United States Patent
Marineau et al.

(10) Patent No.: US 10,787,444 B2
(45) Date of Patent: Sep. 29, 2020

(54) COMPOUNDS FOR THE MODULATION OF MYC ACTIVITY

(71) Applicants: Syros Pharmaceuticals, Inc., Cambridge, MA (US); Christopher Roberts, Belmont, MA (US); Yi Zhang, Belmont, MA (US); Francis Beaumier, Mont-Saint-Hilaire (CA); Luce Lépissier, Montreal (CA)

(72) Inventors: Jason J. Marineau, Franklin, MA (US); Peter B. Rahl, Natick, MA (US); Kevin Sprott, Needham, MA (US); Stephane Ciblat, Montreal (CA); Boubacar Sow, Saint-Laurent (CA); Robin Larouche-Gauthier, Montreal (CA); Lauren Berstler, Somerville, MA (US); Christopher Roberts, Belmont, MA (US); Yi Zhang, Belmont, MA (US); Francis Beaumier, Mont-Saint-Hilaire (CA); Luce Lépissier, Montreal (CA)

(73) Assignee: Syros Pharmaceuticals, Inc., Cambridge, MA (US)

( * ) Notice: Subject to any disclaimer, the term of this patent is extended or adjusted under 35 U.S.C. 154(b) by 0 days.

(21) Appl. No.: 15/579,833

(22) PCT Filed: Jun. 5, 2016

(86) PCT No.: PCT/US2016/035940
§ 371 (c)(1),
(2) Date: Dec. 5, 2017

(87) PCT Pub. No.: WO2016/197078
PCT Pub. Date: Dec. 8, 2016

(65) Prior Publication Data
US 2018/0162851 A1    Jun. 14, 2018

Related U.S. Application Data

(60) Provisional application No. 62/171,775, filed on Jun. 5, 2015.

(51) Int. Cl.
| | | |
|---|---|---|
| C07D 417/04 | (2006.01) | |
| C07D 417/14 | (2006.01) | |
| C07D 495/04 | (2006.01) | |
| C07D 513/02 | (2006.01) | |
| A61P 35/00 | (2006.01) | |

(52) U.S. Cl.
CPC .......... *C07D 417/04* (2013.01); *A61P 35/00* (2018.01); *C07D 417/14* (2013.01); *C07D 495/04* (2013.01); *C07D 513/02* (2013.01)

(58) Field of Classification Search
CPC .................................................. C07D 417/04
See application file for complete search history.

(56) References Cited

U.S. PATENT DOCUMENTS

2011/0053915 A1    3/2011    Ivaschenko et al.

FOREIGN PATENT DOCUMENTS

| EP | 1872795 A1 | 1/2008 | |
|---|---|---|---|
| WO | 2004069149 A2 | 8/2004 | |
| WO | 2008020438 A2 | 2/2008 | |
| WO | WO-2008020438 A2 * | 2/2008 | ........... C07D 495/04 |
| WO | 2012148889 A1 | 11/2012 | |
| WO | 2012154888 A1 | 11/2012 | |

OTHER PUBLICATIONS

STN Chemical Database RN 1329936-46-0 for Propanamide, N-[3-(2-benzothiazolyl)-4,5,6,7-tetrahydro-6-(phenylmethyl)thieno[2,3-c]pyridin-2-yl]-, hydrochloride (1:1) Entered STN: Sep. 8, 2011.*
Online "http://web.archive.org/web/20070202005900/http://www.ambinter.com/" dated Feb. 2, 2007, accessed Feb. 28, 2013.*
Online "http://web.archive.org/web/20070630171813/http://www.enamine.net/index.php?option=com_content&task=view&id=22&menuid=51&PHPSESSID=64a4f248f69d671a413f487bb62c4d90" dated Jun. 30, 2007, accessed Apr. 1, 2015.*
Schönherr "Profound Methyl Effects in Drug Discovery and a Call for New C-H Methylation Reactions" Angew. Chem. Int. Ed. 2013, 52, 12256-12267.*
Wisclicenus, J. "Adolph Strecker's Short Textbook of Organic Chemistry" 1881, Spottiswoode: London, pp. 38-39.*
Yap "Pharmacophore identification of c-Myc inhibitor 10074-G5" Bioorg Med Chem Lett. Jan. 1, 2013; 23(1): 370-374.*

(Continued)

*Primary Examiner* — David K O'Dell
(74) *Attorney, Agent, or Firm* — Goodwin Procter LLP

(57) ABSTRACT

The present invention provides novel compounds of Formula (I) and Formula (II) and pharmaceutically acceptable salts, solvates, hydrates, tautomers, stereoisomers, isotopically labeled derivatives, and compositions thereof. Also provided are methods and kits involving the compounds or compositions for treating or preventing proliferative diseases, e.g., cancers (e.g., breast cancer, prostate cancer, lymphoma, lung cancer, pancreatic cancer, ovarian cancer, neuroblastoma, or colorectal cancer), benign neoplasms, angio genesis, inflammatory diseases, fibrosis (e.g., polycystic kidney disease), autoinflammatory diseases, and autoimmune diseases in a subject.

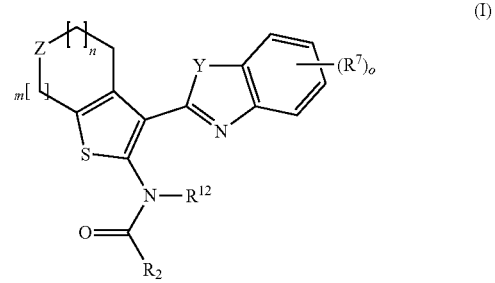

(I)

25 Claims, 129 Drawing Sheets

(56) References Cited

OTHER PUBLICATIONS

Pozharskii et. al. Heterocycles in Life and Society Wiley, 1997, pp. 1-6.*
Pitt "Heteroaromatic Rings of the Future" J. Med. Chem. 2009, 52, 2952-2963.*
"Exploiting Chemical Diversity for Drug Discovery" Edited by Paul A Bartlett and Michael Entzeroth, The Royal Society of Chemistry, 2006, pp. 113-118.*
Rai "Synthesis, biological evaluation, and structure-activity relationships of a novel class of apurinic/apyrimidinic endonuclease 1 inhibitors." Journal of Medicinal Chemistry, 2012, 55(7), 3101-3112.*
STN Chemical Database RN 1330016-73-3 for 2-Thiopheneacetamide, N-[3-(2-benzothiazolyl)-6-ethyl-4,5,6,7-tetrahydrothieno[2,3-c]pyridin-2-yl]-, hydrochloride (1:1) Entered STN: Sep. 8, 2011.*
Fletcher "Small-molecule inhibitors of the Myc oncoprotein" Biochimica et Biophysica Acta, Gene Regulatory Mechanisms (2015), 1849(5), 525-543.*
Richart "c-MYC partners with BPTF in human cancer" Molecular & Cellular Oncology 2016, vol. 3, No. 3, e1152346 (3 pages).*
Shalaby "MYC as Therapeutic Target for Embryonal Tumors: Potential and Challenges" Current Cancer Drug Targets, 2016, 16, 2-21.*
Sharma "Cell line-based platforms to evaluate the therapeutic efficacy of candidate anticancer agents" Nature Reviews Cancer Apr. 2010, vol. 10, 241-253.*
Ocana, A. "Preclinical development of molecular targeted agents for cancer" Nat. Rev. Clin. Oncol. 2011, 8, 200-209.*
Damia "Contemporary pre-clinical development of anticancer agents—What are the optimal preclinical models?" European Journal of Cancer 2009, 45, 2768-2781.*

* cited by examiner

FIG. 1

| # | Structure | NMR/LCMS |
|---|---|---|
| 100 | 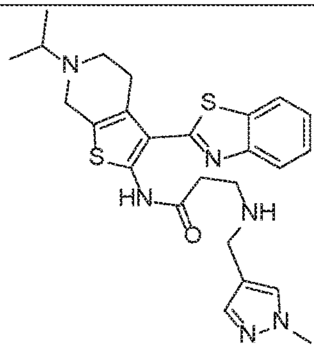 | ¹H NMR (400 MHz, DMSO-d₆) δ 8.14 (d, J=7.34 Hz, 1H), 8.04 (d, J=7.83 Hz, 1H), 7.56 (t, J=7.34 Hz, 2H), 7.46 (d, J=7.34 Hz, 1H), 7.43 (s, 1H), 7.20 (s, 1H), 3.68 (s, 3H), 3.62 (br. s, 2H), 3.57 (s, 2H), 2.80-2.95 (m, 8H), 2.67-2.73 (m, 2H), 1.07 (d, J=5.87 Hz, 6H). LCMS: [M+H]⁺ = 495.15 |
| 101 | 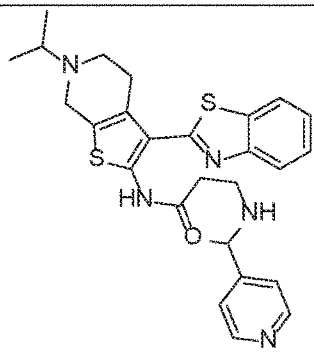 | 1H NMR (400 MHz, Methanol-d4) d 8.77-8.84 (m, 2H), 8.07 (dd, J=8.16, 17.86 Hz, 2H), 7.94 (d, J=6.62 Hz, 2H), 7.59 (t, J=7.50 Hz, 1H), 7.44-7.52 (m, 1H), 4.61-4.80 (m, 2H), 4.50 (br. s., 2H), 3.72-3.87 (m, 2H), 3.51 (dd, J=6.17, 12.79 Hz, 1H), 3.39 (d, J=6.17 Hz, 2H), 3.16-3.23 (m, 2H), 3.08 (t, J=6.17 Hz, 1H), 1.71-1.80 (m, 3H), 1.44-1.53 (m, 6H); LCMS: 506.3 |
| 102 | 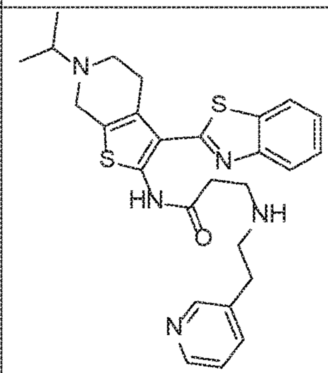 | 1H NMR (400 MHz, Methanol-d4) d 8.82 (s, 1H), 8.76 (d, J=5.40 Hz, 1H), 8.47 (d, J=8.16 Hz, 1H), 8.12 (d, J=8.16 Hz, 1H), 8.07 (d, J=7.91 Hz, 1H), 7.96 (dd, J=5.65, 8.03 Hz, 1H), 7.60 (t, J=7.65 Hz, 1H), 7.47-7.52 (m, 1H), 4.54 (br. s., 2H), 3.94 (br. s., 1H), 3.80 (td, J=6.65, 13.30 Hz, 2H), 3.36-3.66 (m, 8H), 3.22 (t, J=6.40 Hz, 2H), 1.49 (d, J=6.65 Hz, 6H); LCMS: 506.3 |
| 103 | 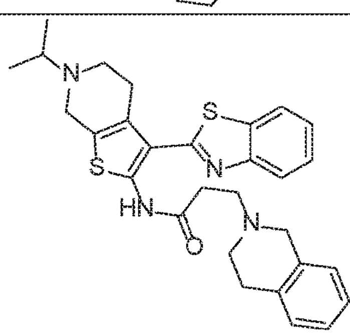 | 1H NMR (400 MHz, Methanol-d4) d 8.18 (d, J=8.38 Hz, 1H), 8.07 (d, J=7.94 Hz, 1H), 7.61 (t, J=7.72 Hz, 1H), 7.46-7.53 (m, 1H), 7.22-7.36 (m, 4H), 4.69 (br. s., 2H), 4.54 (d, J=9.70 Hz, 2H), 3.93 (br. s., 2H), 3.75-3.83 (m, 3H), 3.36-3.57 (m, 6H), 3.26 (br. s., 2H), 1.50 (d, J=6.17 Hz, 6H); LCMS: 517.3 |

FIG. 1 (continued)

| | | |
|---|---|---|
| 104 | 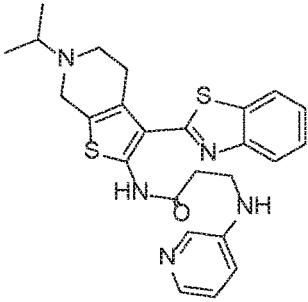 | 1H NMR (400 MHz, Methanol-d4) d 7.98-8.08 (m, 3H), 7.93 (d, J=5.29 Hz, 1H), 7.65-7.76 (m, 2H), 7.58 (t, J=7.28 Hz, 1H), 7.45-7.51 (m, 1H), 4.53 (s, 2H), 3.79 (td, J=6.78, 13.34 Hz, 2H), 3.72 (t, J=6.39 Hz, 2H), 3.44 (br. s., 2H), 3.26 (br. s., 1H), 3.04 (t, J=6.39 Hz, 2H), 1.49 (d, J=6.62 Hz, 6H); LCMS: 478.2 |
| 105 | 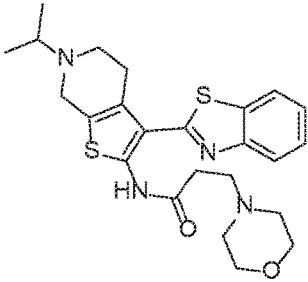 | 1H NMR (400 MHz, Methanol-d4) d 8.02 (d, J=7.50 Hz, 1H), 7.92 (d, J=8.38 Hz, 1H), 7.54 (t, J=7.28 Hz, 1H), 7.42-7.48 (m, 1H), 6.97-7.03 (m, 1H), 6.30-6.39 (m, 2H), 4.53 (br. s., 2H), 3.92 (br. s., 2H), 3.79 (td, J=6.45, 13.12 Hz, 2H), 3.65 (t, J=6.39 Hz, 2H), 3.46 (br. s., 2H), 3.36 (br. s., 2H), 3.26 (br. s., 2H), 2.98 (t, J=6.39 Hz, 2H), 1.49 (d, J=6.62 Hz, 6H); LCMS: 471.2 |
| 106 | 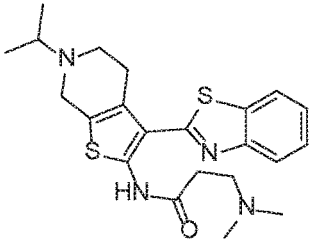 | 1H NMR (400 MHz, Methanol-d4) d 8.15 (d, J=7.94 Hz, 1H), 8.06 (d, J=7.94 Hz, 1H), 7.60 (t, J=7.28 Hz, 1H), 7.45-7.52 (m, 1H), 4.53 (br. s., 2H), 3.80 (td, J=6.62, 13.23 Hz, 2H), 3.60 (t, J=6.39 Hz, 2H), 3.44 (br. s., 3H), 3.24-3.29 (m, 2H), 2.99 (s, 6H), 1.49 (d, J=6.62 Hz, 6H); LCMS: 429.2 |
| 107 | 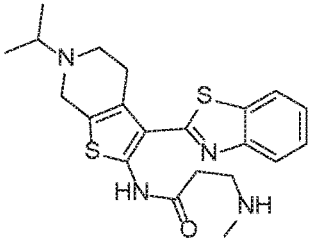 | 1H NMR (400 MHz, Methanol-d4) d 8.02 (d, J=8.38 Hz, 1H), 7.97 (d, J=7.94 Hz, 1H), 7.51 (t, J=7.28 Hz, 1H), 7.37-7.42 (m, 1H), 4.44 (br. s., 2H), 3.81 (br. s., 1H), 3.70 (td, J=6.62, 13.23 Hz, 2H), 3.35 (t, J=6.17 Hz, 4H), 3.05-3.11 (m, 2H), 2.69 (s, 3H), 1.39 (d, J=7.06 Hz, 6H); LCMS: 415.2 |
| 108 | 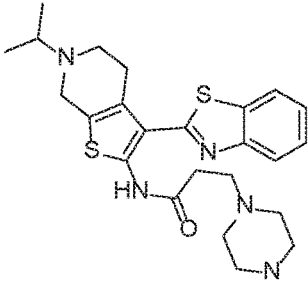 | 1H NMR (400 MHz, Methanol-d4) d 8.11 (d, J=7.94 Hz, 1H), 8.06 (d, J=7.94 Hz, 1H), 7.60 (t, J=7.50 Hz, 1H), 7.46-7.51 (m, 1H), 4.52 (br. s., 2H), 3.93 (br. s., 1H), 3.79 (td, J=6.78, 13.34 Hz, 2H), 3.44 (br. s., 4H), 3.20-3.28 (m, 2H), 3.07-3.15 (m, 3H), 2.88-3.04 (m, 5H), 2.83 (s, 3H), 1.49 (d, J=6.62 Hz, 6H); LCMS: 484.3 |

| | | |
|---|---|---|
| 109 |  | ¹H NMR (400 MHz, Methanol-d4) d 8.09 (dd, J=7.94, 16.32 Hz, 2H), 7.59 (d, J=7.50 Hz, 1H), 7.50 (d, J=7.06 Hz, 1H), 7.43-7.46 (m, 1H), 7.39-7.42 (m, 1H), 7.29-7.33 (m, 2H), 4.54 (br. s., 2H), 3.94 (br. s., 1H), 3.76-3.83 (m, 2H), 3.54 (s, 2H), 3.34-3.39 (m, 4H), 3.18-3.23 (m, 4H), 1.49 (d, J=6.62 Hz, 6H). LCMS: [M+H]⁺ = 539.2. |
| 110 |  | 1H NMR (400 MHz, Methanol-d4) d 8.12 (dd, J=8.03, 18.82 Hz, 2H), 7.63 (t, J=7.53 Hz, 1H), 7.49-7.55 (m, 1H), 4.57 (br. s., 1H), 3.83 (d, J=6.53 Hz, 1H), 3.69-3.73 (m, 2H), 3.52 (t, J=6.53 Hz, 2H), 3.46 (s, 3H), 3.17-3.23 (m, 2H), 1.51 (d, J=6.78 Hz, 6H); LCMS: 459.2 |
| 111 |  | 1H NMR (400 MHz, Methanol-d4) d 8.12 (d, J=7.94 Hz, 1H), 8.06 (d, J=7.94 Hz, 1H), 7.59 (t, J=7.72 Hz, 1H), 7.46-7.51 (m, 1H), 4.53 (br. s., 2H), 3.93 (br. s., 1H), 3.79 (td, J=6.62, 13.23 Hz, 2H), 3.48-3.60 (m, 8H), 3.32-3.38 (m, 4H), 3.22 (t, J=6.17 Hz, 2H), 1.48 (d, J=6.62 Hz, 6H), 1.35 (t, J=7.28 Hz, 6H); LCMS: 500.4 |
| 112 |  | 1H NMR (400 MHz, Methanol-d4) d 8.04 (d, J=7.78 Hz, 1H), 7.91 (d, J=8.03 Hz, 1H), 7.55 (t, J=7.53 Hz, 1H), 7.44-7.50 (m, 1H), 7.21 (t, J=7.78 Hz, 2H), 6.82-6.92 (m, 3H), 4.55 (br. s., 2H), 3.94 (br. s., 1H), 3.75-3.87 (m, 2H), 3.69 (t, J=6.15 Hz, 2H), 3.47 (br. s., 2H), 3.00 (t, J=6.27 Hz, 2H), 1.51 (d, J=6.53 Hz, 6H); LCMS: 477.2 |

FIG. 1 (continued)

| | | |
|---|---|---|
| 113 | *(structure)* | 1H NMR (400 MHz, Methanol-d4) d 8.14 (d, J=7.94 Hz, 1H), 8.06 (d, J=7.94 Hz, 1H), 7.60 (t, J=7.72 Hz, 1H), 7.46-7.52 (m, 1H), 4.53 (br. s., 2H), 3.93 (br. s., 2H), 3.79 (td, J=6.62, 13.23 Hz, 2H), 3.64 (t, J=6.84 Hz, 2H), 3.47 (br. s., 2H), 3.35 (br. s., 1H), 1.49 (d, J=6.62 Hz, 6H); LCMS: 493.2 |
| 114 | *(structure)* | 1H NMR (400 MHz, Methanol-d4) d 8.01 (d, J=7.78 Hz, 1H), 7.85 (d, J=8.03 Hz, 1H), 7.42-7.55 (m, 2H), 7.04 (t, J=7.91 Hz, 1H), 6.28-6.40 (m, 3H), 4.51 (br. s., 2H), 3.90 (br. s., 1H), 3.74-3.83 (m, 2H), 3.66-3.66 (m, 1H), 3.67 (s, 3H), 3.64 (t, J=6.40 Hz, 2H), 3.37-3.43 (m, 2H), 2.94 (t, J=6.40 Hz, 2H), 1.49 (d, J=6.53 Hz, 6H); LCMS: 507.2 |
| 115 | *(structure)* | 1H NMR (400 MHz, Methanol-d4) d 7.98 (d, J=7.50 Hz, 1H), 7.46-7.50 (m, 1H), 7.38-7.42 (m, 1H), 7.01 (d, J=6.62 Hz, 1H), 6.42 (d, J=9.70 Hz, 1H), 6.35 (d, J=11.91 Hz, 1H), 6.24-6.28 (m, 1H), 3.76 (s, 2H), 3.59 (t, J=6.39 Hz, 2H), 3.25 (br. s., 1H), 3.07 (br. s., 2H), 2.95-2.98 (m, 2H), 2.89 (t, J=6.62 Hz, 2H), 1.19 (d, J=6.17 Hz, 6H); LCMS: 495.2 |
| 116 | *(structure)* | 1H NMR (400 MHz, Methanol-d4) d 8.08 (dd, J=7.94, 14.55 Hz, 2H), 7.60 (t, J=7.72 Hz, 1H), 7.53 (br. s., 1H), 7.48 (d, J=5.29 Hz, 4H), 7.28-7.32 (m, 1H), 4.54 (br. s., 2H), 4.32 (s, 2H), 3.80 (td, J=6.62, 13.23 Hz, 2H), 3.50 (t, J=6.62 Hz, 4H), 3.18 (t, J=6.39 Hz, 2H), 2.70 (t, J=6.62 Hz, 1H), 1.49 (d, J=6.62 Hz, 6H); LCMS: 491.3 |

FIG. 1 (continued)

| | | |
|---|---|---|
| 117 | | 1H NMR (400 MHz, Methanol-d4) d 8.09 (dd, J=7.94, 18.08 Hz, 2H), 7.57-7.63 (m, 1H), 7.49 (t, J=7.06 Hz, 1H), 4.52 (br. s., 2H), 3.79 (td, J=6.78, 13.34 Hz, 2H), 3.47 (td, J=6.51, 13.45 Hz, 4H), 3.17 (t, J=6.40 Hz, 2H), 1.83-1.94 (m, 2H), 1.58-1.68 (m, 2H), 1.49 (d, J=6.62 Hz, 6H), 1.38 (d, J=6.62 Hz, 3H), 1.05 (t, J=7.50 Hz, 3H); LCMS: 457.3 |
| 118 | | 1H NMR (400 MHz, Methanol-d4) d 8.09 (d, J=8.03 Hz, 1H), 8.01 (d, J=7.78 Hz, 1H), 7.76 (d, J=8.28 Hz, 2H), 7.58 (t, J=7.40 Hz, 1H), 7.44-7.51 (m, 1H), 6.83 (d, J=8.53 Hz, 2H), 5.15 (t, J=6.40 Hz, 2H), 4.51 (br. s., 2H), 3.75-3.99 (m, 3H), 3.49 (t, J=6.27 Hz, 3H), 1.49 (d, J=6.53 Hz, 6H); LCMS: 545.3 |
| 119 | | 1H NMR (400 MHz, Methanol-d4) d 8.47 (d, J=10.14 Hz, 1H), 8.04 (dd, J=7.94, 13.23 Hz, 2H), 7.52-7.59 (m, 1H), 7.41-7.48 (m, 1H), 4.61 (br. s., 4H), 4.10 (q, J=7.06 Hz, 3H), 3.83 (br. s., 1H), 3.35 (s, 3H), 3.00-3.12 (m, 4H), 2.19-2.32 (m, 4H), 2.01 (s, 3H), 1.24 (t, J=7.28 Hz, 6H); LCMS: 536.3 |
| 120 | | LCMS: [MH]$^+$ =604.23 |

*FIG. 1 (continued)*

| | | |
|---|---|---|
| 121 | (structure) | |
| 122 | (structure) | ¹H NMR (400 MHz, DMSO-d6) δ 12.64 (s, 1H), 8.18 – 8.04 (m, 2H), 7.58 (ddd, $J$ = 8.3, 7.2, 1.2 Hz, 1H), 7.46 (ddd, $J$ = 8.2, 7.2, 1.1 Hz, 1H), 3.62 (s, 2H), 2.90 (p, $J$ = 6.8 Hz, 3H), 2.86 – 2.63 (m, 6H), 2.42 (h, $J$ = 6.6 Hz, 1H), 2.20 (s, 3H), 1.28 (ddd, $J$ = 19.1, 13.4, 6.4 Hz, 2H), 1.07 (d, $J$ = 6.5 Hz, 6H), 0.79 (d, $J$ = 6.5 Hz, 3H), 0.60 (t, $J$ = 7.3 Hz, 3H). LCMS: [M+H]⁺ = 471.25 |
| 123 | (structure) | ¹H NMR (400 MHz, DMSO-d6) δ 12.51 (s, 1H), 9.65 (s, 2H), 8.99 (s, 1H), 8.91 (s, 1H), 8.24 (dd, $J$ = 8.9, 5.3 Hz, 1H), 8.06 (dd, $J$ = 9.9, 2.5 Hz, 1H), 7.42 (td, $J$ = 9.0, 2.6 Hz, 1H), 4.34 (s, 2H), 3.48 (dt, $J$ = 7.9, 3.9 Hz, 2H), 3.25 - 3.15 (m, 6H), 1.82 (dqd, $J$ = 15.1, 7.2, 3.8 Hz, 1H), 1.59 – 1.43 (m, 1H), 1.33 – 1.14 (m, 3H), 0.93 (t, $J$ = 7.5 Hz, 3H). LCMS: [M+H]⁺ =433.20 |
| 124 | (structure) | ¹H NMR (400 MHz, DMSO-d6) δ 12.57 (s, 1H), 9.64 (s, 2H), 8.98-8.88 (m, 2H), 8.18 (dd, $J$ = 14.8, 8.0 Hz, 2H), 7.62 (t, $J$ = 7.7 Hz, 1H), 7.51 (t, $J$ = 7.6 Hz, 1H), 4.34 (s, 2H), 3.52-3.46 (m, 5H), 3.17-3.13 (m, 4H), 1.81 (ddd, $J$ = 12.3, 7.6, 4.4 Hz, 1H), 1.59 – 1.43 (m, 1H), 1.25 (d, $J$ = 6.6 Hz, 3H), 1.00 – 0.81 (m, 3H). LCMS: [M+H]⁺ =415.20 |

FIG. 1 (continued)

| | | |
|---|---|---|
| 125 | [structure] | ¹H NMR (400 MHz, DMSO-d6) δ 8.43 (s, 1H), 8.35 (d, J = 8.4 Hz, 1H), 7.73 (d, J = 8.5 Hz, 1H), 3.82 (s, 2H), 3.12 – 2.82 (m, 6H), 2.71 (t, J = 6.5 Hz, 2H), 2.58 (dt, J = 12.4, 6.3 Hz, 1H), 1.41 – 1.26 (m, 1H), 1.18-1.15 (m, 1H), 0.90 (d, J = 6.3 Hz, 3H), 0.72 (t, J = 7.4 Hz, 3H). LCMS: [M+H]⁺ =483.05 |
| 126 | [structure] | ¹H NMR (DMSO-d₆, 400MHz): δ 12.51 (s, 1H), 10.86 (d, J = 9.5 Hz, 1H), 8.25 (dd, J = 8.6, 4.9 Hz, 1H), 8.05 (d, J = 9.4 Hz, 1H), 7.42 (t, J = 8.9 Hz, 1H), 4.51 (d, J = 14.0 Hz, 1H), 4.44 – 4.33 (m, 1H), 3.88-3.81 (m, 1H), 3.74- 3.64 (m, 1H), 3.21-3.16 (m, 3H), 2.69-2.66 (m, 4 H), 2.36-2.31 (m, 2 H), 1.86-1.81 (m, 1H), 1.57-1.50 (m, 1H), 1.37 (t, J = 7.3 Hz, 6H), 1.24 (d, J = 6.2 Hz, 3H), 0.92 (t, J = 7.3 Hz, 3H). LCMS: [M+H]⁺ = 475.25 |
| 127 | [structure] | ¹H NMR (DMSO-d₆, 400MHz): δ 8.11 (dd, J = 21.0, 8.0 Hz, 2H), 7.57 (t, J = 7.7 Hz, 1H), 7.45 (t, J = 7.6 Hz, 1H), 3.63 (s, 2H), 3.01 (d, J = 8.4 Hz, 2H), 2.96 – 2.79 (m, 7H), 1.22 (d, J = 6.2 Hz, 6H), 1.00 (s, 9H). LCMS: [M+H]⁺ = 457.10 |
| 128 | [structure] | ¹H NMR (DMSO-d₆, 400MHz δ 12.55 (s, 1H), 9.58 (s, 2H), 8.86 (s, 2H), 8.19 (dd, J = 12.2, 8.1 Hz, 2H), 7.62 (t, J = 7.7 Hz, 1H), 7.52 (t, J = 7.6 Hz, 1H), 4.34 (s, 2H), 3.49 (s, 2H), 3.27 (d, J = 7.2 Hz, 3H), 3.22 – 3.07 (m, 4H), 2.60 (d, J = 5.0 Hz, 2H). LCMS: [M+H]⁺ = 373.00 |
| 129 | [structure] | ¹H NMR (DMSO-d₆, 400MHz): 12.57 (s, 1H), 9.69 (s, 2H), 9.02 (s, 2H), 8.19 (dd, J = 11.1, 8.1 Hz, 2H), 7.62 (t, J = 7.6 Hz, 1H), 7.51 (t, J = 7.6 Hz, 1H), 4.33 (s, 2H), 3.48 (t, J = 6.0 Hz, 2H), 3.28-3.20 (m, 3H), 3.19-3.05 (m, 4H), 1.28 (d, J = 6.4 Hz, 6H). LCMS: [M+H]⁺ = 401.05 |

FIG. 1 (continued)

| | | |
|---|---|---|
| 130 | *(structure)* | ¹H NMR (DMSO-$d_6$, 400MHz): 12.61 (d, $J$ = 2.7 Hz, 1H), 10.19 (s, 1H), 9.50 (s, 1H), 8.20 (d, $J$ = 8.0 Hz, 2H), 7.67 – 7.58 (m, 1H), 7.52 (t, $J$ = 7.6 Hz, 1H), 4.34 (s, 2H), 3.56-3.47 (m, 4H), 3.26 – 3.13 (m, 4H), 2.83 (s, 6H). LCMS: [M+H]⁺ = 387.05 |
| 131 | *(structure)* | ¹H NMR (DMSO-$d_6$, 400MHz): δ 12.56 (s, 1H), 9.64 (s, 2H), 9.01 (s, 2H), 8.18 (dd, $J$ = 14.5, 8.1 Hz, 2H), 7.67 – 7.57 (m, 1H), 7.56 – 7.47 (m, 1H), 4.34 (s, 2H), 3.48-3.39 (m, 2H), 3.19-3.05 (m, 6H), 1.33 (s, 9H). LCMS: [M+H]⁺ = 415.05 |
| 132 | *(structure)* | ¹H NMR (DMSO-$d_6$, 400MHz): δ 8.11 (dd, $J$ = 21.8, 8.0 Hz, 2H), 7.76 (s, 2H), 7.57 (t, $J$ = 7.7 Hz, 1H), 7.45 (t, $J$ = 7.6 Hz, 1H), 3.63 (s, 2H), 2.90-2.78 (m, 8H), 2.72-2.65 (m, 2H), 1.07 (d, $J$ = 6.4 Hz, 6H), 0.96 (d, $J$ = 6.2 Hz, 6H). LCMS: [M+H]⁺ = 443.05 |
| 133 | *(structure)* | LCMS: [M]⁺ =480.24 |
| 134 | *(structure)* | ¹H NMR (400 MHz, DMSO-d6) δ 12.56 (s, 1H), 9.64 (s, 2H), 9.00 (s, 2H), 8.18 (dd, $J$ = 17.0, 8.1 Hz, 2H), 7.63 (t, $J$ = 7.7 Hz, 1H), 7.52 (t, $J$ = 7.6 Hz, 1H), 4.34 (s, 2H), 3.63 (t, $J$ = 5.0 Hz, 2H), 3.51 (d, $J$ = 17.0 Hz, 2H), 3.30 – 3.08 (m, 11H). LCMS: [M+H]⁺ =417.05 |

FIG. 1 (continued)

| | | |
|---|---|---|
| 135 | 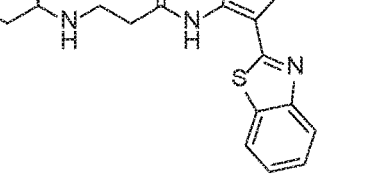 | ¹H NMR (400 MHz, DMSO-$d_6$) δ = 8.13 (d, J=7.96 Hz, 1H), 8.08 (d, J=7.96 Hz, 1H), 7.57 (t, J=7.72 Hz, 1H), 7.42-7.48 (m, 1H), 7.31 (br. s, 2H), 3.62 (s, 2H), 2.86-3.00 (m, 5H), 2.80-2.85 (m, 2H), 2.69 (t, J=6.55 Hz, 2H), 1.28-1.40 (m, 2H), 1.15 (td, J=6.96, 13.69 Hz, 1H), 1.07 (d, J=6.55 Hz, 6H), 0.90 (d, J=6.55 Hz, 3H), 0.71 (t, J=7.49 Hz, 3H). LCMS: [M+H]⁺ = 457.05 |
| 136 | 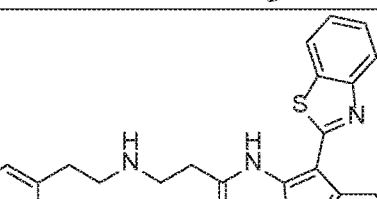 | ¹H NMR (400 MHz, DMSO-d6) δ 12.57 (s, 1H), 9.71 (d, J = 5.4 Hz, 2H), 9.42 (s, 2H), 8.82 (d, J = 2.2 Hz, 1H), 8.75 (d, J = 5.4 Hz, 1H), 8.33 (d, J = 8.0 Hz, 1H), 8.19 (t, J = 8.0 Hz, 2H), 7.86 (dd, J = 8.0, 5.4 Hz, 1H), 7.66 – 7.57 (m, 1H), 7.55 – 7.46 (m, 1H), 4.34 (s, 2H), 3.51 – 3.43 (m, 2H), 3.33 (q, J = 6.2, 5.1 Hz, 4H), 3.19 (q, J = 7.8, 6.9 Hz, 6H). LCMS: [M+H]⁺ =464.05 |
| 137 | 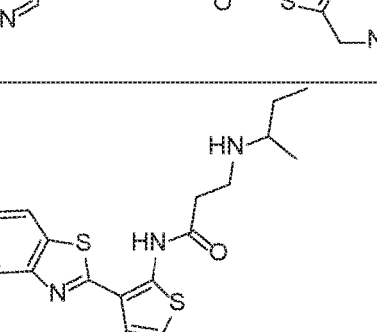 | ¹HNMR (500 MHz, CDCl₃): δ 13.22 (bs, 1H), 8.54 (bs, 1H), 7.93 (d, J = 8.1 Hz, 1H), 7.79 (d, J = 8.0 Hz, 1H), 7.47 (t, J = 7.9 Hz, 1H), 7.33 (t, J = 7.4 Hz, 1H), 4.74 (dt, J = 20.9, 6.3 Hz, 4H), 3.80 – 3.74 (m, 1H), 3.46 (s, 2H), 3.43 – 3.27 (m, 4H), 3.14 – 3.07 (m, 1H), 2.95 (t, J = 5.1 Hz, 2H), 2.72 (t, J = 5.6 Hz, 2H), 1.99-1.91 (m, 1H), 1.72-1.63 (m, 1H), 1.40 (d, J = 6.5 Hz, 3H), 1.02 (t, J = 7.4 Hz, 3H). LCMS: [M+H] = 471.2 |
| 138 | 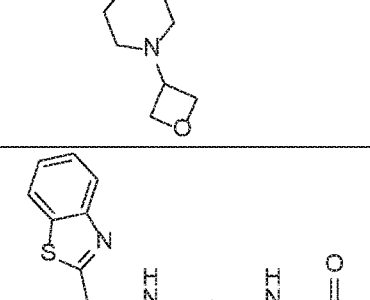 | ¹H NMR (400 MHz, CDCl₃) δ = 13.07 (br. s, 1H), 7.96 (d, J=8.13 Hz, 1H), 7.90 (d, J=7.68 Hz, 1H), 7.51 (t, J=7.68 Hz, 1H), 7.38 (t, J=7.45 Hz, 1H), 4.18 (q, J=6.92 Hz, 2H), 3.76 (m, 2H), 3.47 (s, 2H), 3.13 (t, J=6.32 Hz, 2H), 2.92-3.09 (m, 4H), 2.80 (t, J=6.32 Hz, 2H), 1.46 (d, J=6.32 Hz, 1H), 1.22-1.30 (m, 4H), 1.19 (d, J=6.32 Hz, 6H). LCMS: [M+H]⁺ =487.10 |

*FIG. 1 (continued)*

| | | |
|---|---|---|
| 139 | 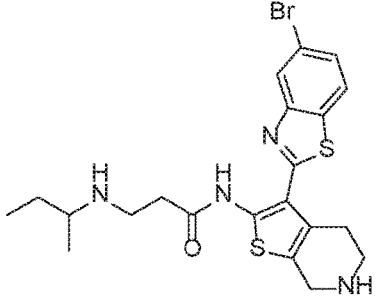 | ¹H NMR (400 MHz, DMSO-$d_6$) δ 12.52 (s, 1H), 9.60 (br. s, 2H), 8.77-8.95 (m, 2H), 8.43 (s, 1H), 8.18 (d, $J$=8.58 Hz, 1H), 7.67 (d, $J$=8.58 Hz, 1H), 4.34 (m, 2H), 3.45-3.53 (m, 3H), 3.11-3.19 (m, 6H), 1.76-1.85 (m, 1H), 1.51 (td, $J$=7.17, 14.11 Hz, 1H), 1.25 (d, $J$=6.32 Hz, 3H), 0.93 (t, $J$=7.22 Hz, 3H). LCMS: [M+H]$^+$ = 495.00 |
| 140 |  | ¹H NMR (400 MHz, DMSO-$d_6$) δ 8.14 – 8.06 (m, 2H), 7.56 (t, $J$ = 8.0 Hz, 1H), 7.44 (t, $J$ = 8.0 Hz, 1H), 3.62 (s, 2H), 2.97 – 2.89 (m, 6H), 2.83 – 2.80 (m, 2H), 2.70 – 2.67 (m, 2H), 1.38 – 1.12 (m, 4H), 1.06 (d, $J$ =6.4 Hz, 6H), 0.89 (d, $J$ =6.8 Hz, 2H), 0.71 (t, $J$ =7.6 Hz, 3H). LCMS: [M+H]$^+$ = 457.10 |
| 141 | 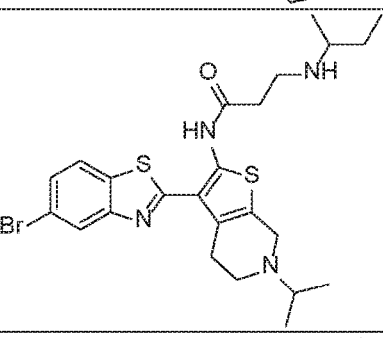 | ¹H NMR (DMSO-$d_6$, 400MHz): δ 8.36 (br. s, 1H), 8.14 (d, $J$=8.55 Hz, 1H), 7.63 (d, $J$=8.79 Hz, 1H), 3.65 (br. s, 2H), 3.28 (br. s, 1H), 3.03-3.18 (m, 3H), 2.82-2.96 (m, 4H), 1.72-1.76 (m, 2H), 1.42-1.52 (m, 2H), 1.39 (d, $J$=6.70 Hz, 1H), 1.21 (d, $J$=6.24 Hz, 3H), 1.00-1.15 (m, 6H), 0.91 (t, $J$=7.28 Hz, 3H). LCMS: [M+H]$^+$ = 535.15 |
| 142 | 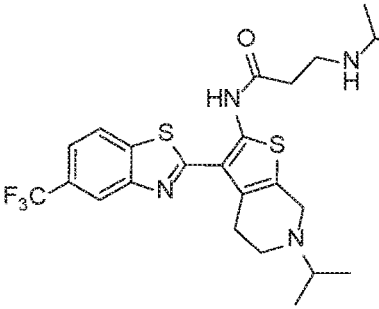 | ¹H NMR (CDCl$_3$, 400MHz): 12.85 (s, 1H), 8.20 (s, 1H), 8.00 (d, $J$ = 8.0 Hz, 1H), 7.61 (d, $J$ = 8.4 Hz, 1H), 3.81 – 3.66 (m, 2H), 3.14 – 3.07 (m, 2H), 3.04-2.92 (m, 5H), 2.80 (t, $J$ = 6.0 Hz, 2H), 2.66 –2.61 (m, 1H), 1.51-1.45 (m, 1H), 1.35 – 1.21 (m, 2H), 1.18 (d, $J$ = 6.4 Hz, 6H), 1.05 (d, $J$ = 6.4 Hz, 3H), 0.88 (t, $J$ = 7.2 Hz, 3H). LCMS: [M+H]$^+$ = 525.2 |

FIG. 1 (continued)

| | | |
|---|---|---|
| 143 | (structure) | ¹H NMR (400 MHz, DMSO-$d_6$) δ 12.55 (s, 1H), 9.62 (br. s, 2H), 9.21 (br. s, 2H), 8.18 (dd, J=7.98, 18.38 Hz, 2H), 7.85 (s, 1H), 7.61 (d, J=7.63 Hz, 1H), 7.58 (s, 1H), 7.51 (t, J=7.51 Hz, 1H), 4.34 (br. s, 2H), 4.05-4.21 (m, 2H), 3.84 (s, 3H), 3.48 (br. s, 2H), 3.09-3.29 (m, 6H). LCMS: [M+H]⁺ = 453.15 |
| 144 | (structure) | ¹H NMR (CDCl₃, 400 MHz): δ 13.09 (s, 1H), 7.96 (d, J = 8.0, 1H), 7.90 (d, J = 7.6 Hz, 1H), 7.51 (t, J = 7.6 Hz, 1H), 7.39 (t, J = 7.6 Hz, 1H), 4.18 (q, J = 7.1 Hz, 2H), 4.03 (s, 2H), 3.46 (s, 2H), 3.31 – 3.23 (m, 2H), 3.12 (t, J = 6.6 Hz, 2H), 2.97 (d, J = 5.8 Hz, 2H), 2.79 (t, J = 6.5 Hz, 2H), 1.26 (t, J = 7.1 Hz, 3H). LCMS: [M+H]⁺ = 445.05 |
| 145 | (structure) | DMSO-d6, δ 8.35 (d, J = 1.8 Hz, 1H), 8.23 (s, 1H), 8.11 (d, J = 8.6 Hz, 1H), 7.60 (dd, J = 8.5, 1.9 Hz, 1H), 3.63 (s, 2H), 3.06 – 2.95 (m, 3H), 2.91 (dd, J = 11.8, 5.3 Hz, 3H), 2.83 (t, J = 5.7 Hz, 2H), 2.77 (t, J = 6.6 Hz, 2H), 2.70 – 2.63 (m, 1H), 1.47 – 1.37 (m, 1H), 1.28 – 1.20 (m, 1H), 1.08 (d, J = 6.5 Hz, 6H), 0.97 (d, J = 6.4 Hz, 3H), 0.78 (t, J = 7.5 Hz, 3H).; LCMS: 535.1/537.0 |
| 146 | (structure) | 1H NMR (CDCl3, 400MHz): 12.85 (s, 1H), 8.20 (s, 1H), 8.00 (d, J = 8.0 Hz, 1H), 7.61 (d, J = 8.4 Hz, 1H), 3.81 – 3.66 (m, 2H), 3.14 – 3.07 (m, 2H), 3.04-2.92 (m, 5H), 2.80 (t, J = 6.0 Hz, 2H), 2.66 –2.61 (m, 1H), 1.51-1.45 (m, 1H), 1.35 – 1.21 (m, 2H), 1.18 (d, J = 6.4 Hz, 6H), 1.05 (d, J = 6.4 Hz, 3H), 0.88 (t, J = 7.2 Hz, 3H); LCMS: 525.2 |

| 147 |  | 1H NMR (400 MHz, DMSO-d6) δ 12.55 (s, 1H), 9.62 (br. s, 2H), 9.21 (br. s, 2H), 8.18 (dd, J=7.98, 18.38 Hz, 2H), 7.85 (s, 1H), 7.61 (d, J=7.63 Hz, 1H), 7.58 (s, 1H), 7.51 (t, J=7.51 Hz, 1H), 4.34 (br. s, 2H), 4.05-4.21 (m, 2H), 3.84 (s, 3H), 3.48 (br. s, 2H), 3.09-3.29 (m, 6H); LCMS: 453.15 |
| --- | --- | --- |
| 148 |  | 1H NMR (CDCl3, 400 MHz): δ 13.09 (s, 1H), 7.96 (d, J = 8.0, 1H), 7.90 (d, J = 7.6 Hz, 1H), 7.51 (t, J = 7.6 Hz, 1H), 7.39 (t, J = 7.6 Hz, 1H), 4.18 (q, J = 7.1 Hz, 2H), 4.03 (s, 2H), 3.46 (s, 2H), 3.31 – 3.23 (m, 2H), 3.12 (t, J = 6.6 Hz, 2H), 2.97 (d, J = 5.8 Hz, 2H), 2.79 (t, J = 6.5 Hz, 2H), 1.26 (t, J = 7.1 Hz, 3H); LCMS: 445.05 |
| 149 |  | DMSO-d6, δ 12.75 (s, 1H), 9.79 – 9.75 (m, 3H), 9.30 (s, 2H), 8.88 (d, J = 2.2 Hz, 1H), 8.44 (d, J = 8.7 Hz, 1H), 8.25 (s, 1H), 7.91 (dd, J = 8.7, 2.3 Hz, 1H), 4.34 (s, 2H), 3.51 – 3.16 (m, 9H), 2.38 (d, J = 0.9 Hz, 3H), 1.29 (d, J = 6.5 Hz, 6H).; LCMS: 481.1 |
| 150 |  | DMSO-d6, δ 12.70 (s, 1 H), 9.49 (dd, J = 1.7, 3.0 Hz, 2 H), 9.11 (d, J = 1.7 Hz, 1 H), 8.89 - 8.77 (m, 2 H), 8.68 (dd, J = 1.1, 4.5 Hz, 1 H), 8.61 (s, 1 H), 8.35 (d, J = 8.4 Hz, 2 H), 7.92 (dd, J = 1.7, 8.4 Hz, 1 H), 7.63 (dd, J = 4.8, 7.5 Hz, 1 H), 4.37 (br. s., 2 H), 3.56 - 3.49 (m, 3 H), 3.22 (d, J = 5.0 Hz, 3 H), 3.17 (d, J = 6.9 Hz, 3 H), 1.28 (d, J = 6.5 Hz, 6 H).; LCMS: 478.1 |

| | | |
|---|---|---|
| 151 |  | CDCl3, δ = 13.22 (s, br, 1 H), 8.47 (s, 1 H), 7.97 (d, J = 8.2 Hz, 1 H), 7.86 (d, J = 7.9 Hz, 1 H), 7.55 - 7.48 (m, 1 H), 7.38 (t, J = 7.6 Hz, 1 H), 4.02 (s, 2 H), 3.36 - 3.19 (m, 5 H), 3.16 - 3.07 (m, 2 H), 2.95 (t, J = 5.7 Hz, 2 H), 1.33 (d, J = 6.6 Hz, 6 H).; LCMS: 467.1 |
| 152 |  | 1H NMR (400 MHz, DMSO-d6) δ 12.47 (s, 1H), 9.70 (s, 2H), 8.98 (br s, 1H), 8.91 (br s, 1H), 8.58 (s, 1H), 8.46 (d, J = 8.4 Hz, 1H), 7.83 (d, J = 8.4 Hz, 1H), 4.34 (s, 2H), 3.48 (q, J = 5.2, 4.5 Hz, 2H), 3.22-3.19 (t, J = 6.4 Hz, 7H), 1.85-1.78 (m, 1H), 1.54 – 1.44 (m, 1H), 1.25 (d, J = 6.4 Hz, 3H), 0.92 (t, J = 7.6 Hz, 3H).; LCMS: 483.05 |
| 153 |  | 1H NMR (400 MHz, DMSO-d6) δ 12.58 (s, 1H), 9.78 (s, 2H), 9.13 (d, J = 11.7 Hz, 2H), 8.18 (t, J = 8.8 Hz, 2H), 7.61 (t, J = 8.0 Hz, 1H), 7.50 (t, J = 8.0 Hz, 1H), 4.33 (s, 2H), 3.47 (t, J = 6.0 Hz, 2H), 3.37 – 3.23 (m, 2H), 3.19 – 3.16 (m, 5H), 1.83 (dqd, J = 11.9, 7.5, 3.9 Hz, 1H), 1.60 – 1.44 (m, 1H), 1.25 (d, J = 6.5 Hz, 3H), 0.92 (t, J = 7.4 Hz, 3H).; LCMS: 415.15 |
| 154 |  | 1H NMR (400 MHz, dmso) δ 12.58 (s, 1H), 9.77 (br. s, 2H), 8.96-9.17 (m, 2H), 8.19 (t, J=8.80 Hz, 2H), 7.61 (t, J=7.58 Hz, 1H), 7.51 (t, J=7.58 Hz, 1H), 4.33 (br. s., 2H), 3.14-3.49 (m, 9H), 1.77-1.90 (m, 1H), 1.46-1.58 (m, 1H), 1.25 (d, J=6.85 Hz, 3H), 0.92 (t, J=7.34 Hz, 3H); LCMS: 415.1 |

*FIG. 1 (continued)*

| | | |
|---|---|---|
| 155 | | 1H NMR (400 MHz, CDCl3) δ 13.08 (s, 1H), 7.91 (dd, J = 12.0, 8.1 Hz, 2H), 7.52 (d, J = 10.8 Hz, 3H), 7.37 (t, J = 7.2 Hz, 1H), 3.82 (s, 2H), 3.74 (s, 2H), 3.14 (t, J = 6.0 Hz, 2H), 2.99-2.92 (m, 5H), 2.83 (t, J = 6.4 Hz, 2H), 1.18 (d, J = 6.4 Hz, 6H).; LCMS: 481.15 |
| 156 | | 1H NMR (400 MHz, DMSO-d6) δ 12.52 (s, 1H), 9.71 (s, 2H), 9.06 (br s, 1H), 8.98 (br s, 1H), 8.24 (dd, J = 8.9, 5.3 Hz, 1H), 8.06 (dd, J = 9.8, 2.5 Hz, 1H), 7.42 (td, J = 9.0, 2.6 Hz, 1H), 4.33 (s, 2H), 3.48 (dt, J = 6.3, 3.6 Hz, 2H), 3.28-3.20 (m, 3H), 3.17 (t, J = 7.6 Hz, 4H), 1.84-1.79 (m, 1H), 1.55-1.47 (m, 1H), 1.25 (d, J = 6.8 Hz, 3H), 0.92 (t, J = 7.2 Hz, 3H).; LCMS: 433.05 |
| 157 | | DMSO-d6, δ 9.65 (br. s, 2H), 8.20 (d, J = 7.9 Hz, 1H), 8.15 (d, J = 8.1 Hz, 1H), 8.06 (br. s, 2H), 7.62 (t, J = 7.7 Hz, 1H), 7.51 (t, J = 7.6 Hz, 1H), 4.33 (br. s, 2H), 3.48 (t, J = 5.8 Hz, 2H), 3.22 – 3.13 (m, 4H), 3.04 (t, J = 6.9 Hz, 2H). 2NH hidden in the water signal; LCMS: 359.1 |
| 158 | | CDCl3, δ 13.29 (br s, 1H), 8.51 (br s, 1H), 7.82 (s, 1H), 7.69 (d, J = 8.2 Hz, 1H), 7.21 (d, J = 8.0 Hz, 1H), 4.01 (s, 2H), 3.38 – 3.16 (m, 6H), 2.93 (s, 2H), 2.71 – 2.63 (m, 1H), 1.98 (d, J = 12.2 Hz, 2H), 1.91 (d, J = 12.7 Hz, 2H), 1.80 (d, J = 12.6 Hz, 1H), 1.61 – 1.30 (m, 12H).; LCMS: 483.2 |

| | | |
|---|---|---|
| 159 |  | DMSO-d6, δ 12.57 (s, 1H), 9.61 (br s, 2H), 9.01 (br s, 2H), 8.29 (dd, J = 8.3, 0.4 Hz, 1H), 8.23 (d, J = 1.2 Hz, 1H), 7.51 (dd, J = 8.3, 1.7 Hz, 1H), 4.35 (s, 2H), 3.50 (t, J = 5.9 Hz, 2H), 3.29 – 3.24 (m, 2H), 3.20 – 3.13 (m, 4H), 2.48 (s, 3H), 2.31 (s, 3H), 1.26 (d, J = 6.5 Hz, 6H).; LCMS: 496.2 |
| 160 |  | CD3OD, δ 8.71 - 8.63 (m, 2 H), 8.51 (s, 2 H), 8.47 (d, J = 1.3 Hz, 1 H), 8.20 (d, J = 8.0 Hz, 1 H), 7.88 - 7.85 (m, 3 H), 4.08 (s, 2 H), 3.47 - 3.37 (m, 4 H), 3.12 (m, J = 6.9 Hz, 4 H), 1.36 - 1.34 (m, 6 H); LCMS: 478.4 |
| 161 |  | CD3OD, δ 8.49 (br. s, 2 H), 8.24 (d, J = 1.2 Hz, 1 H), 8.08 (s, 1 H), 8.01 (d, J = 8.3 Hz, 1 H), 7.94 (s, 1 H), 7.67 (dd, J = 1.6, 8.4 Hz, 1 H), 4.21 (s, 2 H), 3.97 (s, 3 H), 3.50 - 3.41 (m, 5 H), 3.22 - 3.12 (m, 4 H), 1.41 - 1.32 (m, 6 H).; LCMS: 481.3 |
| 162 |  | DMSO-d6, δ 12.54 (s, 1H), 10.49 (br. s, 1H), 8.72 (br. s, 1H), 8.62 (br. s, 1H), 8.57 (s, 1H), 8.04 (d, J = 8.4 Hz, 1H), 7.81 (dd, J = 8.5, 1.6 Hz, 1H), 4.52 (d, J = 16.1 Hz, 1H), 4.45 – 4.35 (m, 1H), 3.88 – 3.78 (m, 1H), 3.73 – 3.64 (m, 1H), 3.21 – 3.07 (m, 3H), 1.85 – 1.75 (m, 1H), 1.55 – 1.46 (m, 1H), 1.39 – 1.35 (m, 5H), 1.25 (d, J = 6.5 Hz, 3H), 0.93 (t, J = 7.5 Hz, 3H). 6H hidden under water signal.; LCMS: 583.2 |

| | | |
|---|---|---|
| 163 |  | DMSO-d6, δ 12.60 (s, 1H), 9.57 (s, 2H), 8.90 (s, 2H), 8.31 (d, J = 6.0 Hz, 1H), 8.30 (s, 1H), 7.63 (dd, J = 8.5, 1.5 Hz, 1H), 6.31 (s, 1H), 4.35 (s, 2H), 3.86 (s, 3H), 3.50 (s, 2H), 3.32 – 3.24 (m, 3H), 3.19 (t, J = 5.5 Hz, 2H), 3.15 (t, J = 7.0 Hz, 2H), 2.21 (s, 3H), 1.27 (d, J = 6.5 Hz, 6H); LCMS: 495.1 |
| 164 |  | CDCl3, δ 8.50 (s, 1H), 7.96 (s, 1H), 7.76 (d, J = 8.2 Hz, 1H), 7.67 (s, 1H), 7.38 (d, J = 8.3 Hz, 1H), 4.01 (s, 2H), 3.92 (s, 3H), 3.40 – 3.16 (m, 6H), 2.94 (t, 2H), 2.47 (s, 3H), 1.37 (s, 3H), 1.36 (s, 3H).; LCMS: 495.3 |
| 165 |  | DMSO-d6, δ 8.27 (s, 1H), 8.16 – 8.04 (m, 1H), 7.56 (ddd, J = 35.5, 8.4, 1.8 Hz, 1H), 6.48 – 6.39 (m, 1H), 4.29 (dd, J = 5.5, 2.7 Hz, 1H), 3.89 (t, J = 5.5 Hz, 2H), 3.15 – 3.04 (m, 2H), 2.98 (dt, J = 26.3, 10.0 Hz, 1H), 2.92 (d, J = 21.6 Hz, 1H), 2.84 (t, J = 6.8 Hz, 1H), 2.58 (d, J = 1.6 Hz, 1H), 2.55 (s, 1H), 1.08 – 1.02 (m, 2H).; LCMS: 483.1 |
| 166 |  | 1H NMR (400 MHz, DMSO-d6): δ 9.80 (s, 2H), 8.17 (dd, J = 12.2, 8.0 Hz, 2H), 7.61 (t, J = 7.2 Hz, 1H), 7.50 (t, J = 8.0 Hz, 1H), 4.32 (s, 2H), 3.90 (s, 2H), 3.50 – 3.42 (m, 2H), 3.33-3.32 (m, 2H), 3.16 (dd, J = 11.0, 6.0 Hz, 4H); LCMS: 417 |

FIG. 1 (continued)

| | | |
|---|---|---|
| 167 | | 1H NMR (400 MHz, DMSO-d6): δ 12.56 (s, 1H), 9.74 (s, 2H), 9.34 (s, 2H), 8.18 (dd, J = 14.1, 8.1 Hz, 2H), 7.79 (s, 2H), 7.61 (t, J = 8.0 Hz, 1H), 7.50 (t, J = 8.0 Hz, 1H), 4.33 (t, J = 4.1 Hz, 2H), 4.10 (t, J = 5.4 Hz, 2H), 3.75 – 3.60 (m, 1H), 3.54 – 3.40 (m, 3H), 3.30 – 3.10 (m, 4H).; LCMS: 439.1 |
| 168 | | 1H NMR (400 MHz, CD3OD): δ 8.14 (d, J = 8.0 Hz, 1H), 8.06 (d, J = 8.0 Hz, 1H), 7.60 (t, J = 8.6 Hz, 1H), 7.49 (t, J = 7.6 Hz, 1H), 4.54 (s, 2H), 3.98 (s, 2H), 3.84-3.76 (m, 2H), 3.62 – 3.51 (m, 3H), 3.45 (s, 2H), 3.22 (d, J = 6.2 Hz, 2H), 1.50 (d, J = 5.9 Hz, 6H).; LCMS: 459.1 |
| 169 | | DMSO-d6, δ 12.72 (br. s, 1H), 9.68 (br. s, 2H), 9.02 (br. s, 2H), 8.49 (d, J = 1.6 Hz, 1H), 8.28 (d, J = 8.4 Hz, 1H), 7.86 – 7.81 (m, 3H), 7.53 (t, J = 7.7 Hz, 2H), 7.43 (t, J = 7.4 Hz, 1H), 4.34 (s, 2H), 3.50 (t, J = 6.0 Hz, 2H), 3.39 – 3.25 (m, 3H; overlaps water signal), 3.23 – 3.15 (m, 4H), 1.28 (d, J = 6.5 Hz, 6H); LCMS: 477.2 |
| 170 | | DMSO-d6, δ 12.67 (s, 1H), 9.57 (s, 1H), 9.23 (s, 1H), 9.03 (s, 1H), 8.31 (s, 1H), 8.19 (d, J = 8.6 Hz, 1H), 7.67 (dd, J = 8.6, 1.8 Hz, 1H), 6.51 – 6.36 (m, 1H), 4.39 – 4.28 (m, 2H), 3.85 – 3.78 (m, 2H), 3.54 – 3.46 (m, 4H), 3.32 – 3.23 (m, 3H), 3.24 – 3.14 (m, J = 6.9 Hz, 4H), 2.93 – 2.79 (m, 2H), 1.28 (d, J = 6.5 Hz, 6H).; LCMS: 482.1 |

| 171 |  | CD3OD, δ 7.03 (s, 1 H), 6.74 (d, J = 8.2 Hz, 1 H), 6.26 (dd, J = 1.2, 8.4 Hz, 1 H), 2.93 (s, 2 H), 2.28 - 2.20 (m, 1 H), 2.20 - 2.11 (m, 5 H), 1.99 - 1.92 (m, 2 H), 1.89 - 1.84 (m, 1 H), 1.72 - 1.65 (m, 1 H), -0.09 (d, J = 6.5 Hz, 6 H).; LCMS: 426.3 |
|---|---|---|
| 173 |  | DMSO-d6, δ 12.66 (s, 1H), 9.55 (s, 2H), 9.00 (s, 2H), 8.65 (d, J = 2.1 Hz, 1H), 8.48 (d, J = 1.6 Hz, 1H), 8.35 (d, J = 8.7 Hz, 1H), 8.14 (d, J = 1.6 Hz, 1H), 7.84 (dd, J = 8.7, 2.2 Hz, 1H), 4.35 (s, 2H), 3.55 – 3.46 (m, 2H), 3.32 – 3.25 (m, 2H), 3.23 – 3.11 (m, 4H), 1.28 (d, J = 6.5 Hz, 6H). 1 x CH missing (overlaping in water signal).; LCMS: 501.2 |
| 174 |  | CD3OD, δ 7.43 (d, J = 1.2 Hz, 1 H), 6.87 (d, J = 8.4 Hz, 1 H), 6.68 (dd, J = 1.3, 8.4 Hz, 1 H), 3.05 (s, 2 H), 2.31 - 2.22 (m, 2 H), 2.12 - 2.04 (m, 3 H), 1.97 (s, 2 H), 1.80 (t, J = 6.5 Hz, 2 H), -0.01 (d, J = 6.5 Hz, 6 H).; LCMS: 469.4 |
| 175 |  | DMSO-d6, δ 12.62 (s, 1H), 9.65 (s, 2H), 8.90 (s, 2H), 8.27 – 8.06 (m, 2H), 7.61 (dd, J = 8.4, 1.6 Hz, 1H), 7.49 – 7.33 (m, 2H), 7.18 (dd, J = 8.7, 0.7 Hz, 1H), 7.09 (td, J = 7.5, 0.9 Hz, 1H), 4.34 (s, 2H), 3.80 (s, 3H), 3.50 (t, J = 5.8 Hz, 2H), 3.26 (s, 2H), 3.20 (t, J = 5.5 Hz, 2H), 3.12 (t, J = 7.1 Hz, 2H), 1.25 (d, J = 6.5 Hz, 6H).; LCMS: 507.4 |

| | | |
|---|---|---|
| 176 |  | DMSO-d6, δ 12.71 (s, 1H), 9.58 (s, 2H), 8.91 (s, 2H), 8.48 (d, J = 1.6 Hz, 1H), 8.27 (d, J = 8.4 Hz, 1H), 7.84 (dd, J = 8.4, 1.8 Hz, 1H), 7.45 (t, J = 7.9 Hz, 1H), 7.42 – 7.37 (m, 1H), 7.35 (t, 1H), 7.01 (ddd, J = 8.1, 2.5, 0.9 Hz, 1H), 4.35 (s, 2H), 3.50 (t, J = 5.8 Hz, 2H), 3.32 – 3.26 (m, 2H), 3.24 – 3.12 (m, 4H), 1.27 (d, J = 6.5 Hz, 6H).; LCMS: 507.4 |
| 177 |  | DMSO-d6, δ 12.72 (s, 1H), 9.58 (s, 2H), 8.92 (s, 2H), 8.42 (d, J = 1.5 Hz, 1H), 8.23 (d, J = 8.4 Hz, 1H), 7.86 – 7.71 (m, 3H), 7.16 – 7.01 (m, 2H), 4.35 (s, 2H), 3.83 (s, 3H), 3.50 (t, J = 5.9 Hz, 2H), 3.31 – 3.26 (m, 2H), 3.26 – 3.11 (m, 4H), 1.27 (d, J = 6.5 Hz, 7H).; LCMS: 507.4 |
| 178 |  | DMSO-d6, δ 12.72 (s, 1H), 9.82-9.59 (m, 3H), 9.23 (br. s, 2H), 8.93 (d, J = 2.1 Hz, 1H), 8.47 (br. s, 1H), 8.45 (d, J = 8.7 Hz, 1H), 7.96 (dd, J = 8.7, 2.3 Hz, 1H), 7.87 (br. s, 1H), 4.35 (br. s, 2H), 3.53 – 3.46 (m, 2H), 3.24 – 3.15 (m, 5H), 1.28 (d, J = 6.5 Hz, 6H). 2H hidden under water signal.; LCMS: 467.2 |
| 179 |  | 1H NMR (400 MHz, DMSO-d6): δ 12.47 (s, 1H), 9.75 (s, 2H), 9.02 (s, 1H), 8.94 (s, 1H), 8.58 (s, 1H), 8.45 (d, J = 8.4 Hz, 1H), 7.82 (d, J = 8.5 Hz, 1H), 4.33 (s, 2H), 3.49 (d, J = 7.0 Hz, 2H), 3.27 (d, J = 7.7 Hz, 1H), 3.18 (q, J = 6.4, 5.7 Hz, 6H), 1.87 – 1.76 (m, 1H), 1.59 – 1.41 (m, 1H), 1.24 (d, J = 6.5 Hz, 3H), 0.92 (t, J = 7.4 Hz, 3H).; LCMS: 483.18 |

| | | |
|---|---|---|
| 180 |  | DMSO-d6, 12.66 (s, 1 H), 9.64 - 9.50 (m, 2 H), 9.09 - 8.91 (m, 2 H), 8.40 (d, J = 1.5 Hz, 1 H), 8.33 (s, 1 H), 8.18 - 8.14 (m, 1 H), 8.05 (d, J = 0.8 Hz, 1 H), 7.74 (dd, J = 1.7, 8.4 Hz, 1 H), 4.35 (t, J = 3.1 Hz, 2 H), 3.91 (s, 3 H), 3.67 - 3.64 (m, 2 H), 3.39 - 3.34 (m, 3 H), 3.24 - 3.13 (m, 7 H).; LCMS: 497.3 |
| 181 |  | DMSO-d6, δ 12.70 (s, 1H), 9.67 (s, 2H), 9.06 (s, 2H), 8.65 (d, J = 1.5 Hz, 1H), 8.35 (d, J = 8.4 Hz, 1H), 8.16 (d, J = 8.5 Hz, 2H), 8.07 (d, J = 8.5 Hz, 2H), 7.93 (dd, J = 8.4, 1.8 Hz, 1H), 4.36 (s, 2H), 3.51 (s, 2H), 3.30 (s, 3H), 3.26 – 3.10 (m, 5H), 1.29 (d, J = 6.5 Hz, 6H).; LCMS: 555.3 |
| 182 |  | DMSO-d6, δ 12.57 (s, 1H), 9.63 (s, 2H), 8.96 (s, 2H), 8.37 (d, J = 1.5 Hz, 1H), 8.25 (s, 1H), 8.13 (d, J = 8.5 Hz, 1H), 7.98 (d, J = 0.7 Hz, 1H), 7.83 (dd, J = 8.5, 1.7 Hz, 1H), 4.34 (br. s, 2H), 3.90 (s, 3H), 3.52 – 3.46 (m, 2H), 3.38-3.32 (m, 1H), 3.31 – 3.24 (m, 2H), 3.18 (t, J = 5.7 Hz, 2H), 3.14 (t, J = 7.1 Hz, 2H), 1.28 (d, J = 6.5 Hz, 6H); LCMS: 481.1 |

| | | |
|---|---|---|
| 183 |  | DMSO-d6, δ 10.08 (s, 1H), 8.33 (s, 1H), 8.22 (s, 1H), 8.18 (d, J = 8.2 Hz, 1H), 7.79 – 7.69 (m, J = 6.1 Hz, 5H), 3.87 (s, 2H), 3.09 (t, 2H), 3.04 (t, 2H), 2.94 – 2.86 (m, 2H), 2.79 (t, 2H), 2.09 (s, 3H), 1.00 (d, J = 6.3 Hz, 6H). NH.HCl not seen as the sample is much diluted.; LCMS: 534.2 |
| 184 |  | CDCl3, δ = 12.56 (s, 1 H), 9.54 - 9.49 (m, 1 H), 8.87 (br. s., 1 H), 8.45 (d, J = 1.9 Hz, 1 H), 8.23 (dd, J = 0.3, 8.6 Hz, 1 H), 7.72 (dd, J = 1.9, 8.6 Hz, 1 H), 4.39 (br. s., 2 H), 3.67 (t, J = 10.2 Hz, 2 H), 3.54 (td, J = 5.0, 5.7 Hz, 3 H), 3.47 - 3.46 (m, 3 H), 3.37 (s, 3 H), 3.28 - 3.11 (m, 7 H).; LCMS: 497.2 |
| 185 |  | 1H NMR (400 MHz, DMSO-d6) δ 12.52 (s, 1H), 9.69 (s, 2H), 9.05 - 8.96 (m, 2H), 8.24 (dd, J = 8.9, 5.3 Hz, 1H), 8.06 (dd, J = 9.8, 2.5 Hz, 1H), 7.42 (td, J = 9.0, 2.5 Hz, 1H), 4.33 (s, 2H), 3.48 - 3.46 (m, 2H), 3.28 (d, J = 7.4 Hz, 2H), 3.21 - 3.12 (m, 5H), 1.82 (tt, J = 11.0, 7.3 Hz, 1H), 1.59 - 1.43 (m, 1H), 1.25 (d, J = 6.5 Hz, 3H), 0.93 (t, J = 7.5 Hz, 3H).; LCMS: 433.12 |
| 186 |  | DMSO-d6, δ 12.49 (s, 1H), 9.64 (br. s, 2H), 9.43 (br. s, 1H), 9.02 (br. s, 2H), 8.62 (d, J = 2.2 Hz, 1H), 8.40 (d, J = 8.8 Hz, 1H), 7.98 (m, 2H), 4.35 (br. s, 2H), 3.67 (br. s, 3H), 3.22 – 3.13 (m, 4H), 3.02 (br. s, 2H), 2.36 (s, 3H), 1.28 (d, J = 6.5 Hz, 6H); LCMS: 481.1 |

FIG. 1 (continued)

| | | |
|---|---|---|
| 187 | | DMSO-d6, δ 12.63 (s, 1H), 9.53 (br. s, 2H), 9.53 (s, 1H), 8.87 (br. s, 2H), 8.75 (d, J = 2.1 Hz, 1H), 8.39 (d, J = 8.7 Hz, 1H), 8.33 (s, 1H), 8.06 (dd, J = 8.7, 2.2 Hz, 1H), 4.35 (br. s, 2H), 3.55 – 3.46 (br. s, 2H), 3.19 (t, J = 6.2 Hz, 2H), 3.16 (t, J = 7.2 Hz, 2H), 1.28 (d, J = 6.5 Hz, 6H). 3H hidden under water signal; LCMS: 468.1 |
| 188 | | DMSO-d6, δ 9.63 - 9.53 (m, 1 H), 8.22 - 8.17 (m, 1 H), 8.09 - 8.08 (m, 1 H), 7.62 (d, J = 8.1 Hz, 1 H), 7.56 (d, J = 8.6 Hz, 2 H), 6.84 (d, J = 8.6 Hz, 2 H), 4.01 - 3.87 (m, 2 H), 3.17 - 3.08 (m, 3 H), 3.00 - 2.86 (m, 5 H), 1.17 - 1.06 (m, 7 H).; LCMS: 493.2 |
| 189 | | 1H NMR (400 MHz, DMSO-d6) δ 12.50 (s, 1H), 9.60 (s, 2H), 8.98 (s, 2H), 8.23 (dd, J = 8.9, 5.3 Hz, 1H), 8.03 (dd, J = 9.9, 2.6 Hz, 1H), 7.42 (td, J = 9.0, 2.6 Hz, 1H), 4.32 (s, 2H), 3.62 (t, J = 5.1 Hz, 2H), 3.51 – 3.35 (m, 2H), 3.32 – 3.28 (m, 5H), 3.17 – 3.09 (m, 6H).; LCMS: 435.3 |
| 190 | | 1H NMR (400 MHz, DMSO-d6/D2O) δ 8.88 (s, 1H), 8.15 (t, J = 7.3 Hz, 2H), 7.72 (s, 1H), 7.61 (t, J = 7.6 Hz, 1H), 7.50 (t, J = 7.4 Hz, 1H), 4.34 - 4.32 (m, 4H), 3.48 (t, J = 5.7 Hz, 2H), 3.35 (q, J = 7.0, 6.5 Hz, 2H), 3.18 – 3.14 (m, 4H).; LCMS: 439 |

FIG. 1 (continued)

| | | |
|---|---|---|
| 191 | 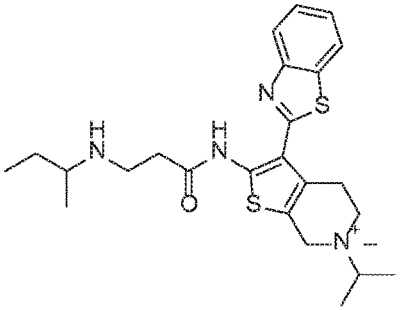 | 1H NMR (400 MHz, DMSO-d6) δ 12.63 (s, 1H), 9.19 (s, 1H), 9.11 (s, 1H), 8.21 (dd, J = 12.5, 8.0 Hz, 2H), 7.62 (t, J = 7.6 Hz, 1H), 7.52 (t, J = 7.5 Hz, 1H), 4.76 (d, J = 15.4 Hz, 1H), 4.65 (d, J = 15.5 Hz, 1H), 3.90 (dp, J = 26.4, 6.3, 5.7 Hz, 2H), 3.71 (dt, J = 12.7, 6.8 Hz, 1H), 3.28 (d, J = 9.3 Hz, 2H), 3.24 – 3.10 (m, 3H), 2.97 (s, 3H), 1.83 (dqd, J = 11.5, 7.4, 3.7 Hz, 1H), 1.60 – 1.37 (m, 7H), 1.26 (d, J = 6.4 Hz, 4H), 0.93 (t, J = 7.4 Hz, 3H).; LCMS: 471 |
| 192 | 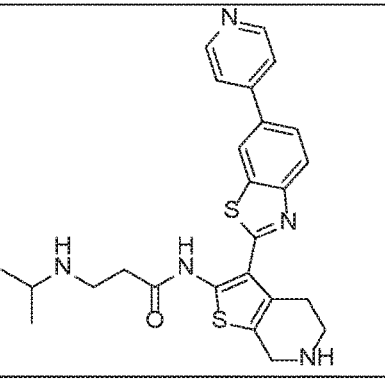 | DMSO-d6+D2O, δ 8.82 (d, J = 6.5 Hz, 2H), 8.78 (d, J = 1.8 Hz, 1H), 8.34 – 8.29 (m, 3H), 8.16 (dd, J = 8.7, 1.9 Hz, 1H), 4.32 (s, 2H), 3.50 (t, J = 6.1 Hz, 2H), 3.35 (hept, J = 6.6 Hz, 1H), 3.28 (t, J = 6.9 Hz, 2H), 3.21 (t, J = 5.7 Hz, 2H), 3.08 (t, J = 6.9 Hz, 2H), 1.24 (d, J = 6.5 Hz, 6H). 5 NH are missing due to D2O; LCMS: 478.2 |
| 193 | 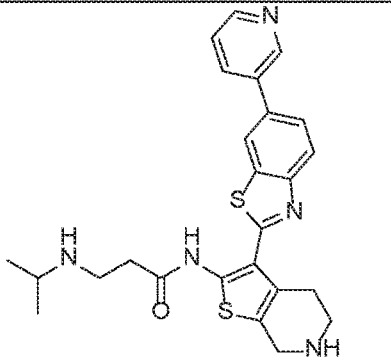 | DMSO-d6+D2O, δ 9.08 (s, 1H), 8.69 (d, J = 4.2 Hz, 1H), 8.60 (d, J = 8.0 Hz, 1H), 8.54 (s, 1H), 8.27 (d, J = 8.5 Hz, 1H), 7.98 (d, J = 8.6 Hz, 1H), 7.92 – 7.85 (m, 1H), 4.31 (br. s, 2H), 3.49 (t, J = 5.5 Hz, 2H), 3.32 (hept, J = 6.5 Hz, 1H), 3.28 (t, J = 6.7 Hz, 2H), 3.23-3.17 (m, 2H), 3.05 (t, J = 6.7 Hz, 2H), 1.23 (d, J = 6.5 Hz, 6H). 5 NH missing due to D2O; LCMS: 478.2 |
| 194 | 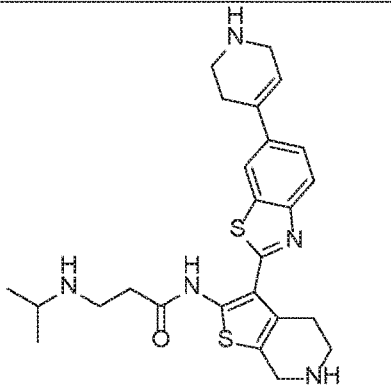 | CD3OD, δ 6.79 (d, J = 1.7 Hz, 1H), 6.73 (d, J = 8.6 Hz, 1H), 6.36 (dd, J = 8.6, 1.8 Hz, 1H), 4.96 – 4.88 (m, 1H), 3.04 (s, 2H), 2.52 (dd, J = 5.5, 2.4 Hz, 2H), 2.26 (t, J = 6.1 Hz, 2H), 2.17 – 2.10 (m, 2H), 2.10 – 2.02 (m, 3H), 1.96 (t, J = 5.7 Hz, 2H), 1.78 (t, J = 6.4 Hz, 2H), 1.52 (ddd, J = 6.2, 3.5, 2.0 Hz, 2H), -0.01 (d, J = 6.6 Hz, 6H).; LCMS: 482.3 |

FIG. 1 (continued)

| | | |
|---|---|---|
| 195 | 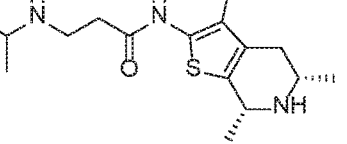 | 1H NMR (400 MHz, DMSO-d6) δ 12.55 (s, 1H), 9.98 (d, J = 9.5 Hz, 1H), 9.35 (d, J = 10.7 Hz, 1H), 8.84 – 8.75 (m, 2H), 8.19 (dd, J = 17.9, 8.1 Hz, 2H), 7.62 (t, J = 7.5 Hz, 1H), 7.52 (t, J = 7.6 Hz, 1H), 4.68 (d, J = 9.3 Hz, 1H), 3.66 (s, 1H), 3.26 (t, J = 6.6 Hz, 2H), 3.10 (t, J = 7.3 Hz, 2H), 2.94 – 2.82 (m, 2H), 1.63 (d, J = 6.6 Hz, 3H), 1.50 (d, J = 6.2 Hz, 3H), 1.30 – 1.08 (m, 6H).; LCMS: 429.2 |
| 196 |  | 1H NMR (400 MHz, DMSO-d6) δ 8.11 (d, J = 8.0 Hz, 2H), 7.56 (t, J = 7.7 Hz, 1H), 7.44 (t, J = 7.4 Hz, 1H), 4.11 (q, J = 6.9 Hz, 1H), 3.18 (q, J = 6.0 Hz, 2H), 2.95 (q, J = 8.0, 6.7 Hz, 3H), 2.78-2.76 (m, 1H), 2.68 (t, J = 6.8 Hz, 2H), 2.39 (dd, J = 15.0, 9.0 Hz, 1H), 1.35 (d, J = 6.9 Hz, 3H), 1.19 (d, J = 6.4 Hz, 3H), 0.92 (d, J = 6.2 Hz, 6H).; LCMS: 429.13 |
| 197 |  | 1H NMR (400 MHz, DMSO-d6) δ 8.14 (d, J = 7.9 Hz, 1H), 8.08 (d, J = 7.9 Hz, 1H), 7.56 (t, J = 7.5 Hz, 1H), 7.44 (t, J = 7.3 Hz, 1H), 7.39 – 7.30 (m, 1H), 4.05 – 3.96 (m, 1H), 3.02 – 2.90 (m, 4H), 2.78 (dd, J = 6.6, 6.2 Hz, 2H), 2.69 (t, J = 6.8 Hz, 2H), 2.48 – 2.37 (m, 1H), 1.33 (d, J = 6.6 Hz, 3H), 1.26 – 1.05 (m, 3H), 0.92 (t, J = 5.0 Hz, 6H).; LCMS: 429.13 |
| 198 |  | 1H NMR (400 MHz, DMSO-d6) δ 8.11 (d, J = 8.0 Hz, 1H), 8.07 (d, J = 8.0 Hz, 1H), 7.57 (t, J = 7.8 Hz, 1H), 7.44 (t, J = 7.7 Hz, 1H), 4.13 (q, J = 6.7 Hz, 1H), 3.20 (dq, J = 14.0, 7.7, 6.1 Hz, 1H), 3.02 – 2.93 (m, 3H), 2.83 (dq, J = 12.5, 6.6, 6.0 Hz, 2H), 2.73 (d, J = 6.7 Hz, 2H), 2.41 (dd, J = 15.4, 8.5 Hz, 2H), 1.36 (d, J = 6.7 Hz, 3H), 1.26 – 1.09 (m, 3H), 0.95 (d, J = 6.2 Hz, 6H).; LCMS: 429.13 |
| 199 | 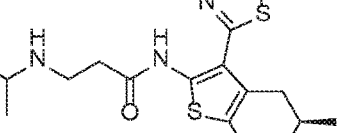 | 1H NMR (400 MHz, DMSO-d6) δ 12.64 (s, 1H), 9.38 (br. s, 2H), 8.18 (dd, J = 8.1, 4.5 Hz, 2H), 7.99 (d, J = 5.7 Hz, 1H), 7.61 (t, J = 7.7 Hz, 1H), 7.49 (t, J = 7.7 Hz, 1H), 4.34 (s, 2H), 3.52 – 3.43 (m, 4H), 3.17 (t, J = 5.6 Hz, 2H), 2.77 (t, J = 6.6 Hz, 2H), 2.00 (q, J = 7.6 Hz, 2H), 0.89 (t, J = 7.6 Hz, 3H).; LCMS: 415.15 |

FIG. 1 (continued)

| | | |
|---|---|---|
| 300 | | 1H NMR (400 MHz, DMSO-d6) δ 12.63 (s, 1H), 9.62 (br. s, 2H), 8.14 (t, J=8.56 Hz, 2H), 7.58 (t, J=7.58 Hz, 1H), 7.46 (t, J=7.58 Hz, 1H), 4.30 (br. s, 2H), 3.50-3.60 (m, 2H), 3.42-3.46 (m, 2H), 3.29-3.38 (m, 1H), 3.14 (d, J=4.40 Hz, 2H), 2.91 (t, J=7.09 Hz, 1H), 2.77-2.84 (m, 1H), 2.06 (s, 1H), 1.97 (s, 2H), 1.38-1.57 (m, 2H), 1.09 (d, J=6.85 Hz, 3H), 0.78 (t, J=7.34 Hz, 3H).; LCMS: 457.3 |
| 301 | | 1H NMR (400 MHz, DMSO-d6) δ 10.06 (s, 2H), 8.61 (s, 2H), 8.19 (d, J = 8.0 Hz, 1H), 8.09 (d, J = 8.1 Hz, 1H), 7.55 (dt, J = 28.7, 7.5 Hz, 2H), 4.42 (s, 2H), 3.47 – 3.36 (m, 4H), 3.25 (s, 3H), 3.09 (d, J = 14.6 Hz, 3H), 2.78 (d, J = 19.7 Hz, 1H), 2.43-2.41 (m, 1H), 1.68-1.64 (m, 1H), 1.39 (dt, J = 15.4, 7.7 Hz, 1H), 1.12 (d, J = 7.2 Hz, 3H), 0.82 (t, J = 7.6 Hz, 3H).; LCMS: 429.13 |
| 302 | | DMSO-d6, δ 12.76 (s, 1H), 9.63 – 9.46 (m, 2H), 9.03 – 8.87 (m, 2H), 7.99 (d, J = 8.9 Hz, 1H), 7.67 (d, J = 2.2 Hz, 1H), 7.27 (dd, J = 9.0, 2.4 Hz, 1H), 4.34 (s, 2H), 3.84 – 3.74 (m, 4H), 3.35 (hept, J = 6.5 Hz, 1H), 3.31 – 3.22 (m, 6H), 3.18 – 3.12 (m, 4H), 1.27 (d, J = 6.5 Hz, 6H). 2H hidden under water signal; LCMS: 486.2 |
| 303 | | DMSO-d6, δ 11.74 (s, 1H), 9.64 (br s, 2H), 8.94 (br s, 2H), 7.85 – 7.78 (m, 2H), 7.48 – 7.44 (m, 2H), 4.33 (br s, 2H), 3.45 (t, J = 6.0 Hz, 2H), 3.36 (hept, J = 6.5 Hz, 1H), 3.30-3.25 (m, 2H), 3.28 (d, J = 5.6 Hz, 5H), 3.14 (t, J = 7.1 Hz, 2H), 1.27 (d, J = 6.5 Hz, 6H).; LCMS: 385.2 |

| | | |
|---|---|---|
| 304 |  | DMSO-d6, δ 12.72 (s, 1H), 9.47 (s, 2H), 8.94 (s, 2H), 7.95 (d, J = 8.9 Hz, 1H), 7.78 (s, 1H), 7.25 (dd, J = 9.0, 2.4 Hz, 1H), 4.27 (s, 2H), 3.86 (s, 4H), 3.42 (s, 2H), 3.21 (dd, J = 12.3, 5.8 Hz, 3H), 3.11 (dd, J = 15.2, 8.1 Hz, 8H), 1.21 (d, J = 6.5 Hz, 6H).; LCMS: 534.2 |
| 305 |  | DMSO-d6, δ 9.64 (br. s, 2 H), 9.31 (br. s, 1 H), 9.07 (br. s, 1 H), 8.25 (d, J = 5.1 Hz, 1 H), 8.23 (d, J = 5.2 Hz, 1 H), 7.66 (ddd, J = 1.1, 7.2, 8.2 Hz, 1 H), 7.55 (ddd, J = 1.1, 7.2, 8.1 Hz, 1 H), 4.38 (br. s., 2 H), 3.93 (td, J = 7.4, 14.4 Hz, 1 H), 3.53 (d, J = 4.1 Hz, 3 H), 3.32 - 3.16 (m, 5 H), 2.29 - 2.16 (m, 1 H), 2.10 - 1.97 (m, 1 H), 1.96 - 1.86 (m, 1 H), 1.78 - 1.67 (m, 1 H); LCMS: 399.2 |
| 306 |  | DMSO-d6, δ 9.98 - 9.84 (m, 1 H), 9.76 (br. s., 2 H), 9.62 - 9.50 (m, 1 H), 8.29 - 8.19 (m, 2 H), 7.66 (dt, J = 1.2, 7.7 Hz, 1 H), 7.59 - 7.51 (m, 1 H), 4.38 (br. s., 2 H), 4.05 - 3.98 (m, 1 H), 3.98 - 3.91 (m, 1 H), 3.85 - 3.75 (m, 2 H), 3.74 - 3.69 (m, 1 H), 3.55 - 3.48 (m, 2 H), 3.35 - 3.27 (m, 1 H), 3.25 - 3.15 (m, 4 H), 3.15 - 3.06 (m, 1 H); LCMS: 415.1 |
| 307 |  | DMSO-d6, δ 12.52 (s, 1H), 9.30 (s, 2H), 8.94 (s, 2H), 8.18 (dd, J = 17.0, 7.9 Hz, 2H), 7.68 – 7.57 (m, 1H), 7.55 – 7.48 (m, 1H), 4.38 (s, 2H), 4.20 (dt, J = 17.7, 10.5 Hz, 4H), 4.06 (dt, J = 9.1, 7.4 Hz, 1H), 3.52 (t, J = 6.0 Hz, 2H), 3.17 (t, J = 5.7 Hz, 2H); LCMS: 371.2 |

FIG. 1 (continued)

| | | |
|---|---|---|
| 308 | 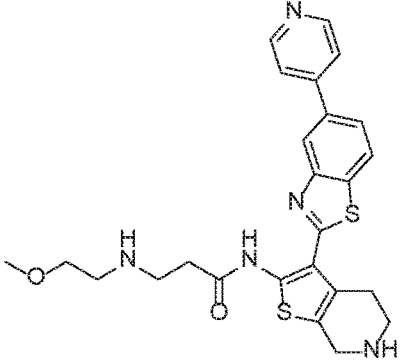 | DMSO-d6+D2O, δ 8.89 (d, J = 6.6 Hz, 2H), 8.80 (d, J = 1.5 Hz, 1H), 8.40 (d, J = 8.5 Hz, 1H), 8.34 (d, J = 6.4 Hz, 2H), 8.07 (dd, J = 8.5, 1.8 Hz, 1H), 4.35 (s, 2H), 3.61 (t, J = 4.9 Hz, 2H), 3.51 (t, J = 6.0 Hz, 2H), 3.34 (t, J = 7.1 Hz, 2H), 3.30 (s, 3H), 3.23 – 3.17 (m, 4H), 3.15 (t, J = 7.0 Hz, 2H). 5 NH missing due to D2O; LCMS: 494.2 |
| 309 | 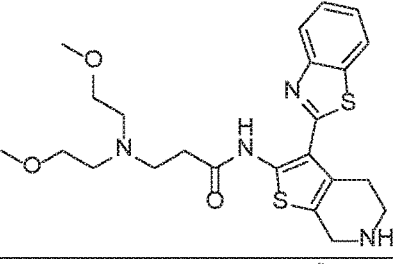 | 1H NMR (400 MHz, DMSO-d6) δ 12.64 (s, 1H), 10.33 (br. s, 1H), 9.76 (br. s, 2H), 8.20 (d, J = 8.31 Hz, 2H), 7.63 (t, J=7.83 Hz, 1H), 7.51 (t, J=7.83 Hz, 1H), 4.33 (br. s, 2H), 3.74 (d, J = 3.91 Hz, 4H), 3.40-3.61 (m, 2H), 3.40-3.51 (m, 6H), 3.30 (s, 6H), 3.22-3.27 (m, 2H), 3.19 (d, J = 4.89 Hz, 2H); LCMS: 475.3 |
| 310 | 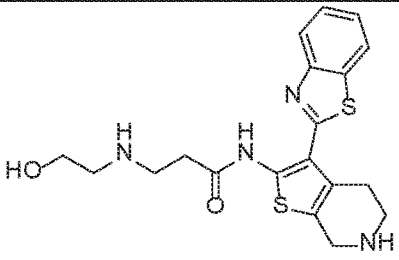 | 1H NMR (400 MHz, DMSO-d6) δ 12.57 (s, 1H), 9.78 (br. s, 2H), 9.05 (br. s, 2H), 8.19 (dd, J=8.31, 11.25 Hz, 2H), 7.58-7.65 (m, 1H), 7.51 (t, J=7.58 Hz, 1H), 5.30 (br. s, 1H), 4.33 (br. s, 2H), 3.70 (t, J=5.14 Hz, 2H), 3.45-3.49 (m, 2H), 3.10-3.22 (m, 6H), 3.04-3.09 (m, 2H); LCMS: 403.15 |
| 311 | 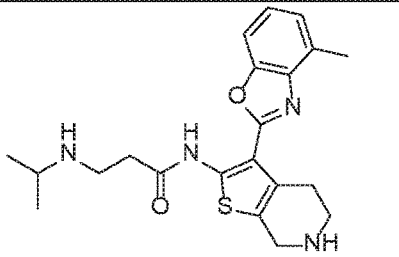 | DMSO-d6, δ 11.92 (s, 1H), 9.58 (s, 2H), 8.88 (s, 2H), 7.60 (d, J = 8.0 Hz, 1H), 7.35 (t, J = 7.8 Hz, 1H), 7.28 (d, J = 7.5 Hz, 1H), 4.33 (s, 2H), 3.46 (t, J = 6.0 Hz, 2H), 3.28 (d, J = 5.6 Hz, 5H), 3.14 (t, J = 7.1 Hz, 2H), 2.64 (s, 3H), 1.27 (d, J = 6.5 Hz, 6H).; LCMS: 399.3 |
| 312 | 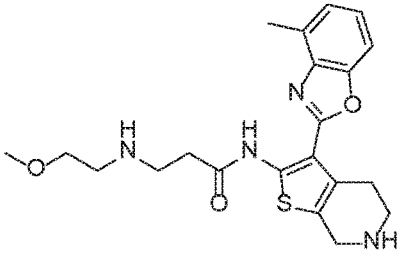 | DMSO-d6, δ 11.93 (s, 1H), 9.58 (s, 2H), 8.93 (s, 2H), 7.60 (d, J = 8.0 Hz, 1H), 7.35 (t, J = 7.8 Hz, 1H), 7.28 (d, J = 7.5 Hz, 1H), 4.33 (s, 2H), 3.65 – 3.60 (m, 2H), 3.46 (s, 2H), 3.32 (s, 3H), 3.28 (t, J = 5.8 Hz, 2H), 3.22 – 3.16 (m, 2H), 3.14 (t, J = 7.2 Hz, 2H), 2.65 (s, 3H).; LCMS: 415.3 |

FIG. 1 (continued)

| | | |
|---|---|---|
| 313 | [structure] | CD3OD, δ 7.28 – 7.01 (m, 4 H), 6.71 (dd, J = 7.9, 19.2 Hz, 1 H), 6.23 (t, J = 7.6 Hz, 1 H), 6.12 (t, J = 15.6 Hz, 1 H), 4.01 – 3.97 (m, 1 H), 3.00 (d, J = 5.0 Hz, 1 H), 2.10 – 2.01 (m, 4 H), 1.72 (d, J = 3.9 Hz, 2 H), 1.52 (d, J = 17.1 Hz, 1 H), 1.11 – 0.99 (m, 3 H), 0.64 – 0.56 (m, 1 H), -0.01 (d, J = 6.5 Hz, 6 H); LCMS: 427.3 |
| 314 | [structure] | 1H NMR (DMSO-d6, 400MHz): δ 12.65 (br. s, 1H), 9.69 (br. s, 2H), 9.03 (br. s, 2H), 8.06 (d, J=8.31 Hz, 1H), 7.97 (s, 1H), 7.35 (d, J=8.31 Hz, 1H), 4.32 (br. s, 2H), 3.63 (t, J=4.89 Hz, 2H), 3.44-3.49 (m, 2H), 3.33 (br. s, 6H), 3.07-3.23 (m, 8H).; LCMS: 431.2 |
| 315 | [structure] | 1H NMR (DMSO-d6, 400MHz): δ 12.56 (br. s, 1H), 9.95 (br. s, 1H), 9.65 (br. s, 1H), 9.19 (br. s, 2H), 8.16-8.22 (m, 2H), 7.61 (t, J=7.58 Hz, 1H), 7.47-7.54 (m, 1H), 4.77 (q, J=6.36 Hz, 1H), 4.66 (d, J=5.87 Hz, 1H), 3.85 (dd, J=6.60, 12.47 Hz, 1H), 3.60-3.62 (m, 1H), 3.64 (t, J=4.89 Hz, 2H), 3.32 (br. s, 3H), 3.10-3.20 (m, 4H), 2.84-2.97 (m, 1H), 1.65 (d, J=6.36 Hz, 3H), 1.53 (d, J=6.36 Hz, 2H), 1.47 (d, J=6.36 Hz, 2H).; LCMS: 445.3 |
| 316 | [structure] | DMSO-d6, δ 12.69 (s, 1H), 9.54 (s, br, 2H), 8.93 (s, br, 2H), 8.05 (d, J = 8.8 Hz, 1H), 7.77 (d, J = 2.3 Hz, 1H), 7.14 (dd, J = 8.8, 2.5 Hz, 1H), 4.41 – 4.27 (m, 2H), 3.90 (s, 3H), 3.56 – 3.44 (m, J = 12.5, 7.1 Hz, 2H), 3.32 – 3.24 (m, J = 12.7, 6.6 Hz, 5H), 3.21 – 3.11 (m, J = 6.7 Hz, 4H), 1.27 (d, J = 6.5 Hz, 6H).; LCMS: 431.2 |
| 317 | [structure] | DMSO-d6, δ 13.09 (s, 1H), 9.64 (s, 2H), 8.91 (s, 2H), 8.12 (d, J = 8.9 Hz, 1H), 7.40 (d, J = 9.0 Hz, 1H), 4.35 (s, 2H), 3.99 (s, 3H), 3.51 (s, 2H), 3.15 (dd, J = 14.1, 6.9 Hz, 4H), 3.08 (dt, J = 12.1, 7.3 Hz, 1H), 1.29 (d, J = 6.5 Hz, 6H), 1.20 (t, J = 7.3 Hz, 1H).; LCMS: 465.2 |

FIG. 1 (continued)

| | | |
|---|---|---|
| 318 | (structure) | 1H NMR (DMSO-d6/D2O, 400MHz): δ 8.13 (dd, J=4.89, 8.80 Hz, 1H), 7.98 (dd, J=1.96, 8.31 Hz, 1H), 7.44 (dt, J=2.20, 8.93 Hz, 1H), 4.29 (br. s, 2H), 3.56 (t, J=4.65 Hz, 2H), 3.46 (t, J=5.38 Hz, 2H), 3.27 (s, 3H), 3.29-3.31 (m, 2H), 3.11-3.18 (m, 4H), 3.02 (t, J=6.85 Hz, 2H).; LCMS: 435.2 |
| 319 | (structure) | 1H NMR (DMSO-d6, 400MHz): δ 12.59 (br. s, 1H), 9.15 (br. s, 1H), 8.08-8.16 (m, 2H), 7.59 (t, J=7.58 Hz, 1H), 7.43-7.49 (m, 1H), 3.77-3.87 (m, 1H), 3.69 (br. s, 2H), 3.58-3.64 (m, 2H), 3.43 (d, J=5.87 Hz, 2H), 2.89-2.99 (m, 4H), 2.85 (d, J=1.96 Hz, 2H), 2.73 (t, J=6.11 Hz, 2H), 2.04 (br. s, 3H), 1.46-1.63 (m, 2H), 1.16 (d, J=6.85 Hz, 3H), 0.81-0.89 (m, 3H).; LCMS: 596.15 |
| 320 | (structure) | 1H NMR (DMSO-d6, 400MHz): δ 13.26 (br. s, 1H), 12.54 (br. s, 1H), 9.32 (br. s, 2H), 8.65 (s, 1H), 8.47 (br. s, 2H), 8.30 (d, J=8.31 Hz, 1H), 8.03 (d, J=8.31 Hz, 1H), 4.36 (br. s, 2H), 3.48-3.55 (m, 2H), 3.35-3.42 (m, 2H), 3.15-3.20 (m, 3H), 3.08 (t, J=6.60 Hz, 2H), 1.21-1.28 (m, 6H).; LCMS: 445.3 |
| 321 | (structure) | 1H NMR (DMSO-d6, 400MHz): δ 12.60 (br. s, 1H), 9.55 (br. s, 2H), 8.90 (br. s, 2H), 8.26 (s, 1H), 8.16 (d, J=8.32 Hz, 1H), 7.66 (d, J=8.31 Hz, 1H), 6.92 (dd, J=11.25, 17.61 Hz, 1H), 6.05 (d, J=17.61 Hz, 1H), 5.40 (d, J=11.25 Hz, 1H), 4.34 (br. s, 2H), 3.48-3.55 (m, 3H), 3.10-3.21 (m, 4H), 1.28 (d, J=6.36 Hz, 6H), 1.15-1.24 (m, 2H).; LCMS: 427.2 |

FIG. 1 (continued)

| | | |
|---|---|---|
| 322 | | 1H NMR (DMSO-d6, 400MHz): δ 12.58 (s, 1H), 9.60 (br. s, 2H), 8.89 (br. s, 2H), 8.25 (d, J=8.58 Hz, 1H), 8.19 (s, 1H), 7.52 (d, J=8.11 Hz, 1H), 4.33 (br. s, 2H), 3.48 (br. s, 2H), 3.10-3.29 (m, 7H), 3.03 (br. s, 3H), 2.98 (br. s, 3H), 1.26 (d, J=6.20 Hz, 6H).; LCMS: 471.85 |
| 323 | | 1H NMR (DMSO-d6/D2O, 400MHz): δ 8.55 (s, 1H), 8.20 (d, J=8.58 Hz, 1H), 7.90 (d, J=8.11 Hz, 1H), 4.30 (br. s, 2H), 3.42-3.50 (m, 6H), 3.29-3.36 (m, 1H), 3.22-3.27 (m, 5H), 3.15 (br. s, 2H), 3.03 (t, J=6.68 Hz, 2H), 1.21 (d, J=6.68 Hz, 6H).; LCMS: 502.35 |
| 324 | | 1H NMR (DMSO-d6, 400MHz): δ 12.74 (s, 1H), 11.35 (br. s, 1H), 9.81 (br. s, 2H), 9.27 (br. s, 2H), 8.37 (s, 1H), 8.30 (d, J=8.21 Hz, 1H), 7.56 (d, J=8.21 Hz, 1H), 4.46-4.64 (m, 1H), 4.34 (br. s, 2H), 3.81-4.10 (m, 2H), 3.44-3.54 (m, 5H), 3.16-3.29 (m, 7H), 2.97-3.07 (m, 1H), 2.82 (br. s, 3H), 1.29 (d, J=6.28 Hz, 6H).; LCMS: 527.2 |
| 325 | | DMSO-d6, δ 10.09 - 9.84 (m, 2 H), 8.79 - 8.45 (m, 2 H), 8.32 (s, 1 H), 8.28 (d, J = 1.0 Hz, 1 H), 8.14 (d, J = 8.4 Hz, 1 H), 8.04 (d, J = 0.6 Hz, 1 H), 7.74 (dd, J = 1.4, 8.4 Hz, 1 H), 4.43 (br. s., 2 H), 3.89 (s, 3 H), 3.46 (br. s., 3 H), 3.41 (d, J = 5.0 Hz, 2 H), 3.26 (s, 3 H), 3.22 - 3.14 (m, 1 H), 3.14 - 3.06 (m, 1 H), 3.06 - 2.97 (m, 1 H), 1.28 - 1.22 (m, 1 H), 1.16 (br. s., 6 H); LCMS: 495.3 |

| 326 |  | DMSO-d6, δ 12.65 (s, 1H), 9.58 (s, 2H), 8.95 (s, 2H), 8.27 (d, J = 1.1 Hz, 1H), 8.17 (d, J = 8.6 Hz, 1H), 7.66 (dd, J = 8.5, 1.8 Hz, 1H), 6.41 (s, 1H), 4.40 – 4.30 (m, 2H), 3.93 (d, J = 2.9 Hz, 2H), 3.50 (d, J = 4.0 Hz, 2H), 3.45 (t, J = 5.6 Hz, 2H), 3.31 – 3.24 (m, 2H), 3.18 (dd, J = 14.7, 7.3 Hz, 4H), 2.98 (s, 3H), 2.76 (d, J = 1.9 Hz, 2H), 1.29 (d, J = 6.5 Hz, 6H).; LCMS: 560.3 |
| --- | --- | --- |
| 327 |  | 1H NMR (400MHz, METHANOL-d4) Shift = 8.78 (br. s., 1H), 8.47 (d, J=4.0 Hz, 1H), 8.40 (d, J=8.8 Hz, 1H), 8.20 (t, J=7.9 Hz, 1H), 8.01 (d, J=9.7 Hz, 1H), 7.91 (t, J=6.8 Hz, 1H), 4.43 (s, 2H), 3.71 - 3.6 1 (m, 4H), 3.50 (t, J=6.6 Hz, 2H), 3.44 - 3.39 (m, 3H), 3.38 - 3.30 (m, 4H), 3.22 - 3.14 (m, J=6.6, 6.6 Hz, 2H); LCMS: 512.1 |
| 328 |  | 1H NMR (400MHz, METHANOL-d4) Shift = 8.40 - 8.28 (m, 3H), 8.15 (d, J=8.4 Hz, 1H), 7.82 (d, J=8.4 Hz, 1H), 7.40 (d, J=8.8 Hz, 1H), 4.42 (br. s., 2H), 3.87 (d, J=4.4 Hz, 4H), 3.74 - 3.66 (m, 6H), 3.64 (t, J=5.7 Hz, 2H), 3.49 (t, J=6.4 Hz, 2H), 3.44 - 3.39 (m, 3H), 3.32 (d, J=5.3 Hz, 4H), 3.18 (t, J=6.4 Hz, 2H); LCMS: 579.1 |

| | | |
|---|---|---|
| 329 |  | 1H NMR (400MHz, METHANOL-d4) Shift = 8.44 (d, J=2.2 Hz, 1H), 8.21 (s, 1H), 8.07 - 7.97 (m, 2H), 7.64 (d, J=8.4 Hz, 1H), 6.90 - 6.82 (m, 1H), 4.44 - 4.28 (m, 4H), 3.72 - 3.64 (m, 2H), 3.61 (t, J=6.0 Hz, 2H), 3.48 (t, J=6.4 Hz, 2H), 3.41 (s, 3H), 3.34 - 3.29 (m, 4H), 3.21 - 3.11 (m, 2H), 1.46 - 1.32 (m, 3H); LCMS: 538.1 |
| 330 |  | 1H NMR (400MHz, METHANOL-d4) Shift = 8.43 (s, 1H), 8.24 (s, 1H), 8.12 (d, J=8.4 Hz, 1H), 8.01 (d, J=8.4 Hz, 1H), 7.79 (d, J=8.4 Hz, 1H), 6.87 (d, J=8.8 Hz, 1H), 4.42 (br. s., 2H), 4.35 (q, J=7.1 Hz, 2H), 3.72 - 3.60 (m, 4H), 3.49 (t, J=6.2 Hz, 2H), 3.45 - 3.39 (m, 3H), 3.32 (d, J=4.9 Hz, 4H), 3.17 (t, J=6.4 Hz, 2H), 1.39 (t, J=7.1 Hz, 3H); LCMS: 538.1 |
| 331 |  | 1H NMR (400MHz, METHANOL-d4) Shift = 8.17 (s, 1H), 7.97 (d, J=8.4 Hz, 1H), 7.63 (d, J=8.4 Hz, 1H), 7.29 - 7.20 (m, 2H), 7.06 - 6.98 (m, 1H), 4.39 (s, 2H), 3.91 (s, 3H), 3.87 (s, 3H), 3.70 - 3.63 (m, 2H), 3.58 (t, J=5.7 Hz, 2H), 3.45 (t, J=6.4 Hz, 2H), 3.40 (s, 3H), 3.31 - 3.26 (m, 4H), 3.14 (t, J=6.4 Hz, 2H); LCMS: 553.1 |

| | | |
|---|---|---|
| 332 |  | 1H NMR (400MHz, METHANOL-d4) Shift = 8.20 (br. s., 1H), 8.06 - 7.95 (m, 1H), 7.81 - 7.69 (m, 3H), 7.55 - 7.44 (m, 1H), 7.39 (d, J=6.6 Hz, 1H), 4.36 (br. s., 2H), 3.73 - 3.65 (m, 2H), 3.61 - 3.45 (m, 4 H), 3.45 - 3.37 (m, 3H), 3.36 - 3.30 (m, 2H), 3.26 - 3.08 (m, 7H), 3.04 (s, 3H); LCMS: 564.1 |
| 333 |  | 1H NMR (400MHz, METHANOL-d4) Shift = 8.13 (br. s., 1H), 8.06 - 8.00 (m, 1H), 7.72 (d, J=7.9 Hz, 1H), 7.15 (d, J=2.6 Hz, 2H), 6.89 (d, J=7.9 Hz, 1H), 5.98 (s, 2H), 4.40 (br. s., 2H), 3.71 - 3.65 (m, 2H ), 3.60 (br. s., 2H), 3.49 (t, J=6.4 Hz, 2H), 3.42 (s, 3H), 3.36 - 3.29 (m, 4H), 3.15 (t, J=6.2 Hz, 2H); LCMS: 537.1 |
| 334 |  | 1H NMR (400MHz, METHANOL-d4) Shift = 8.26 (s, 1H), 8.06 (d, J=7.9 Hz, 1H), 7.80 (d, J=7.9 Hz, 2H), 7.71 (d, J=8.4 Hz, 1H), 7.52 (d, J=8.4 Hz, 2H), 4.40 (s, 2H), 3.76 (br. s., 4H), 3.71 - 3.65 (m, 4H), 3.60 (t, J=5.5 Hz, 3H), 3.48 (t, J=6.4 Hz, 3H), 3.42 - 3.39 (m, 3H), 3.31 (d, J=4.9 Hz, 2H), 3.25 (br. s., 2H), 3.16 (t, J=6.4 Hz, 2H); LCMS: 606.1 |

FIG. 1 (continued)

| | | |
|---|---|---|
| 335 | (structure) | 1H NMR (400MHz, METHANOL-d4) Shift = 8.25 (d, J=1.3 Hz, 1H), 8.08 (s, 1H), 8.04 (d, J=8.4 Hz, 1H), 7.91 (d, J=7.5 Hz, 1H), 7.76 (d, J=7.9 Hz, 1H), 7.66 (dd, J=1.8, 8.4 Hz, 1H), 7.64 - 7.57 (m, 1H), 4.34 (s, 2H), 3.65 - 3.51 (m, 4H), 3.41 (t, J=6.4 Hz, 2H), 3.37 - 3.29 (m, 3H), 3.28 - 3.21 (m, 4H), 3.16 - 3.05 (m, 2H), 2.54 - 2.42 (m, 3H); LCMS: 586 |
| 336 | (structure) | 1H NMR (400MHz, METHANOL-d4) Shift = 8.55 (br. s., 1H), 8.25 (br. s., 1H), 8.08 - 8.00 (m, 2H), 7.66 (d, J=7.9 Hz, 1H), 7.05 (d, J=8.4 Hz, 1H), 4.40 (br. s., 1H), 3.88 (br. s., 2H), 3.70 - 3.56 (m, 2H), 3.52 - 3.45 (m, 1H), 3.42 - 3.30 (m, 4H), 3.18 (br. s., 3H); LCMS: 578.1 |
| 337 | (structure) | 1H NMR (400MHz, METHANOL-d4) Shift = 8.82 (s, 1H), 8.51 (d, J=2.6 Hz, 1H), 8.44 (s, 1H), 8.19 (d, J=8.4 Hz, 1H), 8.05 (d, J=10.1 Hz, 1H), 7.81 (d, J=8.4 Hz, 1H), 4.43 (s, 2H), 3.71 - 3.60 (m, 4H), 3.49 (t, J=6.4 Hz, 2H), 3.45 - 3.39 (m, 3H), 3.39 - 3.33 (m, 2H), 3.31 (d, J=5.3 Hz, 2H), 3.19 (t, J=6.4 Hz, 2H); LCMS: 512 |

*FIG. 1 (continued)*

| | | |
|---|---|---|
| 338 | (structure) | 1H NMR (400MHz, METHANOL-d4) Shift = 8.39 (s, 1H), 8.18 - 8.12 (m, 2H), 8.08 (d, J=7.8 Hz, 1H), 7.81 - 7.75 (m, 2H), 7.73 - 7.66 (m, 1H), 4.45 (br. s., 2H), 3.72 - 3.64 (m, 4H), 3.54 - 3.48 (m, 2H), 3.43 (s, 3H), 3.35 (d, J=9.0 Hz, 4H), 3.25 - 3.18 (m, 2H); LCMS: 518 |
| 339 | (structure) | 1H NMR (400MHz, METHANOL-d4) Shift = 8.21 (s, 1H), 8.07 - 8.01 (m, 3H), 7.79 (d, J=8.4 Hz, 1H), 4.41 (s, 2H), 3.70 - 3.65 (m, 2H), 3.62 (t, J=6.0 Hz, 2H), 3.48 (t, J=6.6 Hz, 2H), 3.42 (s, 3H), 3.31 (d, J=5.3 Hz, 4H), 3.15 (t, J=6.6 Hz, 2H); LCMS: 483 |
| 340 | (structure) | 1H NMR (400MHz, METHANOL-d4) Shift = 8.28 (d, J=5.7 Hz, 2H), 8.17 - 8.12 (m, 1H), 7.64 (d, J=7.5 Hz, 1H), 7.15 - 7.09 (m, 1H), 4.42 (br. s., 2H), 3.65 (dd, J=4.2, 9.0 Hz, 4H), 3.48 (t, J=6.4 Hz, 2H), 3.40 (s, 3H), 3.37 - 3.30 (m, 4H), 3.17 (t, J=6.2 Hz, 2H); LCMS: 530 |

FIG. 1 (continued)

| | | |
|---|---|---|
| 341 | | 1H NMR (400MHz, METHANOL-d4) Shift = 8.25 - 8.15 (m, 1H), 8.13 - 7.97 (m, 2H), 7.82 - 7.70 (m, 2H), 7.03 (t, J=6.0 Hz, 1H), 4.47 - 4.33 (m, 4H), 3.71 - 3.64 (m, 2H), 3.55 (d, J=4.9 Hz, 2H), 3.50 (t, J =6.6 Hz, 2H), 3.44 - 3.36 (m, 3H), 3.35 - 3.30 (m, 2H), 3.26 (br. s., 2H), 3.16 (t, J=6.6 Hz, 2H), 1.41 - 1.25 (m, 3H); LCMS: 538.1 |
| 342 | | 1H NMR (400MHz, METHANOL-d4) Shift = 8.39 (br. s., 1H), 8.35 (d, J=5.3 Hz, 1H), 8.24 (s, 1H), 8.19 - 8.08 (m, 1H), 7.80 (d, J=8.4 Hz, 1H), 7.62 (d, J=5.3 Hz, 1H), 4.42 (s, 2H), 3.72 - 3.57 (m, 4H), 3.50 (t, J=6.4 Hz, 2H), 3.41 (s, 3H), 3.35 - 3.29 (m, 4H), 3.21 (t, J=6.2 Hz, 2H), 2.26 (s, 3H); LCMS: 551 |
| 343 | | 1H NMR (400MHz, METHANOL-d4) Shift = 8.10 (s, 1H), 8.01 (d, J=8.4 Hz, 1H), 7.73 (d, J=8.4 Hz, 1H), 7.53 (d, J=8.4 Hz, 2H), 7.42 (d, J=8.4 Hz, 2H), 4.40 (br. s., 2H), 3.72 - 3.65 (m, 2H), 3.60 (br. s., 2H), 3.49 (t, J=6.2 Hz, 2H), 3.45 - 3.38 (m, 3H), 3.32 (d, J=4.9 Hz, 2H), 3.28 - 3.23 (m, 2H), 3.15 (t, J=6.2 Hz, 2H), 2.86 - 2.72 (m, 3H); LCMS: 565.1 |

*FIG. 1 (continued)*

| | | |
|---|---|---|
| 344 | | 1H NMR (400MHz, METHANOL-d4) Shift = 8.15 - 7.95 (m, 2H), 7.88 - 7.68 (m, 3H), 7.42 (d, J=7.9 Hz, 1H), 4.41 (br. s., 2H), 3.73 - 3.67 (m, 2H), 3.63 (br. s., 2H), 3.51 (t, J=6.6 Hz, 2H), 3.45 - 3.39 (m, 3H), 3.33 (t, J=4.6 Hz, 2H), 3.28 - 3.21 (m, 2H), 3.17 (t, J=6.6 Hz, 2H), 2.47 (br. s., 3H); LCMS: 532.1 |
| 345 | | 1H NMR (400MHz, METHANOL-d4) Shift = 8.82 (s, 2H), 8.32 (s, 1H), 8.13 (d, J=8.4 Hz, 1H), 7.69 (d, J=8.4 Hz, 1H), 7.50 (br. s., 2H), 4.42 (br. s., 2H), 3.66 (dd, J=5.5, 10.4 Hz, 4H), 3.52 - 3.45 (m, 2H), 3.41 - 3.38 (m, 3H), 3.32 (d, J=7.5 Hz, 4H), 3.18 (t, J=6.0 Hz, 2H); LCMS: 510 |
| 346 | | 1H NMR (400MHz, METHANOL-d4) Shift = 8.26 (s, 1H), 8.05 (d, J=8.4 Hz, 1H), 7.71 (d, J=8.4 Hz, 1H), 7.64 (d, J=8.4 Hz, 2H), 7.49 (d, J=8.4 Hz, 2H), 4.42 (s, 2H), 3.74 - 3.60 (m, 4H), 3.48 (t, J=6.4 Hz, 2H), 3.44 - 3.38 (m, 3H), 3.33 (d, J=8.8 Hz, 4H), 3.17 (t, J=6.6 Hz, 2H), 2.79 (s, 3H); LCMS: 565.1 |

*FIG. 1 (continued)*

| 347 | | 1H NMR (400MHz, METHANOL-d4) Shift = 8.22 (d, J=0.9 Hz, 1H), 8.15 (dd, J=1.3, 4.9 Hz, 1H), 8.10 (d, J=8.4 Hz, 1H), 7.77 (ddd, J=1.5, 8.0, 15.5 Hz, 2H), 7.07 (dd, J=5.1, 7.3 Hz, 1H), 4.42 (s, 2H), 3.96 (s, 3H), 3.71 - 3.65 (m, 2H), 3.61 (t, J=5.7 Hz, 2H), 3.49 (t, J=6.6 Hz, 2H), 3.44 - 3.38 (m, 3H), 3.35 - 3.29 (m, 4H), 3.17 (t, J=6.4 Hz, 2H); LCMS: 524.1 |
|---|---|---|
| 348 | | 1H NMR (400MHz, METHANOL-d4) Shift = 8.21 (s, 1H), 8.12 - 8.04 (m, 2H), 7.90 (d, J=7.5 Hz, 1H), 7.78 (dd, J=8.2, 13.0 Hz, 2H), 7.65 - 7.58 (m, 1H), 4.40 (br. s., 2H), 3.68 (d, J=4.9 Hz, 2H), 3.62 (br. s., 2H), 3.49 (d, J=6.2 Hz, 2H), 3.44 - 3.37 (m, 3H), 3.35 - 3.28 (m, 4H), 3.17 (t, J=6.0 Hz, 2H), 2.59 - 2.49 (m, 3H); LCMS: 586 |
| 349 | | 1H NMR (400MHz, METHANOL-d4) Shift = 8.68 (br. s., 1H), 8.42 (s, 2H), 8.14 (d, J=8.4 Hz, 1H), 8.09 (br. s., 1H), 7.77 (d, J=8.4 Hz, 1H), 4.41 (br. s., 2H), 4.04 (s, 3H), 3.71 - 3.58 (m, 4H), 3.54 - 3.45 (m, 2H), 3.40 (s, 3H), 3.30 (d, J=5.7 Hz, 4H), 3.20 (t, J=6.4 Hz, 2H); LCMS: 524 |

FIG. 1 (continued)

| | | |
|---|---|---|
| 350 | (structure) | 1H NMR (400MHz, METHANOL-d4) Shift = 8.40 (s, 1H), 8.13 (d, J=8.4 Hz, 1H), 8.03 (s, 1H), 7.88 - 7.83 (m, 3H), 7.55 (d, J=8.8 Hz, 1H), 4.43 (s, 2H), 4.15 - 4.10 (m, 3H), 3.69 - 3.62 (m, 4H), 3.48 (t, J =6.4 Hz, 2H), 3.40 (s, 3H), 3.37 - 3.30 (m, 4H), 3.23 - 3.15 (m, 2H); LCMS: 547.1 |
| 351 | (structure) | 1H NMR (400MHz, METHANOL-d4) Shift = 8.03 (d, J=7.1 Hz, 2H), 7.82 (br. s., 1H), 7.63 (d, J=8.8 Hz, 1H), 4.39 (s, 2H), 3.71 - 3.63 (m, 2H), 3.58 (t, J=5.7 Hz, 2H), 3.49 (t, J=6.4 Hz, 2H), 3.43 - 3.36 (m, 3H), 3.34 - 3.30 (m, 2H), 3.26 (br. s., 2H), 3.15 (t, J=6.4 Hz, 2H), 2.46 (br. s., 3H); LCMS: 497 |
| 352 | (structure) | 1H NMR (400MHz, METHANOL-d4) Shift = 8.34 (s, 1H), 8.25 - 8.14 (m, 2H), 7.96 - 7.84 (m, 3H), 7.64 (t, J=7.7 Hz, 1H), 4.43 (br. s., 2H), 3.67 (dd, J=5.3, 9.7 Hz, 4H), 3.49 (t, J=6.4 Hz, 2H), 3.45 - 3.39 (m, 3H), 3.37 - 3.30 (m, 4H), 3.17 (t, J=6.2 Hz, 2H); LCMS: 572 |

| | | |
|---|---|---|
| 353 |  | 1H NMR (400MHz, METHANOL-d4) Shift = 8.10 (d, J=8.4 Hz, 1H), 8.02 (s, 1H), 7.43 - 7.37 (m, 1H), 4.42 (s, 2H), 3.68 - 3.60 (m, 4H), 3.46 (t, J=6.4 Hz, 2H), 3.41 - 3.38 (m, 3H), 3.34 (br. s., 2H), 3.29 - 3.26 (m, 2H), 3.15 (t, J=6.4 Hz, 2H), 2.44 - 2.26 (m, 6H); LCMS: 511.1 |
| 354 |  | 1H NMR (400MHz, METHANOL-d4) Shift = 8.16 (d, J=8.2 Hz, 1H), 8.00 (s, 1H), 7.54 (d, J=8.2 Hz, 1H), 4.45 (s, 2H), 3.71 - 3.63 (m, 4H), 3.51 (t, J=6.3 Hz, 2H), 3.43 (s, 3H), 3.35 (d, J=9.4 Hz, 4H), 3.19 (t, J=6.5 Hz, 2H), 2.35 (s, 6H); LCMS: 511.1 |
| 355 |  | 1H NMR (400MHz, METHANOL-d4) Shift = 8.35 (s, 1H), 8.12 - 8.03 (m, 1H), 7.94 (d, J=8.4 Hz, 1H), 6.52 (s, 1H), 4.41 (s, 2H), 3.69 - 3.66 (m, 2H), 3.63 (t, J=6.0 Hz, 2H), 3.49 (t, J=6.6 Hz, 2H), 3.42 (s, 3H), 3.31 (d, J=4.9 Hz, 4H), 3.16 (t, J=6.4 Hz, 2H), 2.35 (s, 3H); LCMS: 497 |

| | | |
|---|---|---|
| 356 |  | 1H NMR (400MHz, METHANOL-d4) Shift = 8.53 (br. s., 1H), 8.36 (s, 1H), 8.30 (br. s., 1H), 8.17 (d, J=8.4 Hz, 1H), 7.91 - 7.80 (m, 2H), 4.43 (br. s., 2H), 4.34 - 4.28 (m, 2H), 3.83 - 3.77 (m, 2H), 3.71 - 3.61 (m, 4H), 3.50 (t, J=6.0 Hz, 2H), 3.45 - 3.39 (m, 6H), 3.32 (d, J=4.4 Hz, 4H), 3.22 - 3.14 (m, 2H); LCMS: 568.1 |
| 357 |  | 1H NMR (400MHz, METHANOL-d4) Shift = 8.37 (s, 1H), 8.20 (d, J=8.2 Hz, 1H), 8.10 (s, 1H), 8.05 (d, J=7.8 Hz, 1H), 7.90 (d, J=8.2 Hz, 1H), 7.78 - 7.73 (m, 1H), 7.70 - 7.64 (m, 1H), 4.45 (s, 2H), 3.72 - 3.65 (m, 4H), 3.51 (t, J=6.3 Hz, 2H), 3.44 (s, 3H), 3.39 - 3.32 (m, 4H), 3.20 (t, J=6.3 Hz, 2H); LCMS: 518.1 |
| 358 |  | 1H NMR (400MHz, METHANOL-d4) Shift = 8.12 - 8.03 (m, 2H), 7.92 - 7.84 (m, 2H), 7.67 (d, J=7.9 Hz, 1H), 4.54 (tt, J=6.6, 13.2 Hz, 1H), 4.32 (br. s., 2H), 3.72 - 3.65 ota (m, 2H), 3.56 - 3.44 (m, 4H), 3.43 - 3.38 (m, 3H), 3.37 - 3.30 (m, 2H), 3.22 - 3.04 (m, 4H), 1.63 - 1.42 (m, 6H); LCMS: 525.1 |

| | | |
|---|---|---|
| 359 |  | 1H NMR (400MHz, METHANOL-d4) Shift = 8.17 (d, J=7.9 Hz, 1H), 8.13 - 8.06 (m, 2H), 7.78 - 7.72 (m, 1H), 7.69 - 7.58 (m, 2H), 7.47 (d, J=7.5 Hz, 1H), 4.39 (br. s., 2H), 3.71 - 3.65 (m, 2H), 3.57 (br. s. , 2H), 3.50 (t, J=6.2 Hz, 2H), 3.44 - 3.37 (m, 3H), 3.34 - 3.30 (m, 2H), 3.24 (br. s., 2H), 3.16 (t, J=6.2 Hz, 2H), 2.81 (s, 3H); LCMS: 571 |
| 360 |  | 1H NMR (400MHz, METHANOL-d4) Shift = 9.20 (br. s., 1H), 8.90 (br. s., 1H), 8.45 (d, J=10.6 Hz, 2H), 8.17 (d, J=7.9 Hz, 1H), 7.80 (d, J=8.4 Hz, 1H), 4.42 (br. s., 2H), 3.71 - 3.60 (m, 4H), 3.49 (t, J=6 .2 Hz, 2H), 3.41 (s, 3H), 3.32 (d, J=4.9 Hz, 4H), 3.20 (t, J=6.4 Hz, 2H); LCMS: 562 |
| 361 |  | 1H NMR (400MHz, METHANOL-d4) Shift = 8.36 (s, 1H), 8.07 - 8.02 (m, 1H), 7.96 (d, J=8.4 Hz, 1H), 7.70 (d, J=1.3 Hz, 1H), 6.75 (d, J=1.3 Hz, 1H), 4.38 (s, 2H), 3.71 - 3.65 (m, 2H), 3.60 (t, J=5.7 Hz, 2H ), 3.49 (t, J=6.6 Hz, 2H), 3.44 - 3.39 (m, 3H), 3.32 (d, J=5.3 Hz, 4H), 3.15 (t, J=6.4 Hz, 2H); LCMS: 483.1 |

FIG. 1 (continued)

| | | |
|---|---|---|
| 362 | | 1H NMR (400MHz, METHANOL-d4) Shift = 8.18 (s, 1H), 8.10 (d, J=7.9 Hz, 1H), 7.76 (d, J=7.9 Hz, 1H), 7.30 (d, J=7.1 Hz, 1H), 7.18 (s, 1H), 7.03 (d, J=7.5 Hz, 1H), 4.59 (s, 2H), 4.43 (br. s., 2H), 3.67 (dd, J=5.1, 9.9 Hz, 4H), 3.50 (t, J=6.2 Hz, 2H), 3.42 (s, 3H), 3.32 (d, J=5.3 Hz, 4H), 3.23 - 3.10 (m, 2H); LCMS: 564 |
| 363 | | 1H NMR (400MHz, METHANOL-d4) Shift = 8.72 - 8.54 (m, 2H), 8.26 - 8.11 (m, 3H), 8.06 (d, J=7.9 Hz, 1H), 4.38 (br. s., 2H), 3.69 (br. s., 2H), 3.65 - 3.55 (m, 2H), 3.50 (br. s., 2H), 3.45 - 3.38 (m, 3H), 3.31 (d, J=15.0 Hz, 4H), 3.20 (br. s., 2H), 2.84 - 2.74 (m, 3H); LCMS: 508.1 |
| 364 | | 1H NMR (400MHz, METHANOL-d4) Shift = 8.21 (s, 1H), 8.07 (d, J=8.4 Hz, 1H), 7.68 - 7.58 (m, 2H), 7.37 - 7.28 (m, 2H), 4.40 (br. s., 2H), 3.69 - 3.63 (m, 2H), 3.59 (br. s., 2H), 3.50 - 3.44 (m, 2H), 3.39 (s, 3H), 3.32 - 3.29 (m, 2H), 3.28 - 3.23 (m, 2H), 3.19 - 3.09 (m, 5H), 3.05 (s, 3H); LCMS: 582.1 |

FIG. 1 (continued)

| | | |
|---|---|---|
| 365 | *(structure)* | 1H NMR (400MHz, METHANOL-d4) Shift = 8.19 (s, 1H), 8.06 (d, J=8.8 Hz, 1H), 7.78 (d, J=8.4 Hz, 1H), 7.65 (d, J=8.4 Hz, 2H), 7.11 (d, J=8.4 Hz, 2H), 4.39 (s, 2H), 4.03 - 3.63 (m, 4H), 3.63 - 3.53 (m, 3H ), 3.48 (t, J=6.4 Hz, 3H), 3.41 (s, 4H), 3.36 - 3.27 (m, 6H), 3.15 (t, J=6.6 Hz, 2H), 2.97 (s, 3H); LCMS: 591.1 |
| 366 | *(structure)* | 1H NMR (400MHz, METHANOL-d4) Shift = 8.81 (s, 1H), 8.73 (d, J=5.3 Hz, 1H), 8.32 - 8.24 (m, 2H), 7.98 (d, J=5.7 Hz, 1H), 7.76 - 7.67 (m, 1H), 4.43 (s, 2H), 3.71 - 3.60 (m, 4H), 3.50 (t, J=6.4 Hz, 2H), 3.44 - 3.38 (m, 3H), 3.38 - 3.30 (m, 4H), 3.23 - 3.16 (m, 2H), 2.54 (s, 3H); LCMS: 508.1 |
| 367 | *(structure)* | 1H NMR (400MHz, METHANOL-d4) Shift = 8.16 - 8.04 (m, 2H), 7.87 (d, J=8.4 Hz, 1H), 7.42 (dd, J=1.5, 8.2 Hz, 1H), 6.98 (d, J=8.4 Hz, 1H), 4.41 (s, 2H), 4.04 (s, 3H), 3.67 - 3.60 (m, 4H), 3.46 (t, J=6.6 Hz, 2H), 3.38 (s, 3H), 3.31 - 3.23 (m, 4H), 3.14 (t, J=6.6 Hz, 2H), 2.47 (s, 3H); LCMS: 538.1 |

FIG. 1 (continued)

| 368 | | 1H NMR (400MHz, METHANOL-d4) Shift = 8.74 (br. s., 2H), 8.30 (s, 1H), 8.20 (d, J=8.4 Hz, 1H), 7.82 - 7.69 (m, 2H), 4.41 (br. s., 2H), 4.18 (s, 3H), 3.72 - 3.65 (m, 2H), 3.61 (br. s., 2H), 3.53 - 3.45 (m, 2H), 3.44 - 3.36 (m, 3H), 3.35 - 3.29 (m, 4H), 3.18 (t, J=6.0 Hz, 2H); LCMS: 524 |
|---|---|---|
| 369 | | 1H NMR (400MHz, METHANOL-d4) Shift = 8.83 (br. s., 1H), 8.75 (d, J=4.9 Hz, 1H), 8.30 - 8.21 (m, 2H), 8.00 (d, J=5.3 Hz, 1H), 7.58 (d, J=8.4 Hz, 1H), 4.42 (s, 2H), 3.70 - 3.59 (m, 4H), 3.46 (t, J=6.6 Hz, 2H), 3.41 - 3.31 (m, 5H), 3.28 - 3.25 (m, 2H), 3.17 (t, J=6.6 Hz, 2H), 2.53 (s, 3H); LCMS: 508.1 |
| 370 | | 1H NMR (400MHz, METHANOL-d4) Shift = 9.02 (br. s., 1H), 8.70 (d, J=7.9 Hz, 1H), 8.40 (s, 1H), 8.15 (d, J=8.4 Hz, 1H), 7.90 (t, J=7.9 Hz, 2H), 4.39 (br. s., 2H), 3.73 - 3.65 (m, 2H), 3.61 (br. s., 2H), 3.50 (t, J=6.0 Hz, 2H), 3.45 - 3.37 (m, 3H), 3.36 - 3.28 (m, 4H), 3.23 - 3.13 (m, 2H), 2.83 - 2.72 (m, 3H); LCMS: 508 |

| | | |
|---|---|---|
| 371 |  | 1H NMR (400MHz, METHANOL-d4) Shift = 9.15 - 9.06 (m, 1H), 8.42 (s, 1H), 8.35 (s, 1H), 8.16 (d, J=8.2 Hz, 1H), 8.08 (d, J=9.0 Hz, 1H), 7.91 (d, J=8.2 Hz, 1H), 7.85 (d, J=9.4 Hz, 1H), 4.44 (s, 2H), 3.74 - 3.65 (m, 4H), 3.54 (t, J=6.3 Hz, 2H), 3.45 (s, 3H), 3.35 (d, J=5.1 Hz, 4H), 3.21 (t, J=6.3 Hz, 2H); LCMS: 534.1 |
| 372 |  | 1H NMR (400MHz, METHANOL-d4) Shift = 8.72 (d, J=4.0 Hz, 1H), 8.40 (d, J=7.1 Hz, 1H), 8.21 (d, J=4.4 Hz, 2H), 7.90 (d, J=5.3 Hz, 1H), 7.52 (d, J=8.4 Hz, 1H), 4.41 (br. s., 2H), 3.64 (br. s., 4H), 3.46 (br. s., 2H), 3.40 - 3.28 (m, 7H), 3.16 (br. s., 2H), 2.72 (s, 3H); LCMS: 508.1 |
| 373 |  | 1H NMR (400MHz, METHANOL-d4) Shift = 9.09 (br. s., 1H), 9.01 (d, J=7.8 Hz, 1H), 8.57 (br. s., 1H), 8.53 - 8.45 (m, 2H), 8.30 (d, J=8.2 Hz, 1H), 8.19 (d, J=8.2 Hz, 1H), 7.98 - 7.89 (m, 2H), 4.44 (br. s ., 2H), 3.72 - 3.63 (m, 4H), 3.52 (br. s., 2H), 3.42 (s, 3H), 3.33 (d, J=4.3 Hz, 4H), 3.23 (br. s., 2H); LCMS: 544.1 |

| 374 |  | 1H NMR (400MHz, METHANOL-d4) Shift = 8.22 - 7.94 (m, 3H), 7.88 - 7.54 (m, 3H), 6.63 (d, J=8.8 Hz, 1H), 4.42 (br. s., 2H), 3.73 - 3.55 (m, 4H), 3.49 (br. s., 2H), 3.44 - 3.38 (m, 3H), 3.36 - 3.29 (m, 4 H), 3.22 - 3.10 (m, 2H); LCMS: 510.1 |
|---|---|---|
| 375 |  | 1H NMR (400MHz, METHANOL-d4) Shift = 8.05 (d, J=8.4 Hz, 1H), 7.94 (s, 1H), 7.34 (d, J=8.4 Hz, 1H), 4.42 (br. s., 2H), 3.78 (s, 3H), 3.68 - 3.59 (m, 4H), 3.46 (t, J=6.6 Hz, 2H), 3.39 (s, 3H), 3.32 (br. s., 2H), 3.29 - 3.26 (m, 2H), 3.14 (t, J=6.4 Hz, 2H), 2.28 (s, 3H), 2.22 (s, 3H); LCMS: 525.1 |
| 376 |  | 1H NMR (400MHz, METHANOL-d4) Shift = 8.64 (s, 2H), 8.18 (s, 1H), 8.06 (d, J=8.4 Hz, 1H), 7.71 (d, J=8.8 Hz, 1H), 4.35 (s, 2H), 3.78 - 3.73 (m, 4H), 3.71 - 3.66 (m, 4H), 3.62 - 3.54 (m, 4H), 3.41 (t, J =6.4 Hz, 2H), 3.34 (s, 3H), 3.26 (d, J=9.3 Hz, 4H), 3.09 (t, J=6.4 Hz, 2H); LCMS: 580 |

FIG. 1 (continued)

| | | |
|---|---|---|
| 377 | *(structure)* | 1H NMR (400MHz, METHANOL-d4) Shift = 8.55 (br. s., 1H), 8.28 (s, 1H), 8.21 - 8.13 (m, 2H), 7.81 (d, J=8.2 Hz, 1H), 4.44 (br. s., 2H), 3.67 (d, J=13.7 Hz, 4H), 3.51 (br. s., 2H), 3.44 (s, 3H), 3.39 - 3.33 (m, 4H), 3.19 (br. s., 2H); LCMS: 577.1 |
| 378 | *(structure)* | 1H NMR (400MHz, METHANOL-d4) Shift = 8.29 (br. s., 1H), 8.14 - 8.02 (m, 1H), 7.95 - 7.83 (m, 2H), 7.72 (d, J=7.8 Hz, 1H), 7.67 - 7.58 (m, 1H), 7.52 (d, J=6.3 Hz, 1H), 4.83 - 4.52 (m, 2H), 4.40 (br. s., 2H), 4.03 (d, J=9.0 Hz, 2H), 3.82 - 3.58 (m, 5H), 3.56 - 3.46 (m, 3H), 3.42 (br. s., 3H), 3.37 - 3.31 (m, 3H), 3.30 - 3.26 (m, 2H), 3.26 - 3.10 (m, 3H), 2.96 (br. s., 3H); LCMS: 619.2 |
| 379 | *(structure)* | 1H NMR (400MHz, METHANOL-d4) Shift = 8.39 - 8.30 (m, 1H), 8.17 (d, J=4.9 Hz, 1H), 8.11 (d, J=8.4 Hz, 1H), 7.87 (d, J=8.4 Hz, 1H), 7.33 (d, J=5.3 Hz, 1H), 7.14 (br. s., 1H), 4.40 (br. s., 2H), 3.96 (d, J=1.3 Hz, 3H), 3.74 - 3.65 (m, 2H), 3.61 (d, J=3.5 Hz, 2H), 3.50 (t, J=6.6 Hz, 2H), 3.46 - 3.36 (m, 3H), 3.35 - 3.28 (m, 4H), 3.17 (t, J=6.6 Hz, 2H); LCMS: 524.1 |

*FIG. 1 (continued)*

| 380 | | 1H NMR (400MHz, METHANOL-d4) Shift = 8.28 - 8.12 (m, 2H), 8.02 - 7.90 (m, 2H), 7.65 (d, J=8.4 Hz, 1H), 7.42 - 7.17 (m, 5H), 5.39 (s, 2H), 4.40 (br. s., 2H), 3.71 - 3.55 (m, 4H), 3.47 (d, J=6.2 Hz, 2H), 3.41 (s, 3H), 3.35 - 3.29 (m, 4H), 3.16 (t, J=6.0 Hz, 2H); LCMS: 573.1 |
|---|---|---|
| 381 | | 1H NMR (400MHz, METHANOL-d4) Shift = 8.25 - 8.14 (m, 2H), 8.04 (dd, J=1.8, 8.4 Hz, 1H), 7.79 (d, J=7.1 Hz, 1H), 7.62 (d, J=7.9 Hz, 1H), 7.07 (dd, J=5.3, 7.1 Hz, 1H), 4.43 - 4.33 (m, 2H), 3.96 (s, 3H), 3.69 - 3.63 (m, 2H), 3.58 (d, J=5.3 Hz, 2H), 3.46 (t, J=6.6 Hz, 2H), 3.43 - 3.34 (m, 3H), 3.29 (s, 2H), 3.27 (br. s., 2H), 3.13 (t, J=6.6 Hz, 2H); LCMS: 524.1 |
| 382 | | 1H NMR (400MHz, METHANOL-d4) Shift = 8.22 (d, J=1.3 Hz, 1H), 8.05 (d, J=8.4 Hz, 1H), 7.99 (d, J=1.8 Hz, 1H), 7.66 (dd, J=1.3, 8.4 Hz, 1H), 7.52 - 7.47 (m, 1H), 4.44 - 4.37 (m, 2H), 3.98 (s, 3H), 3.92 (s, 3H), 3.70 - 3.65 (m, 2H), 3.62 (t, J=6.0 Hz, 2H), 3.48 (t, J=6.6 Hz, 2H), 3.44 - 3.36 (m, 3H), 3.31 (d, J=5.3 Hz, 4H), 3.18 (t, J=6.6 Hz, 2H); LCMS: 554.1 |

*FIG. 1 (continued)*

| | | |
|---|---|---|
| 383 | (structure) | 1H NMR (400MHz, METHANOL-d4) Shift = 9.17 (br. s., 1H), 8.87 (br. s., 1H), 8.53 - 8.34 (m, 2H), 8.21 (d, J=8.4 Hz, 1H), 7.93 (dd, J=1.5, 8.6 Hz, 1H), 4.42 (s, 2H), 3.74 - 3.57 (m, 4H), 3.50 (t, J=6.4 Hz, 2H), 3.46 - 3.37 (m, 3H), 3.32 (dd, J=4.6, 9.5 Hz, 4H), 3.22 - 3.16 (m, 2H); LCMS: 562 |
| 384 | (structure) | 1H NMR (400MHz, METHANOL-d4) Shift = 8.34 (br. s., 1H), 8.20 (s, 1H), 8.15 - 8.07 (m, 1H), 7.78 (d, J=7.9 Hz, 1H), 7.59 - 7.54 (m, 1H), 7.48 (t, J=7.3 Hz, 1H), 7.32 (d, J=6.6 Hz, 1H), 4.41 (br. s., 2H), 3.63 (dd, J=5.1, 9.9 Hz, 4H), 3.46 (t, J=6.6 Hz, 2H), 3.41 - 3.36 (m, 3H), 3.34 - 3.29 (m, 2H), 3.26 (br. s., 2H), 3.14 (t, J=6.6 Hz, 2H); LCMS: 533.1 |
| 385 | (structure) | 1H NMR (400MHz, METHANOL-d4) Shift = 8.16 (d, J=1.3 Hz, 1H), 8.09 - 7.97 (m, 1H), 7.72 (dd, J=1.5, 8.6 Hz, 1H), 7.67 - 7.59 (m, 1H), 6.89 (d, J=7.5 Hz, 1H), 4.43 - 4.32 (m, 2H), 4.01 - 3.88 (m, 3H), 3.72 - 3.64 (m, 2H), 3.51 (td, J=6.3, 17.8 Hz, 4H), 3.44 - 3.35 (m, 3H), 3.34 - 3.29 (m, 2H), 3.26 - 3.20 (m, 2H), 3.15 (t, J=6.6 Hz, 2H), 2.55 - 2.35 (m, 3H); LCMS: 538.1 |

| | | |
|---|---|---|
| 386 |  | 1H NMR (400MHz, METHANOL-d4) Shift = 8.45 (s, 1H), 8.24 (d, J=5.1 Hz, 1H), 8.17 (d, J=8.2 Hz, 1H), 7.83 (d, J=8.2 Hz, 1H), 7.38 (d, J=4.7 Hz, 1H), 7.20 (s, 1H), 4.45 (br. s., 2H), 3.99 (s, 3H), 3.70 - 3.65 (m, 4H), 3.53 - 3.48 (m, 2H), 3.43 (s, 3H), 3.35 (d, J=9.8 Hz, 4H), 3.26 - 3.16 (m, 2H); LCMS: 524.1 |
| 387 |  | 1H NMR (400MHz, METHANOL-d4) Shift = 8.26 (br. s., 1H), 8.13 (br. s., 1H), 8.00 (br. s., 1H), 7.83 (br. s., 1H), 7.53 (br. s., 1H), 4.44 (br. s., 2H), 3.98 (br. s., 3H), 3.95 (s, 3H), 3.67 (d, J=17.2 Hz, 4H), 3.51 (br. s., 2H), 3.44 (s, 3H), 3.33 (br. s., 4H), 3.19 (br. s., 2H); LCMS: 554.1 |
| 388 |  | 1H NMR (400MHz, METHANOL-d4) Shift = 8.19 (s, 1H), 8.09 (d, J=8.4 Hz, 1H), 7.57 - 7.51 (m, 2H), 7.47 - 7.41 (m, 2H), 7.38 (d, J=7.5 Hz, 1H), 4.39 (s, 2H), 3.67 - 3.63 (m, 2H), 3.61 - 3.55 (m, 2H), 3.45 (t, J=6.6 Hz, 2H), 3.39 (s, 3H), 3.29 - 3.24 (m, 4H), 3.09 (t, J=6.6 Hz, 2H), 2.88 (s, 3H); LCMS: 586 |

FIG. 1 (continued)

| | | |
|---|---|---|
| 389 | | 1H NMR (400MHz, METHANOL-d4) Shift = 8.06 - 7.97 (m, 2H), 7.64 (s, 1H), 7.46 (d, J=8.4 Hz, 1H), 4.40 (br. s., 2H), 3.85 (s, 3H), 3.70 - 3.58 (m, 4H), 3.47 (t, J=6.2 Hz, 2H), 3.40 (s, 3H), 3.34 - 3.29 (m, 4H), 3.15 (t, J=6.0 Hz, 2H), 2.44 (s, 3H); LCMS: 511.1 |
| 390 | | 1H NMR (400MHz, METHANOL-d4) Shift = 8.20 (s, 1H), 8.10 (d, J=8.4 Hz, 1H), 7.74 (d, J=8.4 Hz, 1H), 7.63 (t, J=7.7 Hz, 1H), 7.38 - 7.26 (m, 2H), 4.46 - 4.33 (m, 2H), 3.73 - 3.65 (m, 2H), 3.63 - 3.54 (m, 2H), 3.50 (t, J=6.2 Hz, 2H), 3.44 - 3.38 (m, 3H), 3.35 - 3.30 (m, 2H), 3.26 (br. s., 2H), 3.17 (t, J=6.0 Hz, 2H), 3.12 - 3.00 (m, 6H); LCMS: 582.2 |
| 391 | | 1H NMR (400MHz, METHANOL-d4) Shift = 9.10 (d, J=1.8 Hz, 1H), 8.48 (s, 1H), 8.34 (dd, J=2.0, 8.2 Hz, 1H), 8.24 (d, J=8.4 Hz, 1H), 7.97 (dd, J=2.4, 8.2 Hz, 2H), 4.44 (s, 2H), 3.74 - 3.58 (m, 4H), 3.49 (t, J=6.4 Hz, 2H), 3.42 (s, 3H), 3.38 - 3.30 (m, 4H), 3.18 (t, J=6.4 Hz, 2H); LCMS: 519.1 |

FIG. 1 (continued)

| | | |
|---|---|---|
| 392 | | 1H NMR (400MHz, METHANOL-d4) Shift = 8.20 - 8.12 (m, 2H), 8.08 (d, J=7.5 Hz, 1H), 7.75 (t, J=7.1 Hz, 1H), 7.69 - 7.62 (m, 1H), 7.48 (d, J=6.2 Hz, 2H), 4.39 (br. s., 2H), 3.68 - 3.53 (m, 4H), 3.49 - 3.41 (m, 2H), 3.39 - 3.34 (m, 3H), 3.29 - 3.16 (m, 4H), 3.09 (br. s., 2H), 2.79 (s, 3H); LCMS: 571 |
| 393 | | 1H NMR (400MHz, METHANOL-d4) Shift = 8.68 (br. s., 1H), 8.55 (d, J=4.0 Hz, 1H), 8.20 (s, 1H), 8.16 (d, J=8.4 Hz, 1H), 7.61 - 7.52 (m, 2H), 4.42 (br. s., 2H), 3.68 - 3.57 (m, 4H), 3.46 (t, J=6.4 Hz, 2H), 3.39 (s, 3H), 3.33 (br. s., 2H), 3.28 - 3.23 (m, 2H), 3.15 (t, J=6.2 Hz, 2H); LCMS: 528 |
| 394 | | 1H NMR (400MHz, METHANOL-d4) Shift = 8.33 (s, 1H), 8.11 (d, J=8.4 Hz, 1H), 7.85 (d, J=7.9 Hz, 1H), 7.80 - 7.72 (m, 2H), 7.58 (t, J=7.5 Hz, 1H), 7.45 (d, J=7.5 Hz, 1H), 4.42 (s, 2H), 3.70 - 3.59 (m, 4H), 3.48 (t, J=6.6 Hz, 2H), 3.41 (s, 3H), 3.35 - 3.30 (m, 4H), 3.21 - 3.10 (m, 5H), 3.06 (s, 3H); LCMS: 564.1 |

| 395 |  | 1H NMR (400MHz, METHANOL-d4) Shift = 9.13 (s, 2H), 9.09 (s, 1H), 8.36 (s, 1H), 8.17 (d, J=8.4 Hz, 1H), 7.88 (dd, J=1.5, 8.6 Hz, 1H), 4.42 (s, 2H), 3.71 - 3.62 (m, 4H), 3.51 (t, J=6.6 Hz, 2H), 3.42 (s, 3H), 3.33 (t, J=4.6 Hz, 4H), 3.19 (t, J=6.4 Hz, 2H); LCMS: 495 |
| --- | --- | --- |
| 396 |  | 1H NMR (400MHz, METHANOL-d4) Shift = 8.65 (d, J=5.7 Hz, 2H), 8.12 (d, J=11.0 Hz, 1H), 8.01 - 7.94 (m, 1H), 7.56 (d, J=7.9 Hz, 1H), 4.38 (br. s., 2H), 3.80 (d, J=3.5 Hz, 4H), 3.75 (d, J=4.9 Hz, 4H), 3.70 - 3.65 (m, 2H), 3.60 (br. s., 2H), 3.49 (t, J=6.2 Hz, 2H), 3.44 - 3.37 (m, 3H), 3.32 (d, J=4.9 Hz, 2H), 3.28 - 3.23 (m, 2H), 3.18 (t, J=6.2 Hz, 2H); LCMS: 580.2 |
| 397 |  | 1H NMR (400MHz, METHANOL-d4) Shift = 8.47 (br. s., 1H), 8.18 (br. s., 2H), 7.99 (br. s., 1H), 7.81 - 7.67 (m, 2H), 4.36 (br. s., 2H), 3.94 (br. s., 3H), 3.74 - 3.66 (m, 2H), 3.58 (br. s., 2H), 3.51 (t, J=6.2 Hz, 2H), 3.45 - 3.38 (m, 3H), 3.34 (br. s., 2H), 3.26 - 3.12 (m, 4H); LCMS: 524.1 |

*FIG. 1 (continued)*

| | | |
|---|---|---|
| 398 | (structure) | 1H NMR (400MHz, METHANOL-d4) Shift = 8.29 (s, 1H), 8.23 - 8.12 (m, 3H), 7.80 (d, J=8.4 Hz, 1H), 7.48 - 7.41 (m, 1H), 4.43 (s, 2H), 3.70 - 3.61 (m, 4H), 3.50 (t, J=6.4 Hz, 2H), 3.42 (s, 3H), 3.37 - 3.30 (m, 4H), 3.18 (t, J=6.6 Hz, 2H); LCMS: 512 |
| 399 | (structure) | 1H NMR (400MHz, METHANOL-d4) Shift = 8.57 (d, J=2.2 Hz, 1H), 8.37 (s, 1H), 8.31 (dt, J=2.4, 8.0 Hz, 1H), 8.17 (d, J=8.4 Hz, 1H), 7.75 (d, J=7.9 Hz, 1H), 7.21 (dd, J=2.4, 8.6 Hz, 1H), 4.43 (s, 2H), 3.70 - 3.62 (m, 4H), 3.49 (t, J=6.6 Hz, 2H), 3.41 (s, 3H), 3.38 - 3.30 (m, 4H), 3.19 (t, J=6.6 Hz, 2H); LCMS: 512 |
| 400 | (structure) | 1H NMR (400MHz, METHANOL-d4) Shift = 8.43 (d, J=2.2 Hz, 1H), 8.18 (d, J=1.3 Hz, 1H), 8.10 - 7.99 (m, 2H), 7.75 (dd, J=1.5, 8.6 Hz, 1H), 6.88 (d, J=8.8 Hz, 1H), 5.29 - 5.18 (m, 1H), 4.44 - 4.30 (m, 2H), 3.72 - 3.64 (m, 2H), 3.58 (t, J=6.0 Hz, 2H), 3.49 (t, J=6.6 Hz, 2H), 3.45 - 3.36 (m, 3H), 3.34 - 3.30 (m, 2H), 3.28 - 3.22 (m, 2H), 3.16 (t, J=6.6 Hz, 2H), 1.46 - 1.25 (m, 6H); LCMS: 552.1 |

| | | |
|---|---|---|
| 401 |  | 1H NMR (400MHz, METHANOL-d4) Shift = 8.43 (s, 1H), 8.17 (d, J=8.4 Hz, 1H), 7.95 - 7.83 (m, 2H), 7.29 - 7.22 (m, 2H), 4.42 (s, 2H), 3.71 - 3.61 (m, 4H), 3.54 - 3.46 (m, 2H), 3.44 - 3.38 (m, 3H), 3.36 - 3.30 (m, 4H), 3.19 (t, J=6.4 Hz, 2H); LCMS: 509 |
| 402 |  | 1H NMR (400MHz, METHANOL-d4) Shift = 8.18 - 8.07 (m, 2H), 8.01 - 7.91 (m, 2H), 7.72 (d, J=8.4 Hz, 1H), 7.39 - 7.24 (m, 5H), 5.36 (s, 2H), 4.37 (s, 2H), 3.70 - 3.64 (m, 2H), 3.59 (t, J=6.0 Hz, 2H), 3.48 (t, J=6.4 Hz, 2H), 3.44 - 3.38 (m, 3H), 3.29 (br. s., 4H), 3.20 - 3.08 (m, 2H); LCMS: 573.1 |
| 403 |  | 1H NMR (400MHz, METHANOL-d4) Shift = 8.17 - 8.08 (m, 1H), 8.04 (d, J=8.4 Hz, 1H), 7.83 (s, 1H), 7.56 (d, J=8.4 Hz, 1H), 4.42 (s, 2H), 3.70 - 3.60 (m, 4H), 3.48 (t, J=6.4 Hz, 2H), 3.41 (s, 3H), 3.36 - 3.29 (m, 4H), 3.16 (t, J=6.6 Hz, 2H), 2.49 (s, 3H); LCMS: 497 |

FIG. 1 (continued)

| | | |
|---|---|---|
| 404 | (structure) | 1H NMR (400MHz, METHANOL-d4) Shift = 8.94 (s, 2H), 8.36 (d, J=1.3 Hz, 1H), 8.15 (d, J=8.4 Hz, 1H), 7.74 (dd, J=1.8, 8.4 Hz, 1H), 4.43 (s, 2H), 4.07 (s, 3H), 3.70 - 3.62 (m, 4H), 3.49 (t, J=6.6 Hz, 2H), 3.41 (s, 3H), 3.38 - 3.30 (m, 4H), 3.19 (t, J=6.6 Hz, 2H); LCMS: 525 |
| 405 | (structure) | 1H NMR (400MHz, METHANOL-d4) Shift = 9.11 (d, J=1.8 Hz, 1H), 8.47 (s, 1H), 8.36 (dd, J=2.2, 7.9 Hz, 1H), 8.20 (d, J=8.4 Hz, 1H), 7.97 (d, J=7.9 Hz, 1H), 7.83 (dd, J=1.8, 8.4 Hz, 1H), 4.43 (s, 2H), 3.71 - 3.61 (m, 4H), 3.49 (t, J=6.6 Hz, 2H), 3.41 (s, 3H), 3.38 - 3.30 (m, 4H), 3.20 (t, J=6.4 Hz, 2H); LCMS: 519 |
| 406 | (structure) | 1H NMR (400MHz, METHANOL-d4) Shift = 8.44 (s, 1H), 8.02 (d, J=8.2 Hz, 1H), 7.86 (d, J=8.6 Hz, 1H), 7.75 (s, 1H), 6.82 (br. s., 1H), 4.39 (s, 2H), 3.70 (d, J=4.7 Hz, 2H), 3.59 (t, J=5.5 Hz, 2H), 3.51 (t, J=6.3 Hz, 2H), 3.44 (s, 3H), 3.33 (d, J=4.7 Hz, 2H), 3.28 (br. s., 2H), 3.18 (t, J=6.3 Hz, 2H); LCMS: 483.1 |

FIG. 1 (continued)

| | | |
|---|---|---|
| 407 | (structure) | 1H NMR (400MHz, METHANOL-d4) Shift = 8.92 (br. s., 1H), 8.69 (d, J=8.2 Hz, 1H), 8.33 (s, 1H), 8.24 (d, J=8.2 Hz, 1H), 8.13 (d, J=8.2 Hz, 1H), 7.96 (d, J=7.0 Hz, 1H), 7.88 - 7.79 (m, 2H), 7.74 (dd, J=4.5, 8.0 Hz, 1H), 4.45 (s, 2H), 3.70 (t, J=4.5 Hz, 2H), 3.65 (t, J=5.7 Hz, 2H), 3.52 (t, J=6.5 Hz, 2H), 3.44 (s, 3H), 3.39 - 3.32 (m, 4H), 3.22 (t, J=6.5 Hz, 2H); LCMS: 544 |
| 408 | (structure) | 1H NMR (400MHz, METHANOL-d4) Shift = 8.48 - 8.29 (m, 3H), 8.11 (br. s., 1H), 7.71 (br. s., 1H), 7.46 (br. s., 1H), 4.42 (br. s., 2H), 3.89 (br. s., 4H), 3.80 - 3.59 (m, 8H), 3.50 (br. s., 2H), 3.41 (s, 3H), 3.37 - 3.31 (m, 4H), 3.22 (br. s., 2H); LCMS: 579.1 |
| 409 | (structure) | 1H NMR (400MHz, METHANOL-d4) Shift = 9.12 (br. s., 1H), 8.28 (br. s., 1H), 8.20 (d, J=7.8 Hz, 1H), 8.06 (d, J=7.8 Hz, 1H), 7.94 (d, J=8.2 Hz, 1H), 7.57 (d, J=7.8 Hz, 1H), 4.41 (br. s., 2H), 4.04 (s, 3H), 3.74 (br. s., 2H), 3.67 (br. s., 2H), 3.59 (br. s., 2H), 3.42 (s, 5H), 3.28 (br. s., 4H); LCMS: 552.1 |

| | | |
|---|---|---|
| 410 |  | 1H NMR (400MHz, METHANOL-d4) Shift = 8.22 (d, J=1.3 Hz, 1H), 8.04 (d, J=8.4 Hz, 1H), 7.66 (dd, J=1.8, 8.4 Hz, 1H), 7.23 - 7.18 (m, 2H), 6.93 (d, J=8.4 Hz, 1H), 6.00 (s, 2H), 4.42 (s, 2H), 3.69 - 3.60 (m, 4H), 3.48 (t, J=6.6 Hz, 2H), 3.44 - 3.38 (m, 3H), 3.36 - 3.30 (m, 4H), 3.17 (t, J=6.6 Hz, 2H); LCMS: 537 |
| 411 |  | 1H NMR (400MHz, METHANOL-d4) Shift = 9.00 (s, 1H), 8.65 (d, J=11.5 Hz, 2H), 8.47 (d, J=1.3 Hz, 1H), 8.23 (d, J=8.8 Hz, 1H), 7.96 (dd, J=1.8, 8.4 Hz, 1H), 4.42 (s, 2H), 3.71 - 3.66 (m, 2H), 3.63 (t, J=6.0 Hz, 2H), 3.50 (t, J=6.6 Hz, 2H), 3.42 (s, 3H), 3.38 - 3.30 (m, 4H), 3.19 (t, J=6.6 Hz, 2H), 2.69 - 2.50 (m, 3H); LCMS: 508 |
| 412 |  | 1H NMR (400MHz, METHANOL-d4) Shift = 8.41 (d, J=1.3 Hz, 1H), 8.30 (s, 1H), 8.18 (d, J=8.4 Hz, 1H), 8.11 (d, J=7.9 Hz, 1H), 8.00 (d, J=7.9 Hz, 1H), 7.86 - 7.75 (m, 2H), 4.44 (s, 2H), 3.72 - 3.60 (m, 4H), 3.52 - 3.46 (m, 2H), 3.41 (s, 3H), 3.38 - 3.30 (m, 4H), 3.23 - 3.15 (m, 5H); LCMS: 571 |

| | | |
|---|---|---|
| 413 |  | 1H NMR (400MHz, METHANOL-d4) Shift = 9.16 (s, 1H), 8.41 (d, J=16.8 Hz, 2H), 8.17 - 8.06 (m, 2H), 7.89 - 7.76 (m, 2H), 4.42 (br. s., 2H), 3.70 - 3.63 (m, 4H), 3.54 - 3.48 (m, 2H), 3.41 (s, 3H), 3.35 - 3.30 (m, 4H), 3.22 (t, J=6.6 Hz, 2H); LCMS: 534 |
| 414 |  | 1H NMR (400MHz, METHANOL-d4) Shift = 8.25 (br. s., 1H), 8.08 (d, J=7.9 Hz, 1H), 7.94 (s, 2H), 7.80 (d, J=7.9 Hz, 1H), 7.72 - 7.58 (m, 2H), 4.36 (br. s., 2H), 3.72 - 3.65 (m, 2H), 3.60 - 3.45 (m, 4H), 3.44 - 3.37 (m, 3H), 3.35 - 3.30 (m, 2H), 3.24 (br. s., 2H), 3.19 - 3.11 (m, 2H); LCMS: 561 |
| 415 |  | 1H NMR (400MHz, METHANOL-d4) Shift = 8.13 (s, 1H), 8.03 (dd, J=8.2, 15.7 Hz, 2H), 7.72 - 7.63 (m, 1H), 7.63 - 7.55 (m, 1H), 7.49 (d, J=8.4 Hz, 1H), 7.44 (d, J=7.1 Hz, 1H), 4.35 (br. s., 2H), 3.63 (d, J=4.4 Hz, 2H), 3.57 - 3.40 (m, 4H), 3.40 - 3.33 (m, 3H), 3.29 - 3.20 (m, 4H), 3.05 (br. s., 2H), 2.55 - 2.38 (m, 3H); LCMS: 586 |

FIG. 1 (continued)

| | | |
|---|---|---|
| 416 | *(structure)* | 1H NMR (400MHz, METHANOL-d4) Shift = 8.16 (s, 1H), 7.99 (d, J=8.4 Hz, 1H), 7.71 - 7.56 (m, 2H), 6.90 (d, J=7.5 Hz, 1H), 4.37 (s, 2H), 4.01 - 3.84 (m, 3H), 3.69 - 3.61 (m, 2H), 3.57 - 3.49 (m, 2H), 3.4 5 (t, J=6.6 Hz, 2H), 3.42 - 3.35 (m, 3H), 3.29 - 3.19 (m, 4H), 3.17 - 3.06 (m, 2H), 2.53 - 2.38 (m, 3H); LCMS: 538.1 |
| 417 | *(structure)* | 1H NMR (400MHz, METHANOL-d4) Shift = 8.73 (dd, J=1.3, 5.7 Hz, 1H), 8.49 - 8.45 (m, 1H), 8.26 (d, J=8.8 Hz, 1H), 8.20 (d, J=1.3 Hz, 1H), 7.94 (dd, J=6.2, 7.5 Hz, 1H), 7.67 (dd, J=1.3, 8.4 Hz, 1H), 4.43 (s, 2H), 3.71 - 3.60 (m, 4H), 3.50 (t, J=6.6 Hz, 2H), 3.41 (s, 3H), 3.32 (dd, J=4.4, 9.7 Hz, 4H), 3.20 (t, J=6.6 Hz, 2H), 2.75 (s, 3H); LCMS: 508.1 |
| 418 | *(structure)* | 1H NMR (400MHz, METHANOL-d4) Shift = 8.24 (br. s., 1H), 8.02 (d, J=8.4 Hz, 1H), 7.98 - 7.92 (m, 1H), 7.89 (d, J=7.9 Hz, 1H), 7.65 (d, J=8.4 Hz, 1H), 7.48 (d, J=7.9 Hz, 1H), 4.40 (br. s., 2H), 3.73 - 3.66 (m, 2H), 3.65 - 3.57 (m, 2H), 3.49 (t, J=6.4 Hz, 2H), 3.45 - 3.36 (m, 3H), 3.34 - 3.29 (m, 4H), 3.24 - 3.10 (m, 2H), 2.61 - 2.41 (m, 3H); LCMS: 532.1 |

| 419 |  | 1H NMR (400MHz, METHANOL-d4) Shift = 8.22 (d, J=4.0 Hz, 2H), 8.02 (d, J=7.5 Hz, 1H), 7.89 (d, J=6.2 Hz, 2H), 7.71 - 7.56 (m, 2H), 4.38 (br. s., 2H), 3.77 - 3.53 (m, 4H), 3.48 (br. s., 2H), 3.40 (s, 3H ), 3.34 - 3.29 (m, 2H), 3.28 - 3.23 (m, 2H), 3.17 (br. s., 2H); LCMS: 572.1 |
| --- | --- | --- |
| 420 |  | 1H NMR (400MHz, METHANOL-d4) Shift = 8.25 - 8.10 (m, 2H), 7.73 - 7.63 (m, 1H), 7.52 (d, J=1.8 Hz, 1H), 6.51 - 6.41 (m, 1H), 4.42 (s, 2H), 3.92 (s, 3H), 3.72 - 3.58 (m, 4H), 3.49 (t, J=6.4 Hz, 2H), 3.45 - 3.38 (m, 3H), 3.36 - 3.30 (m, 4H), 3.18 (t, J=6.4 Hz, 2H); LCMS: 497 |
| 421 |  | 1H NMR (400MHz, METHANOL-d4) Shift = 8.07 (br. s., 1H), 7.86 (br. s., 1H), 7.43 (d, J=7.5 Hz, 1H), 4.40 (br. s., 2H), 3.80 - 3.64 (m, 5H), 3.61 - 3.46 (m, 4H), 3.45 - 3.37 (m, 3H), 3.31 (br. s., 2H), 3.27 - 3.08 (m, 4H), 2.32 - 2.14 (m, 6H); LCMS: 525.2 |

FIG. 1 (continued)

| | | |
|---|---|---|
| 422 | (structure) | 1H NMR (400MHz, METHANOL-d4) Shift = 8.11 (br. s., 1H), 7.90 (d, J=7.5 Hz, 1H), 7.69 - 7.54 (m, 3H), 7.09 (d, J=7.1 Hz, 2H), 4.31 (br. s., 2H), 3.82 - 3.62 (m, 3H), 3.59 - 3.35 (m, 10H), 3.29 (br. s., 4H), 3.23 - 3.06 (m, 5H), 2.96 (br. s., 4H); LCMS: 591.2 |
| 423 | (structure) | 1H NMR (400MHz, METHANOL-d4) Shift = 8.68 (s, 1H), 8.46 - 8.32 (m, 2H), 8.15 - 8.02 (m, 2H), 7.72 (d, J=8.4 Hz, 1H), 4.46 - 4.32 (m, 4H), 3.84 - 3.78 (m, 2H), 3.73 - 3.66 (m, 2H), 3.65 - 3.58 (m, 2H), 3.50 (t, J=6.4 Hz, 2H), 3.44 (s, 3H), 3.41 (s, 3H), 3.35 - 3.30 (m, 2H), 3.29 - 3.25 (m, 2H), 3.20 (t, J=6.4 Hz, 2H); LCMS: 568.1 |
| 424 | (structure) | 1H NMR (400MHz, METHANOL-d4) Shift = 8.21 (s, 1H), 8.04 (d, J=7.8 Hz, 1H), 7.79 (d, J=8.2 Hz, 1H), 7.35 (d, J=7.0 Hz, 1H), 7.20 (t, J=7.0 Hz, 1H), 6.94 (d, J=7.4 Hz, 2H), 4.37 (br. s., 2H), 3.69 (br. s., 2H), 3.49 (br. s., 4H), 3.43 (s, 3H), 3.36 - 3.32 (m, 2H), 3.21 (br. s., 2H), 3.14 (br. s., 2H); LCMS: 509.1 |

| | | |
|---|---|---|
| 425 |  | 1H NMR (400MHz, METHANOL-d4) Shift = 8.89 (dd, J=1.3, 4.4 Hz, 1H), 8.62 (dd, J=1.3, 8.4 Hz, 1H), 8.33 (s, 1H), 8.18 (d, J=8.4 Hz, 1H), 8.10 (d, J=7.9 Hz, 1H), 7.97 - 7.89 (m, 1H), 7.84 - 7.77 (m, 1H), 7.75 - 7.66 (m, 2H), 4.44 (s, 2H), 3.66 (t, J=6.0 Hz, 2H), 3.64 - 3.58 (m, 2H), 3.44 (t, J=6.6 Hz, 2H), 3.40 - 3.32 (m, 5H), 3.27 - 3.22 (m, 2H), 3.11 (t, J=6.6 Hz, 2H); LCMS: 544 |
| 426 |  | 1H NMR (400MHz, METHANOL-d4) Shift = 9.01 (d, J=4.9 Hz, 1H), 8.82 (d, J=7.9 Hz, 1H), 8.53 (br. s., 1H), 8.46 (br. s., 1H), 8.38 (d, J=9.3 Hz, 1H), 8.25 (dd, J=2.9, 8.6 Hz, 2H), 8.09 - 8.05 (m, 1H), 7.83 (dd, J=4.6, 8.2 Hz, 1H), 4.47 (s, 2H), 3.75 - 3.64 (m, 4H), 3.54 (t, J=6.6 Hz, 2H), 3.46 (s, 3H), 3.39 - 3.34 (m, 4H), 3.22 (t, J=6.4 Hz, 2H); LCMS: 544.1 |
| 427 |  | 1H NMR (400MHz, METHANOL-d4) Shift = 8.99 (br. s., 1H), 8.34 - 8.18 (m, 2H), 8.11 (br. s., 2H), 7.86 (br. s., 1H), 4.43 (br. s., 2H), 3.99 (br. s., 3H), 3.70 (br. s., 5H), 3.55 (br. s., 2H), 3.44 - 3.39 (m, 3H), 3.36 (br. s., 3H), 3.19 (br. s., 2H); LCMS: 552.1 |

FIG. 1 (continued)

| | | |
|---|---|---|
| 428 | (structure) | 1H NMR (400MHz, METHANOL-d4) Shift = 8.23 (d, J=1.3 Hz, 1H), 8.04 (d, J=8.4 Hz, 1H), 7.67 (dd, J=1.8, 8.4 Hz, 1H), 7.45 (dd, J=2.2, 12.3 Hz, 1H), 7.38 (dd, J=1.8, 8.4 Hz, 1H), 7.02 (t, J=8.8 Hz, 1H), 4.42 (s, 2H), 3.71 - 3.57 (m, 4H), 3.48 (t, J=6.6 Hz, 2H), 3.41 (s, 3H), 3.36 - 3.29 (m, 4H), 3.17 (t, J=6.6 Hz, 2H); LCMS: 527 |
| 429 | (structure) | 1H NMR (400MHz, METHANOL-d4) Shift = 8.38 - 8.27 (m, 1H), 8.14 - 8.06 (m, 1H), 7.93 (q, J=8.4 Hz, 4H), 7.76 (dd, J=1.5, 8.6 Hz, 1H), 4.50 - 4.34 (m, 2H), 3.73 - 3.59 (m, 4H), 3.48 (t, J=6.6 Hz, 2H), 3.41 (s, 3H), 3.35 - 3.29 (m, 4H), 3.23 - 3.12 (m, 2H), 2.20 (tt, J=3.6, 6.8 Hz, 1H), 0.63 - 0.42 (m, 4H); LCMS: 612.1 |
| 430 | (structure) | 1H NMR (400MHz, METHANOL-d4) Shift = 8.28 - 8.11 (m, 2H), 8.06 - 7.94 (m, 1H), 7.89 - 7.72 (m, 2H), 7.70 - 7.58 (m, 1H), 7.28 (br. s., 1H), 5.84 (br. s., 1H), 4.45 - 4.31 (m, 2H), 3.73 - 3.64 (m, 2H), 3.63 - 3.54 (m, 2H), 3.53 - 3.45 (m, 2H), 3.44 - 3.36 (m, 3H), 3.36 - 3.28 (m, 3H), 3.25 - 3.14 (m, 3H), 3.13 - 3.02 (m, 3H); LCMS: 574 |

| | | |
|---|---|---|
| 431 |  | 1H NMR (400MHz, METHANOL-d4) Shift = 8.00 (s, 1H), 7.95 - 7.86 (m, 1H), 7.64 (d, J=8.4 Hz, 1H), 7.33 (d, J=12.3 Hz, 1H), 7.26 (d, J=9.3 Hz, 1H), 6.94 (t, J=8.6 Hz, 1H), 4.33 (s, 2H), 3.72 - 3.64 (m, 2H), 3.56 - 3.44 (m, 4H), 3.42 (s, 3H), 3.34 - 3.29 (m, 2H), 3.22 - 3.04 (m, 4H); LCMS: 527.1 |
| 432 |  | 1H NMR (400MHz, METHANOL-d4) Shift = 8.32 (br. s., 1H), 8.11 (d, J=8.4 Hz, 1H), 7.73 (d, J=7.1 Hz, 3H), 7.59 - 7.28 (m, 3H), 4.43 (br. s., 2H), 3.66 (d, J=5.3 Hz, 4H), 3.52 - 3.33 (m, 8H), 3.19 (d, J= 6.2 Hz, 3H); LCMS: 493 |
| 433 |  | 1H NMR (400MHz, METHANOL-d4) Shift = 8.48 (s, 1H), 8.19 (d, J=8.8 Hz, 1H), 7.91 (d, J=7.1 Hz, 1H), 7.81 (dd, J=1.3, 8.4 Hz, 1H), 7.36 (s, 1H), 7.32 (d, J=6.6 Hz, 1H), 4.43 (s, 2H), 3.71 - 3.62 (m, 4H), 3.49 (t, J=6.6 Hz, 2H), 3.41 (s, 3H), 3.36 - 3.30 (m, 4H), 3.24 - 3.19 (m, 2H); LCMS: 509 |

| 434 |  | 1H NMR (400MHz, METHANOL-d4) Shift = 8.31 (s, 1H), 8.11 (d, J=8.4 Hz, 1H), 7.73 (d, J=8.4 Hz, 1H), 7.67 (s, 1H), 7.55 - 7.51 (m, 1H), 7.49 - 7.44 (m, 1H), 7.25 (d, J=8.8 Hz, 1H), 4.43 (s, 2H), 3.70 - 3.61 (m, 4H), 3.49 (t, J=6.6 Hz, 2H), 3.41 (s, 3H), 3.38 - 3.30 (m, 4H), 3.18 (t, J=6.6 Hz, 2H), 3.00 (s, 3H); LCMS: 586 |
| --- | --- | --- |
| 435 |  | 1H NMR (METHANOL-d4, 400MHz): Shift = 8.56 (s, 1H), 8.33 (s, 2H), 8.12 (d, J=8.4 Hz, 1H), 7.71 (dd, J=8.4, 1.3 Hz, 1H), 4.42 (s, 2H), 3.62-3.69 (m, 4H), 3.49 (t, J=6.4 Hz, 2H), 3.41 (s, 3H), 3.30-3.37 (m, 4H), 3.20 ppm (t, J=6.6 Hz, 2H); LCMS: 577.1 |
| 436 |  | 1H NMR (400MHz, METHANOL-d4) Shift = 8.06 (d, J=8.4 Hz, 1H), 7.99 (s, 1H), 7.65 (s, 1H), 7.58 (dd, J=1.3, 8.4 Hz, 1H), 4.41 (s, 2H), 3.84 (s, 3H), 3.71 - 3.65 (m, 2H), 3.60 (t, J=6.0 Hz, 2H), 3.49 (t, J=6.4 Hz, 2H), 3.41 (s, 3H), 3.34 - 3.29 (m, 4H), 3.16 (t, J=6.6 Hz, 2H), 2.43 (s, 3H); LCMS: 511.1 |

| | | |
|---|---|---|
| 437 |  | 1H NMR (400MHz, METHANOL-d4) Shift = 8.21 (s, 1H), 8.15 - 8.11 (m, 1H), 8.04 (d, J=8.4 Hz, 1H), 7.79 (d, J=7.1 Hz, 1H), 7.66 (d, J=8.4 Hz, 1H), 7.06 (dd, J=5.1, 7.3 Hz, 1H), 4.47 - 4.37 (m, 4H), 3.69 - 3.56 (m, 4H), 3.46 (t, J=6.4 Hz, 2H), 3.39 (s, 3H), 3.29 (dd, J=1.5, 3.3 Hz, 4H), 3.13 (t, J=6.4 Hz, 2H), 1.34 (t, J=7.1 Hz, 3H); LCMS: 538.1 |
| 438 |  | 1H NMR (400MHz, METHANOL-d4) Shift = 8.47 (d, J=2.2 Hz, 1H), 8.26 (d, J=1.3 Hz, 1H), 8.10 - 8.04 (m, 2H), 7.68 (dd, J=1.8, 8.4 Hz, 1H), 6.89 (d, J=8.4 Hz, 1H), 5.33 - 5.24 (m, 1H), 4.41 (s, 2H), 3.70 - 3.59 (m, 4H), 3.48 (t, J=6.6 Hz, 2H), 3.41 (s, 3H), 3.31 (d, J=5.3 Hz, 4H), 3.18 (t, J=6.6 Hz, 2H), 1.37 (d, J=6.2 Hz, 6H); LCMS: 552.1 |
| 439 |  | 1H NMR (400MHz, METHANOL-d4) Shift = 8.15 (d, J=8.4 Hz, 1H), 8.01 (d, J=1.3 Hz, 1H), 7.75 (d, J=8.4 Hz, 1H), 7.54 (dd, J=1.3, 8.4 Hz, 1H), 6.87 (d, J=8.4 Hz, 1H), 4.43 (s, 2H), 3.99 (s, 3H), 3.71 - 3.60 (m, 4H), 3.50 (t, J=6.6 Hz, 2H), 3.41 (s, 3H), 3.36 - 3.30 (m, 4H), 3.18 (t, J=6.4 Hz, 2H), 2.45 (s, 3H); LCMS: 538.1 |

FIG. 1 (continued)

| | | |
|---|---|---|
| 440 | | 1H NMR (400MHz, METHANOL-d4) Shift = 9.07 (br. s., 1H), 8.45 (s, 1H), 8.37 (d, J=7.9 Hz, 1H), 8.23 (d, J=8.4 Hz, 1H), 7.97 - 7.88 (m, 2H), 4.43 (br. s., 2H), 3.70 - 3.61 (m, 4H), 3.53 - 3.47 (m, 2H), 3.42 (s, 3H), 3.37 - 3.30 (m, 4H), 3.19 (t, J=6.4 Hz, 2H); LCMS: 562 |
| 441 | | 1H NMR (400MHz, METHANOL-d4) Shift = 8.36 (s, 1H), 8.17 (d, J=8.8 Hz, 1H), 7.89 (d, J=8.4 Hz, 1H), 7.83 (d, J=8.4 Hz, 2H), 7.55 (d, J=7.9 Hz, 2H), 4.43 (s, 2H), 3.82 - 3.62 (m, 10H), 3.49 (t, J=6.6 Hz , 4H), 3.45 - 3.39 (m, 3H), 3.38 - 3.31 (m, 4H), 3.17 (t, J=6.4 Hz, 2H); LCMS: 606.2 |

FIG. 1 (continued)

| | | |
|---|---|---|
| 442 | | 1H NMR (400MHz, METHANOL-d4) Shift = 8.31 (s, 1H), 8.12 (d, J=8.4 Hz, 1H), 7.97 - 7.83 (m, 5H), 4.42 (s, 2H), 3.71 - 3.60 (m, 4H), 3.50 (t, J=6.6 Hz, 2H), 3.42 (s, 3H), 3.35 - 3.29 (m, 4H), 3.18 (t, J =6.6 Hz, 2H), 2.19 (td, J=3.2, 6.8 Hz, 1H), 0.59 - 0.47 (m, 4H); LCMS: 612.1 |
| 443 | | 1H NMR (400MHz, METHANOL-d4) Shift = 8.44 (s, 1H), 8.34 (s, 1H), 8.21 (d, J=8.4 Hz, 1H), 8.01 (d, J=11.5 Hz, 2H), 7.77 (dd, J=1.3, 8.4 Hz, 1H), 4.43 (s, 2H), 3.69 - 3.62 (m, 4H), 3.49 (t, J=6.4 Hz, 2H), 3.41 (s, 3H), 3.37 - 3.30 (m, 4H), 3.20 (t, J=6.6 Hz, 2H); LCMS: 509.1 |
| 444 | | 1H NMR (400MHz, METHANOL-d4) Shift = 8.21 (s, 1H), 8.10 (d, J=8.4 Hz, 1H), 7.79 (dd, J=1.3, 8.4 Hz, 1H), 7.59 (s, 1H), 7.49 - 7.40 (m, 2H), 7.22 (d, J=7.5 Hz, 1H), 4.41 (s, 2H), 3.70 - 3.66 (m, 2H), 3.63 (t, J=6.0 Hz, 2H), 3.49 (t, J=6.4 Hz, 2H), 3.42 (s, 3H), 3.31 (t, J=4.9 Hz, 4H), 3.16 (t, J=6.6 Hz, 2H), 3.00 (s, 3H); LCMS: 586 |

| | | |
|---|---|---|
| 445 |  | 1H NMR (400MHz, METHANOL-d4) Shift = 8.27 (d, J=1.3 Hz, 1H), 8.15 (s, 1H), 8.06 - 7.97 (m, 2H), 7.69 (dd, J=1.5, 8.6 Hz, 1H), 5.07 (s, 2H), 4.42 (s, 2H), 4.25 (q, J=7.1 Hz, 2H), 3.70 - 3.61 (m, 4H), 3.49 (t, J=6.6 Hz, 2H), 3.42 (s, 3H), 3.36 - 3.30 (m, 4H), 3.18 (t, J=6.4 Hz, 2H), 1.29 (t, J=7.1 Hz, 3H); LCMS: 569.1 |
| 446 |  | 1H NMR (400MHz, METHANOL-d4) Shift = 8.70 (s, 1H), 8.56 (d, J=4.9 Hz, 1H), 8.28 - 8.18 (m, 2H), 7.73 (dd, J=1.8, 8.4 Hz, 1H), 7.56 (d, J=5.3 Hz, 1H), 4.43 (s, 2H), 3.70 - 3.62 (m, 4H), 3.50 (t, J=6.6 Hz, 2H), 3.42 (s, 3H), 3.38 - 3.31 (m, 4H), 3.18 (t, J=6.4 Hz, 2H); LCMS: 528 |
| 447 |  | 1H NMR (400MHz, METHANOL-d4) Shift = 8.22 - 8.13 (m, 2H), 7.65 (d, J=8.4 Hz, 1H), 7.49 - 7.40 (m, 1H), 7.11 (t, J=7.9 Hz, 2H), 4.43 (s, 2H), 3.70 - 3.62 (m, 4H), 3.49 (t, J=6.4 Hz, 2H), 3.42 (s, 3H), 3.37 - 3.31 (m, 4H), 3.20 - 3.15 (m, 2H); LCMS: 529 |

| 448 |  | 1H NMR (400MHz, METHANOL-d4) Shift = 8.23 (s, 1H), 8.04 (d, J=8.4 Hz, 1H), 7.65 (d, J=8.4 Hz, 1H), 7.33 (d, J=3.1 Hz, 1H), 7.18 (s, 1H), 4.42 (s, 2H), 3.69 - 3.59 (m, 4H), 3.53 - 3.46 (m, 2H), 3.41 (s, 2H), 3.37 - 3.28 (m, 7H), 3.17 (t, J=6.6 Hz, 2H); LCMS: 548 |
|---|---|---|
| 449 |  | 1H NMR (400MHz, METHANOL-d4) Shift = 8.76 - 8.70 (m, 2H), 8.37 (s, 1H), 8.32 - 8.25 (m, 2H), 8.01 (d, J=8.4 Hz, 1H), 4.42 (s, 2H), 3.72 - 3.60 (m, 4H), 3.50 (t, J=6.4 Hz, 2H), 3.41 (s, 3H), 3.38 - 3.30 (m, 4H), 3.26 - 3.19 (m, 2H), 2.90 - 2.83 (m, 3H); LCMS: 508.1 |
| 450 |  | 1H NMR (400MHz, METHANOL-d4) Shift = 8.27 (d, J=1.3 Hz, 1H), 8.12 (d, J=8.8 Hz, 1H), 8.03 (d, J=2.6 Hz, 1H), 7.78 (dd, J=1.8, 8.8 Hz, 1H), 7.68 (dd, J=2.9, 8.6 Hz, 1H), 4.42 (s, 2H), 3.95 (s, 3H), 3.70 - 3.61 (m, 4H), 3.49 (t, J=6.4 Hz, 2H), 3.42 (s, 3H), 3.36 - 3.30 (m, 4H), 3.17 (t, J=6.6 Hz, 2H); LCMS: 542.1 |

| | | |
|---|---|---|
| 451 |  | 1H NMR (400MHz, METHANOL-d4) Shift = 8.80 (d, J=4.9 Hz, 1H), 8.55 (s, 1H), 8.25 - 8.19 (m, 2H), 8.06 (d, J=4.9 Hz, 1H), 7.91 (d, J=8.8 Hz, 1H), 4.43 (s, 2H), 3.70 - 3.62 (m, 4H), 3.49 (t, J=6.4 Hz, 2H), 3.41 (s, 3H), 3.38 - 3.30 (m, 4H), 3.21 (t, J=6.6 Hz, 2H); LCMS: 562.1 |
| 452 |  | 1H NMR (400MHz, METHANOL-d4) Shift = 8.77 (d, J=5.3 Hz, 1H), 8.55 (d, J=1.8 Hz, 1H), 8.23 (d, J=8.4 Hz, 1H), 8.17 (s, 1H), 8.05 - 8.00 (m, 1H), 4.43 (s, 1H), 3.71 - 3.62 (m, 2H), 3.50 (t, J=6.4 Hz, 1H), 3.42 (s, 1H), 3.38 - 3.31 (m, 4H), 3.19 (t, J=6.6 Hz, 1H); LCMS: 562 |
| 453 |  | 1H NMR (400MHz, METHANOL-d4) Shift = 8.36 (s, 1H), 8.15 (d, J=8.4 Hz, 1H), 8.00 (s, 1H), 7.94 (dd, J=1.5, 8.6 Hz, 1H), 7.85 - 7.81 (m, 2H), 7.52 (d, J=8.8 Hz, 1H), 4.42 (s, 2H), 4.11 (s, 3H), 3.70 - 3.61 (m, 4H), 3.50 (t, J=6.6 Hz, 2H), 3.44 - 3.41 (m, 3H), 3.35 - 3.30 (m, 4H), 3.18 (t, J=6.6 Hz, 2H); LCMS: 547.1 |

*FIG. 1 (continued)*

| 454 | | 1H NMR (400MHz, METHANOL-d4) Shift = 8.30 - 8.23 (m, 2H), 8.19 (d, J=8.4 Hz, 1H), 7.78 (d, J=8.8 Hz, 1H), 7.12 (dd, J=2.6, 7.9 Hz, 1H), 4.43 (s, 2H), 3.70 - 3.61 (m, 4H), 3.51 - 3.46 (m, 2H), 3.42 (s, 3H), 3.37 - 3.30 (m, 4H), 3.18 (t, J=6.6 Hz, 2H); LCMS: 530 |
|---|---|---|
| 455 | | 1H NMR (400MHz, METHANOL-d4) Shift = 8.38 (d, J=1.3 Hz, 1H), 8.16 (d, J=8.4 Hz, 1H), 8.03 - 7.99 (m, 2H), 7.79 (dd, J=1.3, 8.4 Hz, 1H), 7.73 - 7.69 (m, 2H), 4.43 (s, 2H), 3.68 - 3.63 (m, 4H), 3.48 (t, J=6.6 Hz, 2H), 3.41 (s, 3H), 3.36 (t, J=6.0 Hz, 2H), 3.31 (br. s., 2H), 3.19 (t, J=6.6 Hz, 2H); LCMS: 561.1 |
| 456 | | 1H NMR (400MHz, METHANOL-d4) Shift = 8.50 (d, J=1.8 Hz, 1H), 8.27 (d, J=5.3 Hz, 1H), 8.21 (d, J=8.4 Hz, 1H), 7.98 (dd, J=1.5, 8.6 Hz, 1H), 7.70 (d, J=5.3 Hz, 1H), 7.46 (s, 1H), 4.43 (s, 2H), 3.66 (td, J=5.5, 10.7 Hz, 4H), 3.50 (t, J=6.6 Hz, 2H), 3.42 (s, 3H), 3.37 - 3.30 (m, 4H), 3.18 (t, J=6.4 Hz, 2H); LCMS: 512.1 |

| | | |
|---|---|---|
| 457 |  | 1H NMR (400MHz, METHANOL-d4) Shift = 8.35 - 8.31 (m, 2H), 8.10 (d, J=8.4 Hz, 1H), 7.94 (s, 1H), 7.81 (t, J=9.3 Hz, 2H), 7.18 (d, J=7.1 Hz, 1H), 6.73 (d, J=7.1 Hz, 1H), 4.43 (s, 2H), 3.70 - 3.63 (m, 4H), 3.50 (t, J=6.4 Hz, 2H), 3.41 (s, 3H), 3.34 - 3.30 (m, 4H), 3.20 (t, J=6.4 Hz, 2H); LCMS: 560.1 |
| 458 |  | 1H NMR (400MHz, METHANOL-d4) Shift = 8.51 (s, 1H), 8.30 (d, J=5.3 Hz, 1H), 8.20 (d, J=8.4 Hz, 1H), 7.87 (dd, J=1.5, 8.6 Hz, 1H), 7.73 (d, J=5.3 Hz, 1H), 7.50 (s, 1H), 4.43 (s, 2H), 3.72 - 3.59 (m, 4H), 3.49 (t, J=6.6 Hz, 2H), 3.41 (s, 3H), 3.37 - 3.31 (m, 4H), 3.23 - 3.17 (m, J=6.4, 6.4 Hz, 2H); LCMS: 512.1 |
| 459 |  | 1H NMR (400MHz, METHANOL-d4) Shift = 8.16 (d, J=1.3 Hz, 1H), 8.08 (d, J=8.4 Hz, 1H), 7.73 (dd, J=1.5, 8.6 Hz, 1H), 6.29 (br. s., 1H), 4.42 (s, 2H), 3.90 (d, J=2.6 Hz, 2H), 3.69 - 3.61 (m, 4H), 3.49 (td, J=6.2, 11.0 Hz, 4H), 3.41 (s, 3H), 3.32 (d, J=5.3 Hz, 4H), 3.18 - 3.14 (m, 2H), 2.90 (d, J=1.8 Hz, 2H); LCMS: 498.1 |

| 460 |  | 1H NMR (400MHz, METHANOL-d4) Shift = 8.12 - 8.06 (m, 1H), 8.04 - 8.00 (m, 1H), 7.71 - 7.65 (m, 1H), 7.63 - 7.58 (m, 2H), 7.44 (d, J=6.6 Hz, 1H), 4.41 (s, 1H), 3.70 - 3.66 (m, 1H), 3.61 (t, J=6.2 Hz, 1H), 3.49 (t, J=6.4 Hz, 1H), 3.42 (s, 2H), 3.32 (d, J=5.7 Hz, 2H), 3.16 (t, J=6.4 Hz, 1H), 2.49 - 2.45 (m, 1H); LCMS: 586.1 |
| --- | --- | --- |
| 461 |  | 1H NMR (400MHz, METHANOL-d4) Shift = 8.42 (s, 1H), 8.14 - 8.09 (m, 1H), 8.05 - 8.01 (m, 1H), 7.56 (d, J=7.8 Hz, 1H), 7.42 (d, J=7.8 Hz, 1H), 7.16 - 7.10 (m, 1H), 7.06 - 7.00 (m, 1H), 6.93 (s, 1H), 4.4 1 (br. s., 2H), 3.69 (d, J=4.3 Hz, 2H), 3.64 (br. s., 2H), 3.51 (t, J=6.5 Hz, 2H), 3.44 (s, 3H), 3.34 (d, J=5.5 Hz, 4H), 3.19 (t, J=6.3 Hz, 2H); LCMS: 532 |
| 462 |  | 1H NMR (400MHz, METHANOL-d4) Shift = 8.49 (s, 1H), 8.29 (s, 1H), 8.17 (d, J=8.2 Hz, 1H), 8.05 (d, J=8.6 Hz, 1H), 7.83 (d, J=8.6 Hz, 1H), 6.93 (d, J=8.6 Hz, 1H), 4.45 (br. s., 2H), 3.97 (s, 3H), 3.71 - 3.65 (m, 4H), 3.51 (t, J=5.9 Hz, 2H), 3.44 (s, 3H), 3.35 (d, J=9.8 Hz, 4H), 3.19 (t, J=6.1 Hz, 2H); LCMS: 524.1 |

*FIG. 1 (continued)*

| 463 | (structure) | 1H NMR (400MHz, METHANOL-d4) Shift = 8.37 (br. s., 1H), 8.25 (br. s., 1H), 8.10 (d, J=7.4 Hz, 1H), 7.89 (d, J=17.6 Hz, 2H), 7.77 (d, J=6.7 Hz, 1H), 7.59 (br. s., 1H), 4.39 (br. s., 2H), 3.78 (br. s., 2H), 3.63 (br. s., 4H), 3.45 (br. s., 2H), 3.37 (br. s., 6H), 3.28 (br. s., 3H), 3.17 (br. s., 2H), 2.96 (br. s., 6H); LCMS: 607.1 |
|---|---|---|
| 464 | (structure) | 1H NMR (400MHz, METHANOL-d4) Shift = 8.11 - 8.04 (m, 2H), 7.52 - 7.45 (m, 3H), 7.45 - 7.37 (m, 2H), 4.39 (br. s., 2H), 3.67 (t, J=4.3 Hz, 2H), 3.54 (br. s., 2H), 3.48 (t, J=6.3 Hz, 2H), 3.41 (s, 3H), 3.30 - 3.26 (m, 2H), 3.14 (t, J=6.5 Hz, 2H), 1.96 (s, 3H); LCMS: 550.1 |
| 465 | (structure) | 1H NMR (400MHz, METHANOL-d4) Shift = 8.28 (s, 1H), 8.19 (s, 1H), 8.02 (d, J=8.2 Hz, 1H), 7.96 (s, 1H), 7.71 (d, J=8.2 Hz, 1H), 4.60 (td, J=6.7, 13.3 Hz, 1H), 4.44 (s, 2H), 3.72 - 3.63 (m, 4H), 3.51 (t, J=6.1 Hz, 2H), 3.44 (s, 3H), 3.34 (d, J=5.1 Hz, 4H), 3.21 (t, J=6.3 Hz, 2H), 1.57 (d, J=6.7 Hz, 6H); LCMS: 525.1 |

FIG. 1 (continued)

| | | |
|---|---|---|
| 466 | | 1H NMR (400MHz, METHANOL-d4) Shift = 8.25 (s, 1H), 8.05 (d, J=8.2 Hz, 1H), 7.70 (d, J=8.6 Hz, 1H), 7.37 (d, J=7.4 Hz, 1H), 7.26 - 7.17 (m, 1H), 6.95 (d, J=7.0 Hz, 2H), 4.44 (s, 2H), 3.66 (d, J=3.9 Hz, 4H), 3.48 (t, J=6.5 Hz, 2H), 3.41 (s, 3H), 3.35 (br. s., 4H), 3.16 (t, J=6.5 Hz, 2H); LCMS: 509.1 |
| 467 | | 1H NMR (400MHz, DMSO-d6) Shift = 11.73 (s, 1H), 8.58 (s, 1H), 8.23 (d, J=8.4 Hz, 1H), 7.99 (d, J=8.4 Hz, 1H), 7.54 (d, J=7.9 Hz, 1H), 7.42 (d, J=8.4 Hz, 1H), 7.10 (t, J=7.3 Hz, 1H), 7.04 - 6.97 (m, 2H), 4.32 (br. s., 2H), 3.58 (t, J=4.9 Hz, 2H), 3.47 (d, J=5.7 Hz, 4H), 3.29 (br. s., 5H), 3.22 - 3.02 (m, 7H); LCMS: 532.1 |
| 468 | | 1H NMR (400MHz, METHANOL-d4) Shift = 8.50 (s, 1H), 8.05 (d, J=8.4 Hz, 1H), 7.93 (d, J=8.4 Hz, 1H), 7.15 (d, J=7.9 Hz, 1H), 6.96 (t, J=7.7 Hz, 1H), 6.89 (s, 1H), 6.68 (d, J=7.5 Hz, 1H), 4.39 (s, 2H), 4.00 (s, 3H), 3.71 - 3.65 (m, 2H), 3.60 (t, J=6.0 Hz, 2H), 3.51 (t, J=6.4 Hz, 2H), 3.42 (s, 3H), 3.35 - 3.30 (m, 4H), 3.20 (t, J=6.4 Hz, 2H); LCMS: 562 |

FIG. 1 (continued)

| | | |
|---|---|---|
| 469 | (structure) | 1H NMR (400MHz, METHANOL-d4) Shift = 9.24 - 9.16 (m, 1H), 8.96 (s, 1H), 8.35 (s, 1H), 8.15 (d, J=8.6 Hz, 1H), 7.87 (d, J=8.6 Hz, 1H), 4.45 (s, 2H), 3.70 - 3.65 (m, 4H), 3.50 (t, J=6.5 Hz, 2H), 3.44 (s, 3H), 3.38 - 3.34 (m, 4H), 3.18 (t, J=6.3 Hz, 2H); LCMS: 484 |
| 470 | (structure) | 1H NMR (400MHz, METHANOL-d4) Shift = 8.43 (s, 1H), 8.32 (s, 1H), 8.25 (d, J=8.6 Hz, 1H), 8.02 (s, 1H), 7.95 (br. s., 1H), 7.91 (d, J=8.2 Hz, 1H), 4.45 (s, 2H), 3.74 - 3.63 (m, 4H), 3.51 (t, J=6.3 Hz, 2H), 3.44 (s, 3H), 3.40 - 3.32 (m, 4H), 3.21 (t, J=6.3 Hz, 2H); LCMS: 509.1 |
| 471 | (structure) | 1H NMR (400MHz, METHANOL-d4) Shift = 8.58 (s, 1H), 8.44 (d, J=5.5 Hz, 1H), 8.31 (d, J=8.6 Hz, 1H), 8.08 (d, J=8.2 Hz, 1H), 7.72 (br. s., 1H), 7.64 (d, J=5.5 Hz, 1H), 6.99 (br. s., 1H), 4.46 (br. s., 2H), 3.73 - 3.63 (m, 4H), 3.53 (t, J=6.1 Hz, 2H), 3.44 (s, 3H), 3.41 - 3.33 (m, 4H), 3.26 - 3.17 (m, 2H); LCMS: 533.1 |

*FIG. 1 (continued)*

| | | |
|---|---|---|
| 472 | [structure] | 1H NMR (400MHz, METHANOL-d4) Shift = 8.54 (br. s., 1H), 8.41 (br. s., 1H), 8.28 (d, J=8.2 Hz, 1H), 7.94 (d, J=8.2 Hz, 1H), 7.66 (br. s., 1H), 7.57 (d, J=5.1 Hz, 1H), 6.93 (br. s., 1H), 4.46 (br. s., 2H), 3.68 (br. s., 4H), 3.49 (br. s., 2H), 3.45 - 3.35 (m, 5H), 3.34 - 3.31 (m, 2H), 3.20 (br. s., 2H); LCMS: 533.1 |
| 473 | [structure] | 1H NMR (400MHz, METHANOL-d4) Shift = 8.55 (br. s., 1H), 8.39 - 8.24 (m, 2H), 8.19 (d, J=8.2 Hz, 1H), 7.86 (d, J=8.2 Hz, 1H), 7.20 (d, J=8.2 Hz, 1H), 4.44 (s, 2H), 3.67 (dd, J=5.3, 14.3 Hz, 4H), 3.51 (t, J=6.3 Hz, 2H), 3.44 (s, 3H), 3.34 (d, J=4.7 Hz, 4H), 3.26 - 3.15 (m, 2H); LCMS: 512.1 |
| 474 | [structure] | 1H NMR (400MHz, METHANOL-d4) Shift = 8.27 (s, 1H), 8.15 - 8.02 (m, 2H), 7.69 (d, J=6.7 Hz, 2H), 4.44 (s, 2H), 3.97 (s, 3H), 3.73 - 3.60 (m, 4H), 3.49 (t, J=6.5 Hz, 2H), 3.42 (s, 3H), 3.35 (br. s., 4H), 3.17 (t, J=6.3 Hz, 2H); LCMS: 542.1 |

FIG. 1 (continued)

| | | |
|---|---|---|
| 475 | | 1H NMR (400MHz, METHANOL-d4) Shift = 8.16 (d, J=8.6 Hz, 1H), 8.11 (s, 1H), 7.65 (d, J=8.6 Hz, 1H), 7.55 (d, J=7.4 Hz, 1H), 7.50 - 7.35 (m, 3H), 4.45 (s, 2H), 3.72 - 3.61 (m, 4H), 3.51 (t, J=6.3 Hz, 2H), 3.46 - 3.40 (m, 3H), 3.39 - 3.32 (m, 4H), 3.19 (t, J=6.5 Hz, 2H); LCMS: 527 |
| 476 | | 1H NMR (400MHz, METHANOL-d4) Shift = 8.37 (br. s., 1H), 8.22 - 7.86 (m, 2H), 7.83 - 7.63 (m, 1H), 7.12 (br. s., 1H), 6.99 - 6.81 (m, 1H), 6.66 (br. s., 1H), 4.46 - 4.25 (m, 2H), 3.98 (br. s., 3H), 3.83 - 3.35 (m, 9H), 3.35 - 3.30 (m, 3H), 3.16 (br. s., 3H); LCMS: 562.1 |
| 477 | | 1H NMR (400MHz, METHANOL-d4) Shift = 8.21 (s, 1H), 8.08 (d, J=8.6 Hz, 1H), 7.81 (d, J=8.6 Hz, 1H), 7.30 - 7.21 (m, 2H), 7.04 (d, J=8.2 Hz, 1H), 4.43 (s, 2H), 3.94 (s, 3H), 3.87 (s, 3H), 3.69 (t, J=4.3 Hz, 2H), 3.63 (t, J=5.7 Hz, 2H), 3.51 (t, J=6.3 Hz, 2H), 3.44 (s, 3H), 3.33 (br. s., 4H), 3.18 (t, J=6.5 Hz, 2H); LCMS: 553.1 |

*FIG. 1 (continued)*

| | | |
|---|---|---|
| 478 | (structure) | 1H NMR (400MHz, METHANOL-d4) Shift = 8.17 - 8.07 (m, 2H), 7.59 - 7.51 (m, 2H), 7.50 - 7.36 (m, 3H), 4.45 (s, 2H), 3.71 - 3.62 (m, 4H), 3.47 (t, J=6.3 Hz, 2H), 3.43 - 3.34 (m, 5H), 3.28 (br. s., 2H), 3.15 (t, J=6.5 Hz, 2H); LCMS: 527 |
| 479 | (structure) | 1H NMR (400MHz, METHANOL-d4) Shift = 8.18 (s, 1H), 8.05 - 7.96 (m, 1H), 7.61 (d, J=7.9 Hz, 1H), 7.31 (d, J=8.4 Hz, 1H), 7.21 (s, 1H), 7.02 (d, J=8.4 Hz, 1H), 4.59 (s, 2H), 4.43 - 4.34 (m, 2H), 3.71 - 3.65 (m, 2H), 3.62 (t, J=5.7 Hz, 2H), 3.49 (t, J=6.4 Hz, 2H), 3.44 - 3.37 (m, 3H), 3.32 (br. s., 4H), 3.19 (t, J=6.4 Hz, 2H); LCMS: 564.1 |
| 480 | (structure) | 1H NMR (400MHz, METHANOL-d4) Shift = 8.13 (d, J=8.4 Hz, 1H), 8.04 (s, 1H), 7.58 (dd, J=1.3, 8.4 Hz, 1H), 7.49 - 7.34 (m, 4H), 4.43 (s, 2H), 3.69 - 3.62 (m, 4H), 3.49 (t, J=6.6 Hz, 2H), 3.42 (s, 3H), 3.38 - 3.30 (m, 4H), 3.17 (t, J=6.6 Hz, 2H), 1.96 - 1.87 (m, 3H); LCMS: 550.1 |

| | | |
|---|---|---|
| 481 |  | 1H NMR (400MHz, METHANOL-d4) Shift = 9.27 - 9.15 (m, 1H), 8.98 (s, 1H), 8.37 (s, 1H), 8.11 (d, J=8.6 Hz, 1H), 7.76 (d, J=8.2 Hz, 1H), 4.44 (s, 2H), 3.71 - 3.64 (m, 4H), 3.51 (t, J=6.1 Hz, 2H), 3.43 (s, 3H), 3.34 (d, J=5.5 Hz, 4H), 3.21 (t, J=6.3 Hz, 2H); LCMS: 484 |
| 482 |  | 1H NMR (400MHz, METHANOL-d4) Shift = 8.44 (s, 1H), 8.04 (d, J=8.2 Hz, 1H), 7.84 (d, J=8.2 Hz, 1H), 6.58 (br. s., 1H), 4.42 (br. s., 2H), 3.69 (br. s., 2H), 3.63 (br. s., 2H), 3.51 (br. s., 2H), 3.43 (s, 3H), 3.36 - 3.32 (m, 4H), 3.20 (br. s., 2H), 2.46 - 2.29 (m, 3H); LCMS: 497.1 |
| 483 |  | 1H NMR (400MHz, METHANOL-d4) Shift = 8.39 - 8.32 (m, 1H), 8.23 - 8.17 (m, 2H), 7.93 (d, J=8.2 Hz, 1H), 7.60 - 7.54 (m, 1H), 7.53 - 7.46 (m, 1H), 7.34 (d, J=7.0 Hz, 1H), 4.44 (s, 2H), 3.70 (t, J=4.3 Hz, 2H), 3.64 (t, J=5.5 Hz, 2H), 3.52 (t, J=6.3 Hz, 2H), 3.44 (s, 3H), 3.34 (d, J=4.3 Hz, 4H), 3.19 (t, J=6.5 Hz, 2H); LCMS: 533.1 |

*FIG. 1 (continued)*

| 484 | (structure) | 1H NMR (400MHz, METHANOL-d4) Shift = 9.21 (br. s., 3H), 8.48 (s, 1H), 8.23 (d, J=8.2 Hz, 1H), 7.85 (d, J=8.6 Hz, 1H), 4.45 (s, 2H), 3.72 - 3.64 (m, 4H), 3.51 (t, J=6.1 Hz, 2H), 3.43 (s, 3H), 3.36 (d, J=12.5 Hz, 4H), 3.26 - 3.17 (m, 2H); LCMS: 495 |
|---|---|---|
| 485 | (structure) | 1H NMR (400MHz, METHANOL-d4) Shift = 8.21 (d, J=1.3 Hz, 1H), 8.09 - 8.03 (m, 2H), 7.85 - 7.79 (m, 1H), 7.63 (dd, J=1.3, 8.4 Hz, 1H), 6.67 (d, J=9.3 Hz, 1H), 4.42 (s, 2H), 3.68 - 3.62 (m, 4H), 3.49 (t, J=6.4 Hz, 2H), 3.41 (s, 3H), 3.34 - 3.30 (m, 4H), 3.23 - 3.14 (m, 2H); LCMS: 510.2 |
| 486 | (structure) | 1H NMR (400MHz, METHANOL-d4) Shift = 8.67 (s, 2H), 8.27 (s, 1H), 8.16 (d, J=8.4 Hz, 1H), 7.79 (d, J=8.4 Hz, 1H), 4.43 (br. s., 2H), 3.70 - 3.63 (m, 4H), 3.51 - 3.47 (m, 2H), 3.42 (s, 3H), 3.35 (br. s. , 4H), 3.17 (t, J=6.4 Hz, 2H); LCMS: 510.1 |

| | | |
|---|---|---|
| 487 |  | 1H NMR (400MHz, METHANOL-d4) Shift = 9.18 (s, 1H), 8.86 (s, 1H), 8.54 (br. s., 1H), 8.40 (s, 1H), 8.20 (d, J=8.6 Hz, 1H), 7.93 (d, J=8.2 Hz, 1H), 4.46 (s, 2H), 3.73 - 3.64 (m, 4H), 3.53 (t, J=6.3 Hz, 2H), 3.44 (s, 3H), 3.40 - 3.33 (m, 4H), 3.21 (t, J=6.3 Hz, 2H); LCMS: 519 |
| 488 |  | 1H NMR (400MHz, METHANOL-d4) Shift = 8.32 - 8.21 (m, 2H), 8.14 (d, J=8.6 Hz, 1H), 7.94 - 7.73 (m, 3H), 7.33 (br. s., 1H), 5.87 (br. s., 1H), 4.43 (br. s., 2H), 3.72 - 3.62 (m, 4H), 3.55 - 3.49 (m, 2H), 3.44 (br. s., 3H), 3.34 (br. s., 3H), 3.19 (br. s., 3H), 3.06 (s, 2H); LCMS: 574.1 |
| 489 |  | 1H NMR (400MHz, METHANOL-d4) Shift = 8.48 (s, 1H), 8.38 (d, J=4.7 Hz, 1H), 8.32 (br. s., 1H), 8.22 (d, J=8.6 Hz, 1H), 7.97 (d, J=8.2 Hz, 1H), 7.59 (br. s., 1H), 4.45 (br. s., 2H), 3.73 - 3.64 (m, 4H), 3.52 (br. s., 2H), 3.44 (s, 3H), 3.35 (br. s., 4H), 3.21 (br. s., 2H), 2.26 (s, 3H); LCMS: 551.1 |

| 490 |  | 1H NMR (400MHz, METHANOL-d4) Shift = 9.10 (s, 1H), 8.84 (br. s., 1H), 8.71 (s, 1H), 8.51 (br. s., 1H), 8.20 (d, J=7.9 Hz, 1H), 7.84 (d, J=8.4 Hz, 1H), 4.38 (br. s., 2H), 3.72 - 3.64 (m, 2H), 3.59 (br. s., 2H), 3.50 (t, J=6.4 Hz, 2H), 3.40 (s, 3H), 3.34 - 3.30 (m, 2H), 3.23 (t, J=6.4 Hz, 2H), 2.66 (s, 3H); LCMS: 508 |
|---|---|---|
| 491 |  | 1H NMR (400MHz, METHANOL-d4) Shift = 8.20 - 8.12 (m, 2H), 7.69 (d, J=8.2 Hz, 1H), 7.56 - 7.50 (m, 1H), 7.48 - 7.42 (m, 2H), 7.42 - 7.37 (m, 1H), 4.44 (s, 2H), 3.72 - 3.63 (m, 4H), 3.51 (t, J=6.1 Hz, 2H), 3.43 (s, 3H), 3.35 (d, J=5.9 Hz, 4H), 3.22 - 3.12 (m, 2H), 2.83 (s, 3H); LCMS: 586.1 |
| 492 |  | 1H NMR (400MHz, METHANOL-d4) Shift = 8.51 (s, 1H), 8.33 (s, 1H), 8.17 - 8.03 (m, 2H), 7.73 (d, J=8.2 Hz, 1H), 6.95 (d, J=8.6 Hz, 1H), 4.45 (s, 2H), 3.98 (s, 3H), 3.71 - 3.64 (m, 4H), 3.50 (t, J=6.3 Hz, 2H), 3.43 (s, 3H), 3.37 (br. s., 4H), 3.21 (t, J=6.5 Hz, 2H); LCMS: 524 |

| 493 |  | 1H NMR (METHANOL-d4, 400MHz): Shift = 8.31 (s, 1H), 8.23 (br. s., 1H), 8.12 (d, J=8.2 Hz, 1H), 7.84-7.95 (m, 3H), 7.59 (t, J=7.6 Hz, 1H), 4.41 (br. s., 2H), 3.68-3.87 (m, 4H), 3.40-3.67 (m, 9H), 3.30-3.38 (m, 5H), 3.19 (t, J=6.3 Hz, 2H), 3.01 (s, 4H), 2.78 ppm (s, 1H); LCMS: 607.3 |
| --- | --- | --- |
| 494 |  | 1H NMR (400MHz, METHANOL-d4) Shift = 8.80 (s, 1H), 8.74 (d, J=5.5 Hz, 1H), 8.29 (d, J=8.2 Hz, 1H), 8.22 (s, 1H), 8.05 (d, J=5.9 Hz, 1H), 7.69 (d, J=8.6 Hz, 1H), 4.45 (s, 2H), 3.72 - 3.63 (m, 4H), 3.52 (t, J=6.1 Hz, 2H), 3.43 (s, 3H), 3.40 - 3.32 (m, 4H), 3.21 (t, J=6.3 Hz, 2H), 2.64 (s, 3H); LCMS: 508.1 |
| 495 |  | N/A; LCMS: 525.1 |

FIG. 1 (continued)

| | | |
|---|---|---|
| 496 | (structure) | 1H NMR (400MHz, METHANOL-d4) Shift = 9.13 (s, 1H), 8.50 (s, 1H), 8.43 (d, J=7.8 Hz, 1H), 8.24 (d, J=8.2 Hz, 1H), 7.97 (d, J=8.2 Hz, 1H), 7.87 (d, J=8.6 Hz, 1H), 4.44 (s, 2H), 3.70 - 3.65 (m, 4H), 3.50 (t, J=6.3 Hz, 2H), 3.43 (s, 3H), 3.37 (br. s., 4H), 3.26 - 3.18 (m, 2H); LCMS: 562.1 |
| 497 | (structure) | 1H NMR (400MHz, METHANOL-d4) Shift = 8.21 (s, 1H), 8.05 (d, J=8.6 Hz, 1H), 7.64 (d, J=8.2 Hz, 1H), 6.34 (br. s., 1H), 4.43 (s, 2H), 3.92 (br. s., 2H), 3.69 (d, J=4.3 Hz, 2H), 3.64 (t, J=5.7 Hz, 2H), 3.57 - 3.47 (m, 4H), 3.43 (s, 3H), 3.33 (br. s., 4H), 3.21 (t, J=6.3 Hz, 2H), 2.95 (br. s., 2H); LCMS: 498 |
| 498 | (structure) | 1H NMR (400MHz, METHANOL-d4) Shift = 8.27 - 8.04 (m, 2H), 7.79 (d, J=8.6 Hz, 1H), 7.31 (s, 2H), 7.23 - 6.99 (m, 1H), 4.45 (br. s., 2H), 3.85 - 3.59 (m, 5H), 3.52 (br. s., 3H), 3.44 (s, 3H), 3.34 (br. s., 4H), 3.27 - 3.11 (m, 2H); LCMS: 548.1 |

| | | |
|---|---|---|
| 499 |  | N/A; LCMS: 519.1 |
| 500 |  | 1H NMR (400MHz, METHANOL-d4) Shift = 8.68 (d, J=14.9 Hz, 2H), 8.24 (br. s., 2H), 7.87 (br. s., 1H), 7.55 (d, J=8.2 Hz, 1H), 4.45 (s, 2H), 3.67 (br. s., 4H), 3.48 (t, J=6.1 Hz, 2H), 3.43 - 3.32 (m, 7H), 3.23 - 3.15 (m, 2H), 2.56 (s, 3H); LCMS: 508 |
| 501 |  | 1H NMR (400MHz, METHANOL-d4) Shift = 8.37 (s, 1H), 8.20 (d, J=8.2 Hz, 1H), 7.94 - 7.84 (m, 3H), 7.67 - 7.60 (m, 1H), 7.52 (d, J=7.4 Hz, 1H), 4.44 (br. s., 2H), 3.84 (br. s., 2H), 3.74 - 3.59 (m, 5H), 3.51 (t, J=6.1 Hz, 3H), 3.44 (s, 4H), 3.40 - 3.32 (m, 7H), 3.25 - 3.16 (m, 2H), 3.01 - 2.88 (m, 3H); LCMS: 619.2 |

*FIG. 1 (continued)*

| 502 | | 1H NMR (400MHz, METHANOL-d4) Shift = 9.04 (s, 1H), 8.63 (d, J=8.2 Hz, 1H), 8.54 (s, 1H), 8.24 (d, J=8.2 Hz, 1H), 7.85 (t, J=8.4 Hz, 2H), 4.45 (s, 2H), 3.72 - 3.64 (m, 4H), 3.51 (t, J=6.3 Hz, 2H), 3.43 (s, 3H), 3.37 (br. s., 4H), 3.26 - 3.20 (m, 2H), 2.78 (s, 3H); LCMS: 508.1 |
|---|---|---|
| 503 | | 1H NMR (400MHz, METHANOL-d4) Shift = 8.26 - 8.16 (m, 2H), 7.64 - 7.54 (m, 2H), 6.49 (s, 1H), 4.45 (br. s., 2H), 3.95 (s, 3H), 3.67 (br. s., 4H), 3.49 (t, J=6.1 Hz, 2H), 3.42 (s, 3H), 3.40 - 3.32 (m, 4H), 3.18 (t, J=6.1 Hz, 2H); LCMS: 497.1 |
| 504 | | 1H NMR (400MHz, METHANOL-d4) Shift = 8.56 (s, 1H), 8.28 (s, 1H), 8.16 (d, J=8.6 Hz, 1H), 8.04 (d, J=9.0 Hz, 1H), 7.83 (d, J=8.6 Hz, 1H), 7.07 (d, J=8.6 Hz, 1H), 4.44 (s, 2H), 3.89 (d, J=4.7 Hz, 4H), 3.71 - 3.64 (m, 4H), 3.51 (t, J=6.3 Hz, 2H), 3.44 (s, 3H), 3.40 - 3.33 (m, 8H), 3.19 (t, J=6.3 Hz, 2H); LCMS: 578.2 |

| | | |
|---|---|---|
| 505 |  | 1H NMR (DMSO-d6, 400MHz): δ 12.43 (s, 1H), 10.41 (s, 1H), 9.25 (br. s, 2H), 8.62 (d, J=1.47 Hz, 1H), 8.40 (br. s, 2H), 8.28 (d, J=8.31 Hz, 1H), 8.03 (dd, J=1.47, 8.31 Hz, 1H), 7.75 (d, J=7.83 Hz, 2H), 7.32 (t, J=7.83 Hz, 2H), 7.06 (t, J=7.34 Hz, 1H), 4.28-4.34 (m, 2H), 3.42-3.51 (m, 3H), 3.21-3.27 (m, 2H), 3.12 (br. s, 2H), 3.01 (t, J=7.09 Hz, 2H), 1.18 (d, J=6.85 Hz, 6H).; LCMS: 520.3 |
| 506 |  | 1H NMR (DMSO-d6; 400MHz): δ 8.16 (d, J=7.83 Hz, 1H), 8.10 (d, J=8.31 Hz, 1H), 7.53-7.62 (m, 1H), 7.40-7.49 (m, 1H), 4.04 (d, J=6.36 Hz, 1H), 3.25-3.33 (m, 4H), 3.15 (s, 3H), 2.90-3.06 (m, 4H), 2.72 (t, J=5.62 Hz, 4H), 2.38-2.47 (m, 2H), 1.34 (d, J=6.36 Hz, 3H), 1.24 (d, J=5.87 Hz, 3H).; LCMS: 445.3 |
| 507 |  | 1H NMR (DMSO-d6; 400MHz): δ 8.14 (d, J=8.31 Hz, 1H), 8.09 (d, J=8.31 Hz, 1H), 7.57 (t, J=7.58 Hz, 1H), 7.41-7.48 (m, 1H), 6.58 (br. s, 2H), 4.19 (q, J=6.52 Hz, 1H), 3.22-3.29 (m, 2H), 3.16 (s, 3H), 2.96-3.05 (m, 4H), 2.72-2.80 (m, 4H), 2.44 (dd, J=8.56, 15.41 Hz, 2H), 1.39 (d, J=6.36 Hz, 3H), 1.22 (d, J=6.36 Hz, 3H).; LCMS: 445.3 |
| 508 |  | 1H NMR (DMSO-d6; 400MHz): δ 8.16 (d, J=7.83 Hz, 1H), 8.10 (d, J=8.31 Hz, 1H), 7.55-7.61 (m, 1H), 7.42-7.49 (m, 1H), 4.16-4.20 (m, 1H), 3.37-3.42 (m, 3H), 3.20 (s, 3H), 3.06-3.17 (m, 4H), 3.02-3.06 (m, 1H), 2.88 (t, J=5.38 Hz, 2H), 2.81-2.86 (m, 2H), 2.64-2.74 (m, 1H), 2.52-2.59 (m, 1H), 1.40 (d, J=6.85 Hz, 3H), 1.30 (d, J=6.36 Hz, 3H).; LCMS: 445.3 |

| | | |
|---|---|---|
| 509 |  | 1H NMR (DMSO-d6; 400MHz): δ 9.07 (br.s, 2H), 8.16 (d, J=7.83 Hz, 1H), 8.10 (d, J=8.31 Hz, 1H), 7.58 (t, J=7.83 Hz, 1H), 7.43-7.49 (m, 1H), 4.38 (d, J=5.87 Hz, 1H), 3.43 (t, J=5.14 Hz, 2H), 3.21 (s, 3H), 3.13 (t, J=6.85 Hz, 3H), 2.93 (t, J=5.14 Hz, 2H), 2.86 (t, J=6.60 Hz, 2H), 2.71-2.77 (m, 1H), 2.54-2.69 (m, 2H), 1.46 (d, J=6.85 Hz, 3H), 1.30 (d, J=6.36 Hz, 3H).; LCMS: 445.3 |
| 510 |  | 1H NMR (DMSO-d6, 400MHz): δ 12.74 (s, 1H), 11.24 (br. s, 1H), 9.74 (br. s, 2H), 9.39 (br. s, 1H), 9.12 (s, 1H), 9.07 (br. s, 2H), 8.74 (d, J=8.80 Hz, 1H), 8.59 (d, J=4.40 Hz, 1H), 8.44 (d, J=8.31 Hz, 1H), 8.23 (d, J=7.83 Hz, 1H), 7.80-7.88 (m, 1H), 4.41 (br. s, 2H), 3.41-3.61 (m, 5H), 3.21-3.29 (m, 4H), 1.35 (d, J=6.36 Hz, 6H).; LCMS: 521.1 |
| 511 |  | DMSO-d6, δ 8.21 (s, 1H), 8.15 (d, J = 8.5 Hz, 1H), 7.96 (s, 1H), 7.63 (d, J = 8.6 Hz, 1H), 6.40 – 6.36 (m, 1H), 4.28 – 4.23 (m, 2H), 3.95 (d, J = 2.7 Hz, 2H), 3.49 (t, J = 5.6 Hz, 2H), 3.45 – 3.39 (m, 2H), 3.29 – 3.24 (m, 4H), 3.17 – 3.09 (m, 4H), 2.90 (s, 2H), 2.81 (s, 6H), 2.74 – 2.73 (m, 2H), 2.73 – 2.68 (m, 2H), 1.27 (d, J = 6.4 Hz, 6H).; LCMS: 589.4 |
| 512 |  | DMSO-d6, δ 12.60 (s, 1H), 9.52 (s, 2H), 8.87 (s, 2H), 8.11 (d, J = 8.4 Hz, 1H), 8.07 (d, J = 1.7 Hz, 1H), 7.42 (dd, J = 8.5, 1.9 Hz, 1H), 4.34 (s, 2H), 3.49 (s, 2H), 3.36 (sept, J = 6.5 Hz, 1H), 3.28 (t, J = 7.0 Hz, 1H).3.19 – 3.12 (m, 4H), 2.62 (s, 3H), 1.27 (d, J = 6.5 Hz, 6H).; LCMS: 447.2 |

FIG. 1 (continued)

| | | |
|---|---|---|
| 513 | 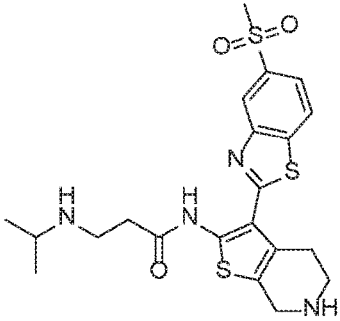 | DMSO-d6, δ 12.47 (s, 1H), 9.69 (s, 2H), 8.94 (s, 2H), 8.71 (d, J = 1.5 Hz, 1H), 8.50 (d, J = 8.4 Hz, 1H), 8.01 (dd, J = 8.4, 1.8 Hz, 1H), 4.34 (s, 2H), 3.49 (s, 2H), 3.38 – 3.26 (m, 6H), 3.21 – 3.15 (m, 4H), 1.28 (d, J = 6.5 Hz, 6H).; LCMS: 479.1 |
| 514 | 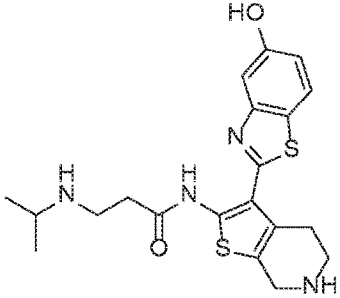 | DMSO-d6, δ 12.61 (s, 1H), 9.93 (s, 1H), 9.54 (s, 2H), 8.85 (s, 2H), 7.94 (d, J = 8.7 Hz, 1H), 7.47 (d, J = 2.3 Hz, 1H), 7.02 (dd, J = 8.7, 2.3 Hz, 1H), 4.33 (s, 2H), 3.48 (s, 2H), 3.41 – 3.33 (m, 1H), 3.30 – 3.23 (m, 2H), 3.15 (t, J = 5.8 Hz, 2H), 3.11 (t, J = 7.0 Hz, 2H), 1.27 (d, J = 6.5 Hz, 6H).; LCMS: 417.1 |
| 515 | 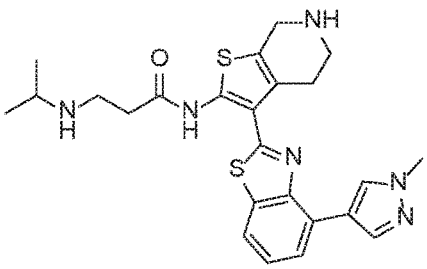 | DMSO-d6, δ 11.99 (s, 1H), 9.64 (s, 2H), 8.82 (s, 2H), 8.45 (s, 1H), 8.24 (d, J = 0.6 Hz, 1H), 8.03 (dd, J = 8.0, 1.1 Hz, 1H), 7.76 (dd, J = 7.5, 1.1 Hz, 1H), 7.50 (t, J = 7.8 Hz, 1H), 4.35 (br. s, 2H), 3.98 (s, 3H), 3.51 – 3.45 (m, 2H), 3.27 – 3.21 (m, 2H), 3.18 (t, J = 5.9 Hz, 2H), 2.96 (t, J = 7.0 Hz, 2H), 1.26 (d, J = 6.5 Hz, 6H). 1H hidden under water signal); LCMS: 481.1 |
| 516 | 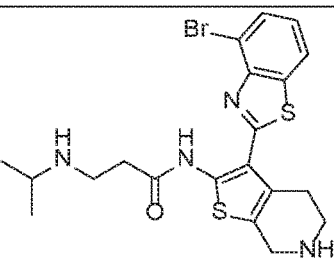 | DMSO-d6+D2O, δ 8.13 (d, J = 7.9 Hz, 1H), 7.83 (d, J = 7.8 Hz, 1H), 7.41 (t, J = 7.9 Hz, 1H), 4.31 (s, 2H), 3.49 (t, J = 6.0 Hz, 2H), 3.32 (hept, J = 6.6 Hz, 1H), 3.28 (t, J = 6.6 Hz, 2H), 3.18 (t, J = 6.1 Hz, 2H), 3.07 (t, J = 6.8 Hz, 2H), 1.23 (d, J = 6.5 Hz, 6H). 5NH missing due to presence of D2O; LCMS: 478.9/ 480.9 |

| | | |
|---|---|---|
| 517 |  | 1H NMR (DMSO-d6, 400MHz): δ 8.69 (d, J=5.87 Hz, 2H), 8.66 (d, J=1.47 Hz, 1H), 8.22 (d, J=8.80 Hz, 1H), 8.04 (dd, J=1.71, 8.56 Hz, 1H), 7.80-7.84 (m, 2H), 4.61-4.70 (m, 1H), 3.68-3.79 (m, 2H), 3.57 (t, J=5.14 Hz, 2H), 3.30 (s, 3H), 3.24-3.28 (m, 2H), 3.13 (t, J=5.14 Hz, 2H), 3.03 (t, J=6.85 Hz, 2H), 2.76-2.86 (m, 2H), 1.58 (d, J=6.36 Hz, 3H), 1.41 (d, J=6.36 Hz, 3H). ; LCMS: 521.85 |
| 518 |  | 1H NMR (DMSO-d6, 400MHz): δ 8.68 (d, J=4.89 Hz, 2H), 8.64 (br. s, 1H), 8.15-8.22 (m, 1H), 7.99-8.05 (m, 1H), 7.82 (d, J=4.89 Hz, 2H), 4.48-4.61 (m, 1H), 3.58-3.69 (m, 2H), 3.47-3.56 (m, 2H), 3.26 (br. s, 3H), 3.18-3.22 (m, 2H), 3.03-3.11 (m, 2H), 2.97 (d, J=5.87 Hz, 2H), 2.65-2.80 (m, 2H), 1.53 (d, J=5.38 Hz, 3H), 1.37 (d, J=5.87 Hz, 3H). ; LCMS: 521.85 |
| 519 |  | 1H NMR (DMSO-d6, 400MHz): δ 9.00 (d, J=1.96 Hz, 1H), 8.61 (dd, J=1.47, 4.89 Hz, 1H), 8.54 (d, J=1.47 Hz, 1H), 8.16-8.21 (m, 2H), 7.94 (dd, J=1.96, 8.31 Hz, 1H), 7.54 (dd, J=5.14, 7.58 Hz, 1H), 4.20 (q, J=6.36 Hz, 1H), 3.22-3.32 (m, 5H), 3.17 (s, 3H), 2.98-3.07 (m, 3H), 2.72-2.81 (m, 4H), 2.46 (d, J=8.80 Hz, 1H), 1.39 (d, J=6.85 Hz, 3H), 1.24 (d, J=6.36 Hz, 3H). ; LCMS: 522.3 |

FIG. 1 (continued)

| 520 | | 1H NMR (DMSO-d6, 400MHz): δ 9.01 (d, J=1.96 Hz, 1H), 8.61 (dd, J=1.71, 4.65 Hz, 1H), 8.54 (d, J=1.96 Hz, 1H), 8.15-8.21 (m, 2H), 7.91-7.97 (m, 1H), 7.54 (dd, J=4.65, 8.07 Hz, 1H), 4.21-4.31 (m, 1H), 3.26-3.36 (m, 5H), 3.19 (s, 3H), 3.03-3.08 (m, 3H), 2.77-2.86 (m, 4H), 1.42 (d, J=6.85 Hz, 3H), 1.26 (d, J=6.36 Hz, 3H).; LCMS: 522.25 |
|---|---|---|
| 521 | | 1H NMR (DMSO-d6, 400MHz): δ 8.70 (d, J=3.91 Hz, 2H), 8.53 (s, 1H), 8.30 (d, J=8.31 Hz, 1H), 7.90 (br. s, 1H), 7.87 (d, J=4.40 Hz, 3H), 6.52 (br. s, 1H), 4.03-4.13 (m, 2H), 3.11 (s, 3H), 2.97-3.08 (m, 4H), 2.74-2.82 (m, 4H), 2.43-2.47 (m, 2H), 1.36 (d, J=5.87 Hz, 3H), 1.27 (d, J=4.89 Hz, 3H).; LCMS: 521.75 |
| 522 | | 1H NMR (DMSO-d6, 400MHz): δ 8.70 (d, J=5.87 Hz, 2H), 8.52 (s, 1H), 8.29 (d, J=8.80 Hz, 1H), 7.90 (s, 1H), 7.86 (d, J=5.38 Hz, 2H), 4.13 (q, J=6.68 Hz, 1H), 3.28 (t, J=5.62 Hz, 3H), 3.21 (dd, J=6.11, 11.49 Hz, 2H), 3.09 (s, 3H), 3.00 (d, J=3.42 Hz, 1H), 2.96 (t, J=6.36 Hz, 2H), 2.69-2.76 (m, 4H), 2.37-2.46 (m, 2H), 1.37 (d, J=6.85 Hz, 3H), 1.21 (d, J=6.36 Hz, 3H).; LCMS: 521.8 |

| | | |
|---|---|---|
| 523 |  | 1H NMR (DMSO-d6, 400MHz): δ 8.61-8.65 (m, 2H), 8.45 (s, 1H), 8.23 (d, J=8.31 Hz, 1H), 7.82-7.84 (m, 1H), 7.80 (d, J=4.89 Hz, 2H), 7.52-7.65 (m, 1H), 6.45 (br. s, 1H), 6.18-6.25 (m, 1H), 4.01-4.10 (m, 1H), 3.07 (s, 3H), 2.94-3.02 (m, 4H), 2.85 (d, J=7.34 Hz, 1H), 2.75 (d, J=4.40 Hz, 3H), 2.69-2.80 (m, 1H), 2.36-2.40 (m, 1H), 1.31 (d, J=5.87 Hz, 3H), 1.22 (d, J=5.38 Hz, 3H).; LCMS: 521.85 |
| 524 |  | 1H NMR (DMSO-d6, 400MHz): δ 9.05 (s, 1H), 8.63 (d, J=3.91 Hz, 1H), 8.46 (br. s, 1H), 8.28 (d, J=8.31 Hz, 1H), 8.22 (d, J=7.83 Hz, 1H), 7.83 (d, J=8.31 Hz, 1H), 7.53-7.59 (m, 1H), 6.52 (s, 1H), 4.12-4.15 (m, 1H), 3.32-3.38 (m, 3H), 3.14 (s, 3H), 3.06 (d, J=5.87 Hz, 4H), 2.83 (d, J=5.87 Hz, 4H), 1.39 (d, J=5.87 Hz, 3H), 1.29 (d, J=4.89 Hz, 3H).; LCMS: 521.8 |
| 525 |  | 1H NMR (DMSO-d6, 400MHz): δ 9.05 (s, 1H), 8.63 (d, J=3.91 Hz, 1H), 8.46 (s, 1H), 8.27 (d, J=8.31 Hz, 1H), 8.22 (d, J=7.34 Hz, 1H), 7.82 (d, J=8.31 Hz, 1H), 7.52-7.59 (m, 2H), 4.20 (d, J=5.87 Hz, 1H), 3.11 (s, 3H), 2.97-3.07 (m, 4H), 2.73-2.80 (m, 5H), 2.43-2.47 (m, 2H), 1.39 (d, J=6.36 Hz, 3H), 1.24 (d, J=5.87 Hz, 3H).; LCMS: 521.85 |

FIG. 1 (continued)

| | | |
|---|---|---|
| 526 | 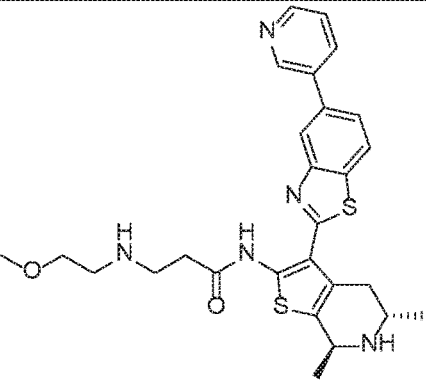 | 1H NMR (DMSO-d6, 400MHz): δ 8.99 (br. s, 1H), 8.57 (d, J=3.91 Hz, 1H), 8.40 (s, 1H), 8.22 (d, J=8.31 Hz, 1H), 8.17 (d, J=7.34 Hz, 1H), 7.77 (d, J=8.31 Hz, 1H), 7.45-7.67 (m, 3H), 6.46 (br. s, 1H), 4.11-4.24 (m, 1H), 3.32-3.39 (m, 3H), 3.12 (s, 3H), 3.05-3.09 (m, 2H), 2.78-2.91 (m, 4H), 2.49-2.62 (m, 2H), 1.37 (d, J=5.87 Hz, 3H), 1.27 (d, J=5.38 Hz, 3H).; LCMS: 521.85 |
| 527 | 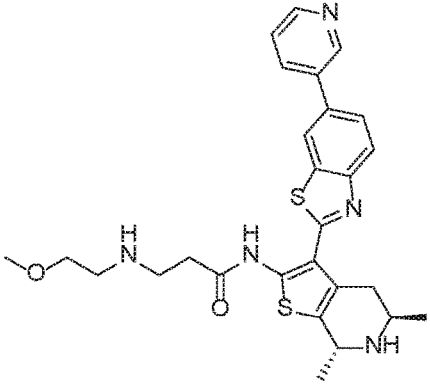 | 1H NMR (DMSO-d6, 400MHz): δ 9.01 (d, J=1.96 Hz, 1H), 8.61 (dd, J=1.47, 4.89 Hz, 1H), 8.56 (d, J=1.47 Hz, 1H), 8.16-8.22 (m, 2H), 7.96 (dd, J=1.96, 8.31 Hz, 1H), 7.55 (dd, J=4.65, 8.07 Hz, 1H), 4.29-4.40 (m, 1H), 3.50 (t, J=5.38 Hz, 2H), 3.28-3.31 (m, 3H), 3.25 (s, 3H), 3.21 (t, J=6.85 Hz, 3H), 3.03 (t, J=5.14 Hz, 2H), 2.95 (t, J=6.60 Hz, 2H), 2.63-2.73 (m, 1H), 1.48 (d, J=6.36 Hz, 3H), 1.38 (d, J=6.36 Hz, 3H).; LCMS: 522.4 |
| 528 | 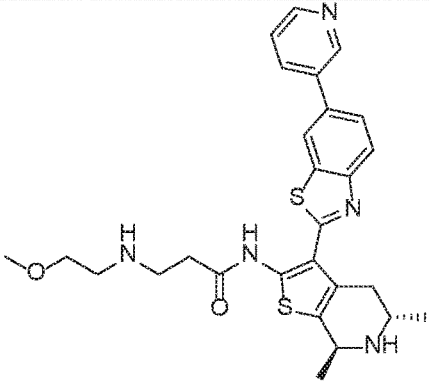 | 1H NMR (CD3OD, 400MHz): δ 8.92 (s, 1H), 8.57 (d, J=2.45 Hz, 1H), 8.38 (br. s, 1H), 8.21 (t, J=7.34 Hz, 2H), 7.89 (d, J=8.31 Hz, 1H), 7.53-7.60 (m, 1H), 4.48 (d, J=6.36 Hz, 1H), 3.59-3.66 (m, 3H), 3.40 (s, 3H), 3.37 (d, J=5.87 Hz, 2H), 3.23-3.29 (m, 1H), 3.17 (br. s, 2H), 3.05-3.10 (m, 2H), 2.76 (dd, J=8.07, 15.41 Hz, 1H), 1.59 (d, J=6.36 Hz, 3H), 1.43 (d, J=6.36 Hz, 3H).; LCMS: 522.4 |
| 529 | 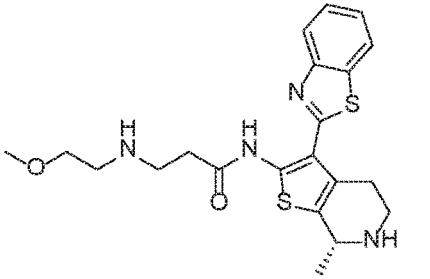 | 1H NMR (DMSO-d6, 400MHz): δ 8.13 (dd, J=8.07, 16.38 Hz, 2H), 7.58 (t, J=7.58 Hz, 1H), 7.46 (t, J=7.58 Hz, 1H), 4.00 (d, J=6.36 Hz, 1H), 3.43-3.46 (m, 1H), 3.29 (dd, J=6.11, 11.49 Hz, 7H), 3.14 (s, 3H), 2.97 (t, J=6.36 Hz, 2H), 2.80-2.87 (m, 2H), 2.72 (t, J=5.38 Hz, 3H), 1.34 (d, J=6.85 Hz, 3H).; LCMS: 430.75 |

| | | |
|---|---|---|
| 530 |  | 1H NMR (DMSO-d6, 400MHz): δ 8.13 (d, J=7.34 Hz, 1H), 8.07 (d, J=8.31 Hz, 1H), 7.56 (dt, J=1.22, 7.70 Hz, 1H), 7.43 (dt, J=1.22, 7.70 Hz, 1H), 3.84 (d, J=2.93 Hz, 2H), 3.25-3.30 (m, 2H), 3.14 (s, 3H), 2.92 (d, J=6.36 Hz, 2H), 2.83-2.89 (m, 2H), 2.66-2.71 (m, 4H), 2.32-2.42 (m, 1H), 1.21 (d, J=6.36 Hz, 3H).; LCMS: 431 |
| 531 |  | 1H NMR (400 MHz, DMSO-d6) δ 12.66 (s, 1H), 9.35 (br. s, 2H), 8.53 (br. s, 2H), 8.12 (s, 1H), 8.10 (d, J=5.38 Hz, 1H), 7.49 (dd, J=0.98, 8.31 Hz, 1H), 5.41 (s, 1H), 4.90-4.97 (m, 1H), 4.37 (br. s, 2H), 3.49-3.55 (m, 2H), 3.28-3.34 (m, 3H), 3.15-3.19 (m, 2H), 3.08 (t, J=6.85 Hz, 2H), 1.41 (d, J=6.36 Hz, 3H), 1.26 (d, J=6.36 Hz, 6H).; LCMS: 445.3 |
| 532 |  | 1H NMR (DMSO-d6, 400MHz): δ 8.70 (d, J=4.40 Hz, 2H), 8.53 (s, 1H), 8.29 (d, J=8.31 Hz, 1H), 7.85-7.91 (m, 3H), 7.50-7.75 (m, 2H), 4.13 (d, J=6.36 Hz, 1H), 3.24-3.28 (m, 2H), 3.20 (br s, 1H), 3.09 (s, 3H), 2.93-3.03 (m, 3H), 2.66-2.77 (m, 4H), 2.34-2.46 (m, 2H), 1.36 (d, J=6.36 Hz, 3H), 1.21 (d, J=5.87 Hz, 3H).; LCMS: 521.85 |
| 533 |  | 1H NMR (DMSO-d6, 400MHz): δ 9.04 (br s, 1H), 8.61 (d, J=3.91 Hz, 1H), 8.45 (s, 1H), 8.26 (d, J=8.32 Hz, 1H), 8.21 (d, J=7.83 Hz, 2H), 7.81 (d, J=8.31 Hz, 2H), 7.50-7.56 (m, 2H), 4.19 (d, J=5.38 Hz, 2H), 3.10 (s, 3H), 2.97-3.06 (m, 4H), 2.72-2.81 (m, 5H), 1.38 (d, J=6.36 Hz, 3H), 1.22 (d, J=5.38 Hz, 4H).; LCMS: 521.85 |

FIG. 1 (continued)

| | | |
|---|---|---|
| 534 | *(structure)* | DMSO-d6, δ 12.02 (s, 1H), 9.30 (s, 2H), 9.19 (d, J = 1.8 Hz, 1H), 8.70 (dd, J = 4.8, 1.6 Hz, 1H), 8.50 (s, 2H), 8.33 (ddd, 1H), 8.29 (dd, J = 8.0, 1.0 Hz, 1H), 7.77 (dd, J = 7.5, 1.0 Hz, 1H), 7.71 – 7.64 (m, 2H), 4.36 (s, 2H), 3.55 – 3.48 (m, 2H), 3.26 (dd, J = 10.9, 5.8 Hz, 3H), 3.18 (t, J = 5.2 Hz, 2H), 2.80 (t, J = 6.7 Hz, 2H), 1.28 (d, J = 6.5 Hz, 6H).; LCMS: 478.1 |
| 535 | *(structure)* | DMSO-d6, δ 8.86 (d, J = 5.8 Hz, 2H), 8.31 (d, J = 8.1 Hz, 1H), 8.20 (d, J = 6.4 Hz, 2H), 7.83 (d, J = 7.2 Hz, 1H), 7.68 (t, J = 7.8 Hz, 1H), 4.32 (s, 2H), 3.48 (t, J = 5.9 Hz, 2H), 3.27 (dt, J = 12.8, 6.3 Hz, 1H), 3.20 – 3.15 (m, J = 6.7 Hz, 4H), 2.69 (t, J = 6.2 Hz, 2H), 1.22 (d, J = 6.5 Hz, 6H).; LCMS: 478.2 |
| 536 | *(structure)* | 1H NMR (DMSO-d6, 400MHz): δ 8.17 (d, J=7.83 Hz, 1H), 8.11 (d, J=8.31 Hz, 1H), 7.58 (t, J=7.58 Hz, 2H), 7.46 (t, J=7.34 Hz, 2H), 3.79 (br s, 1H), 3.29 (d, J=5.87 Hz, 2H), 3.14 (s, 3H), 2.79-2.99 (m, 4H), 2.70 (d, J=5.38 Hz, 4H), 2.31-2.44 (m, 2H), 1.60-1.71 (m, 2H), 1.47-1.58 (m, 2H), 1.03 (d, J=6.36 Hz, 6H).; LCMS: 472.85 |
| 537 | *(structure)* | 1H NMR (DMSO-d6, 400MHz): δ 8.17 (d, J=7.83 Hz, 1H), 8.11 (d, J=7.83 Hz, 1H), 7.58 (t, J=7.83 Hz, 2H), 7.46 (t, J=7.58 Hz, 2H), 3.79 (dd, J=5.38, 8.31 Hz, 1H), 3.27-3.31 (m, 2H), 3.15 (s, 3H), 2.90-2.99 (m, 3H), 2.84 (br s, 1H), 2.67-2.75 (m, 4H), 2.40 (dd, J=8.80, 15.16 Hz, 2H), 1.60-1.71 (m, 2H), 1.53 (td, J=6.79, 14.31 Hz, 2H), 1.03 (q, J=6.85 Hz, 6H).; LCMS: 472.85 |
| 538 | *(structure)* | 1H NMR (DMSO-d6, 400MHz): δ 8.15 (d, J=7.83 Hz, 1H), 8.10 (d, J=7.83 Hz, 1H), 7.57 (t, J=7.34 Hz, 1H), 7.45 (t, J=7.34 Hz, 1H), 3.80-3.93 (m, 2H), 3.27 (br. s, 2H), 3.13 (s, 3H), 2.89-2.99 (m, 4H), 2.69 (d, J=4.89 Hz, 4H), 2.36-2.45 (m, 1H), 1.22 (d, J=4.40 Hz, 3H).; LCMS: 216.2 |

FIG. 1 (continued)

| | | |
|---|---|---|
| 539 | | 1H NMR (DMSO-d6, 400MHz): δ 8.14 (d, J=7.83 Hz, 1H), 8.09 (d, J=8.31 Hz, 1H), 7.64-7.84 (m, 2H), 7.57 (t, J=7.34 Hz, 1H), 7.45 (t, J=7.58 Hz, 1H), 3.63 (s, 2H), 2.93-3.00 (m, 2H), 2.87-2.93 (m, 3H), 2.83 (d, J=5.38 Hz, 2H), 2.72 (t, J=6.36 Hz, 2H), 2.53-2.57 (m, 2H), 1.32 (qd, J=7.25, 14.43 Hz, 2H), 1.07 (d, J=6.36 Hz, 6H), 0.74 (t, J=7.34 Hz, 3H).; LCMS: 443.19 |
| 540 | | 1H NMR (DMSO-d6, 400MHz): δ 12.65 (br. s, 1H), 8.59 (br. s, 1H), 8.19 (d, J=7.34 Hz, 1H), 8.13 (d, J=7.34 Hz, 1H), 7.62 (t, J=6.85 Hz, 1H), 7.48-7.52 (m, 1H), 3.75-3.96 (m, 2H), 3.65 (br. s, 2H), 2.64-3.13 (m, 8H), 1.49-1.71 (m, 2H), 1.35-1.40 (m, 2H), 1.21 (t, J=6.85 Hz, 3H), 1.06-1.11 (m, 3H).; LCMS: 428.85 |
| 541 | | 1H NMR (DMSO-d6, 400MHz): δ 10.01 (br. s, 1H), 8.20 (d, J=7.83 Hz, 1H), 8.15 (d, J=7.83 Hz, 1H), 7.62 (t, J=7.34 Hz, 1H), 7.48-7.55 (m, 1H), 4.55 (d, J=14.67 Hz, 1H), 4.44 (d, J=6.85 Hz, 1H), 4.10 (d, J=15.16 Hz, 5H), 3.65-3.89 (m, 3H), 3.49-3.53 (m, 2H), 2.98-3.03 (m, 2H), 2.21-2.43 (m, 3H), 1.28-1.45 (m, 6H).; LCMS: 440.85 |
| 542 | | 1H NMR (DMSO-d6, 400MHz): δ 8.12 (d, J=7.83 Hz, 1H), 8.08 (d, J=8.32 Hz, 1H), 7.77 (br. s, 2H), 7.56 (t, J=7.58 Hz, 1H), 7.39-7.47 (m, 1H), 3.62 (br. s, 2H), 3.02-3.11 (m, 1H), 2.88-2.97 (m, 4H), 2.66-2.84 (m, 4H), 1.66 (d, J=5.87 Hz, 2H), 1.33-1.54 (m, 5H), 1.20-1.29 (m, 2H), 1.06 (d, J=5.87 Hz, 6H).; LCMS: 468.9 |
| 543 | | DMSO-d6, δ 12.93 (s, 1H), 9.45 (br. s, 2H), 8.77 (br. s, 2H), 7.97 (dd, J = 7.9, 0.9 Hz, 1H), 7.51 (t, J = 7.8 Hz, 1H), 7.45 (d, J = 7.0 Hz, 1H), 4.37 (br. s, 2H), 3.53 (br. s, 2H), 3.22 – 3.13 (m, 4H), 2.68 (s, 3H), 1.29 (d, J = 6.5 Hz, 6H). 3H hidden under water signal; LCMS: 447.1 |

*FIG. 1 (continued)*

| | | |
|---|---|---|
| 544 | 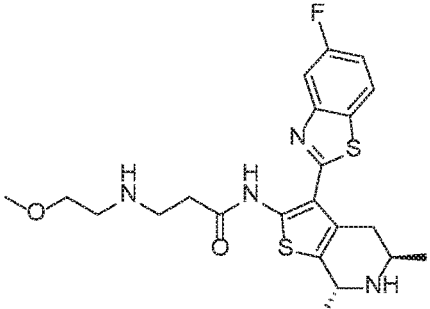 | 1H NMR (DMSO-d6, 400MHz): δ 10.20 (s, 1H), 8.19 (dd, J=5.38, 8.80 Hz, 1H), 7.98 (dd, J=2.20, 10.03 Hz, 1H), 7.35 (dt, J=2.45, 9.05 Hz, 1H), 4.02 (d, J=5.87 Hz, 1H), 3.25-3.29 (m, 2H), 3.14 (s, 3H), 2.89-3.04 (m, 5H), 2.71 (q, J=5.54 Hz, 4H), 2.36-2.46 (m, 2H), 1.33 (d, J=6.85 Hz, 3H), 1.24 (d, J=5.87 Hz, 3H).; LCMS: 462.85 |
| 545 | 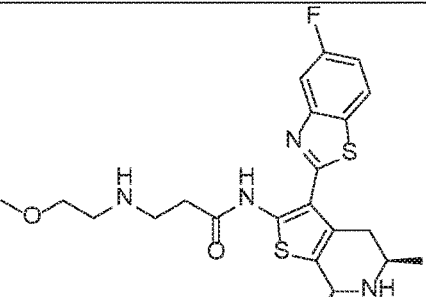 | 1H NMR (DMSO-d6, 400MHz): δ 8.18 (dd, J=5.38, 8.80 Hz, 1H), 7.97 (dd, J=2.20, 10.03 Hz, 1H), 7.35 (dt, J=2.20, 8.93 Hz, 1H), 4.11 (q, J=6.36 Hz, 1H), 3.28 (t, J=5.62 Hz, 3H), 3.16-3.22 (m, 1H), 3.14 (s, 3H), 2.90-2.99 (m, 3H), 2.70 (q, J=5.54 Hz, 4H), 2.38 (dd, J=8.31, 15.16 Hz, 1H), 1.35 (d, J=6.36 Hz, 3H), 1.19 (br d, J=6.36 Hz, 3H).; LCMS: 462.85 |
| 546 | 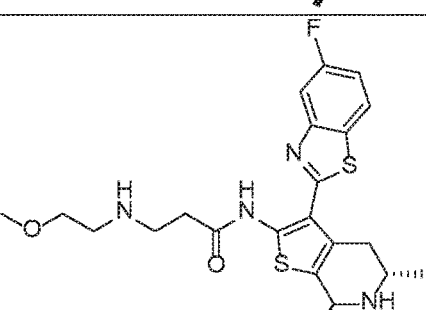 | 1H NMR (DMSO-d6, 400MHz): δ 12.61 (s, 1H), 10.22 (s, 1H), 8.15-8.26 (m, 1H), 7.99 (d, J=9.78 Hz, 1H), 7.37 (t, J=8.80 Hz, 1H), 4.04 (br. s, 1H), 3.97-4.09 (m, 1H), 3.31 (d, J=5.87 Hz, 2H), 3.16 (s, 3H), 2.89-3.06 (m, 4H), 2.73 (br s, 4H), 2.38-2.48 (m, 1H), 1.35 (d, J=5.87 Hz, 3H), 1.25 (d, J=4.89 Hz, 3H).; LCMS: 462.85 |
| 547 | 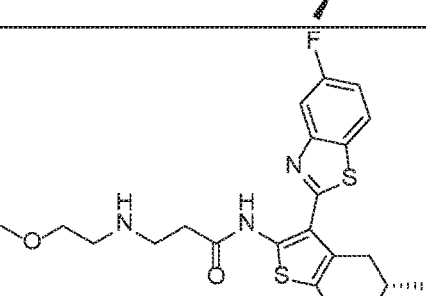 | 1H NMR (DMSO-d6, 400MHz): δ 8.18 (dd, J=5.38, 8.31 Hz, 1H), 7.97 (dd, J=2.20, 10.03 Hz, 1H), 7.35 (dt, J=2.20, 8.93 Hz, 1H), 4.11 (q, J=6.36 Hz, 1H), 3.26-3.30 (m, 3H), 3.16-3.22 (m, 2H), 3.14 (s, 3H), 2.90-2.98 (m, 2H), 2.88-2.99 (m, 1H), 2.70 (q, J=5.54 Hz, 4H), 2.38 (dd, J=8.07, 15.41 Hz, 2H), 1.35 (d, J=6.36 Hz, 3H), 1.19 (d, J=6.36 Hz, 3H).; LCMS: 463.23 |

| | | |
|---|---|---|
| 548 |  | 1H NMR (DMSO-d6/D2O, 400MHz): δ 8.62 (d, J=5.87 Hz, 2H), 8.42 (s, 1H), 8.19 (d, J=8.31 Hz, 1H), 7.82 (d, J=5.87 Hz, 3H), 3.28 (t, J=5.38 Hz, 2H), 3.12-3.23 (m, 2H), 3.07 (s, 3H), 2.66-2.98 (m, 9H), 1.27-1.34 (m, 3H).; LCMS: 507.75 |
| 549 |  | 1H NMR (DMSO-d6/D2O, 400MHz):δ 8.61 (d, J=5.38 Hz, 2H), 8.39 (s, 1H), 8.14-8.21 (m, 1H), 7.80 (d, J=5.38 Hz, 2H), 3.83 (br. s, 2H), 3.29 (t, J=5.38 Hz, 2H), 3.07 (s, 3H), 2.84-2.97 (m, 3H), 2.83-2.99 (m, 1H), 2.64-2.76 (m, 4H), 2.31-2.46 (m, 2H), 1.20 (d, J=5.87 Hz, 3H).; LCMS: 507.9 |
| 550 |  | 1H NMR (DMSO-d6, 400MHz): δ 8.48 (s, 1H), 8.38 (d, J=8.31 Hz, 1H), 7.75 (d, J=8.80 Hz, 1H), 3.81-3.93 (m, 2H), 3.24-3.30 (m, 3H), 3.12 (s, 3H), 2.94 (t, J=6.11 Hz, 4H), 2.66-2.78 (m, 4H), 2.41-2.47 (m, 1H), 1.23 (d, J=6.36 Hz, 3H).; LCMS: 498.8 |
| 551 |  | 1H NMR (DMSO-d6, 400MHz): δ 8.48 (s, 1H), 8.39 (d, J=8.31 Hz, 1H), 7.75 (d, J=8.31 Hz, 1H), 3.89 (s, 2H), 3.23-3.31 (m, 3H), 3.13 (s, 3H), 2.89-3.05 (m, 4H), 2.73 (td, J=5.50, 0.52 Hz, 4H), 2.41-2.47 (m, 1H), 1.24 (d, J=5.87 Hz, 3H).; LCMS: 498.8 |

FIG. 1 (continued)

| | | |
|---|---|---|
| 552 | | 1H NMR (DMSO-d6, 400MHz): δ 12.55 (s, 1H), 10.05 (br. s, 1H), 8.51 (br. s, 2H), 8.22 (d, J=7.83 Hz, 1H), 8.14 (d, J=8.31 Hz, 1H), 7.64 (t, J=7.83 Hz, 1H), 7.53 (t, J=7.58 Hz, 1H), 4.36-4.61 (m, 2H), 3.66-3.90 (m, 2H), 3.19-3.37 (m, 5H), 3.12 (d, J=6.85 Hz, 2H), 2.86 (d, J=4.40 Hz, 2H), 1.90-2.05 (m, 1H), 1.29-1.42 (m, 6H), 0.96 (d, J=6.85 Hz, 6H).; LCMS: 457.24 |
| 553 | | DMSO-d6, δ 12.77 (s, 1H), 9.31 (br. s, 2H), 8.62 (dd, J = 8.1, 1.1 Hz, 1H), 8.47 (br. s, 2H), 8.11 (dd, J = 7.6, 1.1 Hz, 1H), 7.75 (t, J = 7.9 Hz, 1H), 4.39 (br. s, 2H), 3.56 (br. s, 2H), 3.48 (s, 3H), 3.21 (t, J = 5.6 Hz, 2H), 3.14 (t, J = 6.8 Hz, 2H), 1.27 (d, J = 6.5 Hz, 6H). 3H hidden under water signal; LCMS: 479.1 |
| 554 | | DMSO-d6, δ 12.39 (s, 1H), 10.40 (s, 1H), 9.55 (br s, 2H), 8.77 (br s, 2H), 8.01 (d, J = 7.9 Hz, 1H), 7.91 (d, J = 7.4 Hz, 1H), 7.46 (t, J = 8.0 Hz, 1H), 4.35 (s, 2H), 3.50 (s, 2H), 3.35 – 3.17 (m, 7H), 2.29 (s, 3H), 1.26 (d, J = 6.5 Hz, 6H).; LCMS: 458.2 |
| 555 | | 1H NMR (DMSO-d6, 400MHz): δ 12.51 (br. s, 1H), 9.65 (br. s, 1H), 8.90-9.04 (m, 1H), 7.72 (d, J=1.96 Hz, 2H), 6.18 (s, 2H), 4.32 (br. s, 2H), 3.47 (br. s, 2H), 3.23-3.30 (m, 2H), 3.08-3.20 (m, 5H), 1.79-1.84 (m, 1H), 1.44-1.58 (m, 1H), 1.24 (d, J=6.36 Hz, 3H), 0.92 (t, J=7.34 Hz, 3H).; LCMS: 458.9 |
| 556 | | 1H NMR (DMSO-d6, 400MHz): δ 12.51 (br. s, 1H), 9.68 (br. s, 2H), 9.07 (br. s, 2H), 7.72 (d, J=9.29 Hz, 2H), 6.18 (s, 2H), 4.32 (br. s, 2H), 3.64 (t, J=4.89 Hz, 2H), 3.46 (br. s, 2H), 3.33-3.37 (m, 5H), 3.09-3.21 (m, 6H).; LCMS: 460.8 |

FIG. 1 (continued)

| # | Structure | Data |
|---|---|---|
| 557 | 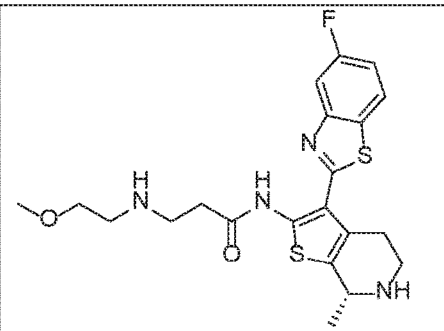 | 1H NMR (DMSO-d6; D2O exchange, 400MHz): δ 8.03-8.14 (m, 1H), 7.91 (d, J=9.78 Hz, 1H), 7.31 (t, J=8.07 Hz, 1H), 3.96 (d, J=5.87 Hz, 1H), 3.20-3.33 (m, 3H), 3.12 (s, 3H), 2.77-2.97 (m, 5H), 2.68 (d, J=5.38 Hz, 4H), 1.32 (d, J=5.87 Hz, 3H).; LCMS: 448.85 |
| 558 | 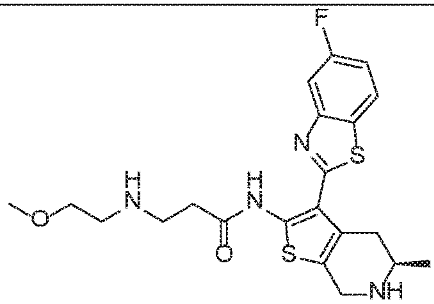 | 1H NMR (DMSO-d6; D2O exchange, 400MHz): δ 8.10 (d, J=5.38 Hz, 1H), 7.89 (d, J=9.29 Hz, 1H), 7.31 (t, J=8.31 Hz, 1H), 3.81-3.85 (m, 2H), 3.25-3.29 (m, 2H), 3.12 (br. s, 3H), 2.86-2.94 (m, 4H), 2.67 (d, J=4.89 Hz, 4H), 2.31-2.45 (m, 2H), 1.98-1.24 (m, 3H).; LCMS: 448.8 |
| 559 | 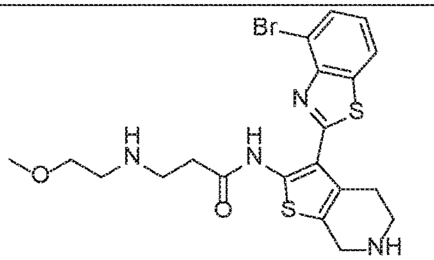 | DMSO-d6, δ 13.12 (s, 1H), 9.56 (s, 2H), 8.96 (s, 2H), 8.23 (d, J = 7.3 Hz, 1H), 7.88 (d, J = 7.7 Hz, 1H), 7.44 (t, J = 7.8 Hz, 1H), 4.35 (s, 2H), 3.74 – 3.43 (m, 6H), 3.23 – 3.14 (m, 6H). 3H hidden under water signal; LCMS: 494.9/ 496.8 |
| 560 | 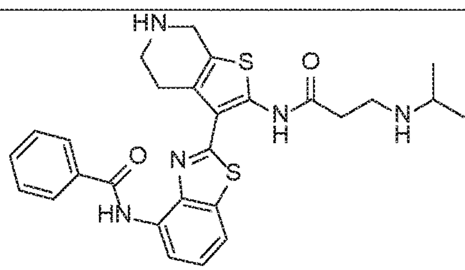 | DMSO-d6, δ 12.19 (s, 1H), 10.68 (s, 1H), 9.50 (br s, 2H), 8.52 (br s, 2H), 8.14 – 8.12 (m, 2H), 8.04 (dd, J = 8.0, 0.9 Hz, 1H), 7.89 (d, J = 7.2 Hz, 1H), 7.68 – 7.59 (m, 3H), 7.55 (t, J = 7.9 Hz, 1H), 4.34 (s, 2H), 3.50 (s, 2H), 3.22 – 3.13 (m, 3H), 3.04 – 2.97 (m, 2H), 2.85 (t, J = 5.9 Hz, 2H), 1.20 (d, J = 6.5 Hz, 6H).; LCMS: 520.1 |
| 561 | 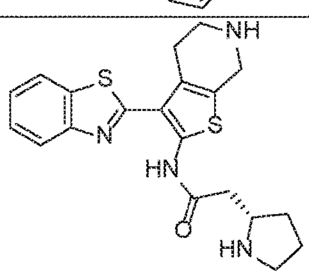 | DMSO-d6, δ 12.60 (s, 1H), 9.58 (s, 2H), 9.25 (s, 1H), 9.01 (s, 1H), 8.20 (t, J = 7.2 Hz, 2H), 7.64 – 7.61 (m, 1H), 7.53 – 7.50 (m, 1H), 4.34 (s, 2H), 3.92 – 3.85 (m, 1H), 3.49 (s, 2H), 3.23 – 3.16 (m, 6H), 2.17 (dtd, J = 11.8, 7.4, 4.2 Hz, 1H), 2.02 – 1.94 (m, 1H), 1.92 – 1.83 (m, 1H), 1.69 (ddd, J = 16.9, 12.8, 8.7 Hz, 1H); LCMS: 399.1 |

FIG. 1 (continued)

| | | |
|---|---|---|
| 562 | (structure) | DMSO-d6, δ 12.60 (s, 1H), 9.58 (s, 2H), 9.25 (s, 1H), 9.01 (s, 1H), 8.20 (t, J = 7.2 Hz, 2H), 7.64 – 7.61 (m, 1H), 7.53 – 7.50 (m, 1H), 4.34 (s, 2H), 3.92 – 3.85 (m, 1H), 3.49 (s, 2H), 3.23 – 3.16 (m, 6H), 2.17 (dtd, J = 11.8, 7.4, 4.2 Hz, 1H), 2.02 – 1.94 (m, 1H), 1.92 – 1.83 (m, 1H), 1.69 (ddd, J = 16.9, 12.8, 8.7 Hz, 1H); LCMS: 399 |
| 563 | (structure) | 1H NMR (DMSO-d6, 400MHz): δ 8.69 (s, 2H), 7.72 (s, 1H), 7.67 (br. s, 1H), 6.18 (s, 2H), 4.27-4.62 (m, 2H), 3.48-3.85 (m, 2H), 3.06-3.20 (m, 4H), 2.63-3.02 (m, 4H), 1.79 (d, J=5.87 Hz, 1H), 1.44-1.58 (m, 2H), 1.29-1.42 (m, 2H), 1.24 (d, J=6.36 Hz, 3H), 1.10 (d, J=4.89 Hz, 3H), 0.92 (t, J=7.34 Hz, 3H).; LCMS: 500.85 |
| 564 | (structure) | 1H NMR (DMSO-d6, 400MHz): δ 8.26 (s, 2H), 8.11 (d, J=8.31 Hz, 1H), 8.01 (s, 1H), 7.67 (d, J=7.83 Hz, 1H), 7.49 (br. s, 1H), 3.98-4.06 (m, 1H), 3.90 (s, 3H), 3.26-3.30 (m, 3H), 3.10-3.14 (m, 3H), 2.91-3.01 (m, 4H), 2.68-2.76 (m, 4H), 2.31-2.46 (m, 2H), 1.33 (d, J=6.85 Hz, 3H), 1.24 (d, J=6.36 Hz, 3H).; LCMS: 524.9 |
| 565 | (structure) | 1H NMR (DMSO-d6, 400MHz): δ 8.26 (br. s, 2H), 8.10 (d, J=8.31 Hz, 1H), 8.01 (s, 1H), 7.67 (d, J=7.83 Hz, 1H), 4.11 (d, J=6.36 Hz, 1H), 3.90 (s, 3H), 3.16-3.29 (m, 4H), 3.12 (s, 3H), 2.95 (d, J=6.36 Hz, 4H), 2.71 (d, J=5.38 Hz, 4H), 2.32-2.43 (m, 2H), 1.36 (d, J=6.36 Hz, 3H), 1.19 (d, J=5.87 Hz, 3H).; LCMS: 524.9 |

FIG. 1 (continued)

| | | |
|---|---|---|
| 566 | *(structure)* | 1H NMR (DMSO-d6, 400MHz): δ 8.26 (br. s, 2H), 8.10 (d, J=8.31 Hz, 1H), 8.00 (br. s, 1H), 7.67 (d, J=7.83 Hz, 1H), 4.01-4.04 (m, 1H), 3.90 (br. s, 3H), 3.19-3.29 (m, 3H), 3.12 (s, 3H), 2.88-3.04 (m, 5H), 2.72 (d, J=5.87 Hz, 4H), 2.32-2.43 (m, 2H), 1.33 (d, J=5.87 Hz, 3H), 1.24 (d, J=4.40 Hz, 3H).; LCMS: 524.85 |
| 567 | *(structure)* | 1H NMR (DMSO-d6, 400MHz): δ 8.31 (d, J=2.93 Hz, 2H), 8.15 (d, J=8.31 Hz, 1H), 8.06 (s, 1H), 7.72 (d, J=8.31 Hz, 1H), 4.12-4.21 (m, 1H), 3.96 (s, 3H), 3.21-3.36 (m, 5H), 3.18 (s, 3H), 2.96-3.06 (m, 3H), 2.77 (q, J=5.54 Hz, 3H), 2.43 (dd, J=8.31, 15.16 Hz, 2H), 1.41 (d, J=6.36 Hz, 3H), 1.28 (br. s, 1H), 1.25 (d, J=6.36 Hz, 3H).; LCMS: 524.9 |
| 568 | *(structure)* | DMSO-d6, δ 12.60 (br. s., 1 H), 9.22 (br. s., 2 H), 8.59 (br. s., 2 H), 8.51 (d, J = 7.9 Hz, 1 H), 8.08 (d, J = 7.6 Hz, 1 H), 7.60 (t, J = 7.9 Hz, 1 H), 4.32 (br. s., 2 H), 3.53 (t, J = 5.0 Hz, 2 H), 3.47 (br. s., 2 H), 3.26 (br. s., 3 H), 3.12 (d, J = 4.4 Hz, 4 H), 3.02 (t, J = 6.8 Hz, 2 H).; LCMS: 442.2 |
| 569 | *(structure)* | 1H NMR (DMSO-d6, 400MHz): δ 8.71-8.80 (m, 2H), 8.57 (s, 1H), 8.30-8.38 (m, 1H), 7.88-8.01 (m, 3H), 4.20 (d, J=5.87 Hz, 1H), 3.39-3.51 (m, 6H), 3.21 (s, 3H), 2.85-3.17 (m, 9H), 1.46 (d, J=6.85 Hz, 3H).; LCMS: 507.85 |

*FIG. 1 (continued)*

| | | |
|---|---|---|
| 570 | *(structure)* | 1H NMR (DMSO-d6, 400MHz): δ 8.17 (dd, J=5.38, 8.80 Hz, 1H), 7.96 (dd, J=2.20, 10.03 Hz, 1H), 7.35 (dt, J=2.20, 8.93 Hz, 1H), 4.04 (d, J=6.36 Hz, 1H), 3.28 (br. s, 2H), 3.16 (s, 3H), 2.90-3.03 (m, 3H), 2.83-2.87 (m, 2H), 2.71-2.79 (m, 4H), 1.36 (d, J=6.85 Hz, 3H), 1.19-1.27 (m, 2H).; LCMS: 499.17 |
| 571 | *(structure)* | 1H NMR (DMSO-d6; D2O exchange, 400MHz): δ 8.10 (br s, 1H), 7.89 (d, J=8.80 Hz, 1H), 7.25-7.34 (m, 1H), 3.83-3.95 (m, 2H), 3.21-3.36 (m, 4H), 3.13 (br. s, 3H), 2.92-3.04 (m, 4H), 2.70-2.78 (m, 4H), 1.21 (d, J=16.63 Hz, 3H).; LCMS: 499.17 |
| 572 | *(structure)* | 1H NMR (DMSO-d6/D2O, 400MHz): δ 8.10 (dd, J=7.34, 19.07 Hz, 2H), 7.59 (d, J=6.36 Hz, 1H), 7.49 (d, J=5.87 Hz, 1H), 3.61 (br. s, 2H), 2.88 (br. s, 3H), 2.79-2.83 (m, 2H), 2.72 (d, J=9.78 Hz, 4H), 2.34-2.43 (m, 2H), 2.21 (br. s, 3H), 1.08 (d, J=3.42 Hz, 6H), 0.82-0.88 (m, 3H).; LCMS: 442.85 |
| 573 | *(structure)* | 1H NMR (DMSO-d6, 400MHz): δ 12.56 (s, 1H), 9.60 (br. s, 2H), 9.36 (br. s, 3H), 9.08 (br. s, 1H), 8.19 (d, J=8.31 Hz, 2H), 7.61 (t, J=7.58 Hz, 1H), 7.50 (t, J=7.58 Hz, 1H), 4.33 (br. s, 2H), 3.77-3.89 (m, 1H), 3.45-3.53 (m, 2H), 3.13-3.34 (m, 8H), 2.85-2.98 (m, 4H), 1.99 (br s, 4H).; LCMS: 467.75 |

| | | |
|---|---|---|
| 574 |  | 1H NMR (DMSO-d6, 400MHz): δ 8.42 (s, 1H), 8.35 (d, J=8.31 Hz, 1H), 7.72 (d, J=8.31 Hz, 1H), 7.46 (br. s, 1H), 3.61 (s, 2H), 2.86-3.04 (m, 5H), 2.79-2.85 (m, 2H), 2.72 (t, J=6.36 Hz, 2H), 2.56-2.63 (m, 1H), 1.29-1.41 (m, 1H), 1.10-1.26 (m, 2H), 1.07 (d, J=6.36 Hz, 6H), 0.91 (d, J=5.87 Hz, 3H), 0.73 (t, J=7.34 Hz, 3H).; LCMS: 524.8 |
| 575 |  | 1H NMR (DMSO-d6, 400MHz): δ 9.94 (br. s, 1H), 8.57 (br. s, 1H), 8.42 (s, 1H), 8.38 (d, J=8.80 Hz, 1H), 7.75 (d, J=8.31 Hz, 1H), 4.29-4.55 (m, 3H), 3.57-3.85 (m, 4H), 3.51 (t, J=4.89 Hz, 3H), 3.12 (br. s, 3H), 3.04 (d, J=6.85 Hz, 3H), 1.22-1.30 (m, 6H), 0.99-1.20 (m, 2H).; LCMS: 526.7 |
| 576 |  | 1H NMR (DMSO-d6/D2O, 400MHz): δ 7.88 (d, J=11.74 Hz, 2H), 4.30 (br. s, 2H), 3.44-3.50 (m, 2H), 3.29 (d, J=4.89 Hz, 2H), 3.14-3.21 (m, 3H), 3.01-2.97 (m, 2H), 2.36 (d, J=4.89 Hz, 6H), 1.66-1.79 (m, 1H), 1.41-1.56 (m, 1H), 1.21 (d, J=6.36 Hz, 3H), 0.89 (t, J=7.34 Hz, 3H).; LCMS: 442.8 |
| 577 |  | 1H NMR (DMSO-d6, 400MHz): δ 12.66 (br. s, 1H), 8.15 (d, J=7.83 Hz, 1H), 8.09 (d, J=8.31 Hz, 1H), 7.58 (t, J=7.34 Hz, 1H), 7.42-7.49 (t, J=7.37 Hz, 1H), 3.63 (s, 2H), 2.79-2.94 (m, 5H), 2.72 (t, J=3.67 Hz, 2H), 2.22-2.29 (m, 2H), 2.21 (s, 3H), 1.21-1.30 (m, 4H), 1.07 (d, J=6.36 Hz, 6H), 0.77-0.89 (m, 2H), 0.65 (t, J=7.34 Hz, 3H).; LCMS: 456.65 |

| | | |
|---|---|---|
| 578 |  | 1H NMR (DMSO-d6; D2O exchange, 400MHz): δ 8.45 (br. s, 1H), 8.38 (d, J=8.31 Hz, 1H), 7.77 (d, J=8.31 Hz, 1H), 3.70 (br. s, 2H), 3.25 (td, J=6.11, 12.23 Hz, 2H), 2.94-3.05 (m, 5H), 2.88-2.93 (m, 2H), 1.70 (td, J=6.42, 12.11 Hz, 1H), 1.37-1.48 (m, 2H), 1.18 (d, J=6.36 Hz, 3H), 1.09 (d, J=6.36 Hz, 6H), 0.88 (t, J=7.34 Hz, 3H).; LCMS: 525.41 |
| 579 |  | 1H NMR (D2O, 400MHz): δ 8.77 (d, J=6.85 Hz, 2H), 8.51 (s, 1H), 8.34 (d, J=6.36 Hz, 2H), 8.19 (d, J=8.80 Hz, 1H), 7.90 (d, J=8.31 Hz, 1H), 4.42 (s, 2H), 3.63 (t, J=6.11 Hz, 2H), 3.40-3.52 (m, 2H), 3.22-3.35 (m, 3H), 3.15 (t, J=6.36 Hz, 2H), 1.77-1.88 (m, 1H), 1.56-1.67 (m, 1H), 1.33 (d, J=6.36 Hz, 3H), 0.97 (t, J=7.58 Hz, 3H).; LCMS: 492.15 |
| 580 |  | 1H NMR (DMSO-d6), δ 12.72 - 12.61 (m, 1 H), 9.46 - 9.36 (m, 2 H), 8.76 - 8.67 (m, 2 H), 8.11 - 8.05 (m, 1 H), 7.91 - 7.86 (m, 1 H), 7.35 - 7.28 (m, 1 H), 4.44 - 4.36 (m, 2 H), 3.58 - 3.49 (m, 2 H), 3.22 - 3.18 (m, 2 H), 3.17 - 3.12 (m, 2 H), 2.25 - 2.11 (m, 1 H), 1.35 - 1.28 (m, 6 H), 1.14 - 1.04 (m, 2 H), 0.89 - 0.79 (m, 2 H).; LCMS: 441.1 |
| 581 |  | 1H NMR (DMSO-d6), δ 12.38 (s, 1H), 10.06 (s, 1H), 9.51 (s br, 2H), 8.78 (s br, 2H), 8.15 (d, J = 8.6 Hz, 1H), 7.99 (d, J = 2.0 Hz, 1H), 7.36 (dd, J = 8.6, 2.1 Hz, 1H), 4.34 (s, 2H), 3.49 (t, J = 5.8 Hz, 2H), 3.31 – 3.26 (m, 3H), 3.16 (t, J = 5.5 Hz, 2H), 3.11 (t, J = 6.9 Hz, 2H), 3.07 (s, 3H), 1.27 (d, J = 6.5 Hz, 6H).; LCMS: 494.2 |

| | | |
|---|---|---|
| 582 |  | DMSO-d6, δ 12.45 (br s, 1H), 10.13 (br s, 1H), 9.71 (br s, 2H), 8.93 (br s, 2H), 8.02 (dd, J = 7.8, 1.2 Hz, 1H), 7.56 – 7.48 (m, 2H), 4.34 (s, 2H), 3.65 – 3.62 (m, 2H), 3.51 – 3.46 (m, 2H), 3.33 – 3.30 (m, 2H), 3.32 (s, 3H), 3.22 – 3.16 (m, 6H), 3.16 (s, 3H).; LCMS: 510.1 |
| 583 |  | DMSO-d6, δ 12.40 (br s, 1H), 9.22 (br s, 2H), 8.66 (br s, 2H), 8.12 (dd, J = 8.0, 1.0 Hz, 1H), 7.80 (d, J = 7.5 Hz, 1H), 7.53 – 7.47 (m, 2H), 6.25 (dd, J = 17.7, 1.3 Hz, 1H), 5.63 (dd, J = 11.1, 1.3 Hz, 1H), 4.37 (s, 2H), 3.62 – 3.59 (m, 2H), 3.52 (t, J = 6.1 Hz, 2H), 3.36-3.29 (m, 5H), 3.22 – 3.15 (m, 4H), 3.06 (t, J = 7.0 Hz, 2H).; LCMS: 443.2 |
| 584 |  | 1H NMR (DMSO-d6, 400MHz): δ 8.09-8.26 (m, 2H), 7.56 (d, J=5.38 Hz, 1H), 3.95 (br. s, 1H), 3.19-3.25 (m, 1H), 3.08-3.15 (m, 3H), 2.86-2.97 (m, 4H), 2.56-2.75 (m, 6H), 2.35-2.45 (m, 3H), 1.28 (d, J=5.87 Hz, 3H), 1.22 (d, J=5.87 Hz, 4H).; LCMS: 513.29 |
| 585 |  | 1H NMR (DMSO-d6, 400MHz): δ 8.48 (s, 1H), 8.38 (d, J=8.31 Hz, 1H), 7.74 (d, J=8.31 Hz, 1H), 4.11 (q, J=6.68 Hz, 1H), 3.27 (t, J=5.62 Hz, 3H), 3.14-3.22 (m, 2H), 3.10-3.14 (m, 3H), 3.00 (d, J=3.91 Hz, 1H), 2.91-2.97 (m, 3H), 2.67-2.75 (m, 5H), 2.41 (dd, J=8.31, 15.16 Hz, 1H), 1.35 (d, J=6.85 Hz, 3H), 1.23 (s, 1H), 1.20 (d, J=6.36 Hz, 3H).; LCMS: 513.29 |

FIG. 1 (continued)

| 586 | 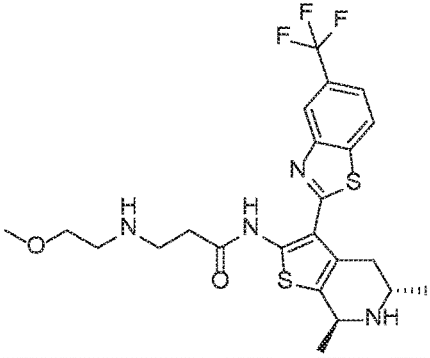 | 1H NMR (DMSO-d6, 400MHz): δ 8.39 (br. s, 1H), 8.33 (d, J=7.83 Hz, 1H), 7.69 (d, J=8.31 Hz, 1H), 3.99 (d, J=6.36 Hz, 1H), 3.46-3.51 (m, 1H), 3.42 (d, J=4.89 Hz, 1H), 3.28 (t, J=5.38 Hz, 2H), 3.10-3.15 (m, 3H), 3.03 (d, J=15.16 Hz, 1H), 2.95-2.99 (m, 1H), 2.92 (t, J=6.36 Hz, 2H), 2.69 (t, J=5.38 Hz, 3H), 2.39-2.47 (m, 2H), 1.31 (d, J=6.36 Hz, 3H), 1.23 (d, J=5.38 Hz, 4H).; LCMS: 513.36 |
| --- | --- | --- |
| 587 | 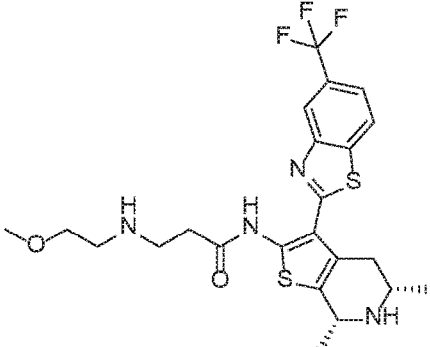 | 1H NMR (DMSO-d6, 400MHz): δ 8.34 (br. s, 1H), 8.30 (d, J=8.31 Hz, 1H), 7.66 (d, J=7.83 Hz, 1H), 4.03-4.10 (m, 1H), 3.29 (t, J=5.62 Hz, 2H), 3.15-3.20 (m, 1H), 3.12-3.14 (s, 3H), 3.07 (d, J=16.14 Hz, 2H), 2.92 (t, J=6.11 Hz, 2H), 2.68 (td, J=5.56, 10.88 Hz, 4H), 2.43 (dd, J=8.56, 15.41 Hz, 2H), 1.34 (d, J=6.85 Hz, 3H), 1.23 (s, 1H), 1.19 (d, J=6.36 Hz, 3H).; LCMS: 513 |
| 588 | 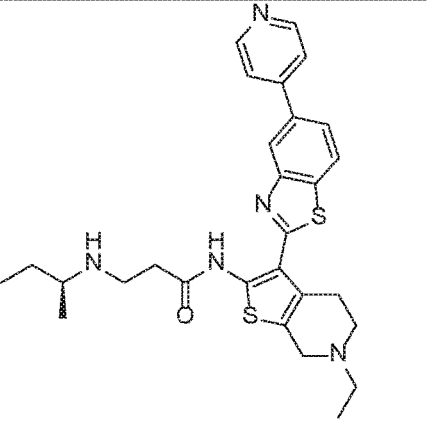 | 1H NMR (DMSO-d6, 400MHz): δ 8.70 (d, J=4.89 Hz, 2H), 8.58 (s, 1H), 8.30 (d, J=8.31 Hz, 1H), 7.91 (d, J=8.31 Hz, 1H), 7.88 (d, J=5.38 Hz, 2H), 3.59 (s, 2H), 3.24 (d, J=6.85 Hz, 2H), 2.93-3.09 (m, 5H), 2.80-2.86 (m, 2H), 2.54-2.64 (m, 2H), 1.60-1.75 (m, 2H), 1.36-1.47 (m, 2H), 1.16 (d, J=5.87 Hz, 3H), 1.11 (t, J=6.85 Hz, 3H), 0.86 (t, J=7.34 Hz, 3H).; LCMS: 520.35 |
| 589 | 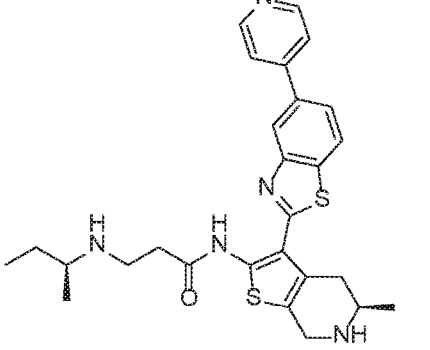 | 1H NMR (DMSO-d6/D2O, 400MHz): δ 8.64 (d, J=5.87 Hz, 2H), 8.40 (s, 1H), 8.20 (d, J=8.31 Hz, 1H), 7.81 (d, J=6.36 Hz, 3H), 2.81-2.99 (m, 5H), 2.69 (t, J=6.60 Hz, 2H), 2.35-2.43 (m, 1H), 1.27-1.37 (m, 1H), 1.20 (d, J=6.36 Hz, 3H), 1.07-1.14 (m, 1H), 0.88 (d, J=6.36 Hz, 3H), 0.66 (t, J=7.34 Hz, 3H).; LCMS: 505.85 |

*FIG. 1 (continued)*

| | | |
|---|---|---|
| 590 | [structure] | 1H NMR (DMSO-d6/D2O, 400MHz): δ 8.62 (d, J=4.89 Hz, 2H), 8.39 (s, 1H), 8.18 (d, J=8.31 Hz, 1H), 7.81 (d, J=5.87 Hz, 3H), 2.87-3.01 (m, 2H), 2.81 (br. s, 3H), 2.69 (t, J=6.36 Hz, 2H), 1.30 (d, J=6.85 Hz, 4H), 1.05-1.19 (m, 2H), 0.88 (d, J=5.87 Hz, 3H), 0.67 (t, J=7.09 Hz, 3H).; LCMS: 505.85 |
| 591 | [structure] | 1H NMR (DMSO-d6, 400MHz): δ 12.62 (br. s, 1H), 8.67 (br. s, 1H), 8.18 (d, J=7.83 Hz, 1H), 8.12 (d, J=8.31 Hz, 1H), 7.61 (t, J=7.58 Hz, 1H), 7.49 (t, J=7.34 Hz, 1H), 4.54 (br. s, 2H), 3.67-3.75 (m, 4H), 3.57 (d, J=4.89 Hz, 5H), 3.42-3.54 (m, 16H), 3.33-3.38 (m, 2H), 3.18-3.23 (m, 2H), 3.09 (t, J=6.36 Hz, 2H), 2.92-2.97 (m, 2H), 2.39-2.46 (m, 4H), 1.44 (s, 9H).; LCMS: 795.45 |
| 592 | [structure] | DMSO-d6, δ 15.55 (br. s, 1H), 11.78 (s, 1H), 9.80 (s, 3H), 9.18 (s, 2H), 8.43 (d, J = 8.1 Hz, 1H), 8.12 (d, J = 24.2 Hz, 1H), 7.91 (d, J = 7.2 Hz, 1H), 7.74 (t, J = 8.0 Hz, 1H), 4.34 (s, 2H), 3.68 (t, J = 5.0 Hz, 2H), 3.53 – 3.27 (m, 7H; overlap with water), 3.24-3.17 (m, 4H), 3.06 (t, J = 7.1 Hz, 2H), 2.47 (s, 3H); LCMS: 497 |
| 593 | [structure] | DMSO-d6, δ 11.58 (s, 1H), 9.56 (s, 2H), 8.90 (s, 2H), 7.72 (d, J = 7.3 Hz, 1H), 7.41 (t, J = 7.9 Hz, 1H), 7.04 (d, J = 7.8 Hz, 1H), 4.34 (t, J = 4.2 Hz, 2H), 3.90 – 3.85 (m, 4H), 3.64 – 3.60 (m, 2H), 3.49 – 3.43 (m, 6H), 3.32 (s, 3H), 3.31 – 3.26 (m, 2H), 3.20 – 3.14 (m, 2H), 3.12 (t, J = 5.9 Hz, 2H), 3.02 (t, J = 7.1 Hz, 2H).; LCMS: 502.1 |

FIG. 1 (continued)

| | | |
|---|---|---|
| 594 | | DMSO-d6, δ 8.17 (s, 1H), 8.01 (d, J = 8.8 Hz, 1H), 7.70 (d, J = 2.4 Hz, 1H), 7.47 (d, J = 8.1 Hz, 1H), 7.15 (dd, J = 8.8, 2.4 Hz, 1H), 7.11 (d, J = 7.8 Hz, 1H), 6.53 (s, 1H), 4.78 – 4.69 (m, 1H), 3.89 (dt, J = 12.3, 4.4 Hz, 3H), 3.53 (ddd, J = 11.8, 9.4, 2.8 Hz, 2H), 3.17 (s, J = 78.9 Hz, 3H), 3.13 – 3.08 (m, 2H), 3.04 – 2.96 (m, 2H), 2.86 (br s, 2H), 2.79 – 2.72 (m, 3H), 2.53 – 2.51 (m, 2H), 2.29 (s, 1H), 2.06 – 1.98 (m, 2H), 1.70 – 1.59 (m, 2H).; LCMS: 517.2 |
| 595 | | 1H NMR (DMSO-d6, 400MHz): δ 8.70 (d, J=5.38 Hz, 2H), 8.56 (s, 1H), 8.30 (d, J=8.31 Hz, 1H), 7.91 (d, J=8.80 Hz, 1H), 7.87 (d, J=5.38 Hz, 2H), 3.47 (br. s, 2H), 3.23 (d, J=6.36 Hz, 2H), 2.91-3.08 (m, 6H), 2.67-2.72 (m, 2H), 2.04-2.08 (m, 2H), 1.83-1.94 (m, 2H), 1.61-1.74 (m, 4H), 1.36-1.46 (m, 1H), 1.22-1.29 (m, 1H), 1.15 (d, J=6.36 Hz, 3H), 0.86 (t, J=7.34 Hz, 3H).; LCMS: 545.7 |
| 596 | | 1H NMR (DMSO-d6, 400MHz): δ 8.14 (d, J=7.83 Hz, 1H), 8.08 (d, J=8.31 Hz, 1H), 7.57 (t, J=7.58 Hz, 1H), 7.46 (t, J=7.58 Hz, 1H), 3.71 (s, 2H), 2.90-3.03 (m, 6H), 2.71 (t, J=6.36 Hz, 2H), 2.58 (dd, J=5.87, 12.23 Hz, 1H), 1.91 (d, J=3.42 Hz, 1H), 1.29-1.42 (m, 1H), 1.10-1.27 (m, 2H), 0.92 (d, J=6.36 Hz, 3H), 0.73 (t, J=7.34 Hz, 3H), 0.51 (d, J=4.40 Hz, 2H), 0.43 (d, J=2.45 Hz, 2H).; LCMS: 454.7 |
| 597 | | DMSO-d6, δ 11.69 (br. s, 1H), 9.36 (s, 2H), 8.72 (br. s, 2H), 8.49 (dd, J = 8.1, 1.0 Hz, 1H), 8.18 (s, 1H), 7.94 (dd, J = 7.7, 1.0 Hz, 1H), 7.85 (s, 1H), 7.76 (t, J = 8.0 Hz, 1H), 4.36 (s, 2H), 3.66 – 3.58 (m, 2H), 3.55 – 3.45 (m, 2H), 3.34 (s, 3H), 3.29 (t, J = 6.8 Hz, 2H), 3.21 (t, J = 4.8 Hz, 2H), 3.12 (t, J = 5.9 Hz, 2H), 2.83 (t, J = 6.9 Hz, 2H), 2.55 (s, 3H); LCMS: 497.1 |

| | | |
|---|---|---|
| 598 |  | DMSO-d6, δ 12.79 (br s, 1H), 9.73 – 8.68 (m, 4H), 8.09 (dd, J = 8.0, 1.0 Hz, 1H), 7.62 (dd, J = 7.3, 0.9 Hz, 1H), 7.52 – 7.48 (m, 1H), 5.48 (br s, 1H), 5.10 (s, 2H), 4.34 (s, 2H), 3.64 – 3.61 (m, 2H), 3.49 (t, J = 6.0 Hz, 2H), 3.34 – 3.30 (m, 2H), 3.32 (s, 3H), 3.21 – 3.13 (m, 6H).; LCMS: 446.9 |
| 599 |  | DMSO-d6, δ 12.68 (br s, 1H), 9.27 (br s, 2H), 8.63 (br s, 2H), 7.96 – 7.92 (m, 1H), 7.38 – 7.34 (m, 2H), 4.29 (s, 2H), 3.54 – 3.52 (m, 2H), 3.44 (t, J = 5.7 Hz, 2H), 3.35 – 3.31 (m, 2H), 3.25 (s, 3H), 3.14 – 3.08 (m, 6H), 3.00 (t, J = 7.0 Hz, 2H), 1.33 (t, J = 7.6 Hz, 3H).; LCMS: 445 |
| 600 |  | DMSO-d6, δ 11.42 (d, J = 46.3 Hz, 1H), 9.23 (d, J = 34.3 Hz, 2H), 8.57 (s, 2H), 7.52 (dd, J = 12.1, 4.2 Hz, 2H), 7.31 (d, J = 53.0 Hz, 1H), 7.06 – 6.93 (m, 1H), 5.16 (d, J = 30.1 Hz, 1H), 4.39 – 3.93 (m, 4H), 3.75 (s, 1H), 3.62 (d, J = 10.5 Hz, 1H), 3.57 (s, 1H), 3.52 – 3.48 (m, 2H), 3.40 (s, 2H), 3.23 (s, 3H), 3.17 (s, 2H), 3.08 (s, 2H), 2.85 – 2.64 (m, 3H).; LCMS: 488 |
| 601 |  | DMSO-d6, δ 12.87 (s, 1 H), 9.71 (dd, J = 1.5, 2.2 Hz, 2 H), 9.36 - 9.30 (m, 2 H), 9.04 (s, 1 H), 8.44 - 8.41 (m, 3 H), 8.15 - 8.12 (m, 1 H), 4.35 (br. s., 2 H), 3.53 - 3.49 (m, 3 H), 3.22 - 3.19 (m, 3 H), 2.97 (s, 1 H), 2.86 (s, 1 H), 2.80 (s, 6 H), 1.32 - 1.29 (m, 6 H), 1.25 - 1.21 (m, 1 H).; LCMS: 506.2 |
| 602 |  | #N/A |

*FIG. 1 (continued)*

| 603 | | #N/A |
|---|---|---|
| 604 | | #N/A |
| 605 | | #N/A |
| 606 | | 1H NMR (DMSO-d6/D2O, 400MHz): δ 8.79 (d, J=6.36 Hz, 2H), 8.74 (s, 1H), 8.33 (d, J=8.31 Hz, 1H), 8.22 (d, J=4.89 Hz, 2H), 8.00 (d, J=8.31 Hz, 1H), 4.31 (br. s, 2H), 3.84-3.87 (m, 1H), 3.48 (t, J=5.62 Hz, 2H), 3.35 (dd, J=5.38, 9.29 Hz, 2H), 3.28 (t, J=6.85 Hz, 2H), 3.17-3.21 (m, 2H), 3.12 (t, J=6.60 Hz, 2H), 2.86-2.95 (m, 3H), 2.84 (d, J=5.38 Hz, 1H), 1.85-2.03 (m, 4H).; LCMS: 544.8 |
| 607 | | 1H NMR (DMSO-d6/D2O, 400MHz): δ 8.14 (t, J=9.05 Hz, 2H), 7.62 (t, J=7.58 Hz, 1H), 7.50 (t, J=7.58 Hz, 1H), 4.33 (s, 2H), 3.49 (t, J=5.87 Hz, 2H), 3.25-3.34 (m, 2H), 3.12-3.22 (m, 3H), 3.02-3.09 (m, 2H), 1.69-1.78 (m, 1H), 1.43-1.54 (m, 1H), 1.22 (d, J=6.36 Hz, 3H), 0.91 (t, J=7.34 Hz, 3H).; LCMS: 415.65 |

FIG. 1 (continued)

| | | |
|---|---|---|
| 608 | (structure) | 1H NMR (DMSO-d6/D2O, 400MHz): δ 8.16 (t, J=8.07 Hz, 2H), 7.61 (t, J=7.58 Hz, 1H), 7.50 (t, J=7.58 Hz, 1H), 4.33 (br. s, 2H), 3.49 (t, J=5.38 Hz, 2H), 3.24-3.30 (m, 2H), 3.15-3.19 (m, 2H), 3.04-3.10 (m, 2H), 2.61 (s, 3H).; LCMS: 373.65 |
| 609 | (structure) | DMSO-d6, δ 12.44 (s, 1H), 9.51 (br s, 2H), 8.74 (br s, 2H), 8.22 (d, J = 8.5 Hz, 1H), 8.20 (d, J = 1.5 Hz, 1H), 7.47 (dd, J = 8.4, 1.8 Hz, 1H), 7.42 – 7.30 (m, 5H), 4.34 (s, 2H), 3.49 (s, 2H), 3.36 – 3.31 (m, 1H), 3.29 – 3.23 (m, 2H), 3.16 (t, J = 5.8 Hz, 2H), 3.09 (t, J = 7.0 Hz, 2H), 1.25 (d, J = 6.5 Hz, 6H).; LCMS: 509.1 |
| 610 | (structure) | DMSO-d6, δ 12.37 (s, 1H), 9.24 (br s, 2H), 8.71 (d, J = 1.7 Hz, 1H), 8.49 – 8.40 (m, 3H), 8.05 – 8.01 (m, 3H), 7.74 – 7.63 (m, 3H), 4.36 (s, 2H), 3.54 – 3.48 (m, 2H), 3.42 – 3.36 (m, 1H), 3.34 – 3.28 (m, 2H), 3.15 (t, J = 5.9 Hz, 2H), 3.11 (t, J = 6.9 Hz, 2H), 1.27 (d, J = 6.5 Hz, 6H).; LCMS: 541.1 |
| 611 | (structure) | DMSO-d6, δ 12.66 (s, 1H), 9.26 (br. s, 2H), 8.63 (br. s, 2H), 8.56 (d, J = 8.1 Hz, 1H), 8.00 (d, J = 7.5 Hz, 1H), 7.69 (t, J = 7.7 Hz, 1H), 4.38 (s, 2H), 3.63 – 3.59 (m, 2H), 3.58 – 3.51 (m, 2H), 3.34 (s, 3H), 3.24 – 3.17 (m, 4H), 3.03 (t, J = 6.9 Hz, 2H). 2H hidden under water signal; LCMS: 484.8 |

| | | |
|---|---|---|
| 612 |  | DMSO-d6, δ 12.40 (br. s, 1 H), 9.45 (br. s, 1 H), 8.74 (s, 1 H), 8.69 (br. s, 2 H), 7.63 (dd, J = 2.4, 6.6 Hz, 1 H), 7.40 - 7.36 (m, 2 H), 7.35 - 7.28 (m, 5 H), 6.95 (tt, J = 1.8, 6.5 Hz, 1 H), 4.39 - 4.32 (m, 2 H), 3.56 (t, J = 5.0 Hz, 2 H), 3.54 - 3.49 (m, 2 H), 3.30 (s, 3 H), 3.29 - 3.23 (m, 2 H), 3.23 - 3.18 (m, 2 H), 3.12 - 3.06 (m, 2 H), 2.99 (t, J = 6.8 Hz, 2 H); LCMS: 508.1 |
| 613 |  | DMSO-d6+D2O, δ 7.68 (d, J = 7.8 Hz, 1H), 7.45 (t, J = 8.1 Hz, 1H), 7.14 (d, J = 7.9 Hz, 1H), 4.31 (s, 2H), 4.02 (s, 3H), 3.60 – 3.56 (m, 2H), 3.48 (t, J = 6.0 Hz, 2H), 3.34 (t, J = 6.9 Hz, 2H), 3.29 (s, 3H), 3.19-3.13 (m, 4H), 3.02 (t, J = 6.9 Hz, 2H). 5 NH missing due to D2O; LCMS: 446.9 |
| 614 |  | DMSO-d6, δ 12.52 (s, 1H), 9.30 (s, 2H), 8.49 (s, 2H), 8.14 (d, J = 8.5 Hz, 1H), 8.11 (d, J = 1.5 Hz, 1H), 7.51 (dd, J = 8.4, 1.8 Hz, 1H), 4.37 (s, 2H), 3.85 – 3.79 (m, 1H), 3.52 (t, J = 5.9 Hz, 2H), 3.43 – 3.27 (m, 3H), 3.15 (t, J = 5.8 Hz, 2H), 3.08 (t, J = 6.9 Hz, 2H), 2.11 – 2.03 (m, 2H), 1.78 – 1.70 (m, 2H), 1.65 – 1.52 (m, 4H), 1.26 (d, J = 6.5 Hz, 6H).; LCMS: 501.1 |
| 615 |  | DMSO-d6, δ 12.47 (s, 1H), 9.30 (br s, 2H), 8.61 (d, J = 1.7 Hz, 1H), 8.50 (d, J = 8.5 Hz, 1H), 8.46 (br s, 2H), 7.98 (dd, J = 8.4, 1.8 Hz, 1H), 4.38 (s, 2H), 3.91 (tt, J = 8.9, 6.8 Hz, 1H), 3.53 (s, 2H), 3.41 – 3.35 (m, 1H), 3.34 – 3.27 (m, 2H), 3.19 (t, J = 5.6 Hz, 2H), 3.11 (t, J = 7.0 Hz, 2H), 1.97 – 1.89 (m, 2H), 1.87 – 1.79 (m, 2H), 1.70 – 1.54 (m, 4H), 1.26 (d, J = 6.5 Hz, 6H).; LCMS: 533.1 |

FIG. 1 (continued)

| | | |
|---|---|---|
| 616 | | DMSO-d6, δ 12.54 (s, 1H), 9.67 (s, 2H), 8.88 (s, 2H), 8.42 – 8.41 (m, 1H), 8.41 (dd, J = 1.9, 0.9 Hz, 1H), 8.32 (d, J = 8.4 Hz, 1H), 7.70 – 7.66 (m, 2H), 7.18 (ddd, J = 7.4, 4.9, 1.0 Hz, 1H), 7.06 (d, J = 8.1 Hz, 1H), 4.34 (s, 2H), 3.52 – 3.46 (m, 2H), 3.36 – 3.29 (m, 1H), 3.28 – 3.22 (m, 2H), 3.19 (t, J = 5.9 Hz, 2H), 3.12 (t, J = 7.1 Hz, 2H), 1.25 (d, J = 6.5 Hz, 6H).; LCMS: 509.9 |
| 617 | | DMSO-d6, δ 11.45 (s, 1H), 9.24 (s, 2H), 8.60 (s, 2H), 7.39 (dd, J = 7.9, 0.9 Hz, 1H), 7.29 (t, J = 7.9 Hz, 1H), 6.48 (dd, J = 7.9, 0.9 Hz, 1H), 5.65 (br. s, 1H), 4.71 – 4.61 (m, 1H), 4.50 (t, J = 8.1 Hz, 2H), 4.36 (s, 2H), 3.94 (dd, J = 8.5, 5.0 Hz, 2H), 3.59 (dd, J = 5.2, 5.2 Hz, 2H), 3.51 – 3.45 (m, 2H), 3.32 (s, 3H), 3.34 – 3.29 (m, 2H), 3.22 – 3.15 (m, 2H), 3.11 (t, J = 6.2 Hz, 2H), 2.98 (t, J = 7.1 Hz, 2H); LCMS: 488 |
| 618 | | 1H NMR (DMSO-d6/D2O, 400MHz): δ 8.66 (d, J=4.40 Hz, 2H), 8.53 (br. s, 1H), 8.27 (d, J=8.31 Hz, 1H), 7.90 (d, J=8.80 Hz, 1H), 7.85 (d, J=4.89 Hz, 2H), 4.17 (br. s, 2H), 3.37 (d, J=12.23 Hz, 2H), 3.30 (d, J=5.87 Hz, 2H), 3.14 (d, J=3.42 Hz, 3H), 3.07 (d, J=6.36 Hz, 2H), 1.66-1.78 (m, 2H), 1.47 (td, J=7.40, 14.06 Hz, 2H), 1.21 (d, J=6.36 Hz, 3H), 0.89 (t, J=7.34 Hz, 3H), 0.53-0.79 (m, 3H).; LCMS: 531.75 |
| 619 | | 1H NMR (DMSO-d6/D2O, 400MHz): δ 7.98-8.07 (m, 2H), 7.52 (t, J=7.58 Hz, 1H), 7.41 (t, J=7.34 Hz, 1H), 4.07 (d, J=6.85 Hz, 2H), 3.48 (br. s, 2H), 2.85-2.99 (m, 4H), 2.72-2.80 (m, 2H), 2.68 (d, J=5.38 Hz, 4H), 1.35 (td, J=6.48, 12.47 Hz, 2H), 1.10-1.24 (m, 2H), 0.90 (d, J=6.36 Hz, 3H), 0.69 (t, J=7.34 Hz, 3H).; LCMS: 505.3 |

*FIG. 1 (continued)*

| | | |
|---|---|---|
| 620 | | 1H NMR (DMSO-d6/D2O, 400MHz): δ 8.10 (d, J=6.85 Hz, 1H), 8.05 (d, J=7.82 Hz, 1H), 7.52-7.58 (m, 1H), 7.43 (t, J=7.09 Hz, 1H), 4.13 (d, J=6.36 Hz, 1H), 2.92-3.07 (m, 3H), 2.59-2.77 (m, 4H), 2.39-2.45 (m, 2H), 1.38-1.44 (m, 1H), 1.36 (d, J=6.36 Hz, 3H), 1.19 (d, J=5.38 Hz, 3H), 0.95 (d, J=5.87 Hz, 3H), 0.73 (t, J=6.85 Hz, 3H).; LCMS: 443.38 |
| 621 | | 1H NMR (DMSO-d6/D2O, 400MHz): δ 8.06 (dd, J=8.07, 14.43 Hz, 2H), 7.54 (t, J=7.58 Hz, 1H), 7.39-7.45 (m, 1H), 3.97 (d, J=5.87 Hz, 2H), 2.85-2.98 (m, 3H), 2.63-2.70 (m, 2H), 2.33-2.46 (m, 2H), 1.31 (d, J=6.36 Hz, 3H), 1.21 (d, J=5.38 Hz, 3H), 1.03-1.17 (m, 2H), 0.89 (d, J=5.87 Hz, 3H), 0.68 (t, J=7.34 Hz, 3H).; LCMS: 443 |
| 622 | | 1H NMR (DMSO-d6, 400MHz): δ 12.56 (s, 1H), 9.46 (s, 1H), 8.81 (br. s, 1H), 8.21 (d, J=7.83 Hz, 1H), 8.15 (d, J=7.82 Hz, 1H), 7.63 (t, J=7.58 Hz, 1H), 7.52 (t, J=7.58 Hz, 1H), 4.35 (br. s, 2H), 4.05 (q, J=6.85 Hz, 2H), 3.71 (t, J=4.65 Hz, 2H), 3.57-3.64 (m, 6H), 3.45-3.53 (m, 19H), 3.18 (d, J=4.89 Hz, 3H), 3.11 (t, J=7.09 Hz, 2H), 2.25-2.35 (m, 2H), 1.17 (t, J=7.09 Hz, 3H).; LCMS: 723.45 |
| 623 | | 1H NMR (DMSO-d6, 400MHz): δ 12.58 (s, 1H), 9.57-9.65 (m, 1H), 8.89-8.98 (m, 1H), 8.18 (dd, J=8.07, 17.85 Hz, 2H), 7.63 (t, J=7.58 Hz, 1H), 7.52 (t, J=7.34 Hz, 1H), 4.34 (br. s, 2H), 3.70-3.75 (m, 2H), 3.28-3.58 (m, 27H), 3.11-3.21 (m, 4H), 2.43 (t, J=5.62 Hz, 2H), 1.18-1.39 (m, 2H).; LCMS: 348.23 |
| 624 | | 1H NMR (DMSO-d6/D2O, 400MHz): δ 8.09 (d, J=7.83 Hz, 1H), 8.04 (d, J=8.31 Hz, 1H), 7.54 (t, J=7.58 Hz, 1H), 7.42 (t, J=7.58 Hz, 1H), 4.03-4.11 (m, 1H), 3.11-3.22 (m, 2H), 2.88-3.00 (m, 2H), 2.67 (t, J=6.11 Hz, 2H), 2.40 (dd, J=7.83, 15.16 Hz, 2H), 1.33 (d, J=6.85 Hz, 3H), 1.28 (d, J=10.27 Hz, 1H), 1.16 (d, J=6.36 Hz, 3H), 1.09-1.15 (m, 1H), 0.88 (d, J=6.36 Hz, 3H), 0.69 (t, J=7.34 Hz, 3H).; LCMS: 443.18 |

| 625 |  | DMSO-d6, δ 8.35 (d, J = 1.8 Hz, 1H), 8.23 (s, 1H), 8.11 (d, J = 8.6 Hz, 1H), 7.60 (dd, J = 8.5, 1.9 Hz, 1H), 3.63 (s, 2H), 3.06 – 2.95 (m, 3H), 2.91 (dd, J = 11.8, 5.3 Hz, 3H), 2.83 (t, J = 5.7 Hz, 2H), 2.77 (t, J = 6.6 Hz, 2H), 2.70 – 2.63 (m, 1H), 1.47 – 1.37 (m, 1H), 1.28 – 1.20 (m, 1H), 1.08 (d, J = 6.5 Hz, 6H), 0.97 (d, J = 6.4 Hz, 3H), 0.78 (t, J = 7.5 Hz, 3H).; LCMS: 535.1/537.0 |

FIG. 2

| Compound No. | Structure | NMR/LCMS |
|---|---|---|
| 200 | 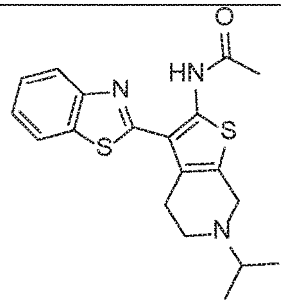 | $^1$H NMR (DMSO-$d_6$, 400MHz):δ 12.58 (s, 1H), 8.14 (dd, $J$=3.42, 7.83 Hz, 2H), 7.58 (t, $J$=7.83 Hz, 1H), 7.41-7.49 (m, 1H), 3.64 (br. s, 2H), 2.79-2.98 (m, 5H), 2.32 (s, 3H), 1.08 (d, $J$=5.87 Hz, 6H). LCMS: [M+H]$^+$ = 372.00 |
| 201 | 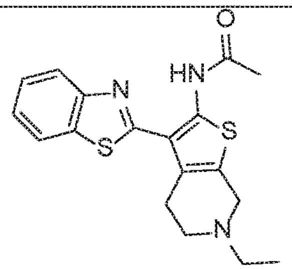 | $^1$H NMR (DMSO-$d_6$, 400MHz): δ 12.59 (br. s, 1H), 8.15 (d, $J$=7.59 Hz, 2H), 7.58 (t, $J$=7.59 Hz, 1H), 7.46 (t, $J$=7.59 Hz, 1H), 3.55 (s, 2H), 2.91-2.95 (m, 2H), 2.76-2.83 (m, 2H), 2.53-2.61 (m, 2H), 2.32 (s, 3H), 1.10 (t, $J$=7.14 Hz, 3H). LCMS: [M+H]$^+$ = 357.90 |
| 202 | 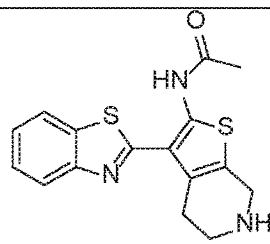 | $^1$H NMR (DMSO-$d_6$, 400MHz): δ 12.50 (s, 1H), 9.48 (br. s, 1H), 8.19 (d, $J$=7.89 Hz, 2H), 7.61 (t, $J$=7.67 Hz, 1H), 7.46-7.52 (m, 1H), 4.31-4.35 (m, 2H), 3.48 (br. s, 2H), 3.15-3.19 (m, 2H), 2.35 (s, 3H). LCMS: [M+H]$^+$ = 329.90 |
| 203 | 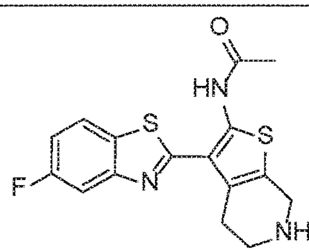 | $^1$H NMR (400 MHz, DMSO-d6) δ 12.44 (s, 1H), 9.38 (s, 2H), 8.23 (dd, $J$ = 8.9, 5.3 Hz, 1H), 8.09 (dd, $J$ = 9.9, 2.5 Hz, 1H), 7.41 (td, $J$ = 9.0, 2.5 Hz, 1H), 4.33 (s, 2H), 3.49 (d, $J$ = 6.5 Hz, 2H), 3.19 – 3.11 (m, 2H), 2.35 (s, 3H). LCMS: [M+H]$^+$ =347.95 |
| 204 | 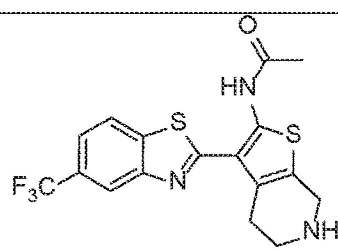 | $^1$H NMR (DMSO-$d_6$, 400MHz): δ 12.40 (s, 1H), 9.42 (s, 2H), 8.65 (s, 1H), 8.44 (d, $J$ = 8.4 Hz, 1H), 7.82 (d, $J$ = 8.4 Hz, 1H), 4.34 (s, 2H), 3.59 – 3.46 (m, 2H), 3.19 (d, $J$ = 6.2 Hz, 2H), 2.39 (s, 3H). LCMS: [M+H]$^+$ =398.00 |

FIG. 2 (continued)

| | | |
|---|---|---|
| 205 | 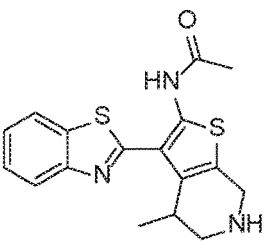 | ¹H NMR (DMSO-d₆, 400MHz): δ 11.95 (s, 1H), 8.17 (dd, J=7.89, 13.59 Hz, 2H), 7.57-7.63 (m, 1H), 7.48-7.53 (m, 1H), 4.23-4.36 (m, 2H), 3.55-3.64 (m, 2H), 3.44-3.51 (m, 1H), 3.37 (d, J=2.19 Hz, 1H), 2.26 (s, 3H), 1.21 (d, J=7.02 Hz, 3H). LCMS: [M+H]⁺ =343.95 |
| 206* | 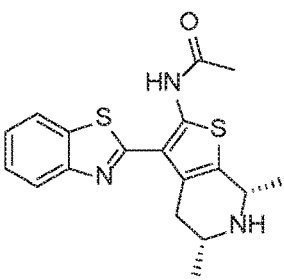 | ¹H NMR (DMSO-d₆, 400MHz): δ 12.51 (s, 1H), 9.69 (d, J=10.64 Hz, 1H), 9.11 (br. s, 1H), 8.19 (d, J=8.32 Hz, 2H), 7.58-7.65 (m, 1H), 7.51 (t, J=7.63 Hz, 1H), 4.69-4.73 (m, 1H), 3.69 (d, J=7.86 Hz, 1H), 3.38-3.40 (m, 1H), 2.78-2.89 (m, 1H), 2.35 (s, 3H), 1.62 (d, J=6.94 Hz, 3H), 1.49 (d, J=6.47 Hz, 3H). LCMS: [M+H]⁺ =358.00 |
| 207 | 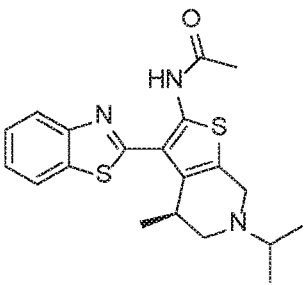 | ¹H NMR (DMSO-d₆, 400MHz): δ 12.42 (s, 1H), 8.15 (t, J=8.55 Hz, 2H), 7.58 (t, J=7.40 Hz, 1H), 7.43-7.50 (m, 1H), 3.76 (d, J=14.80 Hz, 1H), 3.50 (d, J=14.80 Hz, 1H), 3.26-3.31 (m, 1H), 2.89 (td, J=6.47, 12.95 Hz, 1H), 2.80 (d, J=11.10 Hz, 1H), 2.59 (dd, J=3.01, 11.33 Hz, 1H), 2.29 (s, 3H), 1.25 (d, J=6.47 Hz, 3H), 1.07 (dd, J=6.71, 9.94 Hz, 6H). LCMS: [M+H]⁺ = 386.05 |
| 208 | 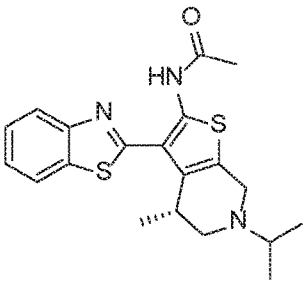 | ¹H NMR (DMSO-d₆, 400MHz): δ 12.42 (s, 1H), 8.15 (t, J=8.32 Hz, 2H), 7.54-7.60 (m, 1H), 7.43-7.50 (m, 1H), 3.76 (d, J=14.80 Hz, 1H), 3.50 (d, J=14.33 Hz, 1H), 3.23-3.30 (m, 1H), 2.89 (td, J=6.47, 12.95 Hz, 1H), 2.80 (d, J=10.64 Hz, 1H), 2.59 (dd, J=3.24, 11.10 Hz, 1H), 2.29 (s, 3H), 1.25 (d, J=6.47 Hz, 3H), 1.07 (dd, J=6.47, 9.71 Hz, 6H). LCMS: [M+H]⁺ = 386.05 |

FIG. 2 (continued)

| | | |
|---|---|---|
| 209 | 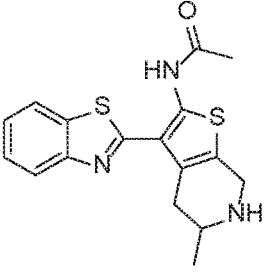 | ¹H NMR (DMSO-d₆, 400MHz): δ 12.61 (br. s, 1H), 8.15 (t, $J$=7.96 Hz, 2H), 7.58 (t, $J$=7.72 Hz, 1H), 7.42-7.51 (m, 1H), 3.88 (m, 2H), 2.85-3.02 (m, 2H), 2.39-2.43 (m, 2H), 2.33 (s, 3H), 1.24 (d, $J$=6.09 Hz, 3H). LCMS-Condition 1: [M+H]⁺ =344.00. |
| 210 | 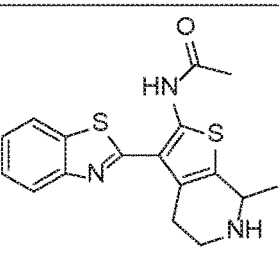 | ¹H NMR (DMSO-d₆, 400MHz): δ 12.61 (br. s, 1H), 8.15 (d, $J$=8.43 Hz, 2H), 7.58 (t, $J$=7.72 Hz, 1H), 7.39-7.51 (m, 1H), 3.98 (d, $J$=6.09 Hz, 1H), 2.90 (dd, $J$=7.02, 12.17 Hz, 2H), 2.82 (m, 3H), 2.33 (s, 3H), 1.34 (d, $J$=6.55 Hz, 3H). LCMS-Condition 1: [M+H]⁺ =343.95 |
| 211* | 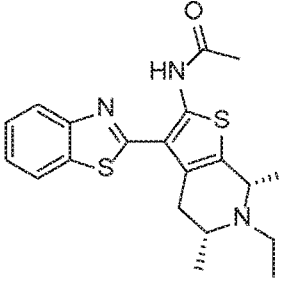 | ¹H NMR (DMSO-d₆, 400MHz): δ 12.60 (d, $J$=14.51 Hz, 1H), 8.16 (t, $J$=7.26 Hz, 2H), 7.58 (t, $J$=7.72 Hz, 1H), 7.45 (t, $J$=7.72 Hz, 1H), 3.97-4.00 (m, 1H), 2.56-3.22 (m, 5H), 2.33 (s, 3H), 1.38-1.42 (m, 3H), 1.18-1.32 (m, 3H), 0.93-1.10 (m, 3H). LCMS: [M+H]⁺ = 386.10 |
| 212 | 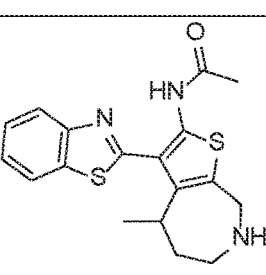 | ¹H NMR (DMSO-d₆, 400MHz): δ 9.24 (br. s, 1H), 8.73 (br. s, 1H), 8.17 (m, 2H), 7.57-7.64 (m, 1H), 7.47-7.55 (m, 1H), 4.37-4.55 (m, 2H), 3.39-3.49 (m, 1H), 2.16 (s, 3H), 2.00-2.12 (m, 1H), 1.86-1.98 (m, 1H), 1.30 (d, $J$=7.10 Hz, 3H). LCMS: [M+H]⁺ = 358.10 |
| 213 | 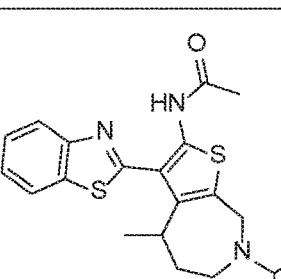 | ¹H NMR (DMSO-d₆, 400MHz): δ 11.66 (br. s, 1H), 8.15 (dd, $J$=8.16, 10.81 Hz, 2H), 7.58 (t, $J$=7.28 Hz, 1H), 7.50 (t, $J$=7.28 Hz, 1H), 3.70-3.88 (m, 2H), 3.54-3.57 (m, 1H), 2.77-3.14 (m, 3H), 2.17 (s, 3H), 2.00 (d, $J$=6.17 Hz, 1H), 1.67-1.69 (m, 1H), 1.29 (d, $J$=7.06 Hz, 3H), 1.03 (d, $J$=10.14 Hz, 6H). LCMS: [M+H]⁺ = 400.05 |

| | | |
|---|---|---|
| 214 |  | ¹H NMR (DMSO-d₆, 400MHz): δ 12.66 (s, 1H), 8.17 (d, J=8.33 Hz, 2H), 7.59 (t, J=7.45 Hz, 1H), 7.46-7.51 (m, 1H), 4.73 (t, J=7.45 Hz, 1H), 3.12-3.25 (m, 2H), 3.03 (d, J=8.77 Hz, 1H), 2.89 (m, 1H), 2.74-2.84 (m, 1H), 2.35 (s, 3H). LCMS: [M+H]⁺ =397.98. |
| 215 |  | ¹H NMR (DMSO-d₆, 400MHz): δ 12.53 (s, 1H), 8.18 (dd, J=7.94, 15.88 Hz, 2H), 7.56-7.61 (m, 1H), 7.47 (t, J=7.50 Hz, 1H), 3.87-4.02 (m, 2H), 3.74 (d, J=2.65 Hz, 1H), 3.12 (dd, J=2.87, 14.77 Hz, 1H), 2.99 (dd, J=5.95, 9.92 Hz, 1H), 2.77-2.87 (m, 1H), 2.33 (s, 3H). LCMS: [M+H]⁺ =397.98. |
| 216 |  | ¹H NMR (DMSO-d₆, 400MHz): δ 12.58 (br. s, 1H), 8.15 (d, J=8.38 Hz, 2H), 7.58 (t, J=7.50 Hz, 1H), 7.43-7.50 (m, 1H), 3.97 (m, 1H), 3.12 (m, 2H), 2.72-2.87 (m, 3H), 2.33 (s, 3H), 1.35 (d, J=6.62 Hz, 3H), 1.11 (d, J=6.17 Hz, 3H), 1.00 (d, J=6.62 Hz, 3H). LCMS: [M+H]⁺ = 386.05 |
| 217 |  | ¹H NMR (400 MHz, DMSO-d6) δ 12.48 (s, 1H), 8.17 (t, J = 7.6 Hz, 2H), 7.59 (t, J = 7.7 Hz, 1H), 7.48 (t, J = 7.6 Hz, 1H), 5.73 (d, J = 51.6 Hz, 1H), 4.00 (dd, J = 17.0, 5.9 Hz, 1H), 3.77 (dd, J = 16.9, 11.1 Hz, 1H), 3.43 (t, J = 15.4 Hz, 1H), 3.04 (d, J = 14.7 Hz, 1H), 2.99 – 2.90 (m, 1H), 2.33 (s, 3H). LCMS: [M+H]⁺ =348.00. |

| | | |
|---|---|---|
| 218* |  | ¹H NMR (400 MHz, DMSO-d6) δ 12.62 (s, 1H), 8.15 (dd, $J$ = 8.8, 7.6 Hz, 2H), 7.57 (ddd, $J$ = 8.3, 7.1, 1.3 Hz, 1H), 7.46 (td, $J$ = 7.6, 7.1, 1.2 Hz, 1H), 4.08 – 3.95 (m, 1H), 3.03 – 2.89 (m, 2H), 2.47 – 2.36 (m, 1H), 2.32 (s, 3H), 1.33 (d, $J$ = 6.5 Hz, 3H), 1.24 (d, $J$ = 5.9 Hz, 3H). LCMS: [M+H]⁺ = 358.00. |
| 219* |  | ¹H NMR (400 MHz, DMSO-d6) δ 12.60 (s, 1H), 8.16 (dd, $J$ = 8.2, 6.6 Hz, 2H), 7.63 – 7.53 (m, 1H), 7.47 (dd, $J$ = 8.1, 6.9 Hz, 1H), 4.10 (s, 1H), 3.00 (d, $J$ = 16.7 Hz, 2H), 2.45 (s, 1H), 2.33 (s, 3H), 1.37 (d, $J$ = 6.5 Hz, 3H), 1.30 – 1.21 (m, 3H). LCMS: [M+H]⁺ = 358.05 |
| 220 |  | ¹H NMR (400 MHz, DMSO-d6) δ 12.51 (s, 1H), 8.16 (t, $J$ = 7.5 Hz, 2H), 7.58 (t, $J$ = 7.7 Hz, 1H), 7.47 (t, $J$ = 7.6 Hz, 1H), 5.87 (d, $J$ = 51.6 Hz, 1H), 3.92 (dd, $J$ = 15.6, 6.1 Hz, 1H), 3.46 (dd, $J$ = 15.4, 10.7 Hz, 1H), 2.95 (p, $J$ = 6.9 Hz, 1H), 2.75 (d, $J$ = 13.6 Hz, 1H), 2.66 (d, $J$ = 13.1 Hz, 1H), 2.33 (s, 3H), 1.08 (dd, $J$ = 6.5, 3.9 Hz, 6H). LCMS: [M+H]⁺ = 390.10. |
| 221 |  | LCMS: [M+H]⁺ =344.00. |

FIG. 2 (continued)

| | | |
|---|---|---|
| 222 | 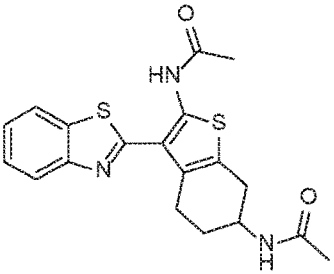 | ¹H NMR (400 MHz, DMSO-d6) δ 12.62 (s, 1H), 8.19 – 8.11 (m, 2H), 8.00 (d, *J* = 7.5 Hz, 1H), 7.62 – 7.53 (m, 1H), 7.51 – 7.41 (m, 1H), 4.06 (t, *J* = 8.3 Hz, 1H), 3.05 (dt, *J* = 15.6, 5.1 Hz, 1H), 2.92 (td, *J* = 15.8, 6.6 Hz, 2H), 2.61 – 2.52 (m, 1H), 2.32 (s, 3H), 2.01 (t, *J* = 9.0 Hz, 1H), 1.83 (s, 4H). LCMS: [M+H]⁺ = 385.90 |
| 223 | 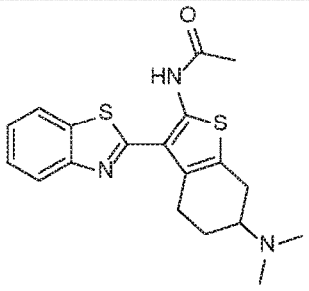 | ¹H NMR (400 MHz, DMSO-d6) δ 12.60 (s, 1H), 8.17 – 8.09 (m, 2H), 7.57 (ddd, *J* = 8.2, 7.1, 1.3 Hz, 1H), 7.50 – 7.41 (m, 1H), 3.06 (dt, *J* = 15.7, 4.4 Hz, 1H), 2.80 (q, *J* = 9.3, 8.5 Hz, 2H), 2.71 – 2.58 (m, 2H), 2.28 (d, *J* = 16.7 Hz, 9H), 2.11 (d, *J* = 12.6 Hz, 1H), 1.68 (dq, *J* = 11.9, 5.1 Hz, 1H). LCMS: [M+H]⁺ = 371.90 |
| 224 | 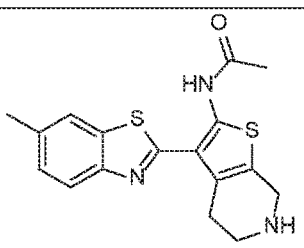 | ¹H NMR (DMSO-*d*₆, 400 MHz): δ 12.52 (s, 1H), 9.36 (s, 2H), 8.06 (d, *J* = 8.3 Hz, 1H), 7.97 (s, 1H), 7.43 (d, *J* = 8.8 Hz, 1H), 4.33 (s, 2H), 3.48-3.42 (m, 2H), 3.15-3.08 (m, 2H), 2.48 (s, 3H), 2.34 (s, 3H). LCMS: [M+H]⁺ = 344.00 |
| 225 | 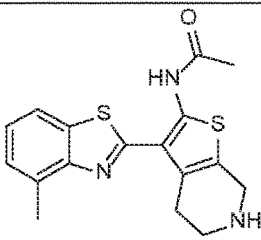 | ¹H NMR (DMSO-*d*₆, 400MHz): δ 12.81 (s, 1H), 9.40 (s, 2H), 8.00 (d, *J* = 7.2 Hz, 1H), 7.44 – 7.37 (m, 2H), 4.34 (s, 2H), 3.50-3.43 (m, 2H), 3.17-3.12 (m, 2H), 2.76 (s, 3H), 2.34 (s, 3H). LCMS: [M+H]⁺ = 343.85 |
| 226 | 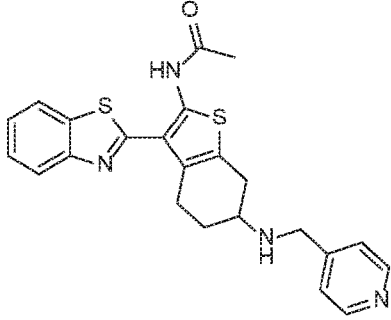 | ¹H NMR (DMSO-*d*₆, 400MHz): δ 12.60 (s, 1H), 8.49 (dt, *J* = 4.5, 1.2 Hz, 2H), 8.15 – 8.12 (m, 2H), 7.57 (ddt, *J* = 8.4, 7.2, 1.2 Hz, 1H), 7.47-7.38 (m, 3H), 3.84 (s, 2H), 3.32 (d, *J* = 1.1 Hz, 2H), 3.05 – 2.97 (m, 3H), 2.91 – 2.70 (m, 1H), 2.30 (s, 3H), 2.18-2.05 (m, 1H), 1.72-1.58 (m, 1H). LCMS: [M+H]⁺ = 435.15 |

| | | |
|---|---|---|
| 227 |  | ¹H NMR (DMSO-$d_6$, 400MHz): 12.56 (s, 1H), 9.69 (br s, 1H), 9.62 (br s, 1H), 9.07 (br s, 1H), 8.97 (br s, 1H), 8.16 (dd, $J$ = 8.0, 5.4 Hz, 2H), 7.59 (t, $J$ = 8.0 Hz, 1H), 7.47 (t, $J$ = 7.6 Hz, 1H), 3.73 (s, 1H), 3.59 (s, 1H), 3.17-3.10 (m, 3H), 3.30 – 3.08 (m, 3H), 2.95-2.80 (m, 3H), 2.32 (s, 3H), 2.29-2.20 (m, 2H), 2.01 – 1.89 (m, 3H). LCMS: [M+H]⁺ =427.05 |
| 228 |  | LCMS: [M+H]⁺ = 527.30 |
| 229 |  | ¹H NMR (400 MHz, DMSO-d6) δ 12.38 (s, 1H), 9.45 – 9.40 (m, 2H), 8.76 (d, $J$ = 1.7 Hz, 1H), 8.33 (d, $J$ = 8.4 Hz, 1H), 8.04 (dd, $J$ = 8.4, 1.6 Hz, 1H), 4.34 (s, 2H), 3.94 (s, 3H), 3.50 (t, $J$ = 6.2 Hz, 2H), 3.18 (t, $J$ = 6.0 Hz, 2H), 2.38 (s, 3H). LCMS: [M+H]⁺ =388.03 |
| 230 |  | ¹H NMR (400 MHz, DMSO-d6) δ 12.63 (s, 1H), 9.51 – 9.44 (m, 2H), 7.96 (d, $J$ = 8.8 Hz, 1H), 7.54 (s, 1H), 7.13 (s, 1H), 4.32 (d, $J$ = 4.3 Hz, 2H), 3.51 – 3.44 (m, 2H), 3.15 (t, $J$ = 6.1 Hz, 2H), 3.04 (s, 6H), 2.36 (s, 3H). LCMS: [M+H]⁺ =372.95. |

FIG. 2 (continued)

| | | |
|---|---|---|
| 231 | 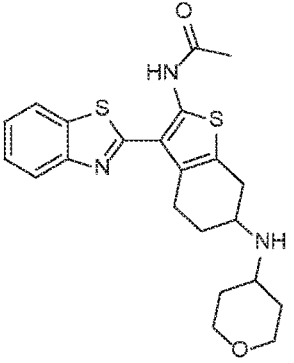 | ¹H NMR (400 MHz, DMSO-d6) δ 12.60 (s, 1H), 8.18 – 8.10 (m, 2H), 7.57 (ddd, J = 8.4, 7.2, 1.2 Hz, 1H), 7.46 (ddd, J = 8.2, 7.2, 1.1 Hz, 1H), 3.83 (dt, J = 11.4, 3.5 Hz, 2H), 3.34-3.31 (m, 1H), 3.29 (d, J = 2.3 Hz, 1H), 3.13 (s, 1H), 3.08 – 2.77 (m, 4H), 2.42 (dd, J = 15.7, 8.6 Hz, 2H), 2.31 (s, 3H), 2.12 – 2.03 (m, 1H), 1.81 – 1.73 (m, 2H), 1.62 (qd, J = 9.7, 5.4 Hz, 1H), 1.33 – 1.17 (m, 2H). LCMS: [M+H]⁺ = 428.10 |
| 232 | 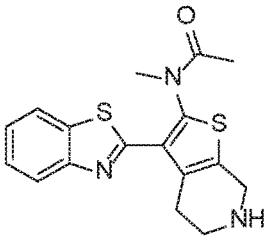 | ¹H NMR (DMSO-d₆, 400MHz): δ 9.63 (br. s, 2H), 8.20 (d, J=7.98 Hz, 1H), 8.08 (d, J=7.98 Hz, 1H), 7.54-7.62 (m, 1H), 7.47-7.54 (m, 1H), 4.42 (br. s, 2H), 3.45-3.49 (m, 2H), 3.35-3.39 (m, 2H), 3.20 (s, 3H), 1.87 (s, 3H). LCMS: [M+H]⁺ =344.00 |
| 233 | 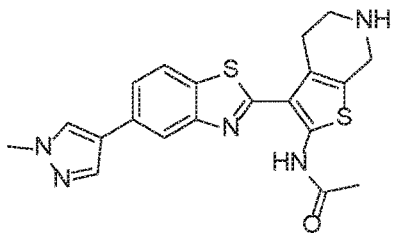 | DMSO-d6, δ 12.58 (s, 1H), 9.57 (s, 2H), 8.36 (d, J = 1.5 Hz, 1H), 8.30 (s, 1H), 8.13 (d, J = 8.4 Hz, 1H), 8.03 (s, 1H), 7.71 (dd, J = 8.4, 1.6 Hz, 1H), 4.32 (s, 2H), 3.90 (s, 3H), 3.49 (t, J = 6.1 Hz, 2H), 3.17 (t, J = 5.9 Hz, 2H), 2.38 (s, 3H).; LCMS: 410.1 |
| 234 | 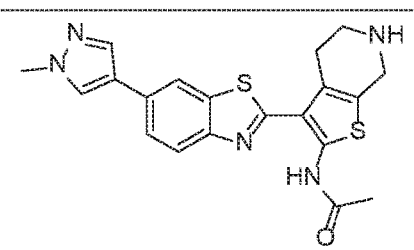 | DMSO-d6, δ 12.48 (s, 1H), 9.47 (br. s, 2H), 8.35 (d, J = 1.4 Hz, 1H), 8.25 (s, 1H), 8.14 (d, J = 8.5 Hz, 1H), 7.98 (d, J = 0.7 Hz, 1H), 7.81 (dd, J = 8.5, 1.8 Hz, 1H), 4.33 (br. s, 2H), 3.90 (s, 3H), 3.54 – 3.45 (m, 2H), 3.17 (t, J = 5.7 Hz, 2H), 2.35 (s, 3H); LCMS: 410.1 |
| 235 | 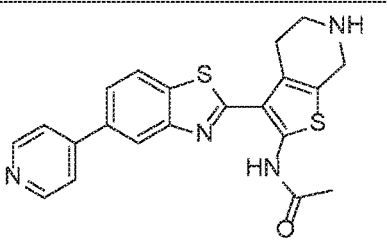 | DMSO-d6, δ 12.54 (s, 1H), 9.48 (s, 2H), 8.86 (d, J = 5.7 Hz, 2H), 8.78 (s, 1H), 8.39 (d, J = 8.4 Hz, 1H), 8.21 (d, J = 3.4 Hz, 2H), 8.04 (dd, J = 8.5, 1.7 Hz, 1H), 4.34 (s, 2H), 3.49 (t, J = 6.1 Hz, 2H), 3.19 (t, J = 5.9 Hz, 2H), 2.40 (s, 3H).; LCMS: 407.1 |

*FIG. 2 (continued)*

| | | |
|---|---|---|
| 236 | | 1H NMR (DMSO-d6, 400MHz): δ 12.46 (br. s, 1H), 7.69 (d, J=13.21 Hz, 2H), 6.16 (br. s, 2H), 3.59-3.74 (m, 3H), 2.79-2.92 (m, 4H), 2.31 (br. s, 3H), 1.01-1.15 (m, 6H); LCMS: 416.2 |
| 237 | | 1H NMR (DMSO-d6, 400MHz): δ 12.42 (br. s, 1H), 9.40 (br. s, 2H), 7.74 (s, 1H), 7.71 (s, 1H), 6.17 (s, 2H), 4.32 (br. s, 2H), 3.46-3.51 (m, 2H), 3.10-3.15 (m, 2H), 2.33 (s, 3H).; LCMS: 373.75 |
| 238 | | DMSO-d6, δ 12.51 (s, 1H), 9.58 – 9.42 (m, 2H), 8.88 (d, J = 5.2 Hz, 2H), 8.85 (d, J = 1.7 Hz, 1H), 8.36 (d, J = 8.6 Hz, 1H), 8.23 (d, J = 4.2 Hz, 2H), 8.19 (dd, J = 8.6, 1.9 Hz, 1H), 4.34 (s, 2H), 3.54 – 3.47 (m, 2H), 3.20 (t, J = 5.8 Hz, 2H), 2.38 (s, 3H); LCMS: 407.1 |

COMPOUNDS FOR THE MODULATION OF MYC ACTIVITY

CROSS REFERENCE TO RELATED APPLICATIONS

The present application is a U.S. National Phase Application under 35 U.S.C. § 371 of International Application PCT/US2016/035940, filed Jun. 5, 2016, which claims priority under 35 U.S.C. § 119(e) to U.S. Provisional Application No. 62/171,775, filed on Jun. 5, 2015. The entire disclosures of each of the foregoing applications are incorporated herein by reference.

BACKGROUND OF THE INVENTION

The transcription factor c-Myc plays an important role in the regulation of cell proliferation, cell growth, apoptosis, the cell cycle, and oncogenesis. c-Myc, a basic helix-loop-helix (bHLH) leucine zipper protein, is the most frequently occurring oncoprotein in a wide range of cancers, including breast, lung, and prostate cancers, where its deregulation provides growth factor-independent growth (Tansey, W. P. *New J Sci* (2014) 2014: 1-27; Dang, C. V. *Cell* (2012) 149:22-35). Myc proteins arise from three distinct gene families, c-myc, N-myc, and L-myc, each of which functions in an analogous manner but exhibits differences in expression levels and potency (Nesbit, C. E. et al, *Oncogene* (1999) 13:3004-3016; Tansey, W. P. *New J Sci* (2014) 2014:1-27; Dang, C. V. *Cell* (2012) 149:22-35). c-Myc requires heterodimerization with the small bHLH leucine zipper protein Max to bind DNA and activate gene transcription. Interaction of c-Myc with Max occurs at all c-Myc-bound genes in the genome and is essential for its oncogencity (Tansey, W. P. *New J Sci* (2014) 2014: 1-27). Further, Max is capable of dimerization with additional bHLH proteins that may influence the c-Myc-Max interaction, such as Mad and Mx11 (Tansey, W. P. *New J Sci* (2014) 2014: 1-27; C. Grandori et al, *Ann Rev Cell Dev Biol* (2000) 16:653-699)

The myc gene is deregulated in cancer through multiple mechanisms including gene amplification, chromosomal translocation, deregulated upstream signaling, and protein stabilization, where the end result is increased levels of the resulting Myc protein (Nesbit, C. E. et al, *Oncogene* (1999) 13:3004-3016). Transgenic mouse models studies have demonstrated that genetic inactivation of myc leads to tumor regression in a range of cancer types (Jain, M. *Science* (2002) 297:102-104; Felsher, D. et al, *Mol Cell* (1999) 4:199-207; Choi, P. S. et al, *Proc Natl Acad Sci USA* (2011) 108:17432-17437; Murphy, D. et al. *Cancer Cell* (2008) 14:447-457; He, T. C. et al, *Science* (1998) 281:1509-1512). In some models, even brief inactivation of Myc significantly improves survival rates (Murphy, D. et al. *Cancer Cell* (2008) 14:447-457; Chesi, M. et al. *Cancer Cell* (2008) 13:167-180; Pelengaris, S. et al, *Mol Cell* (1999) 3:565-577). Additional studies have confirmed these findings in a number of other aggressive tumor models, where the prediction is that Myc inhibitors would have broad utility across multiple cancer types (Hermeking, H. *Curr Cancer Drug Targets* (2003) 3:163-175; Soucek, L. *Nature* (2008) 455:679-683; Konstantinopoulos, P. et al, *JAMA* (2011) 305:2349-2350; Soucek, L. et al, *Nature* (2008) 455:679-683). As such, there is a need to identify compounds that are capable of modulating Myc activity for use as therapeutic agents.

SUMMARY OF THE INVENTION

Figure 1:
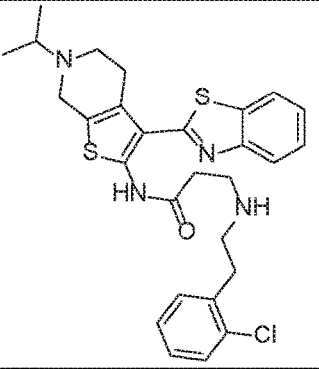
FIG. 1 is a table of exemplary compounds of Formula I.
Figure 1:
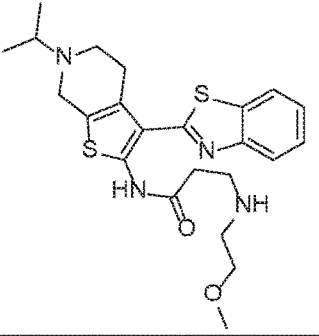
Figure 1:
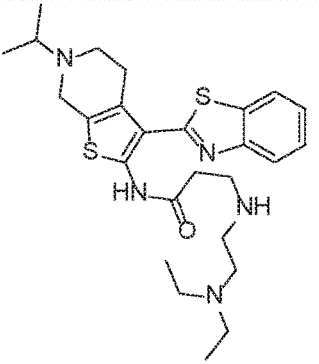
Figure 1:
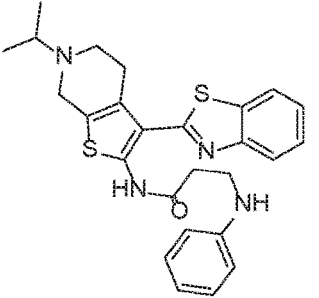
Figure 1:
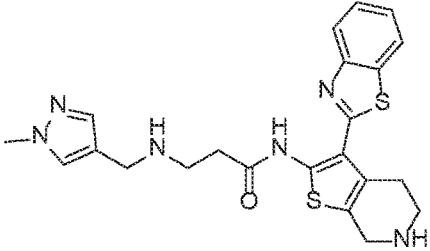
Figure 1:
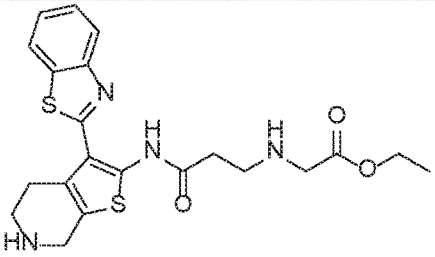
Figure 1:
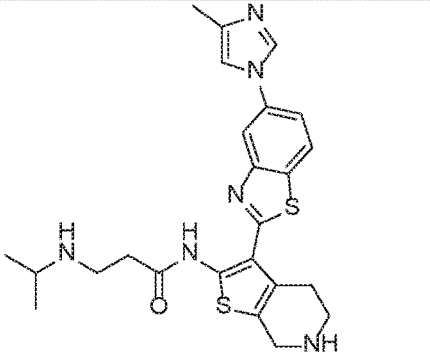
Figure 1:
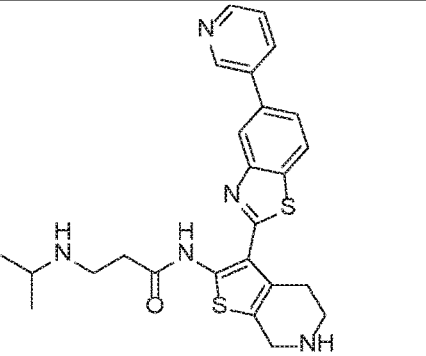
Figure 1:
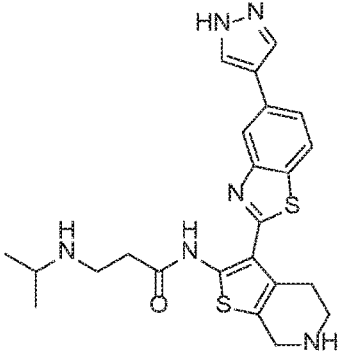
Figure 1:
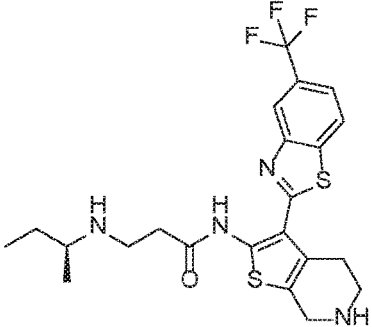
Figure 1:
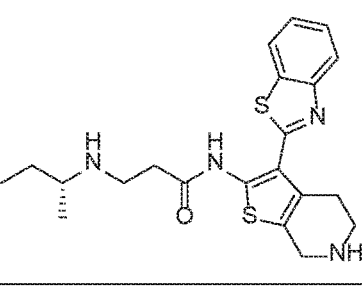
Figure 1:
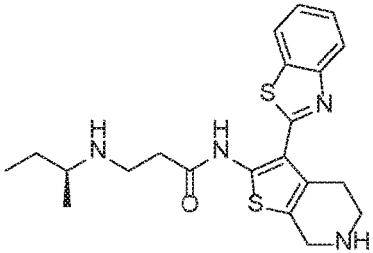
Figure 1:
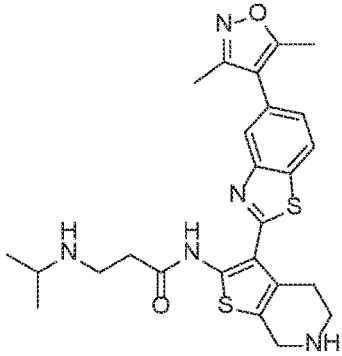
Figure 1:
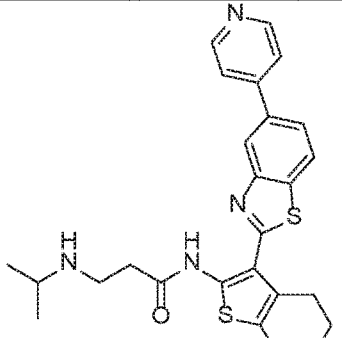
Figure 1:
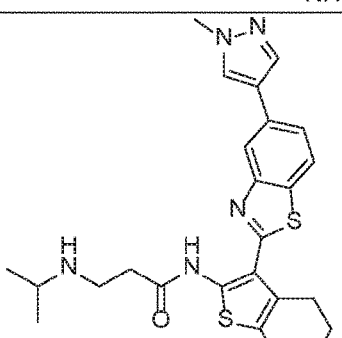
Figure 1:
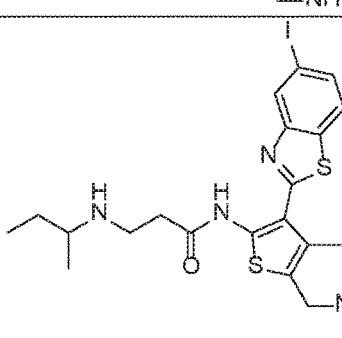
Figure 1:
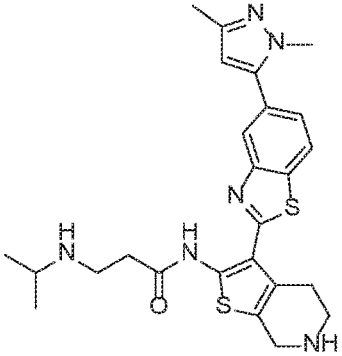
Figure 1:
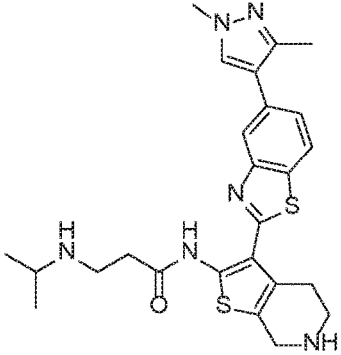
Figure 1:
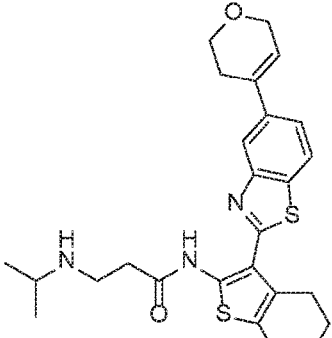
Figure 1:
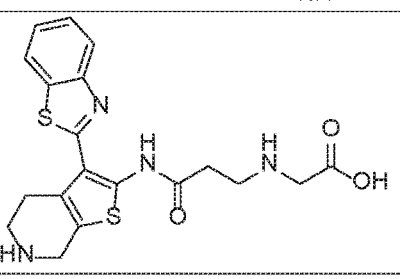
Figure 1:
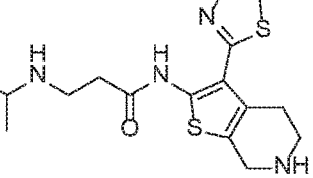
Figure 1:
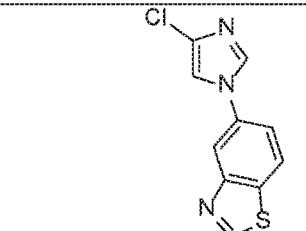
Figure 1:
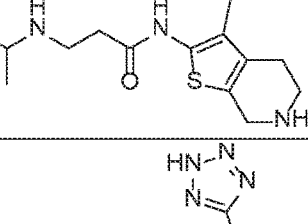
Figure 1:
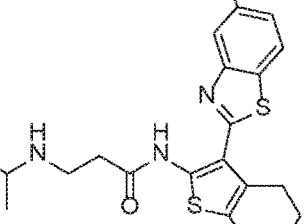
Figure 1:
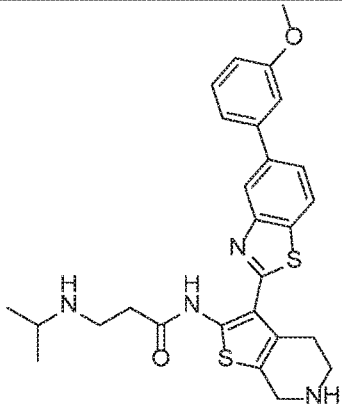
Figure 1:
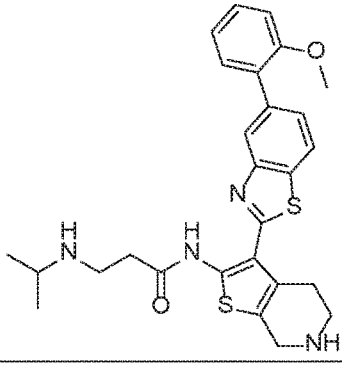
Figure 1:
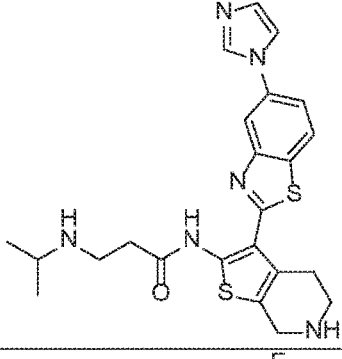
Figure 1:
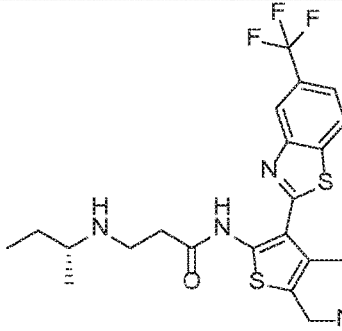
Figure 1:
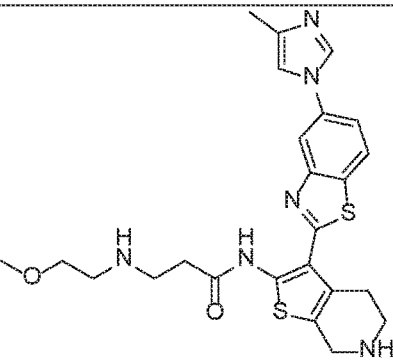
Figure 1:
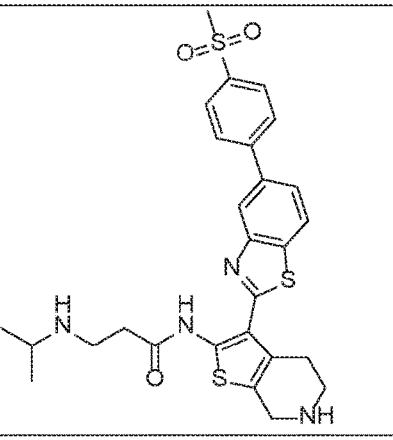
Figure 1:
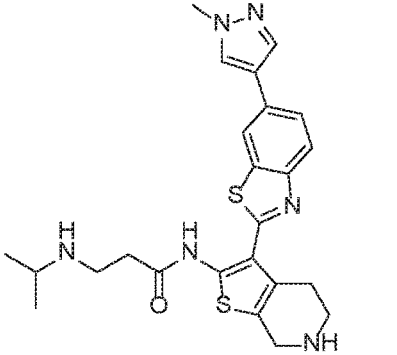
Figure 1:
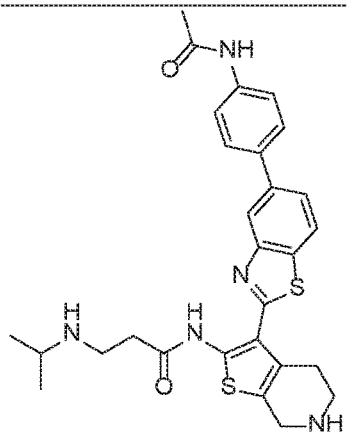
Figure 1:
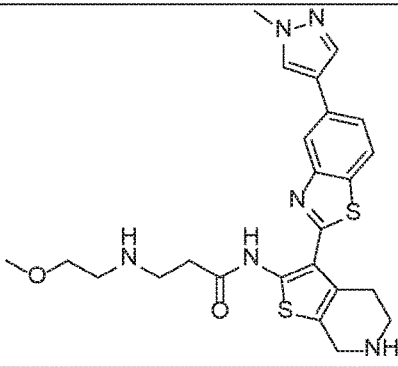
Figure 1:
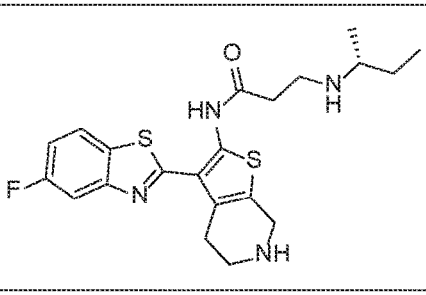
Figure 1:
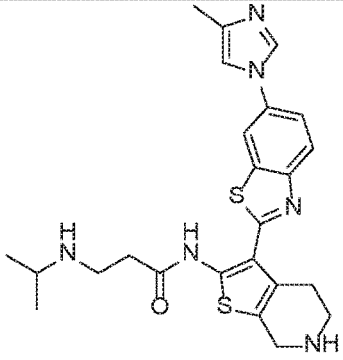
Figure 1:
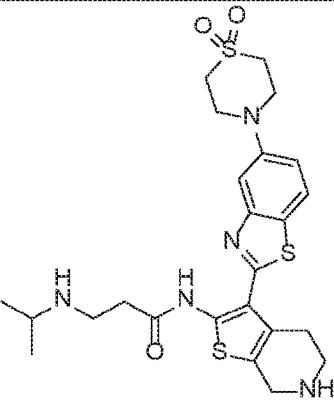
Figure 1:

Figure 1:

Figure 1:
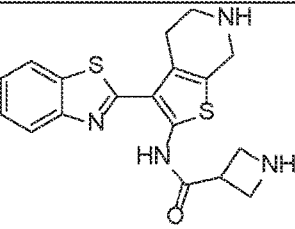
Figure 1:
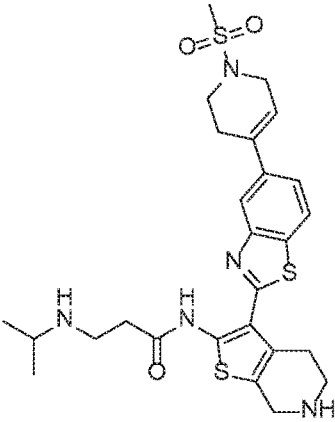
Figure 1:
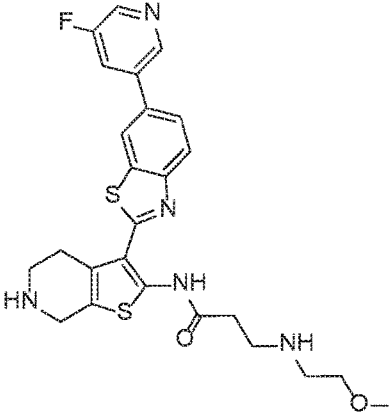
Figure 1:
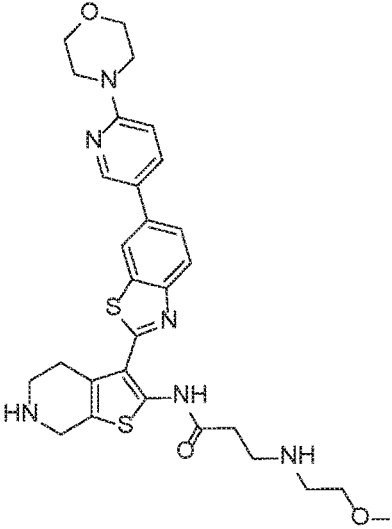
Figure 1:
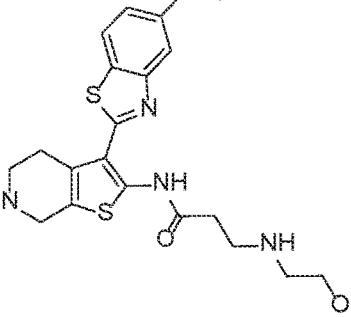
Figure 1:
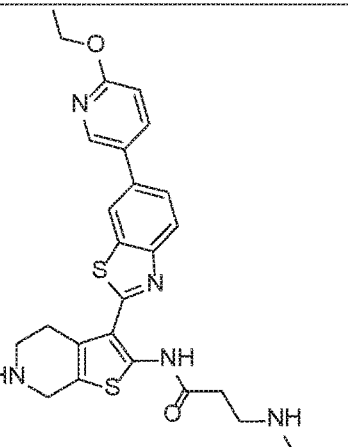
Figure 1:
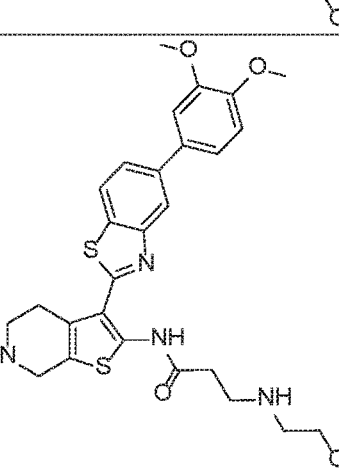
Figure 1:
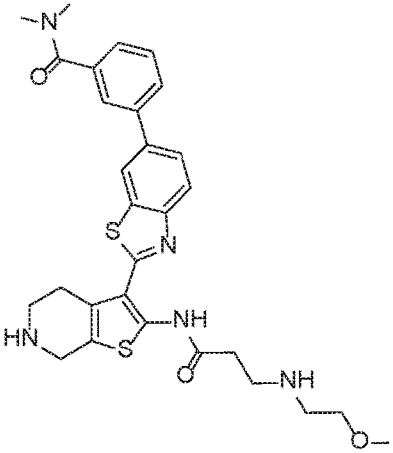
Figure 1:
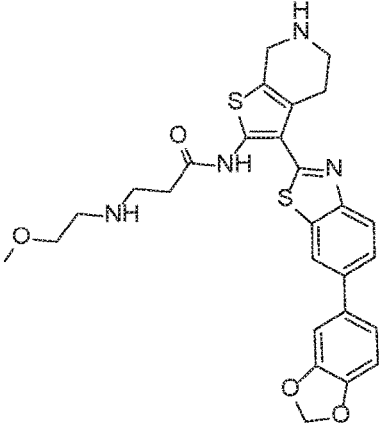
Figure 1:
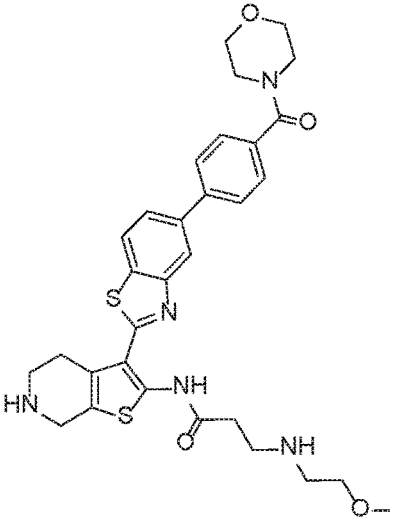
Figure 1:
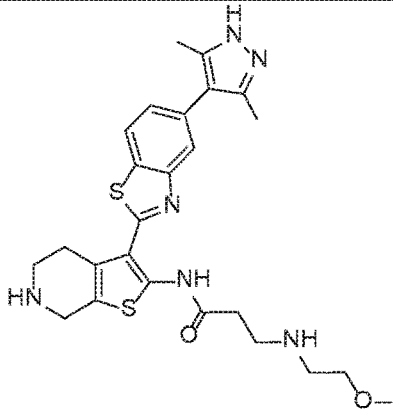
Figure 1:
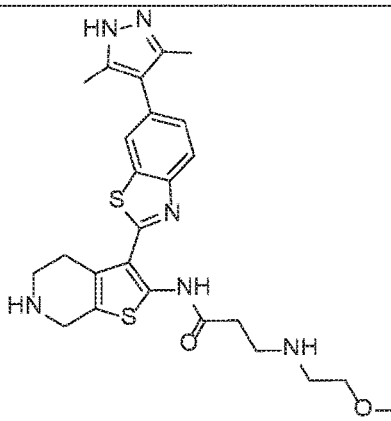
Figure 1:
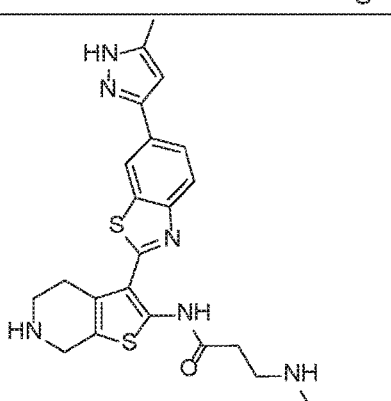
Figure 1:
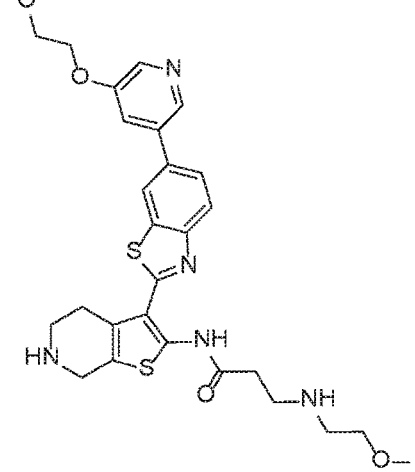
Figure 1:
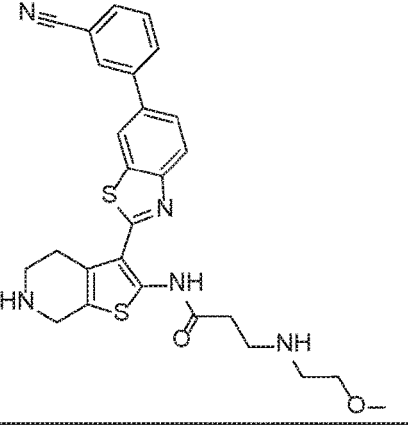
Figure 1:
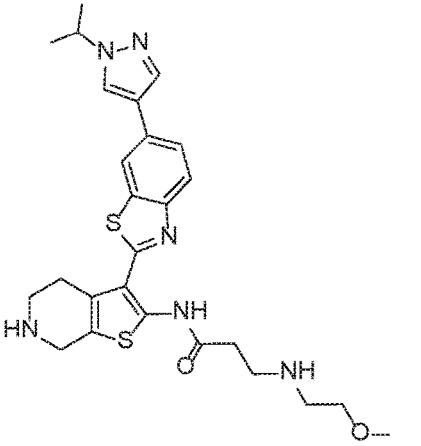
Figure 1:
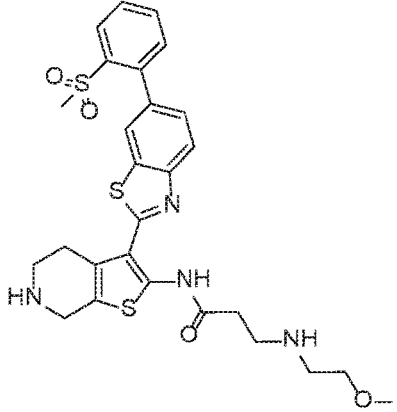
Figure 1:
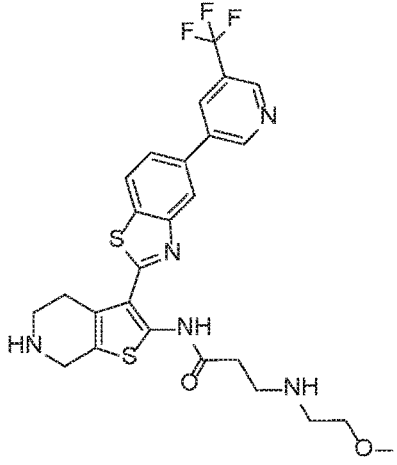
Figure 1:
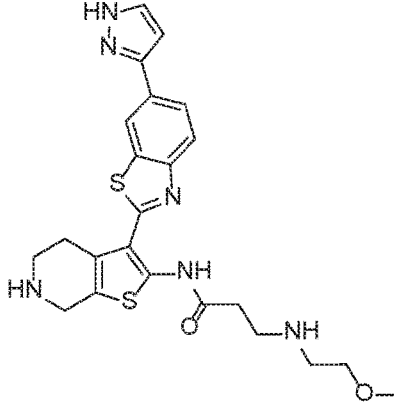
Figure 1:
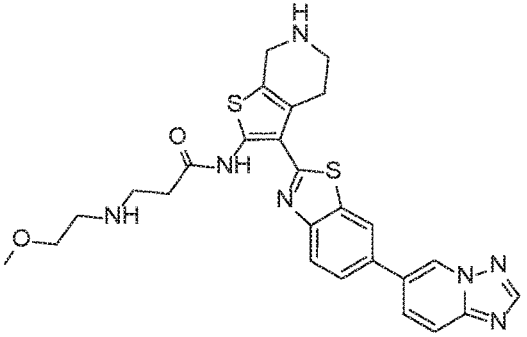
Figure 1:
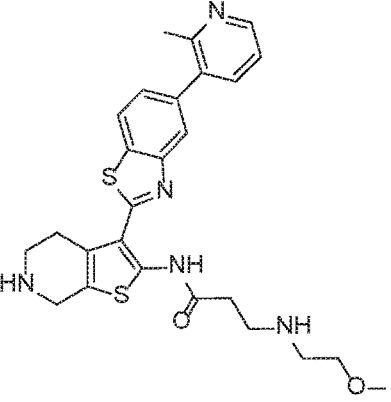
Figure 1:
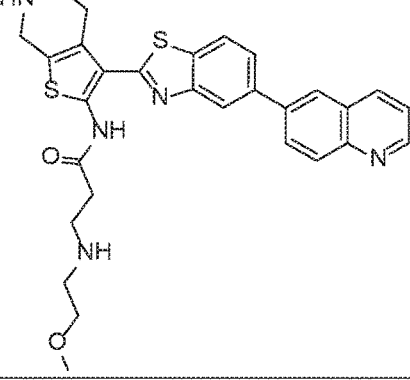
Figure 1:
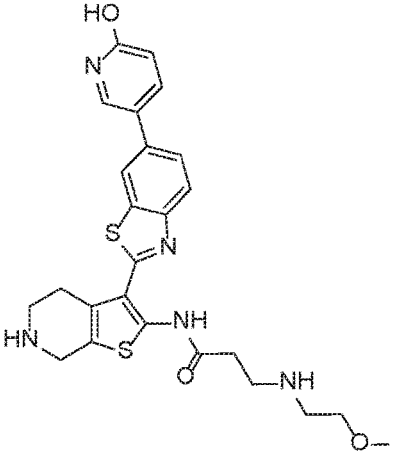
Figure 1:
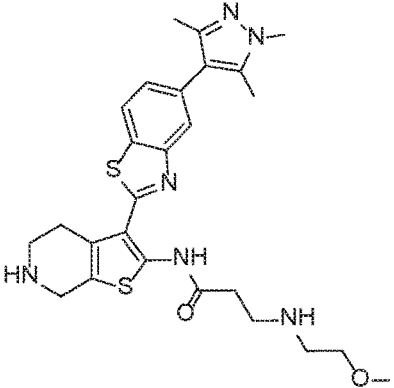
Figure 1:
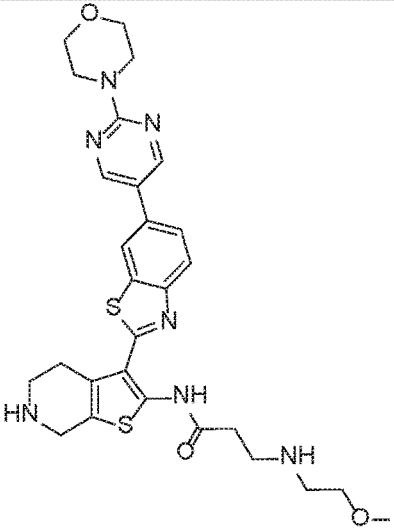
Figure 1:
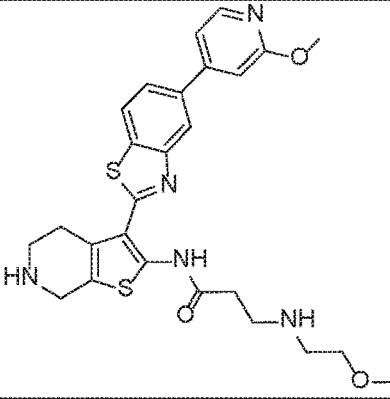
Figure 1:
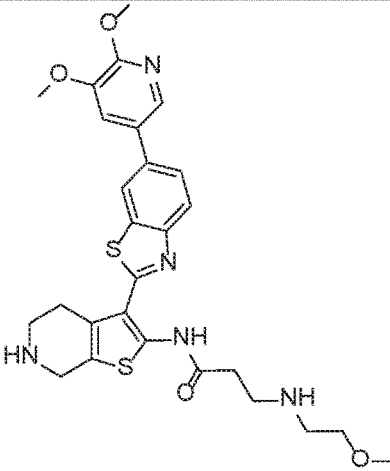
Figure 1:
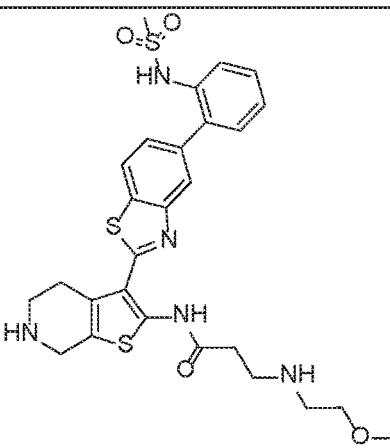
Figure 1:
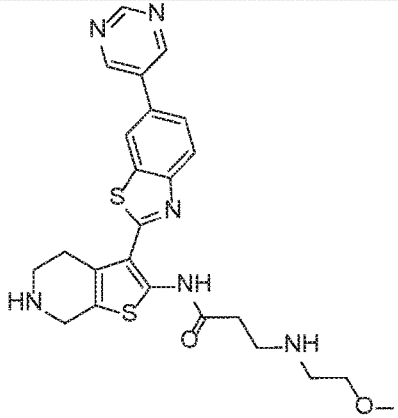
Figure 1:
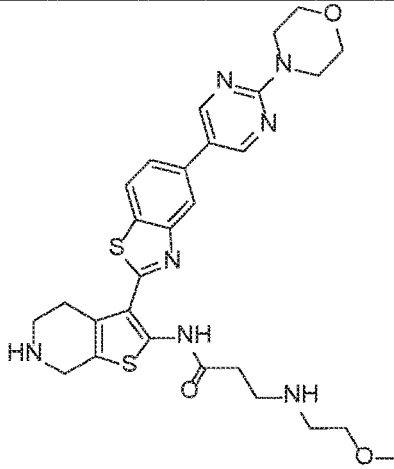
Figure 1:
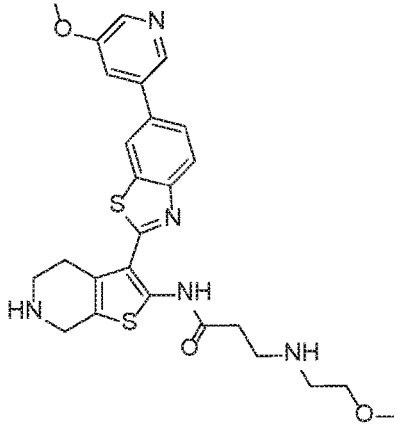
Figure 1:
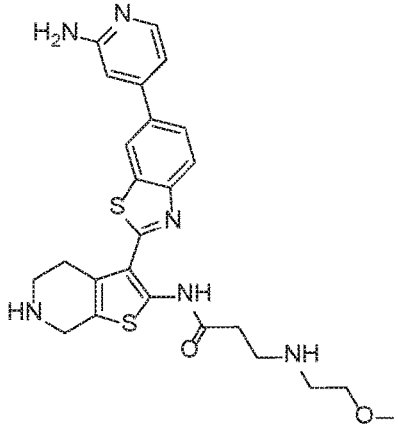
Figure 1:
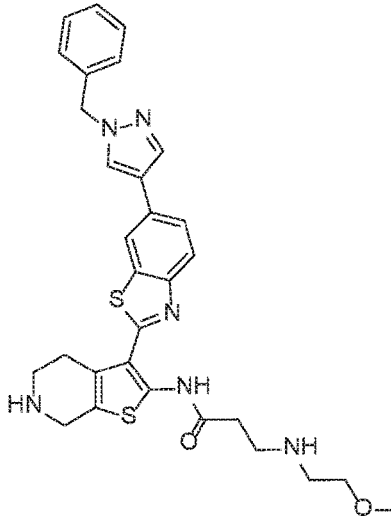
Figure 1:
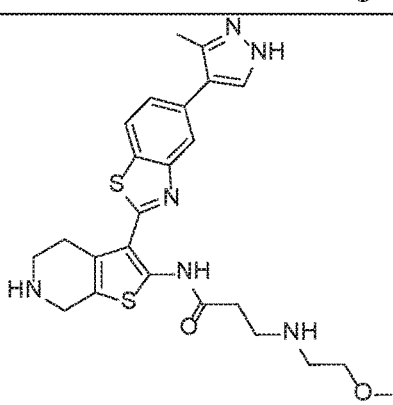
Figure 1:
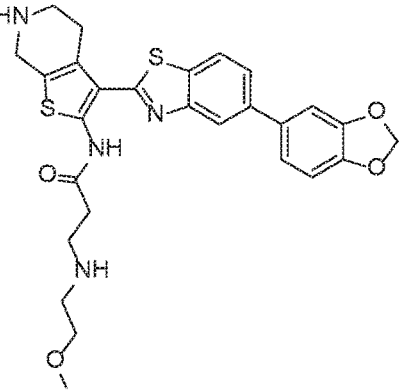
Figure 1:
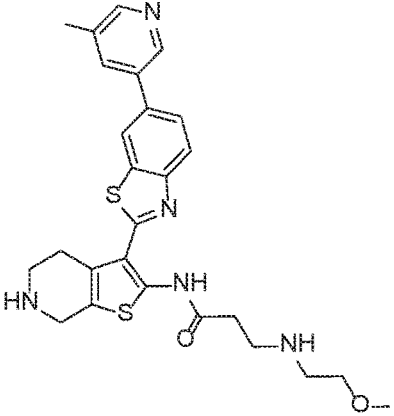
Figure 1:
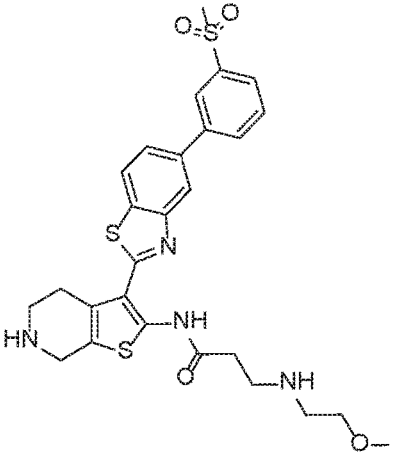
Figure 1:
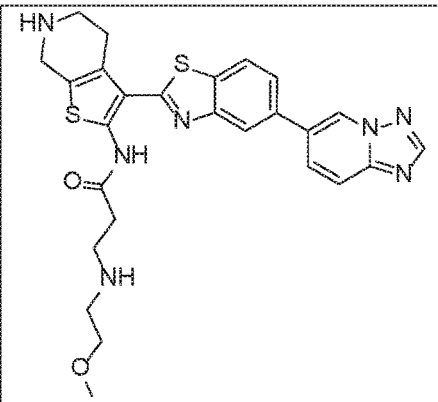
Figure 1:
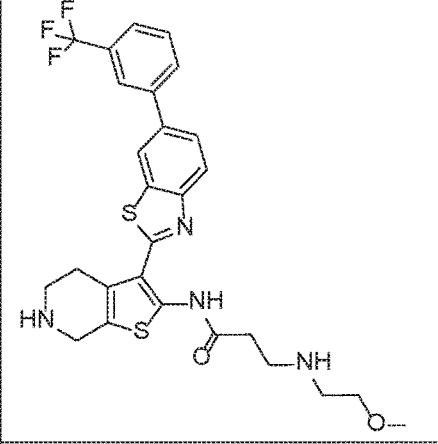
Figure 1:
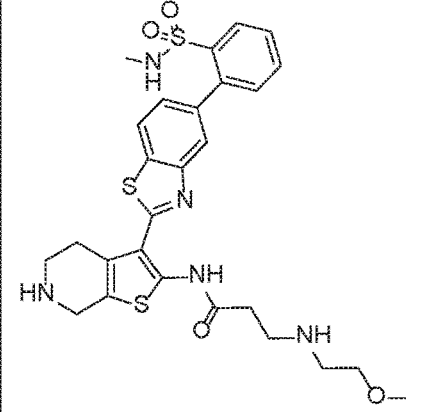
Figure 1:
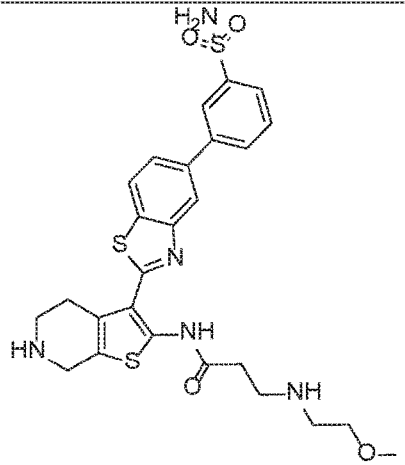
Figure 1:
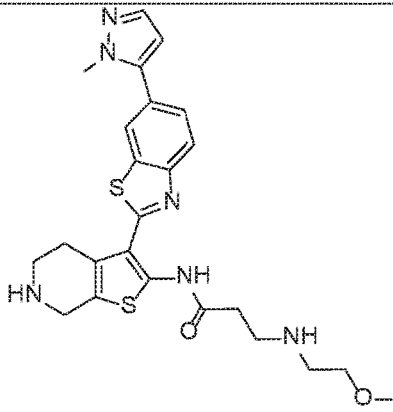
Figure 1:
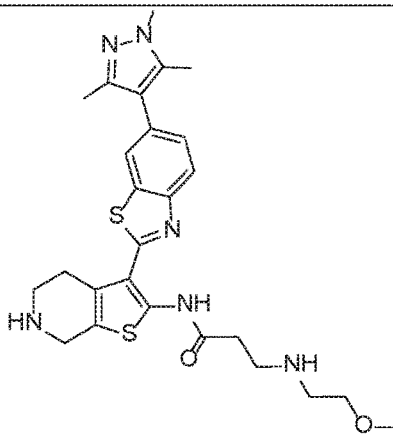
Figure 1:
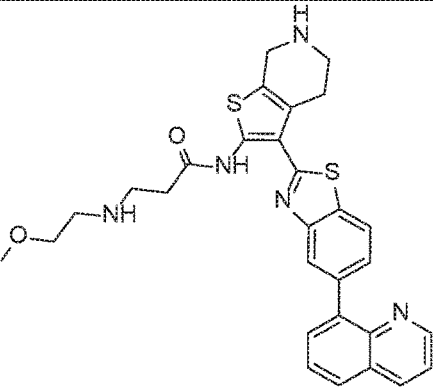
Figure 1:
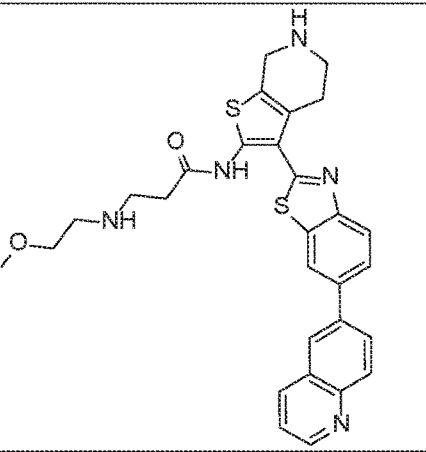
Figure 1:
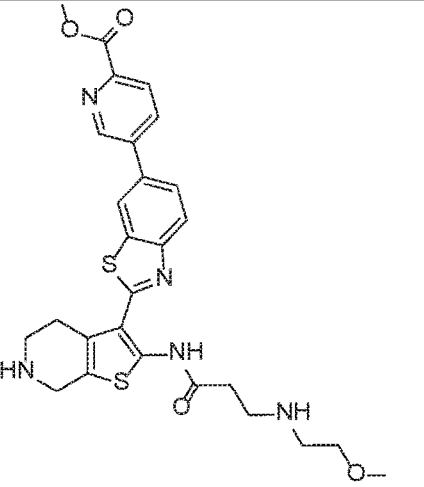
Figure 1:
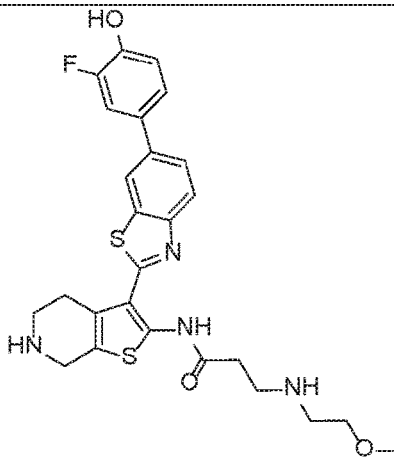
Figure 1:
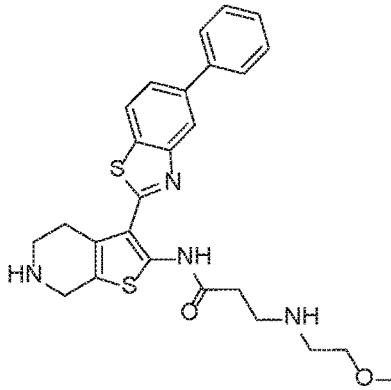
Figure 1:
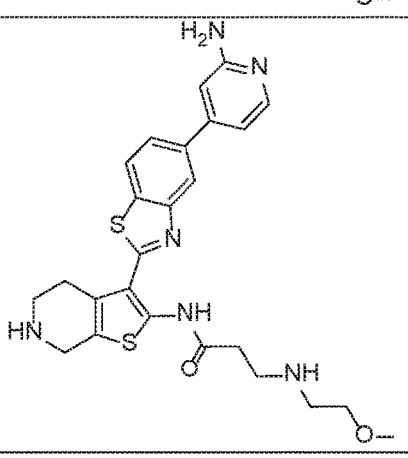
Figure 1:
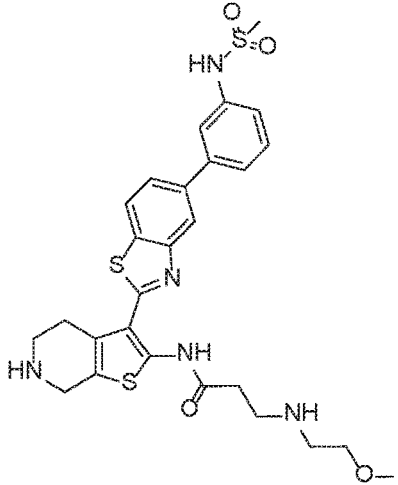
Figure 1:
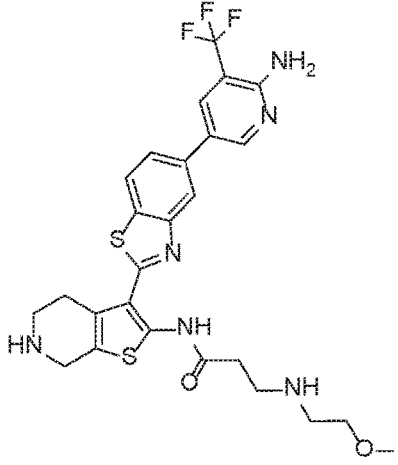
Figure 1:
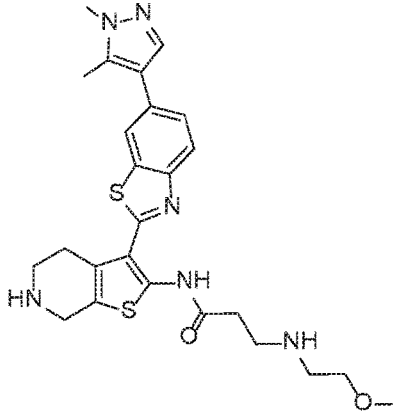
Figure 1:
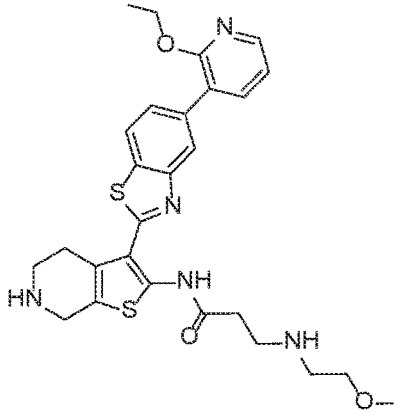
Figure 1:
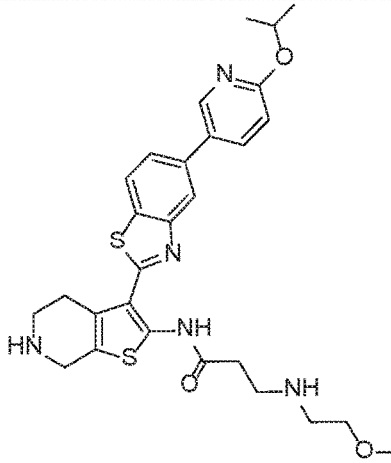
Figure 1:
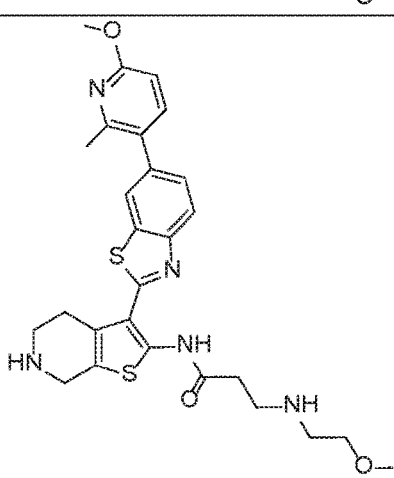
Figure 1:
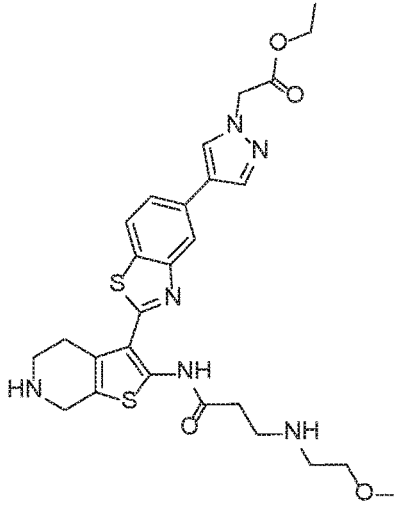
Figure 1:
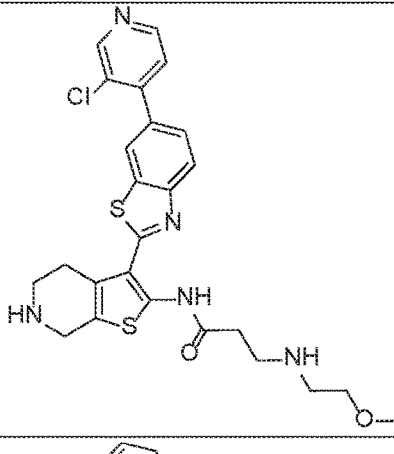
Figure 1:
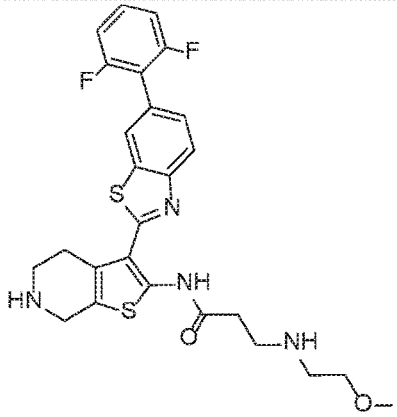
Figure 1:
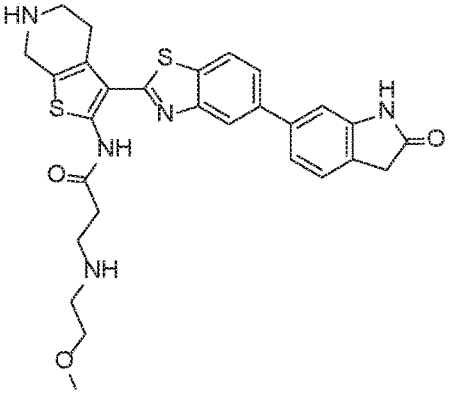
Figure 1:
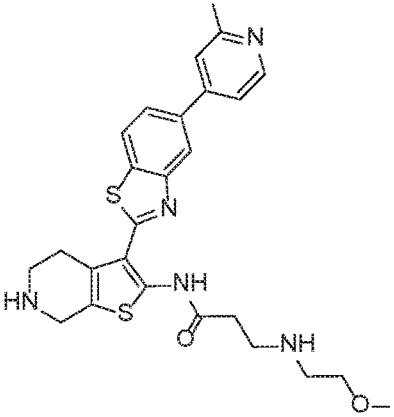
Figure 1:
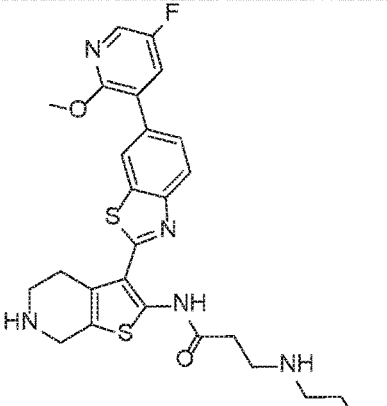
Figure 1:
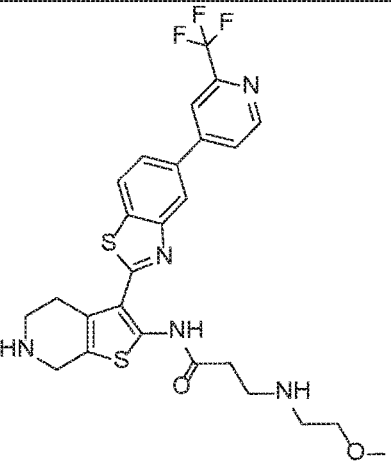
Figure 1:
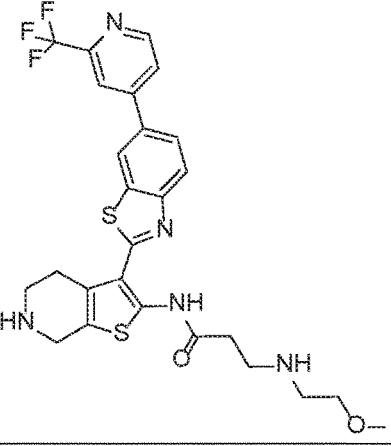
Figure 1:
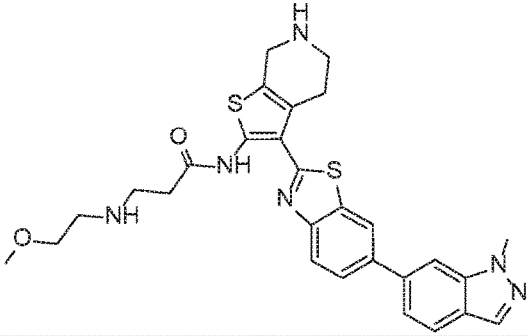
Figure 1:
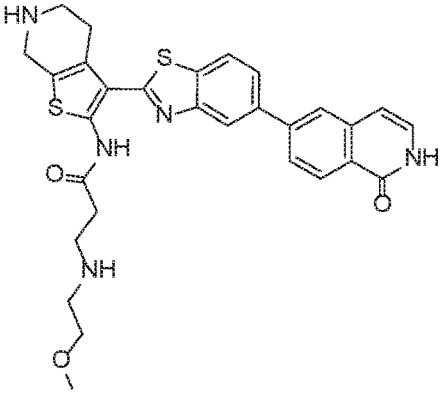
Figure 1:
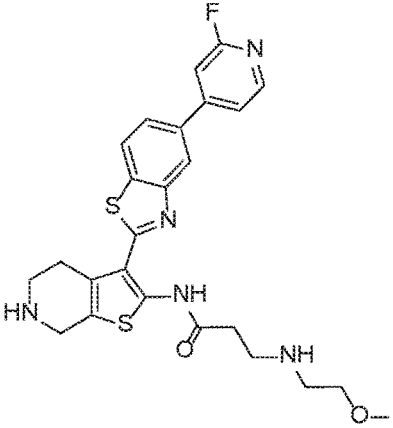
Figure 1:
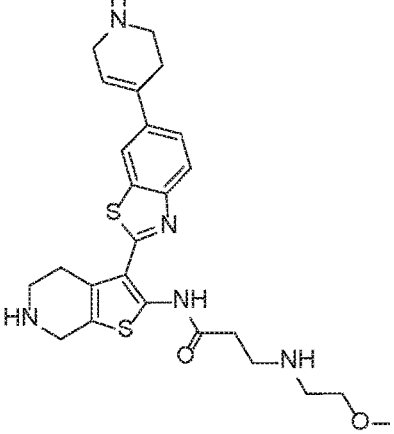
Figure 1:
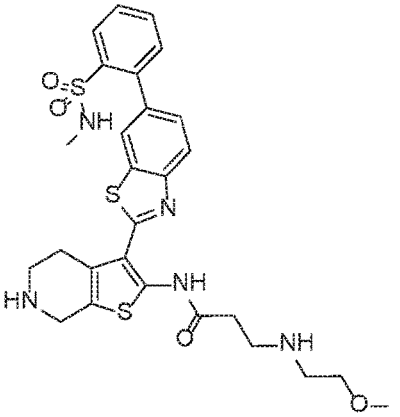
Figure 1:
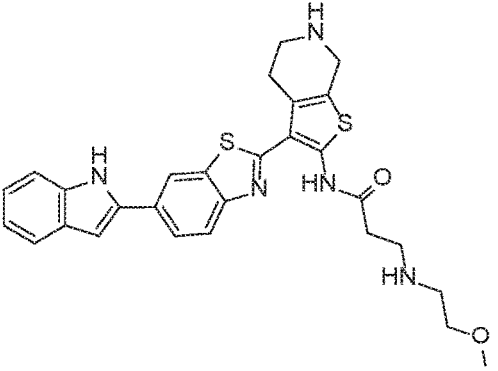
Figure 1:
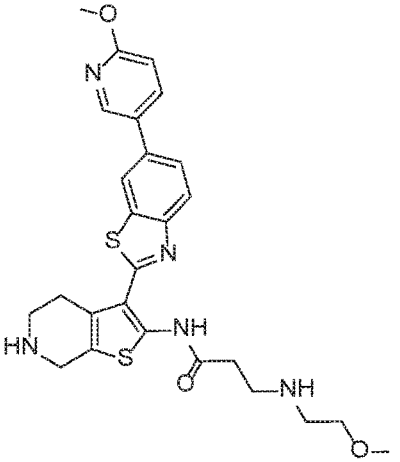
Figure 1:
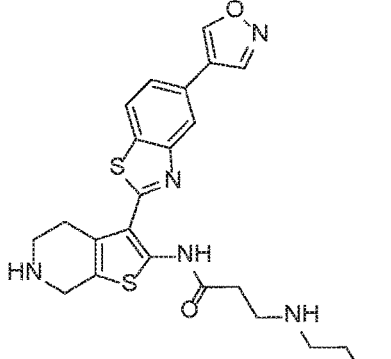
Figure 1:
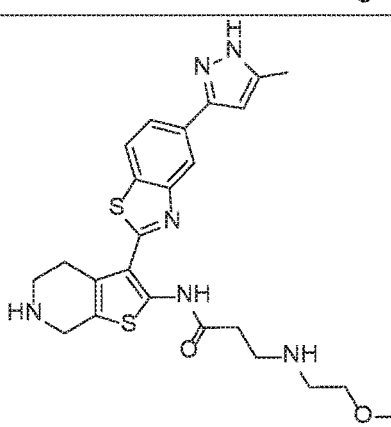
Figure 1:
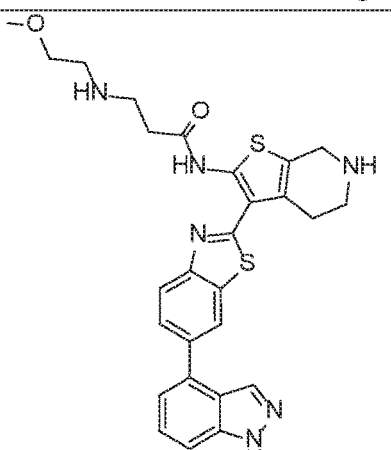
Figure 1:
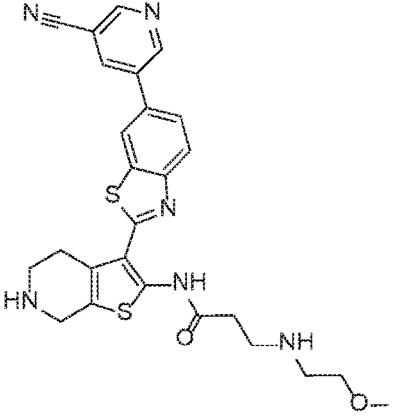
Figure 1:
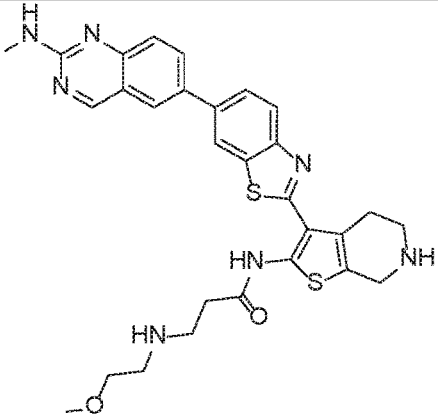
Figure 1:
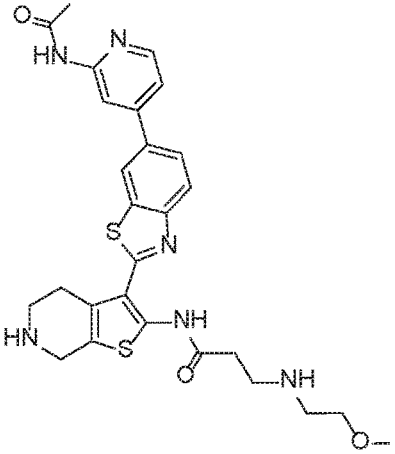
Figure 1:
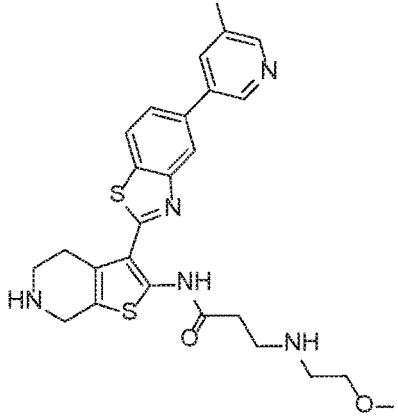
Figure 1:
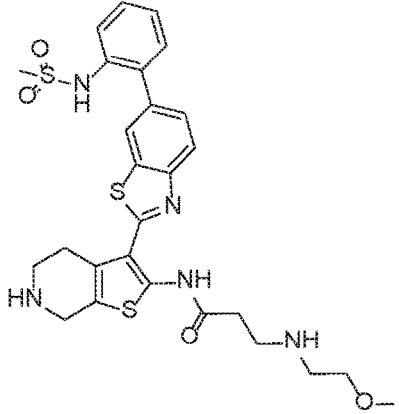
Figure 1:
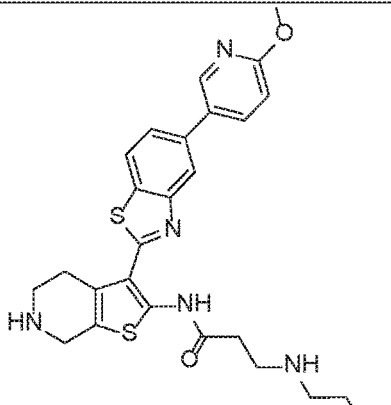
Figure 1:
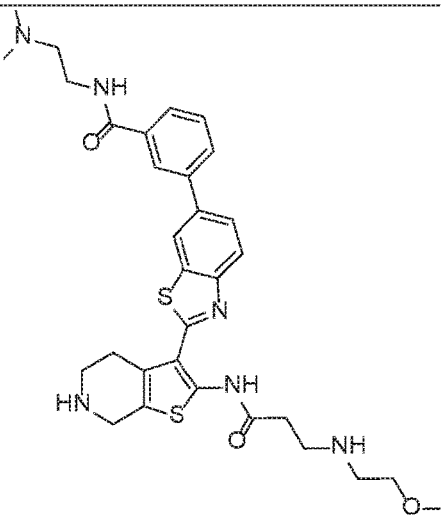
Figure 1:
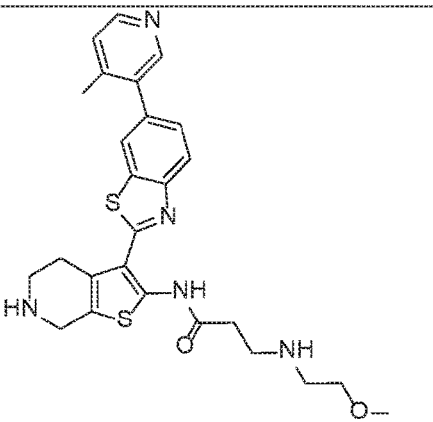
Figure 1:
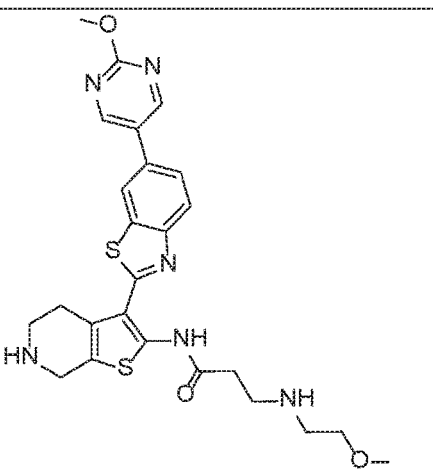
Figure 1:
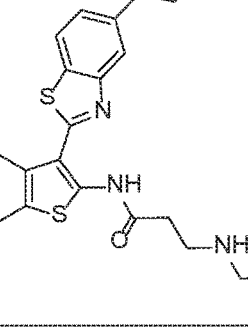
Figure 1:
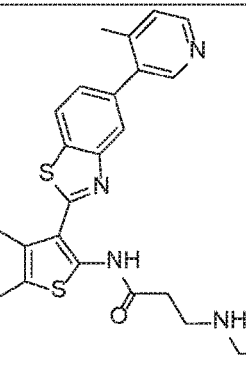
Figure 1:
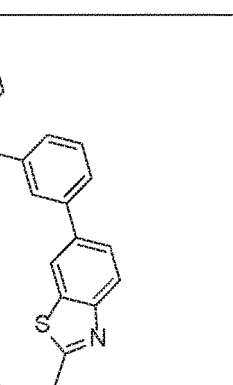
Figure 1:
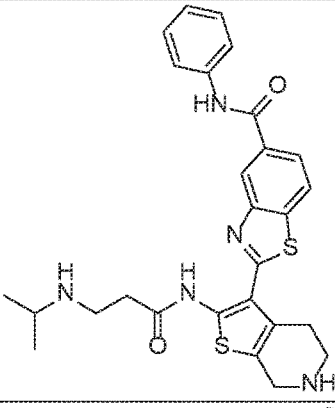
Figure 1:
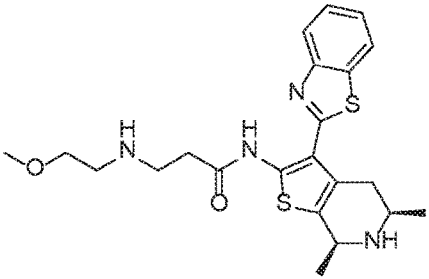
Figure 1:
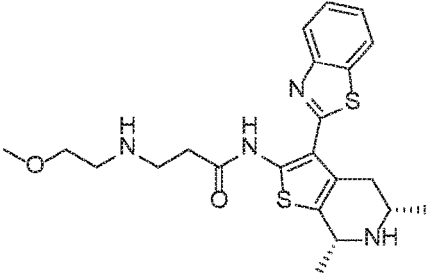
Figure 1:
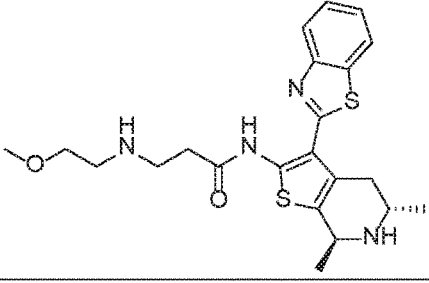
Figure 1:
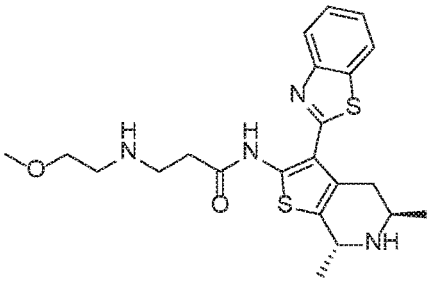
Figure 1:
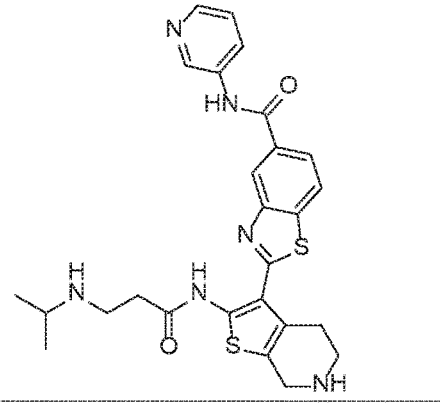
Figure 1:
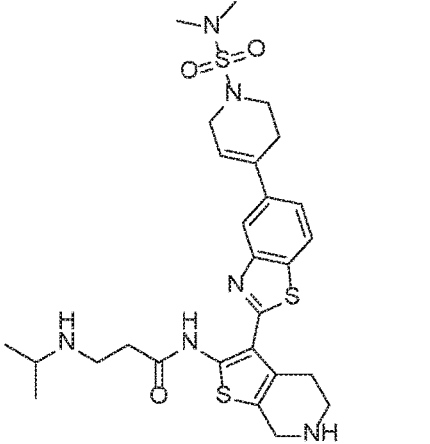
Figure 1:
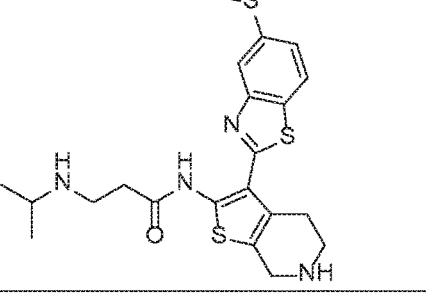
Figure 1:
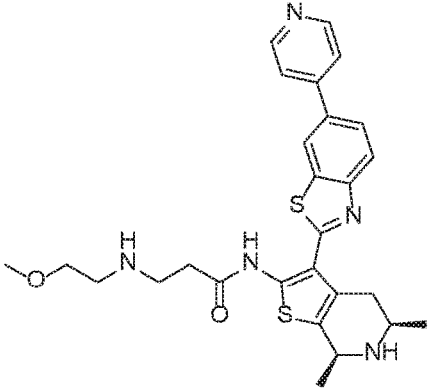
Figure 1:
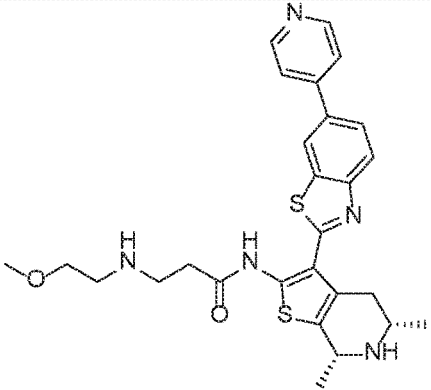
Figure 1:
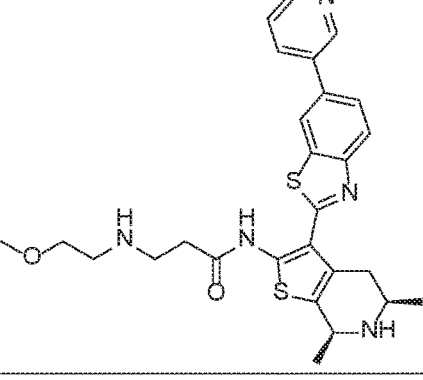
Figure 1:
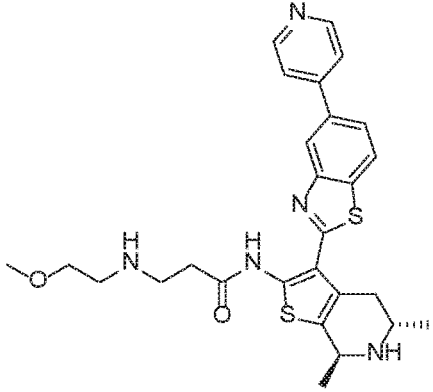
Figure 1:
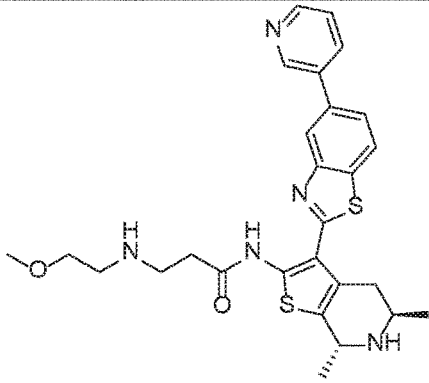
Figure 1:
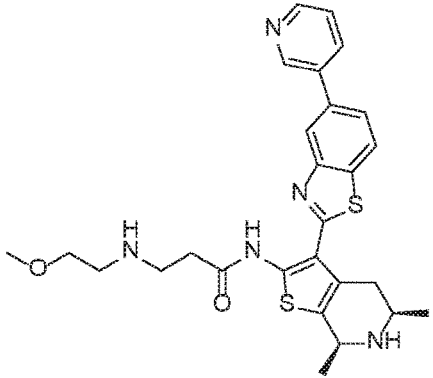
Figure 1:
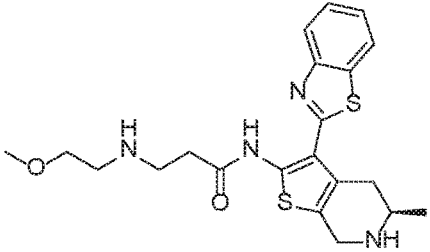
Figure 1:
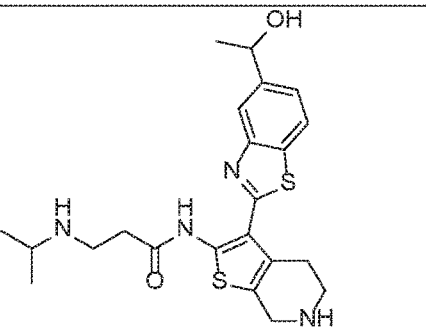
Figure 1:
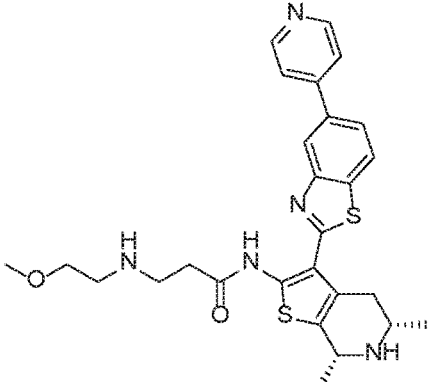
Figure 1:
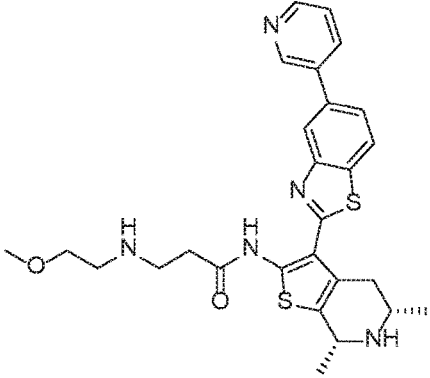
Figure 1:
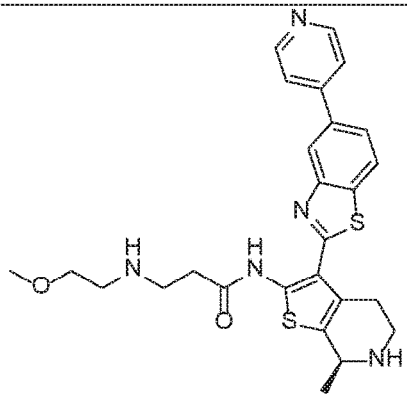
Figure 1:
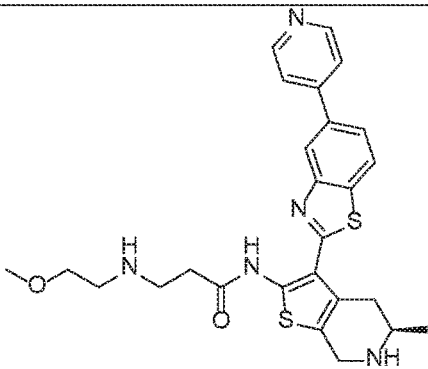
Figure 1:
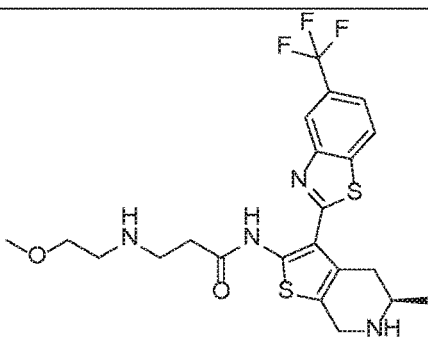
Figure 1:
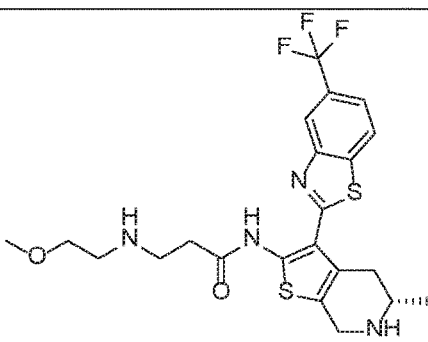
Figure 1:
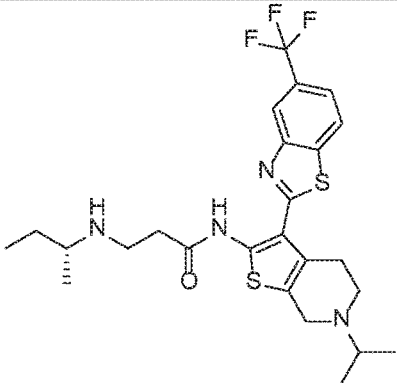
Figure 1:
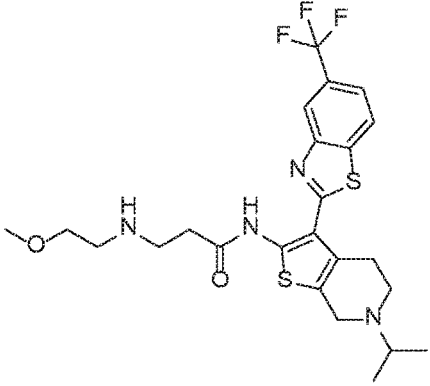
Figure 1:
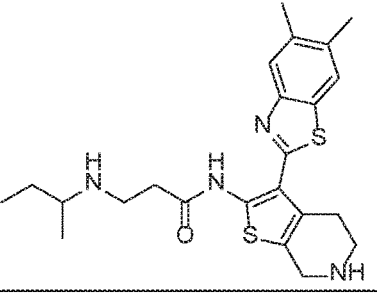
Figure 1:
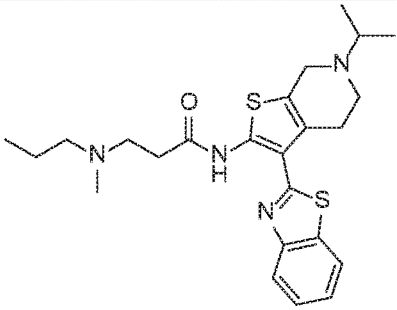
Figure 1:
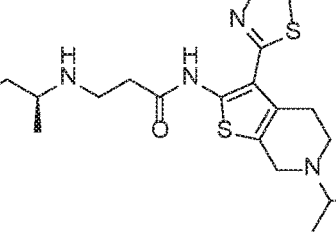
Figure 1:
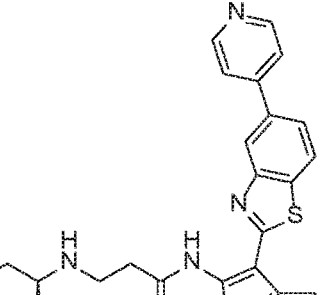
Figure 1:
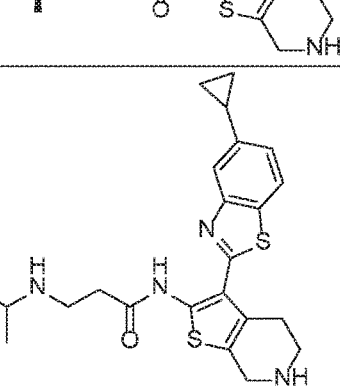
Figure 1:
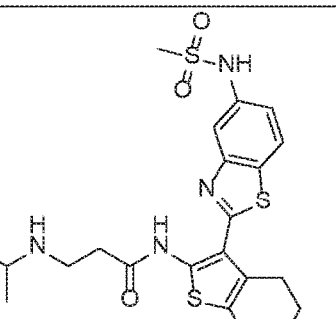
Figure 1:
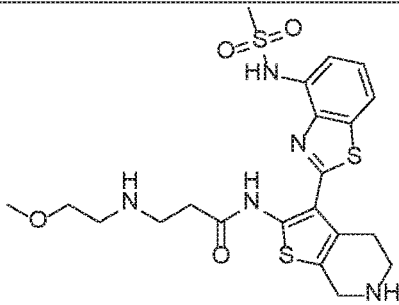
Figure 1:
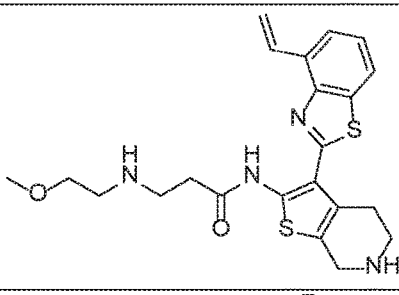
Figure 1:
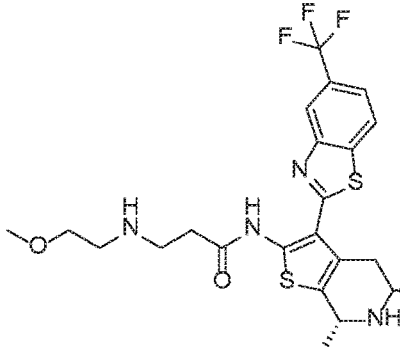
Figure 1:
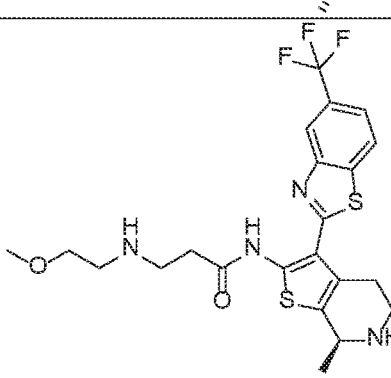
Figure 1:
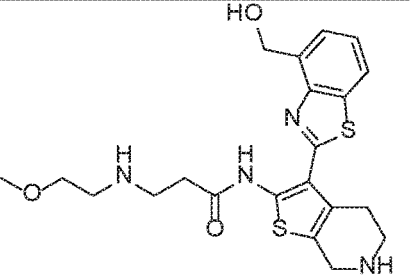
Figure 1:
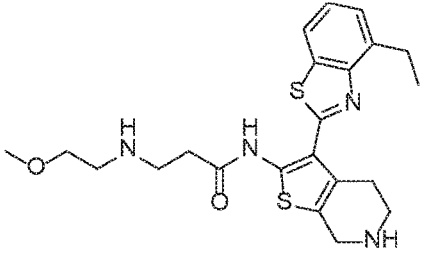
Figure 1:
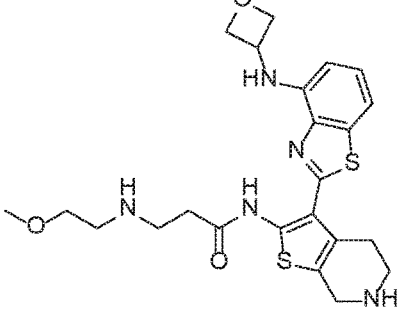
Figure 1:
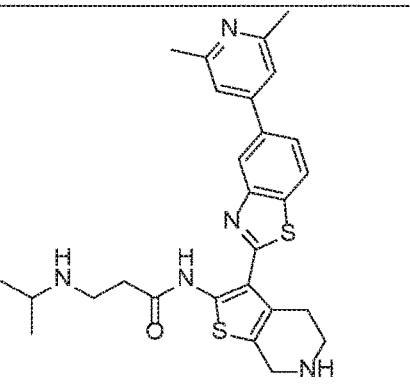
Figure 1:
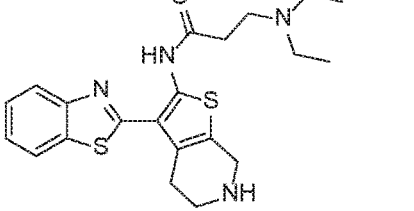
Figure 1:
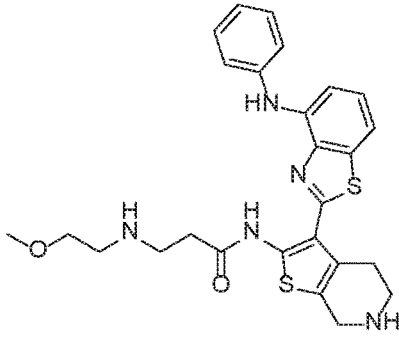
Figure 1:
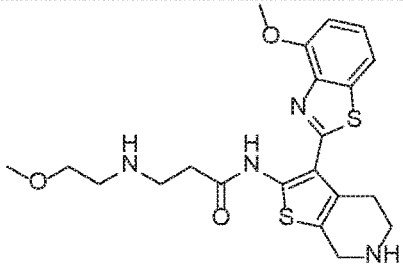
Figure 1:
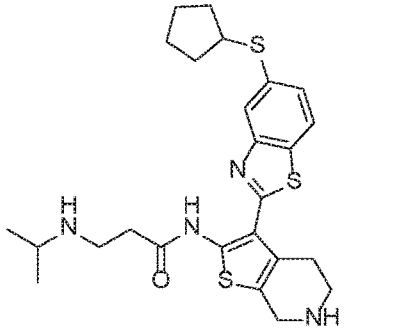
Figure 1:
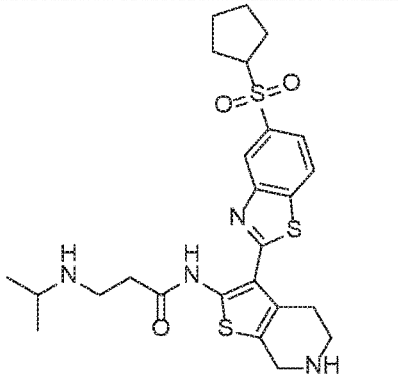
Figure 1:
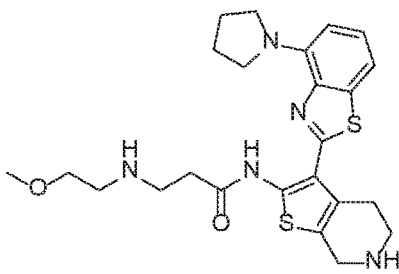

The present invention provides Myc inhibitors, for example c-Myc inhibitors, and in particular selective c-Myc inhibitors of Formulas (I) and (II), and pharmaceutically acceptable salts, solvates, hydrates, tautomers, stereoisomers, isotopically labeled derivatives, and compositions thereof. The present invention further provides methods of using the compounds of the invention, and pharmaceutically acceptable salts, solvates, hydrates, tautomers, stereoisomers, isotopically labeled derivatives, and compositions thereof, to study the inhibition of c-Myc or other Myc family members (e.g., N-Myc or L-Myc), as well as the interaction of c-Myc with DNA or Max. The present invention still further provides methods of using the compounds of the invention, and pharmaceutically acceptable salts, solvates, hydrates, tautomers, stereoisomers, isotopically labeled derivatives, and compositions thereof, as therapeutics for the prevention and/or treatment of diseases associated with overexpression and/or aberrant activity of c-Myc or other Myc family members (e.g., N-Myc or L-Myc). In certain embodiments, the inventive compounds are used for the prevention and/or treatment of proliferative diseases (e.g., cancers (e.g., breast cancer, prostate cancer, lymphoma, lung cancer, pancreatic cancer, ovarian cancer, neuroblastoma, or colorectal cancer), benign neoplasms, angiogenesis, inflammatory diseases, fibrosis (e.g., polycystic kidney disease), autoinflammatory diseases, and autoimmune diseases) in a subject.

In one aspect, the present invention provides compounds of Formula (I) and Formula (II):

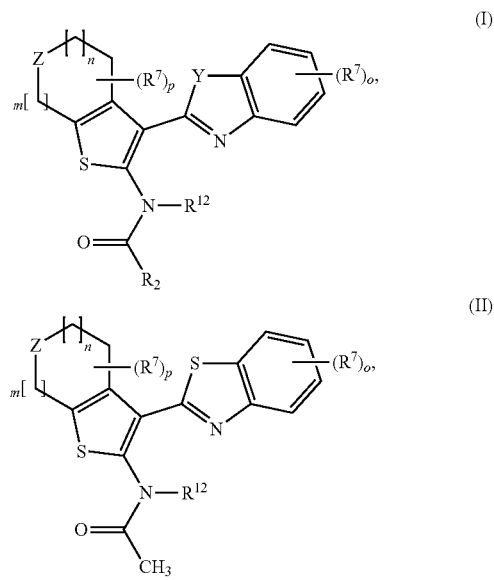

and pharmaceutically acceptable salts, solvates, hydrates, tautomers, stereoisomers, and isotopically labeled derivatives thereof, wherein Y, Z, $R^2$, $R^4$, $R^7$, $R^{12}$, m, n, p, o, and subvariables thereof are as defined herein.

In another aspect, the present invention provides pharmaceutical compositions comprising a compound of Formula (I) or (II), or a pharmaceutically acceptable salt, solvate, hydrate, tautomer, stereoisomer, or isotopically labeled derivative thereof, and optionally a pharmaceutically acceptable excipient. In certain embodiments, the pharmaceutical compositions described herein include a therapeutically effective amount of a compound of Formula (I) or (II), or a pharmaceutically acceptable salt, solvate, hydrate, tautomer, stereoisomer, or isotopically labeled derivative thereof. The pharmaceutical composition may be useful for treating and/or preventing a proliferative or infectious disease.

In another aspect, the present invention provides methods of down-regulating the expression of c-Myc or other Myc family members (e.g., N-Myc or L-Myc) in a cell. In some embodiments, the method comprises contacting the cell with a compound of Formula (I) or (II) or a pharmaceutically acceptable salt, solvate, hydrate, tautomer, stereoisomer, or isotopically labeled derivative thereof, and optionally a pharmaceutically acceptable excipient, or compositions thereof.

In another aspect, the present invention provides methods of inhibiting the activity of c-Myc or other Myc family members (e.g., N-Myc or L-Myc) in a cell. In some embodiments, the method comprises contacting the cell with a compound of Formula (I) or (II) or a pharmaceutically acceptable salt, solvate, hydrate, tautomer, stereoisomer, or isotopically labeled derivative thereof, and optionally a pharmaceutically acceptable excipient, or compositions thereof.

In another aspect, the present invention provides methods of reducing Myc-regulated transcription of a gene in a cell (e.g. reducing transcription regulated by c-Myc, N-Myc, or L-Myc). In some embodiments, the method comprises contacting the cell with a compound of Formula (I) or (II) or a pharmaceutically acceptable salt, solvate, hydrate, tautomer, stereoisomer, or isotopically labeled derivative thereof, and optionally a pharmaceutically acceptable excipient, or compositions thereof.

In another aspect, the present invention provides methods for treating and/or preventing proliferative diseases. Exemplary proliferative diseases include cancers (e.g., breast cancer, prostate cancer, lymphoma, lung cancer, pancreatic cancer, ovarian cancer, neuroblastoma, or colorectal cancer), benign neoplasms, angiogenesis, inflammatory diseases, fibrosis (e.g., polycystic kidney disease), autoinflammatory diseases, and autoimmune diseases. In other embodiments, the present invention provides methods for treating and/or preventing an infectious disease (e.g., a viral infection).

In another aspect, the present invention provides methods for treating a proliferative disease (e.g., cancers (e.g., breast cancer, prostate cancer, lymphoma, lung cancer, pancreatic cancer, ovarian cancer, neuroblastoma, or colorectal cancer), benign neoplasms, angiogenesis, inflammatory diseases, fibrosis (e.g., polycystic kidney disease), autoinflammatory diseases, and autoimmune diseases) characterized by deregulated activity of c-Myc or other Myc family members (e.g., N-Myc or L-Myc). In some embodiments, the deregulated activity of c-Myc or other Myc family members (e.g., N-Myc or L-Myc) comprises deregulation of upstream signaling, gene amplification, or chromosomal translocation by c-Myc or other Myc family members (e.g., N-Myc or L-Myc). In some embodiments, the proliferative disease is characterized by overexpression of c-Myc or other Myc family members (e.g., N-Myc or L-Myc). In some embodiments, the method comprises administering to a subject a compound of Formula (I) or (II) or a pharmaceutically acceptable salt, solvate, hydrate, tautomer, stereoisomer, or isotopically labeled derivative thereof, and optionally a pharmaceutically acceptable excipient, or compositions thereof.

In another aspect, the present invention provides methods for treating a proliferative disease (e.g., cancer (e.g., breast cancer, prostate cancer, lymphoma, or colorectal cancer), benign neoplasm, angiogenesis, inflammatory diseases, autoinflammatory diseases, and autoimmune diseases) characterized by deregulation of other bHLH transcription factors, e.g., MITF, TWIST1, Max, E2A/TCF3, and HES1. In some embodiments, the proliferative disease is characterized by deregulation of the interaction between c-Myc and other bHLH transcription factors, e.g., Max. In some embodiments, the method comprises administering to a subject a compound of Formula (I) or (II) or a pharmaceutically acceptable salt, solvate, hydrate, tautomer, stereoisomer, or isotopically labeled derivative thereof, and optionally a pharmaceutically acceptable excipient, or compositions thereof.

In another aspect, the present invention provides methods for treating a subject determined to exhibit deregulated activity of c-Myc or other Myc family members (e.g., N-Myc or L-Myc). In some embodiments, the deregulated Myc activity comprises overexpression of c-Myc or other Myc family members (e.g., N-Myc or L-Myc). In some embodiments, the method comprises administering to a subject a compound of Formula (I) or (II) or a pharmaceutically acceptable salt, solvate, hydrate, tautomer, stereoisomer, or isotopically labeled derivative thereof, and optionally a pharmaceutically acceptable excipient, or compositions thereof.

In another aspect, the present invention provides methods of reducing transcription of a gene upregulated in a proliferative disease (e.g., cancers (e.g., breast cancer, prostate cancer, lymphoma, lung cancer, pancreatic cancer, ovarian cancer, neuroblastoma, or colorectal cancer), benign neoplasms, angiogenesis, inflammatory diseases, fibrosis (e.g., polycystic kidney disease), autoinflammatory diseases, and autoimmune diseases). In some embodiments, the method comprises administering to a subject a compound of Formula (I) or (II) or a pharmaceutically acceptable salt, solvate, hydrate, tautomer, stereoisomer, or isotopically labeled derivative thereof, and optionally a pharmaceutically acceptable excipient, or compositions thereof.

In another aspect, the present invention provides methods of treating a proliferative disease characterized by Myc addiction (e.g., addiction to c-Myc or other Myc family members, e.g., N-Myc or L-Myc). In some embodiments, the method comprises administering to a subject a compound of Formula (I) or (II) or a pharmaceutically acceptable salt, solvate, hydrate, tautomer, stereoisomer, or isotopically labeled derivative thereof, and optionally a pharmaceutically acceptable excipient, or compositions thereof.

In another aspect, the present invention provides methods of inducing apoptosis of a cell in a biological sample or a subject. In some embodiments, the apoptosis is triggered by c-Myc or other Myc family members (e.g., N-Myc or L-Myc). In some embodiments, the method comprises administering to a subject a compound of Formula (I) or (II) or a pharmaceutically acceptable salt, solvate, hydrate, tautomer, stereoisomer, or isotopically labeled derivative thereof, and optionally a pharmaceutically acceptable excipient, or compositions thereof.

In another aspect, the present invention provides methods of inducing terminal differentiation of a cell in a biological sample or subject. In some embodiments, the terminal differentiation is triggered by c-Myc or other Myc family members (e.g., N-Myc or L-Myc). In some embodiments, the method comprises administering to a subject a compound of Formula (I) or (II) or a pharmaceutically acceptable salt, solvate, hydrate, tautomer, stereoisomer, or isotopically labeled derivative thereof, and optionally a pharmaceutically acceptable excipient, or compositions thereof.

In another aspect, the present invention provides methods of inducing senescence of a cell in a biological sample or subject. In some embodiments, the senescence is triggered by c-Myc or other Myc family members (e.g., N-Myc or L-Myc). In some embodiments, the method comprises administering to a subject a compound of Formula (I) or (II) or a pharmaceutically acceptable salt, solvate, hydrate, tautomer, stereoisomer, or isotopically labeled derivative thereof, and optionally a pharmaceutically acceptable excipient, or compositions thereof.

In another aspect, the present invention provides methods of disrupting the interaction of one or more bHLH transcription factors, e.g., Myc (e.g., c-Myc or other Myc family members (e.g., N-Myc or L-Myc)), MITF, TWIST1, Max, E2A/TCF3, or HES1, with DNA in a cell. In some embodiments, a compound Formula (I) or (II) or a pharmaceutically acceptable salt, solvate, hydrate, tautomer, stereoisomer, or isotopically labeled derivative thereof may disrupt the interaction of one or more bHLH transcription factors, e.g., Myc (e.g., c-Myc or other Myc family members (e.g., N-Myc or L-Myc)), MITF, TWIST1, Max, E2A/TCF3, or HES1, with DNA in a cell.

In another aspect, the present invention provides methods of disrupting the activity of a complex of bHLH transcription factors, e.g., Myc (e.g., c-Myc or other Myc family members (e.g., N-Myc or L-Myc)), MITF, TWIST1, Max, E2A/TCF3, or HES1, in a cell. In some embodiments, a compound Formula (I) or (II) or a pharmaceutically acceptable salt, solvate, hydrate, tautomer, stereoisomer, or isotopically labeled derivative thereof may disrupt the activity of a complex of bHLH transcription factors, e.g., Myc (e.g., c-Myc or other Myc family members (e.g., N-Myc or L-Myc)), MITF, TWIST1, Max, E2A/TCF3, or HES1, in a cell.

In yet another aspect, the present invention provides compounds of Formula (I) or (II), and pharmaceutically acceptable salts, solvates, hydrates, tautomers, stereoisomers, isotopically labeled derivatives, and compositions thereof, for use in the treatment or prevention of an infectious disease in a subject. In certain embodiments, the infectious disease is a viral infection.

Another aspect of the present invention relates to kits comprising a container with a compound of Formula (I) or (II), or a pharmaceutically acceptable salt, solvate, hydrate, tautomer, stereoisomer, or isotopically labeled derivative thereof, or a pharmaceutical composition thereof. In certain embodiments, the kits described herein further include instructions for administering the compound of Formula (I) or (II), or the pharmaceutically acceptable salt, solvate, hydrate, tautomer, stereoisomer, or isotopically labeled derivative thereof, or the pharmaceutical composition thereof.

The details of one or more embodiments of the invention are set forth herein. Other features, objects, and advantages of the invention will be apparent from the Detailed Description, the Figures, the Examples, and the Claims.

Definitions

Definitions of specific functional groups and chemical terms are described in more detail below. The chemical elements are identified in accordance with the Periodic Table of the Elements, CAS version, *Handbook of Chemistry and Physics*, 75$^{th}$ Ed., inside cover, and specific functional groups are generally defined as described therein. Additionally, general principles of organic chemistry, as well as specific functional moieties and reactivity, are described in Thomas Sorrell, *Organic Chemistry*, University Science Books, Sausalito, 1999; Smith and March, *March's Advanced Organic Chemistry*, 5$^{th}$ Edition, John Wiley & Sons, Inc., New York, 2001; Larock, *Comprehensive Organic Transformations*, VCH Publishers, Inc., New York, 1989; and Carruthers, *Some Modern Methods of Organic Synthesis*, 3$^{rd}$ Edition, Cambridge University Press, Cambridge, 1987.

It is to be understood that compounds that have the same molecular formula but differ in the nature or sequence of bonding of their atoms or the arrangement of their atoms in space are termed "isomers". Isomers that differ in the arrangement of their atoms in space are termed "stereoisomers".

Stereoisomers that are not mirror images of one another are termed "diastereomers" and those that are non-superimposable mirror images of each other are termed "enantiomers". When a compound has an asymmetric center, for example, it is bonded to four different groups and a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture".

The term "tautomers" refer to compounds that are interchangeable forms of a particular compound structure, and that vary in the displacement of hydrogen atoms and electrons. Thus, two structures may be in equilibrium through the movement of π electrons and an atom (usually H). For example, enols and ketones are tautomers because they are rapidly interconverted by treatment with either acid or base. Another example of tautomerism is the aci- and nitro-forms of phenylnitromethane that are likewise formed by treatment with acid or base.

Tautomeric forms may be relevant to the attainment of the optimal chemical reactivity and biological activity of a compound of interest.

Unless otherwise stated, structures depicted herein are also meant to include all isomeric (e.g., enantiomeric, diastereomeric, and geometric (or conformational)) forms of the structure; for example, the R and S configurations for each asymmetric center, Z and E double bond isomers, and Z and E conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention. Additionally, unless otherwise stated, structures depicted herein are also meant to include compounds that differ only in the presence of one or more isotopically enriched atoms. For example, compounds having the present structures including the replacement of hydrogen by deuterium or tritium, or the replacement of a carbon by a $^{13}$C- or $^{14}$C-enriched carbon are within the scope of this invention. Such compounds are useful, for example, as analytical tools, as probes in biological assays, or as therapeutic agents in accordance with the present invention.

Where a particular enantiomer is preferred, it may, in some embodiments be provided substantially free of the corresponding enantiomer, and may also be referred to as "optically enriched." "Optically-enriched," as used herein, means that the compound is made up of a significantly greater proportion of one enantiomer. In certain embodiments the compound is made up of at least about 90% by weight of a preferred enantiomer. In other embodiments the compound is made up of at least about 95%, 98%, or 99% by weight of a preferred enantiomer. Preferred enantiomers may be isolated from racemic mixtures by any method known to those skilled in the art, including chiral high pressure liquid chromatography (HPLC) and the formation and crystallization of chiral salts or prepared by asymmetric syntheses. See, for example, Jacques et al., *Enantiomers, Racemates and Resolutions* (Wiley Interscience, New York, 1981); Wilen, et al., *Tetrahedron* 33:2725 (1977); Eliel, E. L. *Stereochemistry of Carbon Compounds* (McGraw-Hill, N Y, 1962); Wilen, S. H. *Tables of Resolving Agents and Optical Resolutions* p. 268 (E. L. Eliel, Ed., Univ. of Notre Dame Press, Notre Dame, Ind. 1972).

The term "aliphatic" or "aliphatic group", as used herein, denotes a hydrocarbon moiety that may be straight-chain (i.e., unbranched), branched, or cyclic (including fused, bridging, and spiro-fused polycyclic) and may be completely saturated or may contain one or more units of unsaturation, but which is not aromatic. Unless otherwise specified, aliphatic groups contain 1-6 carbon atoms. In some embodiments, aliphatic groups contain 1-4 carbon atoms, and in yet other embodiments aliphatic groups contain 1-3 carbon atoms. Suitable aliphatic groups include, but are not limited to, linear or branched, alkyl, alkenyl, and alkynyl groups, and hybrids thereof such as (carbocyclyl) alkyl, (carbocyclyl)alkyl or (carbocyclyl)alkenyl.

The term "alkyl," as used herein, refers to a monovalent saturated, straight- or branched-chain hydrocarbon such as a straight or branched group of 1-12, 1-10, or 1-6 carbon atoms, referred to herein as $C_1$-$C_{12}$ alkyl, $C_1$-$C_{10}$ alkyl, and $C_1$-$C_6$ alkyl, respectively. Examples of alkyl groups include, but are not limited to, methyl, ethyl, n-propyl, isopropyl, n-butyl, iso-butyl, sec-butyl, sec-pentyl, iso-pentyl, tert-butyl, n-pentyl, neopentyl, n-hexyl, sec-hexyl, and the like.

The terms "alkenyl" and "alkynyl" are art-recognized and refer to unsaturated aliphatic groups analogous in length and possible substitution to the alkyls described above, but that contain at least one double or triple bond, respectively. Exemplary alkenyl groups include, but are not limited to, —CH=CH$_2$ and —CH$_2$CH=CH$_2$.

The term "alkylene" refers to the diradical of an alkyl group.

The terms "alkenylene" and "alkynylene" refer to the diradicals of an alkenyl and an alkynyl group, respectively.

The terms "halo" or "halogen" refer to fluorine (fluoro, —F), chlorine (chloro, —Cl), bromine (bromo, —Br), or iodine (iodo, —I).

The term "haloalkyl" refers to a monovalent saturated straight or branched alkyl chain wherein at least one carbon atom in the chain is substituted with a halogen, e.g., F, Cl, Br, or I. In some embodiments, a haloalkyl group may comprise, e.g., 1-12, 1-10, or 1-6 carbon atoms, referred to herein as $C_1$-$C_{12}$ haloalkyl, $C_1$-$C_{10}$ haloalkyl, and $C_1$-$C_6$ haloalkyl. In certain instances, a haloalkyl group comprises 1, 2, 3, or 4 independently selected halogens substituted on 1, 2, 3, or 4 individual carbon atoms in the alkyl chain. In some embodiments, more than one halogen may be substituted on a single carbon atom. Representative haloalkyl groups include —CH$_2$F, —CF$_3$, CH$_2$CH(Cl)CH$_3$, and the like.

The term "haloalkylene" refers to the diradical of a haloalkyl group.

The term "heteroalkyl" refers to a monovalent saturated straight or branched alkyl chain wherein at least one carbon atom in the chain is replaced with a heteroatom, such as O, S, or N. In some embodiments, a heteroalkyl group may comprise, e.g., 1-12, 1-10, or 1-6 carbon atoms, referred to herein as $C_1$-$C_{12}$ heteroalkyl, $C_1$-$C_{10}$ heteroalkyl, and $C_1$-$C_6$ heteroalkyl. In certain instances, a heteroalkyl group comprises 1, 2, 3, or 4 independently selected heteroatoms in place of 1, 2, 3, or 4 individual carbon atoms in the alkyl chain. Representative heteroalkyl groups include —CH$_2$CH$_2$OCH$_3$, —CH$_2$CH$_2$NHCH$_3$, —CH$_2$CH$_2$N(CH$_3$) CH$_3$, and the like.

The term "heteroalkylene" refers to the diradical of a heteralkyl group.

The term "methylene unit" refers to a divalent —CH$_2$— group present in an alkyl, alkenyl, alkynyl, alkylene, alkenylene, or alkynylene moiety.

The term "carbocyclic ring system", as used herein, means a monocyclic, or fused, spiro-fused, and/or bridged bicyclic or polycyclic hydrocarbon ring system, wherein each ring is either completely saturated or contains one or more units of unsaturation, but where no ring is aromatic.

The term "carbocyclyl" refers to a radical of a carbocyclic ring system. Representative carbocyclyl groups include cycloalkyl groups (e.g., cyclopentyl, cyclobutyl, cyclopentyl, cyclohexyl and the like), and cycloalkenyl groups (e.g., cyclopentenyl, cyclohexenyl, cyclopentadienyl, and the like).

The term "aromatic ring system" is art-recognized and refers to a monocyclic, bicyclic or polycyclic hydrocarbon ring system, wherein at least one ring is aromatic.

The term "aryl" refers to a radical of an aromatic ring system. Representative aryl groups include fully aromatic ring systems, such as phenyl, naphthyl, and anthracenyl, and ring systems where an aromatic carbon ring is fused to one or more non-aromatic carbon rings, such as indanyl, phthalimidyl, naphthimidyl, or tetrahydronaphthyl, and the like.

The term "heteroaromatic ring system" is art-recognized and refers to monocyclic, bicyclic or polycyclic ring system wherein at least one ring is both aromatic and comprises a heteroatom; and wherein no other rings are heterocyclyl (as defined below). In certain instances, a ring which is aromatic and comprises a heteroatom contains 1, 2, 3, or 4 independently selected ring heteroatoms in such ring.

The term "heteroaryl" refers to a radical of a heteroaromatic ring system. Representative heteroaryl groups include ring systems where (i) each ring comprises a heteroatom and is aromatic, e.g., imidazolyl, oxazolyl, thiazolyl, triazolyl, pyrrolyl, furanyl, thiophenyl pyrazolyl, pyridinyl, pyrazinyl, pyridazinyl, pyrimidinyl, indolizinyl, purinyl, naphthyridinyl, and pteridinyl; (ii) each ring is aromatic or carbocyclyl, at least one aromatic ring comprises a heteroatom and at least one other ring is a hydrocarbon ring or e.g., indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, carbazolyl, acridinyl, phenazinyl, phenothiazinyl, phenoxazinyl, pyrido[2,3-b]-1,4-oxazin-3(4H)-one, thiazolo-[4,5-c]-pyridinyl, 4,5,6,7-tetrahydrothieno[2,3-c]pyridinyl, 5,6-dihydro-4H-thieno[2,3-c]pyrrolyl, 4,5,6,7,8-tetrahydroquinolinyl and 5,6,7,8-tetrahydroisoquinolinyl; and (iii) each ring is aromatic or carbocyclyl, and at least one aromatic ring shares a bridgehead heteroatom with another aromatic ring, e.g., 4H-quinolizinyl. In certain embodiments, the heteroaryl is a monocyclic or bicyclic ring, wherein each of said rings contains 5 or 6 ring atoms where 1, 2, 3, or 4 of said ring atoms are a heteroatom independently selected from N, O, and S.

The term "heterocyclic ring system" refers to monocyclic, or fused, spiro-fused, and/or bridged bicyclic and polycyclic ring systems where at least one ring is saturated or partially unsaturated (but not aromatic) and comprises a heteroatom. A heterocyclic ring system can be attached to its pendant group at any heteroatom or carbon atom that results in a stable structure and any of the ring atoms can be optionally substituted.

The term "heterocyclyl" refers to a radical of a heterocyclic ring system. Representative heterocyclyls include ring systems in which (i) every ring is non-aromatic and at least one ring comprises a heteroatom, e.g., tetrahydrofuranyl, tetrahydrothienyl, pyrrolidinyl, pyrrolidonyl, piperidinyl, pyrrolinyl, decahydroquinolinyl, oxazolidinyl, piperazinyl, dioxanyl, dioxolanyl, diazepinyl, oxazepinyl, thiazepinyl, morpholinyl, and quinuclidinyl; (ii) at least one ring is non-aromatic and comprises a heteroatom and at least one other ring is an aromatic carbon ring, e.g., 1,2,3,4-tetrahydroquinolinyl; and (iii) at least one ring is non-aromatic and comprises a heteroatom and at least one other ring is aromatic and comprises a heteroatom, e.g., 3,4-dihydro-1H-pyrano[4,3-c]pyridinyl, and 1,2,3,4-tetrahydro-2,6-naphthyridinyl. In certain embodiments, the heterocyclyl is a monocyclic or bicyclic ring, wherein each of said rings contains 3-7 ring atoms where 1, 2, 3, or 4 of said ring atoms are a heteroatom independently selected from N, O, and S.

The term "saturated heterocyclyl" refers to a radical of heterocyclic ring system wherein every ring is saturated, e.g., tetrahydrofuran, tetrahydro-2H-pyran, pyrrolidine, piperidine and piperazine.

"Partially unsaturated" refers to a group that includes at least one double or triple bond. A "partially unsaturated" ring system is further intended to encompass rings having multiple sites of unsaturation, but is not intended to include aromatic groups (e.g., aryl or heteroaryl groups) as herein defined. Likewise, "saturated" refers to a group that does not contain a double or triple bond, i.e., contains all single bonds.

As described herein, compounds of the invention may contain "optionally substituted" moieties. In general, the term "substituted", whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at each position. Combinations of substituents envisioned under this invention are preferably those that result in the formation of stable or chemically feasible compounds. The term "stable", as used herein, refers to compounds that are not substantially altered when subjected to conditions to allow for their production, detection, and, in certain embodiments, their recovery, purification, and use for one or more of the purposes disclosed herein.

Suitable substituents for an optionally substituted alkyl, alkylene, haloalkyl, haloalkylene, heteroalkyl, heteroalkylene, carbocyclyl, heterocyclyl, aryl group and heteroaryl group include halogen, =O, —O(C=S)$R^c$, —C(=O)N$R^dR^e$, —N$R^c$C(=O)$R^c$, —C(=S)N$R^dR^e$, —N$R^c$C(=S)$R^e$, —N$R^e$(C=O) O$R^c$, —O(C=O)N$R^dR^e$, —N$R^c$(C=S) O$R^c$, —O(C=S)N$R^dR^e$, —N$R^c$(C=O)N$R^dR^e$, —N$R^c$(C=S)N$R^dR^e$, —C(=S)$R^c$, —C(=O)$R^c$, $C_1$-$C_6$ alkyl, $C_1$-$C_6$ haloalkyl, $C_1$-$C_6$ heteroalkyl, carbocyclyl, ($C_1$-$C_6$-alkylene)-carbocyclyl, ($C_1$-$C_6$-heteroalkylene)-carbocyclyl, heterocyclyl, ($C_1$-$C_6$-alkylene)-heterocyclyl, ($C_1$-$C_6$-heteroalkylene)-heterocyclyl, aryl, ($C_1$-$C_6$-alkylene)-aryl, ($C_1$-$C_6$-heteroalkylene)-aryl, heteroaryl, ($C_1$-$C_6$-alkylene)-heteroaryl, or ($C_1$-$C_6$-heteroalkylene)-heteroaryl, wherein each of said alkyl, alkylene, heteroalkyl, heteroalkylene, carbocyclyl, heterocyclyl, aryl and heteroaryl are optionally substituted with one or more of halogen, O$R^c$, —NO$_2$, —CN, —N$R^c$C(=O)$R^c$, —N$R^dR^e$, —S(O)$_kR^c$, —C(=O)O$R^c$, —C(=O)N$R^dR^e$, —C(=O)$R^c$, $C_1$-$C_6$ alkyl, $C_1$-$C_6$ haloalkyl, or $C_1$-$C_6$ heteroalkyl, and wherein $R^e$ is hydrogen, hydroxy, $C_1$-$C_6$ alkyl, $C_1$-$C_6$ heteroalkyl, carbocyclyl, ($C_1$-$C_6$-alkylene)-carbocyclyl, ($C_1$-$C_6$-heteroalkylene)-carbocyclyl, heterocyclyl, ($C_1$-$C_6$-alkylene)-heterocyclyl, ($C_1$-$C_6$-heteroalkylene)-heterocyclyl, aryl, ($C_1$-$C_6$-alkylene)-aryl, ($C_1$-$C_6$-heteroalkylene)-aryl, heteroaryl, ($C_1$-$C_6$-alkylene)-heteroaryl, or ($C_1$-$C_6$-heteroalkylene)-heteroaryl, each of which is optionally substituted with one or more of halogen, hydroxy, $C_1$-$C_6$ alkyl, $C_1$-$C_6$ haloalkyl, $C_1$-$C_6$ heteroalkyl, carbocyclyl, heterocyclyl, aryl, or heteroaryl; $R^d$ and $R^e$ are each independently selected from hydrogen, $C_1$-$C_6$ alkyl, or $C_1$-$C_6$ heteroalkyl; and k is 0, 1 or 2.

These and other exemplary substituents are described in more detail in the Detailed Description, Figures, Examples, and Claims. The invention is not intended to be limited in any manner by the above exemplary listing of substituents.

Other Definitions

The following definitions are more general terms used throughout the present application:

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, Berge et al., describe pharmaceutically acceptable salts in detail in *J. Pharmaceutical Sciences*, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid, and perchloric acid or with organic acids such as acetic acid, oxalic acid, maleic acid, tartaric acid, citric acid, succinic acid, or malonic acid or by using other methods known in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and $N^+(C_{1-4}\ alkyl)_4^-$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate, and aryl sulfonate.

The term "solvate" refers to forms of the compound that are associated with a solvent, usually by a solvolysis reaction. This physical association may include hydrogen bonding. Conventional solvents include water, methanol, ethanol, acetic acid, DMSO, THF, diethyl ether, and the like. The compounds of Formula (I) or (II) may be prepared, e.g., in crystalline form, and may be solvated. Suitable solvates include pharmaceutically acceptable solvates and further include both stoichiometric solvates and non-stoichiometric solvates. In certain instances, the solvate will be capable of isolation, for example, when one or more solvent molecules are incorporated in the crystal lattice of a crystalline solid. "Solvate" encompasses both solution-phase and isolable solvates. Representative solvates include hydrates, ethanolates, and methanolates.

The term "hydrate" refers to a compound which is associated with water. Typically, the number of the water molecules contained in a hydrate of a compound is in a definite ratio to the number of the compound molecules in the hydrate. Therefore, a hydrate of a compound may be represented, for example, by the general formula $R \cdot xH_2O$, wherein R is the compound and wherein x is a number greater than 0. A given compound may form more than one type of hydrates, including, e.g., monohydrates (x is 1), lower hydrates (x is a number greater than 0 and smaller than 1, e.g., hemihydrates ($R \cdot 0.5H_2O$)), and polyhydrates (x is a number greater than 1, e.g., dihydrates ($R \cdot 2H_2O$) and hexahydrates ($R \cdot 6H_2O$)).

A "subject" to which administration is contemplated includes, but is not limited to, humans (i.e., a male or female of any age group, e.g., a pediatric subject (e.g., infant, child, adolescent) or adult subject (e.g., young adult, middle-aged adult, or senior adult)) and/or other non-human animals, for example, mammals (e.g., primates (e.g., cynomolgus monkeys, rhesus monkeys); commercially relevant mammals such as cattle, pigs, horses, sheep, goats, cats, and/or dogs) and birds (e.g., commercially relevant birds such as chickens, ducks, geese, and/or turkeys). In certain embodiments, the animal is a mammal. The animal may be a male or female and at any stage of development. A non-human animal may be a transgenic animal.

The terms "administer," "administering," or "administration," as used herein refers to implanting, absorbing, ingesting, injecting, inhaling, or otherwise introducing an inventive compound, or a pharmaceutical composition thereof.

As used herein, the terms "treatment," "treat," and "treating" refer to reversing, alleviating, delaying the onset of, or inhibiting the progress of a "pathological condition" (e.g., a disease, disorder, or condition, or one or more signs or symptoms thereof) described herein. In some embodiments, "treatment," "treat," and "treating" require that signs or symptoms of the disease disorder or condition have developed or have been observed. In other embodiments, treatment may be administered in the absence of signs or symptoms of the disease or condition. For example, treatment may be administered to a susceptible individual prior to the onset of symptoms (e.g., in light of a history of symptoms and/or in light of genetic or other susceptibility factors). Treatment may also be continued after symptoms have resolved, for example, to delay or prevent recurrence.

As used herein, the terms "condition," "disease," and "disorder" are used interchangeably.

An "effective amount" of a compound of Formula (I) or (II) refers to an amount sufficient to elicit the desired biological response, i.e., treating the condition. As will be appreciated by those of ordinary skill in this art, the effective amount of a compound of Formula (I) or (II) may vary depending on such factors as the desired biological endpoint, the pharmacokinetics of the compound, the condition being treated, the mode of administration, and the age and health of the subject. An effective amount encompasses therapeutic and prophylactic treatment. For example, in treating cancer, an effective amount of an inventive compound may reduce the tumor burden or stop the growth or spread of a tumor.

A "therapeutically effective amount" of a compound of Formula (I) or (II) is an amount sufficient to provide a therapeutic benefit in the treatment of a condition or to delay or minimize one or more symptoms associated with the condition. In some embodiments, a therapeutically effective amount is an amount sufficient to provide a therapeutic benefit in the treatment of a condition or to minimize one or more symptoms associated with the condition. A therapeutically effective amount of a compound means an amount of therapeutic agent, alone or in combination with other therapies, which provides a therapeutic benefit in the treatment of the condition. The term "therapeutically effective amount" can encompass an amount that improves overall therapy, reduces or avoids symptoms or causes of the condition, or enhances the therapeutic efficacy of another therapeutic agent.

A "prophylactically effective amount" of a compound of Formula (I) or (II) is an amount sufficient to prevent a condition, or one or more symptoms associated with the condition or prevent its recurrence. A prophylactically effective amount of a compound means an amount of a therapeutic agent, alone or in combination with other agents, which provides a prophylactic benefit in the prevention of the condition. The term "prophylactically effective amount" can encompass an amount that improves overall prophylaxis or enhances the prophylactic efficacy of another prophylactic agent.

A "proliferative disease" refers to a disease that occurs due to abnormal growth or extension by the multiplication of cells (Walker, *Cambridge Dictionary of Biology*; Cambridge University Press: Cambridge, UK, 1990). A proliferative disease may be associated with: 1) the pathological proliferation of normally quiescent cells; 2) the pathological migration of cells from their normal location (e.g., metastasis of neoplastic cells); 3) the pathological expression of proteolytic enzymes such as the matrix metalloproteinases (e.g., collagenases, gelatinases, and elastases); or 4) the pathological angiogenesis as in proliferative retinopathy and tumor metastasis. Exemplary proliferative diseases include cancers (i.e., "malignant neoplasms"), benign neoplasms, angiogenesis, inflammatory diseases, autoinflammatory diseases, and autoimmune diseases.

The terms "neoplasm" and "tumor" are used herein interchangeably and refer to an abnormal mass of tissue wherein the growth of the mass surpasses and is not coordinated with the growth of a normal tissue. A neoplasm or tumor may be "benign" or "malignant," depending on the following characteristics: degree of cellular differentiation (including morphology and functionality), rate of growth, local invasion, and metastasis. A "benign neoplasm" is generally well differentiated, has characteristically slower growth than a malignant neoplasm, and remains localized to the site of origin. In addition, a benign neoplasm does not have the capacity to infiltrate, invade, or metastasize to distant sites. Exemplary benign neoplasms include, but are not limited to, lipoma, chondroma, adenomas, acrochordon, senile angiomas, seborrheic keratoses, lentigos, and sebaceous hyperplasias. In some cases, certain "benign" tumors may later give rise to malignant neoplasms, which may result from additional genetic changes in a subpopulation of the tumor's neoplastic cells, and these tumors are referred to as "pre-malignant neoplasms." An exemplary pre-malignant neoplasm is a teratoma. In contrast, a "malignant neoplasm" is generally poorly differentiated (anaplasia) and has characteristically rapid growth accompanied by progressive infiltration, invasion, and destruction of the surrounding tissue. Furthermore, a malignant neoplasm generally has the capacity to metastasize to distant sites.

As used herein, the term "cancer" refers to a malignant neoplasm (*Stedman's Medical Dictionary*, 25th ed.; Hensyl ed.; Williams & Wilkins: Philadelphia, 1990). Exemplary cancers include, but are not limited to, acoustic neuroma; adenocarcinoma; adrenal gland cancer; anal cancer; angiosarcoma (e.g., lymphangiosarcoma, lymphangioendotheliosarcoma, hemangiosarcoma); appendix cancer; benign monoclonal gammopathy; biliary cancer (e.g., cholangiocarcinoma); bladder cancer; breast cancer (e.g., adenocarcinoma of the breast, papillary carcinoma of the breast, mammary cancer, medullary carcinoma of the breast); brain cancer (e.g., meningioma, glioblastomas, glioma (e.g., astrocytoma, oligodendroglioma), medulloblastoma); bronchus cancer; carcinoid tumor; cervical cancer (e.g., cervical adenocarcinoma); choriocarcinoma; chordoma; craniopharyngioma; colorectal cancer (e.g., colon cancer, rectal cancer, colorectal adenocarcinoma); connective tissue cancer; epithelial carcinoma; ependymoma; endotheliosarcoma (e.g., Kaposi's sarcoma, multiple idiopathic hemorrhagic sarcoma); endometrial cancer (e.g., uterine cancer, uterine sarcoma); esophageal cancer (e.g., adenocarcinoma of the esophagus, Barrett's adenocarcinoma); Ewing's sarcoma; eye cancer (e.g., intraocular melanoma, retinoblastoma); familiar hypereosinophilia; gall bladder cancer; gastric cancer (e.g., stomach adenocarcinoma); gastrointestinal stromal tumor (GIST); germ cell cancer; head and neck cancer (e.g., head and neck squamous cell carcinoma, oral cancer (e.g., oral squamous cell carcinoma), throat cancer (e.g., laryngeal cancer, pharyngeal cancer, nasopharyngeal cancer, oropharyngeal cancer)); hematopoietic cancers (e.g., leukemia such as acute lymphocytic leukemia (ALL) (e.g., B-cell ALL, T-cell ALL), acute myelocytic leukemia (AML) (e.g., B-cell AML, T-cell AML), chronic myelocytic leukemia (CML) (e.g., B-cell CML, T-cell CML), and chronic lymphocytic leukemia (CLL) (e.g., B-cell CLL, T-cell CLL)); lymphoma such as Hodgkin lymphoma (HL) (e.g., B-cell HL, T-cell HL) and non-Hodgkin lymphoma (NHL) (e.g., B-cell NHL such as diffuse large cell lymphoma (DLCL) (e.g., diffuse large B-cell lymphoma), follicular lymphoma, chronic lymphocytic leukemia/small lymphocytic lymphoma (CLL/SLL), mantle cell lymphoma (MCL), marginal zone B-cell lymphomas (e.g., mucosa-associated lymphoid tissue (MALT) lymphomas, nodal marginal zone B-cell lymphoma, splenic marginal zone B-cell lymphoma), primary mediastinal B-cell lymphoma, Burkitt lymphoma, lymphoplasmacytic lymphoma (i.e., Waldenstrom's macroglobulinemia), hairy cell leukemia (HCL), immunoblastic large cell lymphoma, precursor B-lymphoblastic lymphoma and primary central nervous system (CNS) lymphoma; and T-cell NHL such as precursor T-lymphoblastic lymphoma/leukemia, peripheral T-cell lymphoma (PTCL) (e.g., cutaneous T-cell lymphoma (CTCL) (e.g., mycosis fungoides, Sezary syndrome), angioimmunoblastic T-cell lymphoma, extranodal natural killer T-cell lymphoma, enteropathy type T-cell lymphoma, subcutaneous panniculitis-like T-cell lymphoma, and anaplastic large cell lymphoma); a mixture of one or more leukemia/lymphoma as described above; and multiple myeloma (MM)), heavy chain disease (e.g., alpha chain disease, gamma chain disease, mu chain disease); hemangioblastoma; hypopharynx cancer; inflammatory myofibroblastic tumors; immunocytic amyloidosis; kidney cancer (e.g., nephroblastoma a.k.a. Wilms' tumor, renal cell carcinoma); liver cancer (e.g., hepatocellular cancer (HCC), malignant hepatoma); lung cancer (e.g., bronchogenic carcinoma, small cell lung cancer (SCLC), non-small cell lung cancer (NSCLC), adenocarcinoma of the lung); leiomyosarcoma (LMS); mastocytosis (e.g., systemic mastocytosis); muscle cancer; myelodysplastic syndrome (MDS); mesothelioma; myeloproliferative disorder (MPD) (e.g., polycythemia vera (PV), essential thrombocytosis (ET), agnogenic myeloid metaplasia (AMM) a.k.a. myelofibrosis (MF), chronic idiopathic myelofibrosis, chronic myelocytic leukemia (CML), chronic neutrophilic leukemia (CNL), hypereosinophilic syndrome (HES)); neuroblastoma; neurofibroma (e.g., neurofibromatosis (NF) type 1 or type 2, schwannomatosis); neuroendocrine cancer (e.g., gastroenteropancreatic neuroendocrine tumor (GEP-NET), carcinoid tumor); osteosarcoma (e.g., bone cancer); ovarian cancer (e.g., cystadenocarcinoma, ovarian embryonal carcinoma, ovarian adenocarcinoma); papillary adenocarcinoma; pancreatic cancer (e.g., pancreatic adenocarcinoma, intraductal papillary mucinous neoplasm (IPMN), Islet cell tumors); penile cancer (e.g., Paget's disease of the penis and scrotum); pinealoma; primitive neuroectodermal tumor (PNT); plasma cell neoplasia; paraneoplastic syndromes; intraepithelial neoplasms; prostate cancer (e.g., prostate adenocarcinoma); rectal cancer; rhabdomyosarcoma; salivary gland cancer; skin cancer (e.g., squamous cell carcinoma (SCC), keratoacanthoma (KA), melanoma, basal cell carcinoma (BCC)); small bowel cancer (e.g., appendix cancer); soft tissue sarcoma (e.g., malignant fibrous histiocytoma (MFH), liposarcoma, malignant peripheral nerve sheath tumor (MPNST), chondrosarcoma, fibrosarcoma, myxosarcoma); sebaceous gland carcinoma; small intestine cancer; sweat gland carcinoma; synovioma; testicular cancer (e.g., seminoma, testicular embryonal carcinoma); thyroid cancer (e.g., papillary carcinoma of the thyroid, papillary thyroid carcinoma (PTC), medullary thyroid cancer); urethral cancer; vaginal cancer; and vulvar cancer (e.g., Paget's disease of the vulva).

The term "angiogenesis" refers to the formation and the growth of new blood vessels. Normal angiogenesis occurs in the healthy body of a subject for healing wounds and for restoring blood flow to tissues after injury. The healthy body controls angiogenesis through a number of means, e.g., angiogenesis-stimulating growth factors and angiogenesis inhibitors. Many disease states, such as cancer, diabetic blindness, age-related macular degeneration, rheumatoid arthritis, and psoriasis, are characterized by abnormal (i.e., increased or excessive) angiogenesis. Abnormal angiogenesis refers to angiogenesis greater than that in a normal body, especially angiogenesis in an adult not related to normal angiogenesis (e.g., menstruation or wound healing). Abnormal angiogenesis can provide new blood vessels that feed diseased tissues and/or destroy normal tissues, and in the case of cancer, the new vessels can allow tumor cells to escape into the circulation and lodge in other organs (tumor metastases).

As used herein, an "inflammatory disease" refers to a disease caused by, resulting from, or resulting in inflammation. The term "inflammatory disease" may also refer to a dysregulated inflammatory reaction that causes an exaggerated response by macrophages, granulocytes, and/or T-lymphocytes leading to abnormal tissue damage and/or cell death. An inflammatory disease can be either an acute or chronic inflammatory condition and can result from infections or non-infectious causes. Inflammatory diseases include, without limitation, atherosclerosis, arteriosclerosis, autoimmune disorders, multiple sclerosis, systemic lupus erythematosus, polymyalgia rheumatica (PMR), gouty arthritis, degenerative arthritis, tendonitis, bursitis, psoriasis, cystic fibrosis, arthrosteitis, rheumatoid arthritis, inflammatory arthritis, Sjogren's syndrome, giant cell arteritis, progressive systemic sclerosis (scleroderma), ankylosing spondylitis, polymyositis, dermatomyositis, pemphigus, pemphigoid, diabetes (e.g., Type I), myasthenia gravis, Hashimoto's thyroiditis, Graves' disease, Goodpasture's disease, mixed connective tissue disease, sclerosing cholangitis, inflammatory bowel disease, Crohn's disease, ulcerative colitis, pernicious anemia, inflammatory dermatoses, usual interstitial pneumonitis (UIP), asbestosis, silicosis, bronchiectasis, berylliosis, talcosis, pneumoconiosis, sarcoidosis, desquamative interstitial pneumonia, lymphoid interstitial pneumonia, giant cell interstitial pneumonia, cellular interstitial pneumonia, extrinsic allergic alveolitis, Wegener's granulomatosis and related forms of angiitis (temporal arteritis and polyarteritis nodosa), inflammatory dermatoses, hepatitis, delayed-type hypersensitivity reactions (e.g., poison ivy dermatitis), pneumonia, respiratory tract inflammation, Adult Respiratory Distress Syndrome (ARDS), encephalitis, immediate hypersensitivity reactions, asthma, hayfever, allergies, acute anaphylaxis, rheumatic fever, glomerulonephritis, pyelonephritis, cellulitis, cystitis, chronic cholecystitis, ischemia (ischemic injury), reperfusion injury, allograft rejection, host-versus-graft rejection, appendicitis, arteritis, blepharitis, bronchiolitis, bronchitis, cervicitis, cholangitis, chorioamnionitis, conjunctivitis, dacryoadenitis, dermatomyositis, endocarditis, endometritis, enteritis, enterocolitis, epicondylitis, epididymitis, fasciitis, fibrositis, gastritis, gastroenteritis, gingivitis, ileitis, iritis, laryngitis, myelitis, myocarditis, nephritis, omphalitis, oophoritis, orchitis, osteitis, otitis, pancreatitis, parotitis, pericarditis, pharyngitis, pleuritis, phlebitis, pneumonitis, proctitis, prostatitis, rhinitis, salpingitis, sinusitis, stomatitis, synovitis, testitis, tonsillitis, urethritis, urocystitis, uveitis, vaginitis, vasculitis, vulvitis, vulvovaginitis, angitis, chronic bronchitis, osteomyelitis, optic neuritis, temporal arteritis, transverse myelitis, necrotizing fasciitis, and necrotizing enterocolitis.

As used herein, an "autoimmune disease" refers to a disease arising from an inappropriate immune response of the body of a subject against substances and tissues normally present in the body. In other words, the immune system mistakes some part of the body as a pathogen and attacks its own cells. This may be restricted to certain organs (e.g., in autoimmune thyroiditis) or involve a particular tissue in different places (e.g., Goodpasture's disease which may affect the basement membrane in both the lung and kidney). The treatment of autoimmune diseases is typically with immunosuppression, e.g., medications which decrease the immune response. Exemplary autoimmune diseases include, but are not limited to, glomerulonephritis, Goodpasture's syndrome, necrotizing vasculitis, lymphadenitis, peri-arteritis nodosa, systemic lupus erythematosis, rheumatoid, arthritis, psoriatic arthritis, systemic lupus erythematosis, psoriasis, ulcerative colitis, systemic sclerosis, dermatomyositis/polymyositis, anti-phospholipid antibody syndrome, scleroderma, pemphigus vulgaris, ANCA-associated vasculitis (e.g., Wegener's granulomatosis, microscopic polyangiitis), uveitis, Sjogren's syndrome, Crohn's disease, Reiter's syndrome, ankylosing spondylitis, Lyme arthritis, Guillain-Barré syndrome, Hashimoto's thyroiditis, and cardiomyopathy.

The term "autoinflammatory disease" refers to a category of diseases that are similar but different from autoimmune diseases. Autoinflammatory and autoimmune diseases share common characteristics in that both groups of disorders result from the immune system attacking a subject's own tissues and result in increased inflammation. In autoinflammatory diseases, a subject's innate immune system causes inflammation for unknown reasons. The innate immune system reacts even though it has never encountered autoantibodies or antigens in the subject. Autoinflammatory disorders are characterized by intense episodes of inflammation that result in such symptoms as fever, rash, or joint swelling. These diseases also carry the risk of amyloidosis, a potentially fatal buildup of a blood protein in vital organs. Autoinflammatory diseases include, but are not limited to, familial Mediterranean fever (FMF), neonatal onset multisystem inflammatory disease (NOMID), tumor necrosis factor (TNF) receptor-associated periodic syndrome (TRAPS), deficiency of the interleukin-1 receptor antagonist (DIRA), and Behçet's disease.

The term "biological sample" refers to any sample including tissue samples (such as tissue sections and needle biopsies of a tissue); cell samples (e.g., cytological smears (such as Pap or blood smears) or samples of cells obtained by microdissection); samples of whole organisms (such as samples of yeasts or bacteria); or cell fractions, fragments or organelles (such as obtained by lysing cells and separating the components thereof by centrifugation or otherwise). Other examples of biological samples include blood, serum, urine, semen, fecal matter, cerebrospinal fluid, interstitial fluid, mucus, tears, sweat, pus, biopsied tissue (e.g., obtained by a surgical biopsy or needle biopsy), nipple aspirates, milk, vaginal fluid, saliva, swabs (such as buccal swabs), or any material containing biomolecules that is derived from a first biological sample. Biological samples also include those biological samples that are transgenic, such as transgenic oocyte, sperm cell, blastocyst, embryo, fetus, donor cell, or cell nucleus.

DETAILED DESCRIPTION OF CERTAIN EMBODIMENTS OF THE INVENTION

Compounds

In one embodiment of the present invention, provided are compounds of Formula (I):

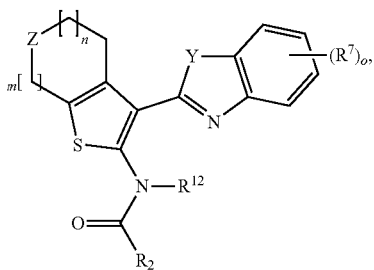

or a pharmaceutically acceptable salt solvate, hydrate, tautomer, or stereoisomer thereof, wherein:

Y is selected from O, S and $N(R^{3a})$;

Z is selected from $C(R^4)(N(R^5)(R^6))$ and $N(R^1)$;

$R^1$ is selected from hydrogen, $C_1$-$C_6$ alkyl, $C_1$-$C_6$ heteroalkyl, ($C_0$-$C_6$ alkylene)-carbocyclyl, ($C_1$-$C_6$ heteroalkylene)-carbocyclyl, ($C_0$-$C_6$ alkylene)-heterocyclyl, ($C_1$-$C_6$ heteroalkylene)-heterocyclyl, ($C_0$-$C_6$ alkylene)-aryl, ($C_1$-$C_6$ heteroalkylene)-aryl, ($C_0$-$C_6$ alkylene)-heteroaryl, ($C_1$-$C_6$ heteroalkylene)-heteroaryl, $CH_2C(O)OR^7$, $CH_2C(O)N(R^{10})(R^{11})$, and $CH_2CH_2N(R^{10})(R^{11})$, wherein:

$R^{10}$ is hydrogen or $C_1$-$C_4$ alkyl;

$R^{11}$ is selected from hydrogen, $C_1$-$C_4$ alkyl, $C_1$-$C_4$ heteroalkyl, ($C_0$-$C_4$ alkylene)-carbocyclyl, ($C_0$-$C_4$ alkylene)-heterocyclyl, ($C_0$-$C_4$ alkylene)-aryl, ($C_0$-$C_4$ alkylene)-heteroaryl, ($C_1$-$C_4$ alkyl)-O—($C_1$-$C_4$ alkyl), ($C_1$-$C_4$ alkyl)-N—($C_1$-$C_4$ alkyl)$_2$, ($C_1$-$C_4$ alkyl)-NH—($C_1$-$C_4$ alkyl), C(O)—($C_1$-$C_4$ alkyl), and C(O)—O—($C_1$-$C_4$ alkyl), or $R^{10}$ and $R^{11}$ are taken together with the nitrogen atom to which they are commonly bound to form a 4-11 membered heterocyclyl or heteroaryl; and any alkyl, alkylene, heteroalkyl, heteroalkylene, heterocyclyl, heteroaryl, aryl or carbocyclyl portion of $R^1$ is optionally substituted;

$R^2$ is selected from $C(R^{2a})(R^{2b})(R^{2c})$, carbocyclyl, aryl, heterocyclyl and heteroaryl, wherein any carbocyclyl, aryl, heterocyclyl and heteroaryl is optionally substituted;

$R^{2a}$ is selected from hydrogen, halogen, —CN, $C_1$-$C_4$ alkyl, $C_1$-$C_4$ heteroalkyl and $C_1$-$C_4$ haloalkyl, wherein any alkyl, heteroalkyl or haloalkyl is optionally substituted;

each of $R^{2b}$ and $R^{2c}$ is independently selected from hydrogen, halogen, —CN, $C_1$-$C_6$ alkyl, $C_1$-$C_6$ heteroalkyl, C(O)($C_1$-$C_6$ alkyl), C(O)($C_1$-$C_6$ heteroalkyl), C(O)O($C_1$-$C_6$ alkyl), C(O)O($C_1$-$C_6$ heteroalkyl), $C(O)N(R^{3a})(R^{3b})$, ($C_0$-$C_6$ alkylene)-carbocyclyl, ($C_1$-$C_6$ heteroalkylene)-carbocyclyl, ($C_0$-$C_6$ alkylene)-heterocyclyl, ($C_1$-$C_6$ heteroalkylene)-heterocyclyl, ($C_0$-$C_6$ alkylene)-aryl, ($C_1$-$C_6$ heteroalkylene)-aryl, ($C_0$-$C_6$ alkylene)-heteroaryl and ($C_1$-$C_6$ heteroalkylene)-heteroaryl, wherein any alkyl, alkylene, heteroalkyl, heteroalkylene, carbocyclyl, heterocyclyl, aryl or heteroaryl portion of $R^{2b}$ and $R^{2c}$ is optionally and independently substituted;

each of $R^{3a}$ and $R^{3b}$ is independently selected from hydrogen, $C_1$-$C_6$ alkyl, or $C_1$-$C_6$ heteroalkyl, each of which is optionally substituted;

each $R^4$ is independently selected from hydrogen, halogen, —CN, $C_1$-$C_8$ alkyl, $C_1$-$C_8$ heteroalkyl, $N(R^{3a})(R^{3b})$, C(O)($C_1$-$C_6$ alkyl), C(O)($C_1$-$C_6$ heteroalkyl), C(O)O($C_1$-$C_6$ alkyl), $C(O)N(R^{3a})(R^{3b})$, ($C_0$-$C_6$ alkylene)-carbocyclyl, ($C_1$-$C_6$ heteroalkylene)-carbocyclyl, ($C_0$-$C_6$ alkylene)-heterocyclyl, ($C_1$-$C_6$ heteroalkylene)-heterocyclyl, ($C_0$-$C_6$ alkylene)-aryl, ($C_1$-$C_6$ heteroalkylene)-aryl, ($C_0$-$C_6$ alkylene)-heteroaryl, and ($C_1$-$C_6$ heteroalkylene)-heteroaryl, wherein any alkyl, alkylene, heteroalkyl, heteroalkylene, carbocyclyl, heterocyclyl, aryl or heteroaryl portion of $R^4$ is optionally and independently substituted;

each of $R^5$ and $R^6$ is independently selected from hydrogen, $C_1$-$C_6$ alkyl, $C_1$-$C_6$ heteroalkyl, C(O)($C_1$-$C_6$ alkyl), C(O)O($C_1$-$C_6$ alkyl), ($C_0$-$C_6$ alkylene)-carbocyclyl, ($C_1$-$C_6$ heteroalkylene)-carbocyclyl, ($C_0$-$C_6$ alkylene)-heterocyclyl, ($C_1$-$C_6$ heteroalkylene)-heterocyclyl, ($C_0$-$C_6$ alkylene)-aryl, ($C_1$-$C_6$ heteroalkylene)-aryl, ($C_0$-$C_6$ alkylene)-heteroaryl, and ($C_1$-$C_6$ heteroalkylene)-heteroaryl, wherein any alkyl, alkylene, heteroalkyl, heteroalkylene, carbocyclyl, heterocyclyl, aryl or heteroaryl portion of each of $R^5$ and $R^6$ is optionally and independently substituted; or $R^5$ and $R^6$ are taken together with the nitrogen atom to which they are commonly bound to form an optionally substituted heterocyclyl;

each $R^7$ is independently selected from halogen, CN, $C_1$-$C_6$ alkyl, $C_1$-$C_6$ heteroalkyl, $N(R^{3a})(R^{3b})$, C(O)($C_1$-$C_6$ alkyl), C(O)O($C_1$-$C_6$ alkyl), ($C_0$-$C_6$ alkylene)-carbocyclyl, ($C_1$-$C_6$ heteroalkylene)-carbocyclyl, ($C_0$-$C_6$ alkylene)-heterocyclyl, ($C_1$-$C_6$ heteroalkylene)-heterocyclyl, ($C_0$-$C_6$ alkylene)-aryl, ($C_1$-$C_6$ heteroalkylene)-aryl, ($C_0$-$C_6$ alkylene)-heteroaryl, and ($C_1$-$C_6$ heteroalkylene)-heteroaryl, wherein any alkyl, alkylene, heteroalkyl, heteroalkylene, carbocyclyl, heterocyclyl, aryl or heteroaryl portion of $R^7$ is optionally and independently substituted;

$R^{12}$ is hydrogen, $C_1$-$C_6$ alkyl, $C_1$-$C_6$ heteroalkyl, ($C_0$-$C_3$ alkylene)-carbocyclyl, ($C_0$-$C_3$ alkylene)-heterocyclyl;

n is 0, 1 or 2;

m is 0, 1 or 2;

n+m=1, 2 or 3;

o is 0, 1, 2, 3 or 4; and p is 0, 1, 2, 3, 4, 5 or 6, wherein when Z is $N(R^1)$, $R^2$ is $-C(R^{2a})(R^{2b})[C(R^{9a})(R^{9b})]_{1-7}-N(R^{17})(R^8)$, wherein each of $R^{17}$ and $R^8$ is independently selected from hydrogen, optionally substituted $C_1$-$C_4$ alkyl, ($C_1$-$C_4$ alkylene)-heterocyclyl, ($C_1$-$C_4$ alkylene)-heteroaryl, and ($C_1$-$C_4$ alkylene)-aryl; or $R^{17}$ and $R^8$ are taken together with the nitrogen atom to which they are commonly bound to form a heterocyclyl or a heteroaryl, wherein any alkyl, alkylene, heterocyclyl, heteroaryl or aryl portion of $R^8$ or $R^{17}$ is optionally substituted;

each $R^{9a}$ and each $R^{9b}$ is independently selected from hydrogen, halogen, —CN, $C_1$-$C_8$ alkyl, ($C_0$-$C_6$ alkylene)-carbocyclyl, ($C_1$-$C_6$ heteroalkylene)-carbocyclyl, ($C_0$-$C_6$ alkylene)-heterocyclyl, ($C_1$-$C_6$ heteroalkylene)-heterocyclyl, ($C_0$-$C_6$ alkylene)-aryl, ($C_1$-$C_6$ heteroalkylene)-aryl, ($C_0$-$C_6$ alkylene)-heteroaryl, and ($C_1$-$C_6$ heteroalkylene)-heteroaryl, and any alkyl, alkylene, heteroalkyl, heteroalkylene, carbocyclyl, heterocyclyl, aryl or heteroaryl portion of $R^{9a}$ or $R^{9b}$ is optionally and independently substituted; and any $R^{9a}$ is optionally taken together with $R^{2b}$ or any $R^{9b}$ and the carbon atom or carbon atoms to which they are respectively bound and including any intervening atoms forms an optionally substituted carbocyclyl, heterocyclyl, aryl, or heteroaryl;
the compound is other than

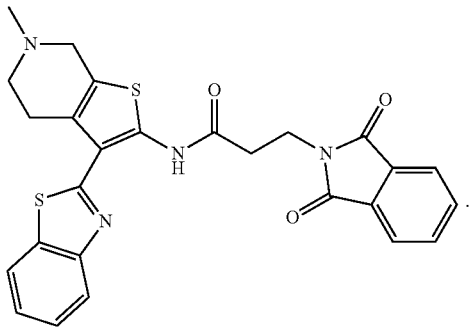 [SMILES: CN1CCc2c(sc(NC(=O)CCN3C(=O)c4ccccc4C3=O)c2-c2nc3ccccc3s2)C1]

In certain embodiments, Y is selected from O and S. In certain embodiments, Y is O. In certain embodiments, Y is S.

In certain embodiments, Y is $N(R^{3a})$, and $R^{3a}$ is hydrogen.

In certain embodiments, Z is additionally selected from $CH(N(R^5)(R^6))$ and $N^+(R^1)_2$.

In certain embodiments, $R^1$ is additionally selected from optionally substituted cycloalkyl.

In certain embodiments, $R^{2c}$ is additionally selected from a polyethylene glycol-$C(O)OR^{20}$ moiety of the formula —$CH_2$—$NR^{17}$—$(CH_2)_{0-1}$—$(CH_2CH_2O)_{3-20}$—$CH_2CH_2$—$R^{20}$, wherein $R^{20}$ is selected from —C(O)OH, —C(O)CH$_3$, —C(O)CH$_2$CH$_3$, —NH$_2$, —CH$_2$NH$_2$, —(CH$_2$)$_2$—NH$_2$, —(CH$_2$)$_3$—NH$_2$ In certain embodiments, $R^{3b}$ is additionally and independently selected from —$S(O)_2$—$C_1$-$C_6$ alkyl, —C(O)—$C_1$-$C_6$ alkyl, —C(O)-aryl, and heterocyclyl, wherein any alkyl, aryl or heterocyclyl portion of $R^{3b}$ is optionally and independently substituted.

In certain embodiments, two $R^4$ are taken together to the carbon ring atom or carbon ring atoms to which they are bound to form a carbocyclic ring that is fused, bridged, or spirofused to ring comprising Z.

In certain embodiments, each $R^7$ is additionally and independently selected from —OH, —$S(O)_2$—$C_1$-$C_6$ alkyl, —S—$C_1$-$C_6$ alkyl, and $C_2$-$C_6$ alkenyl, or two $R^7$ are taken together with the ring carbon atoms to which they are bound to form a heterocyclyl fused to rest of the compound.

In certain embodiments, each $R^{17}$ and $R^8$ is additionally selected from optionally substituted carbocyclyl, optionally substituted $C_1$-$C_6$ heteroalkyl, and —$(CH_2CH_2O)_{3-20}$—$CH_2CH_2R^{20}$.

In certain embodiments, any $R^{9a}$ is additionally and optionally taken together with $R^{17}$ and the atoms to which they are respectively bound and including any intervening atoms forms an optionally substituted heterocyclyl or heteroaryl.

In certain embodiments, Z is $N(R^1)$. In certain embodiments, Z is $N(R^1)$, and $R^1$ is selected from hydrogen, $C_1$-$C_6$ alkyl, $C_1$-$C_6$ heteroalkyl, ($C_0$-$C_6$ alkylene)-heterocyclyl, ($C_1$-$C_6$ heteroalkylene)-heterocyclyl, $CH_2C(O)OR^7$, $CH_2C(O)N(R^{10})(R^{11})$, and $CH_2CH_2N(R^{10})(R^{11})$, wherein $R^{10}$ is hydrogen or methyl and $R^{11}$ is selected from ($C_0$-$C_2$ alkylene)-carbocyclyl, ($C_0$-$C_2$ alkylene)-heterocyclyl, ($C_1$-$C_3$ alkyl)-O—($C_1$-$C_4$ alkyl), and C(O)—O—($C_1$-$C_4$ alkyl), or $R^{10}$ and $R^{11}$ are taken together with the nitrogen to which they are commonly bound to form a 4-11 membered heterocyclyl, and any alkyl, alkylene, heteroalkyl, heteroalkylene, carbocyclyl or heterocyclyl portion of $R^1$ is optionally substituted.

In certain embodiments, $R^1$ is selected from hydrogen, $C_1$-$C_6$ alkyl, $C_1$-$C_6$ heteroalkyl, ($C_0$-$C_6$ alkylene)-heterocyclyl, ($C_1$-$C_6$ heteroalkylene)-heterocyclyl, $CH_2C(O)OR^7$, $CH_2C(O)N(R^{10})(R^{11})$, and $CH_2CH_2N(R^{10})(R^{11})$, wherein $R^{10}$ is hydrogen or methyl and $R^{11}$ is selected from ($C_0$-$C_2$ alkylene)-carbocyclyl, ($C_0$-$C_2$ alkylene)-heterocyclyl, ($C_1$-$C_3$ alkyl)-O—($C_1$-$C_4$ alkyl), and C(O)—O—($C_1$-$C_4$ alkyl), or $R^{10}$ and $R^{11}$ are taken together with the nitrogen to which they are commonly bound to form a 4-11 membered heterocyclyl, and any alkyl, alkylene, heteroalkyl, carbocyclyl or heterocyclyl portion of $R^1$ is optionally substituted with up to three substituents independently selected from halogen, hydroxy, methyl, —NH$_2$, —NH(CH$_3$)—, —N(CH$_3$)$_2$, —CH$_2$NH$_2$, —CH$_2$CH$_2$NH$_2$, and heteroaryl. In certain embodiments, $R^1$ is additionally selected from cycloalkyl optionally substituted with one or two halogen.

In certain embodiments, $R^1$ is selected from hydrogen, methyl, ethyl, isopropyl, oxetan-3-yl, morpholin-4-ylpropan-2-yl, 1-methylpiperazin-4-ylcarbonylmethyl, 2-(pyridin-3-yl)ethylaminocarbonylmethyl, 1-(1H-imidazol-4-yl)methylaminocarbonylmethyl, 3,4-dihydroisoquinolin-2(1H)-ylcarbonylmethyl, 4-(1H-tetrazol-5-yl)phenylaminocarbonylmethyl, 4-(dimethylamino)phenylaminocarbonylmethyl, 1-(4,6-dimethyl-2-oxo-(pyridine-3-yl))methylaminocarbonylmethyl, 2-aminoethyl, 2-(1-methoxy)ethylaminocarbonylmethyl, 2-(morpholin-4-yl)ethyl, and 2-(tert-butoxycarbonylamino)ethyl. In certain embodiments $R^1$ is additionally selected from —(CH$_2$)$_2$NHC(O)CF$_3$, —C(O)OC(CH$_3$)$_3$, cyclobutyl, cyclopropyl, and 3,3-difluorocyclobutyl.

In certain embodiments, $R^1$ is selected from hydrogen, $C_1$-$C_6$ alkyl, and ($C_0$-$C_6$ alkylene)-heterocyclyl, and any alkyl, alkylene, or heterocyclyl portion of $R^1$ is optionally substituted.

In certain embodiments, $R^1$ is selected from hydrogen, methyl, ethyl, isopropyl, ($C_0$-$C_6$ alkylene)-oxetan-3-yl, each of which is optionally substituted. In certain embodiments $R^1$ is additionally selected from cyclobutyl and cyclopropyl, each of which is optionally substituted.

In some embodiments, $R^1$ is selected from hydrogen, methyl, ethyl, and isopropyl. In certain embodiments $R^1$ is additionally selected from cyclobutyl and cyclopropyl. In some embodiments, $R^1$ is hydrogen. In some embodiments, $R^1$ is isopropyl.

In certain embodiments, Z is $C(R^4)(N(R^5)(R^6))$. In certain embodiments, Z is $C(R^4)(N(R^5)(R^6))$, $R^4$ is selected from hydrogen and optionally substituted $C_1$-$C_8$ alkyl and $C_1$-$C_8$ heteroalkyl, $R^5$ is selected from hydrogen and optionally substituted $C_1$-$C_6$ alkyl, and $R^6$ is selected from hydrogen, $C_1$-$C_6$ alkyl, C(O)($C_1$-$C_6$ alkyl), C(O)O($C_1$-$C_6$ alkyl), ($C_0$-$C_6$ alkylene)-heterocyclyl, ($C_0$-$C_6$ alkylene)-heteroaryl, wherein any alkyl, heterocyclyl, or heteroaryl portion of $R^4$, $R^5$ or $R^6$ is optionally and independently substituted. In some embodiments, Z is $C(R^4)(N(R^5)(R^6))$, $R^4$ is selected from hydrogen and optionally substituted $C_1$-$C_8$ alkyl, and $R^5$ and $R^6$ are taken together with the nitrogen atom to which they are commonly bound to form an optionally substituted heterocyclyl.

In certain embodiments, Z is $C(R^4)(N(R^5)(R^6))$, $R^4$ is hydrogen, $R^5$ is selected from hydrogen and $C_1$-$C_6$ alkyl, and $R^6$ is selected from hydrogen, $C_1$-$C_6$ alkyl, C(O)($C_1$-$C_6$ alkyl), C(O)O($C_1$-$C_6$ alkyl), ($C_0$-$C_6$ alkylene)-heterocyclyl, and $(C_0-C_6$ alkylene)-heteroaryl, wherein any alkyl, heterocyclyl, or heteroaryl portion of $R^5$ or $R^6$ is optionally and independently substituted.

In certain embodiments, Z is $C(R^4)(N(R^5)(R^6))$, $R^4$ is hydrogen, $R^5$ is hydrogen or methyl, and $R^6$ is selected from hydrogen, $C_1-C_6$ alkyl, $C(O)(C_1-C_6$ alkyl), $(C_0-C_6$ alkylene)-heterocyclyl, and $(C_0-C_6$ alkylene)-heteroaryl, wherein any alkyl, heterocyclyl, or heteroaryl portion of $R^5$ or $R^6$ is optionally and independently substituted.

In certain embodiments, Z is $C(R^4)(N(R^5)(R^6))$, $R^4$ is hydrogen, $R^5$ is hydrogen or methyl, and $R^6$ is selected from hydrogen, methyl, $C(O)CH_3$, piperidin-4-yl, piperidin-4-ylmethyl, pyridin-4-yl, pyridin-4-ylmethyl, 1-tert-butoxycarbonylpiperidin-4-yl, and tetrahydropyran-4-yl, each of which is optionally and independently substituted.

In certain embodiments, Z is $C(R^4)(N(R^5)(R^6))$, $R^4$ is hydrogen, and each of $R^5$ and $R^6$ is independently selected from hydrogen or $C_1-C_6$ alkyl, wherein any alkyl portion of $R^5$ or $R^6$ is optionally and independently substituted.

In certain embodiments, Z is $C(R^4)(N(R^5)(R^6))$, $R^4$ is hydrogen, and each of $R^5$ and $R^6$ is independently hydrogen or methyl.

In certain embodiments, Z is $C(R^4)(N(R^5)(R^6))$, $R^4$ is hydrogen, and each of $R^5$ and $R^6$ is independently hydrogen.

In certain embodiments, $R^2$ is selected from $C(R^{2a})(R^{2b})(R^{2c})$, carbocyclyl, heterocyclyl, and heteroaryl, each of which is optionally substituted. In certain embodiments, $R^2$ is selected from $C(R^{2a})(R^{2b})(R^{2c})$ and heteroaryl, each of which is optionally substituted.

In certain embodiments, $R^2$ is $C(R^{2a})(R^{2b})(R^{2c})$. In certain embodiments, $R^2$ is $C(R^{2a})(R^{2b})(R^{2c})$, $R^{2a}$ is selected from hydrogen, halogen, $C_1-C_6$ alkyl, and $C_1-C_6$ heteroalkyl, and each of $R^{2b}$ and $R^{2c}$ is independently selected from hydrogen, $C_1-C_6$ alkyl, $C_1-C_6$ heteroalkyl, $C(O)(C_1-C_6$ alkyl), $C(O)(C_1-C_6$ heteroalkyl), $C(O)O(C_1-C_6$ alkyl), $C(O)N(R^{3a})(R^{3b})$, $(C_0-C_6$ alkylene)-carbocyclyl, $(C_1-C_6$ heteroalkylene)-carbocyclyl, $(C_0-C_6$ alkylene)-heterocyclyl, $(C_1-C_6$ heteroalkylene)-heterocyclyl, $(C_0-C_6$ alkylene)-aryl, $(C_1-C_6$ heteroalkylene)-aryl, $(C_0-C_6$ alkylene)-heteroaryl, and $(C_1-C_6$ heteroalkylene)-heteroaryl, wherein any alkyl, alkylene, heteroalkyl, heteroalkylene, carbocyclyl, heterocyclyl, aryl, or heteroaryl portion of $R^{2a}$, $R^{2b}$ and $R^{2c}$ is optionally substituted.

In certain embodiments, $R^2$ is $C(R^{2a})(R^{2b})(R^{2c})$, $R^{2a}$ is hydrogen, and each of $R^{2b}$ and $R^{2c}$ is independently selected from hydrogen, $C_1-C_6$ alkyl, $C_1-C_6$ heteroalkyl, $C(O)(C_1-C_6$ alkyl), $C(O)(C_1-C_6$ heteroalkyl), $C(O)O(C_1-C_6$ alkyl), $C(O)N(R^{3a})(R^{3b})$, $(C_0-C_6$ alkylene)-carbocyclyl, $(C_1-C_6$ heteroalkylene)-carbocyclyl, $(C_0-C_6$ alkylene)-heterocyclyl, $(C_1-C_6$ heteroalkylene)-heterocyclyl, $(C_0-C_6$ alkylene)-aryl, $(C_1-C_6$ heteroalkylene)-aryl, $(C_0-C_6$ alkylene)-heteroaryl, and $(C_1-C_6$ heteroalkylene)-heteroaryl, wherein any alkyl, alkylene, heteroalkyl, heteroalkylene, carbocyclyl, heterocyclyl, aryl, or heteroaryl portion of $R^{2b}$ and $R^{2c}$ is optionally and independently substituted.

In certain embodiments, $R^2$ is $C(R^{2a})(R^{2b})(R^{2c})$, $R^{2a}$ is hydrogen, and each of $R^{2b}$ and $R^{2c}$ is independently selected from hydrogen, $C_1-C_6$ alkyl, $C_1-C_6$ heteroalkyl, $C(O)(C_1-C_6$ alkyl), $C(O)N(R^{3a})(R^{3b})$, $(C_0-C_6$ alkylene)-carbocyclyl, $(C_1-C_6$ heteroalkylene)-carbocyclyl, $(C_0-C_6$ alkylene)-heterocyclyl, $(C_1-C_6$ heteroalkylene)-heterocyclyl, $(C_0-C_6$ alkylene)-aryl, $(C_1-C_6$ heteroalkylene)-aryl, $(C_0-C_6$ alkylene)-heteroaryl, and $(C_1-C_6$ heteroalkylene)-heteroaryl, wherein any alkyl, alkylene, heteroalkyl, heteroalkylene, carbocyclyl, heterocyclyl, aryl, or heteroaryl portion of $R^{2b}$ and $R^{2c}$ is optionally and independently substituted with halogen, hydroxy, $C_1-C_6$ alkyl, $C_1-C_6$ heteroalkyl, =O, O—$(C_1-C_6$ alkyl), heterocyclyl, or heteroaryl, each of which is optionally substituted.

In certain embodiments, $R^2$ is $C(R^{2a})(R^{2b})(R^{2c})$, $R^{2a}$ is hydrogen, $R^{2b}$ is hydrogen or $C_1-C_6$ alkyl, and $R^{2c}$ is selected from hydrogen, $C_1-C_6$ alkyl, $C_1-C_6$ heteroalkyl, $C(O)(C_1-C_6$ alkyl), $C(O)N(R^{3a})(R^{3b})$, $(C_0-C_6$ alkylene)-carbocyclyl, $(C_1-C_6$ heteroalkylene)-carbocyclyl, $(C_0-C_6$ alkylene)-heterocyclyl, $(C_1-C_6$ heteroalkylene)-heterocyclyl, $(C_0-C_6$ alkylene)-aryl, $(C_1-C_6$ heteroalkylene)-aryl, $(C_0-C_6$ alkylene)-heteroaryl, and $(C_1-C_6$ heteroalkylene)-heteroaryl, wherein any alkyl, alkylene, heteroalkyl, heteroalkylene, carbocyclyl, heterocyclyl, aryl, or heteroaryl portion of $R^{2b}$ and $R^{2c}$ is optionally and independently substituted.

In certain embodiments, $R^2$ is $C(R^{2a})(R^{2b})(R^{2c})$, $R^{2a}$ is hydrogen, $R^{2b}$ is hydrogen or $C_1-C_6$ alkyl, and $R^{2c}$ is selected from hydrogen, $C_1-C_6$ alkyl, $C_1-C_6$ heteroalkyl, $C(O)(C_1-C_6$ alkyl), or $C(O)N(R^{3a})(R^{3b})$, wherein any alkyl or heteroalkyl portion of $R^{2c}$ is optionally substituted.

In certain embodiments, $R^2$ is $C(R^{2a})(R^{2b})(R^{2c})$, $R^{2a}$ is hydrogen, $R^{2b}$ is hydrogen, and $R^{2c}$ is selected from hydrogen, $C_1-C_6$ alkyl, $C_1-C_6$ heteroalkyl, $C(O)(C_1-C_6$ alkyl), or $C(O)N(R^{3a})(R^{3b})$, wherein any alkyl or heteroalkyl portion of $R^{2b}$ and $R^{2c}$ is optionally and independently substituted with $C_1-C_6$ alkyl.

In certain embodiments, $R^2$ is $C(R^{2a})(R^{2b})(R^{2c})$, and $R^{2a}$ is hydrogen, $R^{2b}$ is hydrogen or $CH_3$, and $R^{2c}$ is selected from hydrogen, $CH_2NHCH(CH_3)CH_2CH_3$, $CH_2N(CH_3)CH(CH_3)CH_2CH_3$, $CH_2NHCH_3$, $CH_2NHCH_2CH_2OCH_3$, $CH_2N(CH_3)_2$, $CH_2NH(CH_2)_3(OCH_2CH_2)_3CH_2NH_2$, $CH_2NHCH_2CH_2N(CH_2CH_3)_2$, $CH_2NHC(CH_3)_3$, $CH_2NHCH(CH_3)_2$, $CH_2N(CH(CH_3)CH_2CH_3)C(O)OC(CH_3)_3$, $C(O)NHCH(CF_3)_2$, $CH_2SCH(CH_3)CH_2CH_3$, $CH_2S(O)CH(CH_3)CH_2CH_3$, $CH_2S(O)_2CH(CH_3)CH_2CH_3$, $C(O)N(CH_2CH_2OCH_3)_2$, $CH_2CH_2NHC(CH_3)CH_2CH_3$, $CH_2OCH(CH_3)CH_2CH_3$, $CH_2CH(OH)CH(CH_3)CH_2CH_3$, $CH_2C(O)CH(CH_3)CH_2CH_3$, $C(O)NHCH(CF_3)CH_2CH_3$, $C(O)NHCH(CH_3)CH_2CH_3$, $C(CH_3)_2NHCH(CH_3)CH_2CH_3$, $CH(CH_3)NHCH(CH_3)CH_2CH_3$, $CH_2NHC(O)CH_2CH_3$, and $CH_2NHCH_2C(O)OCH_2CH_3$.

In certain embodiments, $R^2$ is $C(R^{2a})(R^{2b})(R^{2c})$, and $R^{2a}$ is hydrogen, $R^{2b}$ is hydrogen or $CH_3$, and $R^{2c}$ is selected from hydrogen, $CH_2NHCH(CH_3)CH_2CH_3$, $CH_2N(CH_3)CH(CH_3)CH_2CH_3$, $CH_2NHCH_3$, $CH_2NHCH_2CH_2OCH_3$, $CH_2N(CH_3)_2$, $CH_2NH(CH_2)_3(OCH_2CH_2)_3CH_2NH_2$, $CH_2NHCH_2CH_2N(CH_2CH_3)_2$, $CH_2NHC(CH_3)_3$, $CH_2NHCH(CH_3)_2$, $CH_2CH_2NHC(CH_3)CH_2CH_3$, and $CH_2OCH(CH_3)CH_2CH_3$.

In certain embodiments, $R^2$ is $C(R^{2a})(R^{2b})(R^{2c})$, $R^{2a}$ is hydrogen, $R^{2b}$ is hydrogen, and $R^{2c}$ is selected from hydrogen, $C_1-C_6$ alkyl, and $C_1-C_6$ heteroalkyl, wherein any alkyl or heteroalkyl portion of $R^{2b}$ and $R^{2c}$ is optionally and independently substituted with $C_1-C_6$ alkyl.

In certain embodiments, $R^2$ is $C(R^{2a})(R^{2b})(R^{2c})$, $R^{2a}$ is hydrogen, $R^{2b}$ is hydrogen, and $R^{2c}$ is selected from hydrogen and $CH_2NHCH(CH_3)CH_2CH_3$. In certain embodiments, $R^2$ is $C(R^{2a})(R^{2b})(R^{2c})$, and each of $R^{2a}$, $R^{2b}$, and $R^{2c}$ is independently hydrogen.

In certain embodiments, $R^2$ is $C(R^{2a})(R^{2b})(R^{2c})$, $R^{2a}$ is hydrogen, $R^{2b}$ is hydrogen or $C_1-C_6$ alkyl, and $R^{2c}$ is selected from hydrogen, $(C_1-C_6$ heteroalkylene)-carbocyclyl, $(C_1-C_6$ heteroalkylene)-heterocyclyl, $(C_1-C_6$ heteroalkylene)-aryl, and $(C_1-C_6$ heteroalkylene)-heteroaryl, wherein any alkyl, heteroalkylene, carbocyclyl, heterocyclyl, aryl, or heteroaryl portion of $R^{2b}$ and $R^{2c}$ is optionally and independently substituted.

In certain embodiments, $R^2$ is $C(R^{2a})(R^{2b})(R^{2c})$, $R^{2a}$ is hydrogen, $R^{2b}$ is hydrogen or $C_1$-$C_6$ alkyl, and $R^{2c}$ is selected from hydrogen, ($C_1$-$C_6$ heteroalkylene)-carbocyclyl, ($C_1$-$C_6$ heteroalkylene)-heterocyclyl, ($C_1$-$C_6$ heteroalkylene)-aryl, and ($C_1$-$C_6$ heteroalkylene)-heteroaryl, wherein any alkyl, heteroalkylene, carbocyclyl, heterocyclyl, aryl, or heteroaryl portion of $R^{2b}$ and $R^{2c}$ is optionally and independently substituted with halogen, hydroxy, $C_1$-$C_6$ alkyl, $C_1$-$C_6$ heteroalkyl, O—($C_1$-$C_6$ alkyl), heterocyclyl, or heteroaryl, each of which is optionally substituted.

In certain embodiments, $R^2$ is $C(R^{2a})(R^{2b})(R^{2c})$, $R^{2a}$ is hydrogen, $R^{2b}$ is hydrogen or $CH_3$, and $R^{2c}$ is selected from hydrogen, 1-(pyridine-4-yl)ethyl-1-aminomethyl, 2,2-(pyridin-3-yl)ethylaminomethyl, 2-(1-(1-methyl-1H-pyrazol-4-yl)methyl)aminomethyl, 1,2,3,4-tetrahydroisoquinolin-2-methyl, pyridin-3-ylaminomethyl, 4-methylpiperazin-1-ylmethyl, morpholin-4-ylmethyl, 2-(2-chlorophenyl) ethylaminomethyl, 1-methylaniline, 4-(1H-tetrazol-5-yl) methylaniline, 2-(3-hydroxyphenyl)aminomethyl, 2-(3-methoxyphenyl)aminomethyl, 2-(3-fluorophenyl) aminomethyl, 1-phenylmethylaminomethyl, 4,6-dimethyl-3-(pyridine-2(1H)-onyl)methylaminomethyl, 1H-pyrrol-2,5-dionyl-aminomethyl, 2-(pyridine-3-yl)ethylaminomethyl, 1-(sec-butyl)piperidin-4-ylmethyl, 1-(sec-butyl)piperidin-3-ylmethyl, 1-(sec-butyl)pyrrolidin-3-ylmethyl, cyclohexylaminomethyl, tetrahydro-2H-pyran-4ylaminomethyl, tetrahydro-2H-thiopyran-4ylaminomethyl, and 4-tetrahydro-2H-thiopyran-1,1-dioxoaminomethyl.

In certain embodiments, $R^2$ is $C(R^{2a})(R^{2b})(R^{2c})$, $R^{2a}$ is hydrogen, $R^{2b}$ is hydrogen or $CH_3$, and $R^{2c}$ is selected from hydrogen, 1-(pyridine-4-yl)ethyl-1-aminomethyl, 2,2-(pyridin-3-yl)ethylaminomethyl, 2-(1-(1-methyl-1H-pyrazol-4-yl)methyl)aminomethyl, 1,2,3,4-tetrahydroisoquinolin-2-methyl, pyridin-3-ylaminomethyl, 4-methylpiperazin-1-ylmethyl, morpholin-4-ylmethyl, 2-(2-chlorophenyl) ethylaminomethyl, 1-methylaniline, 2-(3-hydroxyphenyl) aminomethyl, 2-(3-methoxyphenyl)aminomethyl, 2-(3-fluorophenyl)aminomethyl, 1-phenylmethylaminomethyl, 4,6-dimethyl-3-(pyridine-2(1H)-onyl)methylaminomethyl, and 2-(pyridine-3-yl)ethylaminomethyl.

In certain embodiments, $R^2$ is $C(R^{2a})(R^{2b})(R^{2c})$, $R^{2a}$ is hydrogen, $R^{2b}$ is hydrogen, and $R^{2c}$ is selected from hydrogen, ($C_1$-$C_6$ heteroalkylene)-carbocyclyl, ($C_1$-$C_6$ heteroalkylene)-heterocyclyl, ($C_1$-$C_6$ heteroalkylene)-aryl, and ($C_1$-$C_6$ heteroalkylene)-heteroaryl, wherein any alkyl, heteroalkylene, carbocyclyl, heterocyclyl, aryl, or heteroaryl portion of $R^{2b}$ and $R^{2c}$ is optionally and independently substituted with halogen, hydroxy, $C_1$-$C_6$ alkyl, $C_1$-$C_6$ heteroalkyl, O—($C_1$-$C_6$ alkyl), heterocyclyl, or heteroaryl, each of which is optionally substituted.

In certain embodiments, $R^2$ is optionally substituted carbocyclyl. In certain embodiments, $R^2$ is selected from cyclopropyl, cyclobutyl, cyclopentyl, and cyclohexyl, each of which is optionally substituted.

In certain embodiments, $R^2$ is optionally substituted heterocyclyl. In certain embodiments, $R^2$ is selected from a sulfur-, oxygen-, and nitrogen-containing heterocyclyl, each of which is optionally substituted. In certain embodiments, $R^2$ is selected from a 4-, 5-, and 6-membered heterocyclyl, each of which is optionally substituted. In certain embodiments, $R^2$ is selected from azetidin-3-yl, pyrrolidin-3-yl, tetrahydrofuran-3-yl, piperidin-4-yl, tetrahydropyran-3-yl, and tetrahydrofuran-4-yl, each of which is optionally substituted.

In certain embodiments, $R^2$ is optionally substituted heteroaryl. In certain embodiments, $R^2$ is selected from a sulfur-, oxygen-, and nitrogen-containing heteroaryl, each of which is optionally substituted. In certain embodiments, $R^2$ is selected from a 5- and 6-membered heteroaryl, each of which is optionally substituted. In certain embodiments, $R^2$ is selected from thiophen-2-yl, thiophen-3-yl, pyrrol-2-yl, pyrrol-3-yl, furan-2-yl, and furan-3-yl, each of which is optionally substituted.

In certain embodiments, Z is $N(R^1)$, and $R^2$ is —$C(R^{2a})(R^{2b})[C(R^{9a})(R^{9b})]_{1-7}$—$N(R^{17})(R^8)$. In one aspect of these embodiments, $R^2$ is —$CH_2CH(R^{9a})$—$N(R^{17})(R^8)$, providing a compound of Formula (Ie-2):

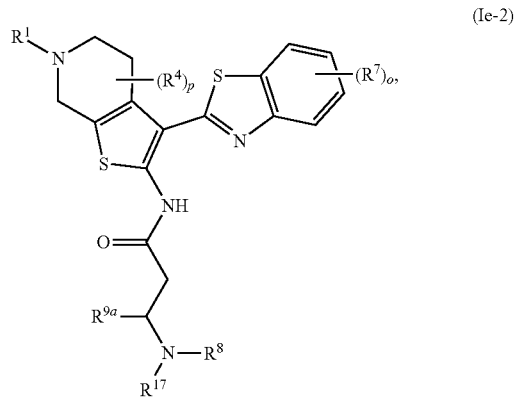

(Ie-2)

wherein $R^{9a}$ is selected from hydrogen or $R^{9a}$ is taken together with $R^{17}$ to form an optionally substituted heterocyclyl, and $R^8$ is as defined for Formula I. In a more specific aspect of Formula Ie-2, $R^{9a}$ is selected from hydrogen or $R^{9a}$ is taken together with $R^{17}$ to form azetidinyl or morpholinyl.

In certain embodiments of Formula Ie-2, $R^{17}$ is selected from hydrogen and —$CH_3$; and $R^8$ is selected from —CH($CH_3$)$CH_2CH_3$, —$CH_3$, —$CH_2CH_2OCH_3$, —$(CH_2)_3$ $(OCH_2CH_2)_3CH_2NH_2$, —$CH_2CH_2N(CH_2CH_3)_2$, —$C$ $(CH_3)_3$, —$CH(CH_3)_2$, —$CH_2CH(CH_3)_2$, —$CH_2CH_3$, —$(CH_2)_2CH_3$, —$CH_2CH_2OH$, —$C(CH_3)CH_2CH_3$, —CH $(CH_3)CH_2CH_3$, —$C(O)CH_2CH_3$, —$C(O)CH_3$, —$CH_2C(O)$ $OCH_2CH_3$, —$(CH_2)_2OCH_3$, —$CH_2C(O)OH$, —$(CH_2CH_2O)_6$—$(CH_2)_2C(O)OH$, —$(CH_2CH_2O)_6$— $(CH_2)_2$ $C(O)OCH_2CH_3$, 1H-pyrazol-4-ylmethyl, 1H-imidazol-4-ylmethyl, cyclopropyl, cyclobutyl, cyclopentyl, bicyclo[1.1.1]pentan-1-yl, octahydrocyclopenta[c]pyrrol-5-yl; or $R^8$ and $R^{17}$ are taken together with the nitrogen atom to which they are bound to form morpholinyl, azetidinyl, or pyrrolidinyl.

In certain embodiments Formula Ie-2, $R^{17}$ is hydrogen; and $R^8$ is selected from —$CH_3$, —$CH_2CH_3$, —$CH(CH_3)_2$, —$C(CH_3)_3$, —$CH_2CH_2OH$, —$(CH_2)_2OCH_3$, —$CH(CH_3)$ $CH_2CH_3$, —$CH_2CH(CH_3)_2$, $CH_2CH_2N(CH_2CH_3)_2$, $(CH_2)_3$ $(OCH_2CH_2)_3CH_2NH_2$, —$(CH_2CH_2O)_6$—$(CH_2)_2C(O)OH$, —$(CH_2CH_2O)_6$—$(CH_2)_2C(O)OCH_2CH_3$, 1H-pyrazol-4-ylmethyl, 1H-imidazol-4-ylmethyl, and octahydrocyclopenta[c]pyrrol-5-yl.

In certain embodiments, $R^4$ is selected from hydrogen, halogen, $C_1$-$C_8$ alkyl, $C_1$-$C_8$ heteroalkyl, $N(R^{3a})(R^{3b})$, $C(O)$ ($C_1$-$C_6$ alkyl), $C(O)O(C_1$-$C_6$ alkyl), $C(O)N(R^{3a})(R^{3b})$, ($C_0$-$C_6$ alkylene)-carbocyclyl, ($C_1$-$C_6$ heteroalkylene)-carbocyclyl, ($C_0$-$C_6$ alkylene)-heterocyclyl, ($C_1$-$C_6$ heteroalkylene)-heterocyclyl, ($C_0$-$C_6$ alkylene)-aryl, and ($C_0$-$C_6$ alkylene)-heteroaryl, wherein any alkyl, alkylene, heteroalkyl, heteroalkylene, carbocyclyl, heterocyclyl, aryl or heteroaryl portion of $R^4$ is optionally and independently substituted.

In certain embodiments, $R^4$ is selected from hydrogen, halogen, $C_1$-$C_8$ alkyl, $C_1$-$C_8$ heteroalkyl, $N(R^{3a})(R^{3b})$, ($C_0$-$C_6$ alkylene)-heterocyclyl, and ($C_0$-$C_6$ alkylene)-heteroaryl, wherein any alkyl, alkylene, heteroalkyl, heterocyclyl or heteroaryl portion of $R^4$ is optionally and independently substituted.

In certain embodiments, $R^4$ is selected from hydrogen, halogen, $C_1$-$C_4$ alkyl, $C_1$-$C_4$ heteroalkyl, $N(R^{3a})(R^{3b})$, and ($C_0$-$C_4$ alkylene)-heteroaryl, wherein each of $R^{3a}$ and $R^{3b}$ is independently selected from hydrogen and $C_1$-$C_4$ alkyl, and any alkyl, alkylene, heteroalkyl, heterocyclyl or heteroaryl portion of $R^4$ is optionally and independently substituted.

In certain embodiments, $R^4$ is selected from hydrogen, halogen, $N(R^{3a})(R^{3b})$, $C_1$-$C_8$ alkyl and $C_1$-$C_8$ heteroalkyl, wherein any alkyl or heteroalkyl portion of $R^4$ is optionally substituted. In certain embodiments, $R^4$ is selected from hydrogen, halogen, $C_1$-$C_4$ alkyl, $NH(C_1$-$C_4$ alkyl), and $N(C_1$-$C_4$ alkyl)$_2$.

In certain embodiments, $R^4$ is selected from hydrogen and optionally substituted $C_1$-$C_4$ alkyl. In certain embodiments, $R^4$ is selected from hydrogen, methyl, ethyl, isopropyl, $CHF_2$, and $CF_3$. In certain embodiments, $R^4$ is hydrogen or methyl. In certain embodiments, $R^4$ is methyl. In certain embodiments, $R^4$ is hydrogen.

In certain embodiments, $R^4$ is $N(R^{3a})(R^{3b})$, and each of $R^{3a}$ and $R^{3b}$ is independently hydrogen or methyl. In some embodiments, $R^4$ is $NH_2$, $NH(CH_3)$, or $N(CH_3)_2$.

In certain embodiments, $R^4$ is halogen. In certain embodiments, $R^4$ is fluoro, chloro, bromo, or iodo.

In certain embodiments, $R^4$ is not hydrogen.

In certain embodiments, two $R^4$ are taken together with the carbon atoms to which they are bound to form a cycloheptyl ring bridged to the ring comprising Z. In one aspect of these embodiments, the resulting bridged ring is

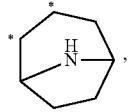

wherein the asterisks denote where the resulting fused ring is bound to the rest of the compound.

In certain embodiments, p is 0, 1, 2, or 3. In certain embodiments, p is 0, 1, or 2. In certain embodiments, p is 0. In certain embodiments, p is 1. In certain embodiments, p is 2.

In certain embodiments, when p is 1 or 2, each $R^4$ is independently selected from hydrogen, halogen, $C_1$-$C_8$ alkyl, $C_1$-$C_8$ heteroalkyl, or $N(R^{3a})(R^{3b})$, wherein each of $R^{3a}$ and $R^{3b}$ is independently hydrogen or $C_1$-$C_4$ alkyl and any alkyl or heteroalkyl portion of $R^4$ is optionally substituted. In certain embodiments, when p is 1 or 2, each $R^4$ is independently halogen or optionally substituted $C_1$-$C_8$ alkyl. In certain embodiments, when p is 1 or 2, each $R^4$ is independently halogen or optionally substituted $C_1$-$C_4$ alkyl. In certain embodiments, when p is 1 or 2, each $R^4$ is independently fluoro, methyl, ethyl, or $CF_3$. In certain embodiments, when p is 1 or 2, each $R^4$ is independently fluoro, methyl, or $CF_3$.

In certain embodiments, when p is 1 or 2, each $R^4$ is independently $N(R^{3a})(R^{3b})$ and each of $R^{3a}$ and $R^{3b}$ is independently hydrogen or $C_1$-$C_4$ alkyl.

In certain embodiments, when p is 1 or 2, each $R^4$ is independently fluoro, chloro, bromo, or iodo.

In certain embodiments, each $R^7$ is independently selected from halogen, $C_1$-$C_6$ alkyl, $C_1$-$C_6$ heteroalkyl, $N(R^{3a})(R^{3b})$, $C(O)(C_1$-$C_6$ alkyl), $C(O)O(C_1$-$C_6$ alkyl), ($C_0$-$C_6$ alkylene)-heterocyclyl, ($C_1$-$C_6$ heteroalkylene)-heterocyclyl, ($C_0$-$C_6$ alkylene)-heteroaryl, and ($C_1$-$C_6$ heteroalkylene)-heteroaryl, wherein any alkyl, alkylene, heteroalkyl, heteroalkylene, heterocyclyl or heteroaryl portion of $R^7$ is optionally and independently substituted.

In certain embodiments, each $R^7$ is independently selected from halogen, $C_1$-$C_6$ alkyl, $N(R^{3a})(R^{3b})$, $C(O)(C_1$-$C_6$ alkyl), and $C(O)O(C_1$-$C_6$ alkyl), wherein any alkyl portion of $R^7$ is optionally and independently substituted.

In certain embodiments, each $R^7$ is independently selected from halogen, $C_1$-$C_6$ alkyl and $C(O)O(C_1$-$C_6$ alkyl), wherein any alkyl portion of each $R^7$ is optionally and independently substituted.

In certain embodiments, one $R^7$ is halogen. In certain embodiments, one $R^7$ is fluoro, chloro, bromo, or iodo.

In certain embodiments, one $R^7$ is $C_1$-$C_6$ alkyl. In certain embodiments, one $R^7$ is methyl, ethyl or isopropyl. In certain embodiments, one $R^7$ is methyl.

In certain embodiments, one $R^7$ is $C(O)O(C_1$-$C_4$ alkyl). In certain embodiments, one $R^7$ is $C(O)OCH_3$.

In certain embodiments, each $R^7$ is independently selected from fluoro, chloro, bromo, methyl, ethyl, isopropyl, and $C(O)OCH_3$.

In certain embodiments, o is 0, 1, 2 or 3. In certain embodiments, o is 0, 1 or 2. In certain embodiments, o is 0 or 1. In certain embodiments, o is 1. In certain embodiments, o is 0.

In certain embodiments, when o is 1, 2, or 3, each $R^7$ is independently selected from halogen, $C_1$-$C_6$ alkyl and $C(O)O(C_1$-$C_6$ alkyl), wherein any alkyl portion of $R^7$ is optionally and independently substituted.

In certain embodiments, when o is 1 or 2, each $R^7$ is independently selected from fluoro, bromo, chloro, methyl, ethyl, isopropyl, and $C(O)OCH_3$.

In certain embodiments, o is 1 or 2, and each $R^7$ is independently selected from —CN, —OH, halogen, $C_1$-$C_6$ alkyl, $C_2$-$C_4$ alkenyl, $C_1$-$C_6$ heteroalkyl, heteroaryl, heterocyclyl, and aryl, wherein each alkyl, alkenyl, heteroalkyl, heteroaryl, heterocyclyl, and aryl are optionally substituted; or when o is 2, two $R^7$ are optionally taken together to form a heterocyclyl fused to the rest of the compound.

In certain embodiments, o is 1 or 2, and each $R^7$ is independently selected from —CN, —OH, fluoro, bromo, chloro, —CH=CH$_2$, optionally substituted $C_1$-$C_2$ alkyl, —O—$C_1$-$C_2$ alkyl, —S(O)$_2$—$C_1$-$C_2$ alkyl, —NH—S(O)$_2$—$C_1$-$C_2$ alkyl, —C(O)—NH—$C_1$-$C_2$ alkyl-O—$C_1$-$C_2$ alkyl, an optionally substituted phenyl, an optionally substituted heteroaryl selected from triazolyl, tetrazolyl, imidazolyl, pyrazolyl, isoxazolyl, pyrimidinyl, pyridinyl, an optionally substituted heterocyclyl selected from azetidinyl, oxetanyl, morpholinyl, tetrahydropyridinyl, dihydropyranyl, triazolylpyridinyl, or two $R^7$ are taken together with two adjacent carbon atoms to which they are bound to form a methylenedioxy or an ethylenedioxy fused to the rest of the compound.

In certain embodiments, each $R^7$ is selected from a heteroaryl, heterocyclyl, and aryl is optionally substituted with up to 3 substituents independently selected from chloro, fluoro, —OH, —CN, —CH$_3$, —CH(CH$_3$)$_2$, —NH$_2$, —OCH$_3$, —S(O)$_2$CH$_3$, —C(O)OCH$_3$, morpholinyl, morpholinylcarbonyl, piperazinyl, methylpiperazinyl, acetamido, N-(2-(dimethylamino)ethyl)aminocarbonyl, dimethylaminocarbonyl, and 1-ethoxycarbonylmethyl.

In certain embodiments, o is 1 or 2, and each $R^7$ is independently selected from fluoro, bromo, chloro, —CN, —OH, —CH$_3$, —CH$_2$CH$_3$, —CF$_3$, —CH(OH)CH$_3$, —CH$_2$OH, —OCH$_3$, —CH=CH$_2$, —C(O)—NH—(CH$_2$)$_2$—OCH$_3$, —NH—S(O)$_2$CH$_3$, —S(O)$_2$CH$_3$, 1,2,5,6-tetrahydropyridin-4-yl, 1-methylsulfonyl-1,2,5,6-tetrahydropyridin-4-yl, 4-(morpholin-4-ylcarbonyl)phenyl, 4-(4-methylpiperazin-1-yl)phenyl, 4-hydroxyphenyl, 4-methoxyphenyl, 4-methylsulfonylphenyl, 4-acetamidophenyl, 3-(N-(2-(dimethylamino)ethyl)aminocarbonyl)phenyl, 3-(dimethylaminocarbonyl)phenyl, 1H-1,2,4-triazol-1-yl, 1H-imidazol-1-yl, 5-chloro-1H-imidazol-1-yl, 1H-pyrazol-5-yl, 1H-pyrazol-4-yl, 1,3-dimethylpyrazol-4-yl, 1,3-dimethylpyrazol-5-yl, 1-isopropyl-1H-pyrazol-4-yl, 1-(1-ethoxycarbonylmethyl)-1H-pyrazol-4-yl, isoxazol-4-yl, 3-hydroxyazetidin-1-yl, oxetan-3-ylamino, pyrimidin-5-yl, 2-aminopyrimidin-5-yl, 2-methoxypyrimidin-5-yl, 5-methyl-1H-pyrazol-3-yl, 1-methyl-1H-pyrazol-4-yl, 4-methyl-1H-imidazol-1-yl, morpholin-4-yl, pyridin-3-yl, pyridin-4-yl, 5-fluoropyridin-3-yl, 2-fluoropyridin-5-yl, 2-fluoropyridin-4-yl, 2-hydroxypyridin-5-yl, 2-aminopyridin-4-yl, 2-methoxycarbonylpyridin-5-yl, 2-acetamidopyridin-4-yl, 2-(piperazin-1-yl)pyridin-5-yl, 5-aminopyridin-3-yl, 2-cyanopyridin-5-yl, 5-methoxypyridin-3-yl, 3,6-dihydro-2H-pyran-4-yl, [1,2,4]triazolo[1,5-a]pyridin-6-yl, 2H-1,2,3,4-tetrazol-5-yl, or two $R^7$ are taken together with two adjacent carbon atoms to which they are bound to form a methylenedioxy fused to the rest of the compound.

In certain embodiments, $R^{12}$ is selected from hydrogen or $C_1$-$C_6$ alkyl. In certain embodiments, $R^{12}$ is hydrogen or methyl. In certain embodiments, $R^{12}$ is hydrogen.

In certain embodiments, n is 0, 1 or 2. In certain embodiments, n is 0. In certain embodiments, n is 1 or 2. In certain embodiments, n is 1. In certain embodiments, n is 2.

In certain embodiments, m is 0. In certain embodiments, m is 1.

In certain embodiments, m is 1 and n is 0, 1, or 2. In certain embodiments, m is 1 and n is 0 or 1. In certain embodiments, m is 1 and n is 1 or 2. In certain embodiments, m is 1 and n is 1. In certain embodiments, m is 1 and n is 0. In certain embodiments, m is 1 and n is 1. In certain embodiments, m is 1 and n is 2.

In certain embodiments, a compound of Formula (I) is isotopically labelled. In certain embodiments, a hydrogen, carbon, nitrogen, or oxygen atom of a compound of Formula (I) is isotopically labeled. In certain embodiments, a nitrogen atom of a compound of Formula (I) is $^{15}$N.

In certain embodiments, a compound of Formula (I) has the structure of Formula (Ia):

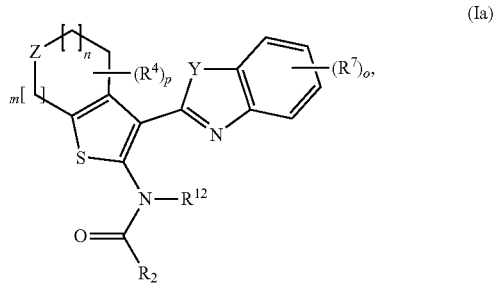

(Ia)

or a pharmaceutically acceptable salt, solvate, hydrate, tautomer, or stereoisomer thereof, wherein:

Y is selected from O and S;

Z is selected from C($R^4$)(N($R^5$)($R^6$)) and N($R^1$);

$R^1$ is selected from hydrogen, $C_1$-$C_6$ alkyl and ($C_0$-$C_6$ alkylene)-heterocyclyl, wherein each alkyl, alkylene or heterocyclyl portion of $R^1$ is optionally substituted;

$R^2$ is selected from C($R^{2a}$)($R^{2b}$)($R^{2c}$), wherein:

$R^{2a}$ is hydrogen;

each of $R^{2b}$ and $R^{2c}$ is independently selected from hydrogen, halogen, $C_1$-$C_6$ alkyl, $C_1$-$C_6$ heteroalkyl, ($C_0$-$C_6$ alkylene)-heterocyclyl, ($C_1$-$C_6$ heteroalkylene)-heterocyclyl, ($C_0$-$C_6$ alkylene)-aryl, ($C_1$-$C_6$ heteroalkylene)-aryl, ($C_0$-$C_6$ alkylene)-heteroaryl, and ($C_1$-$C_6$ heteroalkylene)-heteroaryl, wherein any alkyl, alkylene, heteroalkyl, heteroalkylene, heterocyclyl, aryl or heteroaryl portion of $R^{2b}$ and $R^{2c}$ is optionally and independently substituted;

each of $R^{3a}$ and $R^{3b}$ is independently selected from hydrogen and optionally substituted $C_1$-$C_4$ alkyl;

each $R^4$ is independently selected from hydrogen, halogen, $C_1$-$C_8$ alkyl, $C_1$-$C_8$ heteroalkyl, N($R^{3a}$)($R^{3b}$), wherein any alkyl or heteroalkyl portion of $R^4$ is optionally and independently substituted;

each of $R^5$ and $R^6$ is independently selected from hydrogen, $C_1$-$C_6$ alkyl, C(O)($C_1$-$C_6$ alkyl), ($C_0$-$C_6$ alkylene)-heterocyclyl and ($C_0$-$C_6$ alkylene)-heteroaryl, wherein any alkyl or alkylene of each of $R^5$ and $R^6$ is optionally and independently substituted;

each $R^7$ is independently selected from halogen, $C_1$-$C_6$ alkyl, $C_1$-$C_6$ heteroalkyl, N($R^{3a}$)($R^{3b}$), C(O)($C_1$-$C_6$ alkyl), C(O)O($C_1$-$C_6$ alkyl), wherein any alkyl, alkylene or heteroalkyl portion of $R^7$ is optionally and independently substituted;

$R^{12}$ is hydrogen or $C_1$-$C_6$ alkyl;

n is 0, 1, or 2;

m is 0 or 1;

n+m=1, 2 or 3;

o is 0, 1, 2 or 3; and p is 0, 1, 2, or 3.

In certain embodiments, a compound of Formula (Ia) has the structure of Formula (Ib):

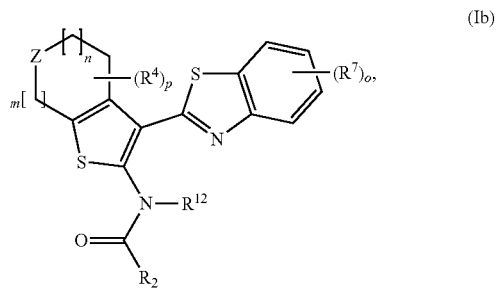

(Ib)

or a pharmaceutically acceptable salt, solvate, hydrate, tautomer, or stereoisomer thereof, wherein each of Z, $R^1$, $R^2$, $R^{2a}$, $R^{2b}$, $R^{2c}$, $R^{3a}$, $R^{3b}$, $R^4$, $R^5$, $R^6$, $R^7$, $R^{12}$, n, m, p, and o are defined as for Formula (Ia).

In certain embodiments, a compound of Formula (Ib) has the structure of Formula (Ib-1):

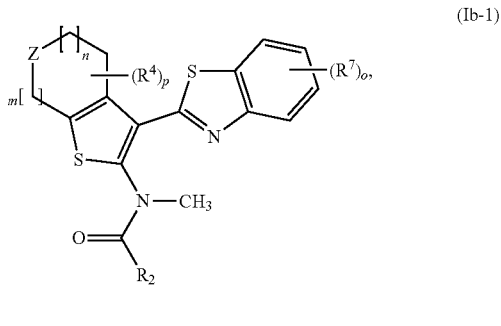

(Ib-1)

or a pharmaceutically acceptable salt, solvate, hydrate, tautomer, or stereoisomer thereof, wherein each of Z, $R^1$, $R^2$, $R^{2a}$, $R^{2b}$, $R^{2c}$, $R^{3a}$, $R^{3b}$, $R^4$, $R^5$, $R^6$, $R^7$, n, m, p, and o are defined as for Formula (Ib).

In certain embodiments, a compound of Formula (Ib-1) has the structure of Formula (Ib-2):

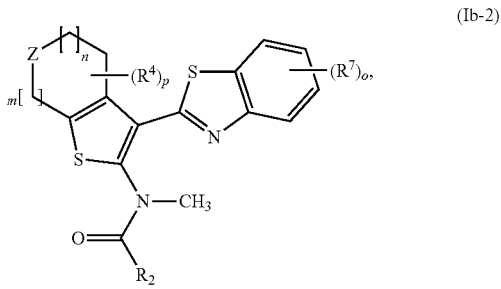

(Ib-2)

or a pharmaceutically acceptable salt, solvate, hydrate, tautomer, or stereoisomer thereof, wherein each of Z, $R^1$, $R^2$, $R^{2a}$, $R^{2b}$, $R^{2c}$, $R^{3a}$, $R^{3b}$, $R^4$, $R^5$, $R^6$, $R^7$, p, and o are defined as for Formula (Ib-1).

In certain embodiments, the compound of Formula (Ib-2) is the compound:

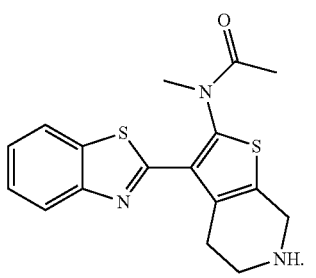 [SMILES: CC(=O)N(C)c1sc2c(c1-c1nc3ccccc3s1)CCNC2]

In certain embodiments, a compound of Formula (Ib) has the structure of Formula (Ic):

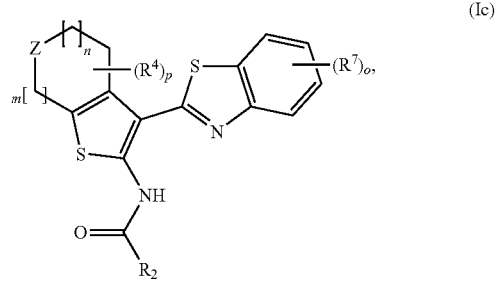

(Ic)

or a pharmaceutically acceptable salt, solvate, hydrate, tautomer, or stereoisomer thereof, wherein each of Z, $R^1$, $R^2$, $R^{2a}$, $R^{2b}$, $R^{2c}$, $R^{3a}$, $R^{3b}$, $R^4$, $R^5$, $R^6$, $R^7$, n, m, p, and o are defined as for Formula (Ib).

In certain embodiments, a compound of Formula (Ic) has the structure of Formula (Ic-1):

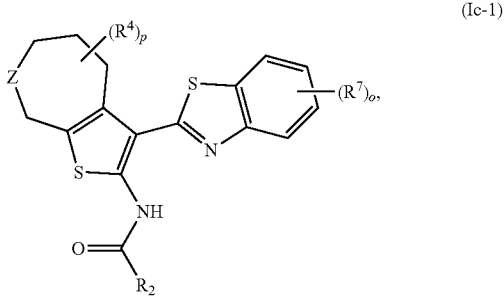

(Ic-1)

or a pharmaceutically acceptable salt, solvate, hydrate, tautomer, or stereoisomer thereof, wherein each of Z, $R^1$, $R^2$, $R^{2a}$, $R^{2b}$, $R^{2c}$, $R^{3a}$, $R^{3b}$, $R^4$, $R^5$, $R^6$, $R^7$, p, and o are defined as for Formula (Ic).

In certain embodiments, the compound of Formula (Ic-1) is the compound:

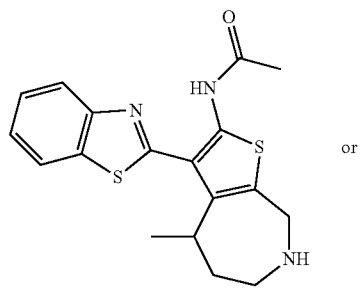

or

-continued

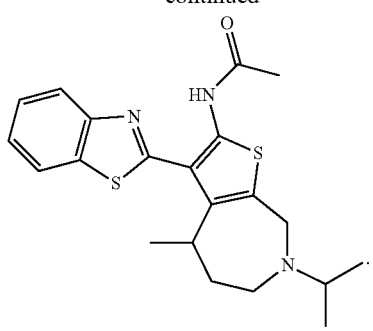

In certain embodiments, a compound of Formula (Ic) has the structure of Formula (Id):

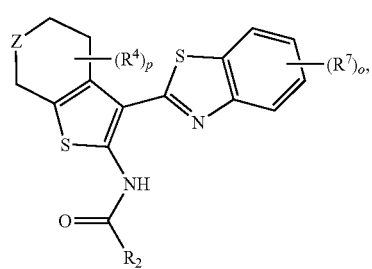

(Ic)

or a pharmaceutically acceptable salt, solvate, hydrate, tautomer, or stereoisomer thereof, wherein each of Z, $R^1$, $R^2$, $R^{2a}$, $R^{2b}$, $R^{2c}$, $R^{3a}$, $R^{3b}$, $R^4$, $R^5$, $R^6$, $R^7$, p, and o are defined as for Formula (Id).

In certain embodiments, a compound of Formula (Id) has the structure of Formula (Id-1):

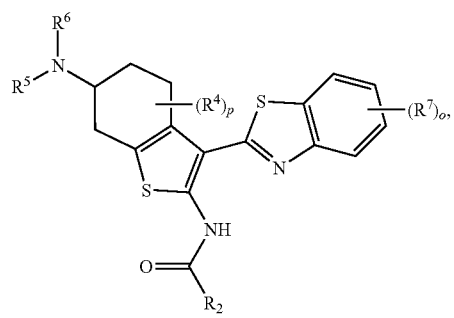

(Id-1)

or a pharmaceutically acceptable salt, solvate, hydrate, tautomer, or stereoisomer thereof, wherein each of $R^2$, $R^{2a}$, $R^{2b}$, $R^{2c}$, $R^{3a}$, $R^{3b}$, $R^4$, $R^5$, $R^6$, $R^7$, p, and o are defined as for Formula (Id).

In certain embodiments, the compound of Formula (Id-1) is the compound:

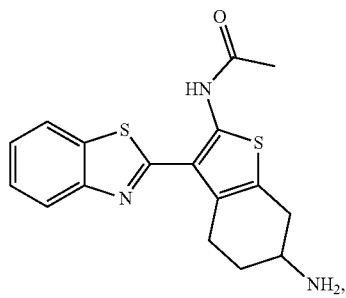

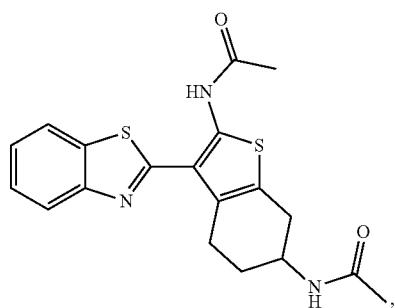

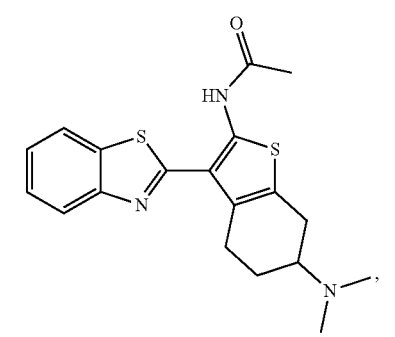

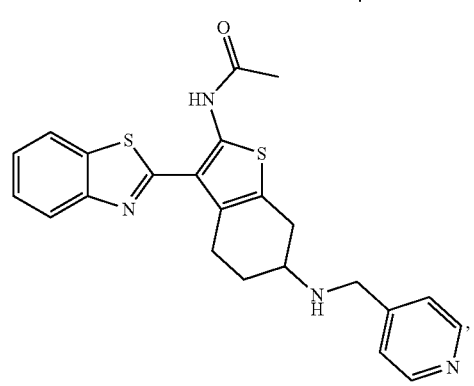

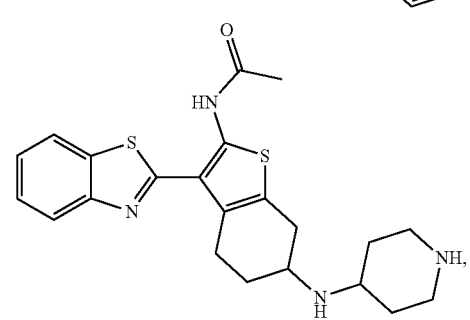

-continued

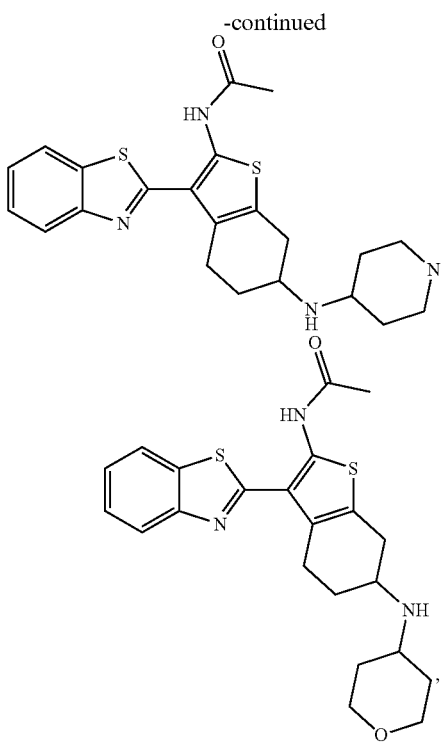

In certain embodiments, a compound of Formula (Id) has the structure of Formula (Ie):

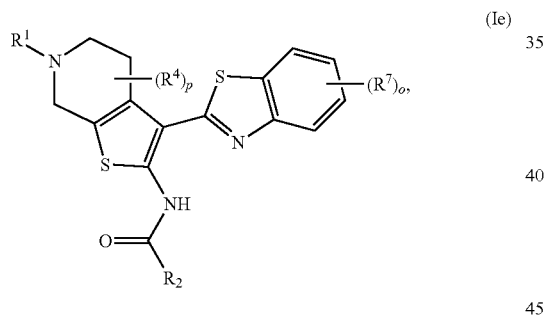

(Ie)

or a pharmaceutically acceptable salt, solvate, hydrate, tautomer, or stereoisomer thereof, wherein each of $R^1$, $R^2$, $R^{2a}$, $R^{2b}$, $R^{2c}$, $R^{3a}$, $R^{3b}$, $R^4$, $R^7$, p, and o are defined as for Formula (Ie).

In certain embodiments, a compound of Formula (Ie) has the structure of Formula (Ie-1):

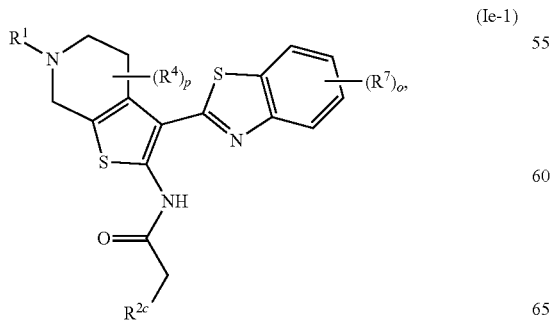

(Ie-1)

or a pharmaceutically acceptable salt, solvate, hydrate, tautomer, or stereoisomer thereof, wherein each of $R^1$, $R^{3a}$, $R^{3b}$, $R^4$, $R^7$, p, and o are defined as for Formula (Ie) and $R^{2c}$ is defined as for Formula (Ia), provided $R^{2c}$ is not hydrogen.

In certain embodiments, the compound of Formula (Ie-1) is the compound:

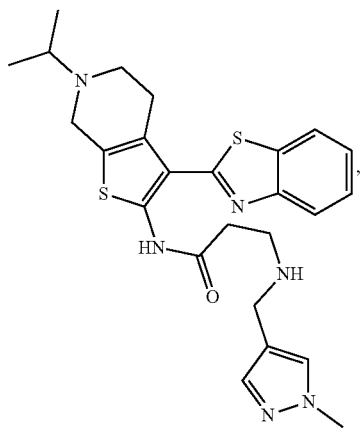

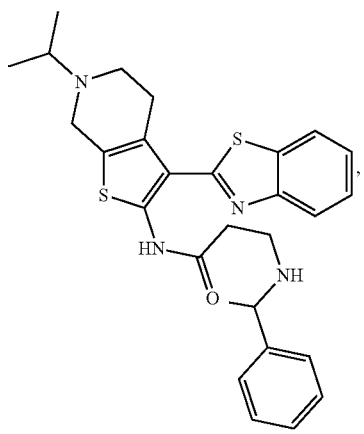

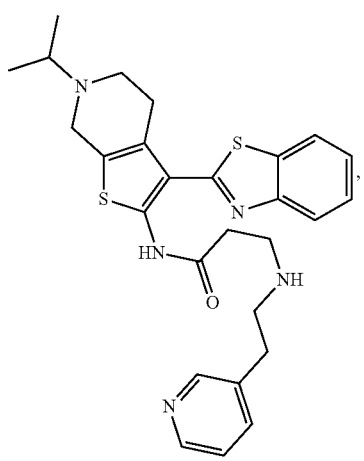

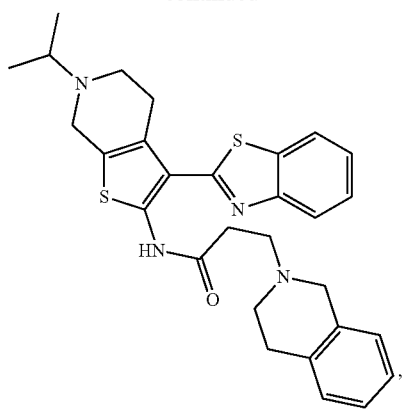,
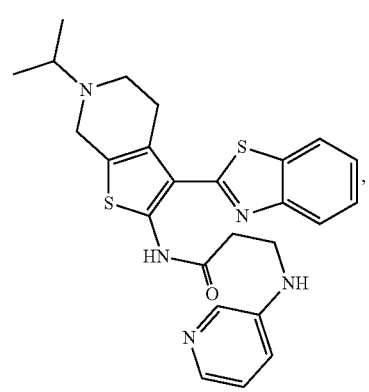,
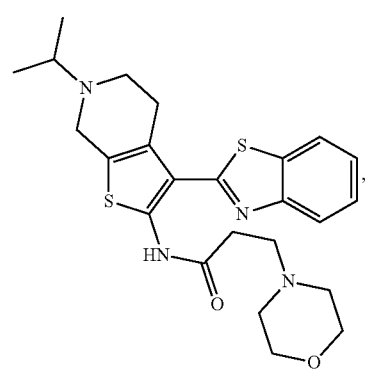,
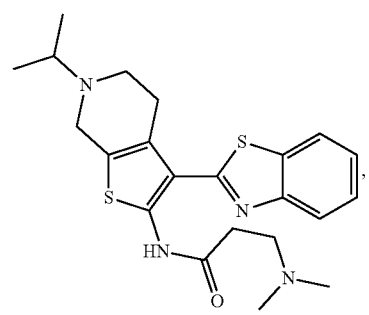,
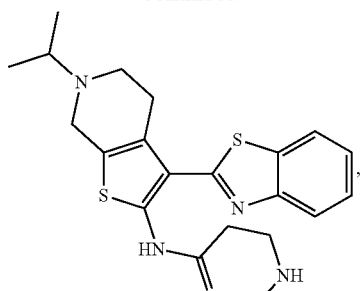,
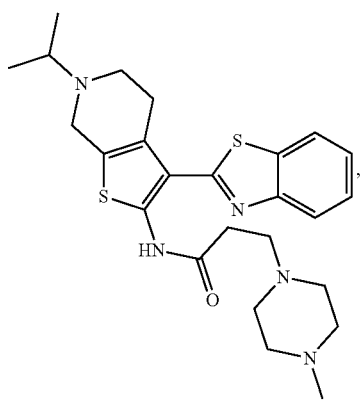,
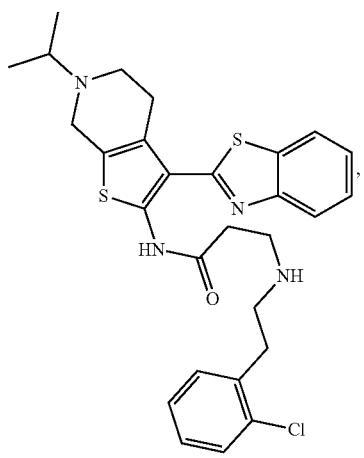,
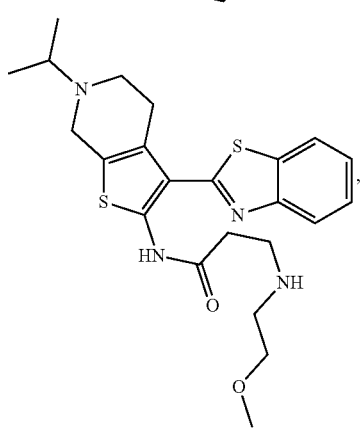, 37
-continued
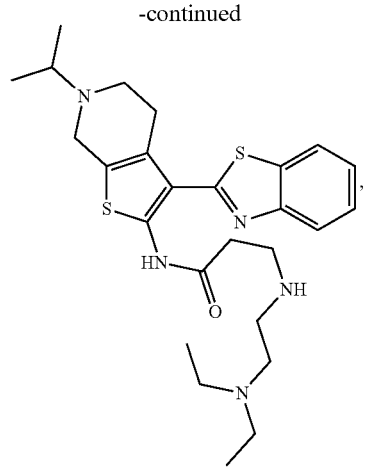
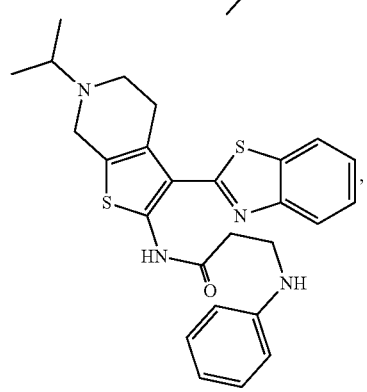
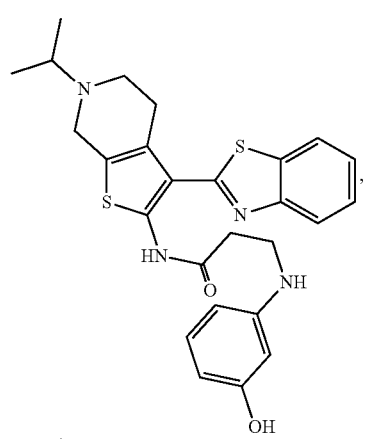
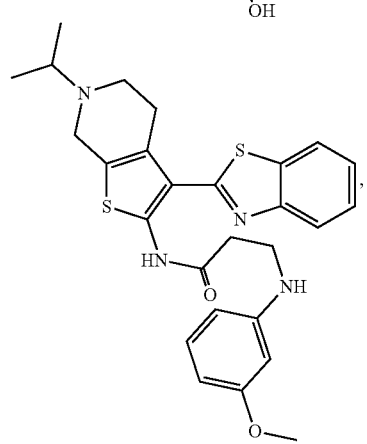
38
-continued
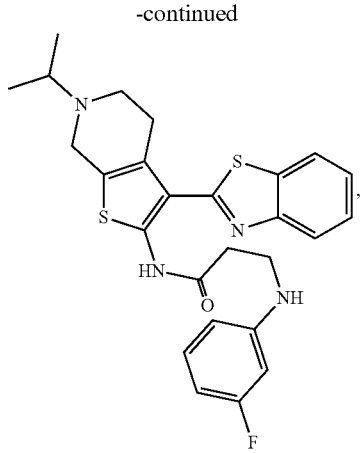
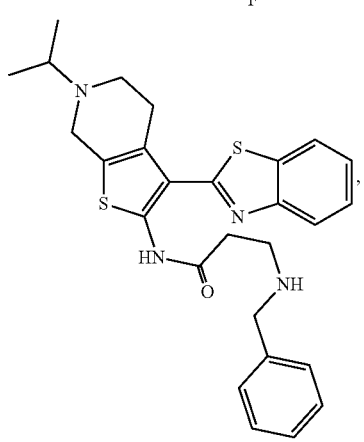
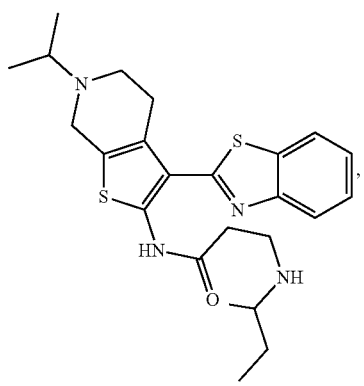
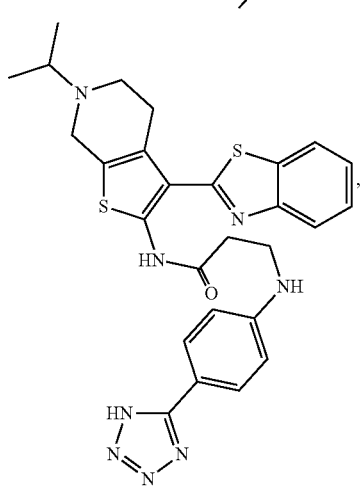

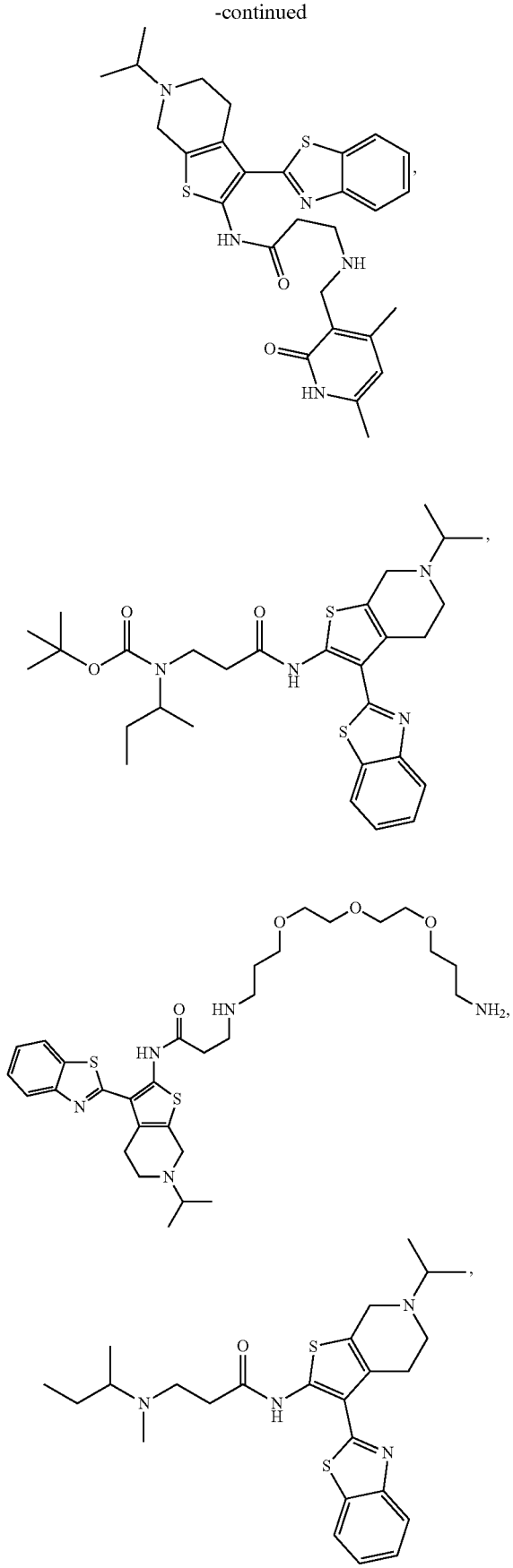
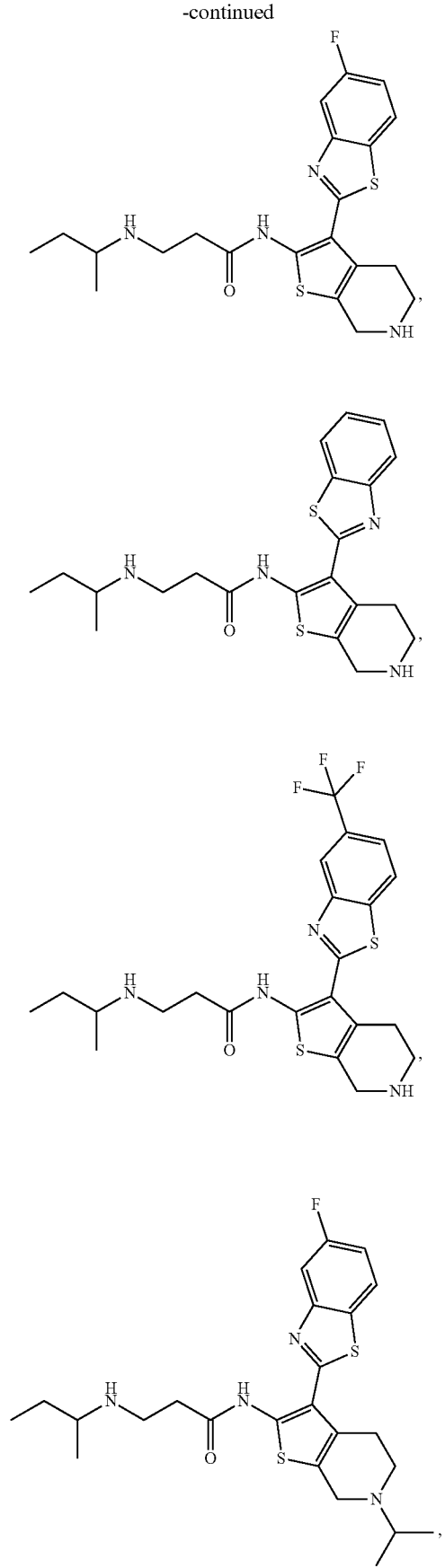

41
-continued
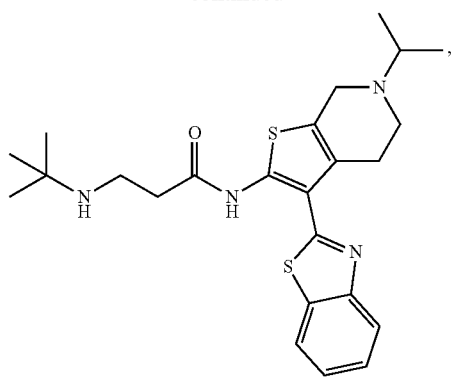
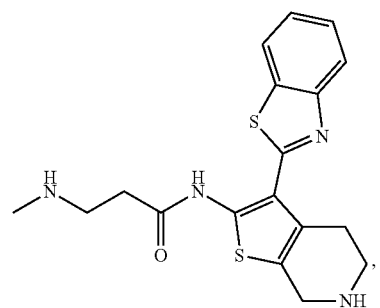
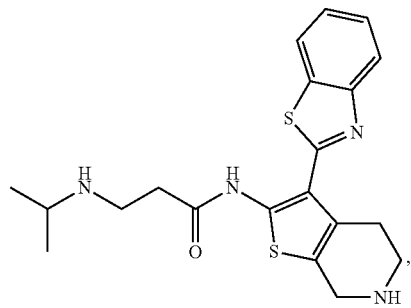
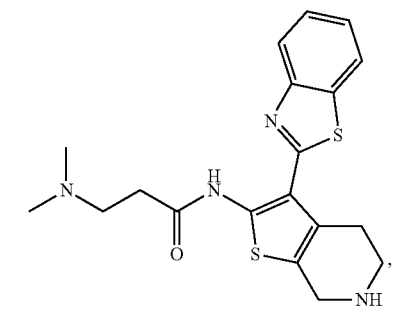
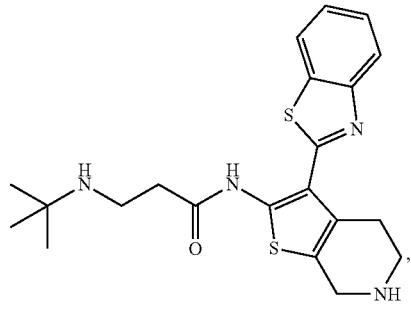
42
-continued
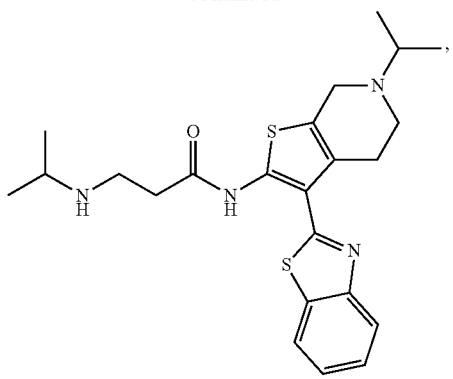
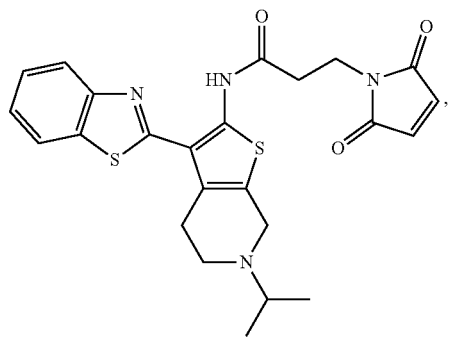
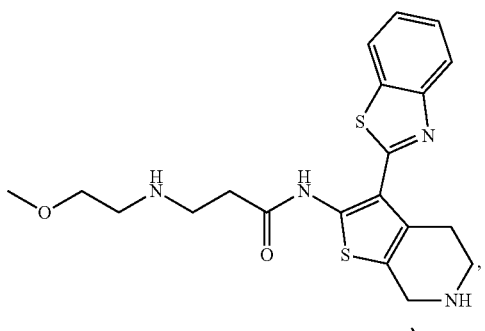
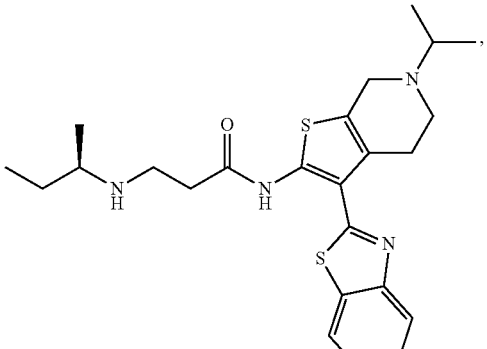
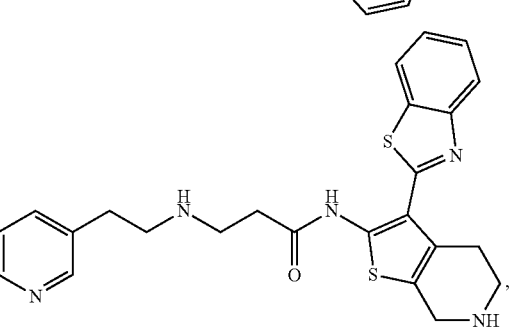

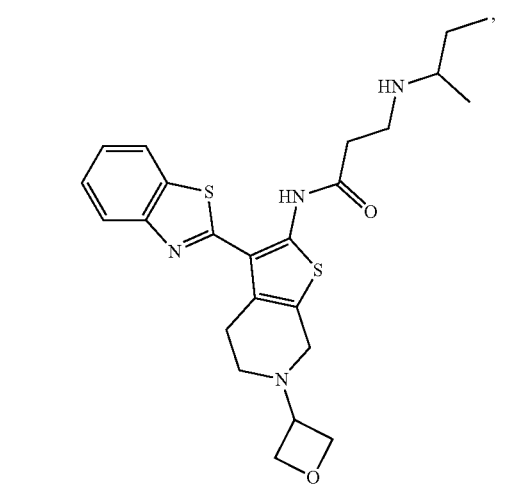
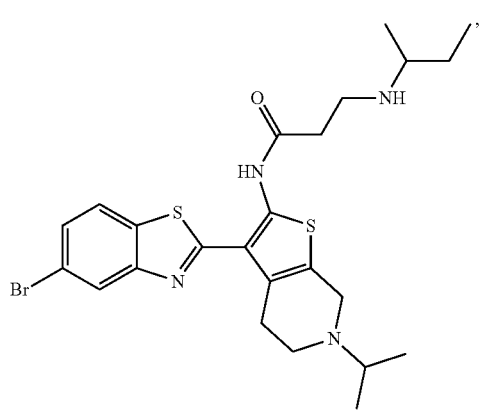
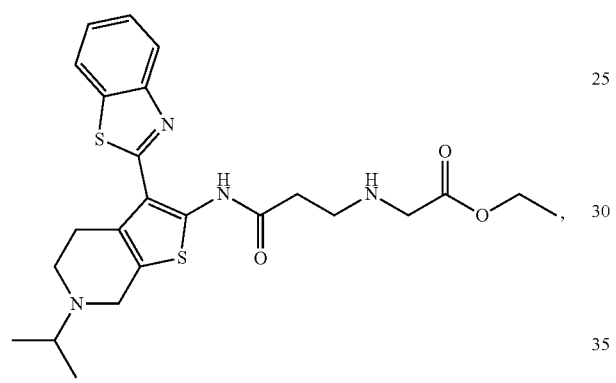
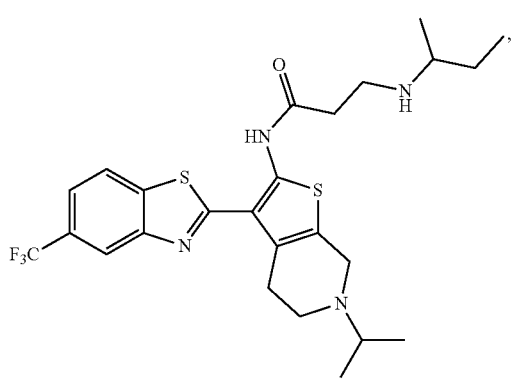
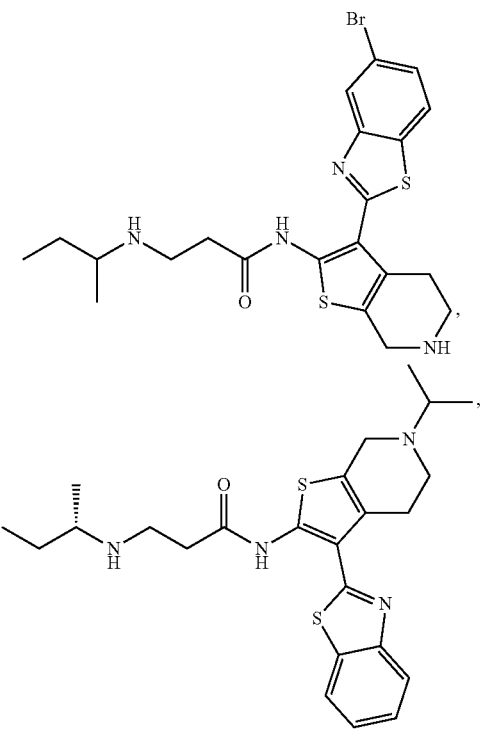
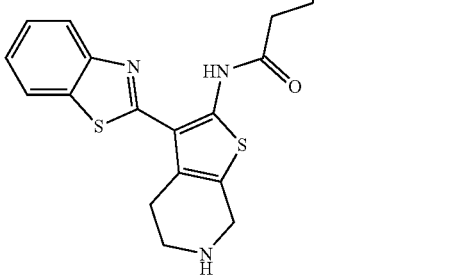
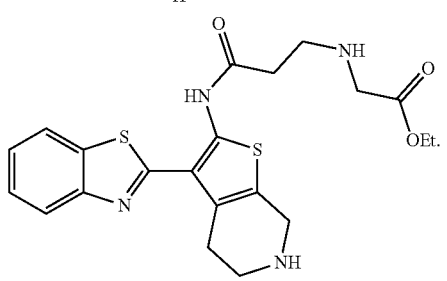

In certain embodiments, the invention provides a compound of Formula (II):

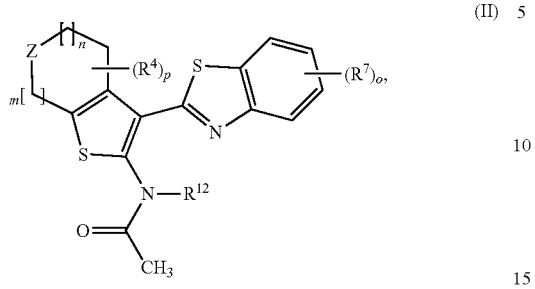

(II)

or a pharmaceutically acceptable salt, solvate, hydrate, tautomer, or stereoisomer thereof, wherein each of Z, $R^4$, $R^7$, $R^{12}$, m, n, o, p, and subvariables thereof are defined as for Formula (I), including all of the embodiments of Formula (I) set forth above.

In some embodiments of Formula II, o is 1, 2, or 3; and at least one $R^7$ is an optionally substituted heterocyclyl or an optionally substituted heteroaryl, or two $R^7$ are taken together with the carbon atoms to which they are bound to form a heteroaryl or heterocyclyl bridged to the rest of the compound. In some aspects of these embodiments, at least one $R^7$ is selected from optionally substituted pyrazolyl or optionally substituted pyridyl. In other aspects of these embodiments, two $R^7$ are taken together with the carbon atoms to which they are bound to form a methylenedioxy or ethylenedioxy fused to the rest of the compound. In some more specific aspects of these embodiments, at least one $R^7$ is selected from 1-methyl-1H-pyrazol-4-yl and pyridin-4-yl, or two $R^7$ are taken together with the carbon atoms to which they are bound to form a methylenedioxy fused to the rest of the compound.

In certain embodiments, the invention provides a compound of Formula (IIa):

(IIa)

or a pharmaceutically acceptable salt, solvate, hydrate, tautomer, or stereoisomer thereof, wherein each of $R^1$, $R^4$, $R^7$, p, o, and subvariables thereof are defined as for Formula (I), including all of the embodiments of Formula (I) set forth above.

In certain embodiments, the compound of Formula (IIa) is the compound:

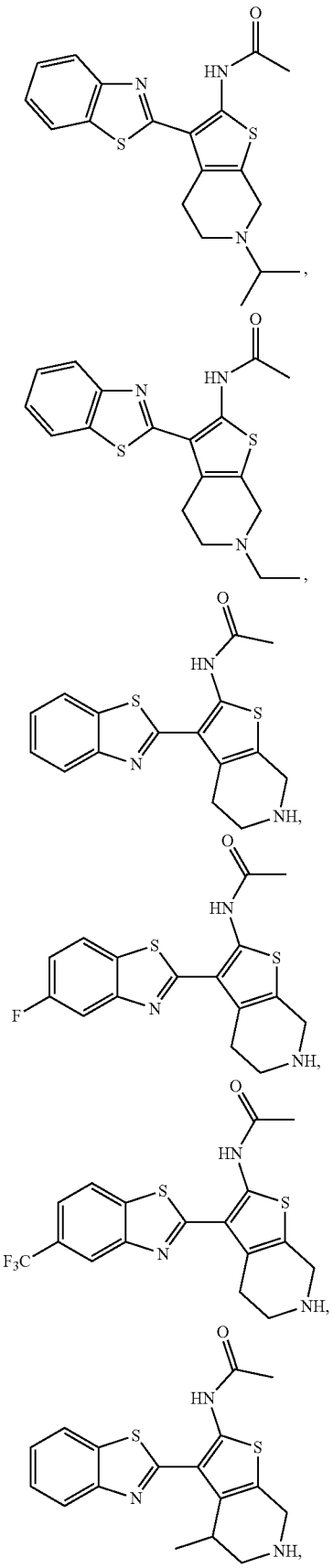

-continued
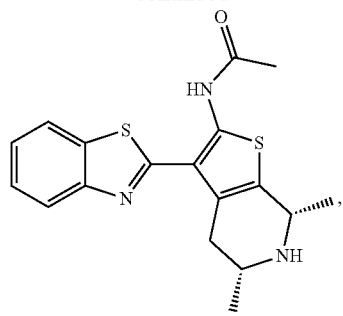
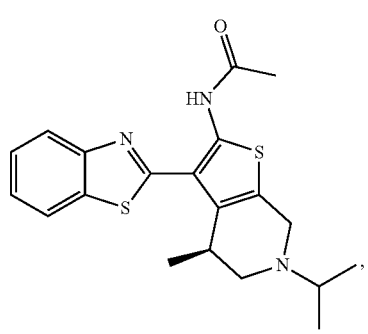
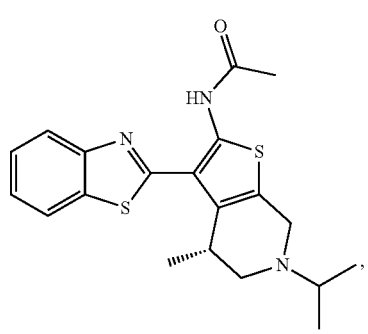
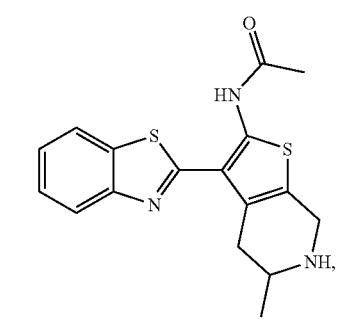
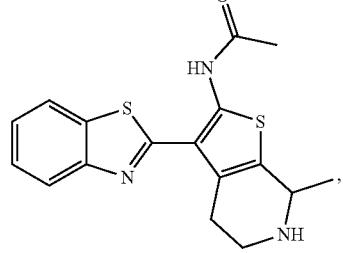
-continued
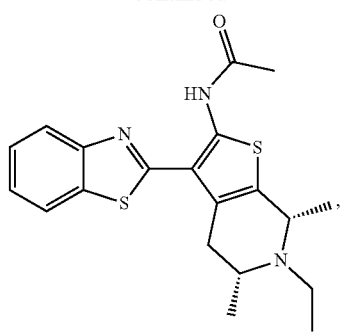
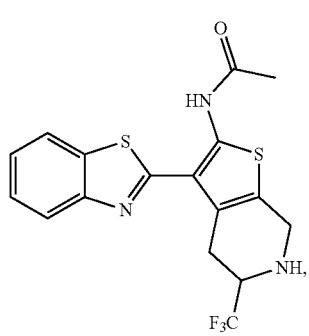
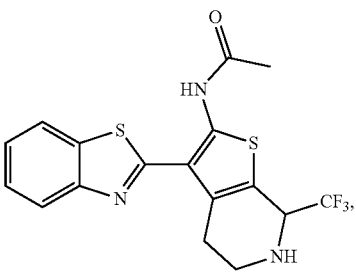
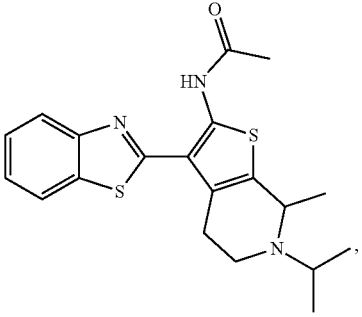
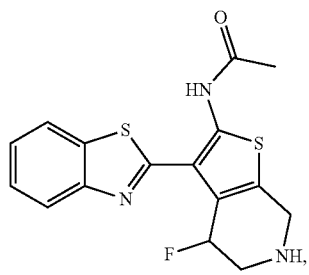

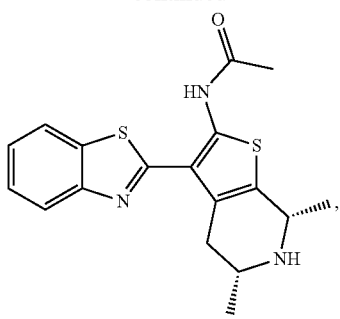
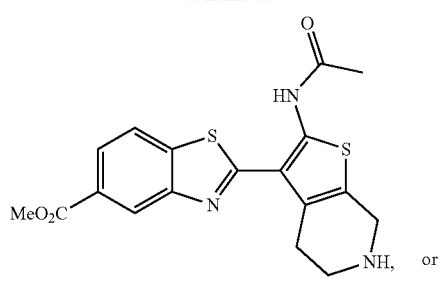
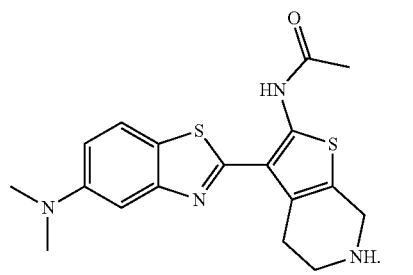
In some embodiments, the compound of Formula (IIa) is a pharmaceutically acceptable salt of any of the foregoing structures.
In certain embodiments, the compound of Formula (IIa) is selected from the compounds:
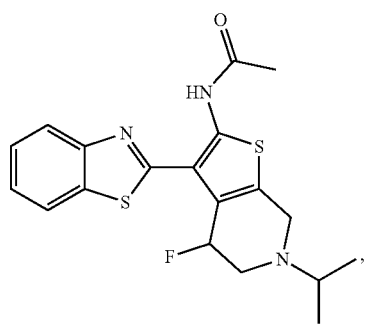
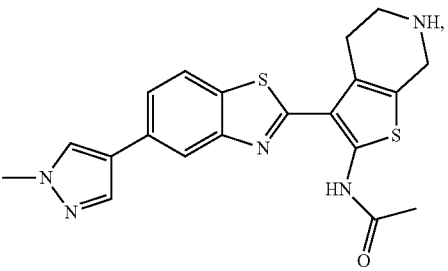
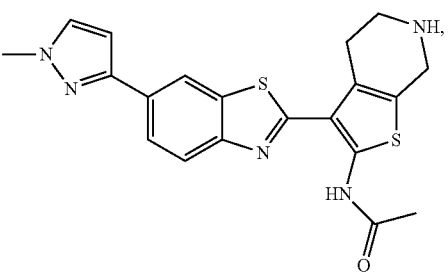
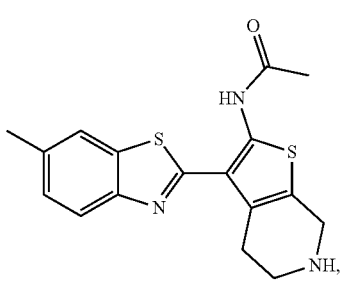
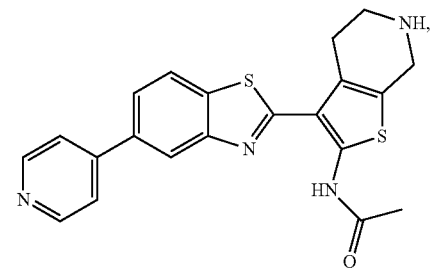

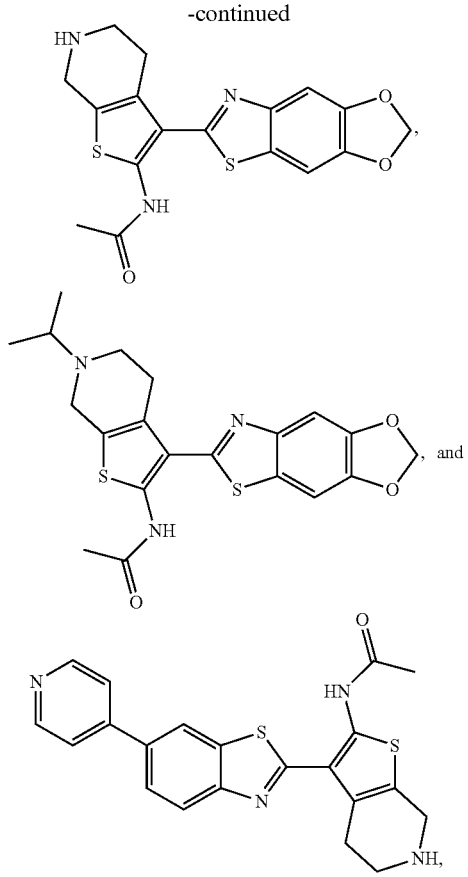

or a pharmaceutically acceptable salt of any of the foregoing.

In certain embodiments, a compound of Formula (II) is isotopically labelled. In certain embodiments, a hydrogen, carbon, nitrogen, or oxygen atom of a compound of Formula (II) is isotopically labeled. In certain embodiments, a nitrogen atom of a compound of Formula (II) is $^{15}N$.

Although, as indicated above, various embodiments and aspects thereof for a variable in Formula (I) or (II), e.g., Formulas (Ia), (Ib), (Ib-1), (Ib-2), (Ic), (Ic-1), (Id), (Id-1), (Ie), (Ie-1), (Ie-2), or (IIa), may be selected from a group of chemical moieties, the invention also encompasses as further embodiments and aspects thereof situations where such variable is: a) selected from any subset of chemical moieties in such a group; and b) any single member of such a group.

Although various embodiments and aspects thereof are set forth (or implied, as discussed in the preceding paragraph) individually for each variable in Formula (I) or (II) above, e.g., Formulas (Ia), (Ib), (Ib-1), (Ib-2), (Ic), (Ic-1), (Id), (Id-1), (Ie), (Ie-1), (Ie-2), or (IIa), the invention encompasses all possible combinations of the different embodiments and aspects for each of the variables in Formula (I) or (II), e.g., Formulas (Ia), (Ib), (Ib-1), (Ib-2), (Ic), (Ic-1), (Id), (Id-1), (Ie), (Ie-1), (Ie-2), or (IIa).

Figure 2:
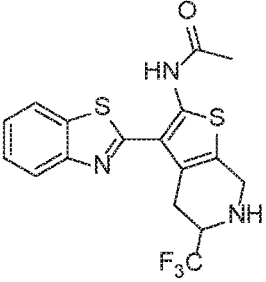
FIG. 2 is a table of exemplary compounds of Formula II.
In the case of compounds marked with "*", the absolute stereochemistry of the compound was not determined but the relative stereochemistry of the indicated chiral centers is known.
Figure 2:
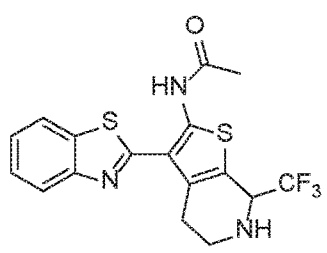
Figure 2:
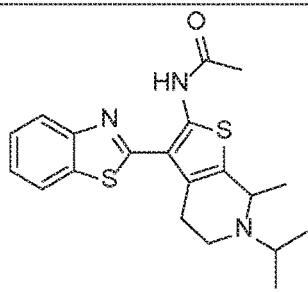
Figure 2:
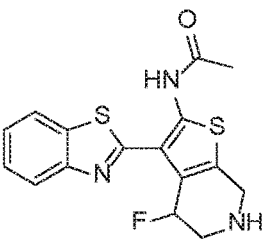
Figure 2:
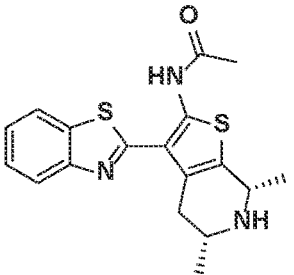
Figure 2:
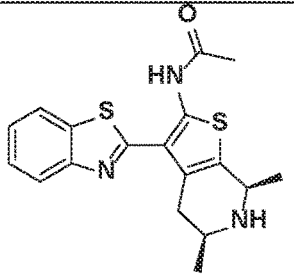
Figure 2:
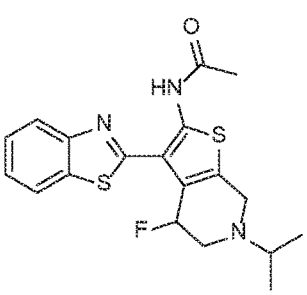
Figure 2:
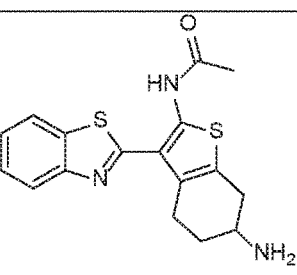
Figure 2:
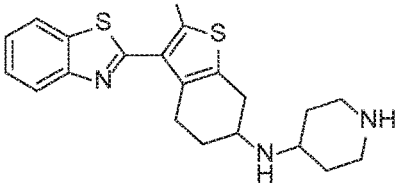
Figure 2:
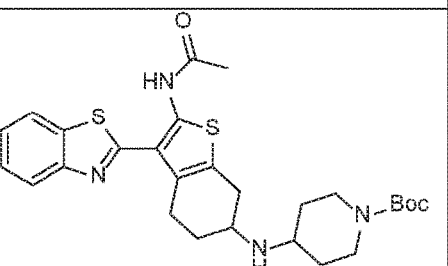
Figure 2:
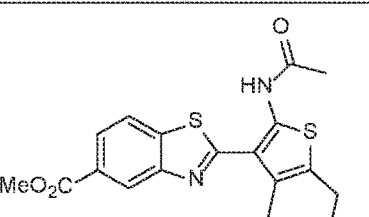
Figure 2:
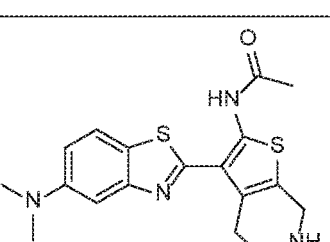

In certain embodiments, the compound of Formula (I) or (II) is selected from the group consisting of any one of the compounds in the tables in FIG. 1 and FIG. 2 and pharmaceutically acceptable salts, solvates, hydrates, tautomers, stereoisomers, and isotopically labeled derivatives thereof.

In certain embodiments, the compound of Formula (I) is selected from the group consisting of any one of the compounds in the table in FIG. 1 and pharmaceutically acceptable salts, solvates, hydrates, tautomers, stereoisomers, and isotopically labeled derivatives thereof.

In certain embodiments, the compound of Formula (II) is selected from the group consisting of any one of the compounds in the table in FIG. 2 and pharmaceutically acceptable salts, solvates, hydrates, tautomers, stereoisomers, and isotopically labeled derivatives thereof.

Pharmaceutical Compositions, Kits, and Administration

The present invention provides pharmaceutical compositions comprising a compound of Formula (I) or (II), e.g., Formulas (Ia), (Ib), (Ib-1), (Ib-2), (Ic), (Ic-1), (Id), (Id-1), (Ie), (Ie-1), (Ie-2), or (IIa), or a pharmaceutically acceptable salt, solvate, hydrate, tautomer, stereoisomer, or isotopically labeled derivative thereof, as described herein, and optionally a pharmaceutically acceptable excipient. In certain embodiments, the pharmaceutical composition of the invention comprises a compound Formula (I) or (II), e.g., Formulas (Ia), (Ib), (Ib-1), (Ib-2), (Ic), (Ic-1), (Id), (Id-1), (Ie), (Ie-1), (Ie-2), or (IIa), or a pharmaceutically acceptable salt thereof, and optionally a pharmaceutically acceptable excipient. In certain embodiments, the compound of Formula (I) or (II), e.g., Formulas (Ia), (Ib), (Ib-1), (Ib-2), (Ic), (Ic-1), (Id), (Id-1), (Ie), (Ie-1), (Ie-2), or (IIa), or a pharmaceutically acceptable salt, solvate, hydrate, tautomer, stereoisomer, or isotopically labeled derivative thereof, is provided in an effective amount in the pharmaceutical composition. In certain embodiments, the effective amount is a therapeutically effective amount. In certain embodiments, the effective amount is a prophylactically effective amount.

Pharmaceutical compositions described herein can be prepared by any method known in the art of pharmacology. In general, such preparatory methods include the steps of bringing the compound of Formula (I) or (II), e.g., a compound of Formulas (Ia), (Ib), (Ib-1), (Ib-2), (Ic), (Ie-1), (Id), (Id-1), (Ie), (Ie-1), (Ie-2), or (IIa), (the "active ingredient") into association with a carrier and/or one or more other accessory ingredients, and then, if necessary and/or desirable, shaping and/or packaging the product into a desired single- or multi-dose unit.

Pharmaceutical compositions can be prepared, packaged, and/or sold in bulk, as a single unit dose, and/or as a plurality of single unit doses. As used herein, a "unit dose" is a discrete amount of the pharmaceutical composition comprising a predetermined amount of the active ingredient. The amount of the active ingredient is generally equal to the dosage of the active ingredient which would be administered to a subject and/or a convenient fraction of such a dosage such as, for example, one-half or one-third of such a dosage.

Relative amounts of the active ingredient, the pharmaceutically acceptable excipient, and/or any additional ingredients in a pharmaceutical composition of the invention will vary, depending upon the identity, size, and/or condition of the subject treated and further depending upon the route by which the composition is to be administered. By way of example, the composition may comprise between about 0.1% and about 100% (w/w) active ingredient.

The term "pharmaceutically acceptable excipient" refers to a non-toxic carrier, adjuvant, diluent, or vehicle that does not destroy the pharmacological activity of the compound with which it is formulated. Pharmaceutically acceptable excipients useful in the manufacture of the pharmaceutical compositions of the invention are any of those that are well known in the art of pharmaceutical formulation and include inert diluents, dispersing and/or granulating agents, surface active agents and/or emulsifiers, disintegrating agents, binding agents, preservatives, buffering agents, lubricating agents, and/or oils. Pharmaceutically acceptable excipients useful in the manufacture of the pharmaceutical compositions of the invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

Compositions of the present invention may be administered orally, parenterally (including subcutaneous, intramuscular, intravenous and intradermal), by inhalation spray, topically, rectally, nasally, buccally, vaginally or via an implanted reservoir. In some embodiments, provided compounds or compositions are administrable intravenously and/or orally.

The term "parenteral" as used herein includes subcutaneous, intravenous, intramuscular, intraocular, intravitreal, intra-articular, intra-synovial, intrasternal, intrathecal, intra-hepatic, intraperitoneal intralesional and intracranial injection or infusion techniques. Preferably, the compositions are administered orally, subcutaneously, intraperitoneally or intravenously. Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium.

Pharmaceutically acceptable compositions of this invention may be orally administered in any orally acceptable dosage form including, but not limited to, capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added. In some embodiments, a provided oral formulation is formulated for immediate release or sustained/delayed release. In some embodiments, the composition is suitable for buccal or sublingual administration, including tablets, lozenges and pastilles. A provided compound can also be in micro-encapsulated form.

Alternatively, pharmaceutically acceptable compositions of this invention may be administered in the form of suppositories for rectal administration. Pharmaceutically acceptable compositions of this invention may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches may also be used.

For ophthalmic use, provided pharmaceutically acceptable compositions may be formulated as micronized suspensions or in an ointment such as petrolatum.

Pharmaceutically acceptable compositions of this invention may also be administered by nasal aerosol or inhalation.

In order to prolong the effect of a drug, it is often desirable to slow the absorption of the drug from subcutaneous or intramuscular injection. This can be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Although the descriptions of pharmaceutical compositions provided herein are principally directed to pharmaceutical compositions which are suitable for administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and/or perform such modification with ordinary experimentation.

Compounds provided herein are typically formulated in dosage unit form, e.g., single unit dosage form, for ease of administration and uniformity of dosage. It will be understood, however, that the total daily usage of the compositions of the present invention will be decided by the attending physician within the scope of sound medical judgment. The specific therapeutically effective dose level for any particular subject or organism will depend upon a variety of factors including the disease being treated and the severity of the disorder; the activity of the specific active ingredient employed; the specific composition employed; the age, body weight, general health, sex and diet of the subject; the time of administration, route of administration, and rate of excretion of the specific active ingredient employed; the duration of the treatment; drugs used in combination or coincidental with the specific active ingredient employed; and like factors well known in the medical arts.

The exact amount of a compound required to achieve an effective amount will vary from subject to subject, depending, for example, on species, age, and general condition of a subject, severity of the side effects or disorder, identity of the particular compound(s), mode of administration, and the like. The desired dosage can be delivered three times a day, two times a day, once a day, every other day, every third day, every week, every two weeks, every three weeks, or every four weeks. In certain embodiments, the desired dosage can be delivered using multiple administrations (e.g., two, three, four, five, six, seven, eight, nine, ten, eleven, twelve, thirteen, fourteen, or more administrations).

In certain embodiments, an effective amount of a compound for administration one or more times a day to a 70 kg adult human may comprise about 0.0001 mg to about 3000 mg, about 0.0001 mg to about 2000 mg, about 0.0001 mg to about 1000 mg, about 0.001 mg to about 1000 mg, about 0.01 mg to about 1000 mg, about 0.1 mg to about 1000 mg, about 1 mg to about 1000 mg, about 1 mg to about 100 mg, about 10 mg to about 1000 mg, or about 100 mg to about 1000 mg, of a compound per unit dosage form.

In certain embodiments, the compounds of Formula (I) or (II), e.g Formulas (Ia), (Ib), (Ib-1), (Ib-2), (Ic), (Ic-1), (Id), (Id-1), (Ie), (Ie-1), (Ie-2), or (IIa), may be at dosage levels sufficient to deliver from about 0.001 mg/kg to about 100 mg/kg, from about 0.01 mg/kg to about 50 mg/kg, preferably from about 0.1 mg/kg to about 40 mg/kg, preferably from about 0.5 mg/kg to about 30 mg/kg, from about 0.01 mg/kg to about 10 mg/kg, from about 0.1 mg/kg to about 10 mg/kg, and more preferably from about 1 mg/kg to about 25 mg/kg, of subject body weight per day, one or more times a day, to obtain the desired therapeutic effect.

It will be appreciated that dose ranges as described herein provide guidance for the administration of provided pharmaceutical compositions to an adult. The amount to be administered to, for example, a child or an adolescent can be determined by a medical practitioner or person skilled in the art and can be lower or the same as that administered to an adult.

It will be also appreciated that a compound or composition, as described herein, can be administered in combination with one or more additional pharmaceutical agents. The compounds or compositions can be administered in combination with additional pharmaceutical agents that improve their bioavailability, reduce and/or modify their metabolism, inhibit their excretion, and/or modify their distribution within the body. It will also be appreciated that the therapy employed may achieve a desired effect for the same disorder, and/or it may achieve different effects.

The compound or composition can be administered concurrently with, prior to, or subsequent to, one or more additional pharmaceutical agents, which may be useful as, e.g., combination therapies. Pharmaceutical agents include therapeutically active agents. Pharmaceutical agents also include prophylactically active agents. Each additional pharmaceutical agent may be administered at a dose and/or on a time schedule determined for that pharmaceutical agent. The additional pharmaceutical agents may also be administered together with each other and/or with the compound or composition described herein in a single dose or administered separately in different doses. The particular combination to employ in a regimen will take into account compatibility of the inventive compound with the additional pharmaceutical agents and/or the desired therapeutic and/or prophylactic effect to be achieved. In general, it is expected that the additional pharmaceutical agents utilized in combination be utilized at levels that do not exceed the levels at which they are utilized individually. In some embodiments, the levels utilized in combination will be lower than those utilized individually.

Exemplary additional pharmaceutical agents include, but are not limited to, anti-proliferative agents, anti-cancer agents, anti-diabetic agents, anti-inflammatory agents, immunosuppressant agents, and a pain-relieving agent. Pharmaceutical agents include small organic molecules such as drug compounds (e.g., compounds approved by the U.S. Food and Drug Administration as provided in the Code of Federal Regulations (CFR)), peptides, proteins, carbohydrates, monosaccharides, oligosaccharides, polysaccharides, nucleoproteins, mucoproteins, lipoproteins, synthetic polypeptides or proteins, small molecules linked to proteins, glycoproteins, steroids, nucleic acids, DNAs, RNAs, nucleotides, nucleosides, oligonucleotides, antisense oligonucleotides, lipids, hormones, vitamins, and cells.

Also encompassed by the invention are kits (e.g., pharmaceutical packs). The inventive kits may be useful for preventing and/or treating a proliferative disease (e.g., cancer (e.g., leukemia, melanoma, multiple myeloma), benign neoplasm, angiogenesis, inflammatory disease, autoinflammatory disease, or autoimmune disease). The kits provided may comprise an inventive pharmaceutical composition or compound and a container (e.g., a vial, ampule, bottle, syringe, and/or dispenser package, or other suitable container). In some embodiments, provided kits may optionally further include a second container comprising a pharmaceutical excipient for dilution or suspension of an inventive pharmaceutical composition or compound. In some embodiments, the inventive pharmaceutical composition or compound provided in the container and the second container are combined to form one unit dosage form.

Thus, in one aspect, provided are kits including a first container comprising a compound described herein, or a pharmaceutically acceptable salt, solvate, hydrate, tautomer, stereoisomer, and isotopically labeled derivative, or a pharmaceutical composition thereof. In certain embodiments, the kit of the invention includes a first container comprising a compound described herein, or a pharmaceutically acceptable salt thereof, or a pharmaceutical composition thereof. In certain embodiments, the kits are useful in preventing and/or treating a proliferative disease in a subject. In certain embodiments, the kits further include instructions for administering the compound, or a pharmaceutically acceptable salt, solvate, hydrate, tautomer, stereoisomer, isotopically and labeled derivative thereof, or a pharmaceutical composition thereof, to a subject to prevent and/or treat a proliferative disease.

Methods of Treatment and Uses

The present invention also provides methods for the treatment or prevention of a proliferative disease (e.g., cancer, benign neoplasm, angiogenesis, inflammatory disease, autoinflammatory disease, or autoimmune disease) or an infectious disease (e.g., a viral disease) in a subject. Such methods comprise the step of administering to the subject in need thereof an effective amount of a compound of Formula (I) or (II), e.g., a compound of Formulas (Ia), (Ib), (Ib-1), (Ib-2), (Ic), (Ic-1), (Id), (Id-1), (Ie), (Ie-1), (Ie-2), or (IIa), or a pharmaceutically acceptable salt, solvate, hydrate, tautomer, stereoisomer, or isotopically labeled derivative thereof, or a pharmaceutical composition thereof. In certain embodiments, the methods described herein include administering to a subject an effective amount of a compound of Formula (I) or (II), e.g., a compound of Formulas (Ia), (Ib), (Ib-1), (Ib-2), (Ic), (Ic-1), (Id), (Id-1), (Ie), (Ie-1), (Ie-2), or (IIa), or a pharmaceutically acceptable salt thereof, or a pharmaceutical composition thereof.

In certain embodiments, the subject being treated is a mammal. In certain embodiments, the subject is a human. In certain embodiments, the subject is a domesticated animal, such as a dog, cat, cow, pig, horse, sheep, or goat. In certain embodiments, the subject is a companion animal such as a dog or cat. In certain embodiments, the subject is a livestock animal such as a cow, pig, horse, sheep, or goat. In certain embodiments, the subject is a zoo animal. In another embodiment, the subject is a research animal such as a rodent, dog, or non-human primate. In certain embodiments, the subject is a non-human transgenic animal such as a transgenic mouse or transgenic pig.

The proliferative disease to be treated or prevented using the compounds of Formula (I) or (II), e.g., a compound of Formulas (Ia), (Ib), (Ib-1), (Ib-2), (Ic), (Ic-1), (Id), (Id-1), (Ie), (Ie-1), (Ie-2), or (IIa), will typically be associated with deregulated activity of c-Myc. Deregulated activity of c-Myc may constitute an elevated and/or an inappropriate (e.g., abnormal) activity of c-Myc. In certain embodiments, c-Myc is not overexpressed, and the activity of c-Myc is elevated and/or inappropriate. In certain other embodiments, c-Myc is overexpressed, and the activity of c-Myc is elevated and/or inappropriate. The compounds Formula (I) or (II), e.g., the compound of Formulas (Ia), (Ib), (Ib-1), (Ib-2), (Ic), (Ic-1), (Id), (Id-1), (Ie), (Ie-1), (Ie-2), or (IIa), and pharmaceutically acceptable salts, solvates, hydrates, tautomers, stereoisomers, isotopically labeled derivatives, and compositions thereof, may inhibit the activity of c-Myc and be useful in treating and/or preventing proliferative diseases.

In other embodiments, the proliferative disease to be treated or prevented using the compounds of Formula (I) or (II), e.g., compounds of Formulas (Ia), (Ib), (Ib-1), (Ib-2), (Ic), (Ic-1), (Id), (Id-1), (Ie), (Ie-1), (Ie-2), or (IIa), may be associated with deregulated activity a Myc family member, e.g., N-Myc or L-Myc. Deregulated activity of a Myc family member (e.g., N-Myc or L-Myc) may constitute an elevated and/or an inappropriate (e.g., abnormal) activity of one or more Myc family members (e.g., N-Myc or L-Myc). In certain embodiments, a Myc family member (e.g., N-Myc or L-Myc) is not overexpressed, and the activity of said Myc family member (e.g., N-Myc or L-Myc) is elevated and/or inappropriate. In certain other embodiments, a Myc family member (e.g., N-Myc or L-Myc) is overexpressed, and the activity of said Myc family member (e.g., N-Myc or L-Myc) is elevated and/or inappropriate. The compounds of Formula (I) or (II), e.g., compounds of Formulas (Ia), (Ib), (Ib-1), (Ib-2), (Ic), (Ic-1), (Id), (Id-1), (Ie), (Ie-1), (Ie-2), or (IIa), and pharmaceutically acceptable salts, solvates, hydrates, tautomers, stereoisomers, isotopically labeled derivatives, and compositions thereof, may inhibit the activity of a Myc family members (e.g., N-Myc or L-Myc) and be useful in treating and/or preventing proliferative diseases.

A proliferative disease may also be associated with inhibition of apoptosis of a cell in a biological sample or subject. All types of biological samples described herein or known in the art are contemplated as being within the scope of the invention. Inhibition of the activity of c-Myc or other Myc family member (e.g., N-Myc or L-Myc) may cause cytotoxicity via induction of apoptosis. The compounds of Formula (I) or (II), e.g., compounds of Formulas (Ia), (Ib), (Ib-1), (Ib-2), (Ic), (Ic-1), (Id), (Id-1), (Ie), (Ie-1), (Ie-2), or (IIa), and pharmaceutically acceptable salts, solvates, hydrates, tautomers, stereoisomers, isotopically labeled derivatives, and compositions thereof, may induce apoptosis, and therefore, may be useful in treating and/or preventing proliferative diseases.

In certain embodiments, the proliferative disease to be treated or prevented using the compounds of Formula (I) or (II), e.g., compounds of Formulas (Ia), (Ib), (Ib-1), (Ib-2), (Ic), (Ic-1), (Id), (Id-1), (Ie), (Ie-1), (Ie-2), or (IIa), is cancer. All types of cancers disclosed herein or known in the art are contemplated as being within the scope of the invention. In certain embodiments, the proliferative disease is a cancer associated with dependence on BCL-2 anti-apoptotic proteins (e.g., MCL-1 and/or XIAP). In certain embodiments, the proliferative disease is a cancer associated with overexpression of Myc. In certain embodiments, the proliferative disease is a hematological malignancy. In certain embodiments, the proliferative disease is a blood cancer. In certain embodiments, the proliferative disease is leukemia. In certain embodiments, the proliferative disease is chronic lymphocytic leukemia (CLL). In certain embodiments, the proliferative disease is acute lymphoblastic leukemia (ALL). In certain embodiments, the proliferative disease is T-cell acute lymphoblastic leukemia (T-ALL). In certain embodiments, the proliferative disease is chronic myelogenous leukemia (CML). In certain embodiments, the proliferative disease is acute myelogenous leukemia (AML). In certain embodiments, the proliferative disease is lymphoma. In certain embodiments, the proliferative disease is melanoma. In certain embodiments, the proliferative disease is multiple myeloma. In certain embodiments, the proliferative disease is a bone cancer. In certain embodiments, the proliferative disease is osteosarcoma. In some embodiments, the proliferative disease is Ewing's sarcoma. In some embodiments, the proliferative disease is triple-negative breast cancer (TNBC). In some embodiments, the proliferative disease is a brain cancer. In some embodiments, the proliferative disease is neuroblastoma. In some embodiments, the proliferative disease is a lung cancer. In some embodiments, the proliferative disease is small cell lung cancer (SCLC). In some embodiments, the proliferative disease is large cell lung cancer. In some embodiments, the proliferative disease is a benign neoplasm. All types of benign neoplasms disclosed herein or known in the art are contemplated as being within the scope of the invention.

In some embodiments, the proliferative disease is associated with angiogenesis. All types of angiogenesis disclosed herein or known in the art are contemplated as being within the scope of the invention.

In certain embodiments, the proliferative disease is an inflammatory disease. All types of inflammatory diseases disclosed herein or known in the art are contemplated as being within the scope of the invention. In certain embodiments, the inflammatory disease is rheumatoid arthritis. In some embodiments, the proliferative disease is an autoinflammatory disease. All types of autoinflammatory diseases disclosed herein or known in the art are contemplated as being within the scope of the invention. In some embodiments, the proliferative disease is an autoimmune disease. All types of autoimmune diseases disclosed herein or known in the art are contemplated as being within the scope of the invention.

The cell described herein may be an abnormal cell. The cell may be in vitro or in vivo. In certain embodiments, the cell is a proliferative cell. In certain embodiments, the cell is a blood cell. In certain embodiments, the cell is a lymphocyte. In certain embodiments, the cell is a cancer cell. In certain embodiments, the cell is a leukemia cell. In certain embodiments, the cell is a CLL cell. In certain embodiments, the cell is a melanoma cell. In certain embodiments, the cell is a multiple myeloma cell. In certain embodiments, the cell is a benign neoplastic cell. In certain embodiments, the cell is an endothelial cell. In certain embodiments, the cell is an immune cell.

In another aspect, the present invention provides methods of down-regulating the expression of c-Myc or other Myc family member (e.g., N-Myc or L-Myc) in a biological sample or subject. In certain embodiments, the present invention provides methods of down-regulating the expression of c-Myc in a biological sample or subject. In another aspect, the present invention provides methods of down-regulating the expression of other bHLH transcription factors, such as MITF, TWIST1, and Max, in a biological sample or subject.

In certain embodiments, the methods described herein comprise the additional step of administering one or more additional pharmaceutical agents in combination with the compounds of Formula (I) or (II), e.g., compounds of Formulas (Ia), (Ib), (Ib-1), (Ib-2), (Ic), (Ic-1), (Id), (Id-1), (Ie), (Ie-1), (Ie-2), or (IIa), a pharmaceutically acceptable salt thereof, or compositions comprising such compound or pharmaceutically acceptable salt thereof. Such additional pharmaceutical agents include, but are not limited to, anti-proliferative agents, anti-cancer agents, anti-diabetic agents, anti-inflammatory agents, immunosuppressant agents, and a pain-relieving agent. The additional pharmaceutical agent(s) may synergistically augment inhibition of c-Myc or other Myc family member (e.g., N-Myc or L-Myc) induced by the inventive compounds or compositions of this invention in the biological sample or subject. In certain embodiments, the additional pharmaceutical agent is flavopiridol, triptolide, SNS-032 (BMS-387032), PHA-767491, PHA-793887, BS-181, (S)—CR8, (R)—CR8, ABT-737, or NU6140. In certain embodiments, the additional pharmaceutical agent is an inhibitor of a mitogen-activated protein kinase (MAPK). In certain embodiments, the additional pharmaceutical agent is an inhibitor of a Bcl-2 protein. In certain embodiments, the additional pharmaceutical agent is an inhibitor of a glycogen synthase kinase 3 (GSK3). In certain embodiments, the additional pharmaceutical agent is an inhibitor of an AGC kinase. In certain embodiments, the additional pharmaceutical agent is an inhibitor of a CaM kinase. In certain embodiments, the additional pharmaceutical agent is an inhibitor of a casein kinase 1. In certain embodiments, the additional pharmaceutical agent is an inhibitor of a STE kinase. In certain embodiments, the additional pharmaceutical agent is an inhibitor of a tyrosine kinase. Thus, the combination of the inventive compounds or compositions and the additional pharmaceutical agent(s) may be useful in treating proliferative diseases resistant to a treatment using the additional pharmaceutical agent(s) without the inventive compounds or compositions.

In yet another aspect, the present invention provides the compounds of compounds of Formula (I) or (II), e.g., compounds of Formulas (Ia), (Ib), (Ib-1), (Ib-2), (Ic), (Ic-1), (Id), (Id-1), (Ie), (Ie-1), (Ie-2), or (IIa), and pharmaceutically acceptable salts, solvates, hydrates, tautomers, stereoisomers, isotopically labeled derivatives, and compositions thereof, for use in the treatment of a proliferative disease in a subject. In certain embodiments, provided by the invention are the compounds described herein, and pharmaceutically acceptable salts and compositions thereof, for use in the treatment of a proliferative disease in a subject. In certain embodiments, provided by the invention are the compounds described herein, and pharmaceutically acceptable salts and compositions thereof, for use in inhibiting cell growth. In certain embodiments, provided by the invention are the compounds described herein, and pharmaceutically acceptable salts and compositions thereof, for use in inducing apoptosis in a cell. In certain embodiments, provided by the invention are the compounds described herein, and pharmaceutically acceptable salts and compositions thereof, for use in inhibiting transcription.

EXAMPLES

In order that the invention described herein may be more fully understood, the following examples are set forth. The synthetic and biological examples described in this application are offered to illustrate the compounds, pharmaceutical compositions, and methods provided herein and are not to be construed in any way as limiting their scope.

The compounds provided herein can be prepared from readily available starting materials using modifications to the specific synthesis protocols set forth below that would be well known to those of skill in the art. It will be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvents used, but such conditions can be determined by those skilled in the art by routine optimization procedures.

Additionally, as will be apparent to those skilled in the art, conventional protecting groups may be necessary to prevent certain functional groups from undergoing undesired reactions. The choice of a suitable protecting group for a particular functional group as well as suitable conditions for protection and deprotection are well known in the art. For example, numerous protecting groups, and their introduction and removal, are described in Greene et al., *Protecting Groups in Organic Synthesis*, Second Edition, Wiley, New York, 1991, and references cited therein.

TABLE 1

| | Abbreviations |
|---|---|
| Ac | acetyl |
| $Ac_2O$ | acetic anyhydride |
| AcOH | acetic acid |
| ACN | acetonitrile |
| aq. | aqueous |
| atm | atmospheres |
| Boc | tert-butoxy carbonyl |
| $Boc_2O$ | di-t-butyl dicarbonate |
| Bn | benzyl |
| DCM | bichloromethane |
| DIPEA | N,N-diisopropyl ethylamine |
| DMF | dmethylformamide |
| DMSO | dimethylsulfoxide |
| DPPA | diphenoxyphosphoryl azide |
| EDTA | ethylenediamine tetraacetic acid |
| ELS, | evaporative light scattering |
| ELSD | detector |
| eq(s). | equivalent(s) |
| EtOAc | ethyl acetate |
| Et | ethyl |
| EtOH | ethanol |
| $Et_3N$, TEA | triethylamine |
| g | gram(s) |
| h | hour(s) |
| Hex | hexanes |
| HOBt | 1-Hydroxybenzotriazole |
| HPLC | high pressure liquid chromatography |
| IPA | isopropanol |
| LCMS; | liquid chromatography mass |
| LC-MS | spectrometry |
| m-CPBA | 3-chloroperoxybenzoic acid |
| MeOH | methanol |
| mg | milligram(s) |
| MHz | megahertz |
| min | minute(s) |
| mL; ml | milliliter(s) |
| MS | mass spectrometry |
| mW | microwave |
| NMe | N-methyl |
| NMR | nuclear magnetic resonance |
| Ph | phenyl |
| pyr | pyridine |
| r.t.; rt; RT | room temperature |
| S., sat. | saturated |
| $T_3P$ | propylphosphonic anhydride |
| TFA | trifluoroacetic acid |
| THF | tetrahydrofuran |
| TLC | thin layer chromatography |

Example 1. Synthesis of N-(3-(benzo[d]thiazol-2-yl)-6-isopropyl-4,5,6,7-tetrahydrothieno[2,3-c]pyridin-2-yl)-3-(tert-butylamino)propanamide (Compound 127)

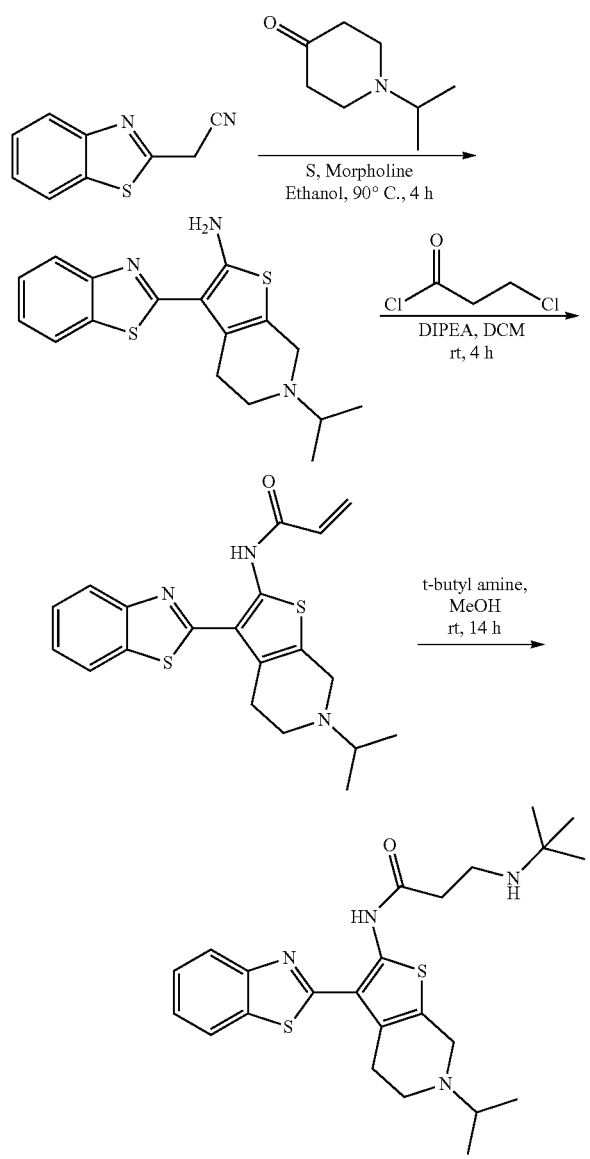

Step 1: 3-(benzo[d]thiazol-2-yl)-6-isopropyl-4,5,6,7-tetrahydrothieno[2,3-c]pyridin-2-amine

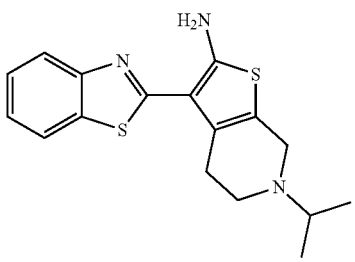

To a stirring solution of 2-(benzo[d]thiazol-2-yl)acetonitrile (5 g, 28.73 mmol) in ethanol (50 mL) was added 1-isopropylpiperidin-4-one (4 g, 28.73 mmol) and morpholine (2.5 mL, 28.73 mmol), and the reaction mixture was heated to 40° C. for 10 min. Sulfur was then added (900 mg, 28.73 mmol) and the resulting mixture heated to 90° C. for 4 h. The reaction progress was monitored by TLC. After the reaction was complete, the mixture was evaporated to dryness resulting in a crude residue which was triturated with methanol. The obtained precipitate was filtered and dried to afford the title compound as a pale yellow solid (4.3 g, 45% yield). LCMS: [M+H]$^+$=330.5; R$_f$=2.12 min.

Step 2: N-(3-(benzo[d]thiazol-2-yl)-6-isopropyl-4,5,6,7-tetrahydrothieno[2,3-c]pyridin-2-yl)acrylamide

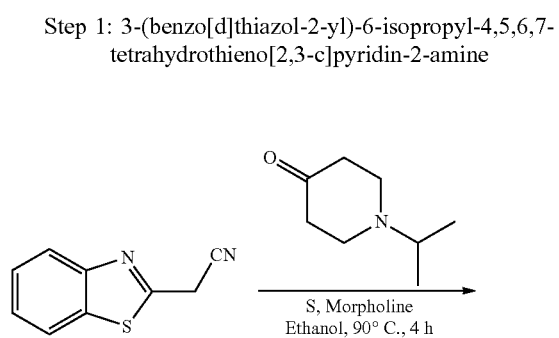

To a solution of 3-(benzo[d]thiazol-2-yl)-6-isopropyl-4,5,6,7-tetrahydrothieno[2,3-c]pyridin-2-amine (3 g, 9.11 mmol) in DCM (30 mL) at 0° C. was added DIPEA (1.57 mL, 9.11 mmol) followed by 3-chloropropanoyl chloride (1.2 g, 9.56 mmol) and the resulting mixture was stirred at room temperature for 4 h. The progress of the reaction was monitored by TLC. After the reaction was complete, the reaction mixture was washed with NaHCO₃ solution. The combined organic layers were dried over Na₂SO₄, filtered, and concentrated to afford crude residue which was purified by column chromatography to afford the title compound as a yellow solid (1.5 g, 44% yield). LCMS: [M+H]⁺=383.95; $R_t$=4.40 min.

Step 3: N-(3-(benzo[d]thiazol-2-yl)-6-isopropyl-4,5,6,7-tetrahydrothieno[2,3-c]pyridin-2-yl)-3-(tert-butylamino)propanamide

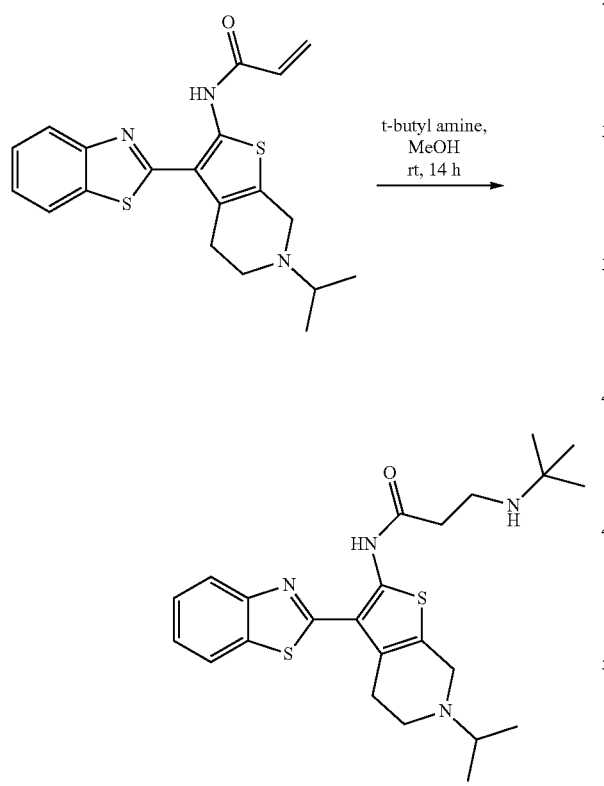

To a solution of N-(3-(benzo[d]thiazol-2-yl)-6-isopropyl-4,5,6,7-tetrahydrothieno[2,3-c]pyridin-2-yl)acrylamide (100 mg, 0.26 mmol) in MeOH (5 mL) was added t-butyl amine (38 mg, 0.52 mmol), and the reaction mixture was stirred at room temperature for 14 h. The reaction progress was monitored by TLC. After the reaction was complete, the mixture was evaporated to dryness. The crude residue was purified by preparative HPLC to afford the title compound as a yellow solid (30 mg, 25%).

Example 2. Synthesis of N-(3-(benzo[d]thiazol-2-yl)-6-isopropyl-4,5,6,7-tetrahydrothieno[2,3-c]pyridin-2-yl)-3-((2-chlorophenethyl)amino)propanamide (Compound 109)

A mixture of N-(3-(benzo[d]thiazol-2-yl)-6-isopropyl-4,5,6,7-tetrahydrothieno[2,3-c]pyridin-2-yl)acrylamide (100.00 mg, 238.10 umol), 2-(2-chlorophenyl)ethan-1-amine (37.05 mg, 238.10 umol), K₂CO₃ (65.82 mg, 476.20 umol) and NaI (17.84 mg, 119.05 umol) in MeCN (2.00 mL) was degassed and purged with N₂ three times. The mixture was stirred at 80° C. for 12 hours under an N₂ atmosphere until LC-MS analysis indicated the reaction was complete. The mixture was concentrated under reduced pressure and the resulting residue was purified by preparative HPLC to give the TFA salt of the title compound (14.20 mg, 26.34 umol, 11.06% yield) was obtained as a white solid.

Compounds 101-108 and 110-119 were prepared in the same manner as described above, using the appropriate amine.

Example 3. Synthesis of 1-amino-N-(3-(benzo[d]
thiazol-2-yl)-6-isopropyl-4,5,6,7-tetrahydrothieno[2,
3-c]pyridin-2-yl)-4,7,10-trioxa-14-azaheptadecan-
17-amide (Compound 120)
Step 1: N-(3-(benzo[d]thiazol-2-yl)-6-isopropyl-4,5,
6,7-tetrahydrothieno[2,3-c]pyridin-2-yl)-1,1,1-triph-
enyl-6,9,12-trioxa-2,16-diazanonadecan-19-amide
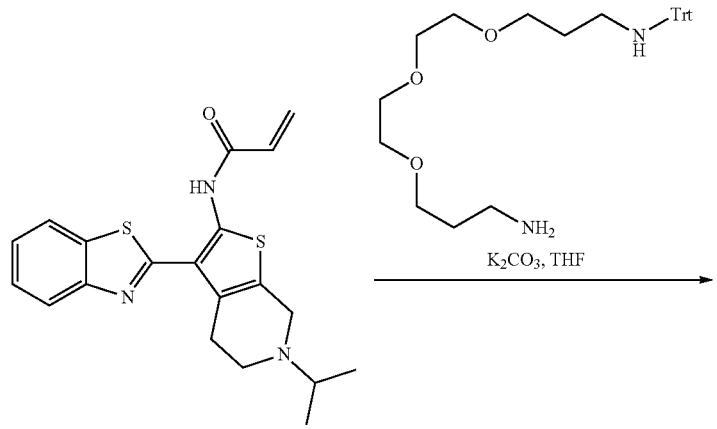
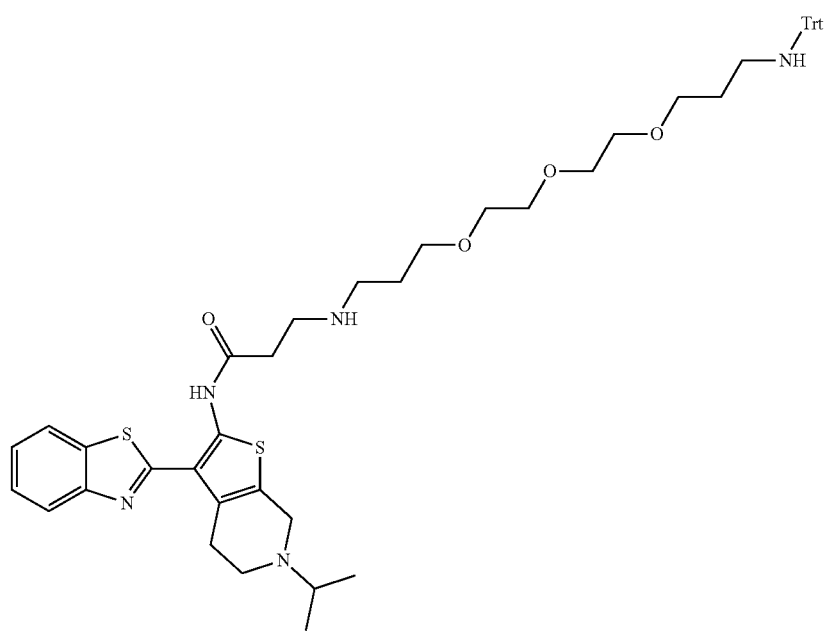

To a stirring solution of N-(3-(benzo[d]thiazol-2-yl)-6-isopropyl-4,5,6,7-tetrahydrothieno[2,3-c]pyridin-2-yl)acrylamide (6.5 mg, 0.0170 mmol) in THF (3.3 mL) was added 3-(2-(2-(3-aminopropoxy)ethoxy)ethoxy)-N-tritylpropan-1-amine (11.8 mg, 0.0255 mmol) and K$_2$CO$_3$ (7 mg, 0.051 mmol) and the reaction was stirred at room temperature for 16 h. Upon completion, the reaction mixture was quenched with aqueous sat. NaHCO$_3$ solution and extracted with 5:1 EtOAc/iPrOH (3×5 mL). The combined organic layers were dried over Na$_2$SO$_4$, filtered, and concentrated under reduced pressure to provide a crude residue which was used directly in the next step. LCMS: [M]$^+$=846.48; R$_t$=2.64 min.

Step 2: 1-amino-N-(3-(benzo[d]thiazol-2-yl)-6-isopropyl-4,5,6,7-tetrahydrothieno[2,3-c]pyridin-2-yl)-4,7,10-trioxa-14-azaheptadecan-17-amide

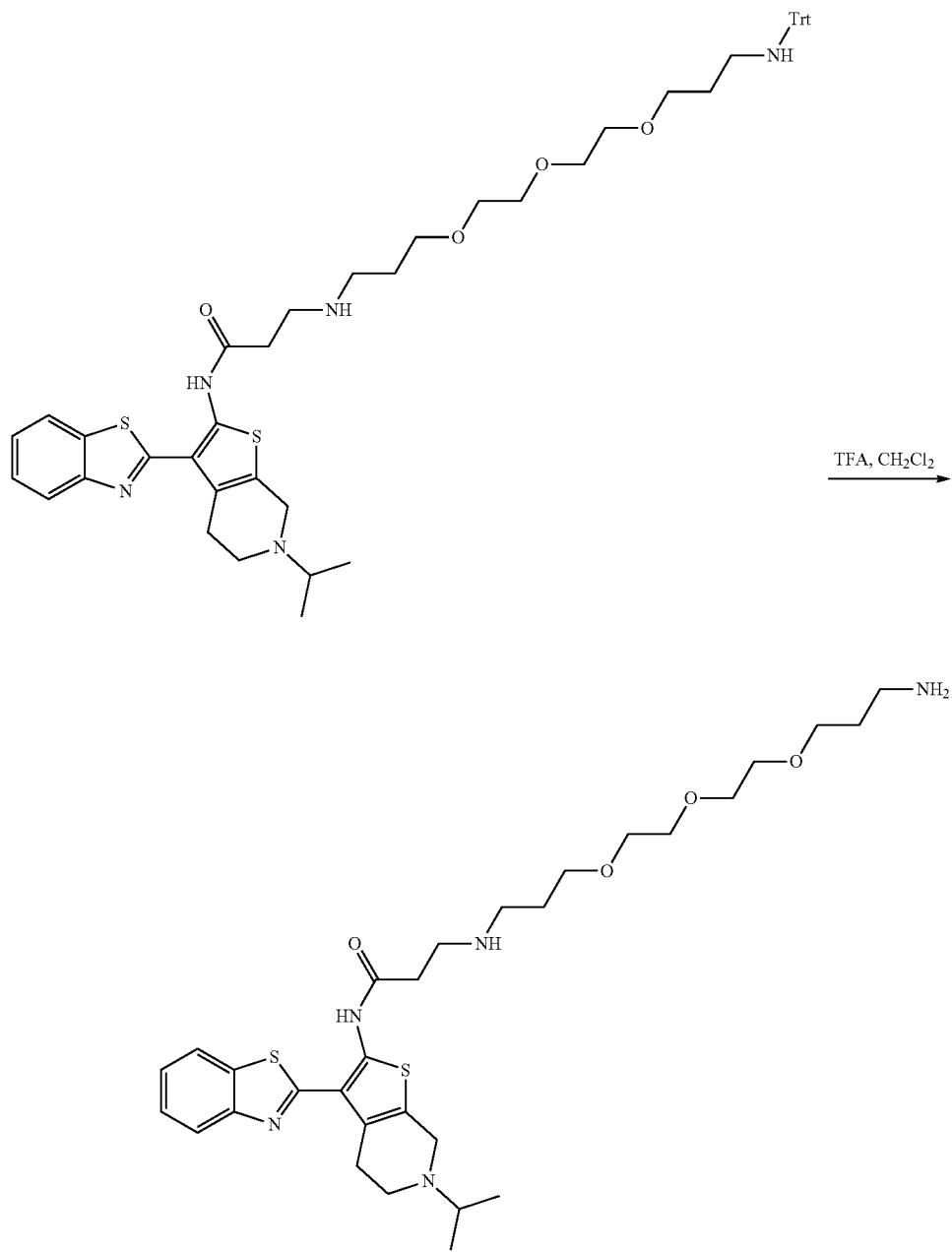

N-(3-(benzo[d]thiazol-2-yl)-6-isopropyl-4,5,6,7-tetrahydrothieno[2,3-c]pyridin-2-yl)-1,1,1-triphenyl-6,9,12-trioxa-2,16-diazanonadecan-19-amide (14.4 mg, 0.0170 mmol) was dissolved in a 5% (v/v) solution of TFA in DCM (2 mL) and stirred at room temperature for 2 h. Upon completion, the reaction mixture was quenched with aqueous sat. NaHCO$_3$ solution and extracted with 5:1 EtOAc/iPrOH (3×5 mL). The combined organic layers were dried over Na$_2$SO$_4$, filtered, and concentrated under reduced pressure to provide a crude residue, which was purified by HPLC (0-100% MeCN in H$_2$O) to afford the title compound as a yellow powder (4.4 mg, 42.9% yield). LCMS: [MH]$^+$=604.23; R$_f$=2.46 min.

Example 4. Synthesis of N-(3-(benzo[d]thiazol-2-yl)-6-isopropyl-4,5,6,7-tetrahydrothieno[2,3-c]pyridin-2-yl)-3-(((1-methyl-1H-pyrazol-4-yl)methyl)amino)propanamide (Compound 100)

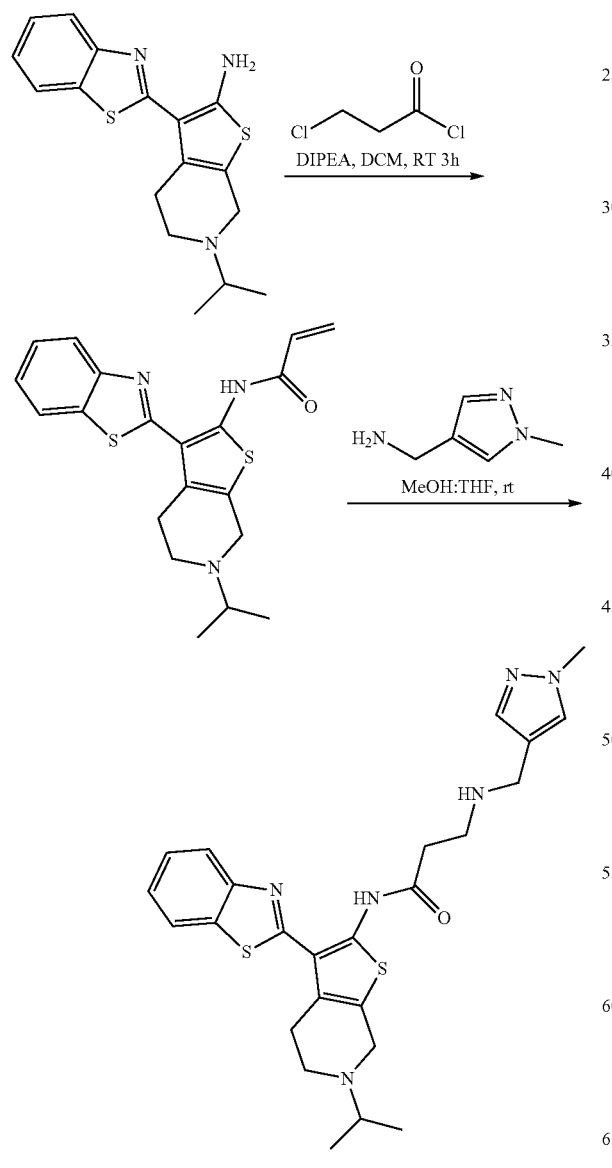

Step 1: N-(3-(benzo[d]thiazol-2-yl)-6-isopropyl-4,5,6,7-tetrahydrothieno[2,3-c]pyridin-2-yl)acrylamide

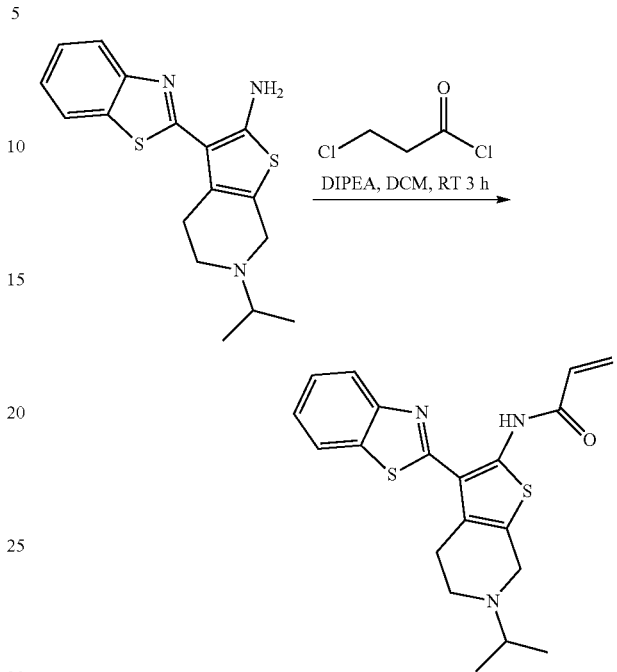

To a solution of 3-(benzo[d]thiazol-2-yl)-6-isopropyl-4,5,6,7-tetrahydrothieno[2,3-c]pyridin-2-amine (1.8 g, 5.45 mmol) in DCM (15 mL) at 0° C. was added DIPEA (1.4 mL, 8.18 mmol) and 3-chloropropanoyl chloride (0.77 mL, 8.18 mmol). The resulting reaction mixture was stirred at room temperature for 3 h. The progress of the reaction was monitored by TLC. After completion, the reaction was concentrated, diluted with water and extracted with ethyl acetate. The combined organic layers were dried over anhydrous Na$_2$SO$_4$, filtered, and concentrated to get a crude residue. The crude compound was purified by silica gel column chromatography eluting with 0-5% MeOH/DCM to afford the title compound as a yellow solid (1.3 g, 62% yield).

Step 2: N-(3-(benzo[d]thiazol-2-yl)-6-isopropyl-4,5,6,7-tetrahydrothieno[2,3-c]pyridin-2-yl)-3-(((1-methyl-1H-pyrazol-4-yl)methyl)amino)propanamide

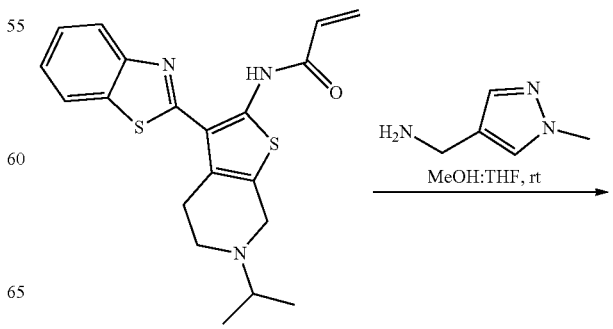

71

-continued

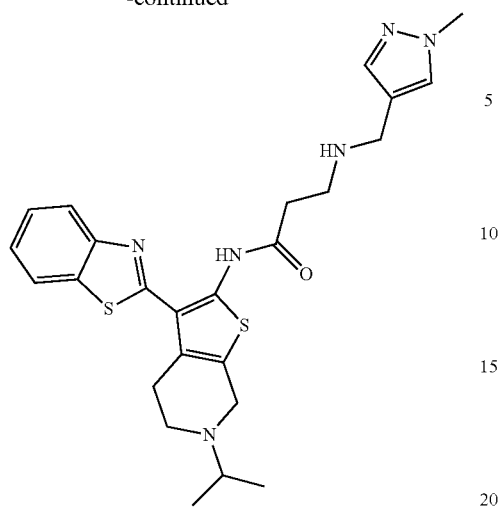

To a solution of N-(3-(benzo[d]thiazol-2-yl)-6-isopropyl-4,5,6,7-tetrahydrothieno[2,3-c]pyridin-2-yl)acrylamide (0.1 g, 0.261 mmol) in methanol:THF (1:2 mL) was added (1-methyl-1H-pyrazol-4-yl)methanamine (0.058 g, 0.522 mmol). The resulting reaction mixture was stirred at room temperature for 2 h. The progress of the reaction was monitored by TLC and LCMS. After completion, the reaction mixture was concentrated up to dryness to get a crude residue. The crude compound was purified by silica gel column chromatography eluting with 0-5% MeOH/DCM to afford the title compound as a brown gummy solid (0.055 g, 43%).

Example 5. Synthesis of tert-butyl (3-((3-(benzo[d]thiazol-2-yl)-6-isopropyl-4,5,6,7-tetrahydrothieno[2,3-c]pyridin-2-yl)amino)-3-oxopropyl)(sec-butyl)carbamate

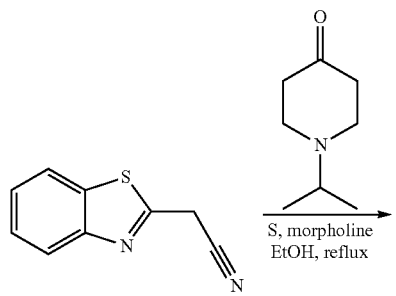

72

-continued

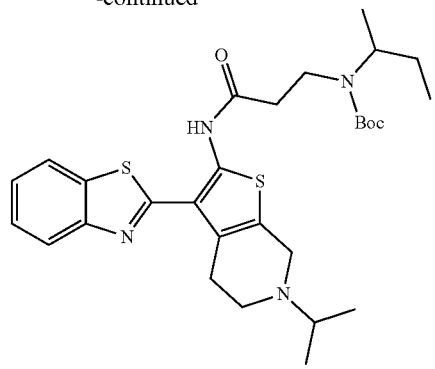

Step 1: 3-(benzo[d]thiazol-2-yl)-6-isopropyl-4,5,6,7-tetrahydrothieno[2,3-c]pyridin-2-amine

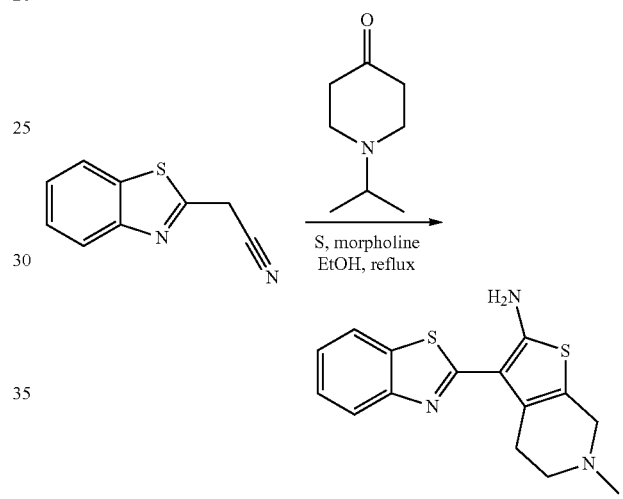

To a solution of 2-(benzo[d]thiazol-2-yl)acetonitrile (0.5 g, 2.87 mmol) in ethanol (10 mL) was added 1-isopropylpiperidin-4-one (0.405 g, 2.87 mmol), elemental sulfur (0.109 g, 2.87 mmol) and morpholine (0.25 g, 2.87 mmol) at room temperature. After the addition, the resulting mixture was heated to reflux at 80° C. for 3 h and monitored by TLC. After completion, the reaction mixture was concentrated under vacuum pressure and the crude compound was purified by triturating with methanol to afford the title compound as a yellow solid (0.7 g, yield 85.4%). This compound was used in the next step without further purification. LCMS: [M+H]$^+$=329.95; R$_t$=2.31 min.

Step 2: tert-butyl (3-((3-(benzo[d]thiazol-2-yl)-6-isopropyl-4,5,6,7-tetrahydrothieno[2,3-c]pyridin-2-yl)amino)-3-oxopropyl)(sec-butyl)carbamate

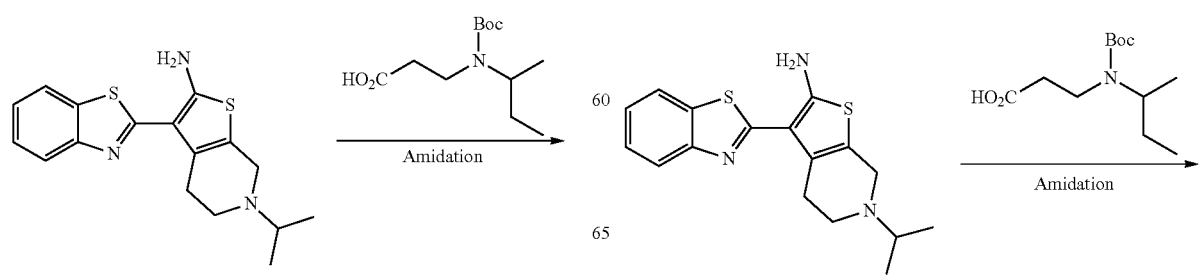

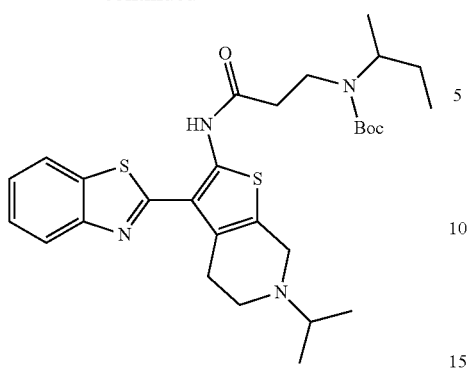

To a solution of 3-(benzo[d]thiazol-2-yl)-6-isopropyl-4,5,6,7-tetrahydrothieno[2,3-c]pyridin-2-amine (0.25 g, 0.759 mmol) in DCM (10 mL), 3-((tert-butoxycarbonyl)(sec-butyl)amino)propanoic acid (0.28 g, 1.14 mmol) and Et$_3$N (0.31 mL, 2.27 mmol) was added T$_3$P (1.2 mL, 1.5 eq, 50 wt % solution in EtOAc) was added at 0° C. The reaction was stirred at room temperature for 16 h and the progress of the reaction was monitored by TLC and LCMS. After completion, the reaction mixture was diluted with water and extracted with DCM and concentrated under reduced pressure to get a crude residue, which purified by preparative HPLC to afford the title compound (0.260 g, yield 61.9%).

Example 6. Synthesis of 3-(sec-butylamino)-N-(3-(5-fluorobenzo[d]thiazol-2-yl)-4,5,6,7-tetrahydrothieno[2,3-c]pyridin-2-yl) propanamide (Compound 123)

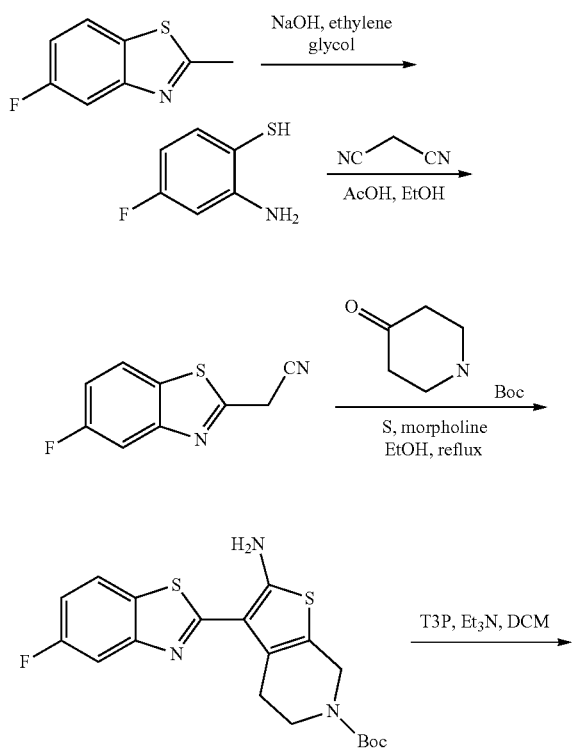

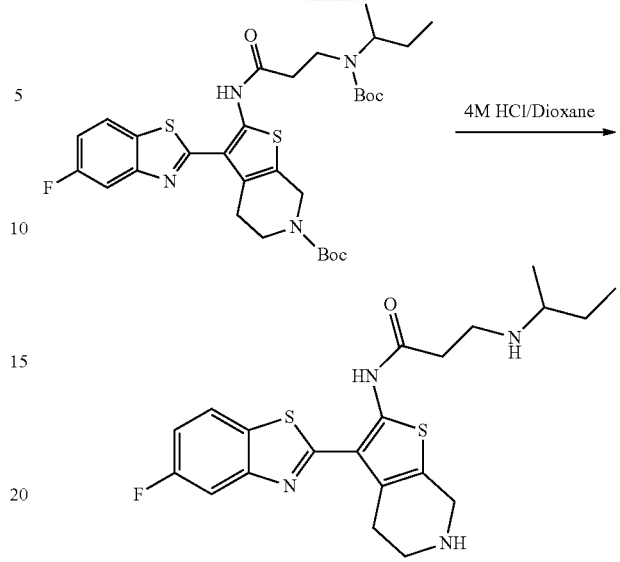

Step 1: 2-amino-4-fluorobenzenethiol

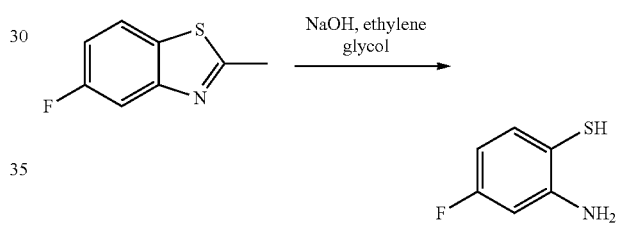

To a solution of 5-fluoro-2-methylbenzo[d]thiazole (1 g, 5.98 mmol) in ethylene glycol (5 mL) was added 8 N NaOH (5 mL). The resulting reaction mixture was stirred at 140° C. for 3 h and was monitored by TLC. After completion, the reaction mixture was cooled to room temperature, acidified with 1N HCl to pH 6 and extracted with DCM. The combined organic layers were dried over anhydrous Na$_2$SO$_4$, filtered, and concentrated under reduced pressure to afford the title compound as a brown oil (0.8 g, yield 94.1%). LCMS: [M+1]$^+$=192.90; R$_t$=2.80 min.

Step 2: 2-(5-fluorobenzo[d]thiazol-2-yl)acetonitrile

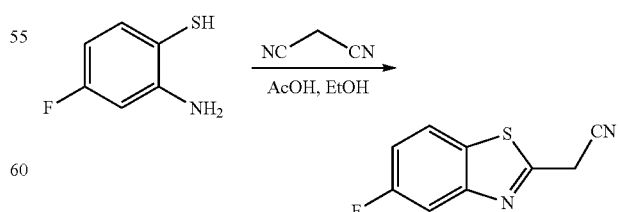

To a solution of 2-amino-4-fluorobenzenethiol (1.6 g, 11.19 mmol) in EtOH (10 mL) was added malononitrile (0.74 g, 11.19 mmol) and AcOH (10 mL). The resulting reaction mixture was stirred at 90° C. for 12 h was monitored by TLC. After completion, the reaction mixture was quenched with water and concentrated under reduced pressure to dryness. The residue was diluted with aqueous sat. NaHCO₃ solution and extracted with ethyl acetate. The combined organic layers were dried over anhydrous Na₂SO₄, filtered, and concentrated to get a crude residue that was purified by silica gel column chromatography eluting with 0-20% ethyl acetate in n-hexane to afford the title compound as a yellow solid (1.1 g, yield 51.4%). LCMS: [M+1]⁺=192.90; R$_f$=2.80 min.

Step 3: tert-butyl 2-amino-3-(5-fluorobenzo[d]thiazol-2-yl)-4,7-dihydrothieno[2,3-c]pyridine-6(5H)-carboxylate

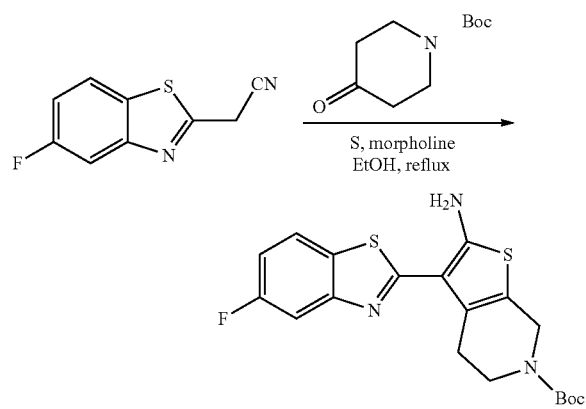

To a solution of 2-(5-fluorobenzo[d]thiazol-2-yl)acetonitrile (0.5 g, 2.60 mmol) in ethanol (10 mL) was added tert-butyl 4-oxopiperidine-1-carboxylate (0.62 g, 3.12 mmol), elemental sulfur (0.12 g, 3.12 mmol) and morpholine (0.27 g, 3.12 mmol) at rt. After the addition, the resulting mixture was heated to reflux at 80° C. for 3 h and monitored by TLC. After completion, the reaction mixture was concentrated under vacuum pressure and the crude compound was purified by triturating with methanol to afford the title compound as a yellow solid (0.98 g, yield 93%). ¹H NMR (400 MHz, DMSO-d6) δ 8.21 (s, 2H), 8.02 (dd, J=8, 3.6 Hz, 1H), 7.71 (dd, J=8, 2.4 Hz, 1H), 7.22-7.17 (m, 1H), 4.35 (s, 2H), 3.65 (t, J=5.2 Hz, 2H), 2.85-2.83 (m, 2H), 1.43 (s, 9H).

Step 4: tert-butyl 2-(3-((tert-butoxycarbonyl)(sec-butyl)amino)propanamido)-3-(5-fluorobenzo[d]thiazol-2-yl)-4,7-dihydrothieno[2,3-c]pyridine-6(5H)-carboxylate

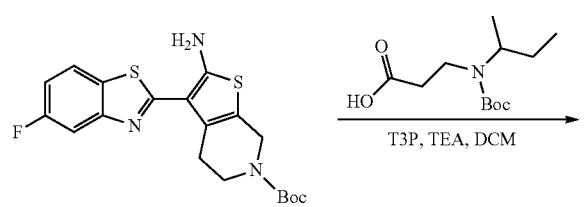

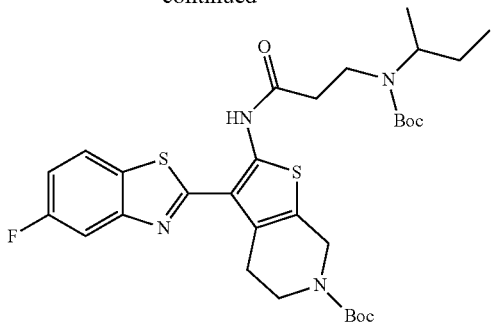

To a solution of tert-butyl 2-amino-3-(5-fluorobenzo[d]thiazol-2-yl)-4,7-dihydrothieno[2,3-c]pyridine-6(5H)-carboxylate (0.25 g, 0.617 mmol) in DCM (5 mL), 3-((tert-butoxycarbonyl)(sec-butyl)amino)propanoic acid (0.23 g, 0.926 mmol), Et₃N (0.43 mL, 0.381 mmol) and T₃P (1.2 mL, 1.85 mmol, 50% in ethyl acetate) was added at 0° C. The reaction was stirred at room temperature for 16 h and the progress of the reaction was monitored by TLC and LCMS. After completion, the reaction mixture was diluted with water, extracted with ethyl acetate and concentrated under reduced pressure to get a crude residue that was purified by preparative HPLC to afford the title compound (0.23 g, yield 59%). LCMS: [M+H]⁺=633.35; R$_t$=4.97 min.

Step 5: 3-(sec-butylamino)-N-(3-(5-fluorobenzo[d]thiazol-2-yl)-4,5,6,7-tetrahydrothieno[2,3-c]pyridin-2-yl) propanamide

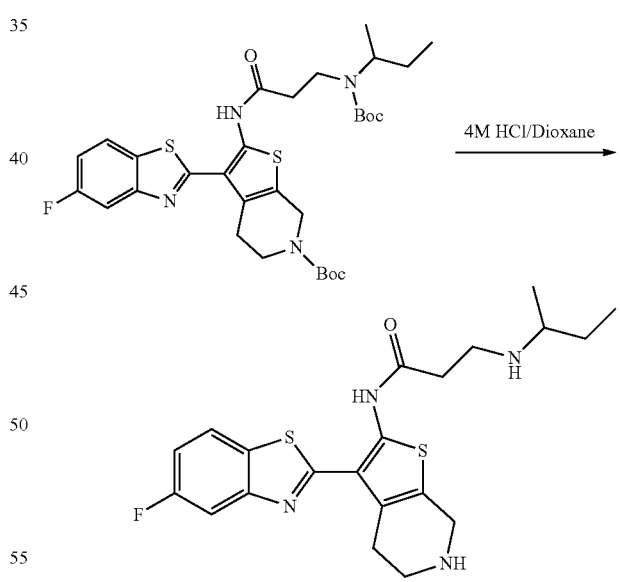

To a solution of tert-butyl 2-(3-((tert-butoxycarbonyl)(sec-butyl)amino)propanamido)-3-(5-fluorobenzo[d]thiazol-2-yl)-4,7-dihydrothieno[2,3-c]pyridine-6(5H)-carboxylate (0.23 g, 0.364 mmol) in dioxane (5 mL) at 0° C. was added 4M HCl in dioxane (1 mL). After addition, the resulting mixture was stirred at room temperature for 2 h. Upon completion, the reaction mixture was concentrated under vacuum pressure resulting in a crude residue which was purified triturating in ether to afford the title compound as a yellow solid (0.08 g HCl salt, yield 53.3%).

Example 7. Synthesis of N-(3-(benzo[d]thiazol-2-yl)-6-isopropyl-4,5,6,7-tetrahydrothieno[2,3-c]pyridin-2-yl)-3-(sec-butylmethyl)amino)propanamide (Compound 122)

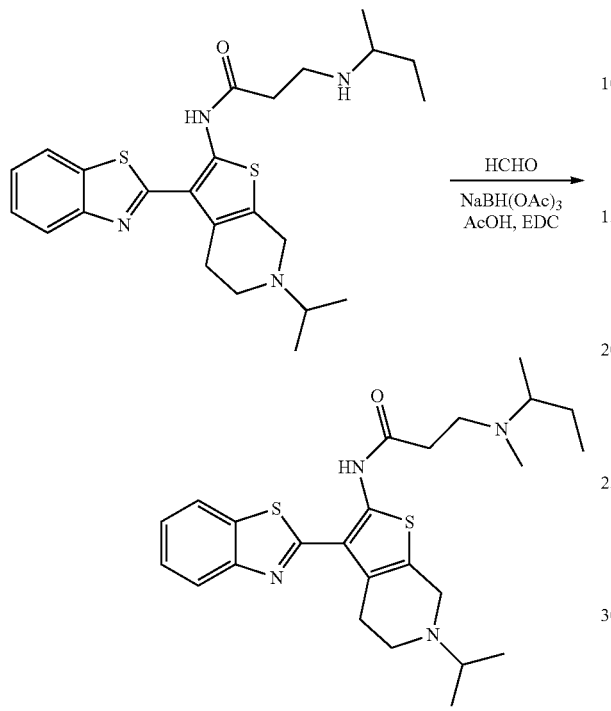

To a stirring solution of N-(3-(benzo[d]thiazol-2-yl)-6-isopropyl-4,5,6,7-tetrahydrothieno[2,3-c]pyridin-2-yl)-3-(sec-butylamino)propanamide (0.08 g, 0.175 mmol) and formalin (0.011 g, 0.351 mmol) in dichloroethane (4 mL) and acetic acid (0.05 mL) was added HCHO, and the reaction was stirred at room temperature for 3 h. Sodium triacetoxyborohydride (0.112 g, 0.526 mmol) was then added at 0° C. and the reaction was stirred at room temperature for 16 h. After the reaction was complete, the mixture was quenched with aqueous sat. NaHCO₃ solution and extracted with 10% MeOH/DCM. The combined organic layers were dried over anhydrous Na₂SO₄, filtered, and concentrated to get a crude residue. The crude compound was purified by preparative HPLC to afford the title compound as a gummy solid (0.042 g, yield 51.2%).

Example 8. Synthesis of N-(3-(benzo[d]thiazol-2-yl)-4,5,6,7-tetrahydrothieno[2,3-c]pyridin-2-yl)-3-(sec-butylamino)propanamide (Compound 124)

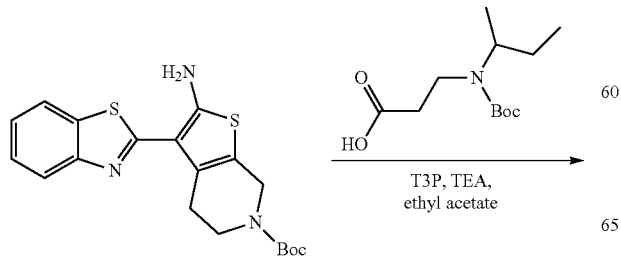

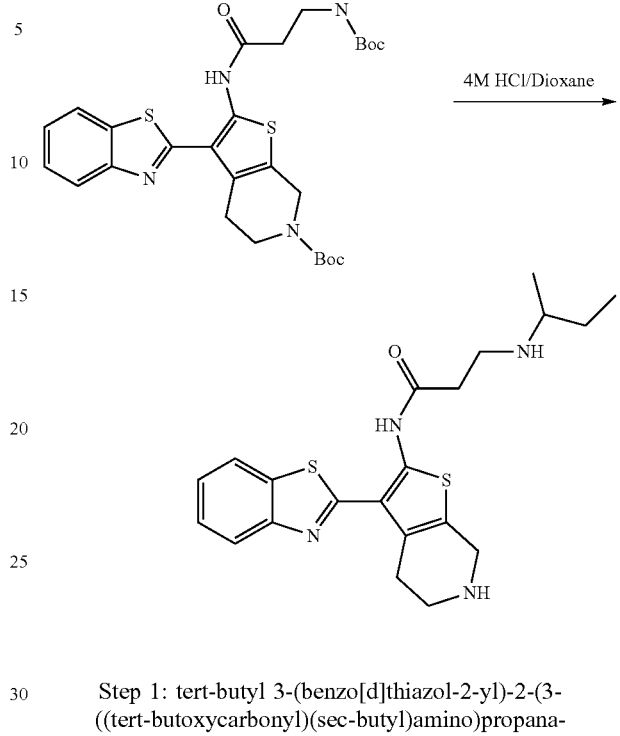

Step 1: tert-butyl 3-(benzo[d]thiazol-2-yl)-2-(3-((tert-butoxycarbonyl)(sec-butyl)amino)propanamido)-4,7-dihydrothieno[2,3-c]pyridine-6(5H)-carboxylate To a stirring solution of tert-butyl 2-amino-3-(benzo[d]thiazol-2-yl)-4,7-dihydrothieno[2,3-c]pyridine-6(5H)-carboxylate (0.25 g, 0.64 mmol) in ethyl acetate (10 mL), 3-((tert-butoxycarbonyl)(sec-butyl)amino)propanoic acid (0.237 g, 0.96 mmol), Et₃N (0.13 g, 1.28 mmol) and T3P (0.305 g, 0.96 mmol) were added at 0° C. The reaction was stirred at room temperature for 16 h and monitored by TLC and LCMS. The reaction was then heated to 60° C. for 12 h. After the reaction was complete, the mixture was diluted with water, extracted with 10% MeOH/DCM, and concentrated under reduced pressure to get a crude residue, which was purified by silica gel column chromatography eluting with 0-5% MeOH/DCM followed by preparative HPLC to afford the title compound (0.2 g, crude). LCMS: [M+1]$^+$= 615.40; $R_t$=4.89 min.

Step 2: N-(3-(benzo[d]thiazol-2-yl)-4,5,6,7-tetrahydrothieno[2,3-c]pyridin-2-yl)-3-(sec-butylamino) propanamide

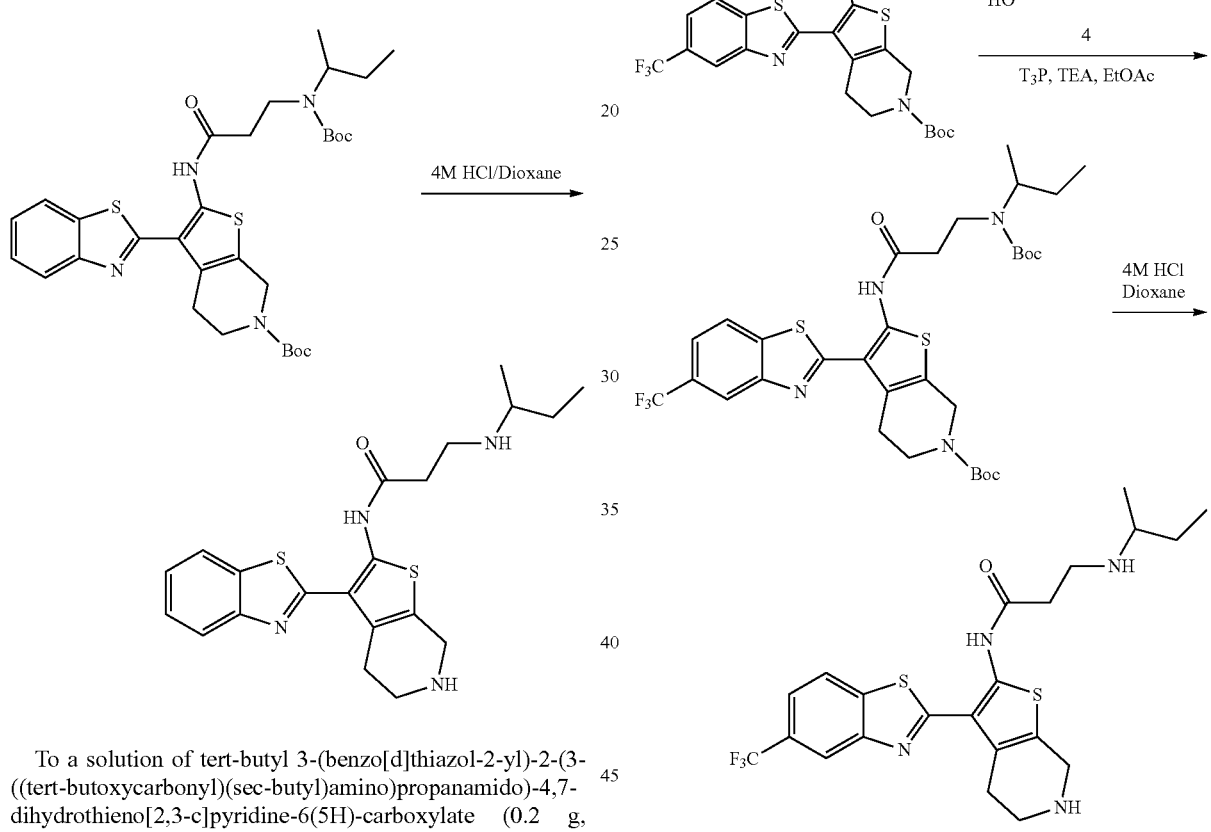

To a solution of tert-butyl 3-(benzo[d]thiazol-2-yl)-2-(3-((tert-butoxycarbonyl)(sec-butyl)amino)propanamido)-4,7-dihydrothieno[2,3-c]pyridine-6(5H)-carboxylate (0.2 g, 0.38 mmol) in dioxane (2 mL) at 0° C. was added 4M HCl in dioxane (2 mL). After the addition, the resulting mixture was stirred at room temperature for 2 h. After completion, the reaction mixture was concentrated under vacuum pressure to give a crude residue which was purified by trituration with ether to afford the title compound as a brown solid (0.06 g HCl salt, 37% yield).

Example 9. Synthesis of 3-(sec-butylamino)-N-(3-(5-(trifluoromethyl) benzo[d]thiazol-2-yl)-4,5,6,7-tetrahydrothieno[2,3-c]pyridin-2-yl) propanamide (Compound 125)

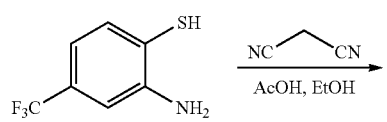

Step 1: 2-(5-(trifluoromethyl)benzo[d]thiazol-2-yl) acetonitrile

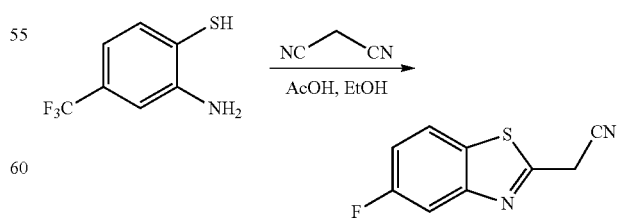

To a stirring solution of 2-amino-4-(trifluoromethyl)benzenethiol (1.5 g, 6.55 mmol) in EtOH (10 mL) was added malononitrile (0.648 g, 9.83 mmol) and AcOH (10 mL). The resulting reaction mixture was stirred at 80° C. for 12 h, and the progress of the reaction was monitored by TLC. After the reaction was complete, the mixture was quenched with water and concentrated under reduced pressure to dryness. The residue was diluted with water and extracted with ethyl acetate, and the combined organic layers were dried over anhydrous Na$_2$SO$_4$, filtered, and concentrated to get a crude residue. The crude compound was purified by silica gel column chromatography eluting with 0-30% ethyl acetate in n-hexane to afford the title compound as a yellow solid (0.9 g, yield 60%).

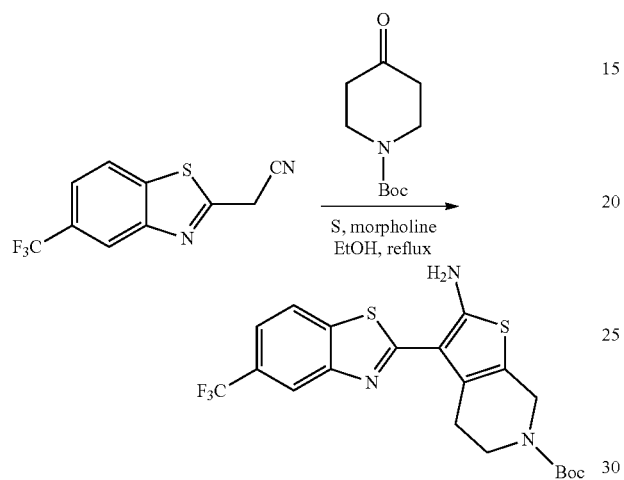

Step 2: tert-butyl 2-amino-3-(5-(trifluoromethyl) benzo[d]thiazol-2-yl)-4,7-dihydrothieno[2,3-c]pyridine-6(5H)-carboxylate To a solution of 2-(5-(trifluoromethyl)benzo[d]thiazol-2-yl)acetonitrile (0.9 g, 3.71 mmol) in ethanol (20 mL) was added tert-butyl 4-oxopiperidine-1-carboxylate (0.74 g, 3.71 mmol), elemental sulfur (0.119 g, 3.71 mmol), and morpholine (0.29 g, 3.71 mmol) at rt. After the addition, the resulting mixture was heated to reflux at 80° C. for 1 h and the progress of the reaction was monitored by TLC. After the reaction was complete, the mixture was concentrated under vacuum pressure and the crude compound was purified by triturating with methanol to afford the title compound as a yellow solid (1.1 g, yield 68.7%). LCMS: [M+H]$^+$=455.80; R$_t$=4.22 min.

Step 3: tert-butyl 2-(3-((tert-butoxycarbonyl)(sec-butyl)amino)propanamido)-3-(5-(trifluoromethyl) benzo[d]thiazol-2-yl)-4,7-dihydrothieno[2,3-c]pyridine-6(5H)-carboxylate

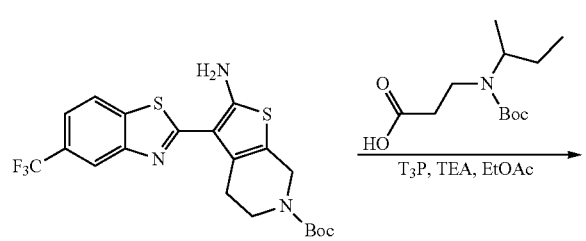

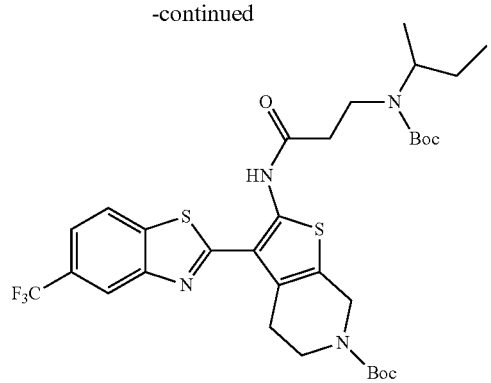

To a solution of tert-butyl 2-amino-3-(5-(trifluoromethyl) benzo[d]thiazol-2-yl)-4,7-dihydrothieno[2,3-c]pyridine-6 (5H)-carboxylate (0.4 g, 0.879 mmol) in ethyl acetate (8 mL), 3-((tert-butoxycarbonyl)(sec-butyl)amino)propanoic acid (0.324 g, 1.32 mmol), Et$_3$N (0.27 g, 2.64 mmol) and T3P (1.2 mL) was added at 0° C. The reaction was stirred at room temperature for 16 h and the progress of the reaction was monitored by TLC and LCMS. After the reaction was complete, the mixture was diluted with water, extracted with ethyl acetate, and concentrated under reduced pressure to afford the title compound (0.25 g, yield 41%). LCMS: [M-Boc+1]$^+$=583.15; R$_t$=5.14 min.

Step 4: 3-(sec-butylamino)-N-(3-(5-(trifluoromethyl)-benzo[d]thiazol-2-yl)-4,5,6,7-tetrahydrothieno[2,3-c]pyridin-2-yl)propanamide

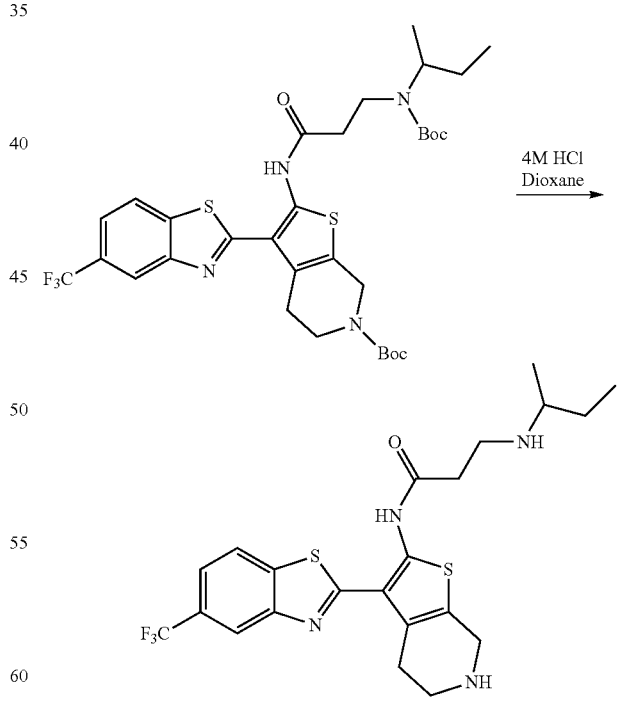

To a solution of tert-butyl 2-(3-((tert-butoxycarbonyl) (sec-butyl)amino)propanamido)-3-(5-(trifluoromethyl) benzo[d]thiazol-2-yl)-4,7-dihydrothieno[2,3-c]pyridine-6 (5H)-carboxylate (0.2 g, 0.293 mmol) in dioxane (5 mL) at 0° C. was added 4M HCl in dioxane (5 mL). After the addition, the resulting mixture was stirred at room temperature for 2 h. After the reaction was complete, the mixture was concentrated under vacuum pressure resulting in a crude residue which was purified by preparative HPLC to afford the title compound as a yellow solid (0.06 g, 42.5% yield).

Example 10. Synthesis of 3-(sec-butylamino)-N-(3-(5-fluorobenzo[d]thiazol-2-yl)-6-isopropyl-4,5,6,7-tetrahydrothieno[2,3-c]pyridin-2-yl)propanamide (Compound 126)

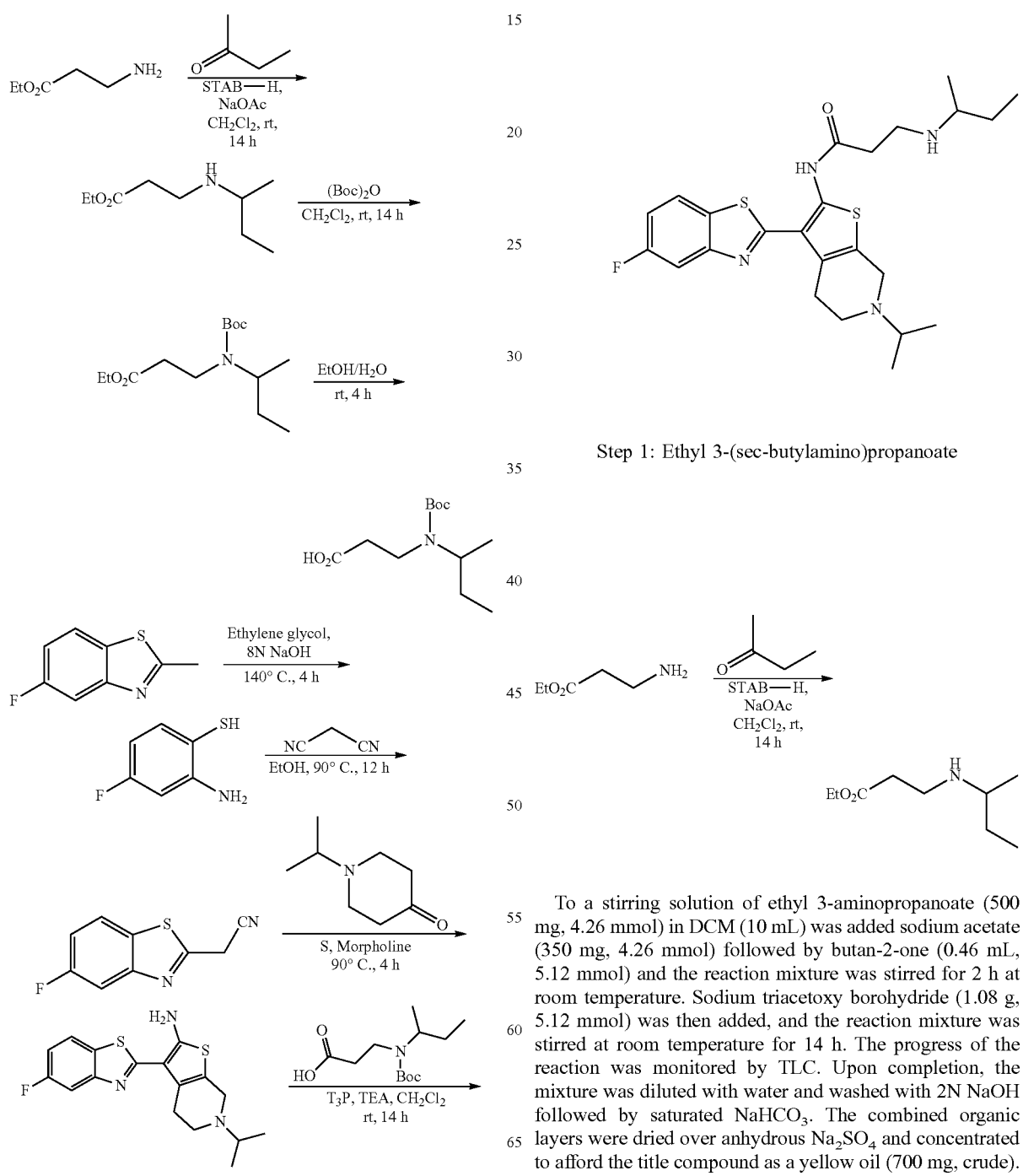

Step 1: Ethyl 3-(sec-butylamino)propanoate

To a stirring solution of ethyl 3-aminopropanoate (500 mg, 4.26 mmol) in DCM (10 mL) was added sodium acetate (350 mg, 4.26 mmol) followed by butan-2-one (0.46 mL, 5.12 mmol) and the reaction mixture was stirred for 2 h at room temperature. Sodium triacetoxy borohydride (1.08 g, 5.12 mmol) was then added, and the reaction mixture was stirred at room temperature for 14 h. The progress of the reaction was monitored by TLC. Upon completion, the mixture was diluted with water and washed with 2N NaOH followed by saturated NaHCO$_3$. The combined organic layers were dried over anhydrous Na$_2$SO$_4$ and concentrated to afford the title compound as a yellow oil (700 mg, crude). ELSD: [M+H]$^+$=173.00; R$_t$=2.84 min.

Step 2: ethyl 3-((tert-butoxycarbonyl)(sec-butyl)amino)propanoate

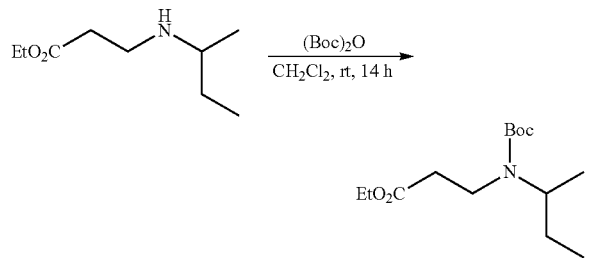

To a solution of ethyl 3-(sec-butylamino)propanoate (700 mg, 4.04 mmol) in DCM (10 mL) was added triethylamine (2.22 mL, 16.16 mmol) followed by DMAP (98 mg, 0.8 mmol) and di-tert-butyl dicarbonate (1.76 mL, 8.08 mmol) and the mixture was stirred at room temperature for 14 h. The reaction progress was monitored by TLC. After the reaction was complete, the mixture was evaporated to dryness to give a crude residue which was purified by column chromatography to afford the title compound as a yellow oil (700 mg, 64% yield). ELSD: $[M+H]^+=274.00$; $R_t=3.06$ min.

Step 3: 3-((tert-butoxycarbonyl)(sec-butyl)amino)propanoic acid

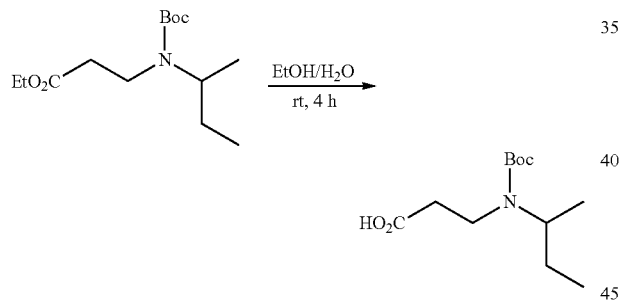

To a solution of ethyl 3-((tert-butoxycarbonyl)(sec-butyl)amino)propanoate (700 mg, 2.56 mmol) in ethanol (1 mL)/water (10 mL) was added NaOH (410 mg, 10.25 mmol) at 0° C., and the reaction was stirred at room temperature for 4 h. The progress of the reaction was monitored by TLC. After the reaction was complete, the mixture was evaporated and neutralized with 1N HCl solution. The aqueous layer was extracted with EtOAc and the combined organic layers were dried over anhydrous $Na_2SO_4$ and concentrated to afford the title compound as a yellow oil (150 mg, 24%). ELSD: $[M-56+1]^+=190$; $R_t=1.39$ min.

Step 4: 2-amino-4-fluorobenzenethiol

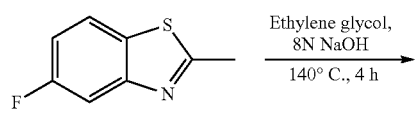 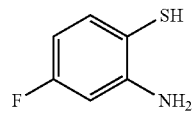

To a stirring solution of 5-fluoro-2-methylbenzo[d]thiazole (2.0 g, 11.97 mmol) in ethylene glycol (20 mL) was added 8N NaOH solution (20 mL) at room temperature and the resulting solution was heated at 140° C. for 4 h. The reaction was monitored by TLC. After the reaction was complete, the mixture was diluted with diethyl ethe, and the pH of the separated aqueous layer was adjusted to 5 with 1N HCl and extracted with EtOAc. The organic layer was dried over anhydrous $Na_2SO_4$ and concentrated under reduced pressure to afford (1.6 g, crude) of title compound as a brown syrup. LCMS: $[M+H]^+=143.3$; $R_t=2.57$ min.

Step 5: 2-(5-fluorobenzo[d]thiazol-2-yl)acetonitrile

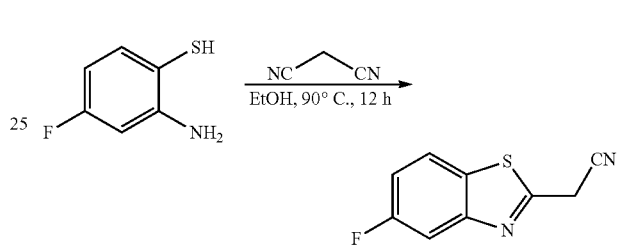

To a solution of 2-amino-4-fluorobenzenethiol (1 g, 11.1 mmol) in ethanol (20 mL) was added acetic acid (10 mL) followed by malononitrile (740 mg, 11.1 mmol) at room temperature. The reaction mixture was heated to 90° C. for 12 h, and the progress was monitored by TLC. After removal of the solvent, the reaction mixture was diluted with EtOAc and washed with saturated $NaHCO_3$ solution. The combined organic layers were dried over anhydrous $Na_2SO_4$ and concentrated to give a crude residue. The crude compound was purified by flash column chromatography to afford the title compound (1.1 g, 51% yield) as a yellow solid. LCMS: $[M+H]^+=192.9$; $R_t=2.08$ min

Step 6: 3-(5-fluorobenzo[d]thiazol-2-yl)-6-isopropyl-4,5,6,7-tetrahydrothieno[2,3-c]pyridin-2-amine

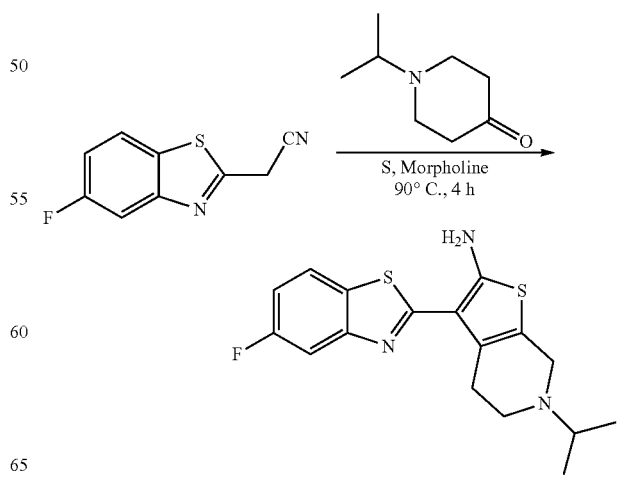

To a solution of 2-(5-fluorobenzo[d]thiazol-2-yl)acetonitrile (200 mg, 1.04 mmol) in ethanol (10 mL) were added 1-isopropylpiperidin-4-one (176 mg, 1.24 mmol) and morpholine (108 mg, 1.24 mmol) at room temperature. The reaction mixture was heated to 40° C. for 10 min, after which was added sulfur (40 mg, 1.24 mmol), and the resulting mixture was heated to 90° C. for 4 h. The progress of the reaction was monitored by TLC. After the reaction was complete, the mixture was evaporated to dryness to afford a crude product that was triturated with methanol to obtain the title compound (280 mg, 78%) as a yellow solid. LCMS: [M+H]$^+$=348.05; R$_t$=2.17 min.

Step 7: tert-butyl sec-butyl(3-((3-(5-fluorobenzo[d]thiazol-2-yl)-6-isopropyl-4,5,6,7-tetrahydrothieno[2,3-c]pyridin-2-yl)amino)-3-oxopropyl)carbamate

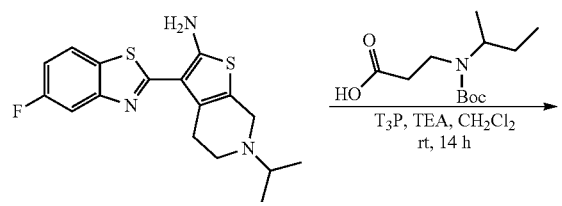

To a solution of 3-(5-fluorobenzo[d]thiazol-2-yl)-6-isopropyl-4,5,6,7-tetrahydrothieno[2,3-c]pyridin-2-amine (250 mg, 0.72 mmol) in DCM (10 mL) at 0° C. was added 3-((tert-butoxycarbonyl)(sec-butyl)amino)propanoic acid (270 mg, 1.08 mmol) and triethylamine (0.49 mL, 3.6 mmol), followed by T$_3$P (0.7 mL, 1.08 mmol). The reaction mixture was stirred at room temperature for 14 h, and the progress was monitored by TLC. After the reaction was complete, the mixture was diluted with DCM and washed with NaHCO$_3$. The combined organic layers were dried over anhydrous Na$_2$SO$_4$ and concentrated to get a crude residue, which was purified by flash column chromatography to afford the title compound as a yellow solid (150 mg, 36% yield). LCMS: [M+H]$^+$=575.35; R$_t$=2.70 min.

Step 8: 3-(sec-butylamino)-N-(3-(5-fluorobenzo[d]thiazol-2-yl)-6-isopropyl-4,5,6,7-tetrahydrothieno[2,3-c]pyridin-2-yl)propanamide

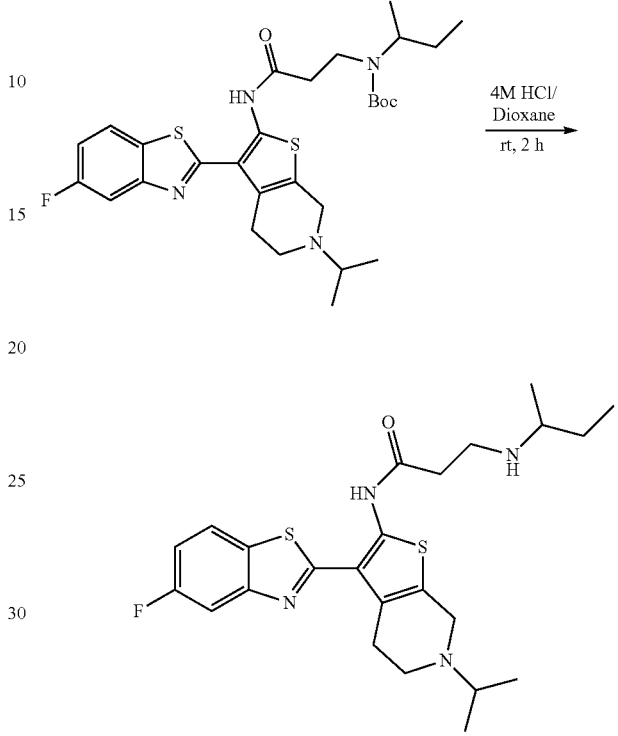

To a solution of tert-butyl sec-butyl(3-((3-(5-fluorobenzo[d]thiazol-2-yl)-6-isopropyl-4,5,6,7-tetrahydrothieno[2,3-c]pyridin-2-yl)amino)-3-oxopropyl)carbamate (150 mg, 0.26 mmol) in dioxane (2 mL) at 0° C. was added 4M HCl in dioxane (5 mL) and the reaction mixture was stirred at room temperature for 2 h. The progress of the reaction was monitored by TLC. After the reaction was complete, the mixture was evaporated to dryness resulting in a crude residue which was purified by triturating with ether and pentane to afford the HCl salt of the title compound as a brown solid (80 mg, 97% yield).

Example 11. Synthesis of N-(3-(benzo[d]thiazol-2-yl)-4,5,6,7-tetrahydrothieno[2,3-c]pyridin-2-yl)-3-(methylamino)propanamide (Compound 128)

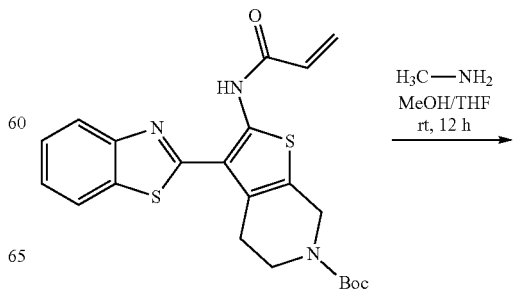

-continued

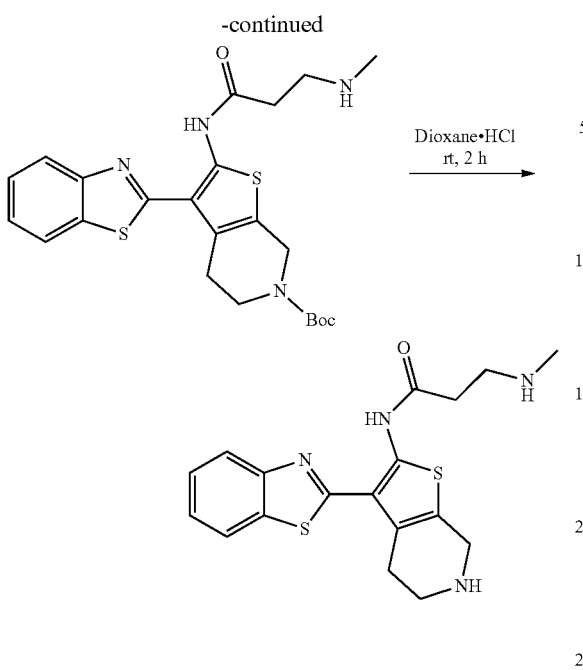

Step 1: tert-butyl 3-(benzo[d]thiazol-2-yl)-2-(3-(methylamino)propanamido)-4,7-dihydrothieno[2,3-c]pyridine-6(5H)-carboxylate

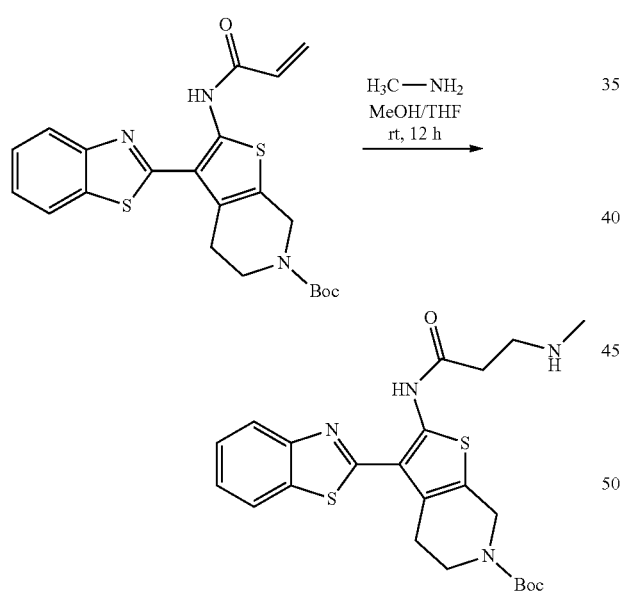

To a stirring solution of tert-butyl 2-acrylamido-3-(benzo[d]thiazol-2-yl)-4,7-dihydrothieno[2,3-c]pyridine-6(5H)-carboxylate (100 mg, 0.22 mmol) in CH$_3$OH/THF (3 mL/3 mL) was added methyl amine (14 mg, 0.45 mmol), and the reaction was stirred at room temperature for 12 h. The reaction progress was monitored by TLC. After the reaction was complete, the mixture was evaporated to dryness resulting in a crude residue which was purified by column chromatography to afford the title compound as a yellow solid (70 mg, 65% yield). LCMS: [M+H]$^+$=473.15; R$_t$=2.42 min.

Step 2: N-(3-(benzo[d]thiazol-2-yl)-4,5,6,7-tetrahydrothieno[2,3-c]pyridin-2-yl)-3-(methylamino)propanamide

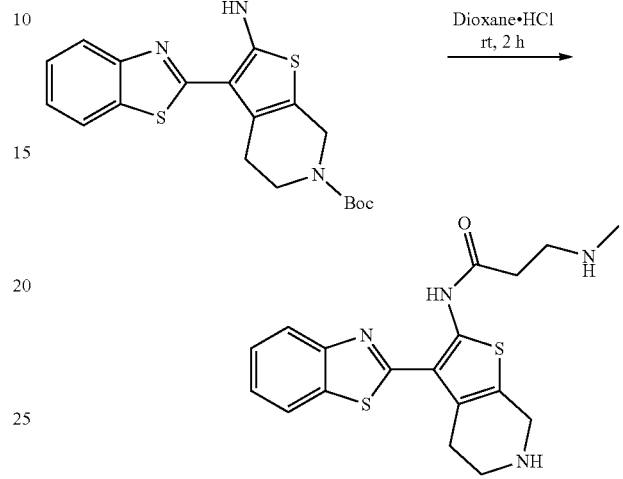

To a solution of tert-butyl 3-(benzo[d]thiazol-2-yl)-2-(3-(methylamino)propanamido)-4,7-dihydrothieno[2,3-c]pyridine-6(5H)-carboxylate (70 mg, 0.14 mmol) in dioxane (2 mL) at 0° C. was added 4M HCl in dioxane (2 mL), and the resulting mixture was stirred at room temperature for 2 h. The reaction progress was monitored by TLC. After the reaction was complete, the mixture was evaporated to dryness resulting in a crude residue which was purified by triturating with methanol and ether to afford the HCl salt of the title compound as an off-white solid (40 mg, 66%).

The synthesis of Compounds 602-605 was similar to the above.

Example 12. Synthesis of N-(3-(benzo[d]thiazol-2-yl)-4,5,6,7-tetrahydrothieno[2,3-c]pyridin-2-yl)-3-(isopropylamino)propanamide (Compound 129)

Step 1: tert-butyl 2-amino-3-(benzo[d]thiazol-2-yl)-4,7-dihydrothieno[2,3-c]pyridine-6(5H)-carboxylate

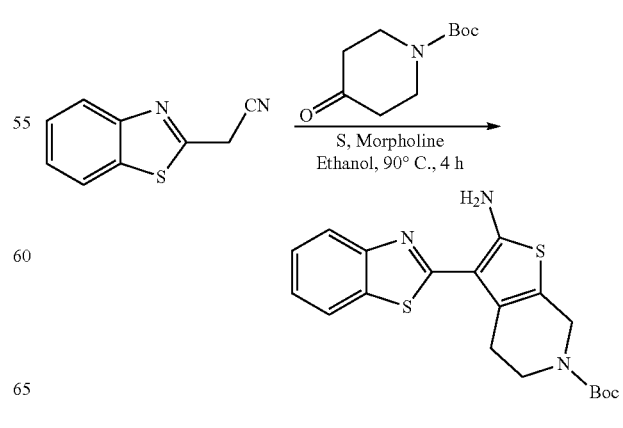

To a stirring solution of 2-(benzo[d]thiazol-2-yl)acetonitrile (5 g, 28.73 mmol) in ethanol (50 mL) was added tert-butyl 4-oxopiperidine-1-carboxylate (5.79 g, 28.73 mmol) followed by morpholine (2.1 g, 28.73 mmol), and the resulting mixture was heated to 40° C. for 10 min. Sulfur (910 mg, 28.73 mmol) was then added, and the reaction mixture was heated to 90° C. for 4 h. The progress of the reaction was monitored by TLC. After the reaction was complete, the mixture was evaporated to dryness resulting in a crude residue which was triturated with methanol. The obtained precipitate was filtered and dried to afford the title compound as a pale yellow solid (7.6 g, 68% yield). LCMS: [M+H]$^+$=388.05; R$_t$=3.90 min.

Step 2: tert-butyl 2-acrylamido-3-(benzo[d]thiazol-2-yl)-4,7-dihydrothieno[2,3-c]pyridine-6(5H)-carboxylate

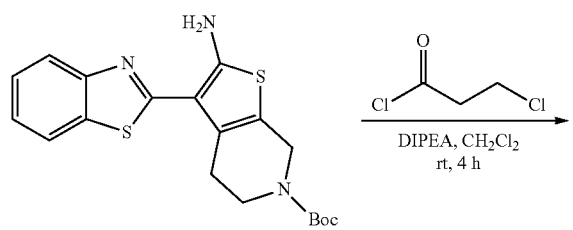

To a solution of tert-butyl 2-amino-3-(benzo[d]thiazol-2-yl)-4,7-dihydrothieno[2,3-c]pyridine-6(5H)-carboxylate (3 g, 9.11 mmol) in DCM (30 mL) at 0° C. was added DIPEA (1.57 mL, 9.11 mmol) followed by 3-chloropropanoyl chloride (1.2 g, 9.56 mmol) and the resulting mixture was stirred at room temperature for 4 h. The progress of the reaction was monitored by TLC. After the reaction was complete, the mixture was washed with NaHCO$_3$. The combined organic layers were dried over anhydrous Na$_2$SO$_4$ and concentrated to afford a crude residue which was purified by flash column chromatography to afford the title compound as a yellow solid (1.5 g, 44% yield). LCMS: [M+H]$^+$=442.00; R$_t$=4.45 min.

Step 3: tert-butyl 3-(benzo[d]thiazol-2-yl)-2-(3-(isopropylamino)propanamido)-4,7-dihydrothieno[2,3-c]pyridine-6(5H)-carboxylate

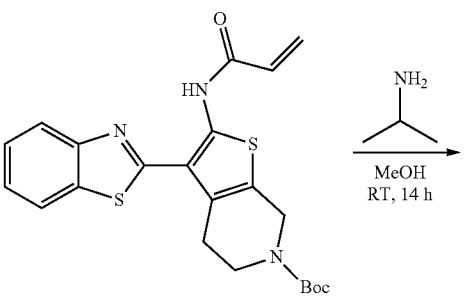

To a solution of tert-butyl 2-acrylamido-3-(benzo[d]thiazol-2-yl)-4,7-dihydrothieno[2,3-c]pyridine-6(5H)-carboxylate (100 mg, 0.22 mmol) in MeOH (2 mL) was added isopropyl amine (26 mg, 0.44 mmol), and the reaction mixture was stirred at room temperature for 14 h. The reaction progress was monitored by TLC. After the reaction was complete, the mixture was evaporated to dryness and the crude residue was purified by column chromatography to afford the title compound as a yellow solid (70 mg, 62%). LCMS: [M+H]$^+$=501.05; R$_t$=2.61 min.

Step 4: N-(3-(benzo[d]thiazol-2-yl)-4,5,6,7-tetrahydrothieno[2,3-c]pyridin-2-yl)-3-(isopropylamino)propanamide

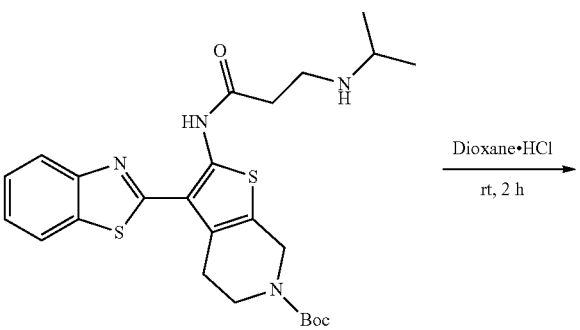

93

-continued

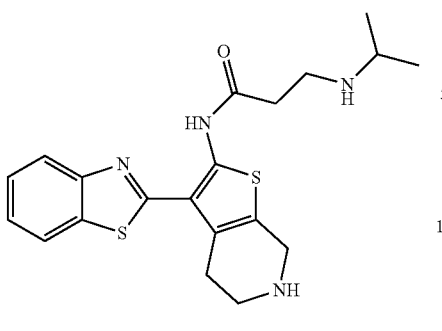

To a solution of tert-butyl 3-(benzo[d]thiazol-2-yl)-2-(3-(isopropylamino)propanamido)-4,7-dihydrothieno[2,3-c]pyridine-6(5H)-carboxylate (70 mg, 0.14 mmol) in dioxane (2 mL) at 0° C. was added 4M HCl in dioxane (2 mL) and the resulting mixture was stirred at room temperature for 2 h. The reaction progress was monitored by TLC. After the reaction was complete, the mixture was evaporated to dryness resulting in a crude residue which was purified by triturating with ether and pentane to afford the HCl salt of the title compound as an off-white solid (45 mg, 80%).

Example 13. Synthesis of N-(3-(benzo[d]thiazol-2-yl)-4,5,6,7-tetrahydrothieno[2,3-c]pyridin-2-yl)-3-(dimethylamino)propanamide (Compound 130)

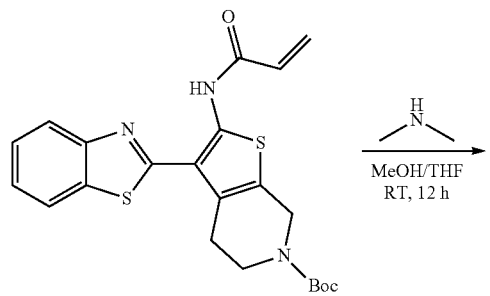

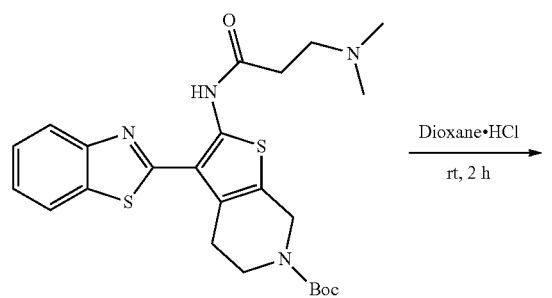

94

Step 1: tert-butyl 3-(benzo[d]thiazol-2-yl)-2-(3-(dimethylamino)propanamido)-4,7-dihydrothieno[2,3-c]pyridine-6(5H)-carboxylate

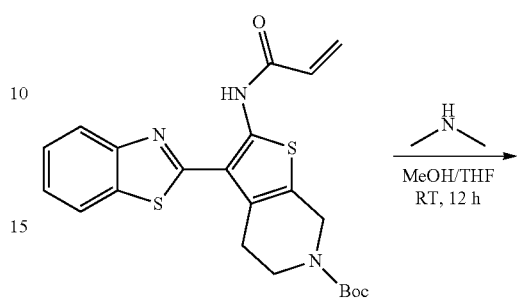

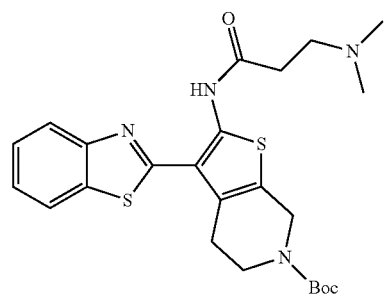

To a stirring solution of tert-butyl 2-acrylamido-3-(benzo[d]thiazol-2-yl)-4,7-dihydrothieno[2,3-c]pyridine-6(5H)-carboxylate (100 mg, 0.22 mmol) in CH$_3$OH/THF (3 mL/3 mL) was added dimethyl amine (20 mg, 0.45 mmol), and the reaction was stirred at room temperature for 12 h. The reaction progress was monitored by TLC. After the reaction was complete, the mixture was evaporated to dryness resulting in a crude residue which was purified by column chromatography to afford the title compound as a yellow solid (80 mg, 73% yield). LCMS: [M+H]$^+$=473.15; R$_t$=2.42 min.

Step 2: N-(3-(benzo[d]thiazol-2-yl)-4,5,6,7-tetrahydrothieno[2,3-c]pyridin-2-yl)-3-(dimethylamino)propanamide

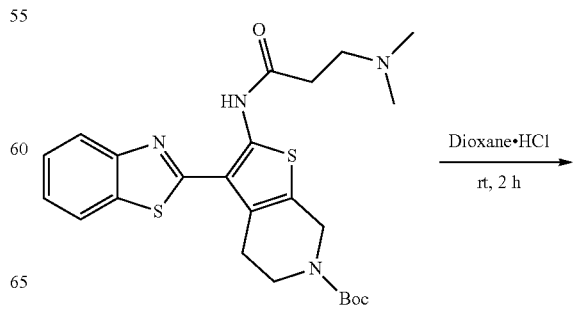

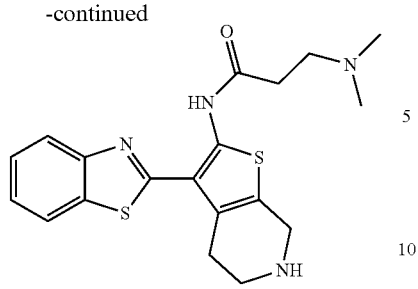

To a solution of tert-butyl 3-(benzo[d]thiazol-2-yl)-2-(3-(dimethylamino)propanamido)-4,7-dihydrothieno[2,3-c]pyridine-6(5H)-carboxylate (80 mg, 0.16 mmol) in dioxane (2 mL) at 0° C. was added 4M HCl in dioxane (2 mL) and the reaction mixture was stirred at room temperature for 2 h. The reaction progress was monitored by TLC. After the reaction was complete, the mixture was evaporated to dryness resulting in a crude residue which was purified by triturating with methanol and ether to afford the HCl salt of the title compound as an off-white solid (60 mg, 87%).

Example 14. Synthesis of N-(3-(benzo[d]thiazol-2-yl)-4,5,6,7-tetrahydrothieno[2,3-c]pyridin-2-yl)-3-(tert-butylamino)propanamide (Compound 131)

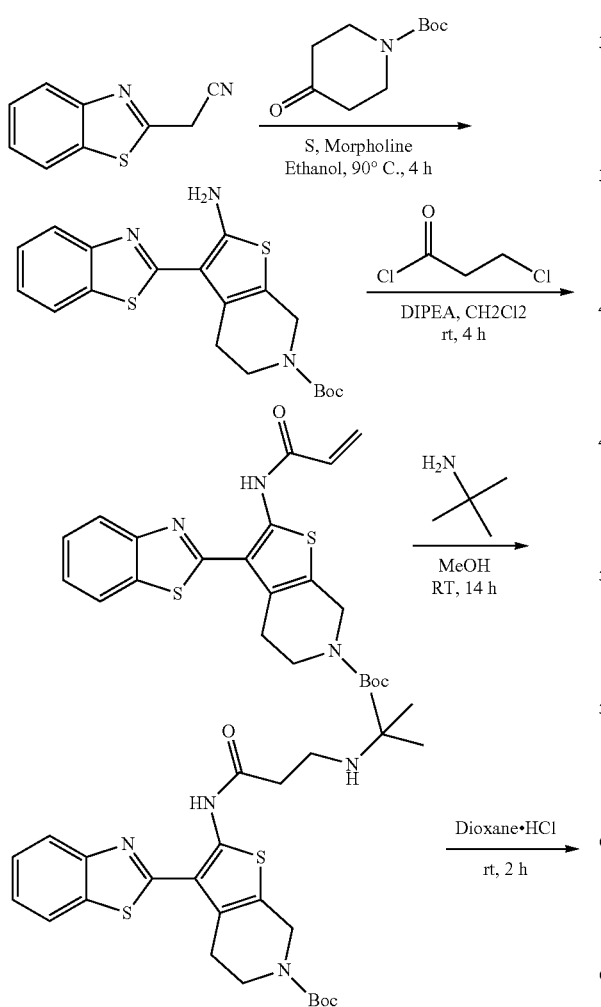

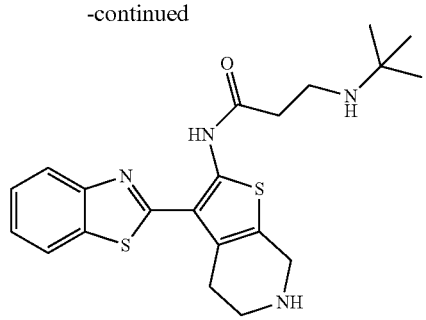

Step 1: tert-butyl 2-amino-3-(benzo[d]thiazol-2-yl)-4,7-dihydrothieno[2,3-c]pyridine-6(5H)-carboxylate

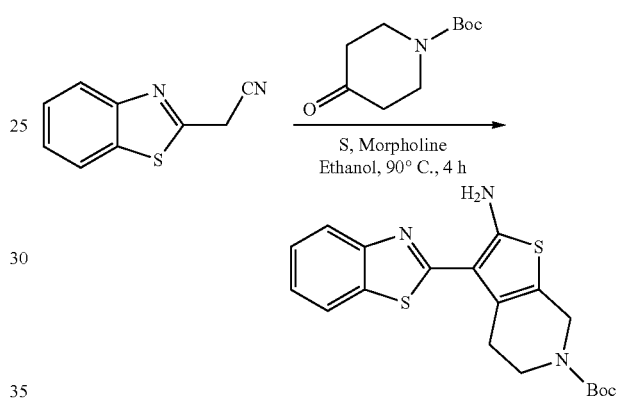

To a stirring solution of 2-(benzo[d]thiazol-2-yl)acetonitrile (5 g, 28.73 mmol) in ethanol (50 mL) was added tert-butyl 4-oxopiperidine-1-carboxylate (5.79 g, 28.73 mmol) and morpholine (2.1 g, 28.73 mmol) at room temperature. After the reaction mixture was heated to 40° C. for 10 min, sulfur (910 mg, 28.73 mmol) was added and the resulting mixture heated to 90° C. for 4 h. The progress of the reaction was monitored by TLC. After the reaction was complete, the mixture was evaporated to dryness resulting in a crude residue which was triturated with methanol. The obtained precipitate was filtered and dried to afford the title compound as a pale yellow solid (7.6 g, 68% yield). LCMS: [M+H]$^+$=388.05; R$_t$=3.90 min.

Step 2: tert-butyl 2-acrylamido-3-(benzo[d]thiazol-2-yl)-4,7-dihydrothieno[2,3-c]pyridine-6(5H)-carboxylate

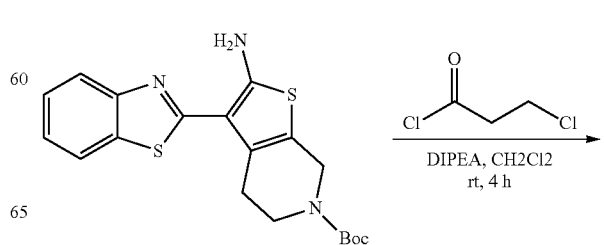

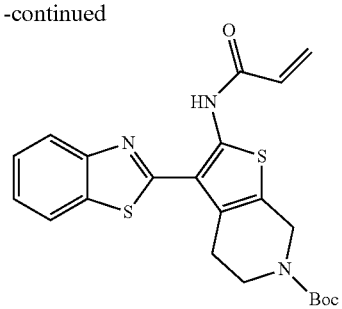

To a solution of tert-butyl 2-amino-3-(benzo[d]thiazol-2-yl)-4,7-dihydrothieno[2,3-c]pyridine-6(5H)-carboxylate (3 g, 9.11 mmol) in DCM (30 mL) at 0° C. was added DIPEA (1.57 mL, 9.11 mmol) followed by 3-chloropropanoyl chloride (1.2 g, 9.56 mmol), and the resulting mixture was stirred at room temperature for 4 h. The reaction progress was monitored by TLC. After the reaction was complete, the mixture was washed with NaHCO$_3$. The combined organic layers were dried over anhydrous Na$_2$SO$_4$ and concentrated to afford a crude residue which was purified by flash column chromatography to afford the title compound as a yellow solid (1.5 g, 44% yield). LCMS: [M+H]$^+$=442.00; R$_t$=4.45 min.

Step 3: tert-butyl 3-(benzo[d]thiazol-2-yl)-2-(3-(tert-butylamino)propanamido)-4,7-dihydrothieno[2,3-c]pyridine-6(5H)-carboxylate

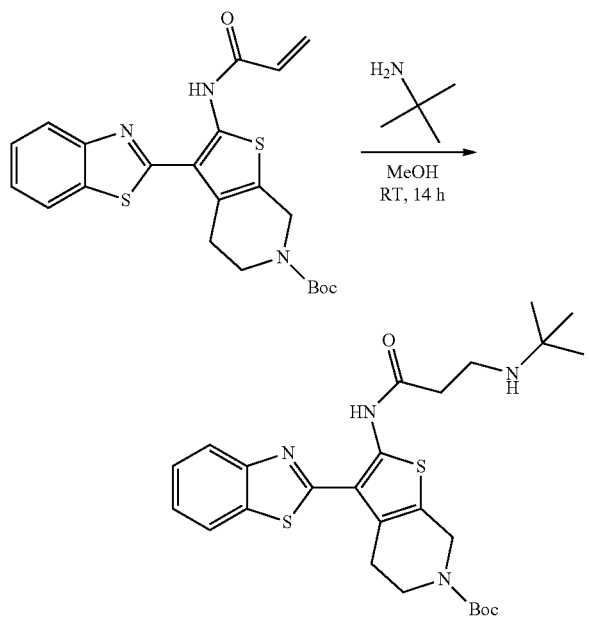

To a solution of tert-butyl 2-acrylamido-3-(benzo[d]thiazol-2-yl)-4,7-dihydrothieno[2,3-c]pyridine-6(5H)-carboxylate (100 mg, 0.22 mmol) in MeOH (2 mL) was added t-butyl amine (33 mg, 0.45 mmol), and the reaction mixture was stirred at room temperature for 14 h. The reaction progress was monitored by TLC. After the reaction was complete, the mixture was evaporated to dryness. The crude residue was purified by flash column chromatography to afford the title compound as a light yellow solid (70 mg, 60%). LCMS: [M+H]$^+$=515.25; R$_t$=2.59 min.

Step 4: N-(3-(benzo[d]thiazol-2-yl)-4,5,6,7-tetrahydrothieno[2,3-c]pyridin-2-yl)-3-(tert-butylamino)propanamide

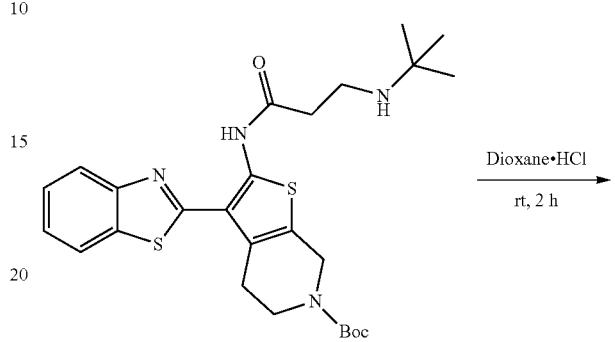

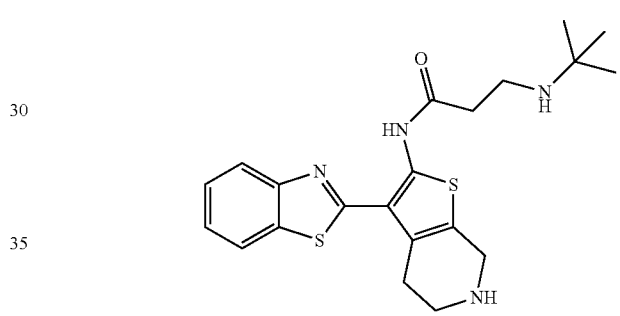

To a solution of tert-butyl 3-(benzo[d]thiazol-2-yl)-2-(3-(tert-butylamino)propanamido)-4,7-dihydrothieno[2,3-c]pyridine-6(5H)-carboxylate (70 mg, 0.13 mmol) in dioxane (2 mL) at 0° C. was added 4M HCl in dioxane (2 mL) and the resulting mixture was stirred at room temperature for 2 h. The reaction was monitored by TLC. After the reaction was complete, the reaction mixture was evaporated to dryness resulting in a crude residue which was purified by triturating with ether and pentane to afford the HCl salt of the title compound as an off-white solid as (60 mg, 91%).

Example 15. Synthesis of N-(3-(benzo[d]thiazol-2-yl)-6-isopropyl-4,5,6,7-tetrahydrothieno[2,3-c]pyridin-2-yl)-3-(isopropylamino)propanamide (Compound 132)

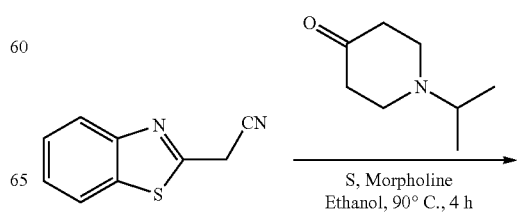

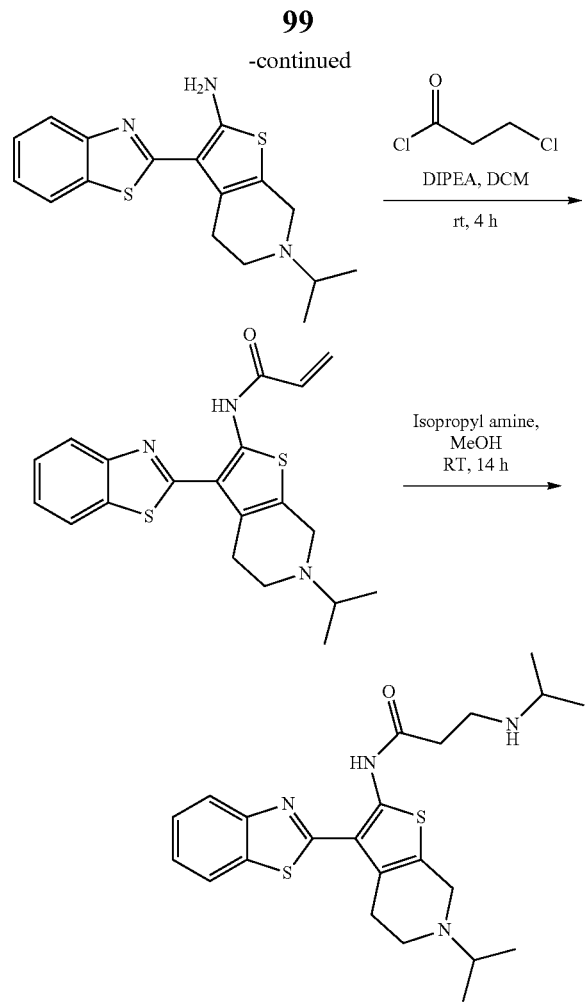

Step 1: 3-(benzo[d]thiazol-2-yl)-6-isopropyl-4,5,6,7-tetrahydrothieno[2,3-c]pyridin-2-amine

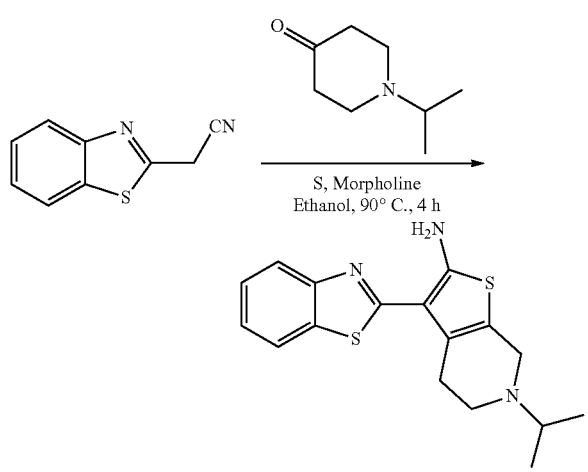

To a stirring solution of 2-(benzo[d]thiazol-2-yl)acetonitrile (5 g, 28.73 mmol) in ethanol (50 mL) was added 1-isopropylpiperidin-4-one (4 g, 28.73 mmol) followed by morpholine (2.5 mL, 28.73 mmol), and the resulting mixture was heated to 40° C. for 10 min. Sulfur (900 mg, 28.73 mmol) was then added, and the reaction mixture heated to 90° C. for 4 h. The progress of the reaction was monitored by TLC. After completion, the reaction mixture was evaporated to dryness resulting in a crude residue which was triturated with methanol. The precipitate obtained was filtered and dried to afford the title compound as a pale yellow solid (4.3 g, 45% yield). LCMS: [M+H]$^+$=330.5; R$_t$=2.12 min.

Step 2: N-(3-(benzo[d]thiazol-2-yl)-6-isopropyl-4,5,6,7-tetrahydrothieno[2,3-c]pyridin-2-yl)acrylamide

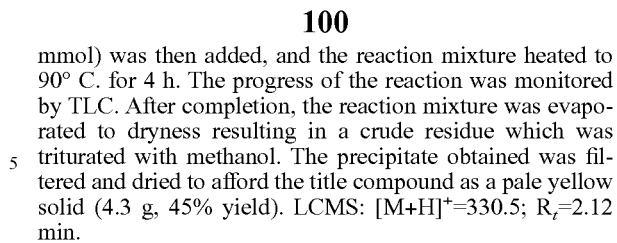

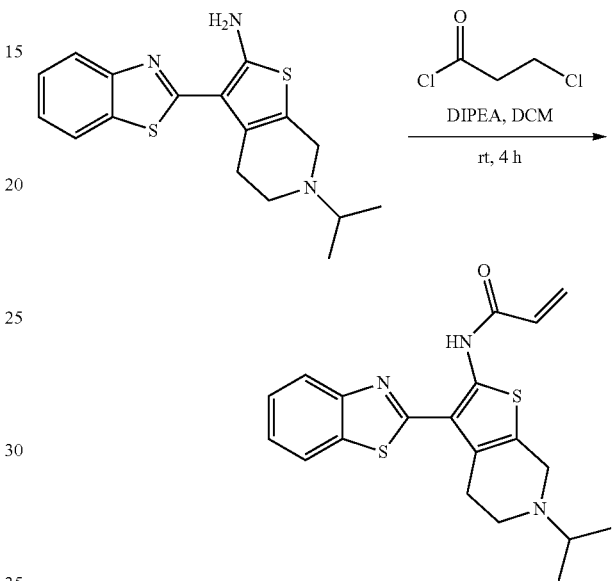

To a solution of 3-(benzo[d]thiazol-2-yl)-6-isopropyl-4,5,6,7-tetrahydrothieno[2,3-c]pyridin-2-amine (3 g, 9.11 mmol) in DCM (30 mL) at 0° C. was added DIPEA (1.57 mL, 9.11 mmol) and 3-chloropropanoyl chloride (1.2 g, 9.56 mmol), and the reaction mixture was stirred at room temperature for 4 h. The reaction progress was monitored by TLC. After the reaction was complete, the reaction mixture was washed with NaHCO$_3$ and the combined organic layers were dried over Na$_2$SO$_4$, filtered, and concentrated to afford a crude residue which was purified by flash column chromatography to afford the title compound as a yellow solid (1.5 g, 44% yield). LCMS: [M+H]$^+$=383.95; R$_t$=4.40 min.

Step 3: N-(3-(benzo[d]thiazol-2-yl)-6-isopropyl-4,5,6,7-tetrahydrothieno[2,3-c]pyridin-2-yl)-3-(isopropylamino)propanamide

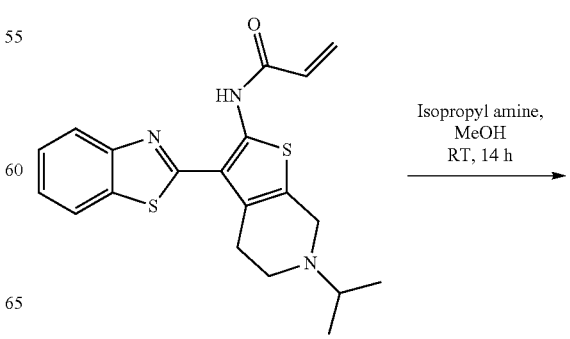

-continued

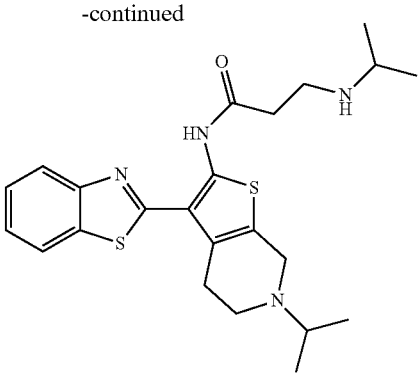

To a solution of N-(3-(benzo[d]thiazol-2-yl)-6-isopropyl-4,5,6,7-tetrahydrothieno[2,3-c]pyridin-2-yl)acrylamide (100 mg, 0.26 mmol) in MeOH (5 mL) was added isopropyl amine (30 mg, 0.52 mmol) and the reaction mixture was stirred at room temperature for 14 h. The progress of the reaction was monitored by TLC. After completion of the reaction, the mixture was evaporated to dryness. The crude residue was purified by preparative HPLC to afford the title compound as a brown solid (35 mg, 30%).

Example 16. Synthesis of N-(3-(benzo[d]thiazol-2-yl)-6-isopropyl-4,5,6,7-tetrahydrothieno[2,3-c]pyridin-2-yl)-3-(2,5-dioxo-2,5-dihydro-1H-pyrrol-1-yl)propanamide (Compound 133)

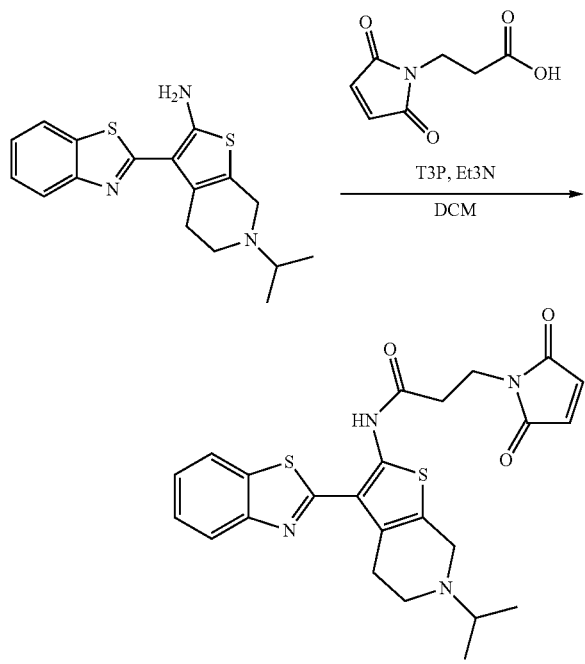

To a stirring solution of 3-(benzo[d]thiazol-2-yl)-6-isopropyl-4,5,6,7-tetrahydrothieno[2,3-c]pyridin-2-amine (15 mg, 0.0455 mmol) in DCM (0.5 mL) was added T$_3$P (50 wt % in EtOAc, 32 uL, 0.0501 mmol) and Et$_3$N (19 uL, 0.137 mmol) and the reaction was stirred at room temperature for 16 h. Upon completion, the reaction mixture was quenched with aqueous sat. NaHCO$_3$ solution and extracted with DCM (3×5 mL). The combined organic layers were washed with brine, dried over Na$_2$SO$_4$, filtered, and concentrated under reduced pressure to provide a crude residue, which was purified by silica gel column chromatography eluting with 0-100% ethyl acetate in n-hexane to afford the title compound as a yellow solid (1.5 mg, yield 6.9%).

Example 17. Synthesis of N-(3-(benzo[d]thiazol-2-yl)-4,5,6,7-tetrahydrothieno[2,3-c]pyridin-2-yl)-3-((2-methoxyethyl)amino)propanamide (Compound 134)

Step 1: tert-butyl 3-(benzo[d]thiazol-2-yl)-2-(3-((2-methoxyethyl)amino)propanamido)-4,7-dihydrothieno[2,3-c]pyridine-6(5H)-carboxylate

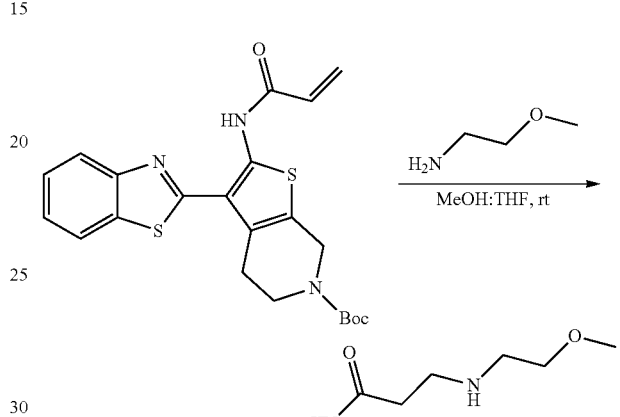

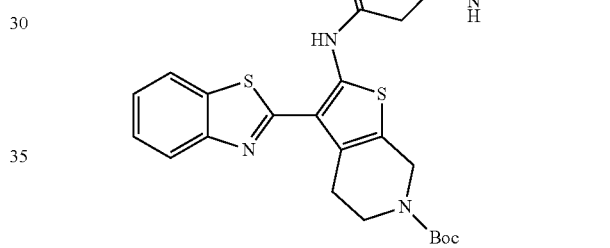

To a solution of tert-butyl 2-acrylamido-3-(benzo[d]thiazol-2-yl)-4,7-dihydrothieno[2,3-c]pyridine-6(5H)-carboxylate (0.1 g, 0.226 mmol) in methanol:THF (1:1.2 mL) was added 2-methoxyethan-1-amine (0.034 g, 0.453 mmol). The resulting mixture was stirred at room temperature for 12 h. The progress of the reaction was monitored by TLC. The reaction mixture was dried under vacuum pressure and the crude compound was purified by silica gel column chromatography eluting with 0-5% MeOH in DCM to afford the title compound as a yellow solid (0.045 g, yield 38.4%). LCMS: [M+H]$^+$=517.15; R$_t$=2.48 min.

Step 2: N-(3-(benzo[d]thiazol-2-yl)-4,5,6,7-tetrahydrothieno[2,3-c]pyridin-2-yl)-3-((2-methoxyethyl)amino)propanamide

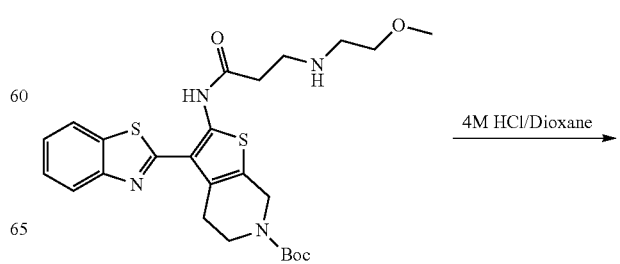

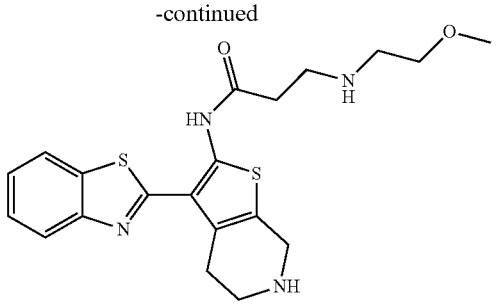

To a solution of tert-butyl 3-(benzo[d]thiazol-2-yl)-2-(3-((2-methoxyethyl)amino)-propanamido)-4,7-dihydrothieno[2,3-c]pyridine-6(5H)-carboxylate (0.045 g, 0.087 mmol) in dioxane (1 mL) at 0° C. was added 4M HCl in dioxane (1.5 mL) and the resulting mixture was stirred at room temperature for 2 h. After completion, the reaction mixture was evaporated to dryness and the resulting crude residue was purified by trituration with ether to afford the title compound as a yellow solid (0.02 g, HCl salt, 50.6% yield).

Example 18. Purification of (S)—N-(3-(benzo[d]thiazol-2-yl)-6-isopropyl-4,5,6,7-tetrahydrothieno[2,3-c]pyridin-2-yl)-3-(sec-butylamino)propanamide (Compound 135)

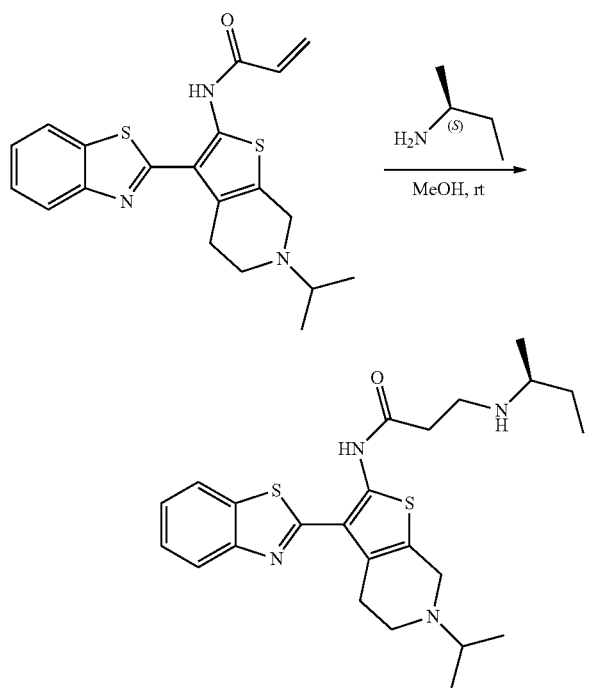

To a stirring solution of N-(3-(benzo[d]thiazol-2-yl)-6-isopropyl-4,5,6,7-tetrahydrothieno[2,3-c]pyridin-2-yl)acrylamide (100 mg, 0.26 mmol) in methanol (1 mL) was added (S)-butan-2-amine (0.05 mL, 0.52 mmol). The reaction was stirred at room temperature for 18 h. The progress of the reaction was monitored by TLC and LCMS. After completion, reaction mixture was diluted with DCM (20 mL) and washed with water (2×10 mL). The combined organic layers were dried over anhydrous Na$_2$SO$_4$ and concentrated under reduced pressure to yield a crude residue, which was purified by preparative TLC to afford the title compound as a brown gummy solid (50 mg, 41% yield).

Example 19. Purification of (R)—N-(3-(benzo[d]thiazol-2-yl)-6-isopropyl-4,5,6,7-tetrahydrothieno[2,3-c]pyridin-2-yl)-3-(sec-butylamino)propanamide (Compound 140)

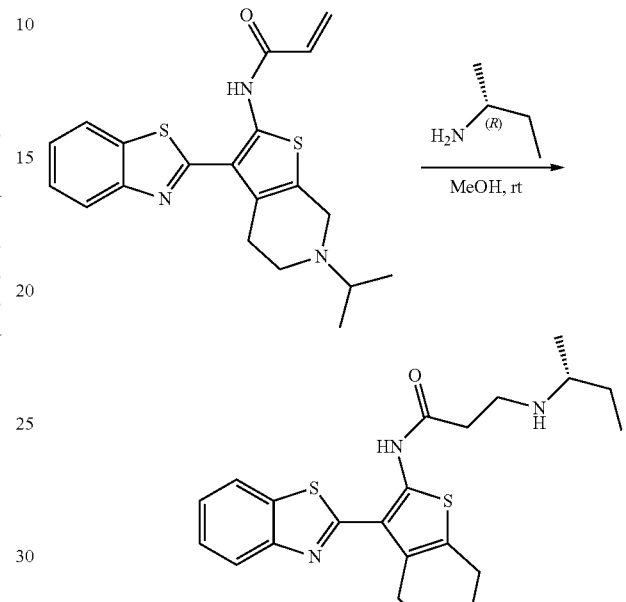

To a stirring solution of N-(3-(benzo[d]thiazol-2-yl)-6-isopropyl-4,5,6,7-tetrahydrothieno[2,3-c]pyridin-2-yl)acrylamide 0.1 g, 0.26 mmol) in methanol (1 mL) was added (R)-butan-2-amine (0.052 mL, 0.52 mmol) and the reaction was incubated at room temperature for 18 h. The progress of the reaction was monitored by TLC and LCMS. After the reaction was complete, the mixture was diluted with DCM (20 mL) and washed with water (2×10 mL). The combined organic layers were dried over anhydrous sodium sulfate, filtered, and concentrated under reduced pressure to yield a crude residue that was purified by preparative TLC to afford the title compound as a brown gummy solid (0.08 g, 66% yield).

Example 20. Synthesis of N-(3-(benzo[d]thiazol-2-yl)-4,5,6,7-tetrahydrothieno[2,3-c]pyridin-2-yl)-3-((2-(pyridin-3-yl) ethyl) amino) propanamide (Compound 136)

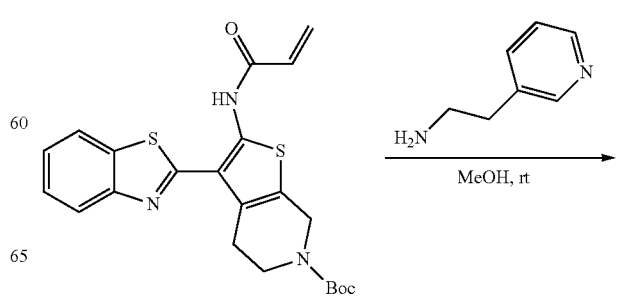

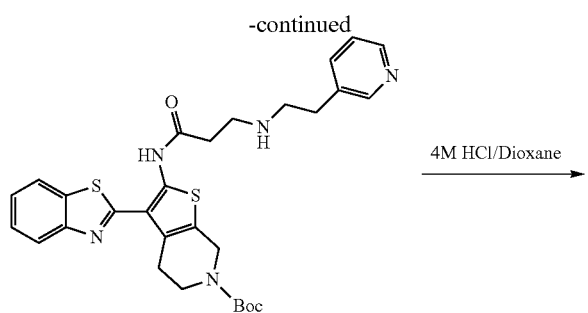

fied by silica gel column chromatography eluting with 0-5% MeOH in DCM to afford the title compound as a yellow solid (0.08 g, yield 63%). LCMS: [M+H]⁺=564.19; $R_t$=2.39 min.

Step 2: N-(3-(benzo[d]thiazol-2-yl)-4,5,6,7-tetrahydrothieno[2,3-c]pyridin-2-yl)-3-((2-(pyridin-3-yl)ethyl)amino)propanamide

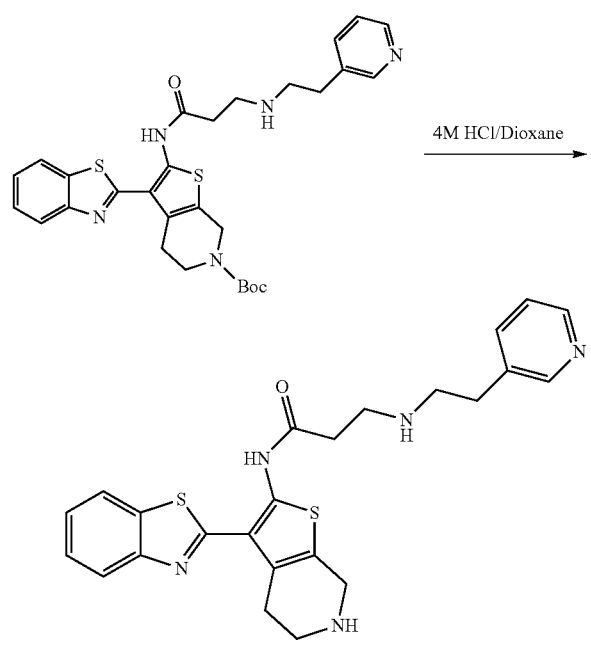

Step 1: tert-butyl 3-(benzo[d]thiazol-2-yl)-2-(3-((2-(pyridin-3-yl)ethyl)amino)propanamido)-4,7-dihydrothieno[2,3-c]pyridine-6(5H)-carboxylate

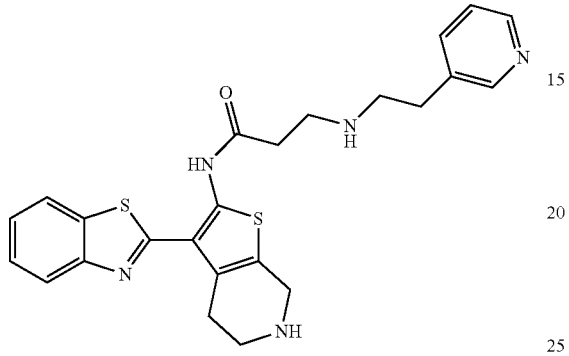

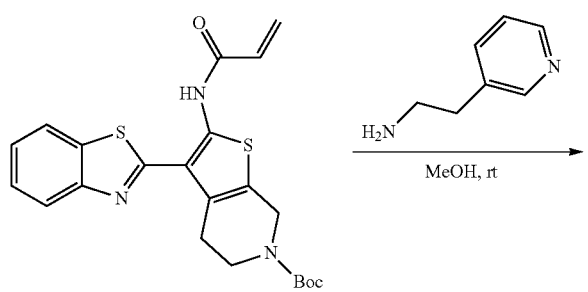

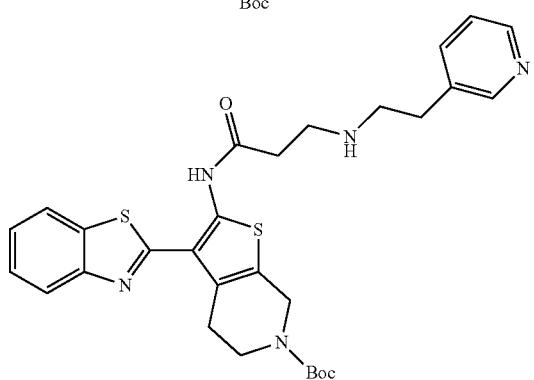

To a solution of tert-butyl 2-acrylamido-3-(benzo[d]thiazol-2-yl)-4,7-dihydrothieno[2,3-c]pyridine-6(5H)-carboxylate (0.1 g, 0.226 mmol) in methanol:THF (1:1, 2 mL) was added 2-(pyridin-3-yl)ethan-1-amine (0.055 g, 0.453 mmol) and the resulting mixture was stirred at room temperature for 12 h. The reaction progress was monitored by TLC. Upon completion, the reaction mixture was dried under vacuum pressure and the crude compound was puri- To a solution of tert-butyl 3-(benzo[d]thiazol-2-yl)-2-(3-((2-(pyridin-3-yl)ethyl)amino)propanamido)-4,7-dihydrothieno[2,3-c]pyridine-6(5H)-carboxylate (0.08 g, 0.142 mmol) in dioxane (1 mL) at 0° C. was added 4M HCl in dioxane (2 mL). After the addition, the resulting mixture was stirred at room temperature for 2 h. Once the reaction was complete, the reaction was evaporated to dryness and the resulting crude residue was purified by trituration with ether to afford the title compound as a yellow solid (0.06 g, HCl salt, 85% yield).

Example 21. Synthesis of N-(3-(benzo[d]thiazol-2-yl)-6-(oxetan-3-yl)-4,5,6,7-tetrahydrothieno[2,3-c]pyridin-2-yl)-3-(sec-butylamino)propanamide (Compound 137)

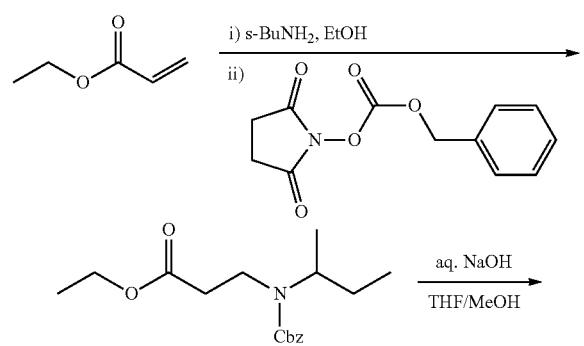

107
-continued

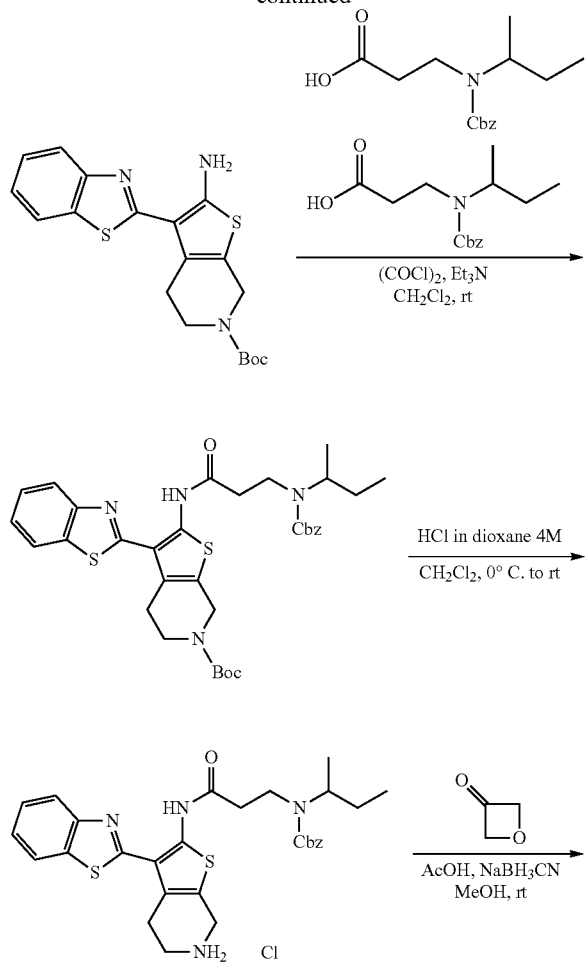

108

Step 1: Ethyl 3-(((benzyloxy)carbonyl)(sec-butyl)amino)propanoate

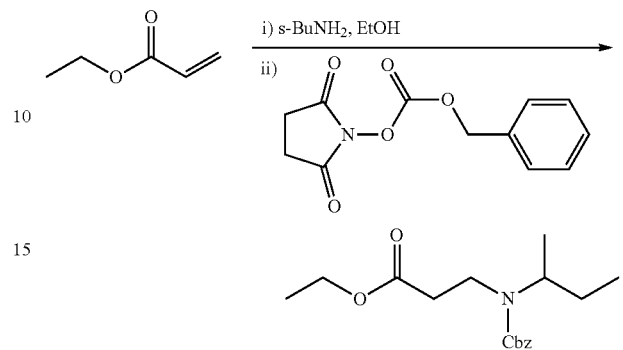

Ethyl acrylate (4.31 g, 43.07 mmol) was added to a solution of s-BuNH$_2$ (3.00 g, 41.02 mmol) in EtOH (103 mL) and stirred for 6 h at room temperature. N-(Benzyloxycarbonyloxy)-succinimide (10.22 g, 41.02 mmol) was added in one portion and the reaction was stirred at room temperature for 16 h. The reaction mixture was concentrated and taken up in EtOAc. The organic layer was washed with 1N NaOH, 1 N HCl then brine, then dried over MgSO$_4$, filtered, and concentrated. The title compound (11.33 g, 90% yield) was obtained as a clear oil and used directly. LCMS: [M+H]+=308.1.

Step 2: 3-(((benzyloxy)carbonyl)(sec-butyl)amino)propanoic acid

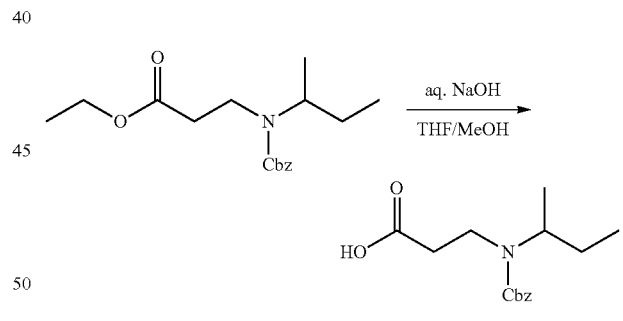

5 N NaOH (37 mL, 184.3 mmol) was added to a solution of ethyl 3-(((benzyloxy)carbonyl)(sec-butyl)amino)propanoate (11.33 g, 36.86 mmol) in 4:1 THF/MeOH (74 mL) at room temperature. The reaction was stirred for 1 h at room temperature, then concentrated, acidified to pH 2 with concentrated HCl, extracted twice with EtOAc, and concentrated. The residue was diluted in 9:1 hexanes/DCM and extracted 3× with diluted NaOH. The aqueous phases were combined, acidified to pH 2 with concentrated HCl, and extracted 3× with EtOAc. The combined organics were washed with brine, dried over MgSO$_4$, filtered, and concentrated to afford the title compound as a clear oil (8.70 g, 85% yield). LCMS: [M+H]+=280.1.

Step 3: tert-butyl 3-(benzo[d]thiazol-2-yl)-2-(3-(((benzyloxy)carbonyl)(sec-butyl)amino)propanamido)-4,7-dihydrothieno[2,3-c]pyridine-6(5H)-carboxylate

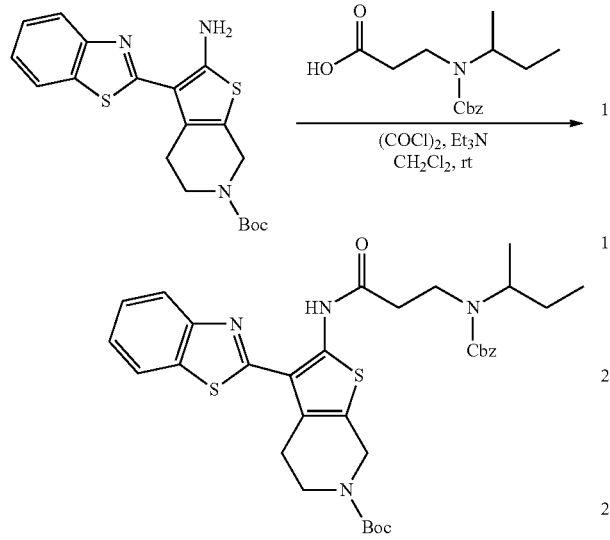

Oxalyl chloride (332 uL, 3.87 mmol) was added to a solution of 3-(((benzyloxy)carbonyl)(sec-butyl)amino)propanoic acid (360 mg, 1.29 mmol) in DCM (6.5 mL) at 0° C. The reaction was allowed to warm to room temperature, and upon completion, the reaction was concentrated to remove excess oxalyl chloride. The crude residue was dissolved in DCM (6.5 mL) and cooled to 0° C. tert-butyl 2-amino-3-(benzo[d]thiazol-2-yl)-4,7-dihydrothieno[2,3-c]pyridine-6 (5H)-carboxylate (500 mg, 1.29 mmol) was then added followed by Et₃N (630 uL, 4.51 mmol). Upon completion, the reaction was quenched with saturated aqueous NH₄Cl and extracted with DCM. The combined organic layers were dried over Na₂SO₄, filtered, and concentrated to afford the crude residue, which was purified by silica gel chromatography eluting with 10-40% EtOAc in hexanes to afford the title compound as an orange solid (455 mg, 54% yield). ¹HNMR (500 MHz, CDCl₃): δ 13.10 (d, J=48.7 Hz, 1H), 8.11 (d, J=7.5 Hz, 1H), 7.90 (d, J=7.5 Hz, 1H), 7.78 (d, J=7.8 Hz, 1H), 7.53-7.46 (m, 1H), 7.43-7.36 (m, 1H), 7.32 (d, J=6.5 Hz, 4H), 7.22 (d, J=17.0 Hz, 1H), 5.14 (dd, J=30.4, 12.1 Hz, 2H), 4.59 (s, 2H), 4.20-3.99 (m, 1H), 3.79 (s, 2H), 3.72-3.63 (m, 1H), 3.61-3.53 (m, 1H), 2.95 (d, J=63.2 Hz, 4H), 1.51 (s, 12H), 1.18 (dd, J=29.6, 6.3 Hz, 3H), 0.92-0.80 (m, 3H). LCMS [M+H]+=649.52, R$_T$ 3.77 min.

Step 4: Benzyl (3-((3-(benzo[d]thiazol-2-yl)-4,5,6,7-tetrahydrothieno[2,3-c]pyridin-2-yl)amino)-3-oxopropyl)(sec-butyl)carbamate

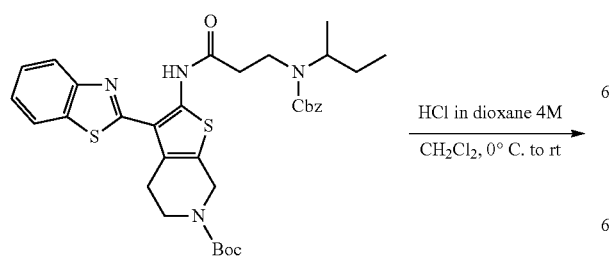

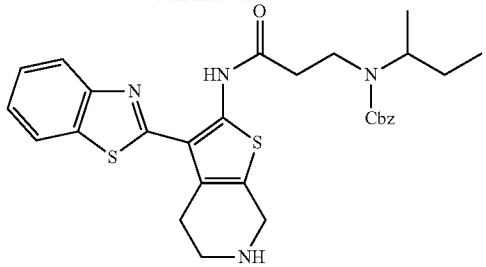

To a solution of tert-butyl 3-(benzo[d]thiazol-2-yl)-2-(3-(((benzyloxy)carbonyl)(sec-butyl)amino)propanamido)-4,7-dihydrothieno[2,3-c]pyridine-6(5H)-carboxylate (200 mg, 0.308 mmol) in dry DCM (3.1 mL) was added HCl in dioxane (771 uL, 3.08 mmol) at 0° C. The reaction was allowed to warm to room temperature and concentrated to afford the crude HCl salt of the title compound as a yellow solid which was used directly in the next reaction. LCMS: [M+H]+=549.48, R$_T$ 2.45 min.

Step 5: Benzyl (3-((3-(benzo[d]thiazol-2-yl)-6-(oxetan-3-yl)-4,5,6,7-tetrahydrothieno[2,3-c]pyridin-2-yl)amino)-3-oxopropyl)(sec-butyl)carbamate

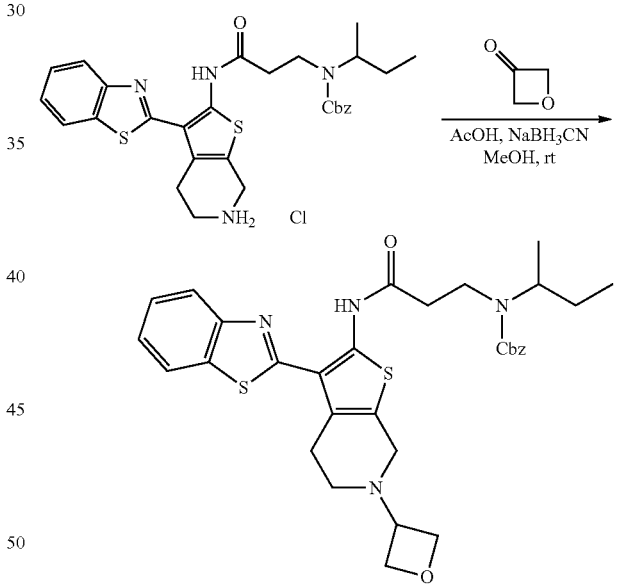

To a solution of benzyl (3-((3-(benzo[d]thiazol-2-yl)-4,5,6,7-tetrahydrothieno[2,3-c]pyridin-2-yl)amino)-3-oxopropyl)(sec-butyl)carbamate hydrochloride (180 mg, 0.308 mmol) in MeOH was added oxetan-3-one (27 uL, 0.462 mmol) and acetic acid (10 uL). The reaction was stirred for 30 min at room temperature and then NaBH₃CN (23 mg, 0.370) was added. Upon completion, the reaction was concentrated and diluted in water. The aqueous layer was extracted with EtOAc and the combined organic layers were dried over Na₂SO₄, filtered, and concentrated. The compound was purified by filtration over a silica gel pad with DCM to afford the title compound as a yellow oil (56 mg, 30% yield over 2 steps). LCMS: [M+H]+=605.36, R$_T$ 2.62 min.

111

Step 6: N-(3-(benzo[d]thiazol-2-yl)-6-(oxetan-3-yl)-4,5,6,7-tetrahydrothieno[2,3-c]pyridin-2-yl)-3-(sec-butylamino)propanamide

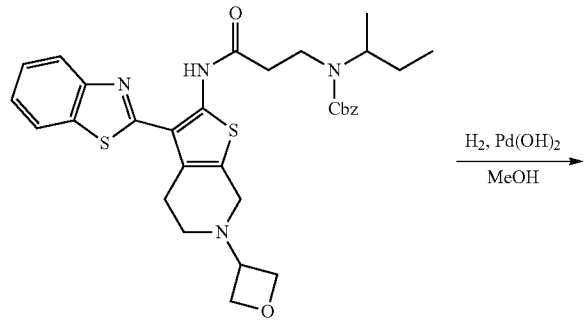

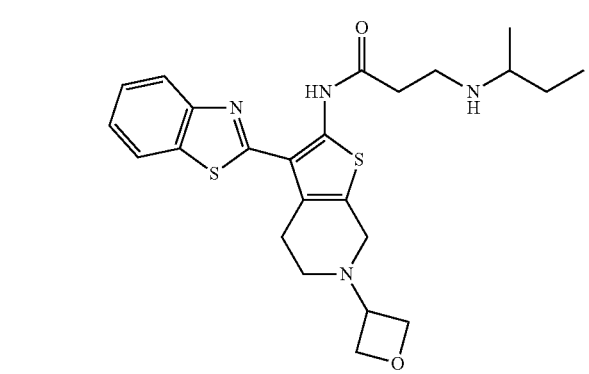 [SMILES: CCC(C)NCCC(=O)Nc1sc2c(c1-c1nc3ccccc3s1)CCN(C1COC1)C2]

Benzyl (3-((3-(benzo[d]thiazol-2-yl)-6-(oxetan-3-yl)-4,5,6,7-tetrahydrothieno[2,3-c]pyridin-2-yl)amino)-3-oxopropyl)(sec-butyl)carbamate (56 mg, 0.0925 mmol) was dissolved in methanol (1 mL). Pearlman's catalyst (10 mg) was added and the vessel purged with 1 atm hydrogen. After 2 days at room temperature, the reaction appeared 90% complete and was filtered over celite and concentrated. Purification by reverse phase C18 HPLC using 0-80% ACN in H₂O/NH₄HCOO followed by lyophilization afforded the title compound as a yellow solid (5.2 mg, 12% yield).

Example 22. Synthesis of Ethyl (3-((3-(benzo[d]thiazol-2-yl)-6-isopropyl-4,5,6,7-tetrahydrothieno[2,3-c]pyridin-2-yl)amino)-3-oxopropyl)glycinate (Compound 138)

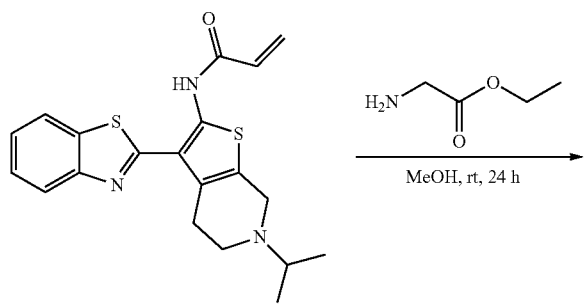

112

-continued

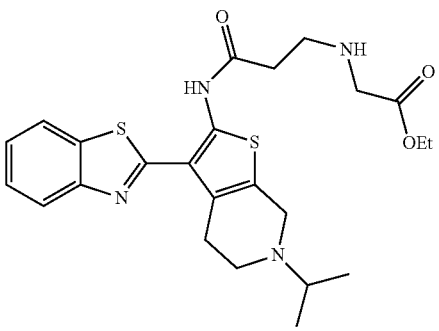

To a stirring solution of N-(3-(benzo[d]thiazol-2-yl)-6-isopropyl-4,5,6,7-tetrahydrothieno[2,3-c]pyridin-2-yl)acrylamide (100 mg, 0.26 mmol) in methanol (2 mL) was added ethyl glycinate (53 mg, 0.52 mmol) and the reaction was stirred at room temperature for 24 h. The progress of the reaction was monitored by TLC and LCMS. After completion, reaction mixture was concentrated under reduced pressure to give a crude residue, which was purified by flash column chromatography eluting with 0-5% MeOH/DCM to afford the title compound as a yellow solid (100 mg, 79% yield).

Example 23. Synthesis of N-(3-(5-bromobenzo[d]thiazol-2-yl)-4,5,6,7-tetrahydrothieno[2,3-c]pyridin-2-yl)-3-(sec-butylamino)propanamide (Compound 139)

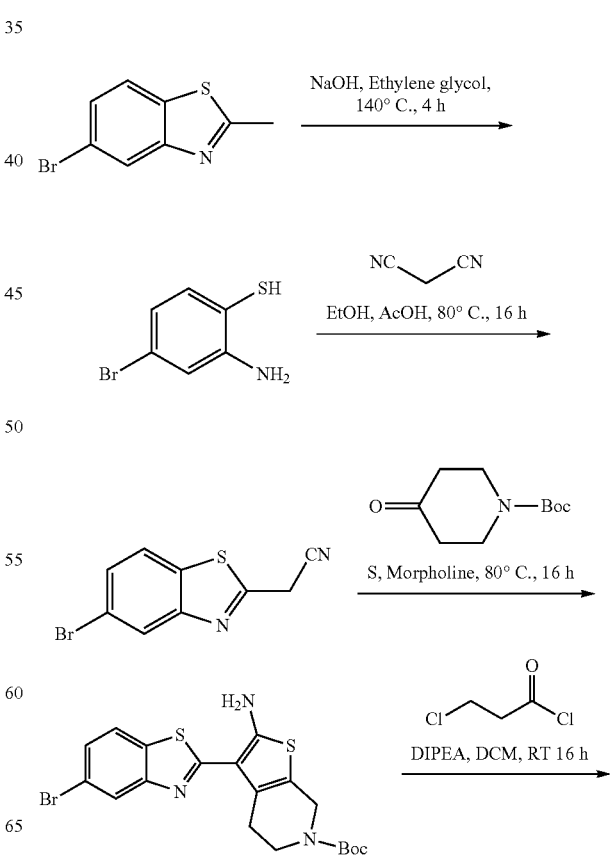

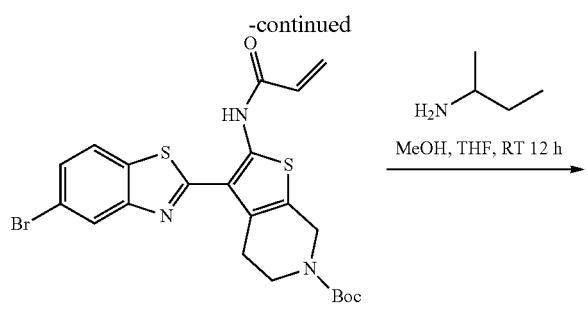

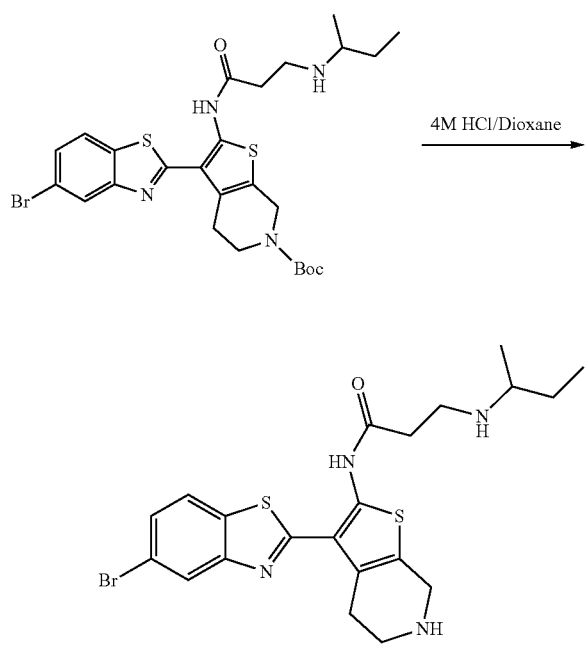

Step 1: 2-Amino-4-bromobenzenethiol

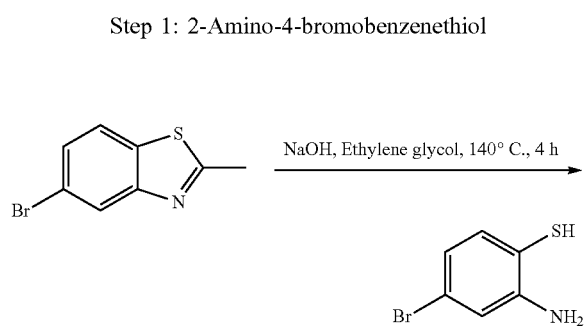

To a stirring solution of 5-bromo-2-methylbenzo[d]thiazole (5 g, 22.02 mmol) in ethylene glycol (50 mL) was added 8N sodium hydroxide solution (50 mL) and the resulting reaction mixture was stirred at 140° C. for 4 h. Progress of the reaction was monitored by TLC and LCMS. After completion, the reaction mixture was concentrated under reduced pressure to get a crude residue, which was purified by triturating it with pentane/ether to afford the title compound as a yellow solid (4.3 g, 96% yield). $^1$H NMR (400 MHz, DMSO-d$_6$) δ=7.09 (d, J=8.33 Hz, 1H), 6.87 (d, J=1.75 Hz, 1H), 6.62 (dd, J=1.75, 8.33 Hz, 1H), 5.16 (br. s, 3H). LCMS: [M+H]$^+$=203.83; R$_t$=3.10 min.

Step 2: 2-(5-bromobenzo[d]thiazol-2-yl)acetonitrile

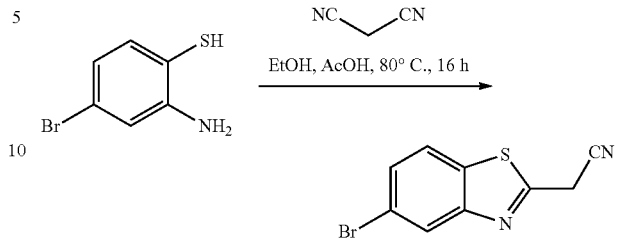

To a stirring solution of 2-amino-4-bromobenzenethiol (4.3 g, 21.07 mmol) in EtOH (60 mL) was added malononitrile (2.8 g, 42.15 mmol) followed by AcOH (0.2 mL) and the resulting reaction mixture was stirred at 80° C. for 16 h. Progress of the reaction was monitored by TLC. After completion, the reaction mixture was quenched with water and concentrated under reduced pressure to dryness. The residue was diluted with water and extracted with ethyl acetate. The combined organic layers were dried over anhydrous Na$_2$SO$_4$ and concentrated to get a crude residue, which was purified by flash column chromatography eluting with 0-30% ethyl acetate in n-hexane to afford the title compound as a yellow solid (4.5 g, yield 85%). $^1$H NMR (400 MHz, DMSO-d$_6$) δ=8.28 (s, 1H), 8.12 (d, J=8.58 Hz, 1H), 7.65 (d, J=8.58 Hz, 1H), 4.78 (s, 2H). LCMS: [M+H]$^+$=254.85; R$_t$=3.02 min.

Step 3: tert-butyl 2-amino-3-(5-bromobenzo[d]thiazol-2-yl)-4,7-dihydrothieno[2,3-c]pyridine-6(5H)-carboxylate

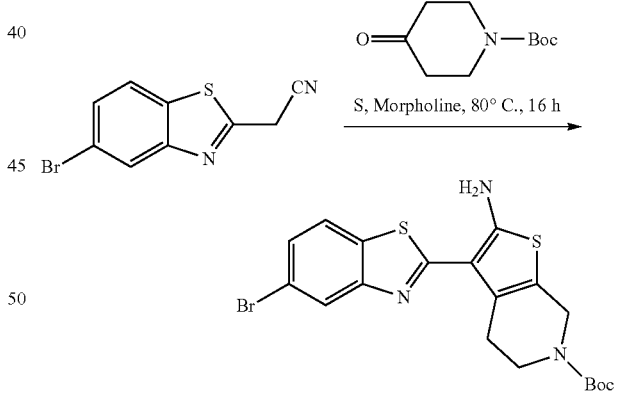

To a solution of 2-(5-bromobenzo[d]thiazol-2-yl)acetonitrile (4.5 g, 17.78 mmol) in ethanol (60 mL) was added tert-butyl 4-oxopiperidine-1-carboxylate (4.2 g, 21.34 mmol), elemental sulfur (0.854 g, 26.67 mmol) and morpholine (3.1 g, 35.57 mmol) and the resulting reaction mixture was heated to reflux at 80° C. for 16 h. Progress of the reaction was monitored by TLC. After completion, the reaction mixture was concentrated under vacuum pressure to give the crude compound, which was purified by flash column chromatography eluting with 30% EtOAc:hexane to afford the title compound as a yellow solid (3 g, 36% yield). $^1$H NMR (400 MHz, DMSO-d$_6$) δ=8.23 (br. s, 2H), 8.11 (s, 1H), 7.97 (d, J=8.58 Hz, 1H), 7.45 (d, J=8.58 Hz, 1H), 4.35 (m, 2H), 3.63-3.68 (m, 2H), 2.81-2.86 (m, 2H), 1.43 (s, 9H).

Step 4: tert-butyl 2-acrylamido-3-(5-bromobenzo[d]thiazol-2-yl)-4,7-dihydrothieno[2,3-c]pyridine-6(5H)-carboxylate

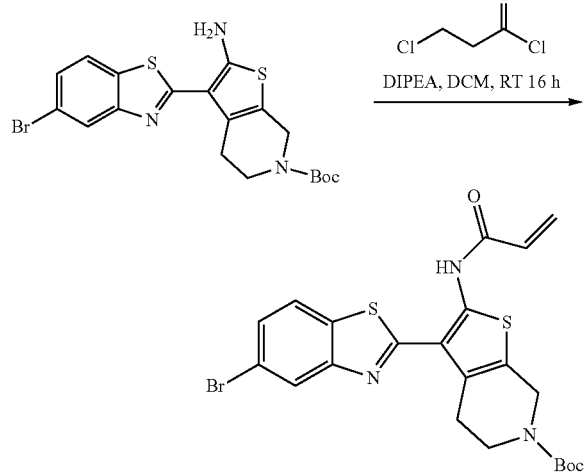

To a solution of tert-butyl 2-amino-3-(5-bromobenzo[d]thiazol-2-yl)-4,7-dihydrothieno[2,3-c]pyridine-6(5H)-carboxylate (0.4 g, 0.858 mmol) in DCM (10 mL) was added 3-chloropropanoyl chloride (0.08 mL, 0.90 mmol) followed by DIPEA (0.3 mL, 1.71 mmol) and the reaction was stirred at room temperature for 16 h. Progress of the reaction was monitored by TLC and LCMS. After completion, reaction mixture was diluted with water, extracted with DCM, and concentrated under reduced pressure to afford a crude residue, which was purified by silica gel (100-200 mesh) column chromatography eluting with 30% EtOAc:hexane to give the title compound as an off yellow solid (0.3 g, yield 67%). $^1$H NMR (400 MHz, DMSO-d$_6$) δ=12.79 (s, 1H), 8.52 (d, J=1.86 Hz, 1H), 8.12 (d, J=8.84 Hz, 1H), 7.62 (dd, J=1.63, 8.61 Hz, 1H), 6.82 (dd, J=10.47, 16.98 Hz, 1H), 6.41 (d, J=16.75 Hz, 1H), 5.98 (d, J=10.23 Hz, 1H), 4.55 (m, 2H), 3.68-3.73 (m, 2H), 2.90-2.96 (m, 2H), 1.44 (s, 9H). LCMS: [M+Na]$^+$=544.09; R$_t$=4.45 min.

Step 5: tert-butyl 3-(5-bromobenzo[d]thiazol-2-yl)-2-(3-(sec-butylamino)propanamido)-4,7-dihydrothieno[2,3-c]pyridine-6(5H)-carboxylate

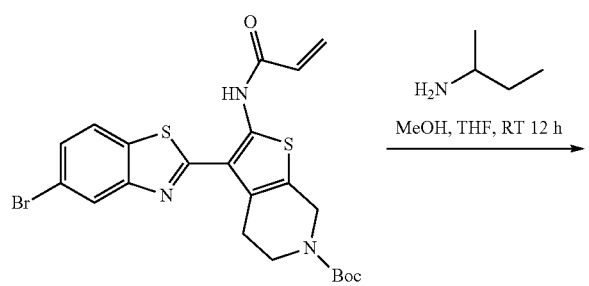

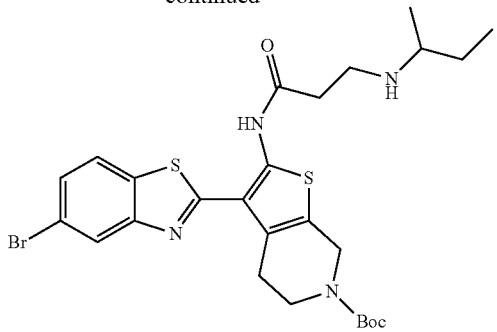

To a solution of tert-butyl 2-acrylamido-3-(5-bromobenzo[d]thiazol-2-yl)-4,7-dihydrothieno[2,3-c]pyridine-6(5H)-carboxylate (125 mg, 0.24 mmol) in methanol:THF (1:2 mL) was added butan-2-amine (35 mg, 0.48 mmol) and the reaction mixture was stirred at room temperature for 12 h. After completion, the reaction mixture was concentrated under vacuum pressure resulting in a crude residue which was purified by silica gel column chromatography eluting with 1-5% methanol in DCM to afford the title compound as a yellow solid (110 mg, 77% yield). $^1$H NMR (400 MHz, DMSO-d$_6$) δ 8.27 (s, 1H), 8.07 (d, J=8.31 Hz, 1H), 7.54-7.59 (m, 1H), 4.50 (m, 2H), 3.65-3.70 (m, 2H), 3.01-3.12 (m, 2H), 2.95-2.99 (m, 2H), 2.73-2.80 (m, 3H), 1.44 (s, 9H), 1.22-1.33 (m, 4H), 1.00 (d, J=5.87 Hz, 3H), 0.79 (t, J=7.34 Hz, 3H). LCMS: [M+H]$^+$=594.95; R$_t$=2.71 min.

Step 6: N-(3-(5-bromobenzo[d]thiazol-2-yl)-4,5,6,7-tetrahydrothieno[2,3-c]pyridin-2-yl)-3-(sec-butylamino)propanamide

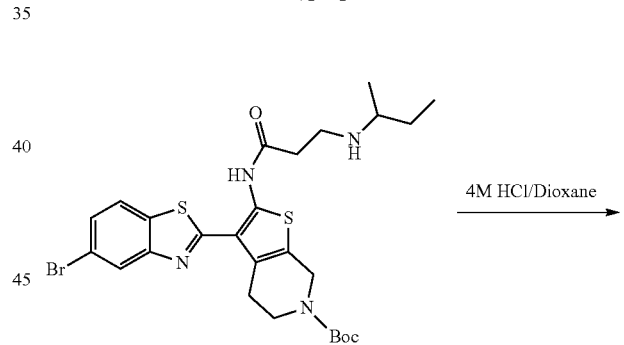

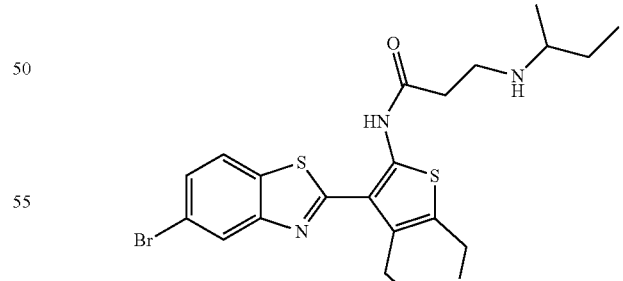

To a solution of tert-butyl 3-(5-bromobenzo[d]thiazol-2-yl)-2-(3-(sec-butylamino)propanamido)-4,7-dihydrothieno[2,3-c]pyridine-6(5H)-carboxylate (110 mg, 0.18 mmol) in dioxane (2 mL) at 0° C. was added 4M HCl in dioxane (2 mL) and the resulting mixture was stirred at room temperature for 2 h. After completion, the reaction mixture was concentrated under vacuum pressure to give a crude residue which was purified by trituration in methanol and diethyl ether to afford the title compound as a yellow solid (70 mg, 67% yield).

Example 24. Synthesis of N-(3-(5-bromobenzo[d]thiazol-2-yl)-6-isopropyl-4,5,6,7-tetrahydrothieno[2,3-c]pyridin-2-yl)-3-(sec-butylamino)propanamide (Compound 141)

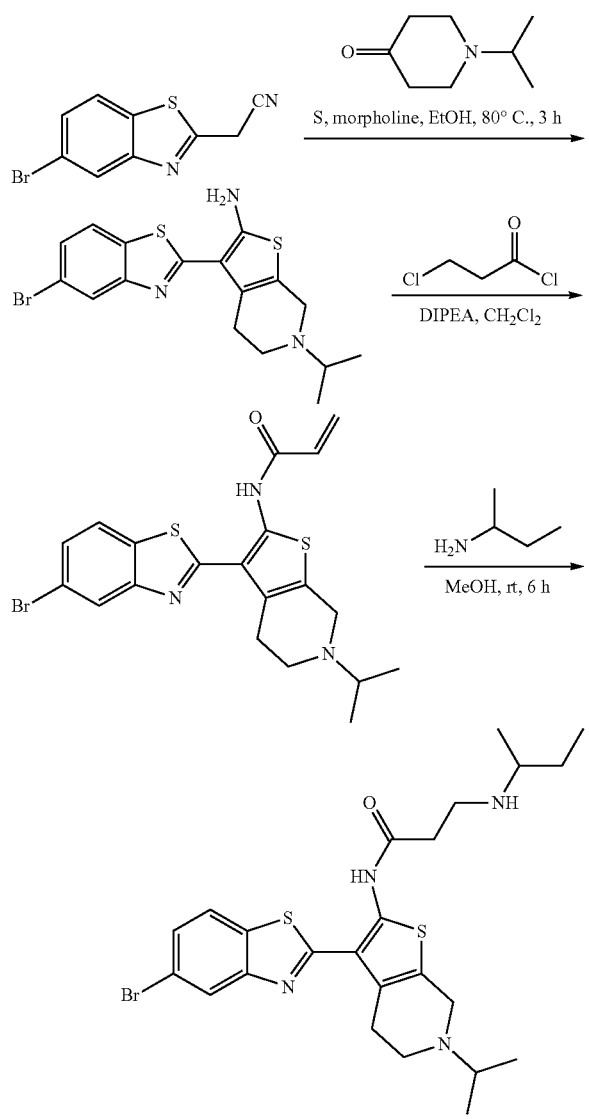

Step 1: 3-(5-bromobenzo[d]thiazol-2-yl)-6-isopropyl-4,5,6,7-tetrahydrothieno[2,3-c]pyridin-2-amine

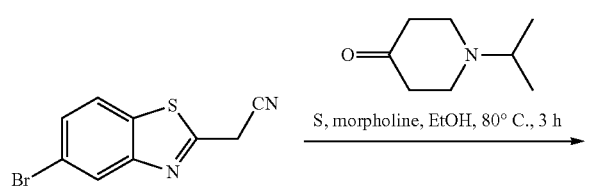

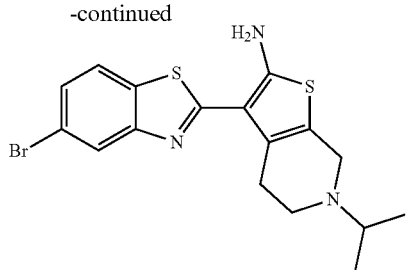

To a solution of 2-(5-bromobenzo[d]thiazol-2-yl)acetonitrile (1.5 g, 5.90 mmol) in ethanol (10 mL) was added 1-isopropylpiperidin-4-one (835 mg, 5.90 mmol), elemental sulfur (224 mg, 5.90 mmol), and morpholine (516 mg, 5.90 mmol) at room temperature. After the addition, the resulting mixture was heated to reflux at 80° C. for 3 h and monitored by TLC. Methanol was added to the reaction mixture and stirred for 20 min. The solid precipitated out and was filtered and dried under vacuum pressure to afford the title compound as a yellow solid (700 mg, yield 29%). $^1$H NMR (DMSO-$d_6$, 400 MHz): δ 8.15 (br. s, 2H), 8.08 (s, 1H), 7.94 (d, J=8.31 Hz, 1H), 7.43 (d, J=8.31 Hz, 1H), 3.45 (br. s, 2H), 2.82-2.87 (m, 1H), 2.74-2.82 (m, 4H), 1.04 (d, J=6.36 Hz, 6H). LCMS: [M+H]$^+$=409.94; $R_t$=2.40 min.

Step 2: N-(3-(5-bromobenzo[d]thiazol-2-yl)-6-isopropyl-4,5,6,7-tetrahydrothieno[2,3-c]pyridin-2-yl) acrylamide

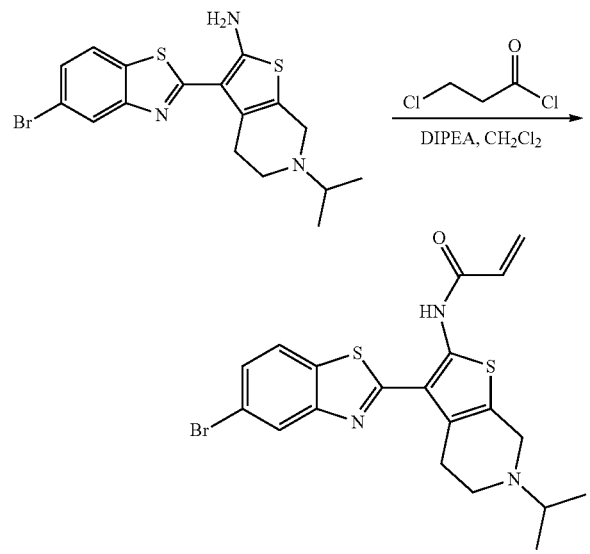

To a solution of 3-(5-bromobenzo[d]thiazol-2-yl)-6-isopropyl-4,5,6,7-tetrahydrothieno[2,3-c]pyridin-2-amine (300 mg, 0.73 mmol) in DCM (3 mL) at 0° C. was added DIPEA (0.25 mL, 1.47 mmol) and 3-chloropropanoyl chloride (112 mg, 0.88 mmol). The reaction was monitored by TLC. After the reaction was complete, the mixture was diluted with DCM and washed with saturated NaHCO$_3$ solution and brine. The combined organic layers were dried over Na$_2$SO$_4$, filtered and concentrated to get a crude residue, which was purified by silica gel column chromatography eluting with 5-10% methanol in DCM to afford the title compound as a yellow solid (200 mg, yield 59%). $^1$H NMR (DMSO-$d_6$, 400

MHz): δ 12.80 (br. s, 1H), 8.47 (s, 1H), 8.08 (d, J=8.27 Hz, 1H), 7.58 (d, J=8.73 Hz, 1H), 6.79 (dd, J=10.34, 16.78 Hz, 1H), 6.39 (d, J=16.55 Hz, 1H), 5.96 (d, J=10.11 Hz, 1H), 3.66 (br. s, 2H), 2.79-2.97 (m, 5H), 1.08 (d, J=5.98 Hz, 6H). LCMS: [M+H]⁺=461.90; R_f=2.45 min.

Step 3: N-(3-(5-bromobenzo[d]thiazol-2-yl)-6-isopropyl-4,5,6,7-tetrahydrothieno[2,3-c]pyridin-2-yl)-3-(sec-butylamino)propanamide

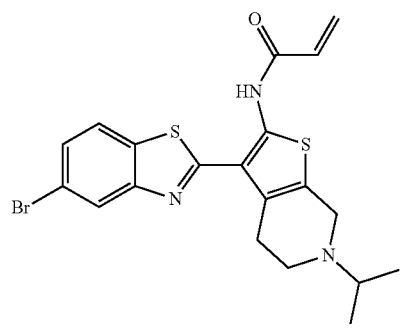
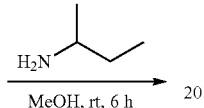
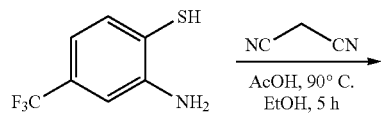

To a solution of N-(3-(5-bromobenzo[d]thiazol-2-yl)-6-isopropyl-4,5,6,7-tetrahydrothieno[2,3-c]pyridin-2-yl)acrylamide (200 mg, 0.43 mmol) in methanol (5 mL) was added butan-2-amine (47 mg, 0.65 mmol). After the addition, the resulting mixture was stirred at room temperature for 6 h. Upon completion, the reaction mixture was evaporated to dryness and the resulting crude residue was purified by silica gel column chromatography eluting with 5% methanol in DCM to afford the title compound as a yellow solid (40 mg, 17% yield).

Example 25. Synthesis of 3-(sec-butylamino)-N-(6-isopropyl-3-(5-(trifluromethyl)benzo[d]thiazol-2-yl)-4,5,6,7-tetrahydrothieno[2,3-c]pyridin-2-yl)propanamide (Compound 142)

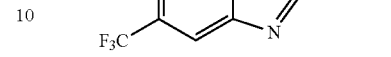
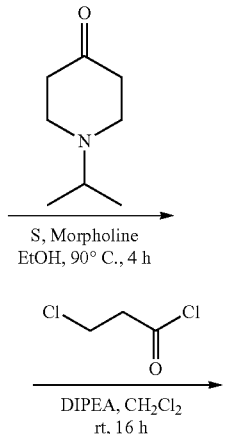
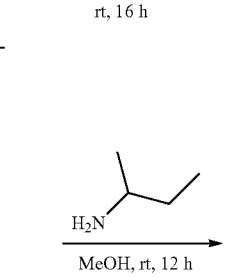
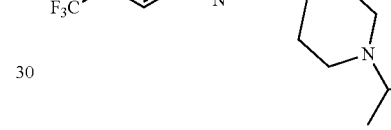

Step 1: 2-(5-(trifluoromethyl)benzo[d]thiazol-2-yl)acetonitrile

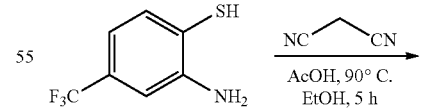
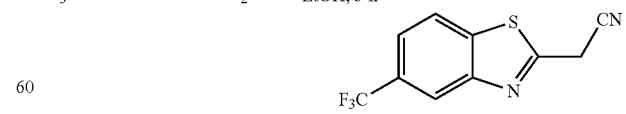

To a solution of 2-amino-4-(trifluoromethyl)benzenethiol (1.5 g, 6.5 mmol) in ethanol (10 mL) was added acetic acid (10 mL) followed by malononitrile (0.64 g, 9.8 mmol) and the reaction mixture was heated to 90° C. for 5 h. The reaction was monitored by TLC. After completion of the reaction, the solvent was removed under reduced pressure and the precipitate obtained was diluted with EtOAc and washed with saturated NaHCO$_3$ solution. The combined organic layers were dried over Na$_2$SO$_4$ and concentrated to afford a crude residue which was purified by flash column chromatography to afford the title compound as an off white solid (750 mg, 50% yield). LCMS: [M+H]$^+$=242.89; R$_t$=3.05 min.

Step 2: 6-isopropyl-3-(5-(trifluoromethyl)benzo[d]thiazol-2-yl)-4,5,6,7-tetrahydrothieno[2,3-c]pyridin-2-amine

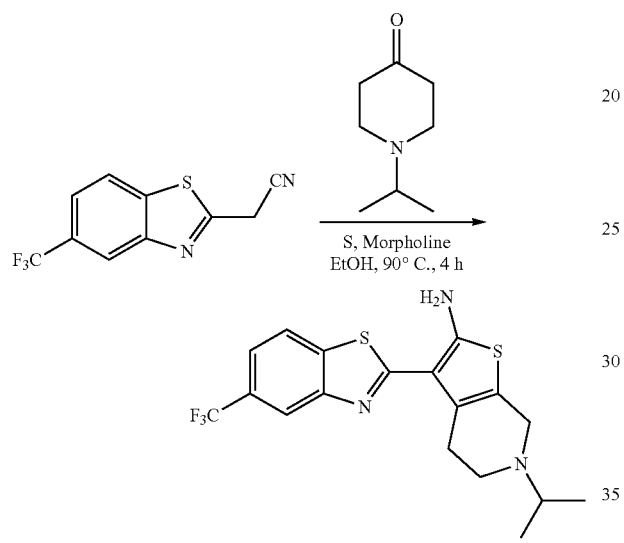

To a solution of 2-(5-(trifluoromethyl)benzo[d]thiazol-2-yl)acetonitrile (700 mg, 2.89 mmol) in ethanol (10 mL) was added 1-isopropylpiperidin-4-one (400 mg, 2.89 mmol), morpholine (251 mg, 2.89 mmol), and the reaction mixture was heated to 40° C. for 10 min. Sulfur (92 mg, 2.89 mmol) was then added, and the resulting mixture heated to 90° C. for 4 h and monitored by TLC. After completion, the reaction mixture was evaporated to yield the crude product, which was purified by flash column chromatography to afford the title compound as a yellow solid (550 mg, 45% yield). LCMS: [M+H]$^+$=398.0; R$_t$=2.32 min.

Step 3: N-(6-isopropyl-3-(5-(trifluoromethyl)benzo[d]thiazol-2-yl)-4,5,6,7-tetrahydrothieno[2,3-c]pyridin-2-yl)acrylamide

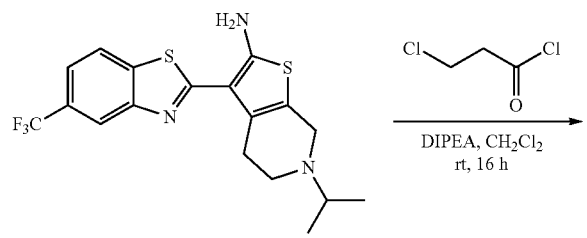

-continued

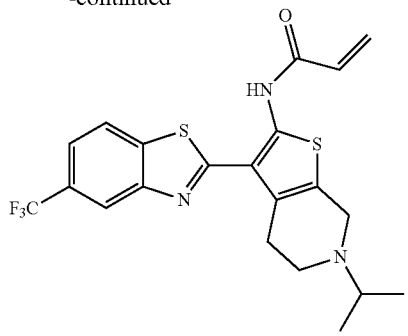

To a solution of 6-isopropyl-3-(5-(trifluoromethyl)benzo[d]thiazol-2-yl)-4,5,6,7-tetrahydrothieno[2,3-c]pyridin-2-amine (500 mg, 1.25 mmol) in DCM (5 mL) at 0° C. was added DIPEA (0.243 mg, 1.88 mmol), followed by 3-chloropropanoyl chloride (0.167 mg, 1.32 mmol) and the reaction mixture was stirred at room temperature for 16 h. The reaction was monitored by TLC, and after completion, was diluted with DCM and water. The organic layer was separated, dried over Na$_2$SO$_4$, and concentrated to give a crude residue which was purified by flash column chromatography to afford the title compound as a yellow solid (200 mg, 35% yield). LCMS: [M+H]$^+$=452.0; R$_t$=2.39 min.

Step 4: 3-(sec-butylamino)-N-(6-isopropyl-3-(5-(trifluoromethyl)benzo[d]thiazol-2-yl)-4,5,6,7-tetrahydrothieno[2,3-c]pyridin-2-yl)propanamide

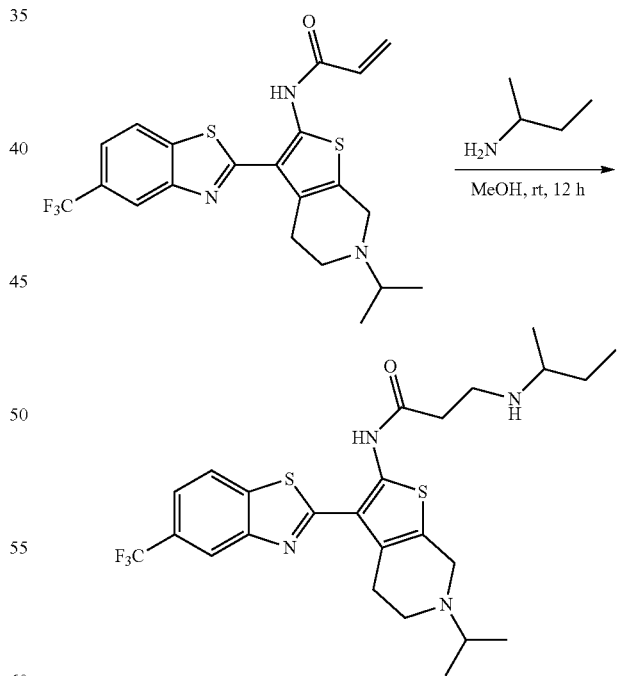

To a stirring solution of N-(6-isopropyl-3-(5-(trifluoromethyl)benzo[d]thiazol-2-yl)-4,5,6,7-tetrahydrothieno[2,3-c]pyridin-2-yl)acrylamide (200 mg, 0.44 mmol) in CH$_3$OH (5 mL) was added butan-2-amine 7 (64 mg, 0.89 mmol) at room temperature and stirred for 12 h. The reaction was monitored by TLC. After completion, the reaction mixture was evaporated to dryness to give a crude residue which was purified by flash column chromatography to afford the title compound the title compound as a yellow solid (80 mg, 13% yield).

Example 26. Synthesis of N-(3-(benzo[d]thiazol-2-yl)-4,5,6,7-tetrahydrothieno[2,3-c]pyridin-2-yl)-3-(((1-methyl-1H-pyrazol-4-yl)methyl)amino)propanamide (Compound 143)

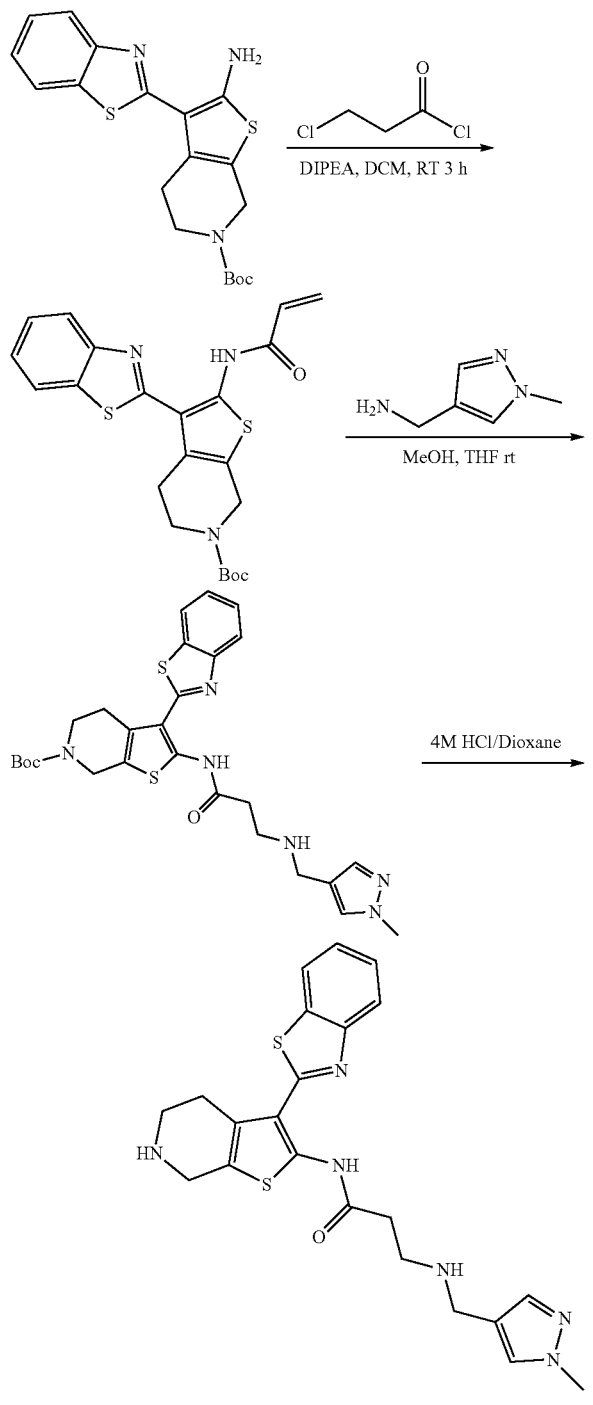

Step 1: tert-butyl 2-acrylamido-3-(benzo[d]thiazol-2-yl)-4,7-dihydrothieno[2,3-c]pyridine-6(5H)-carboxylate

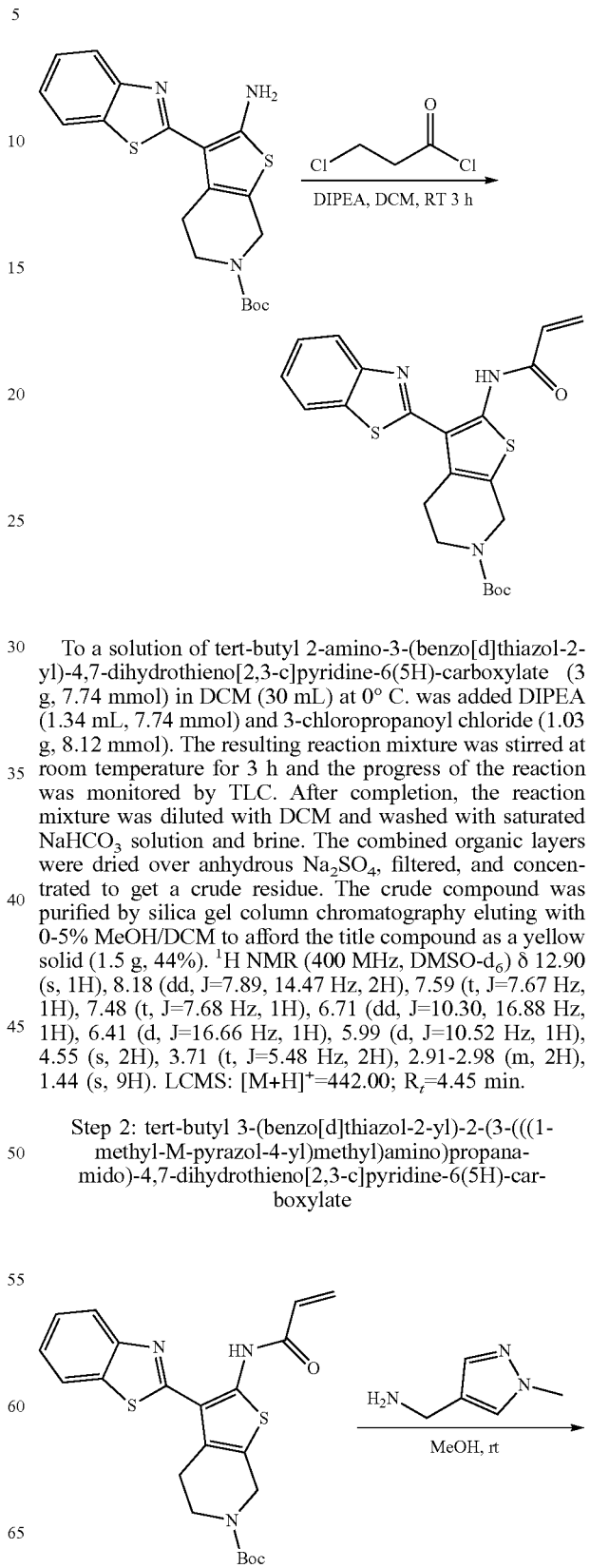

To a solution of tert-butyl 2-amino-3-(benzo[d]thiazol-2-yl)-4,7-dihydrothieno[2,3-c]pyridine-6(5H)-carboxylate (3 g, 7.74 mmol) in DCM (30 mL) at 0° C. was added DIPEA (1.34 mL, 7.74 mmol) and 3-chloropropanoyl chloride (1.03 g, 8.12 mmol). The resulting reaction mixture was stirred at room temperature for 3 h and the progress of the reaction was monitored by TLC. After completion, the reaction mixture was diluted with DCM and washed with saturated NaHCO$_3$ solution and brine. The combined organic layers were dried over anhydrous Na$_2$SO$_4$, filtered, and concentrated to get a crude residue. The crude compound was purified by silica gel column chromatography eluting with 0-5% MeOH/DCM to afford the title compound as a yellow solid (1.5 g, 44%). $^1$H NMR (400 MHz, DMSO-d$_6$) δ 12.90 (s, 1H), 8.18 (dd, J=7.89, 14.47 Hz, 2H), 7.59 (t, J=7.67 Hz, 1H), 7.48 (t, J=7.68 Hz, 1H), 6.71 (dd, J=10.30, 16.88 Hz, 1H), 6.41 (d, J=16.66 Hz, 1H), 5.99 (d, J=10.52 Hz, 1H), 4.55 (s, 2H), 3.71 (t, J=5.48 Hz, 2H), 2.91-2.98 (m, 2H), 1.44 (s, 9H). LCMS: [M+H]$^+$=442.00; R$_f$=4.45 min.

Step 2: tert-butyl 3-(benzo[d]thiazol-2-yl)-2-(3-(((1-methyl-M-pyrazol-4-yl)methyl)amino)propanamido)-4,7-dihydrothieno[2,3-c]pyridine-6(5H)-carboxylate 125
-continued

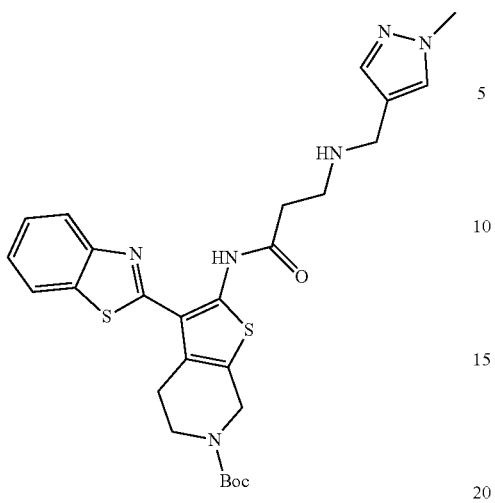

To a solution of tert-butyl 2-acrylamido-3-(benzo[d]thi-azol-2-yl)-4,7-dihydrothieno[2,3-c]pyridine-6(5H)-car-boxylate (0.1 g, 0.226 mmol) in methanol:THF (1:2 mL) was added (1-methyl-1H-pyrazol-4-yl)methanamine (0.050 g, 0.453 mmol). The resulting reaction mixture was stirred at room temperature for 2 h. The progress of the reaction was monitored by TLC and LCMS. After completion, the reaction mixture was concentrated to dryness to get a crude residue. The crude compound was purified by silica gel column chromatography eluting with 0-5% MeOH/DCM to afford the title compound as an off white solid (0.095 g, 76% yield). $^1$H NMR (400 MHz, DMSO-$d_6$) δ 8.14 (d, J=7.83 Hz, 1H), 8.05 (d, J=8.31 Hz, 1H), 7.86 (br. s, 2H), 7.56 (t, J=7.34 Hz, 1H), 7.45-7.48 (m, 1H), 7.44 (s, 1H), 7.22 (s, 1H), 4.52 (br. s, 2H), 3.71-3.74 (m, 2H), 3.69 (s, 3H), 3.61 (s, 2H), 2.90-2.98 (m, 4H), 2.72 (t, J=6.36 Hz, 2H), 1.44 (s, 9H). LCMS: [M+H]$^+$=553.28; R$_t$=2.47 min.

Step 3: N-(3-(benzo[d]thiazol-2-yl)-4,5,6,7-tetrahy-drothieno[2,3-c]pyridin-2-yl)-3-(((1-methyl-1H-pyrazol-4-yl)methyl)amino)propanamide

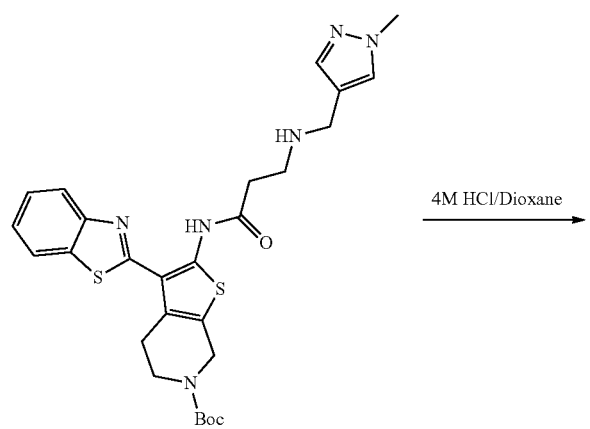

126
-continued

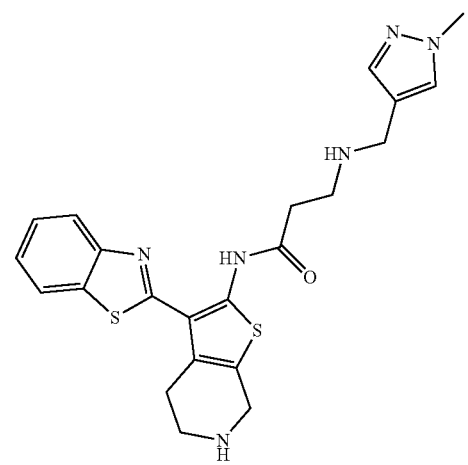

To a solution of tert-butyl 3-(benzo[d]thiazol-2-yl)-2-(3-(((1-methyl-1H-pyrazol-4-yl)methyl)amino)propanamido)-4,7-dihydrothieno[2,3-c]pyridine-6(5H)-carboxylate (0.095 g, 0.172 mmol) in dioxane (1 mL) at 0° C. was added 4M HCl in dioxane (2 mL). After the addition, the resulting mixture was stirred at room temperature for 2 h. After completion, the reaction mixture was evaporated under vacuum resulting in a crude residue. The residue was triturated with methanol, filtered, and washed with diethyl ether and dried to afford the title compound as a yellow solid (0.080 g, 88%).

Example 27. Synthesis of Ethyl (3-((3-(benzo[d]thiazol-2-yl)-4,5,6,7-tetrahydrothieno[2,3-c]pyridin-2-yl)amino)-3-oxopropyl)glycinate (Compound 144)

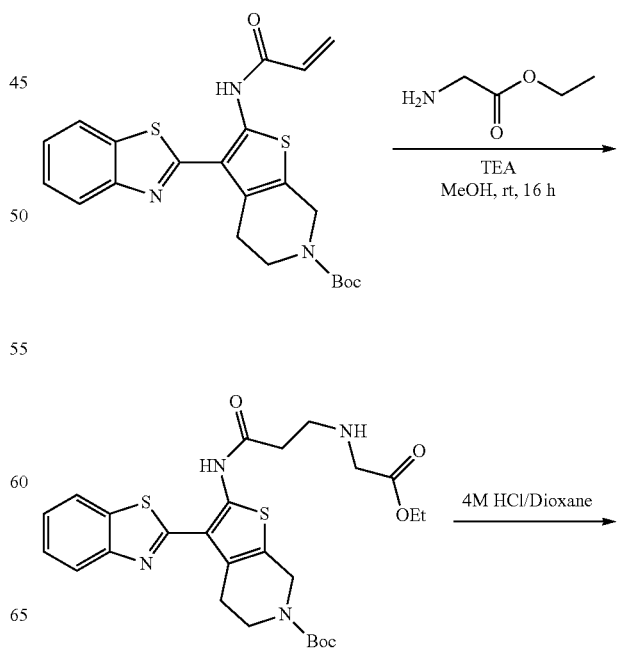

127

-continued

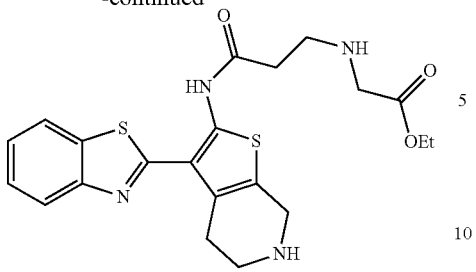

Step 1: tert-butyl 3-(benzo[d]thiazol-2-yl)-2-(3-((2-ethoxy-2-oxoethyl)amino)propanamido)-4,7-dihydrothieno[2,3-c]pyridine-6(5H)-carboxylate

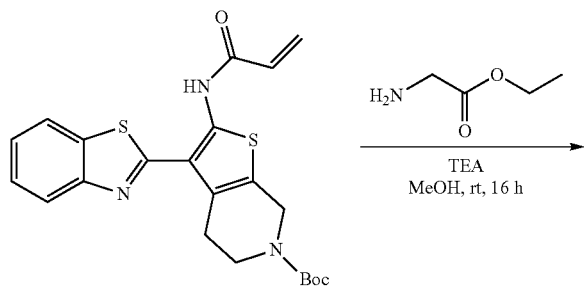

To a stirring solution of tert-butyl 2-acrylamido-3-(benzo[d]thiazol-2-yl)-4,7-dihydrothieno[2,3-c]pyridine-6(5H)-carboxylate (300 mg, 0.68 mmol) in CH₃OH (2 mL) was added ethyl glycinate (141 mg, 1.02 mmol) followed by Et₃N (0.2 mL, 1.36 mmol). The reaction mixture was stirred at room temperature for 16 h and monitored by TLC. After completion, the reaction mixture was evaporated to dryness giving a crude residue which was purified by flash column chromatography to afford the title compound as a pale yellow solid (150 mg, 41% yield). LCMS: [M+H]⁺=545.05; $R_t$=2.57 min.

Step 2: Ethyl (3-((3-(benzo[d]thiazol-2-yl)-4,5,6,7-tetrahydrothieno[2,3-c]pyridin-2-yl)amino)-3-oxopropyl)glycinate

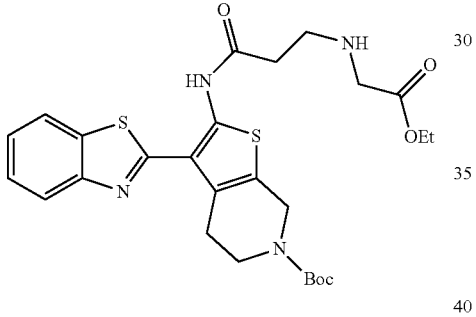

128

-continued

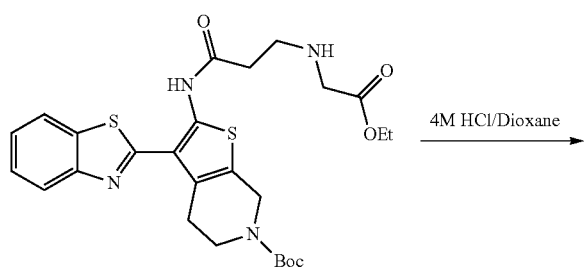

To a solution of tert-butyl 3-(benzo[d]thiazol-2-yl)-2-(3-((2-ethoxy-2-oxoethyl)amino)propanamido)-4,7-dihydrothieno[2,3-c]pyridine-6(5H)-carboxylate (140 mg, 0.257 mmol) in dioxane (2 mL) at 0° C. was added 4M HCl in dioxane (2 mL). The reaction mixture was stirred at room temperature for 2 h and monitored by TLC. After the reaction was complete, the mixture was evaporated to dryness resulting in a crude residue which was purified by preparative HPLC to afford the title compound as a yellow solid (25 mg, 22% yield).

Example 28. Synthesis of N-(3-(benzo[d]thiazol-2-yl)-4,5,6,7-tetrahydrothieno[2,3-c]pyridin-2-yl)acetamide (Compound 202)

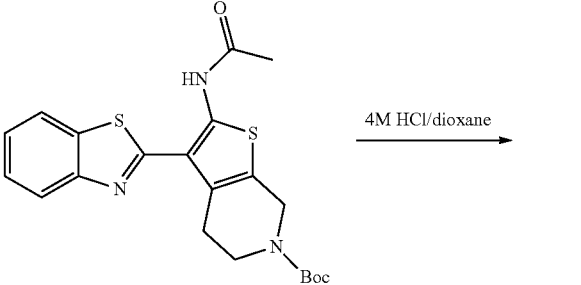

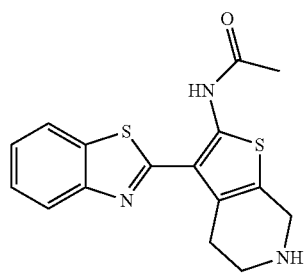

To a solution of tert-butyl 2-acetamido-3-(benzo[d]thiazol-2-yl)-4,7-dihydrothieno[2,3-c]pyridine-6(5H)-carboxylate (200 mg, 1.16 mmol) in dioxane (4 mL) at 0° C. was added 4M HCl in dioxane (4 mL). After the addition, the resulting mixture was stirred at room temperature for 2 h. After completion, the reaction mixture was concentrated under vacuum pressure resulting in a crude residue that was purified by trituration in ether to afford the HCl salt of the title compound as a yellow solid (140 mg, 82% yield).

Example 29. Synthesis of N-(3-(benzo[d]thiazol-2-yl)-6-isopropyl-4,5,6,7-tetrahydrothieno[2,3-c]pyridin-2-yl)acetamide (Compound 200)

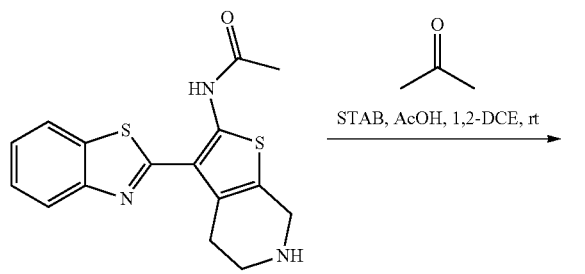

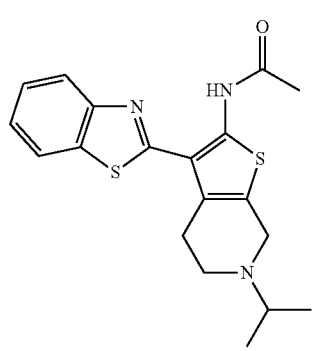

To a solution of acetone (0.18 mL, 2.46 mmol), N-(3-(benzo[d]thiazol-2-yl)-4,5,6,7-tetrahydrothieno[2,3-c]pyridin-2-yl)acetamide (300 mg, 0.82 mmol) in 1,2-dichloroethane (3 mL) was added sodium triacetoxyborohydride (260 mg, 1.23 mmol) followed by AcOH (1 mL) and the mixture was stirred at room temperature for 12 h. After completion of reaction as indicated by LCMS, the reaction mixture was diluted with water (15 mL) and extracted with ethyl acetate (3×10 mL). The combined organic layers were dried over $Na_2SO_4$ and concentrated under vacuum pressure resulting in the crude compound, which was purified using silica gel column chromatography eluting with 0-50% ethyl acetate in n-hexane to afford the title compound (100 mg, yield 32%) as a yellow solid.

Example 30. Synthesis of N-(3-(benzo[d]thiazol-2-yl)-6-ethyl-4,5,6,7-tetrahydrothieno[2,3-c]pyridin-2-yl)acetamide (Compound 201)

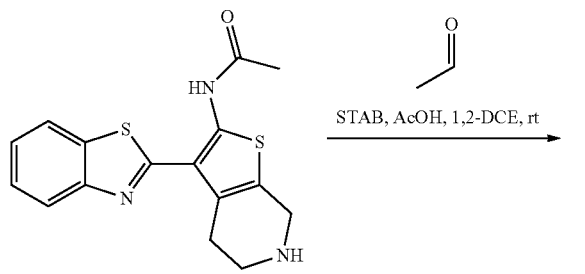

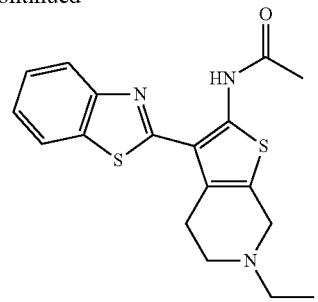

A solution of acetaldehyde (36 mg, 0.82 mmol) and N-(3-(benzo[d]thiazol-2-yl)-4,5,6,7-tetrahydrothieno[2,3-c]pyridin-2-yl)acetamide (100 mg, 0.27 mmol) in DCE (3 mL) was stirred for 2 h at room temperature prior to the addition of sodium triacetoxy borohydride (86 mg, 0.41 mmol) followed by AcOH (1 mL). The resulting mixture was stirred for another 12 h and monitored by LCMS. Upon completion, the mixture was diluted with water (15 mL) and extracted with ethyl acetate (3×10 mL). The combined organic solvents were dried over $Na_2SO_4$ and concentrated under vacuum pressure resulting in the crude compound, which was purified using silica gel column chromatography eluting with 0-5% methanol in DCM to afford the title compound (40 mg, yield 40%) as a yellow solid.

Example 31. Synthesis of N-(3-(5-fluorobenzo[d]thiazol-2-yl)-4,5,6,7-tetrahydrothieno[2,3-c]pyridin-2-yl)acetamide (Compound 203)

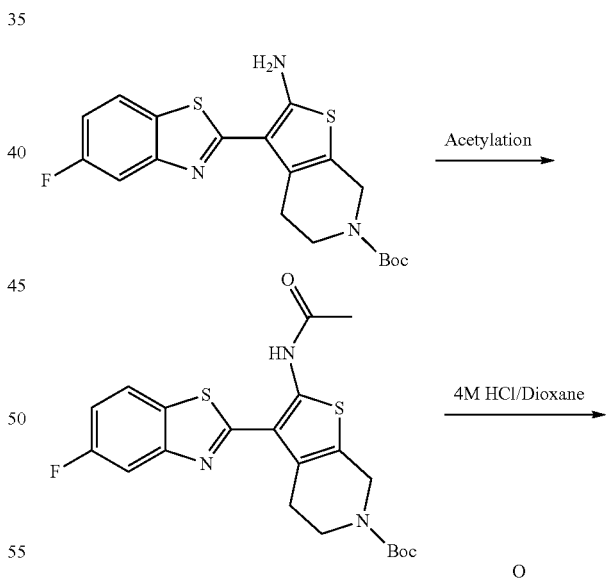

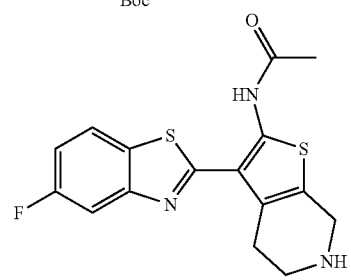

131

Step 1: tert-butyl 2-acetamido-3-(5-fluorobenzo[d]thiazol-2-yl)-4,7-dihydrothieno[2,3-c]pyridine-6(5H)-carboxylate

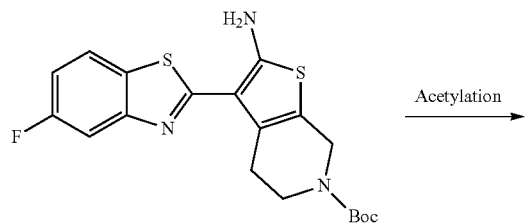

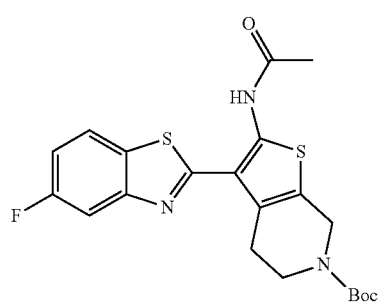

To a solution of tert-butyl 2-amino-3-(5-fluorobenzo[d]thiazol-2-yl)-4,7-dihydrothieno[2,3-c]pyridine-6(5H)-carboxylate (0.15 g, 3.75 mmol) in DCM (5 mL) was added DIPEA (0.13 mL, 7.50 mmol) at 0° C. and stirred for 10 min. To this solution, acetyl chloride (0.032 g, 4.13 mmol) was added at 0° C. The resulting reaction mixture was stirred at room temperature for 16 h and monitored by TLC. After completion, the reaction mixture was diluted with aqueous sat. NaHCO₃ solution and extracted with DCM. The combined organic layers were dried over anhydrous Na₂SO₄, filtered, and concentrated to get a crude residue, which was purified by silica gel column chromatography eluting with a gradient of 0-20% ethyl acetate in n-hexane to afford the title compound as a yellow solid (0.1 g, yield 63%). LCMS: [M+23]⁺=470; $R_f$=3.96 min.

Step 2: N-(3-(5-fluorobenzo[d]thiazol-2-yl)-4,5,6,7-tetrahydrothieno[2,3-c]pyridin-2-yl)acetamide

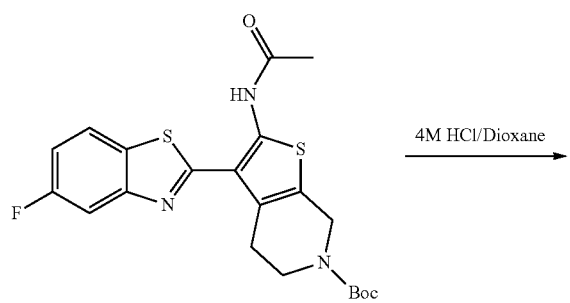

132

-continued

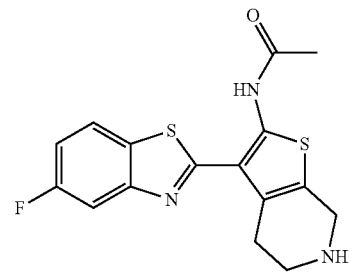

To a solution of tert-butyl 2-acetamido-3-(5-fluorobenzo[d]thiazol-2-yl)-4,7-dihydrothieno[2,3-c]pyridine-6(5H)-carboxylate (0.1 g, 0.223 mmol) in dioxane (2 mL) at 0° C. was added 4M HCl in dioxane (0.5 mL). After the addition, the resulting mixture was stirred at room temperature for 2 h. After completion, the reaction mixture was concentrated under vacuum pressure resulting in a crude residue which was purified by trituration with ether to afford the title compound as an off white solid (0.085 g, HCl salt, 100%).

Example 32. Synthesis of N-(3-(5-(trifluoromethyl)benzo[d]thiazol-2-yl)-4,5,6,7-tetrahydrothieno[2,3-c]pyridin-2-yl)acetamide (Compound 204)

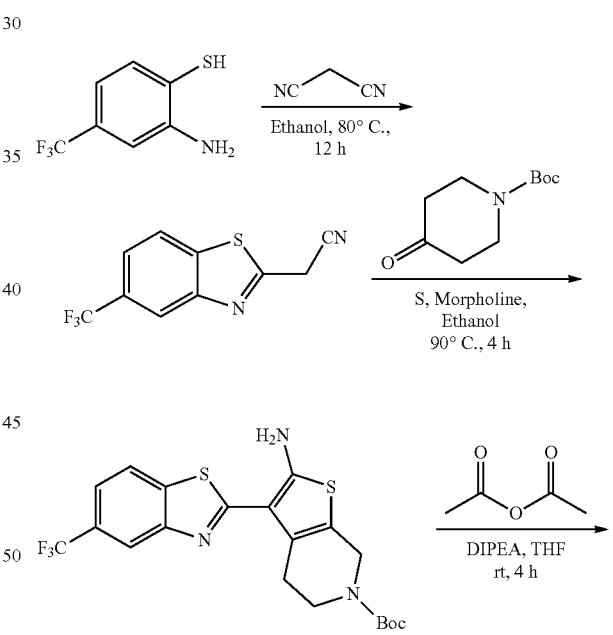

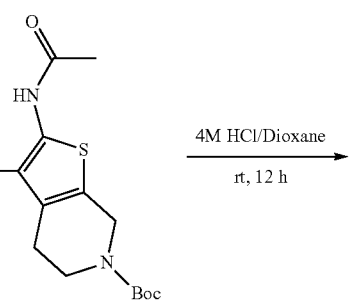

-continued

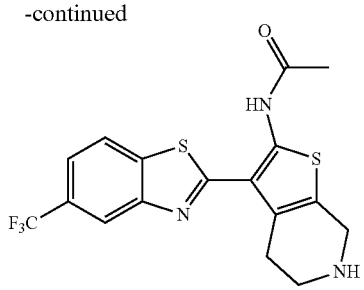

Step 1: 2-(5-(trifluoromethyl)benzo[d]thiazol-2-yl) acetonitrile

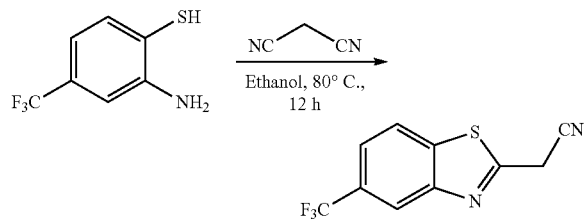

To a stirring solution of 2-amino-4-(trifluoromethyl)benzenethiol (2 g, 8.73 mmol) in ethanol (20 mL) was added acetic acid (10 mL) followed by malononitrile (860 mg, 13.1 mmol) at room temperature. The reaction mixture was heated to 80° C. for 12 h and monitored by TLC. After removal of solvent the reaction mixture was diluted with EtOAc and washed with water. The combined organic layers were dried over anhydrous $Na_2SO_4$ and concentrated to give a crude residue, which was purified by flash column chromatography to afford the title compound as a yellow solid (1.3 g, 62% yield). LCMS: [M+1]$^+$=242.9; $R_f$=2.76 min Step 2: tert-butyl 2-amino-3-(5-(trifluoromethyl) benzo[d]thiazol-2-yl)-4,7-dihydrothieno[2,3-c]pyridine-6(5H)-carboxylate

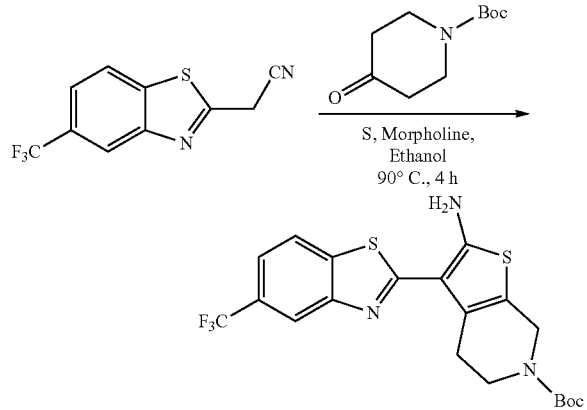

To a solution of 2-(5-(trifluoromethyl)benzo[d]thiazol-2-yl)acetonitrile (900 mg, 3.71 mmol) in ethanol (20 mL) was added tert-butyl 4-oxopiperidine-1-carboxylate (740 mg, 3.71 mmol) followed by morpholine (290 mg, 3.71 mmol) and the reaction mixture was heated to 40° C. for 10 min. Sulfur (119 mg, 3.71 mmol) was then added and the resulting mixture was heated to 90° C. for 4 h. The reaction was monitored by TLC and after completion, was evaporated to dryness resulting in a crude residue which was triturated with methanol. The obtained precipitate was filtered and dried to afford the title compound as a pale yellow solid (1.1 g, 68% yield). $^1$H NMR (DMSO-$d_6$, 400 MHz): δ 8.30 (s, 3H), 8.23 (d, J=7.6 Hz, 1H), 7.60 (d, J=8.0 Hz, 1H), 4.36 (s, 2H), 3.67 (t, J=5.8 Hz, 2H), 2.86 (d, J=5.9 Hz, 2H), 1.44 (s, 9H).

Step 3: tert-butyl 2-acetamido-3-(5-(trifluoromethyl) benzo[d]thiazol-2-yl)-4,7-dihydrothieno[2,3-c]pyridine-6(5H)-carboxylate

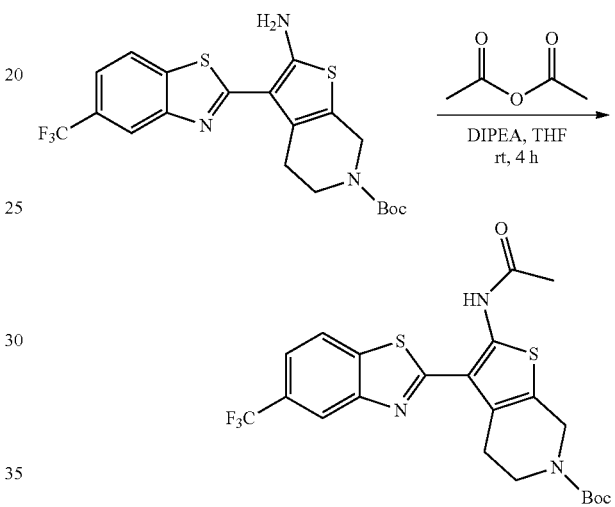

To a solution of tert-butyl 2-amino-3-(5-(trifluoromethyl) benzo[d]thiazol-2-yl)-4,7-dihydrothieno[2,3-c]pyridine-6 (5H)-carboxylate (100 mg, 0.21 mmol) in THF (5 mL) at 0° C. was added DIPEA (0.05 mL, 1.49 mmol), acetic anhydride (22 mg, 0.21 mmol) and the reaction mixture was stirred at room temperature for 4 h. The reaction was monitored by TLC. After completion, the reaction mixture was diluted with EtOAc and washed with water. The combined organic layers were dried over $Na_2SO_4$, filtered, and concentrated to afford the title compound as a yellow liquid (110 mg, crude). LCMS: [M-Boc+1]$^+$=397.90; $R_f$=4.06 min.

Step 4: N-(3-(5-(trifluoromethyl)benzo[d]thiazol-2-yl)-4,5,6,7-tetrahydrothieno[2,3-c]pyridin-2-yl)acetamide hydrochloride

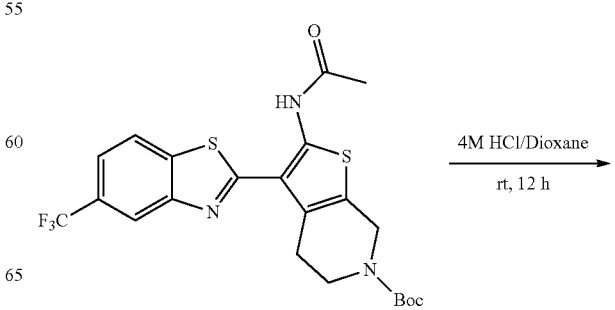

135

-continued

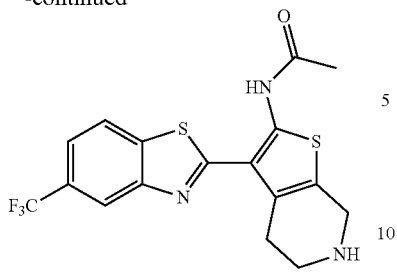

To a solution of tert-butyl 2-acetamido-3-(5-(trifluoromethyl)benzo[d]thiazol-2-yl)-4,7-dihydrothieno[2,3-c]pyridine-6(5H)-carboxylate (110 mg, 0.22 mmol) in dioxane (2 mL) at 0° C. was added 4M HCl in dioxane (2 mL) and the resulting mixture was stirred at room temperature for 12 h. The reaction was monitored by TLC. After completion, the reaction mixture was evaporated to dryness resulting in a crude residue which was purified by preparative HPLC to afford the HCl salt of the title compound as an off-white solid (35 mg, 40% yield).

Example 33. Synthesis of N-(3-(benzo[d]thiazol-2-yl)-4-methyl-4,5,6,7-tetrahydrothieno[2,3-c]pyridin-2-yl)acetamide (Compound 205)

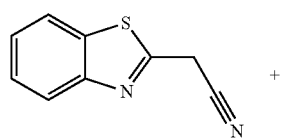

+

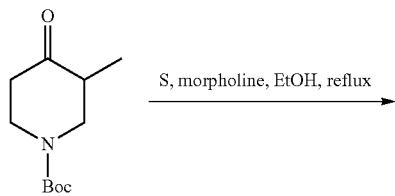
S, morpholine, EtOH, reflux
$\longrightarrow$

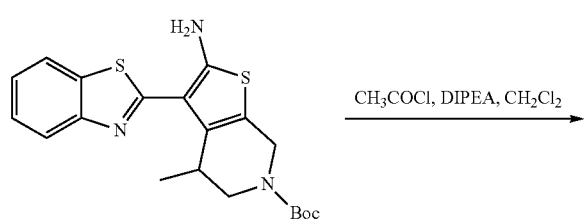
CH$_3$COCl, DIPEA, CH$_2$Cl$_2$
$\longrightarrow$

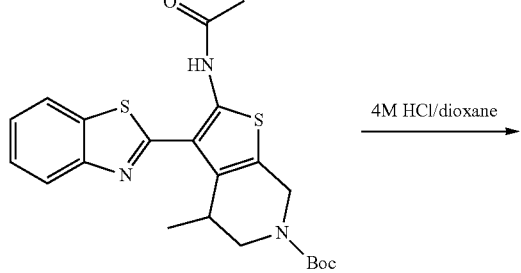
4M HCl/dioxane
$\longrightarrow$

136

-continued

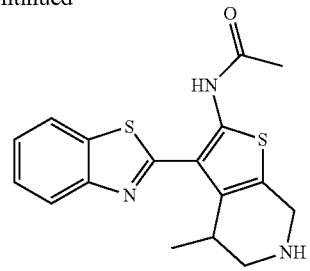

Step 1: tert-butyl 2-amino-3-(benzo[d]thiazol-2-yl)-4-methyl-4,7-dihydrothieno[2,3-c]pyridine-6(5H)-carboxylate

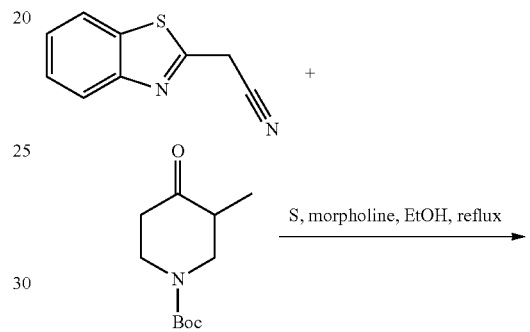
S, morpholine, EtOH, reflux
$\longrightarrow$

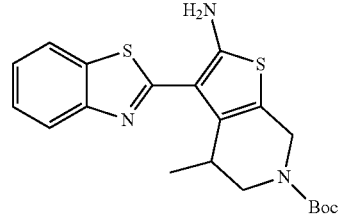

To a solution of 2-(benzo[d]thiazol-2-yl)acetonitrile (500 mg, 2.87 mmol) in ethanol (10 mL) was added tert-butyl 3-methyl-4-oxopiperidine-1-carboxylate (324 mg, 2.87 mmol), elemental sulfur (90 mg, 2.87 mmol) and morpholine (243 mg, 2.87 mmol) at room temperature. After the addition, the resulting mixture was heated to reflux at 85° C. for 12 h. Reaction progress was monitored by TLC. The reaction mixture was concentrated under vacuum pressure and the crude compound was purified by triturating with methanol to afford the title compound as yellow solid (450 mg, yield 39%). LCMS: [M+H]$^+$=401.90; R$_t$=3.89 min.

Step 2: tert-butyl 2-acetamido-3-(benzo[d]thiazol-2-yl)-4-methyl-4,7-dihydrothieno[2,3-c]pyridine-6(5H)-carboxylate

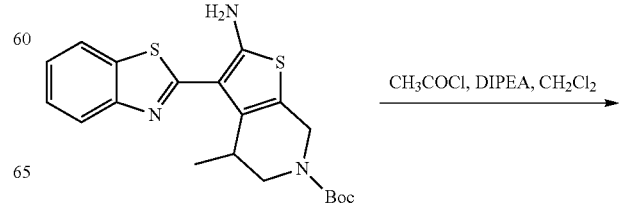
CH$_3$COCl, DIPEA, CH$_2$Cl$_2$
$\longrightarrow$

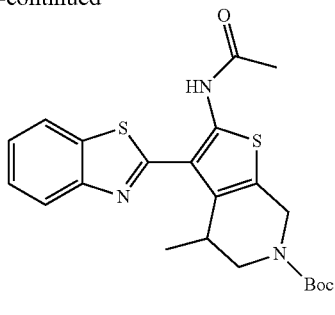

To a solution of tert-butyl 2-amino-3-(benzo[d]thiazol-2-yl)-4-methyl-4,7-dihydrothieno[2,3-c]pyridine-6(5H)-carboxylate (450 mg, 1.12 mmol) in DCM (10 mL) at 0° C. was added DIPEA (0.389 mL, 2.24 mmol) and acetyl chloride (0.12 mL, 1.68 mmol) and the reaction was stirred overnight at room temperature. After completion (monitored by TLC), the reaction mixture was diluted with DCM and washed with saturated NaHCO$_3$ solution and brine. The combined organic layers were dried over Na$_2$SO$_4$, filtered and concentrated to get a crude residue, which was purified by silica gel column chromatography to afford the title compound as off white solid (250 mg, 50% yield). LCMS: [M+H]$^+$=444.0; R$_f$=3.97 min Step 3: N-(3-(benzo[d]thiazol-2-yl)-4-methyl-4,5,6,7-tetrahydrothieno[2,3-c]pyridin-2-yl)acetamide

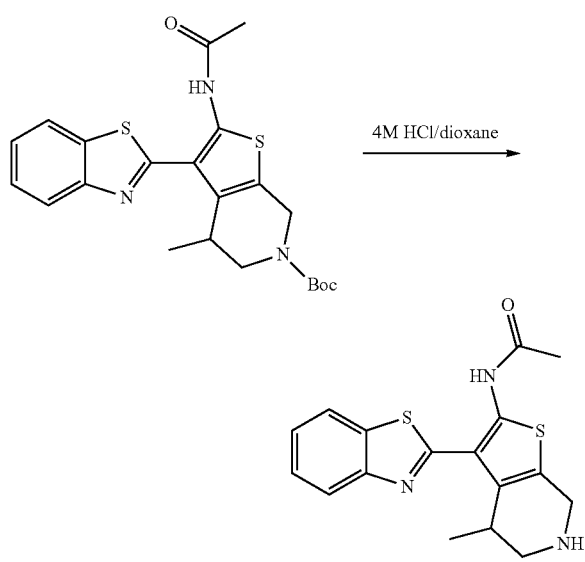

To a solution of tert-butyl 2-acetamido-3-(benzo[d]thiazol-2-yl)-4-methyl-4,7-dihydrothieno[2,3-c]pyridine-6(5H)-carboxylate (250 mg, 0.56 mmol) in dioxane (2.5 mL) at 0° C. was added 4M HCl in dioxane (2.5 mL) and the resulting mixture was stirred at room temperature for 2 h. After completion of reaction, the reaction mixture was evaporated to dryness resulting in a crude residue which was purified by trituration in ether and pentane to afford 200 mg of the HCl salt of the title compound. The salt was taken up in DCM and washed with saturated NaHCO$_3$ solution. The combined organic layers were dried over Na$_2$SO$_4$, filtered and concentrated to get a crude residue, which was purified by silica gel flash column chromatography to afford the title compound as yellow solid (100 mg, 51% yield).

Example 34. Synthesis of N-(3-(benzo[d]thiazol-2-yl)-cis-5,7-dimethyl-4,5,6,7-tetrahydrothieno[2,3-c]pyridin-2-yl)acetamide (Compound 206)

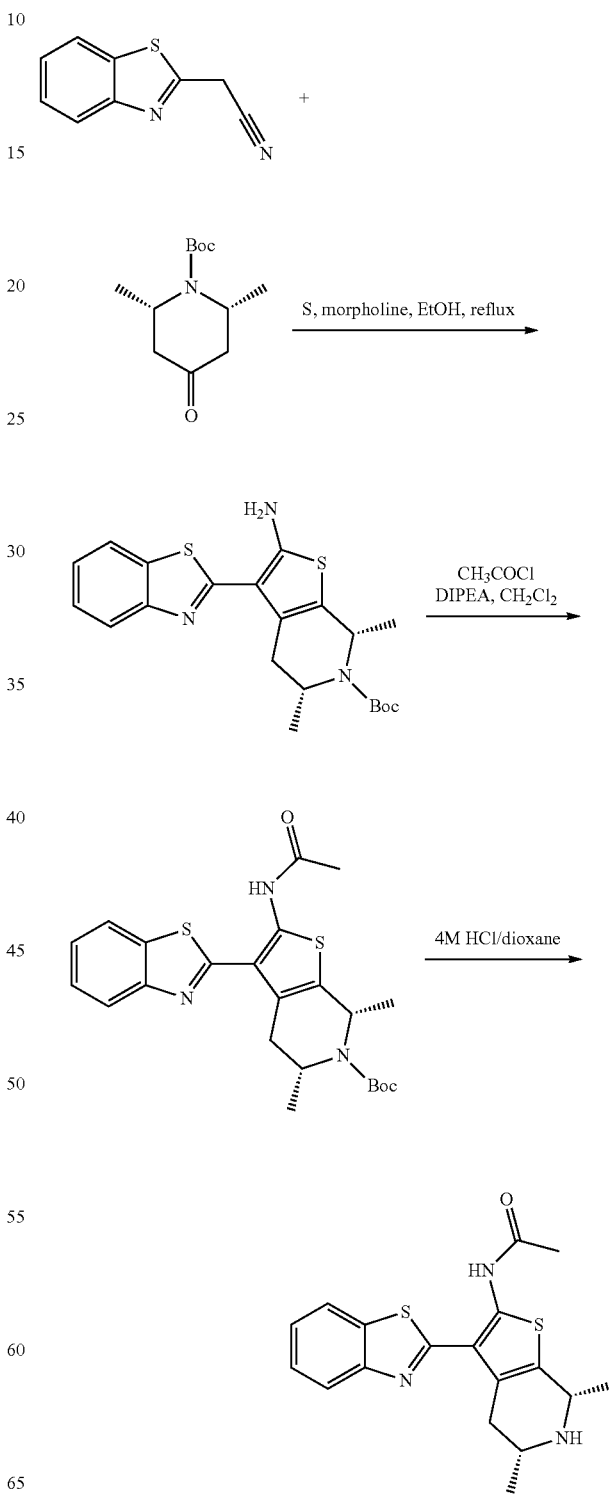

Step 1: tert-butyl 2-amino-3-(benzo[d]thiazol-2-yl)-cis-5,7-dimethyl-4,7-dihydrothieno[2,3-c]pyridine-6(5H)-carboxylate

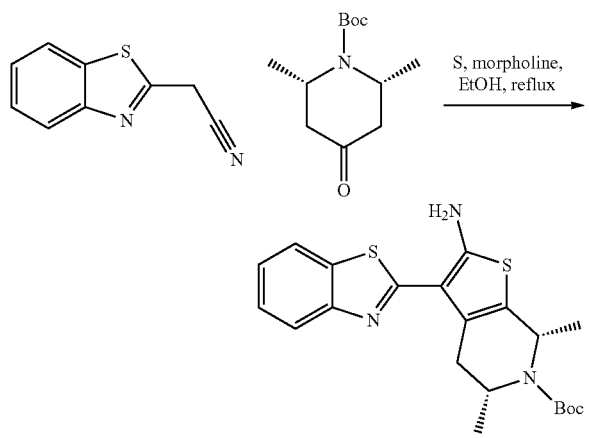

To a solution of 2-(benzo[d]thiazol-2-yl)acetonitrile (1.0 g, 5.74 mmol) in ethanol (10 mL) was added tert-butyl cis-2,6-dimethyl-4-oxopiperidine-1-carboxylate (1.3 g, 5.74 mmol), elemental sulfur (0.184 g, 5.74 mmol) and morpholine (0.5 mL, 5.74 mmol) at room temperature. After the addition, the resulting mixture was heated to reflux at 85° C. for 12 h. Progress of the reaction was monitored by TLC. Upon completion, the reaction mixture was dried under vacuum pressure and the crude compound was purified by triturating with methanol to afford the title compound as off white solid (1 g, yield 42%). LCMS: [M+H]$^+$=416.0; R$_t$=4.03 min

Step 2: tert-butyl 2-acetamido-3-(benzo[d]thiazol-2-yl)-cis-5,7-dimethyl-4,7-dihydrothieno[2,3-c]pyridine-6(5H)-carboxylate

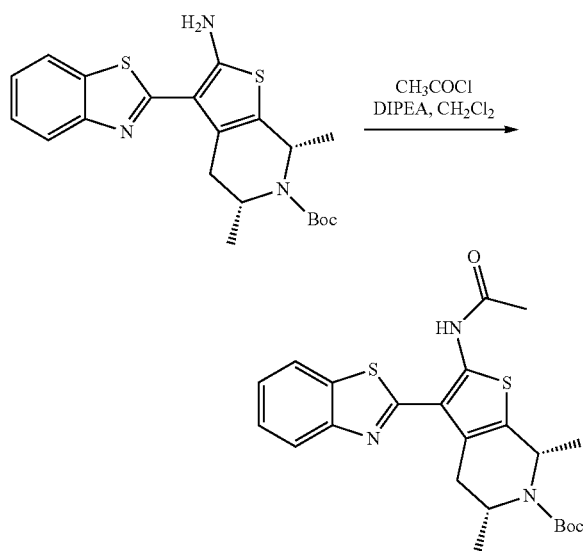

To a solution of tert-butyl 2-amino-3-(benzo[d]thiazol-2-yl)-cis-5,7-dimethyl-4,7-dihydrothieno[2,3-c]pyridine-6(5H)-carboxylate (1 g, 2.40 mmol) in DCM (10 mL) at 0° C. was added DIPEA (0.85 mL, 4.81 mmol) and acetyl chloride (0.3 mL, 4.81 mmol). The reaction was monitored by TLC. After completion, the mixture was diluted with DCM and washed with saturated NaHCO$_3$ solution and brine. The combined organic layers were dried over Na$_2$SO$_4$, filtered and concentrated to get a crude residue, which was purified by silica gel column chromatography eluting with 0-40% ethyl acetate in n-hexane to afford the title compound as an off white solid (500 mg, yield 45%). $^1$H NMR (DMSO-d$_6$, 400 MHz): δ 12.38 (s, 1H), 8.12-8.19 (m, 2H), 7.56-7.62 (m, 1H), 7.43-7.51 (m, 1H), 4.99-5.11 (m, 1H), 4.94 (q, J=6.14 Hz, 1H), 4.80-4.89 (m, 1H), 4.27-4.37 (m, 1H), 3.10 (d, J=4.38 Hz, 1H), 2.97 (d, J=2.19 Hz, 1H), 2.32 (br. s, 3H), 1.51 (d, J=7.02 Hz, 1H), 1.46 (s, 9H), 1.02-1.15 (m, 3H). LCMS: [M+H]$^+$=458.05; R$_t$=4.33 min.

Step 3: N-(3-(benzo[d]thiazol-2-yl)-cis-5,7-dimethyl-4,5,6,7-tetrahydrothieno[2,3-c]pyridin-2-yl)acetamide

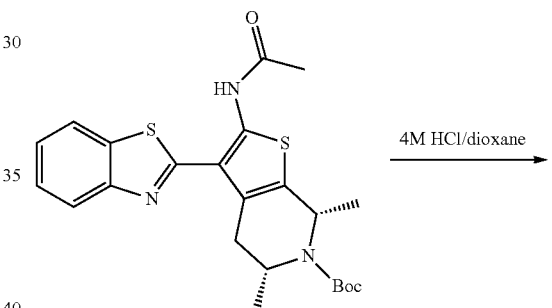

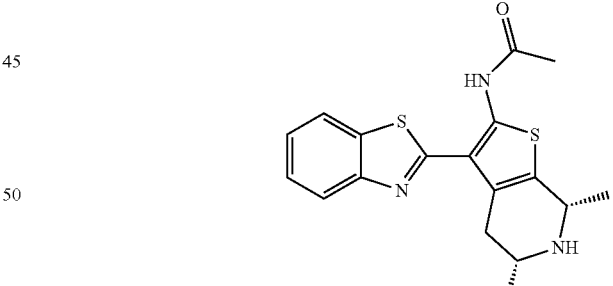

To a solution of tert-butyl 2-amino-3-(benzo[d]thiazol-2-yl)-cis-5,7-dimethyl-4,7-dihydrothieno[2,3-c]pyridine-6(5H)-carboxylate (500 mg, 0.11 mmol) in dioxane (5 mL) at 0° C. was added 4M HCl in dioxane (5 mL). After the addition, the resulting mixture was stirred at room temperature for 2 h. After completion, the reaction mixture was evaporated to dryness and the resulting in a crude residue which was purified by trituration in ether to afford the HCl salt of the title compound as a pale yellow solid (300 mg, 76% yield).

Example 35. Synthesis of (S)—N-(3-(benzo[d]thi-azol-2-yl)-6-isopropyl-4-methyl-4,5,6,7-tetrahydrothieno[2,3-c]pyridin-2-yl)acetamide (Compound 207) and (R)—N-(3-(benzo[d]thiazol-2-yl)-6-isopropyl-4-methyl-4,5,6,7-tetrahydrothieno[2,3-c]pyridin-2-yl)acetamide and (Compound 208)

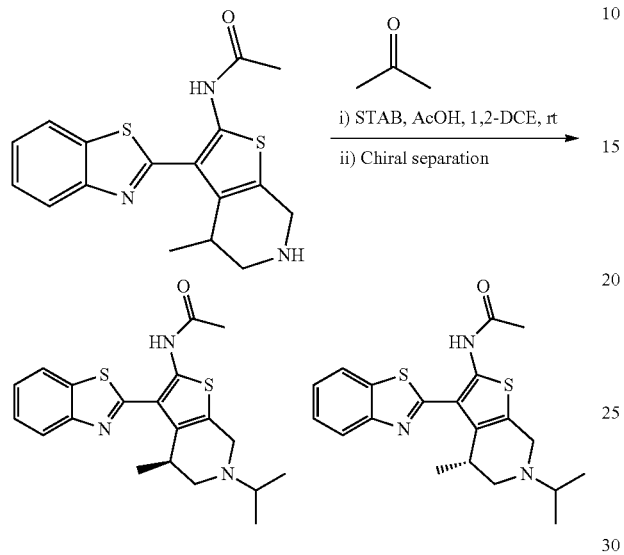

To a solution of N-(3-(benzo[d]thiazol-2-yl)-4-methyl-4,5,6,7-tetrahydrothieno[2,3-c]pyridin-2-yl)acetamide (80 mg, 0.23 mmol) and acetone (40 mg, 0.69 mmol) in DCE (5 mL) was added acetic acid (0.1 mL) and the reaction was stirred for 2 h at room temperature. Sodium triacetoxyborohydride (74 mg, 0.34 mmol) was then added, the reaction was allowed to stir for for another 12 h. The progress of the reaction was monitored by LCMS. After completion, the reaction mixture was diluted with water (15 mL) and extracted with ethyl acetate (3×10 mL). The combined organic layers were dried over $Na_2SO_4$ and concentrated under vacuum pressure to afford 90 mg of the crude compound as a mixture of enantiomers. The enantiomers were separated by using Chiral HPLC to give the title compounds as yellow solids.

Example 36. Synthesis of N-(3-(benzo[d]thiazol-2-yl)-5-methyl-4,5,6,7-tetrahydrothieno[2,3-c]pyridin-2-yl)acetamide (Compound 209) and N-(3-(benzo[d]thiazol-2-yl)-7-methyl-4,5,6,7-tetrahydrothieno[2,3-c]pyridin-2-yl)acetamide (Compound 210)

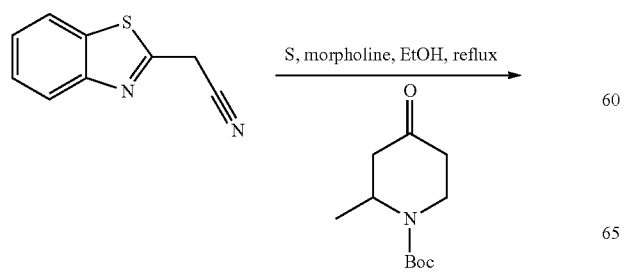

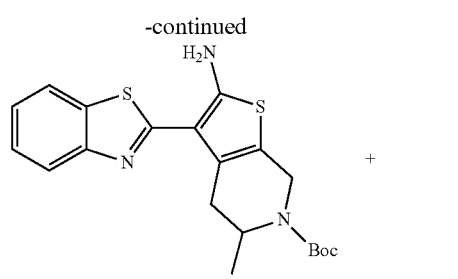

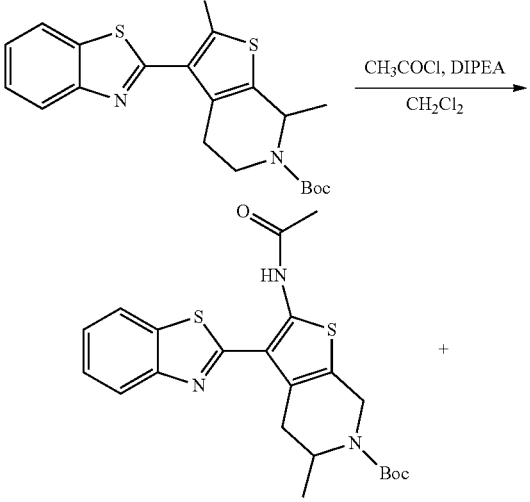

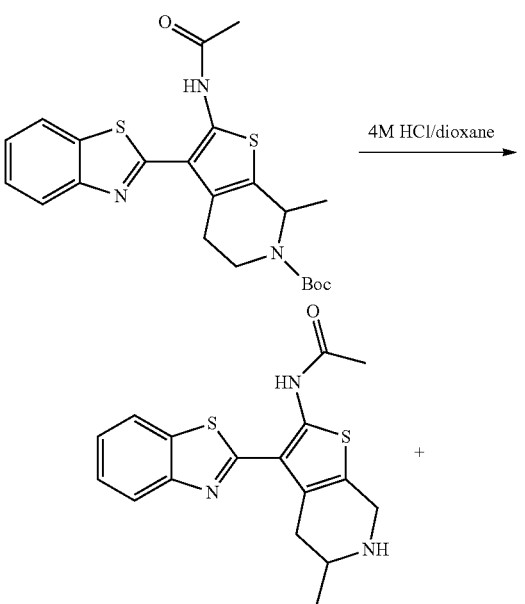

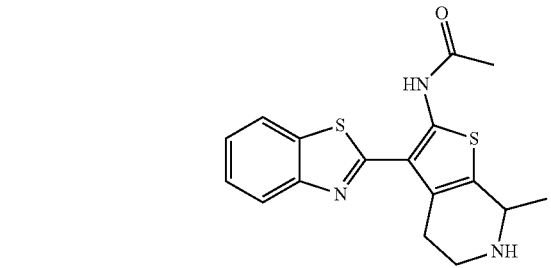 [SMILES: CC(=O)Nc1sc2c(c1-c1nc3ccccc3s1)CCNC2C]

Step 1: tert-butyl 2-amino-3-(benzo[d]thiazol-2-yl)-5-methyl-4,7-dihydrothieno[2,3-c]pyridine-6(5H)-carboxylate and tert-butyl-2-amino-3-(benzo[d]thiazol-2-yl)-7-methyl-4,7-dihydrothieno[2,3-c]pyridine-6(5H)-carboxylate

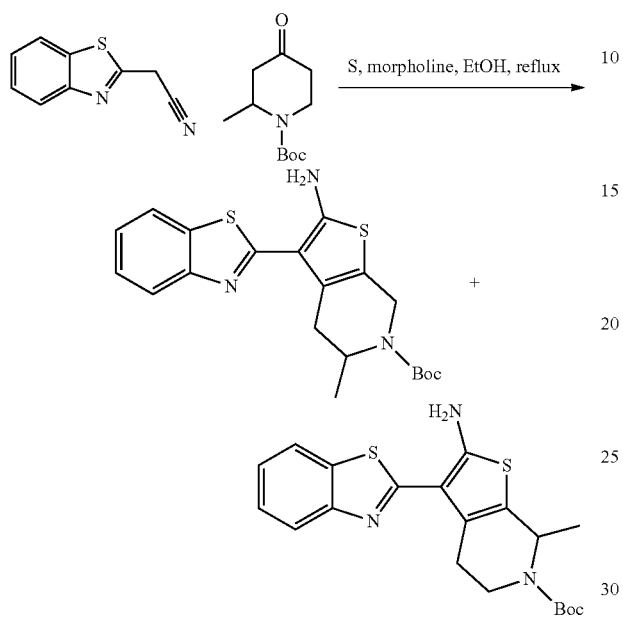

To a solution of 2-(benzo[d]thiazol-2-yl)acetonitrile (1 g, 5.74 mmol) in ethanol (10 mL) was added tert-butyl 2-methyl-4-oxopiperidine-1-carboxylate (1.22 g, 5.74 mmol), elemental sulfur (183 mg, 5.74 mmol), and morpholine (496 mg, 5.74 mmol) at room temperature. After addition, the resulting mixture was heated to reflux at 85° C. for 12 h and monitored by TLC. The reaction mixture was concentrated under vacuum pressure and the crude compound was purified by silica gel column chromatography eluting with 0-30% ethyl acetate in n-hexane to afford the mixture of title compounds as an off white solid (1.5 g, yield 65%). $^1$H NMR (DMSO-$d_6$, 400 MHz): 8.16 (d, J=7.86 Hz, 2H), 8.01 (d, J=7.86 Hz, 1H), 7.90 (d, J=7.86 Hz, 1H), 7.46 (t, J=7.63 Hz, 1H), 7.28-7.35 (m, 1H), 4.60-4.71 (m, 1H), 4.15-4.22 (m, 1H), 3.93-4.05 (m, 1H), 2.65-3.02 (m, 2H), 1.44 (s, 9H), 1.35 (d, J=6.47 Hz, 2H), 1.13 (d, J=6.94 Hz, 1H). LCMS: [M+H]$^+$=402.04; $R_t$=3.74 min.

Step 2: tert-butyl 2-acetamido-3-(benzo[d]thiazol-2-yl)-5-methyl-4,7-dihydrothieno[2,3-c]pyridine-6(5H)-carboxylate and tert-butyl-2-acetamido-3-(benzo[d]thiazol-2-yl)-7-methyl-4,7-dihydrothieno[2,3-c]pyridine-6(5H)-carboxylate

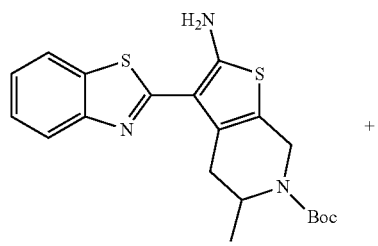

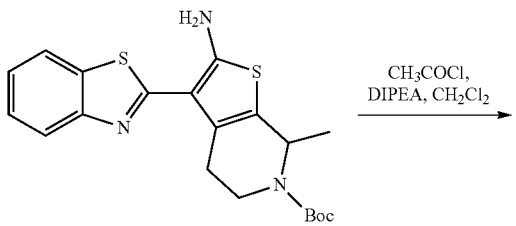

To a solution of a mixture of tert-butyl 2-amino-3-(benzo[d]thiazol-2-yl)-5-methyl-4,7-dihydrothieno[2,3-c]pyridine-6(5H)-carboxylate and tert-butyl-2-amino-3-(benzo[d]thiazol-2-yl)-7-methyl-4,7-dihydrothieno[2,3-c]pyridine-6(5H)-carboxylate (1.5 g, 3.74 mmol) in DCM (10 mL) at 0° C. was added DIPEA (1.3 mL, 7.48 mmol) and acetyl chloride (0.3 mL, 4.11 mmol) and the mixture was stirred at room temperature for 2 h and monitored by TLC. After completion, the reaction mixture was diluted with DCM and washed with saturated NaHCO$_3$ solution and brine. The combined organic layers were dried over Na$_2$SO$_4$, filtered and concentrated to get a crude residue, which was purified by silica gel column chromatography to afford the mixture of title compounds as an off white solid (1.3 g, 78% yield). $^1$H NMR (DMSO-$d_6$, 400 MHz): δ 12.53 (s, 1H), 8.10-8.18 (m, 2H), 7.54-7.62 (m, 1H), 7.43-7.50 (m, 1H), 5.15 (br. s, 1H), 4.66-4.87 (m, 1H), 3.99-4.30 (m, 2H), 2.71-3.20 (m, 3H), 2.32 (s, 3H), 1.46 (s, 9H), 1.12 (d, J=6.85 Hz, 1H). LCMS: [M+H]$^+$=444.10; $R_t$=4.06 min.

145

Step 3: N-(3-(benzo[d]thiazol-2-yl)-5-methyl-4,5,6,7-tetrahydrothieno[2,3-c]pyridin-2-yl)acetamide and N-(3-(benzo[d]thiazol-2-yl)-7-methyl-4,5,6,7-tetrahydrothieno[2,3-c]pyridin-2-yl)acetamide

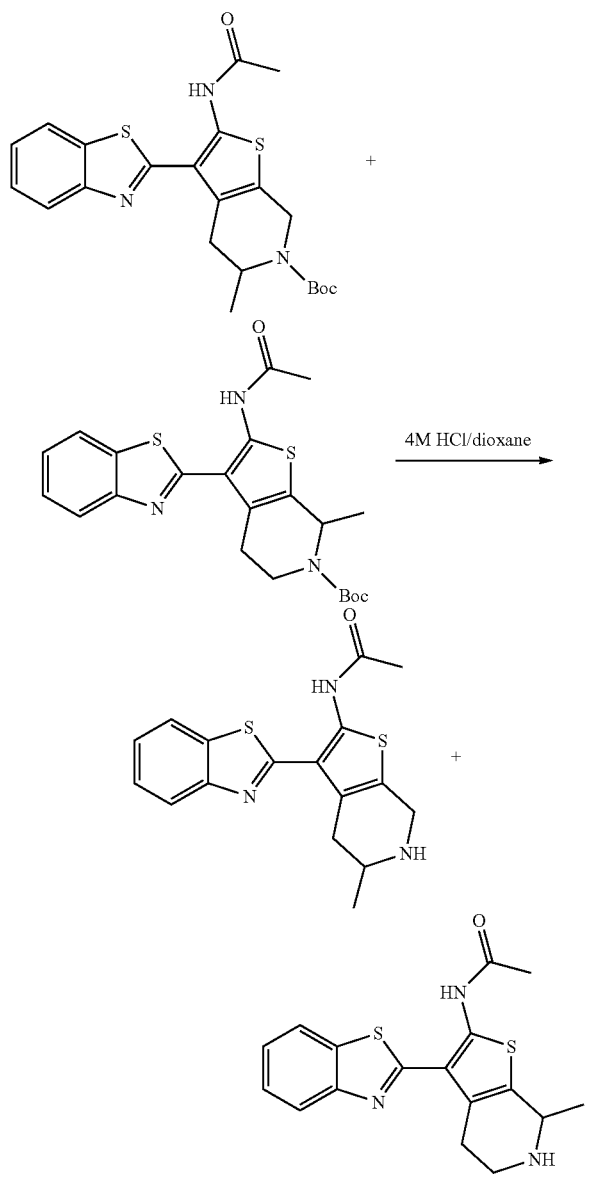

To a solution of a mixture of tert-butyl 2-acetamido-3-(benzo[d]thiazol-2-yl)-5-methyl-4,7-dihydrothieno[2,3-c]pyridine-6(5H)-carboxylate and tert-butyl-2-acetamido-3-(benzo[d]thiazol-2-yl)-7-methyl-4,7-dihydrothieno[2,3-c]pyridine-6(5H)-carboxylate (1.3 g, 2.93 mmol) in dioxane (15 mL) at 0° C. was added 4M HCl in dioxane (13 mL). After the addition, the resulting mixture was stirred at room temperature for 2 h. After completion, the reaction mixture was concentrated under vacuum pressure resulting in a crude residue which was purified by trituration in ether and pentane to afford 1 g mixture of the title compounds. This mixture of compounds was purified by HPLC to afford N-(3-(benzo[d]thiazol-2-yl)-5-methyl-4,5,6,7-tetrahydrothieno[2,3-c]pyridin-2-yl)acetamide (SY-2044) (170 mg) and

146

N-(3-(benzo[d]thiazol-2-yl)-7-methyl-4,5,6,7-tetrahydrothieno[2,3-c]pyridin-2-yl)acetamide (SY-2043) (200 mg) as yellow solids.

Example 37. Synthesis of N-(3-(benzo[d]thiazol-2-yl)-6-ethyl-5,7-dimethyl-4,5,6,7-tetrahydrothieno[2,3-c]pyridin-2-yl)acetamide (Compound 211)

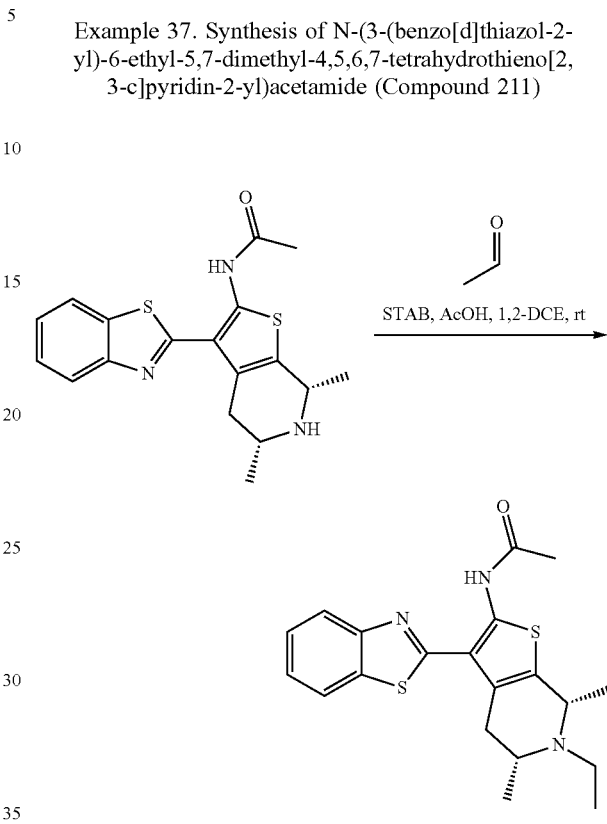

To a solution of acetaldehyde (18 mg, 0.42 mmol) and N-(3-(benzo[d]thiazol-2-yl)-5,7-dimethyl-4,5,6,7-tetrahydrothieno[2,3-c]pyridin-2-yl)acetamide (50 mg, 0.14 mmol) in 1,2-dichloroethane (5 mL) and AcOH (0.1 mL) was added sodium triacetoxyborohydride (44 mg, 0.21 mmol), and the reaction was stirred at room temperature for 12 h. After completion, the reaction mixture was diluted with water (15 mL) and extracted with ethyl acetate (3×10 mL). The combined organic solvents were dried over $Na_2SO_4$ and concentrated under vacuum pressure to provide the crude compound, which was purified using preparative HPLC to afford the title compound (40 mg, yield 74%) as a yellow solid.

Example 38. Synthesis of N-(3-(benzo[d]thiazol-2-yl)-4-methyl-5,6,7,8-tetrahydro-4H-thieno[2,3-c]azepin-2-yl)acetamide (Compound 212)

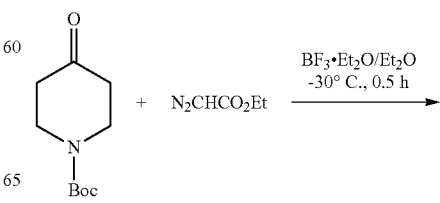

147

-continued

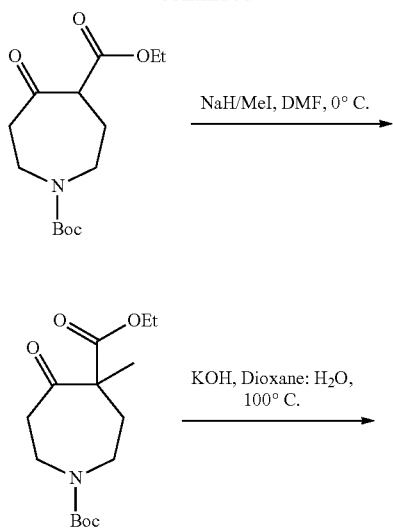

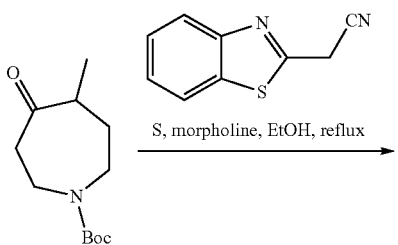

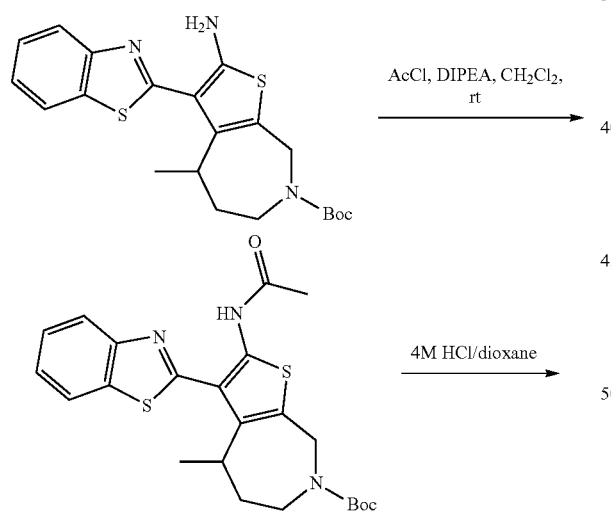

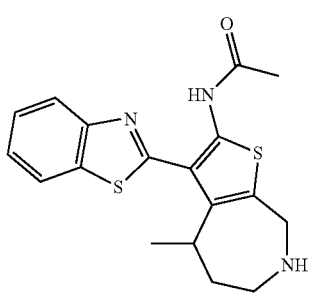 [SMILES: CC(=O)Nc1sc2c(c1-c1nc3ccccc3s1)C(C)CCNC2]

148

Step 1: 1-(tert-butyl) 4-ethyl 5-oxoazepane-1,4-dicarboxylate

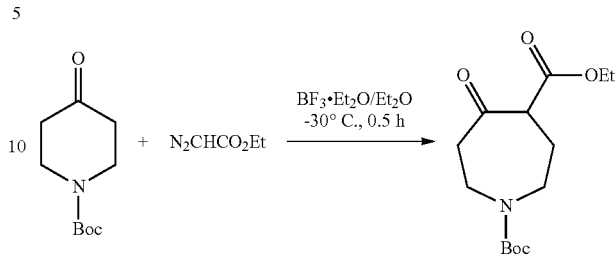

To a stirring solution of N-Boc piperidone (2 g, 10.05 mmol) in THF (20 mL) at −30° C. was added drop wise a solution of BF$_3$ etherate (1.39 mL, 11.0 mmol) and the reaction was stirred for 15 min. Ethyl diazoacetate (1.38 mL, 13.06 mmol) was then added, and the reaction mixture was stirred for another 1 h and monitored by TLC. After the completion, the reaction mixture was quenched with saturated sodium bicarbonate solution and extracted with EtOAc. The combined organic layers were dried over anhydrous Na$_2$SO$_4$ and filtered. The filtrate obtained was concentrated under reduced pressure to get a crude residue which was purified by silica-gel column chromatography eluting with 0-20% ethyl acetate in n-hexane to afford the title compound (1.35 g, yield 47%). $^1$H NMR (CDCl$_3$, 400 MHz): δ 4.22 (d, J=7.34 Hz, 1H), 3.72 (t, J=6.11 Hz, 4H), 2.44 (t, J=6.11 Hz, 4H), 1.50 (s, 9H), 1.44-1.48 (m, 4H), 1.24-1.32 (m, 1H). LCMS: [M-Boc+H]$^+$=185.90; R$_t$=1.66 min.

Step 2: 1-(tert-butyl) 4-ethyl 4-methyl-5-oxoazepane-1,4-dicarboxylate

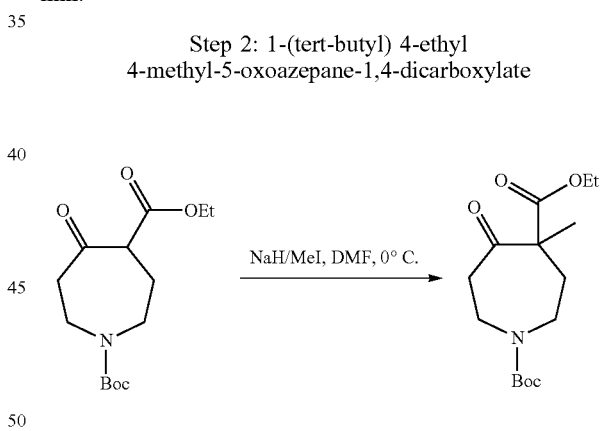

To a stirring solution of 1-(tert-butyl) 4-ethyl 5-oxoazepane-1,4-dicarboxylate (1.3 g, 1 eq) in DMF (10 mL) was added NaH (60% in paraffin oil, 0.18 g, 1 eq) at −5 to 0° C. and the resulting mixture was then stirred at room temperature for 1 h. The reaction mixture was cooled again to −5° C. and methyl iodide (1.62 g, 11.4 mmol) was added. The reaction mixture was allowed to stir for another 3 h at room temperature and monitored by TLC. After the completion of reaction, the reaction mixture as quenched by adding ice water and extracted with ethyl acetate. The combined organic fraction was dried over anhydrous Na$_2$SO$_4$ and concentrated to provide a crude product which was used in the next step without further purification. $^1$H NMR (CDCl$_3$, 400 MHz): δ 4.16-4.30 (m, 2H), 3.66-3.79 (m, 2H), 3.12-3.46 (m, 2H), 2.78-2.83 (m, 2H), 2.44 (t, J=6.21 Hz, 1H), 1.48-1.63 (m, 1H), 1.44 (s, 9H), 1.36 (s, 3H), 1.28 (t, J=7.10 Hz, 3H). LCMS: [M-Boc-H]$^+$=197.90; R$_t$=2.89 min.

Step 3: tert-butyl 4-methyl-5-oxoazepane-1-carboxylate

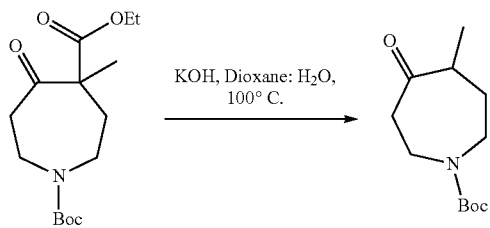 [SMILES: CCOC(=O)C1(C)CCN(C(=O)OC(C)(C)C)CCC1=O ; CC1CCN(C(=O)OC(C)(C)C)CCC1=O]

To a stirring solution of 1-(tert-butyl) 4-ethyl 4-methyl-5-oxoazepane-1,4-dicarboxylate (1.4 g, 4.68 mmol) in dioxane (20 mL) was added solution of 2M KOH solution (11.2 mL) at room temperature. The resulting solution was heated at 100° C. for 16 h monitored by TLC. The reaction mixture was cooled to room temperature, quenched with a saturated solution of sodium chloride and extracted with EtOAc. The combined organic layers were dried over anhydrous $Na_2SO_4$ and filtered. The filtrate obtained was concentrated under reduced pressure to get a crude residue which was purified by silica-gel (100-200 mesh) column chromatography eluting with 0-20% ethyl acetate in n-hexane to afford the title compound (500 mg, yield 47%). $^1$H NMR ($CDCl_3$, 400 MHz): δ 3.67-4.19 (m, 2H), 2.93-3.35 (m, 2H), 2.67-2.89 (m, 2H), 2.52 (d, J=16.22 Hz, 1H), 1.71-1.61 (m, 2H), 1.45 (s, 9H), 1.09 (d, J=6.58 Hz, 3H).

Step 4: tert-butyl 2-amino-3-(benzo[d]thiazol-2-yl)-4-methyl-4,5,6,8-tetrahydro-7H-thieno[2,3-c]azepine-7-carboxylate

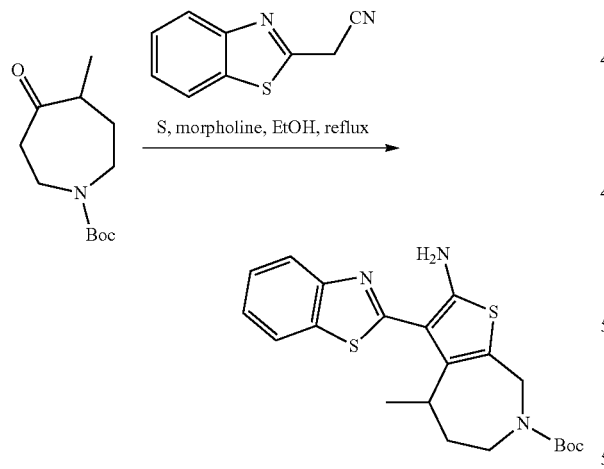

To a solution of 2-(benzo[d]thiazol-2-yl)acetonitrile (440 mg, 2.20 mmol) in ethanol (10 mL) was added tert-butyl 4-methyl-5-oxoazepane-1-carboxylate (500 mg, 2.20 mmol), elemental sulfur (84 mg, 2.20 mmol) and morpholine (0.19 mL, 2.20 mmol) at room temperature. After the addition, the resulting mixture was heated to reflux at 80° C. for 3 h and monitored by TLC. After the completion, the reaction mixture was concentrated under vacuum pressure and the residue obtained was stirred in ethanol for 30 min. The solid precipitated out was filtered and dried to afford the title compound as a yellow solid (200 mg, yield 22%). $^1$H NMR ($CDCl_3$, 400 MHz): δ 8.26 (d, J=7.54 Hz, 1H), 7.87-8.05 (m, 2H), 7.50-7.63 (m, 2H), 4.56 (q, J=6.95 Hz, 2H), 3.74 (br. s, 2H), 3.04 (d, J=4.44 Hz, 4H), 1.49 (t, J=6.88 Hz, 3H), 1.23-1.32 (m, 9H). ESMS: $[M+H]^+$=415.05; $R_t$=0.13 min.

Step 6: tert-butyl 2-acetamido-3-(benzo[d]thiazol-2-yl)-4-methyl-4,5,6,8-tetrahydro-7H-thieno[2,3-c]azepine-7-carboxylate

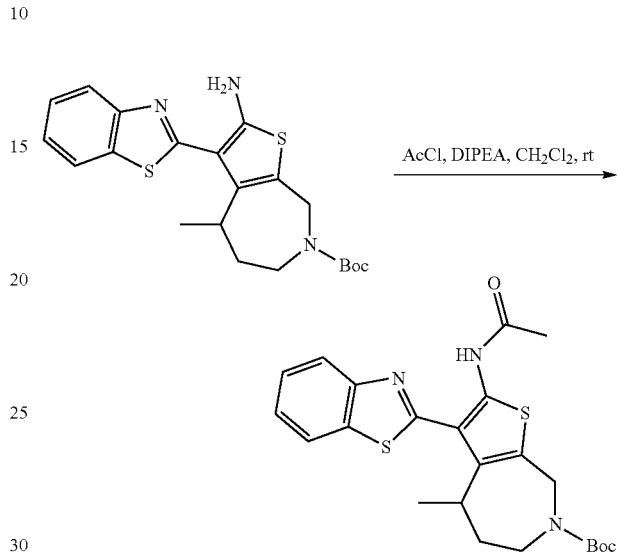

To a solution of tert-butyl 2-amino-3-(benzo[d]thiazol-2-yl)-4-methyl-4,5,6,8-tetrahydro-7H-thieno[2,3-c]azepine-7-carboxylate (350 mg, 0.84 mmol) in DCM (10 mL) at 0° C. was added DIPEA (0.37 mL, 2.10 mmol) and acetyl chloride (0.063 mL, 0.88 mmol) and the reaction was stirred overnight at room temperature. The reaction was monitored by TLC. After completion, the reaction was quenched by the addition of sat. $NaHCO_3$ solution and extracted with 10% $MeOH/CH_2Cl_2$ solution. The combined organic fractions were concentrated to get a crude residue which was purified by preparative HPLC to afford the title compound as an off-white solid (80 mg, 21% yield). $^1$H NMR ($CDCl_3$, 400 MHz): δ 12.97 (br. s, 1H), 7.99 (d, J=7.83 Hz, 1H), 7.91 (d, J=7.83 Hz, 1H), 7.53 (t, J=7.34 Hz, 1H), 7.38-7.45 (m, 1H), 4.52 (d, J=7.83 Hz, 1H), 4.46 (d, J=9.78 Hz, 1H), 3.94-3.97 (m, 1H), 3.75-3.85 (m, 2H), 2.34 (s, 3H), 2.20-2.22 (m, 1H), 1.93 (d, J=11.25 Hz, 1H), 1.55 (s, 3H), 1.43 (s, 9H). LCMS: $[M+H]^+$=458.0; $R_t$=3.76 min.

Step 7: N-(3-(benzo[d]thiazol-2-yl)-4-methyl-5,6,7,8-tetrahydro-4H-thieno[2,3-c]azepin-2-yl)acetamide

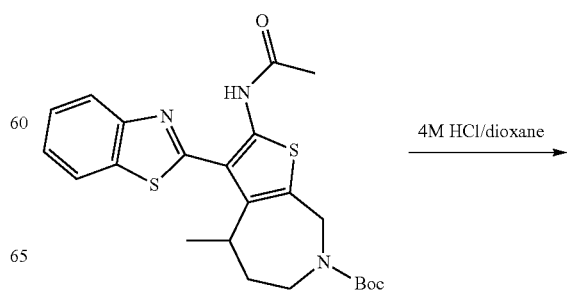

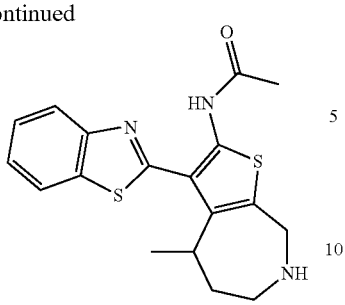

To a solution of tert-butyl 2-acetamido-3-(benzo[d]thiazol-2-yl)-4-methyl-4,5,6,8-tetrahydro-7H-thieno[2,3-c]azepine-7-carboxylate (210 mg, 0.46 mmol) in dioxane (3 mL) at 0° C. was added 4M HCl in dioxane (3 mL). After the addition, the resulting mixture was stirred at room temperature for 2 h and monitored by TLC. After completion, the reaction mixture was concentrated under vacuum pressure resulting in a crude residue, which was purified by trituration in ether and pentane to afford the title compound as an off white solid (150 mg HCl salt, 82% yield).

Example 39. Synthesis of N-(3-(benzo[d]thiazol-2-yl)-7-isopropyl-4-methyl-5,6,7,8-tetrahydro-4H-thieno[2,3-c]azepin-2-yl)acetamide (Compound 213)

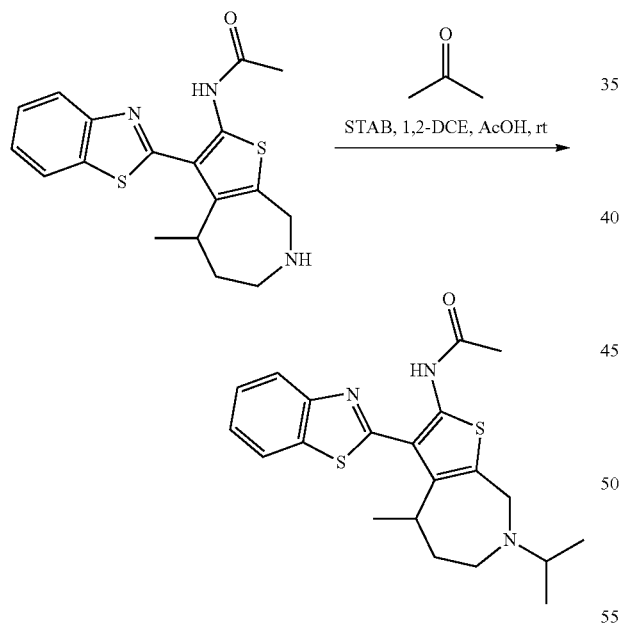

To the solution of N-(3-(benzo[d]thiazol-2-yl)-4-methyl-5,6,7,8-tetrahydro-4H-thieno[2,3-c]azepin-2-yl)acetamide (100 mg, 0.28 mmol) and acetone (0.062 mL, 0.84 mmol) in 1,2-dichloroethane (10 mL) and AcOH (0.1 mL) was added sodium triacetoxyborohydide (89 mg, 0.42 mmol), and the reaction was stirred at room temperature for 3 h. The reaction was monitored by TLC. Upon completion, the reaction mixture was diluted with water (15 mL) and extracted with ethyl acetate (3×10 mL). The combined organic layers were dried over Na$_2$SO$_4$ and concentrated under vacuum pressure resulting in the crude compound, which was purified using preparative HPLC to afford the title compound as a yellow solid (40 mg, yield 36%).

Example 40. N-(3-(benzo[d]thiazol-2-yl)-7-(trifluoromethyl)-4,5,6,7-tetrahydrothieno[2,3-c]pyridin-2-yl)acetamide (Compound 214) and N-(3-(benzo[d]thiazol-2-yl)-5-(trifluoromethyl)-4,5,6,7-tetrahydrothieno[2,3-c]pyridin-2-yl)acetamide (Compound 215)

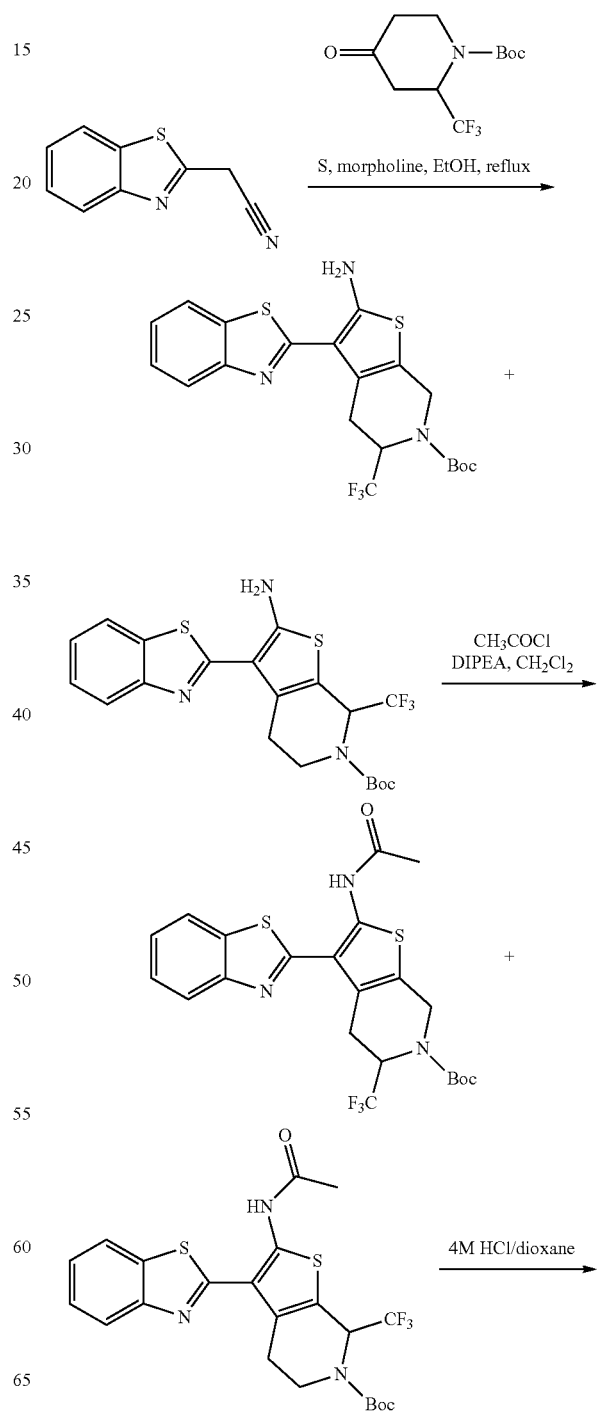

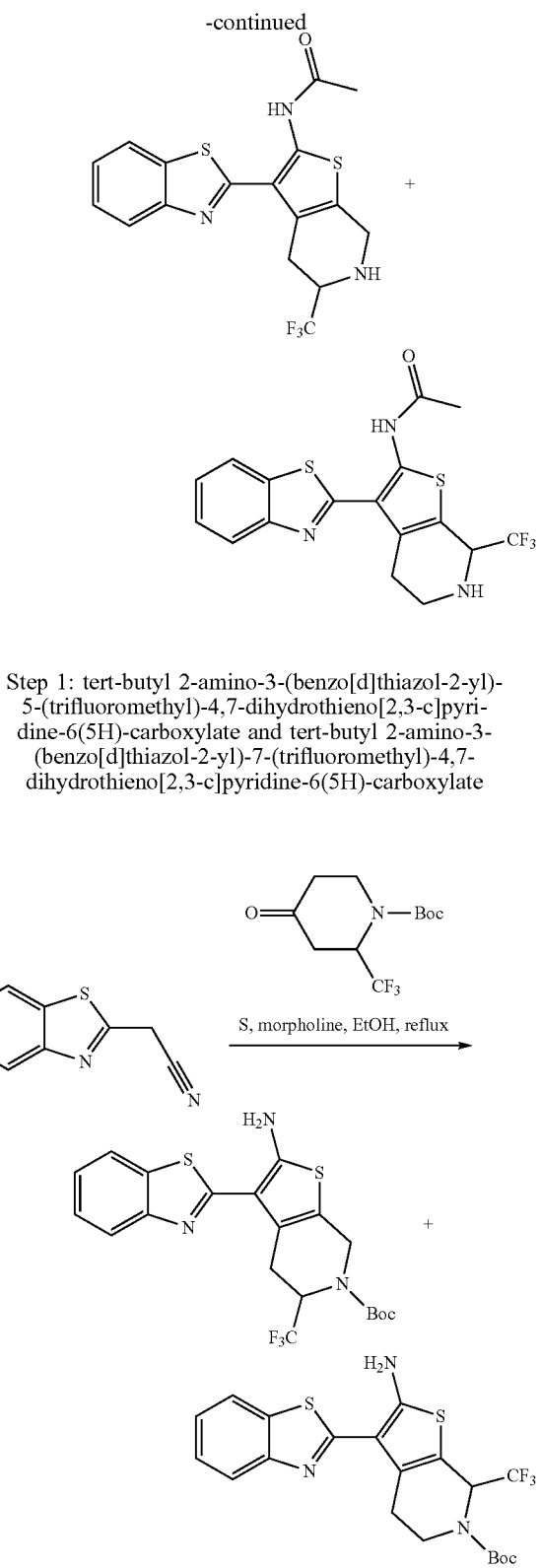

Step 1: tert-butyl 2-amino-3-(benzo[d]thiazol-2-yl)-5-(trifluoromethyl)-4,7-dihydrothieno[2,3-c]pyridine-6(5H)-carboxylate and tert-butyl 2-amino-3-(benzo[d]thiazol-2-yl)-7-(trifluoromethyl)-4,7-dihydrothieno[2,3-c]pyridine-6(5H)-carboxylate To a solution of 2-(benzo[d]thiazol-2-yl)acetonitrile (300 mg, 1.72 mmol) in ethanol (10 mL) was added tert-butyl 4-oxo-2-(trifluoromethyl)piperidine-1-carboxylate (460 mg, 1.72 mmol), elemental sulfur (55 mg, 1.72 mmol) and morpholine (150 mg, 1.72 mmol) at room temperature and the resulting reaction mixture was heated to reflux at 85° C. for 4 h and monitored by TLC. The reaction mixture was dried under vacuum pressure and the crude compound was purified by trituration with methanol to afford the mixture of the title compounds as an off white solid (700 mg, yield 89%). LCMS: [M+H]⁺=456.0; R$_t$=3.50 min, [M+H]⁺= 455.9; R$_t$=3.59 min.

Step 2: tert-butyl 2-acetamido-3-(benzo[d]thiazol-2-yl)-5-(trifluoromethyl)-4,7-dihydrothieno[2,3-c]pyridine-6(5H)-carboxylate and tert-butyl-2-acetamido-3-(benzo[d]thiazol-2-yl)-7-(trifluoromethyl)-4,7-dihydrothieno[2,3-c]pyridine-6(5H)-carboxylate

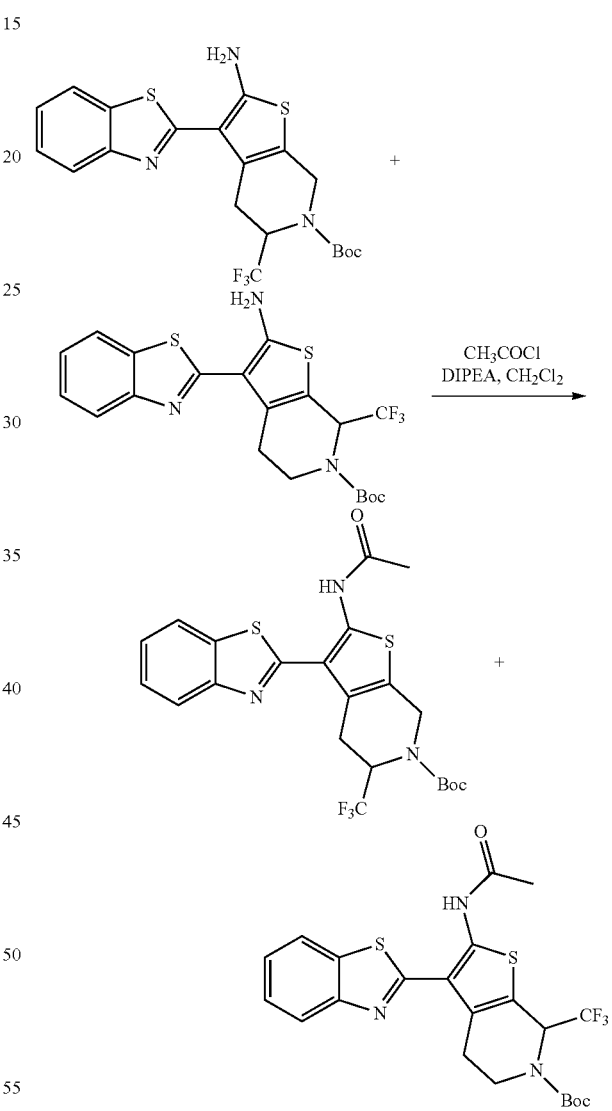

To a solution of mixture of tert-butyl 2-amino-3-(benzo[d]thiazol-2-yl)-5-(trifluoromethyl)-4,7-dihydrothieno[2,3-c]pyridine-6(5H)-carboxylate and tert-butyl 2-amino-3-(benzo[d]thiazol-2-yl)-7-(trifluoromethyl)-4,7-dihydrothieno[2,3-c]pyridine-6(5H)-carboxylate (700 mg, 1.53 mmol) in DCM (10 mL) at 0° C. was added DIPEA (0.67 mL, 3.84 mmol) and acetyl chloride (0.22 mL, 1.61 mmol). The reaction was stirred at room temperature for 4 h and monitored by TLC and LCMS. After completion, the reaction mixture was quenched with saturated NaHCO₃ solution and extracted with DCM. The combined organic layers were dried over Na₂SO₄, filtered, and concentrated to get a crude residue, which was purified by silica gel (100-200 mesh) column chromatography eluting with 0-20% ethyl acetate in n-hexane to afford the mixture of title compounds as an off white solid (500 mg, 65% yield). ¹H NMR (CDCl₃, 400 MHz): δ 7.96-8.11 (m, 1H), 7.90 (d, J=7.34 Hz, 1H), 7.48-7.59 (m, 1H), 7.38-7.47 (m, 1H), 4.98-5.21 (m, 1H), 4.27-4.50 (m, 1H), 3.68 (d, J=18.59 Hz, 1H), 3.26-3.52 (m, 2H), 2.42 (br. s, 3H), 1.50-1.58 (m, 9H). LCMS: [M+H]⁺=497.90; R$_t$=3.65 min, [M+H]⁺=498.00; R$_t$=3.70 min.

Step 3: N-(3-(benzo[d]thiazol-2-yl)-7-(trifluoromethyl)-4,5,6,7-tetrahydrothieno[2,3-c]pyridin-2-yl)acetamide and N-(3-(benzo[d]thiazol-2-yl)-5-(trifluoromethyl)-4,5,6,7-tetrahydrothieno[2,3-c]pyridin-2-yl)acetamide To a solution of mixture of tert-butyl 2-acetamido-3-(benzo[d]thiazol-2-yl)-5-(trifluoromethyl)-4,7-dihydrothieno[2,3-c]pyridine-6(5H)-carboxylate and tert-butyl-2-acetamido-3-(benzo[d]thiazol-2-yl)-7-(trifluoromethyl)-4,7-dihydrothieno[2,3-c]pyridine-6(5H)-carboxylate (500 mg, 1.00 mmol) in dioxane (5 mL) at 0° C. was added 4M HCl in dioxane (5 mL). After the addition, the resulting mixture was stirred at room temperature for 4 h. Upon completion, the reaction mixture was concentrated under vacuum pressure resulting in a crude residue which was purified by trituration in ether and pentane to afford 450 mg crude mixture of the title compounds. The compounds were separated by preparative HPLC to afford N-(3-(benzo[d]thiazol-2-yl)-7-(trifluoromethyl)-4,5,6,7-tetrahydrothieno[2,3-c]pyridin-2-yl)acetamide (80 mg) and N-(3-(benzo[d]thiazol-2-yl)-5-(trifluoromethyl)-4,5,6,7-tetrahydrothieno[2,3-c]pyridin-2-yl)acetamide (65 mg) as yellow solids.

Example 41. Synthesis of N-(3-(benzo[d]thiazol-2-yl)-6-isopropyl-7-methyl-4,5,6,7-tetrahydrothieno[2,3-c]pyridin-2-yl)acetamide (Compound 216)

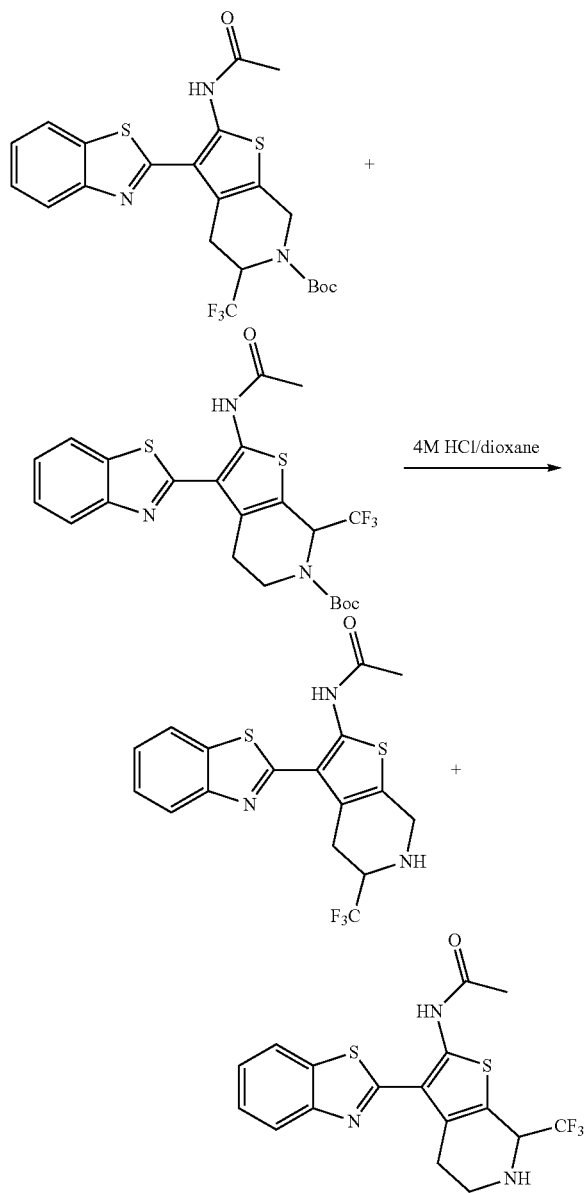

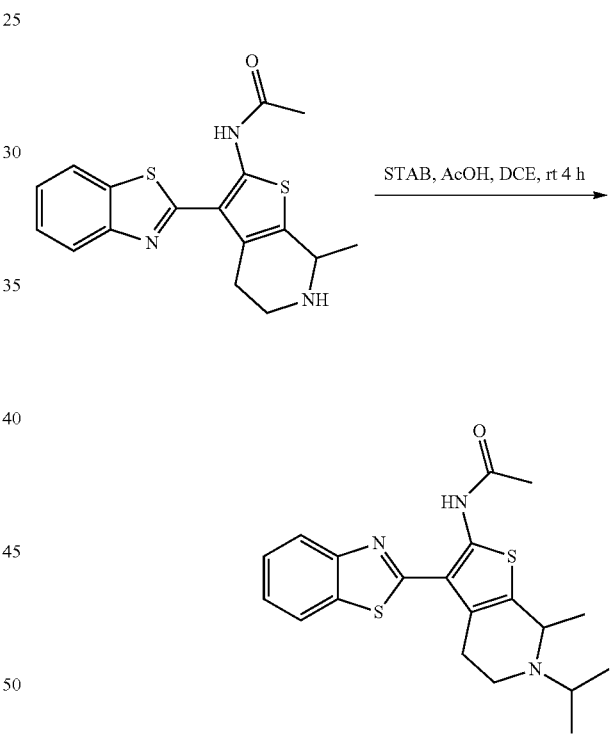

To the solution of N-(3-(benzo[d]thiazol-2-yl)-7-methyl-4,5,6,7-tetrahydrothieno[2,3-c]pyridin-2-yl)acetamide (150 mg, 0.43 mmol) and acetone (0.09 mL, 1.31 mmol) in 1,2-dichloroethane (5 mL) was added AcOH (0.1 mL) followed by sodium triacetoxyborohydride (138 mg, 0.65 mmol). The reaction was stirred at room temperature for 12 h and monitored by TLC. After the reaction was complete, the mixture was diluted with water (15 mL) and extracted with ethyl acetate (3×10 mL). The combined organic fractions were dried over Na₂SO₄ and concentrated in vacuo resulting in the crude compound, which was purified using preparative HPLC to afford the title compound (20 mg, yield 12%) as a yellow solid.

Example 42. Synthesis of N-(3-(benzo[d]thiazol-2-yl)-4-fluoro-4,5,6,7-tetrahydrothieno[2,3-c]pyridin-2-yl) acetamide (Compound 217)

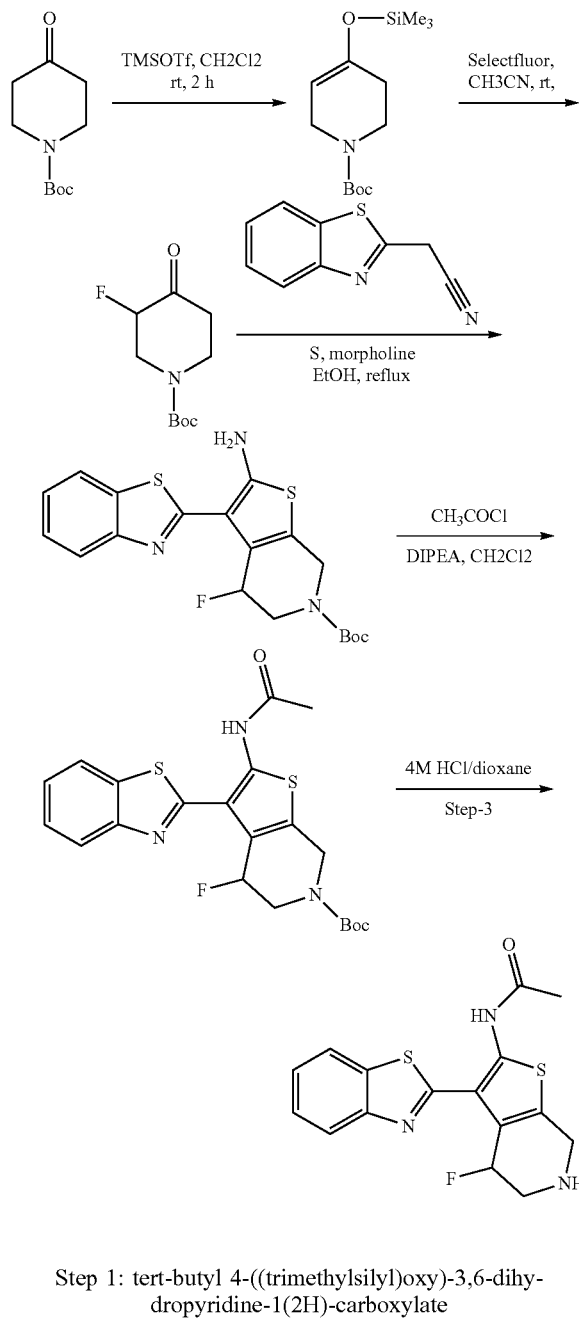

Step 1: tert-butyl 4-((trimethylsilyl)oxy)-3,6-dihydropyridine-1(2H)-carboxylate

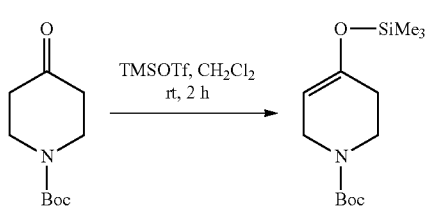 [SMILES: CC(C)(C)OC(=O)N1CCC(=O)CC1 ; CC(C)(C)OC(=O)N1CC=C(O[Si](C)(C)C)CC1]

To a stirring solution of tert-butyl 4-oxopiperidine-1-carboxylate (4 g, 20.08 mmol) in DCM (40 mL) was added TMS-triflate (6.69 g, 30.12 mmol) and TEA (6.09 g, 60.24 mmol). The resulting reaction mixture was stirred at room temperature for 2 h. The reaction progress of was monitored by TLC. After completion, the reaction mixture was concentrated under reduced pressure to dryness. The residue was diluted with water, filtered and concentrated under reduced pressure, then purified by silica gel column chromatography eluting with 0-20% ethyl acetate in n-hexane to afford the title compound as a light yellow oil. (2.3 g, yield 42%). $^1$H NMR (400 MHz, Chloroform-d) δ 4.79 (s, 1H), 3.87 (m, 2H), 3.52 (t, J=5.8 Hz, 2H), 2.10 (m, 2H), 1.46 (s, 9H), 0.19 (s, 9H).

Step 2: tert-butyl 3-fluoro-4-oxopiperidine-1-carboxylate

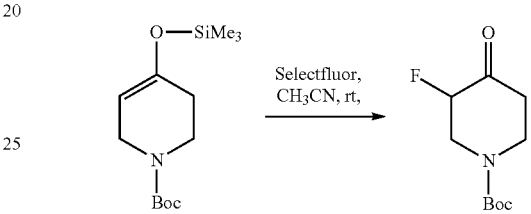

To a solution of tert-butyl 4-((trimethylsilyl)oxy)-3,6-dihydropyridine-1(2H)-carboxylate (4 g, 14.75 mmol) in ACN (150 mL) was added selectfluor (5.76 g, 14.75 mmol). The resulting reaction mixture was stirred at room temperature for 2 h and monitored by TLC. After completion, the reaction mixture was concentrated to get a crude residue that was purified by silica gel column chromatography eluting with 0-30% ethyl acetate in n-hexane to afford the title compound as a white solid (1.3 g, yield 41%).

Step 3: tert-butyl 2-amino-3-(benzo[d]thiazol-2-yl)-4-fluoro-4,7-dihydrothieno[2,3-c]pyridine-6(5H)-carboxylate

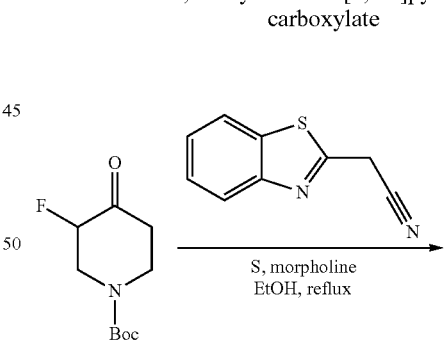

To a solution of 2-(benzo[d]thiazol-2-yl)acetonitrile (1 g, 4.60 mmol) in ethanol (10 mL) was added tert-butyl 3-fluoro-4-oxopiperidine-1-carboxylate (0.801 g, 4.60 mmol), elemental sulfur (0.147 g, 4.60 mmol, and morpholine (0.4 g, 5.74 mmol) at room temperature. After addition, the resulting mixture was heated to reflux at 80° C. for 12 h and monitored by TLC. After completion, the reaction mixture was concentrated under vacuum pressure and the crude compound was purified by triturating with methanol to afford the title compound as a yellow solid (0.6 g, yield 33.3%).

Step 4: tert-butyl 2-acetamido-3-(benzo[d]thiazol-2-yl)-4-fluoro-4,7-dihydrothieno[2,3-c]pyridine-6(5H)-carboxylate

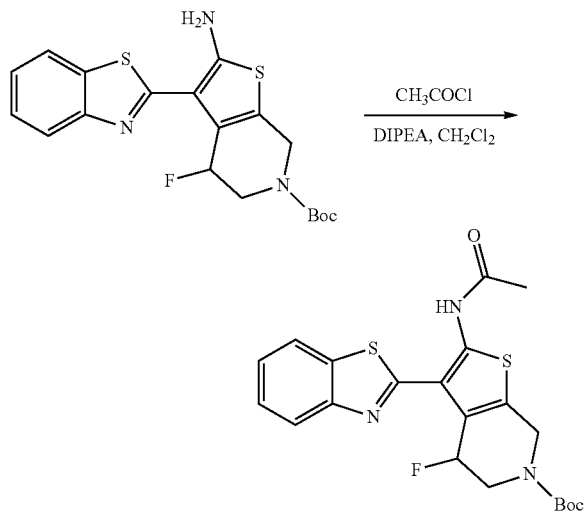

To a solution of tert-butyl 2-amino-3-(benzo[d]thiazol-2-yl)-4-fluoro-4,7-dihydrothieno[2,3-c]pyridine-6(5H)-carboxylate (1 g, 2.46 mmol) in DCM (20 mL) at 0° C. was added DIPEA (0.48 g, 3.69 mmol) and acetyl chloride (0.213 g, 2.71 mmol). The resulting reaction mixture was stirred at room temperature for 2 h and the progress of the reaction was monitored by TLC. After completion, the reaction mixture was diluted with DCM and washed with saturated NaHCO$_3$ solution and brine. The combined organic layers were dried over anhydrous Na$_2$SO$_4$, filtered and concentrated to get a crude residue, which was purified by silica gel column chromatography eluting with 0-20% ethyl acetate in n-hexane to afford the title compound as a yellow solid (0.44 g, yield 51.40%). LCMS: [M+1]$^+$= 448.05; R$_t$=3.56 min.

Step 5: N-(3-(benzo[d]thiazol-2-yl)-4-fluoro-4,5,6,7-tetrahydrothieno[2,3-c]pyridin-2-yl) acetamide

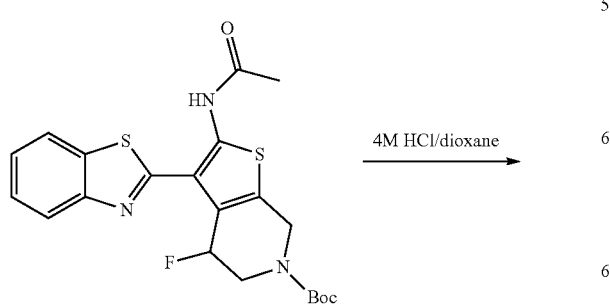

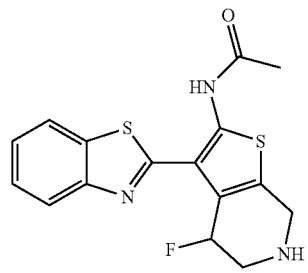

To a solution of tert-butyl 2-acetamido-3-(benzo[d]thiazol-2-yl)-4-fluoro-4,7-dihydrothieno[2,3-c]pyridine-6(5H)-carboxylate (0.05 g, 0.123 mmol) in dioxane (2 mL) at 0° C. was added 4M HCl in dioxane (2 mL). After addition, the resulting mixture was stirred at room temperature for 2 h and then concentrated under vacuum pressure resulting in a crude residue which was purified by preparative HPLC. The compound was taken in methanol and neutralised with carbonate resin, filtered, dried and concentrated under vacuum pressure to afford the title compound as an off white solid (0.015 g, 38.6% yield).

Example 43. Separation of N-((5R,7S)-3-(benzo[d]thiazol-2-yl)-5,7-dimethyl-4,5,6,7-tetrahydrothieno[2,3-c]pyridin-2-yl)acetamide (Compound 218) and N-((5S,7R)-3-(benzo[d]thiazol-2-yl)-5,7-dimethyl-4,5,6,7-tetrahydrothieno[2,3-c]pyridin-2-yl)acetamide (Compound 219)

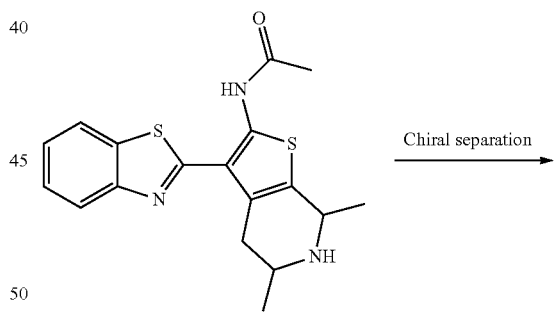

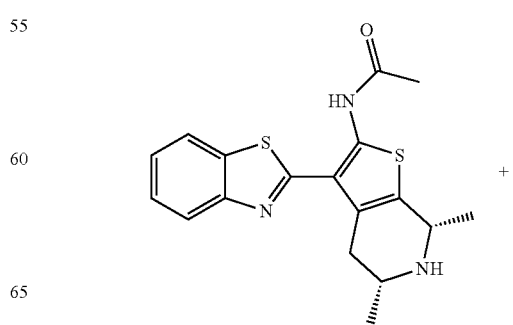

-continued

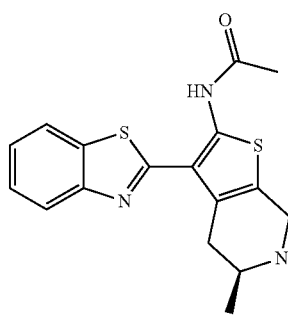

A mixture of stereoisomers was separated by chiral HPLC to provide isomerically pure compounds.

Example 44. Synthesis of N-(3-(benzo[d]thiazol-2-yl)-4-fluoro-6-isopropyl-4,5,6,7-tetrahydrothieno[2,3-c]pyridin-2-yl) acetamide (Compound 220)

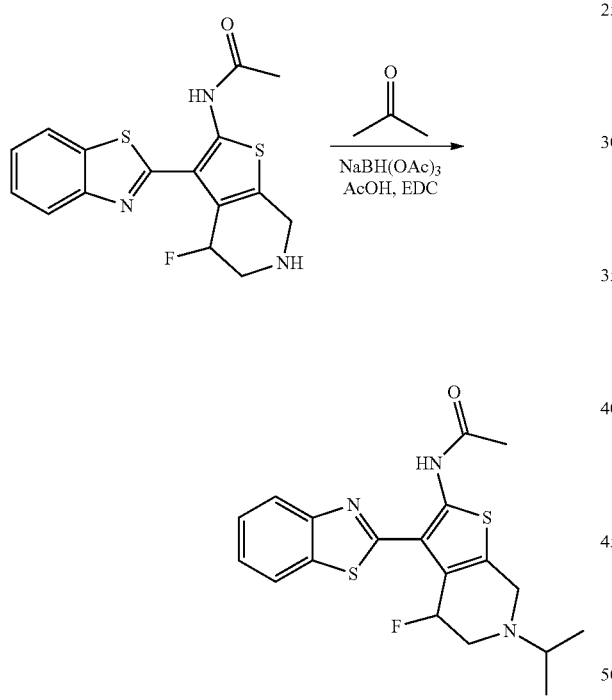

To a stirring solution of N-(3-(benzo[d]thiazol-2-yl)-4-fluoro-4,5,6,7-tetrahydrothieno[2,3-c]pyridin-2-yl)acetamide (0.1 g, 0.287 mmol), propan-2-one (0.083 g, 1.43 mmol) in dichloroethane (4 mL) and acetic acid (0.086 g, 1.43 mmol) was added and the reaction was stirred at room temperature for 15 h. Sodium triacetoxyborohydride (0.303 g, 1.43 mmol) was then added at 0° C. and the reaction was stirred at room temperature for 3 h. After completion, the reaction mixture was quenched with aqueous sat. NaHCO₃ solution and extracted with 10% MeOH/DCM. The combined organic layers were dried over anhydrous Na₂SO₄; filtered and concentrated to get a crude residue, which was purified by preparative HPLC to afford the title compound as a yellow solid (0.01 g, yield 9%).

Example 45. Synthesis of N-(6-amino-3-(benzo[d]thiazol-2-yl)-4,5,6,7-tetrahydrobenzo[b]thiophen-2-yl)acetamide (Compound 221)

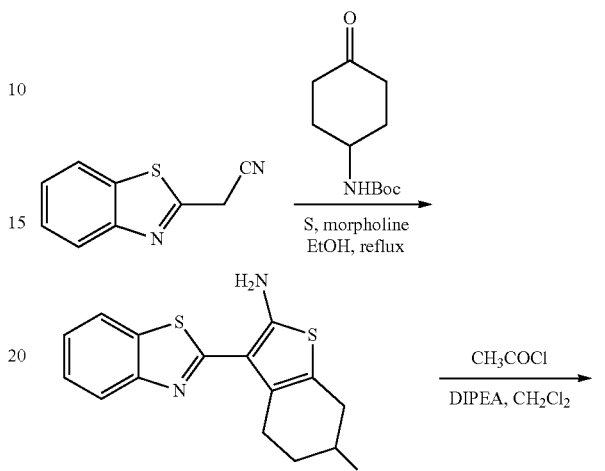

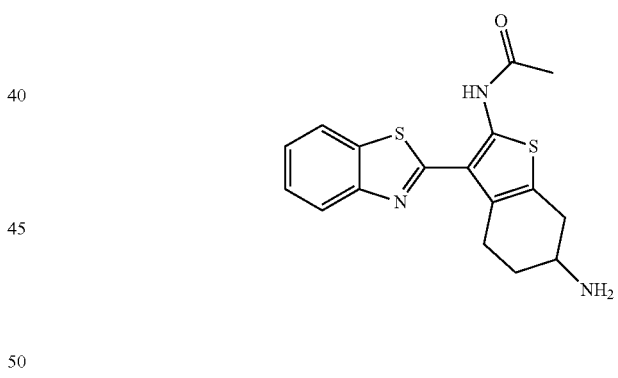

Step 1: tert-butyl (2-amino-3-(benzo[d]thiazol-2-yl)-4,5,6,7-tetrahydrobenzo[b]thiophen-6-yl)carbamate

163

-continued

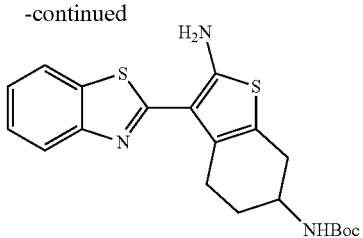

To a solution of 2-(benzo[d]thiazol-2-yl)acetonitrile (4 g, 22.9 mmol) in ethanol (30 mL) was added tert-butyl (4-oxocyclohexyl)carbamate (4.8 g, 22.9 mmol), elemental sulfur (0.732 g, 22.9 mmol), and morpholine (1.9 g, 22.9 mmol) at rt. After the addition, the resulting mixture was heated to reflux at 80° C. for 3 h and monitored by TLC. After completion, the reaction mixture was concentrated under vacuum pressure and the crude compound was purified by triturating with methanol to afford the title compound as a yellow solid (7 g, yield 76%). LCMS: [M+H]$^+$=402.0; R$_t$=3.84 min.

Step 2: tert-butyl (2-acetamido-3-(benzo[d]thiazol-2-yl)-4,5,6,7-tetrahydrobenzo[b]thiophen-6-yl)carbamate

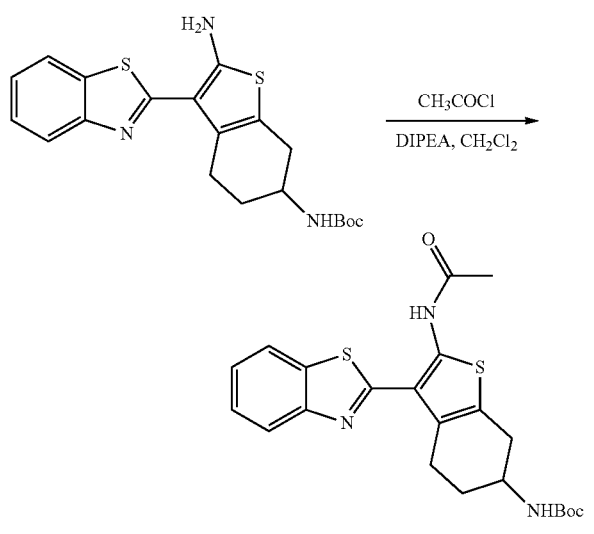

To a solution of tert-butyl (2-amino-3-(benzo[d]thiazol-2-yl)-4,5,6,7-tetrahydrobenzo[b]thiophen-6-yl)carbamate (4 g, 9.97 mmol) in DCM (10 mL) at 0° C. was added DIPEA (3.5 mL, 19.95 mmol) and acetyl chloride (0.8 mL, 11.9 mmol). The resulting reaction mixture was stirred at room temperature for 2 h and monitored by TLC. After completion, the reaction mixture was diluted with DCM and washed with saturated NaHCO$_3$ solution and brine. The combined organic layers were dried over anhydrous Na$_2$SO$_4$, filtered, and concentrated to get a crude residue. The crude compound was purified by silica gel column chromatography eluting with 0-5% MeOH/DCM to afford the title compound as a yellow solid (4 g, crude). LCMS: [M+Na]$^+$=465.95; R$_t$=5.38 min.

164

Step 3: N-(6-amino-3-(benzo[d]thiazol-2-yl)-4,5,6,7-tetrahydrobenzo[b]thiophen-2-yl)acetamide

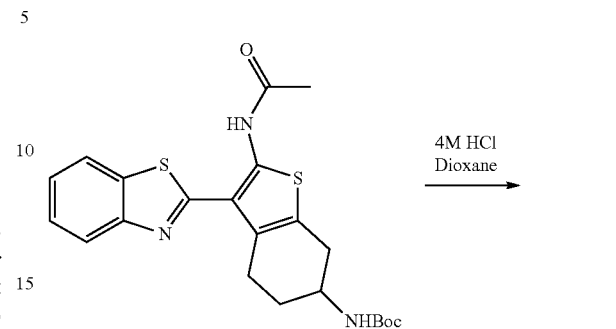

To a solution of tert-butyl (2-acetamido-3-(benzo[d]thiazol-2-yl)-4,5,6,7-tetrahydrobenzo[b]thiophen-6-yl)carbamate (2 g, 4.50 mmol) in dioxane (20 mL) at 0° C. was added 4M HCl in dioxane (10 mL). After addition, the resulting mixture was stirred at room temperature for 2 h. After completion, the reaction mixture was concentrated under vacuum pressure resulting in a crude residue. The compound was taken in methanol and neutralised with carbonate resin; filtered; dried and concentrated under vacuum pressure to afford the title compound (2 g, crude).

Example 46. Synthesis of N,N'-(3-(benzo[d]thiazol-2-yl)-4,5,6,7-tetrahydrobenzo[b]thiophene-2,6-diyl) diacetamide (Compound 222)

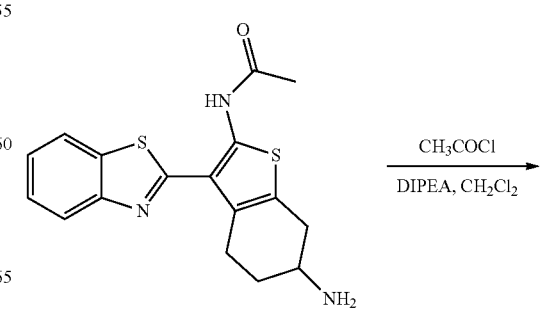

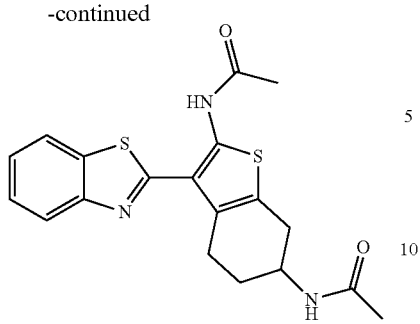

To a solution of N-(6-amino-3-(benzo[d]thiazol-2-yl)-4,5,6,7-tetrahydrobenzo[b]thiophen-2-yl)acetamide (0.1 g, 0.29 mmol) in DCM (10 mL) at 0° C. was added DIPEA (0.055 g, 0.43 mmol) and acetyl chloride (0.029 g, 0.29 mmol). The resulting reaction mixture was stirred at rt for 2 h and monitored by TLC. After completion, the reaction mixture was diluted with DCM and washed with saturated NaHCO₃ solution and brine. The combined organic layers were dried over anhydrous Na₂SO₄, filtered and concentrated to get a crude residue that was purified by silica gel column chromatography eluting with 0-10% MeOH/DCM to afford the title compound as an off white solid (0.07 g, 62% yield).

Example 47. Synthesis of N-(3-(benzo[d]thiazol-2-yl)-6-(dimethylamino)-4,5,6,7-tetrahydrobenzo[b]thiophen-2-yl)acetamide (Compound 223)

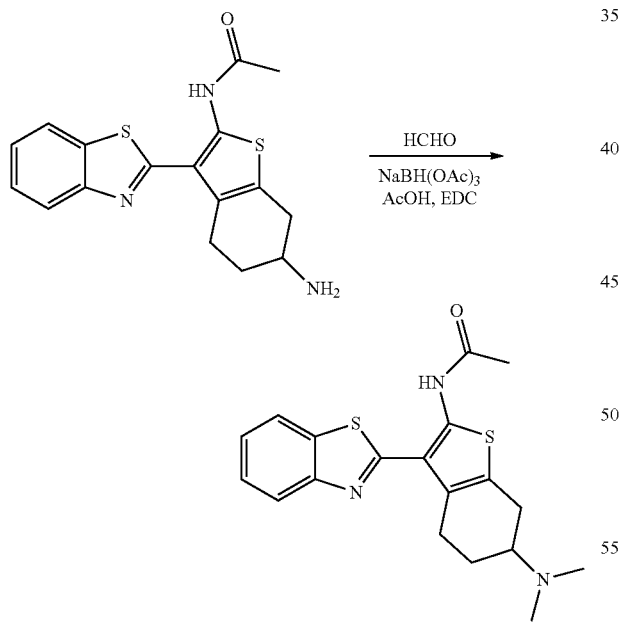

To a stirring solution of N-(6-amino-3-(benzo[d]thiazol-2-yl)-4,5,6,7-tetrahydrobenzo[b]thiophen-2-yl)acetamide (0.1 g, 0.29 mmol) was added formalin (0.055 g, 1.45 mmol) in dichloroethane (5 mL) and acetic acid (0.1 mL). The reaction was stirred at room temperature for 3 h, then sodium triacetoxyborohydride (0.122 g, 0.58 mmol) was added at 0° C. and reaction was stirred at room temperature for 16 h. After completion, the reaction mixture was quenched with aqueous sat. NaHCO₃ solution and extracted with 10% MeOH/DCM. The combined organic layers were dried over anhydrous Na₂SO₄, filtered and concentrated to get a crude residue, which was purified by preparative HPLC to afford the title compound as a light yellow solid (0.08 g, yield 74%).

Example 48. Synthesis of N-(3-(6-methylbenzo[d]thiazol-2-yl)-4,5,6,7-tetrahydrothieno[2,3-c]pyridin-2-yl)acetamide (Compound 224)

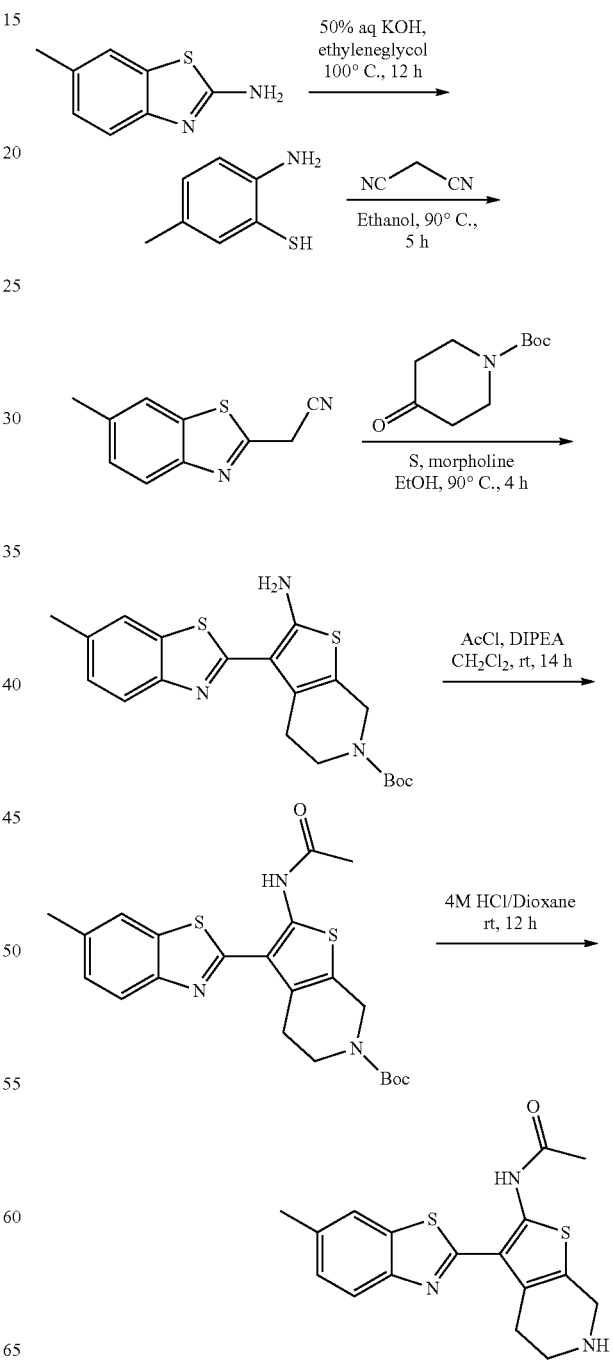

Step 1: 2-amino-5-methylbenzenethiol

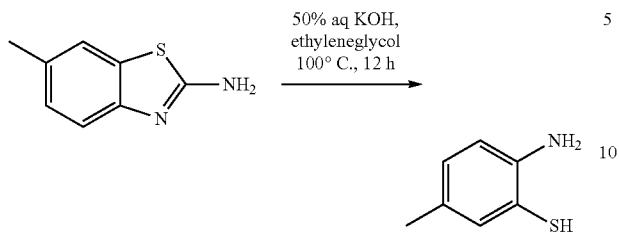

To a stirring solution of 6-methylbenzo[d]thiazol-2-amine (1.6 g, 9.73 mmol) in ethylene glycol (10 mL) was added a 50% KOH aqueous solution (10 mL) at room temperature and the resulting solution was heated at 100° C. for 12 h and monitored by TLC. After completion, the reaction mixture was diluted with diethyl ether and the pH of the aqueous layer was adjusted to 5 with 1N HCl solution and extracted with EtOAc. The organic layer was dried over anhydrous $Na_2SO_4$ and filtered, and the filtrate obtained was concentrated under reduced pressure to afford 1 g of the crude title compound as a brown syrup. LCMS: $[M+H]^+=139.95$; $R_t=3.56$ min.

Step 2: 2-(6-methylbenzo[d]thiazol-2-yl)acetonitrile

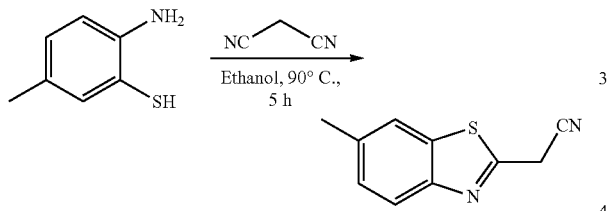

To a solution of 2-amino-5-methylbenzenethiol (1 g, 7.19 mmol) in ethanol (10 mL) was added acetic acid (10 mL) followed by malononitrile (0.95 g, 14.38 mmol) and the reaction mixture was heated to 90° C. for 5 h and monitored by TLC. After removal of solvent the reaction mixture was diluted with EtOAc and washed with saturated $NaHCO_3$ solution. The combined organic layers were dried over $Na_2SO_4$, and concentrated to afford a crude residue that was purified by silica gel column chromatography to afford the title compound as an off white solid (410 mg, 30% yield). LCMS: $[M+H]^+=188.9$; $R_t=4.44$ min.

Step 3: tert-butyl 2-amino-3-(6-methylbenzo[d]thiazol-2-yl)-4,7-dihydrothieno[2,3-c]pyridine-6(5H)-carboxylate

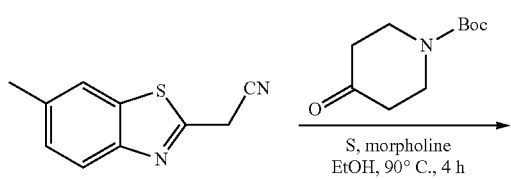

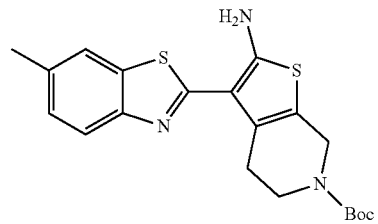

To a solution of 2-(6-methylbenzo[d]thiazol-2-yl)acetonitrile (400 mg, 2.12 mmol) in ethanol (20 mL) was added tert-butyl 4-oxopiperidine-1-carboxylate (507 mg, 2.55 mmol) followed by morpholine (370 mg, 4.24 mmol) and the reaction mixture was heated to 40° C. for 10 min. Sulfur (101 mg, 3.18 mmol) was then added and the resulting solution was heated to 90° C. for 4 h and monitored by TLC. After completion, the reaction mixture was evaporated to dryness resulting in a crude residue which was purified by flash column chromatography to afford the title compound as pale yellow solid (310 mg, 36% yield). LCMS: $[M+H]^+=402.00$; $R_t=4.20$ min.

Step 4: tert-butyl 2-acetamido-3-(6-methylbenzo[d]thiazol-2-yl)-4,7-dihydrothieno[2,3-c]pyridine-6(5H)-carboxylate

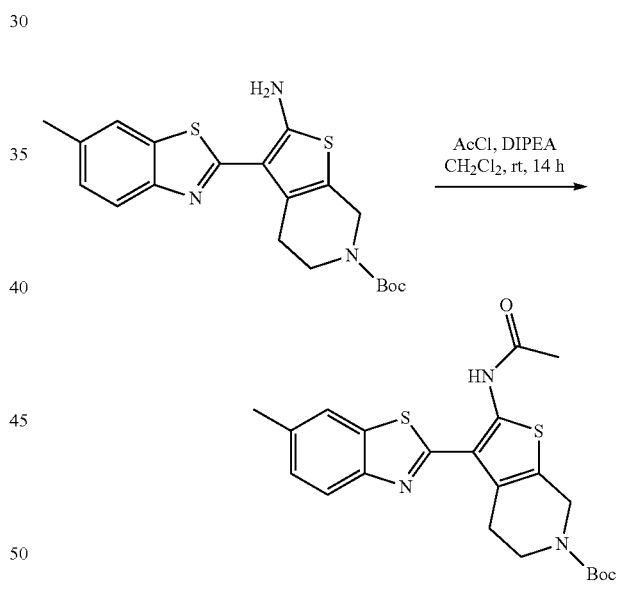

To a solution of tert-butyl 2-amino-3-(6-methylbenzo[d]thiazol-2-yl)-4,7-dihydrothieno[2,3-c]pyridine-6(5H)-carboxylate (200 mg, 0.49 mmol) in DCM (10 mL) at 0° C. was added DIPEA (0.26 mL, 1.49 mmol) followed by acetyl chloride (0.1 mL, 1.54 mmol) and the reaction mixture was stirred at room temperature for 14 h and monitored by TLC. After completion, the reaction mixture was diluted with DCM and washed with 0.5 M HCl solution. The combined organic layers were dried over $Na_2SO_4$, and concentrated to obtain crude residue that was purified by silica gel (100-200 mesh) column chromatography to afford the title compound as an off white solid (165 mg, 75% yield). LCMS: $[M-Boc+1]^+=344.05$; $R_t=4.09$ min.

Step 5: N-(3-(6-methylbenzo[d]thiazol-2-yl)-4,5,6,7-tetrahydrothieno[2,3-c]pyridin-2-yl)acetamide

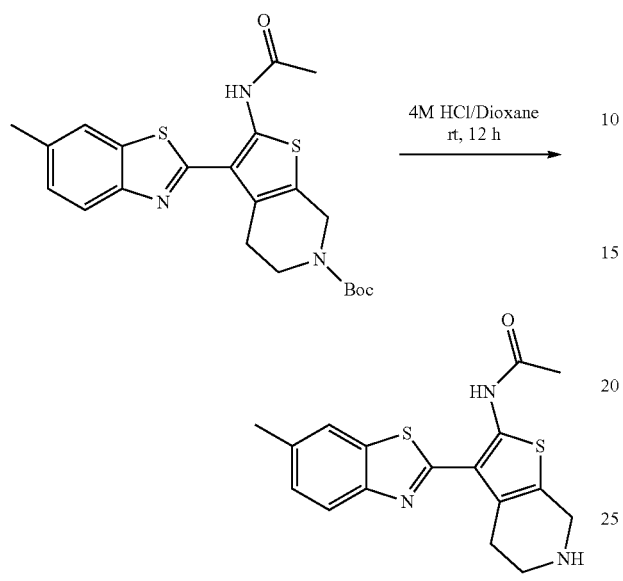

To a solution of tert-butyl 2-acetamido-3-(4-phenylthiazol-2-yl)-4,7-dihydrothieno[2,3-c]pyridine-6(5H)-carboxylate (160 mg, 0.36 mmol) in dioxane (2 mL) at 0° C. was added 4M HCl in dioxane (10 mL) and the reaction mixture was stirred at room temperature for 12 h and monitored by TLC. After completion, the reaction mixture was evaporated to dryness resulting in a crude residue which was purified by triturating with ether and pentane to afford the HCl salt of the title compound as a yellow solid (125 mg, 91% yield).

Example 49. Synthesis of N-(3-(4-methylbenzo[d]thiazol-2-yl)-4,5,6,7-tetrahydrothieno[2,3-c]pyridin-2-yl)acetamide (Compound 225)

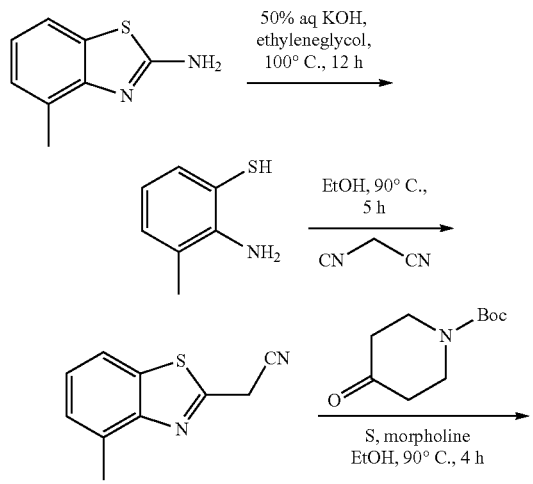

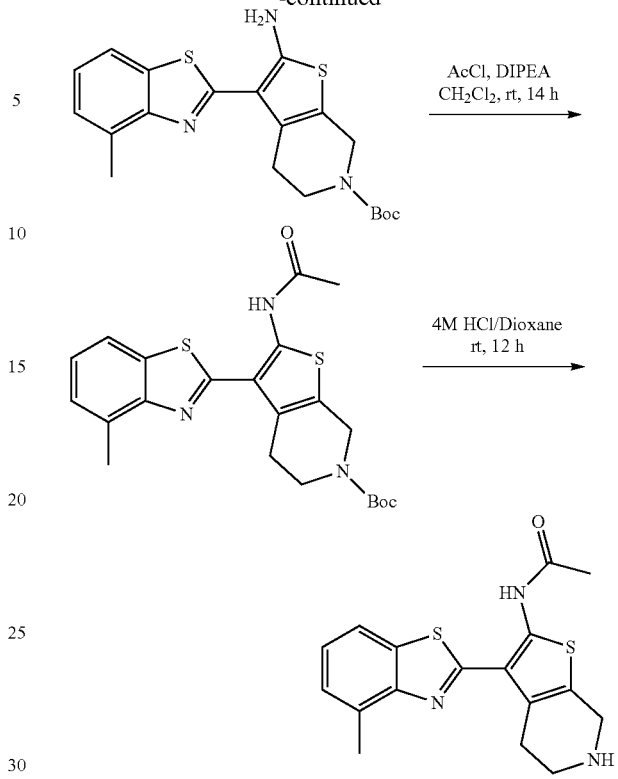

Step 1: 2-amino-3-methylbenzenethiol

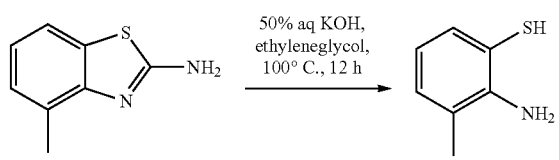

To a stirring solution of 4-methylbenzo[d]thiazol-2-amine 1 (1.6 g, 9.73 mmol) in ethylene glycol (10 mL) was added 50% aq KOH solution (10 mL) at room temperature and the resulting solution was heated at 100° C. for 12 h and monitored by TLC. After completion, the reaction mixture was diluted with diethyl ether and the aqueous layer pH was adjusted to 5 with 1N HCl solution and extracted with EtOAc. The organic layer was dried over anhydrous $Na_2SO_4$ and filtered. The filtrate obtained was concentrated under reduced pressure to afford crude 1 g of the title compound as a brown syrup. LCMS: [M–H]$^+$=138; $R_f$=0.82 min.

Step 2: 2-(4-methylbenzo[d]thiazol-2-yl)acetonitrile

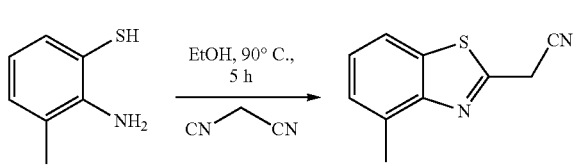

To a solution of 2-amino-3-methylbenzenethiol (1 g, 7.19 mmol) in ethanol (10 mL) was added acetic acid (10 mL) followed by malononitrile (0.95 g, 14.38 mmol) at room temperature. After the reaction mixture was heated to 90° C. for 5 h and monitored by TLC. After the reaction was complete, the mixture was concentrated under reduced pressure. The obtained precipitate was diluted with EtOAc and washed with saturated NaHCO$_3$ solution. The combined organic layers were dried over anhydrous Na$_2$SO$_4$, filtered, and concentrated to afford a crude residue that was purified by flash column chromatography to afford the title compound as an off white solid (170 mg, 12.5% yield). LCMS: [M+H]$^+$=189.00; R$_t$=2.94 min.

Step 3: tert-butyl 2-amino-3-(4-methylbenzo[d]thiazol-2-yl)-4,7-dihydrothieno[2,3-c]pyridine-6(5H)-carboxylate

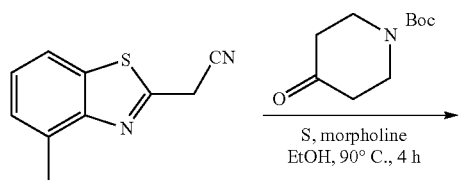

S, morpholine
EtOH, 90° C., 4 h

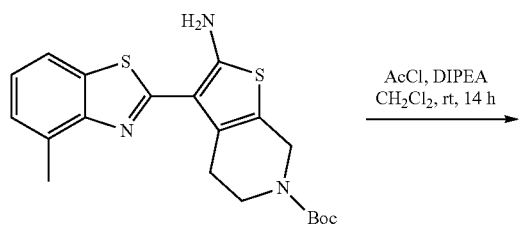

To a solution of 2-(4-methylbenzo[d]thiazol-2-yl)acetonitrile (170 mg, 9.03 mmol) in ethanol (10 mL) was added tert-butyl 4-oxopiperidine-1-carboxylate (216 mg, 1.08 mmol), morpholine (158 mg, 1.80 mmol) at room temperature. The reaction mixture was then heated to 40° C. for 10 min followed by the addition of sulfur (101 mg, 3.18 mmol). The mixture was then heated to 90° C. for 4 h and monitored by TLC. After completion, the reaction mixture was evaporated to dryness to afford (350 mg, crude) of the title compound as a yellow solid. LCMS: [M+H]$^+$=402.00; R$_t$=4.20 min.

Step 4: tert-butyl 2-acetamido-3-(4-methylbenzo[d]thiazol-2-yl)-4,7-dihydrothieno[2,3-c]pyridine-6(5H)-carboxylate

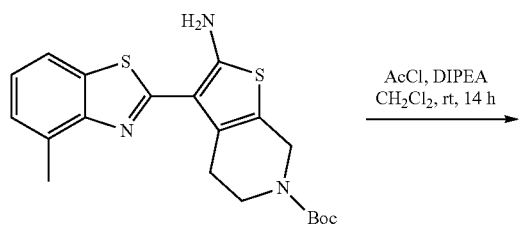

AcCl, DIPEA
CH$_2$Cl$_2$, rt, 14 h

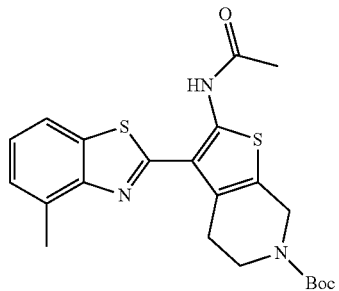

To a solution of tert-butyl 2-amino-3-(4-methylbenzo[d]thiazol-2-yl)-4,7-dihydrothieno[2,3-c]pyridine-6(5H)-carboxylate (300 mg, 0.74 mmol) in DCM (10 mL) at 0° C. was added DIPEA (0.19 mL, 1.12 mmol) and acetyl chloride (0.06 mL, 0.822 mmol). The reaction mixture was then stirred at room temperature for 14 h and monitored by TLC. After completion, the reaction mixture was diluted with DCM and washed with a 0.5 M HCl solution. The combined organic layers were dried over anhydrous Na$_2$SO$_4$, and concentrated to obtain a crude residue which was purified by flash column chromatography to afford the title compound as a yellow solid (70 mg, 21% yield). LCMS: [M+H]$^+$= 444.00; R$_t$=4.50 min.

Step 5: N-(3-(4-methylbenzo[d]thiazol-2-yl)-4,5,6,7-tetrahydrothieno[2,3-c]pyridin-2-yl)acetamide

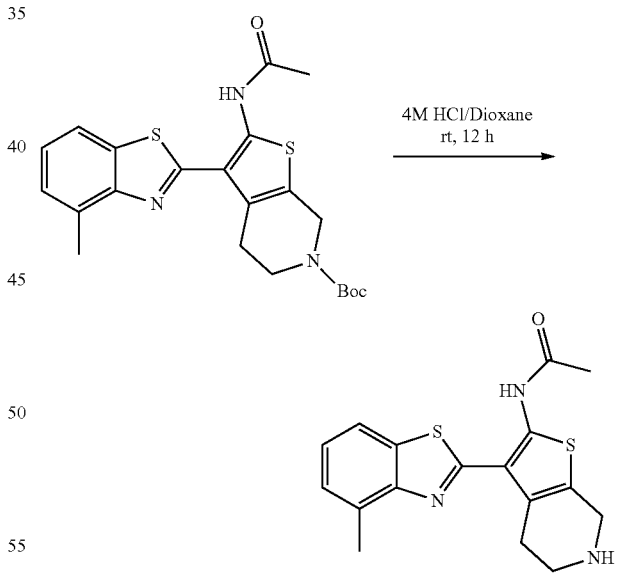

4M HCl/Dioxane
rt, 12 h

To a solution of tert-butyl 2-acetamido-3-(4-methylbenzo[d]thiazol-2-yl)-4,7-dihydrothieno[2,3-c]pyridine-6(5H)-carboxylate (60 mg, 1.35 mmol) in dioxane (2 mL) at 0° C. was added 4M HCl in dioxane (5 mL) and the reaction was stirred at room temperature for 12 h and monitored by TLC. After completion, the reaction mixture was evaporated to dryness resulting in a crude residue which was purified by triturating with ether and pentane to afford the HCl salt of the title compound as a yellow solid (37 mg, 72% yield).

173

Example 50. Synthesis of N-(3-(benzo[d]thiazol-2-yl)-6-((pyridin-4-ylmethyl)amino)-4,5,6,7-tetrahydrobenzo[b]thiophen-2-yl)acetamide (Compound 226)

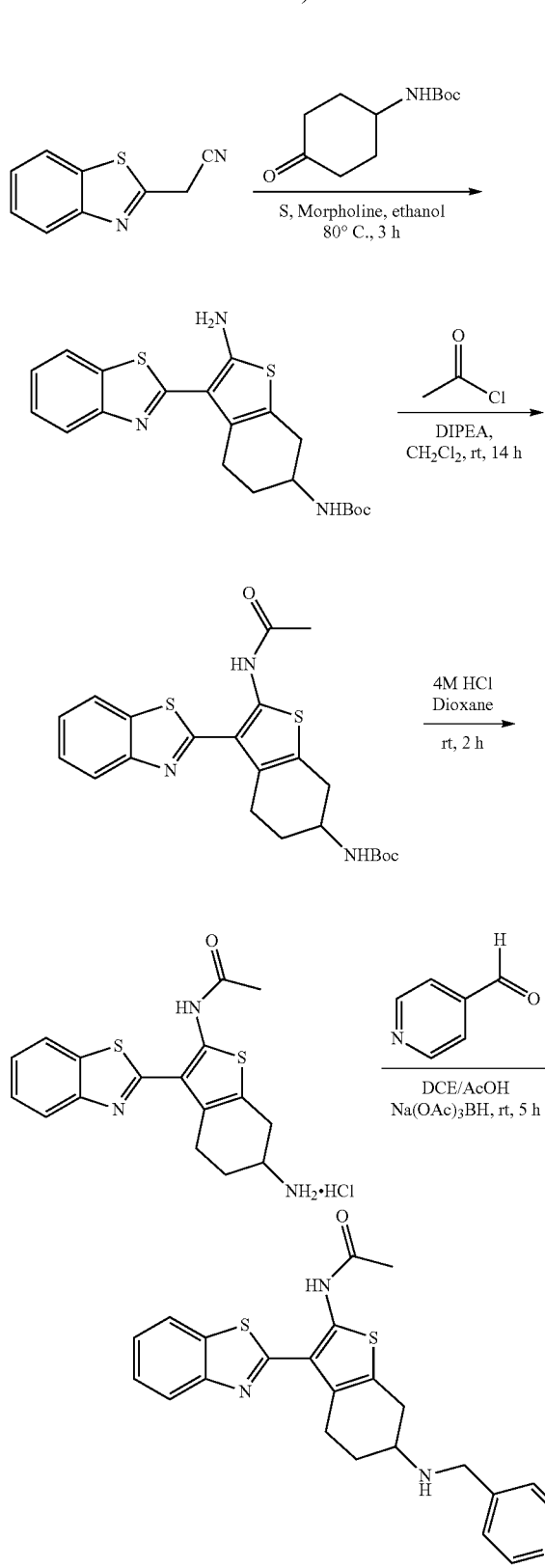

174

Step 1: tert-butyl (2-amino-3-(benzo[d]thiazol-2-yl)-4,5,6,7-tetrahydrobenzo[b]thiophen-6-yl)carbamate

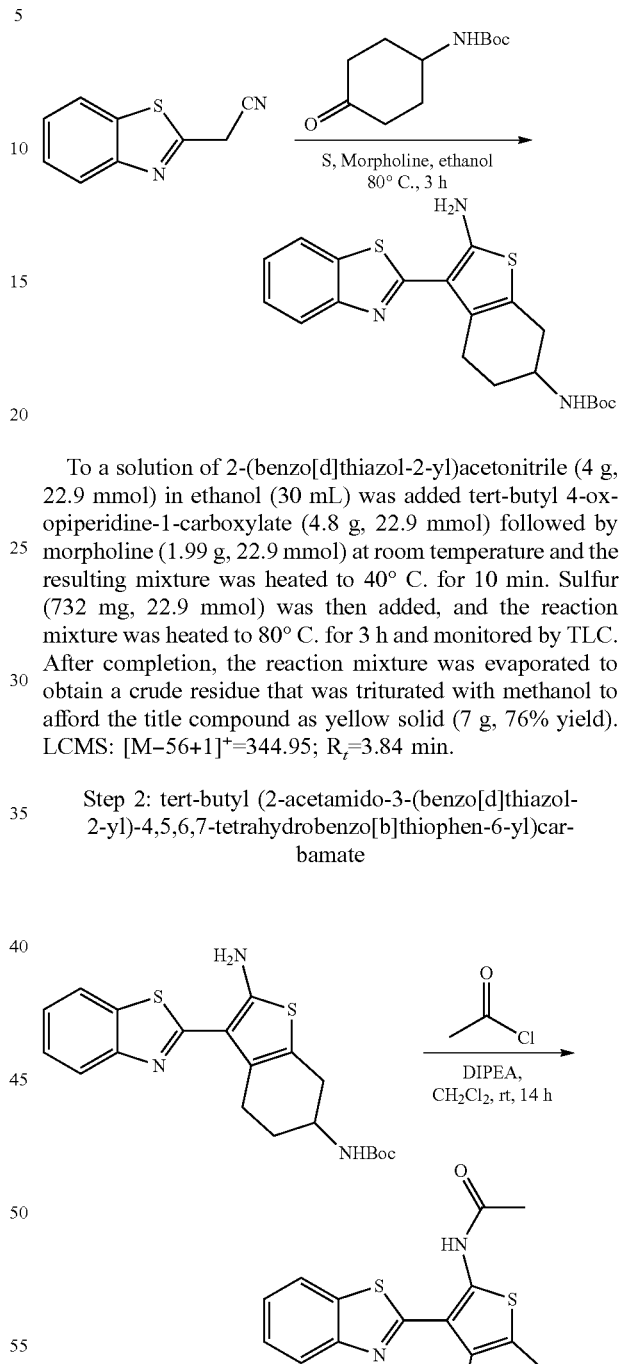

To a solution of 2-(benzo[d]thiazol-2-yl)acetonitrile (4 g, 22.9 mmol) in ethanol (30 mL) was added tert-butyl 4-oxopiperidine-1-carboxylate (4.8 g, 22.9 mmol) followed by morpholine (1.99 g, 22.9 mmol) at room temperature and the resulting mixture was heated to 40° C. for 10 min. Sulfur (732 mg, 22.9 mmol) was then added, and the reaction mixture was heated to 80° C. for 3 h and monitored by TLC. After completion, the reaction mixture was evaporated to obtain a crude residue that was triturated with methanol to afford the title compound as yellow solid (7 g, 76% yield). LCMS: [M−56+1]$^+$=344.95; R$_f$=3.84 min.

Step 2: tert-butyl (2-acetamido-3-(benzo[d]thiazol-2-yl)-4,5,6,7-tetrahydrobenzo[b]thiophen-6-yl)carbamate To a solution of tert-butyl (2-amino-3-(benzo[d]thiazol-2-yl)-4,5,6,7-tetrahydrobenzo[b]thiophen-6-yl)carbamate (4 g, 9.97 mmol) in DCM (20 mL) at 0° C. was added DIPEA (3.5 mL, 19.94 mmol) followed by acetyl chloride (0.8 mL, 11.9 mmol) and the reaction mixture was stirred at room temperature for 14 h and monitored by TLC. After completion, the reaction mixture was diluted with 10% MeOH/

DCM and washed with NaHCO₃ solution. The combined organic layers were dried over Na₂SO₄, filtered and concentrated to afford the title compound as a light yellow coloured solid (4 g, crude). LCMS: [M−56+1]⁺=387.90; $R_t$=5.38 min.

Step 3: N-(6-amino-3-(benzo[d]thiazol-2-yl)-4,5,6,7-tetrahydrobenzo[b]thiophen-2-yl)acetamide

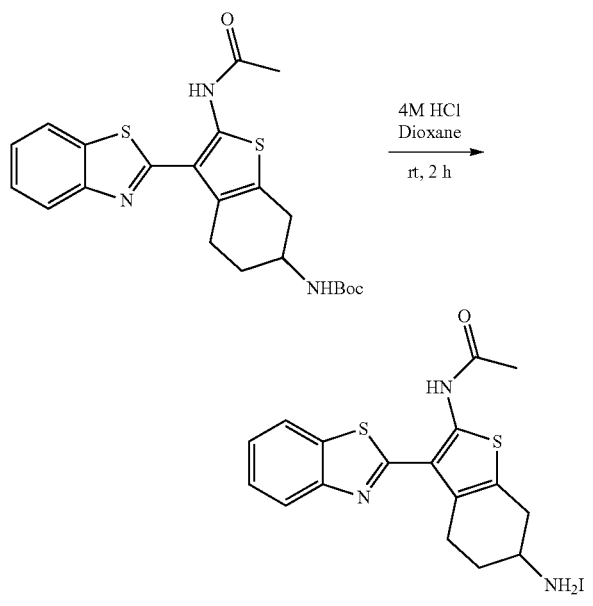

To a solution of tert-butyl (2-acetamido-3-(benzo[d]thiazol-2-yl)-4,5,6,7-tetrahydrobenzo[b]thiophen-6-yl)carbamate (2 g, 4.51 mmol) in dioxane (5 mL) at 0° C. was added 4M HCl in dioxane (20 mL). After the addition, the resulting mixture was stirred at room temperature for 2 h and monitored by TLC. After completion, the reaction mixture was evaporated to dryness resulting in a crude residue which was purified by triturating with ether and pentane to afford the HCl salt of the title compound as a yellow solid (2 g, crude). LCMS: [M+H]⁺=344.00; $R_t$=2.13 min.

Step 4: N-(3-(benzo[d]thiazol-2-yl)-6-((pyridin-4-ylmethyl)amino)-4,5,6,7-tetrahydrobenzo[b]thiophen-2-yl)acetamide

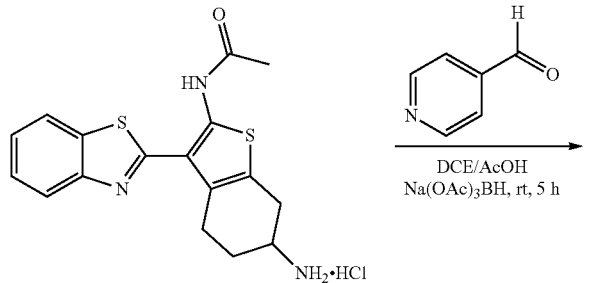

To a stirring solution of N-(6-amino-3-(benzo[d]thiazol-2-yl)-4,5,6,7-tetrahydrobenzo[b]thiophen-2-yl)acetamide (150 mg, 0.43 mmol) in DCE (5 mL) were added 4-formylpyridine (70 mg, 0.64 mmol), sodium triacetoxy borohydride (168 mg, 0.86 mmol) and AcOH (0.3 ml) and the reaction was stirred at room temperature for 5 h and monitored by TLC. After the completion, the reaction mixture was diluted with water and DCM. The combined organic layers were dried over Na₂SO₄, and concentrated to give a crude compound which was purified by flash column chromatography to afford the title compound as a yellow solid (100 mg, 52% yield).

Example 51. Synthesis of tert-butyl 4-((2-acetamido-3-(benzo[d]thiazol-2-yl)-4,5,6,7-tetrahydrobenzo[b]thiophen-6-yl)amino)piperidine-1-carboxylate (Compound 228)

To a stirring solution of N-(6-amino-3-(benzo[d]thiazol-2-yl)-4,5,6,7-tetrahydrobenzo[b]thiophen-2-yl)acetamide (150 mg, 0.43 mmol) in DCE (10 mL) at 0° C. were added tert-butyl 4-oxopiperidine-1-carboxylate (64 mg, 0.65 mmol) and sodium triacetoxy borohydride (181 mg, 0.86 mmol) followed by AcOH (0.3 mL). The resulting solution was stirred at room temperature for 5 h and monitored by TLC. After the completion, the reaction mixture was diluted with water and DCM. The combined organic layers were dried over Na₂SO₄, and concentrated to give a crude residue that was purified by flash column chromatography to afford the title compound as an off white solid (60 mg, 26% yield).

Example 52. Synthesis of N-(3-(benzo[d]thiazol-2-yl)-6-(piperidin-4-ylamino)-4,5,6,7-tetrahydrobenzo[b]thiophen-2-yl)acetamide (Compound 227)

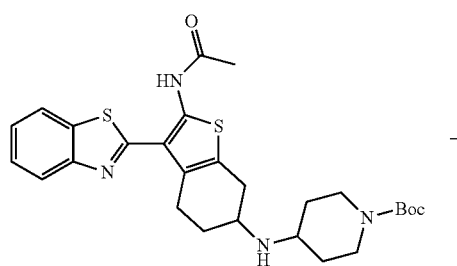

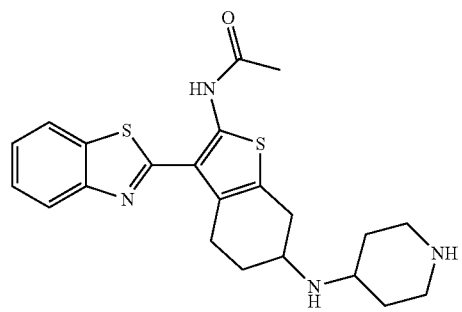

To a solution of tert-butyl 4-((2-acetamido-3-(benzo[d]thiazol-2-yl)-4,5,6,7-tetrahydrobenzo[b]thiophen-6-yl)amino)piperidine-1-carboxylate 7 (60 mg, 0.11 mmol) in dioxane (1 mL) at 0° C. was added 4M HCl in dioxane (5 mL) and the reaction mixture was stirred at room temperature for 2 h and monitored by TLC. After completion, the reaction mixture was evaporated to dryness resulting in a crude residue which was purified by triturating with ether and pentane to afford the HCl salt of the title compound as a yellow solid (45 mg, 95%).

Example 53. Synthesis of Methyl 2-(2-acetamido-4,5,6,7-tetrahydrothieno[2,3-c]pyridin-3-yl)benzo[d]thiazole-5-carboxylate (Compound 229)

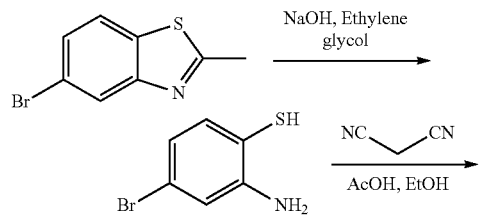

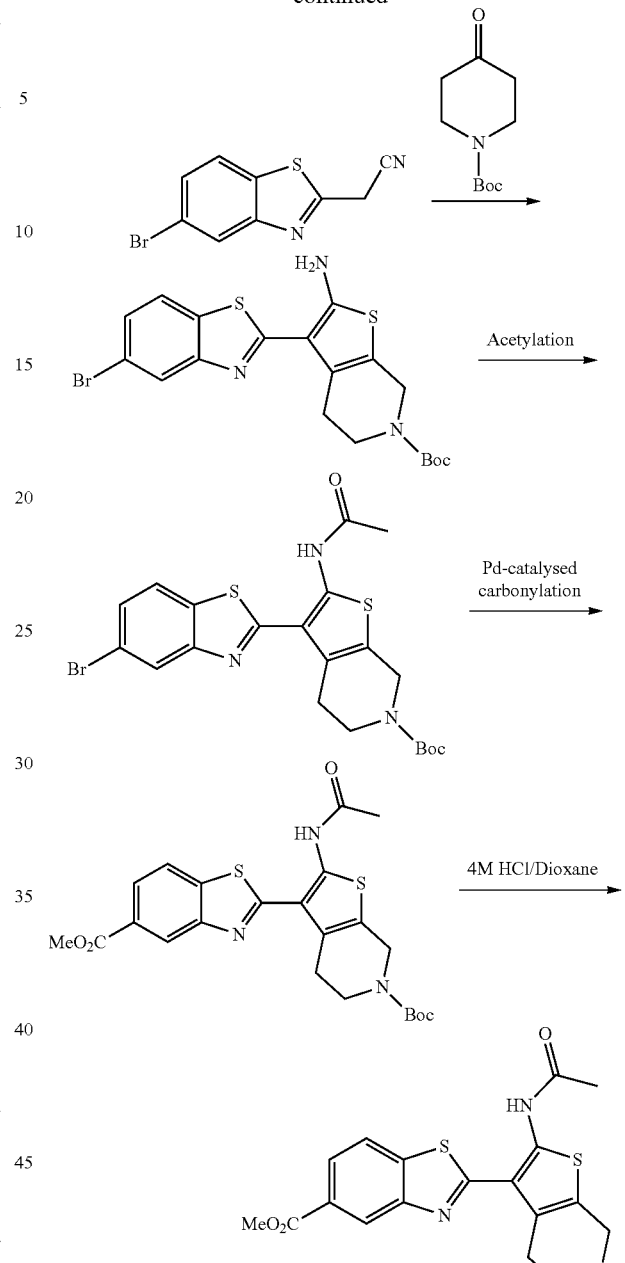

Step 1: 2-amino-4-bromobenzenethiol

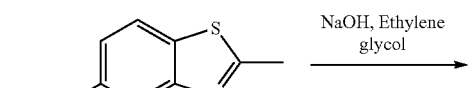

To a solution of 5-bromo-2-methylbenzo[d]thiazole (5 g, 22.03 mmol) in ethylene glycol (50 mL) was added 8 N NaOH (50 mL). The resulting reaction mixture was stirred at 140° C. for 4 h and monitored by TLC. After completion, the reaction mixture was cooled to room temperature, acidified with 1N HCl up to pH 6, and extracted with DCM. The combined organic layers were dried over anhydrous Na$_2$SO$_4$, filtered and concentrated under reduced pressure to afford the title compound as a yellow solid (4.1 g, yield 74%). LCMS: [M−1]$^-$=204; R$_t$=3.81 min.

Step 2: 2-(5-bromobenzo[d]thiazol-2-yl)acetonitrile

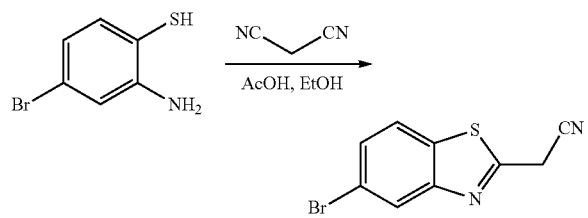

To a solution of 2-amino-4-bromobenzenethiol (3.4 g, 16.6 mmol) in EtOH (20 mL) was added malononitrile (2.19 g, 33.3 mmol) and AcOH (0.1 mL). The resulting reaction mixture was stirred at 90° C. for 12 h and monitored by TLC. After completion, the reaction mixture was quenched with water and concentrated under reduced pressure to dryness. The residue was diluted with aqueous sat. NaHCO$_3$ solution and extracted with ethyl acetate. The combined organic layers were dried over anhydrous Na$_2$SO$_4$, filtered, and concentrated to get a crude residue, which was purified by silica gel column chromatography eluting with 0-20% ethyl acetate in n-hexane to afford the title compound as a yellow solid (3.21 g, yield 76%). LCMS: [M+2]$^+$=254.85; R$_t$=3.02 min.

Step 3: tert-butyl 2-amino-3-(5-bromobenzo[d]thiazol-2-yl)-4,7-dihydrothieno[2,3-c]pyridine-6(5H)-carboxylate

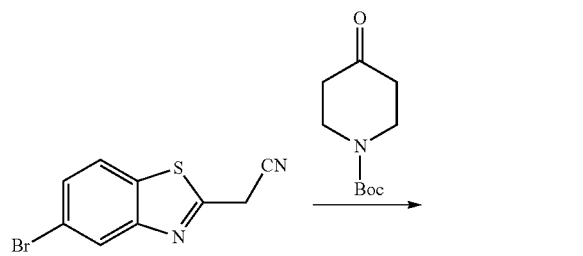

To a solution of 2-(5-bromobenzo[d]thiazol-2-yl)acetonitrile (3.2 g, 12.64 mmol) in ethanol (50 mL) was added tert-butyl 4-oxopiperidine-1-carboxylate (3.02 g, 15.17 mmol), elemental sulfur (0.61 g, 18.98 mmol) and morpholine (2.2 g, 25.28 mmol) and the reaction mixture was heated to reflux at 80° C. for 12 h and monitored by TLC. After completion, the reaction mixture was concentrated under vacuum pressure and the crude compound was purified by triturating with methanol to afford the title compound as a yellow solid (4.6 g, yield 78%). LCMS: [M+1]$^+$=466.05; R$_t$=4.22 min.

Step 4: tert-butyl 2-acetamido-3-(5-bromobenzo[d]thiazol-2-yl)-4,7-dihydrothieno[2,3-c]pyridine-6(5H)-carboxylate

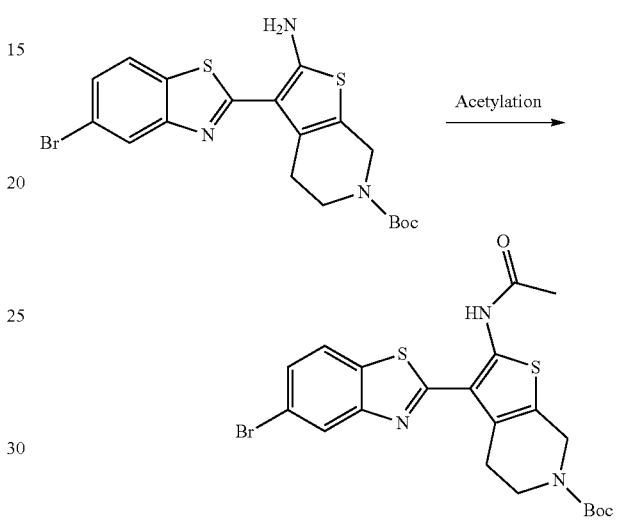

To a solution of tert-butyl 2-amino-3-(5-bromobenzo[d]thiazol-2-yl)-4,7-dihydrothieno[2,3-c]pyridine-6(5H)-carboxylate (4.2 g, 9.01 mmol) in DCM (70 mL) at 0° C. was added DIPEA (7.8 mL, 45.05 mmol) followed by acetyl chloride (1.6 mL, 22.5 mmol) and the reaction mixture was stirred at room temperature for 16 h and monitored by TLC. After completion, the reaction mixture was diluted with aqueous sat. NaHCO$_3$ solution and extracted with DCM. The combined organic layers were dried over anhydrous Na$_2$SO$_4$, filtered and concentrated to get a crude residue that was purified by silica gel column chromatography eluting with 0-20% ethyl acetate in n-hexane to afford the title compound as a yellow solid (1.5 g, yield 33%). LCMS: [M+1]$^+$=508.10; R$_t$=4.34 min.

Step 5: methyl 2-(2-acetamido-6-(tert-butoxycarbonyl)-4,5,6,7-tetrahydrothieno[2,3-c]pyridin-3-yl)benzo[d]thiazole-5-carboxylate

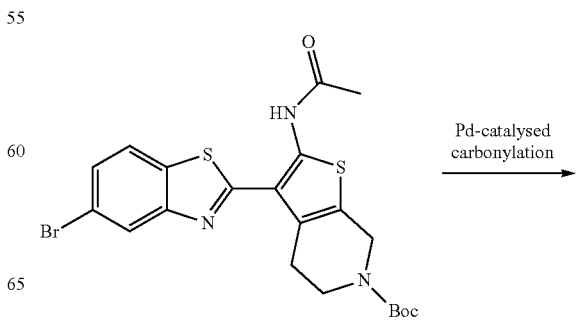

-continued

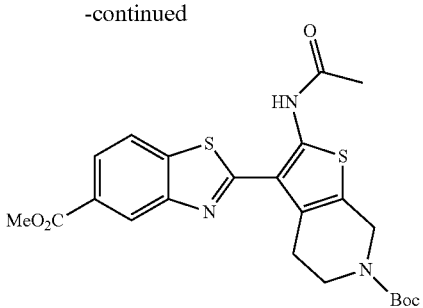

To a stirring solution of tert-butyl 2-acetamido-3-(5-bromobenzo[d]thiazol-2-yl)-4,7-dihydrothieno[2,3-c]pyridine-6(5H)-carboxylate (1 g, 2.14 mmol) in methanol (50 mL) was added triethylamine (0.6 mL, 4.29 mmol) and the reaction mixture was degassed under argon atmosphere for 10 min. Pd(OAc)$_2$ (0.019 g, 0.085 mmol) and Xantphos (0.062 g, 0.107 mmol) were then added, and the reaction mixture was purged with carbon monoxide for 30 min. The reaction mixture was heated to 100° C. for 12 h under the atmosphere of carbon monoxide and monitored by TLC. After complete consumption of starting material, the reaction was quenched with water and extracted with ethyl acetate. The organic layer was separated, washed with brine, dried over anhydrous Na$_2$SO$_4$ and concentrated under reduced pressure to obtain a crude residue, which was purified by column chromatography to afford the title compound as a yellow solid (0.11 g, yield 10%). LCMS: [M+1]$^+$=488.10; R$_f$=3.93 min.

Step 6: Methyl 2-(2-acetamido-4,5,6,7-tetrahydrothieno[2,3-c]pyridin-3-yl)benzo[d]thiazole-5-carboxylate

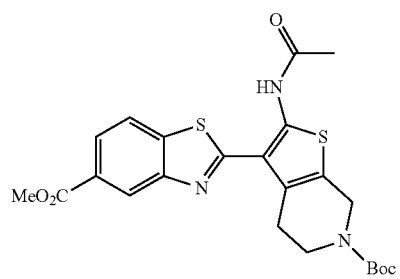

To a solution of methyl 2-(2-acetamido-6-(tert-butoxycarbonyl)-4,5,6,7-tetrahydrothieno[2,3-c]pyridin-3-yl)benzo[d]thiazole-5-carboxylate (0.1 g, 0.205 mmol) in dioxane (2 mL) at 0° C. was added 4M HCl in dioxane (4 mL) and the reaction mixture was stirred at room temperature for 2 h. After completion, the reaction mixture was concentrated under vacuum pressure, resulting in a crude residue was purified trituration with ether to afford the title compound as a yellow solid (0.06 g HCl salt, 69% yield).

Example 54. Synthesis of N-(3-(5-(dimethylamino)benzo[d]thiazol-2-yl)-4,5,6,7-tetrahydrothieno[2,3-c]pyridin-2-yl)acetamide (Compound 230)

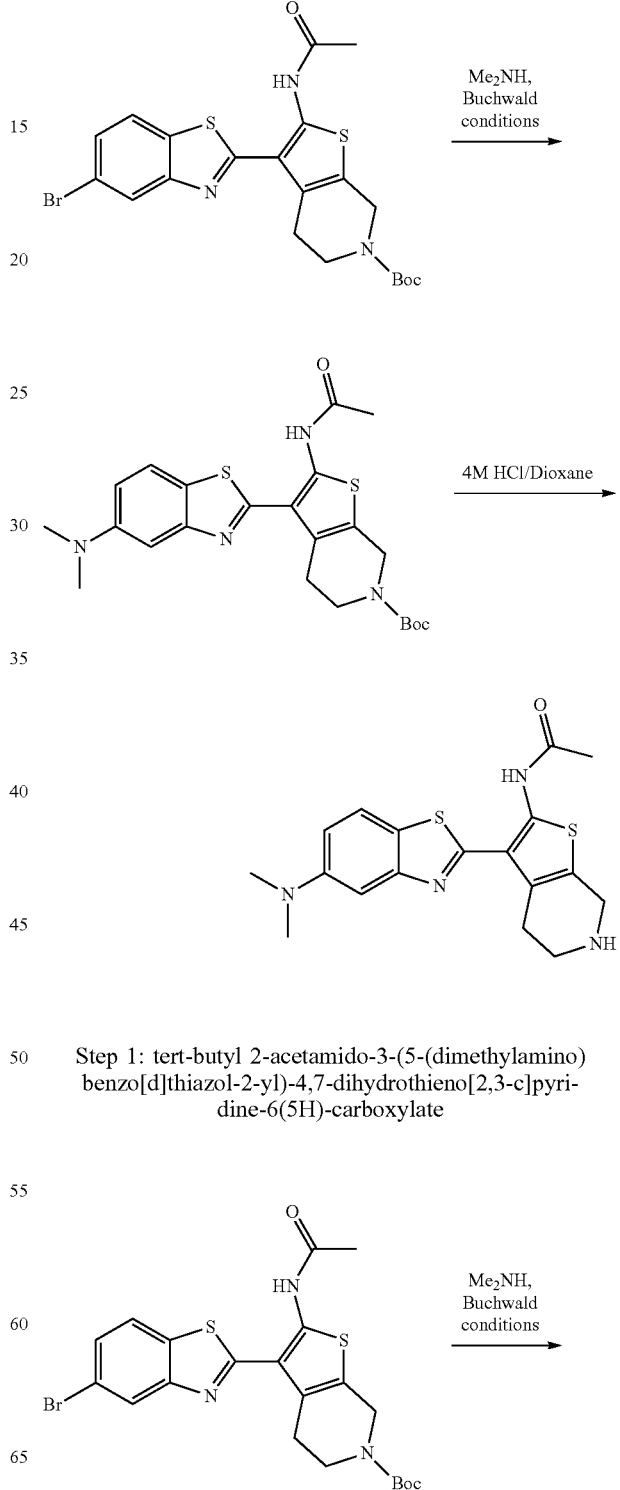

Step 1: tert-butyl 2-acetamido-3-(5-(dimethylamino)benzo[d]thiazol-2-yl)-4,7-dihydrothieno[2,3-c]pyridine-6(5H)-carboxylate -continued

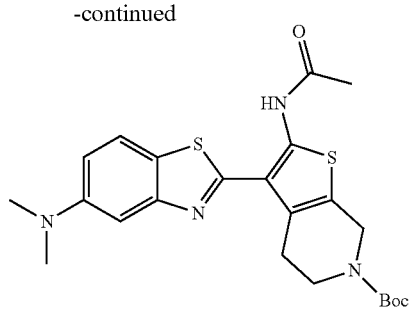

A mixture of tert-butyl 2-acetamido-3-(5-bromobenzo[d]thiazol-2-yl)-4,7-dihydrothieno[2,3-c]pyridine-6(5H)-carboxylate (0.6 g, 1.18 mmol), dimethyl amine (2M in THF, 2.95 mL, 5.90 mmol), and potassium tert-butoxide (0.33 g, 2.95 mmol) in 1,4-dioxane (9 mL) was purged with argon for 10 min, followed by the addition of Xanthphos (0.034 g, 0.059 mmol) and Pd$_2$(dba)$_3$ (0.108 g, 0.118 mmol) was then added. The reaction mixture was stirred at 85° C. overnight and monitored by TLC. After completion of the reaction, the reaction mixture was filtered through celite and evaporated to dryness. The residue was dissolved in ethyl acetate and the organic layer washed with water, brine, dried over anhydrous sodium sulfate and evaporated under reduced pressure. The crude product was purified by column chromatography to afford the title compound as a yellow solid (0.13 g, yield 23%). LCMS: [M−57]$^+$=415; R$_t$=4.04 min.

Step 2: N-(3-(5-(dimethylamino)benzo[d]thiazol-2-yl)-4,5,6,7-tetrahydrothieno[2,3-c]pyridin-2-yl)acetamide

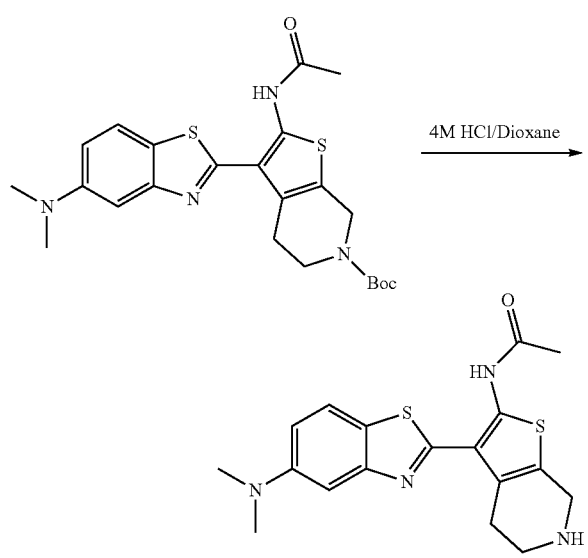

To a solution of tert-butyl 2-acetamido-3-(5-(dimethylamino)benzo[d]thiazol-2-yl)-4,7-dihydrothieno[2,3-c]pyridine-6(5H)-carboxylate (0.11 g, 0.232 mmol) in dioxane (2 mL) at 0° C. was added 4M HCl in dioxane (5 mL) and the reaction mixture was stirred at room temperature for 2 h. After completion, the reaction mixture was concentrated under vacuum pressure, resulting in a crude residue which was purified trituration in ether to afford the title compound as a yellow solid (0.094 g HCl salt, yield 96%).

Example 55. Synthesis of N-(3-(benzo[d]thiazol-2-yl)-6-((tetrahydro-2H-pyran-4-yl)amino)-4,5,6,7-tetrahydrobenzo[b]thiophen-2-yl)acetamide (Compound 231)

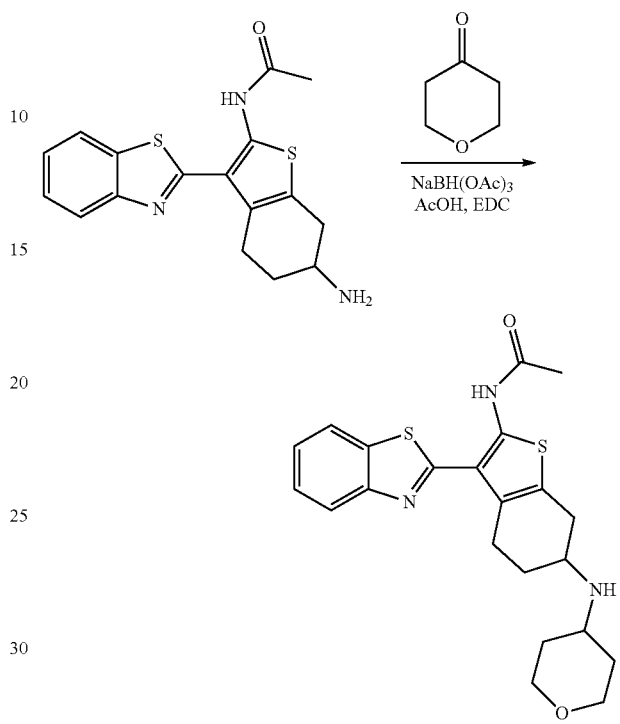

To a stirring solution of N-(6-amino-3-(benzo[d]thiazol-2-yl)-4,5,6,7-tetrahydrobenzo[b]thiophen-2-yl)acetamide (0.15 g, 0.43 mmol) and tetrahydro-4H-pyran-4-one (0.065 g, 0.65 mmol) in dichloroethane (10 mL) was added acetic acid (0.3 mL) and the reaction was stirred at room temperature for 3 h. Sodium triacetoxyborohydride (0.181 g, 0.86 mmol) was then added at 0° C., and the mixture was stirred at room temperature for 12 h. The progress of the reaction was monitored by TLC. After completion, the mixture was quenched with aqueous sat. NaHCO$_3$ solution and extracted with 10% MeOH/DCM. The combined organic layers were dried over anhydrous Na$_2$SO$_4$ and concentrated to get a crude residue, which was purified by silica gel column chromatography eluting with 0-2% MeOH/DCM to afford the title compound as a yellow solid (0.07 g, yield 37%).

Example 56. Synthesis of N-(3-(benzo[d]thiazol-2-yl)-4,5,6,7-tetrahydrothieno[2,3-c]pyridin-2-yl)-N-methylacetamide (Compound 232)

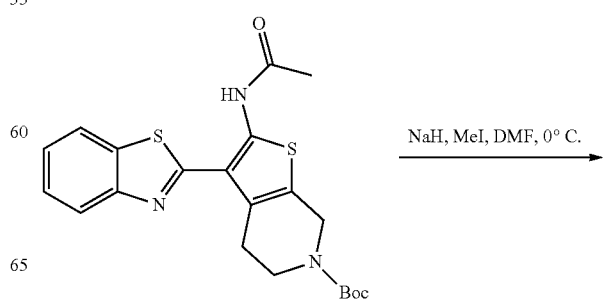

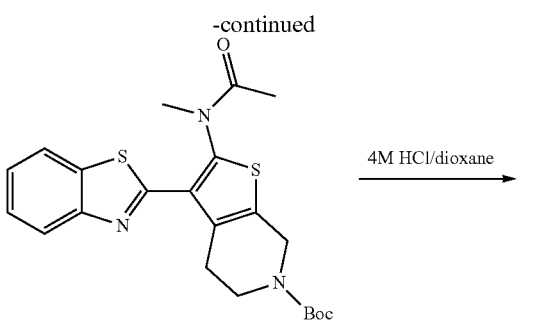

Step 1: tert-butyl 3-(benzo[d]thiazol-2-yl)-2-(N-methylacetamido)-4,7-dihydrothieno[2,3-c]pyridine-6(5H)-carboxylate

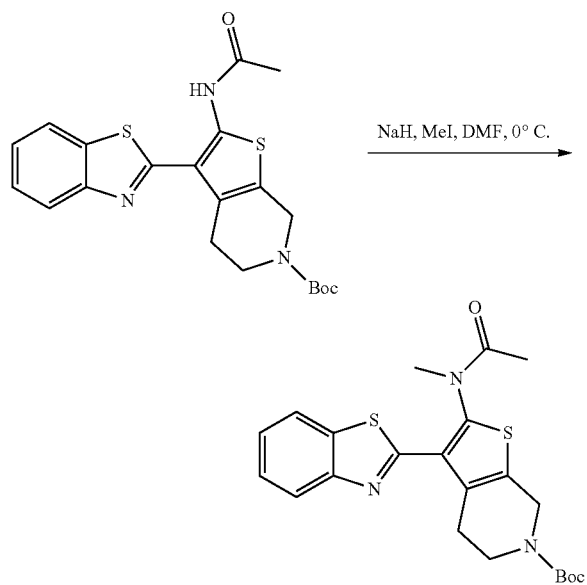

To a solution of tert-butyl 2-acetamido-3-(benzo[d]thiazol-2-yl)-4,7-dihydrothieno[2,3-c]pyridine-6(5H)-carboxylate (200 mg, 0.466 mmol) in DMF (5 mL) at 0° C. was added NaH (17 mg, 0.69 mmol) and the resulting mixture was stirred for 30 min. This was followed by dropwise addition of methyl iodide (328 mg, 2.33 mmol) and the reaction was stirred at room temperature for 12 h. After the completion of reaction (monitored by TLC) the reaction was quenched by the adding ice/water and extracted with EtOAc. The combined organic fractions were dried over anhydrous Na₂SO₄ and concentrated to give a crude residue which was purified by silica-gel flash column chromatography to afford the title compound as an off white solid (100 mg, 48% yield). ¹H NMR (CDCl₃, 400 MHz): δ 8.06 (d, J=8.31 Hz, 1H), 7.90 (d, J=7.83 Hz, 1H), 7.47-7.55 (m, 1H), 7.37-7.45 (m, 1H), 4.64 (m, 2H), 3.77 (t, J=5.38 Hz, 2H), 3.20-3.24 (m, 2H), 1.99 (s, 3H), 1.58 (s, 3H), 1.51 (s, 9H). LCMS: [M+H]⁺=444.04; R_t=3.53 min.

Step 2: N-(3-(benzo[d]thiazol-2-yl)-4,5,6,7-tetrahydrothieno[2,3-c]pyridin-2-yl)-N-methylacetamide

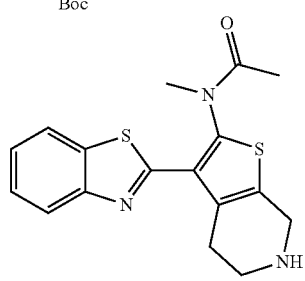

To a solution of tert-butyl 3-(benzo[d]thiazol-2-yl)-2-(N-methylacetamido)-4,7-dihydrothieno[2,3-c]pyridine-6(5H)-carboxylate (100 mg, 0.27 mmol) in dioxane (3 mL) at 0° C. was added 4M HCl in dioxane (1 mL). After the addition, the resulting mixture was stirred at room temperature for 2 h. Upon completion, the reaction mixture was evaporated to dryness and the resulting in a crude residue was triturated in ether and pentane to give crude product (100 mg HCl salt). The salt was further purified by preparative HPLC to afford the title compound as yellow solid (35 mg HCl salt, 41% yield).

Example 57. Synthesis of 3-(Isopropylamino)-N-(3-(5-(pyridin-4-yl)benzo[d]thiazol-2-yl)-4,5,6,7-tetrahydrothieno[2,3-c]pyridin-2-yl)propanamide dihydrochloride (Compound 160)

Ethyl 3-(isopropylamino)propanoate

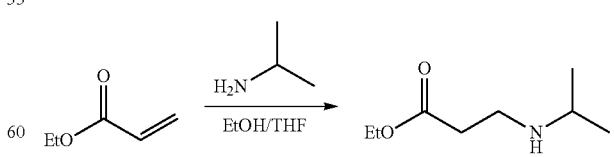

Ethyl acrylate (20.0 g, 200 mmol) was added to a solution of isopropylamine (11.8 g, 200 mmol) in THF/EtOH (1:1, 664 mL) at 0° C. The solution was warmed to RT and stirred for 16 h. The mixture was then concentration to afford the title compound (31.8 g, 100%) as a colorless oil.

Ethyl 3-((tert-butoxycarbonyl)(isopropyl)amino)propanoate

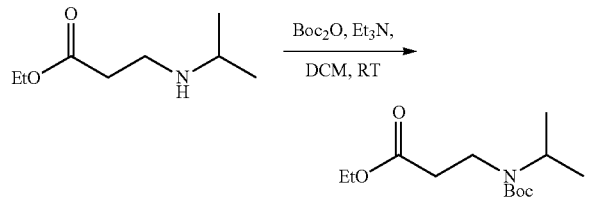

To a solution of ethyl 3-(isopropylamino)propanoate (31.8 g, 200 mmol) in DCM (2 L), were added Et₃N (42 mL, 300 mmol) and Boc₂O. (47.9 g, 220 mmol). The resulted mixture was stirred at RT for 16 h. The reaction was then quenched with an NH₄Cl saturated solution and extracted with DCM. The combined organic phases were dried over Na₂SO₄. and concentrated to afford the title compound (56.1 g, quant.) as a slurry white solid. The crude compound was engaged into the next reaction without further purification.

Ethyl 3-(isopropylamino)propanoate

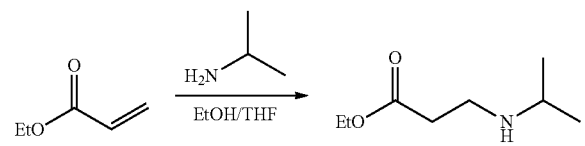

Ethyl acrylate (20.0 g, 200 mmol) was added to a solution of isopropylamine (11.8 g, 200 mmol) in THF/EtOH (1:1, 664 mL) at 0° C. The solution was warmed to RT and stirred for 16 h. The mixture was then concentration to afford the title compound (31.8 g, 100%) as a colorless oil.

3-((tert-Butoxycarbonyl)(isopropyl)amino)propanoic acid

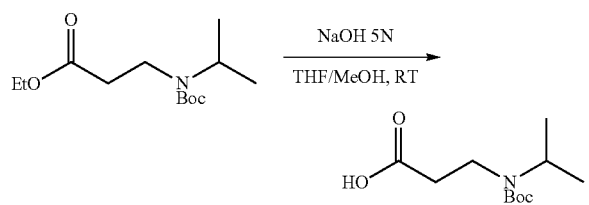

To a solution of ethyl 3-((tert-butoxycarbonyl)(isopropyl)amino)propanoate (57.8 g, 200 mmol) in THF/MeOH (1 L/0.4 L) at 0° C. was added a 5N sodium hydroxide aqueous solution (400 mL, 1000 mmol). The resulted mixture allowed to reach RT and stirred for 16 h. The reaction mixture was cooled to 0° C. and the solution was acidified with KHSO₄ 1 N (1.2 L) then H₂SO₄ 5 N (0.5 L) reaching pH=1 and extracted with EtOAc. The organic phase was concentrated, basified with NaOH 5 N and extracted with water. The aqueous layer was acidified again with concentrated. H₂SO₄ (reach pH=5) and finally extracted with EtOAc. The resulting organic phase was dried over Na₂SO₄, and concentrated to afford the title compound (39 g, 84%) as a white solid.

tert-Butyl 3-(5-bromobenzo[d]thiazol-2-yl)-2-(3-((tert-butoxycarbonyl)(isopropyl)amino)propanamido)-4,5-dihydrothieno[2,3-c]pyridine-6(7H)-carboxylate

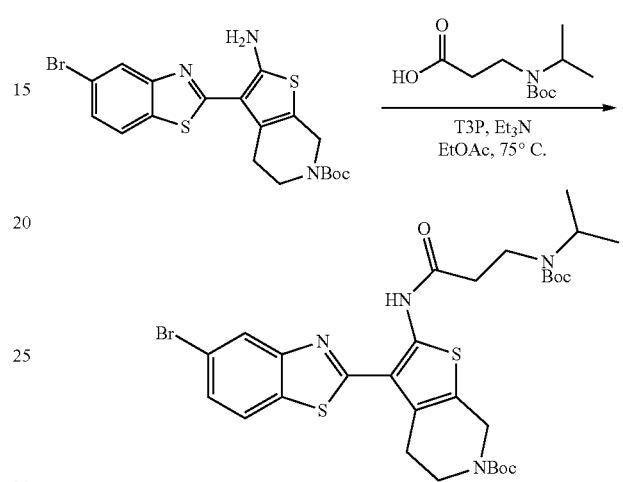

tert-Butyl 2-amino-3-(5-bromobenzo[d]thiazol-2-yl)-4,5-dihydrothieno[2,3-c]pyridine-6(7H)-carboxylate (3.00 g, 6.43 mmol) and 3-((tert-butoxycarbonyl)(isopropyl)amino) propanoic acid (2.23 g, 9.65 mmol) were charged in a 250 mL round-bottom flask equipped with a condenser. EtOAc (64 mL), triethylamine (2.7 mL, 19.3 mmol) and T3P (50% in EtOAc, 9.6 mL, 16.1 mmol) were successively added and the resulting mixture was stirred in a 60° C. oil bath for 14 h. The solution was allowed to cool down at 20° C. and a saturated aqueous solution of NaHCO₃ (200 mL) was added. The resulting mixture was extracted with EtOAc (3×125 mL) and the combined organic layers were dried over anhydrous Na₂SO₄, filtered and concentrated. The obtained residue was purified by SiO₂ chromatography (EtOAc in hexanes, 5 to 40% gradient) to afford the title compound (3.15 g, 72%) as a brown solid.

tert-Butyl 2-(3-((tert-butoxycarbonyl)(isopropyl)amino)propanamido)-3-(5-(pyridin-4-yl)benzo[d]thiazol-2-yl)-4,5-dihydrothieno[2,3-c]pyridine-6(7H)-carboxylate

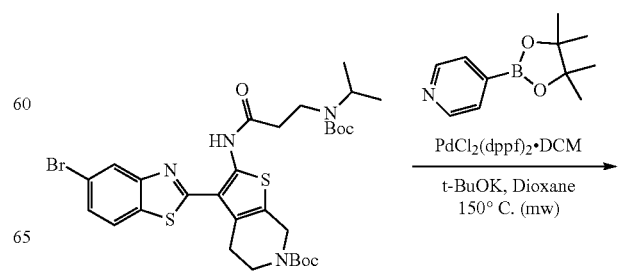

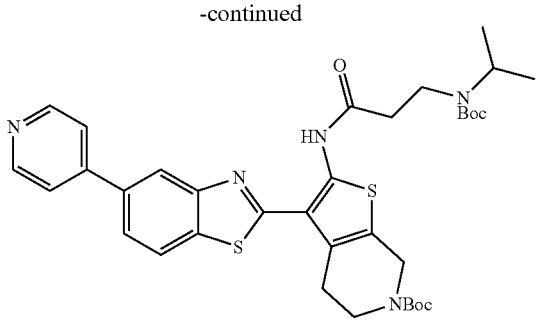

A vial was charged with tert-butyl 3-(5-bromobenzo[d]thiazol-2-yl)-2-(3-((tert-butoxycarbonyl)(isopropyl)amino)propanamido)-4,5-dihydrothieno[2,3-c]pyridine-6(7H)-carboxylate (300 mg, 0.441 mmol), pyridine-4-boronic pinacol ester (181 mg, 0.883 mmol), t-BuOK (149 mg, 1.32 mmol) and Pd(dppf)Cl₂ (36 mg, 0.0441 mmol). The vial was purged with nitrogen and degassed dioxane (2 mL) was added. The vial was sealed and the reaction mixture was stirred under microwave irradiation for 45 min at 150° C. The reaction mixture was concentrated and the resulting residue was purified by SiO₂ chromatography (MeOH in DCM, 0 to 3% gradient) to afford the title compound (210 mg, 70%) as a yellow solid.

3-(isopropylamino)-N-(3-(5-(pyridin-4-yl)benzo[d]thiazol-2-yl)-4,5,6,7-tetrahydrothieno[2,3-c]pyridin-2-yl)propanamide dihydrochloride (Compound 160)

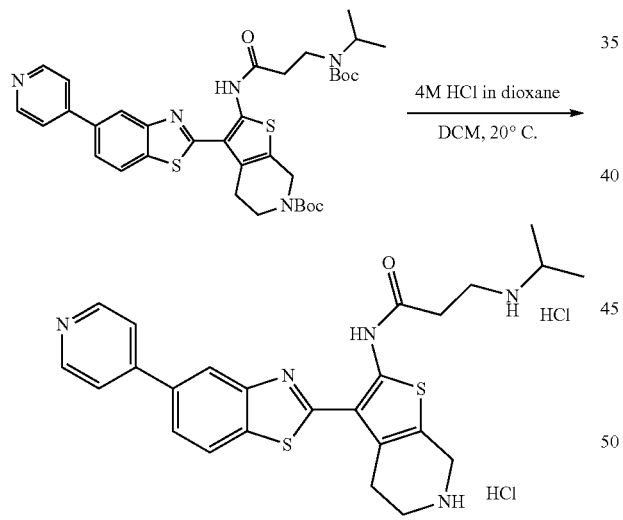

A solution of HCl (4 N in dioxane, 0.50 mL, 2.01 mmol) was added to a solution of tert-butyl 2-(3-((tert-butoxycarbonyl)(isopropyl)amino)propanamido)-3-(5-(pyridin-4-yl)benzo[d]thiazol-2-yl)-4,5-dihydrothieno[2,3-c]pyridine-6(7H)-carboxylate (80 mg, 0.118 mmol) in DCM (2 mL) at 20° C. The reaction mixture was stirred at this temperature for 4 h and it was diluted with Et₂O. The solid was collected by filtration, washed with Et₂O and lyophilized from water to afford the title compound (59 mg, 91%) as a yellow solid. The final deprotection has been performed using 4N HCl in dioxane to afford the title compound.

The synthesis of Compounds 150, 151, 158, 159, 161, 163, 164, 165, 169, 170, 171, 175, 176, 177, 181, 182, 183, 184, 188, 192, 193, 194, 308, 326, 511, 512, 513, 580, 601, 609, 610, 614, 615, 616, was similar to Compound 160 using the appropriate boronic acid ester and, where appropriate, 6-bromo-2-methylbenzothiazole instead of 5-bromo-2-methylbenzothiazole as the starting material. Compound 174 was synthesized by treating Compound 171 with sodium azide and NH₄Cl and deprotecting with 4N HCl in dioxane.

The synthesis of Compounds 233, 234, 235 and 238 were similar to Compound 160 using the appropriate boronic acid ester, acetic acid in the step before the boronic acid and, where appropriate, 6-bromo-2-methylbenzothiazole instead of 5-bromo-2-methylbenzothiazole as the starting material.

Example 58. Synthesis of N-(3-(5-(1H-imidazol-1-yl)benzo[d]thiazol-2-yl)-4,5,6,7-tetrahydrothieno[2,3-c]pyridin-2-yl)-3-(isopropylamino)propanamide dihydrochloride (Compound 178)

tert-Butyl 3-(5-(1H-imidazol-1-yl)benzo[d]thiazol-2-yl)-2-(3-((tert-butoxycarbonyl)(iso-propyl)amino)propanamido)-4,5-dihydrothieno[2,3-c]pyridine-6(7H)-carboxylate

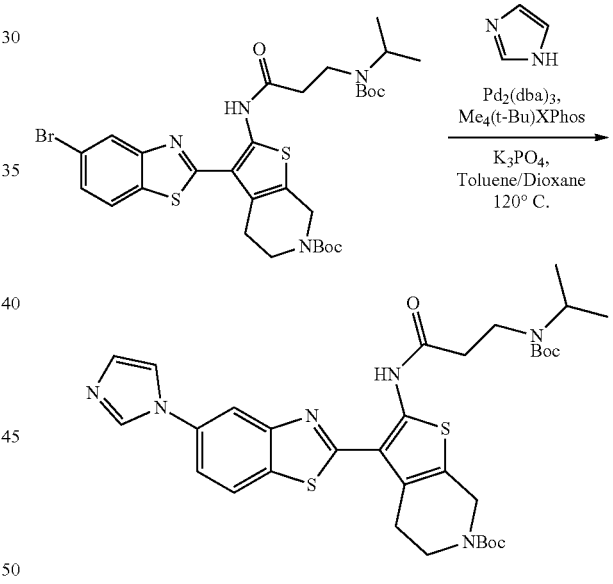

A vial was charged with Pd₂(dba)₃ (5.4 mg, 0.00590 mmol) and Me₄(t-Bu)XPhos (5.7 mg, 0.0118 mmol). The vial was purged with nitrogen and degassed solvents were added (5:1 toluene/dioxane, 1 mL). The mixture was stirred for 3 min at 120° C. and the resulting solution was transferred to a vial that was previously charged with tert-butyl 3-(5-bromobenzo[d]thiazol-2-yl)-2-(3-((tert-butoxycarbonyl)(isopropyl)amino)propanamido)-4,5-dihydrothieno[2,3-c]pyridine-6(7H)-carboxylate (100 mg, 0.147 mmol), imidazole (20 mg, 0.294 mmol) and K₃PO₄ (62 mg, 0.294 mmol) under nitrogen. The vial was sealed and the reaction mixture was stirred in a 120° C. oil bath for 15 h. The reaction mixture was concentrated and the resulting residue was purified by SiO₂ chromatography (MeOH in DCM, 0 to 5% gradient) to afford the title compound (77 mg, 78%) as a yellow solid.

N-(3-(5-(1H-imidazol-1-yl)benzo[d]thiazol-2-yl)-4,5,6,7-tetrahydrothieno[2,3-c]pyridin-2-yl)-3-(isopropylamino)propanamide dihydrochloride (Compound 178)

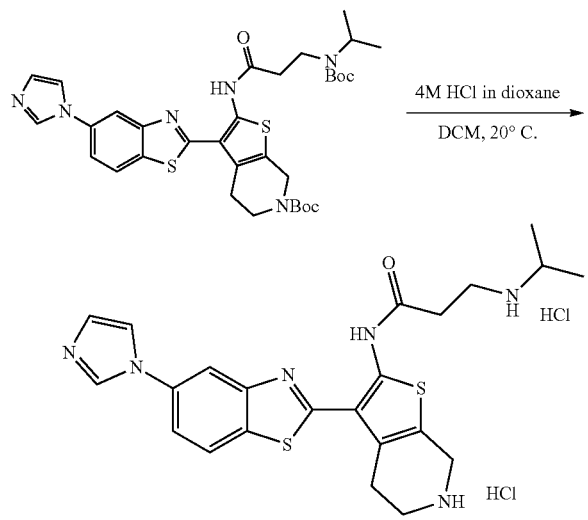

A solution of HCl (4 N in dioxane, 0.43 mL, 1.73 mmol) was added to a solution of tert-butyl 3-(5-(1H-imidazol-1-yl)benzo[d]thiazol-2-yl)-2-(3-((tert-butoxycarbonyl)(isopropyl)amino) propanamido)-4,5-dihydrothieno[2,3-c]pyridine-6(7H)-carboxylate (77 mg, 0.116 mmol) in DCM (0.8 mL) at 20° C. The reaction mixture was stirred at this temperature for 4 h and it was diluted with Et₂O. The solid was collected by filtration, washed with Et₂O and lyophilized from water to afford the title compound (56 mg, 91%) as a yellow solid.

Compounds 149, 173, 180, 186, 187, 302, 304 and 581 were similarly prepared using the appropriate NH-containing heterocycle or heteroaryl to displace the bromine.

Example 59. Synthesis of N-(3-(5-Bromobenzo[d]thiazol-2-yl)-6-isopropyl-4,5,6,7-tetrahydrothieno[2,3-c]pyridin-2-yl)-3-(sec-butylamino)propanamide (Compound 145)

3-(5-Bromobenzo[d]thiazol-2-yl)-4,5,6,7-tetrahydrothieno[2,3-c]pyridin-2-amine

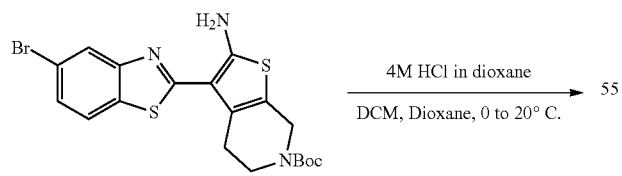

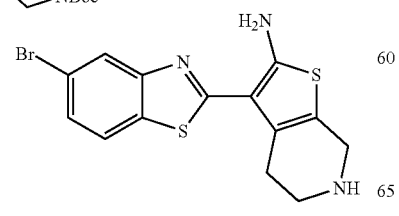

A solution of HCl (4 N in dioxane, 3.2 mL, 12.9 mmol) was added to a solution of tert-butyl 2-amino-3-(5-bromobenzo[d]thiazol-2-yl)-4,5-dihydrothieno[2,3-c]pyridine-6(7H)-carboxylate (600 mg, 1.29 mmol) in DCM (6.4 mL) and dioxane (2.0 mL) at 0° C. The reaction mixture was stirred at 20° C. for 3 h and the volatiles were removed under reduced pressure. The obtained residue was dissolved in warm water followed by the addition of saturated aqueous solution of NaHCO₃. The mixture was extracted with EtOAc (2×) and DCM (2×). Combined organic layers were dried over anhydrous Na₂SO₄, filtered and concentrated to afford the title compound (477 mg, >100% crude yield) as a yellow solid, which was used in the next step without further purification.

3-(5-Bromobenzo[d]thiazol-2-yl)-6-isopropyl-4,5,6,7-tetrahydrothieno[2,3-c]pyridin-2-amine

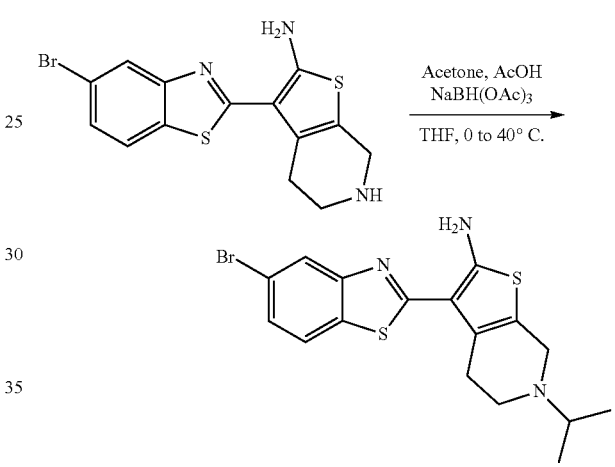

To a 0° C. solution of 3-(5-bromobenzo[d]thiazol-2-yl)-4,5,6,7-tetrahydrothieno[2,3-c]pyridin-2-amine (477 mg, 1.30 mmol) in THF (6.5 mL) were added successively acetone (0.29 mL, 227 mg, 3.91 mmol) and acetic acid (0.075 mL, 78 mg, 1.30 mmol). The reaction mixture was stirred 10 minutes at 0° C. and 2 h at 40° C. A saturated aqueous solution of NaHCO₃ was then added and the mixture was extracted with EtOAc (3×). Combined organic layers were dried over anhydrous Na₂SO₄, filtered and concentrated. The obtained residue was purified by SiO₂ chromatography (MeOH in DCM, 0 to 8% gradient) to afford the title compound (382 mg, 72%) as a brown solid.

tert-Butyl (3-((3-(5-bromobenzo[d]thiazol-2-yl)-6-isopropyl-4,5,6,7-tetrahydrothieno[2,3-c]pyridin-2-yl)amino)-3-oxopropyl)(sec-butyl)carbamate

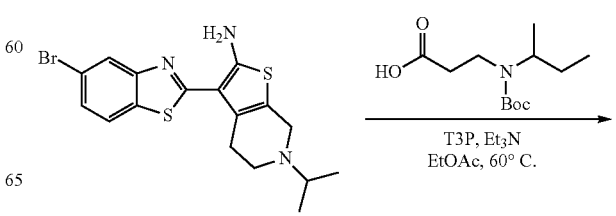

-continued

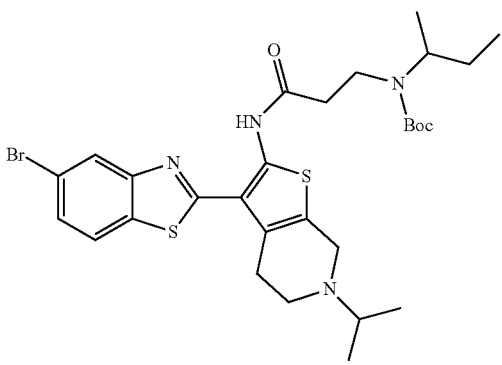

3-(5-bromobenzo[d]thiazol-2-yl)-6-isopropyl-4,5,6,7-tetrahydrothieno[2,3-c]pyridin-2-amine (250 mg, 0.612 mmol) and 3-((tert-butoxycarbonyl)(sec-butyl)amino)propanoic acid (225 mg, 0.918 mmol) were charged in a 25 mL round-bottom flask equipped with a condenser under nitrogen. EtOAc (4.1 mL) was added followed by Et₃N (0.43 mL, 310 mg, 3.06 mmol) and T3P (50% in EtOAc, 1.1 mL, 1.17 g, 1.84 mmol). The reaction mixture was stirred in a 60° C. oil bath for 2.5 h and it was allowed to cool down at room temperature. Saturated aqueous solution of NaHCO₃ was added and the mixture was extracted with EtOAc (3×). Combined organic layers were dried over anhydrous Na₂SO₄, filtered and concentrated. The obtained residue was purified by SiO₂ chromatography (EtOAc in hexanes, 5 to 60% gradient) to afford the title compound (180 mg, 46%) as a yellow solid.

N-(3-(5-Bromobenzo[d]thiazol-2-yl)-6-isopropyl-4,5,6,7-tetrahydrothieno[2,3-c]pyridin-2-yl)-3-(sec-butylamino)propanamide (Compound 145)

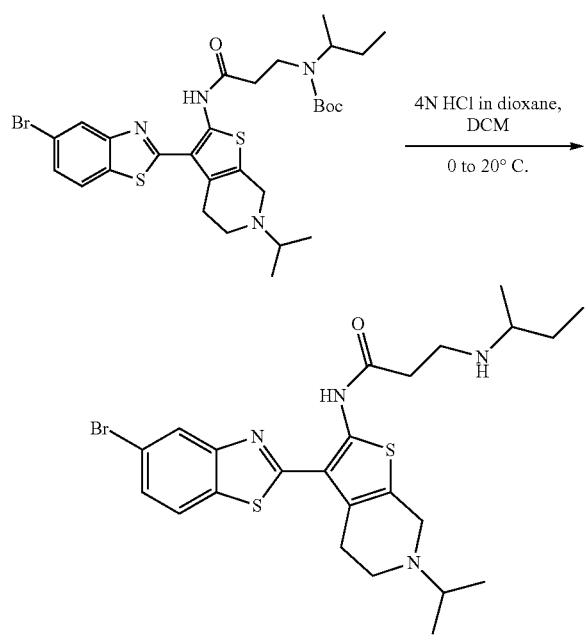

A solution of HCl (4 N in dioxane, 0.39 mL, 1.57 mmol) was added to a solution of tert-Butyl (3-((3-(5-bromobenzo[d]thiazol-2-yl)-6-isopropyl-4,5,6,7-tetrahydrothieno[2,3-c]pyridin-2-yl)amino)-3-oxopropyl)(sec-butyl)carbamate (100 mg, 0.157 mmol) in DCM (0.8 mL) at 0° C. The reaction mixture was stirred at 20° C. for 2.5 h and the volatiles were removed under reduced pressure. The crude product was dissolved in warm water followed by the addition of saturated aqueous solution of NaHCO₃. The resulting suspension was extracted with DCM (3×) and the combined organic layers were dried over anhydrous Na₂SO₄, filtered and concentrated. The obtained residue was purified by reverse phase chromatography (C₁₈, 0.1% HCO₂H/MeCN in H₂O, 5 to 70% gradient) to afford the title compound (66 mg, 79%) as a light yellow solid after lyophilization.

Example 60. Synthesis of 3-(sec-butylamino)-N-(3-(5-iodobenzo[d]thiazol-2-yl)-6-isopropyl-4,5,6,7-tetrahydrothieno[2,3-c]pyridin-2-yl)propanamide dihydrochloride (Compound 162)

2-(5-Iodobenzo[d]thiazol-2-yl)acetonitrile

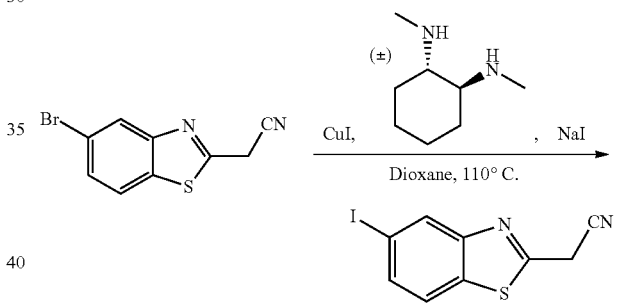

2-(5-Bromobenzo[d]thiazol-2-yl)acetonitrile (2.00 g, 7.90 mmol), copper iodide (75 mg, 0.395 mmol) and sodium iodide (2.37 g, 15.8 mmol) were charged in a 50 mL pressure vessel. The flask was purged with nitrogen. Degassed dioxane (7.9 mL) and trans-N,N'-dimethylcyclohexane-1,2-diamine (0.13 mL, 0.790 mmol) were successively added and the mixture was degassed with nitrogen for an additional 10 min. The reaction mixture was stirred 24 h in a 110° C. oil bath. The solvent was removed under reduced pressure and the obtained residue was purified by SiO₂ chromatography (EtOAc in hexanes, 5 to 45% gradient) to afford the title compound (1.37 g, 58%) as a beige solid.

3-(sec-butylamino)-N-(3-(5-iodobenzo[d]thiazol-2-yl)-6-isopropyl-4,5,6,7-tetrahydrothieno[2,3-c]pyridin-2-yl)propanamide dihydrochloride (Compound 162)

Starting from 2-(5-iodobenzo[d]thiazol-2-yl)acetonitrile, the synthesis of Compound 162 was similar to Compound 145

Example 61. Synthesis of 3-(2-methoxyethyl-amino)-N-(3-(4-vinylbenzo[d]thiazol-2-yl)-4,5,6,7-tetrahydrothieno[2,3-c]pyridin-2-yl)propanamide bis(2,2,2-trifluoroacetate) (Compound 583)

4,6-Dimethylthiazolo[4,5-c]pyridine-2(3H)-thione

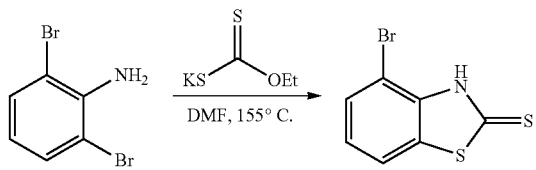

In a 1000 mL round-bottom flask equipped with a condenser under nitrogen were added 2,6-dibromoaniline (20.0 g, 79.7 mmol), potassium ethyl xanthate (25.6 g, 159.4 mmol) and DMF (266 mL). The mixture was heated in a 155° C. oil bath for 18 h and it was allowed to cool down at 20° C. Using an addition funnel, the reaction mixture was added dropwise to a solution of 1N HCl (1000 mL). The obtained beige suspension was filtered and the solid was rinsed with 1N HCl (250 mL) and water (250 mL). Residual water was removed on high vacuum to afford the title compound (19.2 g, 98% crude yield) as a beige solid, which was used in the next step without further purification.

4-Bromo-2-chlorobenzo[d]thiazole

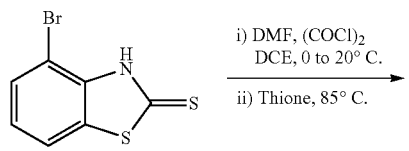

In a 1000 mL round-bottom flask under nitrogen were added DMF (7.9 mL, 101.6 mmol) and DCE (300 mL). Oxalyl chloride (8.6 mL, 101.6 mmol) was added dropwise at 0° C. and the white suspension was allowed to stir at 20° C. for 30 min. 4,6-Dimethylthiazolo[4,5-c]pyridine-2(3H)-thione (10.0 g, 40.6 mmol) was then added directly to the reaction mixture and the flask was mounted with a condenser. The suspension was heated in a 85° C. oil bath for 1.5 h and it was allowed to cool down at 20° C. A saturated aqueous solution of NaHCO₃ (400 mL) and water (100 mL) were added. The resulting mixture was extracted with DCM (2×100 mL) and the combined organic layers were dried over anhydrous Na₂SO₄, filtered and concentrated. In order to get completion, the crude mixture was resubmitted to reaction conditions using DMF (2.4 mL, 30.5 mmol) and oxalyl chloride (2.6 mL, 30.5 mmol) in DCE (30 mL). The crude product obtained after work-up was purified on a SiO₂ pad (EtOAc and DCM in hexane, 4:1:95 gradient) to afford the title compound (8.27 g, 82%) as a beige solid.

2-(4-Bromobenzo[d]thiazol-2-yl)acetonitrile

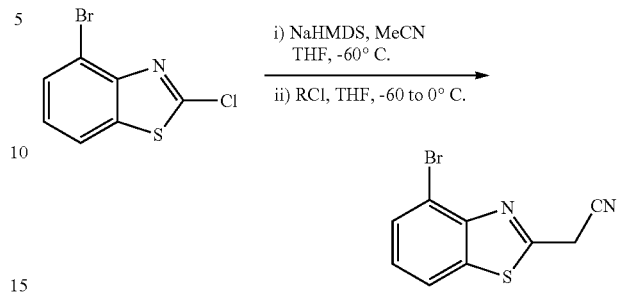

In a 500 mL round-bottom flask equipped with a temperature probe were added NaHMDS (88 mL, 87.8 mmol) and THF (98 mL) under nitrogen. The solution was cooled at −60° C. MeCN (3.1 mL, 58.5 mmol) was added dropwise and the mixture was stirred at the same temperature for 40 min. A solution of 4-bromo-2-chlorobenzo[d]thiazole (7.27 g, 29.3 mmol) in THF (88 mL) was then cannulated to the reaction flask over 15 min and the resulting mixture was stirred at 0° C. for 40 min. A saturated aqueous solution of NH₄Cl (400 mL) and water (400 mL) were added. The resulting mixture was extracted with EtOAc (2×250 mL) and the combined organic layers were washed with brine, dried over anhydrous Na₂SO₄, filtered and concentrated. Trituration of the crude material with EtOAc (2×10 mL) afforded the title compound (7.37 g, 100%) as a brown solid.

tert-Butyl 2-amino-3-(4-bromobenzo[d]thiazol-2-yl)-4,5-dihydrothieno[2,3-c]pyridine-6(7H)-carboxylate

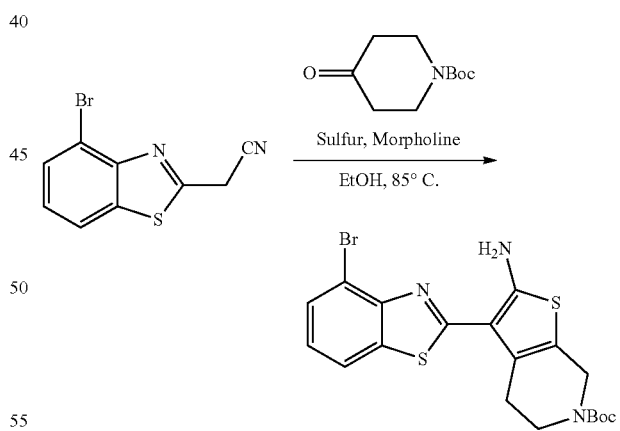

2-(4-Bromobenzo[d]thiazol-2-yl)acetonitrile (6.34 g, 25.0 mmol), N-Boc-4-piperidone (4.99 g, 25.0 mmol) and sulfur (803 mg, 25.0 mmol) were charged in a 500 mL round-bottom flask equipped with a condenser under nitrogen. EtOH (167 mL) and morpholine (2.2 mL, 25.0 mmol) were successively added and the resulting mixture was stirred 14 h in a 85° C. oil bath. The obtained suspension was allowed to cool down at 20° C. and the solid was filtered on Büchner, rinsed with cold EtOH and air dried to afford the title compound (9.81 g, 84%) as a beige solid.

197 tert-Butyl 3-(4-bromobenzo[d]thiazol-2-yl)-2-(3-((tert-butoxycarbonyl)(2-methoxyethyl)amino)propanamido)-4,5-dihydrothieno[2,3-c]pyridine-6(7H)-carboxylate

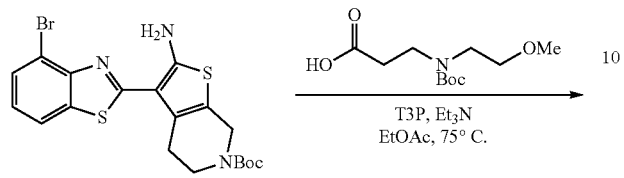

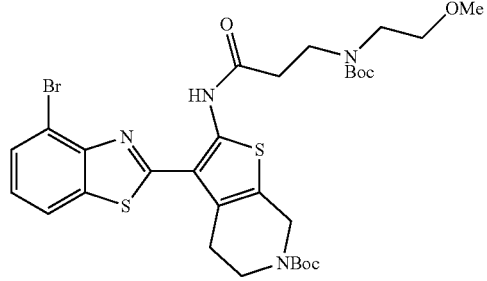

tert-Butyl 2-amino-3-(4-bromobenzo[d]thiazol-2-yl)-4,5-dihydrothieno[2,3-c]pyridine-6(7H)-carboxylate (4.50 g, 9.65 mmol) and a solution of 3-((tert-butoxycarbonyl)(2-methoxyethyl)amino)propanoic acid (3.58 g, 14.5 mmol) in EtOAc (74 mL) were charged in a 350 mL pressure vessel under nitrogen. Triethylamine (4.0 mL, 28.9 mmol) and T3P (50% in EtOAc, 11.5 mL, 19.3 mmol) were successively added and the resulting mixture was stirred in a 75° C. oil bath for 17 h. The solution was allowed to cool down at 20° C. and a saturated aqueous solution of NaHCO$_3$ (100 mL) and water (50 mL) were added. The resulting mixture was extracted with DCM (3×100 mL) and the combined organic layers were dried over anhydrous Na$_2$SO$_4$, filtered and concentrated. The obtained residue was purified by SiO$_2$ chromatography (EtOAc in hexanes, 3 to 35% gradient) to afford the title compound (5.78 g, 86%) as an orange solid.

tert-Butyl 2-(3-(tert-butoxycarbonyl(2-methoxyethyl)amino)propanamido)-3-(4-vinylbenzo[d]thiazol-2-yl)-4,5-dihydrothieno[2,3-c]pyridine-6(7H)-carboxylate

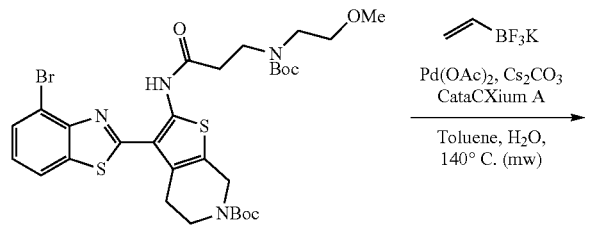

198

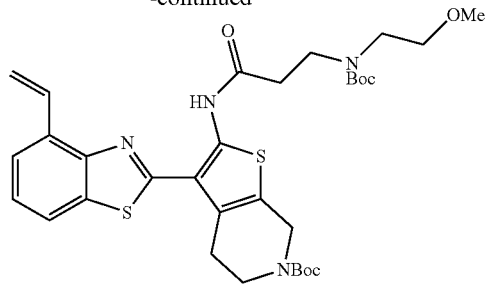

A vial was charged with Pd(OAc)$_2$ (32 mg, 0.144 mmol) and catacXium A (103 mg, 0.287 mmol). The vial was purged with nitrogen and degassed solvents were added (2:1 toluene/water, 7.2 mL). The mixture was stirred for 5 min at 100° C. and the resulting solution was transferred to a vial that was previously charged with tert-butyl 3-(4-bromobenzo[d]thiazol-2-yl)-2-(3-((tert-butoxycarbonyl)(2-methoxyethyl)amino)propanamido)-4,5-dihydrothieno[2,3-c]pyridine-6(7H)-carboxylate (1.00 g, 1.44 mmol), potassium vinyltrifluoroborate (385 mg, 2.88 mmol) and Cs$_2$CO$_3$ (1.41 g, 4.31 mmol) under nitrogen. The vial was sealed and the reaction mixture was stirred in a 140° C. oil bath for 18 h. The solution was diluted with EtOAc, water and a saturated aqueous solution of NH$_4$Cl. The mixture was extracted with EtOAc (3×) and the combined organic layers were washed with brine, dried over anhydrous MgSO$_4$, filtered and concentrated. The obtained residue was purified by SiO$_2$ chromatography (EtOAc in hexanes, 0 to 50% gradient) to afford the title compound (535 mg, 58%) as a brown solid.

3-(2-methoxyethylamino)-N-(3-(4-vinylbenzo[d]thiazol-2-yl)-4,5,6,7-tetrahydrothieno[2,3-c]pyridin-2-yl)propanamide bis(2,2,2-trifluoroacetate) (Compound 583)

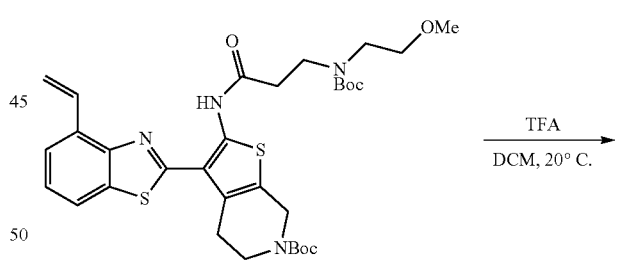

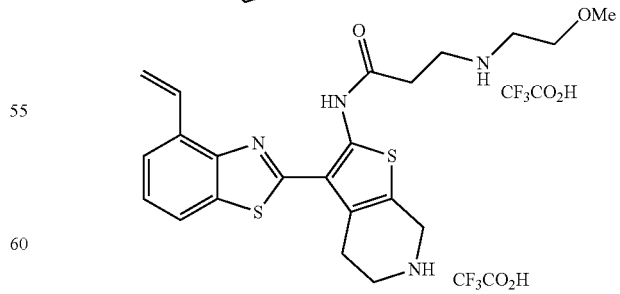

Trifluoroacetic acid (0.65 mL, 8.48 mmol) was added to a solution of tert-butyl 2-(3-(tert-butoxycarbonyl(2-methoxyethyl)amino)propanamido)-3-(4-vinylbenzo[d]thiazol-2-yl)-4,5-dihydrothieno[2,3-c]pyridine-6(7H)-carboxylate (25 mg, 0.389 mmol) in DCM (1.3 mL) at 20° C. The reaction mixture was stirred at this temperature for 2 h and it was concentrated. The resulting oil was lyophilized from water and MeCN to afford the title compound (25 mg, 100%) as a light yellow solid.

Compounds 316, 514, 515, 516, 534, 535, 559, 568, 594, 598, and 599 were synthesized in a similar manner to Compound 583 using the appropriate trifluoroborate.

Example 62. Synthesis of 3-((2-methoxyethyl) amino)-N-(3-(4-(4-methyl-1H-imidazol-1-yl)benzo [d]thiazol-2-yl)-4,5,6,7-tetrahydrothieno[2,3-c]pyridin-2-yl)propanamide trihydrochloride (Compound 592)

tert-Butyl 2-(3-((tert-butoxycarbonyl)(2-methoxyethyl)amino)propanamido)-3-(4-(4-methyl-1H-imidazol-1-yl)benzo[d]thiazol-2-yl)-4,5-dihydrothieno [2,3-c]pyridine-6(7H)-carboxylate

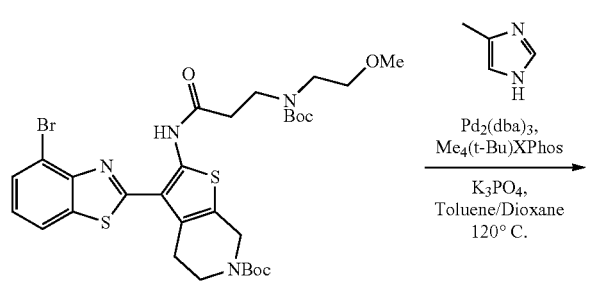

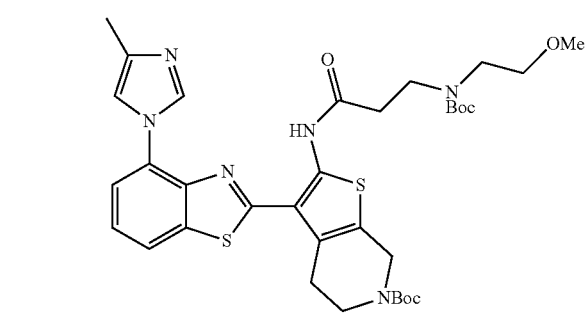

A vial was charged with Pd₂(dba)₃ (5.3 mg, 0.00575 mmol) and Me₄(t-Bu)XPhos (5.5 mg, 0.0115 mmol). The vial was purged with nitrogen and degassed solvents were added (5:1 toluene/dioxane, 1 mL). The mixture was stirred for 3 min at 120° C. and the resulting solution was transferred to a vial that was previously charged with tert-butyl 3-(4-bromobenzo[d]thiazol-2-yl)-2-(3-((tert-butoxycarbonyl)(2-methoxyethyl)amino)propanamido)-4,5-dihydrothieno[2,3-c]pyridine-6(7H)-carboxylate (100 mg, 0.144 mmol), 4-methylimidazole (24 mg, 0.287 mmol) and K₃PO₄ (61 mg, 0.287 mmol) under nitrogen. The vial was sealed and the reaction mixture was stirred in a 120° C. oil bath for 17 h. The reaction mixture was concentrated and the resulting residue was purified by SiO₂ chromatography (MeOH in DCM, 0 to 5% gradient) to afford the title compound (57 mg, 57%) as a yellow solid.

3-((2-Methoxyethyl)amino)-N-(3-(4-(4-methyl-1H-imidazol-1-yl)benzo[d]thiazol-2-yl)-4,5,6,7-tetrahydrothieno[2,3-c]pyridin-2-yl)propanamide trihydrochloride (Compound 592)

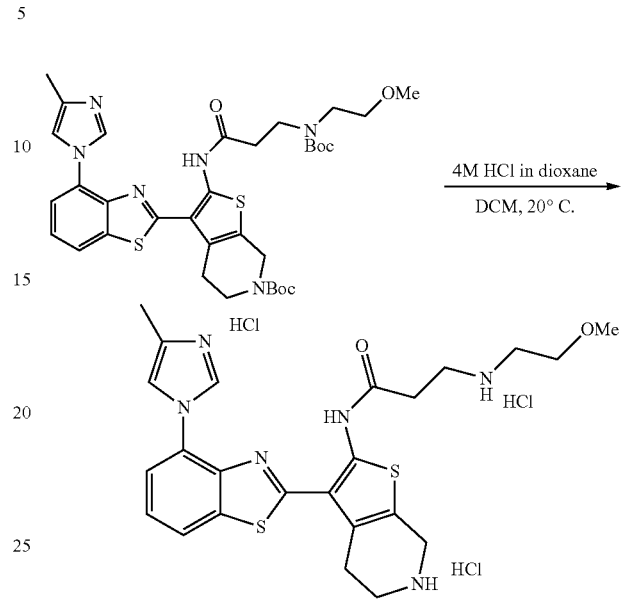

A solution of HCl (4 N in dioxane, 0.82 mL, 3.27 mmol) was added to a solution of tert-butyl 2-(3-((tert-butoxycarbonyl)(2-methoxyethyl)amino)propanamido)-3-(4-(4-methyl-1H-imidazol-1-yl)benzo[d]thiazol-2-yl)-4,5-dihydrothieno[2,3-c]pyridine-6(7H)-carboxylate (57 mg, 0.0819 mmol) in DCM (1.2 mL) at 20° C. The reaction mixture was stirred at this temperature for 5 h and it was diluted with Et₂O. The solid was collected by filtration and washed with Et₂O. The obtained residue was purified by reverse phase chromatography (C₁₈, MeCN in 0.1% HCO₂H/H₂O, 5 to 20% gradient) to afford the title compound (24 mg, 48%) as a yellowish solid after lyophilization.

Compounds 543, 553, 560, 582, 597, 612, 617, and 625 were similarly synthesized using the appropriate NH-containing heterocycle or heteroaryl or NH-linked aryl to displace the bromine.

Example 63. Synthesis of N-(3-(4-Methoxybenzo [d]thiazol-2-yl)-4,5,6,7-tetrahydrothieno[2,3-c]pyridin-2-yl)-3-((2-methoxyethyl)amino)propanamide dihydrochloride (Compound 613)

2-Chloro-4-methoxybenzo[d]thiazole

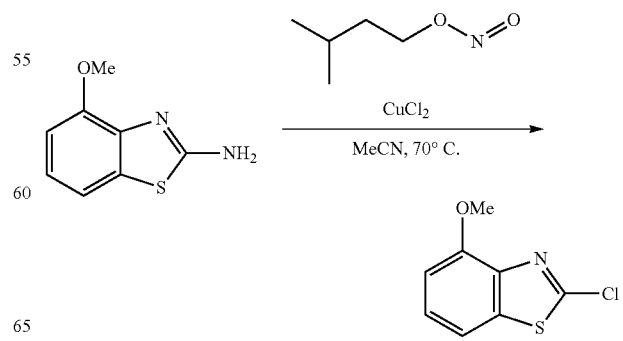

A 500 mL three-necked flask equipped with a condenser under nitrogen was charged with copper(II) chloride (3.36 g, 25.0 mmol), MeCN (71 mL) and isopentyl nitrite (2.2 mL, 16.6 mmol). The suspension was stirred in a 65° C. oil bath for 10 min before adding a solution of 2-amino-4-methoxy-benzothiazole (2.00 g, 11.1 mmol) in MeCN (42 mL). The reaction mixture was stirred in a 65° C. oil bath for 2 h and it was allowed to cool down at 20° C. Water (150 mL) and 1N HCl (100 mL) were added and the resulting mixture was extracted with EtOAc (3×100 mL). Combined organic layers were washed with brine, dried over anhydrous $Na_2SO_4$, filtered and concentrated. The obtained residue was purified by $SiO_2$ chromatography (EtOAc in hexanes, 5 to 15% gradient) to afford the title compound (1.52 g, 69%) as a white solid.

N-(3-(4-Methoxybenzo[d]thiazol-2-yl)-4,5,6,7-tetrahydrothieno[2,3-c]pyridin-2-yl)-3-((2-methoxyethyl)amino)propanamide dihydrochloride (Compound 613)

Starting from 2-chloro-4-methoxybenzo[d]thiazole, the synthesis of Compound 613 is similar to Compound 583. The final deprotection has been performed using 4N HCl in dioxane, affording the title compound.

Example 64. Synthesis of 3-(isopropylamino)-N-(3-(4-methylbenzo[d]oxazol-2-yl)-4,5,6,7-tetrahydrothieno[2,3-c]pyridin-2-yl)propanamide dihydrochloride (Compound 311)

2-(4-Methylbenzo[d]oxazol-2-yl)acetonitrile

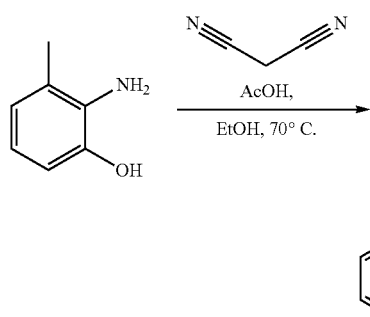

Malononitrile (1.6 g, 24.3 mmol) was added to a solution of 2-amino-3-methylphenol (1 g, 8.12 mmol) in EtOH (20 mL) and acetic acid (3 mL) and the resulting mixture was stirred for 16 h at 100° C. The reaction mixture was concentrated and the residue was taken in DCM. The precipitate was filtered off and the mother liquor were washed with brine (3×), dried over $MgSO_4$, filtered and concentrated under reduced pressure. The residue was purified by $SiO_2$ chromatography (EtOAc in hexanes, 0 to 50% gradient) to afford the title compound (550 mg, 43%) as yellow crystal.

tert-Butyl 2-amino-3-(4-methylbenzo[d]oxazol-2-yl)-4,5-dihydrothieno[2,3-c]pyridine-6(7H)-carboxylate

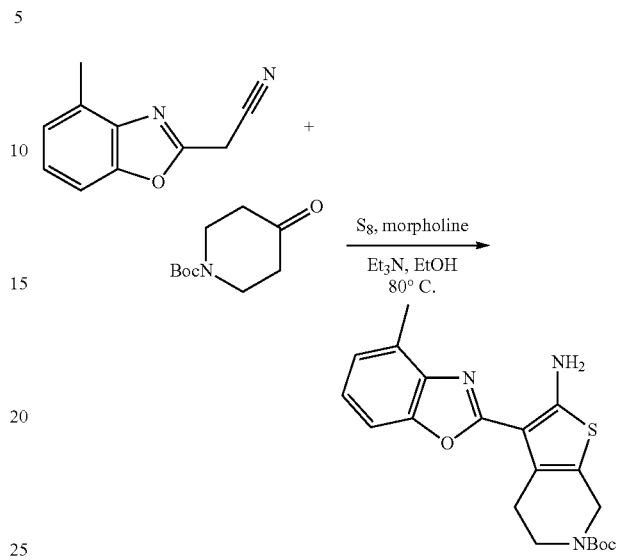

A mixture of 2-(4-methylbenzo[d]oxazol-2-yl)acetonitrile (450 mg, 2.6 mmol), N-Boc-4-piperidone (573 mg, 2.9 mmol), sulfur (92 mg, 2.9 mmol), morpholine (0.25 mL, 2.9 mmol) and triethylamine (0.4 mL, 2.9 mmol) in EtOH (15 mL) was stirred for 16 h at 90° C. The reaction mixture was cooled to RT, concentrated to half of its initial volume and the precipitated solid was collected by filtration. The solid was washed with EtOH and dried under vacuum to afford the title compound (602 mg, 62%).

tert-Butyl 2-(3-((tert-butoxycarbonyl)(isopropyl)amino)propanamido)-3-(4-methylbenzo[d]oxazol-2-yl)-4,5-dihydrothieno[2,3-c]pyridine-6(7H)-carboxylate

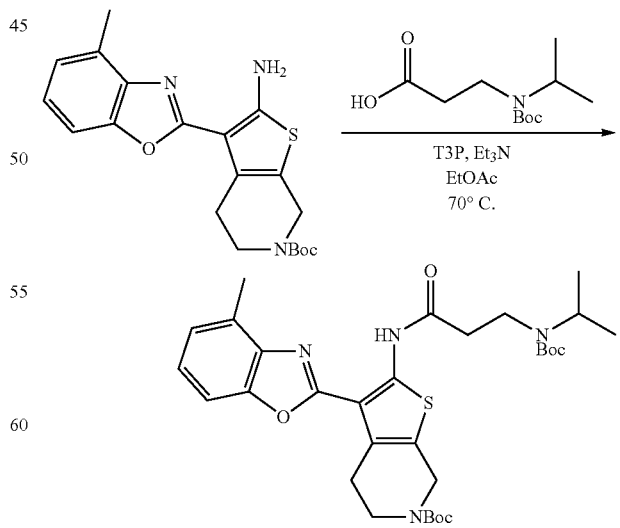

A mixture tert-butyl 2-amino-3-(4-methylbenzo[d]oxazol-2-yl)-4,5-dihydrothieno[2,3-c]pyridine-6(7H)-carboxylate (200 mg, 0.519 mmol), 3-((tert-butoxycarbonyl)(isopropyl)amino)propanoic acid (180 mg, 0.778 mmol), T3P (50% in EtOAc, 1.94 mL, 1.038 mmol) and Et₃N (0.217 mL, 1.557 mmol) in EtOAc (5.2 mL) was stirred for 16 h at 60° C. The reaction mixture was cooled to RT, quenched with saturated water and diluted with EtOAc. The layers were separated, the aqueous phase was extracted with EtOAc, and the combined organic layers were washed with brine, dried over MgSO₄, filtered and concentrated. The residue was purified by reverse phase chromatography (MeCN in a 10 nM aqueous solution of NH₄HCO₂, 30 to 100% gradient) to afford the title compound (170 mg, 55%).

3-(Isopropylamino)-N-(3-(4-methylbenzo[d]oxazol-2-yl)-4,5,6,7-tetrahydrothieno[2,3-c]pyridin-2-yl)propanamide dihydrochloride (Compound 311)

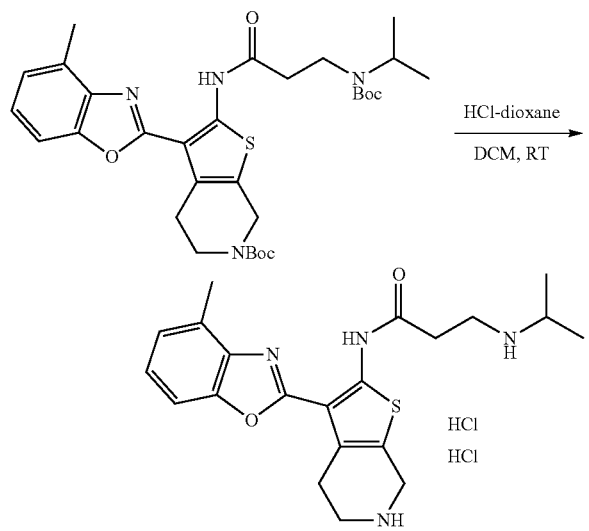

A solution of HCl (4 N in dioxane, 1.0 mL) was added to a solution of tert-butyl 2-(3-((tert-butoxycarbonyl)(isopropyl)amino)propanamido)-3-(4-methylbenzo[d]oxazol-2-yl)-4,5-dihydrothieno[2,3-c]pyridine-6(7H)-carboxylate (170.4 mg, 0.284 mmol) in DCM (2.0 mL) at RT. The resulting mixture was stirred for 2 h at RT and diluted with Et₂O (2.0 mL). The precipitated solid was collected by filtration, washed with Et₂O and lyophilized from water/MeCN to afford the title compound (69.8 mg, 52%) as a yellow solid.

The synthesis of Compounds 302, 312, 554, 593 and 600 were similar to the above.

Example 65. Library I Synthesis of Various Compounds tert-butyl 3-(5-bromo-1,3-benzothiazol-2-yl)-2-(prop-2-enoylamino)-5,7-dihydro-4H-thieno[2,3-c]pyridine-6-carboxylate

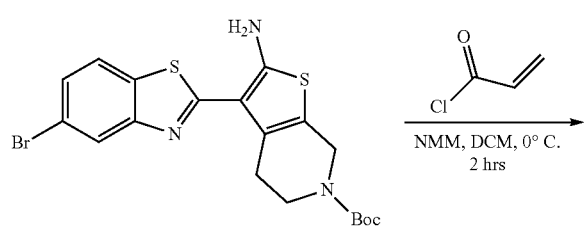

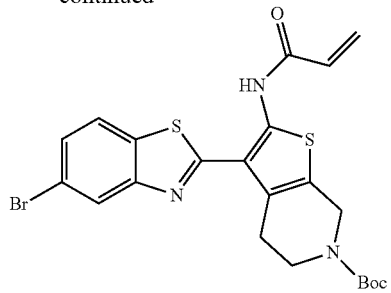

To a solution of tert-butyl 2-amino-3-(5-bromo-1,3-benzothiazol-2-yl)-5,7-dihydro-4H-thieno[2,3-c]pyridine-6-carboxylate (50.00 g, 107.20 mmol, 1.00 eq) in DCM (500.00 mL) was added NMM (32.53 g, 321.61 mmol, 35.36 mL, 3.00 eq) and prop-2-enoyl chloride (19.41 g, 214.40 mmol, 17.48 mL, 2.00 eq) at 0° C. The mixture was stirred at 25° C. for 3 hour. LCMS and TLC (petroleum ether/EtOAc=2/1, Rf=0.51) showed the reaction was complete. The reaction mixture was concentrated under reduced pressure to afford a crude residue. The residue was precipitated with MTBE (500 mL) and the mixture was filtered to obtain the desired product. The title compound (122.00 g, crude) was obtained as a yellow solid.

tert-butyl 3-(5-bromo-1,3-benzothiazol-2-yl)-2-[3-(2-methoxyethylamino)propanoylamino]-5,7-dihydro-4H thieno[2,3c]pyridine-6-carboxylate

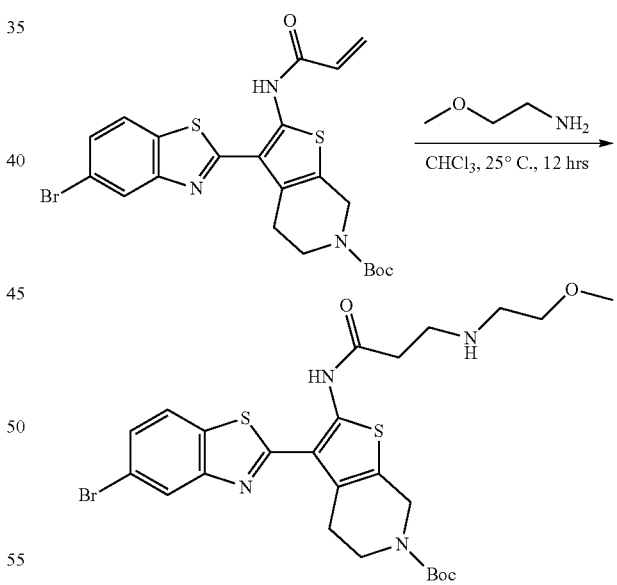

To a solution of tert-butyl 3-(5-bromo-1,3-benzothiazol-2-yl)-2-(prop-2-enoylamino)-5,7-dihydro-4H-thieno[2,3-c]pyridine-6-carboxylate (52.00 g, 99.91 mmol, 1.00 eq) in CHCl3 (600.00 mL) was added NMM (30.32 g, 299.73 mmol, 32.96 mL, 3.00 eq) and 2-methoxyethanamine (21.01 g, 279.75 mmol, 24.43 mL, 2.80 eq) at 25° C. The mixture was stirred at 25° C. for 12 hour. LCMS and TLC (petroleum ether/EtOAc=2/1, Rf=0.51) showed the reaction was complete. The reaction was concentrated under reduced pressure to give a crude residue. The residue was precipitated with MTBE (500 mL) and the mixture was filtered to obtain the desired product. The title compound (51.00 g, 85.63 mmol, 85.71% yield) was obtained as a yellow solid.

General Procedure for Library

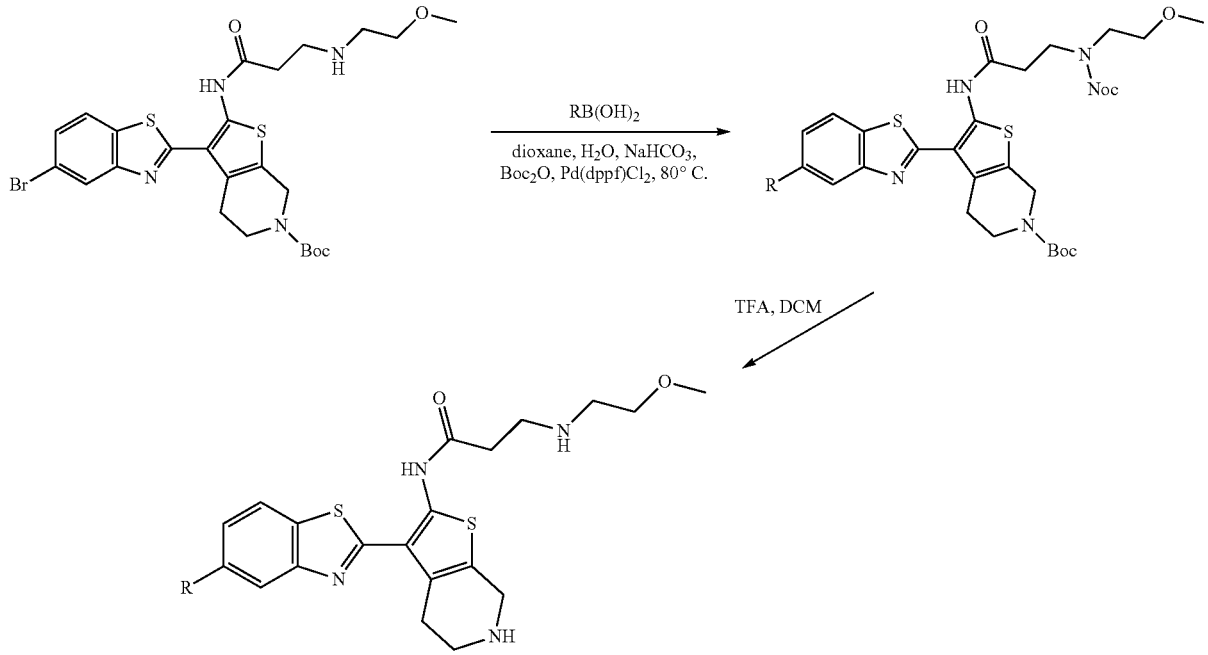

To a solution of tert-butyl 3-(5-bromobenzo[d]thiazol-2-yl)-2-(3-((2-methoxyethyl)amino)propanamido)-4,7-dihydrothieno[2,3-c]pyridine-6(5H)-carboxylate and the appropriate boronic acid (RB(OH)₂; 1.2 eq) in dioxane (3.0 mL), H₂O (2.0 mL) was added NaCO₃ (2 eq), Boc₂O (1.5 eq) and Pd(dppf)Cl₂ (10 mol %) under N₂ atmosphere. The mixture was stirred at 80° C. for 12 hrs at which point, the reaction was complete by LC/MS. The reaction mixture was concentrated and the crude product was purified by preparative HPLC.

To a solution of the Boc-protected product above in DCM (8.0 mL) was added TFA (1.0 mL). The mixture was stirred at 25° C. for 12 hr, at which point the reaction was complete by LC/MS. The reaction mixture was concentrated and the crude product was purified by preparative HPLC to give the various compounds of the invention.

Example 66. Library II Synthesis of Various Compounds 2-amino-5-bromo-benzenethiol

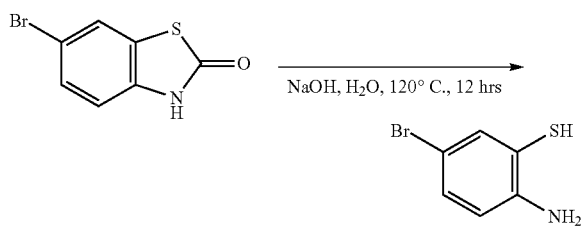

To a solution of 6-bromo-3H-1,3-benzothiazol-2-one (300.00 g, 1.30 mol, 1.00 eq) in water (2.00 L) was added NaOH (520.00 g, 13.00 mol, 10.00 eq). The mixture was stirred at 120° C. for 12 hour. TLC (petroleum ether/EtOAc=2/1, R$_f$=0.51) indicated the reaction was complete. After cooling the solution to 0° C., the pH was adjusted to pH=7 with concentrated HCl (35 mL) keeping the temperature below 35° C. As the hydrochloric acid was added, off-gassing occurred, and solids formed as the pH approached 7. The suspension was filtered and the filtrate concentrated under reduced pressure to afford the title compound (250.00 g, 1.22 mol, 93.85% yield) as a yellow solid.

2-(6-bromo-1,3-benzothiazol-2-yl) acetonitrile

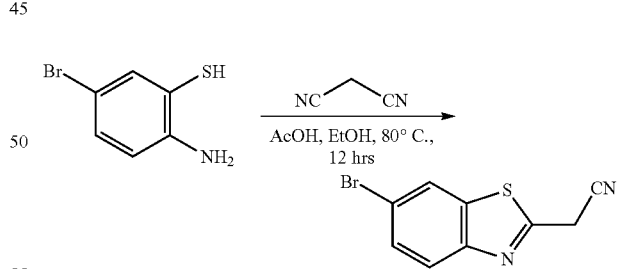

To a solution of 2-amino-5-bromo-benzenethiol (200.00 g, 979.96 mmol, 1.00 eq) in EtOH (1.20 L) was added propanedinitrile (161.84 g, 2.45 mol, 154.13 mL, 2.50 eq) and AcOH (900.00 mL). The mixture was stirred at 120° C. for 12 hour. TLC (petroleum ether/EtOAc=2/1, Rf=0.51) indicated the reaction was complete. The reaction was concentrated under reduced pressure and the residue was taken up in DCM (300 mL). The solution was extracted with 3 N HCl (100 mL×3), dried over anhydrous Na₂SO₄, filtered and concentrated by rotary evaporation. The residue was purified by column chromatography (SiO₂, Petroleum ether/

Ethyl acetate=30:1 to 10:1) to afford the title compound (77.00 g, 304.20 mmol, 31.04% yield) as a yellow solid.

tert-butyl 2-amino-3-(6-bromo-1,3-benzothiazol-2-yl)-5,7-dihydro-4H-thieno[2,3-c]pyridine-6-carboxylate

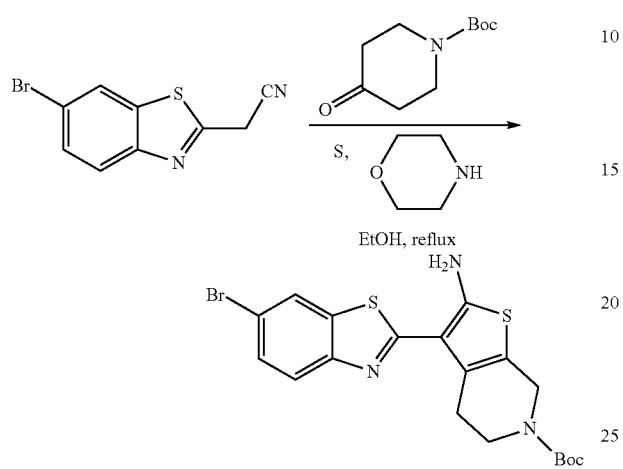

To a solution of 2-(6-bromo-1,3-benzothiazol-2-yl)acetonitrile (25.00 g, 98.77 mmol, 1.00 eq) tert-butyl 4-oxopiperidine-1-carboxylate (15.74 g, 79.02 mmol, 0.80 eq) in EtOH (600.00 mL) was added morpholine (8.60 g, 98.77 mmol, 8.69 mL, 1.00 eq) and sulfur (3.17 g, 98.77 mmol, 1.00 eq). The mixture was stirred at 25° C. for 12 hour. LCMS and TLC (petroleum ether/EtOAc=2/1, Rf=0.51) indicated the reaction was complete. The reaction mixture was concentrated under reduced pressure to provide a crude residue. The residue was triturated with EtOH (500 mL) the title compound (47.00 g) was obtained as a yellow solid which was used directly tert-butyl 3-(6-bromo-1,3-benzothiazol-2-yl)-2-(prop-2-enoylamino)-5,7-dihydro-4H-thieno[2,3-c]pyridine-6-carboxylate

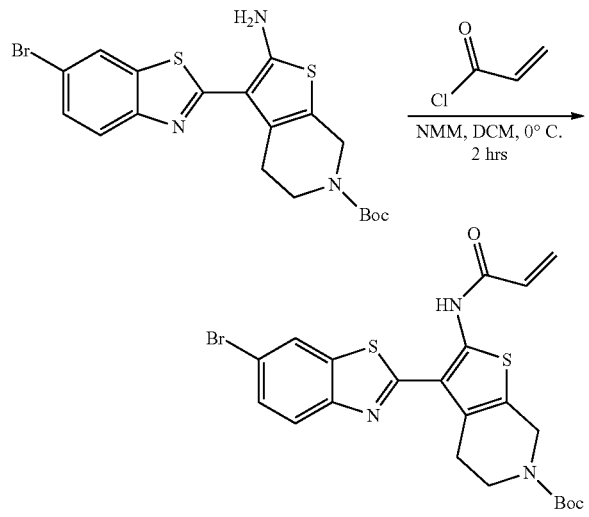

To a solution of tert-butyl 2-amino-3-(6-bromo-1,3-benzothiazol-2-yl)-5,7-dihydro-4H-thieno[2,3-c]pyridine-6-carboxylate (47.00 g, 100.77 mmol, 1.00 eq) in DCM (500.00 mL) was added NMM (30.58 g, 302.31 mmol, 33.24 mL, 3.00 eq) and prop-2-enoyl chloride (18.24 g, 201.54 mmol, 16.43 mL, 2.00 eq) at 0° C. The mixture was stirred at 25° C. for 3 hours. LCMS and TLC (petroleum ether/EtOAc=2/1, Rf=0.51) indicated the reaction was complete. The reaction mixture was concentrated under reduced pressure to provide a residue which was triturated with MTBE (1000 mL) to afford the title compound (74.00 g) as a yellow solid which was used directly.

tert-butyl 3-(6-bromo-1,3-benzothiazol-2-yl)-2-[3-(2-methoxyethylamino)propanoylamino]-5,7-dihydro-4Hthieno[2,3c]pyridine-6-carboxylate

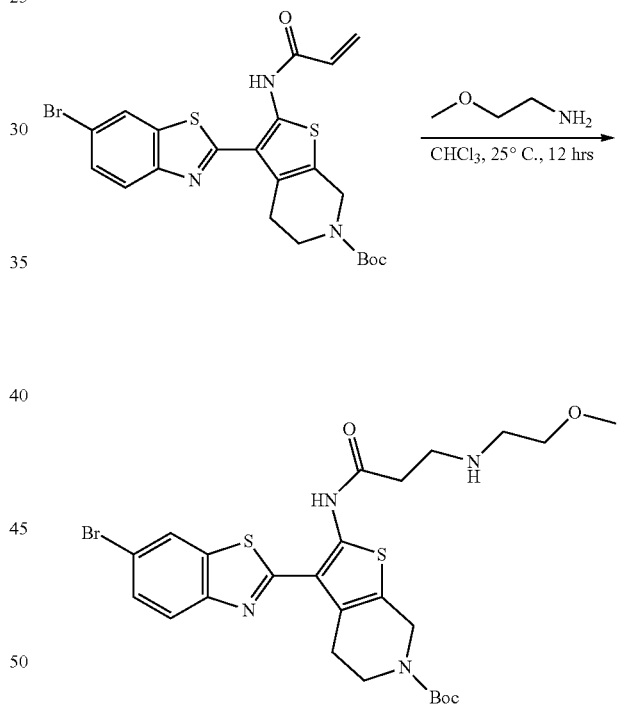

To a solution of tert-butyl 3-(6-bromo-1,3-benzothiazol-2-yl)-2-(prop-2-enoylamino)-5,7-dihydro-4H-thieno[2,3-c]pyridine-6-carboxylate (24.00 g, 46.11 mmol, 1.00 eq) in chloroform (300.00 mL) was added NMM (13.99 g, 138.33 mmol, 15.21 mL, 3.00 eq) and 2-methoxyethanamine (9.70 g, 129.11 mmol, 11.28 mL, 2.80 eq) at 25° C. The mixture was stirred at 25° C. for 12 hour. LCMS and TLC (petroleum ether/EtOAc=2/1, Rf=0.51) indicated the reaction was complete. The reaction mixture was concentrated under reduced pressure to give a residue. The title compound (26.00 g, 43.66 mmol, 94.68% yield) was obtained as a yellow solid.

General Procedure for Preparation of Library

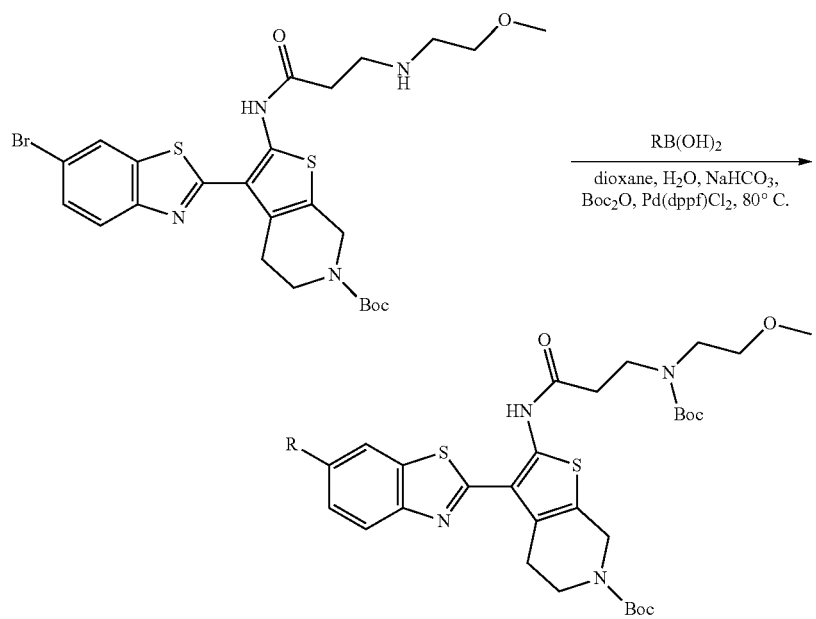

Addition of the appropriate R group onto the benzothiazole and deprotection was achieved as described in the previous example to produce compounds of the invention.

Example 67. Synthesis of 3-(sec-butylamino)-N-(6-isopropyl-3-(5-(trifluoromethyl)benzo[d]thiazol-2-yl)-4,5,6,7-tetrahydrothieno[2,3-c]pyridin-2-yl)propanamide (Compound 146)

Step 1: 2-(5-(trifluoromethyl)benzo[d]thiazol-2-yl)acetonitrile (2

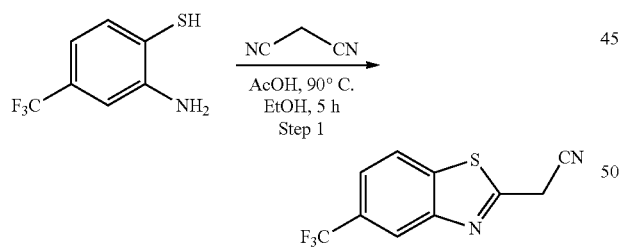

To a solution of 2-amino-4-(trifluoromethyl)benzenethiol (1.5 g, 6.5 mmol) in ethanol (10 mL) was added acetic acid (10 mL) followed by malononitrile (0.64 g, 9.8 mmol) and the reaction mixture was heated to 90° C. for 5 h. Reaction was monitored by TLC. After completion of reaction, solvent was removed under reduced pressure and the precipitate obtained was diluted with EtOAc and washed with saturated NaHCO$_3$ solution. The combined organic layer was dried over Na$_2$SO$_4$ and concentrated to afford a crude residue which was purified by flash column chromatography to afford the title compound as an off white solid (750 mg, 50% yield).

Step 2: 6-isopropyl-3-(5-(trifluoromethyl)benzo[d]thiazol-2-yl)-4,5,6,7-tetrahydrothieno[2,3-c]pyridin-2-amine

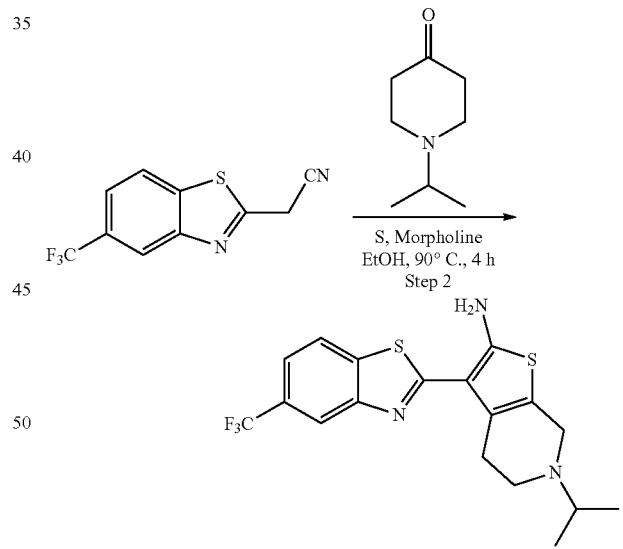

To a solution of 2-(5-(trifluoromethyl)benzo[d]thiazol-2-yl)acetonitrile (700 mg, 2.89 mmol) in ethanol (10 mL) was added 1-isopropylpiperidin-4-one (400 mg, 2.89 mmol), morpholine (251 mg, 2.89 mmol) and the reaction mixture was heated to 40° C. for 10 min. Then was added sulphur (92 mg, 2.89 mmol) and the resulting mixture heated to 90° C. for 4 h. Reaction was monitored by TLC. After completion, the reaction mixture was evaporated to give crude product which was purified by flash column chromatography to afford (550 mg, 45% yield) of the title compound as yellow solid.

Step 3: N-(6-isopropyl-3-(5-(trifluoromethyl)benzo[d]thiazol-2-yl)-4,5,6,7-tetrahydrothieno[2,3-c]pyridin-2-yl)acrylamide (6)

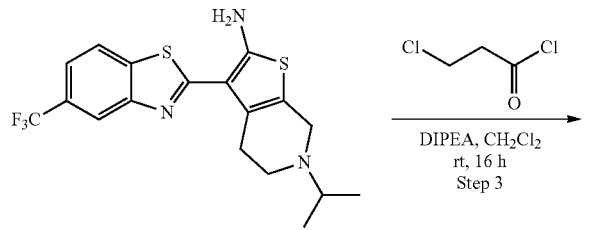

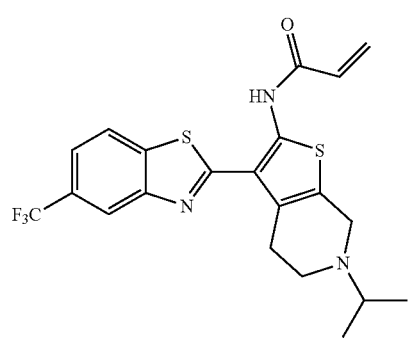

To a solution of 6-isopropyl-3-(5-(trifluoromethyl)benzo[d]thiazol-2-yl)-4,5,6,7-tetrahydrothieno[2,3-c]pyridin-2-amine (500 mg, 1.25 mmol) in DCM (5 mL) at 0° C. was added DIPEA (0.243 mg, 1.88 mmol) followed by 3-chloropropanoyl chloride (0.167 mg, 1.32 mmol) and the reaction mixture was stirred at room temperature for 16 h. Reaction was monitored by TLC. After completion, the reaction mass was diluted with DCM and water. The organic layer was separated, dried over Na$_2$SO$_4$ and concentrated to give crude residue which was purified by flash column chromatography to afford the title compound as yellow solid (200 mg, 35% yield).

Step 4: 3-(sec-butylamino)-N-(6-isopropyl-3-(5-(trifluoromethyl)benzo[d]thiazol-2-yl)-4,5,6,7-tetrahydrothieno[2,3-c]pyridin-2-yl)propanamide (Compound 146)

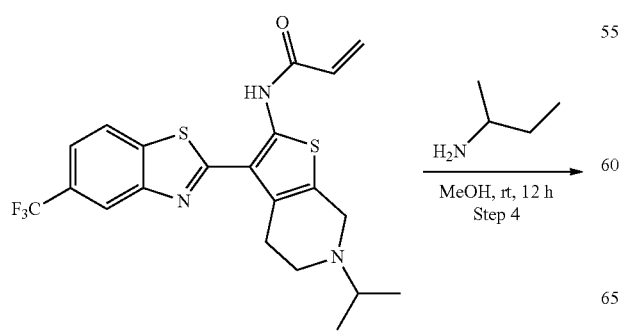

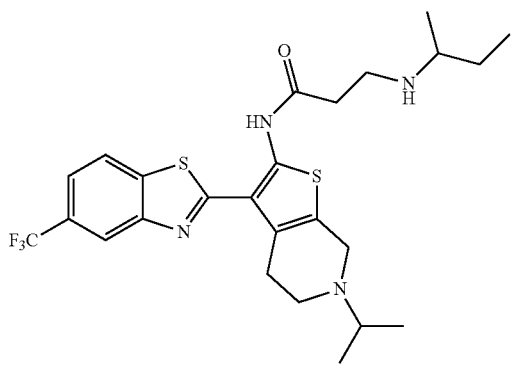

To a stirred solution of N-(6-isopropyl-3-(5-(trifluoromethyl)benzo[d]thiazol-2-yl)-4,5,6,7-tetrahydrothieno[2,3-c]pyridin-2-yl)acrylamide (200 mg, 0.44 mmol) in CH$_3$OH (5 mL) was added butan-2-amine (64 mg, 0.89 mmol) at room temperature and stirred for 12 h. Reaction was monitored by TLC. After completion, the reaction mixture was evaporated to dryness to give crude residue which was purified by flash column chromatography to afford the title compound as yellow solid (80 mg, 13% yield).

Example 68. Synthesis of N-(3-(benzo[d]thiazol-2-yl)-4,5,6,7-tetrahydrothieno[2,3-c]pyridin-2-yl)-3-(((1-methyl-1H-pyrazol-4-yl)methyl)amino)propanamide (Compound 147)

Step 1: tert-butyl 2-acrylamido-3-(benzo[d]thiazol-2-yl)-4,7-dihydrothieno[2,3-c]pyridine-6(5H)-carboxylate (2)

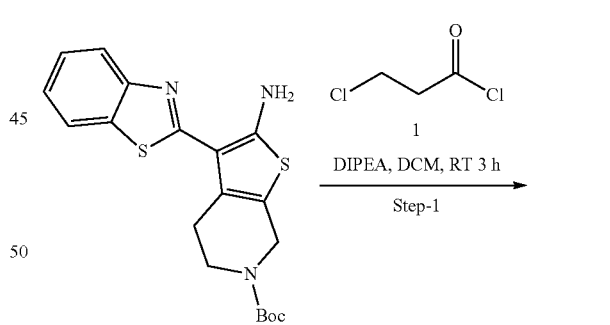

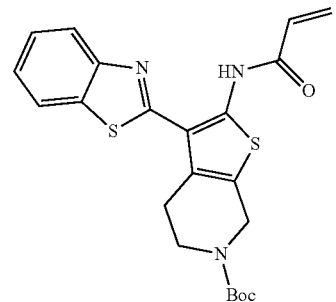

To a solution of tert-butyl 2-amino-3-(benzo[d]thiazol-2-yl)-4,7-dihydrothieno[2,3-c]pyridine-6(5H)-carboxylate (3 g, 7.74 mmol) in DCM (30 mL) at 0° C. was added DIPEA (1.34 mL, 7.74 mmol) and 3-chloropropanoyl chloride (1.03 g, 8.12 mmol). The resulting reaction mixture was stirred at room temperature for 3 h. The progress of the reaction was monitored by TLC. After completion, the reaction mass was diluted with DCM and washed with saturated NaHCO₃ solution and brine. The combined organic layer was dried over anhydrous Na₂SO₄, filtered and concentrated to get a crude residue. The crude compound was purified by silica gel column chromatography eluting with 0-5% MeOH/DCM to afford the title compound as yellow solid (1.5 g, 44%).

Step 2: tert-butyl 3-(benzo[d]thiazol-2-yl)-2-(3-(((1-methyl-M-pyrazol-4-yl)methyl)amino)propanamido)-4,7-dihydrothieno[2,3-c]pyridine-6(5H)-carboxylate (4)

Step 3: N-(3-(benzo[d]thiazol-2-yl)-4,5,6,7-tetrahydrothieno[2,3-c]pyridin-2-yl)-3-(((1-methyl-1H-pyrazol-4-yl)methyl)amino)propanamide (Compound 147)

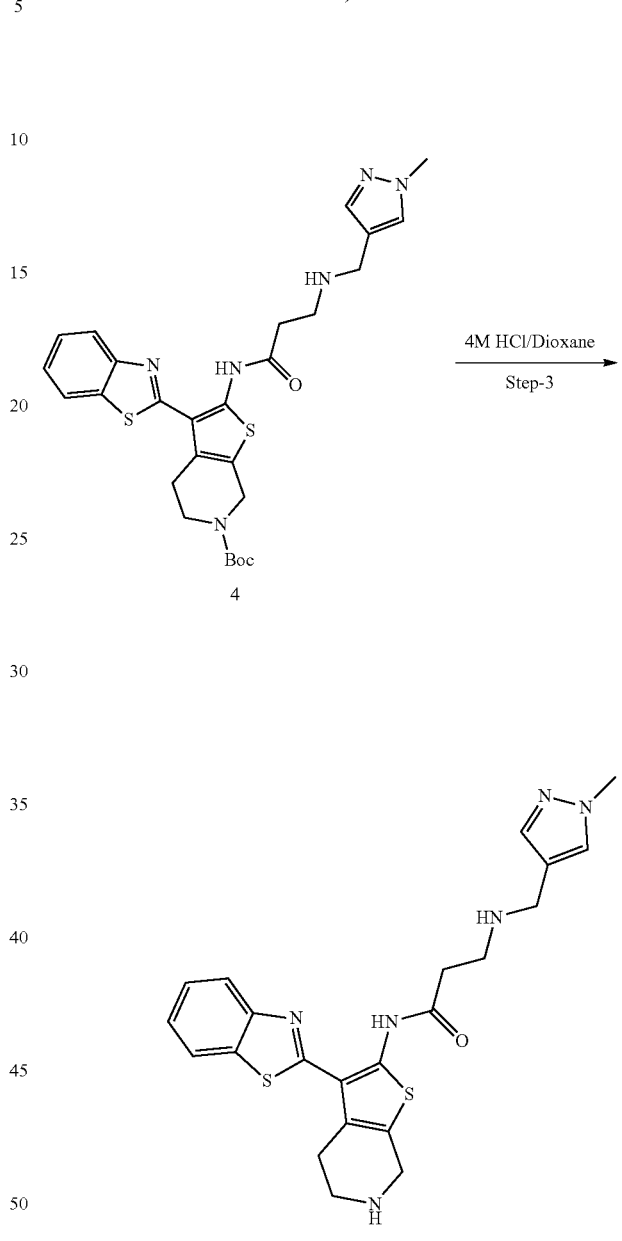

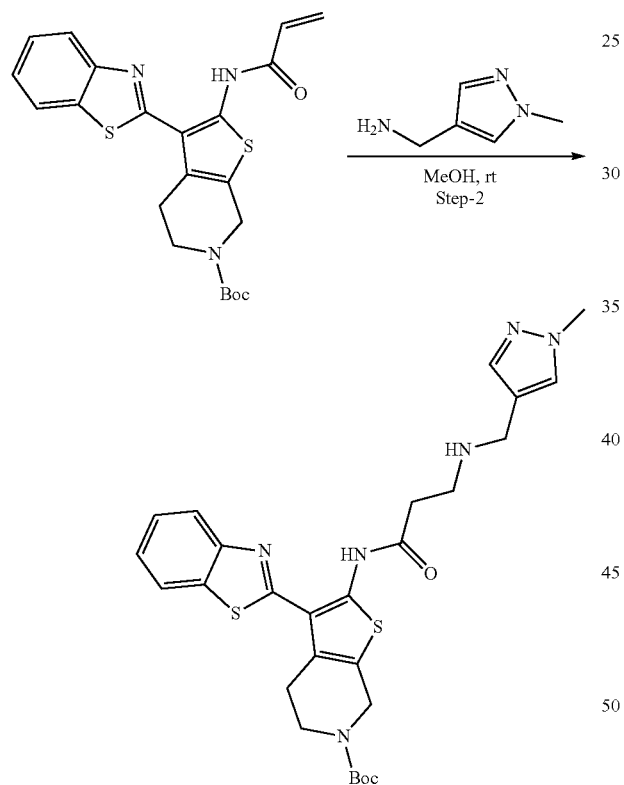

To a solution of tert-butyl 2-acrylamido-3-(benzo[d]thiazol-2-yl)-4,7-dihydrothieno[2,3-c]pyridine-6(5H)-carboxylate (0.1 g, 0.226 mmol) in methanol:THF (1:2 mL) was added (1-methyl-1H-pyrazol-4-yl)methanamine (0.050 g, 0.453 mmol). The resulting reaction mixture was stirred at room temperature for 2 h. The progress of the reaction was monitored by TLC and LCMS. After completion, the reaction mixture was concentrated up to dryness to get a crude residue. The crude compound was purified by silica gel column chromatography eluting with 0-5% MeOH/DCM to afford the title compound as an off white solid (0.095 g, 76% yield).

To a solution of tert-butyl 3-(benzo[d]thiazol-2-yl)-2-(3-(((1-methyl-1H-pyrazol-4-yl)methyl)amino)propanamido)-4,7-dihydrothieno[2,3-c]pyridine-6(5H)-carboxylate 4 (0.095 g, 0.172 mmol) in dioxane (1 mL) at 0° C. was added 4M HCl in dioxane (2 mL). After the addition, the resulting mixture was stirred at room temperature for 2 h. After completion, the reaction mixture was evaporated in vacuum resulting in a crude residue. The residue was triturated with methanol, filtered and washed with diethyl ether and dried to afford the HCl salt of the title compound as a yellow solid (0.080 g, 88%).

Example 69. Synthesis of Ethyl (3-((3-(benzo[d]thiazol-2-yl)-4,5,6,7-tetrahydrothieno[2,3-c]pyridin-2-yl)amino)-3-oxopropyl)glycinate hydrochloride (Compound 148)

Step 1: tert-butyl 3-(benzo[d]thiazol-2-yl)-2-(3-((2-ethoxy-2-oxoethyl)amino)propanamido)-4,7-dihydrothieno[2,3-c]pyridine-6(5H)-carboxylate

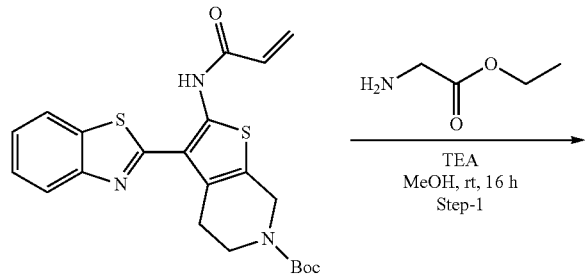

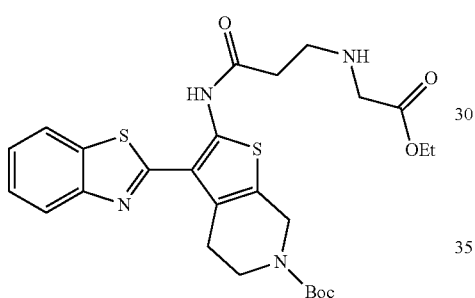

To a stirred solution of tert-butyl 2-acrylamido-3-(benzo[d]thiazol-2-yl)-4,7-dihydrothieno[2,3-c]pyridine-6(5H)-carboxylate (300 mg, 0.68 mmol) in CH₃OH (2 mL) was added ethyl glycinate 2 (141 mg, 1.02 mmol) followed by Et₃N (0.2 mL, 1.36 mmol) and the reaction mixture was stirred at room temperature for 16 h. Reaction was monitored by TLC. After completion, the reaction mixture was evaporated to dryness giving a crude residue which was purified by flash column chromatography to afford the title compound as pale yellow solid (150 mg, 41% yield).

Step 2: Ethyl (3-((3-(benzo[d]thiazol-2-yl)-4,5,6,7-tetrahydrothieno[2,3-c]pyridin-2-yl)amino)-3-oxopropyl)glycinate hydrochloride (Compound 148)

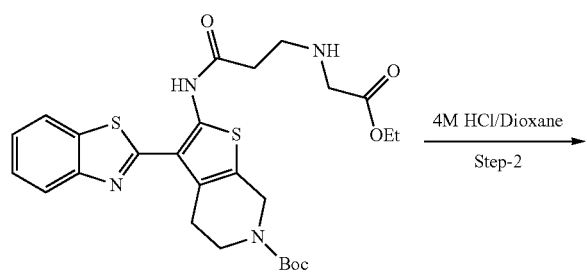

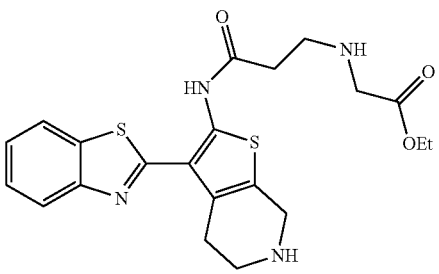

To a solution of tert-butyl 3-(benzo[d]thiazol-2-yl)-2-(3-((2-ethoxy-2-oxoethyl)amino)propanamido)-4,7-dihydrothieno[2,3-c]pyridine-6(5H)-carboxylate 3 (140 mg, 0.257 mmol) in dioxane (2 mL) at 0° C. was added 4M HCl in dioxane (2 mL) and the reaction mixture was stirred at room temperature for 2 h. Reaction was monitored by TLC. After completion, the reaction mixture was evaporated to dryness resulting in a crude residue which was purified by preparative HPLC to afford the HCl salt of the title compound as yellow solid (25 mg, 22% yield).

Example 70. Synthesis of (S)-3-(sec-butylamino)-N-(3-(5-(trifluoromethyl)benzo[d]thiazol-2-yl)-4,5,6,7-tetrahydrothieno[2,3-c]pyridin-2-yl)propanamide (Compound 152)

Step 1: 2-(5-(trifluoromethyl)benzo[d]thiazol-2-yl)acetonitrile (1)

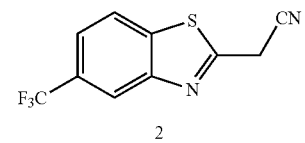

To a stirred solution of 2-amino-4-(trifluoromethyl)benzenethiol 1 (5 g, 21.8 mmol) in EtOH (50 mL) was added malononitrile (2.1 g, 32 mmol) and AcOH (20 mL) and the resulting reaction mixture was stirred at 80° C. for 2 h. Progress of the reaction was monitored by TLC. After completion, the reaction mixture was concentrated under reduced pressure to dryness. The residue was diluted with water and extracted with ethyl acetate. Combined organic layer was dried over anhydrous Na₂SO₄ and concentrated to get a crude residue. The crude compound was purified by flash column chromatography to afford the title compound 2 as yellow solid (4.8 g, 92% yield).

Step 2: tert-butyl 2-amino-3-(5-(trifluoromethyl)benzo[d]thiazol-2-yl)-4,7-dihydrothieno[2,3-c]pyridine-6(5H)-carboxylate(3)

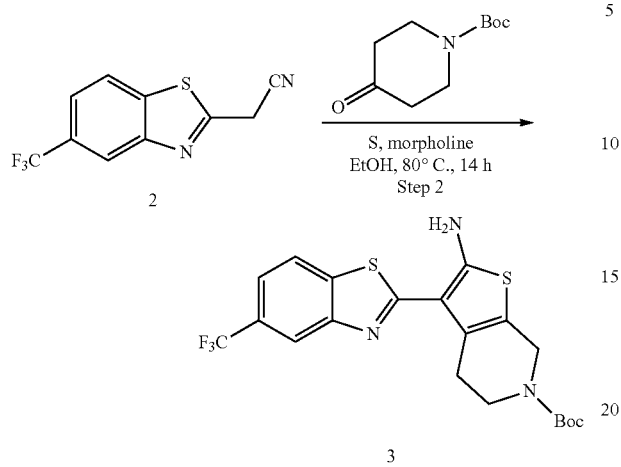

To a solution of 2-(5-(trifluoromethyl)benzo[d]thiazol-2-yl)acetonitrile 2 (4.5 g, 18.5 mmol) in ethanol (50 mL) was added tert-butyl 4-oxopiperidine-1-carboxylate (3.7 g, 18.5 mmol) followed by sulphur (592 mg, 18.5 mmol) and morpholine (1.6 g, 18.5 mmol) and the resulting mixture was heated to 80° C. for 14 h. Progress of the reaction was monitored by TLC. After completion, the reaction mixture was concentrated under reduced pressure to dryness. The residue was diluted with water and extracted with ethyl acetate. Combined organic layer was dried over anhydrous $Na_2SO_4$ and concentrated to get a crude residue. The crude compound was purified by flash column chromatography to afford the title compound 3 as pale yellow solid (6.5 g, 77% yield).

Step 3: tert-butyl 2-acrylamido-3-(5-(trifluoromethyl)benzo[d]thiazol-2-yl)-4,7-dihydrothieno[2,3-c]pyridine-6(5H)-carboxylate (4)

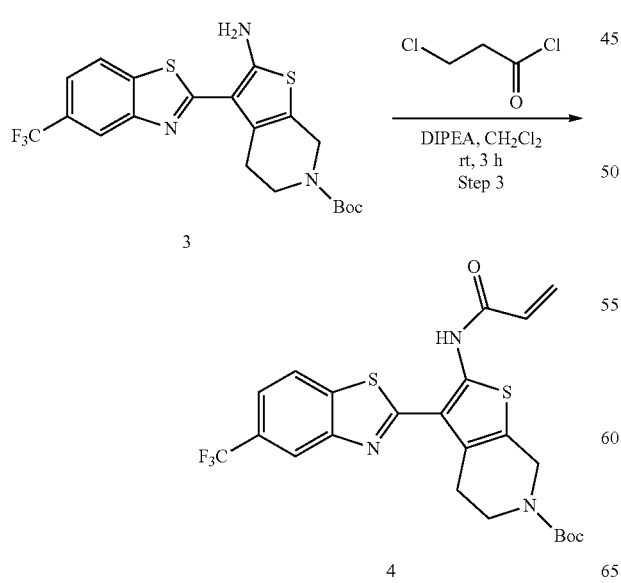

To a solution of tert-butyl 2-amino-3-(5-(trifluoromethyl)benzo[d]thiazol-2-yl)-4,7-dihydrothieno[2,3-c]pyridine-6(5H)-carboxylate 3 (3 g, 6.59 mmol) in DCM (30 mL) was added DIPEA (1.7 mL, 9.89 mmol), 3-chloropropanoyl chloride (0.88 g, 6.82 mmol) at 0° C. and the reaction was stirred at room temperature for 3 h. Progress of the reaction was monitored by TLC. After completion, reaction mixture was diluted with water and extracted with DCM. The combined organic layer was dried over anhydrous $Na_2SO_4$ and concentrated to get a crude residue. The crude compound was purified by flash column chromatography to afford the title compound 4 as yellow solid (3 g, 90% yield).

Step 4: tert-butyl (S)-2-(3-(sec-butylamino)propanamido)-3-(5-(trifluoromethyl)benzo[d]thiazol-2-yl)-4,7-dihydrothieno[2,3-c]pyridine-6(5H)-carboxylate (5)

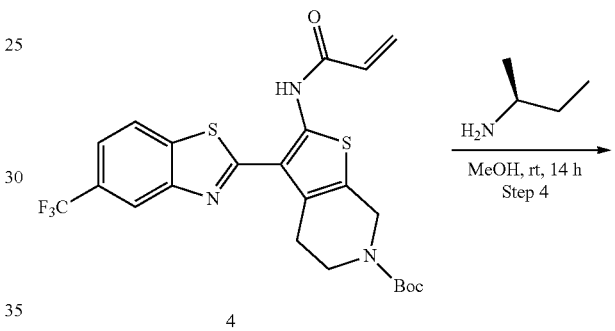

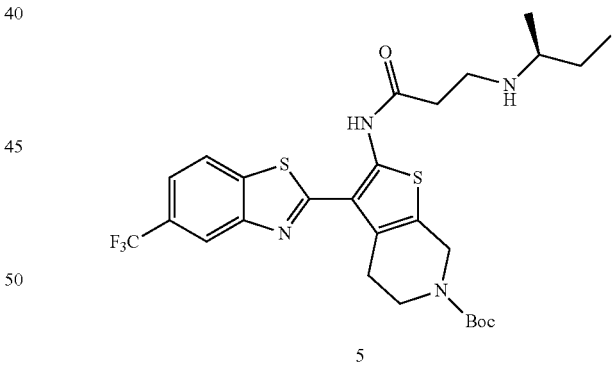

To a solution of tert-butyl 2-acrylamido-3-(5-(trifluoromethyl)benzo[d]thiazol-2-yl)-4,7-dihydrothieno[2,3-c]pyridine-6(5H)-carboxylate 4 (500 mg, 0.98 mmol) in MeOH (10 mL) was added (S)-butan-2-amine (143 mg, 1.96 mmol) and the reaction mixture was stirred at room temperature for 14 h. Reaction was monitored by TLC. After completion, the reaction mass was concentrated to obtained a crude residue. The crude compound was purified by flash column chromatography to afford the title compound 5 as a yellow solid (400 mg, 70% yield).

Step 5: (S)-3-(sec-butylamino)-N-(3-(5-(trifluoromethyl)benzo[d]thiazol-2-yl)-4,5,6,7-tetrahydrothieno[2,3-c]pyridin-2-yl)propanamide hydrochloride

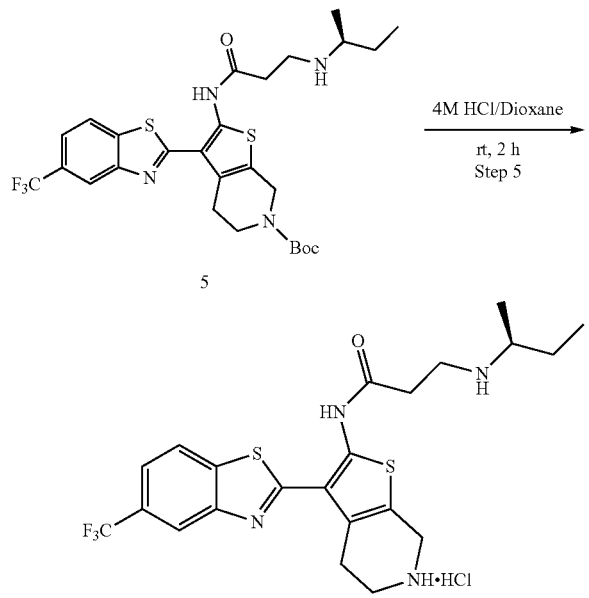

To a solution of tert-butyl (S)-2-(3-(sec-butylamino)propanamido)-3-(5-(trifluoromethyl)benzo[d]thiazol-2-yl)-4,7-dihydrothieno[2,3-c]pyridine-6(5H)-carboxylate 5 (400 mg, 0.68 mmol) in dioxane (5 mL) at 0° C. was added 4M HCl in dioxane (5 mL) and the resulting mixture was stirred at room temperature for 2 h. After completion, the reaction mixture was evaporated in vacuum resulting in a crude residue which was triturated with ether and pentane to afford the HCl salt of the title compound as yellow solid (300 mg, 79% yield).

Example 71. Synthesis of (R)—N-(3-(benzo[d]thiazol-2-yl)-4,5,6,7-tetrahydrothieno[2,3-c]pyridin-2-yl)-3-(sec-butylamino)propanamide (Compound 153) and (S)—N-(3-(benzo[d]thiazol-2-yl)-4,5,6,7-tetrahydrothieno[2,3-c]pyridin-2-yl)-3-(sec-butylamino) propanamide (Compound 154)

Step 1: tert-butyl 2-amino-3-(benzo[d]thiazol-2-yl)-4,7-dihydrothieno[2,3-c]pyridine-6(5H)-carboxylate (2)

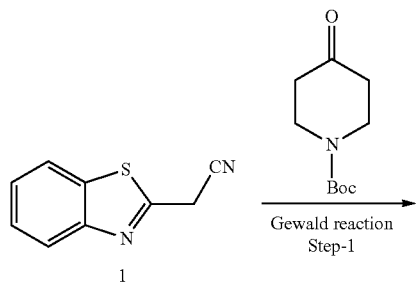

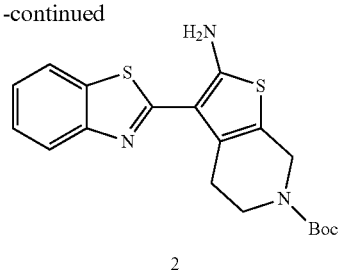

To a solution of 2-(benzo[d]thiazol-2-yl)acetonitrile 1 (5 g, 25.09 mmol) in ethanol (50 mL) was added tert-butyl 4-oxopiperidine-1-carboxylate (4.37 g, 25.09 mmol), elemental sulphur (0.802 g, 25.09 mmol) and morpholine (2.8 g, 25.09 mmol) at room temperature. After the addition, the resulting mixture was heated to reflux at 80° C. for 3 h. The progress of the reaction was monitored by TLC. After completion, the reaction mixture was evaporated in vacuum, The crude compound was purified by silica gel column chromatography eluting with 0-20% ethyl acetate in n-hexane to afford the title compound 2 as light brown solid (7 g, yield 72%).

Step 2: tert-butyl 2-acrylamido-3-(benzo[d]thiazol-2-yl)-4,7-dihydrothieno[2,3-c]pyridine-6(5H)-carboxylate (3)

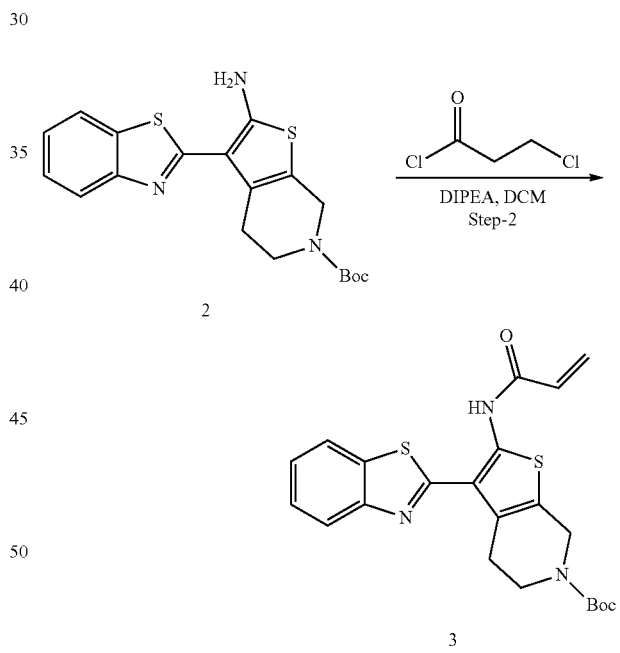

To a solution of tert-butyl 2-amino-3-(benzo[d]thiazol-2-yl)-4,7-dihydrothieno[2,3-c]pyridine-6(5H)-carboxylate 2 (1 g, 2.57 mmol) in DCM (15 mL) was added 3-chloropropanoyl chloride (0.5 g, 3.86 mmol) followed by DIPEA (0.5 g, 3.86 mmol) and the reaction was stirred at room temperature for 16 h. Progress of the reaction was monitored by TLC and LCMS. After completion, reaction mixture was diluted with water and extracted with DCM and concentrated under reduced pressure to afford the crude which was purified by silica gel (100-200 mesh) column chromatography eluting with 20% EtOAc:hexane to give compound 3 as yellow solid (0.9 g, yield 80%).

Step 3a: tert-butyl (R)-3-(benzo[d]thiazol-2-yl)-2-(3-(sec-butylamino)propanamido)-4,7-dihydrothieno[2,3-c]pyridine-6(5H)-carboxylate (4)

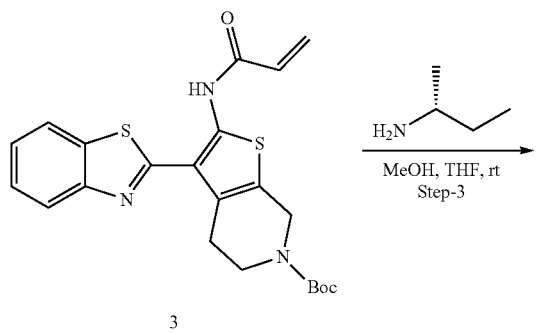

To a solution of tert-butyl 2-acrylamido-3-(benzo[d]thiazol-2-yl)-4,7-dihydrothieno[2,3-c]pyridine-6(5H)-carboxylate 3 (0.3 g, 0.688 mmol) in methanol:THF (1:1, 10 mL) was added (R)-butan-2-amine (0.1 g, 1.36 mmol) and the reaction mixture was stirred at room temperature for 12 h. After completion, the reaction mixture was evaporated in vacuum resulting in a crude residue which was purified by silica gel column chromatography eluting with 2% methanol in DCM to afford the title compound 4 as yellow solid (0.25 g, 72% yield).

Step 4a: (R)—N-(3-(benzo[d]thiazol-2-yl)-4,5,6,7-tetrahydrothieno[2,3-c]pyridin-2-yl)-3-(sec-butylamino) propanamide

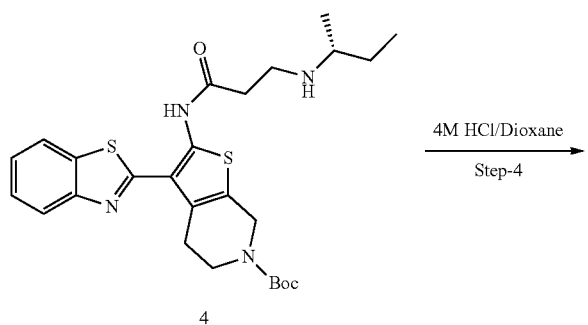

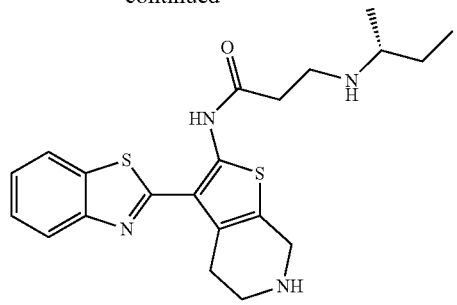

To a solution of tert-butyl (R)-3-(benzo[d]thiazol-2-yl)-2-(3-(sec-butylamino)propanamido)-4,7-dihydrothieno[2,3-c]pyridine-6(5H)-carboxylate 4 (0.22 g, 0.42 mmol) in dioxane (4 mL) at 0° C. was added 4M HCl in dioxane (4 mL) and the resulting mixture was stirred at room temperature for 2 h. After completion, the reaction mixture was evaporated in vacuum resulting in a crude residue which was purified by trituration in methanol and diethyl ether to afford SJMC0130-R HCl salt as yellow solid (0.1 g, 56.4% yield).

Step 3b: tert-butyl (S)-3-(benzo[d]thiazol-2-yl)-2-(3-(sec-butylamino)propanamido)-4,7-dihydrothieno[2,3-c]pyridine-6(5H)-carboxylate (4)

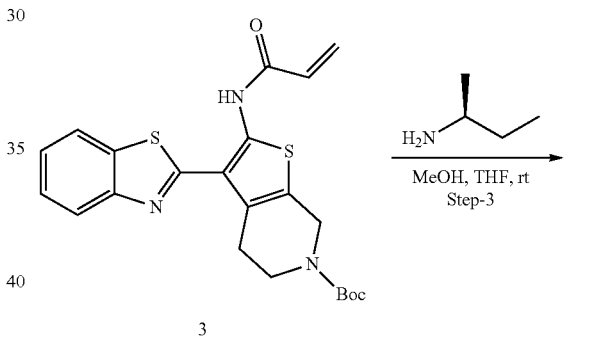

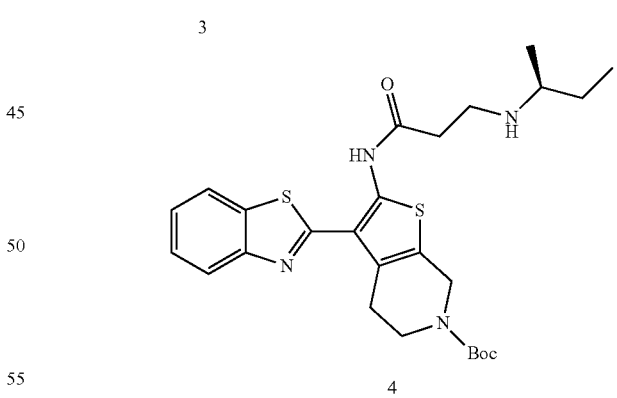

To a solution of tert-butyl 2-acrylamido-3-(benzo[d]thiazol-2-yl)-4,7-dihydrothieno[2,3-c]pyridine-6(5H)-carboxylate 3 (0.3 g, 0.688 mmol) in methanol:THF (1:1, 10 mL) was added (S)-butan-2-amine (0.1 g, 1.36 mmol) and the reaction mixture was stirred at room temperature for 12 h. After completion, the reaction mixture was evaporated in vacuum resulting in a crude residue which was purified by silica gel column chromatography eluting with 2% methanol in DCM to afford the title compound 4 as yellow solid (0.25 g, 72% yield).

Step 4b: (S)—N-(3-(benzo[d]thiazol-2-yl)-4,5,6,7-tetrahydrothieno[2,3-c]pyridin-2-yl)-3-(sec-butylamino) propanamide

Step 1: (1H-pyrazol-4-yl)methanamine (2)

To a stirred solution of 1H-pyrazole-4-carbonitrile 1 (500 mg, 5.37 mmol) in methanol (10 mL), aq NH$_3$ (10 mL) were added Ra—Ni (100 mg) at room temperature in presence of Nitrogen atmosphere. Then the resulting solution was stirred under H$_2$ gas ballon pressure at rt for 12 h. Reaction was monitored by TLC. After the completion, the reaction mixture was filtered through celite and washed with methanol. The filtrate obtained was concentrated under reduced pressure to afford the title compound 2 (250 mg, 48% yield) as colourless oil.

Step 2: 3-(((1H-pyrazol-4-yl)methyl)amino)-N-(3-(benzo[d]thiazol-2-yl)-6-isopropyl-4,5,6,7-tetrahydrothieno[2,3-c]pyridin-2-yl)propanamide

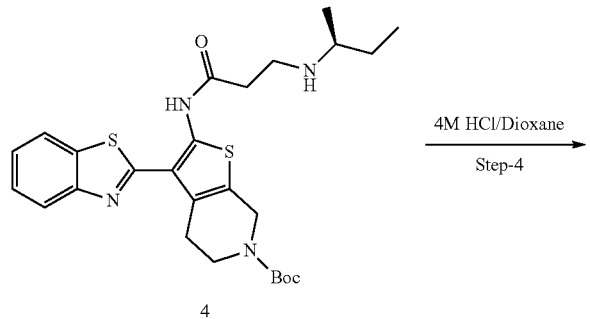

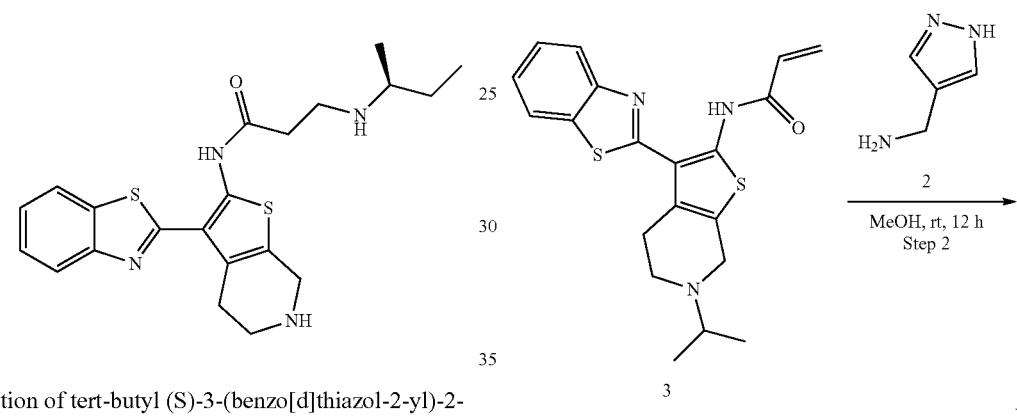

To a solution of tert-butyl (S)-3-(benzo[d]thiazol-2-yl)-2-(3-(sec-butylamino)propanamido)-4,7-dihydrothieno[2,3-c]pyridine-6(5H)-carboxylate 4 (0.25 g, 0.48 mmol) in dioxane (5 mL) at 0° C. was added 4M HCl in dioxane (5 mL) and the resulting mixture was stirred at room temperature for 2 h. After completion, the reaction mixture was evaporated in vacuum resulting in a crude residue which was purified by trituration in methanol and diethyl ether to afford SJMC0130-S HCl salt as yellow solid (0.23 g, quant.).

Example 72. Synthesis of 3-(((1H-pyrazol-4-yl)methyl)amino)-N-(3-(benzo[d]thiazol-2-yl)-6-isopropyl-4,5,6,7-tetrahydrothieno[2,3-c]pyridin-2-yl)propanamide (Compound 155)

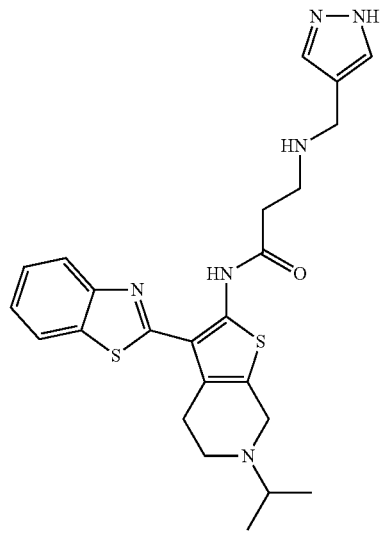

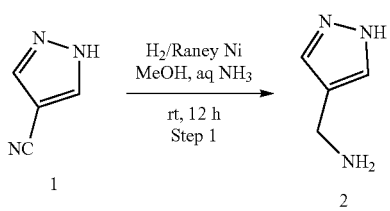 [SMILES: N#Cc1cn[nH]c1 ; NCc1cn[nH]c1]

To a solution of N-(3-(benzo[d]thiazol-2-yl)-6-isopropyl-4,5,6,7-tetrahydrothieno[2,3-c]pyridin-2-yl)acrylamide 3 (100 mg, 0.26 mmol) in methanol (5 mL) was added (1H-pyrazol-4-yl)methanamine 2 (38 mg, 0.39 mmol) at room temperature and stirred for 12 h. Reaction was monitored by TLC. After removal of solvent, the reaction mass was purified by flash column chromatography to afford the title compound as yellow solid (15 mg, 12% yield).

Example 73. Synthesis of (S)-3-(sec-butylamino)-N-(3-(5-fluorobenzo[d]thiazol-2-yl)-4,5,6,7-tetrahydrothieno[2,3-c]pyridin-2-yl)propanamide hydrochloride (Compound 156)

Step 1: 2-amino-4-fluorobenzenethiol (2)

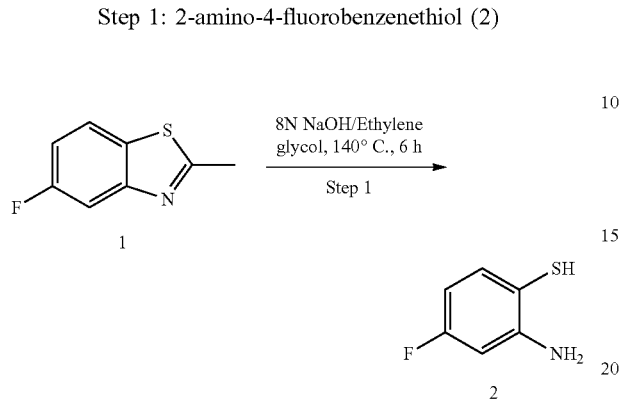

To a stirred solution of 5-fluoro-2-methylbenzo[d]thiazole 1 (1.7 g, 10.16 mmol) in ethylene glycol (10 mL) was added 8N NaOH aqueous solution (10 mL) at room temperature and the resulting solution was heated at 140° C. for 6 h. Reaction was monitored by TLC. After the completion, the reaction mixture was diluted with diethyl ether. The separated aqueous layer pH was adjusted to 5 with 1 N HCl solution and extracted with DCM. The organic layer was dried over anhydrous $Na_2SO_4$ and concentrated under reduced pressure to afford compound 2 (1.3 g, 83% yield) as brown syrup.

Step 2: 2-(5-fluorobenzo[d]thiazol-2-yl)acetonitrile (3)

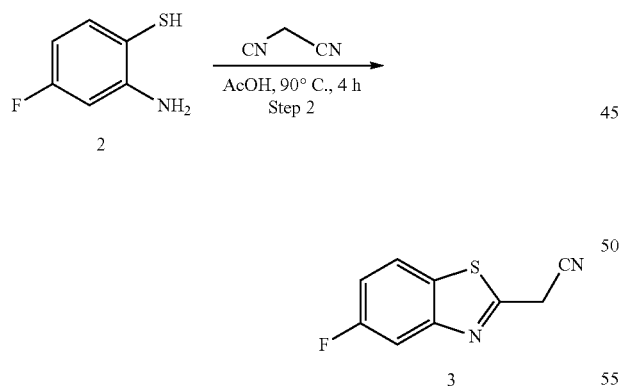

To a solution of 2-amino-4-fluorobenzenethiol 2 (1.3 g, 9.09 mmol) in ethanol (10 mL) were added acetic acid (10 mL), malononitrile (600 mg, 9.09 mmol) at room temperature. After the reaction mixture was heated to 90° C. for 4 h. Reaction was monitored by TLC. After removal of solvent the reaction mass was diluted with EtOAc and washed with saturated $NaHCO_3$ solution. The combined organic layer was dried over anhydrous $Na_2SO_4$ and concentrated to afford the title compound 3 as yellow solid (1.4 g, 80% yield).

Step 3: tert-butyl 2-amino-3-(5-fluorobenzo[d]thiazol-2-yl)-4,7-dihydrothieno[2,3-c]pyridine-6(5H)-carboxylate (4)

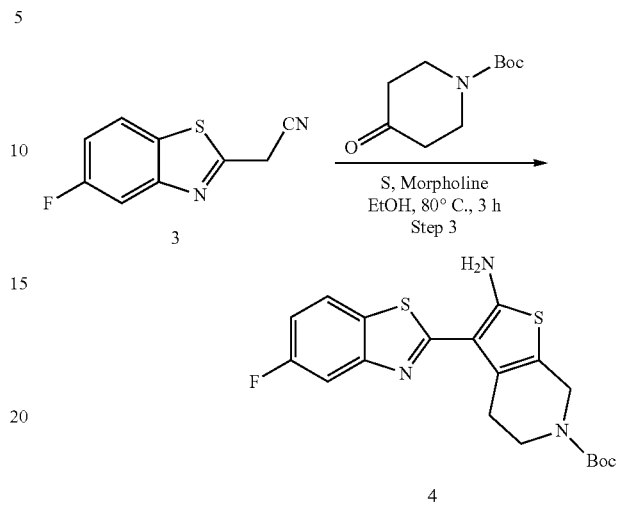

To a solution of 2-(5-fluorobenzo[d]thiazol-2-yl)acetonitrile 3 (1.4 g, 7.24 mmol) in ethanol (20 mL) was added tert-butyl 4-oxopiperidine-1-carboxylate (1.45 g, 7.24 mmol) followed by morpholine (0.63 g, 7.29 mmol) at room temperature and the reaction mixture was heated to 40° C. for 10 min. Then was added sulphur (230 mg, 7.29 mmol) and the resulting solution was heated to 80° C. for 3 h. Reaction was monitored by TLC. After completion, the reaction mixture was evaporated to dryness resulting in a crude residue which was purified by flash column chromatography to afford the title compound 4 as a pale yellow solid (2.1 g, 71% yield).

Step 4: tert-butyl 2-acrylamido-3-(5-fluorobenzo[d]thiazol-2-yl)-4,7-dihydrothieno[2,3-c]pyridine-6(5H)-carboxylate (5)

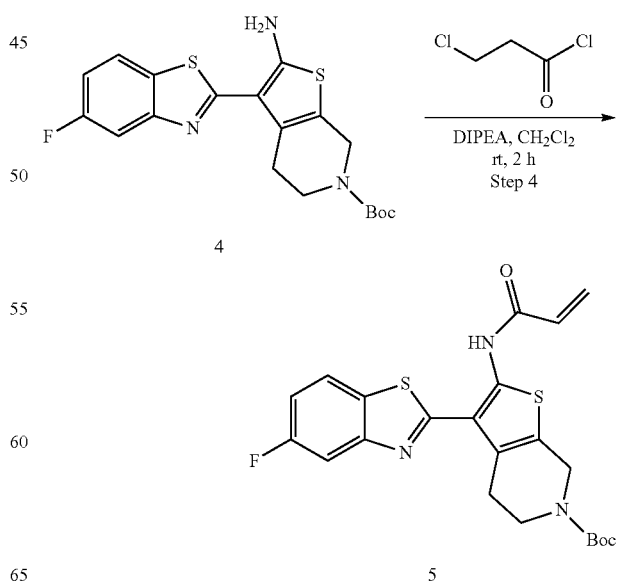

To a solution of tert-butyl 2-amino-3-(5-fluorobenzo[d]thiazol-2-yl)-4,7-dihydrothieno[2,3-c]pyridine-6(5H)-carboxylate 4 (1.1 g, 2.71 mmol) in DCM (15 mL) at 0° C. were added DIPEA (0.66 mL, 4.07 mmol), 3-chloropropanoyl chloride (0.51 g, 4.07 mmol) and the reaction mixture was stirred at room temperature for 2 h. Reaction was monitored by TLC. After completion, the reaction mass was diluted with water. The combined organic layer was dried over anhydrous Na$_2$SO$_4$ and concentrated to get a crude residue. The crude compound was purified by flash column chromatography to afford the title compound 5 as a yellow solid (1.05 g, 85% yield).

Step 5: tert-butyl (5)-2-(3-(sec-butylamino)propanamido)-3-(5-fluorobenzo[d]thiazol-2-yl)-4,7-dihydrothieno[2,3-c]pyridine-6(5H)-carboxylate (6)

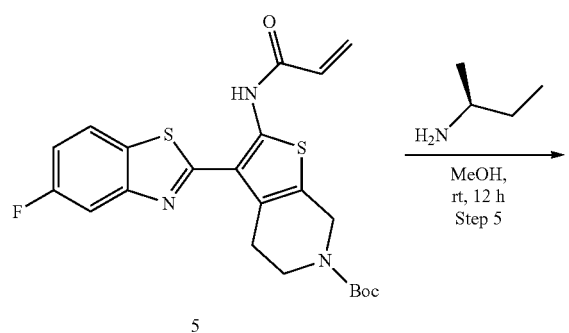

5

To a solution of tert-butyl 2-acrylamido-3-(5-fluorobenzo[d]thiazol-2-yl)-4,7-dihydrothieno[2,3-c]pyridine-6(5H)-carboxylate 5 (500 mg, 1.08 mmol) in MeOH/THF (4 mL/4 mL) were added (S)-butan-2-amine (159 mg, 2.17 mmol) and the reaction mixture was stirred at room temperature for 12 h. Reaction was monitored by TLC. After completion, the reaction mass was evaporated to obtained a crude residue. The crude compound was purified by flash column chromatography to afford the title compound 6 as yellow solid (330 mg, 57% yield).

Step 6: (S)-3-(sec-butylamino)-N-(3-(5-fluorobenzo[d]thiazol-2-yl)-4,5,6,7-tetrahydrothieno[2,3-c]pyridin-2-yl)propanamide hydrochloride (Compound 156)

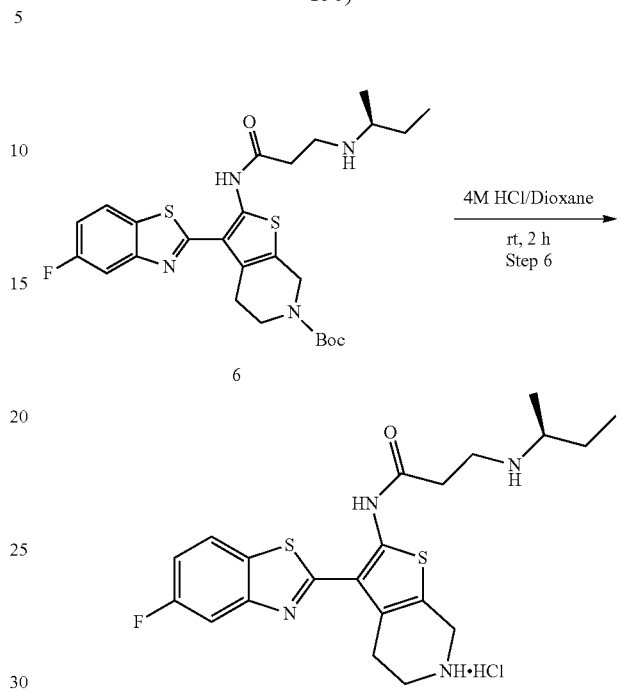

To a solution of tert-butyl (S)-2-(3-(sec-butylamino)propanamido)-3-(5-fluorobenzo[d]thiazol-2-yl)-4,7-dihydrothieno[2,3-c]pyridine-6(5H)-carboxylate 6 (330 mg, 0.52 mmol) in dioxane (3 mL) at 0° C. was added 4M HCl in dioxane (3 mL) and the resulting mixture was stirred at room temperature for 2 h. Reaction was monitored by TLC. After completion, the reaction mixture was evaporated to dryness resulting in a crude residue which was purified by triturating with ether and pentane to afford the title compound as yellow solid (230 mg, 87% yield).

Example 74. Synthesis of (3-((3-(benzo[d]thiazol-2-yl)-4,5,6,7-tetrahydrothieno[2,3-c]pyridin-2-yl)amino)-3-oxopropyl)glycine (Compound 166)

Step 1: tert-butyl 3-(benzo[d]thiazol-2-yl)-2-(3-((2-(tert-butoxy)-2-oxoethyl)amino)propanamido)-4,7-dihydrothieno[2,3-c]pyridine-6(5H)-carboxylate (2)

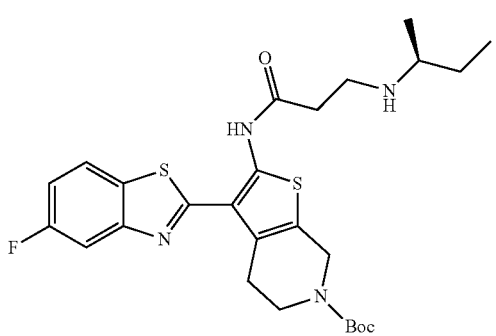

1

-continued

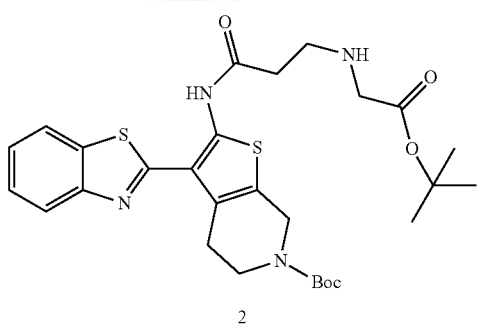

2

To a solution of tert-butyl 2-acrylamido-3-(benzo[d]thiazol-2-yl)-4,7-dihydrothieno[2,3-c]pyridine-6(5H)-carboxylate 1 (400 mg, 0.9 mmol) in MeOH (4 mL) was added tert-butyl glycinate (178 mg, 1.36 mmol) and the reaction mixture was stirred at room temperature for 14 h. Reaction was monitored by TLC. After completion, the reaction mass was evaporated to obtained a crude residue. The crude compound was purified by flash column chromatography to afford the title compound 2 as yellow solid (230 mg, 45% yield).

Step 2: (3-((3-(benzo[d]thiazol-2-yl)-4,5,6,7-tetrahydrothieno[2,3-c]pyridin-2-yl)amino)-3-oxopropyl) glycine

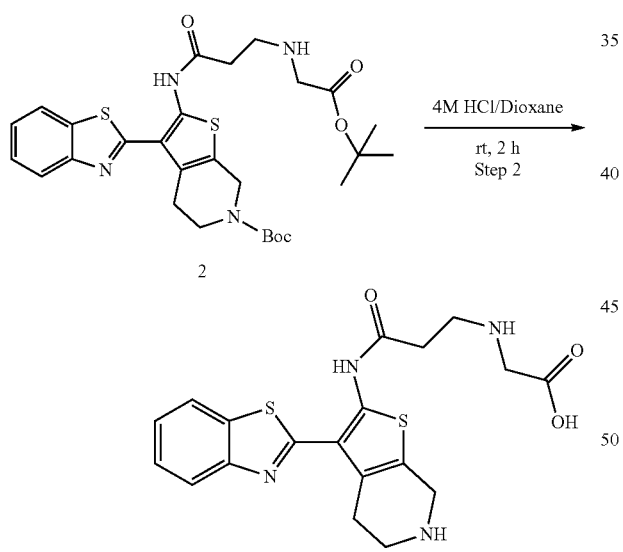

To a solution of tert-butyl 3-(benzo[d]thiazol-2-yl)-2-(3-((2-(tert-butoxy)-2-oxoethyl)amino)propanamido)-4,7-dihydrothieno[2,3-c]pyridine-6(5H)-carboxylate 2 (200 mg, 0.34 mmol) in dioxane (5 mL) at 0° C. was added 4M HCl in dioxane (5 mL) and the resulting mixture was stirred at room temperature for 2 h. Reaction was monitored by TLC. After completion, the reaction mixture was evaporated to dryness resulting in a crude residue which was purified by triturating with ether and pentane to afford the HCl salt of the title compound as yellow solid (100 mg, 65% yield).

Example 75. Synthesis of 3-(((1H-pyrazol-4-yl)methyl)amino)-N-(3-(benzo[d]thiazol-2-yl)-4,5,6,7-tetrahydrothieno[2,3-c]pyridin-2-yl)propanamide (Compound 167)

Step 1: tert-butyl 2-(3-(((1H-pyrazol-4-yl)methyl)amino)propanamido)-3-(benzo[d]thiazol-2-yl)-4,7-dihydrothieno[2,3-c]pyridine-6(5H)-carboxylate (2)

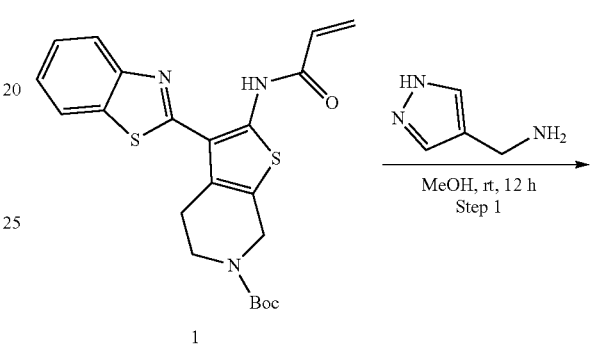

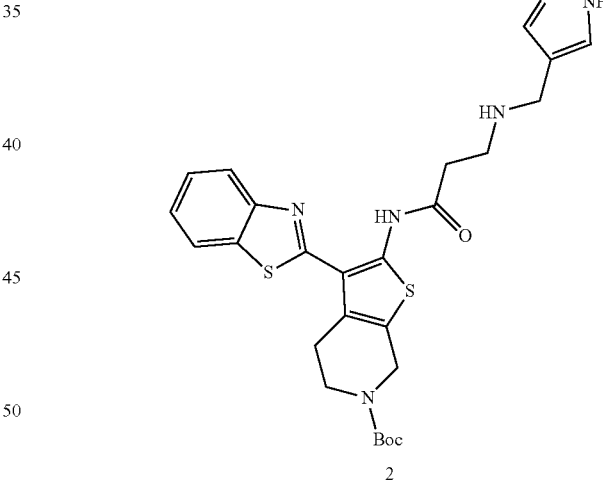

To a solution of tert-butyl 2-acrylamido-3-(benzo[d]thiazol-2-yl)-4,7-dihydrothieno[2,3-c]pyridine-6(5H)-carboxylate 1 (300 mg, 0.68 mmol) in MeOH (5 mL) was added (1H-pyrazol-4-yl)methanamine (99 mg, 1.02 mmol) and the reaction mixture was stirred at room temperature for 12 h. Reaction was monitored by TLC. After completion, the reaction mass was evaporated to obtained a crude residue. The crude compound was purified by flash column chromatography to afford the title compound 2 as yellow solid (250 mg, 68% yield).

Step 2: 3-(((1H-pyrazol-4-yl)methyl)amino)-N-(3-(benzo[d]thiazol-2-yl)-4,5,6,7-tetrahydrothieno[2,3-c]pyridin-2-yl)propanamide

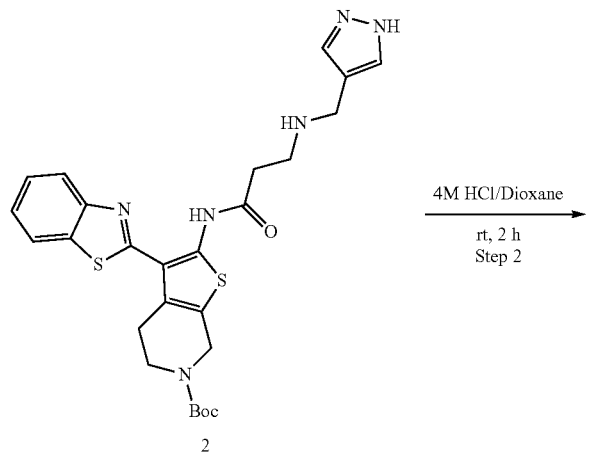

To a solution of tert-butyl 2-(3-(((1H-pyrazol-4-yl)methyl)amino)propanamido)-3-(benzo[d]thiazol-2-yl)-4,7-dihydrothieno[2,3-c]pyridine-6(5H)-carboxylate 2 (150 mg, 0.27 mmol) in dioxane (2 mL) at 0° C. was added 4M HCl in dioxane (5 mL) and the resulting mixture was stirred at room temperature for 2 h. Reaction was monitored by TLC. After completion, the reaction mixture was evaporated to dryness resulting in a crude residue which was purified by triturating with ether and pentane to afford the HCl salt of the title compound as an off-white solid (120 mg, 87% yield).

Example 76. Synthesis of (S)-3-(sec-butylamino)-N-(3-(5-fluorobenzo[d]thiazol-2-yl)-4,5,6,7-tetrahydrothieno[2,3-c]pyridin-2-yl)propanamide hydrochloride (Compound 172)

Step 1: 2-amino-4-fluorobenzenethiol (2)

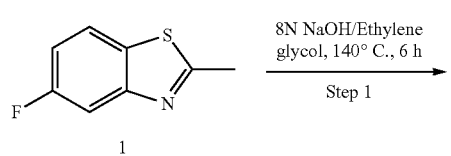

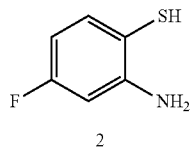

To a stirred solution of 5-fluoro-2-methylbenzo[d]thiazole 1 (1.7 g, 10.16 mmol) in ethylene glycol (10 mL) was added 8N NaOH aqueous solution (10 mL) at room temperature and the resulting solution was heated at 140° C. for 6 h. Reaction was monitored by TLC. After the completion, the reaction mixture was diluted with diethyl ether. The separated aqueous layer pH was adjusted to 5 with 1 N HCl solution and extracted with DCM. The organic layer was dried over anhydrous $Na_2SO_4$ and concentrated under reduced pressure to afford compound 2 (1.3 g, 83% yield) as brown syrup.

Step 2: 2-(5-fluorobenzo[d]thiazol-2-yl)acetonitrile (3)

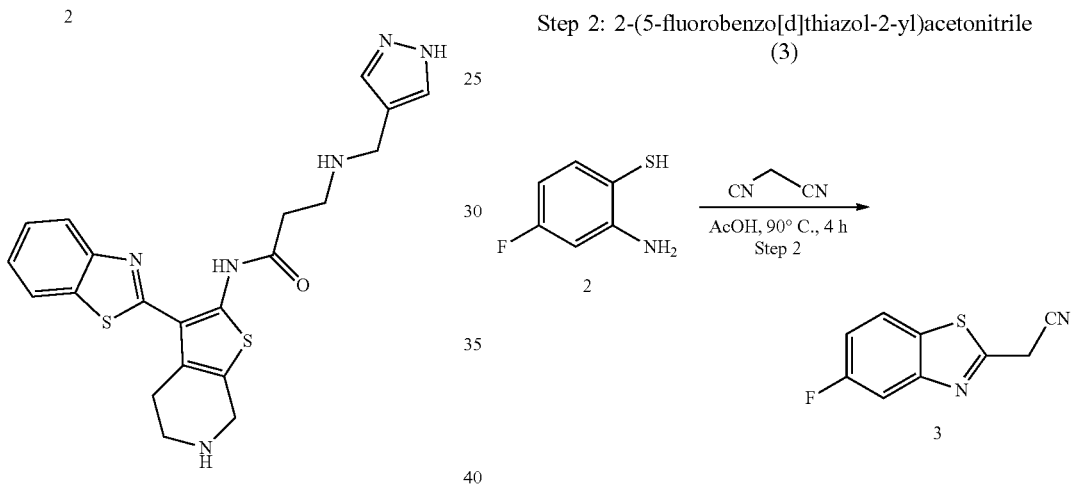

To a solution of 2-amino-4-fluorobenzenethiol 2 (1.3 g, 9.09 mmol) in ethanol (10 mL) were added acetic acid (10 mL), malononitrile (600 mg, 9.09 mmol) at room temperature. After the reaction mixture was heated to 90° C. for 4 h. Reaction was monitored by TLC. After removal of solvent the reaction mass was diluted with EtOAc and washed with saturated $NaHCO_3$ solution. The combined organic layer was dried over anhydrous $Na_2SO_4$ and concentrated to afford the title compound 3 as yellow solid (1.4 g, 80% yield).

Step 3: tert-butyl 2-amino-3-(5-fluorobenzo[d]thiazol-2-yl)-4,7-dihydrothieno[2,3-c]pyridine-6(5H)-carboxylate (4)

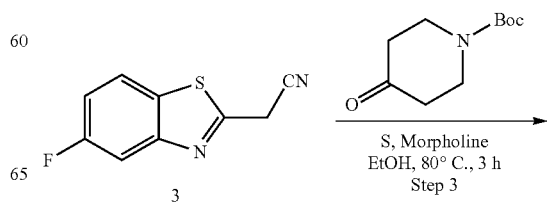

-continued

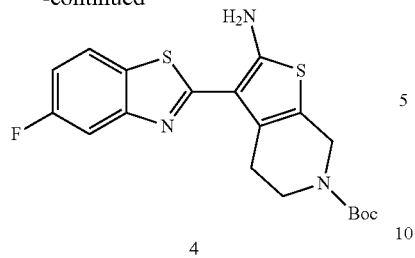

4

To a solution of 2-(5-fluorobenzo[d]thiazol-2-yl)acetonitrile 3 (1.4 g, 7.24 mmol) in ethanol (20 mL) was added tert-butyl 4-oxopiperidine-1-carboxylate (1.45 g, 7.24 mmol) followed by morpholine (0.63 g, 7.29 mmol) at room temperature and the reaction mixture was heated to 40° C. for 10 min. Then was added sulphur (230 mg, 7.29 mmol) and the resulting solution was heated to 80° C. for 3 h. Reaction was monitored by TLC. After completion, the reaction mixture was evaporated to dryness resulting in a crude residue which was purified by flash column chromatography to afford the title compound 4 as a pale yellow solid (2.1 g, 71% yield).

Step 4: tert-butyl 2-acrylamido-3-(5-fluorobenzo[d]thiazol-2-yl)-4,7-dihydrothieno[2,3-c]pyridine-6(5H)-carboxylate (5)

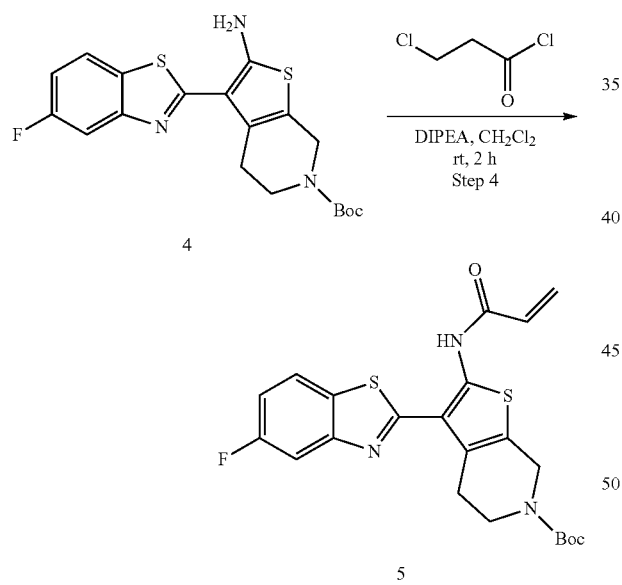

To a solution of tert-butyl 2-amino-3-(5-fluorobenzo[d]thiazol-2-yl)-4,7-dihydrothieno[2,3-c]pyridine-6(5H)-carboxylate 4 (1.1 g, 2.71 mmol) in DCM (15 mL) at 0° C. were added DIPEA (0.66 mL, 4.07 mmol), 3-chloropropanoyl chloride (0.51 g, 4.07 mmol) and the reaction mixture was stirred at room temperature for 2 h. Reaction was monitored by TLC. After completion, the reaction mass was diluted with water. The combined organic layer was dried over anhydrous Na$_2$SO$_4$ and concentrated to get a crude residue. The crude compound was purified by flash column chromatography to afford the title compound 5 as a yellow solid (1.05 g, 85% yield).

Step 5: tert-butyl (S)-2-(3-(sec-butylamino)propanamido)-3-(5-fluorobenzo[d]thiazol-2-yl)-4,7-dihydrothieno[2,3-c]pyridine-6(5H)-carboxylate (6)

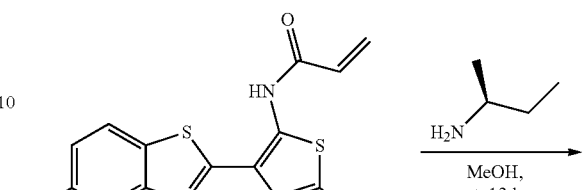

5

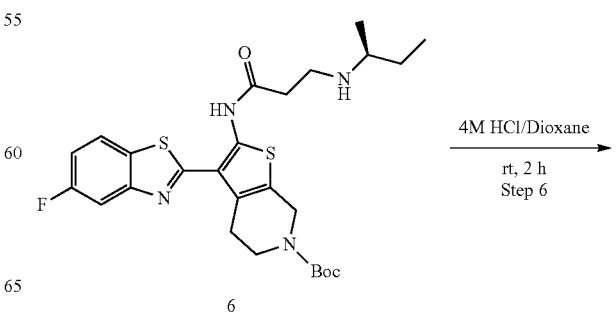

6

To a solution of tert-butyl 2-acrylamido-3-(5-fluorobenzo[d]thiazol-2-yl)-4,7-dihydrothieno[2,3-c]pyridine-6(5H)-carboxylate 5 (500 mg, 1.08 mmol) in MeOH/THF (4 mL/4 mL) were added (S)-butan-2-amine (159 mg, 2.17 mmol) and the reaction mixture was stirred at room temperature for 12 h. Reaction was monitored by TLC. After completion, the reaction mass was evaporated to obtained a crude residue. The crude compound was purified by flash column chromatography to afford the title compound 6 as yellow solid (330 mg, 57% yield).

Step 6: (S)-3-(sec-butylamino)-N-(3-(5-fluorobenzo[d]thiazol-2-yl)-4,5,6,7-tetrahydrothieno[2,3-c]pyridin-2-yl)propanamide hydrochloride

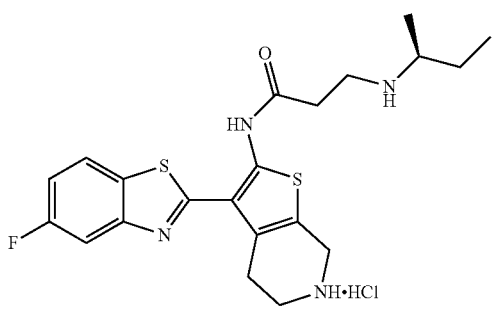

To a solution of tert-butyl (S)-2-(3-(sec-butylamino)propanamido)-3-(5-fluorobenzo[d]thiazol-2-yl)-4,7-dihydrothieno[2,3-c]pyridine-6(5H)-carboxylate 6 (330 mg, 0.52 mmol) in dioxane (3 mL) at 0° C. was added 4M HCl in dioxane (3 mL) and the resulting mixture was stirred at room temperature for 2 h. Reaction was monitored by TLC. After completion, the reaction mixture was evaporated to dryness resulting in a crude residue which was purified by triturating with ether and pentane to afford the HCl salt of the title compound as yellow solid (230 mg, 87% yield).

Example 77. Synthesis of (R)-3-(sec-butylamino)-N-(3-(5-fluorobenzo[d]thiazol-2-yl)-4,5,6,7-tetrahydrothieno[2,3-c]pyridin-2-yl)propanamide (Compound 185)

Step 1: tert-butyl (R)-2-(3-(sec-butylamino)propanamido)-3-(5-fluorobenzo[d]thiazol-2-yl)-4,7-dihydrothieno[2,3-c]pyridine-6(5H)-carboxylate (2)

To a solution of tert-butyl 2-acrylamido-3-(5-fluorobenzo[d]thiazol-2-yl)-4,7-dihydrothieno[2,3-c]pyridine-6(5H)-carboxylate 1 (4 g, 8.714 mmol) in MeOH:THF (1:1, 60 mL), (R)-butan-2-amine (0.95 g, 13.718 mmol) was added. The resulting reaction mixture was stirred at room temperature for 12 h. Progress of the reaction was monitored by TLC. After completion, the reaction mixture was concentrated to dryness under reduced pressure. The crude compound was purified by column chromatography to afford the title compound 2 as yellow solid (3.2 g, yield 69.5%).

Step 2: (R)-3-(sec-butylamino)-N-(3-(5-fluorobenzo[d]thiazol-2-yl)-4,5,6,7-tetrahydrothieno[2,3-c]pyridin-2-yl)propanamide

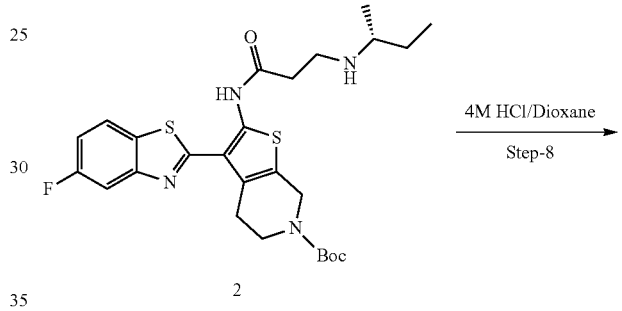

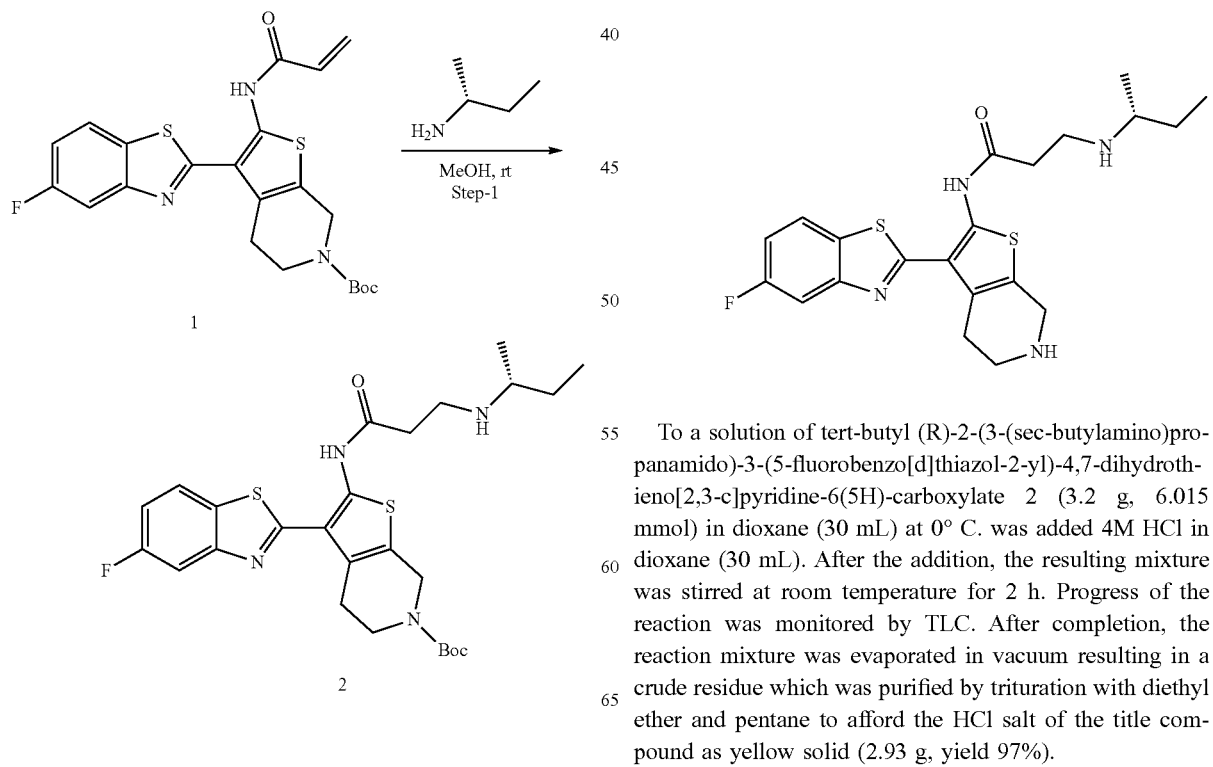

To a solution of tert-butyl (R)-2-(3-(sec-butylamino)propanamido)-3-(5-fluorobenzo[d]thiazol-2-yl)-4,7-dihydrothieno[2,3-c]pyridine-6(5H)-carboxylate 2 (3.2 g, 6.015 mmol) in dioxane (30 mL) at 0° C. was added 4M HCl in dioxane (30 mL). After the addition, the resulting mixture was stirred at room temperature for 2 h. Progress of the reaction was monitored by TLC. After completion, the reaction mixture was evaporated in vacuum resulting in a crude residue which was purified by trituration with diethyl ether and pentane to afford the HCl salt of the title compound as yellow solid (2.93 g, yield 97%).

Example 78. Synthesis of (3-((3-(benzo[d]thiazol-2-yl)-6-isopropyl-4,5,6,7-tetrahydrothieno[2,3-c]pyridin-2-yl)amino)-3-oxopropyl)glycine (Compound 168)

Step 1: tert-butyl (3-((3-(benzo[d]thiazol-2-yl)-6-isopropyl-4,5,6,7-tetrahydrothieno[2,3-c]pyridin-2-yl)amino)-3-oxopropyl)glycinate (2)

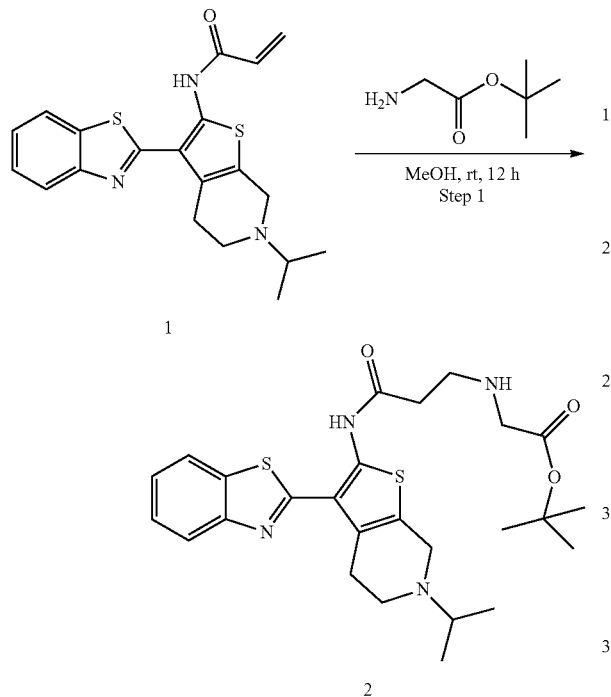

To a solution of N-(3-(benzo[d]thiazol-2-yl)-6-isopropyl-4,5,6,7-tetrahydrothieno[2,3-c]pyridin-2-yl)acrylamide 1 (200 mg, 0.52 mmol) in MeOH (5 mL) was added tert-butyl glycinate (102 mg, 0.78 mmol) and the reaction mixture was stirred at room temperature for 12 h. Reaction was monitored by TLC. After completion, the reaction mass was evaporated to obtained a crude residue. The crude compound was purified by flash column chromatography to afford the title compound 2 as yellow solid (200 mg, 74% yield).

Step 2: (3-((3-(benzo[d]thiazol-2-yl)-6-isopropyl-4,5,6,7-tetrahydrothieno[2,3-c]pyridin-2-yl)amino)-3-oxopropyl)glycine

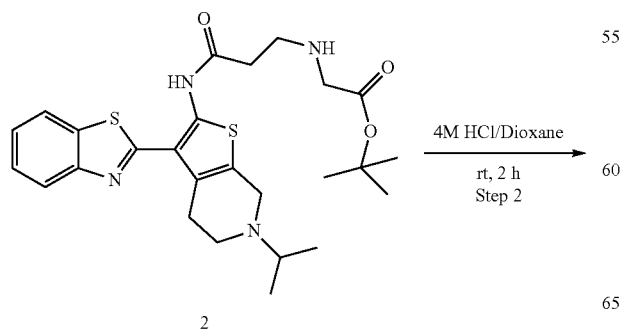

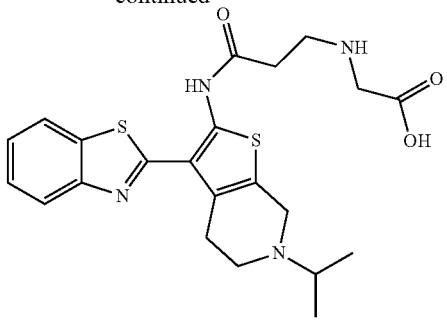

To a solution of tert-butyl (3-((3-(benzo[d]thiazol-2-yl)-6-isopropyl-4,5,6,7-tetrahydrothieno[2,3-c]pyridin-2-yl)amino)-3-oxopropyl)glycinate 2 (180 mg, 0.34 mmol) in dioxane (5 mL) at 0° C. was added 4M HCl in dioxane (5 mL) and the resulting mixture was stirred at room temperature for 2 h. Reaction was monitored by TLC. After completion, the reaction mixture was evaporated to dryness resulting in a crude residue which was purified by triturating with ether and pentane to afford the HCl salt of the title compound as yellow solid (130 mg, 72% yield).

Example 79. Synthesis of N-(3-(5-fluorobenzo[d]thiazol-2-yl)-4,5,6,7-tetrahydrothieno[2,3-c]pyridin-2-yl)-3-((2-methoxyethyl)amino)propanamide (Compound 189)

Step 1: tert-butyl 3-(5-fluorobenzo[d]thiazol-2-yl)-2-(3-((2-methoxyethyl)amino)propanamido)-4,7-dihydrothieno[2,3-c]pyridine-6(5H)-carboxylate (2)

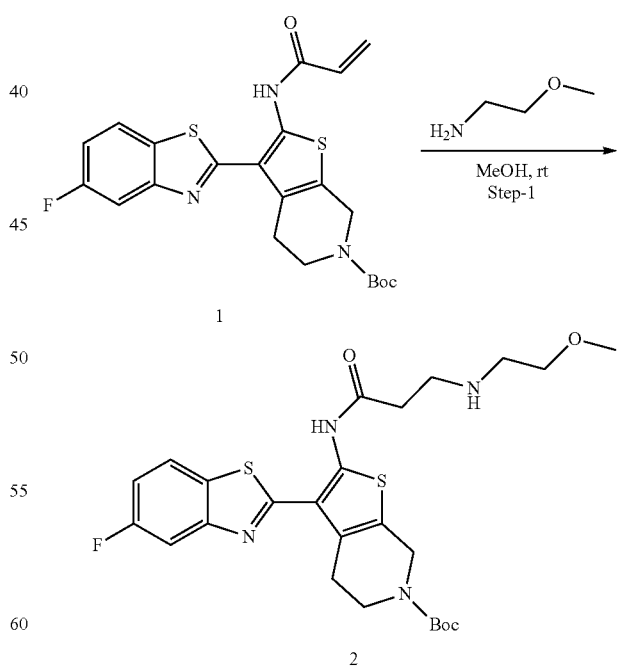

To a solution of tert-butyl 2-acrylamido-3-(5-fluorobenzo[d]thiazol-2-yl)-4,7-dihydrothieno[2,3-c]pyridine-6(5H)-carboxylate 1 (0.15 g, 0.326 mmol) in MeOH:THF (1:1, 4 mL), 2-methoxyethan-1-amine (0.037 g, 0.49 mmol) was added. The resulting reaction mixture was stirred at room temperature for 12 h. Progress of the reaction was monitored by TLC. After completion, the reaction mixture was concentrated to dryness under reduced pressure. The crude compound was purified by column chromatography to afford the title compound 2 as yellow solid (0.133 g, yield 76.43%).

Step 2: N-(3-(5-fluorobenzo[d]thiazol-2-yl)-4,5,6,7-tetrahydrothieno[2,3-c]pyridin-2-yl)-3-((2-methoxyethyl)amino)propanamide

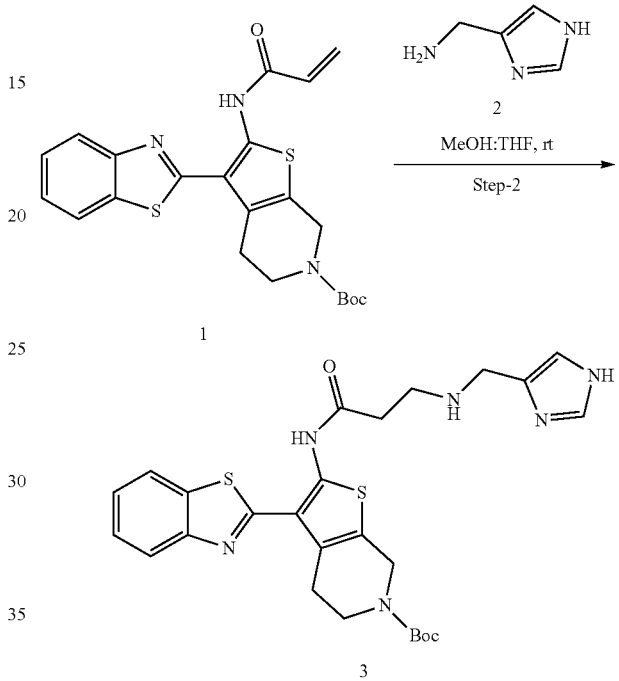

To a solution of tert-butyl 3-(5-fluorobenzo[d]thiazol-2-yl)-2-(3-((2-methoxyethyl)amino)propanamido)-4,7-dihydrothieno[2,3-c]pyridine-6(5H)-carboxylate 2 (0.13 g, 0.243 mmol) in dioxane (1 mL) at 0° C., 4M HCl in dioxane (2 mL) was added. After the addition, the resulting mixture was stirred at room temperature for 2 h. Progress of the reaction was monitored by TLC. After completion, the reaction mixture was evaporated in vacuum resulting in a crude residue which was purified by trituration with diethyl ether and pentane to afford the title compound the HCl salt of the title compound as yellow solid (0.095 g, yield 77.23%).

Example 80. Synthesis of 3-(((1H-imidazol-4-yl)methyl)amino)-N-(3-(benzo[d]thiazol-2-yl)-4,5,6,7-tetrahydrothieno[2,3-c]pyridin-2-yl)propanamide (Compound 190)

Step 1: (1H-imidazol-4-yl)methanamine (2)

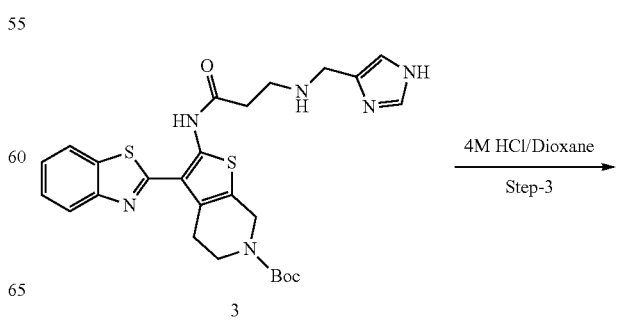

To a stirred solution of compound 4 (0.4 g, 4.29 mmol) in methanol (5 mL), Raney Ni (0.4 g) and aq. NH₃ (0.5 mL) was added and stirred under hydrogen atmosphere (balloon pressure) at room temperature for 15 h. Progress of the reaction was monitored by TLC. After completion of the reaction, the reaction mixture was filtered through a pad of celite and the filtrate was evaporated under reduced pressure to afford title compound 2 as yellow coloured thick oil (0.5 g, crude).

Step 2: tert-butyl 2-(3-(((1H-imidazol-4-yl)methyl)amino)propanamido)-3-(benzo[d]thiazol-2-yl)-4,7-dihydrothieno[2,3-c]pyridine-6(5H)-carboxylate (3)

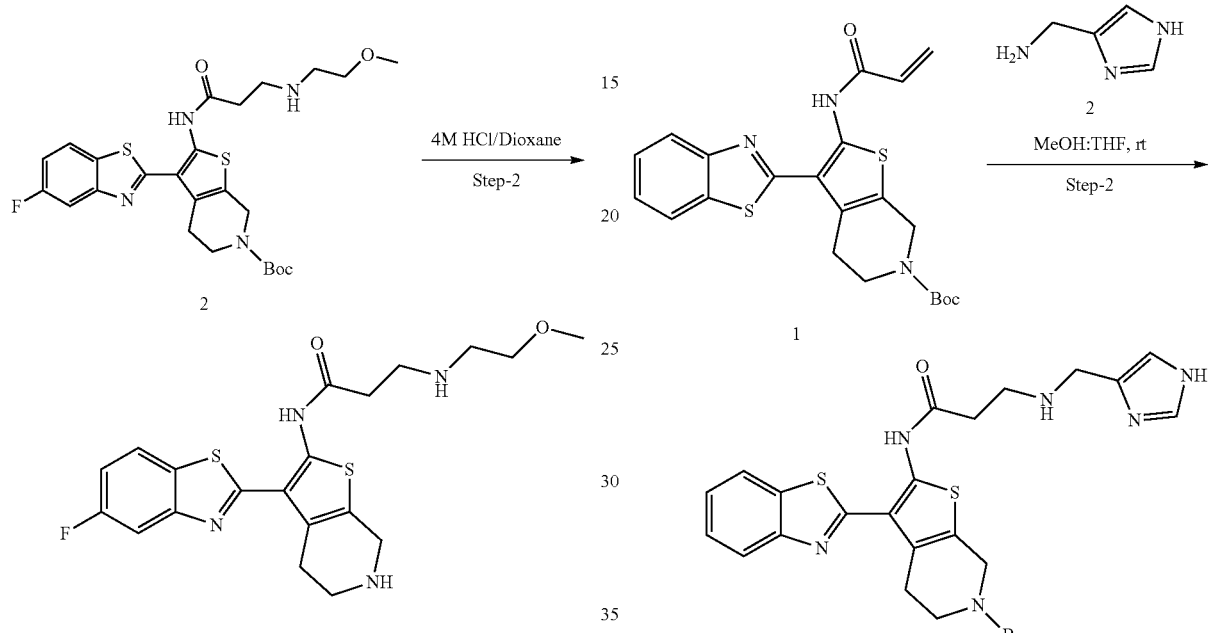

To a solution of tert-butyl 2-acrylamido-3-(benzo[d]thiazol-2-yl)-4,7-dihydrothieno[2,3-c]pyridine-6(5H)-carboxylate 1 (0.6 g, 1.36 mmol) in MeOH:THF (1:1, 10 mL), (1H-imidazol-4-yl)methanamine 2 (0.33 g, 3.40 mmol) was added. The resulting reaction mixture was stirred at room temperature for 12 h. Progress of the reaction was monitored by TLC. After completion, the reaction mixture was concentrated to dryness under reduced pressure. The crude compound was purified by column chromatography to afford the title compound 3

Step 3: 3-(((1H-imidazol-4-yl)methyl)amino)-N-(3-(benzo[d]thiazol-2-yl)-4,5,6,7-tetrahydrothieno[2,3-c]pyridin-2-yl)propanamide

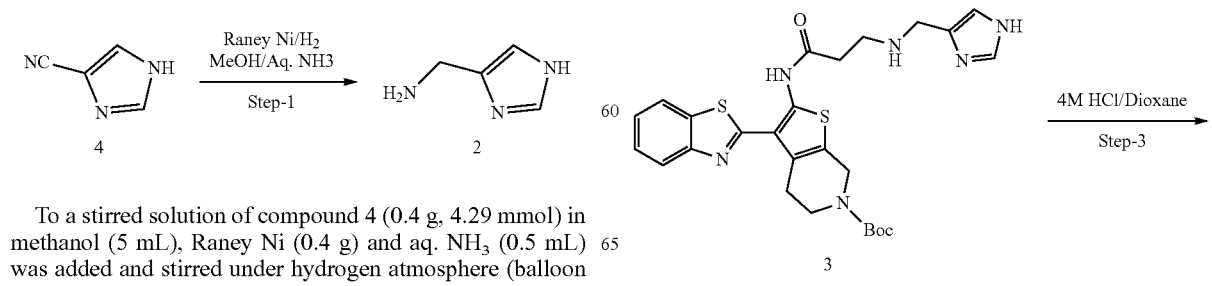

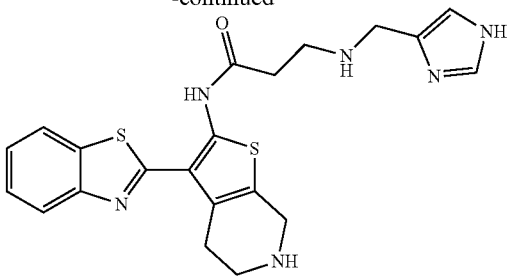

To a solution of tert-butyl 2-(3-(((1H-imidazol-4-yl)methyl)amino)propanamido)-3-(benzo[d]thiazol-2-yl)-4,7-dihydrothieno[2,3-c]pyridine-6(5H)-carboxylate 3 (0.4 g, 0.744 mmol) in dioxane (10 mL) at 0° C., 4M HCl in dioxane (10 mL) was added. After the addition, the resulting mixture was stirred at room temperature for 2 h. Progress of the reaction was monitored by TLC. After completion, the reaction mixture was evaporated in vacuum resulting in a crude residue which was purified by trituration with diethyl ether and pentane to afford the title compound the HCl salt of the title compound as yellow solid (0.3 g, yield 78.89%).

Example 81. Synthesis of 3-(benzo[d]thiazol-2-yl)-2-(3-(sec-butylamino)propanamido)-6-isopropyl-6-methyl-4,5,6,7-tetrahydrothieno[2,3-c]pyridin-6-ium (Compound 191)

Step 1: N-(3-(benzo[d]thiazol-2-yl)-6-isopropyl-4,5,6,7-tetrahydrothieno[2,3-c]pyridin-2-yl)acrylamide (2)

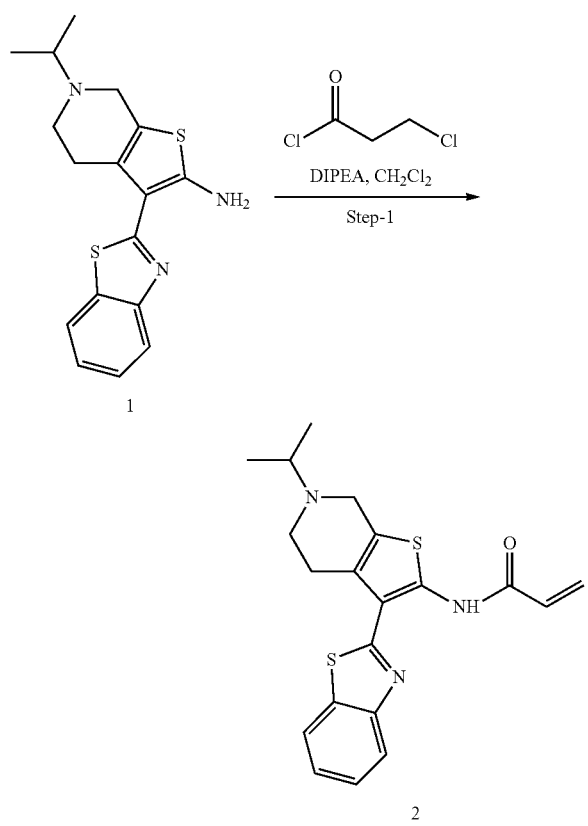

To a solution of 3-(benzo[d]thiazol-2-yl)-6-isopropyl-4,5,6,7-tetrahydrothieno[2,3-c]pyridin-2-amine 1 (3 g, 9.09 mmol) in DCM (30 mL) at 0° C. was added DIPEA (1.75 g, 13.63 mmol) and 3-chloropropanoyl chloride (1.73 g, 13.63 mmol). The resulting reaction mixture was stirred at room temperature for 2 h. Progress of the reaction was monitored by TLC. After completion, the reaction mass was diluted with DCM and washed with water and brine. The combined organic layer was dried over anhydrous Na$_2$SO$_4$, filtered and concentrated to afford the title compound 2 as yellow solid (3 g, crude).

Step 2: N-(3-(benzo[d]thiazol-2-yl)-6-isopropyl-4,5,6,7-tetrahydrothieno[2,3-c]pyridin-2-yl)-3-(sec-butylamino)propanamide (3)

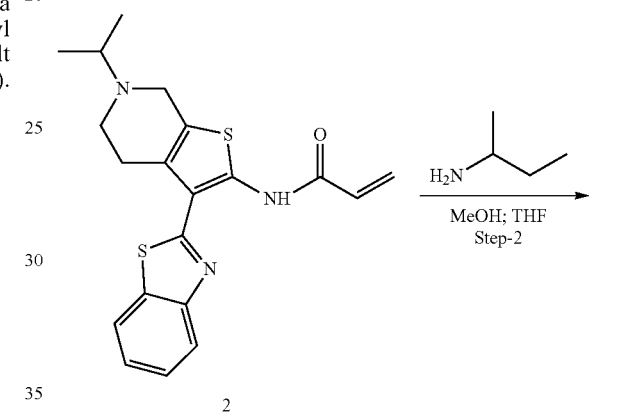

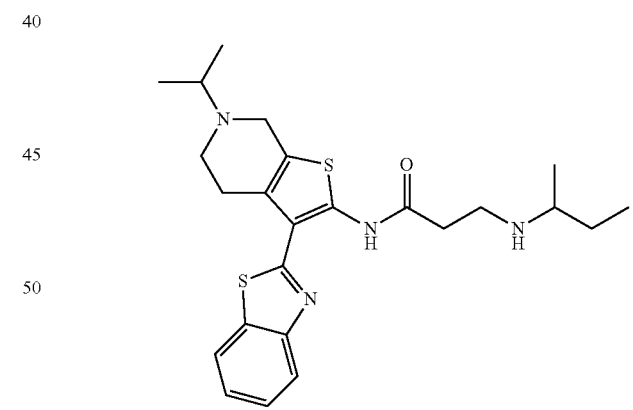

To a solution of N-(3-(benzo[d]thiazol-2-yl)-6-isopropyl-4,5,6,7-tetrahydrothieno[2,3-c]pyridin-2-yl)acrylamide 2 (3 g, 7.85 mmol) in MeOH:THF (100 mL:10 mL), butan-2-amine (1 mL, 11.78 mmol) was added. The resulting reaction mixture was stirred at room temperature for 12 h. Progress of the reaction was monitored by TLC. After completion, the reaction mixture was concentrated to dryness under reduced pressure to afford the title compound 3 as yellow solid (3 g, crude).

243

Step 3: tert-butyl (3-((3-(benzo[d]thiazol-2-yl)-6-isopropyl-4,5,6,7-tetrahydrothieno[2,3-c]pyridin-2-yl)amino)-3-oxopropyl)(sec-butyl)carbamate (4)

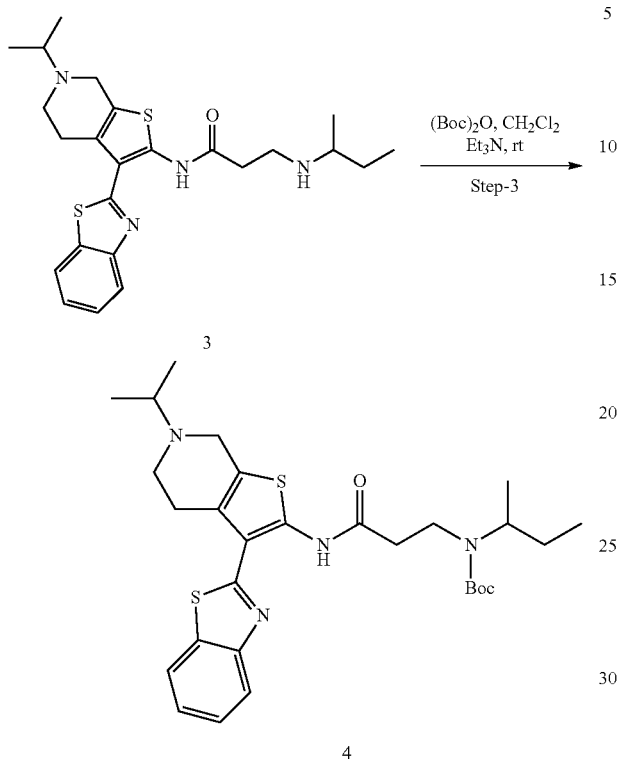

To a stirred solution of N-(3-(benzo[d]thiazol-2-yl)-6-isopropyl-4,5,6,7-tetrahydrothieno[2,3-c]pyridin-2-yl)-3-(sec-butylamino)propanamide 3 (3 g, 6.57) in DCM (50 mL) at 0° C., TEA (1.3 mL, 9.85 mmol) was added and stirred for 15 min followed by the addition of Boc anhydride (1.8 mL, 7.89 mmol) at 0° C. The reaction mixture was stirred at rt for 12 h. Progress of the reaction was monitored by TLC. After completion of the reaction, the reaction mixture was diluted with water and extracted with DCM. The combined organic extracts were washed with brine, dried over anhydrous sodium sulfate and evaporated under reduced pressure. The crude product was purified by column chromatography to afford the title compound 4 as yellow solid (2 g, yield 55%).

Steps 4 and 5: 3-(benzo[d]thiazol-2-yl)-2-(3-(sec-butylamino)propanamido)-6-isopropyl-6-methyl-4,5,6,7-tetrahydrothieno[2,3-c]pyridin-6-ium

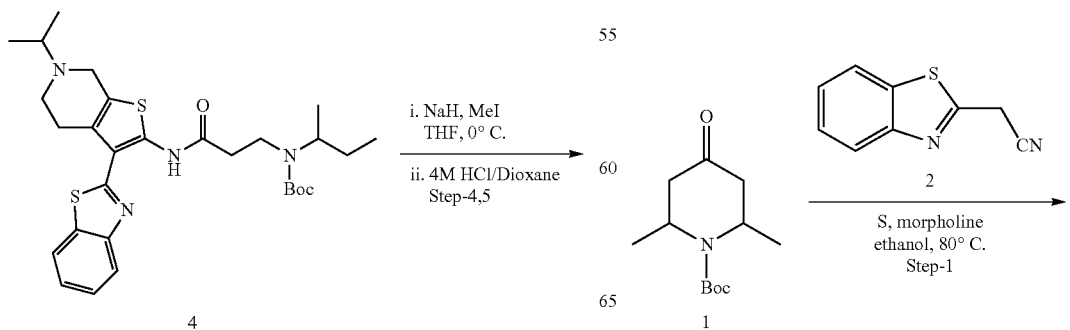

244

-continued

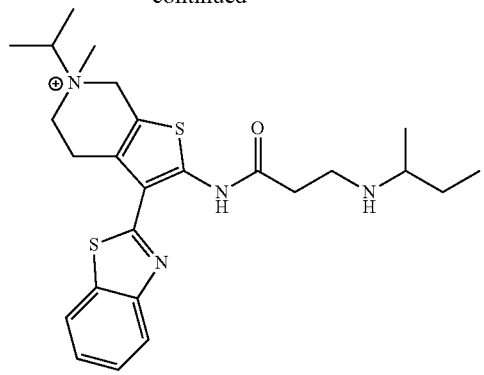

To a stirred solution of tert-butyl (3-((3-(benzo[d]thiazol-2-yl)-6-isopropyl-4,5,6,7-tetrahydrothieno[2,3-c]pyridin-2-yl)amino)-3-oxopropyl)(sec-butyl)carbamate 4 (0.25 g, 0.44 mmol) in dry THF (5 mL) was added NaH (60% dispersion in min.oil, 0.023 g, 0.528 mmol) at 0° C. After stirring the reaction mixture at the same temperature for 10 mins, Methyl iodide (0.095 g, 0.674 mmol) was added and the stirring was continued for another 3 h at rt. The reaction progress was monitored by TLC. After completion of the reaction, it was quenched with water and the resulted solid was filtered, washed with water, dried under vacuum and later was purified by column chromatography to afford the desired product (0.06 g, yield 23%).

To a solution of above Boc protected compound (0.06 g, 0.10 mmol) in dioxane (5 mL) at 0° C. was added 4M HCl in dioxane (2 mL). After the addition, the resulting mixture was stirred at room temperature for 2 h. Progress of the reaction was monitored by TLC. After completion, the reaction mixture was evaporated in vacuum resulting in a crude residue which was purified by trituration with diethyl ether and pentane to afford the title compound the HCl salt of the title compound as yellow solid (0.03 g, yield 56%).

Example 82. Synthesis of N-(3-(benzo[d]thiazol-2-yl)-5,7-dimethyl-4,5,6,7-tetrahydrothieno[2,3-c]pyridin-2-yl)-3-(isopropylamino)propanamide and Separation of Isomers (Compounds 195-198)

Step 1: tert-butyl 2-amino-3-(benzo[d]thiazol-2-yl)-5,7-dimethyl-4,7-dihydrothieno[2,3-c]pyridine-6(5H)-carboxylate (3)

-continued

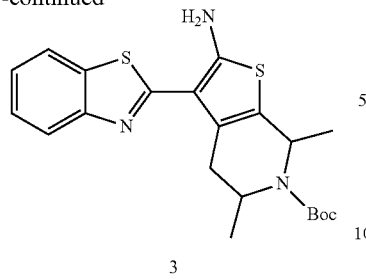

3

To a solution of 2-(benzo[d]thiazol-2-yl)acetonitrile 2 (0.5 g, 2.87 mmol) in ethanol (10 mL) was added tert-butyl 2,6-dimethyl-4-oxopiperidine-1-carboxylate (0.655 g, 2.87 mmol) followed by morpholine (0.375 g, 4.30 mmol) and sulphur (0.138 g, 4.30 mmol) and the resulting mixture heated to 80° C. for 15 h. Progress of the reaction was monitored by TLC. After completion, the reaction mixture was evaporated to give a crude residue. The crude compound was purified by column chromatography to afford the title compound 3 as yellow solid (0.5 g, yield 42%).

Step 2: tert-butyl 2-acrylamido-3-(benzo[d]thiazol-2-yl)-5,7-dimethyl-4,7-dihydrothieno[2,3-c]pyridine-6(5H)-carboxylate (4)

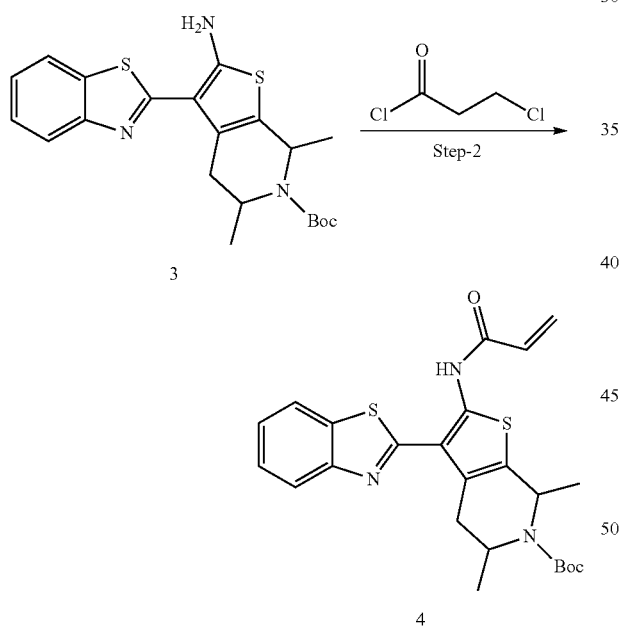

To a solution of tert-butyl 2-amino-3-(benzo[d]thiazol-2-yl)-5,7-dimethyl-4,7-dihydrothieno[2,3-c]pyridine-6(5H)-carboxylate 3 (0.5 g, 1.20 mmol) in DCM (10 mL) at 0° C. was added DIPEA (0.232 g, 1.80 mmol) followed by 3-chloropropanoyl chloride (0.229 g, 1.80 mmol) and the reaction mixture was stirred at room temperature for 12 h. Progress of the reaction was monitored by TLC. After completion, the reaction mass was diluted with 10% MeOH/DCM and washed with NaHCO$_3$ solution. The combined organic layer was washed with water; dried over anhydrous Na$_2$SO$_4$ and concentrated under reduced pressure to afford the compound 4 as yellow solid (0.7 g, crude).

Step 3: tert-butyl 3-(benzo[d]thiazol-2-yl)-2-(3-(isopropylamino)propanamido)-5,7-dimethyl-4,7-dihydrothieno[2,3-c]pyridine-6(5H)-carboxylate (5)

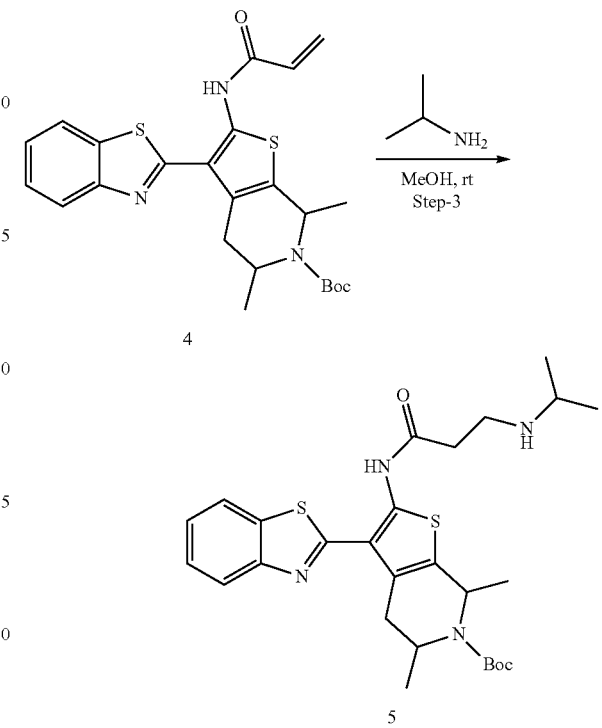

To a solution of tert-butyl 2-acrylamido-3-(benzo[d]thiazol-2-yl)-5,7-dimethyl-4,7-dihydrothieno[2,3-c]pyridine-6(5H)-carboxylate 4 (0.7 g, 1.49 mmol) in MeOH:THF (1:1, 10 mL), propan-2-amine (0.132 g, 2.23 mmol) was added. The resulting reaction mixture was stirred at room temperature for 12 h. Progress of the reaction was monitored by TLC. After completion, the reaction mixture was concentrated to dryness under reduced pressure. The crude compound was purified by column chromatography to afford the title compound 5 as yellow solid (0.5 g, yield 63.36%).

Step 4: 2 N-(3-(benzo[d]thiazol-2-yl)-5,7-dimethyl-4,5,6,7-tetrahydrothieno[2,3-c]pyridin-2-yl)-3-(isopropylamino)propanamide

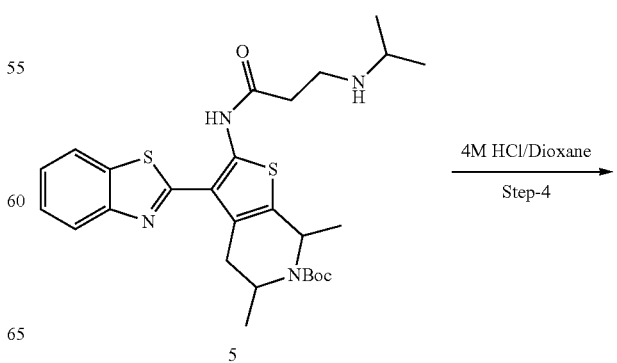

247

-continued

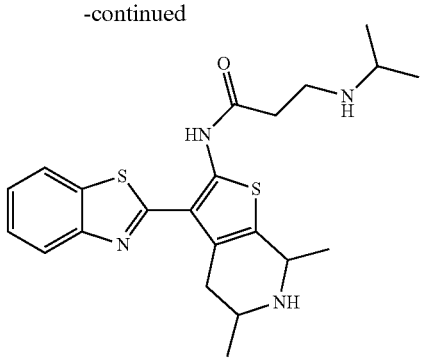

To a solution of tert-butyl 3-(benzo[d]thiazol-2-yl)-2-(3-(isopropylamino)propanamido)-5,7-dimethyl-4,7-dihydrothieno[2,3-c]pyridine-6(5H)-carboxylate 5 (0.5 g, 0.94 mmol) in dioxane (5 mL) at 0° C., 4M HCl in dioxane (5 mL) was added. After the addition, the resulting mixture was stirred at room temperature for 2 h. Progress of the reaction was monitored by TLC. After completion, the reaction mixture was concentrated to dryness under reduced pressure to afford the crude compound title compound.

The crude compound was purified by chiral preparative HPLC to afford Compounds 197 (30 mg, HCl salt), 196 (20 mg), 195 (20 mg) and 198 (30 mg) as yellow solids.

Example 83. Synthesis of N-(3-(benzo[d]thiazol-2-yl)-4,5,6,7-tetrahydrothieno[2,3-c]pyridin-2-yl)-3-propionamidopropanamide (Compound 199)

Step 1: tert-butyl 3-(benzo[d]thiazol-2-yl)-2-(3-propionamidopropanamido)-4,7-dihydrothieno[2,3-c]pyridine-6(5H)-carboxylate (2)

248

To a solution of tert-butyl 2-(3-aminopropanamido)-3-(benzo[d]thiazol-2-yl)-4,7-dihydrothieno[2,3-c]pyridine-6(5H)-carboxylate 1 (0.25 g, 0.54 mmol) in ACN (5 mL), pyridine (0.213 g, 2.7 mmol), HATU (0.308 g, 0.81 mmol) and propionic acid (0.061 g, 0.81 mmol) was added. The resulting reaction mixture was refluxed for 15 h. Progress of the reaction was monitored by TLC. After completion, the reaction mixture was concentrated to dryness under reduced pressure. The residue was diluted with ethyl acetate and washed with $NaHCO_3$ solution. The combined organic layer was washed with water; dried over anhydrous $Na_2SO_4$ and concentrated under reduced pressure. The crude compound was purified by prep. HPLC to afford the title compound 2 as yellow solid (0.05 g, yield 17.86%).

Step 2: N-(3-(benzo[d]thiazol-2-yl)-4,5,6,7-tetrahydrothieno[2,3-c]pyridin-2-yl)-3-propionamidopropanamide

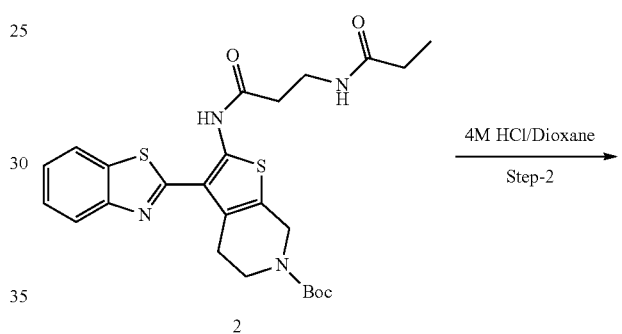

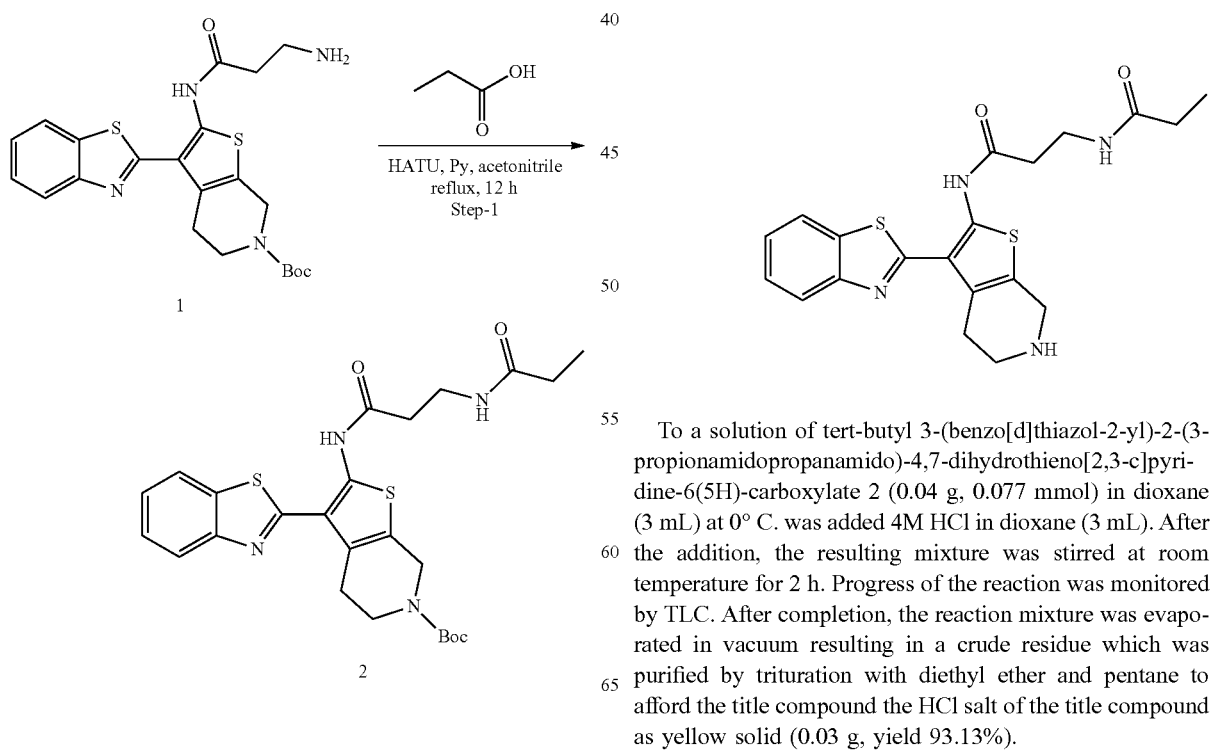

To a solution of tert-butyl 3-(benzo[d]thiazol-2-yl)-2-(3-propionamidopropanamido)-4,7-dihydrothieno[2,3-c]pyridine-6(5H)-carboxylate 2 (0.04 g, 0.077 mmol) in dioxane (3 mL) at 0° C. was added 4M HCl in dioxane (3 mL). After the addition, the resulting mixture was stirred at room temperature for 2 h. Progress of the reaction was monitored by TLC. After completion, the reaction mixture was evaporated in vacuum resulting in a crude residue which was purified by trituration with diethyl ether and pentane to afford the title compound the HCl salt of the title compound as yellow solid (0.03 g, yield 93.13%).

Example 84. Synthesis of N-(3-(benzo[d]thiazol-2-yl)-4,5,6,7-tetrahydrothieno[2,3-c]pyridin-2-yl)-3-(sec-butylamino)-N-methylpropanamide (Compound 301)

Step 1: tert-butyl 3-(benzo[d]thiazol-2-yl)-2-(N-methylacrylamido)-4,7-dihydrothieno[2,3-c]pyridine-6(5H)-carboxylate (2)

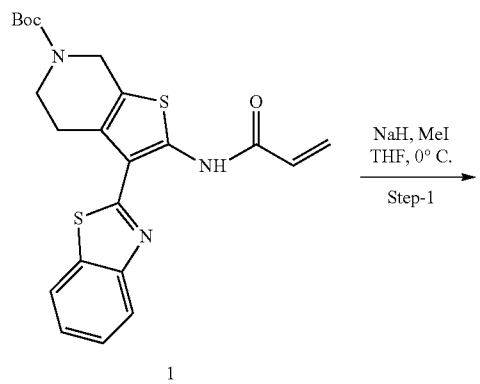

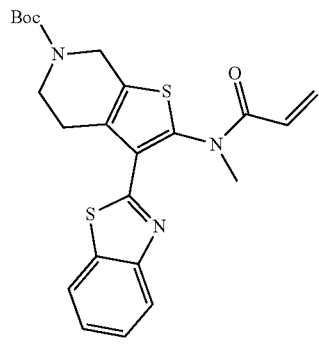

To a stirred solution of tert-butyl 2-acrylamido-3-(benzo[d]thiazol-2-yl)-4,7-dihydrothieno[2,3-c]pyridine-6(5H)-carboxylate 1 (0.25 g, 0.56 mmol) in THF (10 mL) at 0° C., NaH (0.02 g, 0.85 mmol) was added and the reaction was stirred at 0° C. for 30 min. To this solution, MeI (0.119 g, 0.85 mmol) was added at 0° C. The resulting reaction mixture was stirred at rt for 3 h. Progress of the reaction was monitored by TLC. After completion, reaction was quenched with water and extracted with 10% MeOH/DCM. Combined organic layers were dried over anhydrous sodium sulfate and concentrated under reduced pressure. The crude compound was purified by column chromatography to afford the compound 2 as off white solid (0.15 g, yield 58%).

Step 2: tert-butyl 3-(benzo[d]thiazol-2-yl)-2-(3-(sec-butylamino)-N-methylpropanamido)-4,7-dihydrothieno[2,3-c]pyridine-6(5H)-carboxylate (3)

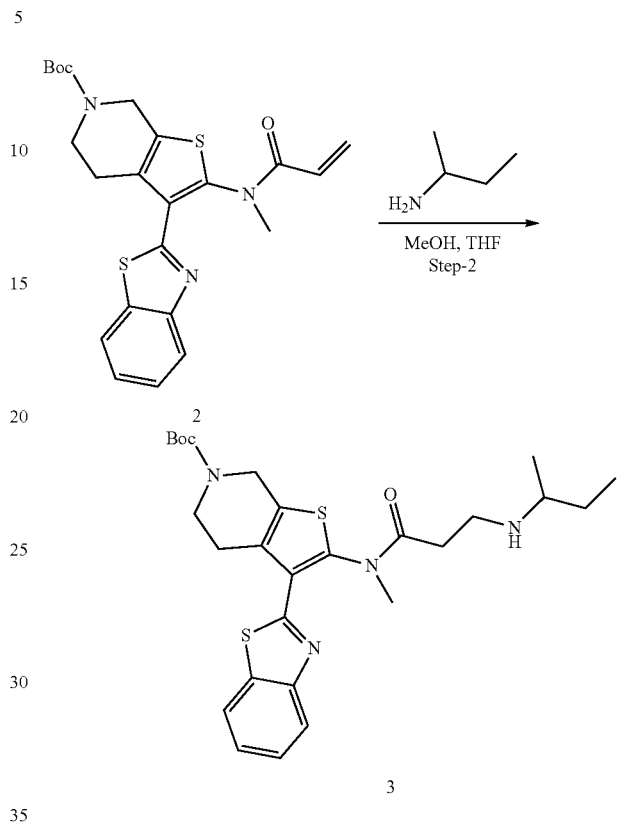

To a solution of tert-butyl 3-(benzo[d]thiazol-2-yl)-2-(N-methylacrylamido)-4,7-dihydrothieno[2,3-c]pyridine-6(5H)-carboxylate 2 (0.15 g, 0.32 mmol) in MeOH:THF (1:1, 20 mL), butan-2-amine (0.036 g, 0.49 mmol) was added. The resulting reaction mixture was stirred at room temperature for 12 h. Progress of the reaction was monitored by TLC. After completion, the reaction mixture was concentrated to dryness under reduced pressure. The crude compound was purified by column chromatography to afford the title compound 3 as yellow solid (0.09 g, yield 52%).

Step 3: N-(3-(benzo[d]thiazol-2-yl)-4,5,6,7-tetrahydrothieno[2,3-c]pyridin-2-yl)-3-(sec-butylamino)-N-methylpropanamide

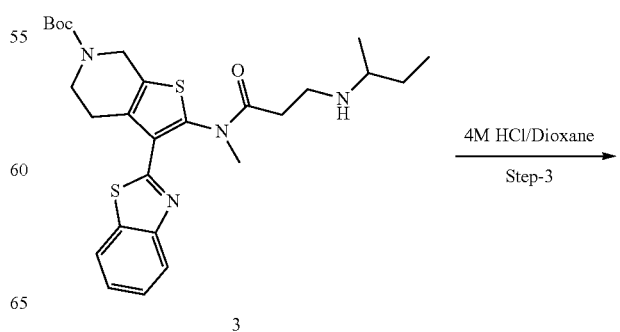

-continued

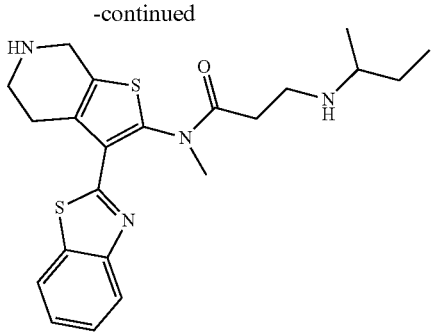

To a solution of tert-butyl 3-(benzo[d]thiazol-2-yl)-2-(3-(sec-butylamino)-N-methylpropanamido)-4,7-dihydrothieno[2,3-c]pyridine-6(5H)-carboxylate 3 (0.09 g, 0.17 mmol) in dioxane (5 mL) at 0° C., 4M HCl in dioxane (3 mL) was added. After the addition, the resulting mixture was stirred at room temperature for 2 h. Progress of the reaction was monitored by TLC. After completion, the reaction mixture was evaporated in vacuum resulting in a crude residue which was purified by trituration with diethyl ether and pentane to afford the HCl salt of the title compound as yellow solid (0.03 g, yield 41%).

Example 85. Synthesis of N-(3-(benzo[d]thiazol-2-yl)-4,5,6,7-tetrahydrothieno[2,3-c]pyridin-2-yl)-3-(bis(2-methoxyethyl)amino)propanamide (Compound 309)

Step 1: tert-butyl 3-(benzo[d]thiazol-2-yl)-2-(3-(bis(2-methoxyethyl)amino)propanamido)-4,7-dihydrothieno[2,3-c]pyridine-6(5H)-carboxylate (1)

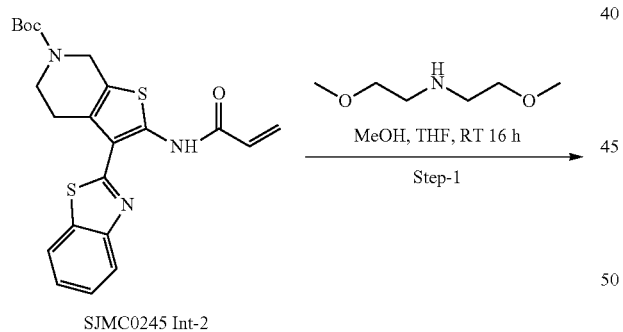

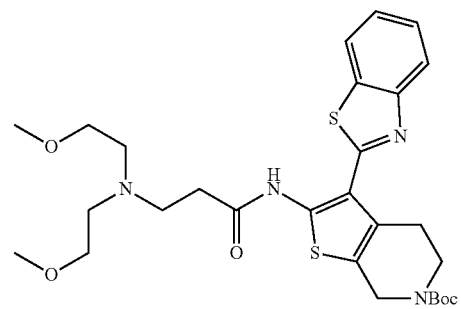

To a stirred solution of tert-butyl 2-acrylamido-3-(benzo[d]thiazol-2-yl)-4,7-dihydrothieno[2,3-c]pyridine-6(5H)-carboxylate SJMC0245 Int-2 (300 mg, 0.68 mmol) in MeOH:THF (10:10 mL) was added bis(2-methoxyethyl)amine (135 mg, 1.02 mmol) and the resulting mixture was stirred at room temperature for 16 h. Progress of the reaction was monitored by TLC. After completion, the reaction mass was concentrated to get a crude residue. This crude compound was purified by column chromatography on silica gel eluting with 2-10% methanol in DCM to afford the title compound 1 as yellow solid (90 mg, yield 23%).

Step 2: N-(3-(benzo[d]thiazol-2-yl)-4,5,6,7-tetrahydrothieno[2,3-c]pyridin-2-yl)-3-(bis(2-methoxyethyl)amino)propanamide

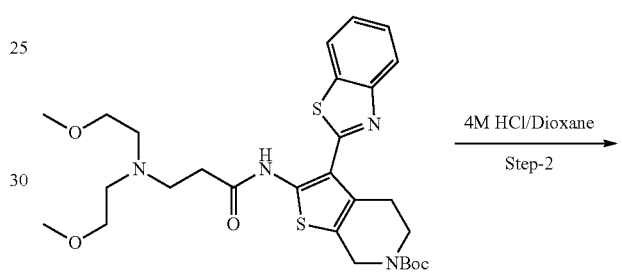

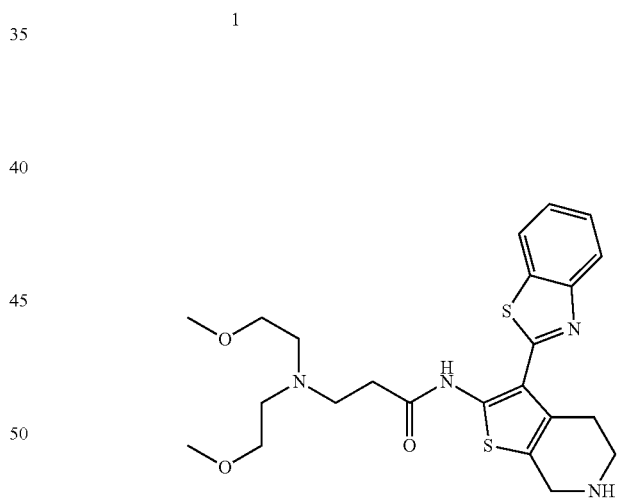

To a solution of tert-butyl 3-(benzo[d]thiazol-2-yl)-2-(3-(bis(2-methoxyethyl)amino)propanamido)-4,7-dihydrothieno[2,3-c]pyridine-6(5H)-carboxylate 1 (90 mg, 0.156 mmol) in dioxane (5 mL) at 0° C. was added 4M HCl in dioxane (5 mL) and the reaction mixture was stirred at room temperature for 2 h. After completion, the reaction mixture was evaporated to dryness and the resulting in the crude residue which was purified by trituration in pentane and diethyl ether to afford the HCl salt of the title compound as yellow solid (35 mg, 41% yield).

Example 86. Synthesis of N-(3-(Benzo[d]thiazol-2-yl)-4,5,6,7-tetrahydrothieno[2,3-c]pyridin-2-yl)-3-((2-hydroxyethyl)amino)propanamide (Compound 310)

Step 1: tert-Butyl 3-(benzo[d]thiazol-2-yl)-2-(3-((2-hydroxyethyl)amino)propanamido)-4,7-dihydrothieno[2,3-c]pyridine-6(5H)-carboxylate (1)

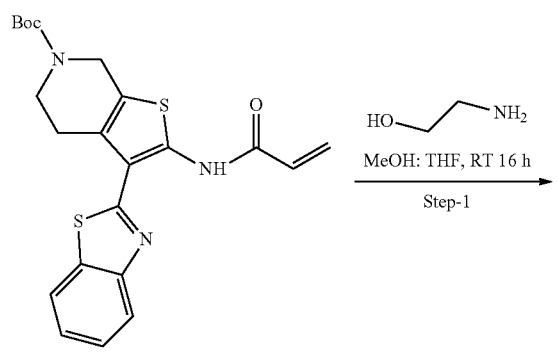

SJMC0245 Int-2

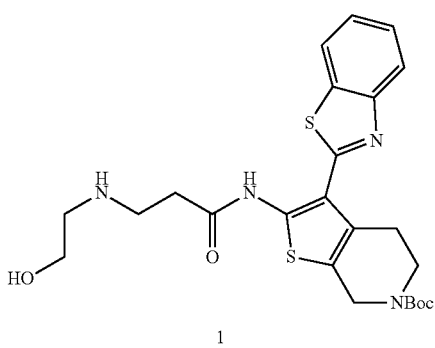

1

To a stirred solution of tert-butyl 2-acrylamido-3-(benzo[d]thiazol-2-yl)-4,7-dihydrothieno[2,3-c]pyridine-6(5H)-carboxylate SJMC0245 Int-2 (200 mg, 0.453 mmol) in MeOH (5 mL) was added 2-aminoethan-1-ol (41 mg, 0.680 mmol) and the resulting mixture was stirred at room temperature for 16 h. Progress of the reaction was monitored by TLC. After completion, the reaction mass was concentrated to get a crude residue. This crude compound was purified by column chromatography on silica gel eluting with 2-10% methanol in DCM to afford the title compound 1 as yellow solid (100 mg, yield 44%).

Step 2: N-(3-(Benzo[d]thiazol-2-yl)-4,5,6,7-tetrahydrothieno[2,3-c]pyridin-2-yl)-3-((2-hydroxyethyl)amino)propanamide

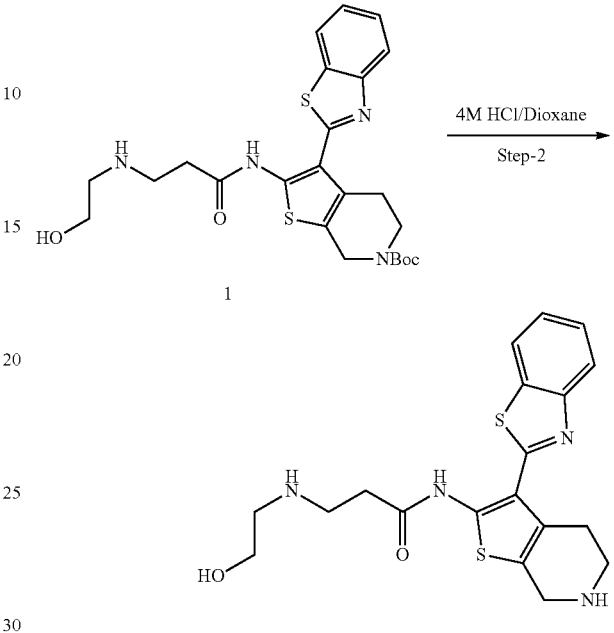

To a solution of tert-butyl 3-(benzo[d]thiazol-2-yl)-2-(3-((2-hydroxyethyl)amino)propanamido)-4,7-dihydrothieno[2,3-c]pyridine-6(5H)-carboxylate 1 (100 mg, 0.199 mmol) in dioxane (5 mL) at 0° C. was added 4M HCl in dioxane (5 mL) and the reaction mixture was stirred at room temperature for 2 h. After completion, the reaction mixture was evaporated to dryness and the resulting in the crude residue which was purified by trituration in pentane and diethyl ether to afford the HCl salt of the title compound as yellow solid (70 mg, 74% yield).

Example 87. Synthesis of 3-((2-Methoxyethyl)amino)-N-(3-(5-methylbenzo[d]thiazol-2-yl)-4,5,6,7-tetrahydrothieno[2,3-c]pyridin-2-yl)propanamide (Compound 314)

Step 1: 2-Amino-4-methylbenzenethiol (2)

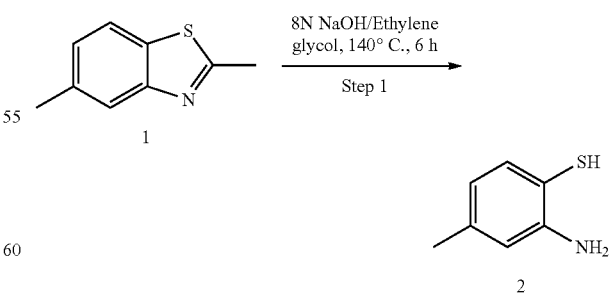

To a solution of 2,5-dimethylbenzo[d]thiazole 1 (2 g, 12.25 mmol) in ethylene glycol (10 mL) was added 8 N NaOH (8 mL). The resulting reaction mixture was stirred at 140° C. for 6 h. Progress of the reaction was monitored by TLC. After completion, the reaction mixture was cooled to room temperature; acidified with 1N HCl up to pH=6 and extracted with ethyl acetate. The combined organic layer was dried over anhydrous Na$_2$SO$_4$; filtered and concentrated under reduced pressure to afford the title compound 2 as yellow solid (1.6 g, yield 94%).

Step 2: 2-(5-Methylbenzo[d]thiazol-2-yl)acetonitrile (3)

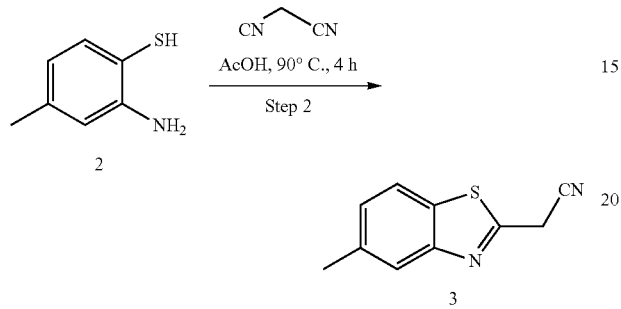

To a solution of 2-amino-4-methylbenzenethiol 2 (1.6 g, 11.51 mmol) in EtOH (15 mL) was added malononitrile (0.76 g, 11.51 mmol) and AcOH (15 mL). The resulting reaction mixture was stirred at 90° C. for 4 h. Progress of the reaction was monitored by TLC. After completion, the reaction mixture was quenched with water and concentrated under reduced pressure to dryness. The residue was diluted with aqueous sat. NaHCO$_3$ solution; extracted with ethyl acetate. Combined organic layer was dried over anhydrous Na$_2$SO$_4$; filtered and concentrated to get a crude residue. The crude compound was purified by silica gel column chromatography eluting with 0-20% ethyl acetate in n-hexane to afford the title compound 3 as yellow solid (1.16 g, yield 54%).

Step 3: tert-Butyl 2-amino-3-(5-methylbenzo[d]thiazol-2-yl)-4,7-dihydrothieno[2,3-c]pyridine-6(5H)-carboxylate (4)

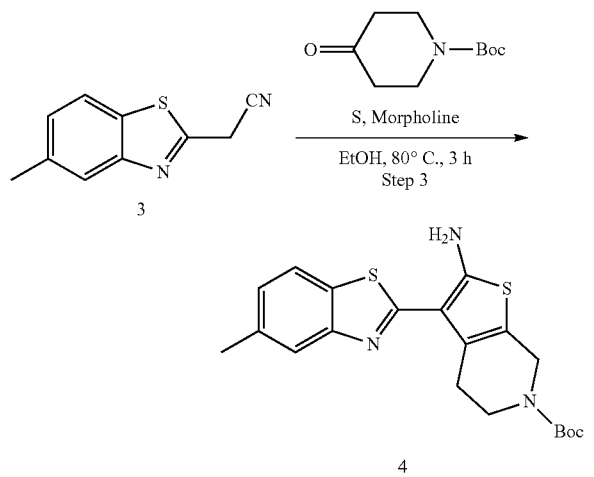

To a solution of 2-(5-methylbenzo[d]thiazol-2-yl)acetonitrile 3 (1.16 g, 6.17 mmol) in ethanol (20 mL) was added tert-butyl 4-oxopiperidine-1-carboxylate (1.23 g, 6.17 mmol), elemental sulphur (0.197 g, 6.17 mmol) and morpholine (0.54 g, 6.17 mmol) at room temperature. After the addition, the resulting mixture was heated to reflux at 80° C. for 3 h. Progress of the reaction was monitored by TLC. After completion, the reaction mixture was evaporated in vacuum resulting in a crude residue which was stirred in methanol. The solid precipitated out was filtered and dried to obtain the crude compound was purified by triturating with n-pentane to afford the title compound 4 as yellow solid (1.7 g, yield 69%).

Step 4: tert-Butyl 2-acrylamido-3-(5-methylbenzo[d]thiazol-2-yl)-4,7-dihydrothieno[2,3-c]pyridine-6(5H)-carboxylate (5)

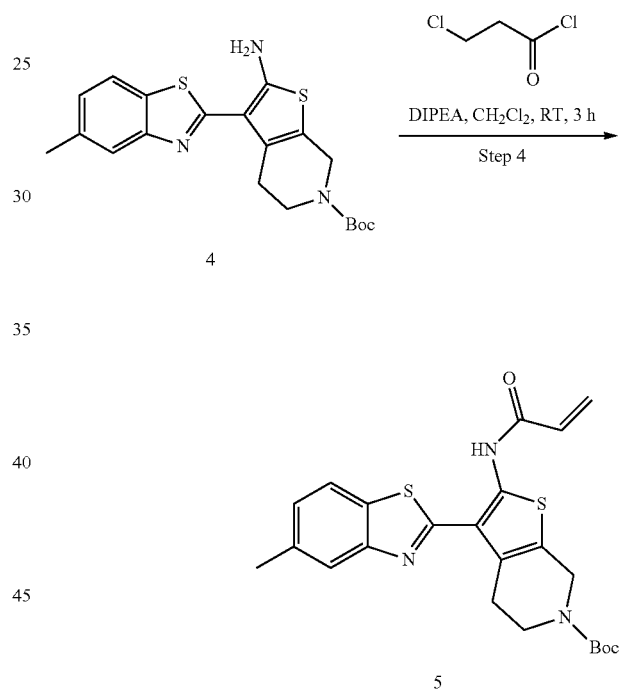

To a solution of tert-butyl 2-amino-3-(5-methylbenzo[d]thiazol-2-yl)-4,7-dihydrothieno[2,3-c]pyridine-6(5H)-carboxylate 4 (1 g, 2.49 mmol) in DCM (10 mL) at 0° C. was added DIPEA (0.65 mL, 3.735 mmol) and 3-chloropropanoyl chloride (0.35 mL, 3.735 mmol). The reaction mixture was stirred at room temperature for 3 h. After completion (monitored by TLC), the reaction mixture was concentrated to dryness under reduced pressure. The crude residue was diluted with water and extracted with ethyl acetate. The combined organic layer was dried over anhydrous Na$_2$SO$_4$; filtered and concentrated to get a crude residue. The crude compound was purified by silica gel column chromatography eluting with a gradient of 10-40% ethyl acetate in n-hexane to afford the title compound 5 as yellow solid (1.1 g, yield 97%).

Step 5: tert-Butyl 2-(3-((2-methoxyethyl)amino)propanamido)-3-(5-methylbenzo[d]thiazol-2-yl)-4,7-dihydrothieno[2,3-c]pyridine-6(5H)-carboxylate (6)

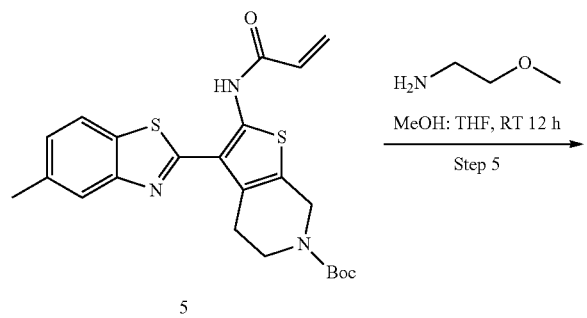

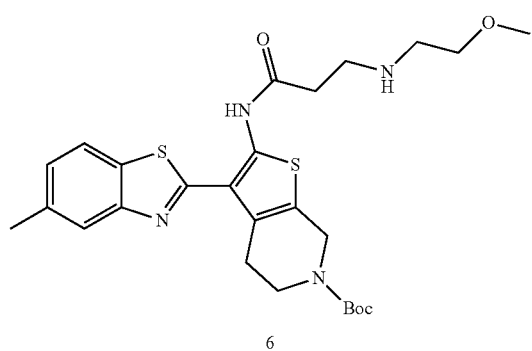

To a solution of tert-butyl 2-acrylamido-3-(5-methylbenzo[d]thiazol-2-yl)-4,7-dihydrothieno[2,3-c]pyridine-6(5H)-carboxylate 5 (0.5 g, 1.098 mmol) in MeOH:THF (1:1, 20 mL) was added 2-methoxyethan-1-amine (0.124 g, 1.648 mmol). The resulting reaction mixture was stirred at room temperature for 12 h. Progress of the reaction was monitored by TLC. After completion, the reaction mixture was concentrated to dryness under reduced pressure. The crude compound was purified by column chromatography eluting with 0-5% methanol in DCM to afford the title compound 6 as yellow solid (0.320 g, yield 55%).

Step 6: 3-((2-Methoxyethyl)amino)-N-(3-(5-methylbenzo[d]thiazol-2-yl)-4,5,6,7-tetrahydrothieno[2,3-c]pyridin-2-yl)propanamide

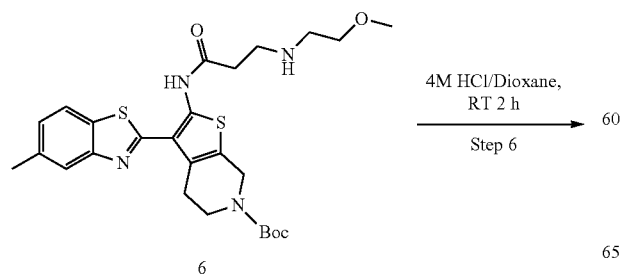

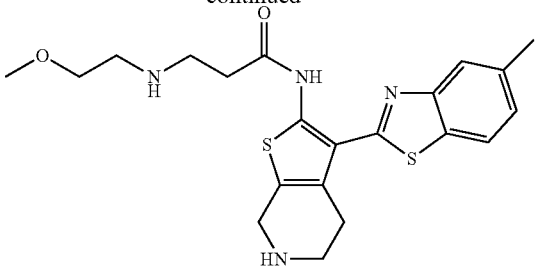

To a solution of tert-butyl 2-(3-((2-methoxyethyl)amino)propanamido)-3-(5-methylbenzo[d]thiazol-2-yl)-4,7-dihydrothieno[2,3-c]pyridine-6(5H)-carboxylate 6 (0.2 g, 0.377 mmol) in dioxane (3 mL) at 0° C. was added 4M HCl in dioxane (4 mL). After the addition, the resulting mixture was stirred at room temperature for 2 h. After completion, the reaction mixture was evaporated in vacuum resulting in a crude residue which was purified by trituration with diethyl ether and n-pentane to afford the HCl salt of the title compound as yellow solid (0.17 g, HCl salt, 90% yield).

Example 88. Synthesis of N-(3-(Benzo[d]thiazol-2-yl)-5,7-dimethyl-4,5,6,7-tetrahydrothieno[2,3-c]pyridin-2-yl)-3-((2-methoxyethyl)amino)propanamide (Compound 315)

Step 1: tert-Butyl 2-acrylamido-3-(benzo[d]thiazol-2-yl)-5,7-dimethyl-4,7-dihydrothieno[2,3-c]pyridine-6(5H)-carboxylate (2)

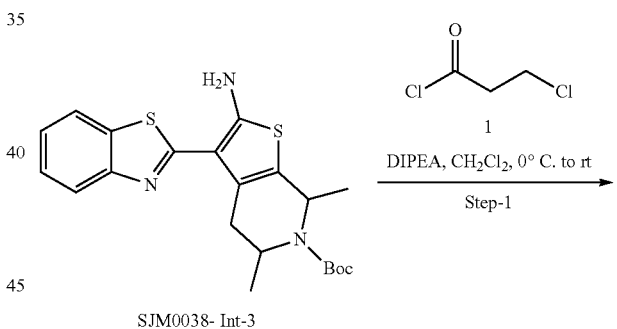

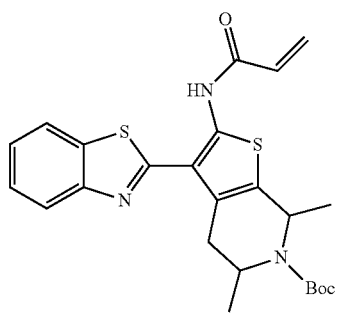

To a solution of tert-butyl 2-amino-3-(5-methylbenzo[d]thiazol-2-yl)-4,7-dihydrothieno[2,3-c]pyridine-6(5H)-carboxylate SJMC0038 Int-3 (0.8 g, 1.927 mmol) in DCM (20 mL) at 0° C. was added DIPEA (1.03 mL, 5.783 mmol) and 3-chloropropanoyl chloride 1 (0.489, 3.855 mmol). The reaction mixture was stirred at room temperature for 15 h.

After completion (monitored by TLC), the reaction mixture was diluted with water and extracted with DCM. The combined organic layer was dried over anhydrous Na$_2$SO$_4$; filtered and concentrated to afford the title compound 2 as yellow solid (0.9 g, crude).

Step 2: tert-Butyl 3-(benzo[d]thiazol-2-yl)-2-(3-((2-methoxyethyl)amino)propanamido)-5,7-dimethyl-4,7-dihydrothieno[2,3-c]pyridine-6(5H)-carboxylate (4)

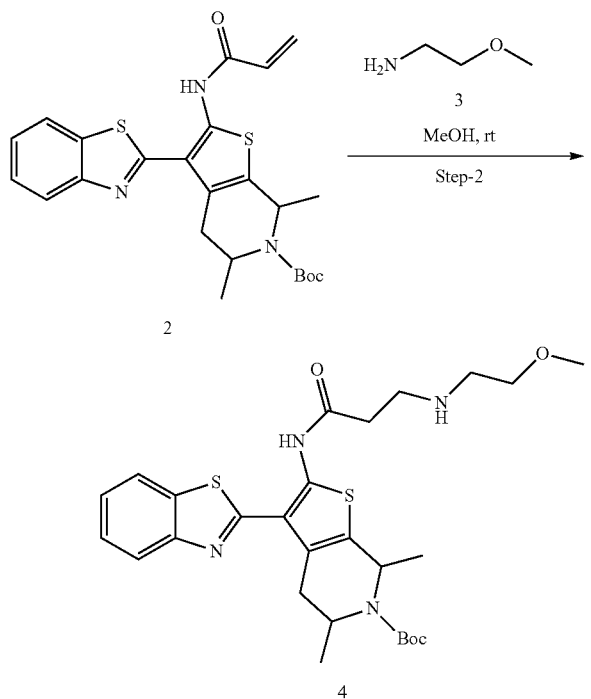

To a solution of tert-butyl 2-acrylamido-3-(benzo[d]thiazol-2-yl)-5,7-dimethyl-4,7-dihydrothieno[2,3-c]pyridine-6 (5H)-carboxylate 2 (0.9 g, 1.914 mmol) in MeOH:THF (1:1, 10 mL) was added 2-methoxyethan-1-amine 3 (0.216 g, 2.872 mmol). The resulting reaction mixture was stirred at room temperature for 15 h. Progress of the reaction was monitored by TLC. After completion, the reaction mixture was concentrated to dryness under reduced pressure. The crude compound was purified by column chromatography eluting with 0-5% methanol in DCM to afford the title compound 4 as yellow solid (0.5 g, yield 48%).

Step 3: N-(3-(Benzo[d]thiazol-2-yl)-5,7-dimethyl-4,5,6,7-tetrahydrothieno[2,3-c]pyridin-2-yl)-3-((2-methoxyethyl)amino)propanamide

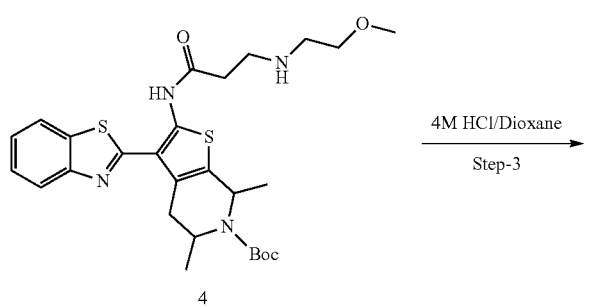

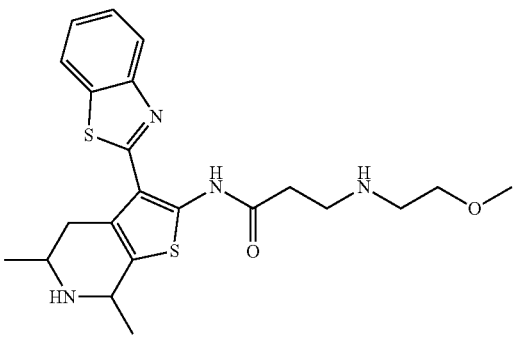

To a solution of N-(3-(benzo[d]thiazol-2-yl)-5,7-dimethyl-4,5,6,7-tetrahydrothieno[2,3-c]pyridin-2-yl)-3-((2-methoxyethyl)amino)propanamide 4 (0.5 g, 0.919 mmol) in dioxane (5 mL) at 0° C. was added 4M HCl in dioxane (5 mL). After the addition, the resulting mixture was stirred at room temperature for 3 h. After completion, the reaction mixture was evaporated in vacuum resulting in a crude residue which was purified by trituration with diethyl ether and n-pentane to afford the HCl salt of the title compound as yellow solid (0.3 g, HCl salt, 63% yield).

Example 89. Synthesis of N-(3-(6-Fluorobenzo[d]thiazol-2-yl)-4,5,6,7-tetrahydrothieno[2,3-c]pyridin-2-yl)-3-((2-methoxyethyl)amino)propanamide (Compound 318)

Step 1: 2-Amino-5-fluorobenzenethiol (2)

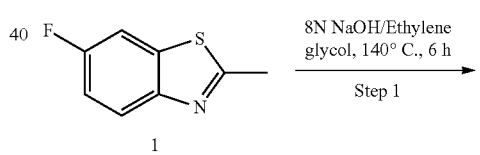

To a solution of 6-fluoro-2-methylbenzo[d]thiazole 1 (2 g, 11.96 mmol) in ethylene glycol (10 mL) was added 8 N NaOH (8 mL). The resulting reaction mixture was stirred at 140° C. for 6 h. Progress of the reaction was monitored by TLC. After completion, the reaction mixture was cooled to room temperature; acidified with 1N HCl up to pH=6 and extracted with ethyl acetate. The combined organic layer was dried over anhydrous Na$_2$SO$_4$; filtered and concentrated under reduced pressure to afford the title compound 2 as yellow solid (1.65 g, yield 96%).

Step 2: 2-(6-Fluorobenzo[d]thiazol-2-yl)acetonitrile (3)

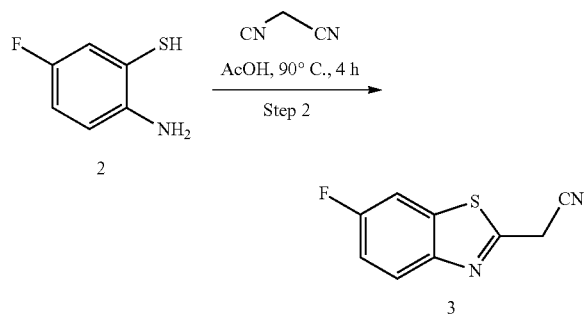

To a solution of 2-amino-5-fluorobenzenethiol 2 (1.65 g, 11.50 mmol) in EtOH (15 mL) was added malononitrile (760 mg, 11.50 mmol) and AcOH (15 mL). The resulting reaction mixture was stirred at 90° C. for 4 h. Progress of the reaction was monitored by TLC. After completion, the reaction mixture was quenched with water and concentrated under reduced pressure to dryness. The residue was diluted with aqueous sat. NaHCO$_3$ solution; extracted with ethyl acetate. Combined organic layer was dried over anhydrous Na$_2$SO$_4$; filtered and concentrated to get a crude residue. The crude compound was purified by silica gel column chromatography eluting with 0-20% ethyl acetate in n-hexane to afford the title compound 3 as yellow solid (920 mg, yield 41%).

Step 3: tert-Butyl 2-amino-3-(6-fluorobenzo[d]thiazol-2-yl)-4,7-dihydrothieno[2,3-c]pyridine-6(5H)-carboxylate (4)

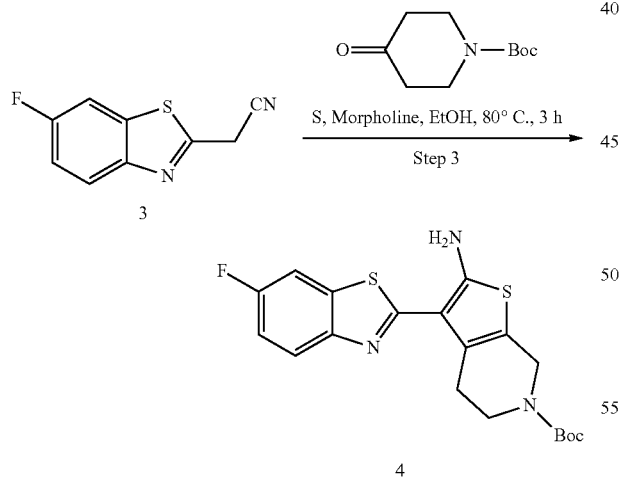

To a solution of 2-(6-fluorobenzo[d]thiazol-2-yl)acetonitrile 3 (920 mg, 4.791 mmol) in ethanol (10 mL) was added tert-butyl 4-oxopiperidine-1-carboxylate (955 mg, 4.791 mmol), elemental sulphur (153 mg, 4.791 mmol) and morpholine (416 mg, 4.791 mmol) at room temperature. After the addition, the resulting mixture was heated to reflux at 80° C. for 3 h. Progress of the reaction was monitored by TLC. After completion, the reaction mixture was evaporated in vacuum resulting in a crude residue which was stirred in methanol. The solid precipitated out was filtered and dried to obtain the crude compound was purified by triturating with n-pentane to afford the title compound 4 as yellow solid (530 mg, yield 28%).

Step 4: tert-Butyl 2-acrylamido-3-(6-fluorobenzo[d]thiazol-2-yl)-4,7-dihydrothieno[2,3-c]pyridine-6(5H)-carboxylate (5)

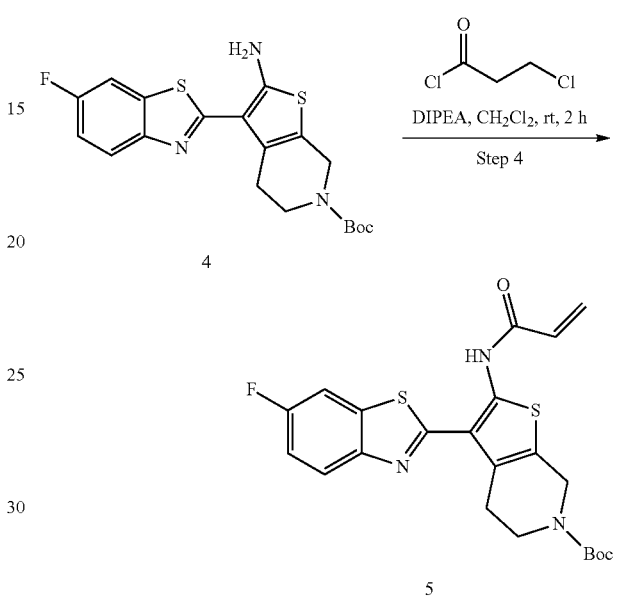

To a solution of tert-butyl 2-amino-3-(6-fluorobenzo[d]thiazol-2-yl)-4,7-dihydrothieno[2,3-c]pyridine-6(5H)-carboxylate 4 (530 mg, 1.308 mmol) in DCM (10 mL) at 0° C. was added DIPEA (0.34 mL, 1.962 mmol) and 3-chloropropanoyl chloride (249 mg, 1.962 mmol). The reaction mixture was stirred at room temperature for 2 h. After completion (monitored by TLC), the reaction mixture was washed with saturated sodium bicarbonate solution and extracted with DCM (thrice). The combined organic layer was dried over anhydrous Na$_2$SO$_4$; filtered and concentrated in vacuo. The crude compound was purified by trituration in diethyl ether and n-pentane to afford the title compound 5 as yellow solid (480 mg, yield 80%).

Step 5: tert-Butyl 3-(6-fluorobenzo[d]thiazol-2-yl)-2-(3-((2-methoxyethyl)amino)propanamido)-4,7-dihydrothieno[2,3-c]pyridine-6(5H)-carboxylate (6)

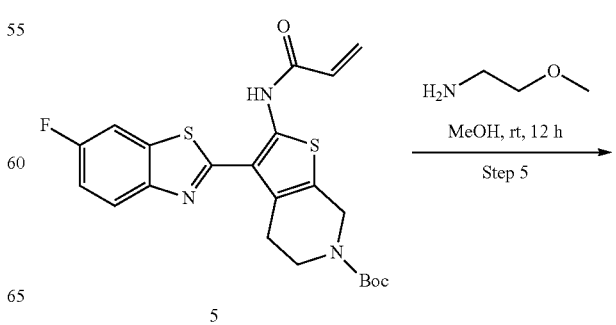

-continued

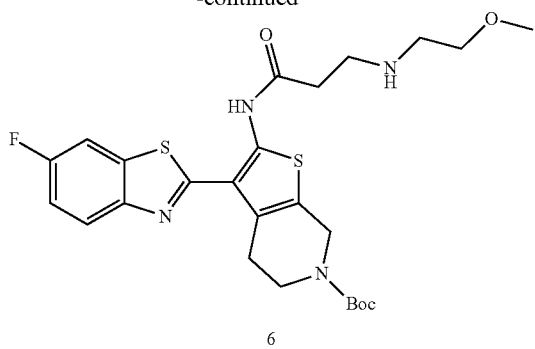

6

To a solution of tert-butyl 2-acrylamido-3-(6-fluorobenzo[d]thiazol-2-yl)-4,7-dihydrothieno[2,3-c]pyridine-6(5H)-carboxylate 5 (480 mg, 1.045 mmol) in MeOH:THF (1:1, 20 mL) was added 2-methoxyethan-1-amine (117 mg, 1.568 mmol). The resulting reaction mixture was stirred at room temperature for 12 h. Progress of the reaction was monitored by TLC. After completion, the reaction mixture was concentrated to dryness under reduced pressure. The residue was washed with water and extracted with DCM (thrice). The combined organic layer was dried over anhydrous $Na_2SO_4$, filtered and concentrated. The crude compound was purified by column chromatography eluting with 0-3% methanol in DCM to afford the title compound 6 as yellow solid (280 mg, yield 50%).

Step 6: N-(3-(6-Fluorobenzo[d]thiazol-2-yl)-4,5,6,7-tetrahydrothieno[2,3-c]pyridin-2-yl)-3-((2-methoxyethyl)amino)propanamide

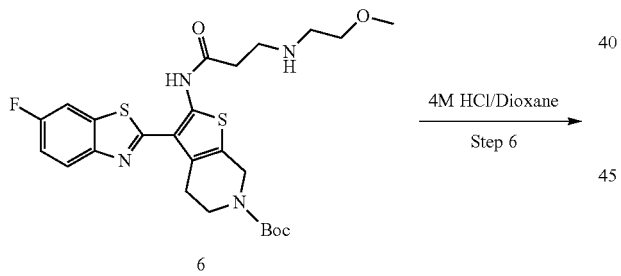

6

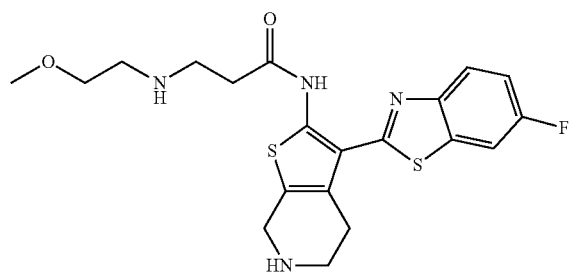

To a solution of tert-butyl 3-(6-fluorobenzo[d]thiazol-2-yl)-2-(3-((2-methoxyethyl)amino)propanamido)-4,7-dihydrothieno[2,3-c]pyridine-6(5H)-carboxylate 6 (180 mg, 0.337 mmol) in dioxane (3 mL) at 0° C. was added 4M HCl in dioxane (3 mL). After the addition, the resulting mixture was stirred at room temperature for 3 h. After completion, the reaction mixture was evaporated in vacuum resulting in a crude residue which was purified by trituration with methanol. The solid obtained was filtered and washed with diethyl ether and n-pentane to afford the HCl salt of the title compound as yellow solid (155 mg, HCl salt, 91% yield).

Example 90. Synthesis of N-(3-(Benzo[d]thiazol-2-yl)-6-(2-(2,2,2-trifluoroacetamido)ethyl)-4,5,6,7-tetrahydrothieno[2,3-c]pyridin-2-yl)-3-(N-(sec-butyl)acetamido)propanamide (Compound 319)

Step 1: tert-Butyl 2-acrylamido-3-(benzo[d]thiazol-2-yl)-4,7-dihydrothieno[2,3-c]pyridine-6(5H)-carboxylate (2)

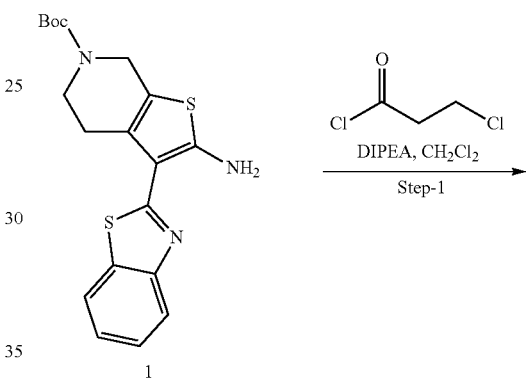

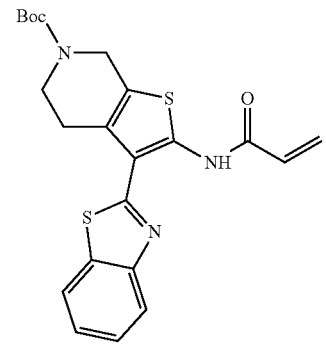

2

To a solution of tert-butyl 2-amino-3-(benzo[d]thiazol-2-yl)-4,7-dihydrothieno[2,3-c]pyridine-6(5H)-carboxylate 1 (3 g, 7.751 mmol) in DCM (50 mL) at 0° C. was added DIPEA (2 mL, 11.62 mmol) and 3-chloropropanoyl chloride (1.47 g, 11.62 mmol). The reaction mixture was stirred at room temperature for 15 h. After completion, the reaction mixture was diluted with water and extracted with DCM. The separated organic layer was washed with saturated $NaHCO_3$ solution and brine. The combined organic layer was dried over anhydrous $Na_2SO_4$, filtered and dried. The crude compound was purified by column chromatography eluting with 0-10% methanol in DCM to afford the title compound 2 as yellow solid (3 g, yield 88%).

Step 2: tert-Butyl 3-(benzo[d]thiazol-2-yl)-2-(3-(sec-butylamino)propanamido)-4,7-dihydrothieno[2,3-c]pyridine-6(5H)-carboxylate (3)

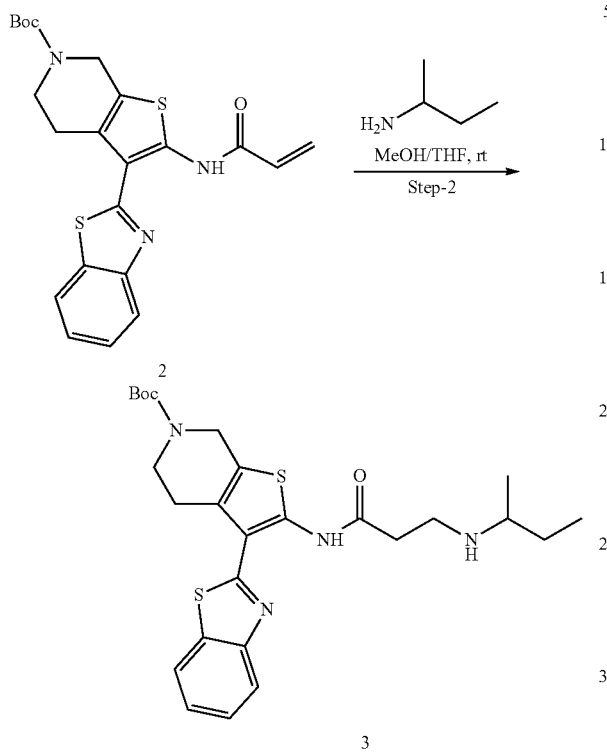

To a solution of tert-butyl 2-acrylamido-3-(benzo[d]thiazol-2-yl)-4,7-dihydrothieno[2,3-c]pyridine-6(5H)-carboxylate 2 (3 g, 6.802 mmol) in MeOH:THF (1:1, 200 mL) was added butan-2-amine (744 mg, 10.20 mmol). The resulting reaction mixture was stirred at room temperature for 3 h. Progress of the reaction was monitored by TLC. After completion, the reaction mixture was diluted with water and extracted with DCM. The separated organic layer was washed with saturated $NaHCO_3$ solution and brine. The combined organic layer was dried over anhydrous $Na_2SO_4$, filtered and dried. The crude compound was purified by column chromatography eluting with 0-10% methanol in DCM to afford the title compound 3 as yellow solid (3.3 g, yield 94%). Reaction was monitored by TLC (TLC system: 10% methanol in DCM; Rf=0.3)

Step 3: tert-Butyl 3-(benzo[d]thiazol-2-yl)-2-(3-(N-(sec-butyl)acetamido)propanamido)-4,7-dihydrothieno[2,3-c]pyridine-6(5H)-carboxylate (4)

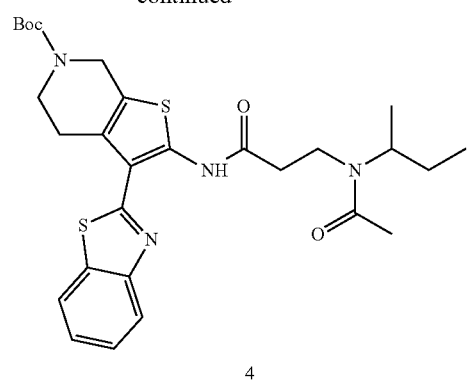

To a solution of tert-butyl 3-(benzo[d]thiazol-2-yl)-2-(3-(sec-butylamino)propanamido)-4,7-dihydrothieno[2,3-c]pyridine-6(5H)-carboxylate 3 (600 mg, 1.167 mmol) in DCM (10 mL) at 0° C. was added DIPEA (0.4 mL, 2.334 mmol) and acetyl chloride (0.08 mL, 1.167 mmol). The reaction mixture was stirred at room temperature for 4 h. After completion (monitored by TLC), the reaction mixture was diluted with saturated $NaHCO_3$ solution and extracted with DCM (thrice). The combined organic layer was dried over anhydrous $Na_2SO_4$; filtered and concentrated to afford the title compound 4 as yellow solid (500 mg, crude).

Step 4: N-(3-(Benzo[d]thiazol-2-yl)-4,5,6,7-tetrahydrothieno[2,3-c]pyridin-2-yl)-3-(N-(sec-butyl)acetamido)propanamide (5)

To a solution of tert-butyl 3-(benzo[d]thiazol-2-yl)-2-(3-(N-(sec-butyl)acetamido)propanamido)-4,7-dihydrothieno[2,3-c]pyridine-6(5H)-carboxylate 4 (500 mg, 0.899 mmol) in dioxane (5 mL) at 0° C. was added 4M HCl in dioxane (5 mL). After the addition, the resulting mixture was stirred at room temperature for 3 h. After completion, the reaction mixture was evaporated in vacuum resulting in a crude residue which was purified by trituration with diethyl ether and methanol to afford the title compound 5 as yellow solid (500 mg crude).

Step 5: tert-Butyl (2-(3-(benzo[d]thiazol-2-yl)-2-(3-(N-(sec-butyl)acetamido)propanamido)-4,7-dihydrothieno[2,3-c]pyridin-6(5H)-yl)ethyl)carbamate (6)

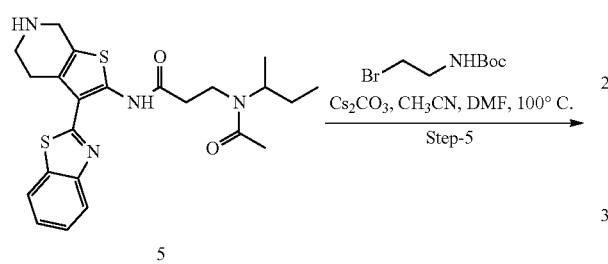

5

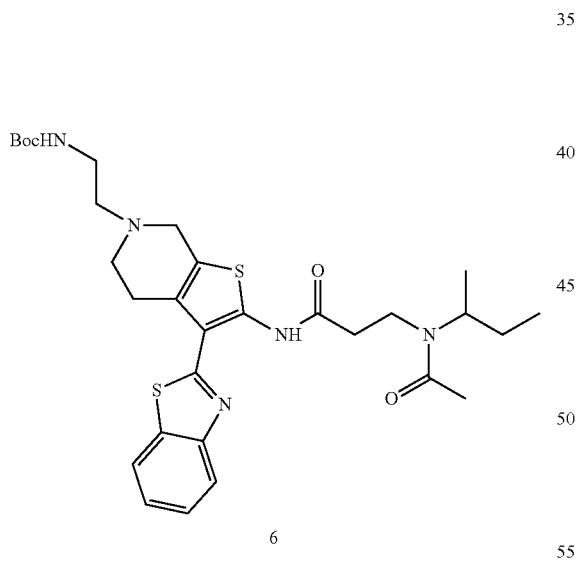

6

To a solution of N-(3-(benzo[d]thiazol-2-yl)-4,5,6,7-tetrahydrothieno[2,3-c]pyridin-2-yl)-3-(N-(sec-butyl)acetamido)propanamide 5 (600 mg, 1.315 mmol) in CH$_3$CN: DMF (30:1.5 mL) was added cesium carbonate (2.13 g, 6.57 mmol) and tert-butyl (2-bromoethyl)carbamate (442 mg, 1.97 mmol) at room temperature. The reaction mixture was further heated to 100° C. and stirred for 16 h. After completion (monitored by TLC), the reaction mixture was diluted with water and extracted with DCM. The separated organic layer was washed with saturated NaHCO$_3$ solution and brine. The combined organic layer was dried over anhydrous Na$_2$SO$_4$, filtered and dried. The crude compound was purified by column chromatography eluting with 0-10% methanol in DCM to afford the title compound 6 as yellow solid (300 mg, yield 38%).

Step 6: N-(6-(2-Aminoethyl)-3-(benzo[d]thiazol-2-yl)-4,5,6,7-tetrahydrothieno[2,3-c]pyridin-2-yl)-3-(N-(sec-butyl)acetamido)propanamide (7)

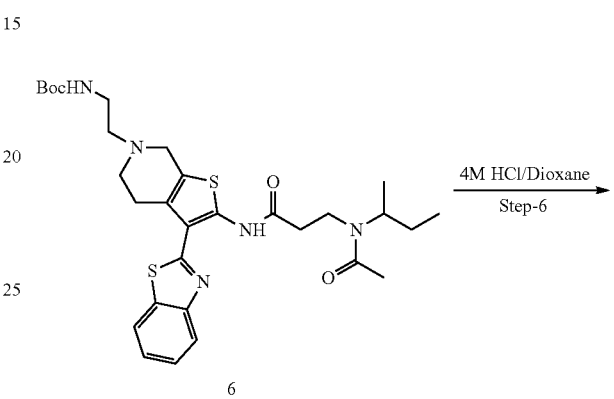

6

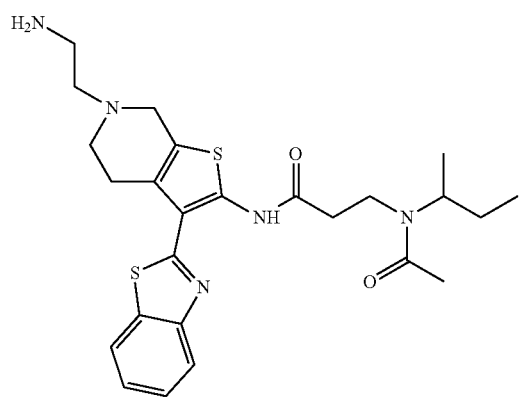

7

To a solution of tert-butyl (2-(3-(benzo[d]thiazol-2-yl)-2-(3-(N-(sec-butyl)acetamido)propanamido)-4,7-dihydrothieno[2,3-c]pyridin-6(5H)-yl)ethyl)carbamate 6 (300 mg, 0.501 mmol) in dioxane (5 mL) at 0° C. was added 4M HCl in dioxane (5 mL). After the addition, the resulting mixture was stirred at room temperature for 3 h. After completion, the reaction mixture was evaporated in vacuum resulting in a crude residue which was purified by trituration with diethyl ether and methanol to afford 7 as yellow solid (320 mg crude).

Step 7: N-(3-(Benzo[d]thiazol-2-yl)-6-(2-(2,2,2-trifluoroacetamido)ethyl)-4,5,6,7-tetrahydrothieno[2,3-c]pyridin-2-yl)-3-(N-(sec-butyl)acetamido)propanamide

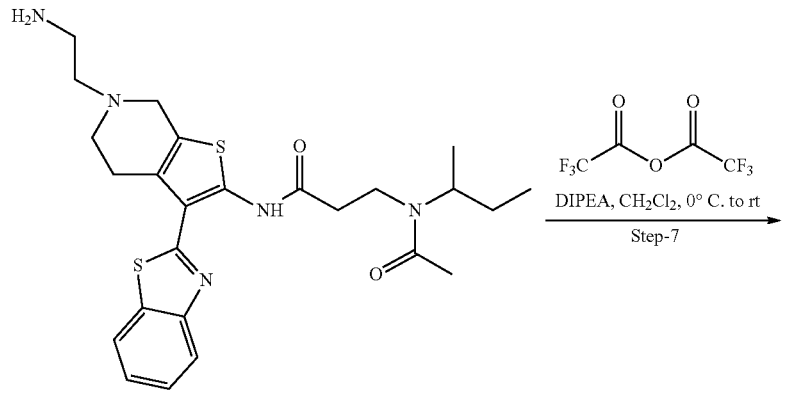

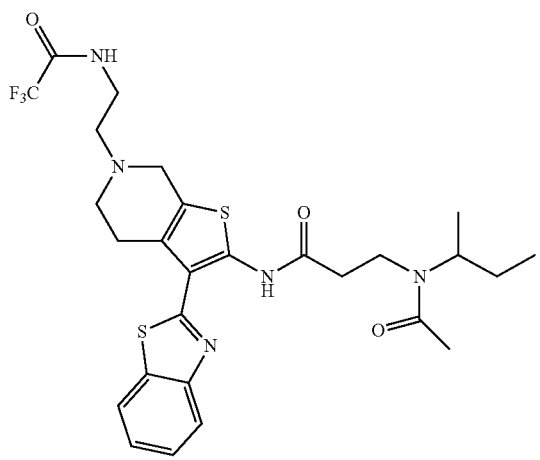

To a solution of N-(6-(2-aminoethyl)-3-(benzo[d]thiazol-2-yl)-4,5,6,7-tetrahydrothieno[2,3-c]pyridin-2-yl)-3-(N-(sec-butyl)acetamido)propanamide 7 (100 mg, 0.20 mmol) in DCM (10 mL) at 0° C. was added DIPEA (0.07 mL, 0.40 mmol) and 2,2,2-trifluoroacetic anhydride (63.1 mg, 0.30 mmol). The reaction mixture was stirred at room temperature for 3 h. After completion (monitored by TLC), the reaction mixture was diluted with water and extracted with DCM. The separated organic layer was washed with saturated $NaHCO_3$ solution and brine. The combined organic layer was dried over anhydrous $Na_2SO_4$, filtered and dried. The crude compound was purified by column chromatography eluting with 0-10% methanol in DCM to afford the title compound as yellow solid (30 mg, yield 25%).

Example 91. Synthesis of 2-(2-(3-(Isopropylamino)propanamido)-4,5,6,7-tetrahydrothieno[2,3-c]pyridin-3-yl)benzo[d]thiazole-5-carboxylic acid (Compound 320)

Step 1: tert-Butyl 2-acrylamido-3-(5-bromobenzo[d]thiazol-2-yl)-4,7-dihydrothieno[2,3-c]pyridine-6(5H)-carboxylate (5)

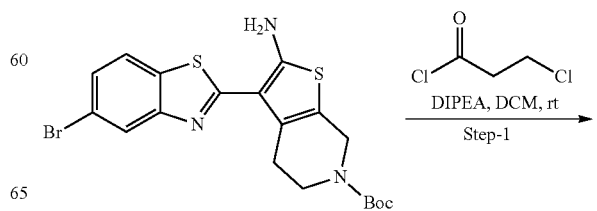

SJMC0017 Int-4

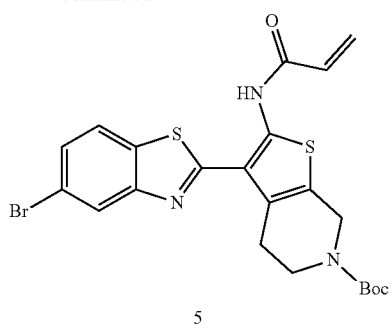

5

To a solution of tert-butyl 2-amino-3-(5-bromobenzo[d]thiazol-2-yl)-4,7-dihydrothieno[2,3-c]pyridine-6(5H)-carboxylate SJMC0017 Int-4 (10 g, 21.50 mmol) in DCM (50 mL) at 0° C. was added DIPEA (7.4 mL, 43.00 mmol). Followed by addition of 3-chloropropanoyl chloride (4 g, 32.25 mmol) and was stirred at room temperature for 2 h. Reaction was monitored by TLC. After the completion of reaction (by LCMS) the reaction mixture was diluted with water and extracted with ethyl acetate. The combined organic layer was dried with anhydrous Na₂SO₄, filtered and concentrated to afford the title compound 5 as yellow solid (10 g, 89% yield).

Step 2: tert-Butyl 3-(5-bromobenzo[d]thiazol-2-yl)-2-(3-(ethylamino)propanamido)-4,7-dihydrothieno[2,3-c]pyridine-6(5H)-carboxylate (6)

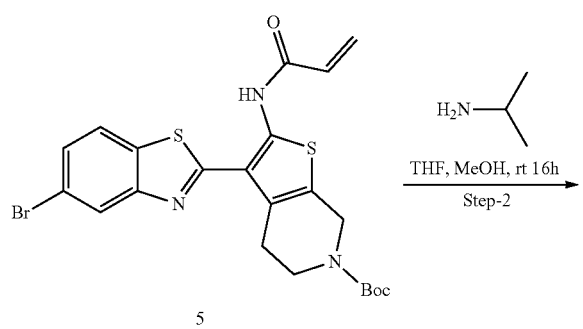

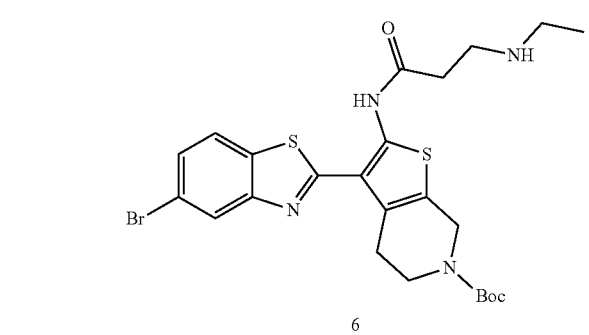

To a solution of tert-butyl 2-acrylamido-3-(5-bromobenzo[d]thiazol-2-yl)-4,7-dihydrothieno[2,3-c]pyridine-6(5H)-carboxylate 5 (9 g, 17.34 mmol) in MeOH:THF (4:1, 40 mL) was added propan-2-amine (2 g, 34.68 mmol). The resulting reaction mixture was stirred at room temperature for 16 h. Progress of the reaction was monitored by TLC. After completion, the reaction mixture was concentrated to dryness under reduced pressure. The crude compound was purified by column chromatography eluting with 0-10% methanol in DCM to afford the title compound 6 as yellow solid (6.1 g, yield 61%).

Step 3: tert-Butyl 2-(3-(isopropylamino)propanamido)-3-(5-vinylbenzo[d]thiazol-2-yl)-4,7-dihydrothieno[2,3-c]pyridine-6(5H)-carboxylate (7)

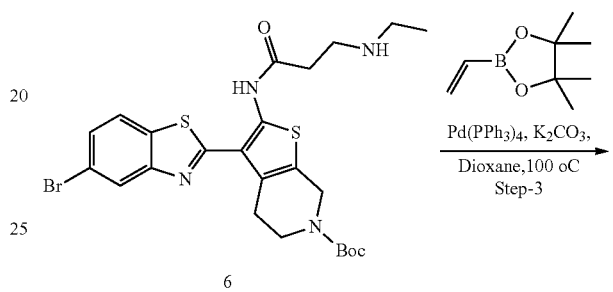

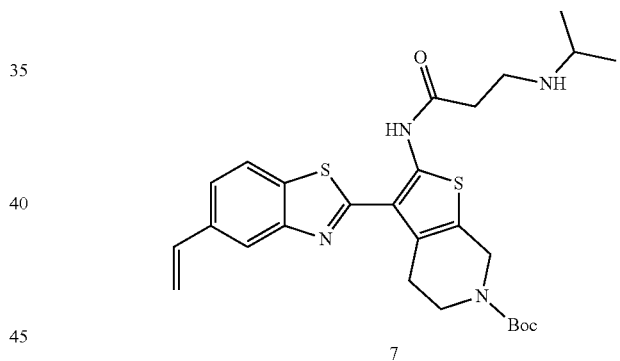

To a solution of tert-butyl 3-(5-bromobenzo[d]thiazol-2-yl)-2-(3-(ethylamino)propanamido)-4,7-dihydrothieno[2,3-c]pyridine-6(5H)-carboxylate 6 (6 g, 10.38 mmol) in dioxane (50 mL) was added K₂CO₃ (2.8 g, 20.7 mmol) and the reaction mixture was degassed under argon atmosphere for 10 min. Followed by addition of Pd(PPh₃)₄ (1.1 g, 1.03 mmol) and 4,4,5,5-tetramethyl-2-vinyl-1,3,2-dioxaborolane (3.99 g, 25.95 mmol) and degassed with argon for another 10 min. The reaction mixture was heated to 100° C. for 16 h. After the completion of reaction (monitored by LCMS), the reaction mixture was diluted with water and extracted with ethyl acetate (thrice). The combined organic layers were dried with anhydrous Na₂SO₄, filtered and concentrated to get a crude residue. This crude compound was purified by silica gel column chromatography eluting with 0-15% ethyl acetate in n-hexane to afford the title compound 7 (4.5 g, 83% yield).

Step 4: tert-Butyl 2-(3-((tert-butoxycarbonyl)(isopropyl)amino)propanamido)-3-(5-vinylbenzo[d]thiazol-2-yl)-4,7-dihydrothieno[2,3-c]pyridine-6(5H)-carboxylate (8)

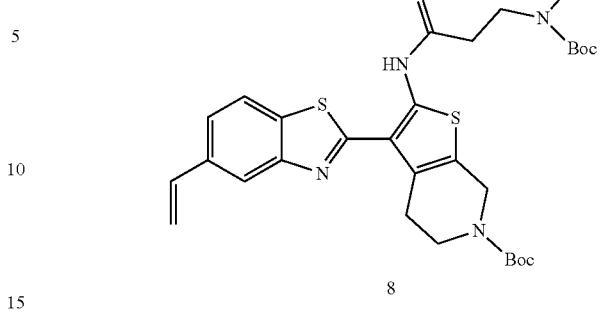

8

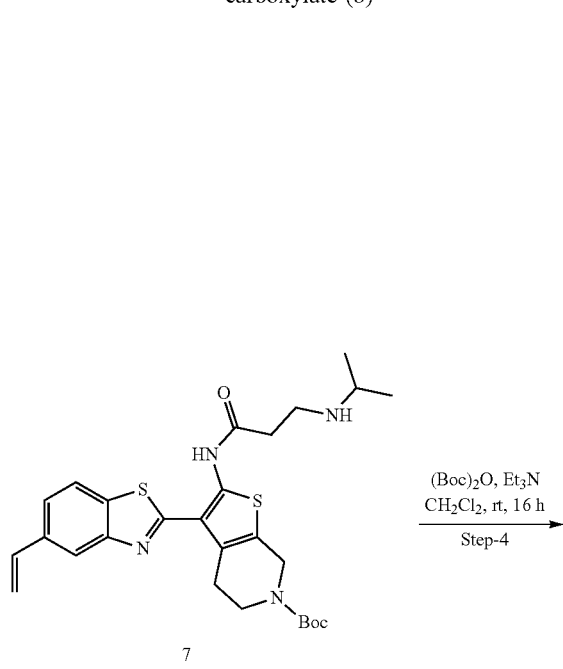

To a solution of tert-butyl 2-(3-(isopropylamino)propanamido)-3-(5-vinylbenzo[d]thiazol-2-yl)-4,7-dihydrothieno[2,3-c]pyridine-6(5H)-carboxylate 7 (4.5 g, 8.55 mmol) in DCM (50 mL) was added triethyl amine (2.3 mL, 17.1 mmol), Boc anhydride (2 g, 9.41 mmol) and stirred at room temperature for 16 h. After the completion of reaction (monitored by LCMS), the reaction was diluted with water and extracted with DCM (thrice). The combined organic layers were dried, filtered and concentrated to afford the title compound 8 (4.8 g, 90% yield).

Step 5: tert-Butyl 2-(3-((tert-butoxycarbonyl)(isopropyl)amino)propanamido)-3-(5-formylbenzo[d]thiazol-2-yl)-4,7-dihydrothieno[2,3-c]pyridine-6(5H)-carboxylate (9)

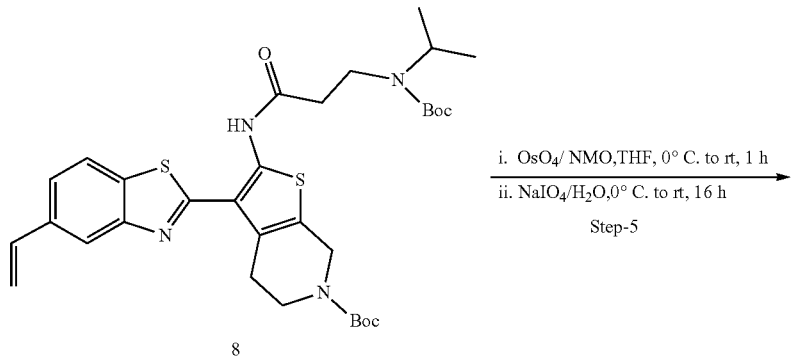

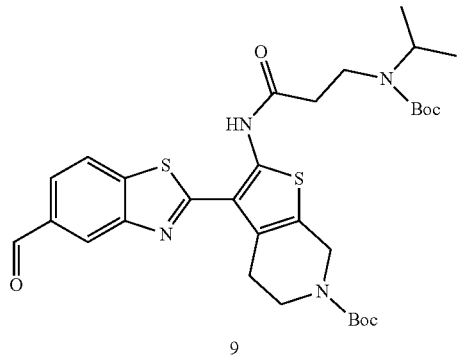

To a solution of tert-butyl 2-(3-((tert-butoxycarbonyl)(isopropyl)amino)propanamido)-3-(5-vinylbenzo[d]thiazol-2-yl)-4,7-dihydrothieno[2,3-c]pyridine-6(5H)-carboxylate 8 (4.2 g, 6.70 mmol) in THF (40 mL) at 0° C. was added NMO (2.3 g, 20.12 mmol) stirred for 15 min and followed by the addition of OsO4 (20 mL, 1M solution in toluene). The reaction mixture was stirred at room temperature for 1 h. To the resulting solution was added water (20 mL) and NaIO$_4$ (4.2 g, 20.12 mmol) and stirred at room temperature for 16 h. After the completion of reaction (monitored by TLC and LCMS), the reaction was quenched with saturated NaHCO$_3$ solution and extracted with ethyl acetate (thrice). The combined organic layers were dried, filtered and concentrated to get a crude residue. This crude compound was purified by silica gel column chromatography eluting with 0-2% methanol in DCM to afford the title compound 9 (3.7 g, yield 88%).

Step 6: 2-(6-(tert-Butoxycarbonyl)-2-(3-((tert-butoxycarbonyl)(isopropyl)amino)propanamido)-4,5,6,7-tetrahydrothieno[2,3-c]pyridin-3-yl)benzo[d]thiazole-5-carboxylic acid (10)

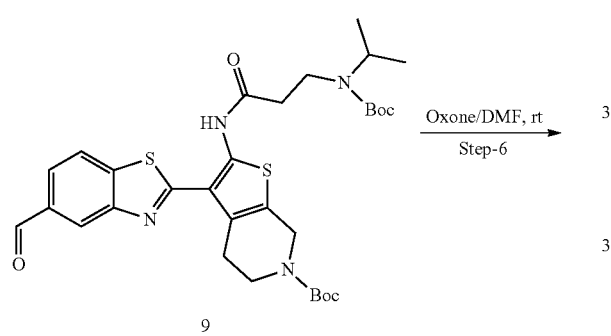

9

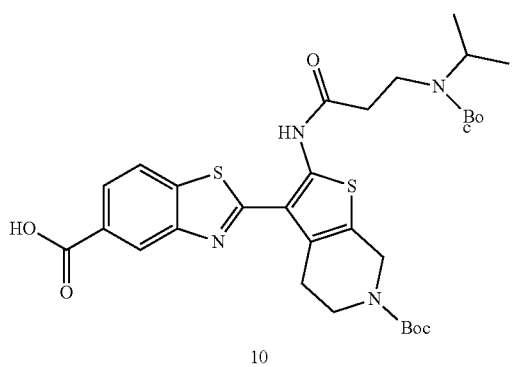

10

To a solution of tert-butyl 2-(3-((tert-butoxycarbonyl)(isopropyl)amino)propanamido)-3-(5-formylbenzo[d]thiazol-2-yl)-4,7-dihydrothieno[2,3-c]pyridine-6(5H)-carboxylate 9 (2.7 g, 4.29 mmol) in DMF (20 mL) was added oxone (5.28 g, 8.59 mmol) and stirred at room temperature for 16 h. After the completion of reaction (monitored by LCMS), the reaction was diluted with water and extracted with DCM (thrice). The combined organic layers were dried, filtered and concentrated to afford the title compound 10 (1.3 g, 48% yield).

Step 7: 2-(2-(3-(Isopropylamino)propanamido)-4,5,6,7-tetrahydrothieno[2,3-c]pyridin-3-yl)benzo[d]thiazole-5-carboxylic acid

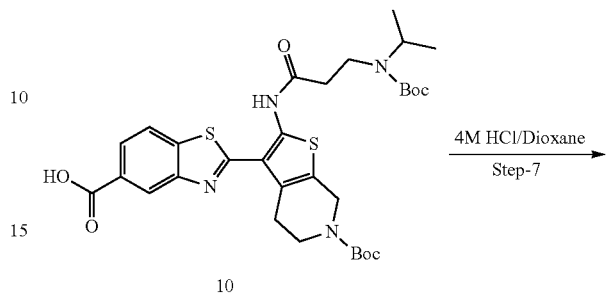

10

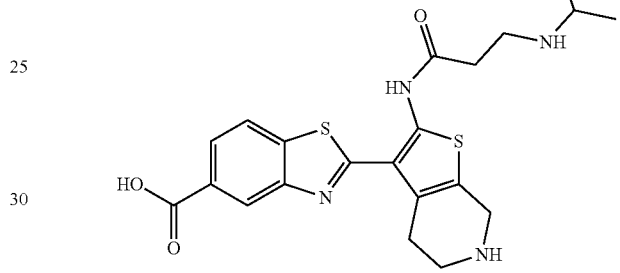

To 2-(6-(tert-butoxycarbonyl)-2-(3-((tert-butoxycarbonyl)(isopropyl)amino)propanamido)-4,5,6,7-tetrahydrothieno[2,3-c]pyridin-3-yl)benzo[d]thiazole-5-carboxylic acid 10 (150 mg, 0.232 mmol) in dioxane (1 mL) at 0° C. was added 4M HCl in dioxane (4 mL). After the addition, the resulting mixture was stirred at room temperature for 2 h. Reaction was monitored by TLC. After completion, the reaction mixture was evaporated in vacuum resulting in a crude residue which was purified by preparative HPLC to afford the HCl salt of the title compound as yellow solid (115 mg, yield 96%).

Example 92. Synthesis of 3-(Isopropylamino)-N-(3-(5-vinylbenzo[d]thiazol-2-yl)-4,5,6,7-tetrahydrothieno[2,3-c]pyridin-2-yl)propanamide (Compound 321)

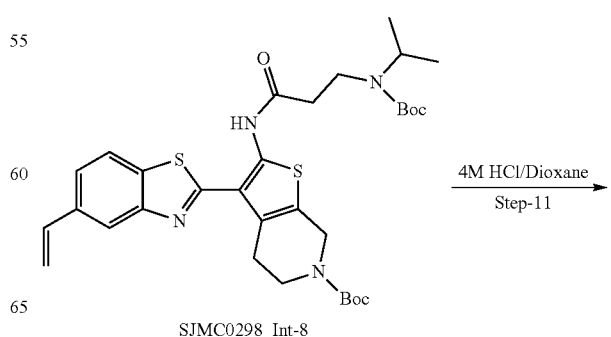

SJMC0298_Int-8

-continued

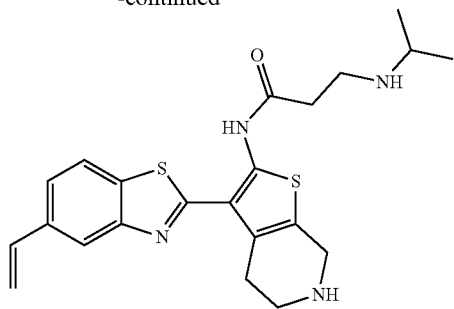

To tert-butyl 2-(3-((tert-butoxycarbonyl)(isopropyl)amino)propanamido)-3-(5-vinylbenzo[d]thiazol-2-yl)-4,7-dihydrothieno[2,3-c]pyridine-6(5H)-carboxylate SJMC0298_Int-8 (100 mg, 0.159 mmol) in dioxane (1 mL) at 0° C. was added 4M HCl in dioxane (2 mL). After the addition, the resulting mixture was stirred at room temperature for 2 h. Reaction was monitored by TLC. After completion, the reaction mixture was evaporated in vacuum resulting in a crude residue which was purified by preparative HPLC to afford the HCl salt of the title compound as yellow solid (30 mg, yield 38%).

Example 93. Synthesis of 2-(2-(3-(Isopropylamino)propanamido)-4,5,6,7-tetrahydrothieno[2,3-c]pyridin-3-yl)-N,N-dimethylbenzo[d]thiazole-5-carboxamide (Compound 322)

Step 1: tert-Butyl 2-(3-((tert-butoxycarbonyl)(isopropyl)amino)propanamido)-3-(5-(dimethylcarbamoyl)benzo[d]thiazol-2-yl)-4,7-dihydrothieno[2,3-c]pyridine-6(5H)-carboxylate

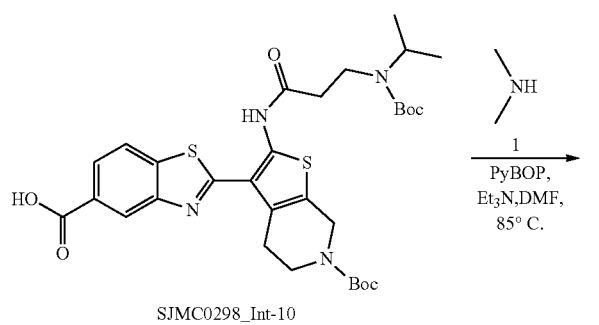

To a solution of 2-(6-(tert-butoxycarbonyl)-2-(3-((tert-butoxycarbonyl)(isopropyl)amino)propanamido)-4,5,6,7-tetrahydrothieno[2,3-c]pyridin-3-yl)benzo[d]thiazole-5-carboxylic acid SJMC0298 Int-10 (250 mg, 0.388 mmol) in DMF (1 mL) was added triethyl amine (0.1 mL, 0.776 mmol), PyBOP (302 mg, 0.582 mmol) and dimethylamine 1 (35 mg, 0.776 mmol) at room temperature. After the addition, the resulting mixture was heated to 85° C. for 12 h. After completion, the reaction mixture was diluted with water and extracted with ethyl acetate (thrice). The combined organic layer was dried over Na₂SO₄, filtered and concentrated in vacuo. The crude compound was purified by column chromatography on silica gel eluting with 0-10% methanol in DCM to afford the title compound 2 as yellow solid (150 mg, 57% yield).

Step 2: 2-(2-(3-(Isopropylamino)propanamido)-4,5,6,7-tetrahydrothieno[2,3-c]pyridin-3-yl)-N,N-dimethylbenzo[d]thiazole-5-carboxamide

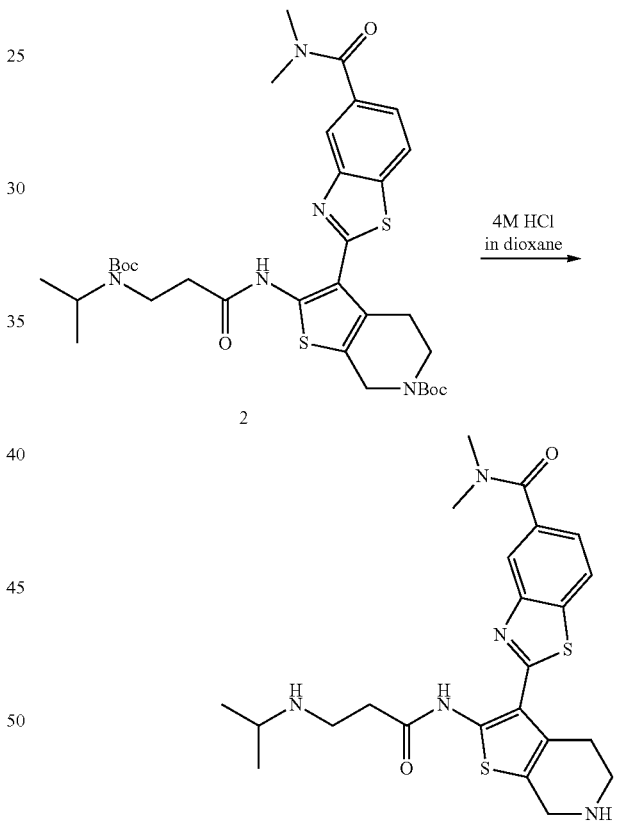

To a solution of tert-butyl 2-(3-((tert-butoxycarbonyl)(isopropyl)amino)propanamido)-3-(5-(dimethylcarbamoyl)benzo[d]thiazol-2-yl)-4,7-dihydrothieno[2,3-c]pyridine-6(5H)-carboxylate 2 (100 mg, 0.175 mmol) in dioxane (1 mL) at 0° C. was added 4M HCl in dioxane (5 mL). After addition, the resulting mixture was stirred at room temperature for 2 h. After completion, the reaction mixture was evaporated to dryness and the resulting in a residue which was triturated in diethyl ether and pentane. The crude compound was purified by preparative HPLC to afford the HCl salt of the title compound as yellow solid (60 mg HCl salt, 63% yield).

Example 94. Synthesis of 2-(2-(3-(Isopropylamino) propanamido)-4,5,6,7-tetrahydrothieno[2,3-c]pyridin-3-yl)-N-(2-methoxyethyl)benzo[d]thiazole-5-carboxamide (Compound 323)

Step 1: tert-Butyl 2-(3-((tert-butoxycarbonyl)(isopropyl)amino)propanamido)-3-(5-((2-methoxyethyl)carbamoyl)benzo[d]thiazol-2-yl)-4,7-dihydrothieno[2,3-c]pyridine-6(5H)-carboxylate (2)

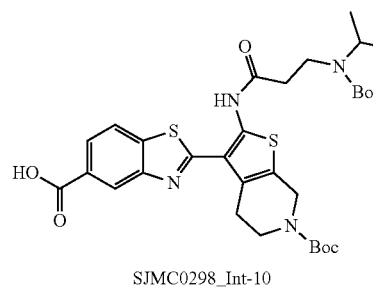

SJMC0298_Int-10

Step 2: 2-(2-(3-(Isopropylamino)propanamido)-4,5,6,7-tetrahydrothieno[2,3-c]pyridin-3-yl)-N-(2-methoxyethyl)benzo[d]thiazole-5-carboxamide

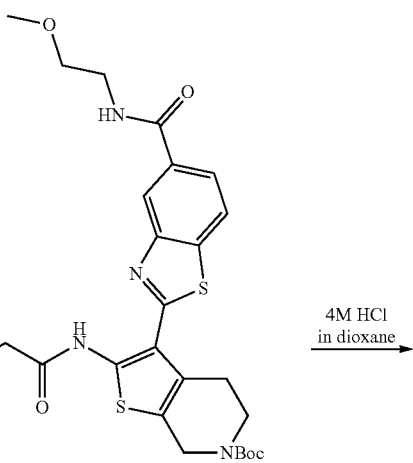

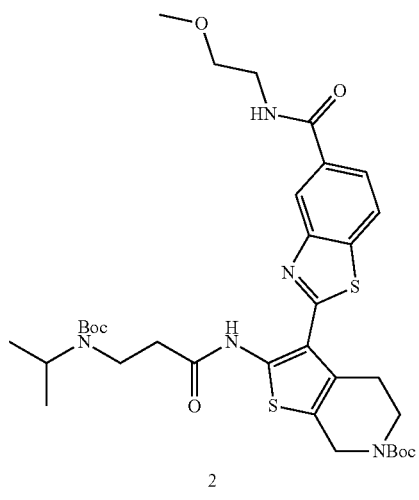

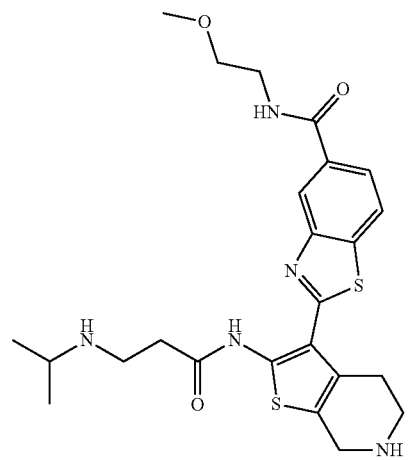

To a solution of 2-(6-(tert-butoxycarbonyl)-2-(3-((tert-butoxycarbonyl)(isopropyl)amino)propanamido)-4,5,6,7-tetrahydrothieno[2,3-c]pyridin-3-yl)benzo[d]thiazole-5-carboxylic acid SJMC0298 Int-10 (250 mg, 0.388 mmol) in DMF (1 mL) was added triethyl amine (0.11 mL, 0.776 mmol), PyBOP (302 mg, 0.582 mmol) and 2-methoxyethan-1-amine 1 (58 mg, 0.776 mmol) at room temperature. After the addition, the resulting mixture was heated to 60° C. for 12 h. After completion, the reaction mixture was diluted with water and extracted with ethyl acetate (thrice). The combined organic layer was dried over $Na_2SO_4$, filtered and concentrated in vacuo. The crude compound was purified by column chromatography on silica gel eluting with 0-10% methanol in DCM to afford the title compound 2 as yellow solid (180 mg, 66% yield).

To a solution of tert-butyl 2-(3-((tert-butoxycarbonyl)(isopropyl)amino)propanamido)-3-(5-((2-methoxyethyl)carbamoyl)benzo[d]thiazol-2-yl)-4,7-dihydrothieno[2,3-c]pyridine-6(5H)-carboxylate 2 (100 mg, 0.142 mmol) in dioxane (1 mL) at 0° C. was added 4M HCl in dioxane (2 mL). After addition, the resulting mixture was stirred at room temperature for 2 h. After completion, the reaction mixture was evaporated to dryness and the resulting in a residue which was triturated in diethyl ether and pentane. The crude compound was purified by preparative HPLC to afford the HCl salt of the title compound as yellow solid (75 mg HCl salt, 92% yield).

281

Example 95. Synthesis of 3-(Isopropylamino)-N-(3-(5-(4-methylpiperazine-1-carbonyl)benzo[d]thiazol-2-yl)-4,5,6,7-tetrahydrothieno[2,3-c]pyridin-2-yl)propanamide (Compound 324)

Step 1: tert-Butyl 2-(3-((tert-butoxycarbonyl)(isopropyl)amino)propanamido)-3-(5-(4-methylpiperazine-1-carbonyl)benzo[d]thiazol-2-yl)-4,7-dihydrothieno[2,3-c]pyridine-6(5H)-carboxylate (2)

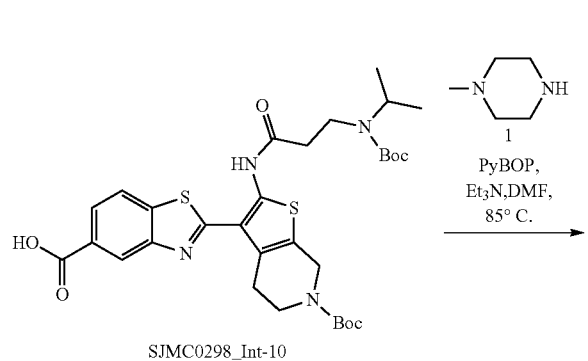

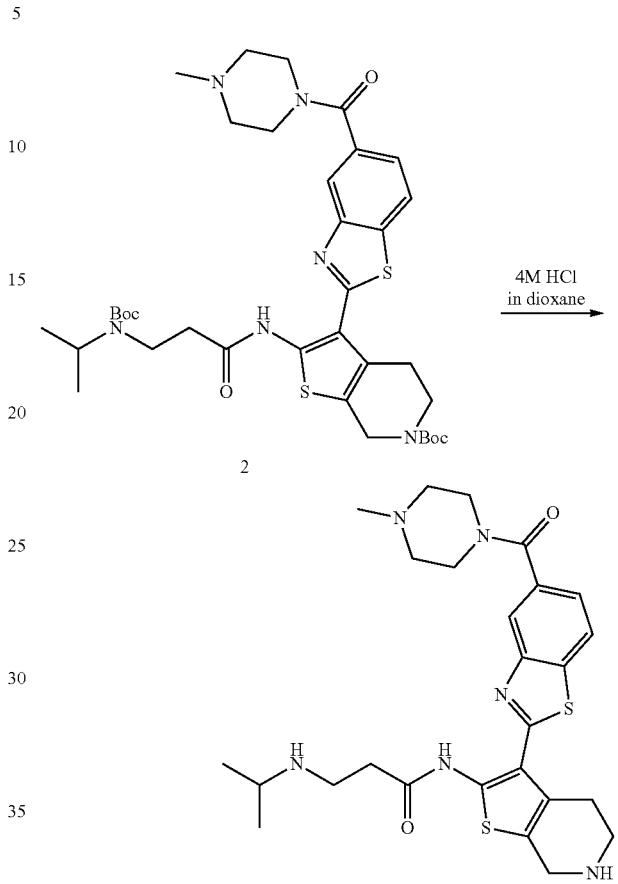

To a solution of 2-(6-(tert-butoxycarbonyl)-2-(3-((tert-butoxycarbonyl)(isopropyl)amino)propanamido)-4,5,6,7-tetrahydrothieno[2,3-c]pyridin-3-yl)benzo[d]thiazole-5-carboxylic acid SJMC0298 Int-10 (200 mg, 0.310 mmol) in DMF (1 mL) was added triethyl amine (0.08 mL, 0.621 mmol), PyBOP (242 mg, 0.465 mmol) and 1-methylpiperazine 1 (62 mg, 0.621 mmol) at room temperature. After the addition, the resulting mixture was heated to 85° C. for 12 h. After completion, the reaction mixture was diluted with water and extracted with ethyl acetate (thrice). The combined organic layer was dried over Na₂SO₄, filtered and concentrated in vacuo. The crude compound was purified by column chromatography on silica gel eluting with 0-10% methanol in DCM to afford the title compound 2 as yellow solid (150 mg, 66% yield).

282

Step 2: 3-(Isopropylamino)-N-(3-(5-(4-methylpiperazine-1-carbonyl)benzo[d]thiazol-2-yl)-4,5,6,7-tetrahydrothieno[2,3-c]pyridin-2-yl)propanamide

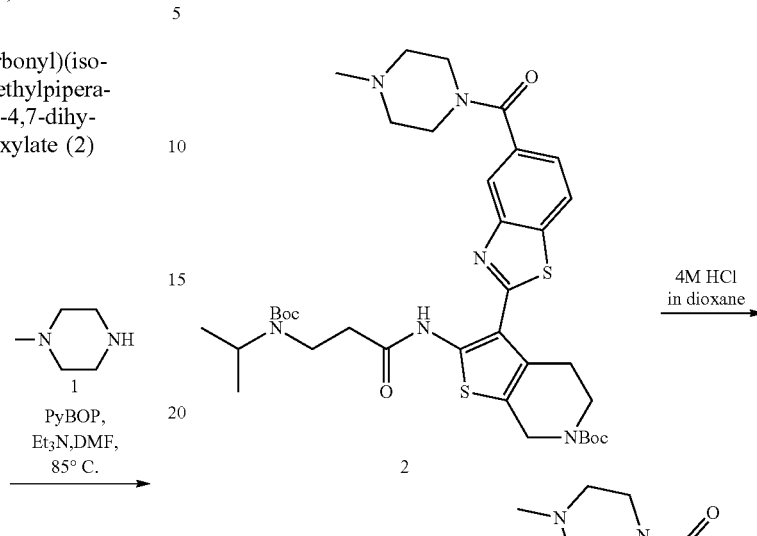

To a solution of tert-butyl 2-(3-((tert-butoxycarbonyl)(isopropyl)amino)propanamido)-3-(5-(4-methylpiperazine-1-carbonyl)benzo[d]thiazol-2-yl)-4,7-dihydrothieno[2,3-c]pyridine-6(5H)-carboxylate 2 (150 mg, 0.206 mmol) in dioxane (1 mL) at 0° C. was added 4M HCl in dioxane (5 mL). After addition, the resulting mixture was stirred at room temperature for 2 h. After completion, the reaction mixture was evaporated to dryness and the resulting in a residue which was triturated in diethyl ether and pentane. The crude compound was purified by preparative HPLC to afford the HCl salt of the title compound as yellow solid (100 mg HCl salt, 76% yield).

Example 96. Synthesis of N-(3-([1,3]Dioxolo[4',5':4,5]benzo[1,2-d]thiazol-6-yl)-4,5,6,7-tetrahydrothieno[2,3-c]pyridin-2-yl)acetamide (Compound 237)

Step 1: 2-([1,3]Dioxolo[4',5':4,5]benzo[1,2-d]thiazol-6-yl)acetonitrile (2)

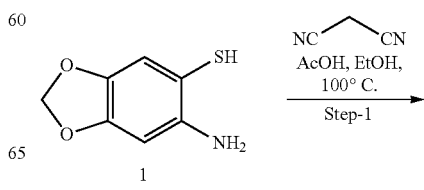

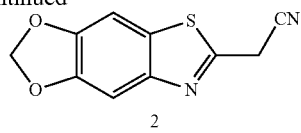

To a solution of 6-aminobenzo[d][1,3]dioxole-5-thiol 1 (100 mg, 0.592 mmol) in EtOH (5 mL) was added malononitrile (39 mg, 0.592 mmol) and AcOH (2 mL). The resulting reaction mixture was stirred at 100° C. for 12 h. Progress of the reaction was monitored by TLC. After completion, the reaction mixture was concentrated under reduced pressure to dryness. The crude compound was purified by column chromatography eluting with 0-20% ethyl acetate in n-hexane to afford the title compound 2 as brown solid (50 mg yield 39%)

Step 2: tert-Butyl 3-([1,3]dioxolo[4',5':4,5]benzo[1,2-d]thiazol-6-yl)-2-amino-4,7-dihydrothieno[2,3-c]pyridine-6(5H)-carboxylate (3)

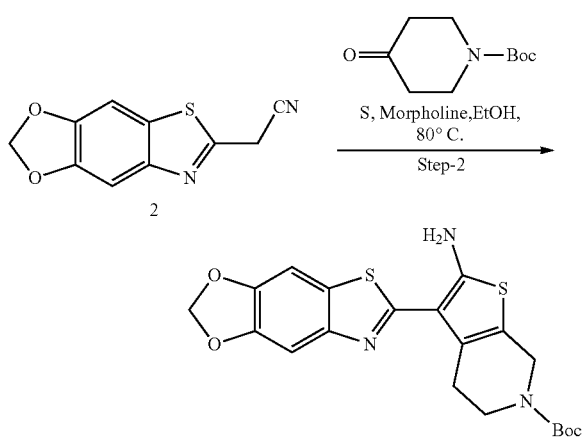

To a solution of 2-([1,3]dioxolo[4',5':4,5]benzo[1,2-d]thiazol-6-yl)acetonitrile 2 (450 g, 2.064 mmol) in ethanol (90 mL) was added tert-butyl 4-oxopiperidine-1-carboxylate (411 mg, 2.064 mmol), elemental sulphur (66 mg, 2.064 mmol) and morpholine (179 mg, 2.064 mmol) at room temperature. After the addition, the resulting mixture was heated to reflux at 80° C. for 3 h. Progress of the reaction was monitored by TLC. After completion, the reaction mixture was evaporated in vacuum up to dryness to afford the title compound 3 as yellow solid (600 mg, crude).

Step 3: tert-Butyl 3-([1,3]dioxolo[4',5':4,5]benzo[1,2-d]thiazol-6-yl)-2-acetamido-4,7-dihydrothieno[2,3-c]pyridine-6(5H)-carboxylate (4)

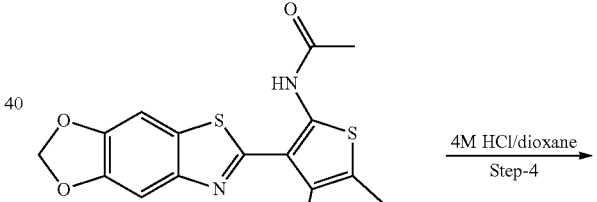

To a solution of tert-butyl 3-([1,3]dioxolo[4',5':4,5]benzo[1,2-d]thiazol-6-yl)-2-amino-4,7-dihydrothieno[2,3-c]pyridine-6(5H)-carboxylate 3 (100 mg, 0.232 mmol) in CH$_2$Cl$_2$ (5 mL) at 0° C. was added DIPEA (0.1 mL, 0.574 mmol) and acetyl chloride (18.2 mL, 0.255 mmol). The reaction mixture was stirred at room temperature for 3 h. After completion (monitored by TLC), the reaction mixture was quenched with saturated sodium bicarbonate solution and extracted with CH$_2$Cl$_2$ (thrice). The combined organic layer was washed with brine and dried with anhydrous Na$_2$SO$_4$, filtered and concentrated. The crude compound was purified by column chromatography eluting with 0-50% ethyl acetate in n-hexane to afford the title compound 4 as light yellow solid (70 mg, 63% yield).

Step 4: N-(3-([1,3]dioxolo[4',5':4,5]benzo[1,2-d]thiazol-6-yl)-4,5,6,7-tetrahydrothieno[2,3-c]pyridin-2-yl)acetamide

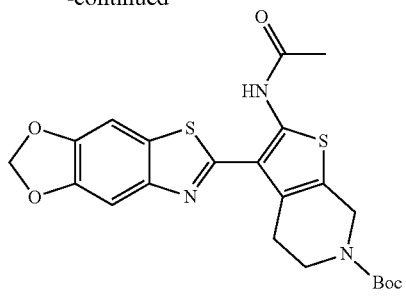

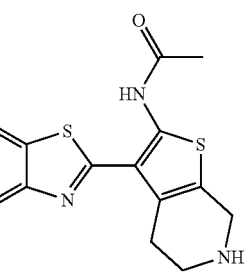

To a solution of tert-butyl 3-([1,3]dioxolo[4',5':4,5]benzo[1,2-d]thiazol-6-yl)-2-acetamido-4,7-dihydrothieno[2,3-c]pyridine-6(5H)-carboxylate 4 (70 mg, 0.147 mmol) in dioxane (5 mL) at 0° C. was added 4M HCl in dioxane (2 mL). After the addition, the resulting mixture was stirred at room temperature for 3 h. After completion, the reaction mixture was evaporated in vacuum resulting in a crude residue which was purified by trituration with methanol. The solid obtained was filtered and washed with diethyl ether and n-pentane to afford the title compound as yellow solid (20 mg, yield 36%).

Example 97. Synthesis of N-(3-([1,3]Dioxolo[4',5': 4,5]benzo[1,2-d]thiazol-6-yl)-6-isopropyl-4,5,6,7-tetrahydrothieno[2,3-c]pyridin-2-yl)acetamide (Compound 236)

Step 1: 2-([1,3]Dioxolo[4',5':4,5]benzo[1,2-d]thiazol-6-yl)acetonitrile (2)

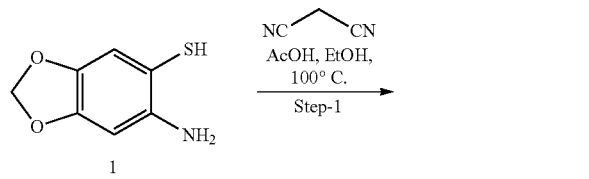

To a solution of 6-aminobenzo[d][1,3]dioxole-5-thiol 1 (400 mg, 2.368 mmol) in EtOH (20 mL) was added malononitrile (156 mg, 2.368 mmol) and AcOH (8 mL). The resulting reaction mixture was stirred at 100° C. for 12 h. Progress of the reaction was monitored by TLC. After completion, the reaction mixture was concentrated under reduced pressure to dryness. The crude compound was purified by column chromatography eluting with 0-30% ethyl acetate in n-hexane to afford the title compound 2 as brown solid (300 mg yield 58%)

Step 2: 3-([1,3]dioxolo[4',5':4,5]benzo[1,2-d]thiazol-6-yl)-6-isopropyl-4,5,6,7-tetrahydrothieno[2,3-c]pyridin-2-amine (3)

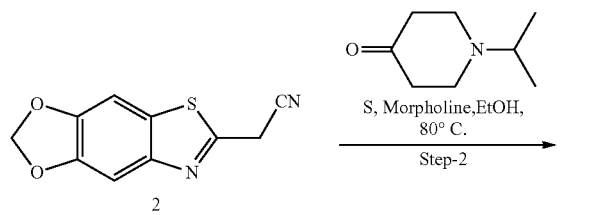

To a solution of 2-([1,3]dioxolo[4',5':4,5]benzo[1,2-d]thiazol-6-yl)acetonitrile 2 (300 mg, 1.376 mmol) in ethanol (20 mL) was added 1-isopropylpiperidin-4-one (194 mg, 1.376 mmol), elemental sulphur (44 mg, 1.376 mmol) and morpholine (119 mg, 1.376 mmol) at room temperature. After the addition, the resulting mixture was heated to reflux at 80° C. for 3 h. Progress of the reaction was monitored by TLC. After completion, the reaction mixture was evaporated in vacuum up to dryness to afford the title compound 3 as off white solid (250 mg, yield 48%).

Step 3: N-(3-([1,3]dioxolo[4',5':4,5]benzo[1,2-d]thiazol-6-yl)-6-isopropyl-4,5,6,7-tetrahydrothieno[2,3-c]pyridin-2-yl)acetamide

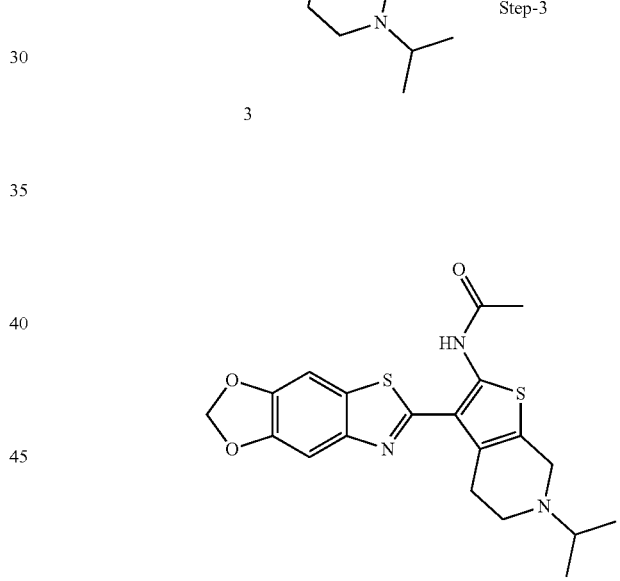

To a solution of 3-([1,3]dioxolo[4',5':4,5]benzo[1,2-d]thiazol-6-yl)-6-isopropyl-4,5,6,7-tetrahydrothieno[2,3-c]pyridin-2-amine 3 (100 mg, 0.263 mmol) in $CH_2Cl_2$ (10 mL) at 0° C. was added DIPEA (0.1 mL, 0.402 mmol) and acetyl chloride (0.02 mL, 0.294 mmol). The reaction mixture was stirred at room temperature for 3 h. After completion (monitored by TLC), the reaction mixture was quenched with saturated sodium bicarbonate solution and extracted with $CH_2Cl_2$ (thrice). The combined organic layer was washed with brine and dried with anhydrous $Na_2SO_4$, filtered and concentrated. The crude compound was purified by column chromatography eluting with 0-50% ethyl acetate in n-hexane to afford the title compound as yellow solid (10 mg, yield 9%).

Example 98. Synthesis of 2-(2-(3-(Isopropylamino) propanamido)-4,5,6,7-tetrahydrothieno[2,3-c]pyridin-3-yl)-N-phenylbenzo[d]thiazole-5-carboxamide (Compound 505)

Step 1: tert-Butyl 2-(3-((tert-butoxycarbonyl)(isopropyl)amino)propanamido)-3-(5-(phenylcarbamoyl)benzo[d]thiazol-2-yl)-4,7-dihydrothieno[2,3-c]pyridine-6(5H)-carboxylate

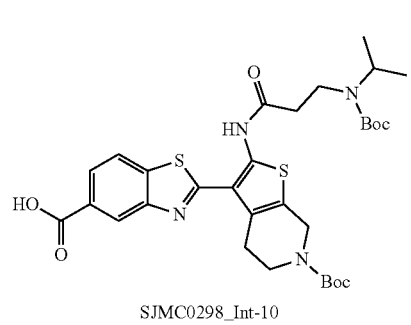

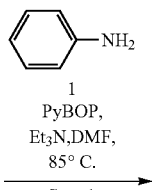

Step 2: 2-(2-(3-(Isopropylamino)propanamido)-4,5,6,7-tetrahydrothieno[2,3-c]pyridin-3-yl)-N-phenylbenzo[d]thiazole-5-carboxamide

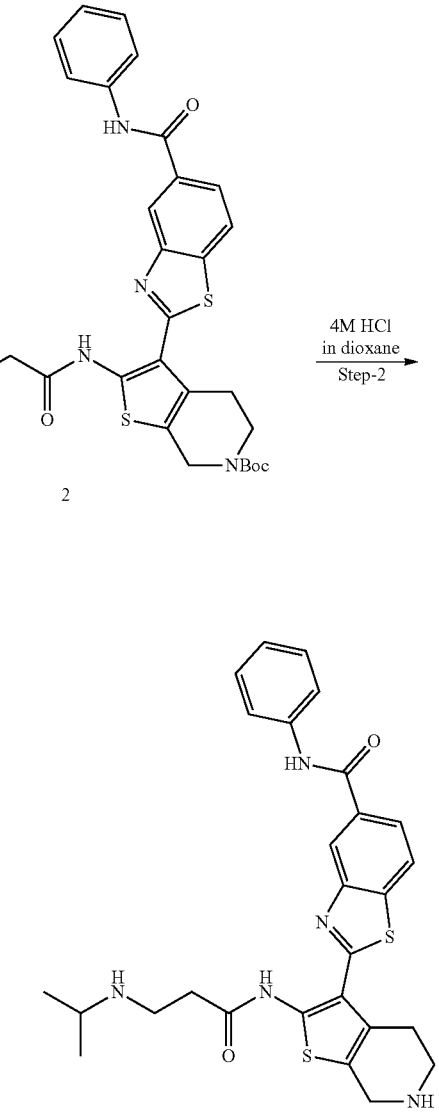

To a solution of 2-(6-(tert-butoxycarbonyl)-2-(3-((tert-butoxycarbonyl)(isopropyl)amino)propanamido)-4,5,6,7-tetrahydrothieno[2,3-c]pyridin-3-yl)benzo[d]thiazole-5-carboxylic acid SJMC0298 Int-10 (100 mg, 0.155 mmol) in DMF (1 mL) was added triethyl amine (0.04 mL, 0.310 mmol), PyBOP (121 mg, 0.232 mmol) and aniline 1 (28 mg, 0.310 mmol) at room temperature. After the addition, the resulting mixture was heated to 85° C. for 12 h. After completion, the reaction mixture was diluted with water and extracted with ethyl acetate (thrice). The combined organic layer was dried over $Na_2SO_4$, filtered and concentrated in vacuo. The crude compound was purified by column chromatography on silica gel eluting with 0-5% methanol in $CH_2Cl_2$ to afford the title compound 2 as yellow solid (80 mg, 72% yield).

To a solution of tert-butyl 2-(3-((tert-butoxycarbonyl)(isopropyl)amino)propanamido)-3-(5-(phenylcarbamoyl)benzo[d]thiazol-2-yl)-4,7-dihydrothieno[2,3-c]pyridine-6(5H)-carboxylate 2 (70 mg, 0.097 mmol) in dioxane (1 mL) at 0° C. was added 4M HCl in dioxane (4 mL). After addition, the resulting mixture was stirred at room temperature for 2 h. After completion, the reaction mixture was evaporated to dryness and the resulting in a residue which was triturated in diethyl ether and pentane. The crude compound was purified by preparative HPLC to afford the HCl salt of the title compound as yellow solid (50 mg HCl salt, 86% yield).

Example 99. Synthesis of N-(3-(Benzo[d]thiazol-2-yl)-5,7-dimethyl-4,5,6,7-tetrahydrothieno[2,3-c]pyridin-2-yl)-3-((2-methoxyethyl)amino)propanamide and Separation of Isomers (Compounds 506-509)

Step 1: tert-Butyl 2-acrylamido-3-(benzo[d]thiazol-2-yl)-5,7-dimethyl-4,7-dihydrothieno[2,3-c]pyridine-6(5H)-carboxylate (6

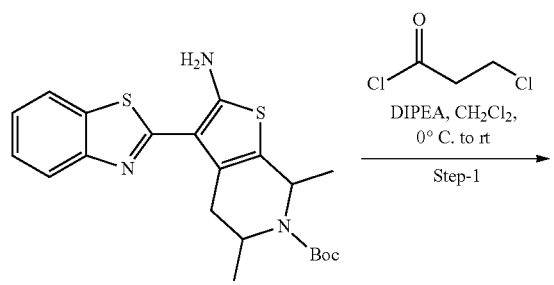

To a solution of tert-butyl 2-amino-3-(benzo[d]thiazol-2-yl)-5,7-dimethyl-4,7-dihydrothieno[2,3-c]pyridine-6(5H)-carboxylate SJMC0111 Int-5 (800 mg, 1.927 mmol) in CH$_2$Cl$_2$ (20 mL) was added DIPEA (1.03 mL, 5.783 mmol) at room temperature and stirred for 20 min. To the resulting solution at 0° C. was added 3-chloropropanoyl chloride (489 mg, 3.855 mmol) and stirred at room temperature for 15 h. Reaction was monitored by TLC. After the completion of reaction (by LCMS) the reaction mixture was diluted with water and extracted with CH$_2$Cl$_2$. The combined organic layer was dried with anhydrous Na$_2$SO$_4$, filtered and concentrated to afford the title compound 6 as yellow solid (900 mg, crude).

Step 2: tert-Butyl 3-(benzo[d]thiazol-2-yl)-2-(3-((2-methoxyethyl)amino)propanamido)-5,7-dimethyl-4,7-dihydrothieno[2,3-c]pyridine-6(5H)-carboxylate (7)

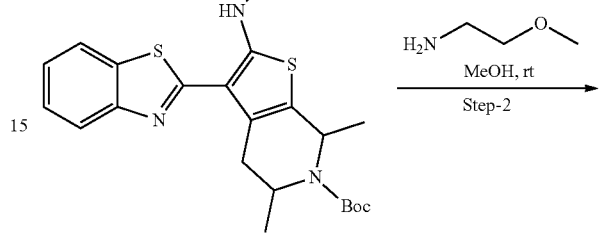

To a solution of tert-butyl 2-acrylamido-3-(benzo[d]thiazol-2-yl)-5,7-dimethyl-4,7-dihydrothieno[2,3-c]pyridine-6(5H)-carboxylate 6 (900 mg, 1.914 mmol) in MeOH:THF (1:1, 10 mL) was added 2-methoxyethan-1-amine (0.25 mL, 2.87 mmol). The resulting reaction mixture was stirred at room temperature for 15 h. Progress of the reaction was monitored by TLC. After completion, the reaction mixture was concentrated to dryness under reduced pressure. The crude compound was purified by column chromatography eluting with 0-2% methanol in CH$_2$Cl$_2$ to afford the title compound 7 as yellow solid (500 mg, yield 48%).

Step 3: N-(3-(Benzo[d]thiazol-2-yl)-5,7-dimethyl-4,5,6,7-tetrahydrothieno[2,3-c]pyridin-2-yl)-3-((2-methoxyethyl)amino)propanamid

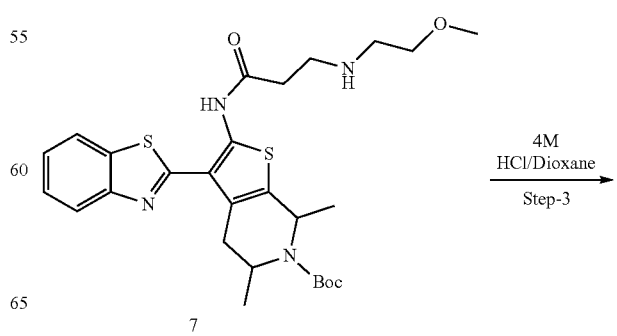

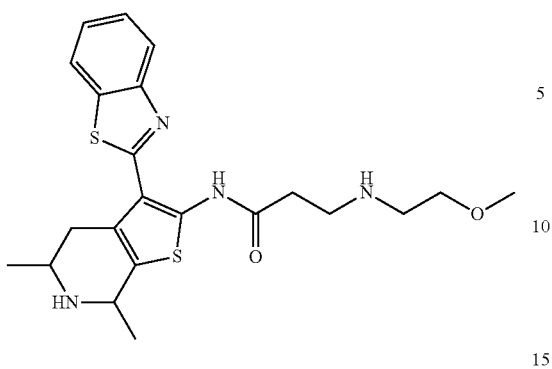

To tert-butyl 3-(benzo[d]thiazol-2-yl)-2-(3-((2-methoxyethyl)amino)propanamido)-5,7-dimethyl-4,7-dihydrothieno[2,3-c]pyridine-6(5H)-carboxylate 7 (500 mg, 0.919 mmol) in dioxane (5 mL) at 0° C. was added 4M HCl in dioxane (5 mL). After the addition, the resulting mixture was stirred at room temperature for 2 h. Reaction was monitored by TLC. After completion, the reaction mixture was evaporated in vacuum resulting in a crude residue which was triturated by diethyl ether and n-pentane to afford the title compound as brown semisolid (300 mg, yield 73%).

The chiral separation for the racemic title compound (Column: CHIRALPAK IC, 250 mm*4.6 mm*5 um; Mobile Phase: A: n-Hexane+0.1% TEA, B: ETOH: DCM (85:15)+0.1% TEA; Flow rate: 1.0 ml/min; Gradient isocratic: 45% B) afforded Compounds 506-509.

Example 100. Synthesis of 2-(2-(3-(Isopropylamino)propanamido)-4,5,6,7-tetrahydrothieno[2,3-c]pyridin-3-yl)-N-(pyridin-3-yl)benzo[d]thiazole-5-carboxamide (Compound 510)

Step 1: tert-Butyl 2-(3-((tert-butoxycarbonyl)(isopropyl)amino)propanamido)-3-(5-(pyridin-3-ylcarbamoyl)benzo[d]thiazol-2-yl)-4,7-dihydrothieno[2,3-c]pyridine-6(5H)-carboxylate (2)

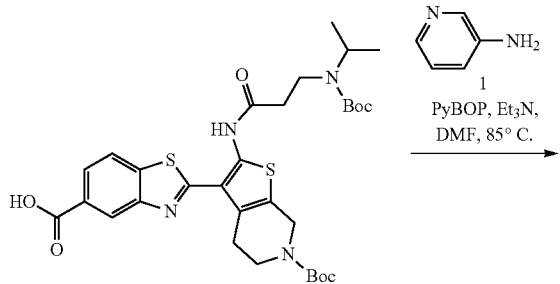

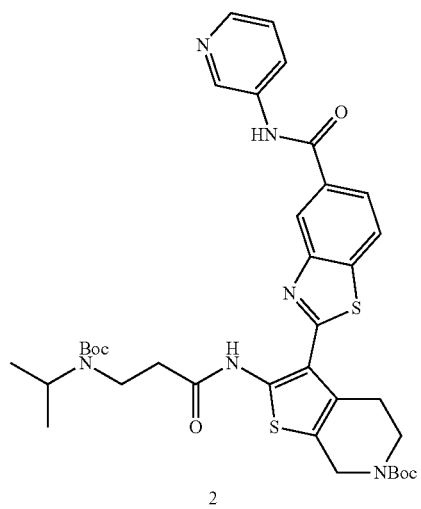

To a solution of 2-(6-(tert-butoxycarbonyl)-2-(3-((tert-butoxycarbonyl)(isopropyl)amino)propanamido)-4,5,6,7-tetrahydrothieno[2,3-c]pyridin-3-yl)benzo[d]thiazole-5-carboxylic acid SJMC0298 Int-10 (200 mg, 0.310 mmol) in DMF (2 mL) was added triethyl amine (0.12 mL, 0.931 mmol), PyBOP (242 mg, 0.465 mmol) and pyridin-3-amine 1 (43 mg, 0.465 mmol) at room temperature. After the addition, the resulting mixture was heated to 85° C. for 12 h. After completion, the reaction mixture was diluted with water and extracted with ethyl acetate (thrice). The combined organic layer was dried over Na₂SO₄, filtered and concentrated in vacuo. The crude compound was purified by column chromatography on silica gel eluting with 0-5% methanol in CH₂Cl₂ to afford the title compound 2 as yellow solid (40 mg, 18% yield).

Step 2: 2-(2-(3-(Isopropylamino)propanamido)-4,5,6,7-tetrahydrothieno[2,3-c]pyridin-3-yl)-N-(pyridin-3-yl)benzo[d]thiazole-5-carboxamide

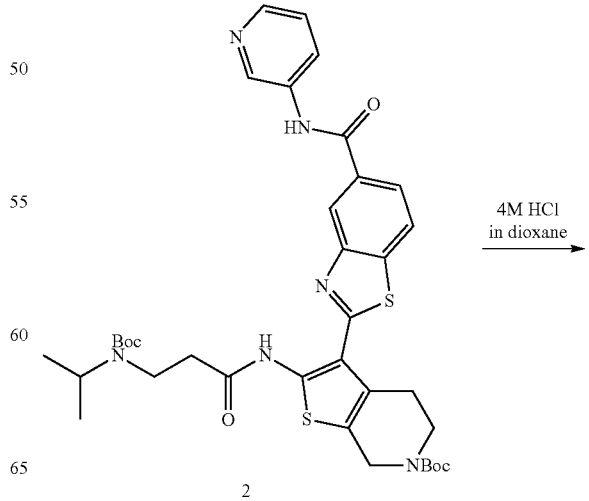

293

-continued

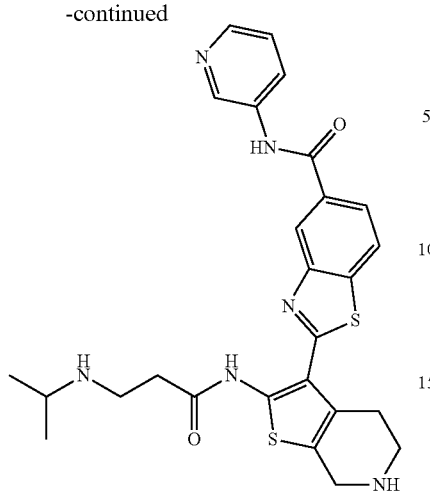

To a solution of tert-butyl 2-(3-((tert-butoxycarbonyl) (isopropyl)amino)propanamido)-3-(5-(pyridin-3-ylcarbamoyl)benzo[d]thiazol-2-yl)-4,7-dihydrothieno[2,3-c]pyridine-6(5H)-carboxylate 2 (30 mg, 0.041 mmol) in dioxane (1 mL) at 0° C. was added 4M HCl in dioxane (1 mL). After addition, the resulting mixture was stirred at room temperature for 2 h. After completion, the reaction mixture was evaporated to dryness and the resulting in a residue which was triturated in diethyl ether and pentane. The crude compound was purified by preparative HPLC to afford the HCl salt of the title compound as yellow solid (15 mg HCl salt, 62% yield).

Example 101. Synthesis of N-(5,7-Dimethyl-3-(6-(pyridin-3-yl)benzo[d]thiazol-2-yl)-4,5,6,7-tetrahydrothieno[2,3-c]pyridin-2-yl)-3-((2-methoxyethyl) amino)propanamide and Separation of Isomers (Compounds 517 and 518)

Step 1: 2-Amino-5-bromobenzenethiol (2)

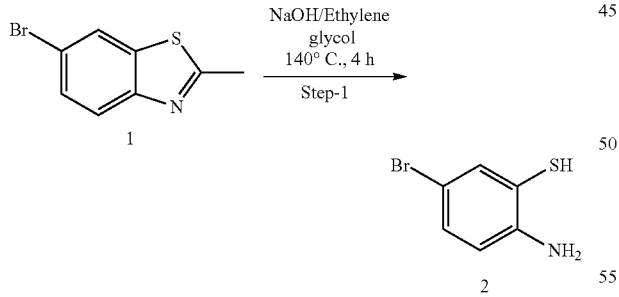

To a solution of 6-bromo-2-methylbenzo[d]thiazole 1 (2 g, 8.771 mmol) in ethylene glycol (20 mL) was added 8 N NaOH (10 mL). The resulting reaction mixture was stirred at 140° C. for 4 h. Progress of the reaction was monitored by TLC. After completion, the reaction mixture was cooled to room temperature; acidified with 1N HCl up to pH=6 and extracted with ethyl acetate. The combined organic layer was dried over anhydrous $Na_2SO_4$; filtered and concentrated under reduced pressure to afford the title compound 2 as brown oil (1.8 g, crude).

294

Step 2: 2-(6-Bromobenzo[d]thiazol-2-yl)acetonitrile (3)

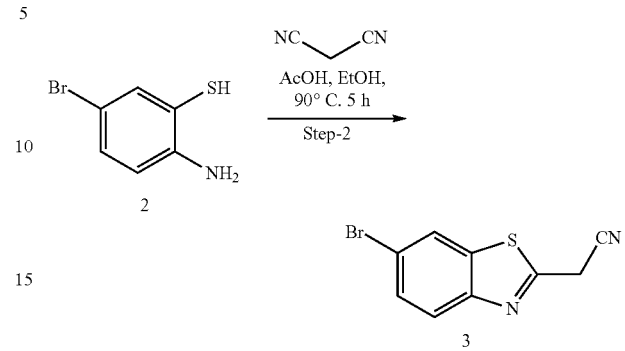

To a solution of 2-amino-5-bromobenzenethiol 2 (1.8 g, 8.823 mmol) in EtOH (20 mL) was added malononitrile (700 mg, 10.58 mmol) and AcOH (20 mL). The resulting reaction mixture was stirred at 90° C. for 5 h. Progress of the reaction was monitored by TLC. After completion, the reaction mixture was concentrated under reduced pressure to dryness. The residue was azeotroped with toluene and dried to afford the title compound 3 as brown solid (900 mg yield 40%)

Step 3: tert-Butyl 2-amino-3-(6-bromobenzo[d]thiazol-2-yl)-5,7-dimethyl-4,7-dihydrothieno[2,3-c] pyridine-6(5H)-carboxylate (4)

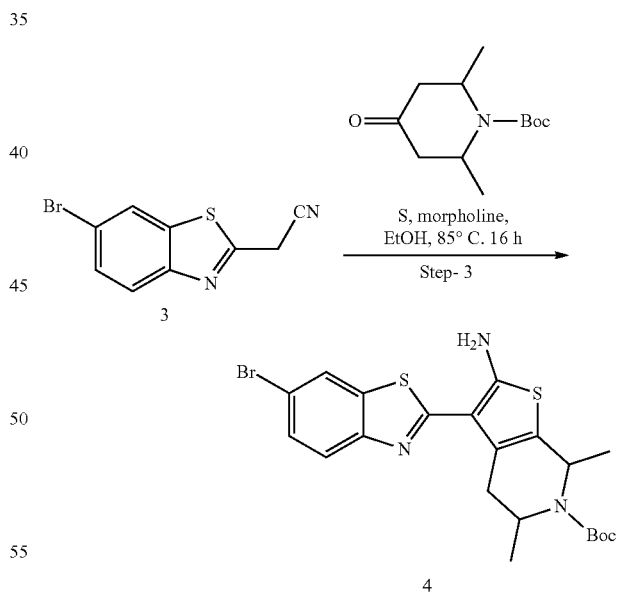

To a solution of 2-(6-bromobenzo[d]thiazol-2-yl)acetonitrile 3 (900 mg, 3.571 mmol) in ethanol (10 mL) was added tert-butyl 2,6-dimethyl-4-oxopiperidine-1-carboxylate (977 mg, 4.285 mmol), elemental sulphur (140 mg, 4.285 mmol) and morpholine (370 mg, 4.285 mmol) at room temperature. After the addition, the resulting mixture was heated to reflux at 85° C. for 16 h. Progress of the reaction was monitored by TLC. After completion, the reaction mixture was evaporated in vacuum up to dryness. The crude compound was purified by column chromatography eluting with 0-10% ethyl acetate in n-hexane to afford the title compound 4 as off white solid (900 mg, yield 51%).

Step 4: tert-Butyl 2-acrylamido-3-(6-bromobenzo[d]thiazol-2-yl)-5,7-dimethyl-4,7-dihydrothieno[2,3-c]pyridine-6(5H)-carboxylate (5)

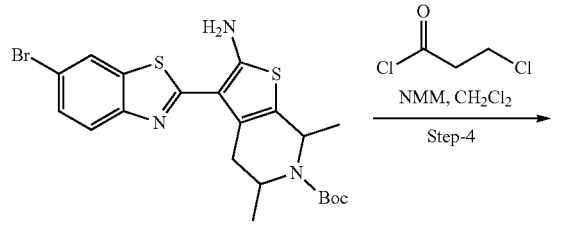

4

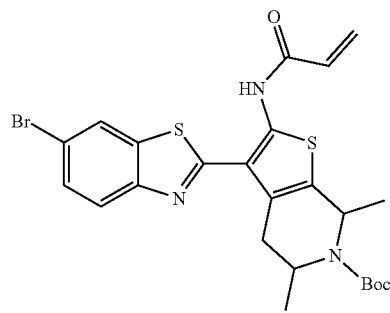

5

To a solution of tert-butyl 2-amino-3-(6-bromobenzo[d]thiazol-2-yl)-5,7-dimethyl-4,7-dihydrothieno[2,3-c]pyridine-6(5H)-carboxylate 4 (900 mg, 1.825 mmol) in CH$_2$Cl$_2$ (20 mL) at 0° C. was added N-methyl morpholine (0.62 mL, 4.563 mmol) and 3-chloropropanoyl chloride (340 mg, 2.738 mmol). The reaction mixture was stirred at room temperature for 2 h. After completion (monitored by TLC), the reaction mixture was concentrated in vacuo. The crude compound was purified by column chromatography eluting with 0-5% methanol in CH$_2$Cl$_2$ to afford the title compound 5 as yellow solid (1.4 g crude).

Step 5: tert-Butyl 3-(6-bromobenzo[d]thiazol-2-yl)-2-(3-((2-methoxyethyl)amino)propanamido)-5,7-dimethyl-4,7-dihydrothieno[2,3-c]pyridine-6(5H)-carboxylate (6)

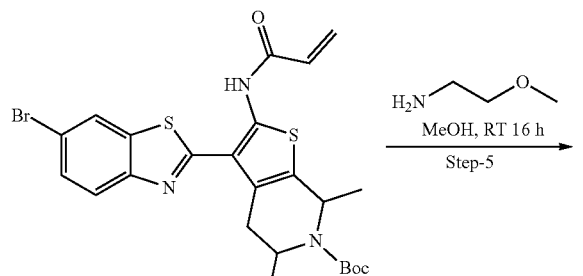

5

-continued

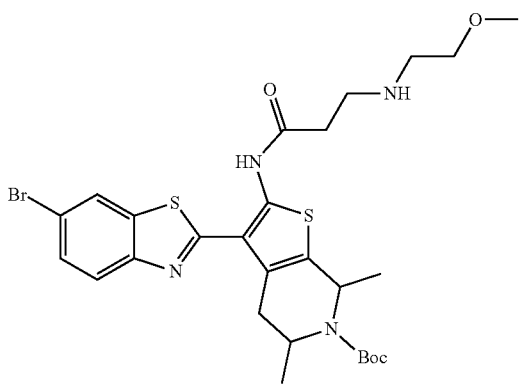

6

To a solution of tert-butyl 2-acrylamido-3-(6-bromobenzo[d]thiazol-2-yl)-5,7-dimethyl-4,7-dihydrothieno[2,3-c]pyridine-6(5H)-carboxylate 5 (1.4 g, 2.55 mmol) in MeOH (20 mL) was added 2-methoxyethan-1-amine (0.45 mL, 5.11 mmol). The resulting reaction mixture was stirred at room temperature for 16 h. Progress of the reaction was monitored by TLC. After completion, the reaction mixture was concentrated to dryness under reduced pressure. The residue was washed with water and extracted with CH$_2$Cl$_2$ (thrice). The combined organic layer was dried over anhydrous Na$_2$SO$_4$, filtered and concentrated. The crude compound was purified by column chromatography eluting with 0-5% methanol in CH$_2$Cl$_2$ to afford the title compound 6 as yellow solid (600 mg, yield 38%).

Step 6: tert-Butyl 2-(3-((2-methoxyethyl)amino)propanamido)-5,7-dimethyl-3-(6-(pyridin-4-yl)benzo[d]thiazol-2-yl)-4,7-dihydrothieno[2,3-c]pyridine-6(5H)-carboxylate (7)

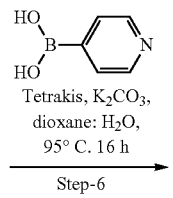

Tetrakis, K$_2$CO$_3$, dioxane: H$_2$O, 95° C. 16 h

6

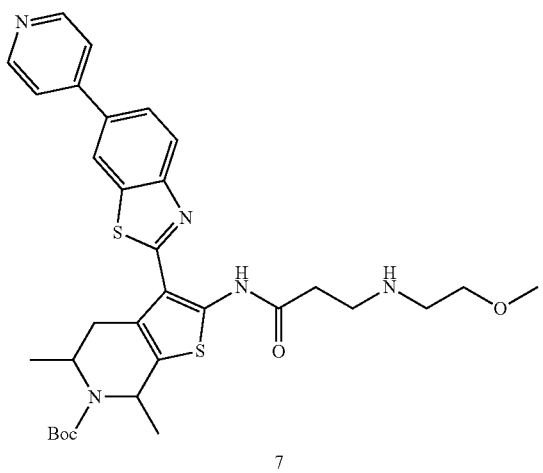

7

To a solution of tert-butyl 3-(6-bromobenzo[d]thiazol-2-yl)-2-(3-((2-methoxyethyl)amino)propanamido)-5,7-dimethyl-4,7-dihydrothieno[2,3-c]pyridine-6(5H)-carboxylate 6 (250 mg, 0.40 mmol) in dioxane (10 mL) was added solution of K$_2$CO$_3$ (138 mg, 1.00 mmol) in water (0.5 mL) and degassed under argon atmosphere for 10 min. Followed by addition of Pd(PPh$_3$)$_4$ (46 mg, 0.04 mmol) and pyridin-4-ylboronic acid (74 mg, 0.60 mmol) and degassed with argon for another 10 min. The reaction mixture was heated to 95° C. for 16 h. After the completion of reaction (monitored by LCMS), the reaction mixture was diluted with water and extracted with ethyl acetate (thrice). The combined organic layers were dried with anhydrous Na$_2$SO$_4$, filtered and concentrated to get a crude residue. This crude compound was purified by silica gel column chromatography eluting with 0-5% methanol in CH$_2$Cl$_2$ to afford the title compound 7 (150 mg, yield 60%).

Step 7: N-(5,7-Dimethyl-3-(6-(pyridin-4-yl)benzo[d]thiazol-2-yl)-4,5,6,7-tetrahydrothieno[2,3-c]pyridin-2-yl)-3-((2-methoxyethyl)amino)propanamide

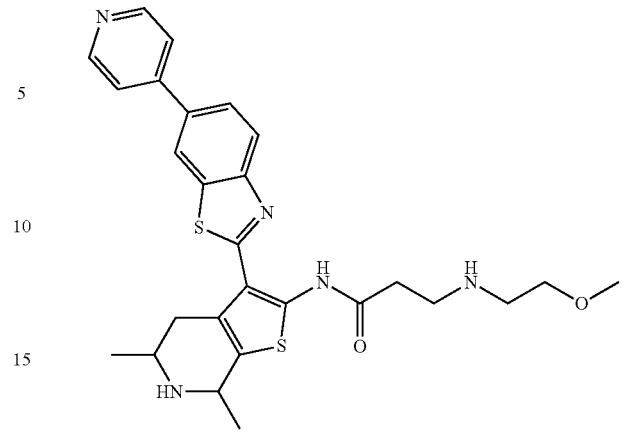

To a solution of tert-butyl 2-(3-((2-methoxyethyl)amino)propanamido)-5,7-dimethyl-3-(6-(pyridin-4-yl)benzo[d]thiazol-2-yl)-4,7-dihydrothieno[2,3-c]pyridine-6(5H)-carboxylate 7 (150 mg, 0.241 mmol) in dioxane (1 mL) at 0° C. was added 4M HCl in dioxane (1 mL). After the addition, the resulting mixture was stirred at room temperature for 3 h. After completion, the reaction mixture was evaporated in vacuum resulting in a crude residue which was purified by trituration with methanol. The solid obtained was filtered and washed with diethyl ether and n-pentane to afford the title compound as yellow solid (130 mg, yield 93%). The chiral separation for the mixture (Column: CHIRALPAK; IA3, 150 mm*4.6 mm*3 um; Mobile Phase: A: n-Hexane+ 0.1% TEA; B: ETOH:DCM (85:15)+0.1% TEA; Flow rate: 1.0 ml/min; Isocratic:20% B) afforded Compounds 517 and 518).

Example 102. Synthesis of N-(5,7-Dimethyl-3-(6-(pyridin-3-yl)benzo[d]thiazol-2-yl)-4,5,6,7-tetrahydrothieno[2,3-c]pyridin-2-yl)-3-((2-methoxyethyl)amino)propanamide and Separation of Isomers (Compounds 518 and 519)

Step 1: tert-Butyl 2-(3-((2-methoxyethyl)amino)propanamido)-5,7-dimethyl-3-(6-(pyridin-3-yl)benzo[d]thiazol-2-yl)-4,7-dihydrothieno[2,3-c]pyridine-6(5H)-carboxylate (7)

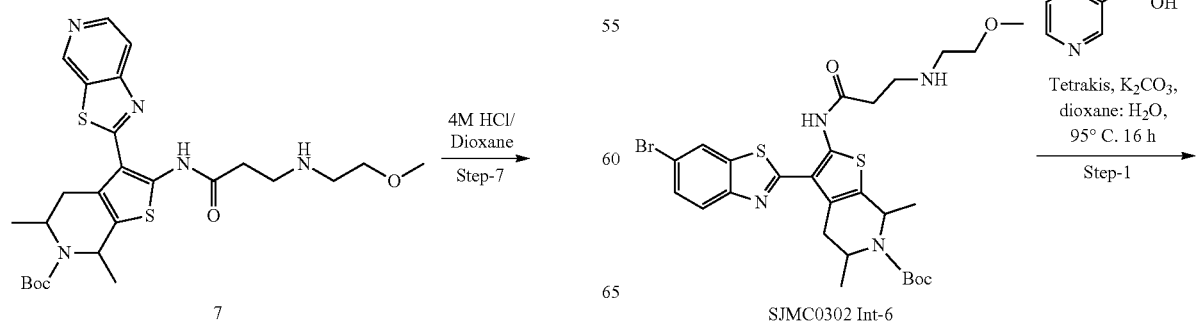

SJMC0302 Int-6

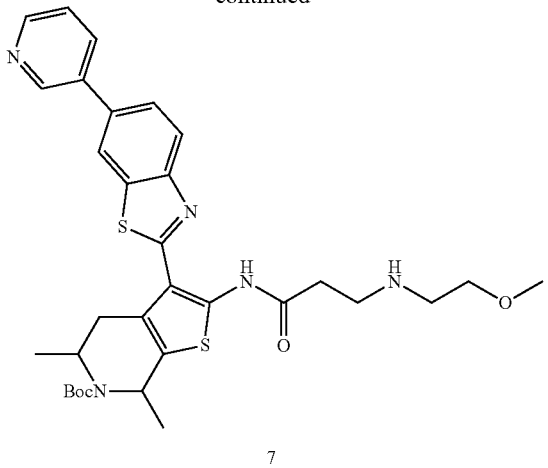

7

To a solution of tert-butyl 3-(6-bromobenzo[d]thiazol-2-yl)-2-(3-((2-methoxyethyl)amino)propanamido)-5,7-dimethyl-4,7-dihydrothieno[2,3-c]pyridine-6(5H)-carboxylate SJMC0302 Int-6 (550 mg, 0.88 mmol) in dioxane (20 mL) was added solution of K₂CO₃ (303 mg, 2.20 mmol) in water (1 mL) and degassed under argon atmosphere for 10 min. Followed by addition of Pd(PPh₃)₄ (100 mg, 0.088 mmol) and pyridin-3-ylboronic acid (160 mg, 1.320 mmol) and degassed with argon for another 10 min. The reaction mixture was heated to 100° C. for 16 h. After the completion of reaction (monitored by LCMS), the reaction mixture was diluted with water and extracted with ethyl acetate (thrice). The combined organic layers were dried with anhydrous Na₂SO₄, filtered and concentrated to get a crude residue. This crude compound was purified by silica gel column chromatography eluting with 0-5% methanol in CH₂Cl₂ to afford the title compound 7 (350 mg, yield 65%).

Step 2: N-(5,7-Dimethyl-3-(6-(pyridin-3-yl)benzo[d]thiazol-2-yl)-4,5,6,7-tetrahydrothieno[2,3-c]pyridin-2-yl)-3-((2-methoxyethyl)amino)propanamide

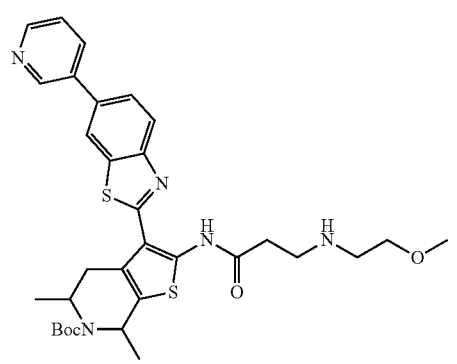

7

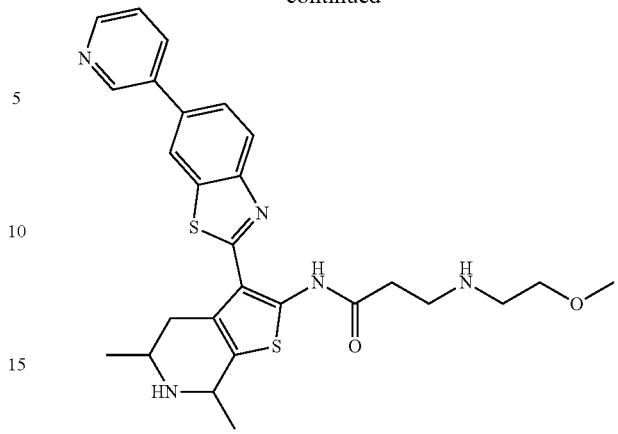

To a solution of tert-butyl 2-(3-((2-methoxyethyl)amino)propanamido)-5,7-dimethyl-3-(6-(pyridin-3-yl)benzo[d]thiazol-2-yl)-4,7-dihydrothieno[2,3-c]pyridine-6(5H)-carboxylate 7 (350 mg, 0.562 mmol) in dioxane (5 mL) at 0° C. was added 4M HCl in dioxane (5 mL). After the addition, the resulting mixture was stirred at room temperature for 2 h. After completion, the reaction mixture was evaporated in vacuum resulting in a crude residue which was purified by trituration with methanol. The solid obtained was filtered and washed with diethyl ether and n-pentane to afford the title compound as yellow solid (330 mg crude). The chiral separation for the title compound (Column: CHIRALPAK; IA3, 150 mm*4.6 mm*3 um; Mobile Phase: A: n-Hexane+0.1% DEA; B: ETOH; Flow rate: 1.0 ml/min; Isocratic:20% B) afforded Compounds 519 and 520.

Example 103. Synthesis of N-((5S,7R)-5,7-dimethyl-3-(5-(pyridin-4-yl)benzo[d]thiazol-2-yl)-4,5,6,7-tetrahydrothieno[2,3-c]pyridin-2-yl)-3-((2-methoxyethyl)amino)propanamide and Separation of Isomers (Compound 521, 522, 523 and 532)

Step 1: 2-Amino-4-bromobenzenethiol (2)

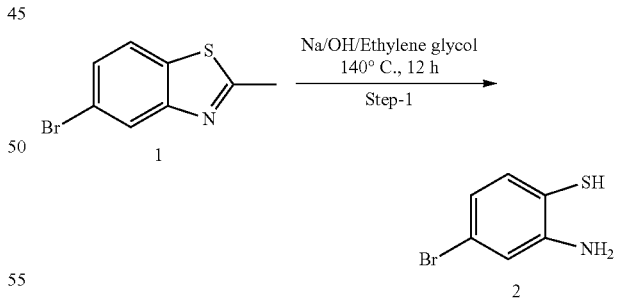

To a solution of 5-bromo-2-methylbenzo[d]thiazole 1 (5 g, 21.92 mmol) in ethylene glycol (50 mL) was added 8 N NaOH (25 mL). The resulting reaction mixture was stirred at 140° C. for 3 h. Progress of the reaction was monitored by TLC. After completion, the reaction mixture was cooled to room temperature; acidified with 1N HCl up to pH=6 and extracted with ethyl acetate (thrice). The combined organic layer was dried over anhydrous Na₂SO₄; filtered and concentrated under reduced pressure to afford the title compound 2 as yellow solid (4.3 g, crude).

Step 2: 2-(5-Bromobenzo[d]thiazol-2-yl)acetonitrile (3)

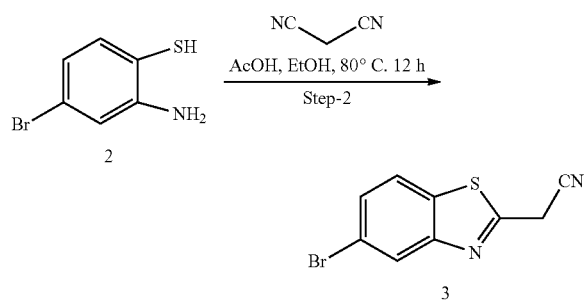

To a solution of 2-amino-4-bromobenzenethiol 2 (4.3 g, 21.07 mmol) in EtOH (40 mL) was added malononitrile (1.4 g, 21.07 mmol) and AcOH (40 mL). The resulting reaction mixture was stirred at 80° C. for 12 h. Progress of the reaction was monitored by TLC. After completion, the reaction mixture was concentrated under reduced pressure to dryness. The crude compound was purified by column chromatography eluting with 0-20% ethyl acetate in n-hexane to afford the title compound 3 as brown solid (1.9 g yield 36%)

Step 3: tert-Butyl 2-amino-3-(5-bromobenzo[d]thiazol-2-yl)-5,7-dimethyl-4,7-dihydrothieno[2,3-c]pyridine-6(5H)-carboxylate (4)

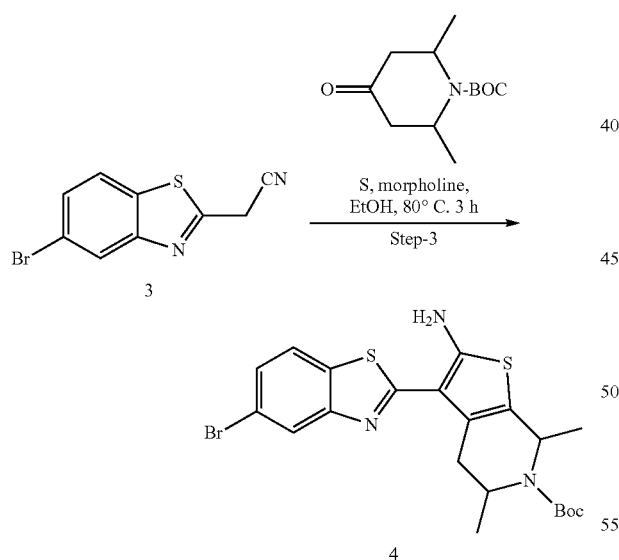

To a solution of 2-(5-bromobenzo[d]thiazol-2-yl)acetonitrile 3 (1.9 g, 7.539 mmol) in ethanol (20 mL) was added tert-butyl 2,6-dimethyl-4-oxopiperidine-1-carboxylate (1.72 g, 7.539 mmol), elemental sulphur (241 mg, 7.539 mmol) and morpholine (656 mg, 7.539 mmol) at room temperature. After the addition, the resulting mixture was heated to reflux at 80° C. for 3 h. Progress of the reaction was monitored by TLC. After completion, the reaction mixture was evaporated in vacuum up to dryness. The crude compound was purified by column chromatography eluting with 0-20% ethyl acetate in n-hexane to afford the title compound 4 as off white solid (1.7 g, yield 45%).

Step 4: tert-Butyl 2-acrylamido-3-(5-bromobenzo[d]thiazol-2-yl)-5,7-dimethyl-4,7-dihydrothieno[2,3-c]pyridine-6(5H)-carboxylate (5)

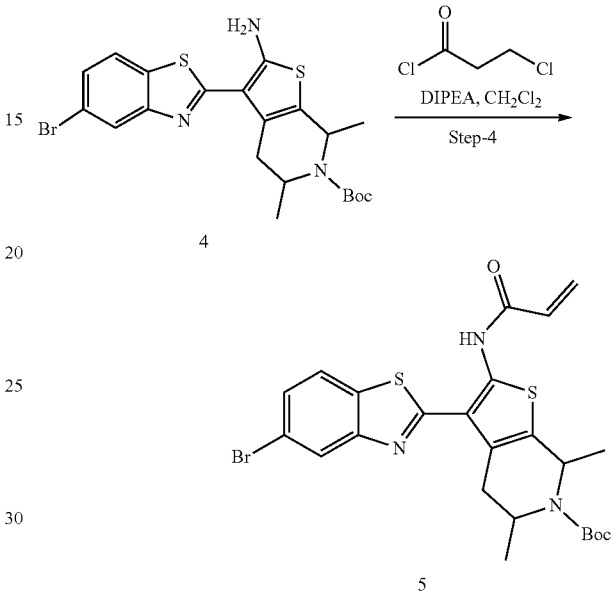

To a solution of tert-butyl 2-amino-3-(5-bromobenzo[d]thiazol-2-yl)-5,7-dimethyl-4,7-dihydrothieno[2,3-c]pyridine-6(5H)-carboxylate 4 (1.5 g, 3.042 mmol) in CH$_2$Cl$_2$ (25 mL) at 0° C. was added DIPEA (0.78 mL, 4.563 mmol) and 3-chloropropanoyl chloride (0.43 mL, 4.563 mmol). The reaction mixture was stirred at room temperature for 2 h. After completion (monitored by TLC), the reaction mixture was concentrated in vacuo. The crude compound was purified by column chromatography eluting with 0-5% methanol in CH$_2$Cl$_2$ to afford the title compound 5 as light brown solid (1.7 g crude).

Step 5: tert-Butyl 3-(5-bromobenzo[d]thiazol-2-yl)-2-(3-((2-methoxyethyl)amino)propanamido)-5,7-dimethyl-4,7-dihydrothieno[2,3-c]pyridine-6(5H)-carboxylate (6)

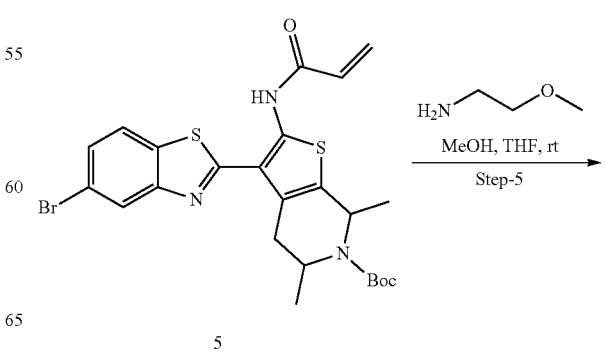

-continued

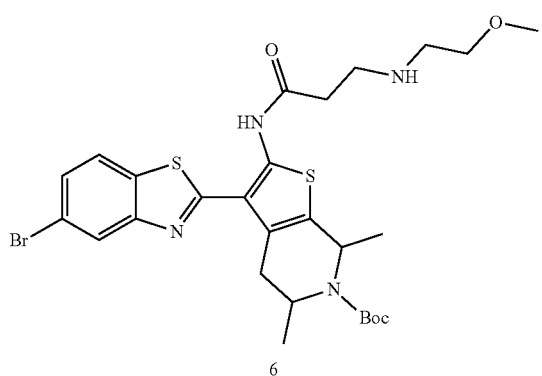

6

-continued

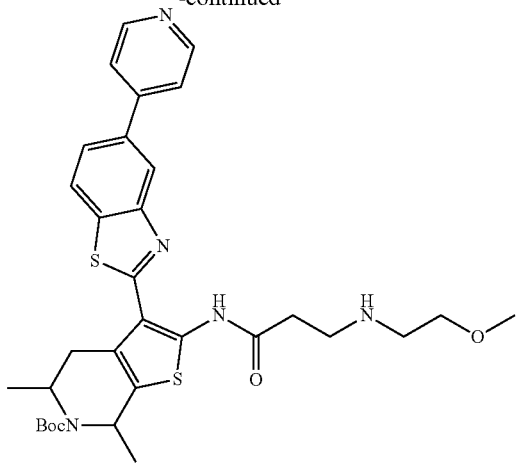

8

To a solution of tert-butyl 2-acrylamido-3-(5-bromobenzo[d]thiazol-2-yl)-5,7-dimethyl-4,7-dihydrothieno[2,3-c]pyridine-6(5H)-carboxylate 5 (1.7 g, 3.102 mmol) in MeOH (15 mL) was added 2-methoxyethan-1-amine (0.35 mL, 4.653 mmol). The resulting reaction mixture was stirred at room temperature for 16 h. Progress of the reaction was monitored by TLC. After completion, the reaction mixture was concentrated to dryness under reduced pressure. The residue was washed with water and extracted with CH$_2$Cl$_2$ (thrice). The combined organic layer was dried over anhydrous Na$_2$SO$_4$, filtered and concentrated. The crude compound was purified by column chromatography eluting with 0-5% methanol in CH$_2$Cl$_2$ to afford the title compound 6 as yellow solid (1.16 g, yield 90%).

Step 6: tert-Butyl 2-(3-((2-methoxyethyl)amino)propanamido)-5,7-dimethyl-3-(5-(pyridin-4-yl)benzo[d]thiazol-2-yl)-4,7-dihydrothieno[2,3-c]pyridine-6(5H)-carboxylate (8)

To a solution of tert-butyl 3-(5-bromobenzo[d]thiazol-2-yl)-2-(3-((2-methoxyethyl)amino)propanamido)-5,7-dimethyl-4,7-dihydrothieno[2,3-c]pyridine-6(5H)-carboxylate 6 (550 mg, 0.884 mmol) in dioxane (10 mL) was added solution of K$_2$CO$_3$ (305 mg, 2.211 mmol) in water (1 mL) and degassed under argon atmosphere for 10 min. Followed by addition of Pd(PPh$_3$)$_4$ (102 mg, 0.08 mmol) and pyridin-4-ylboronic acid 7 (163 mg, 1.326 mmol) and degassed with argon for another 10 min. The reaction mixture was heated to 100° C. for 12 h. After the completion of reaction (monitored by LCMS), the reaction mixture was diluted with water and extracted with CH$_2$Cl$_2$ (thrice). The combined organic layers were dried with anhydrous Na$_2$SO$_4$, filtered and concentrated to get a crude residue. This crude compound was purified by silica gel column chromatography eluting with 0-8% methanol in CH$_2$Cl$_2$ to afford the title compound 8 (360 mg, yield 65%).

Step 7: N-(5,7-dimethyl-3-(5-(pyridin-4-yl)benzo[d]thiazol-2-yl)-4,5,6,7-tetrahydrothieno[2,3-c]pyridin-2-yl)-3-((2-methoxyethyl)amino)propanamide

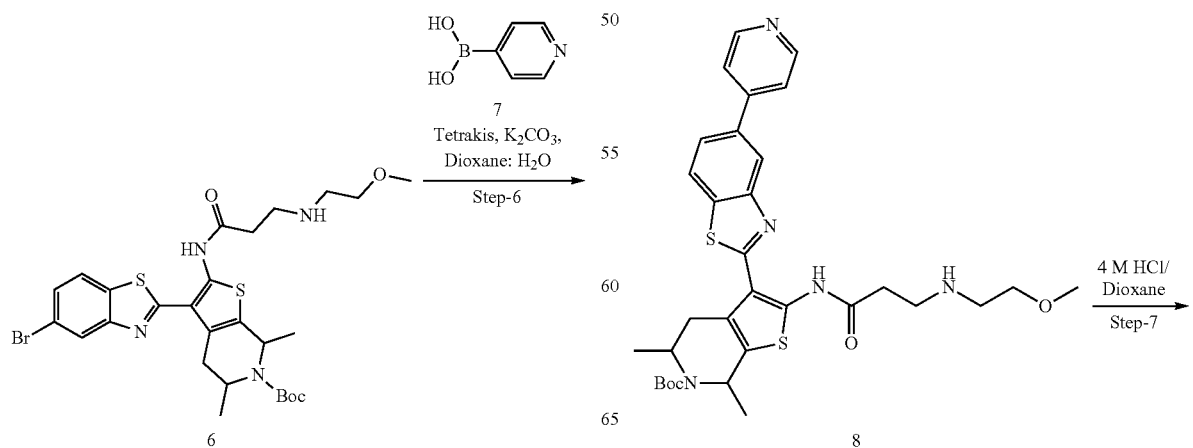

-continued

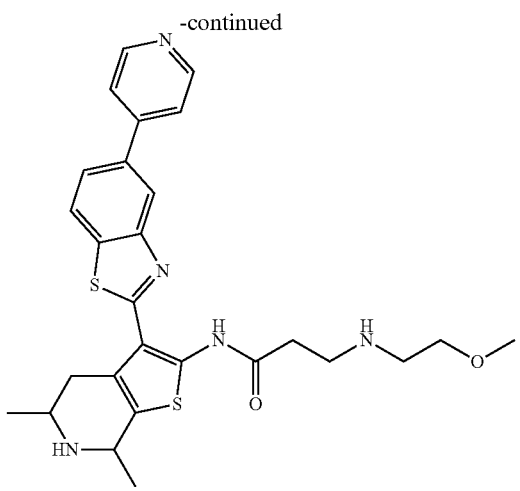

To a solution of tert-butyl 2-(3-((2-methoxyethyl)amino)propanamido)-5,7-dimethyl-3-(5-(pyridin-4-yl)benzo[d]thiazol-2-yl)-4,7-dihydrothieno[2,3-c]pyridine-6(5H)-carboxylate 8 (360 mg, 0.579 mmol) in dioxane (3 mL) at 0° C. was added 4M HCl in dioxane (4 mL). After the addition, the resulting mixture was stirred at room temperature for 3 h. After completion, the reaction mixture was evaporated in vacuum resulting in a crude residue which was purified by trituration with methanol. The solid obtained was filtered and washed with diethyl ether and n-pentane to afford the title compound as yellow solid (340 mg, crude). The chiral separation for the mixture (Column: CHIRALPAK, IC, 250 mm*4.6 mm*5 um; Mobile Phase: A: n-Hexane+0.1% TEA; B: ETOH:DCM (85:15)+0.1% TEA; Flow rate: 1.0 ml/min; Isocratic: 70% B) afforded Compounds 521, 522, 523 and 532.

Example 104. Synthesis of N-((5S,7R)-5,7-dimethyl-3-(5-(pyridin-4-yl)benzo[d]thiazol-2-yl)-4,5,6,7-tetrahydrothieno[2,3-c]pyridin-2-yl)-3-((2-methoxyethyl)amino)propanamide (Compound 532)

Step 1: 2-Amino-4-bromobenzenethiol (2)

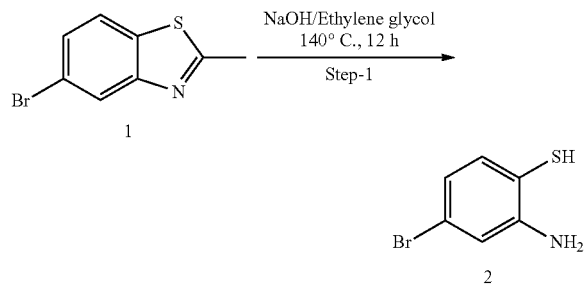

To a solution of 5-bromo-2-methylbenzo[d]thiazole 1 (5 g, 21.92 mmol) in ethylene glycol (50 mL) was added 8 N NaOH (25 mL). The resulting reaction mixture was stirred at 140° C. for 3 h. Progress of the reaction was monitored by TLC. After completion, the reaction mixture was cooled to room temperature; acidified with 1N HCl up to pH=6 and extracted with ethyl acetate (thrice). The combined organic layer was dried over anhydrous Na₂SO₄; filtered and concentrated under reduced pressure to afford the title compound 2 as yellow solid (4.3 g, crude).

Step 2: 2-(5-Bromobenzo[d]thiazol-2-yl)acetonitrile (3)

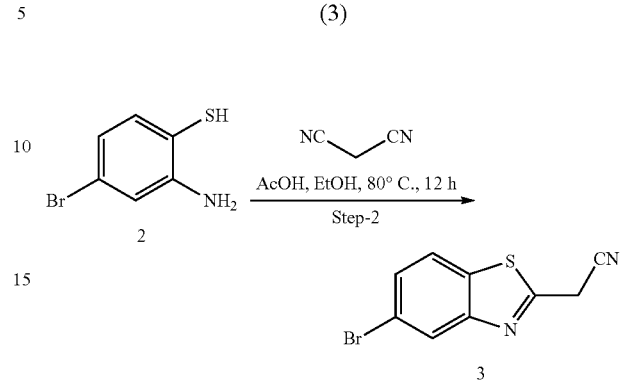

To a solution of 2-amino-4-bromobenzenethiol 2 (4.3 g, 21.07 mmol) in EtOH (40 mL) was added malononitrile (1.4 g, 21.07 mmol) and AcOH (40 mL). The resulting reaction mixture was stirred at 80° C. for 12 h. Progress of the reaction was monitored by TLC. After completion, the reaction mixture was concentrated under reduced pressure to dryness. The crude compound was purified by column chromatography eluting with 0-20% ethyl acetate in n-hexane to afford the title compound 3 as brown solid (1.9 g yield 36%)

Step 3: tert-Butyl 2-amino-3-(5-bromobenzo[d]thiazol-2-yl)-5,7-dimethyl-4,7-dihydrothieno[2,3-c]pyridine-6(5H)-carboxylate (4)

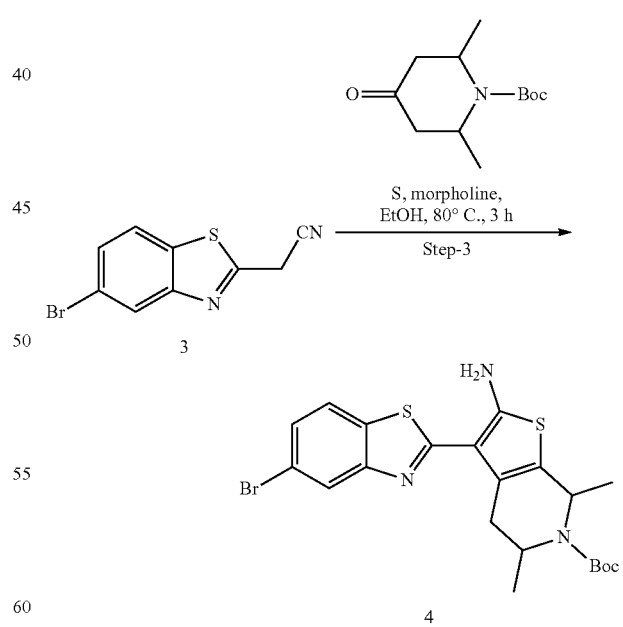

To a solution of 2-(5-bromobenzo[d]thiazol-2-yl)acetonitrile 3 (1.9 g, 7.539 mmol) in ethanol (20 mL) was added tert-butyl 2,6-dimethyl-4-oxopiperidine-1-carboxylate (1.72 g, 7.539 mmol), elemental sulphur (241 mg, 7.539 mmol) and morpholine (656 mg, 7.539 mmol) at room temperature.

After the addition, the resulting mixture was heated to reflux at 80° C. for 3 h. Progress of the reaction was monitored by TLC. After completion, the reaction mixture was evaporated in vacuum up to dryness. The crude compound was purified by column chromatography eluting with 0-20% ethyl acetate in n-hexane to afford the title compound 4 as off white solid (1.7 g, yield 45%).

Step 4: tert-Butyl 2-acrylamido-3-(5-bromobenzo[d]thiazol-2-yl)-5,7-dimethyl-4,7-dihydrothieno[2,3-c]pyridine-6(5H)-carboxylate (5)

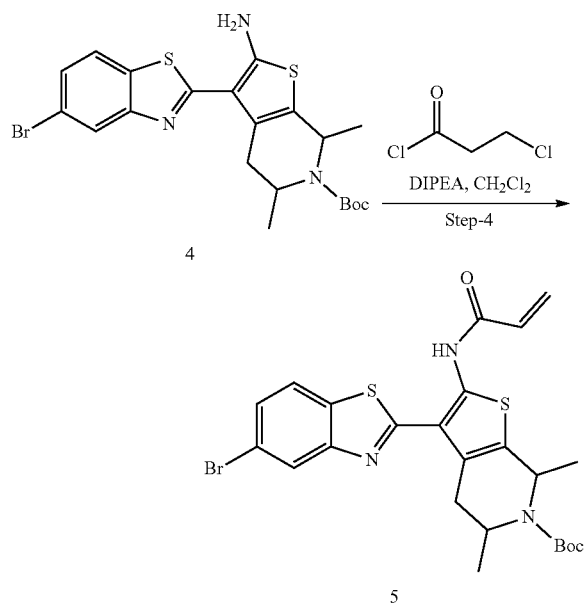

To a solution of tert-butyl 2-amino-3-(5-bromobenzo[d]thiazol-2-yl)-5,7-dimethyl-4,7-dihydrothieno[2,3-c]pyridine-6(5H)-carboxylate 4 (1.5 g, 3.042 mmol) in CH$_2$Cl$_2$ (25 mL) at 0° C. was added DIPEA (0.78 mL, 4.563 mmol) and 3-chloropropanoyl chloride (0.43 mL, 4.563 mmol). The reaction mixture was stirred at room temperature for 2 h. After completion (monitored by TLC), the reaction mixture was concentrated in vacuo. The crude compound was purified by column chromatography eluting with 0-5% methanol in CH$_2$Cl$_2$ to afford the title compound 5 as light brown solid (1.7 g crude).

Step 5: tert-Butyl 3-(5-bromobenzo[d]thiazol-2-yl)-2-(3-((2-methoxyethyl)amino)propanamido)-5,7-dimethyl-4,7-dihydrothieno[2,3-c]pyridine-6(5H)-carboxylate (6)

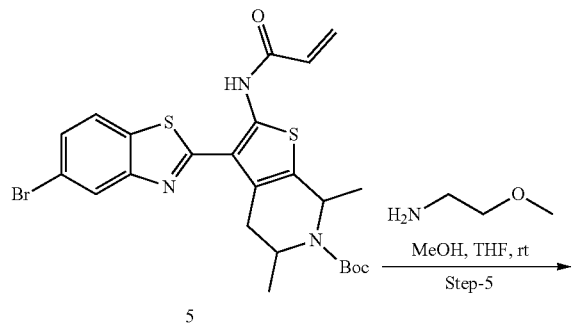

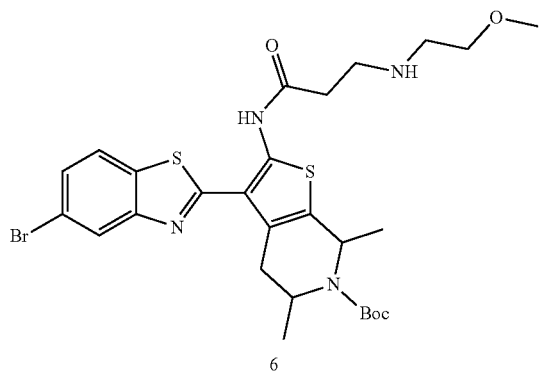

To a solution of tert-butyl 2-acrylamido-3-(5-bromobenzo[d]thiazol-2-yl)-5,7-dimethyl-4,7-dihydrothieno[2,3-c]pyridine-6(5H)-carboxylate 5 (1.7 g, 3.102 mmol) in MeOH (15 mL) was added 2-methoxyethan-1-amine (0.35 mL, 4.653 mmol). The resulting reaction mixture was stirred at room temperature for 16 h. Progress of the reaction was monitored by TLC. After completion, the reaction mixture was concentrated to dryness under reduced pressure. The residue was washed with water and extracted with CH$_2$Cl$_2$ (thrice). The combined organic layer was dried over anhydrous Na$_2$SO$_4$, filtered and concentrated. The crude compound was purified by column chromatography eluting with 0-5% methanol in CH$_2$Cl$_2$ to afford the title compound 6 as yellow solid (1.16 g, yield 90%).

Step 6: tert-Butyl 2-(3-((2-methoxyethyl)amino)propanamido)-5,7-dimethyl-3-(5-(pyridin-4-yl)benzo[d]thiazol-2-yl)-4,7-dihydrothieno[2,3-c]pyridine-6(5H)-carboxylate (8)

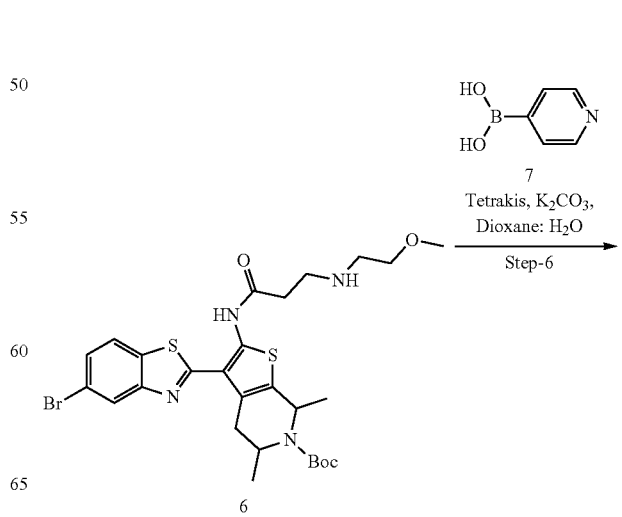

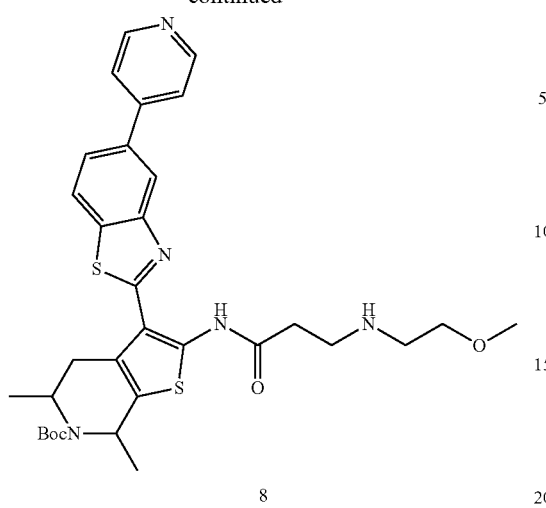

8

To a solution of tert-butyl 3-(5-bromobenzo[d]thiazol-2-yl)-2-(3-((2-methoxyethyl)amino)propanamido)-5,7-dimethyl-4,7-dihydrothieno[2,3-c]pyridine-6(5H)-carboxylate 6 (550 mg, 0.884 mmol) in dioxane (10 mL) was added solution of K$_2$CO$_3$ (305 mg, 2.211 mmol) in water (1 mL) and degassed under argon atmosphere for 10 min. Followed by addition of Pd(PPh$_3$)$_4$ (102 mg, 0.08 mmol) and pyridin-4-ylboronic acid 7 (163 mg, 1.326 mmol) and degassed with argon for another 10 min. The reaction mixture was heated to 100° C. for 12 h. After the completion of reaction (monitored by LCMS), the reaction mixture was diluted with water and extracted with CH$_2$Cl$_2$ (thrice). The combined organic layers were dried with anhydrous Na$_2$SO$_4$, filtered and concentrated to get a crude residue. This crude compound was purified by silica gel column chromatography eluting with 0-8% methanol in CH$_2$Cl$_2$ to afford the title compound 8 (360 mg, yield 65%).

Step 7: N-(5,7-dimethyl-3-(5-(pyridin-4-yl)benzo[d]thiazol-2-yl)-4,5,6,7-tetrahydrothieno[2,3-c]pyridin-2-yl)-3-((2-methoxyethyl)amino)propanamide

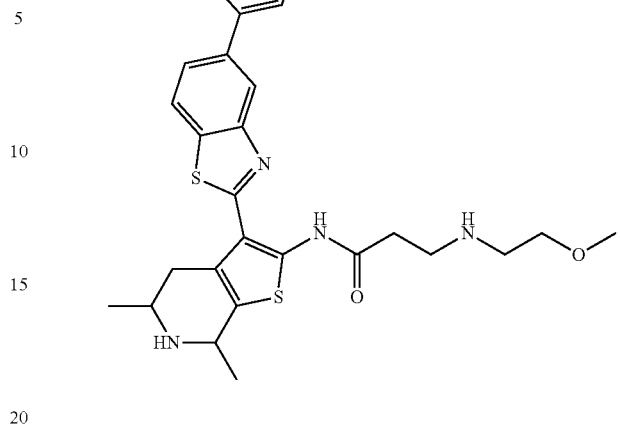

To a solution of tert-butyl 2-(3-((2-methoxyethyl)amino)propanamido)-5,7-dimethyl-3-(5-(pyridin-4-yl)benzo[d]thiazol-2-yl)-4,7-dihydrothieno[2,3-c]pyridine-6(5H)-carboxylate 8 (360 mg, 0.579 mmol) in dioxane (3 mL) at 0° C. was added 4M HCl in dioxane (4 mL). After the addition, the resulting mixture was stirred at room temperature for 3 h. After completion, the reaction mixture was evaporated in vacuum resulting in a crude residue which was purified by trituration with methanol. The solid obtained was filtered and washed with diethyl ether and n-pentane to afford the title compound as yellow solid (340 mg, crude). Chiral separation (Column: CHIRALPAK, IC, 250 mm*4.6 mm*5 um; Mobile Phase: A: n-Hexane+0.1% TEA; B: ETOH:DCM (85:15)+0.1% TEA; Flow rate: 1.0 ml/min; Isocratic: 70% B) afforded Compound 532.

Example 105. Synthesis of N-((5S,7R)-5,7-Dimethyl-3-(5-(pyridin-3-yl)benzo[d]thiazol-2-yl)-4,5,6,7-tetrahydrothieno[2,3-c]pyridin-2-yl)-3-((2-methoxyethyl)amino)propanamide (Compound 533)

Step 1: tert-Butyl 2-(3-((2-methoxyethyl)amino)propanamido)-5,7-dimethyl-3-(5-(pyridin-3-yl)benzo[d]thiazol-2-yl)-4,7-dihydrothieno[2,3-c]pyridine-6(5H)-carboxylate (1)

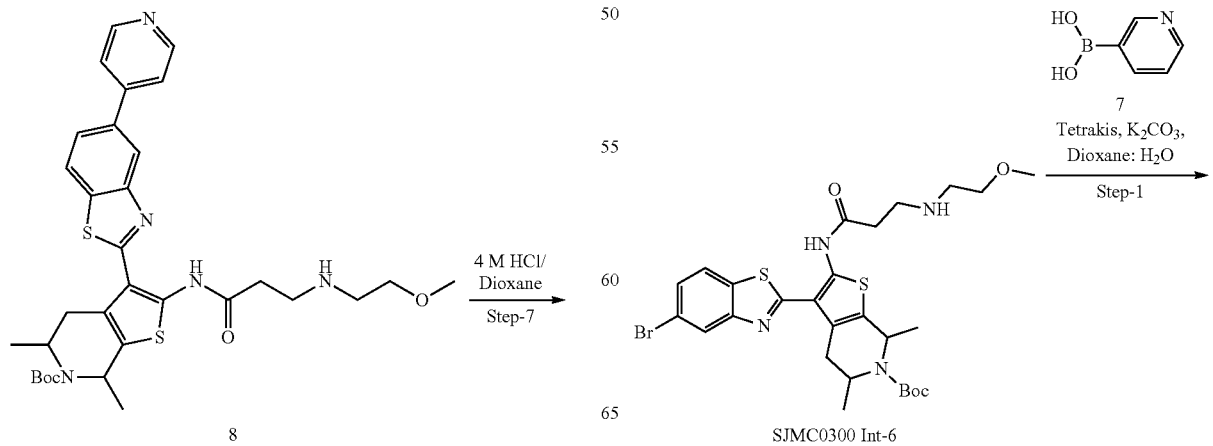

SJMC0300 Int-6

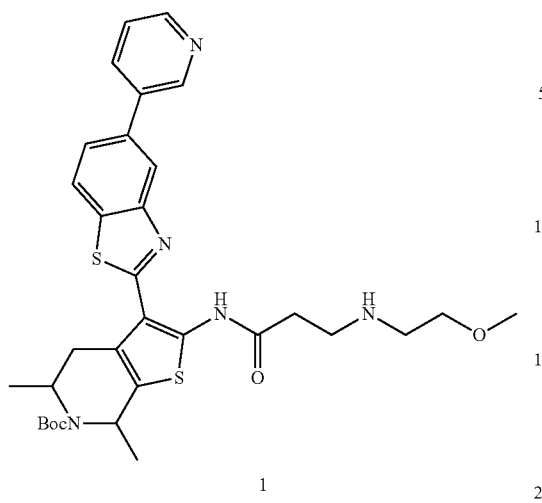

1

To a solution of tert-butyl 3-(5-bromobenzo[d]thiazol-2-yl)-2-(3-((2-methoxyethyl)amino)propanamido)-5,7-dimethyl-4,7-dihydrothieno[2,3-c]pyridine-6(5H)-carboxylate SJMC0300 Int-6 (550 mg, 0.884 mmol) in dioxane (10 mL) was added solution of K₂CO₃ (305 mg, 2.211 mmol) in water (1 mL) and degassed under argon atmosphere for 10 min. Followed by addition of Pd(PPh₃)₄ (102 mg, 0.08 mmol) and pyridin-3-ylboronic acid 7 (163 mg, 1.326 mmol) and degassed with argon for another 10 min. The reaction mixture was heated to 100° C. for 12 h. After the completion of reaction (monitored by LCMS), the reaction mixture was diluted with water and extracted with CH₂Cl₂ (thrice). The combined organic layers were dried with anhydrous Na₂SO₄, filtered and concentrated to get a crude residue. This crude compound was purified by silica gel column chromatography eluting with 0-8% methanol in CH₂Cl₂ to afford the title compound 1 (300 mg, yield 55%).

Step 2: N-(5,7-Dimethyl-3-(5-(pyridin-3-yl)benzo[d]thiazol-2-yl)-4,5,6,7-tetrahydrothieno[2,3-c]pyridin-2-yl)-3-((2-methoxyethyl)amino)propanamide

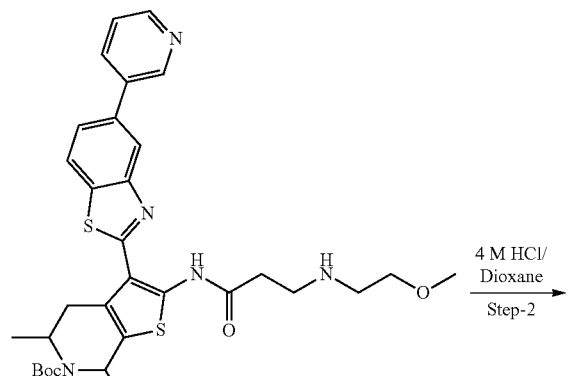

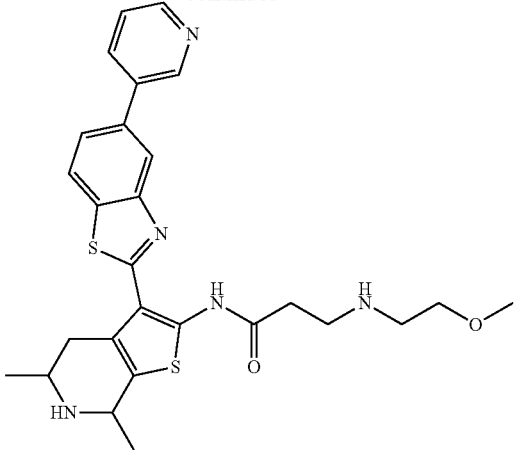

To a solution of tert-butyl 2-(3-((2-methoxyethyl)amino)propanamido)-5,7-dimethyl-3-(5-(pyridin-3-yl)benzo[d]thiazol-2-yl)-4,7-dihydrothieno[2,3-c]pyridine-6(5H)-carboxylate 1 (300 mg, 0.483 mmol) in dioxane (4 mL) at 0° C. was added 4M HCl in dioxane (5 mL). After the addition, the resulting mixture was stirred at room temperature for 2 h. After completion, the reaction mixture was evaporated in vacuum resulting in a crude residue which was purified by trituration with methanol. The solid obtained was filtered and washed with diethyl ether and n-pentane to afford the title compound as yellow solid (284 mg, crude). Chiral separation (Column: CHIRALPAK, IC, 250 mm*4.6 mm*5 um; Mobile Phase: A: n-Hexane+0.1% TEA; B: ETOH:DCM (85:15)+0.1% TEA; Flow rate: 1.20 ml/min; Isocratic: 70% B) afforded Compound 533.

Example 106. Synthesis of N-(3-(Benzo[d]thiazol-2-yl)-5,7-diethyl-4,5,6,7-tetrahydrothieno[2,3-c]pyridin-2-yl)-3-((2-methoxyethyl)amino)propanamide and Separation of Isomers (Compounds 536 and 537)

Step 1: 1-Benzyl-2,6-diethylpiperidin-4-one (2)

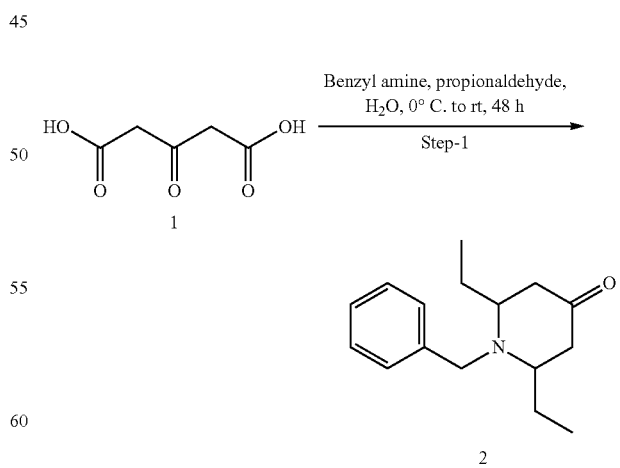

To a solution of 3-oxopentanedioic acid 1 (10 g, 68.44 mmol) in water (50 mL) was added propionaldehyde (9.8 mL, 136.89 mmol) and stirred at room temperature for 15 min. The reaction mixture was cooled to 0° C. and followed by addition of benzyl amine (7.4 mL, 68.44 mmol) and stirred at room temperature for 48 h. Progress of the reaction was monitored by TLC. After completion, the reaction mixture was cooled to room temperature; acidified with 1N HCl up to pH=2 and neutralised with saturated NaHCO₃ solution and extracted with ethyl acetate (thrice). The combined organic layer was dried over anhydrous Na₂SO₄; filtered and concentrated under reduced pressure. The crude compound was purified by column chromatography eluting with 0-10% ethyl acetate in n-hexane to afford the title compound 2 as brown oil (8.25 g, yield 49%).

Step 2: tert-Butyl 2,6-diethyl-4-oxopiperidine-1-carboxylate (3)

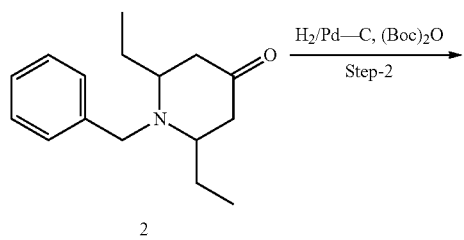

To a solution of 1-benzyl-2,6-diethylpiperidin-4-one 2 (4 g, 16.32 mmol) in IPA (50 mL) was added Boc anhydride (5.33 g, 24.48 mmol) and 10% Pd/c (1 g). The resulting reaction mixture was stirred at room temperature under hydrogen atmosphere for 15 h. Progress of the reaction was monitored by TLC. After completion, the reaction mixture was filtered through a pad of Celite and the filtrate was concentrated under reduced pressure to dryness. The crude compound was purified by column chromatography eluting with 0-10% ethyl acetate in n-hexane to afford the title compound 3 as brown solid (4 g yield 96%)

Step 3: tert-Butyl 2-amino-3-(benzo[d]thiazol-2-yl)-5,7-diethyl-4,7-dihydrothieno[2,3-c]pyridine-6(5H)-carboxylate (5)

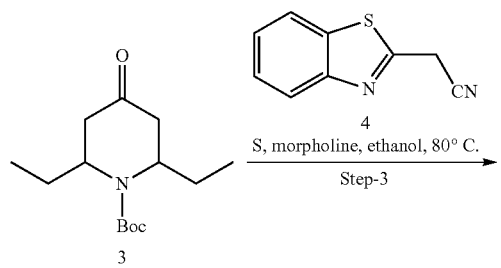

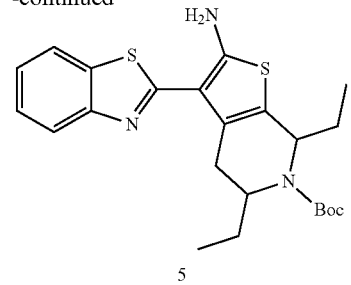

To a solution of 2-(benzo[d]thiazol-2-yl)acetonitrile 4 (2 g, 11.49 mmol) in ethanol (30 mL) was added tert-butyl 2,6-diethyl-4-oxopiperidine-1-carboxylate 3 (2.93 g, 11.49 mmol), elemental sulphur (551 mg, 17.23 mmol) and morpholine (1.49 g, 17.23 mmol) at room temperature. After the addition, the resulting mixture was heated to reflux at 80° C. for 3 h. Progress of the reaction was monitored by TLC. After completion, the reaction mixture was evaporated in vacuum up to dryness. The crude compound was triturated with methanol to afford the title compound 5 as yellow solid (2.1 g crude).

Step 4: tert-Butyl 2-acrylamido-3-(benzo[d]thiazol-2-yl)-5,7-diethyl-4,7-dihydrothieno[2,3-c]pyridine-6(5H)-carboxylate (6)

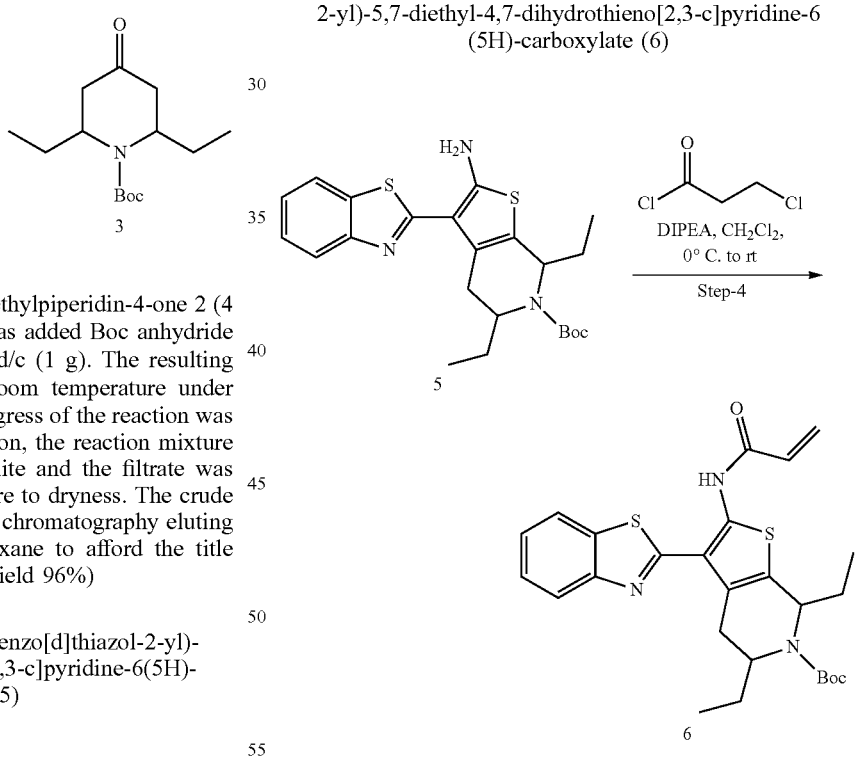

To a solution of tert-butyl 2-amino-3-(benzo[d]thiazol-2-yl)-5,7-diethyl-4,7-dihydrothieno[2,3-c]pyridine-6(5H)-carboxylate 5 (2 g, 4.504 mmol) in CH₂Cl₂ (30 mL) at 0° C. was added DIPEA (2.4 mL, 13.51 mmol) and 3-chloropropanoyl chloride (0.86 mL, 9.009 mmol). The reaction mixture was stirred at room temperature for 2 h. After completion (monitored by TLC), the reaction mixture was concentrated in vacuo. The crude compound was purified by column chromatography eluting with 0-20% ethyl acetate in n-hexane to afford the title compound 6 as yellow solid (3 g crude).

315

Step 5: tert-Butyl 3-(benzo[d]thiazol-2-yl)-5,7-diethyl-2-(3-((2-methoxyethyl)amino)propanamido)-4,7-dihydrothieno[2,3-c]pyridine-6(5H)-carboxylate (7)

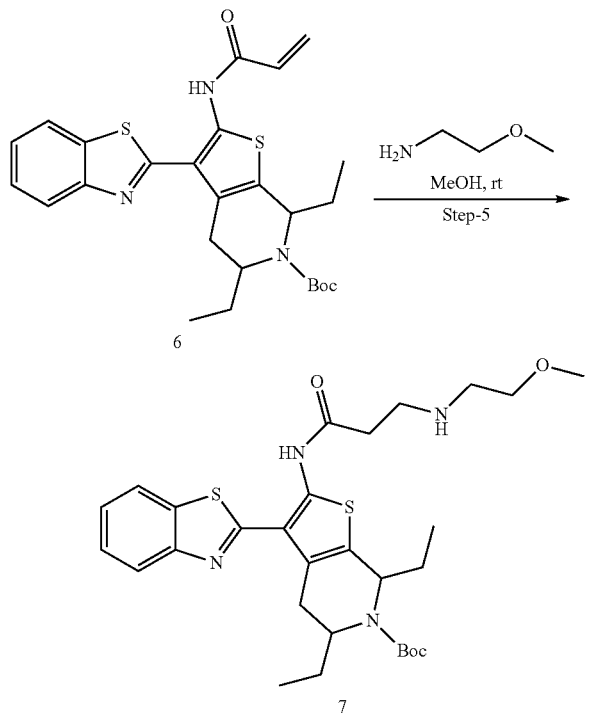

To a solution of tert-butyl 2-acrylamido-3-(benzo[d]thiazol-2-yl)-5,7-diethyl-4,7-dihydrothieno[2,3-c]pyridine-6(5H)-carboxylate 6 (3 g, 6.024 mmol) in MeOH:THF (1:1, 20 mL) was added 2-methoxyethan-1-amine (0.78 mL, 9.036 mmol). The resulting reaction mixture was stirred at room temperature for 16 h. Progress of the reaction was monitored by TLC. After completion, the reaction mixture was concentrated to dryness under reduced pressure. The residue was washed with water and extracted with $CH_2Cl_2$ (thrice). The combined organic layer was dried over anhydrous $Na_2SO_4$, filtered and concentrated. The crude compound was purified by column chromatography eluting with 0-5% methanol in $CH_2Cl_2$ to afford the title compound 7 as yellow solid (1.3 g, yield 37%).

Step 6: N-(3-(Benzo[d]thiazol-2-yl)-5,7-diethyl-4,5,6,7-tetrahydrothieno[2,3-c]pyridin-2-yl)-3-((2-methoxyethyl)amino)propanamide

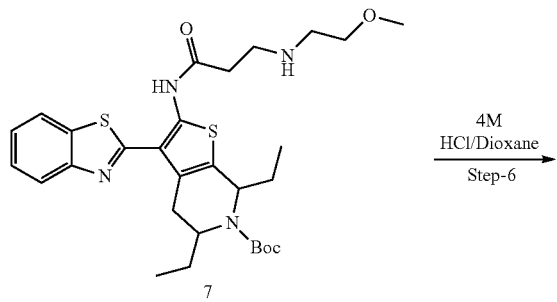

316

-continued

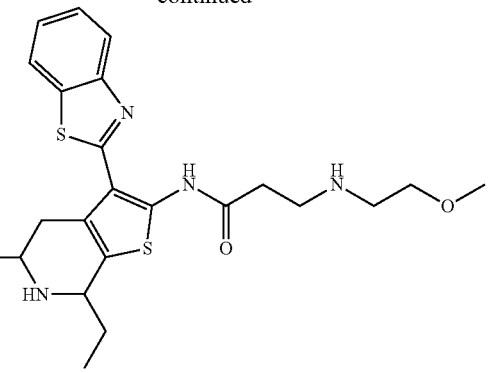

To a solution of tert-butyl 3-(benzo[d]thiazol-2-yl)-5,7-diethyl-2-(3-((2-methoxyethyl)amino)propanamido)-4,7-dihydrothieno[2,3-c]pyridine-6(5H)-carboxylate 7 (1.1 g, 1.919 mmol) in dioxane (20 mL) at 0° C. was added 4M HCl in dioxane (10 mL). After the addition, the resulting mixture was stirred at room temperature for 3 h. After completion, the reaction mixture was evaporated in vacuum resulting in a crude residue which was purified by trituration with methanol. The solid obtained was filtered and washed with diethyl ether and n-pentane to afford the title compound as yellow solid (1 g, HCl salt, crude). Chiral separation (Column: CHIRALART; 250 mm*4.6 mm*5 um; Mobile Phase: A: n-Hexane+0.1% TEA; B: ETOH: DCM (85:15)+0.1% TEA; Flow rate: 1.0 ml/min; Isocratic: 50% B) afforded Compounds 536 and 537.

Example 107. Synthesis of (S)—N-(3-(Benzo[d]thiazol-2-yl)-5-methyl-4,5,6,7-tetrahydrothieno[2,3-c]pyridin-2-yl)-3-((2-methoxyethyl)amino)propanamide (Compound 538)

Step 1: tert-Butyl 2-acrylamido-3-(benzo[d]thiazol-2-yl)-5-methyl-4,7-dihydrothieno[2,3-c]pyridine-6(5H)-carboxylate compound and tert-butyl 2-acrylamido-3-(benzo[d]thiazol-2-yl)-7-methyl-4,7-dihydrothieno[2,3-c]pyridine-6(5H)-carboxylate (5 and 6)

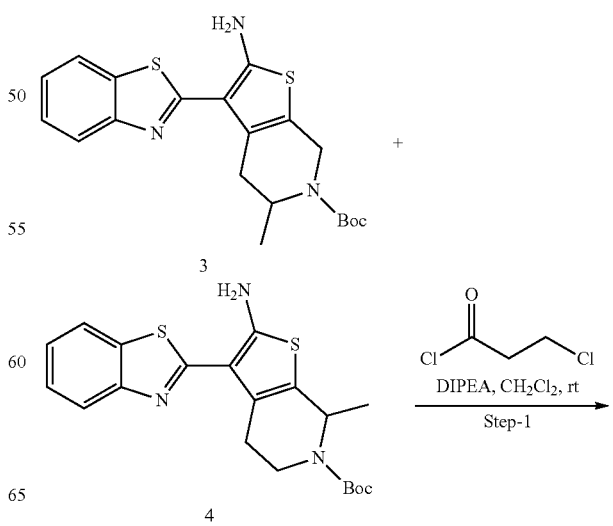

317
-continued

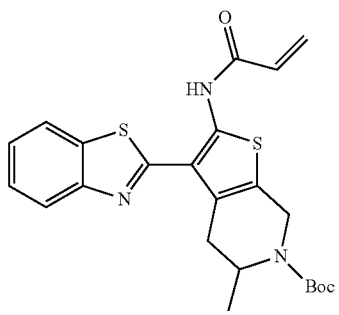

318
-continued

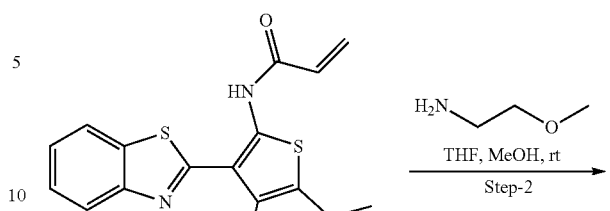

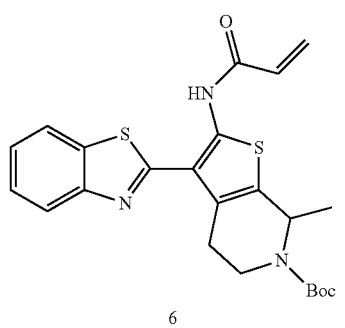

6

To a solution of 3 and 4 (800 mg, 1.99 mmol) in CH$_2$Cl$_2$ (10 mL) was added DIPEA (0.5 mL, 2.99 mmol) at room temperature and stirred for 20 min. To the resulting solution at 0° C. was added 3-chloropropanoyl chloride (380 mg, 2.99 mmol) and stirred at room temperature for 15 h. Reaction was monitored by TLC. After the completion of reaction (by LCMS) the reaction mixture was diluted with water and extracted with CH$_2$Cl$_2$. The combined organic layer was dried with anhydrous Na$_2$SO$_4$, filtered and concentrated to afford the title compound 5 and 6 as yellow solid (700 mg, crude).

Step 2: tert-Butyl 3-(benzo[d]thiazol-2-yl)-2-(3-((2-methoxyethyl)amino)propanamido)-5-methyl-4,7-dihydrothieno[2,3-c]pyridine-6(5H)-carboxylate compound and tert-butyl 3-(benzo[d]thiazol-2-yl)-2-(3-((2-methoxyethyl)amino) propanamido)-7-methyl-4,7-dihydrothieno[2,3-c]pyridine-6(5H)-carboxylate (7 and 8)

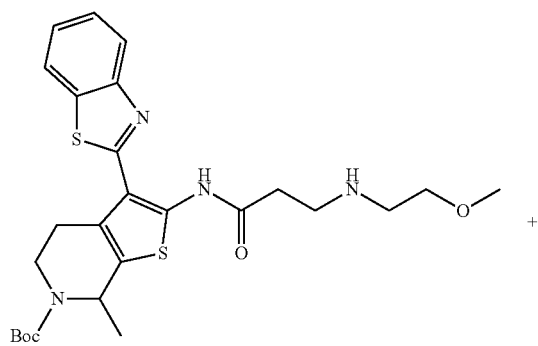

7

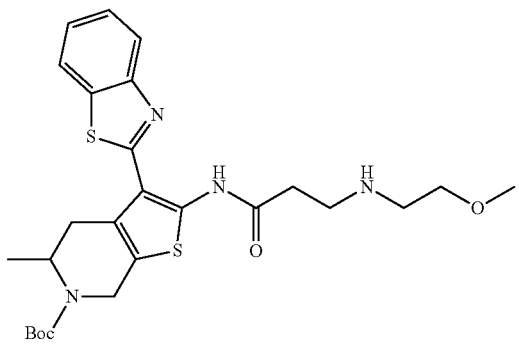

8

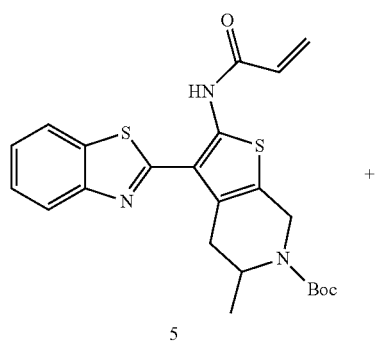

5

To a mixture of 5 and 6 (700 mg, 1.54 mmol) in MeOH:THF (1:1, 20 mL) was added 2-methoxyethan-1-amine (173 mg, 2.31 mmol). The resulting reaction mixture was stirred at room temperature for 15 h. Progress of the reaction was monitored by TLC. After completion, the reaction mixture was concentrated to dryness under reduced pressure. The crude compound was purified by column chromatography eluting with 0-10% methanol in CH$_2$Cl$_2$ to afford the title compound 7 and 8 as yellow solid (600 mg, yield 73%).

Step 3: N-(3-(Benzo[d]thiazol-2-yl)-5-methyl-4,5,6,7-tetrahydrothieno[2,3-c]pyridin-2-yl)-3-((2-methoxyethyl)amino)propanamide compound and N-(3-(Benzo[d]thiazol-2-yl)-7-methyl-4,5,6,7-tetrahydrothieno[2,3-c]pyridin-2-yl)-3-((2-methoxyethyl)amino)propanamide

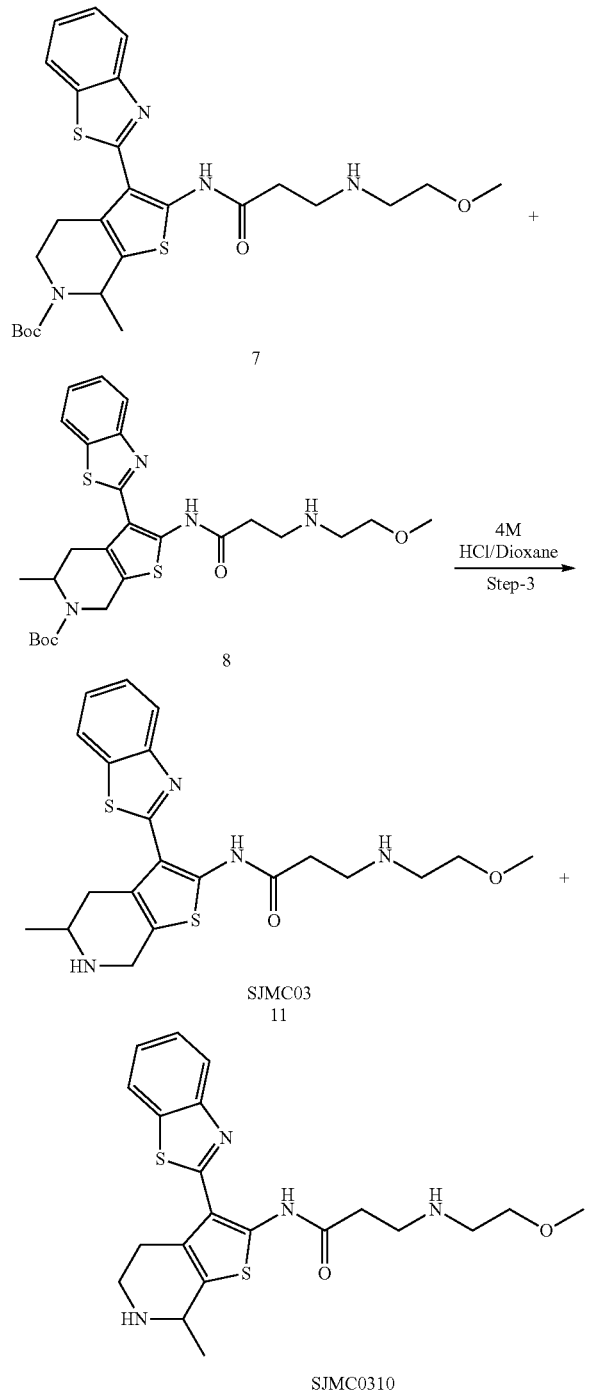

To mixture of 7 and 8 (600 mg, 1.132 mmol) in dioxane (10 mL) at 0° C. was added 4M HCl in dioxane (5 mL). After the addition, the resulting mixture was stirred at room temperature for 2 h. Reaction was monitored by TLC. After completion, the reaction mixture was evaporated in vacuum resulting in a crude residue which was triturated by diethyl ether and n-pentane to afford a mixture of the title compounds as yellow solid (600 mg, crude). Chiral separation (Column: CHIRALPAK; 250 mm*4.6 mm*5 um; Mobile Phase: A: n-Hexane+0.1% TEA; B: ETOH: DCM (85:15)+0.1% TEA; Flow rate: 1.0 ml/min; Isocratic: 50% B) afforded Compound 538.

Example 108. Synthesis of N-(3-(Benzo[d]thiazol-2-yl)-6-isopropyl-4,5,6,7-tetrahydrothieno[2,3-c]pyridin-2-yl)-3-(propylamino)propanamide (Compound 539)

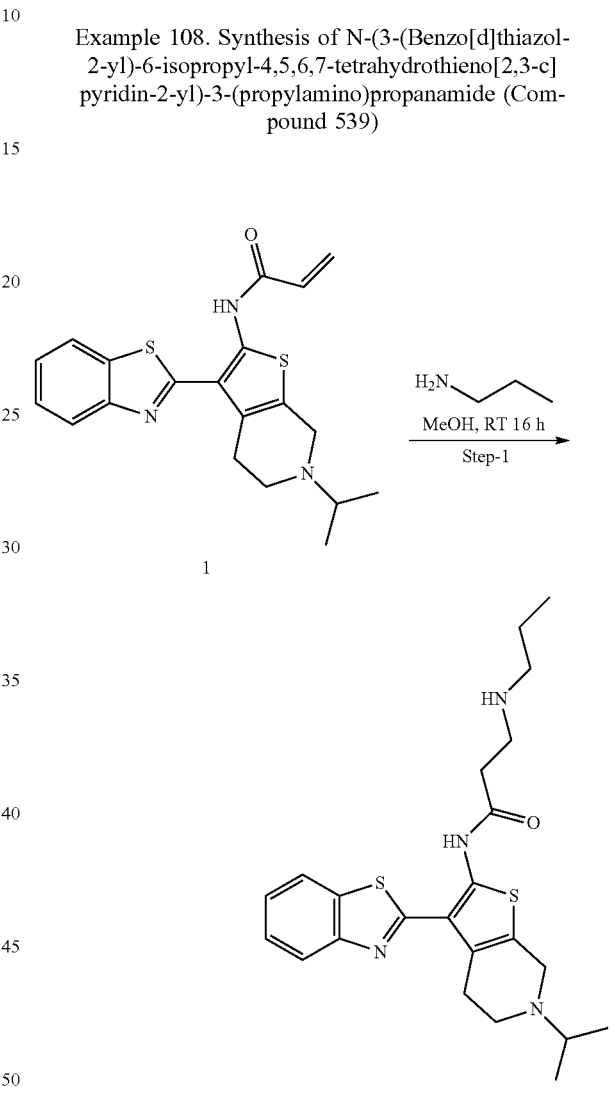

To a solution of N-(3-(benzo[d]thiazol-2-yl)-6-isopropyl-4,5,6,7-tetrahydrothieno[2,3-c]pyridin-2-yl)acrylamide 1 (200 mg, 0.522 mmol) in MeOH (2 mL) was added propan-1-amine (0.08 mL, 1.044 mmol). The resulting reaction mixture was stirred at room temperature for 16 h. Progress of the reaction was monitored by TLC. After completion, the reaction mixture was concentrated to dryness under reduced pressure. The crude residue was dissolved in $CH_2Cl_2$ and washed with water. The combined organic layers were dried with anhydrous $Na_2SO_4$, filtered and concentrated to get a crude residue. This crude compound was purified by silica gel flash (230-400 mesh) column chromatography eluting with 0-5% methanol in $CH_2Cl_2$ to afford the title compound as yellow solid (150 mg, yield 65%).

Example 109. Synthesis of N-(3-(Benzo[d]thiazol-2-yl)-6-isopropyl-4,5,6,7-tetrahydrothieno[2,3-c]pyridin-2-yl)-3-(ethylamino)propanamide (Compound 540)

Example 110. Synthesis of 3-(Azetidin-1-yl)-N-(3-(benzo[d]thiazol-2-yl)-6-isopropyl-4,5,6,7-tetrahydrothieno[2,3-c]pyridin-2-yl)propanamide (Compound 541)

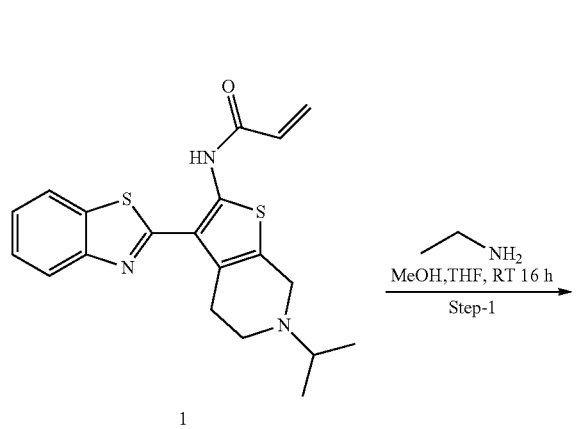

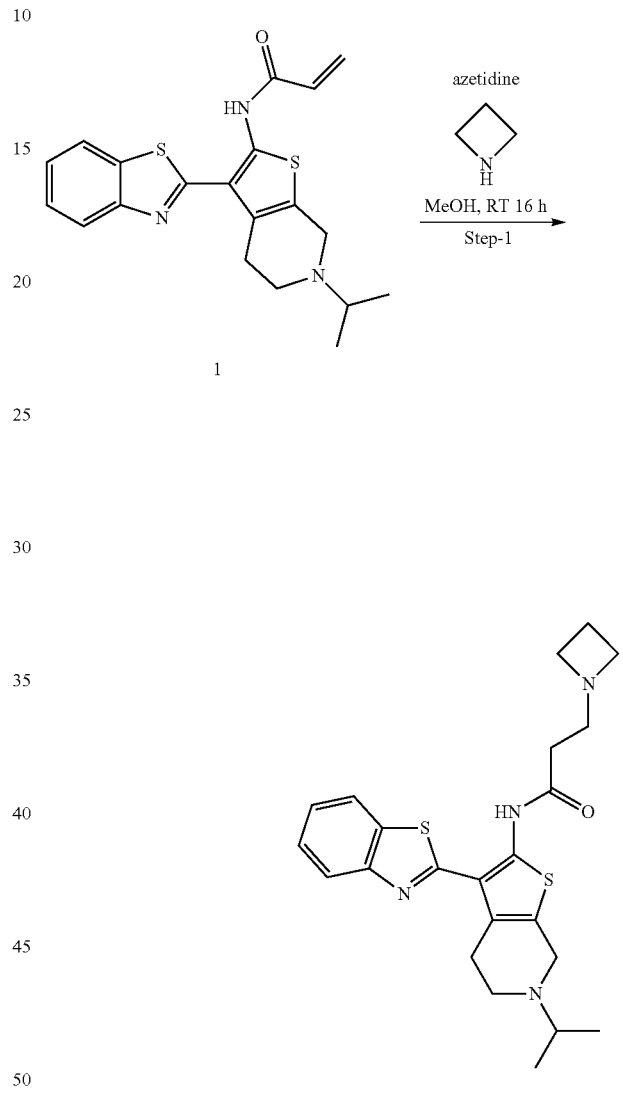

To a solution of N-(3-(benzo[d]thiazol-2-yl)-6-isopropyl-4,5,6,7-tetrahydrothieno[2,3-c]pyridin-2-yl)acrylamide 1 (150 mg, 0.391 mmol) in MeOH:THF (1:1, 10 mL) was added ethanamine (26 mg, 0.587 mmol). The resulting reaction mixture was stirred at room temperature for 16 h. Progress of the reaction was monitored by TLC. After completion, the reaction mixture was concentrated to dryness under reduced pressure. The crude compound was purified by silica gel flash (230-400 mesh) column chromatography eluting with 0-5% methanol in $CH_2Cl_2$ to afford the title compound as yellow solid (15 mg, yield 9%).

To a solution of N-(3-(benzo[d]thiazol-2-yl)-6-isopropyl-4,5,6,7-tetrahydrothieno[2,3-c]pyridin-2-yl)acrylamide 1 (100 mg, 0.261 mmol) in MeOH (2 mL) was added azetidine (29 mg, 0.522 mmol). The resulting reaction mixture was stirred at room temperature for 16 h. Progress of the reaction was monitored by TLC. After completion, the reaction mixture was concentrated to dryness under reduced pressure. The crude residue was dissolved in $CH_2Cl_2$ and washed with water. The combined organic layers were dried with anhydrous $Na_2SO_4$, filtered and concentrated to get a crude residue. This crude compound was purified by silica gel column chromatography eluting with 0-50% ethyl acetate in n-hexane to afford Compound 541 as yellow solid (15 mg, yield 13%).

Example 111. Synthesis of N-(3-(Benzo[d]thiazol-2-yl)-6-isopropyl-4,5,6,7-tetrahydrothieno[2,3-c]pyridin-2-yl)-3-(cyclopentylamino)propanamide (Compound 542)

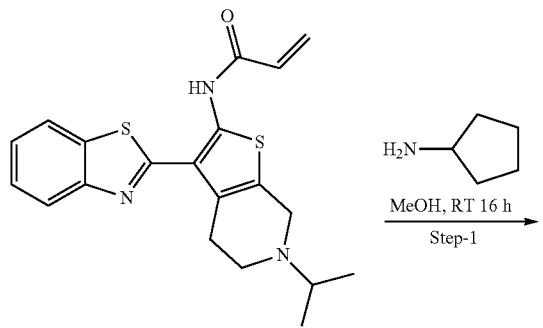

To a solution of N-(3-(benzo[d]thiazol-2-yl)-6-isopropyl-4,5,6,7-tetrahydrothieno[2,3-c]pyridin-2-yl)acrylamide 1 (100 mg, 0.261 mmol) in MeOH (2 mL) was added cyclopentanamine (44 mg, 0.522 mmol). The resulting reaction mixture was stirred at room temperature for 16 h. Progress of the reaction was monitored by TLC. After completion, the reaction mixture was concentrated to dryness under reduced pressure. The crude residue was dissolved in $CH_2Cl_2$ and washed with water. The combined organic layers were dried with anhydrous $Na_2SO_4$, filtered and concentrated to get a crude residue. This crude compound was purified by silica gel column chromatography eluting with 0-5% methanol in $CH_2Cl_2$ to afford Compound 542 as yellow solid (60 mg, yield 49%).

Example 112. Synthesis of N-(3-(5-Fluorobenzo[d]thiazol-2-yl)-5,7-dimethyl-4,5,6,7-tetrahydrothieno[2,3-c]pyridin-2-yl)-3-((2-methoxyethyl)amino)propanamide and Separation of Isomers (Compounds 544-547)

Step 1: 2-Amino-4-fluorobenzenethiol (2)

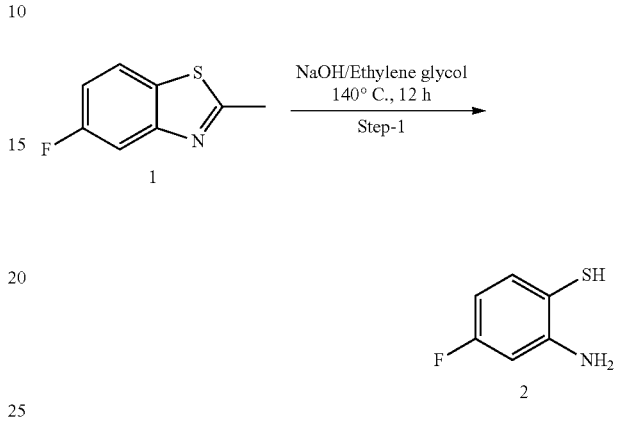

To a solution of 5-fluoro-2-methylbenzo[d]thiazole 1 (5 g, 29.90 mmol) in ethylene glycol (50 mL) was added 8 N NaOH (25 mL). The resulting reaction mixture was stirred at 140° C. for 3 h. Progress of the reaction was monitored by TLC. After completion, the reaction mixture was cooled to room temperature; acidified with 1N HCl up to pH=6 and extracted with ethyl acetate (thrice). The combined organic layer was dried over anhydrous $Na_2SO_4$; filtered and concentrated under reduced pressure to afford the title compound 2 as brown oil (4.2 g, crude).

Step 2: 2-(5-Fluorobenzo[d]thiazol-2-yl)acetonitrile (3)

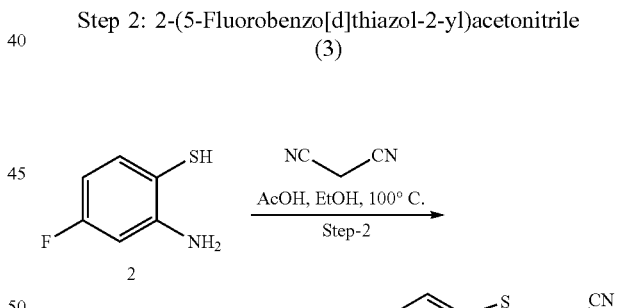

To a solution of 2-amino-4-fluorobenzenethiol 2 (4.2 g, 29.37 mmol) in EtOH (30 mL) was added malononitrile (1.94 g, 29.37 mmol) and AcOH (30 mL). The resulting reaction mixture was stirred at 80° C. for 12 h. Progress of the reaction was monitored by TLC. After completion, the reaction mixture was concentrated under reduced pressure to dryness. The crude compound was purified by column chromatography eluting with 0-20% ethyl acetate in n-hexane to afford the title compound 3 as brown solid (3.72 g yield 66%)

Step 3: tert-Butyl 2-amino-3-(5-fluorobenzo[d]thi-
azol-2-yl)-5,7-dimethyl-4,7-dihydrothieno[2,3-c]
pyridine-6(5H)-carboxylate (4)

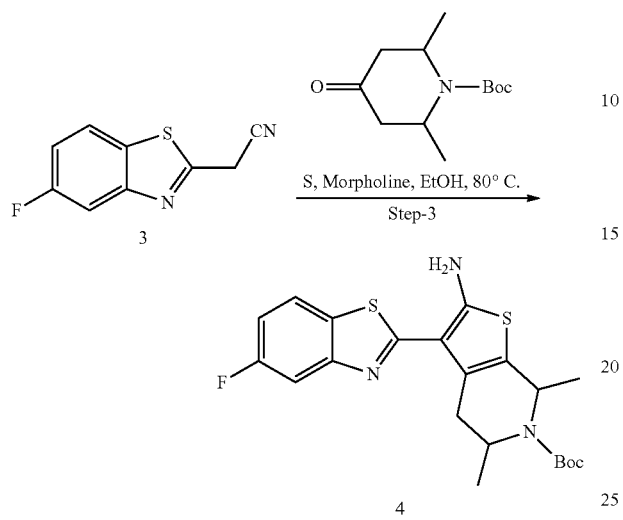

To a solution of 2-(5-fluorobenzo[d]thiazol-2-yl)acetonitrile 3 (1.5 g, 7.812 mmol) in ethanol (20 mL) was added tert-butyl 2,6-dimethyl-4-oxopiperidine-1-carboxylate (1.78 g, 7.812 mmol), elemental sulphur (250 mg, 7.812 mmol) and morpholine (670 mg, 7.812 mmol) at room temperature. After the addition, the resulting mixture was heated to reflux at 80° C. for 3 h. Progress of the reaction was monitored by TLC. After completion, the reaction mixture was evaporated in vacuum up to dryness. The crude compound was purified by column chromatography eluting with 0-20% ethyl acetate in n-hexane to afford the title compound 4 as off white solid (1.65 g, yield 58%).

Step 4: tert-Butyl 2-acrylamido-3-(5-fluorobenzo[d]
thiazol-2-yl)-5,7-dimethyl-4,7-dihydrothieno[2,3-c]
pyridine-6(5H)-carboxylate (5)

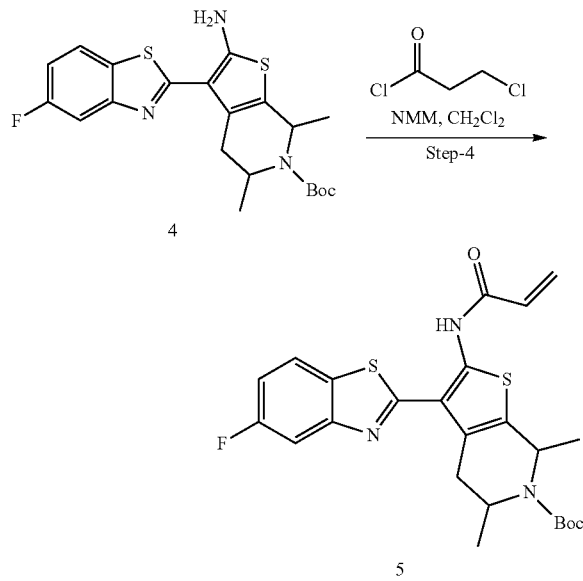

To a solution of tert-butyl 2-amino-3-(5-fluorobenzo[d]thiazol-2-yl)-5,7-dimethyl-4,7-dihydrothieno[2,3-c]pyridine-6(5H)-carboxylate 4 (1.6 g, 3.695 mmol) in $CH_2Cl_2$ (25 mL) at 0° C. was added DIPEA (0.95 mL, 5.542 mmol) and 3-chloropropanoyl chloride (700 mg, 5.542 mmol). The reaction mixture was stirred at room temperature for 2 h. After completion (monitored by TLC), the reaction mixture was concentrated to dryness under reduced pressure to afford the title compound 5 as light brown solid (2.1 g crude).

Step 5: tert-Butyl 3-(5-fluorobenzo[d]thiazol-2-yl)-
2-(3-((2-methoxyethyl)amino)propanamido)-5,7-
dimethyl-4,7-dihydrothieno[2,3-c]pyridine-6(5H)-
carboxylate (6)

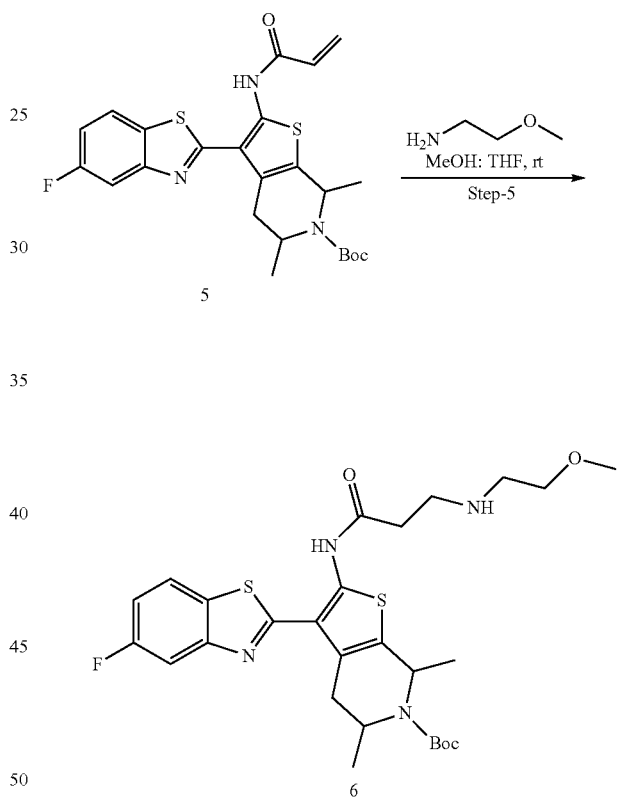

To a solution of tert-butyl 2-acrylamido-3-(5-fluorobenzo[d]thiazol-2-yl)-5,7-dimethyl-4,7-dihydrothieno[2,3-c]pyridine-6(5H)-carboxylate 5 (2.1 g, 4.312 mmol) in MeOH:THF (1:1, 30 mL) was added 2-methoxyethan-1-amine (0.48 g, 6.468 mmol). The resulting reaction mixture was stirred at room temperature for 16 h. Progress of the reaction was monitored by TLC. After completion, the reaction mixture was concentrated to dryness under reduced pressure. The residue was washed with water and extracted with $CH_2Cl_2$ (thrice). The combined organic layer was dried over anhydrous $Na_2SO_4$, filtered and concentrated. The crude compound was purified by column chromatography eluting with 0-5% methanol in $CH_2Cl_2$ to afford the title compound 6 as yellow solid (1.07 g, yield 44%).

Step 6: N-(3-(5-Fluorobenzo[d]thiazol-2-yl)-5,7-dimethyl-4,5,6,7-tetrahydrothieno[2,3-c]pyridin-2-yl)-3-((2-methoxyethyl)amino)propanamid

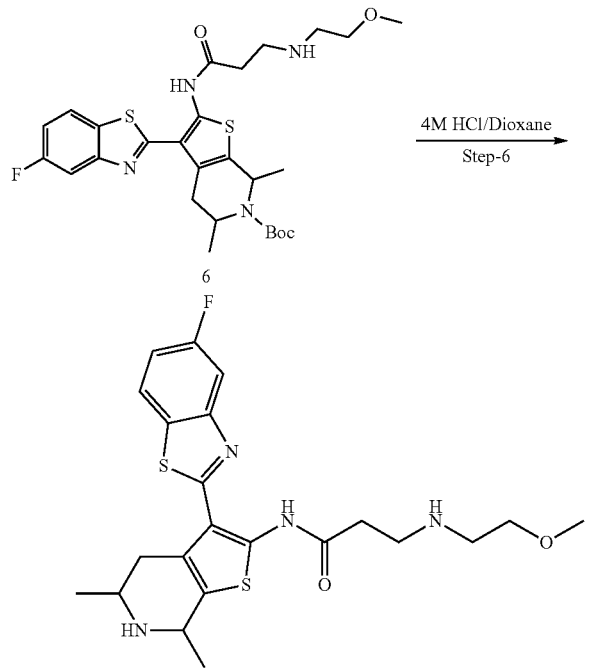

To a solution of tert-butyl 3-(5-fluorobenzo[d]thiazol-2-yl)-2-(3-((2-methoxyethyl)amino)propanamido)-5,7-dimethyl-4,7-dihydrothieno[2,3-c]pyridine-6(5H)-carboxylate 6 (1 g, 1.779 mmol) in dioxane (5 mL) at 0° C. was added 4M HCl in dioxane (10 mL). After the addition, the resulting mixture was stirred at room temperature for 3 h. After completion, the reaction mixture was evaporated in vacuum resulting in a crude residue which was purified by trituration with methanol. The solid obtained was filtered and washed with diethyl ether and n-pentane to afford the title compound as yellow solid (400 mg, yield 42%). Chiral separation (CHIRALART-SC, 250 mm×4.6 mm, 5 µm; Mobile Phase: A: n-Hexane+0.1% TEA; B: ETOH: DCM (85:15)+0.1% TEA; Flow rate: 1.20 mL/min; Isocratic: 60% B) afforded Compounds 544, 545, 546 and 547.

Example 113. Synthesis of 3-((2-Methoxyethyl)amino)-N-(7-methyl-3-(5-(pyridin-4-yl)benzo[d]thiazol-2-yl)-4,5,6,7-tetrahydrothieno[2,3-c]pyridin-2-yl)propanamide and Separation of Isomers (Compounds 548 and 569) and 3-((2-Methoxyethyl)amino)-N-(5-methyl-3-(5-(pyridin-4-yl)benzo[d]thiazol-2-yl)-4,5,6,7-tetrahydrothieno[2,3-c]pyridin-2-yl)propanamide (Compound 549)

Step 1: 2-Amino-4-bromobenzenethiol (2)

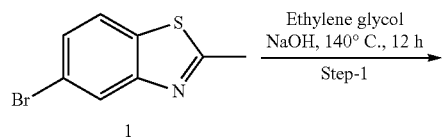

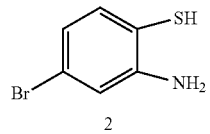

To a solution of 5-bromo-2-methylbenzo[d]thiazole 1 (5 g, 21.92 mmol) in ethylene glycol (50 mL) was added 8 N NaOH (25 mL). The resulting reaction mixture was stirred at 140° C. for 12 h. Progress of the reaction was monitored by TLC (30% ethyl acetate in n-hexane). After completion, the reaction mixture was cooled to room temperature; acidified with 1N HCl up to pH=6 and extracted with ethyl acetate (thrice). The combined organic layer was dried over anhydrous Na₂SO₄; filtered and concentrated under reduced pressure to afford the title compound 2 as yellow solid (5 g, crude).

Step 2: 2-(5-Bromobenzo[d]thiazol-2-yl)acetonitrile (3)

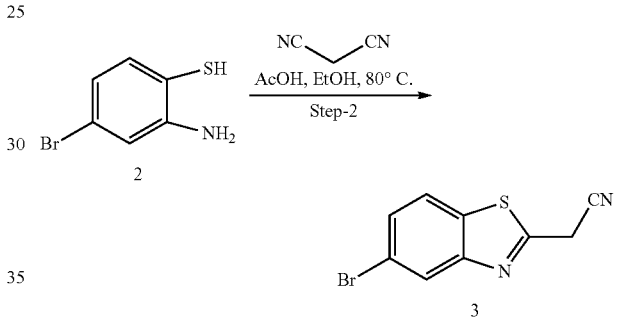

To a solution of 2-amino-4-bromobenzenethiol 2 (5 g, 24.63 mmol) in EtOH (250 mL) was added malononitrile (1.6 g, 24.63 mmol) and AcOH (5 mL). The resulting reaction mixture was stirred at 80° C. for 4 h. Progress of the reaction was monitored by TLC (30% ethyl acetate in n-hexane). After completion, the reaction mixture was concentrated under reduced pressure to dryness. The crude compound was purified by column chromatography eluting with 0-20% ethyl acetate in n-hexane to afford the title compound 3 as brown solid (4 g yield 64%)

Step 3: tert-Butyl 2-amino-3-(5-bromobenzo[d]thiazol-2-yl)-5-methyl-4,7-dihydrothieno[2,3-c]pyridine-6(5H)-carboxylate and tert-Butyl 2-amino-3-(5-bromobenzo[d]thiazol-2-yl)-7-methyl-4,7-dihydrothieno[2,3-c]pyridine-6(5H)-carboxylate (4 and 5)

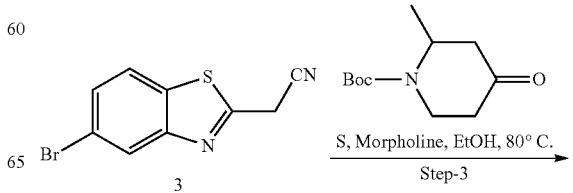

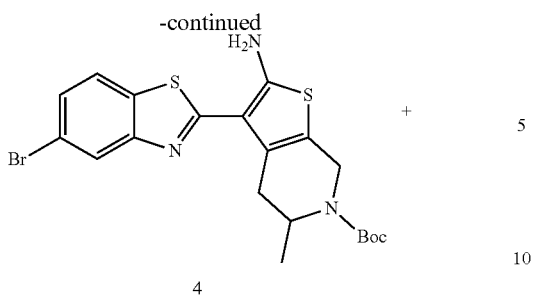

4

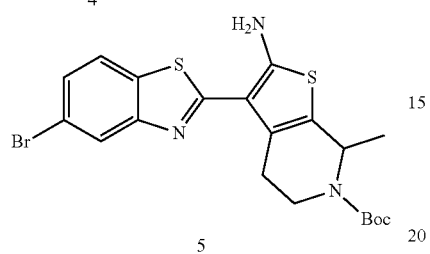

5

To a solution of 2-(5-bromobenzo[d]thiazol-2-yl)acetonitrile 3 (1.5 g, 5.952 mmol) in ethanol (20 mL) was added tert-butyl 2-methyl-4-oxopiperidine-1-carboxylate (1.26 g, 5.952 mmol), elemental sulphur (190 mg, 5.952 mmol) and morpholine (0.5 mL, 5.952 mmol) at room temperature. After the addition, the resulting mixture was heated to reflux at 80° C. for 16 h. Progress of the reaction was monitored by TLC. After completion, the reaction mixture was evaporated in vacuum up to dryness. The crude compound was purified by column chromatography eluting with 0-30% ethyl acetate in n-hexane to afford the title compound 4 and 5 as off white solid (1 g, yield 36%).

Step 4: tert-Butyl 2-acrylamido-3-(5-bromobenzo[d]thiazol-2-yl)-5-methyl-4,7-dihydrothieno[2,3-c]pyridine-6(5H)-carboxylate and tert-Butyl 2-acrylamido-3-(5-bromobenzo[d]thiazol-2-yl)-7-methyl-4,7-dihydrothieno[2,3-c]pyridine-6(5H)-carboxylate (6 and 7)

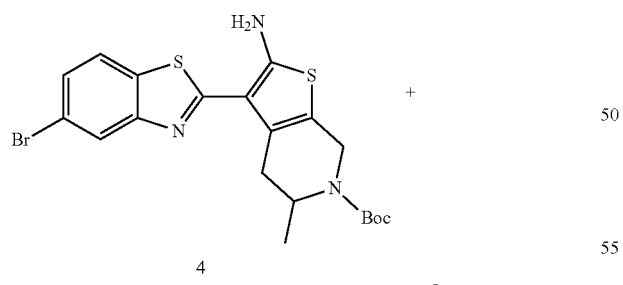

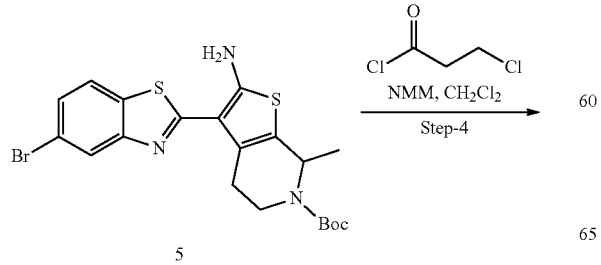

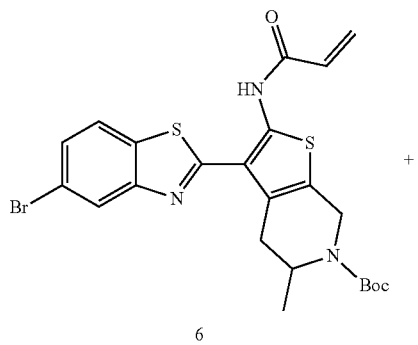

6

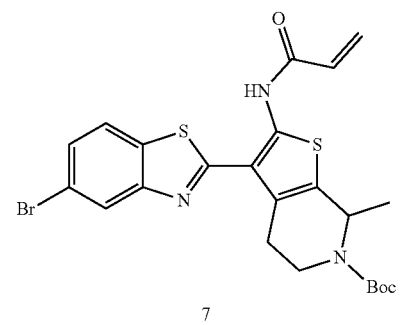

7

To a solution of 4 and 5 (1 g, 2.087 mmol) in CH$_2$Cl$_2$ (20 mL) at 0° C. was added DIPEA (1 mL, 6.260 mmol) and 3-chloropropanoyl chloride (530 mg, 4.175 mmol). The reaction mixture was stirred at room temperature for 2 h. After completion (monitored by TLC), the reaction mixture was concentrated to dryness under reduced pressure to afford the title compound 6 and 7 as light brown solid (1.2 g crude).

Step 5: tert-Butyl 3-(5-bromobenzo[d]thiazol-2-yl)-2-(3-((2-methoxyethyl)amino)propanamido)-5-methyl-4,7-dihydrothieno[2,3-c]pyridine-6(5H)-carboxylate and tert-Butyl 3-(5-bromobenzo[d]thiazol-2-yl)-2-(3-((2-methoxyethyl)amino)propanamido)-7-methyl-4,7-dihydrothieno[2,3-c]pyridine-6(5H)-carboxylate (8 and 9)

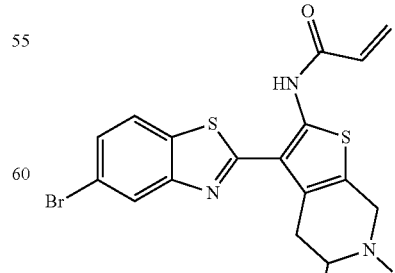

6

331
-continued

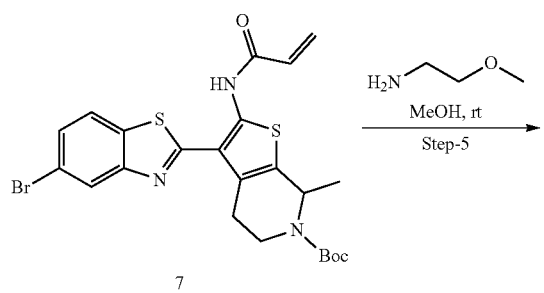

7

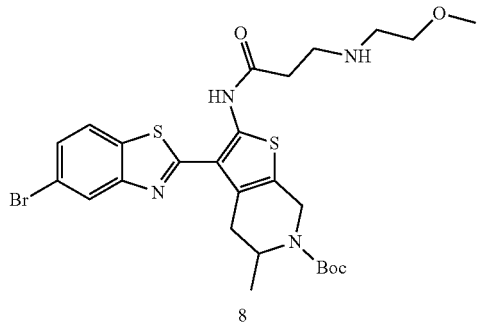

8

+

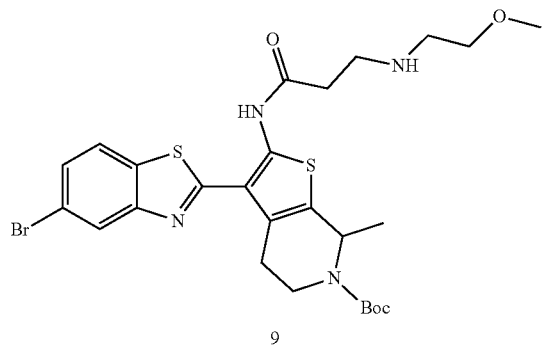

9

To a solution of 6 and 7 (1.2 g, 2.251 mmol) in MeOH (10 mL) was added 2-methoxyethan-1-amine (300 mg, 4.502 mmol). The resulting reaction mixture was stirred at room temperature for 16 h. Progress of the reaction was monitored by TLC. After completion, the reaction mixture was concentrated to dryness under reduced pressure. The crude compound was purified by column chromatography eluting with 0-30% ethyl acetate in n-hexane to afford the title compound 8 and 9 as yellow solid (1.2 g, yield 88%).

332

Step 6: tert-Butyl 2-(3-((2-methoxyethyl)amino)propanamido)-5-methyl-3-(5-(pyridin-4-yl)benzo[d]thiazol-2-yl)-4,7-dihydrothieno[2,3-c]pyridine-6(5H)-carboxylate and tert-Butyl 2-(3-((2-methoxyethyl)amino)propanamido)-7-methyl-3-(5-(pyridin-4-yl)benzo[d]thiazol-2-yl)-4,7-dihydrothieno[2,3-c]pyridine-6(5H)-carboxylate (10 and 11)

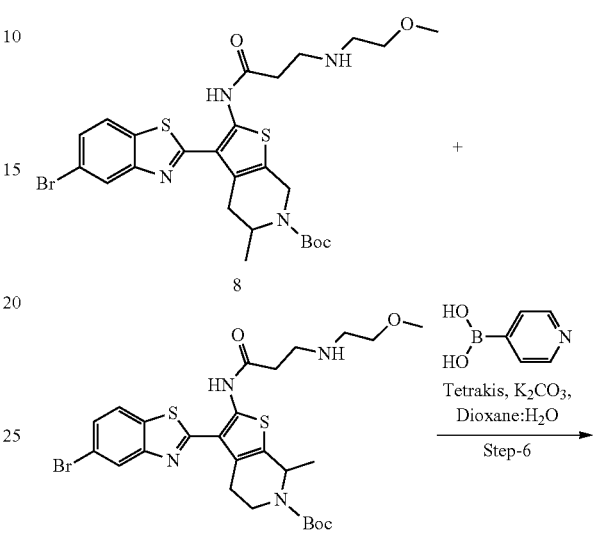

To a solution of 8 and 9 (500 mg, 0.822 mmol) in dioxane (5 mL) was added solution of K₂CO₃ (226 mg, 1.644 mmol) in water (0.5 mL) and degassed under argon atmosphere for 10 min. Followed by addition of Pd(PPh₃)₄ (94 mg, 0.082 mmol) and pyridin-4-ylboronic acid (150 mg, 1.23 mmol) and degassed with argon for another 10 min. The reaction mixture was heated to 100° C. for 16 h. After the completion of reaction (monitored by LCMS), the reaction mixture was diluted with water and extracted with ethyl acetate (thrice). The combined organic layers were dried with anhydrous Na₂SO₄, filtered and concentrated to get a crude residue. This crude compound was purified by silica gel column chromatography eluting with 0-10% methanol in CH₂Cl₂ to afford the title compound 10 and 11 (200 mg, yield 40%).

Step 7: 3-((2-Methoxyethyl)amino)-N-(7-methyl-3-(5-(pyridin-4-yl)benzo[d]thiazol-2-yl)-4,5,6,7-tetrahydrothieno[2,3-c]pyridin-2-yl)propanamide and 3-((2-Methoxyethyl)amino)-N-(5-methyl-3-(5-(pyridin-4-yl)benzo[d]thiazol-2-yl)-4,5,6,7-tetrahydrothieno[2,3-c]pyridin-2-yl)propanamide

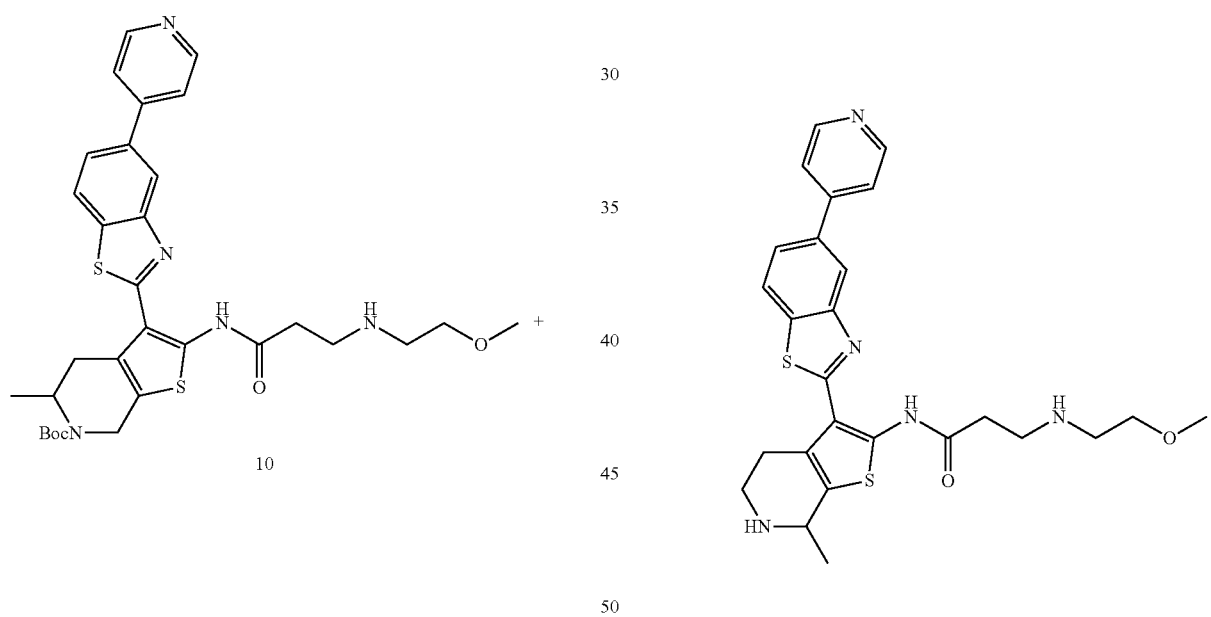

10

11

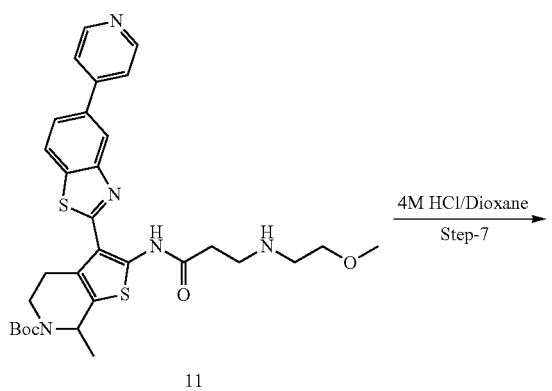

4M HCl/Dioxane
Step-7

-continued

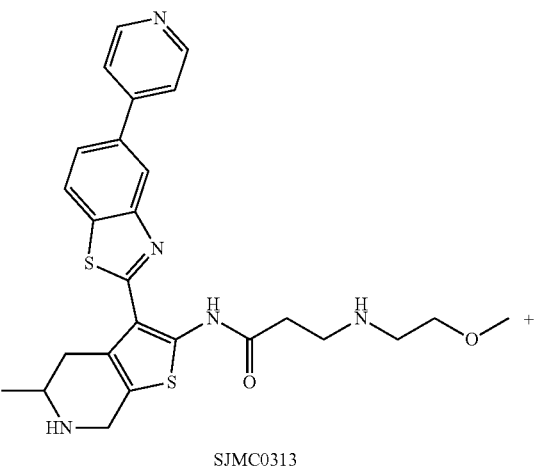

SJMC0313

To a solution of 10 and 11 (200 mg, 0.329 mmol) in dioxane (1 mL) at 0° C. was added 4M HCl in dioxane (2 mL). After the addition, the resulting mixture was stirred at room temperature for 2 h. After completion, the reaction mixture was evaporated in vacuum resulting in a crude residue which was purified by trituration with methanol. The solid obtained was filtered and washed with diethyl ether and n-pentane to afford the title compound as yellow solid (200 mg, crude). Chiral separation (Column: CHIRALART-SC, 250 mm×4.6 mm, 5 μm; Mobile Phase: A: n-Hexane+0.1% TEA; B: ETOH: DCM (85:15)+0.1% TEA; Flow rate: 1.0 mL/min; Isocratic: 70% B) afforded Compounds 548, 569, 549 and an isomer of Compound 549.

Example 114. Synthesis of 3-((2-Methoxyethyl)amino)-N-(5-methyl-3-(5-(trifluoromethyl)benzo[d]thiazol-2-yl)-4,5,6,7-tetrahydrothieno[2,3-c]pyridin-2-yl)propanamide and Separation of Isomers (Compounds 550 and 551)

Step 1: 2-(5-(Trifluoromethyl)benzo[d]thiazol-2-yl)acetonitrile (2)

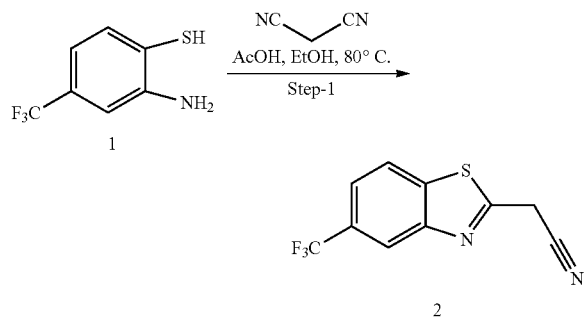

To a solution of 2-amino-4-(trifluoromethyl)benzenethiol 1 (5 g, 25.91 mmol) in EtOH (50 mL) was added malononitrile (1.71 g, 25.91 mmol) and AcOH (10 mL). The resulting reaction mixture was stirred at 80° C. for 4 h. Progress of the reaction was monitored by TLC (30% ethyl acetate in n-hexane). After completion, the reaction mixture was concentrated under reduced pressure to dryness. The crude compound was purified by column chromatography eluting with 0-20% ethyl acetate in n-hexane to afford the title compound 2 as brown solid (3 g yield 48%)

Step 2: tert-Butyl 2-amino-5-methyl-3-(5-(trifluoromethyl)benzo[d]thiazol-2-yl)-4,7-dihydrothieno[2,3-c]pyridine-6(5H)-carboxylate and tert-Butyl 2-amino-7-methyl-3-(5-(trifluoromethyl)benzo[d]thiazol-2-yl)-4,7-dihydrothieno[2,3-c]pyridine-6(5H)-carboxylate (4 and 5)

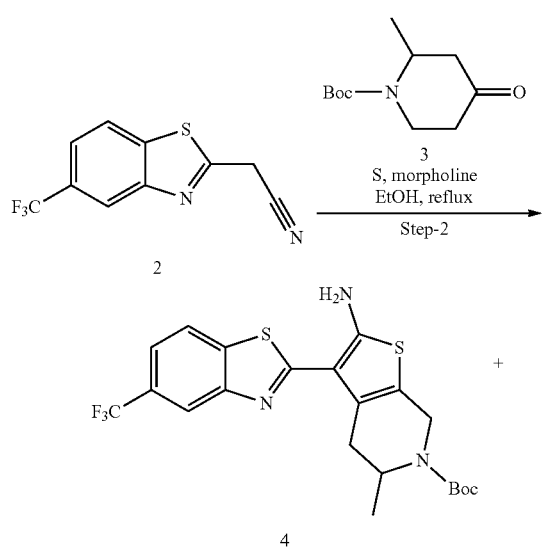

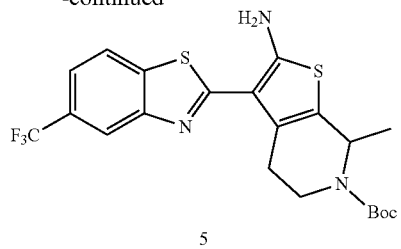

To a solution of 2-(5-(trifluoromethyl)benzo[d]thiazol-2-yl)acetonitrile 2 (1.5 g, 6.198 mmol) in ethanol (10 mL) was added tert-butyl 2-methyl-4-oxopiperidine-1-carboxylate 3 (1.3 g, 6.198 mmol), elemental sulphur (198 mg, 6.198 mmol) and morpholine (0.53 mL, 6.198 mmol) at room temperature. After the addition, the resulting mixture was heated to reflux at 80° C. for 16 h. Progress of the reaction was monitored by TLC. After completion, the reaction mixture was evaporated in vacuum up to dryness. The crude compound was purified by column chromatography eluting with 0-30% ethyl acetate in n-hexane to afford the title compound 4 and 5 as off white solid (800 mg, yield 27%).

Step 3: tert-Butyl 2-acrylamido-5-methyl-3-(5-(trifluoromethyl)benzo[d]thiazol-2-yl)-4,7-dihydrothieno[2,3-c]pyridine-6(5H)-carboxylate and tert-Butyl 2-acrylamido-7-methyl-3-(5-(trifluoromethyl)benzo[d]thiazol-2-yl)-4,7-dihydrothieno[2,3-c]pyridine-6(5H)-carboxylate (6 and 7)

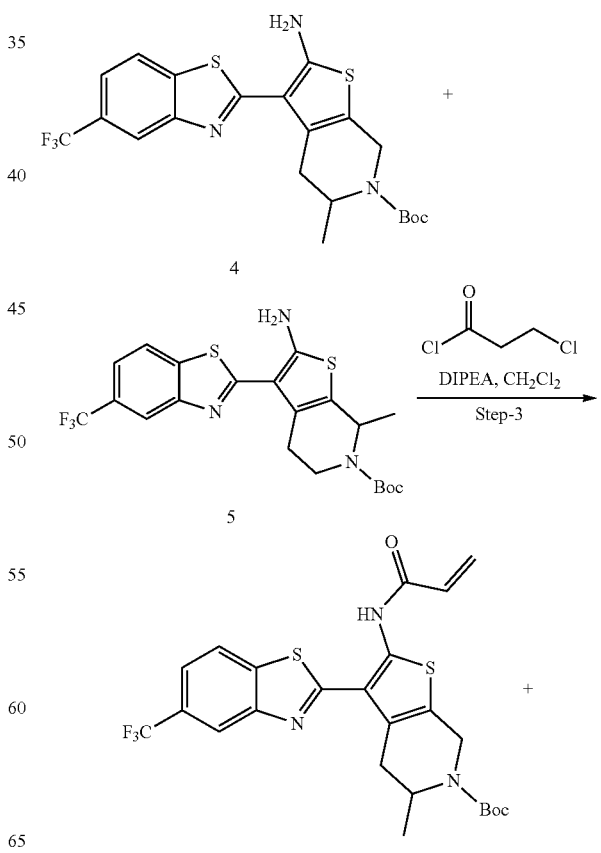

-continued

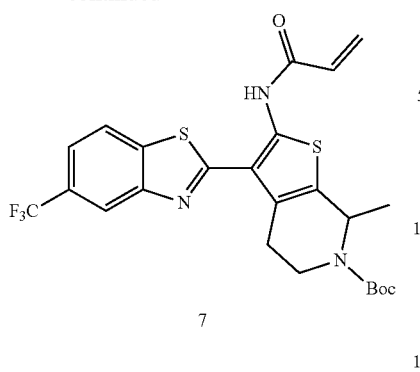

7

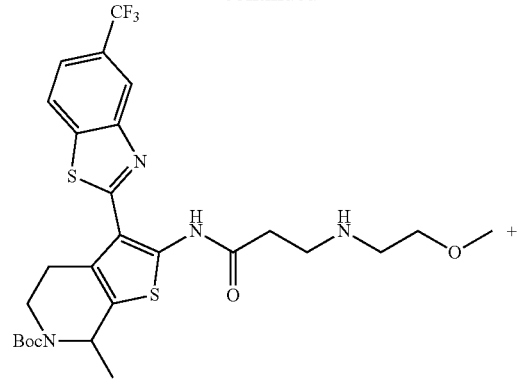

8

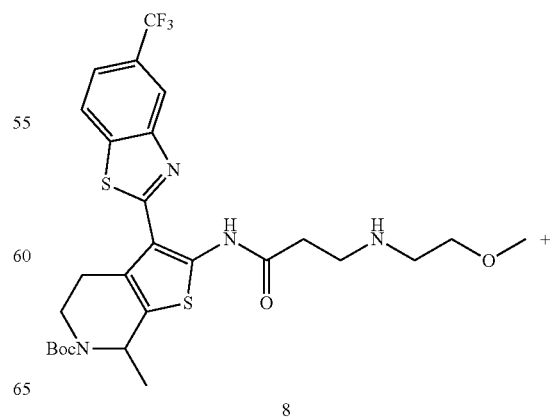

9

To a solution of 4 and 5 (800 mg, 1.705 mmol) in CH$_2$Cl$_2$ (15 mL) at 0° C. was added DIPEA (0.59 mL, 3.411 mmol) and 3-chloropropanoyl chloride (324 mg, 2.558 mmol). The reaction mixture was stirred at room temperature for 2 h. After completion (monitored by TLC), the reaction mixture was concentrated to dryness under reduced pressure to afford the title compound 6 and 7 as light brown solid (890 mg crude).

Step 4: 3-((2-Methoxyethyl)amino)-N-(5-methyl-3-(5-(trifluoromethyl)benzo[d]thiazol-2-yl)-4,5,6,7-tetrahydrothieno[2,3-c]pyridin-2-yl)propanamide and 3-((2-Methoxyethyl)amino)-N-(7-methyl-3-(5-(trifluoromethyl)benzo[d]thiazol-2-yl)-4,5,6,7-tetrahydrothieno[2,3-c]pyridin-2-yl)propanamide (8 and 9)

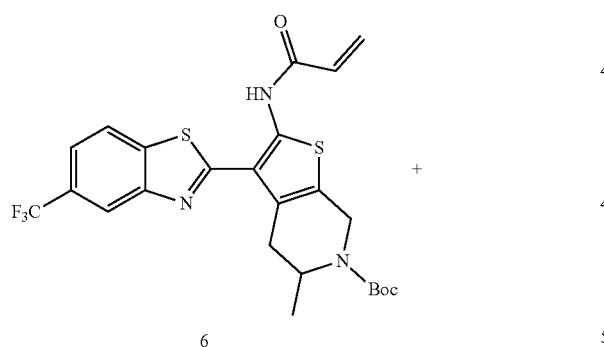

6

To a solution of 6 and 7 (800 mg, 1.529 mmol) in MeOH (5 mL) was added 2-methoxyethan-1-amine (230 mg, 3.059 mmol). The resulting reaction mixture was stirred at room temperature for 16 h. Progress of the reaction was monitored by TLC. After completion, the reaction mixture was concentrated to dryness under reduced pressure. The crude compound was purified by column chromatography eluting with 0-30% ethyl acetate in n-hexane to afford the title compound 8 and 9 as yellow solid (600 mg, yield 65%).

Step 7: 3-((2-Methoxyethyl)amino)-N-(5-methyl-3-(5-(trifluoromethyl)benzo[d]thiazol-2-yl)-4,5,6,7-tetrahydrothieno[2,3-c]pyridin-2-yl)propanamide and 3-((2-Methoxyethyl)amino)-N-(7-methyl-3-(5-(trifluoromethyl) benzo[d]thiazol-2-yl)-4,5,6,7-tetrahydrothieno[2,3-c]pyridin-2-yl)propanamide

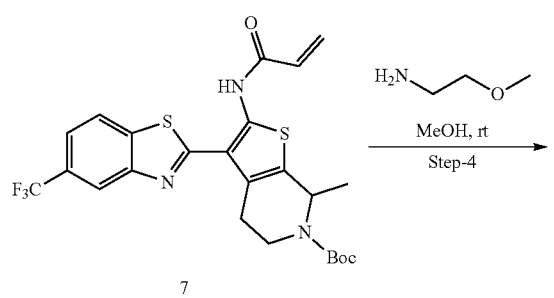

7

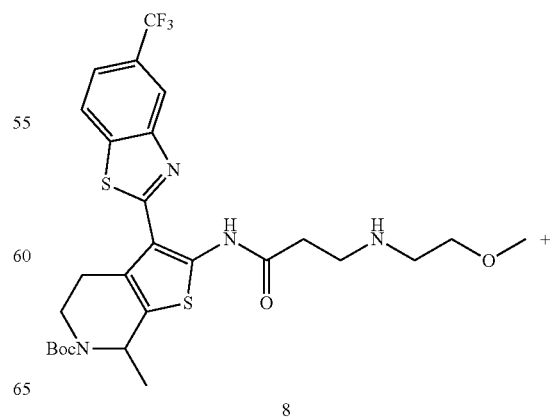

8

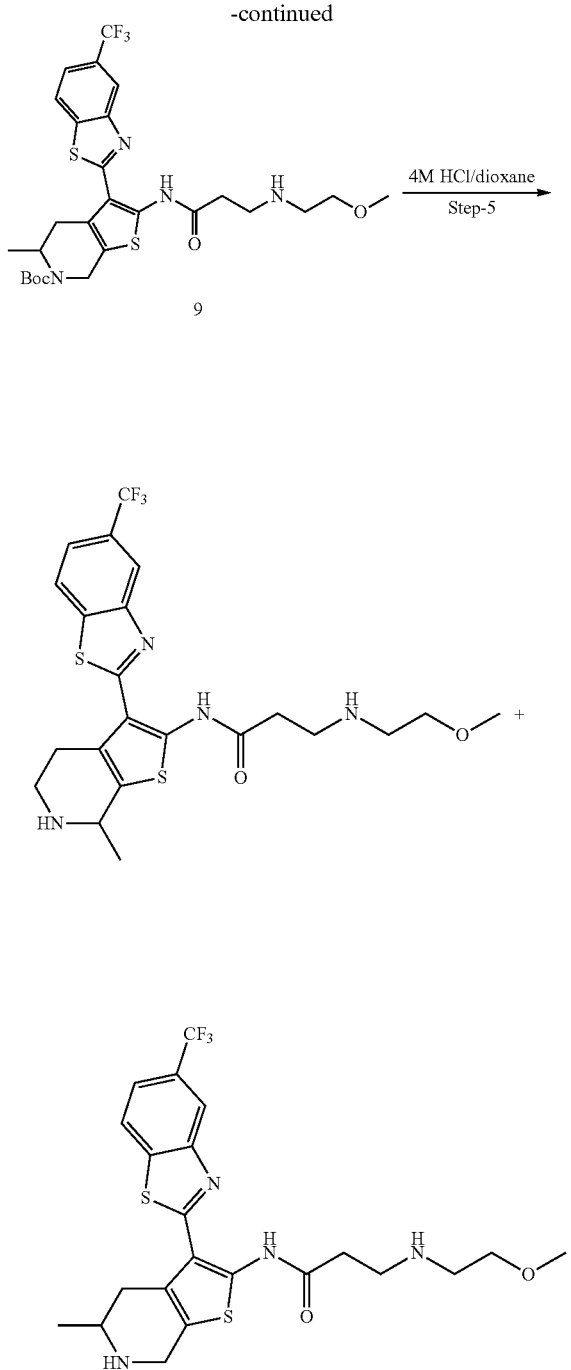

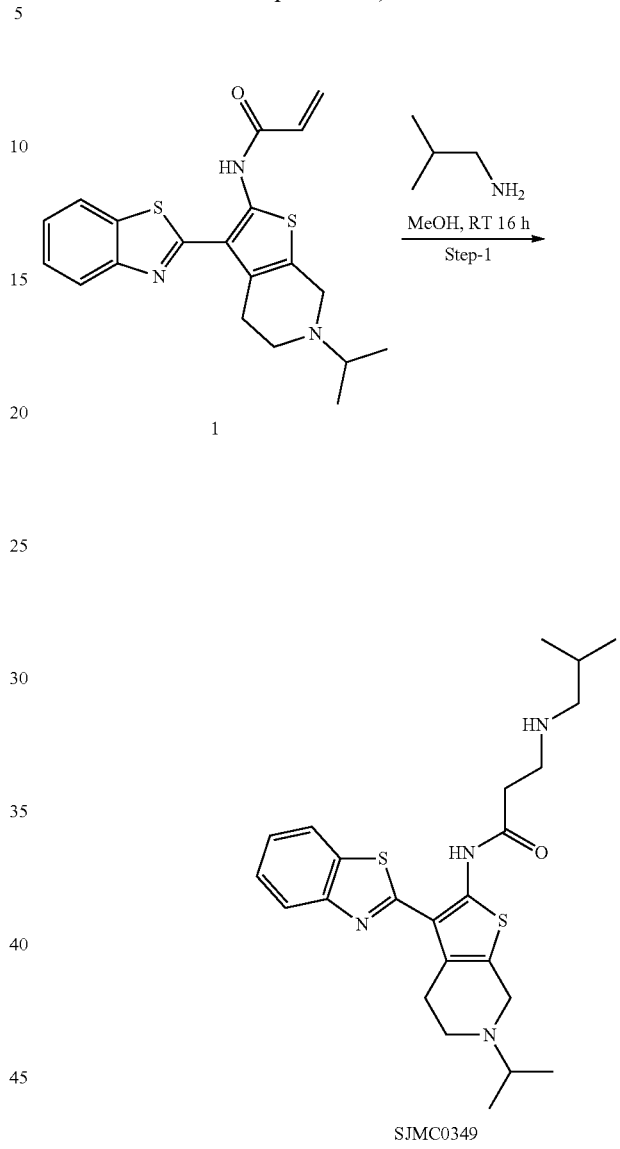

Example 115. Synthesis of N-(3-(Benzo[d]thiazol-2-yl)-6-isopropyl-4,5,6,7-tetrahydrothieno[2,3-c]pyridin-2-yl)-3-(isobutylamino)propanamide (Compound 552)

To a solution of 8 and 9 (150 mg, 0.251 mmol) in dioxane (1 mL) at 0° C. was added 4M HCl in dioxane (2 mL). After the addition, the resulting mixture was stirred at room temperature for 2 h. After completion, the reaction mixture was evaporated in vacuum resulting in a crude residue which was purified by trituration with methanol. The solid obtained was filtered and washed with diethyl ether and n-pentane to afford the title compound as yellow solid (100 mg, yield 70%). Chiral separation f (Column: CHIRALART Cellulose-SC, 250 mm×4.6 mm, 5 μm; Mobile Phase: A: n-Hexane+0.1% TEA; B: ETOH: DCM (85:15)+0.1% TEA; Flow rate: 1.0 mL/min; Isocratic: 50% B) afforded Compounds 550 and 551.

To a solution of N-(3-(benzo[d]thiazol-2-yl)-6-isopropyl-4,5,6,7-tetrahydrothieno[2,3-c]pyridin-2-yl)acrylamide 1 (100 mg, 0.261 mmol) in MeOH (2 mL) was added 2-methylpropan-1-amine (0.05 mL, 0.522 mmol). The resulting reaction mixture was stirred at room temperature for 16 h. Progress of the reaction was monitored by TLC. After completion, the reaction mixture was concentrated to dryness under reduced pressure. The crude residue was dissolved in $CH_2Cl_2$ and washed with water. The combined organic layers were dried with anhydrous $Na_2SO_4$, filtered and concentrated to get a crude residue. This crude compound was purified by silica gel column chromatography eluting with 0-50% ethyl acetate in n-hexane to afford the TFA salt of Compound 552 as yellow solid (40 mg, yield 33%).

Example 116. Synthesis of N-(3-([1,3]Dioxolo[4',5': 4,5]benzo[1,2-d]thiazol-6-yl)-4,5,6,7-tetrahydrothieno[2,3-c]pyridin-2-yl)-3-(sec-butylamino)propanamide (Compound 555)

Step 1: tert-Butyl 3-([1,3]dioxolo[4',5':4,5]benzo[1,2-d]thiazol-6-yl)-2-acrylamido-4,7-dihydrothieno[2,3-c]pyridine-6(5H)-carboxylate (5)

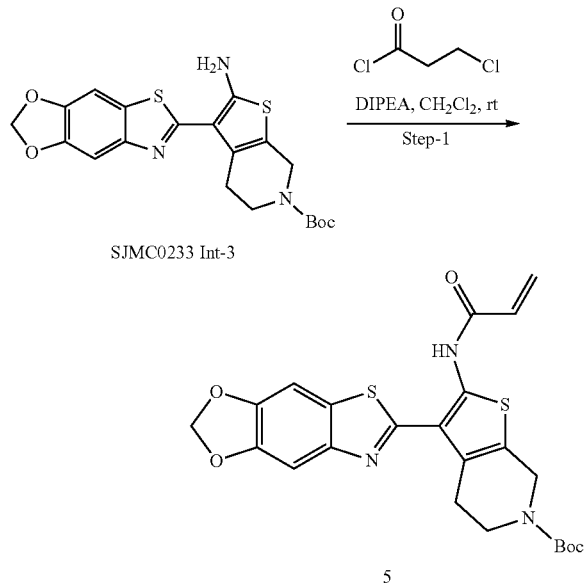

To a solution of tert-butyl 3-([1,3]dioxolo[4',5':4,5]benzo[1,2-d]thiazol-6-yl)-2-amino-4,7-dihydrothieno[2,3-c]pyridine-6(5H)-carboxylate SJMC0233 Int-3 (300 mg, 0.697 mmol) in DCM (20 mL) was added DIPEA (0.37 mL, 2.073 mmol) at room temperature and stirred for 20 min. To the resulting solution at 0° C. was added 3-chloropropanoyl chloride (175 mg, 1.395 mmol) and stirred at room temperature for 15 h. Reaction was monitored by TLC. After the completion of reaction (by LCMS) the reaction mixture was diluted with water and extracted with CH$_2$Cl$_2$ (thrice). The combined organic layer was dried with anhydrous Na$_2$SO$_4$, filtered and concentrated to afford the title compound 5 as yellow solid (400 mg, crude).

Step 2: tert-Butyl 3-([1,3]dioxolo[4',5':4,5]benzo[1,2-d]thiazol-6-yl)-2-(3-(sec-butylamino)propanamido)-4,7-dihydrothieno[2,3-c]pyridine-6(5H)-carboxylate (6)

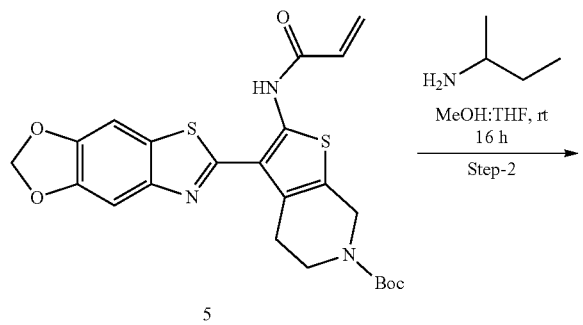

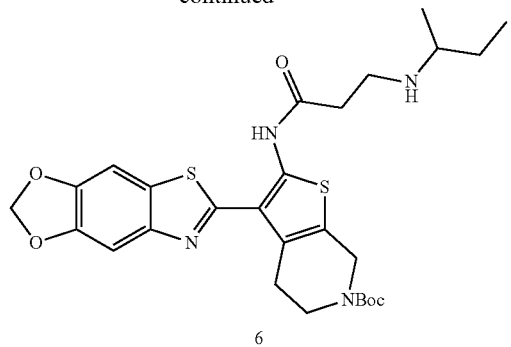

To a solution of tert-butyl 3-([1,3]dioxolo[4',5':4,5]benzo[1,2-d]thiazol-6-yl)-2-acrylamido-4,7-dihydrothieno[2,3-c]pyridine-6(5H)-carboxylate 5 (150 mg, 0.309 mmol) in MeOH:THF (1:1, 20 mL) was added butan-2-amine (34 mg, 0.463 mmol). The resulting reaction mixture was stirred at room temperature for 16 h. Progress of the reaction was monitored by TLC. After completion, the reaction mixture was concentrated to dryness under reduced pressure. The crude compound was purified by column chromatography eluting with 0-10% methanol in CH$_2$Cl$_2$ to afford the title compound 6 as yellow solid (100 mg, yield 58%).

Step 3: N-(3-([1,3]Dioxolo[4',5':4,5]benzo[1,2-d]thiazol-6-yl)-4,5,6,7-tetrahydrothieno[2,3-c]pyridin-2-yl)-3-(sec-butylamino)propanamide

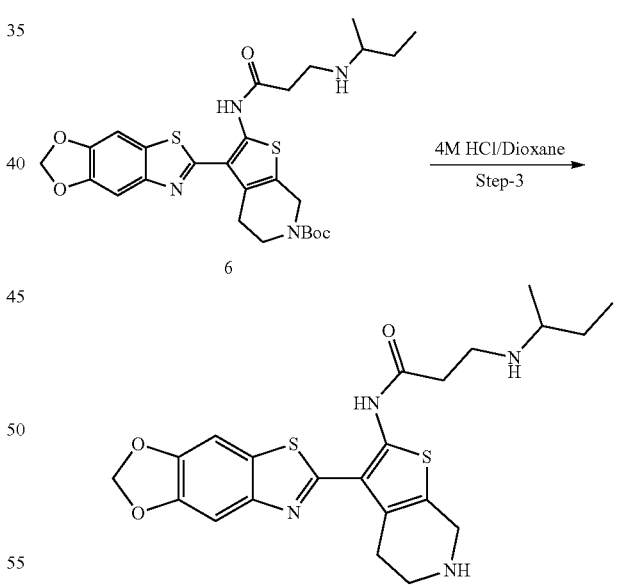

To a solution of tert-butyl 3-([1,3]dioxolo[4',5':4,5]benzo[1,2-d]thiazol-6-yl)-2-(3-(sec-butylamino)propanamido)-4,7-dihydrothieno[2,3-c]pyridine-6(5H)-carboxylate 6 (100 mg, 0.179 mmol) in dioxane (5 mL) at 0° C. was added 4M HCl in dioxane (5 mL). After the addition, the resulting mixture was stirred at room temperature for 3 h. Reaction was monitored by TLC. After completion, the reaction mixture was evaporated in vacuum resulting in a crude residue which was triturated by diethyl ether and n-pentane to afford Compound 555 as yellow solid (60 mg, yield 73%).

Example 117. Synthesis of N-(5,7-Dimethyl-3-(5-(1-methyl-1H-pyrazol-4-yl)benzo[d]thiazol-2-yl)-4,5,6,7-tetrahydrothieno[2,3-c]pyridin-2-yl)-3-((2-methoxyethyl)amino)propanamide and Separation of Isomers (Compounds 564-567)
Step 1: tert-Butyl 2-(3-((2-methoxyethyl)amino)propanamido)-5,7-dimethyl-3-(5-(1-methyl-1H-pyrazol-4-yl)benzo[d]thiazol-2-yl)-4,7-dihydrothieno[2,3-c]pyridine-6(5H)-carboxylate (5)
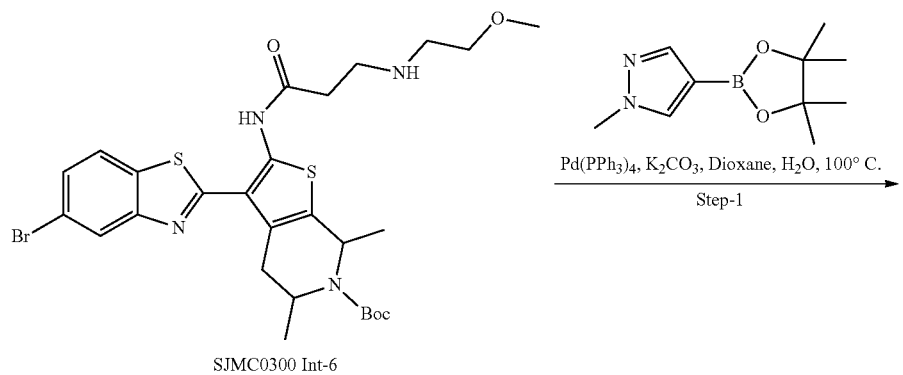
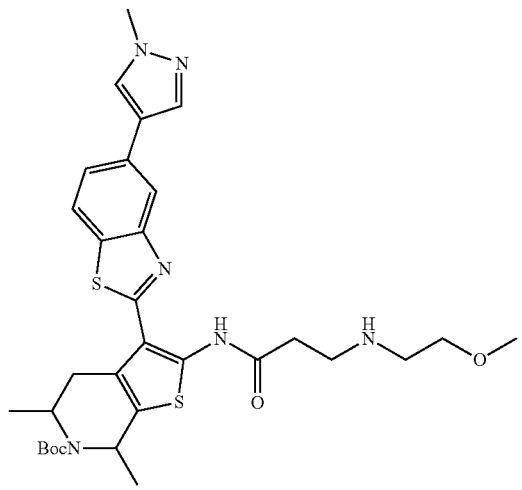

To a solution of tert-butyl 3-(5-bromobenzo[d]thiazol-2-yl)-2-(3-((2-methoxyethyl)amino)propanamido)-5,7-dimethyl-4,7-dihydrothieno[2,3-c]pyridine-6(5H)-carboxylate SJMC0300_Int-6 (500 mg, 0.803 mmol) in dioxane (10 mL) was added K$_2$CO$_3$ (277 mg, 2.01 mmol) in water (1 mL) and the reaction mixture was degassed under argon atmosphere for 10 min. Followed by addition of Pd(PPh$_3$)$_4$ (92 mg, 0.08 mmol) and 1-methyl-4-(4,4,5,5-tetramethyl-1,3,2-dioxaborolan-2-yl)-1H-pyrazole (250 mg, 1.205 mmol) and degassed with argon for another 20 min. The reaction mixture was heated to 100° C. for 16 h. After the completion of reaction (monitored by LCMS), the reaction mixture was diluted with water and extracted with ethyl acetate (thrice). The combined organic layers were dried with anhydrous Na$_2$SO$_4$, filtered and concentrated to get a crude residue. This crude compound was purified by silica gel column chromatography eluting with 0-6% methanol in CH$_2$Cl$_2$ to afford the title compound 7 as yellow solid (160 mg, 32% yield).

Step 2: N-(5,7-Dimethyl-3-(5-(1-methyl-1H-pyrazol-4-yl)benzo[d]thiazol-2-yl)-4,5,6,7-tetrahydrothieno[2,3-c]pyridin-2-yl)-3-((2-methoxyethyl)amino)propanamide

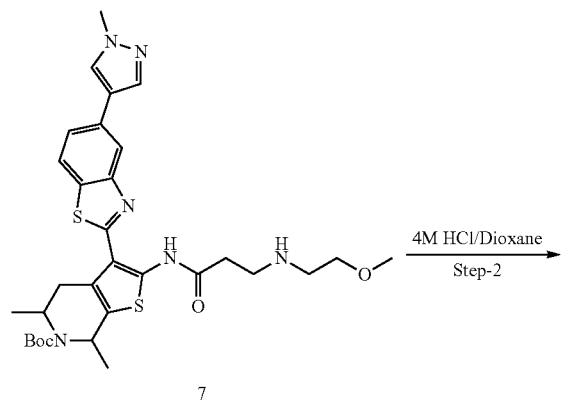

To a solution of tert-butyl 2-(3-((2-methoxyethyl)amino)propanamido)-5,7-dimethyl-3-(5-(1-methyl-1H-pyrazol-4-yl)benzo[d]thiazol-2-yl)-4,7-dihydrothieno[2,3-c]pyridine-6(5H)-carboxylate 7 (160 mg, 0.256 mmol) in dioxane (2 mL) at 0° C. was added 4M HCl in dioxane (2 mL). After the addition, the resulting mixture was stirred at room temperature for 3 h. After completion, the reaction mixture was evaporated in vacuum resulting in a crude residue which was purified by trituration with methanol. The solid obtained was filtered and washed with diethyl ether and n-pentane to afford the title compound as yellow solid (90 mg, yield 54%). Chiral separation f (Column: YMC CHIRALART-CELLULOSE-SC; 250 mm*4.6 mm*5 um; Mobile Phase: A: n-Hexane+0.1% TEA; B: ETOH: DCM (85:15)+0.1% TEA; Flow rate: 1.0 ml/min; Isocratic: 70% B) afforded Compounds 564, 565, 566, and 567.

Example 118. Synthesis of 3-((((S)-sec-butyl)amino)-N-(5,7-dimethyl-3-(5-(trifluoromethyl)benzo[d]thiazol-2-yl)-4,5,6,7-tetrahydrothieno[2,3-c]pyridin-2-yl)propanamide and Separation of Isomers (Compounds 584-587)

Step 1: tert-Butyl 2-amino-5,7-dimethyl-3-(5-(trifluoromethyl)benzo[d]thiazol-2-yl)-4,7-dihydrothieno[2,3-c]pyridine-6(5H)-carboxylate (2)

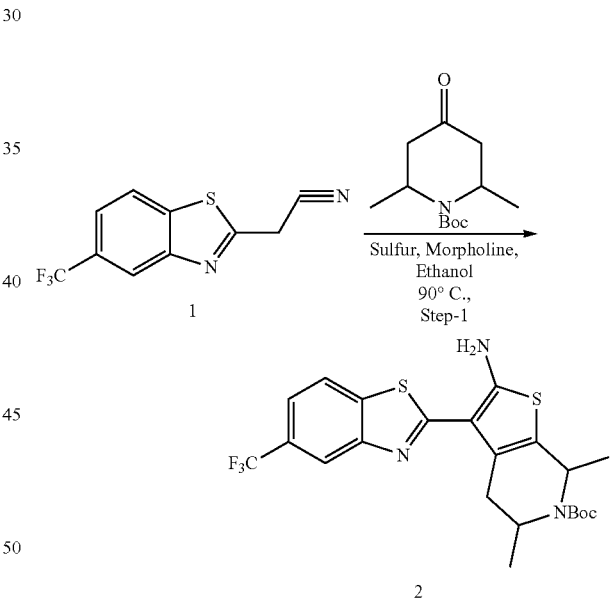

To a solution of 2-(5-(trifluoromethyl)benzo[d]thiazol-2-yl)acetonitrile 1 (0.500 g, 2.05 mmol), elemental sulphur (0.065 g, 2.05 mmol) and morpholine (0.2 mL, 2.05 mmol) was added tert-butyl 2,6-dimethyl-4-oxopiperidine-1-carboxylate (0.467 g, 2.05 mmol) at room temperature and the resulting reaction mixture was heated to reflux at 85° C. for 3 h. Reaction was monitored by TLC. After the completion, reaction mixture was evaporated to dryness on rotavapour and the crude compound. This crude compound was purified by silica gel column chromatography eluting with 0-10% methanol in CH$_2$Cl$_2$ to afford title compound 4 as yellow solid 2 as brown solid (0.300 g, 30%).

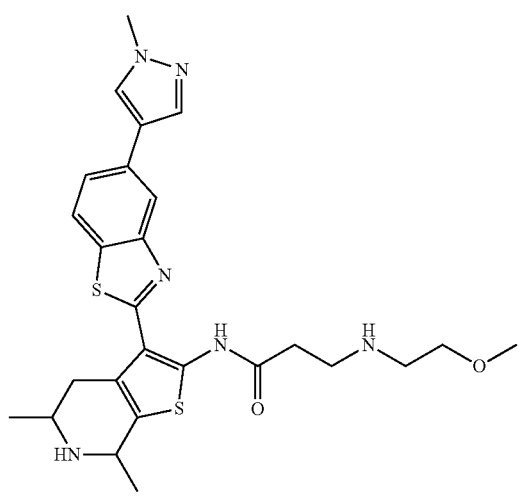

Step 2: tert-Butyl 2-acrylamido-5,7-dimethyl-3-(5-(trifluoromethyl)benzo[d]thiazol-2-yl)-4,7-dihydrothieno[2,3-c]pyridine-6(5H)-carboxylate (3)

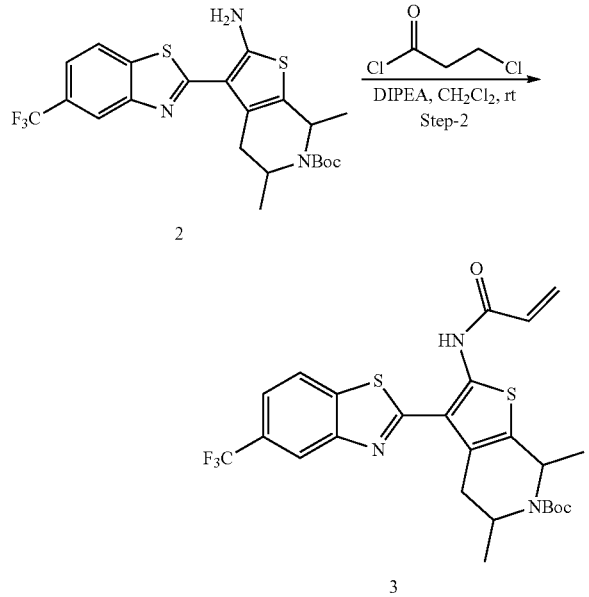

To a solution of tert-butyl 2-amino-5,7-dimethyl-3-(5-(trifluoromethyl)benzo[d]thiazol-2-yl)-4,7-dihydrothieno[2,3-c]pyridine-6(5H)-carboxylate (2) (380 mg, 0.786 mmol) in CH$_2$Cl$_2$ (10 mL) at 0° C. was added DIPEA (202 mg, 1.57 mmol) followed by 3-chloro propionyl chloride (150 mg, 1.180 mmol). Reaction mixture was stirred at room temperature for 3 h. Reaction was monitored by TLC. After completion, the reaction mixture was diluted with CH$_2$Cl$_2$ and washed with saturated NaHCO$_3$ solution and brine. The separated organic layer was dried over Na$_2$SO$_4$, filtered and concentrated in vacuum to get a crude compound 3 brown solid (2.0 g crude).

Step 3: tert-Butyl 2-(3-(((S)-sec-butyl)amino)propanamido)-5,7-dimethyl-3-(5-(trifluoromethyl)benzo[d]thiazol-2-yl)-4,7-dihydrothieno[2,3-c]pyridine-6(5H)-carboxylate (4)

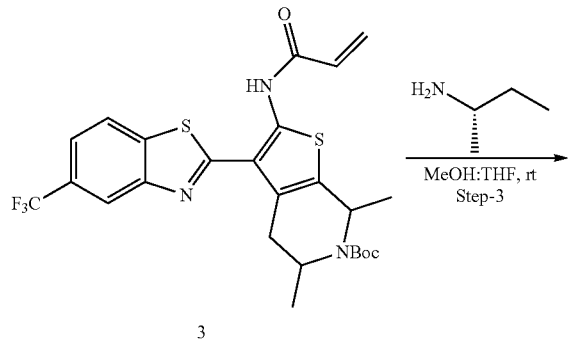

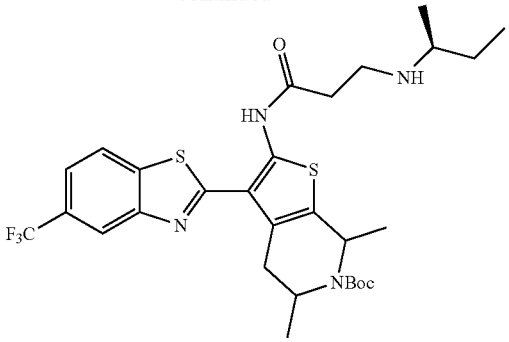

To a solution of tert-butyl 2-acrylamido-5,7-dimethyl-3-(5-(trifluoromethyl)benzo[d]thiazol-2-yl)-4,7-dihydrothieno[2,3-c]pyridine-6(5H)-carboxylate 3 (320 mg, 0.595 mmol) in MeOH:THF (1:1, 10 mL) was added (S) 2-methoxyethylamine (89 mg, 1.19 mmol). The resulting reaction mixture was stirred at room temperature for 16 h. Progress of the reaction was monitored by TLC. After completion, the reaction mixture was concentrated to dryness under reduced pressure. The crude residue was dissolved in CH$_2$Cl$_2$ and washed with water. The combined organic layers were dried with anhydrous Na$_2$SO$_4$, filtered and concentrated to get a crude residue. This crude compound was purified by silica gel column chromatography eluting with 0-10% methanol in CH$_2$Cl$_2$ to afford title compound 4 as yellow solid (200 mg, yield 55%).

Step 4: 3-(((S)-sec-butyl)amino)-N-(5,7-dimethyl-3-(5-(trifluoromethyl)benzo[d]thiazol-2-yl)-4,5,6,7-tetrahydrothieno[2,3-c]pyridin-2-yl)propanamide

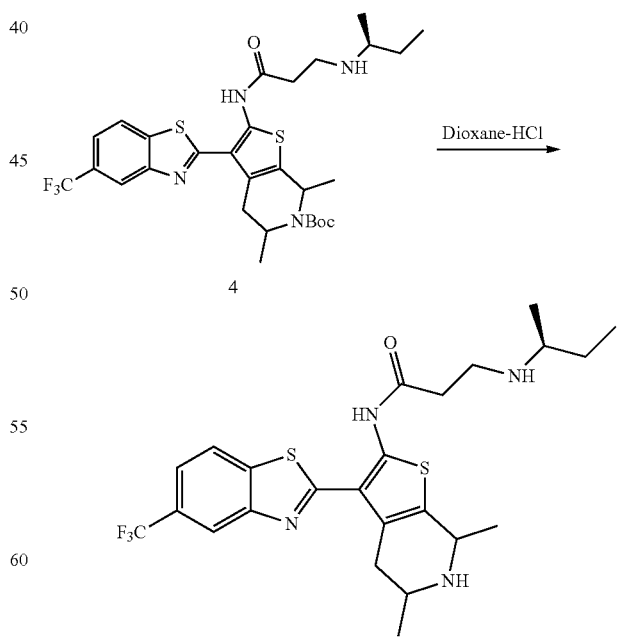

To a solution of tert-butyl 2-(3-(((S)-sec-butyl)amino) propanamido)-5,7-dimethyl-3-(5-(trifluoromethyl)benzo[d]thiazol-2-yl)-4,7-dihydrothieno[2,3-c]pyridine-6(5H)-carboxylate (4) (180 mg, 0.262 mmol) in dioxane (2 mL) at 0° C. was added 4M HCl in dioxane (2 mL) and the reaction mixture was stirred at room temperature for 4 h. After completion of the reaction (monitored by TLC), the reaction mixture was evaporated to dryness on rotavapour and residue was purified by trituration in ether and pentane to afford mixture of isomers as yellow solid. This mixture of isomers was purified by preparative HPLC separation to afford Compound 584 (20 mg, 11.6%), Compound 587 (20 mg, 11.6%), and Compound 586 (22 mg, 12.7%) and Compound 585 (25 mg, 14.5%).

Example 119. Synthesis of 3-((((S)-sec-butyl)amino)-N—((R)-5-methyl-3-(5-(pyridin-4-yl)benzo[d]thiazol-2-yl)-4,5,6,7-tetrahydrothieno[2,3-c]pyridin-2-yl)propanamide (Compound 589) and 3-(((S)-sec-butyl)amino)-N—((R)-7-methyl-3-(5-(pyridin-4-yl)benzo[d]thiazol-2-yl)-4,5,6,7-tetrahydrothieno[2,3-c]pyridin-2-yl)propanamide (Compound 590)

Step 1: tert-Butyl (R)-2-amino-3-(5-bromobenzo[d]thiazol-2-yl)-5-methyl-4,7-dihydrothieno[2,3-c]pyridine-6(5H)-carboxylate and tert-Butyl (R)-2-amino-3-(5-bromobenzo[d]thiazol-2-yl)-7-methyl-4,7-dihydrothieno[2,3-c]pyridine-6(5H)-carboxylate (2 and 3)

To a solution of 2-(5-bromobenzo[d]thiazol-2-yl)acetonitrile 1 (0.70 g, 2.77 mmol), elemental sulphur (88 mg, 2.77 mmol) and morpholine (0.24 mg, 2.77 mmol) in ethanol (20 mL) was added tert-butyl (R)-2-methyl-4-oxopiperidine-1-carboxylate (0.59 g, 2.77 mmol) at room temperature and the resulting reaction mixture was heated to reflux at 85° C. for 3 h. Reaction was monitored by TLC. After the completion, reaction mixture was evaporated to dryness on rotavapour and the crude compound was triturated in methanol and dried to afford the pure compound 2 and 3 as brown solid (0.5 g, 38.4%).

Step 2: tert-Butyl (R)-2-acrylamido-3-(5-bromobenzo[d]thiazol-2-yl)-5-methyl-4,7-dihydrothieno[2,3-c]pyridine-6(5H)-carboxylate (4) and tert-Butyl (R)-2-acrylamido-3-(5-bromobenzo[d]thiazol-2-yl)-7-methyl-4,7-dihydrothieno[2,3-c]pyridine-6(5H)-carboxylate (5)

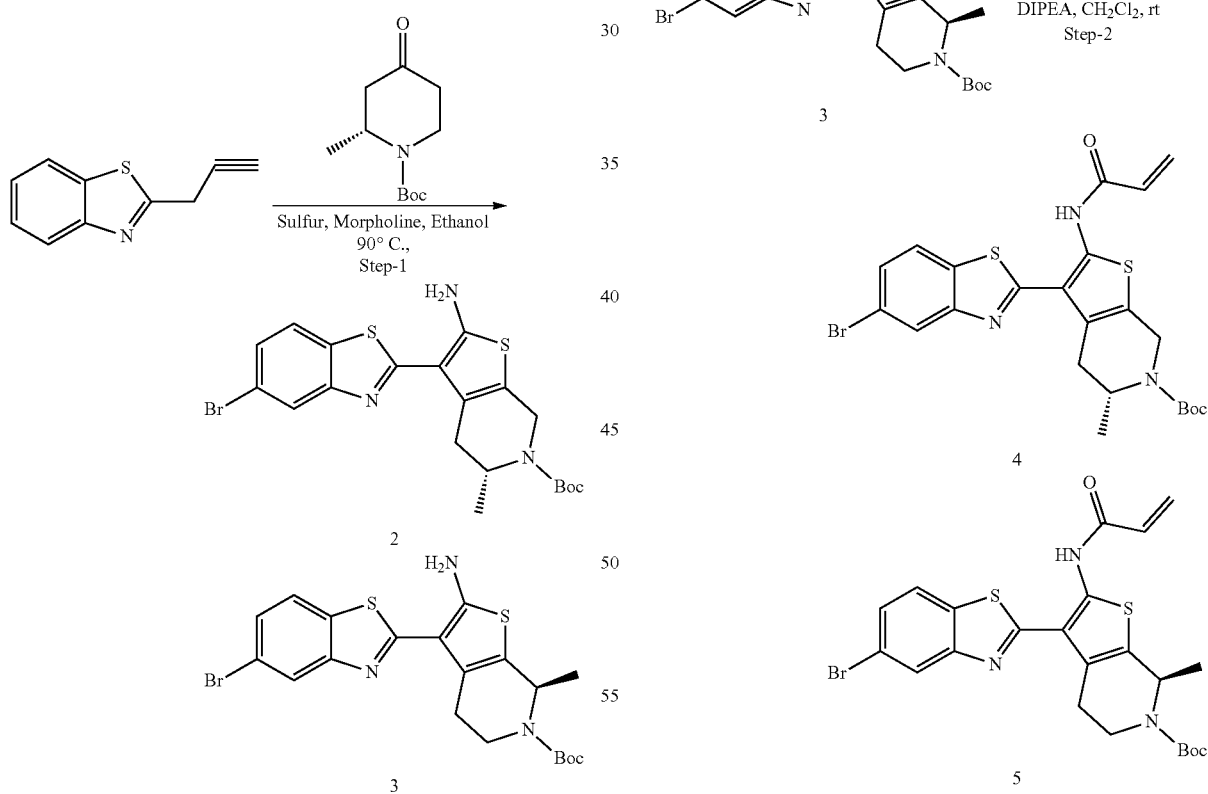

To a solution of 2 and 3 (0.46 g, 0.958 mmol) in CH$_2$Cl$_2$ (10 mL) at 0° C. was added DIPEA (0.25 g, 1.91 mmol) and 3-chloro propionyl chloride (0.182 g, 1.43 mmol). Reaction mixture was stirred at room temperature for 3 h. Reaction was monitored by TLC. After completion, the reaction mixture was diluted with CH$_2$Cl$_2$ and washed with saturated NaHCO$_3$ solution and brine. The separated organic layer was dried over Na$_2$SO$_4$, filtered and concentrated in vacuum to get a crude compound 4 and 5 brown solid (0.5 g, 98%).
Step 3: tert-Butyl (R)-3-(5-bromobenzo[d]thiazol-2-yl)-2-(3-(((S)-sec-butyl)amino)propanamido)-5-methyl-4,7-dihydrothieno[2,3-c]pyridine-6(5H)-carboxylate and tert-Butyl (R)-3-(5-bromobenzo[d]thiazol-2-yl)-2-(3-(((S)-sec-butyl)amino)propanamido)-7-methyl-4,7-dihydrothieno[2,3-c]pyridine-6(5H)-carboxylate (6 and 7)
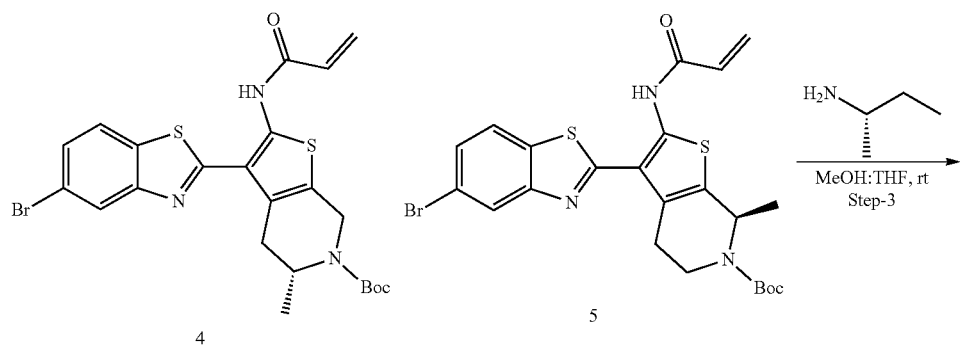
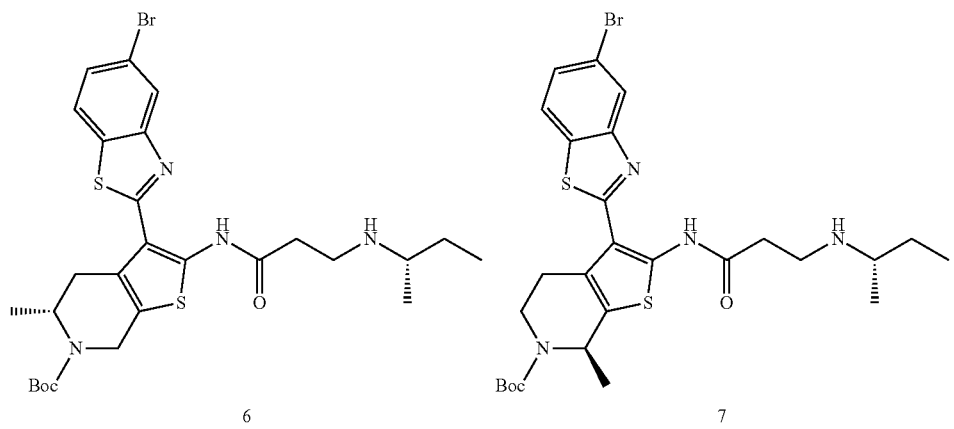

To a solution of 4 and 5 (0.46 g, 0.804 mmol) in MeOH (5 mL) was added (5) 2 aminobutane (90 mg, 0.804 mmol). The resulting reaction mixture was stirred at room temperature for 16 h. Progress of the reaction was monitored by TLC. After completion, the reaction mixture was concentrated to dryness under reduced pressure. The crude residue was dissolved in $CH_2Cl_2$ and washed with water. The combined organic layers were dried with anhydrous $Na_2SO_4$, filtered and concentrated to get a crude residue. This crude compound was purified by silica gel column chromatography eluting with 0-10% methanol in $CH_2Cl_2$ to afford title compound 6 and 7 as yellow solid (0.37 g, yield 75.9%).

Step 4: tert-Butyl (R)-2-(3-(((S)-sec-butyl)amino)propanamido)-5-methyl-3-(5-(pyridin-4-yl)benzo[d]thiazol-2-yl)-4,7-dihydrothieno[2,3-c]pyridine-6(5H)-carboxylate and tert-Butyl (R)-2-(3-(isopropylamino)propanamido)-7-methyl-3-(5-(pyridin-4-yl)benzo[d]thiazol-2-yl)-4,7-dihydrothieno[2,3-c]pyridine-6(5H)-carboxylate (9 and 10)

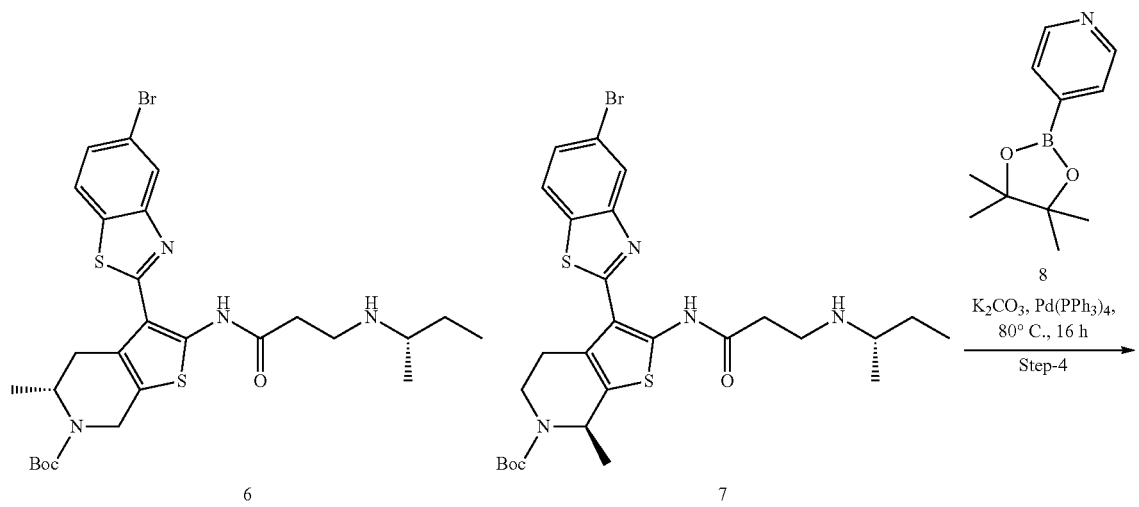

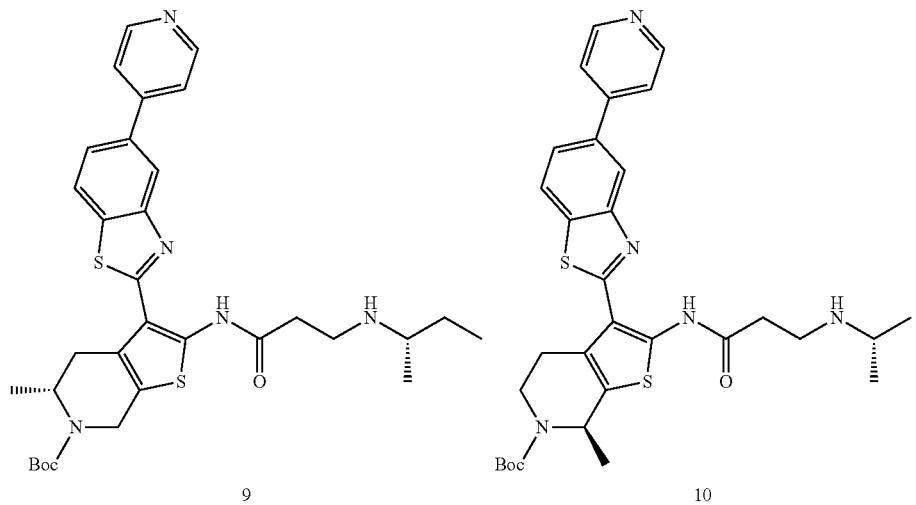

To a solution of 6 and 7 (350 mg, 0.577 mmol) in dioxane (10 mL) was added K₂CO₃ (199 mg, 1.443 mmol) in water (1 mL) and the reaction mixture was degassed under argon atmosphere for 10 min. Followed by addition of Pd(PPh₃)₄ (66 mg, 0.057 mmol) and 4-(4,4,5,5-tetramethyl-1,3,2-dioxaborolan-2-yl)pyridine (106 mg, 0.86 mmol) and degassed with argon for another 20 min. The reaction mixture was heated to 100° C. for 16 h. After the completion of reaction (monitored by LCMS), the reaction mixture was diluted with water and extracted with ethyl acetate (thrice). The combined organic layers were dried with anhydrous Na₂SO₄, filtered and concentrated to get a crude residue.

This crude compound was purified by silica gel column chromatography eluting with 0-6% methanol in CH₂Cl₂ to afford the title compound 9 and 10 as yellow solid (180 mg, 51.5% yield).

Step 5: 3-(((S)-sec-butyl)amino)-N—((R)-5-methyl-3-(5(pyridin-4-yl)benzo[d]thiazol-2-yl)-4,5,6,7-tetrahydrothieno[2,3-c]pyridin-2-yl)propanamide (Compound 589) and 3-(((S)-sec-butyl)amino)-N—((R)-7-methyl-3-(5-pyridin-4-yl)benzo[d]thiazol-2-yl)-4,5,6,7-tetrahydrothieno[2,3-c]pyridin-2-yl) propanamide (Compound 590)

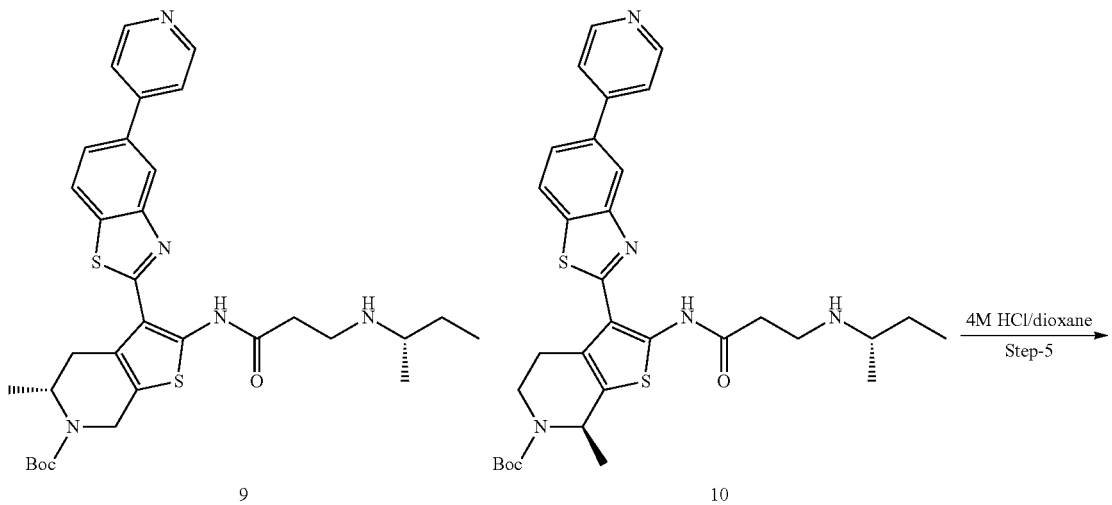

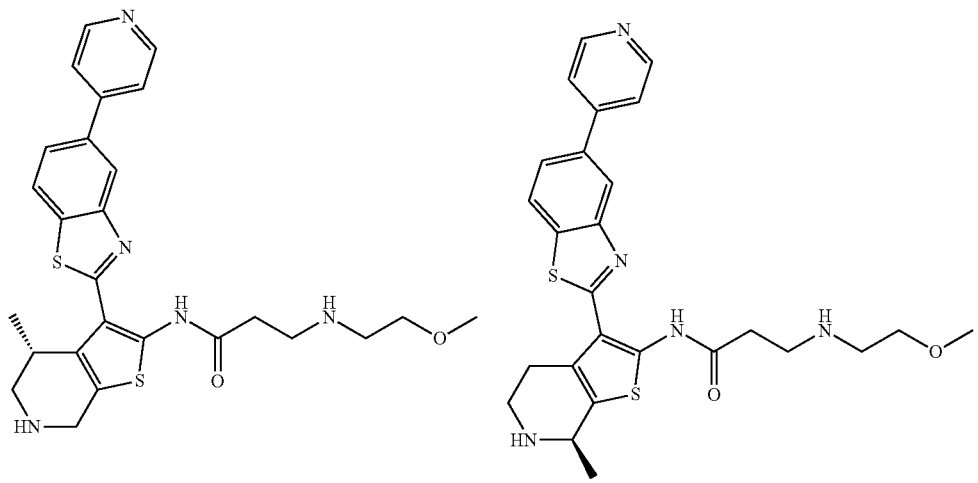

To a solution of 9 and 10 (180 mg, 0.297 mmol) in dioxane (5 mL) at 0° C. was added 4M HCl in dioxane (5 mL). After the addition, the resulting mixture was stirred at room temperature for 3 h. After completion, the reaction mixture was evaporated in vacuum resulting in a crude residue which was purified by triturating with methanol. The solid obtained was filtered and washed with diethyl ether and n-pentane to afford a mixture of the title compounds as yellow solid (150 mg, yield 74%). This mixture of compounds was purified by preparative HPLC separation (Column: CHIRALART CELLULOSE SC, 250 mm×4.6 mm, 5 μm; Mobile Phase: A: 0.1% TEA in N-Hexane; B: ETOH: DCM (85:15)+0.1% TEA; Flow rate: 1.0 mL/min; ISOCRATIC: 80% B) to afford Compound 589 (30 mg, 16.4%) and Compound 590 (30 mg, 16.4%) as yellow solid.

Example 120. Synthesis of N1-(3-(benzo[d]thiazol-2-yl)-4,5,6,7-tetrahydrothieno[2,3-c]pyridin-2-yl)-N25-((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)-7,10,13,16,19,22-hexaoxa-4-azapentacosanediamide (Compound 591)

Step 1: 17-Hydroxy-3,6,9,12,15-pentaoxaheptadecyl 4-methyl benzenesulfonate

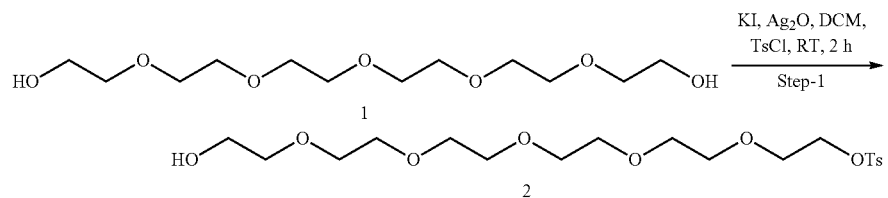

To a solution of hexaethylene glycol (5 g, 17.71 mmol) in dichloromethane (50 mL) was added silver oxide (6.15 g, 26.56 mmol) and potassium iodide (0.587 g, 3.54 mmol) followed by slowly addition of tosyl chloride (3.71 g, 19.48 mmol) and the reaction mixture stirred at room temperature for 2 h. Progress of the reaction was monitored by TLC. After completion, the reaction mixture was concentrated to dryness under reduced pressure. The crude residue was dissolved in $CH_2Cl_2$ and filtered through pad of Celite. Filtrate was washed with water and brine. The combined organic layers were dried with anhydrous $Na_2SO_4$, filtered and concentrated to get a crude residue. This crude compound was purified by silica gel column chromatography eluting with 0-5% methanol in $CH_2Cl_2$ to afford title compound 2 as colourless slurry (3.2 g, yield 41%).

Step 2: 17-Azido-3,6,9,12,15-pentaoxaheptadecan-1-ol

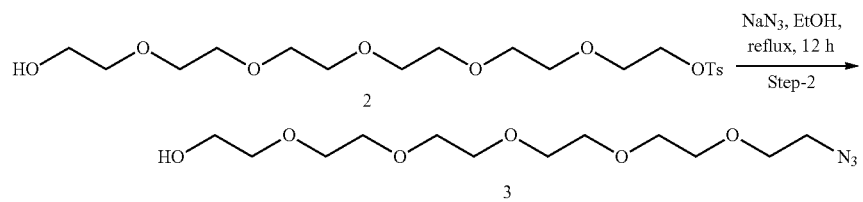

To a solution of 17-hydroxy-3,6,9,12,15-pentaoxaheptadecyl 4-methyl benzenesulfonate (3 g, 6.87 mmol) in ethanol (100 mL) was added sodium azide (1.34 g, 20.61 mmol) and the reaction mixture reflux for 15 h. Progress of the reaction was monitored by TLC. After completion, the reaction mixture was concentrated to dryness under reduced pressure. The crude residue was dissolved in CH$_2$Cl$_2$ and filtered through pad of Celite. Filtrate was concentrated to get title compound 3 as clear slurry (2 g, yield 94%).

Step 3: Ethyl 1-azido-3,6,9,12,15,18-hexaoxahenicosan-21-oate (4)

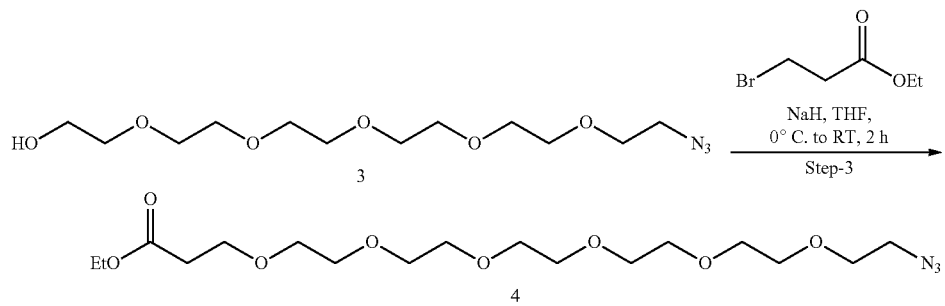

To a solution of 17-azido-3,6,9,12,15-pentaoxaheptadecan-1-ol 3 (1.5 g, 4.88 mmol) in THF (20 mL) at 0° C. was added sodium hydride (0.175 g, 7.30 mmol) in portions within 1 h. Then to it ethyl 3-bromopropanoate (0.811 mL, 6.34 mmol) was added and the reaction mixture stirred at 0° C. to room temperature for 2 h. Progress of the reaction was monitored by TLC. After completion, reaction mixture diluted with ethyl acetate and quenched with saturated NH$_4$Cl and extracted with ethyl acetate. The combined organic layers were dried with anhydrous Na$_2$SO$_4$, filtered and concentrated to get a crude residue. This crude compound was purified by silica gel column chromatography eluting with 0-5% methanol in CH$_2$Cl$_2$ to afford title compound 4 as clear slurry (1.6 g, yield 75%).

Step 4: Ethyl 1-amino-3,6,9,12,15,18-hexaoxahenicosan-21-oate

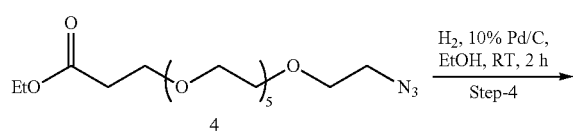

To a solution of ethyl 1-azido-3,6,9,12,15,18-hexaoxahenicosan-21-oate 4 (1.6 g, 3.926 mmol) in ethanol (20 mL) was added 10% Pd/C (200 mg) and the reaction mixture stirred at room temperature under hydrogen gas for 1 h. Progress of the reaction was monitored by TLC. After completion, reaction mixture filtered through a pad of Celite and concentrated. This crude compound was purified by silica gel column chromatography eluting with 3-10% methanol in CH$_2$Cl$_2$ to afford title compound 5 as clear slurry (0.93 g, yield 62%).

Step 5: tert-Butyl 3-(benzo[d]thiazol-2-yl)-2-(4-oxo-3,7,10,13,16,19,22-heptaoxa-25-azaoctacosan-28-amido)-4,7-dihydrothieno[2,3-c]pyridine-6(5H)-carboxylate

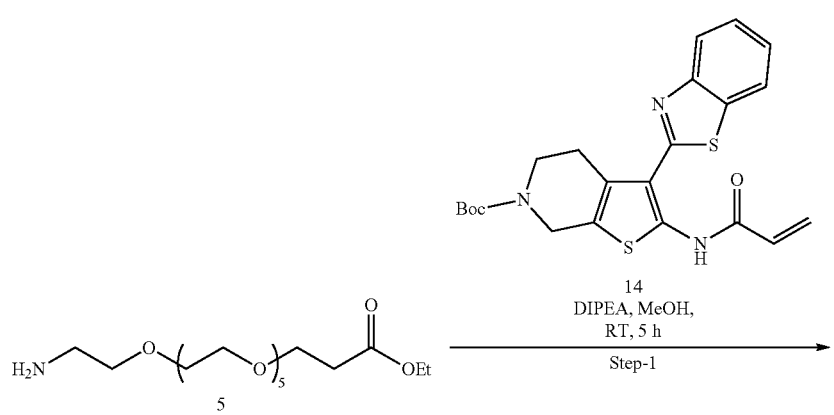

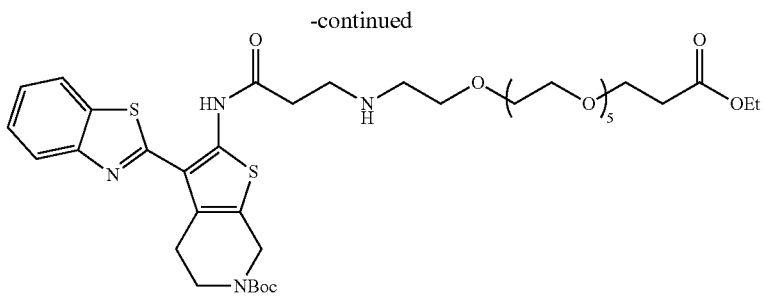

15

To a solution of ethyl 1-amino-3,6,9,12,15,18-hexaoxa-henicosan-21-oate (0.9 g, 2.359 mmol) in methanol (10 mL) was added dIIsopropyl ethylamine (1.2 mL, 7.07 mmol) followed by tert-butyl 2-acrylamido-3-(benzo[d]thiazol-2-yl)-4,7-dihydrothieno[2,3-c]pyridine-6(5H)-carboxylate 14 (1.14 g, 2.595 mmol). The resulting reaction mixture was stirred at room temperature for 16 h. Progress of the reaction was monitored by TLC. After completion, the reaction mixture was concentrated to dryness under reduced pressure. This crude compound was purified by silica gel column chromatography eluting with 0-5% methanol in CH$_2$Cl$_2$ to afford title compound 15 as yellow slurry (405 mg, yield 21%).

Step 6: 1-((3-(Benzo[d]thiazol-2-yl)-6-(tert-butoxycarbonyl)-4,5,6,7-tetrahydrothieno[2,3-c]pyridin-2-yl)amino)-1-oxo-7,10,13,16,19,22-hexaoxa-4-azapentacosan-25-oic acid (SY-3506)

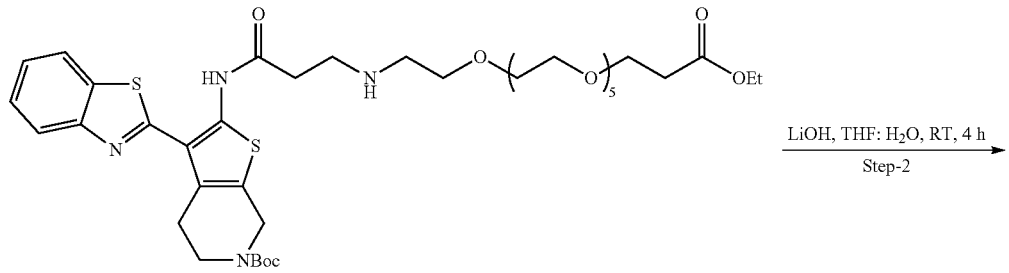

15

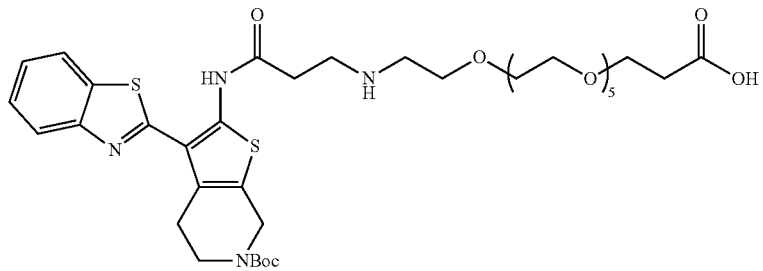

16

To a solution of tert-butyl 3-(benzo[d]thiazol-2-yl)-2-(4-oxo-3,7,10,13,16,19,22-heptaoxa-25-azaoctacosan-28-amido)-4,7-dihydrothieno[2,3-c]pyridine-6(5H)-carboxylate 15 (110 mg, 0.133 mmol) in THF:water (4:1; 2 mL) was added lithium hydroxide (19 mg, 0.801 mmol). After the addition, the resulting mixture was stirred at room temperature for 4 h. After completion, the reaction mixture was evaporated to dryness and the resulting in a crude residue was dissolved in water and acidifies with dilute HCl and extracted with ethyl acetate. Organic layer was dried over anhydrous sodium sulphate and concentrate under vacuum to obtained crude product, which was purified by triturating in diethyl ether and pentane to afford compound 16 as pale yellow slurry (85 mg, yield 80%).

Step-7: tert-Butyl-3-(benzo[d]thiazol-2-yl)-2-((S)-27-((2S,4R)-4-hydroxy-2-((4-(4-methylthiazol-5-yl)benzyl)carbamoyl) pyrrolidine-1-carbonyl)-28,28-dimethyl-25-oxo-7,10,13,16,19,22-hexaoxa-4,26-diazanonacosanamido)-4,7-dihydrothieno[2,3-c]pyridine-6(5H)-carboxylate

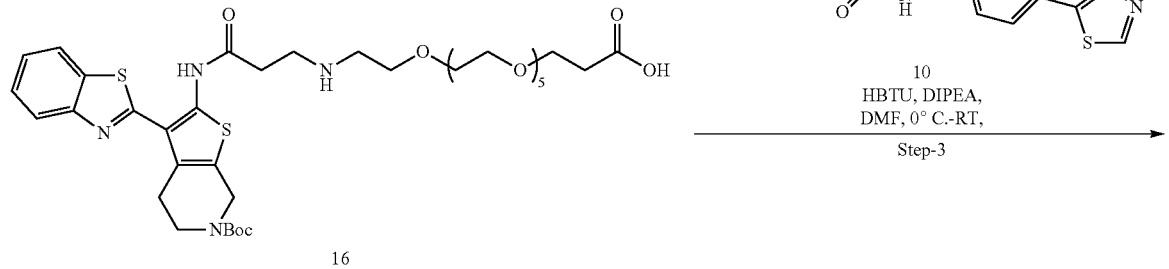

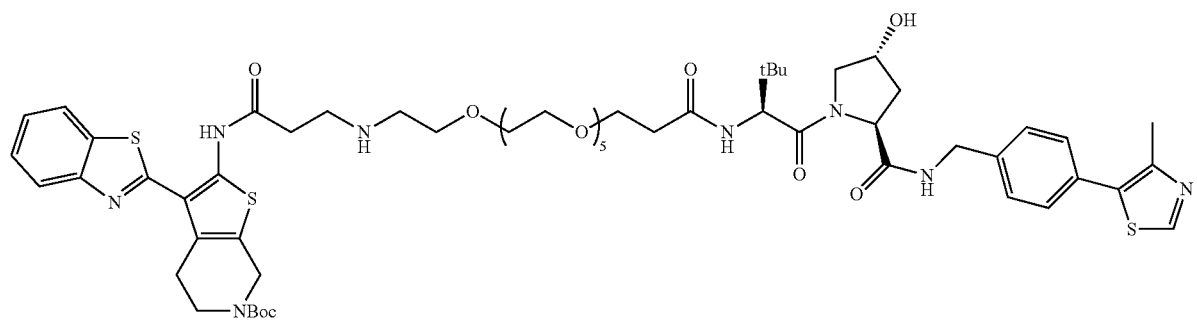

To a solution of 1-((3-(benzo[d]thiazol-2-yl)-6-(tert-butoxycarbonyl)-4,5,6,7-tetrahydrothieno[2,3-c]pyridin-2-yl)amino)-1-oxo-7,10,13,16,19,22-hexaoxa-4-azapentacosan-25-oic acid 16 (85 mg, 0.106 mmol) in dimethyl formamide (2 mL) were added HBTU (60 mg, 0.159 mmol) and dIIsopropyl ethyl amine (0.055 mL, 0.318 mmol) and stirred at room temperature for 30 min. Then to it (2S,4R)-1-((S)-2-amino-3,3-dimethylbutanoyl)-4-hydroxy-N-(4-(4-methylthiazol-5-yl)benzyl)pyrrolidine-2-carboxamide 10 (51 mg, 0.117 mmol) was added and the reaction mixture stirred at room temperature for h. After completion (monitored by TLC), the reaction mixture was diluted with dichloromethane and washed with dilute HCl solution and brine solution.

Organic layer was dried over anhydrous sodium sulphate and concentrate under vacuum to obtained crude product. The crude compound was purified by column chromatography eluting with 2-10% methanol in dichloromethane to afford the title compound 17 as pale yellow solid (32 mg, yield 25%).

Step 8: N1-(3-(benzo[d]thiazol-2-yl)-4,5,6,7-tetrahydrothieno[2,3-c]pyridin-2-yl)-N25-((5)-1-((2S,4R)-4-hydroxy-2-((4-(4-methyl thiazol-5-yl)benzyl)carbamoyl)pyrrolidin-1-yl)-3,3-dimethyl-1-oxo butan-2-yl)-7,10,13,16,19,22-hexaoxa-4-azapentacosanediamide

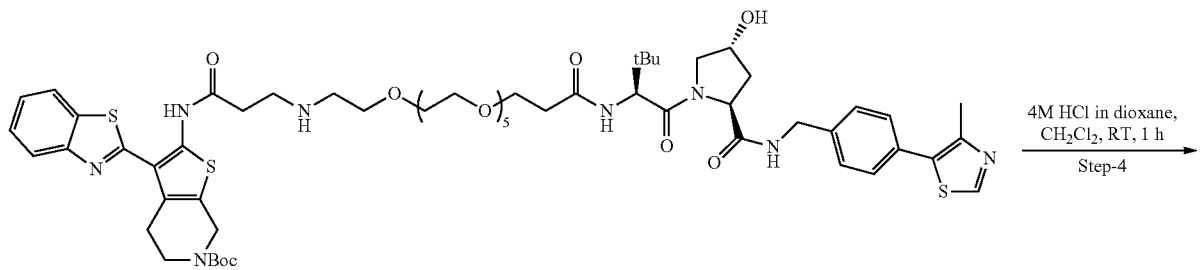

17

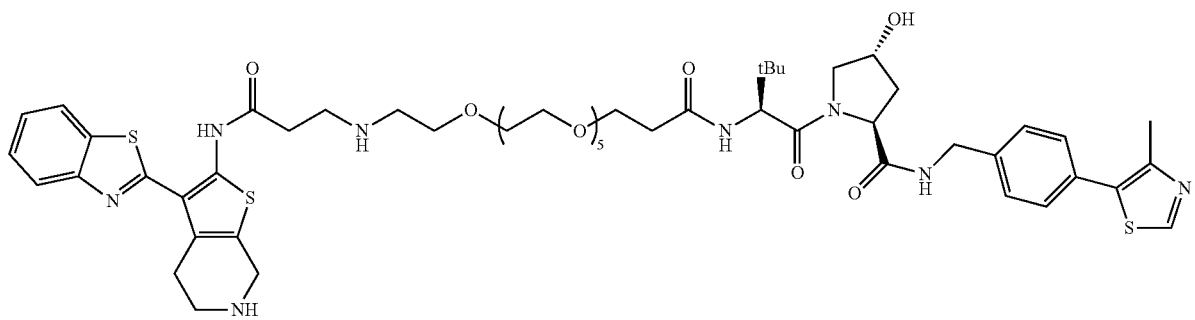

SJMC0412

To a solution of tert-butyl-3-(benzo[d]thiazol-2-yl)-2-((S)-27-((2S,4R)-4-hydroxy-2-((4-(4-methylthiazol-5-yl)benzyl)carbamoyl)pyrrolidine-1-carbonyl)-28,28-dimethyl-25-oxo-7,10,13,16,19,22-hexaoxa-4,26-diazanonacosanamido)-4,7-dihydrothieno[2,3-c]pyridine-6(5H)-carboxylate 17 (30 mg 0.0248 mmol) in CH₂Cl₂ (1 mL) at 0° C. was added 4M HCl in dioxane (0.3 mL). After the addition, the resulting mixture was stirred at room temperature for 1 h. After completion, the reaction mixture was evaporated to dryness and the resulting in a crude residue was purified by Prep HPLC to afford the title compound as yellow solid (6 mg, yield 21%).

Example 121. Synthesis of (S)-3-(sec-butylamino)-N-(6-cyclobutyl-3-(5-(pyridin-4-yl)benzo[d]thiazol-2-yl)-4,5,6,7-tetrahydrothieno[2,3-c]pyridin-2-yl)propanamide (Compound 595)

Step 1: 3-(5-Bromobenzo[d]thiazol-2-yl)-6-cyclobutyl-4,5,6,7-tetrahydrothieno[2,3-c]pyridin-2-amine (2)

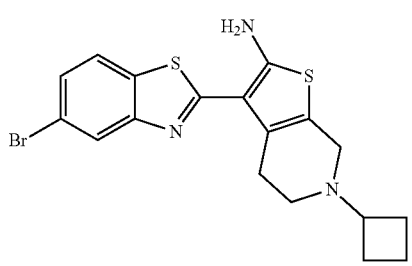

1

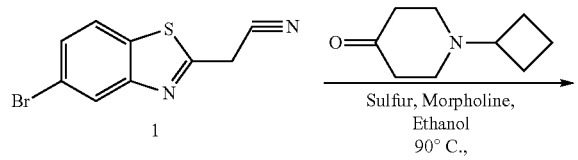

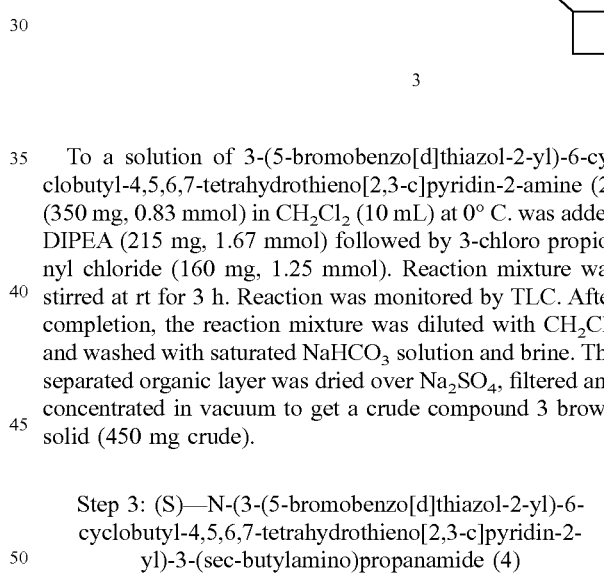

2

To a solution of 2-(5-bromobenzo[d]thiazol-2-yl)acetonitrile 1 (400 mg, 1.58 mmol), elemental sulphur (50 mg, 1.58 mmol) and morpholine (138 mg, 1.57 mmol) in ethanol (20 mL) was added 1-cyclobutyl-4-oxo-piperidine (241 mg, 1.58 mmol) at room temperature and the resulting reaction mixture was heated to reflux at 85° C. for 3 h. Reaction was monitored by TLC. After the completion, reaction mixture was evaporated to dryness on rotavapour and the crude compound was triturated in methanol and dried to afford the pure compound 2 as brown solid (350 mg crude).

Step 2: N-(3-(5-bromobenzo[d]thiazol-2-yl)-6-cyclobutyl-4,5,6,7-tetrahydrothieno[2,3-c]pyridin-2-yl)acrylamide (3)

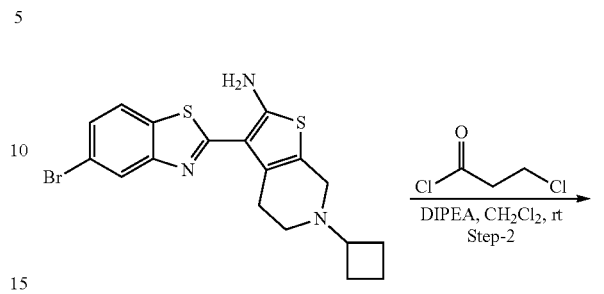

2

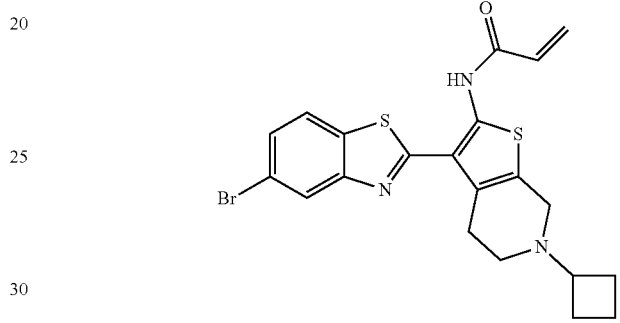

3

To a solution of 3-(5-bromobenzo[d]thiazol-2-yl)-6-cyclobutyl-4,5,6,7-tetrahydrothieno[2,3-c]pyridin-2-amine (2) (350 mg, 0.83 mmol) in CH₂Cl₂ (10 mL) at 0° C. was added DIPEA (215 mg, 1.67 mmol) followed by 3-chloro propionyl chloride (160 mg, 1.25 mmol). Reaction mixture was stirred at rt for 3 h. Reaction was monitored by TLC. After completion, the reaction mixture was diluted with CH₂Cl₂ and washed with saturated NaHCO₃ solution and brine. The separated organic layer was dried over Na₂SO₄, filtered and concentrated in vacuum to get a crude compound 3 brown solid (450 mg crude).

Step 3: (S)—N-(3-(5-bromobenzo[d]thiazol-2-yl)-6-cyclobutyl-4,5,6,7-tetrahydrothieno[2,3-c]pyridin-2-yl)-3-(sec-butylamino)propanamide (4)

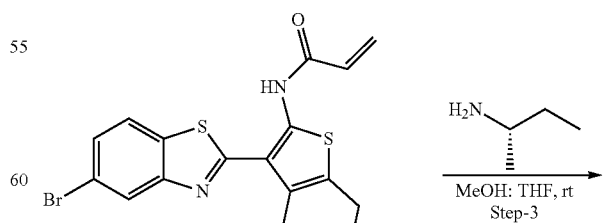

3

-continued

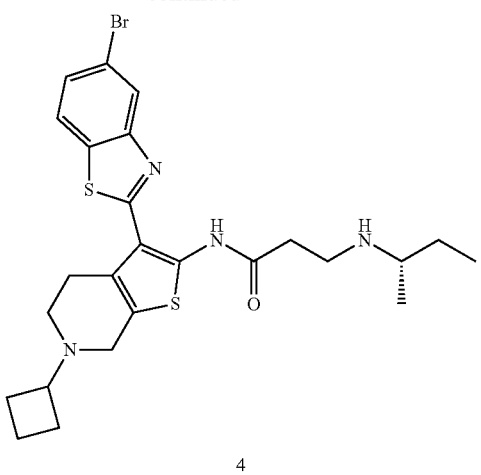

4

To a solution of N-(3-(5-bromobenzo[d]thiazol-2-yl)-6-cyclobutyl-4,5,6,7-tetrahydrothieno[2,3-c]pyridin-2-yl)acrylamide 3 (0.45 g, 0.95 mmol) in MeOH (10 mL) was added (5) 2 aminobutane (70 mg, 0.95 mmol). The resulting reaction mixture was stirred at room temperature for 16 h. Progress of the reaction was monitored by TLC. After completion, the reaction mixture was concentrated to dryness under reduced pressure. The crude residue was dissolved in CH$_2$Cl$_2$ and washed with water. The combined organic layers were dried with anhydrous Na$_2$SO$_4$, filtered and concentrated to get a crude residue. This crude compound was purified by silica gel column chromatography eluting with 0-10% methanol in DCM to afford title compound 4 as yellow solid (250 mg, yield 48.1%).

Step 4: (S)-3-(sec-butylamino)-N-(6-cyclobutyl-3-(5-(pyridin-4-yl)benzo[d]thiazol-2-yl)-4,5,6,7-tetrahydrothieno[2,3-c]pyridin-2-yl)propanamide -continued

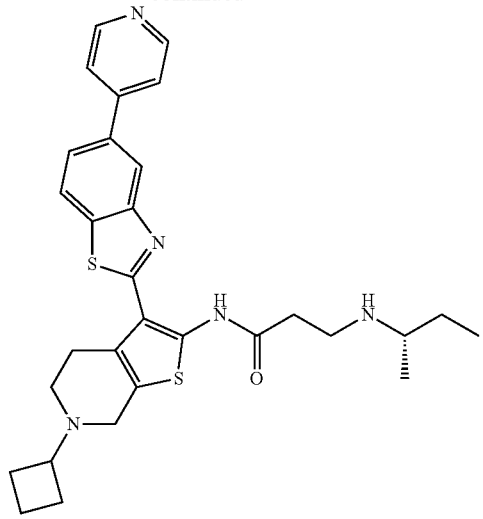

To a solution of (S)—N-(3-(5-bromobenzo[d]thiazol-2-yl)-6-cyclobutyl-4,5,6,7-tetrahydrothieno[2,3-c]pyridin-2-yl)-3-(sec-butylamino)propanamide 4 (250 mg, 0.457 mmol) in dioxane (10 mL) was added K$_2$CO$_3$ (157 mg, 1.14 mmol) in water (1 mL) and the reaction mixture was degassed under argon atmosphere for 10 min. Followed by addition of Pd(PPh$_3$)$_4$ (56 mg, 0.204 mmol) and 4-(4,4,5,5-tetramethyl-1,3,2-dioxaborolan-2-yl)pyridine (83 mg, 0.68 mmol) and degassed with argon for another 20 min. The reaction mixture was heated to 100° C. for 16 h. After the completion of reaction (monitored by LCMS), the reaction mixture was diluted with water and extracted with ethyl acetate (thrice). The combined organic layers were dried with anhydrous Na$_2$SO$_4$, filtered and concentrated to get a crude residue. This crude compound was purified by silica gel column chromatography eluting with 0-6% methanol in CH$_2$Cl$_2$ to afford the title compound as yellow solid (85 mg, 34% yield).

Example 122. Synthesis of (S)—N-(3-(benzo[d]thiazol-2-yl)-6-cyclopropyl-4,5,6,7-tetrahydrothieno[2,3-c]pyridin-2-yl)-3-(sec-butylamino)propanamide (Compound 596)

Step 1: 3-(Benzo[d]thiazol-2-yl)-6-cyclopropyl-4,5,6,7-tetrahydrothieno[2,3-c]pyridin-2-amine (2)

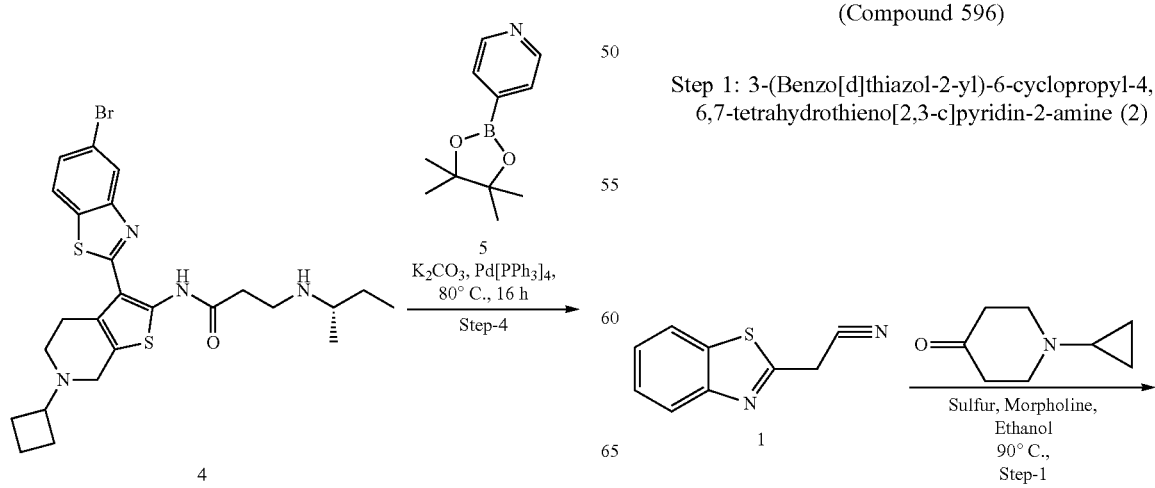

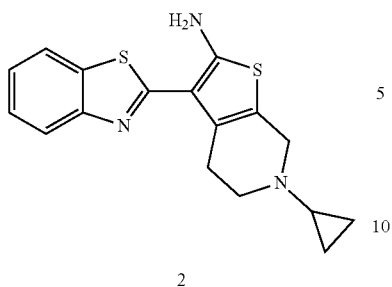

2

To a solution of 2-(benzo[d]thiazol-2-yl)acetonitrile 1 (290 mg, 1.16 mmol), elemental sulphur (53 mg, 1.66 mmol) and morpholine (145 mg, 1.66 mmol) in ethanol (10 mL) was added 1-cyclopropyl-4-oxo-piperidine (231 mg, 1.66 mmol) at room temperature and the resulting reaction mixture was heated to reflux at 85° C. for 3 h. Reaction was monitored by TLC. After the completion, reaction mixture was evaporated to dryness on rotavapour and the crude compound was triturated in methanol and dried to afford the pure compound 2 as brown solid (290 mg, 53.3%).

Step 2: N-(3-(benzo[d]thiazol-2-yl)-6-cyclopropyl-4,5,6,7-tetrahydrothieno[2,3-c]pyridin-2-yl)acrylamide (3)

To a solution of 3-(benzo[d]thiazol-2-yl)-6-cyclopropyl-4,5,6,7-tetrahydrothieno[2,3-c]pyridin-2-amine (2) (290 mg, 0.88 mmol) in CH$_2$Cl$_2$ (10 mL) at 0° C. was added DIPEA (172 mg, 1.33 mmol) followed by 3-chloro propionyl chloride (169 mg, 1.33 mmol). Reaction mixture was stirred at room temperature for 3 h. Reaction was monitored by TLC. After completion, the reaction mixture was diluted with CH$_2$Cl$_2$ and washed with saturated NaHCO$_3$ solution and brine. The separated organic layer was dried over Na$_2$SO$_4$, filtered and concentrated in vacuum to get a crude compound. Crude was purified by silica gel column chromatography to afford pure compound 3 as brown solid (160 mg, 47.47%).

Step 3: (S)—N-(3-(benzo[d]thiazol-2-yl)-6-cyclopropyl-4,5,6,7-tetrahydrothieno[2,3-c]pyridin-2-yl)-3-(sec-butylamino)propanamide

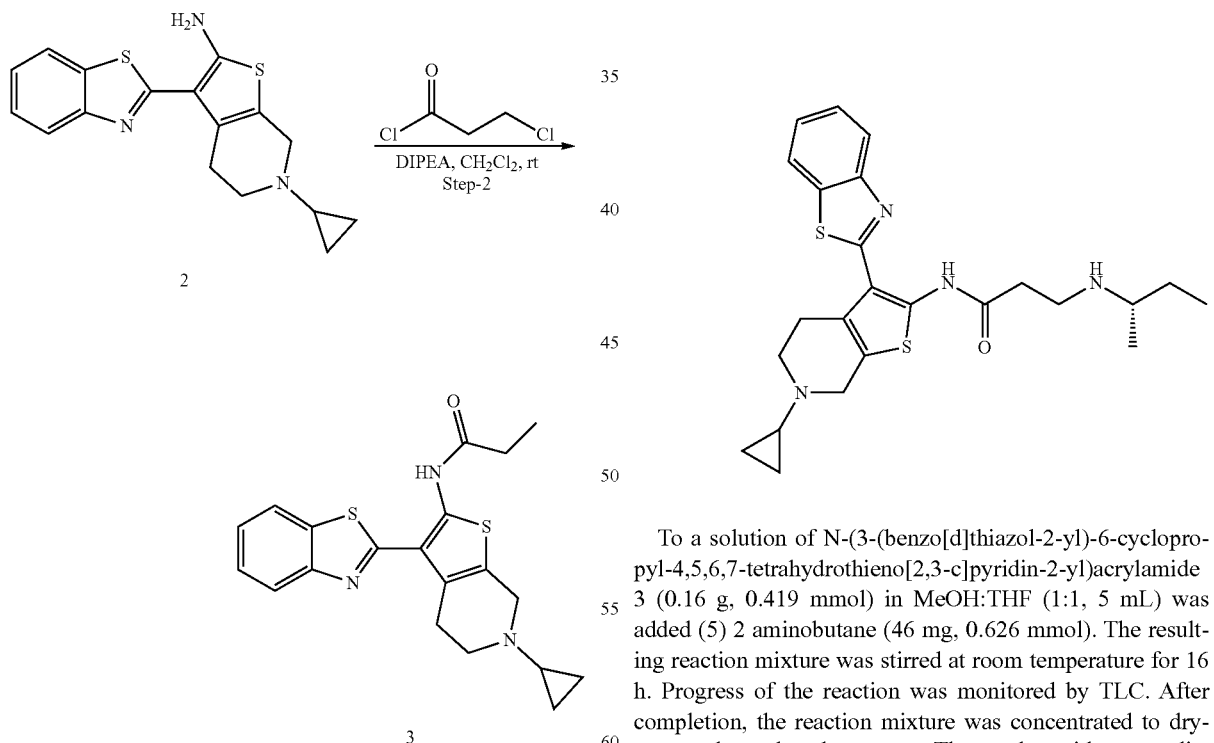

To a solution of N-(3-(benzo[d]thiazol-2-yl)-6-cyclopropyl-4,5,6,7-tetrahydrothieno[2,3-c]pyridin-2-yl)acrylamide 3 (0.16 g, 0.419 mmol) in MeOH:THF (1:1, 5 mL) was added (5) 2 aminobutane (46 mg, 0.626 mmol). The resulting reaction mixture was stirred at room temperature for 16 h. Progress of the reaction was monitored by TLC. After completion, the reaction mixture was concentrated to dryness under reduced pressure. The crude residue was dissolved in CH$_2$Cl$_2$ and washed with water. The combined organic layers were dried with anhydrous Na$_2$SO$_4$, filtered and concentrated to get a crude residue. This crude compound was purified by silica gel column chromatography eluting with 0-10% methanol in CH$_2$Cl$_2$ to afford title compound as yellow solid (25 mg, yield 13.1%).

Example 123. Synthesis of 14(3-(Benzo[d]thiazol-2-yl)-4,5,6,7-tetrahydrothieno[2,3-c]pyridin-2-yl)amino)-1-oxo-7,10,13,16,19,22-hexaoxa-4-azapentacosan-25-oic acid (Compound 623)

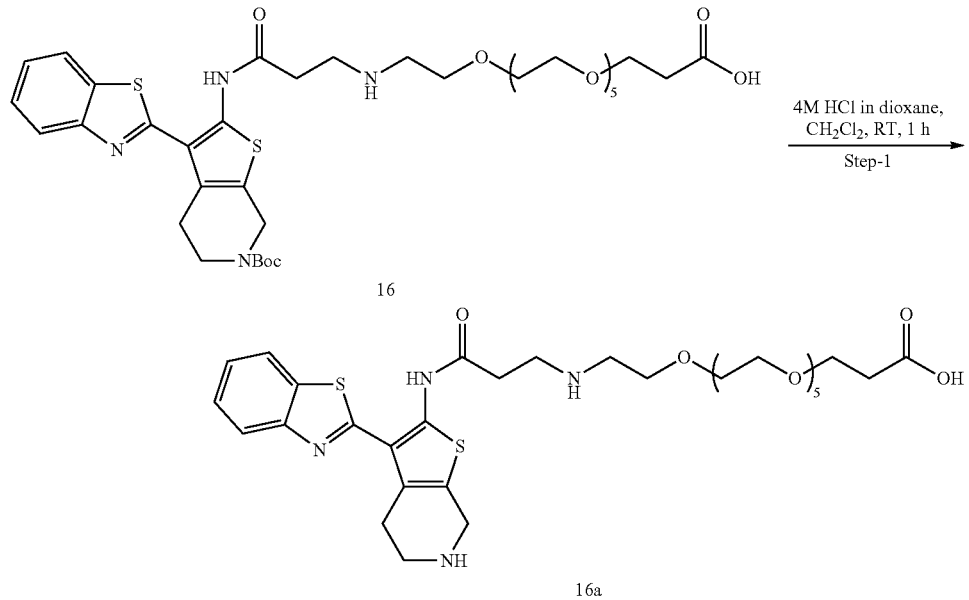

To a solution of 1-((3-(benzo[d]thiazol-2-yl)-6-(tert-butoxycarbonyl)-4,5,6,7-tetrahydro thieno[2,3-c]pyridin-2-yl)amino)-1-oxo-7,10,13,16,19,22-hexaoxa-4-azapentacosan-25-oic acid 16 (40 mg, 0.050 mmol) in CH$_2$Cl$_2$ (1 mL) at 0° C. was added 4M HCl in dioxane (0.3 mL). After the addition, the resulting mixture was stirred at room temperature for 1 h. After completion, the reaction mixture was evaporated to dryness and the resulting in a crude residue was purified by preparative HPLC to afford the HCl salt of the title compound as brown solid (28 mg, yield 77%).

Example 124. Synthesis of Ethyl 1-((3-(benzo[d]thiazol-2-yl)-4,5,6,7-tetrahydrothieno[2,3-c]pyridin-2-yl)amino)-1-oxo-7,10,13,16,19,22-hexaoxa-4-azapentacosan-25-oate (Compound 622)

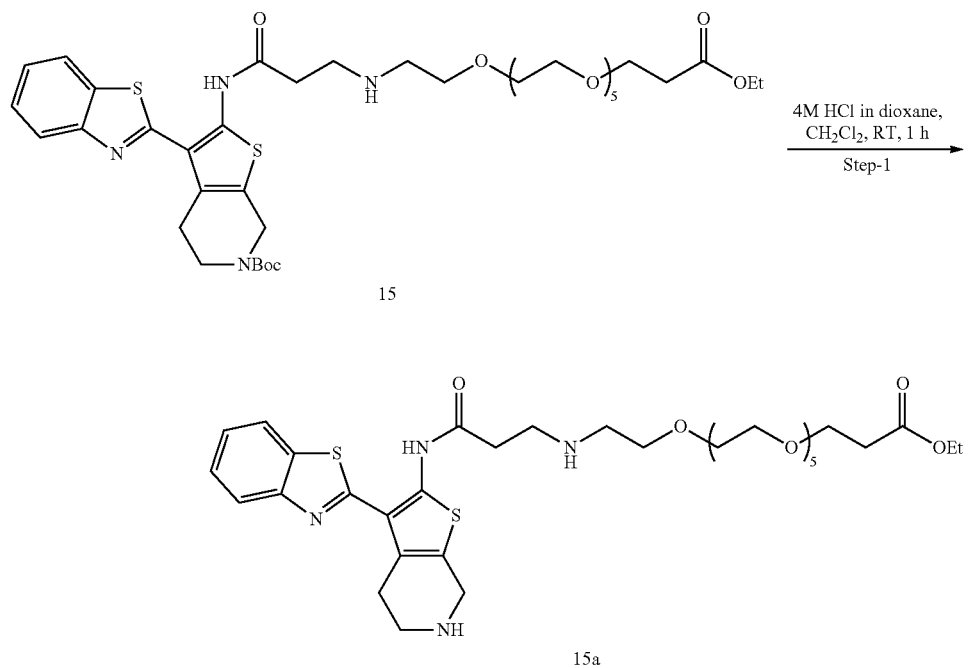

To a solution of tert-butyl 3-(benzo[d]thiazol-2-yl)-2-(4-oxo-3,7,10,13,16,19,22-heptaoxa-25-azaoctacosan-28-amido)-4,7-dihydrothieno[2,3-c]pyridine-6(5H)-carboxylate from the previous example 15 (250 mg, 0.303 mmol) in CH$_2$Cl$_2$ (2 mL) at 0° C. was added 4M HCl in dioxane (0.3 mL). After the addition, the resulting mixture was stirred at room temperature for 1 h. After completion, the reaction mixture was evaporated to dryness and the resulting in a crude residue was purified by Prep HPLC to afford the title compound as brown solid (96 mg, yield 43%).

Example 125. Synthesis of N-(3-(benzo[d]thiazol-2-yl)-5,7-dimethyl-4,5,6,7-tetrahydrothieno[2,3-c]pyridin-2-yl)-3-(((S)-sec-butyl)amino)propanamide and Separation of Isomers (Compounds 620, 621 and 624)

Step 1: tert-Butyl 2-amino-3-(benzo[d]thiazol-2-yl)-5,7-dimethyl-4,7-dihydrothieno[2,3-c]pyridine-6(5H)-carboxylate (2)

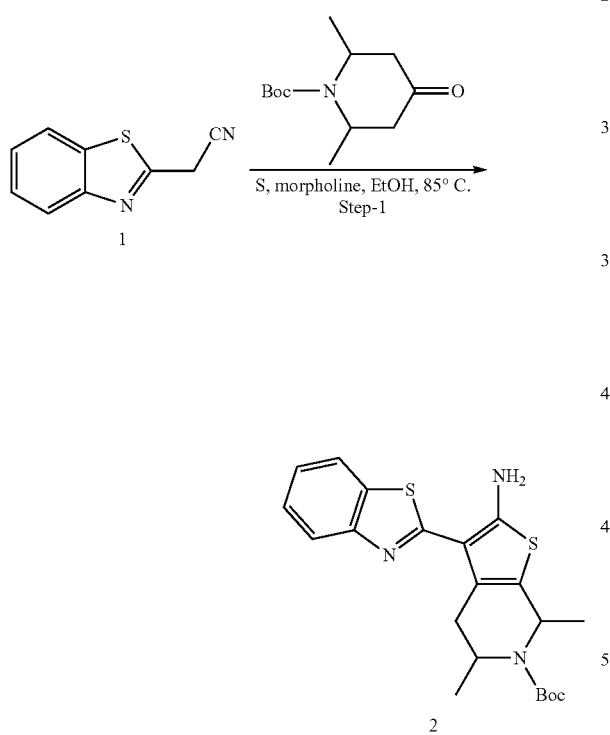

To a solution of 2-(benzo[d]thiazol-2-yl)acetonitrile 1 (800 mg, 4.597 mmol), elemental sulphur (147 mg, 4.597 mmol) and morpholine (399 mg, 4.597 mmol) in ethanol (20 mL) was added tert-butyl 2,6-dimethyl-4-oxopiperidine-1-carboxylate (1.04 g, 4.597 mmol) at room temperature and the resulting reaction mixture was heated to reflux at 85° C. for 12 h. Reaction was monitored by TLC. After the completion, reaction mixture was evaporated to dryness on rotavapour. The crude compound was purified by silica gel column chromatography eluting with 0-30% ethyl acetate in n-hexane to afford the title compound 2 as brown solid (600 mg, 31.5%).

Step 2: tert-Butyl 2-acrylamido-3-(benzo[d]thiazol-2-yl)-5,7-dimethyl-4,7-dihydrothieno[2,3-c]pyridine-6(5H)-carboxylate (3)

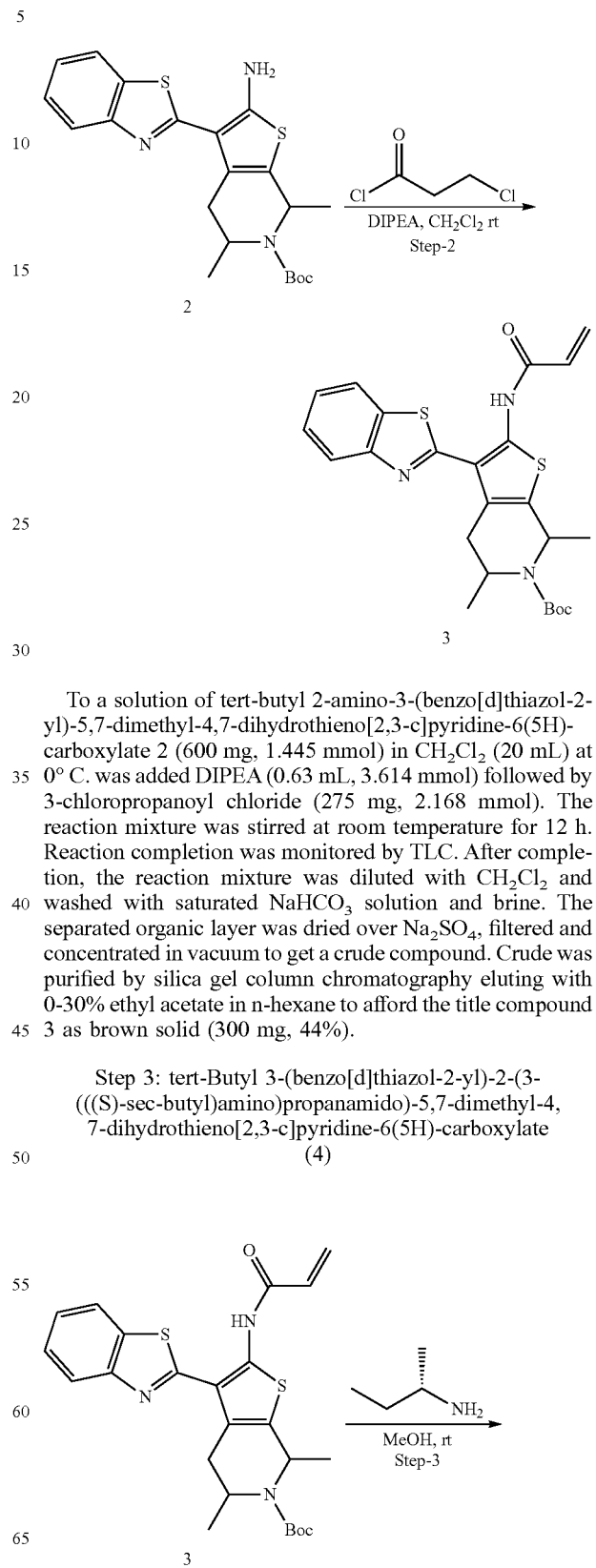

To a solution of tert-butyl 2-amino-3-(benzo[d]thiazol-2-yl)-5,7-dimethyl-4,7-dihydrothieno[2,3-c]pyridine-6(5H)-carboxylate 2 (600 mg, 1.445 mmol) in CH$_2$Cl$_2$ (20 mL) at 0° C. was added DIPEA (0.63 mL, 3.614 mmol) followed by 3-chloropropanoyl chloride (275 mg, 2.168 mmol). The reaction mixture was stirred at room temperature for 12 h. Reaction completion was monitored by TLC. After completion, the reaction mixture was diluted with CH$_2$Cl$_2$ and washed with saturated NaHCO$_3$ solution and brine. The separated organic layer was dried over Na$_2$SO$_4$, filtered and concentrated in vacuum to get a crude compound. Crude was purified by silica gel column chromatography eluting with 0-30% ethyl acetate in n-hexane to afford the title compound 3 as brown solid (300 mg, 44%).

Step 3: tert-Butyl 3-(benzo[d]thiazol-2-yl)-2-(3-(((S)-sec-butyl)amino)propanamido)-5,7-dimethyl-4,7-dihydrothieno[2,3-c]pyridine-6(5H)-carboxylate (4)

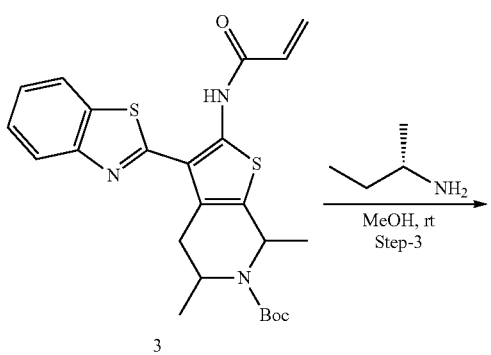

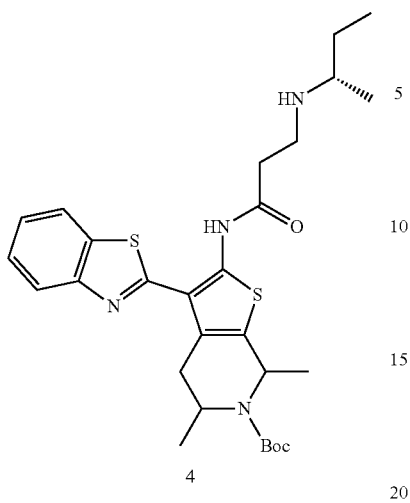

4

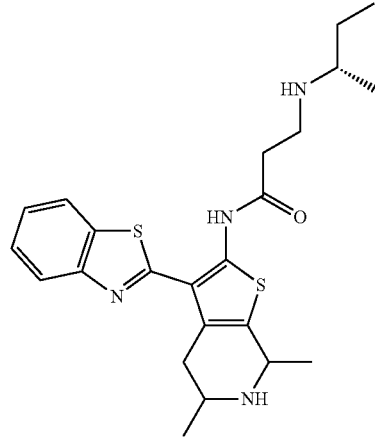

To a solution of tert-butyl 2-acrylamido-3-(benzo[d]thiazol-2-yl)-5,7-dimethyl-4,7-dihydrothieno[2,3-c]pyridine-6(5H)-carboxylate 3 (300 mg, 0.639 mmol) in MeOH:THF (1:1, 10 mL) was added (S)-butan-2-amine (47 mg, 0.639 mmol). The resulting reaction mixture was stirred at room temperature for 15 h. Progress of the reaction was monitored by TLC. After completion, the reaction mixture was concentrated to dryness under reduced pressure. The crude residue was dissolved in $CH_2Cl_2$ and washed with water. The combined organic layers were dried with anhydrous $Na_2SO_4$, filtered and concentrated to get a crude residue. This crude compound was purified by silica gel column chromatography eluting with 0-5% methanol in $CH_2Cl_2$ to afford title compound 4 as yellow solid (185 mg, yield 53%).

Step 4: N-(3-(benzo[d]thiazol-2-yl)-5,7-dimethyl-4,5,6,7-tetrahydrothieno[2,3-c]pyridin-2-yl)-3-(((S)-sec-butyl)amino)propanamide To a solution of tert-butyl 3-(benzo[d]thiazol-2-yl)-2-(3-(((S)-sec-butyl)amino)propanamido)-5,7-dimethyl-4,7-dihydrothieno[2,3-c]pyridine-6(5H)-carboxylate 4 (185 mg, 0.340 mmol) in dioxane (5 mL) at 0° C. was added 4M HCl in dioxane (5 mL). After the addition, the resulting mixture was stirred at room temperature for 3 h. After completion, the reaction mixture was evaporated in vacuum resulting in a crude residue which was purified by triturating with methanol. The solid obtained was filtered and washed with diethyl ether and n-pentane to afford the racemic title compound as yellow solid (220 mg). This mixture of isomers was purified by preparative HPLC separation to afford Compound 624 (30 mg), Compound 621 (40 mg) and Compound 620 (20 mg) as yellow solids.

Example 126. Synthesis of (R)-3-(sec-butylamino)-N-(3-(5-(trifluoromethyl)benzo[d]thiazol-2-yl)-4,5,6,7-tetrahydrothieno[2,3-c]pyridin-2-yl)propanamide (Compound 179)

Step 1: tert-butyl (R)-2-(3-(sec-butylamino)propanamido)-3-(5-(trifluoromethyl)benzo[d]thiazol-2-yl)-4,7-dihydrothieno[2,3-c]pyridine-6(5H)-carboxylate (2)

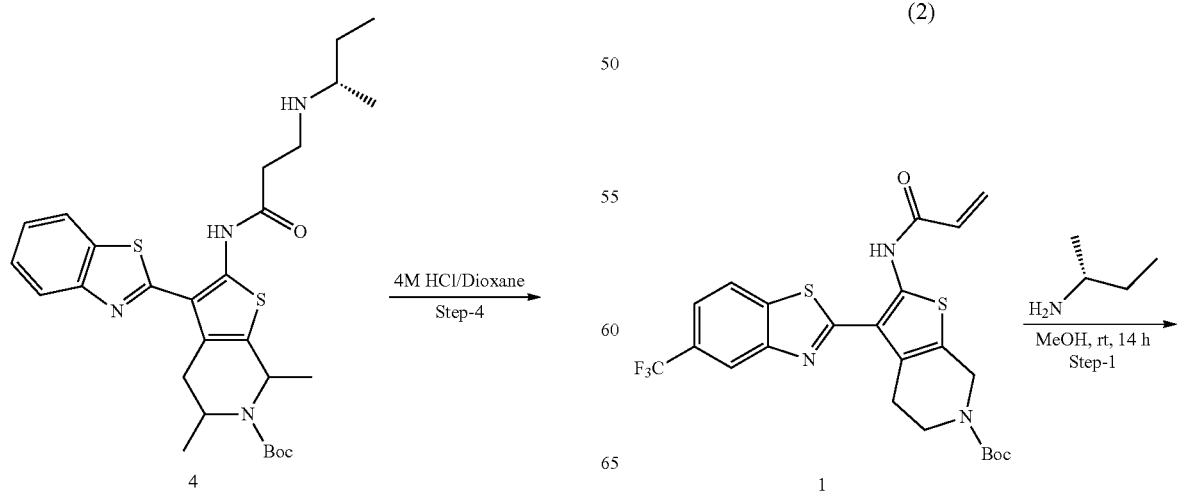

-continued

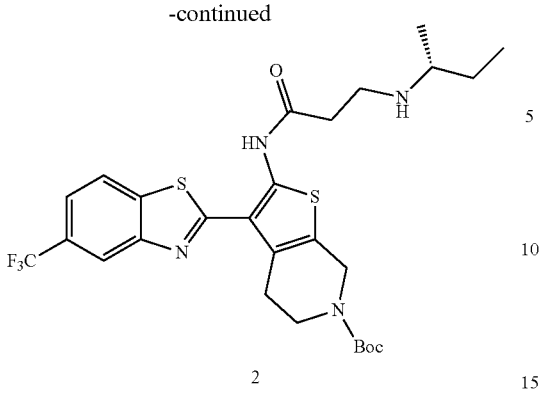

2

To a solution of tert-butyl 2-acrylamido-3-(5-(trifluoromethyl)benzo[d]thiazol-2-yl)-4,7-dihydrothieno[2,3-c]pyridine-6(5H)-carboxylate 1 (4 g, 7.85 mmol) in MeOH (40 mL)/THF (20 mL) were added (R)-butan-2-amine (688 mg, 9.42 mmol) and the reaction mixture was stirred at room temperature for 14 h. Reaction was monitored by TLC. After completion, the reaction mass was concentrated to obtained a crude residue. The crude compound was purified by flash column chromatography to afford the title compound 2 as a yellow solid (1.8 g, 40% yield).

Step 2: (R)-3-(sec-butylamino)-N-(3-(5-(trifluoromethyl)benzo[d]thiazol-2-yl)-4,5,6,7-tetrahydrothieno[2,3-c]pyridin-2-yl)propanamide

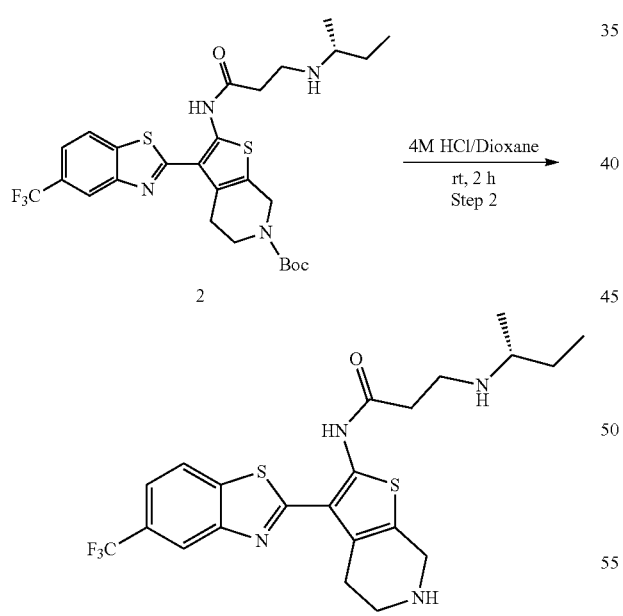

To a solution of tert-butyl (R)-2-(3-(sec-butylamino)propanamido)-3-(5-(trifluoromethyl)benzo[d]thiazol-2-yl)-4,7-dihydrothieno[2,3-c]pyridine-6(5H)-carboxylate 2 (1.8 g, 3.09 mmol) in dioxane (5 mL) at 0° C. was added 4M HCl in dioxane (15 mL) and the resulting mixture was stirred at room temperature for 2 h. After completion, the reaction mixture was evaporated in vacuum resulting in a crude residue which was triturated with ether and pentane to afford the title compound as yellow solid (1.3 g, 67% yield).

Example 127. Synthesis of N-(3-([1,3]Dioxolo[4',5': 4,5]benzo[1,2-d]thiazol-6-yl)-4,5,6,7-tetrahydrothieno[2,3-c]pyridin-2-yl)-3-((2-methoxyethyl)amino) propanamide (Compound 556)

Step 1: tert-Butyl 3-([1,3]dioxolo[4',5':4,5]benzo[1,2-d]thiazol-6-yl)-2-(3-((2-methoxyethyl)amino)propanamido)-4,7-dihydrothieno[2,3-c]pyridine-6(5H)-carboxylate (1)

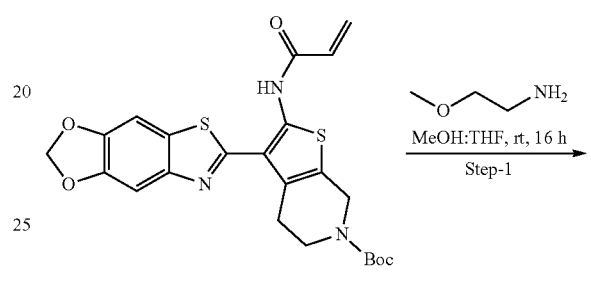

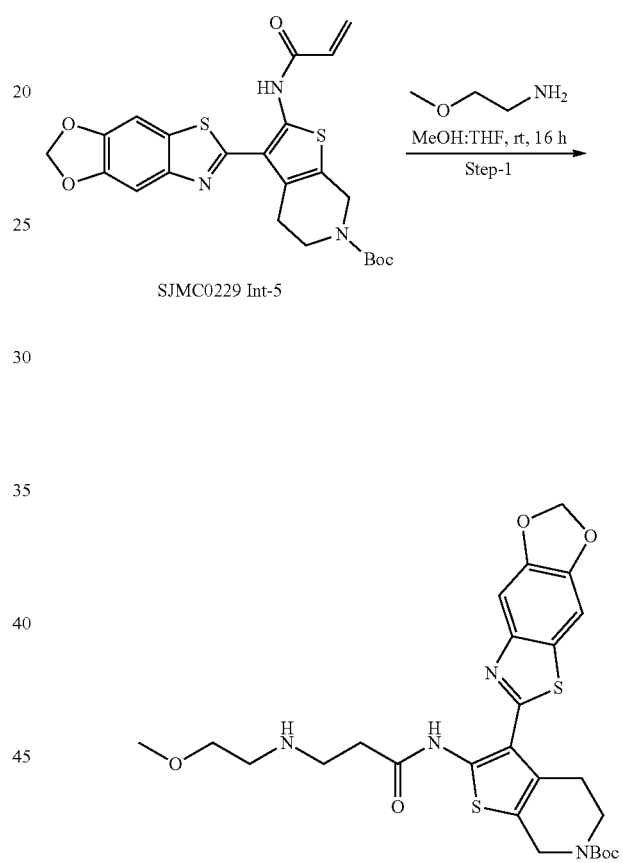

To a solution of tert-butyl 3-([1,3]dioxolo[4',5':4,5]benzo[1,2-d]thiazol-6-yl)-2-acrylamido-4,7-dihydrothieno[2,3-c]pyridine-6(5H)-carboxylate SJMC0229 Int-5 (150 mg, 0.309 mmol) in MeOH:THF (1:1, 20 mL) was added 2-methoxyethan-1-amine (35 mg, 0.463 mmol). The resulting reaction mixture was stirred at room temperature for 16 h. Progress of the reaction was monitored by TLC. After completion, the reaction mixture was concentrated to dryness under reduced pressure. The crude compound was purified by column chromatography eluting with 0-10% methanol in CH$_2$Cl$_2$ to afford the title compound 1 as yellow solid (100 mg, yield 58%).

Step 2: N-(3-([1,3]Dioxolo[4',5':4,5]benzo[1,2-d]thiazol-6-yl)-4,5,6,7-tetrahydrothieno[2,3-c]pyridin-2-yl)-3-((2-methoxyethyl)amino)propanamide

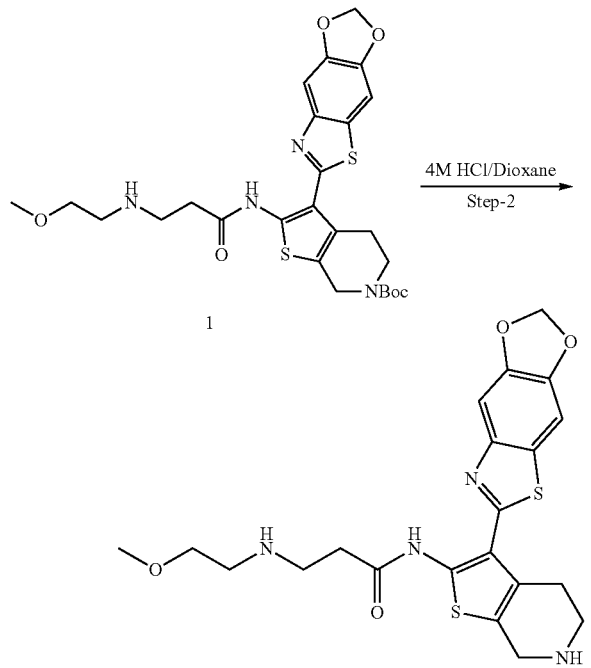

To a solution of tert-butyl 3-([1,3]dioxolo[4',5':4,5]benzo[1,2-d]thiazol-6-yl)-2-(3-((2-methoxyethyl)amino)propanamido)-4,7-dihydrothieno[2,3-c]pyridine-6(5H)-carboxylate 1 (100 mg, 0.178 mmol) in dioxane (5 mL) at 0° C. was added 4M HCl in dioxane (5 mL). After the addition, the resulting mixture was stirred at room temperature for 3 h. Reaction was monitored by TLC. After completion, the reaction mixture was evaporated in vacuum resulting in a crude residue which was triturated by diethyl ether and n-pentane to afford the HCl salt of the title compound as yellow solid (75 mg, yield 79%).

Example 128. Synthesis of N-(3-(5-Fluorobenzo[d]thiazol-2-yl)-7-methyl-4,5,6,7-tetrahydrothieno[2,3-c]pyridin-2-yl)-3-((2-methoxyethyl)amino)propanamide and N-(3-(5-Fluorobenzo[d]thiazol-2-yl)-5-methyl-4,5,6,7-tetrahydrothieno[2,3-c]pyridin-2-yl)-3-((2-methoxyethyl)amino)propanamide and Separation of Isomers (Compounds 557, 558, 570 and 571)

Step 1: tert-Butyl 2-amino-3-(5-fluorobenzo[d]thiazol-2-yl)-5-methyl-4,7-dihydrothieno[2,3-c]pyridine-6(5H)-carboxylate and tert-Butyl 2-amino-3-(5-fluorobenzo[d]thiazol-2-yl)-7-methyl-4,7-dihydrothieno[2,3-c]pyridine-6(5H)-carboxylate (3 and 4)

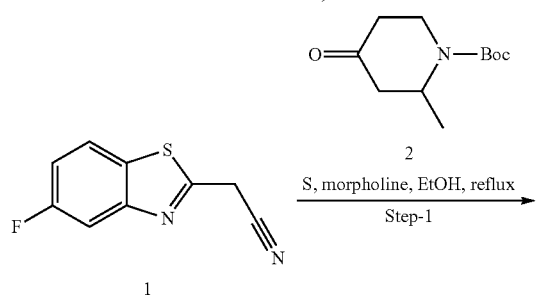

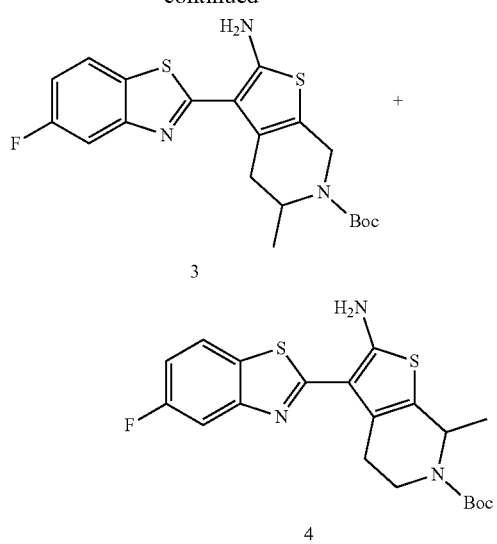

To a solution of 2-(5-fluorobenzo[d]thiazol-2-yl)acetonitrile 1 (1.35 g, 7.032 mmol) in ethanol (15 mL) was added tert-butyl 2-methyl-4-oxopiperidine-1-carboxylate 2 (1.50 g, 7.032 mmol), elemental sulphur (225 mg, 7.032 mmol) and morpholine (611 mg, 7.032 mmol) at room temperature. After the addition, the resulting mixture was heated to reflux at 80° C. for 3 h. Progress of the reaction was monitored by TLC. After completion, the reaction mixture was evaporated in vacuum up to dryness. The crude compound was purified by column chromatography eluting with 0-20% ethyl acetate in n-hexane to afford the title compound 3 and 4 as off white solid (2.8 g, yield 95%).

Step 2: tert-Butyl 2-acrylamido-3-(5-fluorobenzo[d]thiazol-2-yl)-5-methyl-4,7-dihydrothieno[2,3-c]pyridine-6(5H)-carboxylate and tert-Butyl 2-acrylamido-3-(5-fluorobenzo[d]thiazol-2-yl)-7-methyl-4,7-dihydrothieno[2,3-c]pyridine-6(5H)-carboxylate (5 and 6)

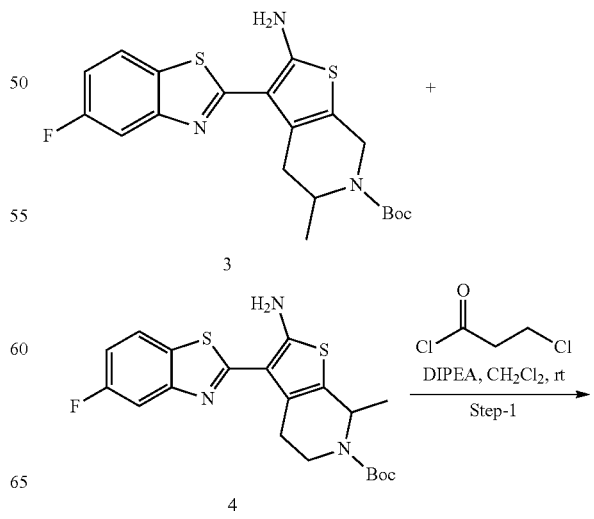

383
-continued

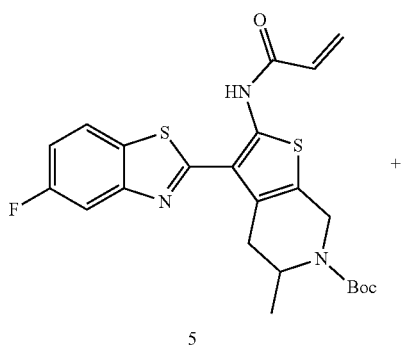

5

384
-continued

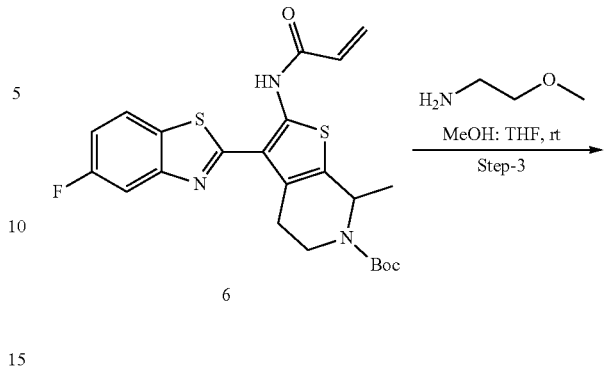

6

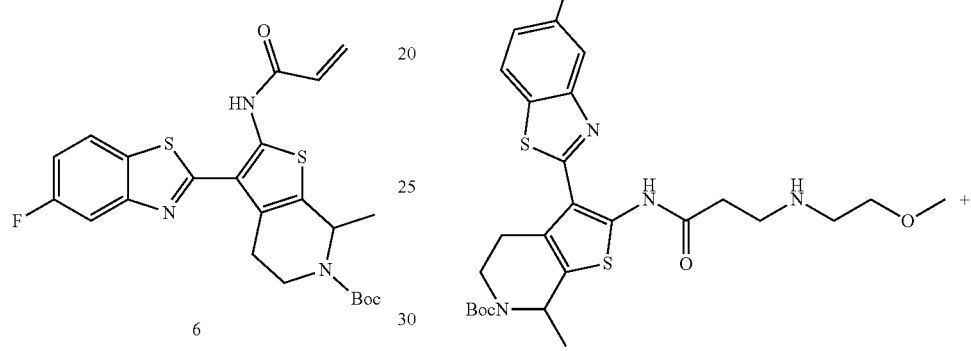

7

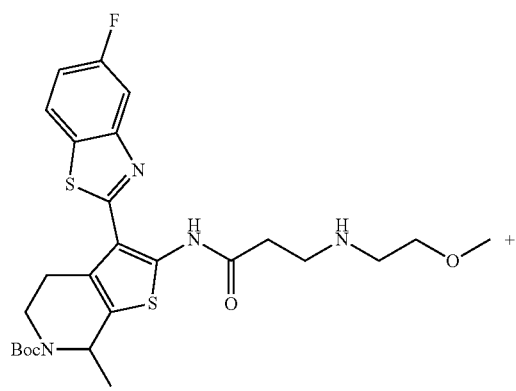

6

To a solution of mixture 3 and 4 (1.5 g, 3.579 mmol) in CH$_2$Cl$_2$ (25 mL) at 0° C. was added DIPEA (0.92 mL, 5.369 mmol) and 3-chloropropanoyl chloride (680 mg, 5.369 mmol). The reaction mixture was stirred at room temperature for 2 h. After completion (monitored by TLC), the reaction mixture was concentrated to dryness under reduced pressure to afford the title compound 5 and 6 as light brown solid (2.1 g crude).

Step 3: tert-Butyl 3-(5-fluorobenzo[d]thiazol-2-yl)-2-(3-((2-methoxyethyl)amino)propanamido)-7-methyl-4,7-dihydrothieno[2,3-c]pyridine-6(5H)-carboxylate and tert-Butyl 3-(5-fluorobenzo[d]thiazol-2-yl)-2-(3-((2-methoxyethyl)amino)propanamido)-5-methyl-4,7-dihydrothieno[2,3-c]pyridine-6(5H)-carboxylate (7 and 8)

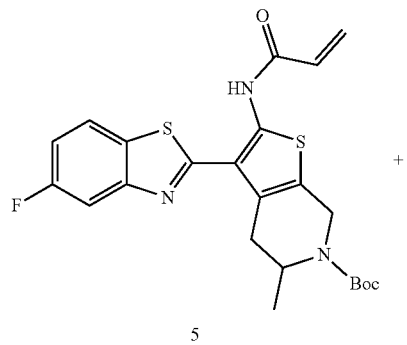

5

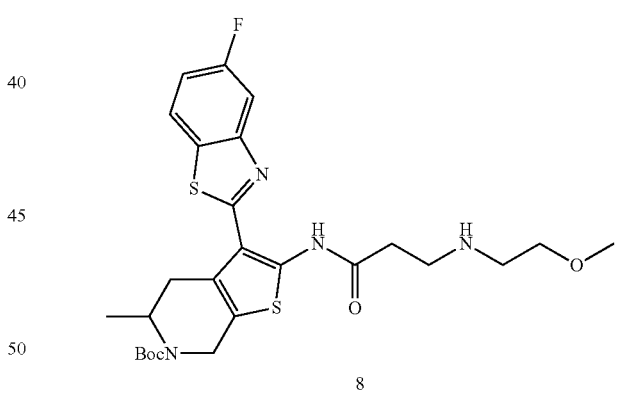

8

To a solution of mixture 5 and 6 (2.1 g, 4.439 mmol) in MeOH:THF (1:1, 30 mL) was added 2-methoxyethan-1-amine (500 mg, 6.659 mmol). The resulting reaction mixture was stirred at room temperature for 16 h. Progress of the reaction was monitored by TLC. After completion, the reaction mixture was concentrated to dryness under reduced pressure. The residue was washed with water and extracted with CH$_2$Cl$_2$ (thrice). The combined organic layer was dried over anhydrous Na$_2$SO$_4$, filtered and concentrated. The crude compound was purified by column chromatography eluting with 0-5% methanol in CH$_2$Cl$_2$ to afford the title compound 7 and 8 as yellow solid (1.23 g, yield 51%).

Step 4: N-(3-(5-Fluorobenzo[d]thiazol-2-yl)-7-methyl-4,5,6,7-tetrahydrothieno[2,3-c]pyridin-2-yl)-3-((2-methoxyethyl)amino)propanamide and N-(3-(5-Fluorobenzo[d]thiazol-2-yl)-5-methyl-4,5,6,7-tetrahydrothieno[2,3-c]pyridin-2-yl)-3-((2-methoxyethyl)amino)propanamide

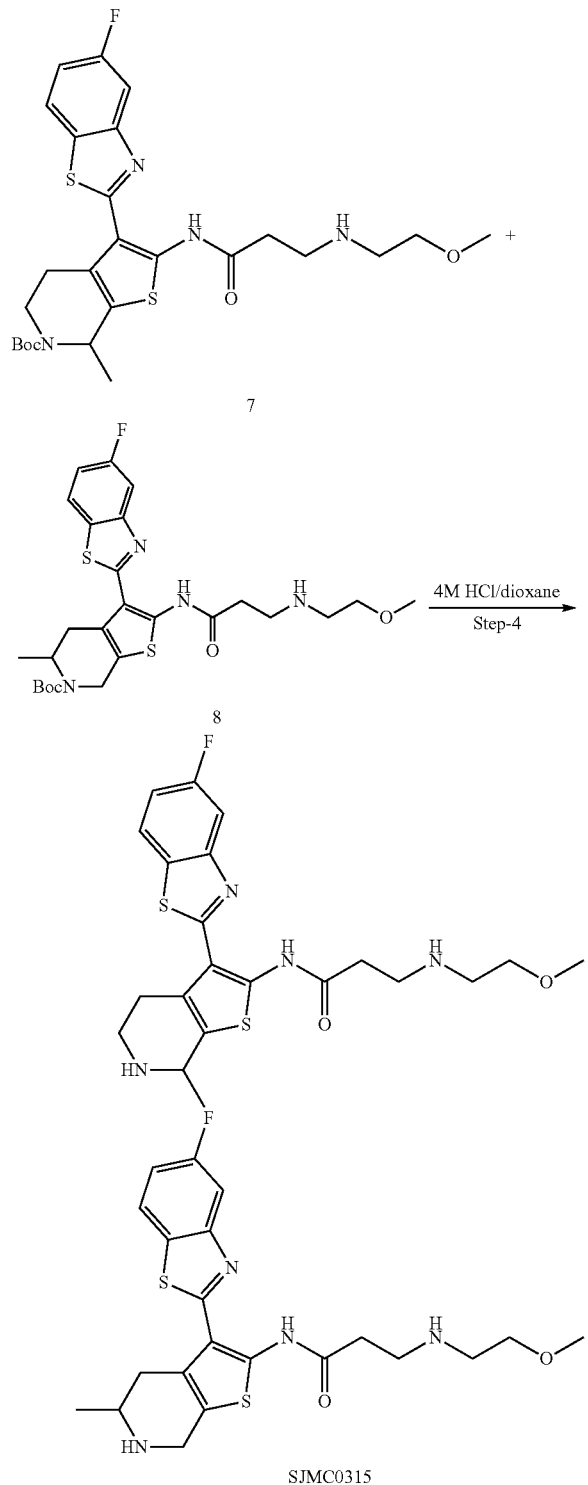

To a solution of 7 and 8 (1.23 g, 2.244 mmol) in dioxane (10 mL) at 0° C. was added 4M HCl in dioxane (10 mL). After the addition, the resulting mixture was stirred at room temperature for 3 h. After completion, the reaction mixture was evaporated in vacuum resulting in a crude residue which was purified by trituration with methanol. The solid obtained was filtered and washed with diethyl ether and n-pentane to afford a mixture of the title compounds as yellow solid (1.1 g, yield 95%). The chiral separation for the mixture (Column: CHIRALART-CELLULOSE SC, 250 mm×4.6 mm, 5 µm; Mobile Phase: A: n-Hexane+0.1% TEA; B: ETOH:DCM (85:15)+0.1% TEA; Flow rate: 1.0 mL/min; Isocratic: 80% B) afforded Compounds 557, 558, 570 and 571.

Example 129. Synthesis of N-(3-([1,3]Dioxolo[4',5':4,5]benzo[1,2-d]thiazol-6-yl)-6-isopropyl-4,5,6,7-tetrahydrothieno[2,3-c]pyridin-2-yl)-3-(sec-butylamino)propanamide (Compound 563)

Step 1: N-(3-([1,3]Dioxolo[4',5':4,5]benzo[1,2-d]thiazol-6-yl)-6-isopropyl-4,5,6,7-tetrahydrothieno[2,3-c]pyridin-2-yl)acrylamide (1)

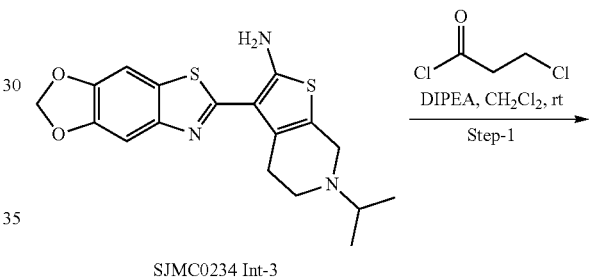

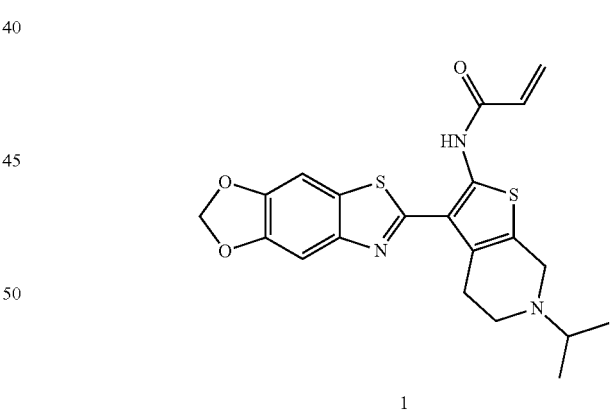

To a solution of 3-([1,3]dioxolo[4',5':4,5]benzo[1,2-d]thiazol-6-yl)-6-isopropyl-4,5,6,7-tetrahydrothieno[2,3-c]pyridin-2-amine SJMC0234_Int-3 (120 g, 0.321 mmol) in CH₂Cl₂ (10 mL) at 0° C. was added DIPEA (0.16 mL, 0.965 mmol) and 3-chloropropanoyl chloride (81 mg, 0.643 mmol). The reaction mixture was stirred at room temperature for 16 h. After completion (monitored by TLC), the reaction mixture was concentrated in vacuo. The crude compound was purified by column chromatography eluting with 0-20% ethyl acetate in n-hexane to afford the title compound 1 as light brown solid (120 mg crude).

387

Step 2: N-(3-([1,3]Dioxolo[4',5':4,5]benzo[1,2-d]thiazol-6-yl)-6-isopropyl-4,5,6,7-tetrahydrothieno[2,3-c]pyridin-2-yl)-3-(sec-butylamino)propanamide

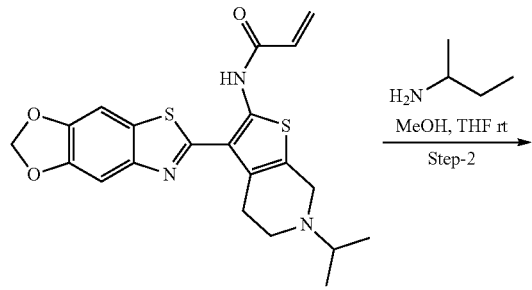

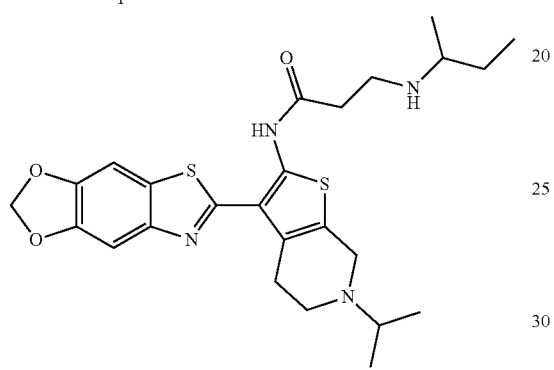

To a solution of N-(3-([1,3]dioxolo[4',5':4,5]benzo[1,2-d]thiazol-6-yl)-6-isopropyl-4,5,6,7-tetrahydrothieno[2,3-c]pyridin-2-yl)acrylamide 1 (120 mg, 0.281 mmol) in MeOH:THF (1:1, 20 mL) was added 2-methoxyethan-1-amine (31 mg, 0.421 mmol). The resulting reaction mixture was stirred at room temperature for 16 h. Progress of the reaction was monitored by TLC. After completion, the reaction mixture was concentrated to dryness under reduced pressure. The crude compound was purified by column chromatography eluting with 0-10% methanol in DCM to afford the title compound as yellow solid (10 mg, 7% yield).

Example 130. Synthesis of N-(3-(Benzo[d]thiazol-2-yl)-6-isopropyl-4,5,6,7-tetrahydrothieno[2,3-c]pyridin-2-yl)-3-(ethylmethyl)amino)propanamide (Compound 572)

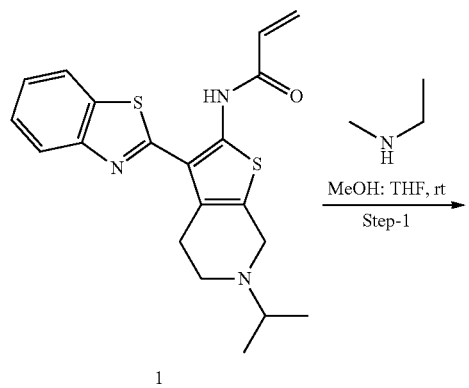

388

-continued

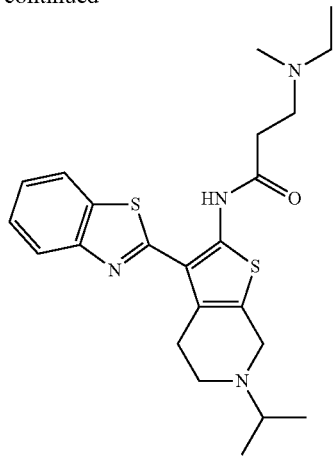

To a solution of N-(3-(benzo[d]thiazol-2-yl)-6-isopropyl-4,5,6,7-tetrahydrothieno[2,3-c]pyridin-2-yl)acrylamide 1 (200 mg, 0.521 mmol) in MeOH:THF (1:1; 10 mL) was added N-methylethanamine (46 mg, 0.781 mmol). The resulting reaction mixture was stirred at room temperature for 16 h. Progress of the reaction was monitored by TLC. After completion, the reaction mixture was concentrated to dryness under reduced pressure. The crude residue was dissolved in $CH_2Cl_2$ and washed with water. The combined organic layers were dried with anhydrous $Na_2SO_4$, filtered and concentrated to get a crude residue. This crude compound was purified by silica gel column chromatography eluting with 0-10% methanol in $CH_2Cl_2$ to afford Compound 572 as red sticky oil (15 mg, yield 6%).

Example 131. Synthesis of N-(3-(Benzo[d]thiazol-2-yl)-4,5,6,7-tetrahydrothieno[2,3-c]pyridin-2-yl)-3-(((3aR,5s,6aS)-octahydrocyclopenta[c]pyrrol-5-yl)amino)propanamide (Compound 573)

Step 1: tert-Butyl (3aR,5r,6aS)-5-hydroxyhexahydrocyclopenta[c]pyrrole-2(1H)-carboxylate (2)

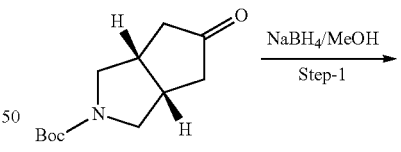

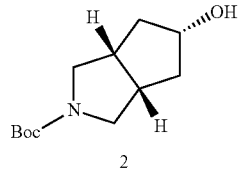

To a solution of tert-butyl (3aR,6aS)-5-oxohexahydrocyclopenta[c]pyrrole-2(1H)-carboxylate 1 (1 g, 4.438 mmol) in methanol (15 mL) at 0° C. was added sodium borohydride (250 mg, 6.658 mmol) and stirred at room temperature for 1 h. Progress of the reaction was monitored by TLC. After completion, the reaction mixture was quenched with water and extracted with ethyl acetate (thrice). The combined Step 2: tert-Butyl (3aR,5r,6aS)-5-((methylsulfonyl)oxy)hexahydrocyclopenta[c]pyrrole-2(1H)-carboxylate (3)

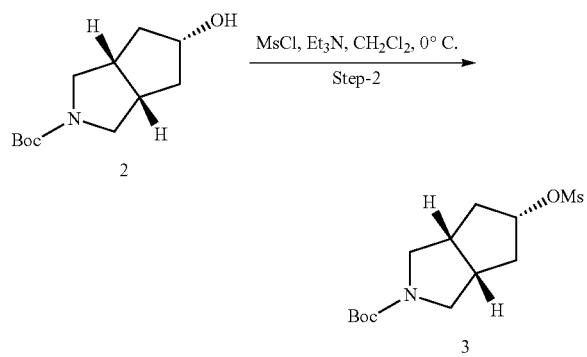

To a solution of tert-butyl (3aR,5r,6aS)-5-hydroxyhexahydrocyclopenta[c]pyrrole-2(1H)-carboxylate 2 (1.1 g, 4.845 mmol) in CH$_2$Cl$_2$ (20 mL) at 0° C. was added triethyl amine (1.32 mL, 9.691 mmol) and mesyl chloride (0.56 mL, 7.268 mmol). The resulting reaction mixture was stirred at room temperature for 3 h. Progress of the reaction was monitored by TLC. After completion, the reaction mixture was diluted with water and extracted with CH$_2$Cl$_2$ (thrice). The combined organic layer was dried over anhydrous Na$_2$SO$_4$; filtered and concentrated under reduced pressure to afford the title compound 3 as brown solid (1.56 g crude).

Step 3: tert-Butyl (3aR,5s,6aS)-5-azidohexahydrocyclopenta[c]pyrrole-2(1H)-carboxylate (4)

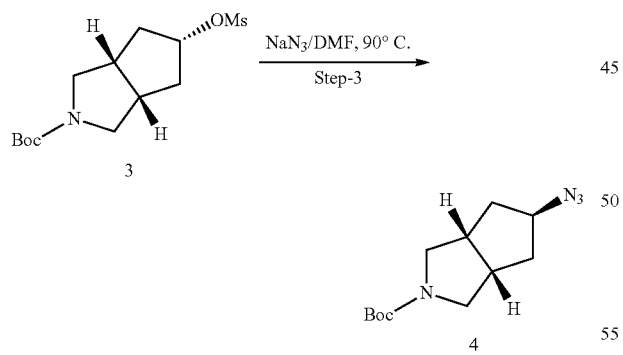

To a solution of tert-butyl (3aR,5r,6aS)-5-((methylsulfonyl)oxy)hexahydrocyclopenta[c]pyrrole-2(1H)-carboxylate 3 (1 g, 3.278 mmol) in DMF (10 mL) was added sodium azide (310 mg, 4.918 mmol) at room temperature. After the addition, the resulting mixture was heated to 90° C. for 3 h. Progress of the reaction was monitored by TLC. After completion, the reaction mixture was evaporated in vacuum up to dryness. The residue was diluted with water and extracted with CH$_2$Cl$_2$ (thrice). The combined organic layer was dried over anhydrous Na$_2$SO$_4$; filtered and concentrated under reduced pressure. The crude compound was purified by column chromatography eluting with 0-40% ethyl acetate in n-hexane to afford the title compound 4 as off white solid (500 mg, yield 60%).

Step 4: tert-Butyl (3aR,5s,6aS)-5-aminohexahydrocyclopenta[c]pyrrole-2(1H)-carboxylate (5)

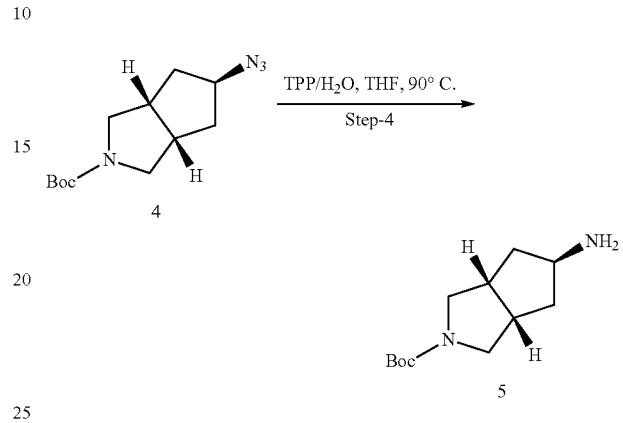

To a solution of tert-butyl (3aR,5s,6aS)-5-azidohexahydrocyclopenta[c]pyrrole-2(1H)-carboxylate 4 (500 mg, 1.984 mmol) in THF:H$_2$O (4:1; 10 mL) was added triphenyl phosphine (1.03 g, 3.968 mmol) at room temperature. The reaction mixture was heated to 90° C. for 2 h. After completion (monitored by TLC), the reaction mixture was evaporated in vacuum. The residue was dissolved in water and extracted with CH$_2$Cl$_2$ (thrice). The combined organic layer was dried over anhydrous Na$_2$SO$_4$; filtered and concentrated under reduced pressure. The crude compound was purified by basic alumina column chromatography eluting with 0-10% methanol in CH$_2$Cl$_2$ to afford the title compound 5 as light brown solid (340 mg, yield 76%).

Step 5: tert-Butyl 3-(benzo[d]thiazol-2-yl)-2-(3-(((3aR,5s,6aS)-2-(tert-butoxycarbonyl)octahydrocyclopenta[c]pyrrol-5-yl)amino)propanamido)-4,7-dihydrothieno[2,3-c]pyridine-6(5H)-carboxylate (7)

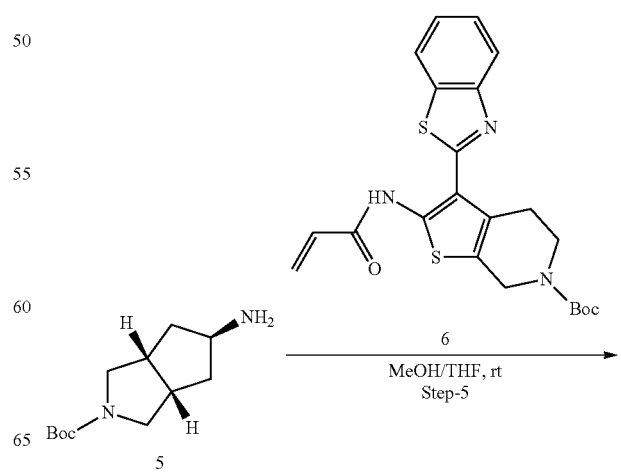

-continued

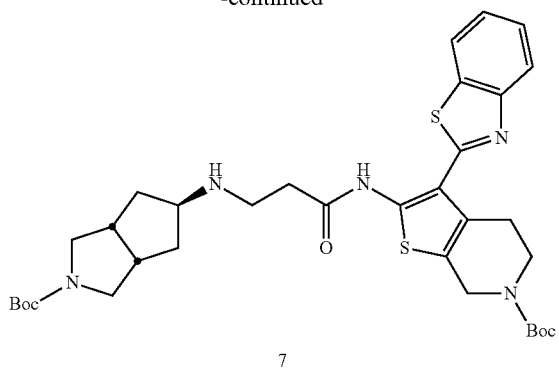

7

To a solution of tert-butyl 2-acrylamido-3-(benzo[d]thiazol-2-yl)-4,7-dihydrothieno[2,3-c]pyridine-6(5H)-carboxylate 6 (200 mg, 0.453 mmol) in MeOH:THF (1:1, 4 mL) was added tert-butyl (3aR,5s,6aS)-5-aminohexahydrocyclopenta[c]pyrrole-2(1H)-carboxylate 5 (123 mg, 0.544 mmol). The resulting reaction mixture was stirred at room temperature for 16 h. Progress of the reaction was monitored by TLC. After completion, the reaction mixture was concentrated to dryness under reduced pressure. The residue was washed with water and extracted with $CH_2Cl_2$ (thrice). The combined organic layer dried over anhydrous $Na_2SO_4$; filtered and concentrated under reduced pressure. The crude compound was purified by column chromatography eluting with 0-5% methanol in $CH_2Cl_2$ to afford the title compound 7 as yellow solid (102 mg, yield 34%).

Step 6: N-(3-(Benzo[d]thiazol-2-yl)-4,5,6,7-tetrahydrothieno[2,3-c]pyridin-2-yl)-3-(((3aR,5s,6aS)-octahydrocyclopenta[c]pyrrol-5-yl)amino)propanamide

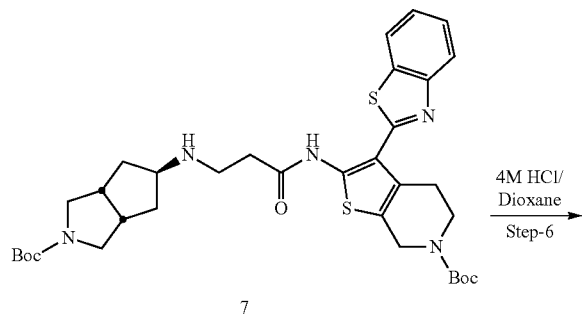

7

4M HCl/ Dioxane
Step-6

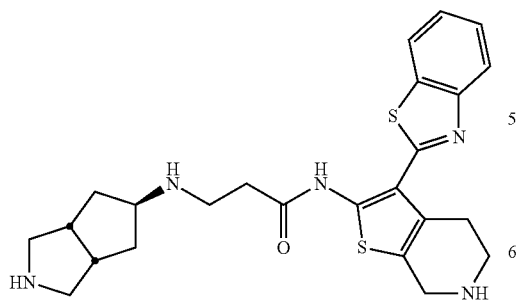

To a solution of tert-butyl 3-(benzo[d]thiazol-2-yl)-2-(3-(((3aR,5s,6aS)-2-(tert-butoxycarbonyl)octahydrocyclopenta[c]pyrrol-5-yl)amino)propanamido)-4,7-dihydrothieno[2,3-c]pyridine-6(5H)-carboxylate 7 (100 mg, 0.149 mmol) in dioxane (1 mL) at 0° C. was added 4M HCl in dioxane (3 mL). After the addition, the resulting mixture was stirred at room temperature for 3 h. After completion, the reaction mixture was evaporated in vacuum resulting in a crude residue which was purified by trituration with methanol. The solid obtained was filtered and washed with diethyl ether and n-pentane to afford the HCl salt of Compound 573 as yellow solid (85 mg, yield 98%).

Example 132. Synthesis of (R)-3-(sec-butylamino)-N-(6-isopropyl-3-(5-(trifluoromethyl)benzo[d]thiazol-2-yl)-4,5,6,7-tetrahydrothieno[2,3-c]pyridin-2-yl)propanamide (Compound 574)

Step 1: 6-Isopropyl-3-(5-(trifluoromethyl)benzo[d]thiazol-2-yl)-4,5,6,7-tetrahydrothieno[2,3-c]pyridin-2-amine (2)

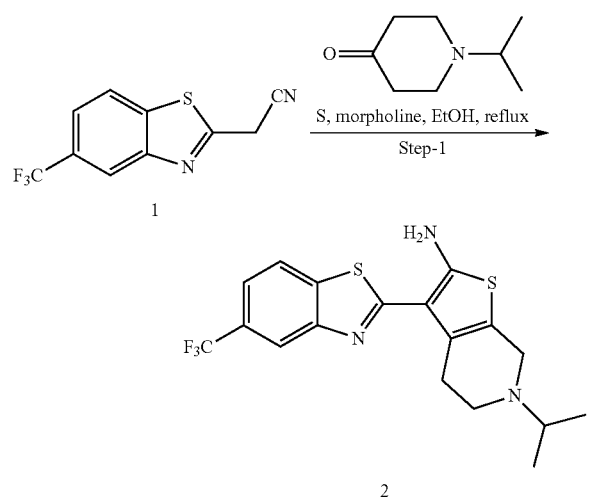

To a solution of 2-(5-(trifluoromethyl)benzo[d]thiazol-2-yl)acetonitrile 1 (2 g, 8.264 mmol) in ethanol (20 mL) was added 1-isopropylpiperidin-4-one (1.16 g, 8.264 mmol), elemental sulphur (264 mg, 8.264 mmol) and morpholine (700 mg, 8.264 mmol) at room temperature. After the addition, the resulting mixture was heated to reflux at 80° C. for 16 h. Progress of the reaction was monitored by TLC. After completion, the reaction mixture was evaporated in vacuum up to dryness. The crude compound was purified by column chromatography eluting with 0-40% ethyl acetate in n-hexane to afford the title compound 2 as off white solid (2 g, yield 62%).

Step 2: N-(6-Isopropyl-3-(5-(trifluoromethyl)benzo[d]thiazol-2-yl)-4,5,6,7-tetrahydrothieno[2,3-c]pyridin-2-yl)acrylamide (3)

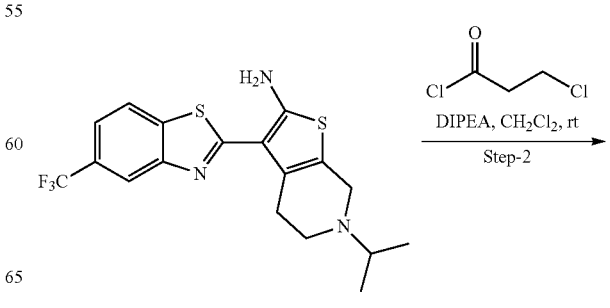

-continued

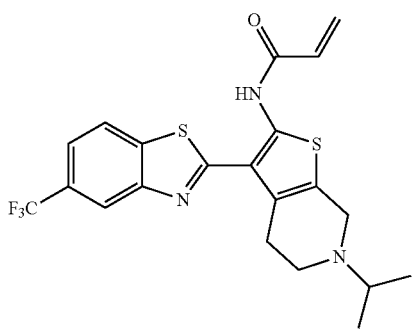

3

To a solution of 6-isopropyl-3-(5-(trifluoromethyl)benzo[d]thiazol-2-yl)-4,5,6,7-tetrahydrothieno[2,3-c]pyridin-2-amine 2 (2 g, 5.037 mmol) in CH$_2$Cl$_2$ (20 mL) at 0° C. was added DIPEA (1.75 mL, 10.07 mmol) and 3-chloropropanoyl chloride (950 mg, 7.556 mmol). The reaction mixture was stirred at room temperature for 2 h. After completion (monitored by TLC), the reaction mixture was concentrated to dryness under reduced pressure to afford the title compound 3 as light brown solid (2 g crude).

Step 3: (R)-3-(sec-butylamino)-N-(6-isopropyl-3-(5-(trifluoromethyl)benzo[d]thiazol-2-yl)-4,5,6,7-tetrahydrothieno[2,3-c]pyridin-2-yl)propanamide

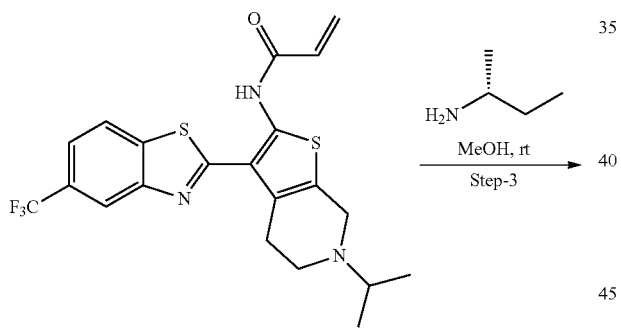

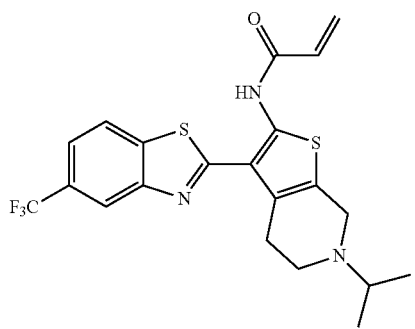

SJMC0429

To a solution of N-(6-isopropyl-3-(5-(trifluoromethyl)benzo[d]thiazol-2-yl)-4,5,6,7-tetrahydrothieno[2,3-c]pyridin-2-yl)acrylamide 3 (300 mg, 0.665 mmol) in MeOH (5 mL) was added (R)-butan-2-amine (97 mg, 1.330 mmol). The resulting reaction mixture was stirred at room temperature for 16 h. Progress of the reaction was monitored by TLC. After completion, the reaction mixture was concentrated to dryness under reduced pressure. The crude compound was purified by column chromatography eluting with 0-10% methanol in CH$_2$Cl$_2$ to afford the title compound as yellow solid (30 mg, yield 8.6%).

Example 133. Synthesis of N-(6-Isopropyl-3-(5-(trifluoromethyl)benzo[d]thiazol-2-yl)-4,5,6,7-tetrahydrothieno[2,3-c]pyridin-2-yl)-3-((2-methoxyethyl)amino) propanamide (Compound 575)

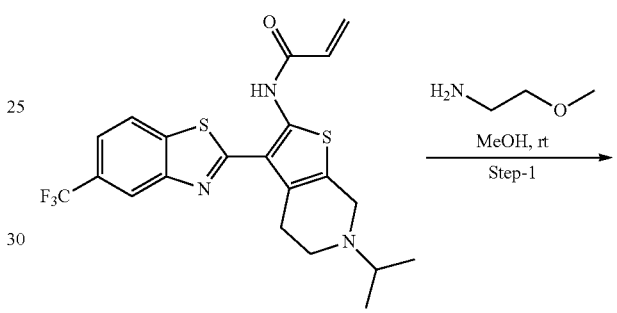

SJMC0429_Int-3

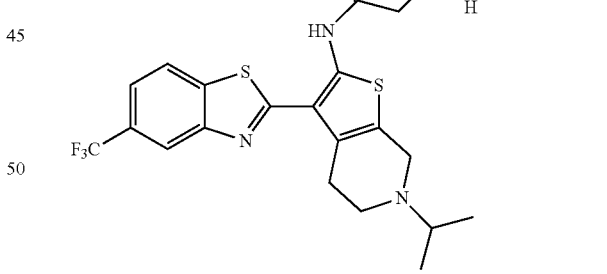

To a solution of N-(6-isopropyl-3-(5-(trifluoromethyl)benzo[d]thiazol-2-yl)-4,5,6,7-tetrahydrothieno[2,3-c]pyridin-2-yl)acrylamide SJMC0429_Int-3 (300 mg, 0.665 mmol) in MeOH (5 mL) was added 2-methoxyethan-1-amine (99 mg, 1.330 mmol). The resulting reaction mixture was stirred at room temperature for 16 h. Progress of the reaction was monitored by TLC. After completion, the reaction mixture was concentrated to dryness under reduced pressure. The crude compound was purified by column chromatography eluting with 0-10% methanol in CH$_2$Cl$_2$ to afford the title compound as yellow solid (18 mg, yield 5.2%).

Example 134. Synthesis of 3-(sec-Butylamino)-N-(3-(5,6-dimethylbenzo[d]thiazol-2-yl)-4,5,6,7-tetrahydrothieno[2,3-c]pyridin-2-yl)propanamide (Compound 576)

Step 1: tert-Butyl 2-acrylamido-3-(5,6-dimethylbenzo[d]thiazol-2-yl)-4,7-dihydrothieno[2,3-c]pyridine-6(5H)-carboxylate (2)

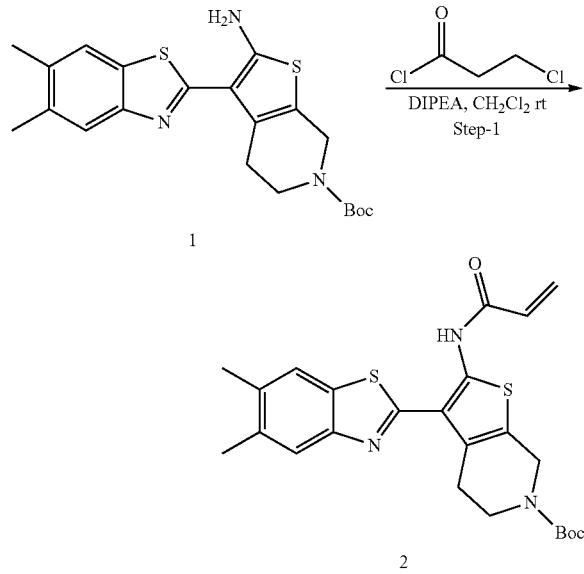

To a solution of tert-butyl 2-amino-3-(5,6-dimethylbenzo[d]thiazol-2-yl)-4,7-dihydrothieno[2,3-c]pyridine-6(5H)-carboxylate 1 (260 mg, 0.626 mmol) in $CH_2Cl_2$ (75 mL) at 0° C. was added dii23sopropylethylamine (0.16 mL, 0.939 mmol) and 3-chloropropanoyl chloride (0.089 mL, 0.939 mmol). The reaction mixture was stirred at room temperature for 2 h. After completion (monitored by TLC), the reaction mixture was diluted with $CH_2Cl_2$ and organic layer was washed with saturated solution of sodium bicarbonate and brine solution. Organic layer was dried over anhydrous sodium sulphate and concentrate under vacuum to obtained crude product. The crude compound was purified by column chromatography eluting with 15% ethyl acetate in n-hexane to afford the title compound 2 as light brown solid (110 mg, yield 38%).

Step-2: tert-Butyl 2-(3-(sec-butylamino)propanamido)-3-(5,6-dimethylbenzo[d]thiazol-2-yl)-4,7-dihydrothieno[2,3-c]pyridine-6(5H)-carboxylate (3)

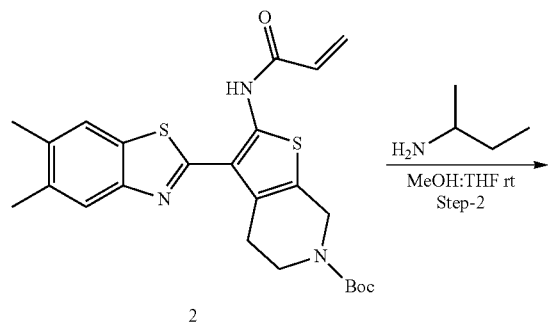

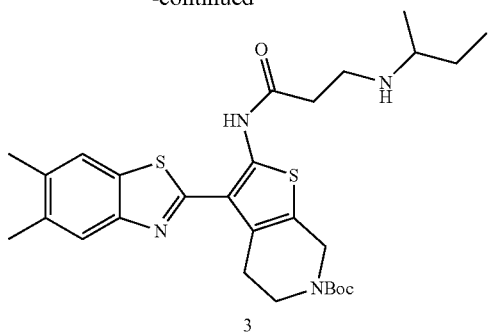

To a solution of tert-butyl 2-acrylamido-3-(5,6-dimethylbenzo[d]thiazol-2-yl)-4,7-dihydrothieno[2,3-c]pyridine-6(5H)-carboxylate 2 (110 mg, 0.234 mmol) in MeOH:THF (1:1; 10 mL) was added (S) 2-amino butane (20.5 mg, 0.281 mmol). The resulting reaction mixture was stirred at room temperature for 16 h. Progress of the reaction was monitored by TLC. After completion, the reaction mixture was concentrated to dryness under reduced pressure. The crude residue was dissolved in $CH_2Cl_2$ and washed with water. The combined organic layers were dried with anhydrous $Na_2SO_4$, filtered and concentrated to get a crude residue. This crude compound was purified by silica gel column chromatography eluting with 0-10% methanol in $CH_2Cl_2$ to afford 3 as yellow solid (80 mg, yield 63%).

Step 3: 3-(sec-Butylamino)-N-(3-(5,6-dimethylbenzo[d]thiazol-2-yl)-4,5,6,7-tetrahydrothieno[2,3-c]pyridin-2-yl)propanamide

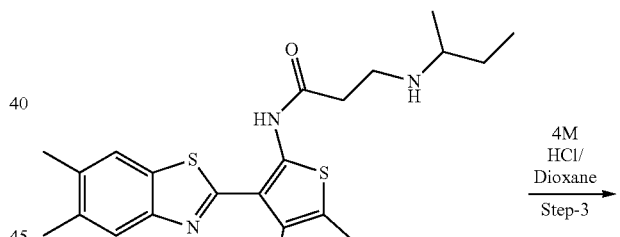

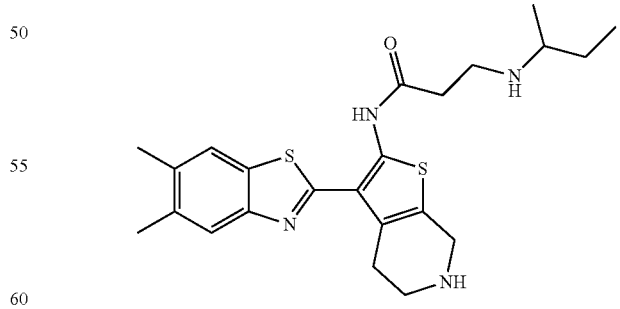

To a solution of tert-butyl 2-(3-(sec-butylamino)propanamido)-3-(5,6-dimethylbenzo[d]thiazol-2-yl)-4,7-dihydrothieno[2,3-c]pyridine-6(5H)-carboxylate 3 (80 mg, 0.147 mmol) in dioxane (1 mL) at 0° C. was added 4M HCl in dioxane (2 mL). After the addition, the resulting mixture was stirred at room temperature for 5 h. After completion, the reaction mixture was evaporated to dryness and the resulting in a crude residue was purified by trituration in diethyl ether and pentane to afford the HCl salt of the title compound as yellow solid (40 mg HCl salt, yield 40%).

Example 135. Synthesis of N-(3-(benzo[d]thiazol-2-yl)-6-isopropyl-4,5,6,7 tetrahydrothieno[2,3-c]pyridin-2-yl)-3-(sec-butyl(methyl)amino)propanamide (Compound 577)

Step 1: N-(3-(benzo[d]thiazol-2-yl)-6-isopropyl-4,5,6,7-tetrahydrothieno[2,3-c]pyridin-2-yl)acrylamide (2)

Step-2: N-(3-(benzo[d]thiazol-2-yl)-6-isopropyl-4,5,6,7-tetrahydrothieno[2,3-c]pyridin-2-yl)-3-(sec-butyl(methyl)amino)propanamide

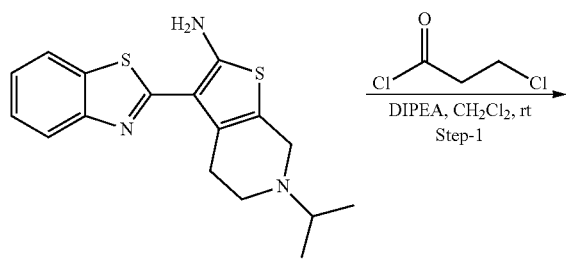

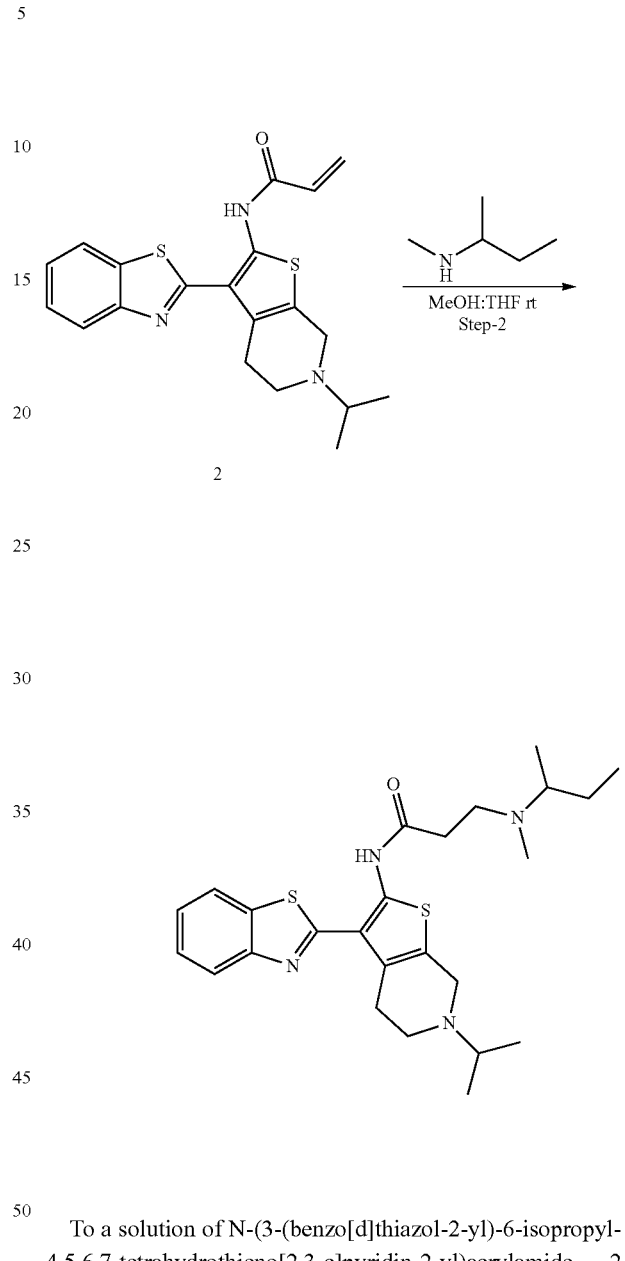

To a solution of 3-(benzo[d]thiazol-2-yl)-6-isopropyl-4,5,6,7-tetrahydrothieno[2,3-c]pyridin-2-amine 1 (1.2 g, 3.64 mmol) in $CH_2Cl_2$ (20 mL) at 0° C. was added diisopropylethylamine (1.57 mL, 9.11 mmol) and 3-chloropropanoyl chloride (0.55 mL, 4.37 mmol). The reaction mixture was stirred at room temperature for 2 h. After completion (monitored by TLC), the reaction mixture was diluted with dichloromethane and organic layer was washed with Saturated solution of sodium bicarbonate and brine solution. Organic layer was dried over anhydrous sodium sulphate and concentrate under vacuum to obtained crude product. The crude compound was purified by column chromatography eluting with 15% Ethyl acetate in Hexane to afford the title compound 2 as light brown solid (800 mg, yield 57%).

To a solution of N-(3-(benzo[d]thiazol-2-yl)-6-isopropyl-4,5,6,7-tetrahydrothieno[2,3-c]pyridin-2-yl)acrylamide 2 (400 mg, 1.04 mmol) in MeOH:THF (1:1; 10 mL) was added N-methylbutan-2-amine (0.16 mL, 1.56 mmol). The resulting reaction mixture was stirred at room temperature for 16 h. Progress of the reaction was monitored by TLC. After completion, the reaction mixture was concentrated to dryness under reduced pressure. The crude residue was dissolved in $CH_2Cl_2$ and washed with water. The combined organic layers were dried with anhydrous $Na_2SO_4$, filtered and concentrated to get a crude residue. This crude compound was purified by silica gel column chromatography eluting with 0-10% methanol in $CH_2Cl_2$ to afford the title compound as yellow solid (110 mg, yield 23%).

Example 136. Synthesis of (S)-3-(sec-butylamino)-N-(6-isopropyl-3-(5-(trifluoromethyl) benzo[d]thiazol-2-yl)-4,5,6,7-tetrahydrothieno[2,3-c]pyridin-2-yl)propanamide (Compound 578)

Step 1: 6-Isopropyl-3-(5-(trifluoromethyl)benzo[d]thiazol-2-yl)-4,5,6,7-tetrahydrothieno[2,3-c]pyridin-2-amine (2)

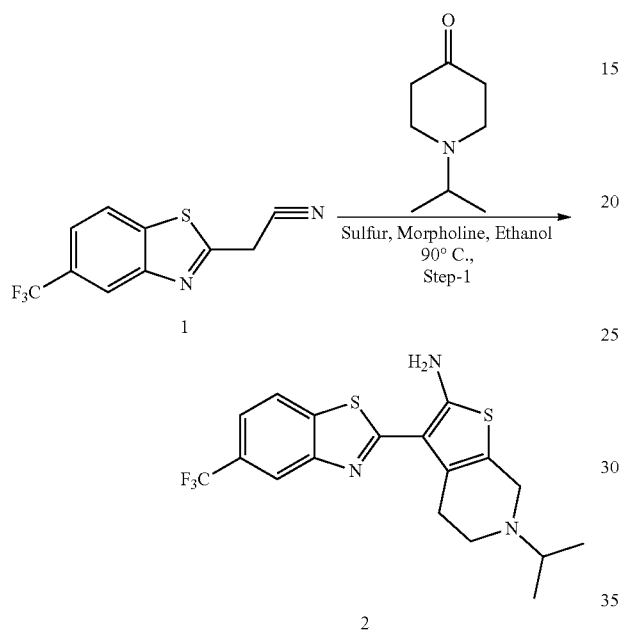

To a solution of 2-(5-(trifluoromethyl)benzo[d]thiazol-2-yl)acetonitrile 1 (2.0 g, 8.2 mmol), elemental sulphur (0.26 g, 8.2 mmol) and morpholine (0.7 g, 8.2 mmol) was added 1-isopropyl-4-oxopiperidine-(1.16 g, 8.2 mmol) at room temperature and the resulting reaction mixture was heated to reflux at 85° C. for 3 h. Reaction was monitored by TLC. After the completion, reaction mixture was evaporated to dryness on rotavapour and the crude compound was triturated in methanol and dried to afford the pure compound 2 as brown solid (2.0 g crude).

Step 2: N-(6-isopropyl-3-(5-(trifluoromethyl)benzo[d]thiazol-2-yl)-4,5,6,7-tetrahydrothieno[2,3-c]pyridin-2-yl)acrylamide (3)

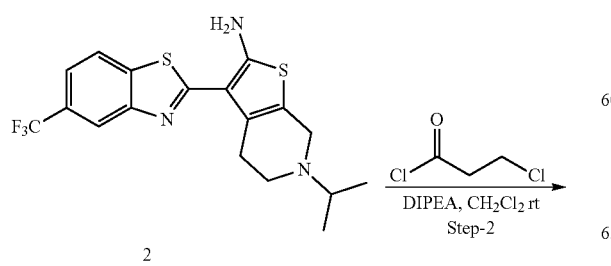

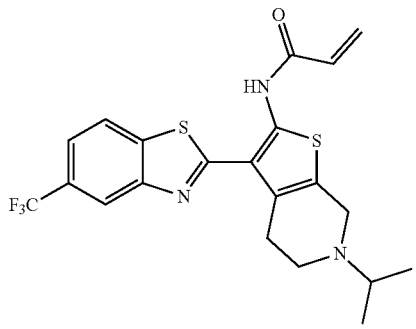

To a solution of 6-isopropyl-3-(5-(trifluoromethyl)benzo[d]thiazol-2-yl)-4,5,6,7-tetrahydrothieno[2,3-c]pyridin-2-amine 2 (2 g, 5.0 mmol) in $CH_2Cl_2$ (20 mL) at 0° C. was added DIPEA (1.29 g, 10.0 mmol) followed by 3-chloro propionyl chloride (0.95 g, 5.5 mmol). Reaction mixture was stirred at room temperature for 3 h. Reaction was monitored by TLC. After completion, the reaction mixture was diluted with $CH_2Cl_2$ and washed with saturated $NaHCO_3$ solution and brine. The separated organic layer was dried over $Na_2SO_4$, filtered and concentrated in vacuum to get a crude compound 3 brown solid (2.0 g crude).

Step 3: (S)-3-(sec-butylamino)-N-(6-isopropyl-3-(5-(trifluoromethyl)benzo[d]thiazol-2-yl)-4,5,6,7-tetrahydrothieno[2,3-c]pyridin-2-yl)propanamide

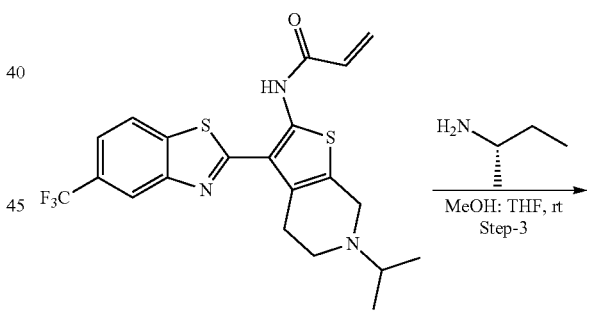

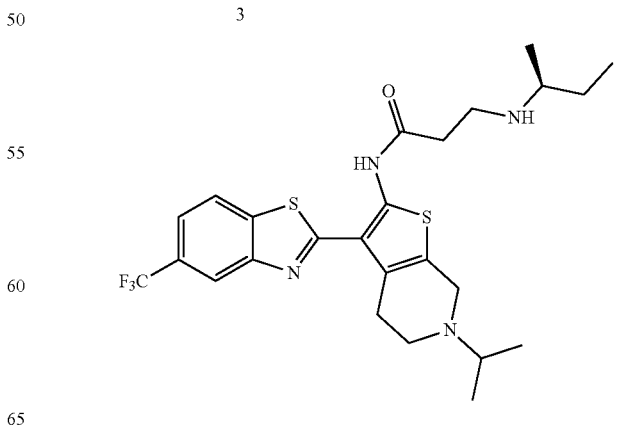

To a solution of N-(6-isopropyl-3-(5-(trifluoromethyl)benzo[d]thiazol-2-yl)-4,5,6,7-tetrahydrothieno[2,3-c]pyridin-2-yl)acrylamide 3 (300 mg, 0.665 mmol) in MeOH (50 mL) was added (S) 2-aminobutane (97 mg, 1.33 mmol). The resulting reaction mixture was stirred at room temperature for 16 h. Progress of the reaction was monitored by TLC. After completion, the reaction mixture was concentrated to dryness under reduced pressure. The crude residue was dissolved in $CH_2Cl_2$ and washed with water. The combined organic layers were dried with anhydrous $Na_2SO_4$, filtered and concentrated to get a crude residue. This crude compound was purified by silica gel column chromatography eluting with 0-10% methanol in $CH_2Cl_2$ to afford the title compound as yellow solid (25 mg, yield 7.2%).

Example 137. Synthesis of (S)-3-(sec-butylamino)-N-(3-(5-(pyridin-4-yl)benzo[d]thiazol-2-yl)-4,5,6,7-tetrahydrothieno[2,3-c]pyridin-2-yl)Propanamide (Compound 579)

Step 1: tert-butyl 2-amino-3-(5-bromobenzo[d]thiazol-2-yl)-4,7-dihydrothieno[2,3-c]pyridine-6(5H)-carboxylate (2)

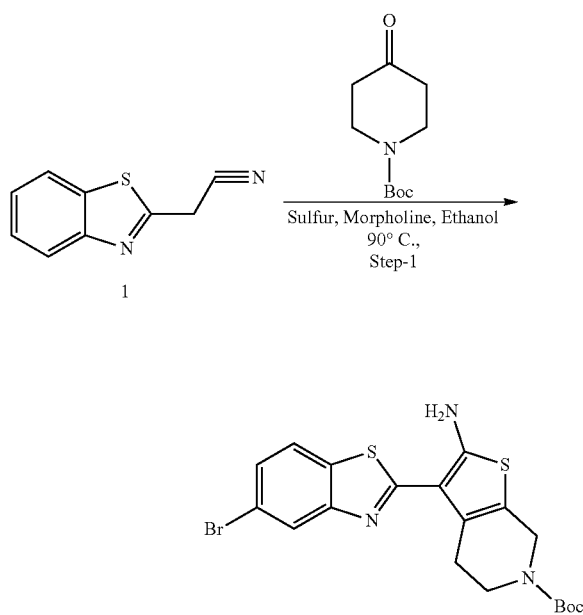

To a solution of 2-(5-bromobenzo[d]thiazol-2-yl)acetonitrile 1 (14.0 g, 55 mmol), elemental sulphur (1.7 g, 55 mmol) and morpholine (4.8 g, 55 mmol) was added tert-butyl 4-oxopiperidine-1-carboxylate (11.0 g, 55 mmol) at room temperature and the resulting reaction mixture was heated to reflux at 85° C. for 3 h. Reaction was monitored by TLC. After the completion, reaction mixture was evaporated to dryness on rotavapour and the crude compound was triturated in methanol and dried to afford the pure compound 2 as brown solid (21.5 g crude).

Step-2: tert-Butyl 2-acrylamido-3-(5-bromobenzo[d]thiazol-2-yl)-4,7-dihydrothieno[2,3-c]pyridine-6(5H)-carboxylate (3)

To a solution of tert-butyl 2-amino-3-(5-bromobenzo[d]thiazol-2-yl)-4,7-dihydrothieno[2,3-c]pyridine-6(5H)-carboxylate (2) (20 g, 43 mmol) in $CH_2Cl_2$ (100 mL) at 0° C. was added DIPEA (11 g, 64.5 mmol) followed by 3-chloro propionyl chloride (8.1 g, 86 mmol). Reaction mixture was stirred at room temperature for 3 h. Reaction was monitored by TLC. After completion, the reaction mixture was diluted with $CH_2Cl_2$ and washed with saturated $NaHCO_3$ solution and brine. The separated organic layer was dried over $Na_2SO_4$, filtered and concentrated in vacuum to get a crude compound 3 brown solid (15 g crude).

Step 3: tert-Butyl (S)-3-(5-bromobenzo[d]thiazol-2-yl)-2-(3-(sec-butylamino)propanamido)-4,7-dihydrothieno[2,3-c]pyridine-6(5H)-carboxylate (4)

-continued

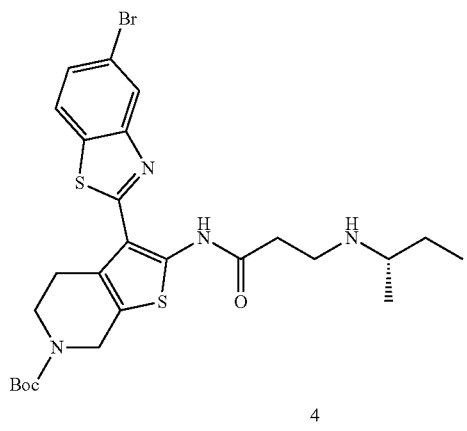

4

-continued

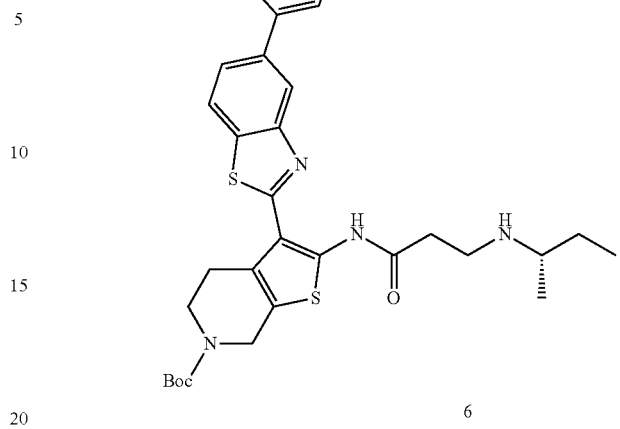

6

To a solution of tert-butyl 2-acrylamido-3-(5-bromobenzo[d]thiazol-2-yl)-4,7-dihydrothieno[2,3-c]pyridine-6(5H)-carboxylate 3 (0.5 g, 0.96 mmol) in MeOH:THF (1:1, 10 mL) was added (S) 2 aminobutane (105 mg, 1.45 mmol). The resulting reaction mixture was stirred at room temperature for 16 h. Progress of the reaction was monitored by TLC. After completion, the reaction mixture was concentrated to dryness under reduced pressure. The crude residue was dissolved in $CH_2Cl_2$ and washed with water. The combined organic layers were dried with anhydrous $Na_2SO_4$, filtered and concentrated to get a crude residue. This crude compound was purified by silica gel column chromatography eluting with 0-10% methanol in $CH_2Cl_2$ to afford title compound 4 as yellow solid (0.5 g, yield 87%).

Step 4: tert-Butyl (S)-2-(3-(sec-butylamino)propanamido)-3-(5-(pyridin-4-yl)benzo[d]thiazol-2-yl)-4,7-dihydrothieno[2,3-c]pyridine-6(5H)-carboxylate (6)

To a solution of tert-butyl (S)-3-(5-bromobenzo[d]thiazol-2-yl)-2-(3-(sec-butylamino)propanamido)-4,7-dihydrothieno[2,3-c]pyridine-6(5H)-carboxylate 4 (500 mg, 0.84 mmol) in dioxane (10 mL) was added $K_2CO_3$ (291 mg, 2.11 mmol) in water (1 mL) and the reaction mixture was degassed under argon atmosphere for 10 min. Followed by addition of $Pd(PPh_3)_4$ (97 mg, 0.084 mmol) and 4-(4,4,5,5-tetramethyl-1,3,2-dioxaborolan-2-yl)pyridine (155 mg, 1.26 mmol) and degassed with argon for another 20 min. The reaction mixture was heated to 100° C. for 16 h. After the completion of reaction (monitored by LCMS), the reaction mixture was diluted with water and extracted with ethyl acetate (thrice). The combined organic layers were dried with anhydrous $Na_2SO_4$, filtered and concentrated to get a crude residue. This crude compound was purified by silica gel column chromatography eluting with 0-6% methanol in $CH_2Cl_2$ to afford the title compound 6 as yellow solid (400 mg, 80% yield).

Step 5: (S)-3-(sec-butylamino)-N-(3-(5-(pyridin-4-yl)benzo[d]thiazol-2-yl)-4,5,6,7-tetrahydrothieno[2,3-c]pyridin-2-yl)propanamide

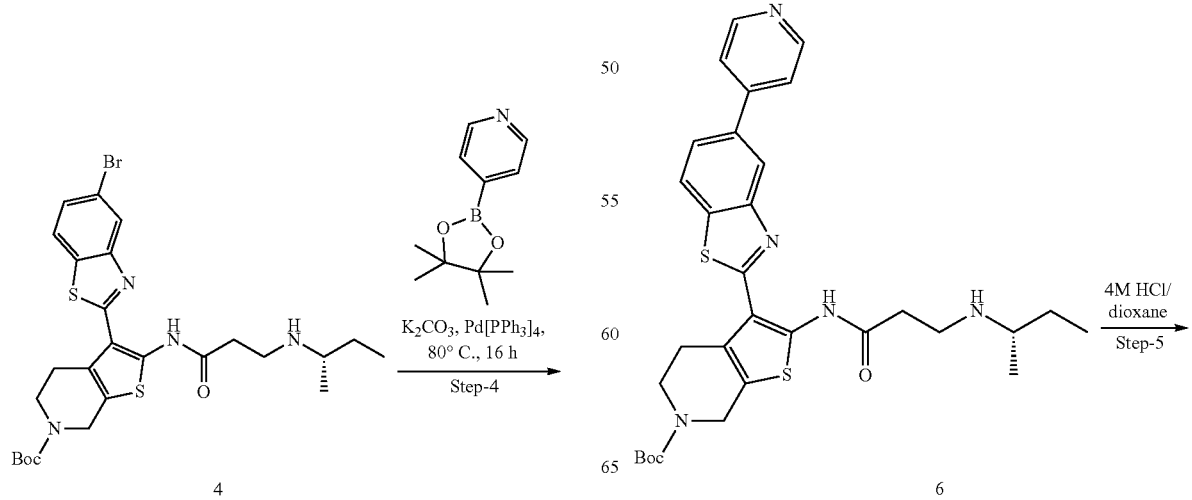

-continued

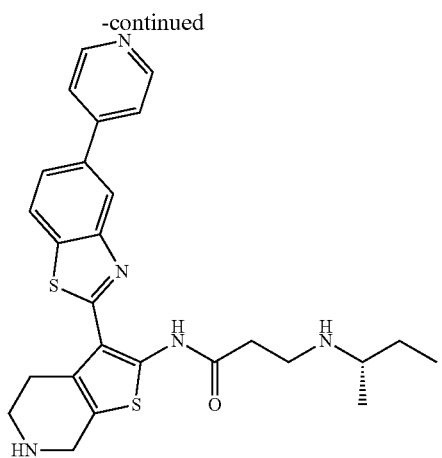

To a solution of tert-butyl (S)-2-(3-(sec-butylamino)propanamido)-3-(5-(pyridin-4-yl)benzo[d]thiazol-2-yl)-4,7-dihydrothieno[2,3-c]pyridine-6(5H)-carboxylate 6 (200 mg, 0.337 mmol) in dioxane (5 mL) at 0° C. was added 4M HCl in dioxane (5 mL). After the addition, the resulting mixture was stirred at room temperature for 3 h. After completion, the reaction mixture was evaporated in vacuum resulting in a crude residue which was purified by trituration with methanol. The solid obtained was filtered and washed with diethyl ether and n-pentane to afford the HCl salt of the title compound as yellow solid (150 mg, yield 74%).

Example 138. Synthesis of (S)-3-(sec-butylamino)-N-(6-ethyl-3-(5-(pyridin-4-yl)benzo[d]thiazol-2-yl)-4,5,6,7-tetrahydrothieno[2,3-c]pyridin-2-yl)propanamide (Compound 588)

Step 1: 3-(5-Bromobenzo[d]thiazol-2-yl)-6-ethyl-4,5,6,7-tetrahydrothieno[2,3-c]pyridin-2-amine (2)

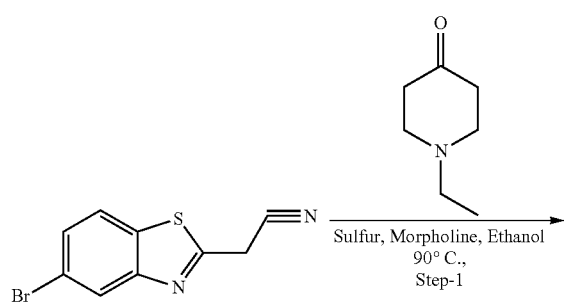

To a solution of 2-(5-bromobenzo[d]thiazol-2-yl)acetonitrile 1 (1.0 g, 3.9 mmol), elemental sulphur (126 mg, 3.9 mmol) and morpholine (345 mg, 3.9 mmol) in ethanol (20 mL) was added 1-ethyl-4-oxo-piperidine (500 mg, 3.9 mmol) at room temperature and the resulting reaction mixture was heated to reflux at 85° C. for 3 h. Reaction was monitored by TLC. After the completion, reaction mixture was evaporated to dryness on rotavapour and the crude compound was triturated in methanol and dried to afford the pure compound 2 as brown solid (1.0 g crude).

Step 2: N-(3-(5-bromobenzo[d]thiazol-2-yl)-6-ethyl-4,5,6,7-tetrahydrothieno[2,3-c]pyridin-2-yl)acrylamide (3)

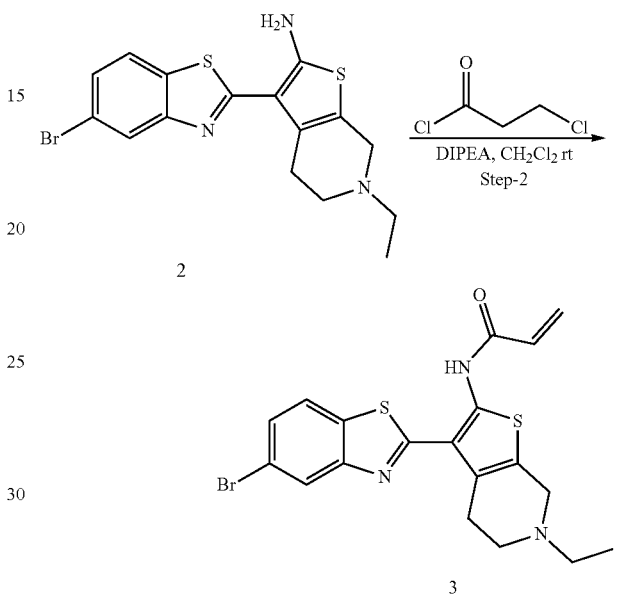

To a solution of 3-(5-bromobenzo[d]thiazol-2-yl)-6-ethyl-4,5,6,7-tetrahydrothieno[2,3-c]pyridin-2-amine 2 (0.8 g, 2.03 mmol) in $CH_2Cl_2$ (15 mL) at 0° C. was added DIPEA (0.52 g, 4.07 mmol) followed by 3-chloro propionyl chloride (0.387 g, 3.05 mmol). Reaction mixture was stirred at room temperature for 3 h. Reaction was monitored by TLC. After completion, the reaction mixture was diluted with $CH_2Cl_2$ and washed with saturated $NaHCO_3$ solution and brine. The separated organic layer was dried over $Na_2SO_4$, filtered and concentrated in vacuum to get a crude compound 3 as brown solid (0.9 g crude).

Step 3: (S)—N-(3-(5-bromobenzo[d]thiazol-2-yl)-6-ethyl-4,5,6,7-tetrahydrothieno[2,3-c]pyridin-2-yl)-3-(sec-butylamino)propanamide (4)

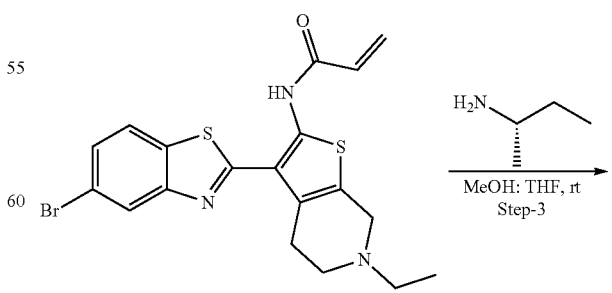

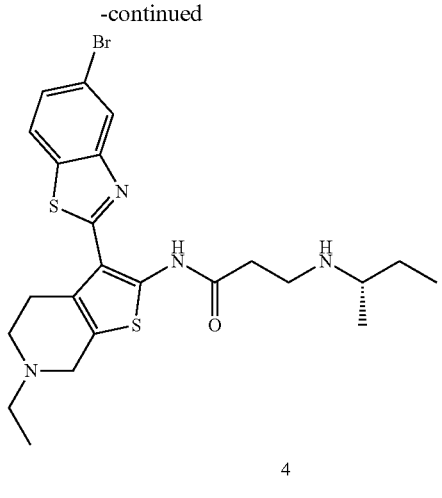

4

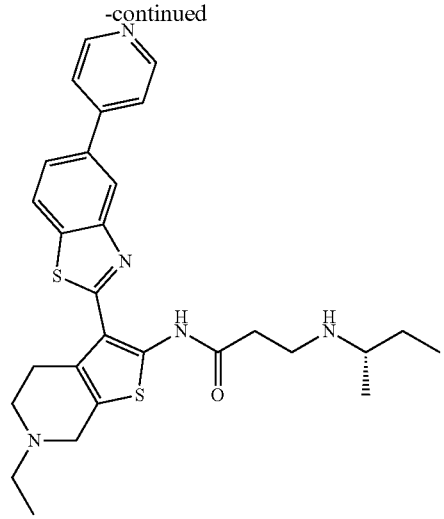

To a solution of N-(3-(5-bromobenzo[d]thiazol-2-yl)-6-ethyl-4,5,6,7-tetrahydrothieno[2,3-c]pyridin-2-yl)acrylamide 3 (0.9 g, 2.013 mmol) in MeOH (10 mL) was added (S) 2 aminobutane (0.146 mg, 2.013 mmol). The resulting reaction mixture was stirred at room temperature for 16 h. Progress of the reaction was monitored by TLC. After completion, the reaction mixture was concentrated to dryness under reduced pressure. The crude residue was dissolved in $CH_2Cl_2$ and washed with water. The combined organic layers were dried with anhydrous $Na_2SO_4$, filtered and concentrated to get a crude residue. This crude compound was purified by silica gel column chromatography eluting with 0-10% methanol in $CH_2Cl_2$ to afford title compound 4 as yellow solid (0.35 g, yield 33.6%).

Step 4: (S)-3-(sec-butylamino)-N-(6-ethyl-3-(5-(pyridin-4-yl)benzo[d]thiazol-2-yl)-4,5,6,7-tetrahydrothieno[2,3-c]pyridin-2-yl)propanamide To a solution of (S)—N-(3-(5-bromobenzo[d]thiazol-2-yl)-6-ethyl-4,5,6,7-tetrahydrothieno[2,3-c]pyridin-2-yl)-3-(sec-butylamino)propanamide 4 (300 mg, 0.576 mmol) in dioxane (10 mL) was added $K_2CO_3$ (200 mg, 1.44 mmol) in water (1 mL) and the reaction mixture was degassed under argon atmosphere for 10 min. Followed by addition of $Pd(PPh_3)_4$ (67 mg, 0.057 mmol) and 4-(4,4,5,5-tetramethyl-1,3,2-dioxaborolan-2-yl)pyridine (105 mg, 0.865 mmol) and degassed with argon for another 20 min. The reaction mixture was heated to 100° C. for 16 h. After the completion of reaction (monitored by LCMS), the reaction mixture was diluted with water and extracted with ethyl acetate (thrice). The combined organic layers were dried with anhydrous $Na_2SO_4$, filtered and concentrated to get a crude residue. This crude compound was purified by silica gel column chromatography eluting with 0-6% methanol in DCM to afford the title compound as yellow solid (400 mg, 80% yield).

Example 139. Synthesis of 3-4(3aR,5s,6aS)-octahydrocyclopenta[c]pyrrol-5-yl)amino)-N-(3-(5-(pyridin-4-yl)benzo[d]thiazol-2-yl)-4,5,6,7-tetrahydrothieno[2,3-c]pyridin-2-yl)propanamide (Compound 606)

Step 1: tert-Butyl 3-(5-bromobenzo[d]thiazol-2-yl)-2-(3-(((3aR,5s,6aS)-2-(tert-butoxycarbonyl)octahydrocyclopenta[c]pyrrol-5-yl)amino)propanamido)-4,7-dihydrothieno[2,3-c]pyridine-6(5H)-carboxylate (3)

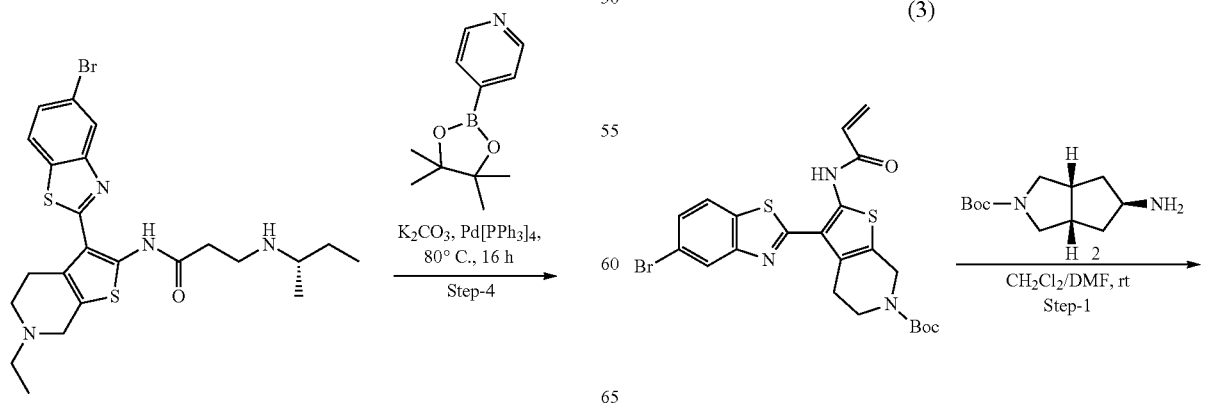

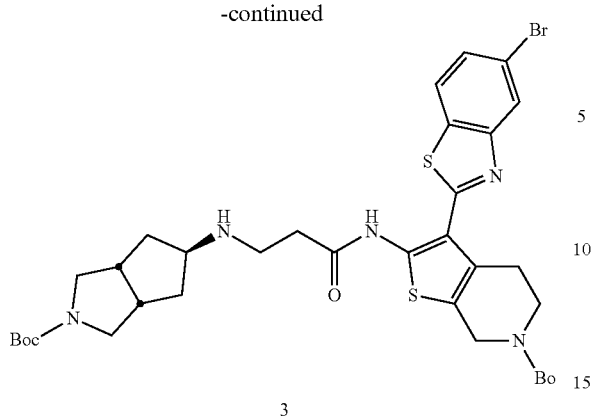

3

To a solution of tert-butyl 2-acrylamido-3-(5-bromobenzo[d]thiazol-2-yl)-4,7-dihydrothieno[2,3-c]pyridine-6(5H)-carboxylate 1 (300 mg, 0.578 mmol) in CH$_2$Cl$_2$:DMF (1:1, 4 mL) was added tert-butyl (3aR,5s,6aS)-5-aminohexahydrocyclopenta[c]pyrrole-2(1H)-carboxylate 2 (195 mg, 0.867 mmol). The resulting reaction mixture was stirred at room temperature for 16 h. Progress of the reaction was monitored by TLC. After completion, the reaction mixture was concentrated to dryness under reduced pressure. The residue was washed with water and extracted with CH$_2$Cl$_2$ (thrice). The combined organic layer dried over anhydrous Na$_2$SO$_4$; filtered and concentrated under reduced pressure. The crude compound was purified by column chromatography eluting with 0-5% methanol in CH$_2$Cl$_2$ to afford the title compound 3 as yellow solid (280 mg, yield 65%).

Step 2: tert-Butyl 2-(3-(((3aR,5s,6aS)-2-(tert-butoxycarbonyl)octahydrocyclopenta[c]pyrrol-5-yl)amino)propanamido)-3-(5-(pyridin-4-yl)benzo[d]thiazol-2-yl)-4,7-dihydrothieno[2,3-c]pyridine-6(5H)-carboxylate (4)

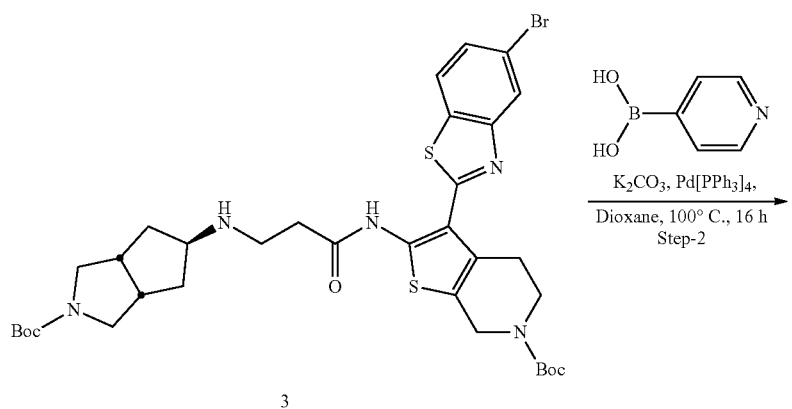

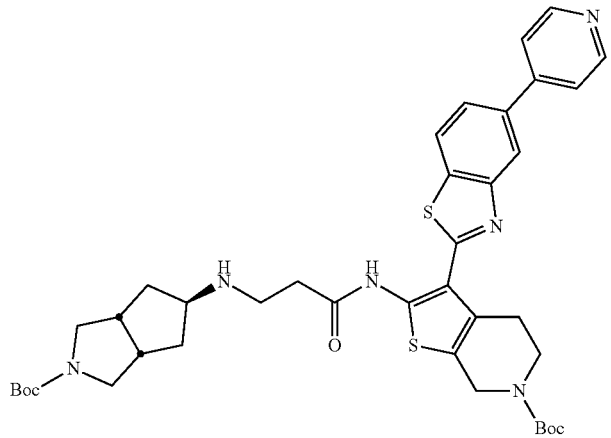

4

To a solution of tert-butyl 3-(5-bromobenzo[d]thiazol-2-yl)-2-(3-(((3aR,5s,6aS)-2-(tert-butoxycarbonyl)octahydrocyclopenta[c]pyrrol-5-yl)amino)propanamido)-4,7-dihydrothieno[2,3-c]pyridine-6(5H)-carboxylate 3 (280 mg, 0.375 mmol) in dioxane (10 mL) was added K$_2$CO$_3$ (103 mg, 0.751 mmol) in water (0.7 mL) and the reaction mixture was degassed under argon atmosphere for 10 min. Followed by addition of Pd(PPh$_3$)$_4$ (43 mg, 0.037 mmol) and pyridin-4-ylboronic acid (68 mg, 0.56 mmol) and degassed with argon for another 20 min. The reaction mixture was heated to 100° C. for 12 h. After the completion of reaction (monitored by LCMS), the reaction mixture was diluted with water and extracted with ethyl acetate (thrice). The combined organic layers were dried with anhydrous Na$_2$SO$_4$, filtered and concentrated to get a crude residue. This crude compound was purified by silica gel column chromatography eluting with 0-8% methanol in CH$_2$Cl$_2$ to afford the title compound 3 as yellow solid (120 mg, 43% yield).

Step 3: 3-(((3aR,5s,6aS)-octahydrocyclopenta[c]pyrrol-5-yl)amino)-N-(3-(5-(pyridin-4-yl)benzo[d]thiazol-2-yl)-4,5,6,7-tetrahydrothieno[2,3-c]pyridin-2-yl)propanamide

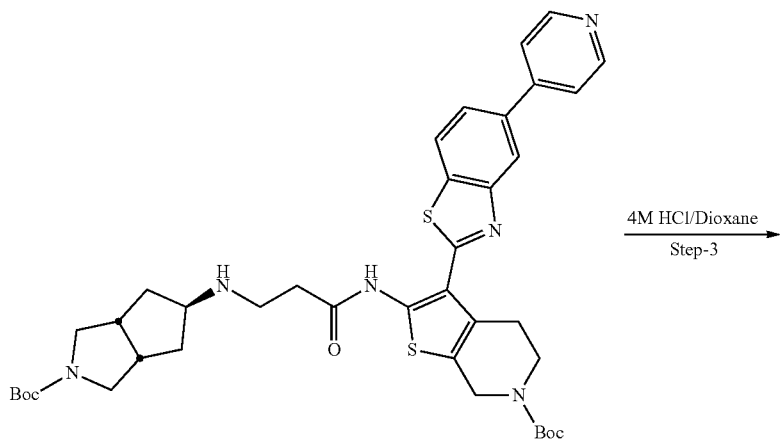

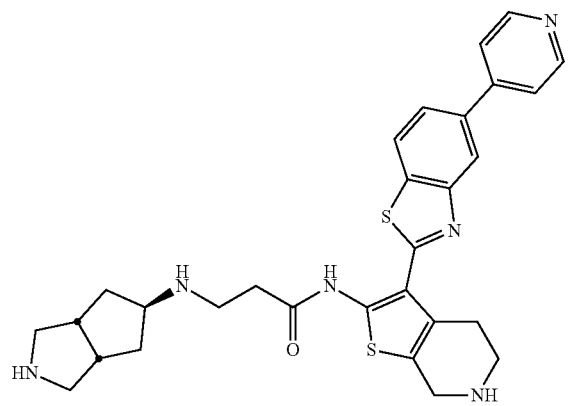

To a solution of tert-butyl 2-(3-(((3aR,5s,6aS)-2-(tert-butoxycarbonyl)octahydrocyclopenta[c]pyrrol-5-yl)amino)propanamido)-3-(5-(pyridin-4-yl)benzo[d]thiazol-2-yl)-4,7-dihydrothieno[2,3-c]pyridine-6(5H)-carboxylate 4 (120 mg, 0.161 mmol) in dioxane (2 mL) at 0° C. was added 4M HCl in dioxane (3 mL). After the addition, the resulting mixture was stirred at room temperature for 3 h. After completion, the reaction mixture was evaporated in vacuum resulting in a crude residue which was purified by trituration with methanol. The solid obtained was filtered and washed with diethyl ether and n-pentane to afford the HCl salt of the title compound as yellow solid (60 mg, yield 57%).

Example 140. Synthesis of N-(3-(benzo[d]thiazol-2-yl)-4,5,6,7-tetrahydrothieno[2,3-c]pyridin-2-yl)-3-(sec-butylamino)propanamide (Compound 607)

Step 1: 2-(Benzo[d]thiazol-2-yl)acetonitrile (3)

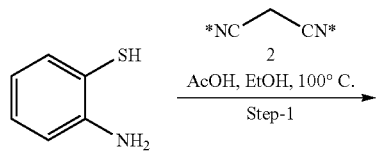

To a solution of 2-aminobenzenethiol 1 (225 mg, 1.80 mmol) in ethanol (5 mL) was added malononitrile (122 mg, 1.80 mmol) and AcOH (5 mL). The resulting reaction mixture was stirred at 90° C. for 5 h. Progress of the reaction was monitored by TLC. After completion, the reaction mixture was concentrated under reduced pressure to dryness. The crude compound was purified by silica gel column chromatography eluting with 0-30% ethyl acetate in n-hexane to afford the title compound 2 as brown solid (150 mg, yield 47%)

Step 2: tert-Butyl 2-amino-3-(benzo[d]thiazol-2-yl)-4,7-dihydrothieno[2,3-c]pyridine-6(5H)-carboxylate (5)

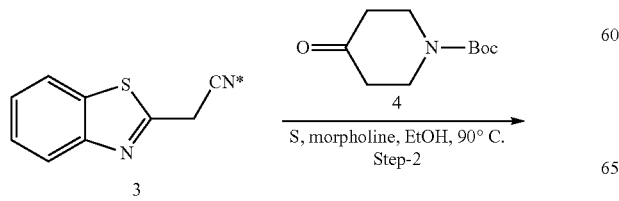

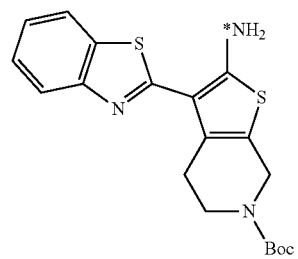

To a solution of 2-(benzo[d]thiazol-2-yl)acetonitrile 3 (150 mg, 0.857 mmol) in ethanol (10 mL) was added tert-butyl 4-oxopiperidine-1-carboxylate 4 (170 mg, 0.857 mmol), elemental sulphur (27 mg, 0.857 mmol) and morpholine (74 mg, 0.857 mmol) at room temperature. After the addition, the resulting mixture was heated to reflux at 90° C. for 3 h. Progress of the reaction was monitored by TLC. After completion, the reaction mixture was evaporated in vacuum up to dryness. The crude compound was purified by column chromatography eluting with 0-5% methanol in $CH_2Cl_2$ to afford the title compound 3 as off white solid (150 mg, yield 45%).

Step 3: tert-Butyl 2-acrylamido-3-(benzo[d]thiazol-2-yl)-4,7-dihydrothieno[2,3-c]pyridine-6(5H)-carboxylate (6)

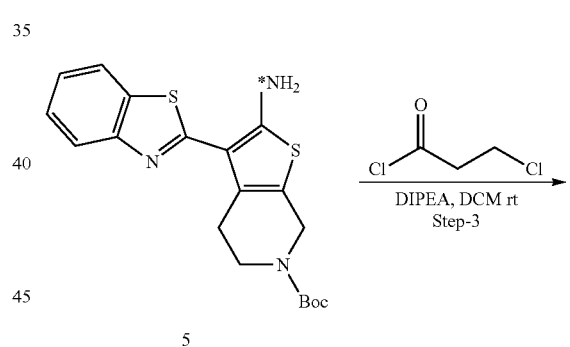

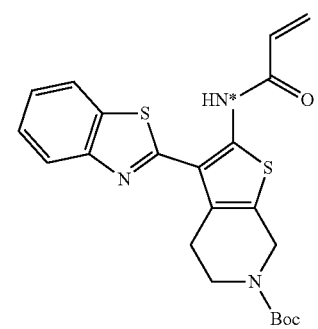

To a solution of tert-butyl 2-amino-3-(benzo[d]thiazol-2-yl)-4,7-dihydrothieno[2,3-c]pyridine-6(5H)-carboxylate 5 (150 mg, 0.386 mmol) in CH$_2$Cl$_2$ (5 mL) at 0° C. was added DIPEA (0.09 mL, 0.579 mmol) and 3-chloropropanoyl chloride (0.05 mL, 0.579 mmol). The reaction mixture was stirred at room temperature for 3 h. After completion (monitored by TLC), the reaction mixture was quenched with saturated NaHCO$_3$ and extracted with dichloromethane (thrice). The combined organic layer was dried over anhydrous sodium sulphate and concentrated up to dryness. The crude compound was purified by column chromatography eluting with 0-5% methanol in CH$_2$Cl$_2$ to afford the title compound 4 as light brown solid (110 mg, yield 65%).

Step 4: tert-Butyl 3-(benzo[d]thiazol-2-yl)-2-(3-(sec-butylamino)propanamido)-4,7-dihydrothieno[2,3-c]pyridine-6(5H)-carboxylate (7)

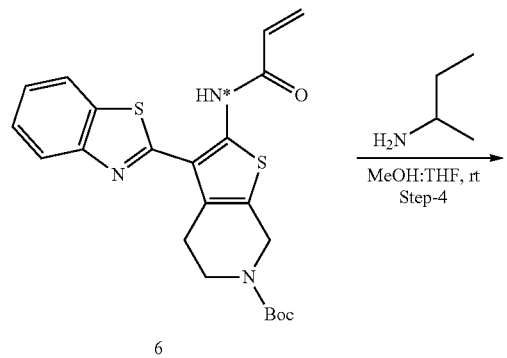

h. Progress of the reaction was monitored by TLC. After completion, the reaction mixture was concentrated to dryness under reduced pressure. The residue was washed with water and extracted with CH$_2$Cl$_2$ (thrice). The combined organic layer was dried over anhydrous Na$_2$SO$_4$, filtered and concentrated. The crude compound was purified by column chromatography eluting with 0-3% methanol in CH$_2$Cl$_2$ to afford the title compound 7 as yellow solid (70 mg, yield 55%).

Step 5: N-(3-(benzo[d]thiazol-2-yl)-4,5,6,7-tetrahydrothieno[2,3-c]pyridin-2-yl)-3-(sec-butylamino)propanamide

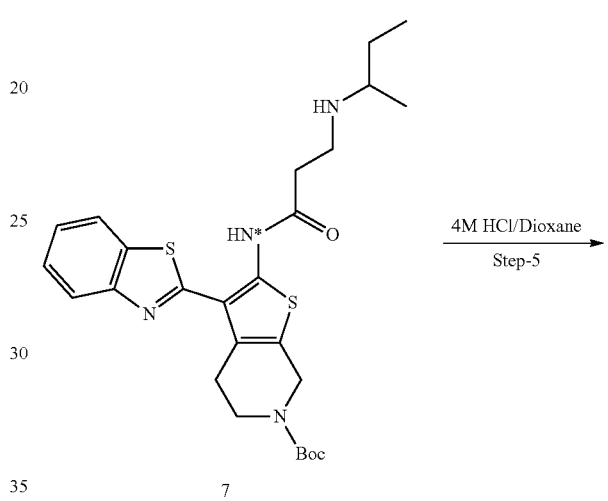

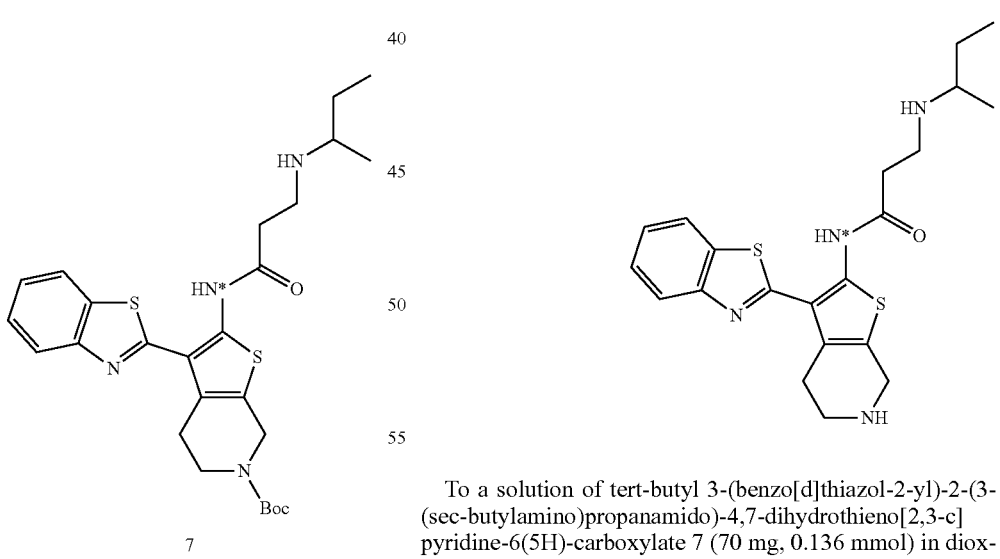

To a solution of tert-butyl 2-acrylamido-3-(benzo[d]thiazol-2-yl)-4,7-dihydrothieno[2,3-c]pyridine-6(5H)-carboxylate 6 (110 mg, 0.248 mmol) in MeOH:THF (1:1, 3 mL) was added butan-2-amine (27 mg, 0.373 mmol). The resulting reaction mixture was stirred at room temperature for 12

To a solution of tert-butyl 3-(benzo[d]thiazol-2-yl)-2-(3-(sec-butylamino)propanamido)-4,7-dihydrothieno[2,3-c]pyridine-6(5H)-carboxylate 7 (70 mg, 0.136 mmol) in dioxane (1 mL) at 0° C. was added 4M HCl in dioxane (1.5 mL). After the addition, the resulting mixture was stirred at room temperature for 3 h. After completion, the reaction mixture was evaporated in vacuum resulting in a crude residue which was triturated with methanol. The solid obtained was filtered and washed with diethyl ether and n-pentane to afford the HCl salt of the title compound as yellow solid (45 mg, yield 68%).

Example 141. Synthesis of N-(3-(benzo[d]thiazol-2-yl)-4,5,6,7-tetrahydrothieno[2,3-c]pyridin-2-yl)-3-(methyl-$^{15}$N-amino)propanamide hydrochloride (Compound 608)

Step 1: tert-Butyl 3-(benzo[d]thiazol-2-yl)-2-(3-(methyl-$^{15}$N-amino)propanamido)-4,7-dihydrothieno[2,3-c]pyridine-6(5H)-carboxylate (2)

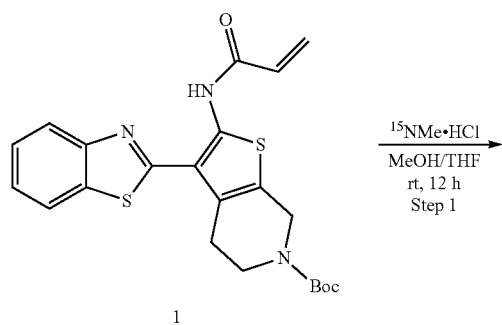

To a stirred solution of tert-butyl 2-acrylamido-3-(benzo[d]thiazol-2-yl)-4,7-dihydrothieno[2,3-c]pyridine-6(5H)-carboxylate (100 mg, 0.22 mmol) in CH$_3$OH:THF (1:1; 6 mL) were added $^{15}$N-methyl amine hydrochloride (30 mg, 0.45 mmol) at room temperature and stirred for 12 h. Reaction was monitored by TLC. After completion, the reaction mixture was evaporated to dryness resulting in a crude residue which was purified by column chromatography to afford the title compound 2 as yellow solid (45 mg, 42% yield).

Step 2: N-(3-(benzo[d]thiazol-2-yl)-4,5,6,7-tetrahydrothieno[2,3-c]pyridin-2-yl)-3-(methyl-$^{15}$N-amino)propanamide hydrochloride

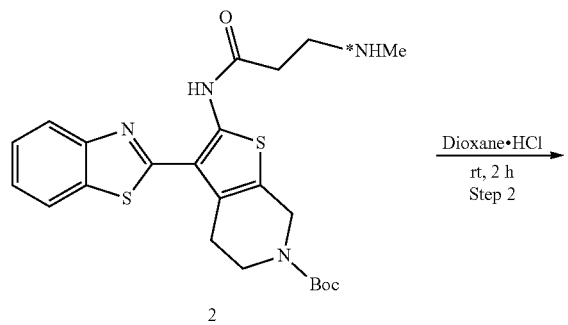

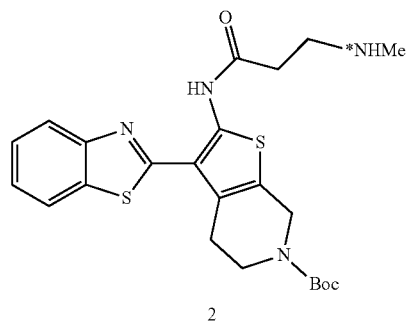

To a solution of tert-butyl 3-(benzo[d]thiazol-2-yl)-2-(3-(methyl-$^{15}$N-amino)propanamido)-4,7-dihydrothieno[2,3-c]pyridine-6(5H)-carboxylate 2 (45 mg, 0.095 mmol) in dioxane (1 mL) at 0° C. was added 4M HCl in dioxane (1 mL) and the resulting mixture was stirred at room temperature for 2 h. Reaction was monitored by TLC. After completion, the reaction mixture was evaporated to dryness resulting in a crude residue which was purified by triturating with methanol and ether to afford HCl salt of the title compounds as an off-white solid (25 mg, 59.5%).

Example 142. Synthesis of (S)-3-(sec-butylamino)-N-(6-cyclopropyl-3-(5-(pyridin-4-yl)benzo[d]thiazol-2-yl)-4,5,6,7-tetrahydrothieno[2,3-c]pyridin-2-yl)propanamide (Compound 618)

Step 1: 3-(5-Bromobenzo[d]thiazol-2-yl)-6-cyclopropyl-4,5,6,7-tetrahydrothieno[2,3-c]pyridin-2-amine (3)

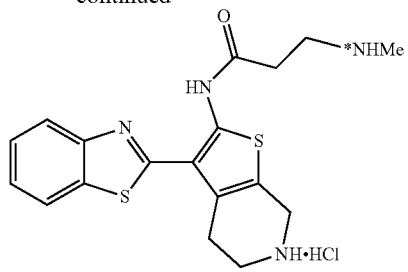

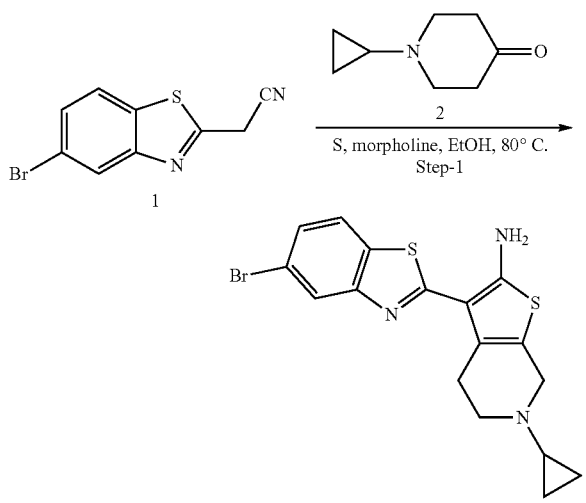

To a solution of 2-(5-bromobenzo[d]thiazol-2-yl)acetonitrile 1 (700 mg, 2.777 mmol), elemental sulphur (88 mg, 2.777 mmol) and morpholine (241 mg, 2.777 mmol) in ethanol (20 mL) was added 1-cyclopropylpiperidin-4-one 2 (383 mg, 2.777 mmol) at room temperature and the resulting reaction mixture was heated to reflux at 80° C. for 16 h. Reaction was monitored by TLC. After the completion, reaction mixture was evaporated to dryness on rotavapour and the crude compound was triturated in methanol and dried to afford the pure compound 3 as brown solid (760 mg, 67%).

Step 2: N-(3-(5-bromobenzo[d]thiazol-2-yl)-6-cyclopropyl-4,5,6,7-tetrahydrothieno[2,3-c]pyridin-2-yl)acrylamide (4)

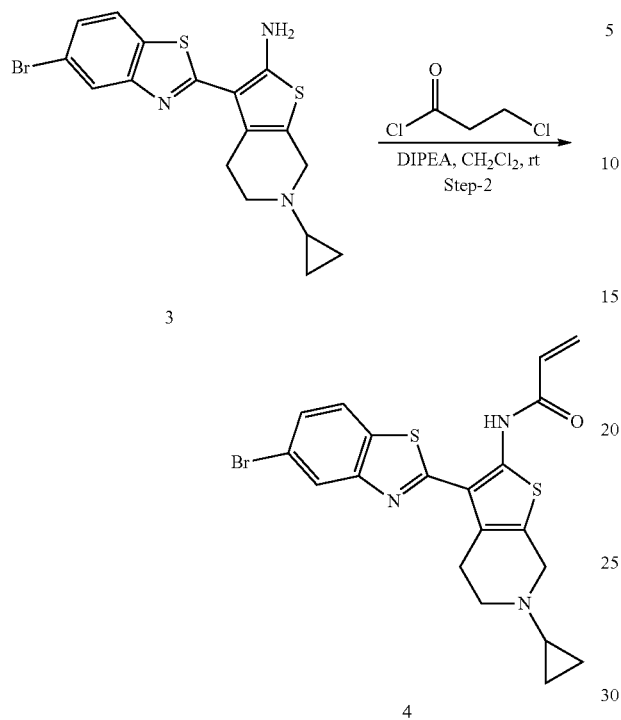

To a solution of 3-(5-bromobenzo[d]thiazol-2-yl)-6-cyclopropyl-4,5,6,7-tetrahydrothieno[2,3-c]pyridin-2-amine 3 (400 mg, 0.987 mmol) in $CH_2Cl_2$ (15 mL) at 0° C. was added DIPEA (234 mg, 1.975 mmol) followed by 3-chloropropanoyl chloride (188 mg, 1.4814 mmol). Reaction mixture was stirred at room temperature for 3 h. Reaction was monitored by TLC. After completion, the reaction mixture was diluted with $CH_2Cl_2$ and washed with saturated $NaHCO_3$ solution and brine. The separated organic layer was dried over $Na_2SO_4$, filtered and concentrated in vacuum to afford the title compound 4 as brown solid (400 mg crude).

Step 3: (S)—N-(3-(5-bromobenzo[d]thiazol-2-yl)-6-cyclopropyl-4,5,6,7-tetrahydrothieno[2,3-c]pyridin-2-yl)-3-(sec-butylamino)propanamide (5)

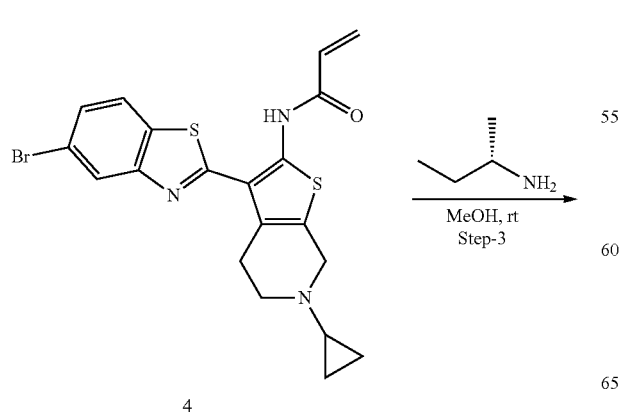

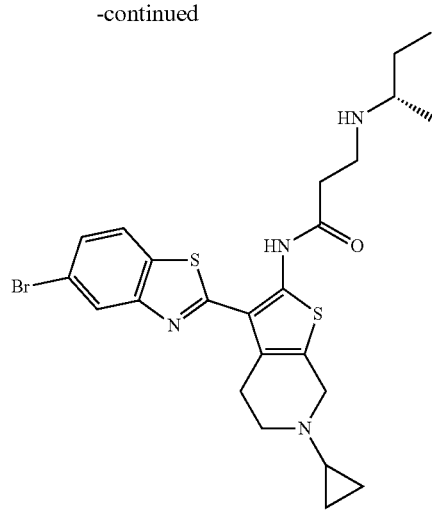

To a solution of N-(3-(5-bromobenzo[d]thiazol-2-yl)-6-cyclopropyl-4,5,6,7-tetrahydrothieno[2,3-c]pyridin-2-yl) acrylamide 4 (400 mg, 0.871 mmol) in MeOH (10 mL) was added (S)-butan-2-amine (63 mg, 0.871 mmol). The resulting reaction mixture was stirred at room temperature for 16 h. Progress of the reaction was monitored by TLC. After completion, the reaction mixture was concentrated to dryness under reduced pressure. The crude residue was dissolved in $CH_2Cl_2$ and washed with water. The combined organic layers were dried with anhydrous $Na_2SO_4$, filtered and concentrated to get a crude residue. This crude compound was purified by silica gel column chromatography eluting with 0-10% methanol in $CH_2Cl_2$ to afford title compound 5 as yellow solid (300 mg, yield 86%).

Step 4: (S)-3-(sec-butylamino)-N-(6-cyclopropyl-3-(5-(pyridin-4-yl)benzo[d]thiazol-2-yl)-4,5,6,7-tetrahydrothieno[2,3-c]pyridin-2-yl)propanamide

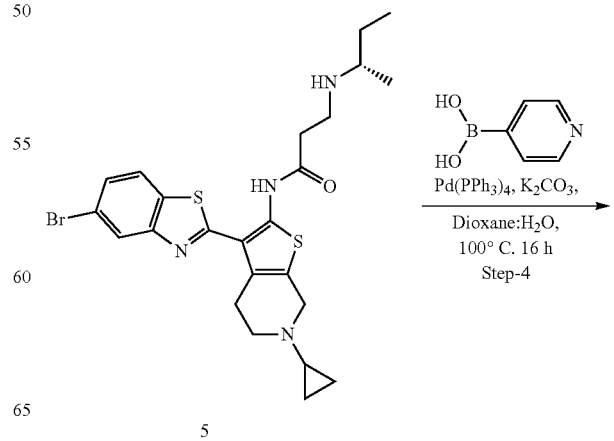

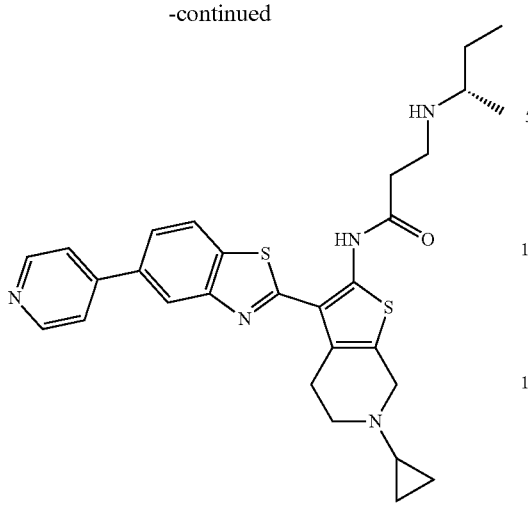

To a solution of (S)—N-(3-(5-bromobenzo[d]thiazol-2-yl)-6-cyclopropyl-4,5,6,7-tetrahydrothieno[2,3-c]pyridin-2-yl)-3-(sec-butylamino)propanamide 5 (300 mg, 0.563 mmol) in dioxane (10 mL) was added $K_2CO_3$ (194 mg, 1.409 mmol) in water (0.7 mL) and the reaction mixture was degassed under argon atmosphere for 10 min. Followed by addition of Pd(PPh$_3$)$_4$ (65 mg, 0.056 mmol) and pyridin-4-ylboronic acid (103 mg, 0.845 mmol) and degassed with argon for another 20 min. The reaction mixture was heated to 100° C. for 16 h. After the completion of reaction (monitored by LCMS), the reaction mixture was diluted with water and extracted with ethyl acetate (thrice). The combined organic layers were dried with anhydrous $Na_2SO_4$, filtered and concentrated to get a crude residue. This crude compound was purified by silica gel column chromatography eluting with 0-10% methanol in DCM to afford the title compound as yellow solid (25 mg, yield 8.3%).

Example 143. Synthesis of (S)—N-(3-(benzo[d]thiazol-2-yl)-6-(3,3-difluorocyclobutyl)-4,5,6,7-tetrahydrothieno[2,3-c]pyridin-2-yl)-3-(sec-butylamino)propanamide (Compound 619)

Step 1: tert-Butyl (3,3-difluorocyclobutyl)carbamate (2)

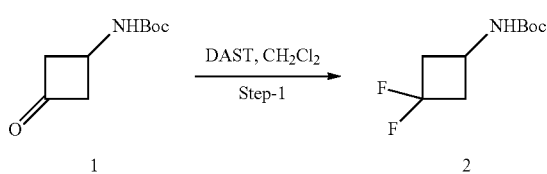 [SMILES: CC(C)(C)OC(=O)NC1CC(=O)C1 ; CC(C)(C)OC(=O)NC1CC(F)(F)C1]

To a solution of tert-butyl (3-oxocyclobutyl)carbamate 1 (600 mg, 3.239 mmol) in $CH_2Cl_2$ (10 mL) at 0° C. was added DAST (1.04 g, 6.478 mmol). The reaction mixture was allowed to attain room temperature and stirred for 18 h. After completion (monitored by TLC), the reaction mixture was quenched with saturated $NaHCO_3$ solution. The combined organic layer was washed with brine, dried over $Na_2SO_4$, filtered and concentrated in vacuum. The crude compound was purified by silica gel column chromatography eluting with 0-5% ethyl acetate in n-hexane to afford the title compound to afford the title compound 2 as white solid (450 mg, yield 67%).

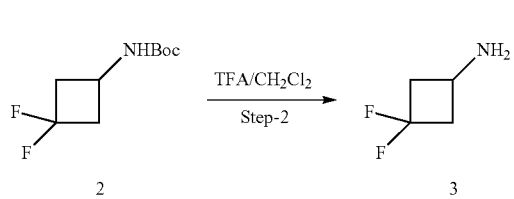 [SMILES: CC(C)(C)OC(=O)NC1CC(F)(F)C1 ; NC1CC(F)(F)C1]

Step 2: 3,3-Difluorocyclobutan-1-amine (3)

To a solution of tert-butyl (3,3-difluorocyclobutyl)carbamate 2 (400 mg, 1.930 mmol) in $CH_2Cl_2$ (7 mL) at 0° C. was added trifluoroacetic acid (1 mL, 13.06 mmol). The reaction mixture was allowed to attain room temperature and stirred for 5 h. After completion (monitored by TLC), the reaction mixture was concentrated in vacuum up to dryness to afford the title compound 3 as brown solid (600 mg crude).

Step 3: 1-(3,3-Difluorocyclobutyl)piperidin-4-one (5)

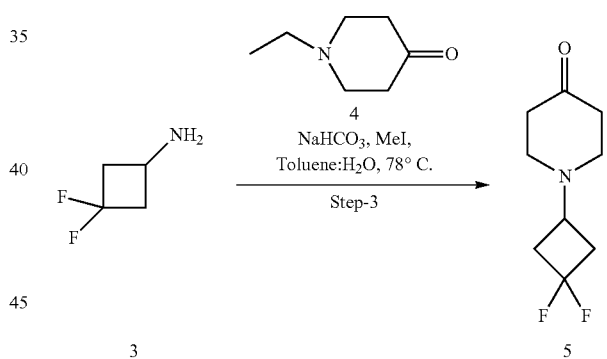

To a solution of 1-ethylpiperidin-4-one 4 (600 mg, 4.717 mmol) in acetone (10 mL) was added methyl amine (0.6 mL, 0.943 mmol) slowly at room temperature and stirred for 3 h. The slurry was filtered and the solid residue obtained was washed with acetone and dried well. The solid obtained was added to a solution of 3,3-difluorocyclobutan-1-amine 3 (505 mg, 4.717 mmol) in toluene (5 mL) followed by saturated $NaHCO_3$ aqueous solution (3 mL) addition at room temperature. The reaction mixture was stirred at room temperature for 10 min and further heated to 78° C. for 12 h. After the completion (monitored by TLC), the organic layer was separated and the aqueous layer was extracted with ethyl acetate (thrice). The combined organic layer was washed with brine, dried over $Na_2SO_4$, filtered and concentrated in vacuum. The crude compound was purified by silica gel column chromatography eluting with 0-5% methanol in $CH_2Cl_2$ to afford the title compound 5 as oil (400 mg, 45%).

Step 4: 3-(Benzo[d]thiazol-2-yl)-6-(3,3-difluorocyclobutyl)-4,5,6,7-tetrahydrothieno[2,3-c]pyridin-2-amine (6)

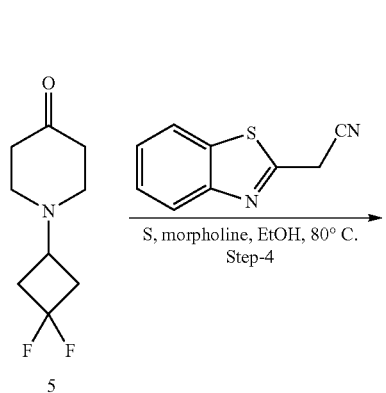

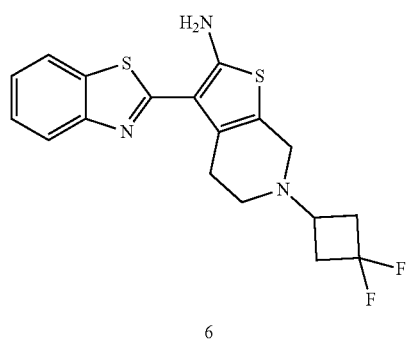

To a solution of 2-(benzo[d]thiazol-2-yl)acetonitrile (100 mg, 0.574 mmol), elemental sulphur (18 mg, 0.574 mmol) and morpholine (49.6 mg, 0.574 mmol) in ethanol (3 mL) was added 1-(3,3-difluorocyclobutyl)piperidin-4-one 5 (98 mg, 0.574 mmol) at room temperature and the resulting reaction mixture was heated to reflux at 80° C. for 3 h. Reaction was monitored by TLC. After the completion, reaction mixture was evaporated to dryness on rotavapour and the crude compound was triturated in methanol and dried to afford the pure compound 6 as brown solid (460 mg, 70%).

Step 5: N-(3-(benzo[d]thiazol-2-yl)-6-(3,3-difluorocyclobutyl)-4,5,6,7-tetrahydrothieno[2,3-c]pyridin-2-yl)acrylamide (7)

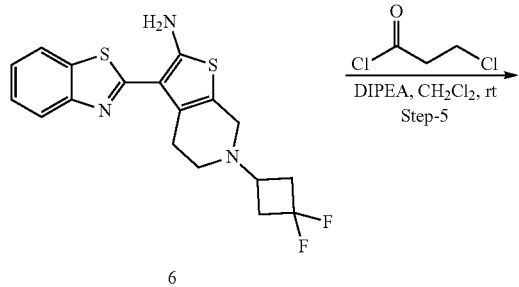

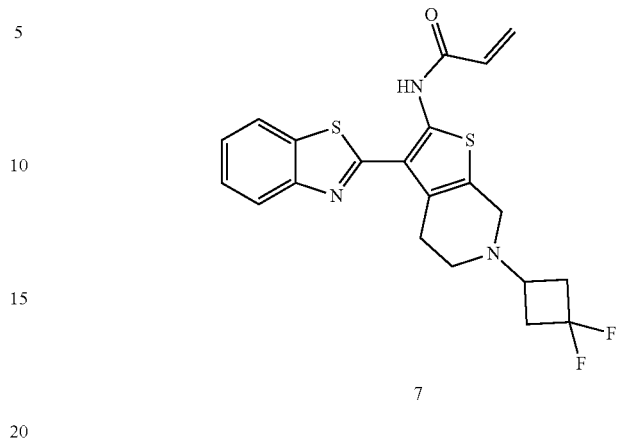

To a solution of 3-(benzo[d]thiazol-2-yl)-6-(3,3-difluorocyclobutyl)-4,5,6,7-tetrahydrothieno[2,3-c]pyridin-2-amine 6 (400 mg, 1.058 mmol) in $CH_2Cl_2$ (10 mL) at 0° C. was added DIPEA (0.69 mL, 3.950 mmol) followed by 3-chloropropanoyl chloride (201 mg, 1.587 mmol). Reaction mixture was stirred at room temperature for 15 h. Reaction was monitored by TLC. After completion, the reaction mixture was diluted with $CH_2Cl_2$ and washed with saturated $NaHCO_3$ solution and brine. The separated organic layer was dried over $Na_2SO_4$, filtered and concentrated in vacuum to afford the title compound 7 as brown solid (600 mg crude).

Step 6: (S)—N-(3-(benzo[d]thiazol-2-yl)-6-(3,3-difluorocyclobutyl)-4,5,6,7-tetrahydrothieno[2,3-c]pyridin-2-yl)-3-(sec-butylamino)propanamid

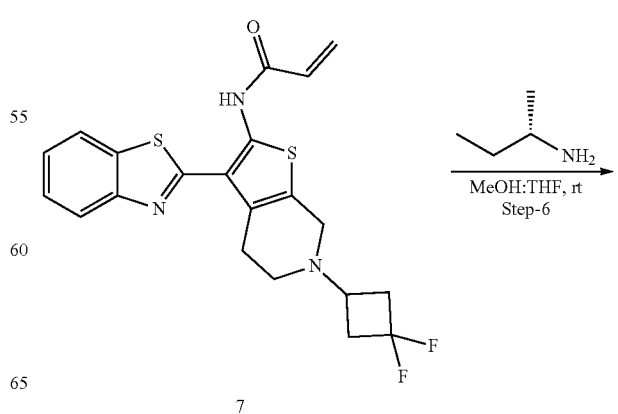

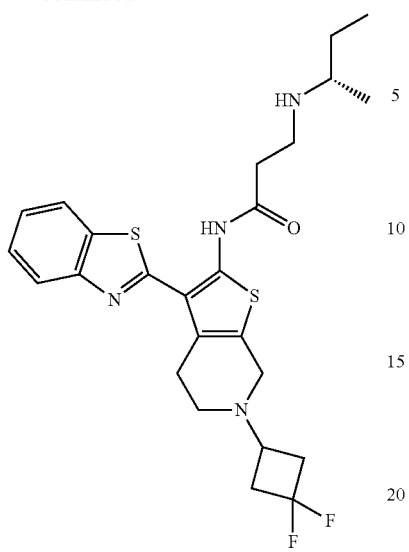

To a solution of N-(3-(benzo[d]thiazol-2-yl)-6-(3,3-difluorocyclobutyl)-4,5,6,7-tetrahydrothieno[2,3-c]pyridin-2-yl)acrylamide 7 (600 mg, 1.388 mmol) in MeOH:THF (1:1, 10 mL) was added (S) 2 aminobutane (101.6 mg, 1.388 mmol). The resulting reaction mixture was stirred at room temperature for 16 h. Progress of the reaction was monitored by TLC. After completion, the reaction mixture was concentrated to dryness under reduced pressure. The crude residue was dissolved in DCM and washed with water. The combined organic layers were dried with anhydrous Na₂SO₄, filtered and concentrated to get a crude residue. This crude compound was purified by silica gel column chromatography eluting with 0-5% methanol in DCM to afford title compound as yellow solid (80 mg, yield 11.4%).

Example 144. Synthesis of (R)-3-(sec-butylamino)-N-(3-(5-(trifluoromethyl)benzo[d]thiazol-2-yl)-4,5,6,7-tetrahydrothieno[2,3-c]pyridin-2-yl)propanamide (Compound 179)

Step 1: tert-butyl (R)-2-(3-(sec-butylamino)propanamido)-3-(5-(trifluoromethyl)benzo[d]thiazol-2-yl)-4,7-dihydrothieno[2,3-c]pyridine-6(5H)-carboxylate (2)

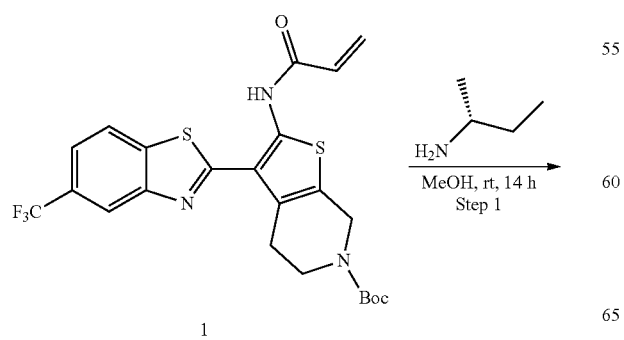

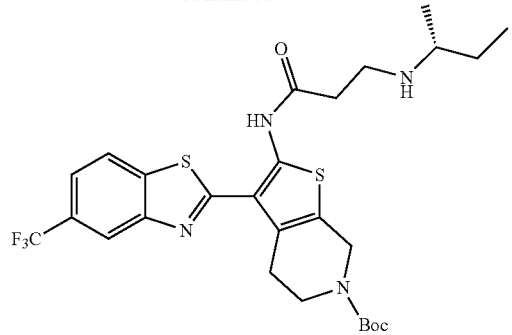

To a solution of tert-butyl 2-acrylamido-3-(5-(trifluoromethyl)benzo[d]thiazol-2-yl)-4,7-dihydrothieno[2,3-c]pyridine-6(5H)-carboxylate 1 (4 g, 7.85 mmol) in MeOH (40 mL)/THF (20 mL) were added (R)-butan-2-amine (688 mg, 9.42 mmol) and the reaction mixture was stirred at room temperature for 14 h. Reaction was monitored by TLC. After completion, the reaction mass was concentrated to obtained a crude residue. The crude compound was purified by flash column chromatography to afford the title compound 2 as a yellow solid (1.8 g, 40% yield).

Step 2: (R)-3-(sec-butylamino)-N-(3-(5-(trifluoromethyl)benzo[d]thiazol-2-yl)-4,5,6,7-tetrahydrothieno[2,3-c]pyridin-2-yl)propanamide

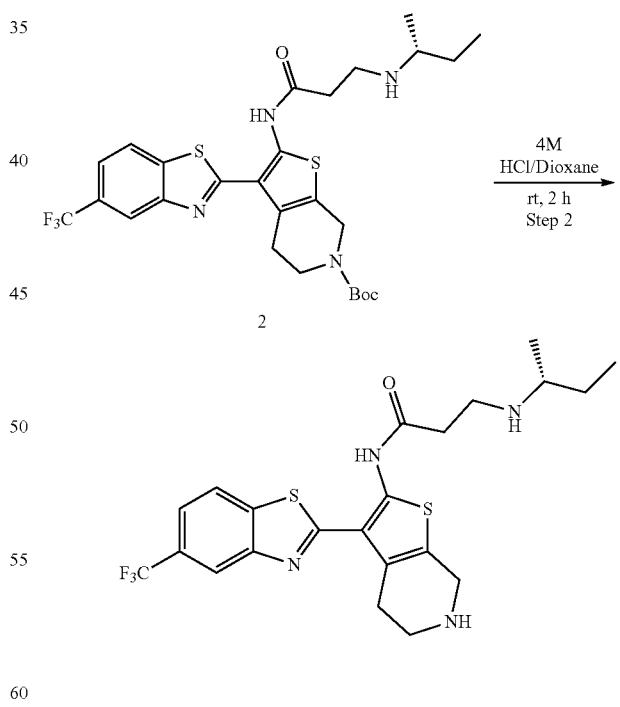

To a solution of tert-butyl (R)-2-(3-(sec-butylamino)propanamido)-3-(5-(trifluoromethyl)benzo[d]thiazol-2-yl)-4,7-dihydrothieno[2,3-c]pyridine-6(5H)-carboxylate (1.8 g, 3.09 mmol) in dioxane (5 mL) at 0° C. was added 4M HCl in dioxane (15 mL) and the resulting mixture was stirred at room temperature for 2 h. After completion, the reaction mixture was evaporated in vacuum resulting in a crude residue which was triturated with ether and pentane to afford the title compound as yellow solid (1.3 g, 67% yield).

Example 145. Synthesis of N-(5,7-Dimethyl-3-(6-(pyridin-3-yl)benzo[d]thiazol-2-yl)-4,5,6,7-tetrahydrothieno[2,3-c]pyridin-2-yl)-3-((2-methoxyethyl)amino)propanamide and Separation of Isomers (Compounds 519, 520, 527, and 528)

Step 1: tert-Butyl 2-(3-((2-methoxyethyl)amino)propanamido)-5,7-dimethyl-3-(6-(pyridin-3-yl)benzo[d]thiazol-2-yl)-4,7-dihydrothieno[2,3-c]pyridine-6(5H)-carboxylate (7)

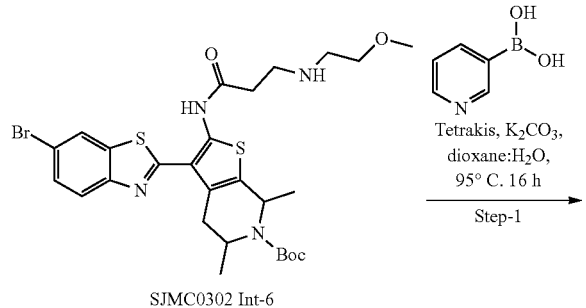

SJMC0302 Int-6

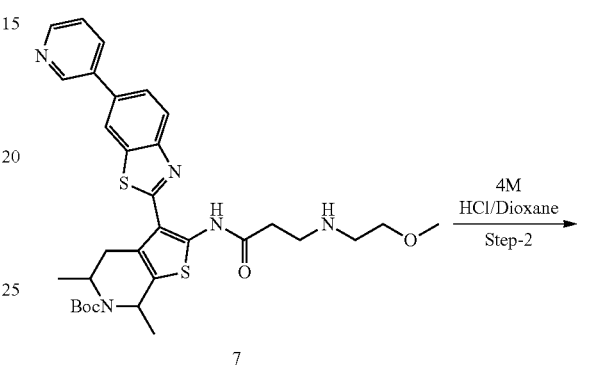

Step 2: N-(5,7-Dimethyl-3-(6-(pyridin-3-yl)benzo[d]thiazol-2-yl)-4,5,6,7-tetrahydrothieno[2,3-c]pyridin-2-yl)-3-((2-methoxyethyl)amino)propanamide

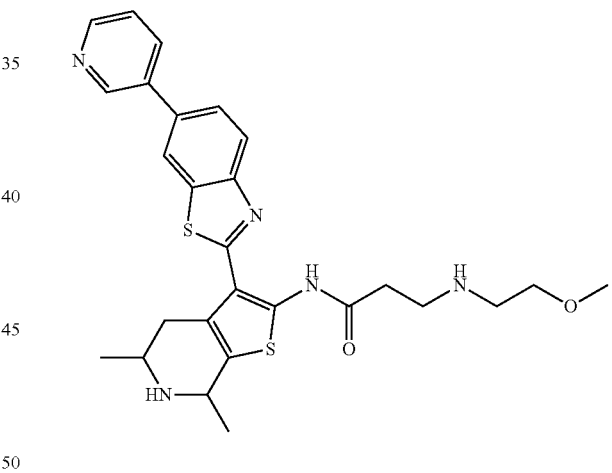

To a solution of tert-butyl 3-(6-bromobenzo[d]thiazol-2-yl)-2-(3-((2-methoxyethyl)amino)propanamido)-5,7-dimethyl-4,7-dihydrothieno[2,3-c]pyridine-6(5H)-carboxylate (550 mg, 0.88 mmol) in dioxane (20 mL) was added solution of $K_2CO_3$ (303 mg, 2.20 mmol) in water (1 mL) and degassed under argon atmosphere for 10 min. Followed by addition of $Pd(PPh_3)_4$ (100 mg, 0.088 mmol) and pyridin-3-ylboronic acid (160 mg, 1.320 mmol) and degassed with argon for another 10 min. The reaction mixture was heated to 100° C. for 16 h. After the completion of reaction (monitored by LCMS), the reaction mixture was diluted with water and extracted with ethyl acetate (thrice). The combined organic layers were dried with anhydrous $Na_2SO_4$, filtered and concentrated to get a crude residue. This crude compound was purified by silica gel column chromatography eluting with 0-5% methanol in $CH_2Cl_2$ to afford the title compound 7 (350 mg, yield 65%).

To a solution of tert-butyl 2-(3-((2-methoxyethyl)amino)propanamido)-5,7-dimethyl-3-(6-(pyridin-3-yl)benzo[d]thiazol-2-yl)-4,7-dihydrothieno[2,3-c]pyridine-6(5H)-carboxylate 7 (350 mg, 0.562 mmol) in dioxane (5 mL) at 0° C. was added 4M HCl in dioxane (5 mL). After the addition, the resulting mixture was stirred at room temperature for 2 h. After completion, the reaction mixture was evaporated in vacuum resulting in a crude residue which was purified by trituration with methanol. The solid obtained was filtered and washed with diethyl ether and n-pentane to afford the title compound as yellow solid (330 mg crude). The chiral separation for the mixture (Column: CHIRALPAK; IA3, 150 mm*4.6 mm*3 um; Mobile Phase: A: n-Hexane+0.1% DEA; B: ETOH; Flow rate: 1.0 ml/min; Isocratic: 20% B) afforded the separated title compounds.

Example 146. Synthesis of N-((5S,7R)-5,7-Dimethyl-3-(5-(pyridin-3-yl)benzo[d]thiazol-2-yl)-4,5,6,7-tetrahydrothieno[2,3-c]pyridin-2-yl)-3-((2-methoxyethyl)amino)propanamide and Separation of Isomers (Compounds 524, 525, 526 and 533)

Step 1: tert-Butyl 2-(3-((2-methoxyethyl)amino)propanamido)-5,7-dimethyl-3-(5-(pyridin-3-yl)benzo[d]thiazol-2-yl)-4,7-dihydrothieno[2,3-c]pyridine-6(5H)-carboxylate (1)

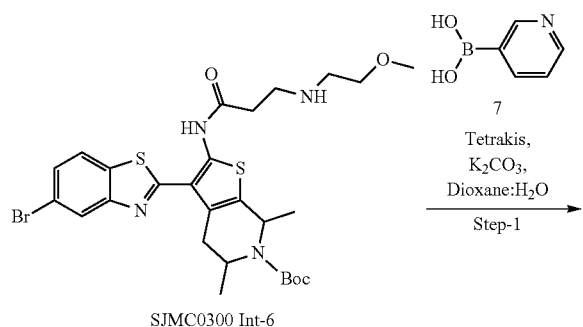

Step 2: N-(5,7-Dimethyl-3-(5-(pyridin-3-yl)benzo[d]thiazol-2-yl)-4,5,6,7-tetrahydrothieno[2,3-c]pyridin-2-yl)-3-((2-methoxyethyl)amino)propanamide

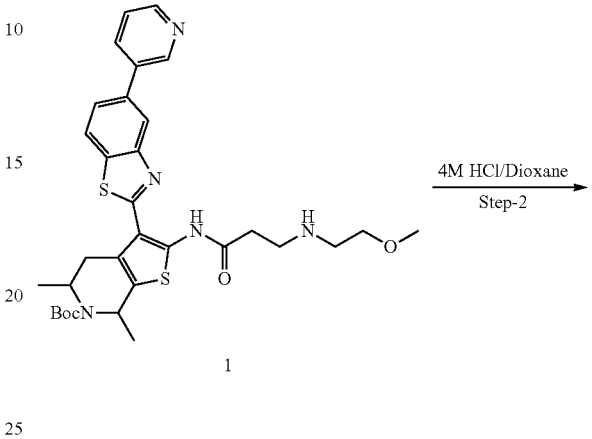

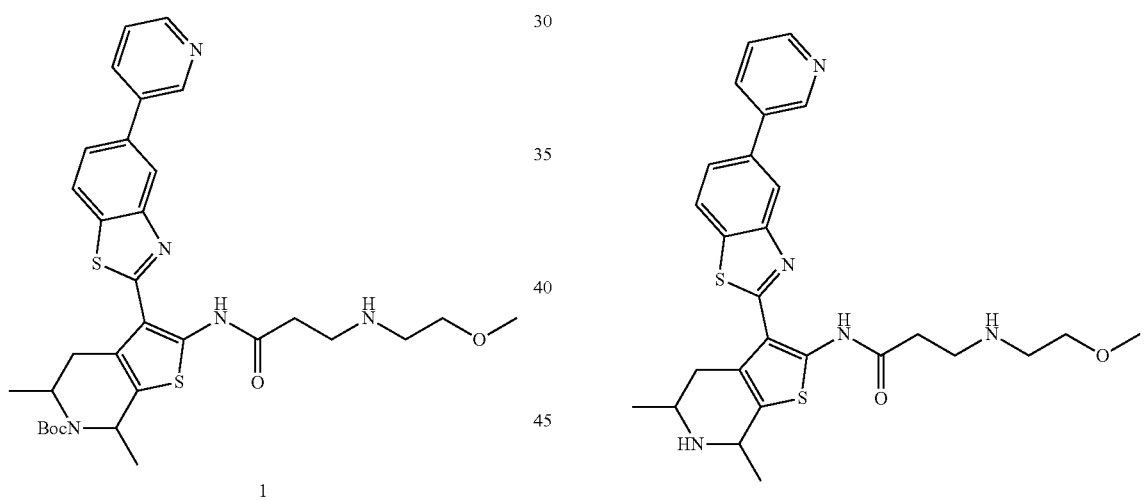

To a solution of tert-butyl 3-(5-bromobenzo[d]thiazol-2-yl)-2-(3-((2-methoxyethyl)amino)propanamido)-5,7-dimethyl-4,7-dihydrothieno[2,3-c]pyridine-6(5H)-carboxylate (550 mg, 0.884 mmol) in dioxane (10 mL) was added solution of K₂CO₃ (305 mg, 2.211 mmol) in water (1 mL) and degassed under argon atmosphere for 10 min. Followed by addition of Pd(PPh₃)₄ (102 mg, 0.08 mmol) and pyridin-3-ylboronic acid 7 (163 mg, 1.326 mmol) and degassed with argon for another 10 min. The reaction mixture was heated to 100° C. for 12 h. After the completion of reaction (monitored by LCMS), the reaction mixture was diluted with water and extracted with CH₂Cl₂ (thrice). The combined organic layers were dried with anhydrous Na₂SO₄, filtered and concentrated to get a crude residue. This crude compound was purified by silica gel column chromatography eluting with 0-8% methanol in CH₂Cl₂ to afford the title compound 1 (300 mg, yield 55%).

To a solution of tert-butyl 2-(3-((2-methoxyethyl)amino)propanamido)-5,7-dimethyl-3-(5-(pyridin-3-yl)benzo[d]thiazol-2-yl)-4,7-dihydrothieno[2,3-c]pyridine-6(5H)-carboxylate 1 (300 mg, 0.483 mmol) in dioxane (4 mL) at 0° C. was added 4M HCl in dioxane (5 mL). After the addition, the resulting mixture was stirred at room temperature for 2 h. After completion, the reaction mixture was evaporated in vacuum resulting in a crude residue which was purified by trituration with methanol. The solid obtained was filtered and washed with diethyl ether and n-pentane to afford the title compound as yellow solid (284 mg, crude). The chiral separation for the mixture (Column: CHIRALPAK, IC, 250 mm*4.6 mm*5 um; Mobile Phase: A: n-Hexane+0.1% TEA; B: ETOH: DCM (85:15)+0.1% TEA; Flow rate: 1.20 ml/min; Isocratic: 70% B) afforded the separated title compounds.

Example 147. Synthesis of (S)—N-(3-(Benzo[d]thiazol-2-yl)-5-methyl-4,5,6,7-tetrahydrothieno[2,3-c]pyridin-2-yl)-3-((2-methoxyethyl)amino)propanamide and Separation of Isomers (Compounds 529, 530, and 538)

Step 1: tert-Butyl 2-acrylamido-3-(benzo[d]thiazol-2-yl)-5-methyl-4,7-dihydrothieno[2,3-c]pyridine-6(5H)-carboxylate compound and tert-butyl 2-acrylamido-3-(benzo[d]thiazol-2-yl)-7-methyl-4,7-dihydrothieno[2,3-c]pyridine-6(5H)-carboxylate (5 and 6)

reaction (by LCMS) the reaction mixture was diluted with water and extracted with $CH_2Cl_2$. The combined organic layer was dried with anhydrous $Na_2SO_4$, filtered and concentrated to afford the title compounds as a yellow solid (700 mg, crude).

Step 2: tert-Butyl 3-(benzo[d]thiazol-2-yl)-2-(3-((2-methoxyethyl)amino)propanamido)-5-methyl-4,7-dihydrothieno[2,3-c]pyridine-6(5H)-carboxylate compound and tert-butyl 3-(benzo[d]thiazol-2-yl)-2-(3-((2-methoxyethyl)amino) propanamido)-7-methyl-4,7-dihydrothieno[2,3-c]pyridine-6(5H)-carboxylate (7 and 8)

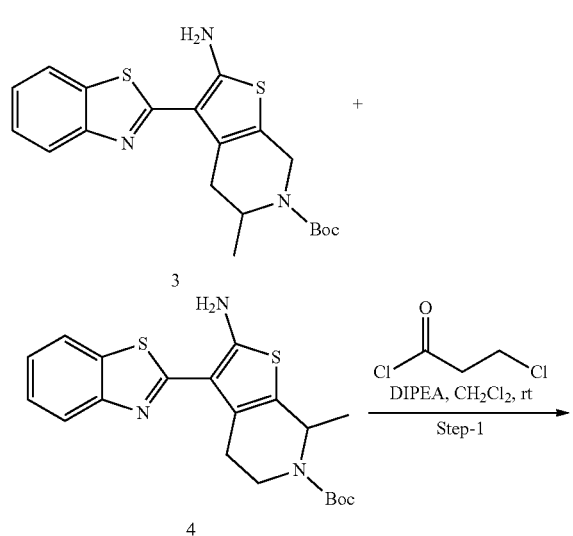

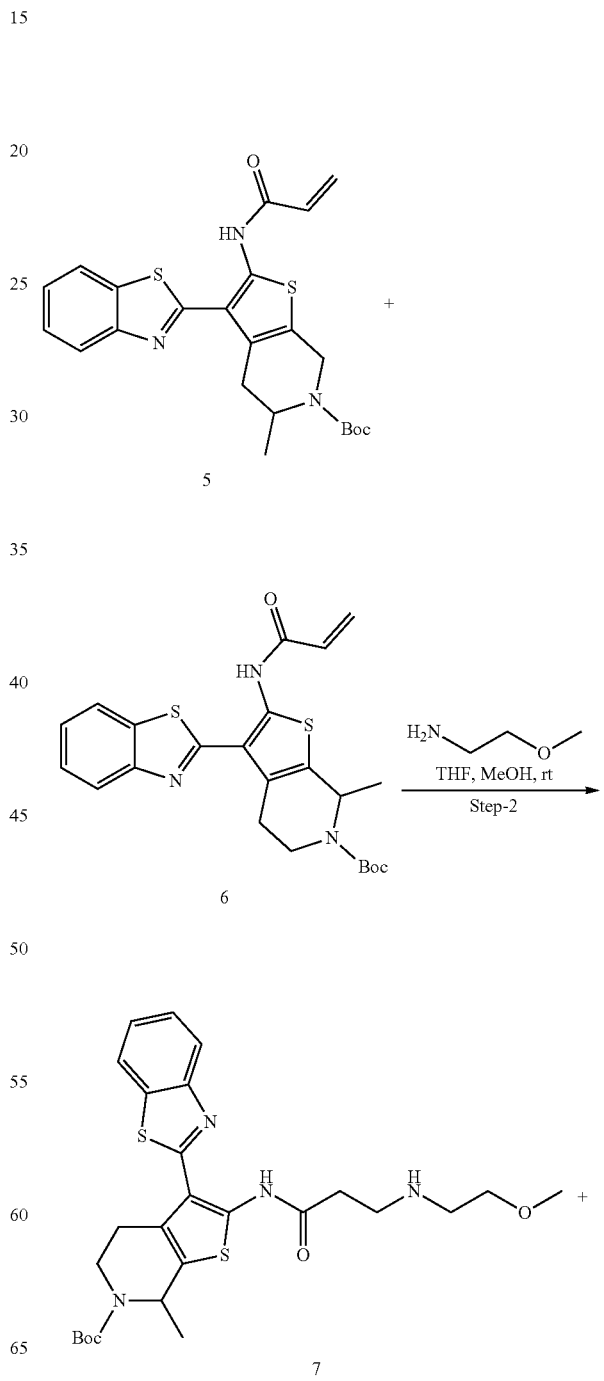

To a solution of 3 and 4 (800 mg, 1.99 mmol) in $CH_2Cl_2$ (10 mL) was added DIPEA (0.5 mL, 2.99 mmol) at room temperature and stirred for 20 min. To the resulting solution at 0° C. was added 3-chloropropanoyl chloride (380 mg, 2.99 mmol) and stirred at room temperature for 15 h. Reaction was monitored by TLC. After the completion of

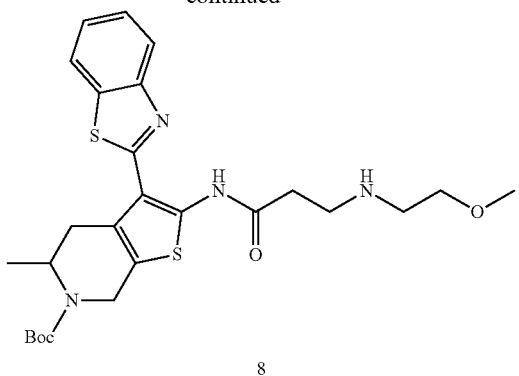

8

To a mixture of 5 and 6 (700 mg, 1.54 mmol) in MeOH:THF (1:1, 20 mL) was added 2-methoxyethan-1-amine (173 mg, 2.31 mmol). The resulting reaction mixture was stirred at room temperature for 15 h. Progress of the reaction was monitored by TLC. After completion, the reaction mixture was concentrated to dryness under reduced pressure. The crude compound was purified by column chromatography eluting with 0-10% methanol in $CH_2Cl_2$ to afford the title compounds 7 and 8 as yellow solid (600 mg, yield 73%).

Step 3: N-(3-(Benzo[d]thiazol-2-yl)-5-methyl-4,5,6,7-tetrahydrothieno[2,3-c]pyridin-2-yl)-3-((2-methoxyethyl)amino)propanamide compound and N-(3-(Benzo[d]thiazol-2-yl)-7-methyl-4,5,6,7-tetrahydrothieno[2,3-c]pyridin-2-yl)-3-((2-methoxyethyl)amino)propanamide

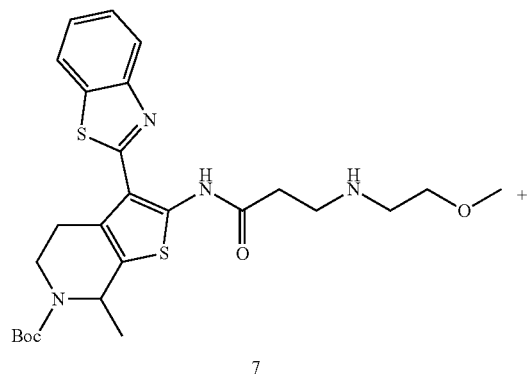

7

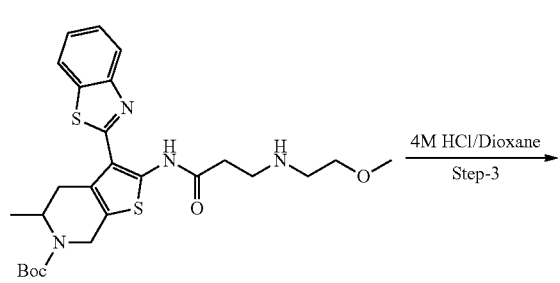

8

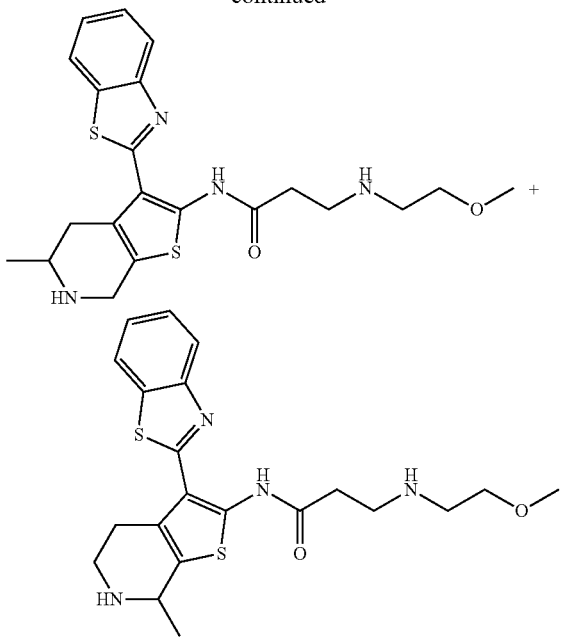

To mixture of 7 and 8 (600 mg, 1.132 mmol) in dioxane (10 mL) at 0° C. was added 4M HCl in dioxane (5 mL). After the addition, the resulting mixture was stirred at room temperature for 2 h. Reaction was monitored by TLC. After completion, the reaction mixture was evaporated in vacuum resulting in a crude residue which was triturated by diethyl ether and n-pentane to afford a mixture of the title compounds as yellow solid (600 mg, crude). Chiral separation (Column: CHIRALPAK; 250 mm*4.6 mm*5 um; Mobile Phase: A: n-Hexane+0.1% TEA; B: ETOH: DCM (85:15)+ 0.1% TEA; Flow rate: 1.0 ml/min; Isocratic: 50% B) of the mixture afforded the isolated title compounds.

Example 148. Synthesis of N-((5S,7R)-5,7-Dimethyl-3-(5-(pyridin-3-yl)benzo[d]thiazol-2-yl)-4,5,6,7-tetrahydrothieno[2,3-c]pyridin-2-yl)-3-((2-methoxyethyl)amino)propanamide and Separation of Isomers (Compounds 524, 525, 526 and 533)

Step 1: tert-Butyl 2-(3-((2-methoxyethyl)amino)propanamido)-5,7-dimethyl-3-(5-(pyridin-3-yl)benzo[d]thiazol-2-yl)-4,7-dihydrothieno[2,3-c]pyridine-6(5H)-carboxylate (1)

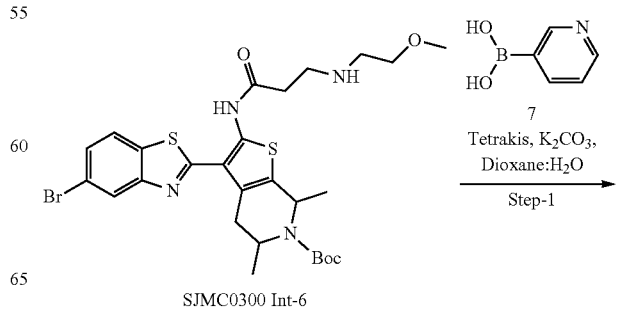

SJMC0300 Int-6

-continued

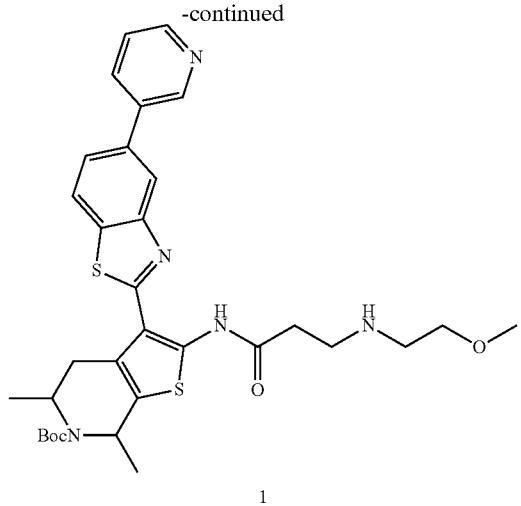

-continued

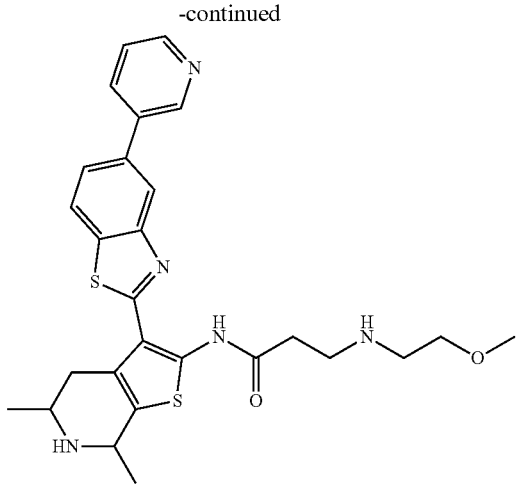

To a solution of tert-butyl 3-(5-bromobenzo[d]thiazol-2-yl)-2-(3-((2-methoxyethyl)amino)propanamido)-5,7-dimethyl-4,7-dihydrothieno[2,3-c]pyridine-6(5H)-carboxylate (550 mg, 0.884 mmol) in dioxane (10 mL) was added solution of K$_2$CO$_3$ (305 mg, 2.211 mmol) in water (1 mL) and degassed under argon atmosphere for 10 min. Followed by addition of Pd(PPh$_3$)$_4$ (102 mg, 0.08 mmol) and pyridin-3-ylboronic acid 7 (163 mg, 1.326 mmol) and degassed with argon for another 10 min. The reaction mixture was heated to 100° C. for 12 h. After the completion of reaction (monitored by LCMS), the reaction mixture was diluted with water and extracted with CH$_2$Cl$_2$ (thrice). The combined organic layers were dried with anhydrous Na$_2$SO$_4$, filtered and concentrated to get a crude residue. This crude compound was purified by silica gel column chromatography eluting with 0-8% methanol in CH$_2$Cl$_2$ to afford the title compound 1 (300 mg, yield 55%).

Step 2: N-(5,7-Dimethyl-3-(5-(pyridin-3-yl)benzo[d]thiazol-2-yl)-4,5,6,7-tetrahydrothieno[2,3-c]pyridin-2-yl)-3-((2-methoxyethyl)amino)propanamide To a solution of tert-butyl 2-(3-((2-methoxyethyl)amino)propanamido)-5,7-dimethyl-3-(5-(pyridin-3-yl)benzo[d]thiazol-2-yl)-4,7-dihydrothieno[2,3-c]pyridine-6(5H)-carboxylate 1 (300 mg, 0.483 mmol) in dioxane (4 mL) at 0° C. was added 4M HCl in dioxane (5 mL). After the addition, the resulting mixture was stirred at room temperature for 2 h. After completion, the reaction mixture was evaporated in vacuum resulting in a crude residue which was purified by trituration with methanol. The solid obtained was filtered and washed with diethyl ether and n-pentane to afford the title compound as yellow solid (284 mg, crude). The chiral separation for the mixture (Column: CHIRALPAK, IC, 250 mm*4.6 mm*5 um; Mobile Phase: A: n-Hexane+0.1% TEA; B: ETOH: DCM (85:15)+0.1% TEA; Flow rate: 1.20 ml/min; Isocratic: 70% B) afforded the separated title compounds.

Example 149. Synthesis of N-((5S,7R)-5,7-Dimethyl-3-(5-(pyridin-3-yl)benzo[d]thiazol-2-yl)-4,5,6,7-tetrahydrothieno[2,3-c]pyridin-2-yl)-3-((2-methoxyethyl)amino)propanamide and Separation of Isomers (Compounds 524, 525, 526 and 533)

Step 1: tert-Butyl 2-(3-((2-methoxyethyl)amino)propanamido)-5,7-dimethyl-3-(5-(pyridin-3-yl)benzo[d]thiazol-2-yl)-4,7-dihydrothieno[2,3-c]pyridine-6(5H)-carboxylate (1)

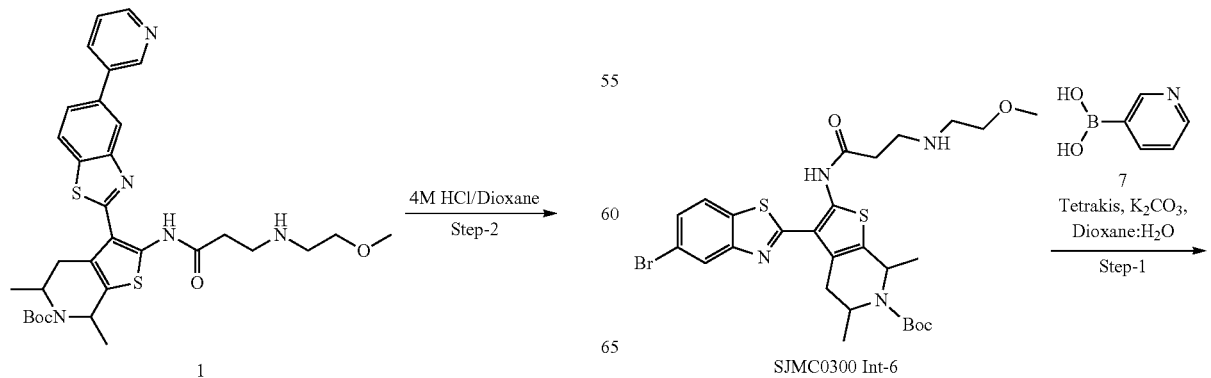

SJMC0300 Int-6

437
-continued

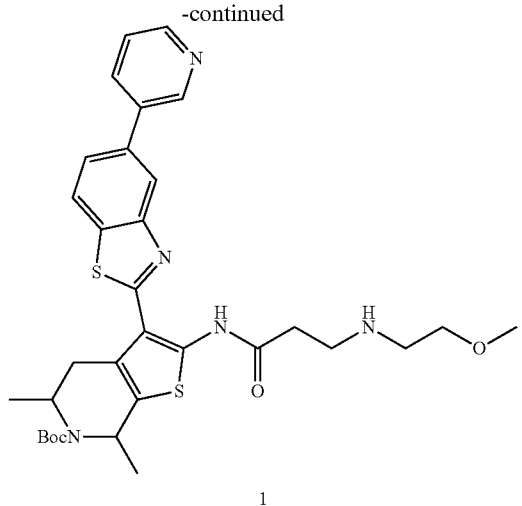

1

To a solution of tert-butyl 3-(5-bromobenzo[d]thiazol-2-yl)-2-(3-((2-methoxyethyl)amino)propanamido)-5,7-dimethyl-4,7-dihydrothieno[2,3-c]pyridine-6(5H)-carboxylate SJMC0300 Int-6 (550 mg, 0.884 mmol) in dioxane (10 mL) was added solution of $K_2CO_3$ (305 mg, 2.211 mmol) in water (1 mL) and degassed under argon atmosphere for 10 min. Followed by addition of $Pd(PPh_3)_4$ (102 mg, 0.08 mmol) and pyridin-3-ylboronic acid 7 (163 mg, 1.326 mmol) and degassed with argon for another 10 min. The reaction mixture was heated to 100° C. for 12 h. After the completion of reaction (monitored by LCMS), the reaction mixture was diluted with water and extracted with $CH_2Cl_2$ (thrice). The combined organic layers were dried with anhydrous $Na_2SO_4$, filtered and concentrated to get a crude residue. This crude compound was purified by silica gel column chromatography eluting with 0-8% methanol in $CH_2Cl_2$ to afford the title compound 1 (300 mg, yield 55%).

Step 2: N-(5,7-Dimethyl-3-(5-(pyridin-3-yl)benzo[d]thiazol-2-yl)-4,5,6,7-tetrahydrothieno[2,3-c]pyridin-2-yl)-3-((2-methoxyethyl)amino)propanamide

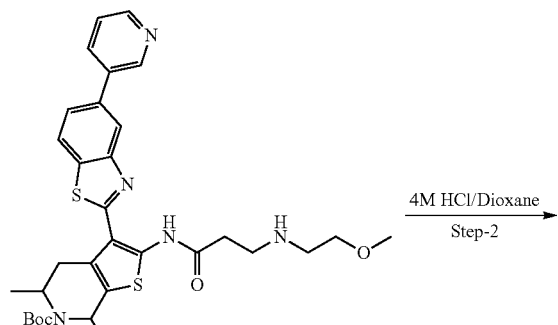

1

438
-continued

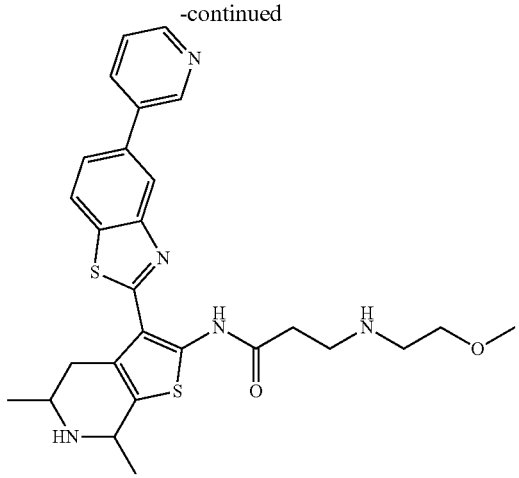

To a solution of tert-butyl 2-(3-((2-methoxyethyl)amino)propanamido)-5,7-dimethyl-3-(5-(pyridin-3-yl)benzo[d]thiazol-2-yl)-4,7-dihydrothieno[2,3-c]pyridine-6(5H)-carboxylate 1 (300 mg, 0.483 mmol) in dioxane (4 mL) at 0° C. was added 4M HCl in dioxane (5 mL). After the addition, the resulting mixture was stirred at room temperature for 2 h. After completion, the reaction mixture was evaporated in vacuum resulting in a crude residue which was purified by trituration with methanol. The solid obtained was filtered and washed with diethyl ether and n-pentane to afford the title compound as yellow solid (284 mg, crude). The chiral separation for the mixture (Column: CHIRALPAK, IC, 250 mm*4.6 mm*5 um; Mobile Phase: A: n-Hexane+0.1% TEA; B: ETOH: DCM (85:15)+0.1% TEA; Flow rate: 1.20 ml/min; Isocratic: 70% B) afforded the separated title compounds.

Example 150. c-Myc/Max/Ebox DNA AlphaScreen Assay

Compounds of the invention were assayed for c-Myc/Max/EBox activity as described in the following protocol. Human $his_6$-c-Myc and $his_6$-Max were used with biotinylated DNA containing a single Ebox sequence (biotinG-GAAGCAGACCACGTGGTCTGCTTCC) purchased from MWG Operon. Free c-Myc was generated from $his_6$-c-Myc through thrombin cleavage of the $his_6$ tag. For 384-well plate assays, 10 µL of a 2× solution of free c-Myc (20 nM final), $Ni^{2+}$ coated Acceptor Beads (25 µg/ml final), and biotinylated Ebox oligo (10 nM final) were added to 384-well plates with a Biotek EL406 liquid handler. 50 nL of compounds from stock plates were added by pin transfer using a Janus Workstation (PerkinElmer), allowing the compounds to interact with c-Myc prior to c-Myc binding with Max. In the current assay, DMSO was not allowed to exceed 2% v/v of the assay. 10 µl of 2× master mix containing streptavidin-coated donor beads (25 µg/ml final) and $his_6$-Max (5 nM) were added. AlphaScreen measurements were performed on an Envision plate reader (PerkinElmer) utilizing the manufacturer's protocol.

Both master mixes were made in room temperature assay buffer (50 mM HEPES, 150 mM NaCl, 0.2% w/v BSA, 0.02% w/v Tween20, 40 µg/ml glycogen, 500 µM DTT, pH 8.0, wherein both DTT and glycogen were added fresh). Alpha beads were added to respective master solutions. All subsequent steps were performed in low light conditions. Solution 1:2× solution of components with final concentrations of c-Myc Ni-coated Acceptor Beads (25 µg/ml), and biotinylated Ebox oligo (10 nM). Solution 2:2× solution of streptavidin-coated donor beads (25 µg/ml final) and his$_6$-Max 10 µL. Solution 1 was added to 384-well plate (AlphaPlate-384, PerkinElmer) with Biotek EL406 liquid handler and the plates were centrifuged very briefly. 50 nL of compounds from stock plates were added by pin transfer using a Janus Workstation. Solution 2 (10 µl) was added with the liquid handler. Plates were sealed with foil to block light exposure and prevent evaporation. Plates were very briefly centrifuged followed by 2 hour incubation. AlphaScreen measurements were performed on an Envision 2104 utilizing the manufacturer's protocol. Excitation was at 680 nm for donor bead release of singlet oxygen and emission was read with a bandpass filter from 520-620 nm. Glycogen: Roche Diagnostics #10901393001. Plate 1536: Perkin Elmer, 6004350. Plate 384: Perkin Elmer, 6005350. Nickel-His Alpha Beads: 6760619R. The data from this assay are summarized in Tables 3 and 4 below (Myc/Max/DNA Activity).

Example 151. Cell Viability Assay

Compounds of the invention were assayed for cell viability using the human small lung cancer cell line H2171 as described in the following protocol. Cells were counted and adjusted to 20,000 cells/mL. Using a Biotek EL406, 50 µL of cells in media were distributed into 384 well white plates from Thermo. Immediately after plating, compound in DMSO was distributed to plates. Compounds were added to plates using a 50 nL 384 well pin transfer manifold on a Janus workstation. Stocks were arrayed in 10 point dose response in DMSO stock in 384 well Greiner compound plates. After the addition of compounds, plates were incubated for three days in a 37° C. incubator. Cell viability was read out using ATPlite from Perkin Elmer. Lyophilized powder was resuspended in lysis buffer and diluted 1:2 with deionized water. 25 µL of this solution was added to each well using the Biotek liquid handler. Plates were incubated for 15 minutes at room temperature before signal was read on an Envision Plate Reader. The data from this assay are summarized in Tables 2 and 3 below (H2171 activity).

Tables 2 and 3. Biological Assay Data of Selected Compounds of the Invention

The results of the assays described in Examples 57 and 58 are summarized in the following tables, where "A" represents a calculated IC$_{50}$ of less than 300 nM; "B" represents a calculated IC$_{50}$ of between 300 nM and less than 1 µM; "C" represents a calculated IC$_{50}$ of between 1 µM and less than 10 µM; "D" represents a value of greater than 10 µM; "*" is a value above the assay detection limit; and "NT" represents a value that was not obtained. Table 2 represents the assay results from the compounds depicted in FIG. 1, and Table 3 represents the assay results from compounds depicted in FIG. 2.

TABLE 2

| Compound # | Myc/Max/DNA Activity | H2171 Activity |
| --- | --- | --- |
| 100 | B | A |
| 101 | C | NT |
| 102 | B | B |
| 103 | D | NT |
| 104 | C | NT |
| 105 | B | A |
| 106 | B | A |

TABLE 2-continued

| Compound # | Myc/Max/DNA Activity | H2171 Activity |
| --- | --- | --- |
| 107 | A | A |
| 108 | B | B |
| 109 | D | NT |
| 110 | B | C |
| 111 | B | C |
| 112 | D | NT |
| 113 | C | NT |
| 114 | C | NT |
| 115 | D | NT |
| 116 | C | C |
| 117 | B | A |
| 118 | D | NT |
| 119 | C | NT |
| 120 | A | NT |
| 121 | D | NT |
| 122 | A | B |
| 123 | A | A |
| 124 | A | A |
| 125 | B | B |
| 126 | A | A |
| 127 | B | B |
| 128 | A | A |
| 129 | A | A |
| 130 | A | A |
| 131 | A | B |
| 132 | B | B |
| 133 | D | C |
| 134 | A | A |
| 135 | A | A |
| 136 | C | B |
| 137 | C | D |
| 138 | B | NT |
| 139 | A | NT |
| 140 | A | A |
| 141 | NT | B |
| 142 | A | A |
| 143 | NT | A |
| 144 | NT | NT |
| 145 | NT | B |
| 146 | A | A |
| 147 | NT | A |
| 148 | NT | D |
| 149 | A | A |
| 150 | A | A |
| 151 | A | A |
| 152 | A | A |
| 153 | B | A |
| 154 | B | A |
| 155 | A | A |
| 156 | A | A |
| 157 | A | A |
| 158 | D | B |
| 159 | C | B |
| 160 | B | B |
| 161 | A | A |
| 162 | NT | C |
| 163 | A | B |
| 164 | A | C |
| 165 | A | A |
| 166 | B | NT |
| 167 | A | NT |
| 168 | B | NT |
| 169 | B | NT |
| 170 | A | NT |
| 171 | A | NT |
| 173 | A | A |
| 174 | A | NT |
| 175 | A | NT |
| 176 | C | NT |
| 177 | C | NT |
| 178 | A | A |
| 179 | A | A |
| 180 | A | A |
| 181 | A | A |
| 182 | A | A |
| 183 | B | NT |
| 184 | A | A |

TABLE 2-continued

| Compound # | Myc/Max/DNA Activity | H2171 Activity |
|---|---|---|
| 185 | A | A |
| 186 | A | A |
| 187 | A | NT |
| 188 | A | B |
| 189 | A | A |
| 190 | A | A |
| 191 | A | C |
| 192 | A | A |
| 193 | A | A |
| 194 | A | A |
| 195 | A | A |
| 196 | B | A |
| 197 | C | B |
| 198 | C | A |
| 199 | C | C |
| 300 | C | C |
| 301 | C | C |
| 302 | A | A |
| 303 | B | A |
| 304 | B | A |
| 305 | B | NT |
| 306 | B | NT |
| 307 | A | NT |
| 308 | A | A |
| 309 | D | A |
| 310 | A | A |
| 311 | B | NT |
| 312 | B | NT |
| 313 | C | A |
| 314 | A | A |
| 315 | B | A |
| 316 | A | A |
| 317 | A | B |
| 318 | B | A |
| 319 | D | B |
| 320 | B | A |
| 321 | B | A |
| 322 | B | A |
| 323 | A | A |
| 324 | B | C |
| 325 | D | C |
| 326 | A | B |
| 327 | B | A |
| 328 | D | NT |
| 329 | B | A |
| 330 | C | NT |
| 331 | D | NT |
| 332 | B | A |
| 333 | D | NT |
| 334 | A | A |
| 335 | B | A |
| 336 | A | NT |
| 337 | A | A |
| 338 | B | A |
| 339 | A | A |
| 340 | B | A |
| 341 | D | NT |
| 342 | A | A |
| 343 | C | A |
| 344 | D | NT |
| 345 | A | A |
| 346 | C | NT |
| 347 | C | NT |
| 348 | B | A |
| 349 | A | A |
| 350 | B | NT |
| 351 | B | A |
| 352 | B | A |
| 353 | C | NT |
| 354 | D | NT |
| 355 | A | A |
| 356 | D | NT |
| 357 | C | NT |
| 358 | A | A |
| 359 | D | NT |
| 360 | B | A |
| 361 | A | A |
| 362 | D | NT |
| 363 | B | A |
| 364 | B | A |
| 365 | A | A |
| 366 | D | A |
| 367 | D | NT |
| 368 | D | NT |
| 369 | C | A |
| 370 | B | A |
| 371 | C | NT |
| 372 | C | A |
| 373 | D | NT |
| 374 | A | A |
| 375 | C | A |
| 376 | D | NT |
| 377 | D | NT |
| 378 | C | NT |
| 379 | B | A |
| 380 | C | A |
| 381 | D | NT |
| 382 | C | NT |
| 383 | D | A |
| 384 | C | NT |
| 385 | D | NT |
| 386 | B | A |
| 387 | C | NT |
| 388 | C | A |
| 389 | B | A |
| 390 | B | NT |
| 391 | A | A |
| 392 | D | NT |
| 393 | D | NT |
| 394 | A | A |
| 395 | B | A |
| 396 | B | A |
| 397 | C | NT |
| 398 | D | NT |
| 399 | A | B |
| 400 | D | NT |
| 401 | B | A |
| 402 | C | NT |
| 403 | B | B |
| 404 | A | A |
| 405 | A | A |
| 406 | A | A |
| 407 | D | NT |
| 408 | B | B |
| 409 | A | A |
| 410 | D | NT |
| 411 | C | A |
| 412 | B | A |
| 413 | A | A |
| 414 | D | NT |
| 415 | D | NT |
| 416 | C | NT |
| 417 | D | NT |
| 418 | D | NT |
| 419 | B | B |
| 420 | C | A |
| 421 | D | NT |
| 422 | B | A |
| 423 | B | A |
| 424 | D | NT |
| 425 | D | NT |
| 426 | D | NT |
| 427 | C | NT |
| 428 | D | NT |
| 429 | D | NT |
| 430 | D | NT |
| 431 | D | NT |
| 432 | C | NT |
| 433 | A | A |
| 434 | C | A |
| 435 | C | A |
| 436 | B | A |
| 437 | C | B |
| 438 | C | A |

TABLE 2-continued

| Compound # | Myc/Max/DNA Activity | H2171 Activity |
|---|---|---|
| 439 | D | NT |
| 440 | D | NT |
| 441 | B | NT |
| 442 | D | NT |
| 443 | A | A |
| 444 | B | A |
| 445 | A | A |
| 446 | D | NT |
| 447 | D | NT |
| 448 | D | NT |
| 449 | B | A |
| 450 | D | NT |
| 451 | B | A |
| 452 | D | NT |
| 453 | D | NT |
| 454 | D | NT |
| 455 | D | NT |
| 456 | A | A |
| 457 | D | NT |
| 458 | A | A |
| 459 | A | A |
| 460 | D | NT |
| 461 | D | NT |
| 462 | C | NT |
| 463 | B | NT |
| 464 | D | NT |
| 465 | A | A |
| 466 | C | NT |
| 467 | D | NT |
| 468 | C | NT |
| 469 | A | A |
| 470 | B | A |
| 471 | D | NT |
| 472 | C | NT |
| 473 | B | A |
| 474 | C | NT |
| 475 | D | NT |
| 476 | C | NT |
| 477 | D | NT |
| 478 | C | NT |
| 479 | C | NT |
| 480 | D | NT |
| 481 | A | A |
| 482 | B | A |
| 483 | C | NT |
| 484 | A | B |
| 485 | A | B |
| 486 | B | A |
| 487 | C | NT |
| 488 | D | A |
| 489 | B | A |
| 490 | B | A |
| 491 | D | NT |
| 492 | C | A |
| 493 | A | A |
| 494 | D | NT |
| 495 | C | NT |
| 496 | C | A |
| 497 | A | A |
| 498 | C | NT |
| 499 | B | B |
| 500 | C | A |
| 501 | B | NT |
| 502 | B | A |
| 503 | B | A |
| 504 | A | A |
| 505 | C | A |
| 506 | B | C |
| 507 | B | A |
| 508 | C | A |
| 509 | C | A |
| 510 | B | A |
| 511 | B | A |
| 512 | B | A |
| 513 | A | D |
| 514 | A | B |
| 515 | A | A |
| 516 | A | A |
| 517 | A | A |
| 518 | C | NT |
| 519 | A | A |
| 520 | C | B |
| 521 | A | A |
| 522 | A | A |
| 523 | C | B |
| 524 | A | B |
| 525 | A | A |
| 526 | C | B |
| 527 | B | A |
| 528 | B | B |
| 529 | A | A |
| 530 | C | A |
| 531 | A | NT |
| 532 | D | B |
| 533 | C | B |
| 534 | A | A |
| 535 | A | A |
| 536 | B | A |
| 537 | D | A |
| 538 | B | NT |
| 539 | B | NT |
| 540 | B | A |
| 541 | B | A |
| 542 | B | A |
| 543 | B | A |
| 544 | A | A |
| 545 | A | A |
| 546 | D | A |
| 547 | C | A |
| 548 | A | A |
| 549 | A | A |
| 550 | A | A |
| 551 | A | A |
| 552 | A | A |
| 553 | A | A |
| 554 | B | A |
| 555 | A | A |
| 556 | A | A |
| 557 | A | A |
| 558 | A | NT |
| 559 | A | A |
| 560 | C | NT |
| 561 | C | A |
| 562 | B | A |
| 563 | A | A |
| 564 | A | A |
| 565 | A | A |
| 566 | C | A |
| 567 | C | A |
| 568 | A | A |
| 569 | C | C |
| 570 | C | A |
| 571 | A | A |
| 572 | B | A |
| 573 | B | B |
| 574 | A | A |
| 575 | A | A |
| 576 | A | A |
| 577 | D | D |
| 578 | B | A |
| 579 | A | A |
| 580 | B | A |
| 581 | A | A |
| 582 | C | A |
| 583 | A | A |
| 584 | A | A |
| 585 | A | A |
| 586 | D | A |
| 587 | D | B |
| 588 | A | A |
| 589 | A | A |
| 590 | A | A |
| 591 | D | A |
| 592 | A | A |

TABLE 2-continued

| Compound # | Myc/Max/DNA Activity | H2171 Activity |
|---|---|---|
| 593 | D | B |
| 594 | B | A |
| 595 | A | B |
| 596 | D | B |
| 597 | B | A |
| 598 | A | A |
| 599 | A | A |
| 600 | A | A |
| 601 | D | A |
| 602 | B | A |
| 603 | C | B |
| 604 | B | A |
| 605 | C | B |
| 606 | A | B |
| 607 | A | A |
| 608 | NT | NT |
| 609 | D | B |
| 610 | B | A |
| 611 | A | A |
| 612 | D | B |
| 613 | C | B |
| 614 | D | A |
| 615 | B | A |
| 616 | C | A |
| 617 | A | A |
| 618 | A | A |
| 619 | C | A |
| 620 | C | C |
| 621 | D | C |
| 622 | A | A |
| 623 | A | A |
| 624 | A | A |
| 625 | A | NT |

TABLE 3

| Compound # | Myc/Max/DNA Activity | H2171 Activity |
|---|---|---|
| 200 | B | C |
| 201 | C | C |
| 202 | C | A |
| 203 | C | C |
| 204 | C | C |
| 205 | D | D |
| 206 | C | C |
| 207 | C | NT |
| 208 | C | NT |
| 209 | C | NT |
| 210 | C | NT |
| 211 | C | NT |
| 212 | D | NT |
| 213 | D | NT |
| 214 | D | NT |
| 215 | D | NT |
| 216 | D | NT |
| 217 | D | A |
| 218 | C | A |
| 219 | C | A |
| 220 | C | D |
| 221 | D | D |
| 222 | D | NT |
| 223 | C | D |
| 224 | B | D |
| 225 | B | A |
| 226 | D | A |
| 227 | D | A |
| 228 | D | NT |
| 229 | B | A |
| 230 | C | D |
| 231 | C | A |
| 232 | D | D |
| 233 | B | A |
| 234 | B | B |

TABLE 3-continued

| Compound # | Myc/Max/DNA Activity | H2171 Activity |
|---|---|---|
| 235 | B | A |
| 236 | B | B |
| 237 | C | B |
| 238 | NT | B |

EQUIVALENTS

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process.

Furthermore, the invention encompasses all variations, combinations, and permutations in which one or more limitations, elements, clauses, and descriptive terms from one or more of the listed claims are introduced into another claim. For example, any claim that is dependent on another claim can be modified to include one or more limitations found in any other claim that is dependent on the same base claim. Where elements are presented as lists, e.g., in Markush group format, each subgroup of the elements is also disclosed, and any element(s) can be removed from the group. It should it be understood that, in general, where the invention, or aspects of the invention, is/are referred to as comprising particular elements and/or features, certain embodiments of the invention or aspects of the invention consist, or consist essentially of, such elements and/or features. For purposes of simplicity, those embodiments have not been specifically set forth in haec verba herein. It is also noted that the terms "comprising" and "containing" are intended to be open and permits the inclusion of additional elements or steps. Where ranges are given, endpoints are included. Furthermore, unless otherwise indicated or otherwise evident from the context and understanding of one of ordinary skill in the art, values that are expressed as ranges can assume any specific value or sub-range within the stated ranges in different embodiments of the invention, to the tenth of the unit of the lower limit of the range, unless the context clearly dictates otherwise.

This application refers to various issued patents, published patent applications, journal articles, and other publications, all of which are incorporated herein by reference. If there is a conflict between any of the incorporated references and the instant specification, the specification shall control. In addition, any particular embodiment of the present invention that falls within the prior art may be explicitly excluded from any one or more of the claims. Because such embodiments are deemed to be known to one of ordinary skill in the art, they may be excluded even if the exclusion is not set forth explicitly herein. Any particular embodiment of the invention can be excluded from any claim, for any reason, whether or not related to the existence of prior art.

Those skilled in the art will recognize or be able to ascertain using no more than routine experimentation many equivalents to the specific embodiments described herein. The scope of the present embodiments described herein is not intended to be limited to the above Description, but rather is as set forth in the appended claims. Those of ordinary skill in the art will appreciate that various changes and modifications to this description may be made without departing from the spirit or scope of the present invention, as defined in the following claims.

What is claimed is:

1. A compound of structural formula I:

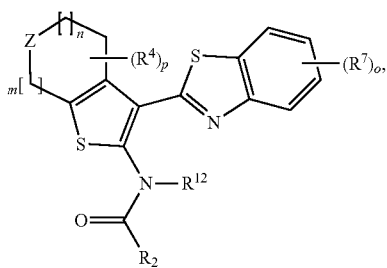

(I)

or a pharmaceutically acceptable salt or isotopically labeled derivative thereof, wherein:

Y is S;

Z is $N(R^1)$;

$R^1$ is selected from hydrogen, $C_1$-$C_6$ alkyl, and ($C_0$ alkylene)-carbocyclyl;

$R^{12}$ is hydrogen;

$R^2$ is —$C(R^{2a})(R^{2b})[C(R^{9a})(R^{9b})]_{1-7}$—$N(R^{17})(R^8)$;

$R^{2a}$ is selected from hydrogen, $C_1$-$C_4$ alkyl, and $C_1$-$C_4$ heteroalkyl;

$R^{2b}$ is selected from hydrogen, $C_1$-$C_6$ alkyl, $C_1$-$C_6$ heteroalkyl, ($C_0$-$C_6$ alkylene)-heteroaryl, and —$CH_2$—$NR^{17}$—$(CH_2)_{0-1}$—$(CH_2CH_2O)_{3-20}$—$CH_2CH_2$—$R^{20}$, wherein:

each $R^{9a}$ and each $R^{9b}$ is independently selected from hydrogen, halogen, —CN, $C_1$-$C_8$ alkyl, ($C_0$-$C_6$ alkylene)-carbocyclyl, ($C_1$-$C_6$ heteroalkylene)-carbocyclyl, ($C_0$-$C_6$ alkylene)-heterocyclyl, ($C_1$-$C_6$ heteroalkylene)-heterocyclyl, ($C_0$-$C_6$ alkylene)-aryl, ($C_1$-$C_6$ heteroalkylene)-aryl, ($C_0$-$C_6$ alkylene)-heteroaryl, and ($C_1$-$C_6$ heteroalkylene)-heteroaryl;

each $R^{17}$ and $R^8$ is independently selected from hydrogen, $C_1$-$C_4$ alkyl, $C_1$-$C_6$ heteroalkyl, ($C_1$-$C_4$ alkylene)-heterocyclyl, ($C_1$-$C_4$ alkylene)-heteroaryl, carbocyclyl, —$(CH_2CH_2O)_{3-20}$—$CH_2CH_2R^{20}$, and ($C_1$-$C_4$ alkylene)-aryl;

$R^{20}$ is selected from —C(O)OH, —C(O)$CH_3$, —C(O)$CH_2CH_3$, —$NH_2$, —$CH_2NH_2$, —$(CH_2)_2$—$NH_2$, and —$(CH_2)_3$—$NH_2$;

and wherein any alkyl portion of $R^{2b}$ optionally substituted with one or more methyl;

each $R^4$ is $C_1$-$C_8$ alkyl;

each $R^7$ is independently selected from halogen, —CN, —OH, —S(O)$_2$—$C_1$-$C_6$ alkyl, —S—$C_1$-$C_6$ alkyl, $C_1$-$C_6$ alkyl, $C_2$-$C_6$ alkenyl, $C_1$-$C_6$ heteroalkyl, $N(R^{3a})(R^{3b})$, $C(O)(C_1$-$C_6$ alkyl), $C(O)O(C_1$-$C_6$ alkyl), ($C_0$-$C_6$ alkylene)-carbocyclyl, ($C_1$-$C_6$ heteroalkylene)-carbocyclyl, ($C_0$-$C_6$ alkylene)-heterocyclyl, ($C_1$-$C_6$ heteroalkylene)-heterocyclyl, ($C_0$-$C_6$ alkylene)-aryl, ($C_1$-$C_6$ heteroalkylene)-aryl, ($C_0$-$C_6$ alkylene)-heteroaryl, and ($C_1$-$C_6$ heteroalkylene)-heteroaryl, wherein any alkyl, alkylene, heteroalkyl, heteroalkylene, heterocyclyl or heteroaryl portion of $R^7$ is optionally and independently substituted; or two $R^7$ are taken together with the ring carbon atoms to which they are bound to form a heterocyclyl fused to rest of the compound;

$R^{3a}$ is hydrogen;

$R^{3b}$ is —S(O)$_2$—$C_1$-$C_6$ alkyl or heterocyclyl;

n is 1;

m is 1;

o is 0, 1, or 2; and p is 0, 1, or 2.

2. The compound of claim 1 or the pharmaceutically acceptable salt or isotopically labeled derivative thereof, wherein $R^1$ is hydrogen.

3. The compound of claim 1 or the pharmaceutically acceptable salt or isotopically labeled derivative thereof, wherein $R^1$ is selected from ethyl and cyclopropyl.

4. The compound of claim 1 or the pharmaceutically acceptable salt or isotopically labeled derivative thereof, wherein $R^{2a}$ is $C_1$-$C_4$ alkyl.

5. The compound of claim 1 or the pharmaceutically acceptable salt or isotopically labeled derivative thereof, wherein each $R^4$ is $C_1$ alkyl.

6. The compound of claim 1 or the pharmaceutically acceptable salt or isotopically labeled derivative thereof, wherein p is zero (0).

7. The compound of claim 1 or the pharmaceutically acceptable salt or isotopically labeled derivative thereof, wherein p is 1.

8. The compound of claim 1 or the pharmaceutically acceptable salt or isotopically labeled derivative thereof, wherein p is 2.

9. The compound of claim 1 or the pharmaceutically acceptable salt or isotopically labeled derivative thereof, wherein each $R^7$ is independently selected from —CN, —OH, halogen, $C_1$-$C_6$ alkyl, $C_2$-$C_4$ alkenyl, $C_1$-$C_6$ heteroalkyl, heteroaryl, heterocyclyl, and aryl, and wherein any alkyl, heteroalkyl, heterocyclyl or heteroaryl portion of $R^7$ is optionally and independently substituted.

10. The compound of claim 9 or the pharmaceutically acceptable salt or isotopically labeled derivative thereof, wherein each $R^7$ is independently selected from fluoro, bromo, chloro, —CN, —OH, —$CH_3$, —$CH_2CH_3$, —$CF_3$, —CH(OH)$CH_3$, —$CH_2OH$, —$OCH_3$, —CH═$CH_2$, 1,2,5,6-tetrahydropyridin-4-yl, 1-methylsulfonyl-1,2,5,6-tetrahydropyridin-4-yl, 4-(morpholin-4-ylcarbonyl)phenyl, 4-(4-methylpiperazin-1-yl)phenyl, 4-hydroxyphenyl, 4-methoxyphenyl, 4-methyl sulfonylphenyl, 4-acetamidophenyl, 3-(N-(2-(dimethylamino)ethyl)aminocarbonyl)phenyl, 3-(dimethylaminocarbonyl)phenyl, 1H-1,2,4-triazol-1-yl, 1H-imidazol-1-yl, 5-chloro-1H-imidazol-1-yl, 1H-pyrazol-5-yl, 1H-pyrazol-4-yl, 1,3-dimethylpyrazol-4-yl, 1,3-dimethylpyrazol-5-yl, 1-isopropyl-1H-pyrazol-4-yl, 1-(1-ethoxycarbonylmethyl)-1H-pyrazol-4-yl, isoxazol-4-yl, 3-hydroxyazetidin-1-yl, oxetan-3-ylamino, pyrimidin-5-yl, 2-aminopyrimidin-5-yl, 2-methoxypyrimidin-5-yl, 5-methyl-1H-pyrazol-3-yl, 1-methyl-1H-pyrazol-4-yl, 4-methyl-1H-imidzaol-1-yl, morpholin-4-yl, pyridin-3-yl, pyridin-4-yl, 5-fluoropyridin-3-yl, 2-fluoropyridin-5-yl, 2-fluoropyridin-4-yl, 2-hydroxypyridin-5-yl, 2-aminopyridin-4-yl, 2-methoxycarbonylpyridin-5-yl, 2-acetamidopyridin-4-yl, 2-(piperazin-1-yl)pyridin-5-yl, 5-aminopyridin-3- yl, 2-cyanopyridin-5-yl, 5-methoxypyridin-3-yl, 3,6-dihydro-2H-pyran-4-yl, [1,2,4]triazolo[1,5-a]pyridin-6-yl, and 2H-1,2,3,4-tetrazol-5-yl.

11. The compound of claim 1 or the pharmaceutically acceptable salt or isotopically labeled derivative thereof, wherein o is zero (0) or 1.

12. The compound of claim 11 or the pharmaceutically acceptable salt or isotopically labeled derivative thereof, wherein o is zero (0).

13. The A compound of structural formula I:

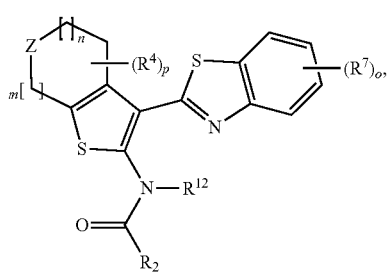

(I)

or a pharmaceutically acceptable salt or isotopically labeled derivative thereof, wherein:

Y is S;

Z is $N(R^1)$;

$R^1$ is selected from hydrogen, $C_1$-$C_6$ alkyl, and ($C_0$ alkylene)-carbocyclyl;

$R^{12}$ is hydrogen;

$R^2$ is —$C(R^{2a})(R^{2b})[C(R^{9a})(R^{9b})]_{1-7}$—$N(R^{17})(R^8)$;

$R^{2a}$ is selected from hydrogen, $C_1$-$C_4$ alkyl, and $C_1$-$C_4$ heteroalkyl;

$R^{2b}$ is selected from hydrogen, $C_1$-$C_6$ alkyl, $C_1$-$C_6$ heteroalkyl, ($C_0$-$C_6$ alkylene)-heteroaryl, and —$CH_2$—$NR^{17}$—$(CH_2)_{0-1}$—$(CH_2CH_2CH_2O)_{3-20}$—$CH_2CH_2$—$R^{20}$, wherein any alkyl portion of $R^{2b}$ is optionally substituted with one or more methyl;

each $R^{9a}$ and each $R^{9b}$ is independently selected from hydrogen, halogen, —CN, $C_1$-$C_8$ alkyl, ($C_0$-$C_6$ alkylene)-carbocyclyl, ($C_1$-$C_6$ heteroalkylene)-carbocyclyl, ($C_0$-$C_6$ alkylene)-heterocyclyl, ($C_1$-$C_6$ heteroalkylene)-heterocyclyl, ($C_0$-$C_6$ alkylene)-aryl, ($C_1$-$C_6$ heteroalkylene)-aryl, ($C_0$-$C_6$ alkylene)-heteroaryl, and ($C_1$-$C_6$ heteroalkylene)-heteroaryl;

$R^{17}$ is selected from —$CH(CH_3)CH_2CH_3$, —$CH_3$, —$CH_2CH_2OCH_3$, —$(CH_2)_3(OCH_2CH_2)_3CH_2NH_2$, —$CH_2CH_2N(CH_2CH_3)_2$, —$C(CH_3)_3$, —$CH(CH_3)_2$, —$CH_2CH(CH_3)_2$, —$CH_2CH_3$, —$(CH_2)_2CH_3$, —$CH_2CH_2OH$, —$C(CH_3)CH_2CH_3$, —$CH(CH_3)CH_2CH_3$, —$C(O)CH_2CH_3$, —$C(O)CH_3$, —$CH_2C(O)OCH_2CH_3$, —$(CH_2)_2OCH_3$, and —$CH_2C(O)OH$ $R^8$ is independently selected from hydrogen, $C_1$-$C_4$ alkyl, $C_1$-$C_6$ heteroalkyl, ($C_1$-$C_4$ alkylene)-heterocyclyl, ($C_1$-$C_4$ alkylene)-heteroaryl, carbocyclyl, —$(CH_2CH_2O)_{3-20}$—$CH_2CH_2R^{20}$, and ($C_1$-$C_4$ alkylene)-aryl;

$R^{20}$ is selected from —$C(O)OH$, —$C(O)CH_3$, —$C(O)CH_2CH_3$, —$NH_2$, —$CH_2NH_2$, —$(CH_2)_2$—$NH_2$, and —$(CH_2)_3$—$NH_2$;

each $R^4$ is $C_1$-$C_8$ alkyl;

each $R^7$ is independently selected from halogen, —CN, —OH, —$S(O)_2$—$C_1$-$C_6$ alkyl, —$S$—$C_1$-$C_6$ alkyl, $C_1$-$C_6$ alkyl, $C_2$-$C_6$ alkenyl, $C_1$-$C_6$ heteroalkyl, $N(R^{3a})(R^{3b})$, $C(O)(C_1$-$C_6$ alkyl), $C(O)O(C_1$-$C_6$ alkyl), ($C_0$-$C_6$ alkylene)-carbocyclyl, ($C_1$-$C_6$ heteroalkylene)-carbocyclyl, ($C_0$-$C_6$ alkylene)-heterocyclyl, ($C_1$-$C_6$ heteroalkylene)-heterocyclyl, ($C_0$-$C_6$ alkylene)-aryl, ($C_1$-$C_6$ heteroalkylene)-aryl, ($C_0$-$C_6$ alkylene)-heteroaryl, and ($C_1$-$C_6$ heteroalkylene)-heteroaryl, wherein each alkyl is optionally substituted with halogen; or two $R^7$ are taken together with the ring carbon atoms to which they are bound to form a heterocyclyl fused to rest of the compound;

$R^{3a}$ is hydrogen;

$R^{3b}$ is —$S(O)_2$—$C_1$-$C_6$ alkyl or heterocyclyl;

n is 1;

m is 1;

o is 0, 1, or 2; and p is 0, 1, or 2.

14. A pharmaceutically acceptable composition comprising a compound of claim 1 or the pharmaceutically acceptable salt or isotopically labeled derivative thereof and a pharmaceutically acceptable carrier.

15. A method for treating a cancer in a subject in need thereof, the method comprising administering to the subject a compound of claim 1 or the pharmaceutically acceptable salt or isotopically labeled derivative thereof.

16. The method of claim 15, wherein the cancer is a breast cancer, prostate cancer, lymphoma, lung cancer, pancreatic cancer, ovarian cancer, neuroblastoma, or colorectal cancer.

17. The method of claim 16, wherein the lung cancer is small cell lung cancer.

18. The method of claim 15, wherein the subject has been determined to have deregulated c-Myc activity prior to administration of the compound or the pharmaceutically acceptable salt or isotopically labeled derivative thereof.

19. The method of claim 15, wherein the subject has been diagnosed with a cancer associated with overexpression of Myc prior to administration of the compound or the pharmaceutically acceptable salt or isotopically labeled derivative thereof.

20. The compound of claim 1 or the pharmaceutically acceptable salt or isotopically labeled derivative thereof, wherein the compound is Compound 107

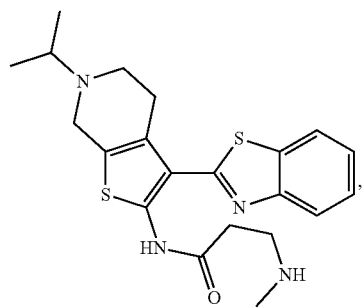

Compound 123
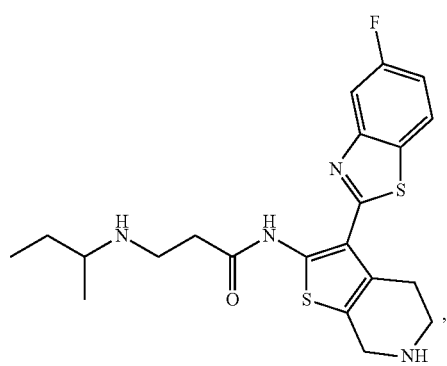
Compound 124
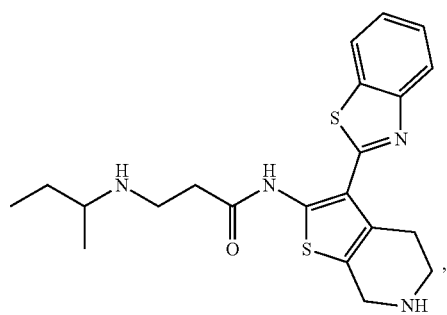
Compound 126
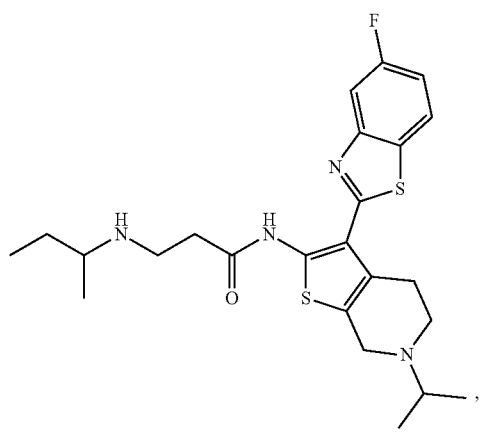
Compound 128
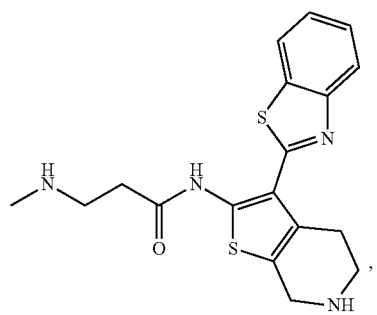
Compound 129
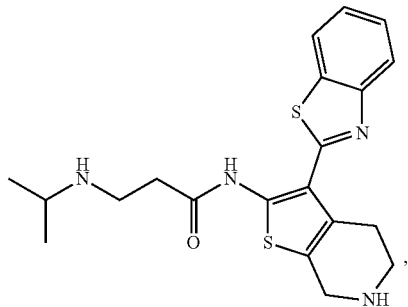
Compound 130
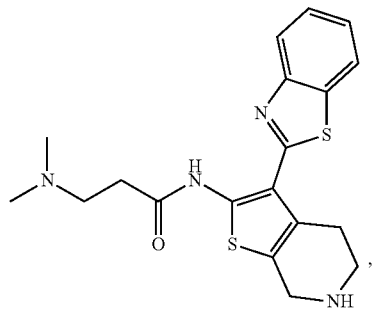
Compound 134
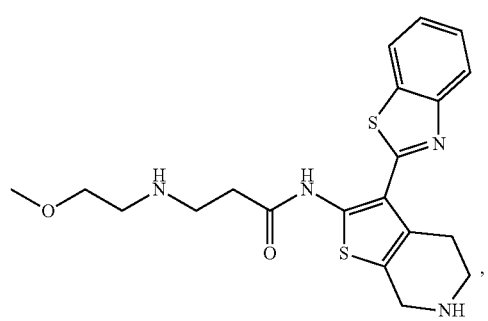
Compound 135
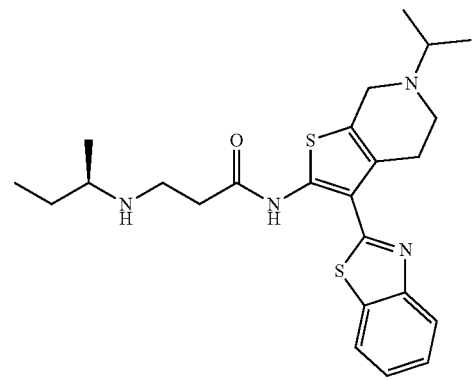

Compound 142
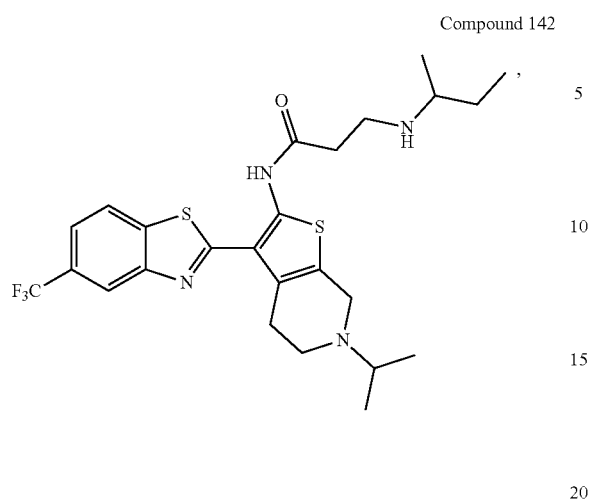
Compound 146
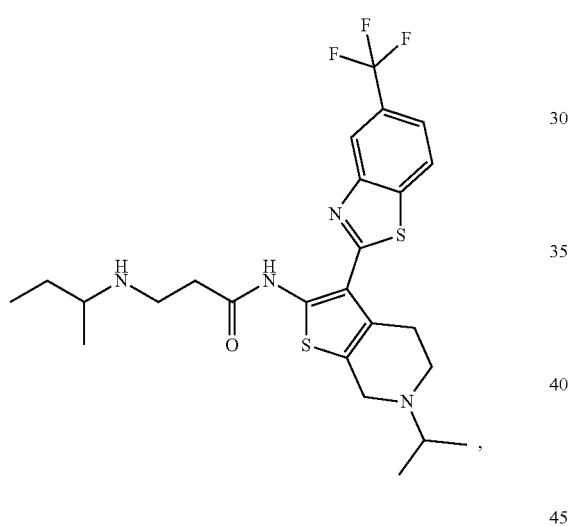
Compound 149
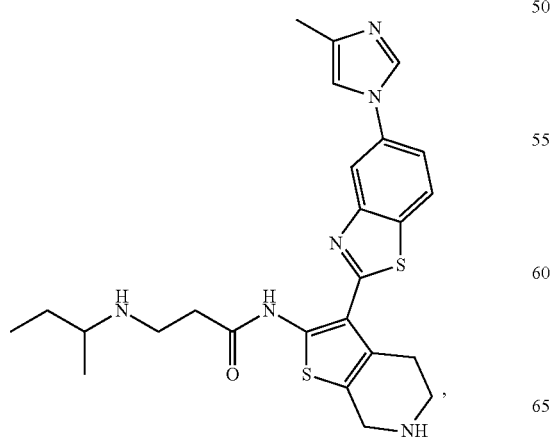
Compound 150
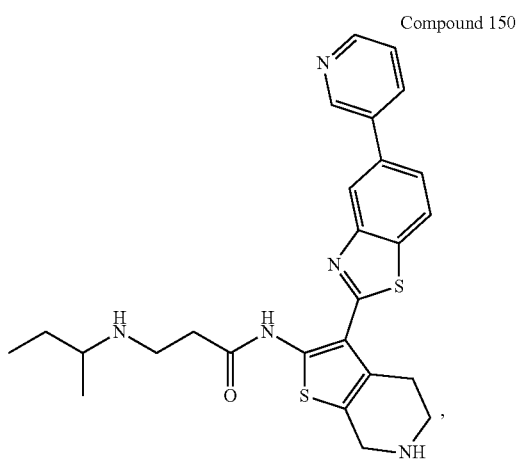
Compound 151
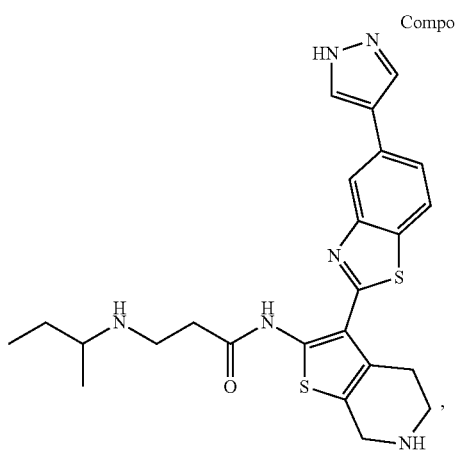
Compound 152
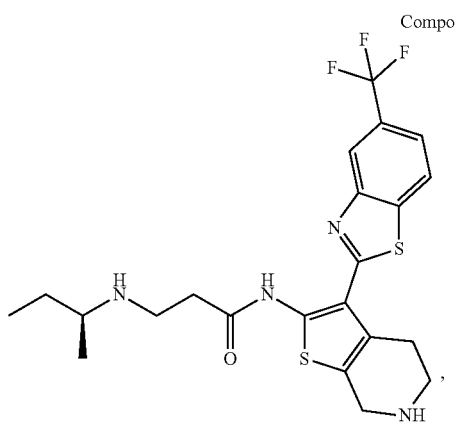

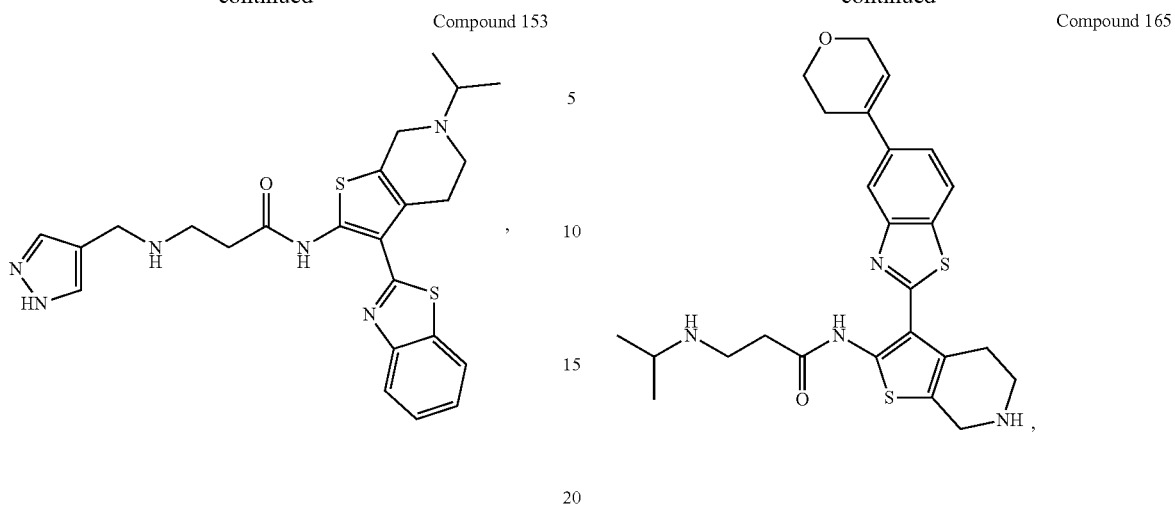

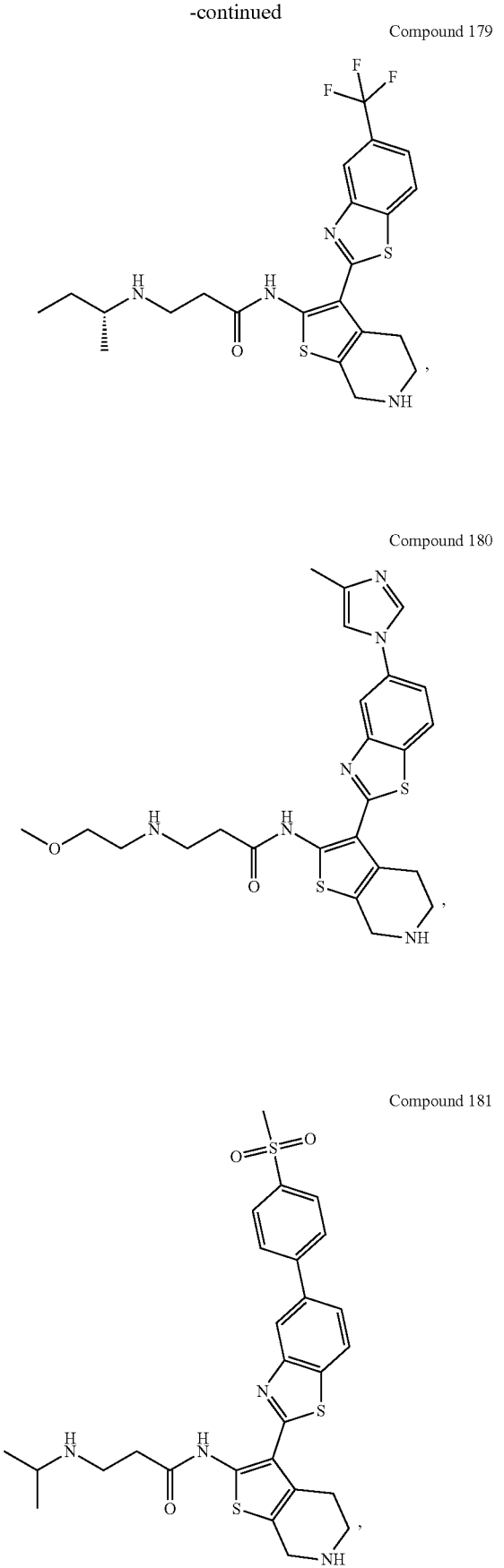
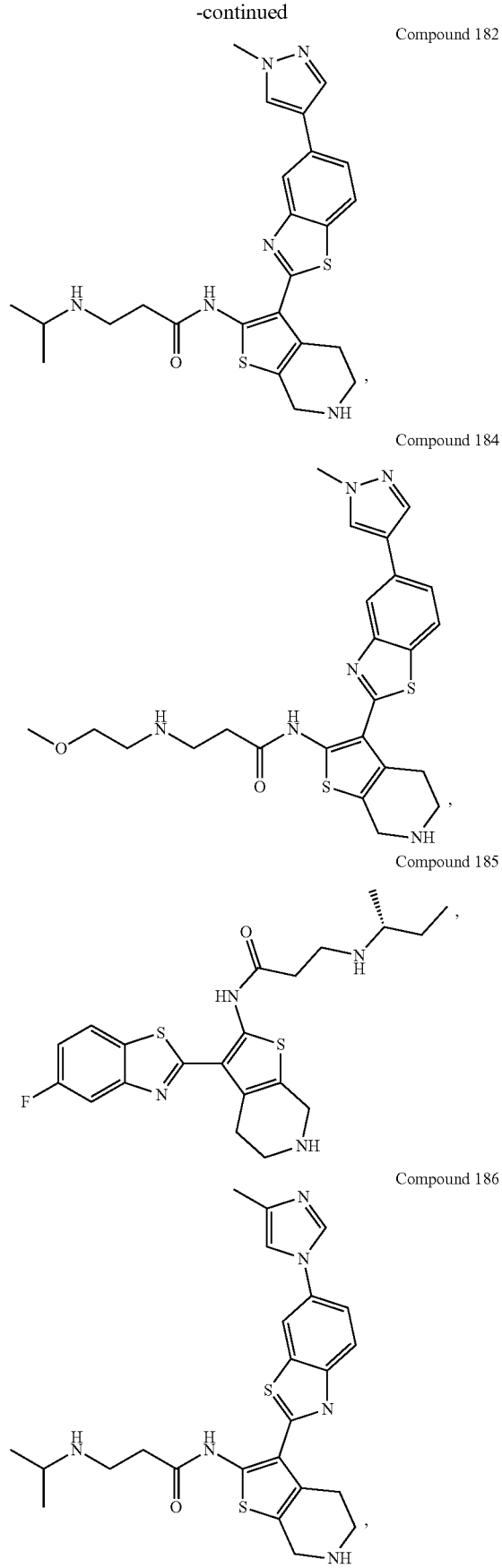

Compound 189
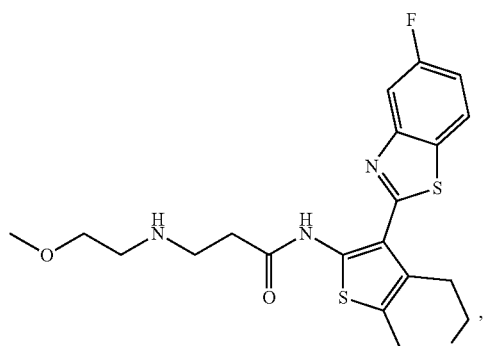
Compound 192
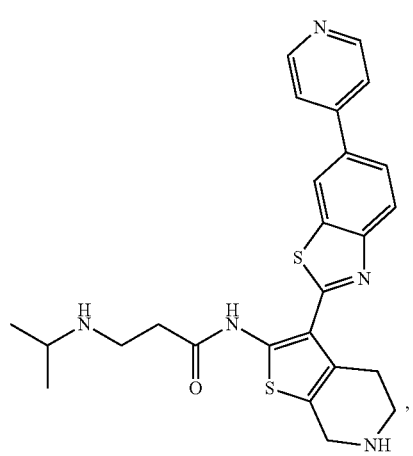
Compound 193
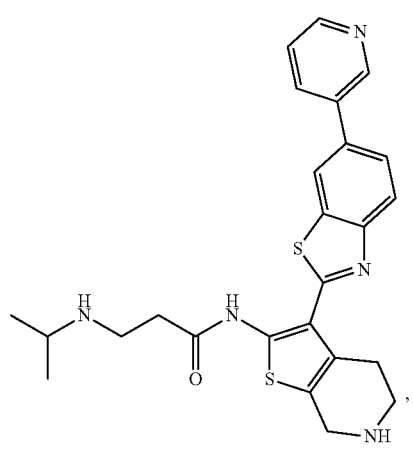
Compound 194
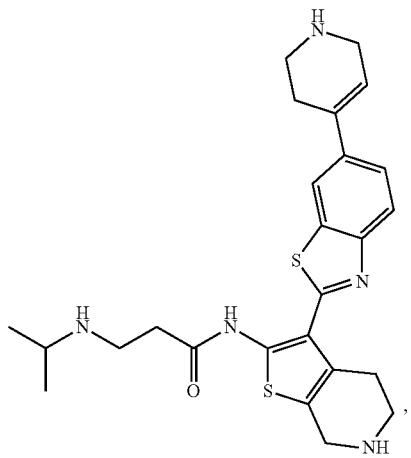
Compound 195
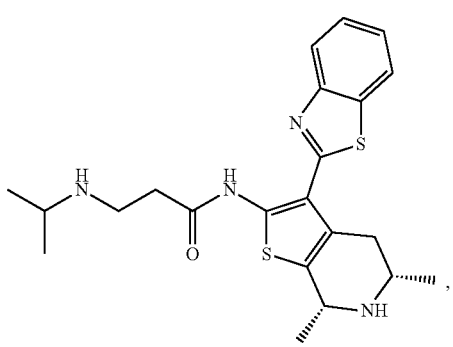
Compound 302
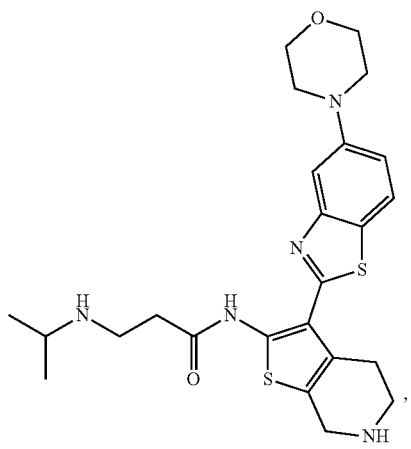

461
-continued
Compound 308
Compound 310
Compound 314
Compound 316
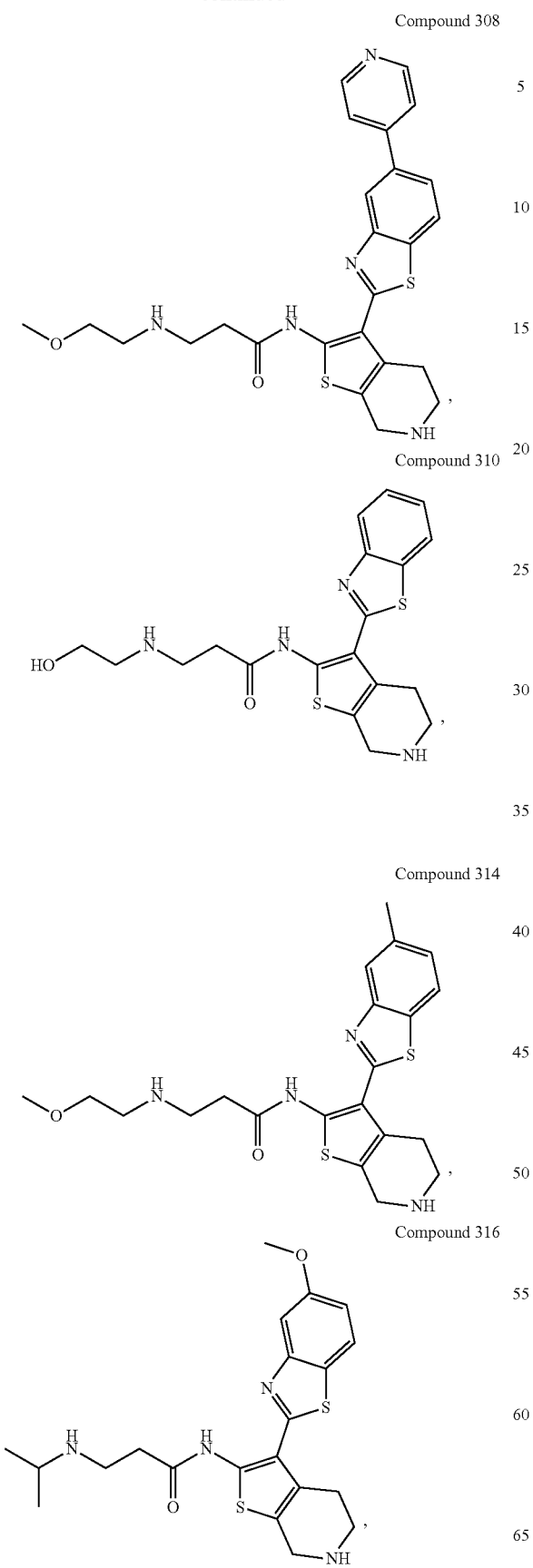
462
-continued
Compound 334
Compound 337
Compound 339
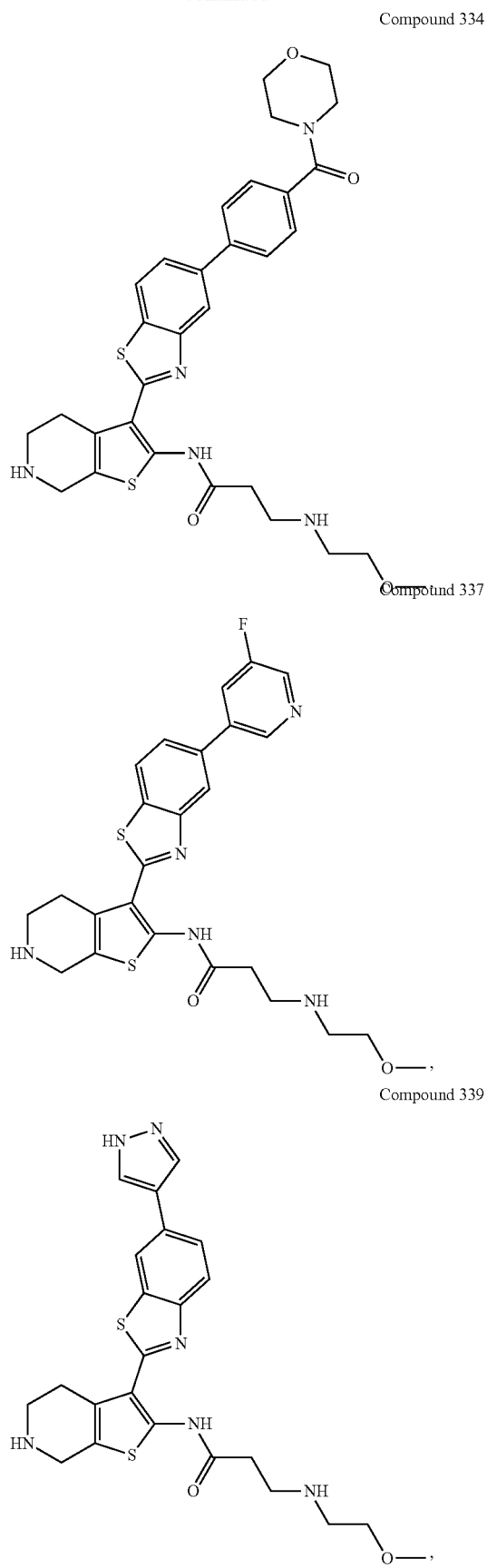

Compound 342
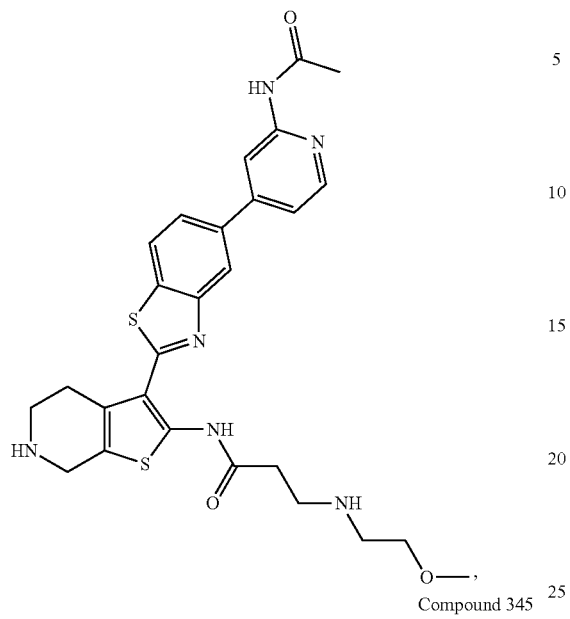
Compound 345
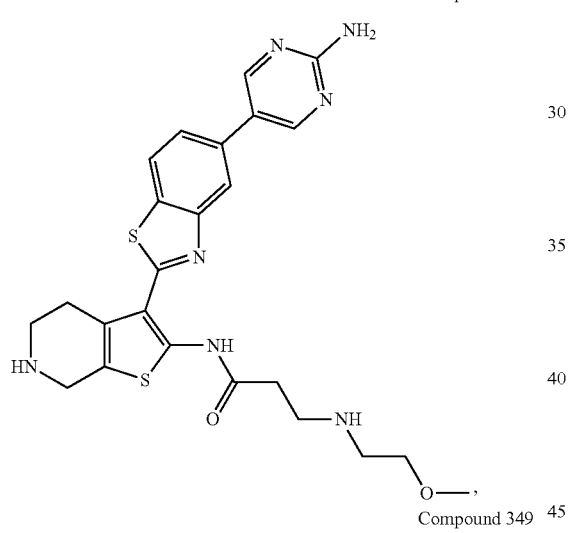
Compound 349
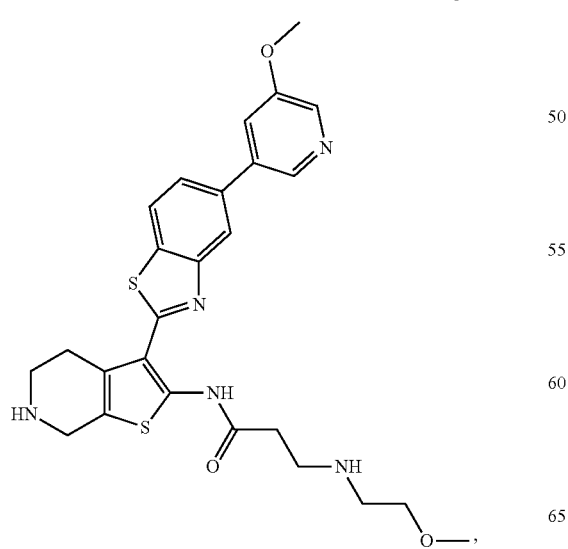
Compound 355
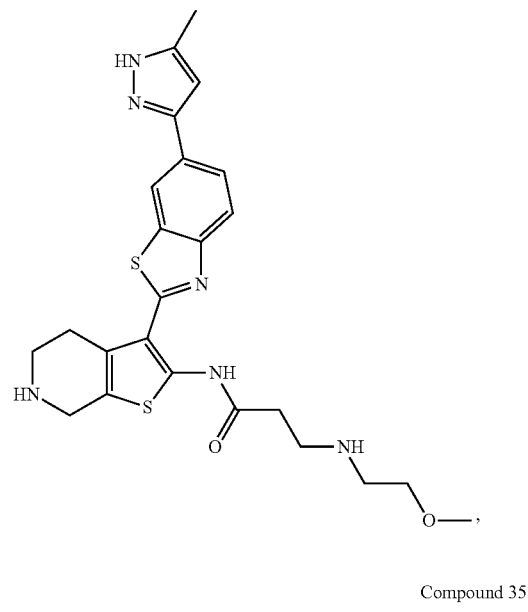
Compound 358
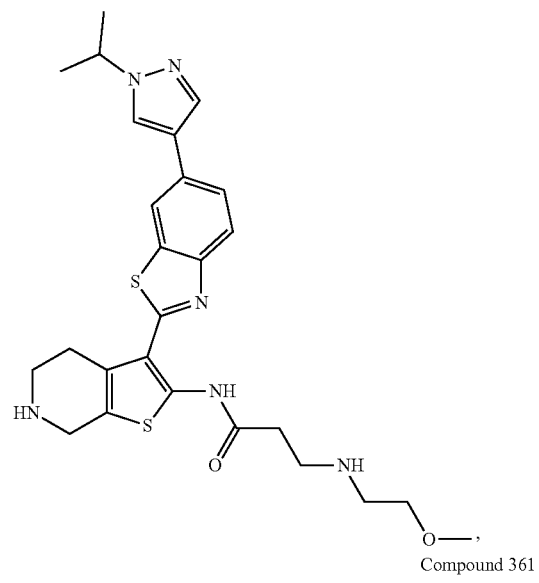
Compound 361

Compound 365
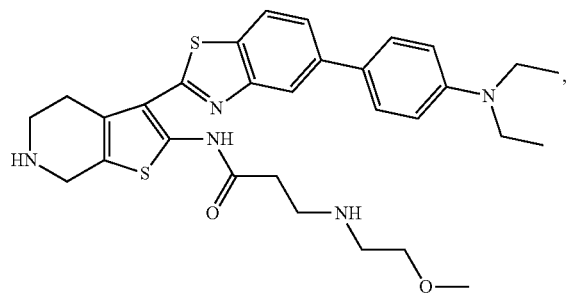
Compound 374
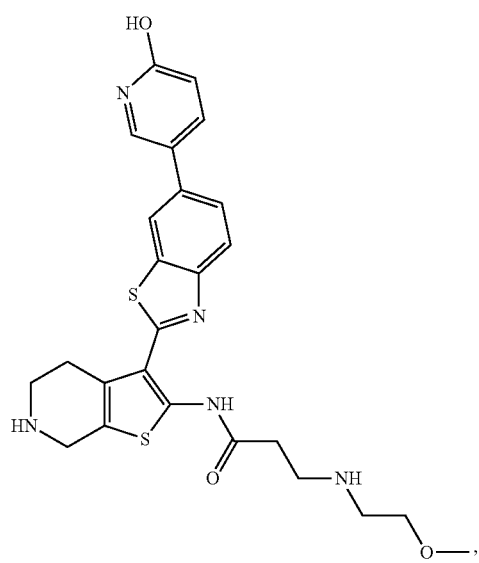
Compound 391
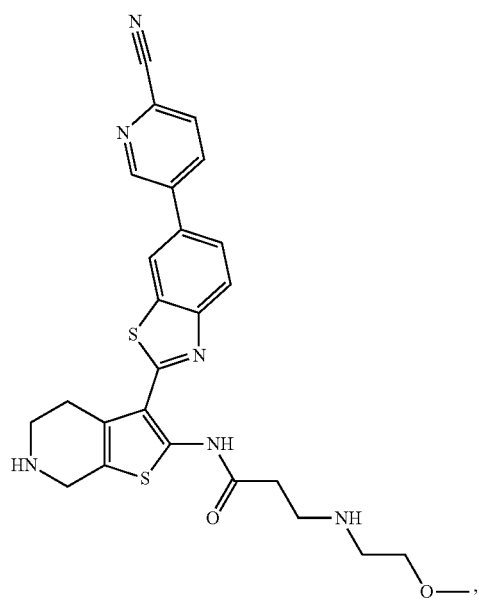
Compound 394
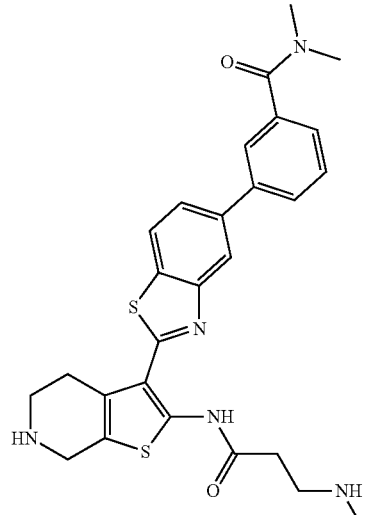
Compound 404
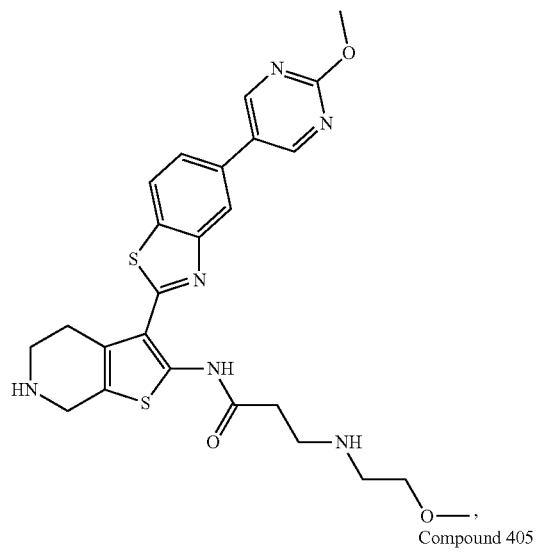
Compound 405
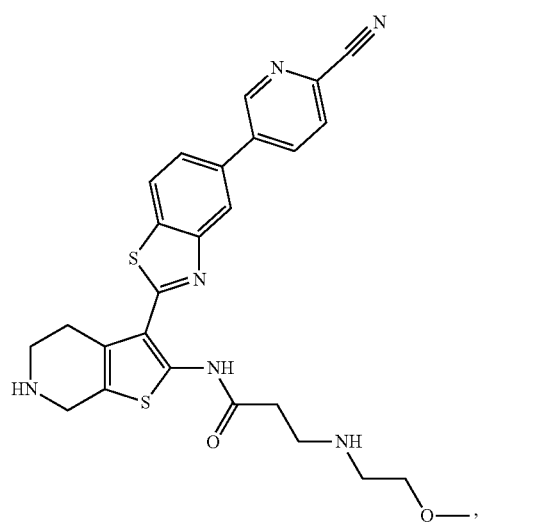

Compound 406
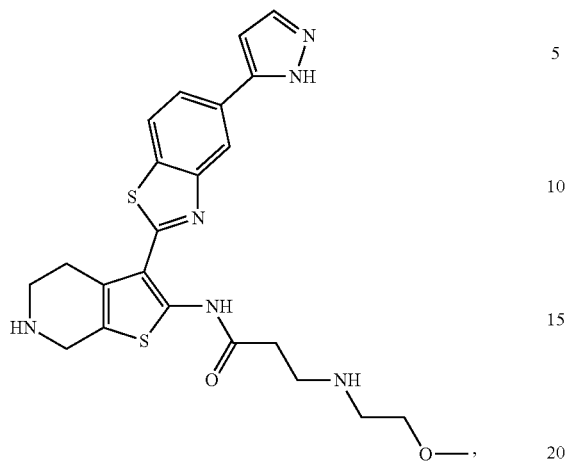
Compound 409
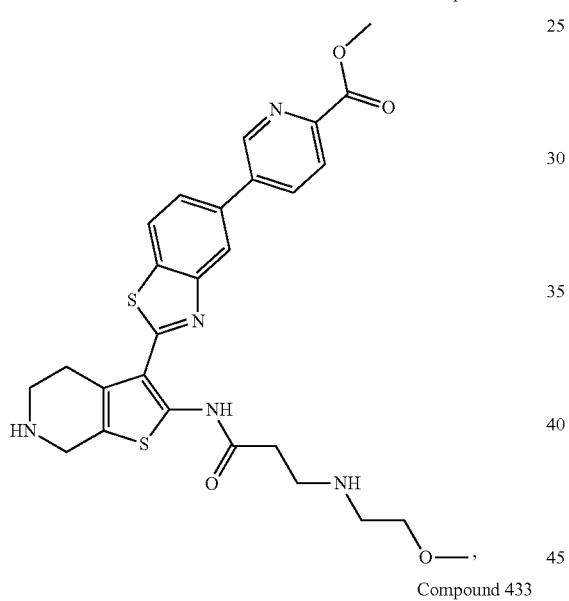
Compound 433
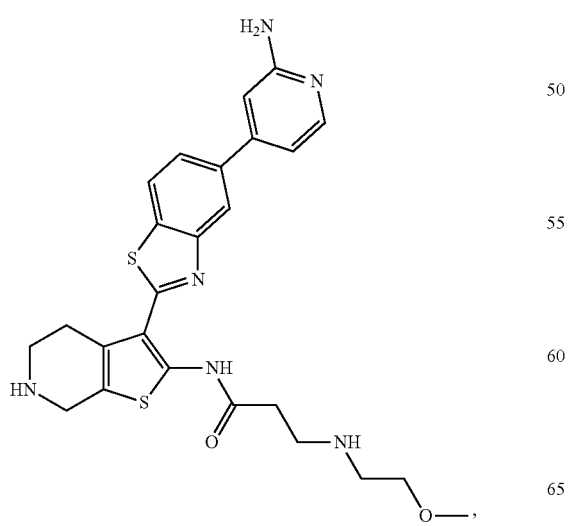
Compound 443
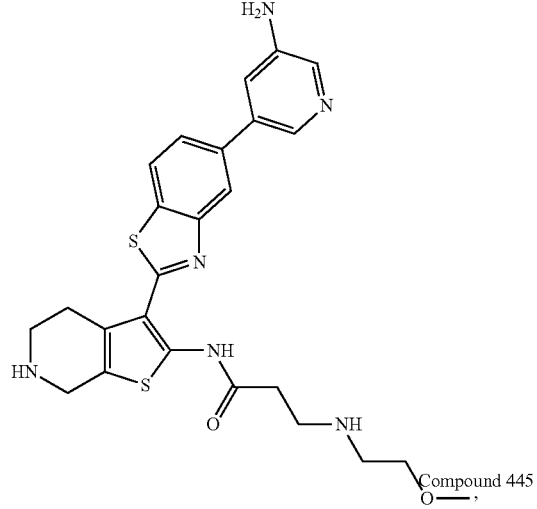
Compound 445
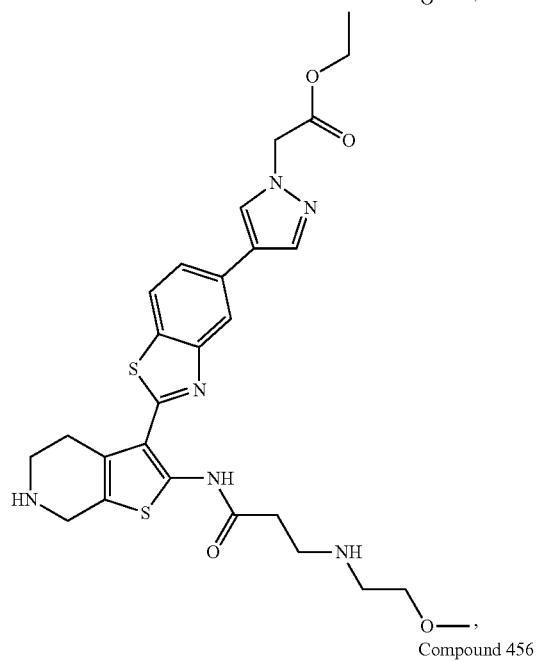
Compound 456
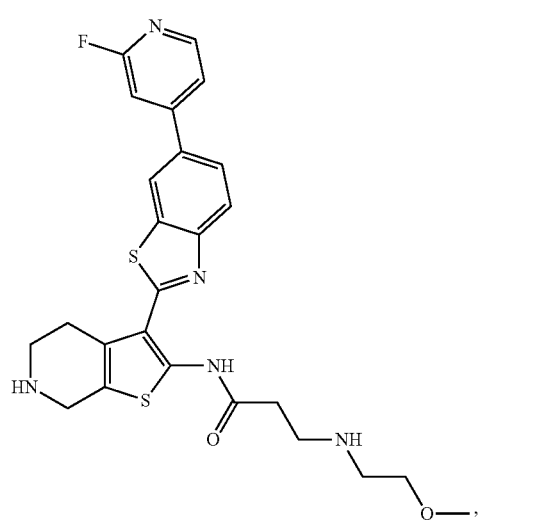

Compound 458
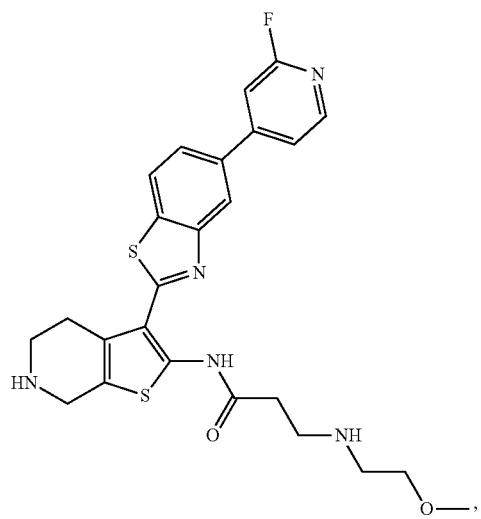
Compound 459
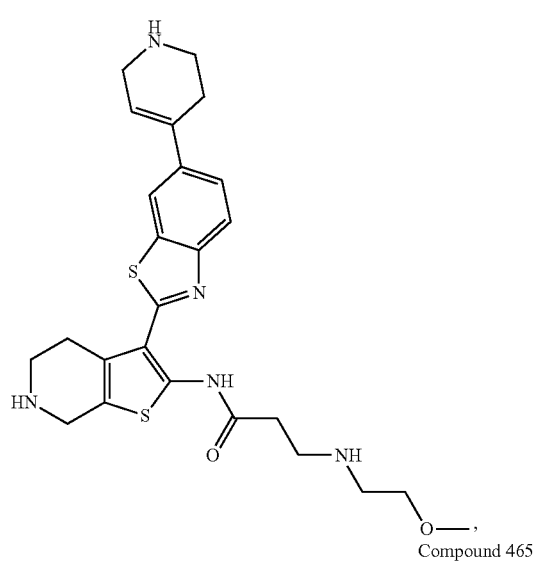
Compound 465
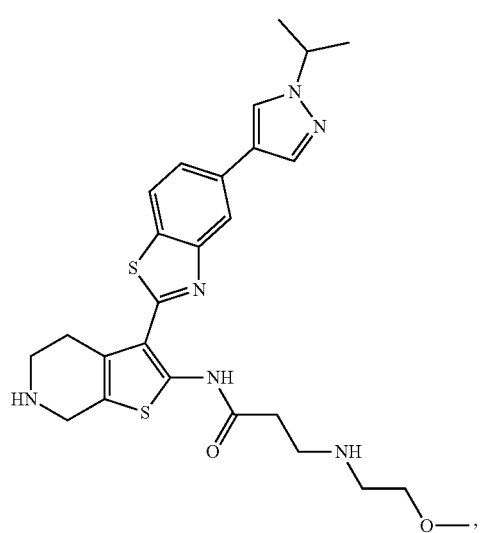
Compound 469
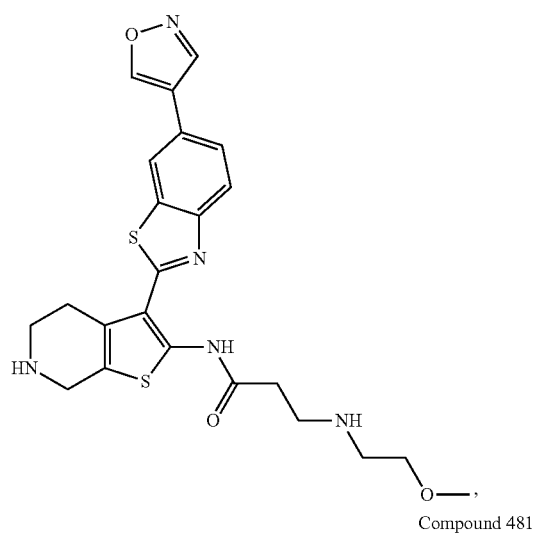
Compound 481
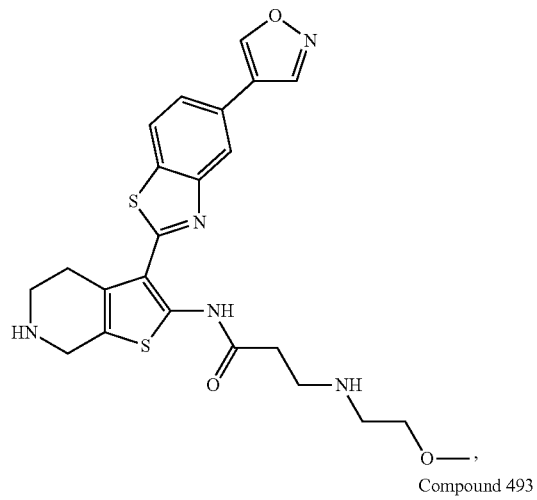
Compound 493
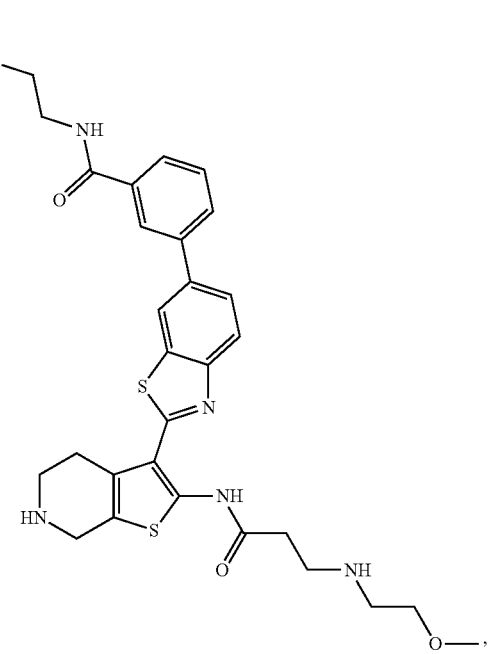

Compound 497
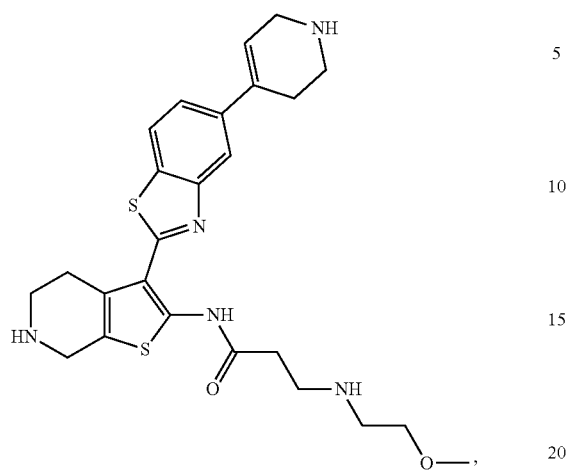
Compound 504
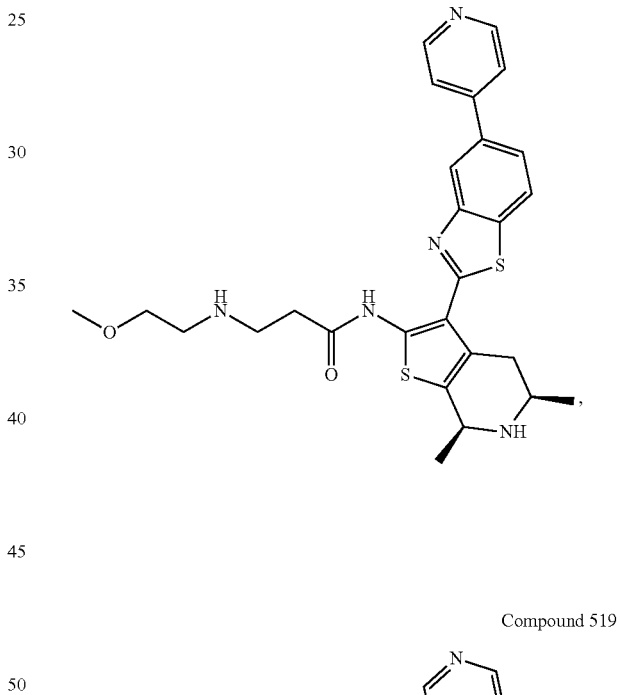
Compound 515
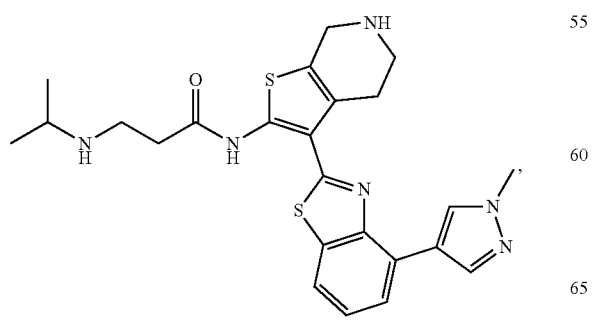
Compound 516
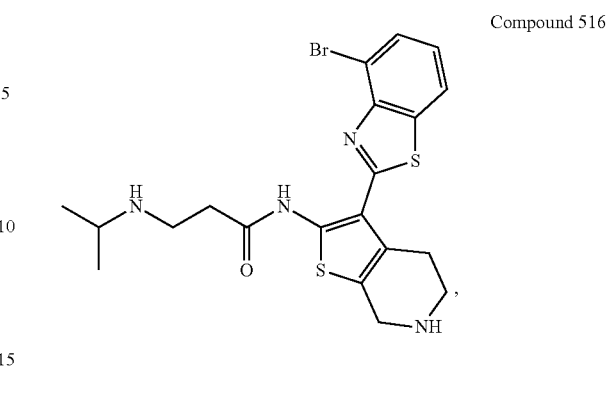
Compound 517
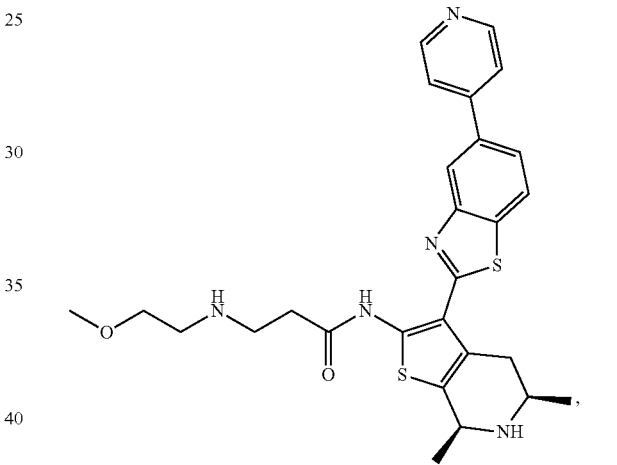
Compound 519
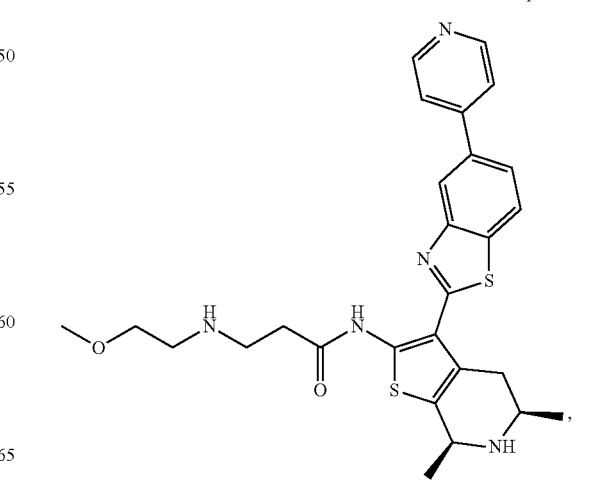

-continued
Compound 521
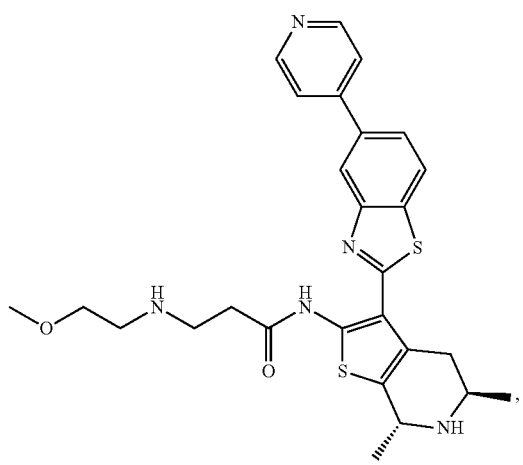
Compound 522
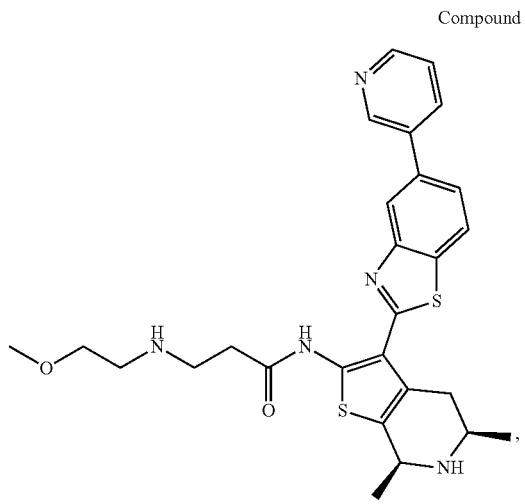
Compound 525
-continued
Compound 529
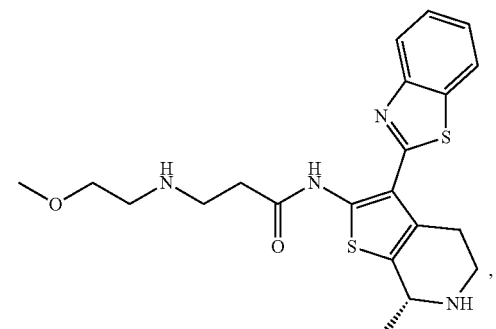
Compound 534
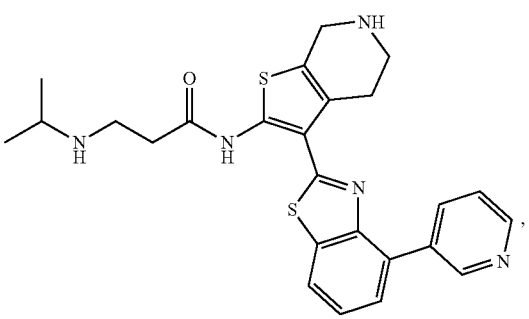
Compound 535
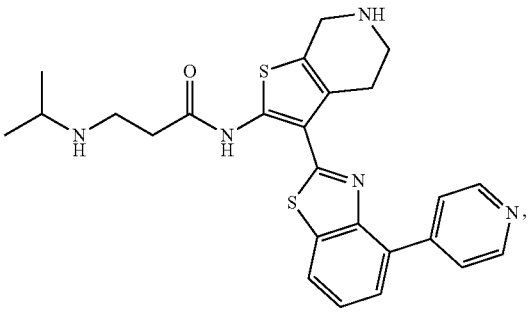
Compound 544
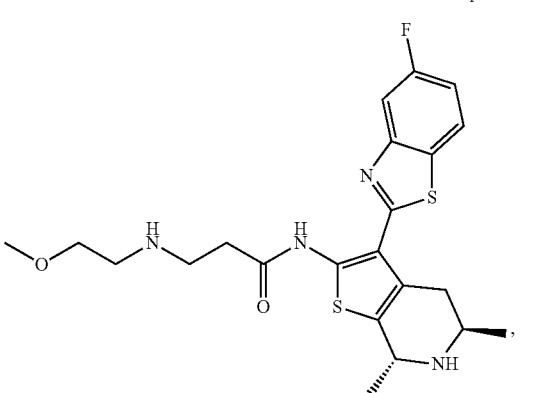

Compound 545
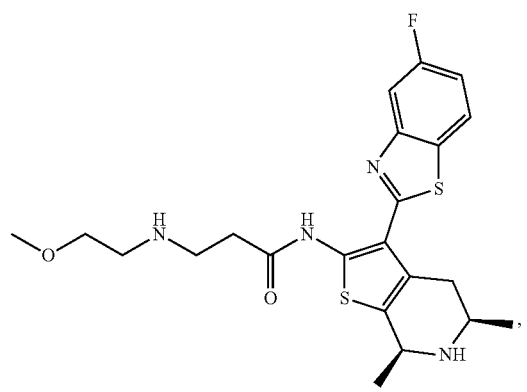
Compound 550
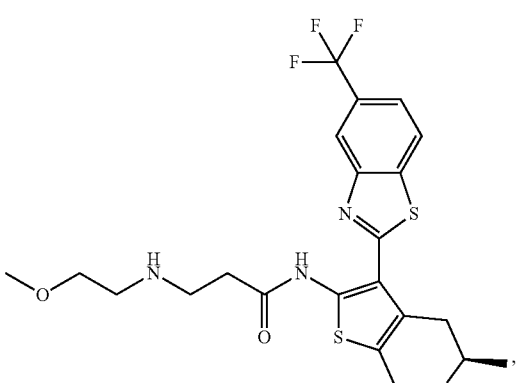
Compound 548
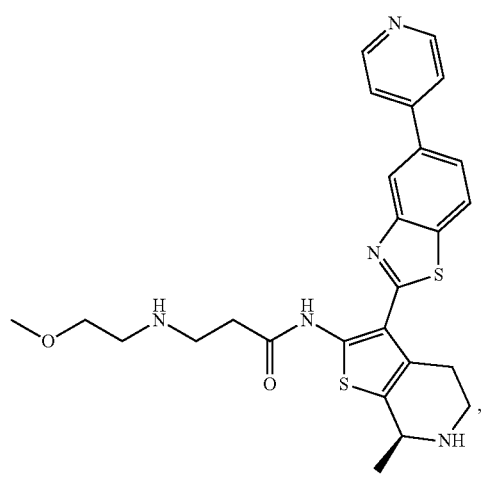
Compound 551
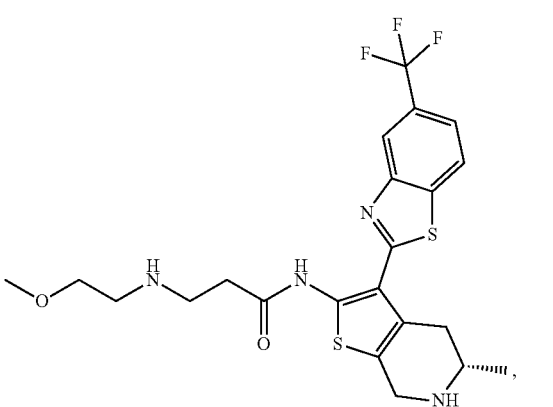
Compound 552
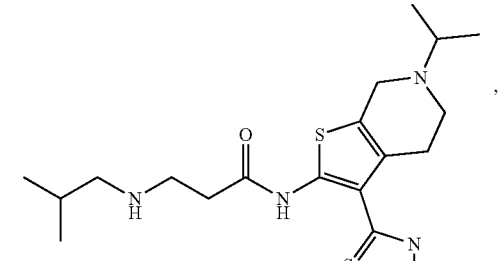
Compound 549
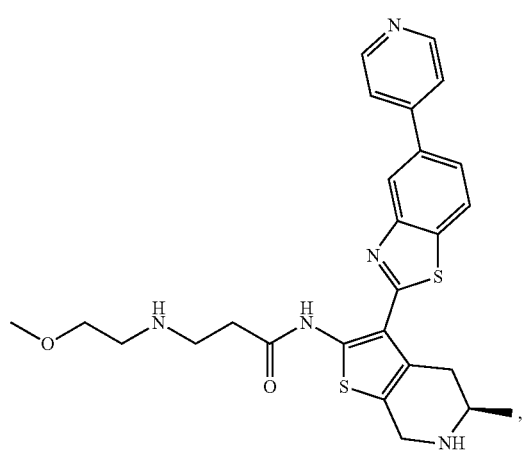
Compound 553
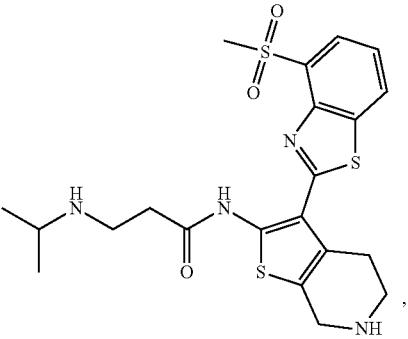

Compound 555
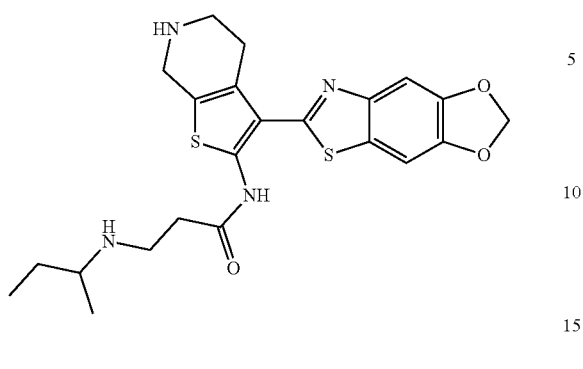
Compound 556
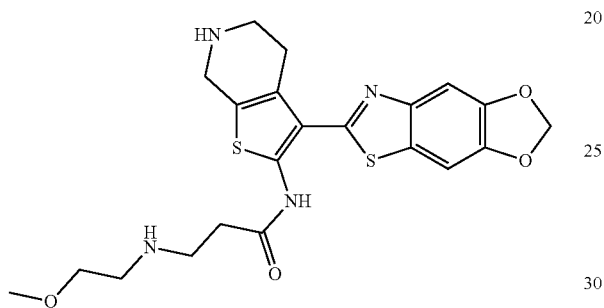
Compound 557
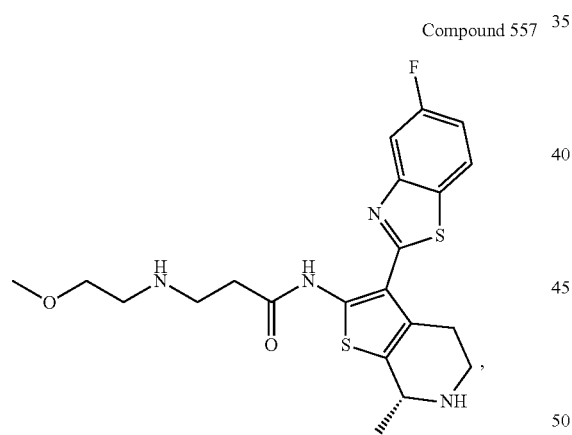
Compound 559
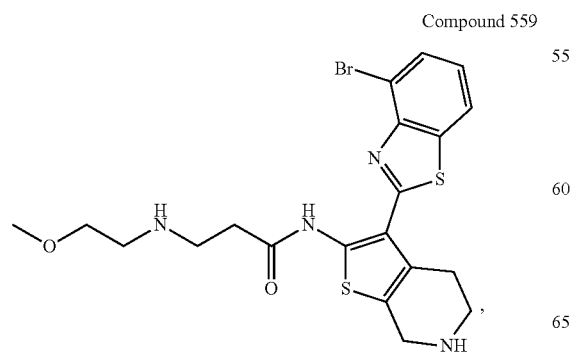
Compound 563
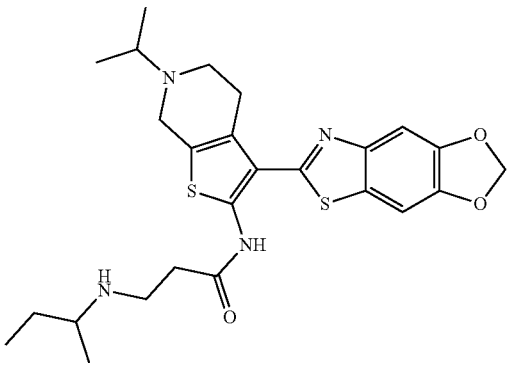
Compound 564
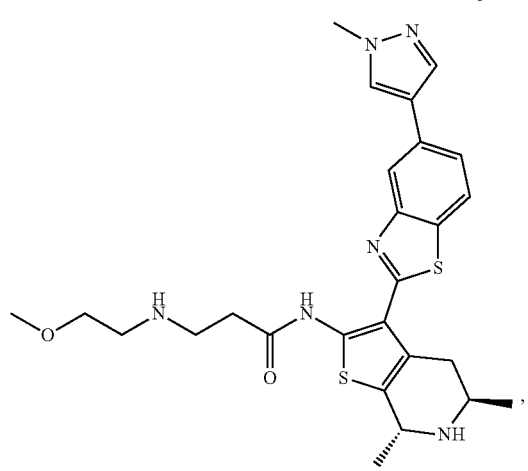
Compound 565
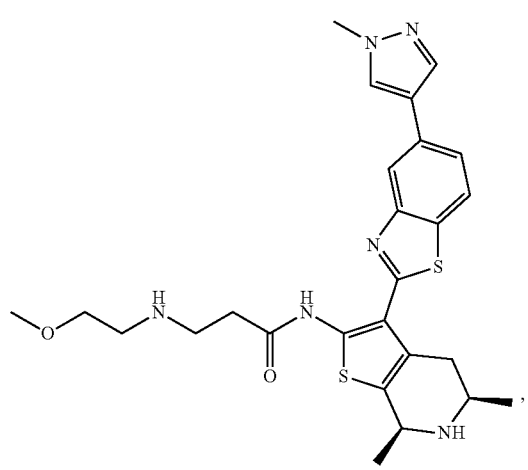

Compound 568
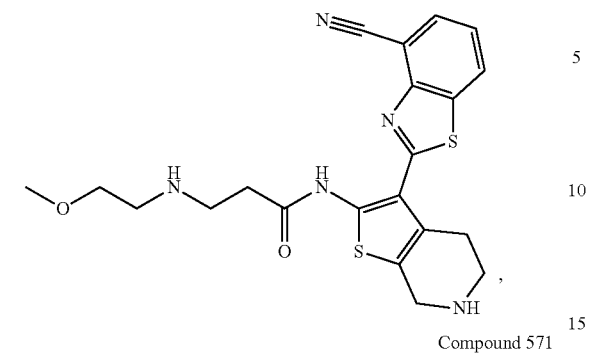
Compound 571
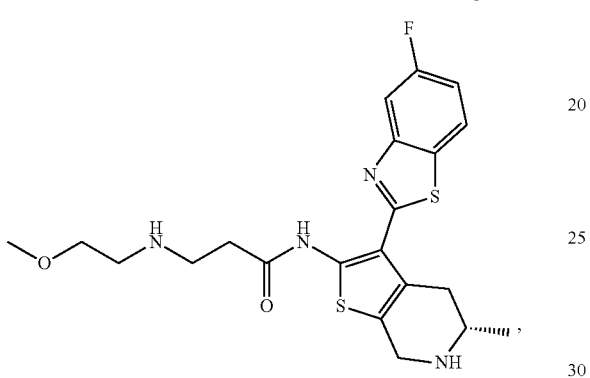
Compound 575
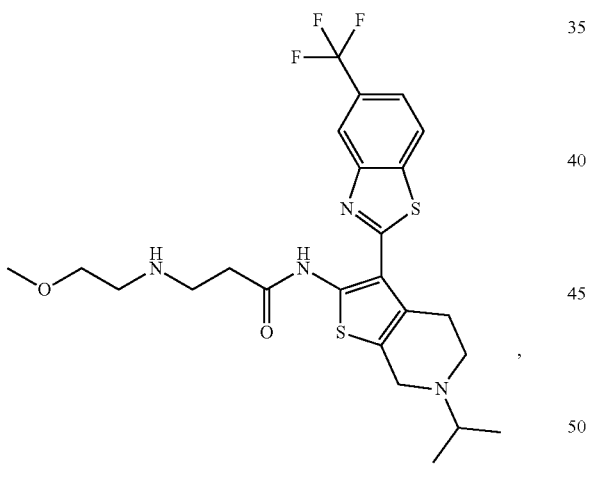
Compound 576
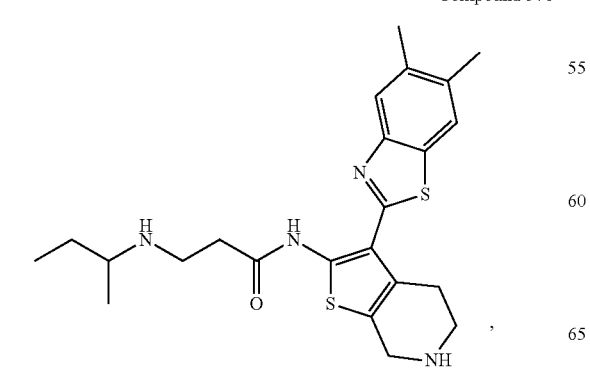
Compound 579
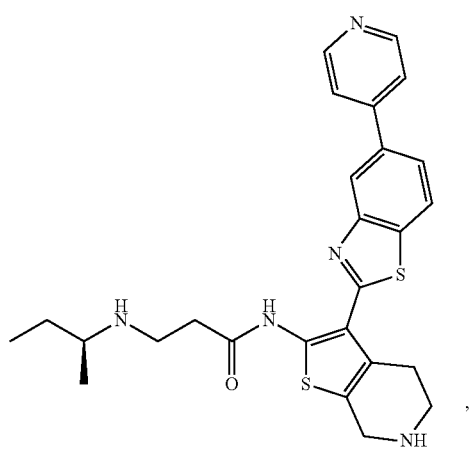
Compound 581
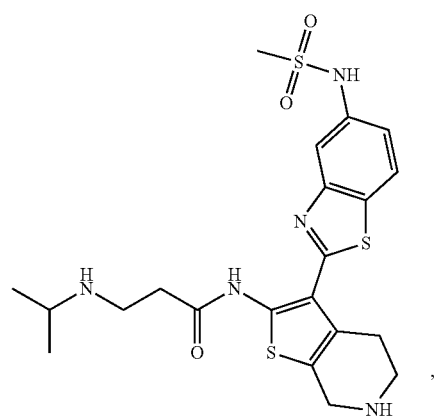
Compound 583
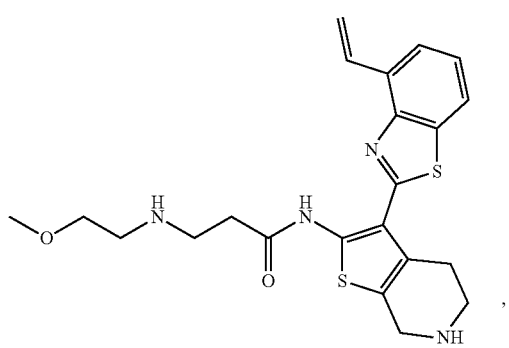

Compound 584
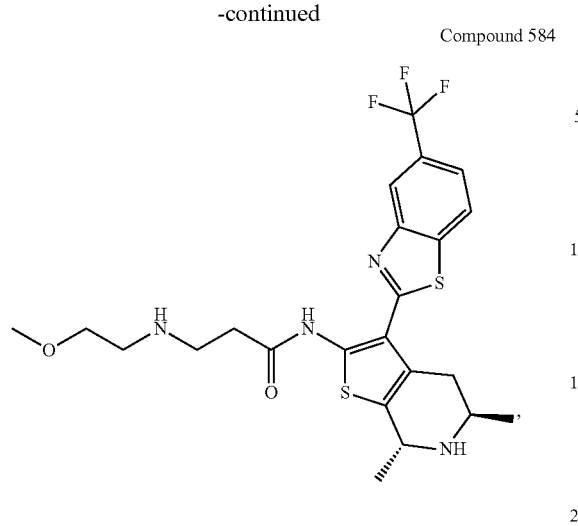
Compound 585
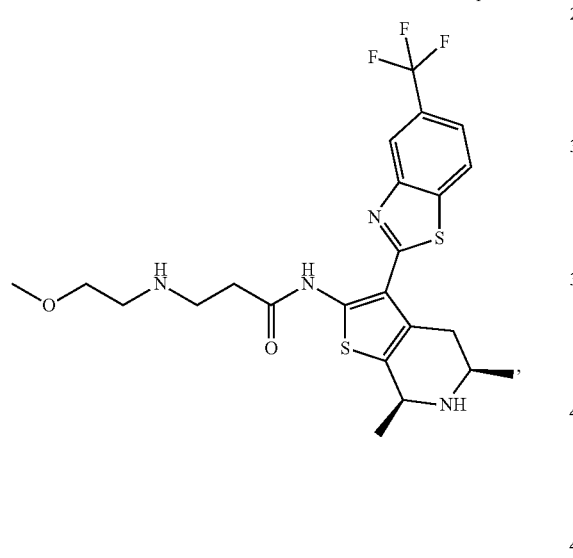
Compound 588
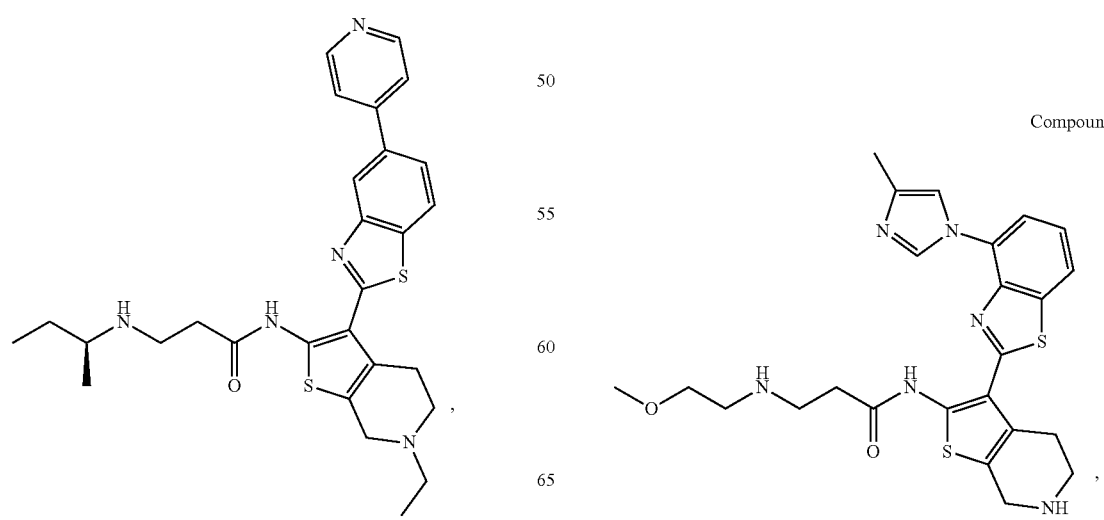
Compound 589
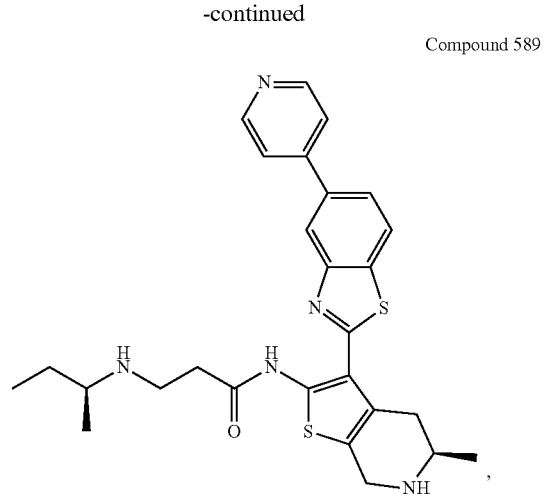
Compound 588
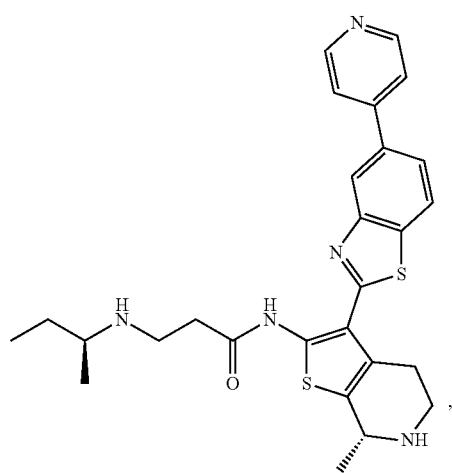
Compound 592
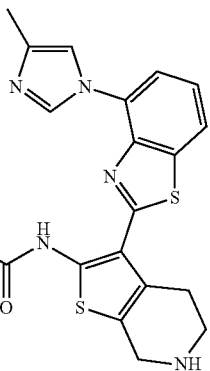

Compound 598
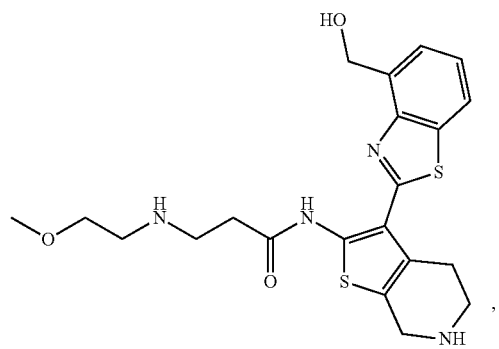
Compound 611
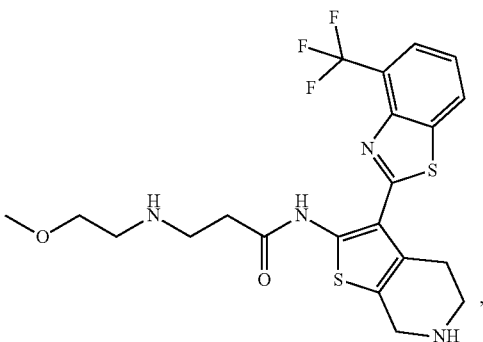
Compound 599
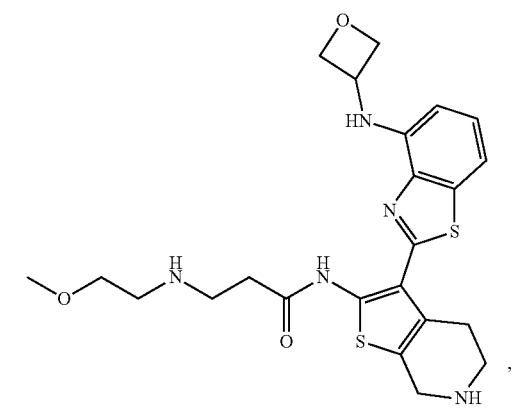
Compound 618
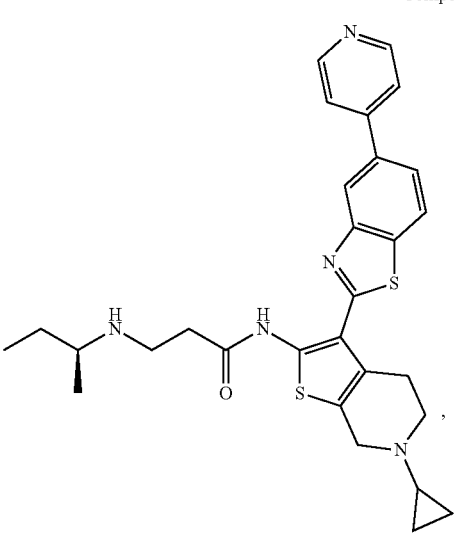
Compound 600
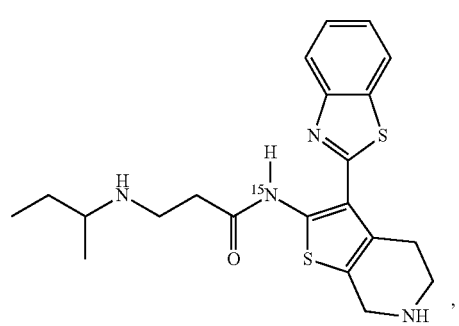
Compound 622
Compound 607
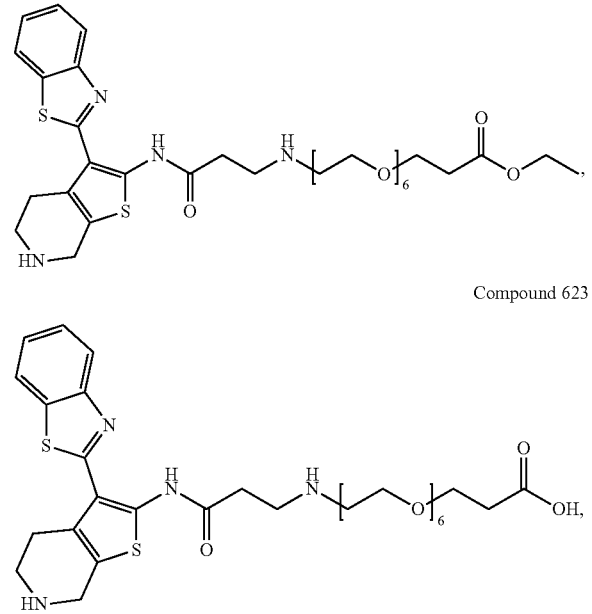
Compound 623

Compound 624

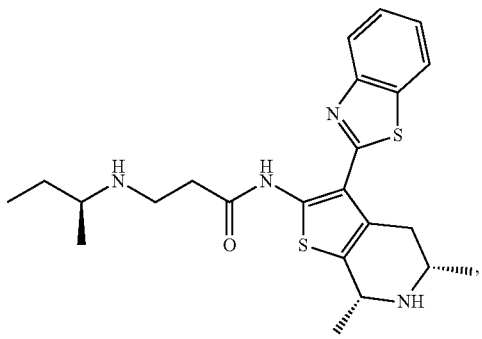

or a pharmaceutically acceptable salt, tautomer, or stereoisomer or isotopically labeled derivative thereof.

21. The compound of claim 1 or the pharmaceutically acceptable salt or isotopically labeled derivative thereof, wherein $R^{2a}$ and $R^{2b}$ are each hydrogen.

22. The compound of claim 1, wherein the compound conforms to structural formula I and excludes the pharmaceutically acceptable salt or the isotopically labeled derivative thereof.

23. The compound of claim 1, wherein the compound is in the form of the pharmaceutically acceptable salt.

24. The compound of claim 1, wherein the compound is in the form of the isotopically labeled derivative.

25. A pharmaceutically acceptable composition comprising a compound of claim 13 or the pharmaceutically acceptable salt or isotopically labeled derivative thereof and a pharmaceutically acceptable carrier.

* * * * *